US011639370B2

(12) United States Patent
Franti et al.

(10) Patent No.: US 11,639,370 B2
(45) Date of Patent: May 2, 2023

(54) ANTIGEN DELIVERY PLATFORMS

(71) Applicant: GLAXOSMITHKLINE BIOLOGICALS SA, Rixensart (BE)

(72) Inventors: Michael Franti, Redding, CT (US); Anders Lilja, Somerville, MA (US); Rebecca Loomis, Philadelphia, PA (US); Peter W. Mason, Somerville, MA (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 17/360,320

(22) Filed: Jun. 28, 2021

(65) Prior Publication Data

US 2022/0119455 A1 Apr. 21, 2022

Related U.S. Application Data

(60) Division of application No. 16/114,621, filed on Aug. 28, 2018, now Pat. No. 11,078,237, which is a continuation of application No. 13/878,835, filed as application No. PCT/US2011/055834 on Oct. 11, 2011, now abandoned.

(60) Provisional application No. 61/391,960, filed on Oct. 11, 2010.

(51) Int. Cl.

| | |
|---|---|
| ***C07K 14/005*** | (2006.01) |
| ***A61K 39/12*** | (2006.01) |
| ***C12N 15/86*** | (2006.01) |
| ***A61K 39/00*** | (2006.01) |

(52) U.S. Cl.

CPC ............ *C07K 14/005* (2013.01); *A61K 39/12* (2013.01); *C12N 15/86* (2013.01); *A61K 2039/5256* (2013.01); *A61K 2039/53* (2013.01); *A61K 2039/55555* (2013.01); *C07K 2319/92* (2013.01); *C12N 2710/16122* (2013.01); *C12N 2710/16134* (2013.01); *C12N 2710/16722* (2013.01); *C12N 2710/16734* (2013.01); *C12N 2770/36143* (2013.01); *C12N 2830/20* (2013.01); *C12N 2840/203* (2013.01)

(58) Field of Classification Search

CPC .. C07K 14/005; C07K 2319/92; A61K 39/12; A61K 2039/5256; A61K 2039/55555; A61K 2039/53; C12N 2710/16122; C12N 2710/16134; C12N 2710/16722; C12N 2710/16734; C12N 2770/36143; C12N 2830/20; C12N 2840/203; C12N 15/86; A61P 37/04; A61P 31/22

See application file for complete search history.

(56) References Cited

U.S. PATENT DOCUMENTS

| | | | |
|---|---|---|---|
| 5,013,556 | A | 5/1991 | Woodie et al. |
| 5,279,833 | A | 1/1994 | Rose |
| 5,459,127 | A | 10/1995 | Feigner et al. |
| 5,474,914 | A | 12/1995 | Spaete |
| 5,750,390 | A | 5/1998 | Thompson et al. |
| 5,814,482 | A | 9/1998 | Dubensky, Jr. et al. |
| 5,843,723 | A | 12/1998 | Dubensky, Jr |
| 5,885,613 | A | 3/1999 | Holland |
| 5,965,434 | A | 10/1999 | Wolff et al. |
| 5,972,704 | A | 10/1999 | Draper et al. |
| 6,009,406 | A | 12/1999 | Nick |
| 6,015,686 | A | 1/2000 | Dubensky et al. |
| 6,048,546 | A | 4/2000 | Sasaki et al. |
| 6,060,308 | A | 5/2000 | Parrington |
| 6,090,406 | A | 7/2000 | Popescu et al. |
| 6,156,558 | A | 12/2000 | Johnston et al. |
| 6,395,302 | B1 | 5/2002 | Hennink et al. |
| 6,432,925 | B1 | 8/2002 | Hoon et al. |
| 6,602,705 | B1 | 8/2003 | Barnett et al. |
| 6,610,321 | B2 | 8/2003 | Huang et al. |
| 6,790,449 | B2 | 9/2004 | Collins |
| 6,815,432 | B2 | 11/2004 | Wheeler et al. |
| 6,858,225 | B2 | 2/2005 | Semple et al. |
| 6,890,554 | B2 | 5/2005 | Jessee et al. |
| 7,250,404 | B2 | 7/2007 | Feigner et al. |
| 7,303,881 | B2 | 12/2007 | Huang et al. |
| 7,384,923 | B2 | 6/2008 | Gregoriadis |
| 7,422,902 | B1 | 9/2008 | Wheeler et al. |
| 7,442,381 | B2 | 10/2008 | Smith et al. |
| 7,557,200 | B2 | 7/2009 | Wu et al. |
| 7,604,803 | B2 | 10/2009 | Bacon et al. |

(Continued)

FOREIGN PATENT DOCUMENTS

| | | |
|---|---|---|
| BR | 112012001666-0 | 9/2019 |
| EP | 0786522 | 7/1997 |

(Continued)

OTHER PUBLICATIONS

Kimura et al. "Recombinant Varicella-Zoster Virus Glycoproteins E and I: Immunologic Responses and Clearance of Virus in a Guinea Pig Model of Chronic Uveitis", 1998 Journal of Infectious Diseases 178:310-317.

Kimura et al. "Varicella-Zoster Virus Glycoproteins E and I Expressed in Insect Cells Form a Heterodimer That Requires the N-Terminal Domain of Glycoprotein I", 1997 Virology 233:382-391.

Macagno et al., "Isolation of Human Monoclonal Antibodies That Potently Neutralize Human Cytomegalovirus Infection by Targeting Different Epitopes on the gH/gL/UL128-131A Complex", 2010 Journal of Virology 84 (2):1005-1013.

(Continued)

*Primary Examiner* — Rachel B Gill

(57) ABSTRACT

The invention relates to platforms for delivery of herpes virus proteins to cells, particularly proteins that form complexes in vivo. In some embodiments these proteins and the complexes they form elicit potent neutralizing antibodies. Thus, presentation of herpes virus proteins using such platforms permits the generation of broad and potent immune responses useful for vaccine development.

19 Claims, 53 Drawing Sheets

Specification includes a Sequence Listing.

(56) References Cited

U.S. PATENT DOCUMENTS

| | | | |
|---|---|---|---|
| 7,691,405 | B2 | 4/2010 | Chen et al. |
| 7,745,651 | B2 | 6/2010 | Heyes et al. |
| 7,799,565 | B2 | 9/2010 | MacLachlan et al. |
| 7,811,812 | B2 | 10/2010 | Dubensky et al. |
| 7,862,829 | B2 | 1/2011 | Johnston et al. |
| 7,977,091 | B2 | 7/2011 | Dubensky et al. |
| 8,058,069 | B2 | 11/2011 | Yaworski et al. |
| 8,338,583 | B2 | 12/2012 | Michaeli |
| 8,877,206 | B2 | 11/2014 | Chen et al. |
| 9,254,265 | B2 | 2/2016 | Geall et al. |
| 9,504,651 | B2 | 11/2016 | MacLachlan et al. |
| 9,770,463 | B2 | 9/2017 | Geall et al. |
| 9,801,897 | B2 | 10/2017 | Geall et al. |
| 9,801,987 | B2 | 10/2017 | Farnan et al. |
| 10,188,748 | B2 | 1/2019 | Mulbe et al. |
| 10,487,332 | B2 | 11/2019 | Geall |
| 10,532,067 | B2 | 1/2020 | Geall et al. |
| 10,906,867 | B2 | 2/2021 | Brito et al. |
| 11,026,964 | B2 | 6/2021 | Geall et al. |
| 11,058,762 | B2 | 7/2021 | Geall et al. |
| 11,078,237 | B2 | 8/2021 | Franti et al. |
| 11,291,635 | B2 | 4/2022 | Geall et al. |
| 11,291,682 | B2 | 4/2022 | Geall et al. |
| 11,324,770 | B2 | 5/2022 | Geall et al. |
| 2003/0091591 | A1 | 5/2003 | Xiong et al. |
| 2003/0096397 | A1 | 5/2003 | Schlesinger |
| 2003/0124134 | A1 | 7/2003 | Edwards et al. |
| 2003/0138453 | A1 | 7/2003 | O'Hagan et al. |
| 2003/0203865 | A1 | 10/2003 | Harvie |
| 2003/0212022 | A1 | 11/2003 | Vogel et al. |
| 2003/0232058 | A1 | 12/2003 | Dubensky, Jr. |
| 2004/0142025 | A1 | 7/2004 | MacLachlan et al. |
| 2004/0208848 | A1 | 10/2004 | Smith et al. |
| 2004/0228842 | A1 | 11/2004 | Lu et al. |
| 2005/0032730 | A1 | 2/2005 | Von Der Mulbe et al. |
| 2005/0042230 | A1 | 2/2005 | Anderson et al. |
| 2005/0064026 | A1 | 3/2005 | Garidel et al. |
| 2005/0064595 | A1 | 3/2005 | Maclachlan et al. |
| 2005/0118566 | A1 | 6/2005 | Escriou et al. |
| 2005/0266550 | A1 | 12/2005 | Rayner et al. |
| 2006/0002991 | A1 | 1/2006 | Essler et al. |
| 2006/0051405 | A1 | 3/2006 | Maclachlan et al. |
| 2006/0063732 | A1 | 3/2006 | Vogel et al. |
| 2006/0083780 | A1 | 4/2006 | Heyes et al. |
| 2006/0177819 | A1 | 8/2006 | Smith et al. |
| 2006/0240554 | A1 | 10/2006 | Chen et al. |
| 2006/0251620 | A1 | 11/2006 | Ivanova |
| 2007/0014805 | A1 | 1/2007 | Dalencon et al. |
| 2007/0118094 | A1 | 5/2007 | Bingham et al. |
| 2007/0207526 | A1 | 9/2007 | Coit |
| 2008/0057080 | A1 | 3/2008 | Luke et al. |
| 2008/0085870 | A1 | 4/2008 | Hermanson et al. |
| 2008/0187545 | A1 | 8/2008 | Shenk et al. |
| 2008/0249046 | A1 | 10/2008 | MacLachlan et al. |
| 2008/0260698 | A1 | 10/2008 | Weaver |
| 2008/0311158 | A1 | 12/2008 | Merola |
| 2009/0068221 | A1 | 3/2009 | Morrison |
| 2009/0075384 | A1 | 3/2009 | Kamrud |
| 2009/0104226 | A1 | 4/2009 | Perri et al. |
| 2009/0143323 | A1 | 6/2009 | Bavari |
| 2010/0040650 | A1 | 2/2010 | Crowe et al. |
| 2010/0092481 | A1 | 4/2010 | Lanzavecchia |
| 2010/0173980 | A1 | 7/2010 | Valliant et al. |
| 2010/0196492 | A1 | 8/2010 | Green et al. |
| 2010/0285112 | A1 | 11/2010 | Novobrantseva |
| 2010/0324120 | A1 | 12/2010 | Chen |
| 2011/0053893 | A1 | 3/2011 | Wu et al. |
| 2011/0070260 | A1 | 3/2011 | Baric et al. |
| 2011/0076335 | A1 | 3/2011 | Yaworski et al. |
| 2011/0117125 | A1 | 5/2011 | Hope et al. |
| 2011/0200582 | A1 | 8/2011 | Baryza |
| 2011/0200667 | A1 | 8/2011 | Contreras et al. |
| 2011/0229969 | A1 | 9/2011 | Sandig et al. |
| 2011/0244026 | A1 | 10/2011 | Guild et al. |
| 2011/0300205 | A1 | 12/2011 | Geall |
| 2011/0305727 | A1 | 12/2011 | Swanson et al. |
| 2012/0030901 | A1 | 2/2012 | Manninen et al. |
| 2012/0100207 | A1 | 4/2012 | Motokui et al. |
| 2012/0156251 | A1 | 6/2012 | Brito et al. |
| 2012/0177677 | A1 | 7/2012 | Carmon |
| 2012/0195936 | A1 | 8/2012 | Carten et al. |
| 2012/0237546 | A1 | 9/2012 | Singh et al. |
| 2012/0251618 | A1 | 10/2012 | Schrum |
| 2013/0101609 | A1 | 4/2013 | O'Hagan et al. |
| 2013/0149375 | A1 | 6/2013 | Geall |
| 2013/0164289 | A1 | 6/2013 | McVoy et al. |
| 2013/0171185 | A1 | 7/2013 | Settembre et al. |
| 2013/0171241 | A1 | 7/2013 | Geall |
| 2013/0177639 | A1 | 7/2013 | Geall et al. |
| 2013/0177640 | A1 | 7/2013 | Geall et al. |
| 2013/0183355 | A1 | 7/2013 | Jain et al. |
| 2013/0189351 | A1 | 7/2013 | Geall |
| 2013/0195968 | A1 | 8/2013 | Geall |
| 2013/0195969 | A1 | 8/2013 | Geall et al. |
| 2013/0202684 | A1 | 8/2013 | Geall |
| 2013/0225409 | A1 | 8/2013 | Allen et al. |
| 2013/0245105 | A1 | 9/2013 | De Fougerolles et al. |
| 2013/0295043 | A1 | 11/2013 | Kallen |
| 2014/0023673 | A1 | 1/2014 | Weiner |
| 2014/0030292 | A1 | 1/2014 | Franti et al. |
| 2014/0044751 | A1 | 2/2014 | Dormitzer |
| 2014/0141070 | A1 | 5/2014 | Geall et al. |
| 2014/0193484 | A1 | 7/2014 | Bertholet Girardin et al. |
| 2014/0212498 | A1 | 7/2014 | Brito et al. |
| 2014/0220083 | A1 | 8/2014 | Brito et al. |
| 2014/0227346 | A1 | 8/2014 | Geall et al. |
| 2014/0242152 | A1 | 8/2014 | Geall et al. |
| 2014/0248314 | A1 | 9/2014 | Swanson et al. |
| 2014/0255472 | A1 | 9/2014 | Geall |
| 2014/0271829 | A1 | 9/2014 | Lilja et al. |
| 2014/0275227 | A1 | 9/2014 | Hoge et al. |
| 2014/0303232 | A1 | 10/2014 | Baryza et al. |
| 2014/0348863 | A1 | 11/2014 | Bianchi et al. |
| 2015/0017251 | A1 | 1/2015 | La et al. |
| 2016/0024157 | A1 | 1/2016 | Masignani et al. |
| 2016/0129105 | A1 | 5/2016 | Muibe et al. |
| 2018/0094033 | A1 | 4/2018 | Telford et al. |
| 2019/0343862 | A1 | 11/2019 | Geall |
| 2020/0048636 | A1 | 2/2020 | Geall |
| 2020/0069793 | A1 | 3/2020 | Ciaramella |
| 2020/0113830 | A1 | 4/2020 | Geall et al. |
| 2020/0113831 | A1 | 4/2020 | Geall et al. |
| 2020/0230058 | A1 | 7/2020 | Geall et al. |
| 2020/0323896 | A1 | 10/2020 | Geall |
| 2021/0290755 | A1 | 8/2021 | Geall et al. |
| 2021/0268013 | A1 | 9/2021 | Geall et al. |
| 2022/0054525 | A1 | 2/2022 | Geall et al. |
| 2022/0056449 | A1 | 2/2022 | Geall |
| 2022/0119455 | A1 | 4/2022 | Franti et al. |
| 2022/0192997 | A1 | 6/2022 | Geall et al. |
| 2022/0213149 | A1 | 7/2022 | Franti et al. |

FOREIGN PATENT DOCUMENTS

| | | |
|---|---|---|
| EP | 1083232 | 3/2001 |
| EP | 0880360 | 10/2002 |
| EP | 1392341 | 3/2004 |
| EP | 1637144 | 3/2006 |
| EP | 1764089 | 3/2007 |
| EP | 2338478 | 6/2011 |
| EP | 2510099 | 10/2012 |
| EP | 2578685 | 4/2013 |
| EP | 2791160 | 10/2014 |
| EP | 2590626 | 10/2015 |
| EP | 2591114 | 6/2016 |
| EP | 2590676 | 8/2016 |
| EP | 3336082 | 6/2018 |
| EP | 2750707 | 10/2018 |
| EP | 3318248 | 4/2019 |
| EP | 3492109 | 6/2019 |
| EP | 2591103 | 8/2019 |
| EP | 3611266 | 2/2020 |
| EP | 3682905 | 7/2020 |
| EP | 2729126 | 12/2020 |

(56) References Cited

FOREIGN PATENT DOCUMENTS

| | | | |
|---|---|---|---|
| JP | 2000505802 | | 5/2000 |
| JP | 2007112768 | | 5/2007 |
| JP | 2007521247 | | 8/2007 |
| JP | 2008501729 | | 1/2008 |
| JP | 2009510097 | | 3/2009 |
| JP | 2009539845 | | 11/2009 |
| JP | 2010025644 | | 2/2010 |
| JP | 2010528591 | | 8/2010 |
| JP | 2011504802 | | 2/2011 |
| WO | WO8900812 | | 2/1989 |
| WO | WO9011092 | | 10/1990 |
| WO | WO9219752 | | 11/1992 |
| WO | WO1993024640 | | 12/1993 |
| WO | WO9527721 | | 10/1995 |
| WO | WO9608235 | | 3/1996 |
| WO | 96/17072 | A2 | 6/1996 |
| WO | WO9728818 | | 8/1997 |
| WO | WO1997030170 | | 8/1997 |
| WO | WO1998010748 | | 3/1998 |
| WO | WO1998051278 | | 11/1998 |
| WO | WO1999011808 | | 3/1999 |
| WO | WO9928487 | | 6/1999 |
| WO | WO9930733 | | 6/1999 |
| WO | WO1999052503 | | 10/1999 |
| WO | WO9955310 | | 11/1999 |
| WO | WO0003683 | | 1/2000 |
| WO | WO2000000617 | | 1/2000 |
| WO | WO200129233 | | 4/2001 |
| WO | WO200179253 | | 10/2001 |
| WO | WO0193836 | | 12/2001 |
| WO | WO2002002606 | | 1/2002 |
| WO | WO200209645 | | 2/2002 |
| WO | WO2002026209 | | 4/2002 |
| WO | WO2002034771 | | 5/2002 |
| WO | WO2002061113 | | 8/2002 |
| WO | WO02074920 | | 9/2002 |
| WO | WO2002072027 | | 9/2002 |
| WO | WO2002079239 | | 10/2002 |
| WO | WO2002095023 | | 11/2002 |
| WO | WO2002098443 | | 12/2002 |
| WO | WO2003018054 | | 3/2003 |
| WO | WO2003068190 | | 8/2003 |
| WO | WO2004076645 | | 9/2004 |
| WO | WO2004098509 | | 11/2004 |
| WO | WO2005002619 | | 1/2005 |
| WO | WO2005007689 | | 1/2005 |
| WO | WO2005032582 | | 4/2005 |
| WO | WO2005046621 | | 5/2005 |
| WO | WO2005060934 | | 7/2005 |
| WO | WO2005111066 | | 11/2005 |
| WO | WO2005113781 | | 12/2005 |
| WO | WO2005113782 | | 12/2005 |
| WO | WO2005120152 | | 12/2005 |
| WO | WO2005121348 | | 12/2005 |
| WO | WO2006053646 | | 5/2006 |
| WO | WO2006061643 | | 6/2006 |
| WO | WO2006078294 | | 7/2006 |
| WO | WO2006089264 | | 8/2006 |
| WO | WO2006091517 | | 8/2006 |
| WO | WO2006092607 | | 9/2006 |
| WO | WO2006094756 | | 9/2006 |
| WO | WO2006110413 | | 10/2006 |
| WO | WO2006138004 | | 12/2006 |
| WO | WO2007014754 | | 2/2007 |
| WO | WO2007024708 | | 3/2007 |
| WO | 2007041270 | A1 | 4/2007 |
| WO | WO2007036366 | | 4/2007 |
| WO | WO2007047749 | | 4/2007 |
| WO | WO2007049155 | | 5/2007 |
| WO | WO2007107304 | | 9/2007 |
| WO | 2007146024 | A2 | 12/2007 |
| WO | WO2007149518 | | 12/2007 |
| WO | WO2008020330 | | 2/2008 |
| WO | WO2008033966 | | 3/2008 |
| WO | WO2008051245 | | 5/2008 |
| WO | WO2008083949 | | 7/2008 |
| WO | WO2008103276 | | 8/2008 |
| WO | WO2008137758 | | 11/2008 |
| WO | 2008148068 | A1 | 12/2008 |
| WO | WO2008155141 | | 12/2008 |
| WO | WO2009003975 | | 1/2009 |
| WO | WO2009016515 | | 2/2009 |
| WO | WO2009026328 | | 2/2009 |
| WO | WO2009031043 | | 3/2009 |
| WO | WO2009040443 | | 4/2009 |
| WO | WO2009042794 | | 4/2009 |
| WO | 2009068485 | A1 | 6/2009 |
| WO | WO2009074861 | | 6/2009 |
| WO | WO2009079185 | | 6/2009 |
| WO | WO2009086558 | | 7/2009 |
| WO | WO2009104092 | | 8/2009 |
| WO | WO2009109860 | | 9/2009 |
| WO | WO2009111088 | | 9/2009 |
| WO | WO2009127230 | | 10/2009 |
| WO | WO2009132131 | | 10/2009 |
| WO | WO2009132206 | | 10/2009 |
| WO | WO2009146867 | | 12/2009 |
| WO | WO2009156852 | | 12/2009 |
| WO | 2010/007463 | A1 | 1/2010 |
| WO | 2010/007533 | A2 | 1/2010 |
| WO | WO2010015098 | | 2/2010 |
| WO | WO2010019718 | | 2/2010 |
| WO | WO2010036948 | | 4/2010 |
| WO | WO2010042877 | | 4/2010 |
| WO | WO2010053572 | | 5/2010 |
| WO | WO2010054401 | | 5/2010 |
| WO | WO2010059689 | | 5/2010 |
| WO | WO2010088537 | | 8/2010 |
| WO | WO2010119343 | | 10/2010 |
| WO | WO2010144740 | | 12/2010 |
| WO | WO2011001780 | | 1/2011 |
| WO | WO2011005799 | | 1/2011 |
| WO | WO2011008974 | | 1/2011 |
| WO | WO2011012316 | | 2/2011 |
| WO | WO2011068810 | | 6/2011 |
| WO | WO2011071860 | | 6/2011 |
| WO | WO2011071931 | | 6/2011 |
| WO | WO2011075656 | | 6/2011 |
| WO | WO2011076807 | | 6/2011 |
| WO | WO2011112717 | | 9/2011 |
| WO | WO2011127316 | | 10/2011 |
| WO | WO2011140627 | | 11/2011 |
| WO | 2012006378 | | 1/2012 |
| WO | WO2012006369 | | 1/2012 |
| WO | WO2012006372 | | 1/2012 |
| WO | WO2012006376 | | 1/2012 |
| WO | WO2012006377 | | 1/2012 |
| WO | WO2012006380 | | 1/2012 |
| WO | WO2012019168 | | 2/2012 |
| WO | 2012030901 | | 3/2012 |
| WO | 2012034025 | | 3/2012 |
| WO | WO2012031043 | | 3/2012 |
| WO | WO2012031046 | | 3/2012 |
| WO | WO2012045075 | | 4/2012 |
| WO | WO2012045082 | | 4/2012 |
| WO | WO2012135805 | | 10/2012 |
| WO | WO2012158736 | | 11/2012 |
| WO | WO2012170889 | | 12/2012 |
| WO | WO2013006825 | | 1/2013 |
| WO | WO2013006837 | | 1/2013 |
| WO | WO2013033563 | | 3/2013 |
| WO | WO2013039861 | | 3/2013 |
| WO | WO2013052523 | | 4/2013 |
| WO | WO2013090648 | | 6/2013 |
| WO | WO2013096709 | | 6/2013 |
| WO | WO2013130161 | | 9/2013 |
| WO | WO2013151663 | | 10/2013 |
| WO | WO2013151664 | | 10/2013 |
| WO | WO2013151665 | | 10/2013 |
| WO | WO2013151666 | | 10/2013 |
| WO | WO2013151667 | | 10/2013 |
| WO | WO2013151668 | | 10/2013 |
| WO | WO2013151669 | | 10/2013 |
| WO | WO2013151670 | | 10/2013 |

(56) References Cited

FOREIGN PATENT DOCUMENTS

| | | |
|---|---|---|
| WO | WO2013151671 | 10/2013 |
| WO | WO2013151672 | 10/2013 |
| WO | WO2013151736 | 10/2013 |
| WO | WO2014081507 | 5/2014 |
| WO | WO2014152211 | 9/2014 |
| WO | WO2014160243 | 10/2014 |
| WO | WO2017049245 | 3/2017 |
| WO | WO2017075531 | 5/2017 |
| WO | WO2018089790 | 5/2018 |
| WO | WO2020106946 | 5/2020 |
| WO | WO2021038508 | 3/2021 |
| WO | WO2022137133 | 6/2022 |

OTHER PUBLICATIONS

Reap et al., "Cellular and Humoral Immune Responses to Alphavirus Replicon Vaccines Expressing Cytomegalovirus pp. 65, IE1, and gB Proteins", Clin. Vaccine Immunol. Jun. 2007; 14(6):748-55. Epub Apr. 18, 2007.
Chee et al., "Hypothetical Protein UL128", UniProtKB/Swiss-Prot: P16837, Dep. Feb. 1, 1991.
Davison AJ, UL131A [Human Herpesvirus 5]. NCBI Reference Sequence: YP_081566.1, Dep. Sep. 16, 2004.
Davison AJ, UL130 [Human Herpesvirus 5]. NCBI Reference Sequence: YP_081565.1, Dep. Sep. 16, 2004.
Davison AJ, UL115; gL [Human Herpesvirus 5]. NCBI Reference Sequence: YP_081555.1, Dep. Sep. 16, 2004.
Davison AJ, UL75; gH [Human Herpesvirus 5]. NCBI Reference Sequence: YP_081523.1, Dep. Sep. 16, 2004.
Dolan et al, "Genetic Content of Wild-Type Human Cytomegalovirus", J. Gen. Virol. May 2004; 85(Pt 5):1301-12.
Hahn et al, "Deletion Mapping of the Encephalomyocarditis Virus Primary Cleavage Site". J. Virol. Aug. 2001; 75 (15):7215-8.
Corresponding parent U.S. Appl. No. 16/114,621, filed Aug. 28, 2018.
U.S. Appl. No. 61/223,347, filed Jul. 6, 2009, Geall et al.
U.S. Appl. No. 61/280,510, filed Nov. 4, 2009, Cullis et al.
U.S. Appl. No. 61/223,347, priority document to WO2011005799.
Aberle, "Humeral and Cellular Immune Response to RNA Immunization with Flavivirus Replicons Derived from Tick-Borne Encephalitis Virus", Journal of Virology; 2005; pp. 15107-15113; vol. 79(24).
Acheampong, Samuel et al.; "Ionization and transfection activity of n-methyl-substituted carbamoylcholesterol derivatives", Journal of Biophysical Chemistry, vol. 2, No. 2, 53-62; 2011.
Adler et al., "Role of human cytomegalovirus UL131A in cell type-specific virus entry and release," J. Gen. Virol., 2006, 87:2451-2460.
Aissaoui et al.: "Efficient topical delivery of plasmid DNA to lung in vivo mediated by putative triggered, PEGylated pDNA nanoparticles", Journal of Controlled Release, Elsevier, Amsterdam, NL, vol. 154, No. 3, Jun. 4, 2011 Jun. 4, 2011), pp. 275-284.
Amidi et al. "Antigen-expressing immunostimulatory liposomes as a genetically programmable synthetic vaccine." Systems and Synthetic Biology, vol. 5, 2011, pp. 21-31. (Year: 2011).
Amidi et al. "Optimization and quantification of protein synthesis inside liposomes." Journal of Liposome Research, vol. 20(1), 2010, pp. 73-83. (Year: 2010).
Amidi, "Induction of humoral and cellular immune responses by antigen-expressing immunostimulatory liposomes." Journal of Controlled Release; Aug. 1, 2012; p. 3, left-hand column p. 20, lines 13-14 example 1.
Anderson et al. "Incorporation of pseudouridine into mRNA enhances translation by diminishing PKR activation," Nucleic Acids Research, 38(17):5884-5892 (2010).
Anonymous, "Mengovirus", Wikipedia, (Apr. 25, 2020), pp. 1-2, URL: https://en.wikipedia.org/wiki/Mengovirus.
Arvin AM, Gershon AA. Live attenuated varicella vaccine. Annu Rev Microbial. 1996;50:59-100.
Atwood, et al., "Comprehensive Supramolecular Chemistry II" Gen. Prin. of SupraMol. Chem. and Mol. Recogn.; pp. 141-143.
Auxiliary requests 1, 2 and 3 (claims 1-13) filed in relation to the Opposition of European Patent No. 2590676B1 Appln No. 11741348. 4) (6 pages).
Babiuk, S., et al., "Electroporation improves the efficacy of DNA vaccines in large animals," Vaccine; 2002, pp. 3399-3408; vol. 20(27-28).
Bagarazzi, M. L., et al., "Immunotherapy against HPV16118 generates potent TH1 and cytotoxic cellular immune responses," Science Translational Medicine; 2012; vol. 4(155), pp. 1-14.
Bailey et al., "Modulation of membrane fusion by asymmetric transbilayer distributions of amino lipids," Biochemistry, 33:12573-80 (1994).
Balasuriya et al., "Expression of the two major envelope proteins of equine arteritis virus as a heterodimer is necessary for induction of neutralizing antibodies in mice immunized with recombinant Venezuelan equine encephalitis virus replicon particles," J. Virol., 2000, 74(22):10623-10630.
Barai, V.N. et al. Production of highly purified RNA from yeast using calcium. Applied Biochemistry and Microbiology. 1995; 31(5): 421-424.
Barichello JM, et al., Complexation of siRNA and pDNA with cationic liposomes: the important aspects in lipoplex preparation, Methods Mil. Biol., 2010, 605: 461-72 (Nov. 21, 2009).
Barnett et al., "Antibody-Mediated Protection against Mucosa! Simian-Human Immunodeficiency Virus Challenge of Macaques Immunized with Alphavirus Replicon Particles and Boosted with Trimeric Envelope Glycoprotein in MF59 Adjuvant," Journal of Virology, 84(12):5975-5985 (2010).
Barratt, "Therapeutic applications of colloidal drug carriers." PSTT, 2000, vol. 3, No. 5, pp. 163-171.
Bauer et al., "Toll-like receptors (TLRs) and innate immunity", Handbook of Experimental Pharmacology, ISBN 978-3-540-72166-6, 2008, pp. i-xi, 1-240, and a cover page (2008).
Bernstein et al., "Randomized, double-blind, Phase 1 trial of an alphavirus replicon vaccine for cytomegalovirus in CMV seronegative adult volunteers," Vaccine, 28:484-493 (2010).
Bettinger T et al. (2001) Nucleic Acids Research 29(18): 3882-3891.
Biochemistry/Lubert Stryer (1995) 4th Ed.: title pages and p. 23.
Blakney, "The next generation of RNA vaccines: self-amplifying RNA." Document obtained from https://portlandpress.com/biochemist/article/43/4/14/229206/The-next-generation-of-RNA-vaccines-self on Sep. 20, 2021, originally published Aug. 2021, pp. 14-17. (Year: 2021).
BMGF Report, "Summary of stability data for licensed vaccines," Working in Tandem Ltd, 2012, pp. 1-17.
Bogers, et al., "Macaques Primed with Self-Amplifying RNA Vaccines Expressing HIV-1 Envelope and Boosted with Recombinant Protein Show Potent T- and B-Cell Responses" poster at the AIDS Vaccine 2012 meeting; Sep. 9-12, 2012; Boston, MA USA.
Bogers, et al., "Potent Immune Responses in Rhesus Macaques Induced by Nonviral Delivery of a Self-amplifying RNA Vaccines Expressing HIV Type 1 Envelope With a Cationic Nanoemulsion." J. Infectious Disease; 2015; pp. 947-955; vol. 211.
Boxus, M., et al., "DNA immunization with plasmids encoding fusion and nucleocapsid proteins of bovine respiratory synctial virus induces a strong cell-mediated immunity and protects calves against challenge," Journal of Virology; 2007; pp. 6879-6889; vol. 81(13).
Bramwell, "The rational design of vaccines," (DDT. 2005; 10(22): 1527-1534).
Bringmann et al., "RNA Vaccines in Cancer Treatment," Journal of Biomedicine and Biotechnology, 2010:1-12 (2010).
Brito et al., "Self-Amplifying mRNAVaccines", Advances in Genetics, vol. 89; p. 179-233; 2015.
Brito et al., "A Cationic Nanoemulsion for the delivery of next-generation RNA vaccines," Molecular Therapy, 2014; pp. 2118-2129, vol. 22.
Britt et al., "Cell surface expression of human cytomegalovirus (HCMV) gp55-116 (GB): use of HCMV-recombinant vaccinia virus-infected cells in analysis of the human neutralizing antibody response," J. Virol., 1990, 64(3):1079-1085.

(56) References Cited

OTHER PUBLICATIONS

Britt et al., "Cytomegalovirus," In Fields Virology, 3rd edition, BN Fields, DM Knipe, PM Howley (ed.), Philadelphia, PA, Lippincott-Raven, 1996, pp. 2493-2523.
Britt et al., "Human cytomegalovirus virion proteins," Hum. Immunol., 2004, 65:395-402.
Broz, et al. "Newly described pattern recognition receptors team up against intracellular pathogents", Nat. Rev. Immunol. 13:8: 551-565 (2013).
Buyens et al., "Elucidating the encapsulation of short interfering RNA in PEGylated cationic liposomes," Langmuir, 25(9) :4886-4891 (2009).
Buza, J. et al., "CD14+ cells are required for IL-12 response in bovine blood mononuclear cells activated with Toll-like receptor (TLR) 7 and TLR8 ligands", Vet. Immunol. Immunopath. 126(3-4): 273-282 (2008)—XP025676816.
Cannon, G., et al., "RNA Based Vaccines", DNA Cell Biol., 21(12): 953-961 (2002).
Caplen, "Nucleic acid transfer using cationic lipids." Methods in Mol Biol.; 2000; pp. 1-19; vol. 133.
Carine et al., "Vaccination of calves using the BRSV nucleocapsid protein in a DNA prime-protein boost strategy stimulates cell-mediated immunity and protects the lungs against BRSV replication and pathology," Vaccine Elsevier Ltd, GB, 26(37):4840-4848 (2008).
Carralot, J.P., et al., "Polarization of immunity induced by direct injection of naked sequence-stabilized mRNA vaccines", Cell. Mole. Life Sci. 61(18): 2418-2424 (2004)—XP002355208.
U.S. Appl. No. 61/223,347, filed Jul. 6, 2009.
U.S. Appl. No. 61/265,653, filed Dec. 1, 2009.
U.S. Appl. No. 61/361,780, filed Jul. 6, 2010.
U.S. Appl. No. 61/361,794, filed Jul. 6, 2010.
Cha et al., "Human cytomegalovirus clinical isolates carry at least 19 genes not found in laboratory strains," J. Virol., 1996, 70(1):78-83.
Chambers, et al., "Vaccination of mice and cattle with plasmid DNA encoding the Mycobacterium bovis antigent MPB83." Clinical Infection Diseases; 2000; pp. S283-S287; vol. 30(3).
Chee et al., "Analysis of the protein-coding content of the sequence of human cytomegalovirus strain AD169," Curr. Top. Microbiol. Immunol., 1990, 154:125-169.
Cheng et al., "Enhancement of Sindbis virus self-replicating RNA vaccine potency by linkage of Mycobacterium tuberculosis heat shock protein 70 gene to an antigen gene", Journal of Immunology, 166:6218-6226 (2001).
Cheng WF, Hung CF, Lee CN, Su YN, Chang MC, He L, Wu TC, Chen CA, Hsieh CY. Naked RNA vaccine controls tumors with down-regulated MHC class 1 expression through NK cells and perforin-dependent pathways. Eur J Immunol. Jul. 2004;34(7):1892-900.
Cheng, W.F., et al., "Enhancement of Sindbis Virus Self-Replicating RNA Vaccine Potency by Linkage of Herpes Simplex Virus Type 1 VP22 Protein to Antigen", J. Viral. 75(5): 2368-2376 (2001) -XP002201711.
Chiaramoni et al. "Liposome/DNA systems: correlation between hydrophobicity and DNA conformational changes" Journal of Biological Physics, 34(1-2), 179-88 (2008).
Chrai et al., "Liposomes: A Review Part 1: Manufacturing Issues," Biotech Trends, Pharmaceutical Technology, 28-34 (2002).
Communication of the Board of Appeals pursuant to Art. 15(1) of the Rules of Procedure of the Boards of Appeal issued on Mar. 25, 2021, in European Patent Application Publication No. 2590676.
Compton et al., "Receptors and immune sensors: the complex entry path of human cytomegalovirus," Trends Cell. Bio., 2004, 14(1):5-8.
Conry, et al., "Characterization of a Messenger RNA Polynucleotide Vaccine Vector." Cancer Research; 1995; pp. 1397-1400; vol. 55.
Cox, et al., "Bovine herpesvirus 1: immune responses in mice and cattle injected with plasmid DNA." Journal of Virology; 1993; pp. 5664-5667; vol. 67(9).
Crooke Stanley T., (Ed.), "Antisense Drug Technology: Principles, Strategies, and Applications," 2nd ed., Chapter 9 (2008), pp. 237-270.
Cui, et al., DNA Vaccine, Advances in Genetics; 2005; pp. 257-289; vol. 54.
Cavagna, et al.; "7—Signs and Work of Man"; The National Park of the Casentine Forests; 2003; pp. 175.
Davis, et al., "DNA vaccine for hepatitis B Evidence for immunogenicity in chimpanzees and comparison with other vaccines." Proc. Natl Acad Sci USA; 1996; pp. 7213-7218; vol. 93.
Davison et al., "The human cytomegalovirus genome revisited: comparison with the chimpanzee cytomegalovirus genome," J. Gen. Virol., 2003, 84:17-28.
Declaration Andrew Geall dated Sep. 11, 2014.
Declaration by Prof. Peter Liljestrom, dated Mar. 31, 2019 submitted in EP 2591114.
Declaration by Prof. Peter Liljestrom, dated Aug. 7, 2018 submitted in EP 2591114.
Declaration by Russell Johnson cited in EP2729126 on Jul. 4, 2018 and in opposition filed on Sep. 23, 2021 (4 pages).
Declaration of Professor Liljestrom dated Dec. 11, 2018 submitted in EP2590676, itself having annexes A-G.
Declaration of Russell N. Johnson dated Dec. 10, 2018.
Deering, et al., "Nucleic acid vaccines: prospects for non-viral delivery of mRNA vaccines." Expert Opinion Drug Delivery; 2014; pp. 885-899; vol. 11(6).
Defang et al., "Induction of neutralizing antibodies to Hendra and Nipah glycoproteins using a Venezuelan equine encephalitis virus in vivo expression system," Vaccine Elsevier Ltd. GB,29(2):212-220 (2010).
Diebold, S.S., et al., "Innate Antiviral Responses by Means of TLR7-Mediated Recognition of Single-Stranded RNA", Science 303(5663): 1529-1531 (2004).
Dunn et al., "Functional profiling of a human cytomegalovirus genome," Proc. Natl. Acad. Sci. USA, 2003, 100 (24):14223-14228.
Dupuis et al., "Dendritic cells internalize vaccine adjuvant after intramuscular injection", Cellular Immunology, 186:18-27 (1998).
Dupuis et al., "Distribution of DNA vaccines determines their immunogenicity after intramuscular injection in mice," Journal of Immunology, 165:2850-2858 (2000).
El Ouahabi, A et al., "Double long-chain amidine liposome-mediated self replicating RNA transfection", FEBS Letters, 380(1-2): 108-112 (1996).
Elbashir et al., "Duplexes of 21-nucleotide RNAs mediate RNA interference in cultured mammalian cells." Nature, 2001, 411(6836), 494-498.
Elkington et al., "Ex Vivo Profiling of CD8+ -T-Cell Responses to Human Cytomegalovirus Reveals Broad and Multispecific Reactivities in Healthy Virus Carriers," Journal of Virology (2003), vol. 77, No. 9, pp. 5226-5240.
Elliott et al., "Alphavirus replicon particles encoding the fusion or attachment glycoproteins of respiratory syncytial virus elicit protective immune responses in BALB/c mice and functional serum antibodies in rhesus macaques," Vaccine Elsevier Ltd, GB, 25(41):7132-7144, (2007).
Encyclopedia Britannica House Mouse; 2005, p. 963.
EP12738679.5 Third Party Observations in accordance with Article 115 EPC; Mar. 8, 2019.
Er, et al., "The encapsulation and release of guanosine from PEGylated liposomes." Journal of Liposome Research, 2009, vol. 19, No. 1, pp. 29-36.
Espuelas, Socorro, et al., "Effect of synthetic lipopeptides formulated in liposomes on the maturation of human dendritic cells," Molecular Immunology 42 (2005): 721-729, and Corrigendum, Molecular Immunology 43 (2006) 772.
Evers, M., et al., "State-of-the-Art Design and Rapid-Mixing Production Techniques of Lipid Nanoparticles for Nucleic Acid Delivery", Small Methods, 2:1-20, (2018).
Excerpt from "Chemical Book" on DLinDMA Sep. 9, 2021.
Excerpt from "Comprehensive Supermolecular Chemistry II" 2017; vol. 1.

(56) References Cited

OTHER PUBLICATIONS

Faure, et al., "Control of the in vivo Biodistribution of Hybrid Nanoparticles with Different Poly(ethylene glycol) Coatings." Small, 2009, vol. 5, No. 22, pp. 2565-2575.

Felgner, et al., "Lipofection: A Highly Efficient, Lipid-Mediated DNA-Transfection Procedure." Proc. Natl. Acad. Sci. USA; 1987pp. 7413-7417; vol. 84.

Fenske, "Liposomal Nanomedicines: An Emerging Field", Toxicologic Pathology; 2008; pp. 21-29; vol. 36, No. 1.

Final Decision and Upheld Claims from EP2591114, European Equivalent of U.S. Appl. No. 13/808,153, dated Nov. 27, 2018.

Fleeton et al., "Self-Replicative RNA Vaccines Elicit Protection against Influenza A Virus, Respiratory Syncytial Virus, and a Tickborne Encephalitis Virus", Journal of Infectious Diseases 183:1395-1398 (2001).

Fraenkel-Conrat et al., (Ed.), Virology second edition, Prentice-Hall Inc., Englewood Cliffs, New Jersey; 1988; from Chapter 3, "Enveloped Plus-strand RNA Viruses:Togaviridae", pp. 96-103.

Fraenkel-Conrat, "Togaviridae", Virology second edition, Prentice-Hall Inc.; 1988; p. 2 p. 99.

Freddolino, et al., "Molecular Dynamics Simulations of the Complete Satellite Tobacco Mosaic Virus." Structure; 2006; pp. 437-449; vol. 14.

Frolov et al., "Alphavirus-based expression vectors: Strategies and applications," 93 Proceedings of the National Academy of Sciences USA (1996).

Fynan, E.F., et al., DNA vaccines: Protective immunizations by parenteral, mucosal, and gene-gun inoculations; Proc Natl Acad Sci.; 1993; pp. 11478-11482; vol. 90.

Gamvrellis A et al. Vaccines that facilitate antigen entry into dendritic cells. Immunol Cell Biol. Oct. 2004; 82(5): 506-516.

Gao & Hui, Gene Therapy 8 (2001), 855-863.

Garcia-Valcarcel M, Fowler WJ, Harper DR, Jeffries DJ, Layton GT. Induction of neutralizing antibody and T-cell responses to varicella-zoster virus (VZV) using Ty-virus-like particles carrying fragments of glycoprotein E (gE). Vaccine. Apr. 1997-May 15(6-7): 709-19.

Geall, A. et al., "Nonviral delivery of self-amplifying RNA vaccines." Proceedings of the National Academy of Sciences of the United States of America, 2012, 109(36), 14604-14609.

Geall, et al. "Using self-amplifying mRNA vaccines to facilitate a rapid response to pandemic influenza" Eur. Pharm. Review 19:3 20-23 (2014).

Geisbert, et al., "Postexposure Protection of Guinea Pigs against a Lethal Ebola Virus Challenge Is Conferred by RNA Interference", Journal of Infectious Diseases; 2006; pp. 1650-1657; vol. 193.

Genini et al., "Serum antibody response to the gH/gL/pUL 128-131 five protein complex of Serum antibody response to the gH/gL/pUL 128-131 five-protein complex of human cytomegalovirus (HCMV) in primary and reactivated HCMV infections," Journal of Clinical Virology, 52:113-118 (2011).

Giraud A, Ataman-Onal Y, Battail N, Piga N, Brand D, Mandrand B, Verrier B. Generation of monoclonal antibodies to native human immunodeficiency virus type 1 envelope glycoprotein by immunization of mice with naked RNA. J Virol Methods. Apr. 1999;79(l):75-84.

Giuliani et al., "A universal vaccine for serogroup B meningococcus," Proc. Natl. Acad. Sci. U. S. A, 2006, vol. 103, No. 29, pp. 10834-10839.

Glaxosmithkline, SAM/Protein Mixed Modality Study Data, PowerPoint presentation (2019).

Gonçalves, et al. The effect of liposome size on the final 1 ipid/DNA ratio of cationic lipoplexes. Biophysical Journal, 86 (3), 1554-63 (2004).

Graham, Barney, "Biological challenges and technological opportunities for respiratory syncytial virus vaccine development," Immunological Reviews, 239(1):149-166 (2011).

Graham, et al., "Priming Immunization Determines T Helper Cytokine mRNA Expression Patterns in Lungs of Mice Challenged with Respiratory Syncytial Virus." The Journal of Immunology; Aug. 15, 1993; pp. 2032-2040; vol. 151, No. 4.

Granstein, et al., "Induction of Anti-Tumor Immunity with Epidermal Cells Pulsed with Tumor-Derived RNA or Intradermal Administration of RNA." Journal of Investigative Dermatology; 2000; pp. 632-636; vol. 114(4).

Greer, C, et al., "A chimeric alphavirus RNA replicon gene-based vaccine for human parainfluenza virus type 3 induces protective immunity against intranasal virus challenge", Vaccine 25(3): 481-489 (2007)-XP005798901.

Hamm et al., "Immunostimulatory RNA is a potent inducer of antigen -specific cytotoxic and hum oral immune response in vivo," International Immunology, 2007, vol. 19(3); 297-304.

Harvey et al. Kunjin Virus Replicon Vectors for Human Immunodeficiency Virus Vaccine Development 2003 Journal of Virology vol. 77 No. 14 pp. 7796-7803.

Hatakeyama, et al., "Systemic delivery of siRNA to tumors using a lipid nanoparticle containing a tumorspecific cleavable PEG-lipid." Biomaterials, 2011, vol. 32, pp. 4306-4316.

Heidel, J.D., et al., "Administration in non-human primates of escalating intravenous doses of targeted nanoparticles containing ribonucleotide reductase subunit M2 siRNA," Proc. Natl Acad Sci USA; 2007; pp. 5715-5721; vol. 104(14).

Herweijer et al., "Self-amplifying vectors for gene delivery," Advanced Drug Delivery Reviews, 27; 1997; pp. 5-16.

Heyes et al., "Cationic lipid saturation influences intracellular delivery of encapsulated nucleic acids," J Control Release; vol. 107; 2005; pp. 276-287.

Hidmark et al., "Humoral Responses against Coimmunized Protein Antigen but Not against Alphavirus-Encoded Antigens Require Alpha/Beta Interferon Signaling," Journal of Virology, 80(14):7100-7110 (2006).

Hiroshi, et al., "Replication of Genetic Information with Self-Encoded Replicase in Liposomes." ChemBioChem; Oct. 13, 2008; pp. 2403-2410; vol. 9(15).

Ho, "Cytomegalovirus," In Principles and Practice of Infectious Diseases, GL Mandell, RG Douglas, and JE Bennett (ed.), Wiley, New York, NY, 1979, pp. 1307-1323.

Hobom et al., "Fast screening procedures for random transposon libraries of cloned herpesvirus genomes: mutational analysis of human cytomegalovirus envelope glycoprotein genes," J. Virol., 2000, 74(17):7720-7729.

Hoerr et al. "In vivo application of RNA leads to induction of specific cytotoxic T lymphocytes and antibodies" Eur. J. Immunol. 30; pp. 1-7; 2000.

Hoerr, I, Tissue Engineering 13(4): 886-887; 2007.

Hofmann et al., "Physiochemical Properties of Bile Acids and their Relationship to Biological Properties: An Overview of the Problem," J Lip Res., vol. 25, (1984), pp. 1477-1489.

Hope, et al., "Chapter 8: Reduction of Liposome Size and Preparation of unilamellar Vesicles by Extrusion Techniques," Liposome Technology; 1993; pp. 123-139; vol. 1.

Hornung, et al., "5'-Triphosphate RNA Is the Ligand for RIG-I" Science; 2006; vol. 314; pp. 994-997.

Huang, et al., "Immunization with a bovine herpesvirus 1 glycoprotein B DNA vaccine induces cytotoxic T-lymphocyte responses in mice and cattle," Journal of General Virology; 2005; pp. 887-898; vol. 86(4).

Iavarone et al., "A Point Mutation in the Amino Terminus of TLR7 Abolishes Signaling without Affecting Ligand Binding", J. Immunol, (2011), vol. 186, pp. 4213-4222.

Imagines Immunization Merriam Webster's Medical Desk Dictionary; 1993; pp. 326-327.

Immordino, et al., "Stealth liposomes: review of the basic science, rationala, and clinical application, Existing and potential." International Journal of Nanomedicine, 2006, vol. 1, pp. 297-315.

International Search Report for International Application No. PCT/2012/045847 dated Oct. 10, 2012.

International Search Report for International Application No. PCT/2012/045854 dated May 9, 2014.

Jeffs et al., "A Scalable, Extrusion-Free Method for Efficient Liposomal Encapsulation of Plasmid DNA," Pharmaceutical Research (Mar. 2005), vol. 22, No. 3, pp. 362-372.

(56) References Cited

OTHER PUBLICATIONS

Johanning et al., "A Sindbis virus mRNA polynucleotide vector achieves prolonged and high level heterologous gene expression in vivo," Nucleic Acids Res, (1995), vol. 23, pp. 1495-1501.
Johnson signed Declaration dated Oct. 22, 2020 (9 pages).
Johnson, T, et al., "TLR9 agonist, but not TLR7/8, functions as an adjuvant to diminish FI-RSV vaccine-enhanced disease, while either agonist used as therapy during primary RSV infection increases disease severity", Vaccine 27 (23): 3045-3052 (2009).
Jones et al. "DNA vaccination protects against an influenza challenge in a double-blind randomised placebo-controlled phase 1b clinical trial" Vaccine 27 (2009): 2506-2512.
Ju J., et al., Int. J. Mol. Sci. 16:5666-5681; 2015.
Kamrud KI, Alterson K, Custer M, Dudek J, Goodman C, Owens G, Smith JF. Development and characterization of promoterless helper RNAs for the production of alphavirus replicon particle. J Gen Virol. Jul. 2010;91(Pt 7):1723-7. Epub Feb. 24, 2010.
Kariko, et al., "mRNA Is an Endogenous Ligand for Toll-like Receptor 3*"; The Journal of Biological Chemistry; 2004; vol. 279, No. 13; pp. 12542-12550.
Kariko, et al., "Suppression of RNA Recognition by Toll-like Receptors: The Impact of Nucleoside Modification and the Evolutionary Origin of RNA"; Immunity; 2005; vol. 23; pp. 165-175.
Kawano, et al., "Effects of Polyethylene Glycol Spacer Length and Ligand Density on Folate Receptor Targeting of Liposomal Doxorubicin In Vitro." Journal of Drug Delivery, 2011, vol. 2011, No. 160967, pp. 1-6.
Khan, K. H., "DNA vaccines: roles against diseases," GERMS; 2013; pp. 26-35; vol. 3(1).
Kinnan, et al., "Enhanced Immunogenicity to Mycobacterium tuberculosis by Vaccination with an Alphavirus Plasmid Replicon Expressing Antigen 85A" Infection and Immunity; 2003; pp. 575-579; vol. 71(1).
Kirman, et al., "Enhanced Immunogenicity to Mycobacterium tuberculosis by Vaccination with an Alphavirus Plasmid Replicon Expressing Antigen BSA" Infection and Immunity; 2003; pp. 575-579; vol. 71(1).
Kita et al.: "Replication of Genetic Information with Self-Encoded Replicase in Liposomes", CHEMBIOCHEM, vol. 9, No. 15, Oct. 13, 2008 (Oct. 13, 2008), pp. 2403-2410.
Klibanov A L et al.: "Amphipathic polyethyleneglycols effectively prolong the circulation time of liposomes", Febs Letters, Elsevier, Amsterdam, NL, vol. 268, No. 1, Jul. 30, 1990 (Jul. 30, 1990), pp. 235-237.
Knipe et al., "Fields Virology," 4th edition, Lippincott Williams & Wilkins, 2001; pp. 690-692; vol. 1, p. 2.
Kofler, et al. "Mimicking live flavivirus immunization with a noninfectious RNA vaccine." Proc. Natl. Acad. Sci. USA; 2004; pp. 1951-1956; vol. 101(7).
Kornbluth at al. "Immunostimulatory combinations: designing the next generation of vaccine adjuvants," Journal of Leukocyte Biology, 2006, vol. 80, pp. 1084-1102.
Kulkarni, et al., "Factors affecting microencapsulation of drugs in liposomes", Journal of Microencapsulation, 12(3), 229-46. (1995).
Kumar et al., "Toll-like receptors and innate immunity," Biochemical and Biophysical Research Communications, 388:621-625 (2009).
Kumar, et al., "Single histidine residue in head-group region is sufficient to impart remarkable gene transfection properties to cationic lipids: evidence for histidine-mediated membrane fusion at acidic pH". Gene Therapy; 2003; vol. 10; pp. 1206-1215.
Kumar, et al., Molecular Therapy 9(S1): S258-S259, 2004.
Kutinova et al., "Immune response to vaccinia virus recombinants expressing glycoproteins gE, GB, gH, and gL of varicella-zoster virus," Virol., 2001, 280:211-220.
Kutzler, et al., "DNA vaccines; ready for prime time?" Nature Reviews; Genetics; 2008; pp. 776-788; vol. 9(10).
Lazzaro et al., "CDS T-cell priming upon mRNA vaccination is restricted to bone-marrow-derived antigen -presenting cells and may involve antigen transfer from myocytes," Immunology, 146:312-326 (2015).
Lee et al., "Multiagent vaccines vectored by Venezuelan equine encephalitis virus replicon elicits immune responses to Marburg virus and protection against anthrax and botulinum neurotoxin in mice," Vaccine, Elsevier, Amsterdam, NL, vol. 24, No. 47-48; pp. 6886-6892; Nov. 17, 2006.
Lee, et al., "Venezuelan Equine Encephalitis Virus-Vectored Vaccines Protect Mice Against Anthrax Spore Challenge." Infection and Immunity; 2003; pp. 1491-1496; vol. 71.
Leitner et al. "DNA and RNA-based vaccines: principles, progress and prospects" Vaccine 18:765-77 (1999).
Levine, et al., Vaccine development strategies for improving immunization: the role of modern immunology. Nature Immunol.; 2004; pp. 460-464; vol. 5(5).
Levy; "Quantitation of supercoiled circular content in plasmid DNA solutions using a fluorescence based method", Nucleic Acids Res.; 2000; 28:e57.
Li et al., "Protection against Respiratory Syncytial Virus Infection by DNA Immunization," J Exp Med., vol. 188, (1998), pp. 681-688.
Liljestrom, et al., "A new generation of animal cell expression vectors based on the Semliki Forest virus replicon," Biotechnology, 9:1356-1361 (1991).
Liljestrom, et al., "In vitro mutagenesis of a full-length cDNA clone of Semliki Forest virus: the small 6,000-molecular-weight membrane protein modulates virus release," Journal of Virology, Aug. 1991; 65(8): 4107-4113.
Liu Y & Huang L (2010) Molecular therapy 18(4): 669-670.
Ljungberg et al., "Increased Immunogenicity of a DNA-Launched Venezuelan Equine Encephalitis Virus-Based Replicon DNA Vaccine," Journal of Virology, Dec. 2007, pp. 13412-13423.
Ljungman et al., "Definitions of cytomegalovirus infection and disease in transplant recipients," Clin. Infect. Dis., 2002, 34:1094-1097.
Lobue, et al. "Multivalent norovirus vaccines induce strong mucosal and systemic blocking antibodies against multiple strains." Vaccine; 2006; pp. 5220-5234; vol. 24.
Lonez, et al., "Cationic liposomal lipids: From gene carriers to cell signaling." Progress in Lipid Research; 2008; pp. 340-347; vol. 47(5).
Lorenzi, et al. "Intranasal vaccination with messenger RNA as a new approach in gene therapy: use against tuberculosis," BMC Biotechnology 10.1 (2010): 1-11.
Lu, et al., "Optimization of methods to achieve mRNA-mediated transfection of tumor cells in vitro and in vivo employing cationic liposome vectors," Cancer Gene Ther., l(4):245-252 (1994) (abstract).
Lundstrom et al., "Biology and application of alphaviruses in gene therapy", Gene Therapy; vol. 12; Suppl 1; pp. S92-S97, 2005.
Lundstrom, "Semliki Forest Virus Vectors for Gene Therapy," Expert Opinion on Biological Therapy, vol. 3, No. 5, (2003), pp. 771-777.
Lv et al., "Toxicity of cationic lipids and cationic polymers in gene delivery." Journal of Controlled Release, vol. 114 (2006), pp. 100-109. (Year: 2006).
Lyubchenko, et al., "Visualization of supercoiled DNA with atomic force microscopy in situ" Proc. Natl. Acad Sci. USA; 1997; pp. 496-501; vol. 94.
Mackey et al. "mRNA-based cancer vaccine: prevention of B16 melanoma progression and metastasis by systemic injection of MARTI mRNA histidylated lipopolyplexes." Cancer Gene Therapy, vol. 14, (2007) pp. 802-814. (Year: 2007).
MacLachlan, I., "Liposomal formulations for nucleic acid delivery", Antisense Drug Technologies, 2nd Edition, Chapter 9, 237-270, 2007.
Mahato RI, Water insoluble and soluble lipids for gene delivery, Adv. Drug Delivery Rev.,2005, 57(5):699-712.
Malone et al., "Cationic liposome-mediated RNA transfection ", Proc. Natl. Acad. Sci. (PNAS) USA: Biochemistry; 86:16; 6077-6081; 1989.
Manning, et al., "Infectivity of Liposomally Encapsulated Nucleic Acids Isolated From EMC Virus and Scrapie- Infected Mouse Brain," Intervirology; vol. 20; 1983; pp. 164-168.
Martin, et al., "Characterization of formaldehyde-inactivated poliovirus preparations made from live-attenuated strains." Journal of General Virology; 2003; pp. 1781-1788; vol. 84.

(56) References Cited

OTHER PUBLICATIONS

Martinon et al. "Induction of virus-specific cytotoxic T lymphocytes in vivo by liposome-entrapped mRNA," Eur. J. Immuno. 1993.23: 1719-1722.
Matsuura, et al., "Polycation liposome-mediated gene transfer in vivo," Biochimica et Biophysica Acta, vol. 1612, 2003, pp. 136-143.
Maurer, et al., "Spontaneous Entrapment of Polynucleotides upon Electrostatic Interaction with Ethanol-Destabilized Cationic Liposomes" Biophys Journal; vol. 80; 2001; pp. 2310-2326.
McGlone, et al., "Pig Production: Biological Principles and Applications" Chapter 8; 2000; pp. 99.
Merriam-Webster definition of "virion" (downloaded Mar. 14, 2016).
Mocarski et al., "Cytomegalovirus and their replication," In Fields Virology, 4th edition, vol. 2, 2001, DM Knipe and PM Howley (ed.), Lippincott Williams and Wilkins, Philadelphia, PA, pp. 2629-2673.
Mockey, et al., "mRNA-based cancer vaccine: prevention of B16 melanoma progression and metastatis by systemic injection of MARTI mRNA histidylated lipopolyplexes." Cancer Gene Therapy; 2007; pp. 802-814; vol. 14(9).
Mok et al., "Venezuelan equine encephalitis virus replicon particles encoding respiratory syncytial virus surface glycoproteins induce protective mucosal responses in mice and cotton rats," Journal of Virology, The American Society for Microbiology, 81(24):13710-13722 (2007).
Morris-Downes, et al., "A recombinant Semliki Forest virus particle vaccine encoding the prME and NS1 proteins of louping ill virus is effective in a sheep challenge model." Vaccine; 2001; pp. 3877-3884; vol. 19.
Mosca et al., "Molecular and cellular signatures of human vaccine adjuvants," Proc. Natl. Acad. Sci. USA, 105:10501-10506(2008).
Mossman, "Protection against Lethal Simian Immunodeficiency Virus SIVsmmPBj14 Disease by a Recombinant Semliki Forest Virus gp160 Vaccines and by a gp120 Subunit Vaccine." J. Virology; 1996; pp. 1953-1960; vol. 70.
Murphy et al., "Coding potential of laboratory and clinical strains of cytomegalovirus," Proc. Natl. Acad. Sci. USA, 2003, 100(25):14976-14981.
Na Slund et al. "Role of innate signalling pathways in the immunogenicity of alphaviral replicon-based vaccines," Virology Journal, 8(1):36 (2011).
Narang, et al., Bioconjugate Chem. 16 (2005), 156-166.
NCBI reference sequence. "Homo sapiens coagulation factor VIII (F8), transcript variant 1, mRNA." Mar. 2016, pp. 1-18.
Notice of Opposition in relation to European Patent No. 259110381 (Appln No. 11736498.4) dated May 28, 2020 (44 pages).
Notice of Opposition in relation to European Patent No. 2591103B1 (Appln No. 11736498.4) dated May 27, 2020 (17 pages).
Obata, "Evaluation of pH-responsive liposomes containing amino acid- based zwitterionic lipids for improving intracellular drug delivery in vitro and in vivo", Journal of Controlled Release; 2010; pp. 267-276; vol. 142, No. 2.
O'Hagan et al., "Induction of potent immune responses by cationic microparticles with adsorbed human. Immunodeficiency virus DNA vaccines," J Virology, (2001), vol. 75, pp. 9037-9043.
Opponents arguments by Dr. Georg Schnappauf filed on Jan. 14, 2022, in opposition to European Patent No. 2591103.
Opponents arguments by Janssen Vaccines & Prevention B.V. filed on Jan. 14, 2022 in opposition to European Patent No. 2591103.
Opposition Document D60 - Declaration of Russell N. Johnson from EP2591114, European Equivalent of U.S. Appl. No. 13/808,153, filed Aug. 8, 2018.
Organism overview of Encephalomyocarditis virus and of Poliovirus obtained from PubMed "Encephalomyocarditis virus." retrieved on Jun. 4, 2019 from https://www.ncbi.nlm.mih.gov/genome/?term=encephalomyocarditis+virus, and "Enterovirus C" retrieved on Jun. 4, 2019 from https://www.ncbi.nlm.nih.gov/genome/?term=poliovirus[orgn].
Ott, et al., "A Cationic sub-micron emulsion [lv159/DOTAP] is an effective delivery system for DNA vaccines," Journal of Controlled Release; 2002; pp. 1-5; vol. 79(1-3).
Oussoren, et al., "Lymphatic Uptake and Biodistribution of Liposomes After Subcutaneous Injection: III. Influence of Surface Modification with Poly(ethyleneglycol)." Pharmaceutical Research, 1997, vol. 14, No. 10, pp. 1479-1484.
Papahadjopoulos, et al., "Cochleate Lipid Cylinders: Formation by Fusion of Unilamellar Lipid Vesicles" Biochim et Biophys Acta; 1975; pp. 483-491; vol. 394.
Papahadjopoulos, et al., "Incorporation of Macromolecules within Large Unilamellar Vesicles (LUV)" Annals NY Academy of Sciences; 1978; pp. 259-267.
Pascolo, "Vaccination With Messenger RNA." Methods in Molecular Medicine, 2006, vol. 127, pp. 23-40.
Patentee's Reply to Opposition in relation to European Patent No. 2591103B1 (Appln No. 11736498.4) dated Oct. 23, 2020 (28 pages).
Peng et al., "The gH-gL complex of herpes simplex virus (HSV) stimulates neutralizing antibody and protects mice against HSV type 1 challenge," J. Virol., 1998, 72(1):65-72.
Perri, S., et al., "An Alphavirus Replicon Particle Chimera Derived from Venezuelan Equine Encephalitis and Sindbis Viruses is a Potent Gene-Based Vaccine Delivery Vector." J. Virol.; 2003; p. 10394-10403; vol. 77 (19).
Phumiamorn, et al., "Induction of humoral and cell-mediated immunity to hepatitis B surface antigen by a novel adjuvant activity of Oka varicella vaccine." Journal of General Virology; 2003; pp. 287-291; vol. 84.
Pomeroy et al., "Cyotmegalovirus: epidemiology and infection control," Am. J. Infect. Control, 1987, 15(3):107-119.
Preliminary Opposition Opinion from EP2591114 (U.S. Appl. No. 13/808,153), European Equivalent of U.S. Appl. No. 13/808,153, dated Feb. 23, 2018.
Pschyrembel, Klinisches Wortenbuch Immunisiserung, Immunreaktion; 1997; pp. 747-748.
Pushko, P. et al., Virology, 239: 389-401(1997).
Qa'Dan et al., "ph-Induced Conformational Changes in Clostridium Difficile Toxin B," Infect & Immun., vol. 68, (2000), pp. 2470-2474.
Ramana, et al., "Development of a liposomal nanodelivery system for nevirapine." Journal of Biomedical Science, 2010, 17:57, pp. 1-9.
Rayner, et al., "Alphavirus vectors and vaccination", Reviews in Medical Virology; 2002; pp. 279-296; vol. 12.
Reap et al., Development and preclinical evaluation of an alphavirus replicon particle vaccine for cytomegalovirus, Vaccine, Elsevier Ltd, GB, 25(42):7441-7449, (2007).
Ren et al., "Immunogene therapy of recurrent glioblastoma multiforme with a liposomally encapsulated replication-incompetent Semliki forest virus vector carrying the human interleukin-12 gene—a phase 1/11 clinical protocol", J. Neuro-Oncology, 2003, 64:147-154.
Rishi R Goel, et al., "Distinct antibody and memory B cell responses in SARS-COV-2 naive and recovered individuals after mRNA vaccination," Science Immunology, vol. 6, eabi6950, Apr. 2021, pp. 1-13; 2021.
Rodriguez A, et al. Cancer Chemother Pharmacol 74:151-166, 2014.
Rodriguez-Gascon et al., Development of nucleic acid vaccines: use of self-amplifying RNA in lipid nanoparticles, International Journal of Nanomedicine, 2014, vol. 9(1), 1833-1843.
Roldao A Mellado MC Castilho LR Carrondo MJ Alves PM. Virlike particles in vaccine development. Expert Rev Vaccines. Oct. 2010;9(10):1149-76.
Rubin, "Clinical approach to infection in the compromised host," In Infection in the Organ Transplant Recipient, 4th edition, R Rubin and LS Young (ed.), Kluwer Academic Press, New York, NY, 2002, pp. 573-679.
Ryckman et al., "Characterization of the human cytomegalovirus gH/gL/UL128-131 complex that mediates entry into epithelial and endothelial cells," J. Virol., 2008, 82(1):60-70.
Ryckman et al., "Human cytomegalovirus TR strain glycoprotein O acts as a chaperone promoting gH/gL incorporation into virions, but is not present in virions," J. Virol., 2010, 84(5):2597-2609.

(56) References Cited

OTHER PUBLICATIONS

Sacco, et al., "The Average Body Surface Area of Adult Cancer Patients in the Uk: A Multicentre Retrospective Study." PLoS ONE; 2010; pp. 1-6; vol. 5(1).
Saccoccio, Frances Maria, "Thesis: CMV Vaccine Development based on Epithelial Entry Mediators UL128, UL130, and UL131," Jun. 3, 2011, Retrieved from the Internet: URL: https//digarchiveJibrary.vcu.edu/bit streamjhandle/10156/3452/SACCOCCIO FRANCES PhD.pdf?sequence=l-l retrieved on Mar. 18, 2014] Impact on future vaccine design; p. 160 (2011). Chapter: Peptides To UL130 and UL131. Neutralize CMV Infection of Mucosal Epithelial Cells; p. 96.
Sadzuka et al., J. Liposome Res., 13(2), 157-172 (2003).
Saeki, Y., et al., "Development and Characterization of Cationic Liposomes Conjugated with HVJ (Sendai Virus): reciprocal Effect of Cationic Lipid For In Vitro and In Vivo Gene Transfer", Human gene Therapy, 8(17): 2133-2141 (1997).
Saenz-Badillos, et al., "RNA as a tumor vaccine: a review of the literature", Experimental Dermatology; 2001; pp. 143-154; vol. 10, Issue 3.
Samad et al. (2007). Liposomal drug delivery systems: an updated review. Curr Drug Deliv. Oct. 2007;4(4):297-305.
Sawai et al., "A Novel Method of Cell-Specific mRNA Transfection" 64 Molecular Genetics and Metabolism 44-51 (1998).
Saxena et al., "Induction of immune responses and protection in mice against rabies using a self-replicating RNA vaccine encoding rabies virus glycoprotein," Veterinary Microbiology; vol. 136(1-2); 2009; pp. 36-44.
Schedin-Weiss et al., "Antiangiogenic Forms of Antithrombin Specifically Bind to the Anticoagulant Heparin Sequence," Biochemistry, vol. 47, (2008), pp. 13610-13619.
Scheel, et al., "Toll-like receptor-dependent activation of several human blood cell types by protamine-condensed rnRNA"; European Journal of Immunology; 2005; pp. 1557-1566.
Schirrmacher et al., "Intra-pinna anti-tumor vaccination with self-replicating infectious RNA or with DNA encoding a model tumor antigen and a cytokine" Gene Therapy; 2000; pp. 1137-1146; vol. 7.
Schleiss MR. Cytomegalovirus vaccine development. Curr Top Microbiol Immunol. 2008;325:361-82.
Schlesinger et al., "Alphavirus vectors for gene expression and vaccines," Current Opinion in Biotechnology, 1999, 10:434-439.
Schoenmaker, et al., mRNA-lipid nanoparticle COVID-19 vaccines: Structure and stability, International Journal of Pharmaceutics 601; 120586, pp. 1-13; 2021.
Search Report issued in EP Application No. 21298987.3, dated May 25, 2022.
Semple et al. Efficient encapsulation of antisense oligonucleotides in lipid vesicles using ionizable aminolipids: formation of novel small multilamellar vesicle structures. Biochimica et Biophysica Acta (BBA)—Biomembranes, vol. 1510, 2001, pp. 152-166.
Semple et al., "Rational design of cationic lipids for siRNA delivery," Nature Biotechnology, v. 28 :172-176 (2010).
Shade RO Blundell MC Cotmore SF Tattersall P Astell CR. unknown protein [Human parvovirus B19]. GenBank: AAA66867.1 Dep. 05171995.
Sharma, et al., "To scale or not to scale: the principles of does extrapolation." British Journal of Pharmacology; 2009; pp. 907-921; vol. 157.
Shimamura et al., "Human cytomegalovirus infection elicits a glycoprotein M (gM)/gN-specific virusneutralizing antibody response," J. Virol., 2006, 80(9):4591-4600.
Silva, et al. "Effect of ultrasound parameters for unilamellar liposome preparation" Ultrasonics Sonochemistry, 17(3), 628-32 (2010).
Singh et al., "The Effect of CTAB Concentration in Cationic PLG Microparticles on DNA Adsorption and in Vivo Performance," Pharmaceutical Research, (2003), vol. 20, pp. 247-251.
Singh, et al., "Cationic microparticles: A potent delivery system for DNA vaccines" Proc Natl Acad Sci USA; 2000; pp. 811-816; vol. 97(2).
Smerdou, et al., "Non-viral amplification systems for gene transfer: Vectors based on alphaviruses," Curr Opin Mal Ther; 1999; pp. 244-251; vol. 1(2).
Smith Korsholm, Karen, et al. "The adjuvant mechanism of cationic dimethyldioctadecylammonium liposomes," Immunology 121(2) (2007): 216-226.
Soong et al., "PEG Molecular Weight and Lateral Diffusion of PEG-ylated Lipids in Magnetically Aligned Bicelles," BBA, (2007), pp. 1805-1814.
Spelios et al., Biophys. Chem. 129 (2007), 137-147.
Sriwongsitanont, et al. "Physiochemical Properties of PEG-Grafted Liposomes." Chem Pharm Bull; 2002; pp. 1238-1244; vol. 50(9).
Stagno et al., "Cytomegalovirus," In Infectious Diseases of the Fetus and Newborn Infant, 6th edition, JS Remington and JO Klein (ed.), WB Saunders, Philadelphia, PA, 1995, pp. 312-353.
Stedman's Medical Dictionary; 27th Edition; Lippincott, Williams & Wilkins; published 2000, p. 1963.
Strauss, J. H. et al., Microbiological Reviews, 58(3): 491-562 (1994) (excerpt).
Strejan, "Suppression of Chronic-Relapsing Experimental Allergic Encephalomyelitis in Strain-13 Guinea Pigs by Administration of Liposome-Associated Myelin Basic Protein", Journal of Neuroimmunology; vol. 7; 1984; pp. 27-41.
Stuart, et al., "A new liposomal formulation for antisense oligodeoxynucleotides with small size, high incorporation efficiency and good stability", Biochimica et Biophysica Acta, 1463(2), 219-29 (2000).
Submission filed by the patentee (then applicant) in the examination proceedings (Jun. 26, 2017).
Sugiyama, T., "Immunoadjuvant effects of polyadenylic:polyuridylic acids through TLR3 and TLR7", Int. Immunolo. 20 (1): 1-9 (2008)—XP002665154.
Szoka, et al., "Procedure for preparation of liposomes with large internal aqueous space and high capture by reverse -phase evaporation," Proc Natl Acad Sci USA, 75(9) (1978): 4194-4198.
Tannous, et al., Secreted blood reporters: Insights and applications, Biotechnol. Adv., 2011, 29(6):997-1003.
Taylor, et al., "DNA vaccination against respiratory syncytial virus in young calves." Vaccine; 2005; pp. 1242-1250; vol. 23(10).
ThermoFisher Scientific, "Ribosomal RNA Sizes", submitted in EP Opposition against Application No. EP 2591103 on Jan. 14, 2022, 1 page.
Third Party Observations under Art. 115 EPC Nov. 3, 2016, from EP Appl. No. 11736499.2; pp. 1-17.
Thompson et al., "Mucosal and systemic adjuvant activity of alphavirus replicon particles," Proceedings of the National Academy of Sciences,103{10):3722-3727 (2006).
Tonkin, D. R. et al., Vaccine, 28(18): 3238-3246 (2010).
Torchilin, et al., "Poly(ethylene glycol) on the liposome surface: on the mechanism of polymer-coated liposome longevity." Biochimica et Biophysica Acta, 1994, vol. 1195, pp. 11-20.
Tranchant, I et al. (2004) J Gene Med 6: S24-S35.
Tseng et al., "Liposomes incorporated with cholesterol for drug release triggered by magnetic field," Journal of Medical and Biological Engineering, vol. 27, No. 1 (2007), 29-34.
Tubulekas et al., "Alphavirus expression vectors and their use as recombinant vaccines: a minireview" 190 Gene 191-195 (1997).
U.S. Appl. No. 17/560,019, filed Dec. 22, 2021.
U.S. Appl. No. 17/511,762, filed Oct. 27, 2021.
U.S. Appl. No. 17/512,258, filed Oct. 27, 2021.
U.S. Appl. No. 17/560,052, filed Dec. 22, 2021.
U.S. Appl. No. 17/560,059, filed Dec. 22, 2021.
U.S. Appl. No. 17/560,092, filed Dec. 22, 2021.
U.S. Appl. No. 17/560,116, filed Dec. 22, 2021.
U.S. Appl. No. 17/560,138, filed Dec. 22, 2021.
U.S. Appl. No. 61/529,878, filed Aug. 31, 2011.
Uddin SN, Biotechnology and Molecular Biology Review 2(3): 058-067, 2007.
Ulmer, et al., "Heterologous Protection Against Influenza by Injection of DNA Encoding a Viral Protein." Science; 1993; pp. 1745-1749; vol. 259.
U.S. Appl. No. 16/714,877, filed Dec. 16, 2019.
U.S. Appl. No. 17/808,519, filed Jun. 23, 2022.

(56) References Cited

OTHER PUBLICATIONS

U.S. Appl. No. 17/848,294, filed Jun. 23, 2022.
U.S. Appl. No. 17/848,299, filed Jun. 23, 2022.
U.S. Appl. No. 17/848,337, filed Jun. 23, 2022.
U.S. Appl. No. 61/361,828, filed Jul. 6, 2010.
Vadjy, et al., "Mucosal adjuvants and delivery systems for protein-, DNA- and RNA-based vaccines." Immunol. Cell Biol.; 2004; pp. 617-627; vol. 82(6).
Van Bleek et al., "RSV 2010: Recent advances in research on respiratory syncytial virus and other pneumoviruses," Vaccine, 29{43):7285-7291 (2011).
Varnum et al., "Identification of proteins in human cytomegalovirus (HCMV) particles: the HCMV proteome," J. Virol., 2004, 78(20):10960-10966.
Vasiueva et al., "Identification of a novel function of the alphavirus capping apparatus," Journal of Biological Chemistry, 2000; 275(23):17281-17287.
Vassilev, et al., "Microparticle-mediated RNA immunization against bovine viral diarrhea virus." Vaccine; 2001; pp. 2012-2019; vol. 19.
Vignuzzi, et al., "Naked RNA immunization with replicons derived from poliovirus and Semliki Forest virus genomes for the generation of a cytotoxic T cell response against the influenza A virus nucleoprotein." Journal of General Virology; 2001; pp. 1737-1747; vol. 82(7).
Wang et al., "Human cytomegalovirus virion protein complex required for epithelial and endothelial cell tropism," Proc. Natl. Acad. Sci. USA, 2005, 102(5):18153-18158.
Wang, et al., "pH-sensitive immunoliposomes mediate target-cell-specific delivery and controlled expression of a foreign gene in mouse." Proc. Natl. Acad. Sci. USA; 1987; pp. 7851-7855; vol. 84.
Ward, et al., "Generation of CTL responses using Kunjin replicon RNA" Immunology and Cell Biology; 2003; pp. 73-78; vol. 81(1).
Weide, et al., "Direct Injection of Protamine-protected mRNA: Results of a Phase 1/2 Vaccination Trial in Metastatic Melanoma Patients." Journal of Immunotherapy; 2009; pp. 498-507; vol. 32(5).
Weide, et al., "Results of the First Phase 1111 Clinical Vaccination Trial with Direct Injection of mRNA," Journal of Immunotherapy; 2008; pp. 180-188; vol. 31(2).
Whitehead et al., "Knocking down barriers: advances in siRNA delivery" Nature Reviews Drug Discovery; 2009; pp. 129-138; vol. 8.
Wille et al., "A human cytomegalovirus gO-null mutant fails to incorporate gH/gL into the virion envelope and is unable to enter fibroblasts and epithelial and endothelial cells," J. Virol., 2010, 84(5):2585-2596.
Wilson et al., "Biological properties of poliovirus encapsulated in lipid vesicles: Antibody resistance and infectivity in virus-resistant cells", Proc. Natl. Acad. Sci. USA; 1977; pp. 3471-3475; vol. 74, No. 8.
Wilson, et al., "The Introduction of Poliovirus RNA into Cells via Lipid Vesicles (Liposomes)." Cell, 1979, vol. 17, pp. 77-84.
Wilson, Kaley et al.; "The combination of stabilized plasmid lipid particles and lipid nanoparticle encapsulated CpG containing oligodexoynucleotides as a systemic genetic vaccine", The Journal of Gene Medicine; 11; pp. 14-25; 2009.
Wloch, et al., "Safety and Immunogenicity of A Bivalent of Cmv Dna Vaccine in Healthy in Healthy Adult Subjects." J Infect Dis; 2008; pp. 1634-1642; vol. 197(12).
Xiong et al., "Sindbis virus: an efficient, broad host range vector for gene expression in animal cells," Science, 243:1188-1191 (1989).
Xu et al., "Characterization of immune Responses Elicited in Macaques Immunized Sequentially with Chimeric VEE/ SIN Alphavirus Replicon Particles Expressing SIVGag and/or HIVEnv and with Recombinant HIVgp140Env Protein," Aids Research and Human Retroviruses, Mary Ann Liebert, 22(10):1022-1030 (2006).
Xu et al., "Sequential priming and boosting with heterologous HIV immunogens predominantly stimulated T cell immunity against conserved epitopes," AIDS; 20(18); 2293-2303; Nov. 28, 2006.
Xu, et al., "Clinical Trials and Translational Medicine Commentary: Drug Delivery Trends in Clinical Trials and Translational Medicine: Challenges and Opportunities in the Delivery of Nucleic Acid-Based Therapeutics," Journal of Pharmaceutical Sciences, vol. 100, No. 1, (2011), pp. 38-52.
Xu, Y., et al., Physicochemical characterization and purification of cationic lipoplexes, Biophys J., 1999, 77(1):341-53.
Yamamoto, et al. "Current prospects for mRNA gene delivery". Eur. J. of Pharma and Biopharm 71, 484-489 (2009).
Yang, J-P., et al., "Overcoming the inhibitory effect of serum on lipofection by increasing the charge ratio of cationic liposome to DNA," Gene Therapy, vol. 4, 1997, pp. 950-960; 1997.
Yi, et al., "A Cationic Lipid Emulsion/DNA Complex as a Physically Stable and Serum-Resistant Gene Delivery." Pharmaceutical Research; 2000; pp. 314-320; vol. 17.
Ying et al. "Cancer therapy using a self-replicating RNA vaccine" Nat. Med.; vol. 5; pp. 823-827; 1999.
Yoder, et al., "Role of Complement in Neutralization of Respiratory Syncytial Virus" J Med Virol., 2004; pp. 688-694; vol. 72.
Yoffe, "Predicting the sizes of large RNA molecules" PNAS; vol. 105; 2008; pp. 16153-16158.
Yoneyama, et al., "RIG-1 family RNA helicases: cytoplasmic sensor for antiviral innate immunity," Cytokine & Growth Factor Review S, (2007), vol. 18, pp. 545-551.
Yoon, et al.," DNA-Mediated Immunization of Mice with Plasmid Encoding HBs Antigen." J. Korean Med Sci; 1999; pp. 187-192; vol. 14.
Yu et al., Journal of Pharmaceutical Sciences 98(9): 3278-3289; 2009.
Zhang, et al., "Ionization Behavior of Amino Lipids for siRNA Delivery: Determination of Ionization Constants, SAR, and the Impact of Lipid pKa on Cationic Lipid-Biomembrane Interactions." Languir: The ACS Journal of Surfaces and Colloids, ACS;2011; pp. 1907-1914; vol. 15(5).
Zhao, QQ., et al., N/P ratio significantly influences the transfection efficiency and cytotoxicity of a polyethylenimine/chitosan/DNA complex, Biol. Pharm. Bull., 2009, 32(4):706-10.
Zhou, et al. "RNA Melanoma Vaccine: Induction of Antitumor Immunity by Human Glycoprotein 100 mRNA Immunization." Human Gene Therapy; 1999; pp. 2719-2724; vol. 10(16).
Zhou, X., et al., "Self-replicating Semliki Forest virus RNA as recombinant vaccine", Vaccine 12(16): 1510-1514 (1994).
Zhu et al. "Vaccines for Gonorrhea: Can We Rise to the Challenge?" Frontiers in Microbiology, vol. 2, Jan. 1, 2011, 13 pages.
Zhu et al., Science, 261: 209-211 (1993).
Zhu L & Mahato RI, Expert Opin Drug Deliv. 7(10): 1209-1226, 2010.
Zimmermann et al., "RNAi-mediated gene silencing in non-human primates," Nature, vol. 441, pp. 111-114 (2006).
Zuckerman, "Principles and Practice of Travel Medicine," 2001, pp. 165-183.
Zuckerman, The importance of injecting vaccines into muscle, BMJ, vol. 321, pp. 1237-1238 (2000).
Patel et al., "The Importance of Apparent pKa in the Development of Nanoparticles Encapsulating siRNA and mRNA," Trends Pharmacol Sci., vol. 42, No. 6, (2021), pp. 448-460.
Eastman et al., "Influence of Phospholipid Asymmetry on Fusion between Large Unilamellar Vesicles," Biochemistry, vol. 31, (1992), pp. 4262-4268.
Declaration by Russell Johnson dated Sep. 21, 2022 in opposition filed in EP2591103, Int'l filing date Jul. 6, 2012, (2 pages).
Hwang et al., "alpha-Methylprednisolone Conjugated Cyclodextrin Polymer-Based Nanoparticles for Rheumatoid Arthritis Therapy," International Journal of Nanomedicine, 2008, 3(3), 359-371.
Bettinger, T., et al., "Recent Developments in RNA-BASED strategies for cancer gene therapy", Current Opinion in Molecular Therapeutics, Current Drugs, London, GB, vol. 3, No. 2, Apr. 1, 2001, pp. 116-124.
Van Der Velden, W., et al., "Vector Design for Optimal Protein Expression", Sep. 1, 2001, p. 576.
Geldmacher et al.: "Therapeutic vaccination for cancer immunotherapy: Antigen selection and clinical responses", Human Vaccines, vol. 7, No. supl, Jan. 1, 2011 (Jan. 1, 2011), pp. 115-119.

(56) References Cited

OTHER PUBLICATIONS

Pascolo S., "Messenger RNA-based vaccines", Expert Opinion On Biological The, Informa Healthcare, Ashley, London; GB, vol. 4, No. 8, Aug. 1, 2004 (Aug. 1, 2004), pp. 1285-1294.
EP12722942.5 (Moderna's submission of Jul. 9, 2018).
Agris et al., (1999) "Thermodynamic Contribution of Nucleoside Modifications to Yeast tRNAphe Anticodon Stem Loop Analogs," Acta Biochimica Polonica, vol. 46, No. 1, pp. 163-172.
Anderson et al., Nucleic Acids Research (2011), 39(21), 9329, published online on Aug. 3, 2011.
Andries et al., (2015) Sep. 3, 2015 "N(1)-Methylpseudouridine-Incorporated mRNA Outperforms Pseudouridine-Incorporated mRNA by Providing Enhanced Protein Expression and Reduced Immunogenicity in Mammalian Cell Lines and Mice," Journal of Controlled Release, vol. 217, pp. 337-344.
Annex to the communication in Opposition against EP 3 492 109 Bl by the Opposition Division Apr. 13, 2022.
A-Plus™ Poly(A) Polymerase Tailing Kit Protocol Nov. 16, 2006 (Capture Date).
Aso and Yoshioka: "Effect of freezing rate on physical stability of lyophilized cationic liposomes", Chem Pharm. Bull. 53(3) 301-204 (2005).
Brand et al., Biochem. J. (1978), 169, 71-77.
Chang et al. 2008 Nov. 19, 2007 "Synthesis and Solution Conformation Studies of 3-substituted Uridine and Pseudouridine Derivatives," Bioorganic & Medicinal Chemistry, vol. 16, pp. 2676-2686.
Chatterjee et al., (2012) Mar. 2012 "The Archaeal COG1901/DUF358 SPOUT-Methyltransferase Members, Together with Pseudouridine Synthase Pus10, Catalyze the Formation of 1-Methylpseudouridine at Position 54 of tRNA," RNA, vol. 18, pp. 421-433.
Chen et al. "An Overview of Liposome Lyophilization and its Future Potential," Journal of Controlled Release 142 (2010) 299-311.
Christ: "Gefriertrocknung mit System" (with D6a, a timestamp, showing that this document was available as of Jan. 22, 2010).
Christ: "Smart Freeze Drying" Manual Jan. 2010.
Cortesi et al.: Effect of DNA complexation and freeze-drying on the physicochemical characteristics of cationic liposomes', Antisense & Nucleic Acid Drug Development 10:205-215(2000).
CRC Handbook of Chemistry and Physics, 101st Edition, CRC Press 2020—Section 6 vapor pressure of ice.
Drug Discovery Handbook, edited by Shayne Cox Gad, Wiley Interscience, 2005; Chapter 27: RNA-based therapies, pp. 1259 to 1308.
Earl and Townsend (1977) Jun. 1977 "A Chemical Synthesis of the Nucleoside I-Methylpseudouridine," J. Heterocyclic Chem, vol. 15, pp. 699-700.
Eberhardt et al. "Modulation of mRNA Stability as a Novel Therapeutic Approach," Pharmacology & Therapeutics 114 (2007) 56-73.
Excerpt of textbook "The immune system" by Peter Parham, Third edition, (2009) Cover page, Table contents and pp. 49 and 50 common general knowledge.
F.F. Davis, F.W. Allen (1957) "Ribonucleic Acids from Yeast which Contain a Fifth Nucleotide".
Janeway CA Jr, Travers P. Walport M, et al. Immunobiology: The Immune System in Health and Disease. 5th edition. New York: Garland Science; 2001. Induced innate responses to infection. Part 1, Chapter 2, "Induced innate responses to infection" pp. 87-106. Available from: https://www.ncbi.nlm.nih.oov/books/NBK27122/.
Jones et al.: "Long-term storage of DNA-free RNA for use in vaccine studies", BioTechniques 43:675-681 (Nov. 2007).
Kariko (2008) "Incorporation of Pseudouridine into mRNA yields Superior Nonimmunogenic Vector with Increased Translational Capacity and Biological Stability," Mol Ther., vol. 16, No. 11, pp. 1833-1840.
Kariko and Weissman, (2007) "Naturally Occurring Nucleoside Modifications Suppress the Immunostimulatory Activity of RNA: Implication for Therapeutic RNA Development," Curr Opin Drug Disc & Dev., vol. 10, No. 5, pp. 524-532.
Kariko et al., (2005) "Suppression of RNA Recognition by Toll-Like Receptors: The Impact of Nucleoside Modification and the Evolutionary Origin of RNA," Immunity, vol. 23, pp. 165-175.
Kariko et al., (2012) "Increased Erythropoiesis in Mice Injected with Submicrogram Quantities of Pseudouridine--Containing mRNA Encoding Erythropoietin," Mal Ther 20(5):948-53.
Kariko et al., Nucleic Acids Research (2011), 39 (21), e142, published online on Sep. 2, 2011.
Kariko, Muramatsu, Welsh, Ludwig, Kato, Akira and Weissman (2008) Incorporation of Pseudouridine Into mRNA Yields Superior Nonimmunogenic Vector With Increased Translational Capacity and Biological Stability. Molecular Therapy vol. 16 No. 11, 1833-1840.
Kierzek & Kierzek et al., (2001) Jun. 21, 2001 "Influence of N6-Isopentenyladenosine (k6A) on Thermal Stability of RNA Duplexes," Biophysical Chemistry, vol. 91, pp. 135-140.
Molina et al.: The stability of lyophilized lipid/DNA complexes during prolonged storage', Journal of Pharmaceutical Sciences, vol. 93, No. 9, Sep. 2004.
Montana et al. "Employment of Cationic Solid-Lipid Nanoparticles as RNA Carriers," Bioconjugate Chem. 2007, 18, 302-308.
Motorin & Helm (2009) Dec. 8, 2009 "RNA Nucleotide Methylation," Advanced Review, vol. 2, pp. 611-631.
Motorin & Helm (2011) Sep./Oct. 2011 "5-Methylcytosine in RNA: Detection, Enzymatic Formation and Biological Functions," Nucleic Acids Research, vol. 38, No. 5, pp. 1415-1430.
Kit Protocol Nov. 16, 2006 (Capture Date).
Nucleic Acids in Innate Immunity, Various Authors (2008) CRC Press.
Operating manual freeze-dryer Alpha 1 -4 LCS plus and Alpha 2-4 LSC plus by Christ, revised version of Dec. 16, 2013.
Pang et al., (1982) Apr. 1982 "Structure of a Modified Nucleoside in Archaebacterial tRNA which Replaces Ribosylthymine," The Journal of Biological Chemistry, vol. 257, No. 7, pp. 3589-3592.
Post-filed evidence submitted on Jun. 12, 2014 during prosecution of EP2578685 B1 (D1a).
Post-filing experimental evidence submitted by the Patentee during the examination phase of EP 18 153 312.6 on Apr. 5, 2019.
Reichman et al., (1977) Feb. 1977 The Journal of Antibiotics, vol. XXX, No. 2, pp. 129-131.
Reijenga et al., "Development of Methods for the Determination of pKa Values," Analytical Chemistry Insights, vol. 8, (2013), pp. 53-71.
Robbins et al., (2007) Sep. 1, 2007 "2'-0-Methyl-Modified RNAs Act as TLR7 Antagonists," Mol. Ther. Vol. 15, No. 9, pp. 1663-1669.
Sahin et al., Nature Reviews Drug Discovery (2014), 13, 759-780, published online on Sep. 19, 2014.
Schlake et al., "Developing mRNA-Vaccine Technologies," RNA Biology (2012), 9 (11), 1319-1330, published in Nov. 2012.
D. Liu and L. Huang Journal of Liposome Research 2(1): 57-66 (1992).
Su et al In Vitro and in Vivo mRNA Delivery using Lipid-Enveloped pH-Responsive Polymer Nanoparticles, Molecular Pharmaceutics, vol. 8, (2011) pp. 774-787.
Submitted claims to the EPO on 30. Sep. 2008 in the case EP 06 81 3536.7 (EP1979364) prior art under Art. 54(2) EPC.
Tang et al. "Design of Freeze-Drying Processes for Pharmaceuticals: Practical Advice," Pharmaceutical Research, vol. 21, No. 2, Feb. 2004.
Tcherepanova et al., "Ectopic Expression of a Truncated CD40L Protein from Synthetic Post-Transcriptionally Capped RNA in Dendritic Cells Induces High Levels of IL-12 Secretion," BMC Molecular Biology 2008, 9:90.
The International Association for the Properties of Water and Steam, Pizer\ Czech Republic, Sep. 2011.
U.S. Appl. No. 61/494,745, filed Jun. 8, 2011.
U.S. Appl. No. 61/494,882, filed Jun. 8, 2011.
Van Winden EC, "Freeze-drying of liposomes: theory and practice "Methods Enzymol. 2003; 367:99-110.
VirTis Advantage Plus marketing brochure 2008.
VirTis Advantage Plus specification sheet 2013.

(56) References Cited

OTHER PUBLICATIONS

Weissman et al., "HIV Gag mRNATransfection of Dendritic Cells (DC) Delivers Encoded Antigen to MHC Class I and II Molecules, Causes DC Maturation, and Induces a Potent Human in Vitro Primary Immune Response," The Journal of Immunology, 2000, 165 (8), 4710, published on Oct. 15, 2000.
Wisse et al. 2008 "The Size of Endothelial Fenestrae in Human Liver Sinusoids: Implications for Hepatocyte-Directed Gene Transfer," Gene Therapy, vol. 15, pp. 1193-1199.
Yadava et al., Effect of lyophilization and freeze-thawing on the stability of siRNA-liposome complexes'. AAPS Pharm Sci Tech, vol. 9. No.2, Jun. 2008.
Yarian et al., (1999) Sep. 1, 1999 "Structural and Functional Roles of the N1- and N3-Protons of ψ at tRNA's Position 39," Nucleic Acids Research, vol. 27, No. 17, pp. 3542-3549.
Zust et al., (2011) Feb. 2011 "Ribose 2'-O-Methylation Provides a Molecular Signature for the Distinction of Self and Non-self mRNA Dependent on the RNA Sensor Mda5,"Nature Immunology, vol. 12, No. 2, pp. 137-144.
U.S. Appl. No. 61/404,413, filed Oct. 1, 2010.
U.S. Appl. No. 61/542,533, filed Oct. 2, 2011.
U.S. Appl. No. 61/570,690, filed Dec. 14, 2011.
U.S. Appl. No. 61/576,705, filed Dec. 16, 2011.
U.S. Appl. No. 61/578,271, filed Dec. 21, 2011.
U.S. Appl. No. 61/618,862, filed Apr. 2, 2012.
Mann et al., "DNA Transfer into Vascular Smooth Muscle using Fusigenic Sendai Virus (HJV)-Liposomes," Molecular and Cellular Biochemistry, vol. 172, (1997), pp. 3-12.
Kitajima et al., "Efficient Transfer of Synthetic Ribozymes into Cells using Hemagglutinating Virus of Japan (HVJ)-Cationic Liposomes," The Jounral of Biological Chemistry, vol. 272, No. 43, (1997), pp. 27099-27106.
Willis et al., "Liposome-Anchored Vascular Endothelial Growth Factor Aptamers," Bioconjugate Chem., vol. 9, (1998), pp. 573-582.
Bai et al., "Gene Transfer to Vein Graft Wall by HVJ-Liposome Method: Time Course and Localization fo Gene Expression," Ann Thorac Surg, vol. 66, (1998), pp. 814-820.
Mandal et al., "Delivery of Macromolecules into Cytosol using Liposomes Containing Hemolysin," Methods in Enzymology, vol. 372, (2003), pp. 319-339.
Kawauchi et al., "Gene Therapy for Attenuating Cardiac Allograft Arteriopathy using Ex Vivo E2F Decoy Transfection by HVJ-AVE-Liposome Method in Mice and Nonhuman Primates," Circulation Research, (2000), pp. 1063-1068.
Hobo et al., "Improving Dendritic Cell Vaccine Immunogenicity by Silencing PD-1 Ligands using siRNA-lipid Nanoparticles Combined with Antigen mRNA Electroporation," Cancer Immunol Immunother, vol. 62, (2013), pp. 285-297.
Hobo et al., "Immunogenicity of Dendritic Cells Pulsed with MAGE3, Survivin and B-Cell Maturation Antigen mRNA for Vaccination of Multiple Myeloma Patients," Cancer Immunol Immunother, vol. 62, (2013), pp. 1381-1392.
Kreiter et al., "Tumor Vaccination using Messenger RNA: Prospects of a Future Therapy," Current Opinion in Immunology, vol. 23, (2011), pp. 399-406.
Zimmer et al., "RNA Replicons—A New Approach for Influenza Virus Immunoprophylaxis," Viruses, vol. 2, (2010), pp. 413-434.
Dwarki et al., "Cationic Liposome-Mediated RNA Transfection," Methods in Enzymology, vol. 217, (1993), pp. 644-654.
Leroueil PR, et al., "Wide varieties of cationic nanoparticles induce defects in supported lipid bilayers" Nano Lett. Feb. 2008;8(2):420-4. Epub Jan. 25, 2008. (Year: 2008).
Szebeni J, et al., "Activation of complement by therapeutic liposomes and other lipid excipient-based therapeutic products: prediction and prevention," Adv Drug Deliv Rev. Sep. 16, 2011;63(12):1020-30. Epub Jul. 14, 2011. (Year: 2011).
Szebeni J., "Complement activation-related pseudoallergy: a stress reaction in blood triggered by nanomedicines and biolocials," Mol Immunol. Oct. 2014;61(2):163-73. Epub Aug. 12, 2014. (Year: 2014).

Bahl K, Senn JJ, Yuzhakov O, Bulychev A, Brito LA, Hassett KJ, Laska ME, et al. "Preclinical and Clinical Demonstration of Immunogenicity by mRNA Vaccines against H10N8 and H7N9 Influenza Viruses," Mol Ther. Jun. 7, 2017;25(6):1316-1327. Epub Apr. 27, 2017. Erratum in: Mol Ther. Aug. 3, 2022;30(8):2874. (Year: 2017).
Szebeni J, Storm G." Complement activation as a bioequivalence issue relevant to the development of generic liposomes and other nanoparticulate drugs," Biochem Biophys Res Commun. Dec. 18, 2015;468(3):490-7. doi: 10.1016/j.bbrc.2015.06.177. Epub Jul. 14, 2015. PMID: 26182876. (Year: 2015).
Ernsting MJ, Murakami M, Roy A, Li SD. "Factors controlling the pharmacokinetics, biodistribution and intratumoral penetration of nanoparticles," J Control Release. Dec. 28, 2013;172(3):782-94. doi: 10.1016/j.jconrel.2013.09.013. Epub Sep. 25, 2013. PMID: 24075927; PMCID: PMC3891171. (Year: 2013).
Chen S, Tam YYC, Lin PJC, Sung MMH, Tam YK, Cullis PR. "Influence of particle size on the in vivo potency of lipid nanoparticle formulations of siRNA," J Control Release. Aug. 10, 2016;235:236-244. doi: 10.1016/j.jconrel.2016.05.059. Epub May 26, 2016. PMID: 27238441. (Year: 2016).
Xue HY, Guo P, Wen WC, Wong HL. "Lipid-Based Nanocarriers for RNA Delivery," Curr Pharm Des. 2015;21(22):3140-7. doi: 10.2174/1381612821666150531164540. PMID: 26027572; PMCID: PMC4618487. (Year: 2015).
Hassett KJ, Benenato KE, Jacquinet E, Lee A, Woods A, Yuzhakov O, Himansu S, Deterling J, Geilich BM, Ketova T, Mihai C, Lynn A, McFadyen I, et al., "Optimization of Lipid Nanoparticles for Intramuscular Administration of mRNA Vaccines," Mol Ther Nucleic Acids. Apr. 15, 2019;15:1-11. Epub Feb. 7, 2019. (Year: 2019).
Poveda C, Biter AB, Bottazzi ME, Strych U. "Establishing Preferred Product Characterization for the Evaluation of RNA Vaccine Antigens," Vaccines (Basel). Sep. 27, 2019;7(4):131. doi: 10.3390/vaccines7040131. PMID: 31569760; PMCID: PMC6963847. (Year: 2019).
Durbin AF, Wang C, Marcotrigiano J, Gehrke L. "RNAs Containing Modified Nucleotides Fail To Trigger RIG-I Conformational Changes for Innate Immune Signaling," mBio. Sep. 2, 20160;7(5):e00833-16. doi: 10.1128/mBio.00833-16. PMID: 27651356; PMCID: PMC5030355. (Year: 2016).
Woodward M, Marko A, Galea S, Eagel B, Straus W, "Varicella Virus Vaccine Live: A 22-Year Review of Postmarketing Safety Data," Open Forum Infect Dis. Aug. 1, 2019;6(8):ofz295. doi: 10.1093/ofid/ofz295. PMID: 31392326; PMCID: PMC6685817. (Year: 2019).
Depledge DP, Yamanishi K, Gomi Y, Gershon AA, Breuer J. "Deep Sequencing of Distinct Preparations of the Live Attenuated Varicella-Zoster Virus Vaccine Reveals a Conserved Core of Attenuating Single-Nucleotide Polymorphisms," J Viral. Sep. 12, 2016;90 (19):8698-704. (Year: 2016).
Shah RA, Limmer AL, Nwannunu CE, Patel RR, Mui UN, Tyring SK. "Shingrix for Herpes Zoster: A Review," Skin Therapy Lett. Jul. 2019;24(4):5-7. PMID: 31339679. (Year: 2019).
Freer G, Pistello M. "Varicella-zoster virus infection: natural history, clinical manifestations, immunity and current and future vaccination strategies," New Microbial. Apr. 2018;41(2):95-105. Epub Mar. 2, 2018. PMID: 29498740. (Year: 2018).
Monslow MA, Elbashir S, Sullivan NL, Thiriot DS, Ahl P, Smith J, et al. "Immunogenicity generated by mRNA vaccine encoding VZV gE antigen is comparable to adjuvanted subunit vaccine and better than live attenuated vaccine in nonhuman primates," Vaccine. Aug. 10, 2020;38(36):5793-5802. Epub Jul. 20, 2020. (Year: 2020).
Office Action issued in U.S. Appl. No. 17/560,052, dated Jul. 12, 2022.
Office Action issued in U.S. Appl. No. 17/560,138, dated Aug. 23, 2022.
Office Action issued in U.S. Appl. No. 17/560,092, dated Aug. 4, 2022.
Office Action issued in U.S. Appl. No. 17/560,059, dated Jul. 15, 2022.
Office Action issued in U.S. Appl. No. 17/560,116, dated May 31, 2022.

(56) References Cited

OTHER PUBLICATIONS

Office Action issued in U.S. Appl. No. 13/808,080 dated May 25, 2022.
Office Action issued in U.S. Appl. No. 17/560,019, dated May 31, 2022.
Office Action issued in U.S. Appl. No. 17/696,143, dated Aug. 30, 2022.
Office Action issued in U.S. Appl. No. 17/511,762, dated Sep. 15, 2022.
Office Action issued in U.S. Appl. No. 16/837,115, dated Apr. 22, 2022.
Office Action issued in U.S. Appl. No. 16/714,891, dated May 26, 2022.
McGown, "Uv Absorbance Measurements of DNA in Microplates," BioTechniques, vol. 28, (2000), pp. 60-64.
Office Action, dated Nov. 23, 2022, in U.S. Appl. No. 17/560,019.
Office Action, dated Nov. 23, 2022, in U.S. Appl. No. 17/560,052.
Office Action, dated Nov. 25, 2022, in U.S. Appl. No. 17/560,059.
Office Action, dated Dec. 8, 2022, in U.S. Appl. No. 17/560,116.
Feigner et al., "Cationic Lipid-Mediated Transfection in Mammalian Cells: Lipofection," J Tiss Cult Meth., vol. 15, (1993), pp. 63-38.
Akinc et al., "The Onpattro Story and the Clinical Translatioin of Nanomedicines Containing Nucleic Acid-Based Drugs," Nature Nanotechnology, vol. 14, (2019), pp. 1084-1087.
Ambegia et al., "Stabilized Plasmid-Lipid Particles Containing PEG-diacylglycerols Exhibit Extended Circulation Lifetimes and Tumor Selective Gene Expression," Biochimica et Piophysica Acta., vol. 1669, (2005), pp. 155-163.
Banerjee, "5'Terminal Cap Structure in Eucaryotic Messenger Ribonucleic Acids," Microbiological Reviews, vol. 44, No. 2, (1980), pp. 175-205.
Declaration of Kimberly J. Hassett, dated Nov. 18, 2021.
Cox et al., "Plasmid DNA and Messenger RNA for Therapy," Handbook of Pharmaceutical Biotechnology, Chapter 7.2, (2007), pp. 971-1011.
Bangs et al., "Mass Spectrometry of mRNA Cap 4 from Trypanosomatids Reveals Two Novel Nucleosides," The Journal of Biological Chemistry, vol. 267, No. 14, (1992), pp. 9805-9815.
Pascolo, "Vaccination with Messenger RNA (mRNA)," Handboook of Experimental Pharmacology, vol. 183, (2008), pp. 221-235.
Furuichi et al., "Viral and Cellular mRNA Capping: Past and Prospects," Advances in Virus Research, vol. 55, (2000), pp. 135-184.
Fechter et al., "Recognition of mRNA Cap Structures by Viral and Cellular Proteins," Journal fo General Virology, vol. 86, (2005), pp. 1239-1249.
Pardi et al., "Nucleoside-Modified mRNA Vaccines Induce Potent T Follicular Helper and Germinal Center B Cell Responses," Journal of Experimental Medicine, vol. 215, No. 6, (2018), pp. 1571-1588.
Morais et al., "The Critical Contribution of Pseudouridine to mRNA COVID-19 Vaccines," Frontiers in Cell and Development Biology, vol. 9, (2021), pp. 1-9.
Hess et al., "Vaccination with mRNAs encoding Tumor-Associated Antigens and Granulocyte-Macrophage Colony-Stimulating Factor Efficiently Primes CTL Responses, but is Insufficient to Overcome Tolerance to a Model Tumor/Self Antigen,," Cancer Immunol Immunother, vol. 55, (2006), pp. 672-683.
Lambert et al., "Intradermal Vaccine Delivery: Will New Delivery Systems Transform Vaccine Administration?" Vaccine, vol. 26, (2008), pp. 3197-3208.
Li et al., Low-pH-Sensitive Poly(ethylene glycol) (PEG)-Stabilized Plasmid Nanolipoparticles: Effects of PEG Chain Length, Lipid Composition and Assembly Conditions on Gene Delivery, The Journal of Gene Medicine, vol. 7, (2005), pp. 67-79.
Patentee Submission to EPO in EP Application No. 11758014.2, dated Nov. 13, 2018.
Roos, "Europe Approves Sanofi's Intradermal Flu Vaccine," University of Minnesota Center for Infections Disease Research and Policy [online: cidrap.umn.edu/news-perspective/2009/02/europe-approves-sanofis-intradermal-flu-vaccine], (2009), pp. 1-2.
"ProductlnfoNow," Modern Drug Discovery, vol. 6, No. 6, (2003), pp. 57-62.
Print-out of the entry for the m7G(5')ppp(5')G RNA Cap Structure Analog from the New England Biolabs homepage, from Apr. 2010, pp. 1-2.
Print-out of the entry for the ScriptCap™ m7G Capping System from the Epicentre Biotechnologies Homepage from Nov. 2006, pp. 1-2.
Santos et al., "Design of Peptide-Targeted Liposomes Containing Nucleic Acids," Biochimica et Biophysica Acta, vol. 1798, (2010), pp. 433-441.
Spikevax Patient Information, European Medicines Agency, (2022), pp. 1-5.
Sticchi et al., "The Intradermal Vaccination: Past Experiences and Current Perspectives," J Prev Med Hyg, vol. 51, (2010), pp. 7-14.
van den Berg et al., "Shielding the Cationic Charge of Nanoparticle-Formulated Dermal DNA Vaccines is Essential for Antigen Expression and Immunogenicity," Journal of Controlled Release, vol. 141, (2010), pp. 234-240.
Sonoke et al., "Tumor Regression in Mice by Delivery of Liposomes," Cancer Research, vol. 68, (2008), pp. 8843-8851.
Kim et al., "Enhanced siRNA Delivery using Cationic Liposomes with new Polyarginine-Conjugated PEG-Lipid," International Journal of Pharmaceutics, vol. 392, (2010), pp. 141-147.
Office Action, dated Dec. 21, 2022, issued in U.S. Appl. No. 16/656,929.
Office Action, dated Jan. 20, 2023, issued in U.S. Appl. No. 17/512,258.
Office Action, dated Jan. 24, 2023, issued in U.S. Appl. No. 17/696,143.

BHKV cells infected with alphavirus
IP: mIgG or mouse α-gH
IB: rabbit α-gH + rabbit α-gL

MRC-5/TB40-UL32-EGFP without complement

ARPE-19 cells, without complement

MRC-5 cells, without complement

ATAGGCGGCGCATGAGAGAAGCCCAGACCAATTACCTACCCAAAATGGAGAAAGTTC
ACGTTGACATCGAGGAAGACAGCCCATTCCTCAGAGCTTTGCAGCGGAGCTTCCCGC
AGTTTGAGGTAGAAGCCAAGCAGGTCACTGATAATGACCATGCTAATGCCAGAGCGT
TTTCGCATCTGGCTTCAAAACTGATCGAAACGGAGGTGGACCCATCCGACACGATCC
TTGACATTGGAAGTGCGCCCGCCCGCAGAATGTATTCTAAGCACAAGTATCATTGTA
TCTGTCCGATGAGATGTGCGGAAGATCCGGACAGATTGTATAAGTATGCAACTAAGC
TGAAGAAAAACTGTAAGGAAATAACTGATAAGGAATTGGACAAGAAAATGAAGGAGC
TCGCCGCCGTCATGAGCGACCCTGACCTGGAAACTGAGACTATGTGCCTCCACGACG
ACGAGTCGTGTCGCTACGAAGGGCAAGTCGCTGTTTACCAGGATGTATACGCGGTTG
ACGGACCGACAAGTCTCTATCACCAAGCCAATAAGGGAGTTAGAGTCGCCTACTGGA
TAGGCTTTGACACCACCCCTTTTATGTTTAAGAACTTGGCTGGAGCATATCCATCAT
ACTCTACCAACTGGGCCGACGAAACCGTGTTAACGGCTCGTAACATAGGCCTATGCA
GCTCTGACGTTATGGAGCGGTCACGTAGAGGGATGTCCATTCTTAGAAAGAAGTATT
TGAAACCATCCAACAATGTTCTATTCTCTGTTGGCTCGACCATCTACCACGAGAAGA
GGGACTTACTGAGGAGCTGGCACCTGCCGTCTGTATTTCACTTACGTGGCAAGCAAA
ATTACACATGTCGGTGTGAGACTATAGTTAGTTGCGACGGGTACGTCGTTAAAAGAA
TAGCTATCAGTCCAGGCCTGTATGGGAAGCCTTCAGGCTATGCTGCTACGATGCACC
GCGAGGGATTCTTGTGCTGCAAAGTGACAGACACATTGAACGGGGAGAGGGTCTCTT
TTCCCGTGTGCACGTATGTGCCAGCTACATTGTGTGACCAAATGACTGGCATACTGG
CAACAGATGTCAGTGCGGACGACGCGCAAAAACTGCTGGTTGGGCTCAACCAGCGTA
TAGTCGTCAACGGTCGCACCCAGAGAAACACCAATACCATGAAAAATTACCTTTTGC
CCGTAGTGGCCCAGGCATTTGCTAGGTGGGCAAAGGAATATAAGGAAGATCAAGAAG
ATGAAAGGCCACTAGGACTACGAGATAGACAGTTAGTCATGGGGTGTTGTTGGGCTT
TTAGAAGGCACAAGATAACATCTATTTATAAGCGCCCGGATACCCAAACCATCATCA
AAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCAC
CTCTCATTACCGCCGAGGACGTACAAGAAGCTAAGTGCGCAGCCGATGAGGCTAAGG
AGGTGCGTGAAGCCGAGGAGTTGCGCGCAGCTCTACCACCTTTGGCAGCTGATGTTG
AGGAGCCCACTCTGGAAGCCGATGTAGACTTGATGTTACAAGAGGCTGGGGCCGGCT
CAGTGGAGACACCTCGTGGCTTGATAAAGGTTACCAGCTACGATGGCGAGGACAAGA
TCGGCTCTTACGCTGTGCTTTCTCCGCAGGCTGTACTCAAGAGTGAAAAATTATCTT
GCATCCACCCTCTCGCTGAACAAGTCATAGTGA

FIG 14A

TAACACACTCTGGCCGAAAAGGGCGTTATGCCGTGGAACCATACCATGGTAAAGTAG
TGGTGCCAGAGGGACATGCAATACCCGTCCAGGACTTTCAAGCTCTGAGTGAAAGTG
CCACCATTGTGTACAACGAACGTGAGTTCGTAAACAGGTACCTGCACCATATTGCCA
CACATGGAGGAGCGCTGAACACTGATGAAGAATATTACAAAACTGTCAAGCCCAGCG
AGCACGACGGCGAATACCTGTACGACATCGACAGGAAACAGTGCGTCAAGAAAGAAC
TAGTCACTGGGCTAGGGCTCACAGGCGAGCTGGTGGATCCTCCCTTCCATGAATTCG
CCTACGAGAGTCTGAGAACACGACCAGCCGCTCCTTACCAAGTACCAACCATAGGGG
TGTATGGCGTGCCAGGATCAGGCAAGTCTGGCATCATTAAAAGCGCAGTCACCAAAA
AAGATCTAGTGGTGAGCGCCAAGAAAGAAAACTGTGCAGAAATTATAAGGGACGTCA
AGAAAATGAAAGGGCTGGACGTCAATGCCAGAACTGTGGACTCAGTGCTCTTGAATG
GATGCAAACACCCCGTAGAGACCCTGTATATTGACGAAGCTTTTGCTTGTCATGCAG
GTACTCTCAGAGCGCTCATAGCCATTATAAGACCTAAAAAGGCAGTGCTCTGCGGGG
ATCCCAAACAGTGCGGTTTTTTTAACATGATGTGCCTGAAAGTGCATTTTAACCACG
AGATTTGCACACAAGTCTTCCACAAAAGCATCTCTCGCCGTTGCACTAAATCTGTGA
CTTCGGTCGTCTCAACCTTGTTTTACGACAAAAAAATGAGAACGACGAATCCGAAAG
AGACTAAGATTGTGATTGACACTACCGGCAGTACCAAACCTAAGCAGGACGATCTCA
TTCTCACTTGTTTCAGAGGGTGGGTGAAGCAGTTGCAAATAGATTACAAAGGCAACG
AAATAATGACGGCAGCTGCCTCTCAAGGGCTGACCCGTAAAGGTGTGTATGCCGTTC
GGTACAAGGTGAATGAAAATCCTCTGTACGCACCCACCTCAGAACATGTGAACGTCC
TACTGACCCGCACGGAGGACCGCATCGTGTGGAAAACACTAGCCGGCGACCCATGGA
TAAAAACACTGACTGCCAAGTACCCTGGGAATTTCACTGCCACGATAGAGGAGTGGC
AAGCAGAGCATGATGCCATCATGAGGCACATCTTGGAGAGACCGGACCCTACCGACG
TCTTCCAGAATAAGGCAAACGTGTGTTGGGCCAAGGCTTTAGTGCCGGTGCTGAAGA
CCGCTGGCATAGACATGACCACTGAACAATGGAACACTGTGGATTATTTTGAAACGG
ACAAAGCTCACTCAGCAGAGATAGTATTGAACCAACTATGCGTGAGGTTCTTTGGAC
TCGATCTGGACTCCGGTCTATTTTCTGCACCCACTGTTCCGTTATCCATTAGGAATA
ATCACTGGGATAACTCCCCGTCGCCTAACATGTACGGGCTGAATAAAGAAGTGGTCC
GTCAGCTCTCTCGCAGGTACCCACAACTGCCTCGGGCAGTTGCCACTGGAAGAGTCT
ATGACATGAACACTGGTACACTGCGCAATTATGATCCGCGCATAAACCTAGTACCTG
TAAACAGAAGACTGCCTCATGCTTTAGTCCTCCACCATAATGAACACCCACAGAGTG
ACTTTTCTTCATTCGTCAGCAAATTGAAGGGCAGAACTGTCCTGGTGGTCGGGGAAA
AGTTGTCCGTCCCAGGCAAAATGGTTGACTGGT

FIG. 14B

TGTCAGACCGGCCTGAGGCTACCTTCAGAGCTCGGCTGGATTTAGGCATCCCAGGTG
ATGTGCCCAAATATGACATAATATTTGTTAATGTGAGGACCCCATATAAATACCATC
ACTATCAGCAGTGTGAAGACCATGCCATTAAGCTTAGCATGTTGACCAAGAAAGCTT
GTCTGCATCTGAATCCCGGCGGAACCTGTGTCAGCATAGGTTATGGTTACGCTGACA
GGGCCAGCGAAAGCATCATTGGTGCTATAGCGCGGCAGTTCAAGTTTTCCCGGGTAT
GCAAACCGAAATCCTCACTTGAAGAGACGGAAGTTCTGTTTGTATTCATTGGGTACG
ATCGCAAGGCCCGTACGCACAATCCTTACAAGCTTTCATCAACCTTGACCAACATTT
ATACAGGTTCCAGACTCCACGAAGCCGGATGTGCACCCTCATATCATGTGGTGCGAG
GGGATATTGCCACGGCCACCGAAGGAGTGATTATAAATGCTGCTAACAGCAAAGGAC
AACCTGGCGGAGGGGTGTGCGGAGCGCTGTATAAGAAATTCCCGGAAAGCTTCGATT
TACAGCCGATCGAAGTAGGAAAAGCGCGACTGGTCAAAGGTGCAGCTAAACATATCA
TTCATGCCGTAGGACCAAACTTCAACAAAGTTTCGGAGGTTGAAGGTGACAAACAGT
TGGCAGAGGCTTATGAGTCCATCGCTAAGATTGTCAACGATAACAATTACAAGTCAG
TAGCGATTCCACTGTTGTCCACCGGCATCTTTTCCGGGAACAAAGATCGACTAACCC
AATCATTGAACCATTTGCTGACAGCTTTAGACACCACTGATGCAGATGTAGCCATAT
ACTGCAGGGACAAGAAATGGGAAATGACTCTCAAGGAAGCAGTGGCTAGGAGAGAAG
CAGTGGAGGAGATATGCATATCCGACGACTCTTCAGTGACAGAACCTGATGCAGAGC
TGGTGAGGGTGCATCCGAAGAGTTCTTTGGCTGGAAGGAAGGGCTACAGCACAAGCG
ATGGCAAAACTTTCTCATATTTGGAAGGGACCAAGTTTCACCAGGCGGCCAAGGATA
TAGCAGAAATTAATGCCATGTGGCCCGTTGCAACGGAGGCCAATGAGCAGGTATGCA
TGTATATCCTCGGAGAAAGCATGAGCAGTATTAGGTCGAAATGCCCCGTCGAAGAGT
CGGAAGCCTCCACACCACCTAGCACGCTGCCTTGCTTGTGCATCCATGCCATGACTC
CAGAAAGAGTACAGCGCCTAAAAGCCTCACGTCCAGAACAAATTACTGTGTGCTCAT
CCTTTCCATTGCCGAAGTATAGAATCACTGGTGTGCAGAAGATCCAATGCTCCCAGC
CTATATTGTTCTCACCGAAAGTGCCTGCGTATATTCATCCAAGGAAGTATCTCGTGG
AAACACCACCGGTAGACGAGACTCCGGAGCCATCGGCAGAGAACCAATCCACAGAGG
GGACACCTGAACAACCACCACTTATAACCGAGGATGAGACCAGGACTAGAACGCCTG
AGCCGATCATCATCGAAGAGGAAGAAGAGGATAGCATAAGTTTGCTGTCAGATGGCC
CGACCCACCAGGTGCTGCAAGTCGAGGCAGACATTCACGGGCCGCCCTCTGTATCTA
GCTCATCCTGGTCCATTCCTCATGCATCCGACTTTGATGTGGACAGTTTATCCATAC
TTGACACCCTGGAGGGAGCTAGCGTGACCAGCGGGGCAACGTCAGCCGAGACTAACT
CTTACTTCGCAAAGAGTATGGAGTTTCTGGCGC

FIG. 14C

GACCGGTGCCTGCGCCTCGAACAGTATTCAGGAACCCTCCACATCCCGCTCCGCGCA
CAAGAACACCGTCACTTGCACCCAGCAGGGCCTGCTCGAGAACCAGCCTAGTTTCCA
CCCCGCCAGGCGTGAATAGGGTGATCACTAGAGAGGAGCTCGAGGCGCTTACCCCGT
CACGCACTCCTAGCAGGTCGGTCTCGAGAACCAGCCTGGTCTCCAACCCGCCAGGCG
TAAATAGGGTGATTACAAGAGAGGAGTTTGAGGCGTTCGTAGCACAACAACAATGAC
GGTTTGATGCGGGTGCATACATCTTTTCCTCCGACACCGGTCAAGGGCATTTACAAC
AAAAATCAGTAAGGCAAACGGTGCTATCCGAAGTGGTGTTGGAGAGGACCGAATTGG
AGATTTCGTATGCCCCGCGCCTCGACCAAGAAAAAGAAGAATTACTACGCAAGAAAT
TACAGTTAAATCCCACACCTGCTAACAGAAGCAGATACCAGTCCAGGAAGGTGGAGA
ACATGAAAGCCATAACAGCTAGACGTATTCTGCAAGGCCTAGGGCATTATTTGAAGG
CAGAAGGAAAAGTGGAGTGCTACCGAACCCTGCATCCTGTTCCTTTGTATTCATCTA
GTGTGAACCGTGCCTTTTCAAGCCCCAAGGTCGCAGTGGAAGCCTGTAACGCCATGT
TGAAAGAGAACTTTCCGACTGTGGCTTCTTACTGTATTATTCCAGAGTACGATGCCT
ATTTGGACATGGTTGACGGAGCTTCATGCTGCTTAGACACTGCCAGTTTTTGCCCTG
CAAAGCTGCGCAGCTTTCCAAAGAAACACTCCTATTTGGAACCCACAATACGATCGG
CAGTGCCTTCAGCGATCCAGAACACGCTCCAGAACGTCCTGGCAGCTGCCACAAAAA
GAAATTGCAATGTCACGCAAATGAGAGAATTGCCCGTATTGGATTCGGCGGCCTTTA
ATGTGGAATGCTTCAAGAAATATGCGTGTAATAATGAATATTGGGAAACGTTTAAAG
AAAACCCCATCAGGCTTACTGAAGAAAACGTGGTAAATTACATTACCAAATTAAAAG
GACCAAAAGCTGCTGCTCTTTTTGCGAAGACACATAATTTGAATATGTTGCAGGACA
TACCAATGGACAGGTTTGTAATGGACTTAAAGAGAGACGTGAAAGTGACTCCAGGAA
CAAAACATACTGAAGAACGGCCCAAGGTACAGGTGATCCAGGCTGCCGATCCGCTAG
CAACAGCGTATCTGTGCGGAATCCACCGAGAGCTGGTTAGGAGATTAAATGCGGTCC
TGCTTCCGAACATTCATACACTGTTTGATATGTCGGCTGAAGACTTTGACGCTATTA
TAGCCGAGCACTTCCAGCCTGGGGATTGTGTTCTGGAAACTGACATCGCGTCGTTTG
ATAAAAGTGAGGACGACGCCATGGCTCTGACCGCGTTAATGATTCTGGAAGACTTAG
GTGTGGACGCAGAGCTGTTGACGCTGATTGAGGCGGCTTTCGGCGAAATTTCATCAA
TACATTTGCCCACTAAAACTAAATTTAAATTCGGAGCCATGATGAAATCTGGAATGT
TCCTCACACTGTTTGTGAACACAGTCATTAACATTGTAATCGCAAGCAGAGTGTTGA
GAGAACGGCTAACCGGATCACCATGTGCAGCATTCATTGGAGATGACAATATCGTGA
AAGGAGTCAAATCGGACAAATTAATGGCAGACAGGTGCGCCACCTGGTTGAATATGG
AAGTCAAGATTATAGATGCTGTGGTGGGCGAGA

FIG. 14D

AAGCGCCTTATTTCTGTGGAGGGTTTATTTTGTGTGACTCCGTGACCGGCACAGCGT
GCCGTGTGGCAGACCCCCTAAAAAGGCTGTTTAAGCTTGGCAAACCTCTGGCAGCAG
ACGATGAACATGATGATGACAGGAGAAGGGCATTGCATGAAGAGTCAACACGCTGGA
ACCGAGTGGGTATTCTTTCAGAGCTGTGCAAGGCAGTAGAATCAAGGTATGAAACCG
TAGGAACTTCCATCATAGTTATGGCCATGACTACTCTAGCTAGCAGTGTTAAATCAT
TCAGCTACCTGAGAGGGGCCCCTATAACTCTCTACGGCTAACCTGAATGGACTACGA
CATAGTCTAGTCGACGCCACCATGAGGCCTGGCCTGCCCTCCTACCTGATCATCCTG
GCCGTGTGCCTGTTCAGCCACCTGCTGTCCAGCAGATACGGCGCCGAGGCCGTGAGC
GAGCCCCTGGACAAGGCTTTCCACCTGCTGCTGAACACCTACGGCAGACCCATCCGG
TTTCTGCGGGAGAACACCACCCAGTGCACCTACAACAGCAGCCTGCGGAACAGCACC
GTCGTGAGAGAGAACGCCATCAGCTTCAACTTTTTCCAGAGCTACAACCAGTACTAC
GTGTTCCACATGCCCAGATGCCTGTTTGCCGGCCCTCTGGCCGAGCAGTTCCTGAAC
CAGGTGGACCTGACCGAGACACTGGAAAGATACCAGCAGCGGCTGAATACCTACGCC
CTGGTGTCCAAGGACCTGGCCAGCTACCGGTCCTTTAGCCAGCAGCTCAAGGCTCAG
GATAGCCTCGGCGAGCAGCCTACCACCGTGCCCCCTCCCATCGACCTGAGCATCCCC
CACGTGTGGATGCCTCCCCAGACCACCCCTCACGGCTGGACCGAGAGCCACACCACC
TCCGGCCTGCACAGACCCCACTTCAACCAGACCTGCATCCTGTTCGACGGCCACGAC
CTGCTGTTTAGCACCGTGACCCCCTGCCTGCACCAGGGCTTCTACCTGATCGACGAG
CTGAGATACGTGAAGATCACCCTGACCGAGGATTTCTTCGTGGTCACCGTGTCCATC
GACGACGACACCCCCATGCTGCTGATCTTCGGCCACCTGCCCAGAGTGCTGTTCAAG
GCCCCCTACCAGCGGGACAACTTCATCCTGCGGCAGACCGAGAAGCACGAGCTGCTG
GTGCTGGTCAAGAAGGACCAGCTGAACCGGCACTCCTACCTGAAGGACCCCGACTTC
CTGGACGCCGCCCTGGACTTCAACTACCTGGACCTGAGCGCCCTGCTGAGAAACAGC
TTCCACAGATACGCCGTGGACGTGCTGAAGTCCGGACGGTGCCAGATGCTCGATCGG
CGGACCGTGGAGATGGCCTTCGCCTATGCCCTCGCCCTGTTCGCCGCTGCCAGACAG
GAAGAGGCTGGCGCCCAGGTGTCAGTGCCCAGAGCCCTGGATAGACAGGCCGCCCTG
CTGCAGATCCAGGAATTCATGATCACCTGCCTGAGCCAGACCCCCCCTAGAACCACC
CTGCTGCTGTACCCCACAGCCGTGGATCTGGCCAAGAGGGCCCTGTGGACCCCCAAC
CAGATCACCGACATCACAAGCCTCGTGCGGCTCGTGTACATCCTGAGCAAGCAGAAC
CAGCAGCACCTGATCCCCCAGTGGGCCCTGAGACAGATCGCCGACTTCGCCCTGAAG
CTGCACAAGACCCATCTGGCCAGCTTTCTGAGCGCCTTCGCCAGGCAGGAACTGTAC
CTGATGGGCAGCCTGGTCCACAGCATGCTGGTG

FIG. 14E

CATACCACCGAGCGGCGGGAGATCTTCATCGTGGAGACAGGCCTGTGTAGCCTGGCC
GAGCTGTCCCACTTTACCCAGCTGCTGGCCCACCCTCACCACGAGTACCTGAGCGAC
CTGTACACCCCCTGCAGCAGCAGCGGCAGACGGGACCACAGCCTGGAACGGCTGACC
AGACTGTTCCCCGATGCCACCGTGCCTGCTACAGTGCCTGCCGCCCTGTCCATCCTG
TCCACCATGCAGCCCAGCACCCTGGAAACCTTCCCCGACCTGTTCTGCCTGCCCCTG
GGCGAGAGCTTTAGCGCCCTGACCGTGTCCGAGCACGTGTCCTACATCGTGACCAAT
CAGTACCTGATCAAGGGCATCAGCTACCCCGTGTCCACCACAGTCGTGGGCCAGAGC
CTGATCATCACCCAGACCGACAGCCAGACCAAGTGCGAGCTGACCCGGAACATGCAC
ACCACACACAGCATCACCGTGGCCCTGAACATCAGCCTGGAAAACTGCGCTTTCTGT
CAGTCTGCCCTGCTGGAATACGACGATACCCAGGGCGTGATCAACATCATGTACATG
CACGACAGCGACGACGTGCTGTTCGCCCTGGACCCCTACAACGAGGTGGTGGTGTCC
AGCCCCCGGACCCACTACCTGATGCTGCTGAAGAACGGCACCGTGCTGGAAGTGACC
GACGTGGTGGTGGACGCCACCGACAGCAGACTGCTGATGATGAGCGTGTACGCCCTG
AGCGCCATCATCGGCATCTACCTGCTGTACCGGATGCTGAAAACCTGCTGATAATCT
AGACGGCGCGCCCACCCAGCGGCCGCCTATAACTCTCTACGGCTAACCTGAATGGAC
TACGACATAGTCTAGTCGACGCCACCATGTGCAGAAGGCCCGACTGCGGCTTCAGCT
TCAGCCCTGGACCCGTGATCCTGCTGTGGTGCTGCCTGCTGCTGCCTATCGTGTCCT
CTGCCGCCGTGTCTGTGGCCCCTACAGCCGCCGAGAAGGTGCCAGCCGAGTGCCCCG
AGCTGACCAGAAGATGCCTGCTGGGCGAGGTGTTCGAGGGCGACAAGTACGAGAGCT
GGCTGCGGCCCCTGGTCAACGTGACCGGCAGAGATGGCCCCCTGAGCCAGCTGATCC
GGTACAGACCCGTGACCCCCGAGGCCGCCAATAGCGTGCTGCTGGACGAGGCCTTCC
TGGATACCCTGGCCCTGCTGTACAACAACCCCGACCAGCTGAGAGCCCTGCTGACCC
TGCTGTCCAGCGACACCGCCCCCAGATGGATGACCGTGATGCGGGGCTACAGCGAGT
GTGGAGATGGCAGCCCTGCCGTGTACACCTGCGTGGACGACCTGTGCAGAGGCTACG
ACCTGACCAGACTGAGCTACGGCCGGTCCATCTTCACAGAGCACGTGCTGGGCTTCG
AGCTGGTGCCCCCCAGCCTGTTCAACGTGGTGGTGGCCATCCGGAACGAGGCCACCA
GAACCAACAGAGCCGTGCGGCTGCCTGTGTCTACAGCCGCTGCACCTGAGGGCATCA
CACTGTTCTACGGCCTGTACAACGCCGTGAAAGAGTTCTGCCTCCGGCACCAGCTGG
ATCCCCCCCTGCTGAGACACCTGGACAAGTACTACGCCGGCCTGCCCCCAGAGCTGA
AGCAGACCAGAGTGAACCTGCCCGCCCACAGCAGATATGGCCCTCAGGCCGTGGACG
CCAGATGATAATCTAGACGGCGCGCCCACCCACCTGCAGGATACAGCAGCAATTGGC
AAGCTGCTTACATAGAACTCGCGGCGATTGGCA

FIG. 14F

TGCCGCCTTAAAATTTTTATTTTATTTTTCTTTTCTTTTCCGAATCGGATTTTGTTT
TTAATATTTCAAAAAAAAAAAAAAAAAAAAAAAAAAAAAAAAAAAGGGTCGGCATGG
CATCTCCACCTCCTCGCGGTCCGACCTGGGCATCCGAAGGAGGACGCACGTCCACTC
GGATGGCTAAGGGAGAGCCACGTTTAAACGCTAGAGCAAGACGTTTCCCGTTGAATA
TGGCTCATAACACCCCTTGTATTACTGTTTATGTAAGCAGACAGTTTTATTGTTCAT
GATGATATATTTTTATCTTGTGCAATGTAACATCAGAGATTTTGAGACACAACGTGG
CTTTGTTGAATAAATCGAACTTTTGCTGAGTTGAAGGATCAGATCACGCATCTTCCC
GACAACGCAGACCGTTCCGTGGCAAAGCAAAAGTTCAAAATCACCAACTGGTCCACC
TACAACAAAGCTCTCATCAACCGTGGCTCCCTCACTTTCTGGCTGGATGATGGGGCG
ATTCAGGCCTGGTATGAGTCAGCAACACCTTCTTCACGAGGCAGACCTCAGCGCTAG
CGGAGTGTATACTGGCTTACTATGTTGGCACTGATGAGGGTGTCAGTGAAGTGCTTC
ATGTGGCAGGAGAAAAAAGGCTGCACCGGTGCGTCAGCAGAATATGTGATACAGGAT
ATATTCCGCTTCCTCGCTCACTGACTCGCTACGCTCGGTCGTTCGACTGCGGCGAGC
GGAAATGGCTTACGAACGGGGCGGAGATTTCCTGGAAGATGCCAGGAAGATACTTAA
CAGGGAAGTGAGAGGGCCGCGGCAAAGCCGTTTTTCCATAGGCTCCGCCCCCCTGAC
AAGCATCACGAAATCTGACGCTCAAATCAGTGGTGGCGAAACCCGACAGGACTATAA
AGATACCAGGCGTTTCCCCCTGGCGGCTCCCTCGTGCGCTCTCCTGTTCCTGCCTTTC
GGTTTACCGGTGTCATTCCGCTGTTATGGCCGCGTTTGTCTCATTCCACGCCTGACA
CTCAGTTCCGGGTAGGCAGTTCGCTCCAAGCTGGACTGTATGCACGAACCCCCCGTT
CAGTCCGACCGCTGCGCCTTATCCGGTAACTATCGTCTTGAGTCCAACCCGGAAAGA
CATGCAAAAGCACCACTGGCAGCAGCCACTGGTAATTGATTTAGAGGAGTTAGTCTT
GAAGTCATGCGCCGGTTAAGGCTAAACTGAAAGGACAAGTTTTGGTGACTGCGCTCC
TCCAAGCCAGTTACCTCGGTTCAAAGAGTTGGTAGCTCAGAGAACCTTCGAAAAACC
GCCCTGCAAGGCGGTTTTTTCGTTTTCAGAGCAAGAGATTACGCGCAGACCAAAACG
ATCTCAAGAAGATCATCTTATTAAGGGGTCTGACGCTCAGTGGAACGAAAACTCACG
TTAAGGGATTTTGGTCATGAGATTATCAAAAAGGATCTTCACCTAGATCCTTTTAAA
TTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATC
TGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTATC
CGCCTCCATCCAGTCTATTAATTGTTGCCGGGA

FIG. 14G

AGCTAGAGTAAGTAGTTCGCCAGTTAATAGTTTGCGCAACGTTGTTGCCATTGCTGC
AGGCATCGTGGTGTCACGCTCGTCGTTTGGTATGGCTTCATTCAGCTCCGGTTCCCA
ACGATCAAGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCATGGTTAT
GGCAGCACTGCATAATTCTCTTACTGTCATGCCATCCGTAAGATGCTTTTCTGTGAC
TGGTGAGTACTCAACCAAGTCATTCTGAGAATAGTGTATGCGGCGACCGAGTTGCTC
TTGCCCGGCGTCAACACGGGATAATACCGCGCCACATAGCAGAACTTTAAAAGTGCT
CATCATTGGAAAACGTTCTTCGGGGCGAAAACTCTCAAGGATCTTACCGCTGTTGAG
ATCCAGTTCGATGTAACCCACTCGTGCACCCAACTGATCTTCAGCATCTTTTACTTT
CACCAGCGTTTCTGGGTGAGCAAAAACAGGAAGGCAAAATGCCGCAAAAAAGGGAAT
AAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAA
TAAACAAATAGGGGTTCCGCGCACATTTCCCCGAAAAGTGCCACCTGACGTGTCGAG
ACGCGTAATACGACTCACTATAG

Plasmid encoding p15-T7G-TC83R-merlinCMV-gH-sg.gL (A160)

FIG. 14H

ATAGGCGGCGCATGAGAGAAGCCCAGACCAATTACCTACCCAAAATGGAGAAAGTTC
ACGTTGACATCGAGGAAGACAGCCCATTCCTCAGAGCTTTGCAGCGGAGCTTCCCGC
AGTTTGAGGTAGAAGCCAAGCAGGTCACTGATAATGACCATGCTAATGCCAGAGCGT
TTTCGCATCTGGCTTCAAAACTGATCGAAACGGAGGTGGACCCATCCGACACGATCC
TTGACATTGGAAGTGCGCCCGCCCGCAGAATGTATTCTAAGCACAAGTATCATTGTA
TCTGTCCGATGAGATGTGCGGAAGATCCGGACAGATTGTATAAGTATGCAACTAAGC
TGAAGAAAAACTGTAAGGAAATAACTGATAAGGAATTGGACAAGAAAATGAAGGAGC
TCGCCGCCGTCATGAGCGACCCTGACCTGGAAACTGAGACTATGTGCCTCCACGACG
ACGAGTCGTGTCGCTACGAAGGGCAAGTCGCTGTTTACCAGGATGTATACGCGGTTG
ACGGACCGACAAGTCTCTATCACCAAGCCAATAAGGGAGTTAGAGTCGCCTACTGGA
TAGGCTTTGACACCACCCCTTTTATGTTTAAGAACTTGGCTGGAGCATATCCATCAT
ACTCTACCAACTGGGCCGACGAAACCGTGTTAACGGCTCGTAACATAGGCCTATGCA
GCTCTGACGTTATGGAGCGGTCACGTAGAGGGATGTCCATTCTTAGAAAGAAGTATT
TGAAACCATCCAACAATGTTCTATTCTCTGTTGGCTCGACCATCTACCACGAGAAGA
GGGACTTACTGAGGAGCTGGCACCTGCCGTCTGTATTTCACTTACGTGGCAAGCAAA
ATTACACATGTCGGTGTGAGACTATAGTTAGTTGCGACGGGTACGTCGTTAAAAGAA
TAGCTATCAGTCCAGGCCTGTATGGGAAGCCTTCAGGCTATGCTGCTACGATGCACC
GCGAGGGATTCTTGTGCTGCAAAGTGACAGACACATTGAACGGGGAGAGGGTCTCTT
TTCCCGTGTGCACGTATGTGCCAGCTACATTGTGTGACCAAATGACTGGCATACTGG
CAACAGATGTCAGTGCGGACGACGCGCAAAAACTGCTGGTTGGGCTCAACCAGCGTA
TAGTCGTCAACGGTCGCACCCAGAGAAACACCAATACCATGAAAAATTACCTTTTGC
CCGTAGTGGCCCAGGCATTTGCTAGGTGGGCAAAGGAATATAAGGAAGATCAAGAAG
ATGAAAGGCCACTAGGACTACGAGATAGACAGTTAGTCATGGGGTGTTGTTGGGCTT
TTAGAAGGCACAAGATAACATCTATTTATAAGCGCCCGGATACCCAAACCATCATCA
AAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCAC
CTCTCATTACCGCCGAGGACGTACAAGAAGCTAAGTGCGCAGCCGATGAGGCTAAGG
AGGTGCGTGAAGCCGAGGAGTTGCGCGCAGCTCTACCACCTTTGGCAGCTGATGTTG
AGGAGCCCACTCTGGAAGCCGATGTAGACTTGATGTTACAAGAGGCTGGGGCCGGCT
CAGTGGAGACACCTCGTGGCTTGATAAAGGTTACCAGCTACGATGGCGAGGACAAGA
TCGGCTCTTACGCTGTGCTTTCTCCGCAGG

FIG. 15A

CTGTACTCAAGAGTGAAAAATTATCTTGCATCCACCCTCTCGCTGAACAAGTCATAG
TGATAACACACTCTGGCCGAAAAGGGCGTTATGCCGTGGAACCATACCATGGTAAAG
TAGTGGTGCCAGAGGGACATGCAATACCCGTCCAGGACTTTCAAGCTCTGAGTGAAA
GTGCCACCATTGTGTACAACGAACGTGAGTTCGTAAACAGGTACCTGCACCATATTG
CCACACATGGAGGAGCGCTGAACACTGATGAAGAATATTACAAAACTGTCAAGCCCA
GCGAGCACGACGGCGAATACCTGTACGACATCGACAGGAAACAGTGCGTCAAGAAAG
AACTAGTCACTGGGCTAGGGCTCACAGGCGAGCTGGTGGATCCTCCCTTCCATGAAT
TCGCCTACGAGAGTCTGAGAACACGACCAGCCGCTCCTTACCAAGTACCAACCATAG
GGGTGTATGGCGTGCCAGGATCAGGCAAGTCTGGCATCATTAAAAGCGCAGTCACCA
AAAAAGATCTAGTGGTGAGCGCCAAGAAAGAAAACTGTGCAGAAATTATAAGGGACG
TCAAGAAAATGAAAGGGCTGGACGTCAATGCCAGAACTGTGGACTCAGTGCTCTTGA
ATGGATGCAAACACCCCGTAGAGACCCTGTATATTGACGAAGCTTTTGCTTGTCATG
CAGGTACTCTCAGAGCGCTCATAGCCATTATAAGACCTAAAAAGGCAGTGCTCTGCG
GGGATCCCAAACAGTGCGGTTTTTTAACATGATGTGCCTGAAAGTGCATTTTAACC
ACGAGATTTGCACACAAGTCTTCCACAAAAGCATCTCTCGCCGTTGCACTAAATCTG
TGACTTCGGTCGTCTCAACCTTGTTTTACGACAAAAAAATGAGAACGACGAATCCGA
AAGAGACTAAGATTGTGATTGACACTACCGGCAGTACCAAACCTAAGCAGGACGATC
TCATTCTCACTTGTTTCAGAGGGTGGGTGAAGCAGTTGCAAATAGATTACAAAGGCA
ACGAAATAATGACGGCAGCTGCCTCTCAAGGGCTGACCCGTAAAGGTGTGTATGCCG
TTCGGTACAAGGTGAATGAAAATCCTCTGTACGCACCCACCTCAGAACATGTGAACG
TCCTACTGACCCGCACGGAGGACCGCATCGTGTGGAAAACACTAGCCGGCGACCCAT
GGATAAAAACACTGACTGCCAAGTACCCTGGGAATTTCACTGCCACGATAGAGGAGT
GGCAAGCAGAGCATGATGCCATCATGAGGCACATCTTGGAGAGACCGGACCCTACCG
ACGTCTTCCAGAATAAGGCAAACGTGTGTTGGGCCAAGGCTTTAGTGCCGGTGCTGA
AGACCGCTGGCATAGACATGACCACTGAACAATGGAACACTGTGGATTATTTTGAAA
CGGACAAAGCTCACTCAGCAGAGATAGTATTGAACCAACTATGCGTGAGGTTCTTTG
GACTCGATCTGGACTCCGGTCTATTTTCTGCACCCACTGTTCCGTTATCCATTAGGA
ATAATCACTGGGATAACTCCCCGTCGCCTAACATGTACGGGCTGAATAAAGAAGTGG
TCCGTCAGCTCTCTCGCAGGTACCCACAACTGCCTCGGGCAGTTGCCACTGGAAGAG
TCTATGACATGAACACTGGTACACTGCGCAATTATGATCCGCGCATAAACCTAGTAC
CTGTAAACAGAAGACTGCCTCATGCTTTAGTCCTCCACCATAATGAACACCCACAGA
GTGACTTTTCTTCATTCGTCAGCAAATTGAAGG

FIG. 15B

GCAGAACTGTCCTGGTGGTCGGGGAAAAGTTGTCCGTCCCAGGCAAAATGGTTGACT
GGTTGTCAGACCGGCCTGAGGCTACCTTCAGAGCTCGGCTGGATTTAGGCATCCCAG
GTGATGTGCCCAAATATGACATAATATTTGTTAATGTGAGGACCCCATATAAATACC
ATCACTATCAGCAGTGTGAAGACCATGCCATTAAGCTTAGCATGTTGACCAAGAAAG
CTTGTCTGCATCTGAATCCCGGCGGAACCTGTGTCAGCATAGGTTATGGTTACGCTG
ACAGGGCCAGCGAAAGCATCATTGGTGCTATAGCGCGGCAGTTCAAGTTTTCCCGGG
TATGCAAACCGAAATCCTCACTTGAAGAGACGGAAGTTCTGTTTGTATTCATTGGGT
ACGATCGCAAGGCCCGTACGCACAATCCTTACAAGCTTTCATCAACCTTGACCAACA
TTTATACAGGTTCCAGACTCCACGAAGCCGGATGTGCACCCTCATATCATGTGGTGC
GAGGGGATATTGCCACGGCCACCGAAGGAGTGATTATAAATGCTGCTAACAGCAAAG
GACAACCTGGCGGAGGGGTGTGCGGAGCGCTGTATAAGAAATTCCCGGAAAGCTTCG
ATTTACAGCCGATCGAAGTAGGAAAAGCGCGACTGGTCAAAGGTGCAGCTAAACATA
TCATTCATGCCGTAGGACCAAACTTCAACAAAGTTTCGGAGGTTGAAGGTGACAAAC
AGTTGGCAGAGGCTTATGAGTCCATCGCTAAGATTGTCAACGATAACAATTACAAGT
CAGTAGCGATTCCACTGTTGTCCACCGGCATCTTTTCCGGGAACAAAGATCGACTAA
CCCAATCATTGAACCATTTGCTGACAGCTTTAGACACCACTGATGCAGATGTAGCCA
TATACTGCAGGGACAAGAAATGGGAAATGACTCTCAAGGAAGCAGTGGCTAGGAGAG
AAGCAGTGGAGGAGATATGCATATCCGACGACTCTTCAGTGACAGAACCTGATGCAG
AGCTGGTGAGGGTGCATCCGAAGAGTTCTTTGGCTGGAAGGAAGGGCTACAGCACAA
GCGATGGCAAAACTTTCTCATATTTGGAAGGGACCAAGTTTCACCAGGCGGCCAAGG
ATATAGCAGAAATTAATGCCATGTGGCCCGTTGCAACGGAGGCCAATGAGCAGGTAT
GCATGTATATCCTCGGAGAAAGCATGAGCAGTATTAGGTCGAAATGCCCCGTCGAAG
AGTCGGAAGCCTCCACACCACCTAGCACGCTGCCTTGCTTGTGCATCCATGCCATGA
CTCCAGAAAGAGTACAGCGCCTAAAAGCCTCACGTCCAGAACAAATTACTGTGTGCT
CATCCTTTCCATTGCCGAAGTATAGAATCACTGGTGTGCAGAAGATCCAATGCTCCC
AGCCTATATTGTTCTCACCGAAAGTGCCTGCGTATATTCATCCAAGGAAGTATCTCG
TGGAAACACCACCGGTAGACGAGACTCCGGAGCCATCGGCAGAGAACCAATCCACAG
AGGGGACACCTGAACAACCACCACTTATAACCGAGGATGAGACCAGGACTAGAACGC
CTGAGCCGATCATCATCGAAGAGGAAGAAGAGGATAGCATAAGTTTGCTGTCAGATG
GCCCGACCCACCAGGTGCTGCAAGTCGAGGCAGACATTCACGGGCCGCCCTCTGTAT
CTAGCTCATCCTGGTCCATTCCTCATGCATCCGACTTTGATGTGGACAGTTTATCCA
TACTTGACACCCTGGAGGGAGCTAGCGTGACCA

FIG. 15C

GCGGGGCAACGTCAGCCGAGACTAACTCTTACTTCGCAAAGAGTATGGAGTTTCTGG
CGCGACCGGTGCCTGCGCCTCGAACAGTATTCAGGAACCCTCCACATCCCGCTCCGC
GCACAAGAACACCGTCACTTGCACCCAGCAGGGCCTGCTCGAGAACCAGCCTAGTTT
CCACCCCGCCAGGCGTGAATAGGGTGATCACTAGAGAGGAGCTCGAGGCGCTTACCC
CGTCACGCACTCCTAGCAGGTCGGTCTCGAGAACCAGCCTGGTCTCCAACCCGCCAG
GCGTAAATAGGGTGATTACAAGAGAGGAGTTTGAGGCGTTCGTAGCACAACAACAAT
GACGGTTTGATGCGGGTGCATACATCTTTTCCTCCGACACCGGTCAAGGGCATTTAC
AACAAAAATCAGTAAGGCAAACGGTGCTATCCGAAGTGGTGTTGGAGAGGACCGAAT
TGGAGATTTCGTATGCCCCGCGCCTCGACCAAGAAAAAGAAGAATTACTACGCAAGA
AATTACAGTTAAATCCCACACCTGCTAACAGAAGCAGATACCAGTCCAGGAAGGTGG
AGAACATGAAAGCCATAACAGCTAGACGTATTCTGCAAGGCCTAGGGCATTATTTGA
AGGCAGAAGGAAAAGTGGAGTGCTACCGAACCCTGCATCCTGTTCCTTTGTATTCAT
CTAGTGTGAACCGTGCCTTTTCAAGCCCCAAGGTCGCAGTGGAAGCCTGTAACGCCA
TGTTGAAAGAGAACTTTCCGACTGTGGCTTCTTACTGTATTATTCCAGAGTACGATG
CCTATTTGGACATGGTTGACGGAGCTTCATGCTGCTTAGACACTGCCAGTTTTTGCC
CTGCAAAGCTGCGCAGCTTTCCAAAGAAACACTCCTATTTGGAACCCACAATACGAT
CGGCAGTGCCTTCAGCGATCCAGAACACGCTCCAGAACGTCCTGGCAGCTGCCACAA
AAAGAAATTGCAATGTCACGCAAATGAGAGAATTGCCCGTATTGGATTCGGCGGCCT
TTAATGTGGAATGCTTCAAGAAATATGCGTGTAATAATGAATATTGGGAAACGTTTA
AAGAAAACCCCATCAGGCTTACTGAAGAAAACGTGGTAAATTACATTACCAAATTAA
AAGGACCAAAAGCTGCTGCTCTTTTTGCGAAGACACATAATTTGAATATGTTGCAGG
ACATACCAATGGACAGGTTTGTAATGGACTTAAAGAGAGACGTGAAAGTGACTCCAG
GAACAAAACATACTGAAGAACGGCCCAAGGTACAGGTGATCCAGGCTGCCGATCCGC
TAGCAACAGCGTATCTGTGCGGAATCCACCGAGAGCTGGTTAGGAGATTAAATGCGG
TCCTGCTTCCGAACATTCATACACTGTTTGATATGTCGGCTGAAGACTTTGACGCTA
TTATAGCCGAGCACTTCCAGCCTGGGGATTGTGTTCTGGAAACTGACATCGCGTCGT
TTGATAAAAGTGAGGACGACGCCATGGCTCTGACCGCGTTAATGATTCTGGAAGACT
TAGGTGTGGACGCAGAGCTGTTGACGCTGATTGAGGCGGCTTTCGGCGAAATTTCAT
CAATACATTTGCCCACTAAAACTAAATTTAAATTCGGAGCCATGATGAAATCTGGAA
TGTTCCTCACACTGTTTGTGAACACAGTCATTAACATTGTAATCGCAAGCAGAGTGT
TGAGAGAACGGCTAACCGGATCACCATGTGCAGCATTCATTGGAGATGACAATATCG
TGAAAGGAGTCAAATCGGACAAATTAATGGCAG

FIG. 15D

ACAGGTGCGCCACCTGGTTGAATATGGAAGTCAAGATTATAGATGCTGTGGTGGGCG
AGAAAGCGCCTTATTTCTGTGGAGGGTTTATTTTGTGTGACTCCGTGACCGGCACAG
CGTGCCGTGTGGCAGACCCCCTAAAAAGGCTGTTTAAGCTTGGCAAACCTCTGGCAG
CAGACGATGAACATGATGATGACAGGAGAAGGGCATTGCATGAAGAGTCAACACGCT
GGAACCGAGTGGGTATTCTTTCAGAGCTGTGCAAGGCAGTAGAATCAAGGTATGAAA
CCGTAGGAACTTCCATCATAGTTATGGCCATGACTACTCTAGCTAGCAGTGTTAAAT
CATTCAGCTACCTGAGAGGGGCCCCTATAACTCTCTACGGCTAACCTGAATGGACTA
CGACATAGTCTAGTCGACGCCACCATGAGGCCTGGCCTGCCCTCCTACCTGATCATC
CTGGCCGTGTGCCTGTTCAGCCACCTGCTGTCCAGCAGATACGGCGCCGAGGCCGTG
AGCGAGCCCCTGGACAAGGCTTTCCACCTGCTGCTGAACACCTACGGCAGACCCATC
CGGTTTCTGCGGGAGAACACCACCCAGTGCACCTACAACAGCAGCCTGCGGAACAGC
ACCGTCGTGAGAGAGAACGCCATCAGCTTCAACTTTTTCCAGAGCTACAACCAGTAC
TACGTGTTCCACATGCCCAGATGCCTGTTTGCCGGCCCTCTGGCCGAGCAGTTCCTG
AACCAGGTGGACCTGACCGAGACACTGGAAAGATACCAGCAGCGGCTGAATACCTAC
GCCCTGGTGTCCAAGGACCTGGCCAGCTACCGGTCCTTTAGCCAGCAGCTCAAGGCT
CAGGATAGCCTCGGCGAGCAGCCTACCACCGTGCCCCCTCCCATCGACCTGAGCATC
CCCCACGTGTGGATGCCTCCCCAGACCACCCCTCACGGCTGGACCGAGAGCCACACC
ACCTCCGGCCTGCACAGACCCCACTTCAACCAGACCTGCATCCTGTTCGACGGCCAC
GACCTGCTGTTTAGCACCGTGACCCCCTGCCTGCACCAGGGCTTCTACCTGATCGAC
GAGCTGAGATACGTGAAGATCACCCTGACCGAGGATTTCTTCGTGGTCACCGTGTCC
ATCGACGACGACACCCCCATGCTGCTGATCTTCGGCCACCTGCCCAGAGTGCTGTTC
AAGGCCCCCTACCAGCGGGACAACTTCATCCTGCGGCAGACCGAGAAGCACGAGCTG
CTGGTGCTGGTCAAGAAGGACCAGCTGAACCGGCACTCCTACCTGAAGGACCCCGAC
TTCCTGGACGCCGCCCTGGACTTCAACTACCTGGACCTGAGCGCCCTGCTGAGAAAC
AGCTTCCACAGATACGCCGTGGACGTGCTGAAGTCCGGACGGTGCCAGATGCTCGAT
CGGCGGACCGTGGAGATGGCCTTCGCCTATGCCCTCGCCCTGTTCGCCGCTGCCAGA
CAGGAAGAGGCTGGCGCCCAGGTGTCAGTGCCCAGAGCCCTGGATAGACAGGCCGCC
CTGCTGCAGATCCAGGAATTCATGATCACCTGCCTGAGCCAGACCCCCCCTAGAACC
ACCCTGCTGCTGTACCCCACAGCCGTGGATCTGGCCAAGAGGGCCCTGTGGACCCCC
AACCAGATCACCGACATCACAAGCCTCGTGCGGCTCGTGTACATCCTGAGCAAGCAG
AACCAGCAGCACCTGATCCCCCAGTGGGCCCTGAGACAGATCGCCGACTTCGCCCTG
AAGCTGCACAAGACCCATCTGGCCAGCTTTCTG

FIG. 15E

AGCGCCTTCGCCAGGCAGGAACTGTACCTGATGGGCAGCCTGGTCCACAGCATGCTG
GTGCATACCACCGAGCGGCGGGAGATCTTCATCGTGGAGACAGGCCTGTGTAGCCTG
GCCGAGCTGTCCCACTTTACCCAGCTGCTGGCCCACCCTCACCACGAGTACCTGAGC
GACCTGTACACCCCCTGCAGCAGCAGCGGCAGACGGGACCACAGCCTGGAACGGCTG
ACCAGACTGTTCCCCGATGCCACCGTGCCTGCTACAGTGCCTGCCGCCCTGTCCATC
CTGTCCACCATGCAGCCCAGCACCCTGGAAACCTTCCCCGACCTGTTCTGCCTGCCC
CTGGGCGAGAGCTTTAGCGCCCTGACCGTGTCCGAGCACGTGTCCTACATCGTGACC
AATCAGTACCTGATCAAGGGCATCAGCTACCCCGTGTCCACCACAGTCGTGGGCCAG
AGCCTGATCATCACCCAGACCGACAGCCAGACCAAGTGCGAGCTGACCCGGAACATG
CACACCCACACACAGCATCACCGTGGCCCTGAACATCAGCCTGGAAAACTGCGCTTTC
TGTCAGTCTGCCCTGCTGGAATACGACGATACCCAGGGCGTGATCAACATCATGTAC
ATGCACGACAGCGACGACGTGCTGTTCGCCCTGGACCCCTACAACGAGGTGGTGGTG
TCCAGCCCCCGGACCCACTACCTGATGCTGCTGAAGAACGGCACCGTGCTGGAAGTG
ACCGACGTGGTGGTGGACGCCACCGACTGATAATCTAGACGGCGCGCCCACCCAGCG
GCCGCCTATAACTCTCTACGGCTAACCTGAATGGACTACGACATAGTCTAGTCGACG
CCACCATGTGCAGAAGGCCCGACTGCGGCTTCAGCTTCAGCCCTGGACCCGTGATCC
TGCTGTGGTGCTGCCTGCTGCTGCCTATCGTGTCCTCTGCCGCCGTGTCTGTGGCCC
CTACAGCCGCCGAGAAGGTGCCAGCCGAGTGCCCCGAGCTGACCAGAAGATGCCTGC
TGGGCGAGGTGTTCGAGGGCGACAAGTACGAGAGCTGGCTGCGGCCCCTGGTCAACG
TGACCGGCAGAGATGGCCCCCTGAGCCAGCTGATCCGGTACAGACCCGTGACCCCCG
AGGCCGCCAATAGCGTGCTGCTGGACGAGGCCTTCCTGGATACCCTGGCCCTGCTGT
ACAACAACCCCGACCAGCTGAGAGCCCTGCTGACCCTGCTGTCCAGCGACACCGCCC
CCAGATGGATGACCGTGATGCGGGGCTACAGCGAGTGTGGAGATGGCAGCCCTGCCG
TGTACACCTGCGTGGACGACCTGTGCAGAGGCTACGACCTGACCAGACTGAGCTACG
GCCGGTCCATCTTCACAGAGCACGTGCTGGGCTTCGAGCTGGTGCCCCCCAGCCTGT
TCAACGTGGTGGTGGCCATCCGGAACGAGGCCACCAGAACCAACAGAGCCGTGCGGC
TGCCTGTGTCTACAGCCGCTGCACCTGAGGGCATCACACTGTTCTACGGCCTGTACA
ACGCCGTGAAAGAGTTCTGCCTCCGGCACCAGCTGGATCCCCCCCTGCTGAGACACC
TGGACAAGTACTACGCCGGCCTGCCCCCAGAGCTGAAGCAGACCAGAGTGAACCTGC
CCGCCCACAGCAGATATGGCCCTCAGGCCGTGGACGCCAGATGATAATCTAGACGGC
GCGCCCACCCACCTGCAGGATACAGCAGCAATTGGCAAGCTGCTTACATAGAACTCG
CGGCGATTGGCATGCCGCCTTAAAATTTTTATT

FIG. 15F

TTATTTTTCTTTTCTTTTCCGAATCGGATTTTGTTTTTAATATTTCAAAAAAAAAAA
AAAAAAAAAAAAAAAAAAAAAAAAAGGGTCGGCATGGCATCTCCACCTCCTCGCGGTC
CGACCTGGGCATCCGAAGGAGGACGCACGTCCACTCGGATGGCTAAGGGAGAGCCAC
GTTTAAACGCTAGAGCAAGACGTTTCCCGTTGAATATGGCTCATAACACCCCTTGTA
TTACTGTTTATGTAAGCAGACAGTTTTATTGTTCATGATGATATATTTTTATCTTGT
GCAATGTAACATCAGAGATTTTGAGACACAACGTGGCTTTGTTGAATAAATCGAACT
TTTGCTGAGTTGAAGGATCAGATCACGCATCTTCCCGACAACGCAGACCGTTCCGTG
GCAAAGCAAAAGTTCAAAATCACCAACTGGTCCACCTACAACAAAGCTCTCATCAAC
CGTGGCTCCCTCACTTTCTGGCTGGATGATGGGGCGATTCAGGCCTGGTATGAGTCA
GCAACACCTTCTTCACGAGGCAGACCTCAGCGCTAGCGGAGTGTATACTGGCTTACT
ATGTTGGCACTGATGAGGGTGTCAGTGAAGTGCTTCATGTGGCAGGAGAAAAAAGGC
TGCACCGGTGCGTCAGCAGAATATGTGATACAGGATATATTCCGCTTCCTCGCTCAC
TGACTCGCTACGCTCGGTCGTTCGACTGCGGCGAGCGGAAATGGCTTACGAACGGGG
CGGAGATTTCCTGGAAGATGCCAGGAAGATACTTAACAGGGAAGTGAGAGGGCCGCG
GCAAAGCCGTTTTTCCATAGGCTCCGCCCCCCTGACAAGCATCACGAAATCTGACGC
TCAAATCAGTGGTGGCGAAACCCGACAGGACTATAAAGATACCAGGCGTTTCCCCTG
GCGGCTCCCTCGTGCGCTCTCCTGTTCCTGCCTTTCGGTTTACCGGTGTCATTCCGC
TGTTATGGCCGCGTTTGTCTCATTCCACGCCTGACACTCAGTTCCGGGTAGGCAGTT
CGCTCCAAGCTGGACTGTATGCACGAACCCCCCGTTCAGTCCGACCGCTGCGCCTTA
TCCGGTAACTATCGTCTTGAGTCCAACCCGGAAAGACATGCAAAAGCACCACTGGCA
GCAGCCACTGGTAATTGATTTAGAGGAGTTAGTCTTGAAGTCATGCGCCGGTTAAGG
CTAAACTGAAAGGACAAGTTTTGGTGACTGCGCTCCTCCAAGCCAGTTACCTCGGTT
CAAAGAGTTGGTAGCTCAGAGAACCTTCGAAAAACCGCCCTGCAAGGCGGTTTTTTC
GTTTTCAGAGCAAGAGATTACGCGCAGACCAAAACGATCTCAAGAAGATCATCTTAT
TAAGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATC
AATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGG
AAGGGCCGAGCGCAGAAGTGGTCCTGCAACTTTATCCGCCTCCATCCAGTCTATTAA
TTGTTGCCGGGAAGCTAGAGTAAGTAGTTCGCC

FIG. 15G

AGTTAATAGTTTGCGCAACGTTGTTGCCATTGCTGCAGGCATCGTGGTGTCACGCTC
GTCGTTTGGTATGGCTTCATTCAGCTCCGGTTCCCAACGATCAAGGCGAGTTACATG
ATCCCCCATGTTGTGCAAAAAAGCGGTTAGCTCCTTCGGTCCTCCGATCGTTGTCAG
AAGTAAGTTGGCCGCAGTGTTATCACTCATGGTTATGGCAGCACTGCATAATTCTCT
TACTGTCATGCCATCCGTAAGATGCTTTTCTGTGACTGGTGAGTACTCAACCAAGTC
ATTCTGAGAATAGTGTATGCGGCGACCGAGTTGCTCTTGCCCGGCGTCAACACGGGA
TAATACCGCGCCACATAGCAGAACTTTAAAAGTGCTCATCATTGGAAAACGTTCTTC
GGGGCGAAAACTCTCAAGGATCTTACCGCTGTTGAGATCCAGTTCGATGTAACCCAC
TCGTGCACCCAACTGATCTTCAGCATCTTTTACTTTCACCAGCGTTTCTGGGTGAGC
AAAAACAGGAAGGCAAAATGCCGCAAAAAAGGGAATAAGGGCGACACGGAAATGTTG
AATACTCATACTCTTCCTTTTTCAATATTATTGAAGCATTTATCAGGGTTATTGTCT
CATGAGCGGATACATATTTGAATGTATTTAGAAAAATAAACAAATAGGGGTTCCGCG
CACATTTCCCCGAAAAGTGCCACCTGACGTGTCGAGACGCGTAATACGACTCACTAT
AG

Plasmid encoding p15-T7G-TC83R-merlinCMV-gHsol-sg.gL
(A322)

FIG. 15H

ATAGGCGGCGCATGAGAGAAGCCCAGACCAATTACCTACCCAAAATGGAGAAAGTTC
ACGTTGACATCGAGGAAGACAGCCCATTCCTCAGAGCTTTGCAGCGGAGCTTCCCGC
AGTTTGAGGTAGAAGCCAAGCAGGTCACTGATAATGACCATGCTAATGCCAGAGCGT
TTTCGCATCTGGCTTCAAAACTGATCGAAACGGAGGTGGACCCATCCGACACGATCC
TTGACATTGGAAGTGCGCCCGCCCGCAGAATGTATTCTAAGCACAAGTATCATTGTA
TCTGTCCGATGAGATGTGCGGAAGATCCGGACAGATTGTATAAGTATGCAACTAAGC
TGAAGAAAAACTGTAAGGAAATAACTGATAAGGAATTGGACAAGAAAATGAAGGAGC
TCGCCGCCGTCATGAGCGACCCTGACCTGGAAACTGAGACTATGTGCCTCCACGACG
ACGAGTCGTGTCGCTACGAAGGGCAAGTCGCTGTTTACCAGGATGTATACGCGGTTG
ACGGACCGACAAGTCTCTATCACCAAGCCAATAAGGGAGTTAGAGTCGCCTACTGGA
TAGGCTTTGACACCACCCCTTTTATGTTTAAGAACTTGGCTGGAGCATATCCATCAT
ACTCTACCAACTGGGCCGACGAAACCGTGTTAACGGCTCGTAACATAGGCCTATGCA
GCTCTGACGTTATGGAGCGGTCACGTAGAGGGATGTCCATTCTTAGAAAGAAGTATT
TGAAACCATCCAACAATGTTCTATTCTCTGTTGGCTCGACCATCTACCACGAGAAGA
GGGACTTACTGAGGAGCTGGCACCTGCCGTCTGTATTTCACTTACGTGGCAAGCAAA
ATTACACATGTCGGTGTGAGACTATAGTTAGTTGCGACGGGTACGTCGTTAAAAGAA
TAGCTATCAGTCCAGGCCTGTATGGGAAGCCTTCAGGCTATGCTGCTACGATGCACC
GCGAGGGATTCTTGTGCTGCAAAGTGACAGACACATTGAACGGGGAGAGGGTCTCTT
TTCCCGTGTGCACGTATGTGCCAGCTACATTGTGTGACCAAATGACTGGCATACTGG
CAACAGATGTCAGTGCGGACGACGCGCAAAAACTGCTGGTTGGGCTCAACCAGCGTA
TAGTCGTCAACGGTCGCACCCAGAGAAACACCAATACCATGAAAAATTACCTTTTGC
CCGTAGTGGCCCAGGCATTTGCTAGGTGGGCAAAGGAATATAAGGAAGATCAAGAAG
ATGAAAGGCCACTAGGACTACGAGATAGACAGTTAGTCATGGGGTGTTGTTGGGCTT
TTAGAAGGCACAAGATAACATCTATTTATAAGCGCCCGGATACCCAAACCATCATCA
AAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCAC
CTCTCATTACCGCCGAGGACGTACAAGAAGCTAAGTGCGCAGCCGATGAGGCTAAGG
AGGTGCGTGAAGCCGAGGAGTTGCGCGCAGCTCTACCACCTTTGGCAGCTGATGTTG
AGGAGCCCACTCTGGAAGCCGATGTAGACTTGATGTTACAAGAGGCTGGGGCCGGCT
CAGTGGAGACACCTCGTGGCTTGATAAAGGTTACCAGCTACGATGGCGAGGACAAGA
TCGGCTCTTACGCTGTGCTTTCTCCGCAGG

FIG. 16A

CTGTACTCAAGAGTGAAAAATTATCTTGCATCCACCCTCTCGCTGAACAAGTCATAG
TGATAACACACTCTGGCCGAAAAGGGCGTTATGCCGTGGAACCATACCATGGTAAAG
TAGTGGTGCCAGAGGGACATGCAATACCCGTCCAGGACTTTCAAGCTCTGAGTGAAA
GTGCCACCATTGTGTACAACGAACGTGAGTTCGTAAACAGGTACCTGCACCATATTG
CCACACATGGAGGAGCGCTGAACACTGATGAAGAATATTACAAAACTGTCAAGCCCA
GCGAGCACGACGGCGAATACCTGTACGACATCGACAGGAAACAGTGCGTCAAGAAAG
AACTAGTCACTGGGCTAGGGCTCACAGGCGAGCTGGTGGATCCTCCCTTCCATGAAT
TCGCCTACGAGAGTCTGAGAACACGACCAGCCGCTCCTTACCAAGTACCAACCATAG
GGGTGTATGGCGTGCCAGGATCAGGCAAGTCTGGCATCATTAAAAGCGCAGTCACCA
AAAAAGATCTAGTGGTGAGCGCCAAGAAAGAAAACTGTGCAGAAATTATAAGGGACG
TCAAGAAAATGAAAGGGCTGGACGTCAATGCCAGAACTGTGGACTCAGTGCTCTTGA
ATGGATGCAAACACCCCGTAGAGACCCTGTATATTGACGAAGCTTTTGCTTGTCATG
CAGGTACTCTCAGAGCGCTCATAGCCATTATAAGACCTAAAAAGGCAGTGCTCTGCG
GGGATCCCAAACAGTGCGGTTTTTTAACATGATGTGCCTGAAAGTGCATTTTAACC
ACGAGATTTGCACACAAGTCTTCCACAAAAGCATCTCTCGCCGTTGCACTAAATCTG
TGACTTCGGTCGTCTCAACCTTGTTTTACGACAAAAAAATGAGAACGACGAATCCGA
AAGAGACTAAGATTGTGATTGACACTACCGGCAGTACCAAACCTAAGCAGGACGATC
TCATTCTCACTTGTTTCAGAGGGTGGGTGAAGCAGTTGCAAATAGATTACAAAGGCA
ACGAAATAATGACGGCAGCTGCCTCTCAAGGGCTGACCCGTAAAGGTGTGTATGCCG
TTCGGTACAAGGTGAATGAAAATCCTCTGTACGCACCCACCTCAGAACATGTGAACG
TCCTACTGACCCGCACGGAGGACCGCATCGTGTGGAAAACACTAGCCGGCGACCCAT
GGATAAAAACACTGACTGCCAAGTACCCTGGGAATTTCACTGCCACGATAGAGGAGT
GGCAAGCAGAGCATGATGCCATCATGAGGCACATCTTGGAGAGACCGGACCCTACCG
ACGTCTTCCAGAATAAGGCAAACGTGTGTTGGGCCAAGGCTTTAGTGCCGGTGCTGA
AGACCGCTGGCATAGACATGACCACTGAACAATGGAACACTGTGGATTATTTTGAAA
CGGACAAAGCTCACTCAGCAGAGATAGTATTGAACCAACTATGCGTGAGGTTCTTTG
GACTCGATCTGGACTCCGGTCTATTTTCTGCACCCACTGTTCCGTTATCCATTAGGA
ATAATCACTGGGATAACTCCCCGTCGCCTAACATGTACGGGCTGAATAAAGAAGTGG
TCCGTCAGCTCTCTCGCAGGTACCCACAACTGCCTCGGGCAGTTGCCACTGGAAGAG
TCTATGACATGAACACTGGTACACTGCGCAATTATGATCCGCGCATAAACCTAGTAC
CTGTAAACAGAAGACTGCCTCATGCTTTAGTCCTCCACCATAATGAACACCCACAGA
GTGACTTTTCTTCATTCGTCAGCAAATTGAAGG

FIG. 16B

GCAGAACTGTCCTGGTGGTCGGGGAAAAGTTGTCCGTCCCAGGCAAAATGGTTGACT
GGTTGTCAGACCGGCCTGAGGCTACCTTCAGAGCTCGGCTGGATTTAGGCATCCCAG
GTGATGTGCCCAAATATGACATAATATTTGTTAATGTGAGGACCCCATATAAATACC
ATCACTATCAGCAGTGTGAAGACCATGCCATTAAGCTTAGCATGTTGACCAAGAAAG
CTTGTCTGCATCTGAATCCCGGCGGAACCTGTGTCAGCATAGGTTATGGTTACGCTG
ACAGGGCCAGCGAAAGCATCATTGGTGCTATAGCGCGGCAGTTCAAGTTTTCCCGGG
TATGCAAACCGAAATCCTCACTTGAAGAGACGGAAGTTCTGTTTGTATTCATTGGGT
ACGATCGCAAGGCCCGTACGCACAATCCTTACAAGCTTTCATCAACCTTGACCAACA
TTTATACAGGTTCCAGACTCCACGAAGCCGGATGTGCACCCTCATATCATGTGGTGC
GAGGGGATATTGCCACGGCCACCGAAGGAGTGATTATAAATGCTGCTAACAGCAAAG
GACAACCTGGCGGAGGGGTGTGCGGAGCGCTGTATAAGAAATTCCCGGAAAGCTTCG
ATTTACAGCCGATCGAAGTAGGAAAAGCGCGACTGGTCAAAGGTGCAGCTAAACATA
TCATTCATGCCGTAGGACCAAACTTCAACAAAGTTTCGGAGGTTGAAGGTGACAAAC
AGTTGGCAGAGGCTTATGAGTCCATCGCTAAGATTGTCAACGATAACAATTACAAGT
CAGTAGCGATTCCACTGTTGTCCACCGGCATCTTTTCCGGGAACAAAGATCGACTAA
CCCAATCATTGAACCATTTGCTGACAGCTTTAGACACCACTGATGCAGATGTAGCCA
TATACTGCAGGGACAAGAAATGGGAAATGACTCTCAAGGAAGCAGTGGCTAGGAGAG
AAGCAGTGGAGGAGATATGCATATCCGACGACTCTTCAGTGACAGAACCTGATGCAG
AGCTGGTGAGGGTGCATCCGAAGAGTTCTTTGGCTGGAAGGAAGGGCTACAGCACAA
GCGATGGCAAAACTTTCTCATATTTGGAAGGGACCAAGTTTCACCAGGCGGCCAAGG
ATATAGCAGAAATTAATGCCATGTGGCCCGTTGCAACGGAGGCCAATGAGCAGGTAT
GCATGTATATCCTCGGAGAAAGCATGAGCAGTATTAGGTCGAAATGCCCCGTCGAAG
AGTCGGAAGCCTCCACACCACCTAGCACGCTGCCTTGCTTGTGCATCCATGCCATGA
CTCCAGAAAGAGTACAGCGCCTAAAAGCCTCACGTCCAGAACAAATTACTGTGTGCT
CATCCTTTCCATTGCCGAAGTATAGAATCACTGGTGTGCAGAAGATCCAATGCTCCC
AGCCTATATTGTTCTCACCGAAAGTGCCTGCGTATATTCATCCAAGGAAGTATCTCG
TGGAAACACCACCGGTAGACGAGACTCCGGAGCCATCGGCAGAGAACCAATCCACAG
AGGGGACACCTGAACAACCACCACTTATAACCGAGGATGAGACCAGGACTAGAACGC
CTGAGCCGATCATCATCGAAGAGGAAGAAGAGGATAGCATAAGTTTGCTGTCAGATG
GCCCGACCCACCAGGTGCTGCAAGTCGAGGCAGACATTCACGGGCCGCCCTCTGTAT
CTAGCTCATCCTGGTCCATTCCTCATGCATCCGACTTTGATGTGGACAGTTTATCCA
TACTTGACACCCTGGAGGGAGCTAGCGTGACCA

FIG. 16C

GCGGGGCAACGTCAGCCGAGACTAACTCTTACTTCGCAAAGAGTATGGAGTTTCTGG
CGCGACCGGTGCCTGCGCCTCGAACAGTATTCAGGAACCCTCCACATCCCGCTCCGC
GCACAAGAACACCGTCACTTGCACCCAGCAGGGCCTGCTCGAGAACCAGCCTAGTTT
CCACCCCGCCAGGCGTGAATAGGGTGATCACTAGAGAGGAGCTCGAGGCGCTTACCC
CGTCACGCACTCCTAGCAGGTCGGTCTCGAGAACCAGCCTGGTCTCCAACCCGCCAG
GCGTAAATAGGGTGATTACAAGAGAGGAGTTTGAGGCGTTCGTAGCACAACAACAAT
GACGGTTTGATGCGGGTGCATACATCTTTTCCTCCGACACCGGTCAAGGGCATTTAC
AACAAAAATCAGTAAGGCAAACGGTGCTATCCGAAGTGGTGTTGGAGAGGACCGAAT
TGGAGATTTCGTATGCCCCGCGCCTCGACCAAGAAAAAGAAGAATTACTACGCAAGA
AATTACAGTTAAATCCCACACCTGCTAACAGAAGCAGATACCAGTCCAGGAAGGTGG
AGAACATGAAAGCCATAACAGCTAGACGTATTCTGCAAGGCCTAGGGCATTATTTGA
AGGCAGAAGGAAAAGTGGAGTGCTACCGAACCCTGCATCCTGTTCCTTTGTATTCAT
CTAGTGTGAACCGTGCCTTTTCAAGCCCCAAGGTCGCAGTGGAAGCCTGTAACGCCA
TGTTGAAAGAGAACTTTCCGACTGTGGCTTCTTACTGTATTATTCCAGAGTACGATG
CCTATTTGGACATGGTTGACGGAGCTTCATGCTGCTTAGACACTGCCAGTTTTTGCC
CTGCAAAGCTGCGCAGCTTTCCAAAGAAACACTCCTATTTGGAACCCACAATACGAT
CGGCAGTGCCTTCAGCGATCCAGAACACGCTCCAGAACGTCCTGGCAGCTGCCACAA
AAAGAAATTGCAATGTCACGCAAATGAGAGAATTGCCCGTATTGGATTCGGCGGCCT
TTAATGTGGAATGCTTCAAGAAATATGCGTGTAATAATGAATATTGGGAAACGTTTA
AAGAAAACCCCATCAGGCTTACTGAAGAAAACGTGGTAAATTACATTACCAAATTAA
AAGGACCAAAAGCTGCTGCTCTTTTTGCGAAGACACATAATTTGAATATGTTGCAGG
ACATACCAATGGACAGGTTTGTAATGGACTTAAAGAGAGACGTGAAAGTGACTCCAG
GAACAAAACATACTGAAGAACGGCCCAAGGTACAGGTGATCCAGGCTGCCGATCCGC
TAGCAACAGCGTATCTGTGCGGAATCCACCGAGAGCTGGTTAGGAGATTAAATGCGG
TCCTGCTTCCGAACATTCATACACTGTTTGATATGTCGGCTGAAGACTTTGACGCTA
TTATAGCCGAGCACTTCCAGCCTGGGGATTGTGTTCTGGAAACTGACATCGCGTCGT
TTGATAAAAGTGAGGACGACGCCATGGCTCTGACCGCGTTAATGATTCTGGAAGACT
TAGGTGTGGACGCAGAGCTGTTGACGCTGATTGAGGCGGCTTTCGGCGAAATTTCAT
CAATACATTTGCCCACTAAAACTAAATTTAAATTCGGAGCCATGATGAAATCTGGAA
TGTTCCTCACACTGTTTGTGAACACAGTCATTAACATTGTAATCGCAAGCAGAGTGT
TGAGAGAACGGCTAACCGGATCACCATGTGCAGCATTCATTGGAGATGACAATATCG
TGAAAGGAGTCAAATCGGACAAATTAATGGCAG

FIG. 16D

ACAGGTGCGCCACCTGGTTGAATATGGAAGTCAAGATTATAGATGCTGTGGTGGGCG
AGAAAGCGCCTTATTTCTGTGGAGGGTTTATTTTGTGTGACTCCGTGACCGGCACAG
CGTGCCGTGTGGCAGACCCCCTAAAAAGGCTGTTTAAGCTTGGCAAACCTCTGGCAG
CAGACGATGAACATGATGATGACAGGAGAAGGGCATTGCATGAAGAGTCAACACGCT
GGAACCGAGTGGGTATTCTTTCAGAGCTGTGCAAGGCAGTAGAATCAAGGTATGAAA
CCGTAGGAACTTCCATCATAGTTATGGCCATGACTACTCTAGCTAGCAGTGTTAAAT
CATTCAGCTACCTGAGAGGGGCCCCTATAACTCTCTACGGCTAACCTGAATGGACTA
CGACATAGTCTAGTCGACGCCACCATGGAAAGCCGGATCTGGTGCCTGGTCGTGTGC
GTGAACCTGTGCATCGTGTGCCTGGGAGCCGCCGTGAGCAGCAGCAGCACCAGAGGC
ACCAGCGCCACACACAGCCACCACAGCAGCCACACCACCTCTGCCGCCCACAGCAGA
TCCGGCAGCGTGTCCCAGAGAGTGACCAGCAGCCAGACCGTGTCCCACGGCGTGAAC
GAGACAATCTACAACACCACCCTGAAGTACGGCGACGTCGTGGGCGTGAATACCACC
AAGTACCCCTACAGAGTGTGCAGCATGGCCCAGGGCACCGACCTGATCAGATTCGAG
CGGAACATCGTGTGCACCAGCATGAAGCCCATCAACGAGGACCTGGACGAGGGCATC
ATGGTGGTGTACAAGAGAAACATCGTGGCCCACACCTTCAAAGTGCGGGTGTACCAG
AAGGTGCTGACCTTCCGGCGGAGCTACGCCTACATCCACACCACATACCTGCTGGGC
AGCAACACCGAGTACGTGGCCCCTCCCATGTGGGAGATCCACCACATCAACAGCCAC
AGCCAGTGCTACAGCAGCTACAGCCGCGTGATCGCCGGCACAGTGTTCGTGGCCTAC
CACCGGGACAGCTACGAGAACAAGACCATGCAGCTGATGCCCGACGACTACAGCAAC
ACCCACAGCACCAGATACGTGACCGTGAAGGACCAGTGGCACAGCAGAGGCAGCACC
TGGCTGTACCGGGAGACATGCAACCTGAACTGCATGGTCACCATCACCACCGCCAGA
AGCAAGTACCCTTACCACTTCTTCGCCACCTCCACCGGCGACGTGGTGGACATCAGC
CCCTTCTACAACGGCACCAACCGGAACGCCAGCTACTTCGGCGAGAACGCCGACAAG
TTCTTCATCTTCCCCAACTACACCATCGTGTCCGACTTCGGCAGACCCAACAGCGCT
CTGGAAACCCACAGACTGGTGGCCTTTCTGGAACGGGCCGACAGCGTGATCAGCTGG
GACATCCAGGACGAGAAGAACGTGACCTGCCAGCTGACCTTCTGGGAGGCCTCTGAG
AGAACCATCAGAAGCGAGGCCGAGGACAGCTACCACTTCAGCAGCGCCAAGATGACC
GCCACCTTCCTGAGCAAGAAACAGGAAGTGAACATGAGCGACTCCGCCCTGGACTGC
GTGAGGGACGAGGCCATCAACAAGCTGCAGCAGATCTTCAACACCAGCTACAACCAG
ACCTACGAGAAGTATGGCAATGTGTCCGTGTTCGAGACAACAGGCGGCCTGGTGGTG
TTCTGGCAGGGCATCAAGCAGAAAAGCCTGGTGGAGCTGGAACGGCTCGCCAACCGG
TCCAGCCTGAACCTGACCCACAACCGGACCAAG

FIG. 16E

CGGAGCACCGACGGCAACAACGCAACCCACCTGTCCAACATGGAAAGCGTGCACAAC
CTGGTGTACGCACAGCTGCAGTTCACCTACGACACCCTGCGGGGCTACATCAACAGA
GCCCTGGCCCAGATCGCCGAGGCTTGGTGCGTGGACCAGCGGCGGACCCTGGAAGTG
TTCAAAGAGCTGTCCAAGATCAACCCCAGCGCCATCCTGAGCGCCATCTACAACAAG
CCTATCGCCGCCAGATTCATGGGCGACGTGCTGGGCCTGGCCAGCTGCGTGACCATC
AACCAGACCAGCGTGAAGGTGCTGCGGGACATGAACGTGAAAGAGAGCCCAGGCCGC
TGCTACTCCAGACCCGTGGTCATCTTCAACTTCGCCAACAGCTCCTACGTGCAGTAC
GGCCAGCTGGGCGAGGACAACGAGATCCTGCTGGGGAACCACCGGACCGAGGAATGC
CAGCTGCCCAGCCTGAAGATCTTTATCGCCGGCAACAGCGCCTACGAGTATGTGGAC
TACCTGTTCAAGCGGATGATCGACCTGAGCAGCATCTCCACCGTGGACAGCATGATC
GCCCTGGACATCGACCCCCTGGAAAACACCGACTTCCGGGTGCTGGAACTGTACAGC
CAGAAAGAGCTGCGGAGCAGCAACGTGTTCGACCTGGAAGAGATCATGCGGGAGTTC
AACAGCTACAAGCAGCGCGTGAAATACGTGGAGGACAAGGTGGTGGACCCCCTGCCT
CCTTACCTGAAGGGCCTGGACGACCTGATGAGCGGACTGGGCGCTGCCGGAAAAGCC
GTGGGAGTGGCCATTGGAGCTGTGGGCGGAGCTGTGGCCTCTGTCGTGGAAGGCGTC
GCCACCTTTCTGAAGAACCCCTTCGGCGCCTTCACCATCATCCTGGTGGCCATTGCC
GTCGTGATCATCACCTACCTGATCTACACCCGGCAGCGGAGACTGTGTACCCAGCCC
CTGCAGAACCTGTTCCCCTACCTGGTGTCCGCCGATGGCACCACAGTGACCAGCGGC
TCCACCAAGGATACCAGCCTGCAGGCCCCACCCAGCTACGAAGAGAGCGTGTACAAC
AGCGGCAGAAAGGGCCCTGGCCCTCCCAGCTCTGATGCCAGCACAGCCGCCCCTCCC
TACACCAACGAGCAGGCCTACCAGATGCTGCTGGCCCTGGCTAGACTGGATGCCGAG
CAGAGGGCCCAGCAGAACGGCACCGACAGCCTGGATGGCAGAACCGGCACCCAGGAC
AAGGGCCAGAAGCCCAACCTGCTGGACCGGCTGCGGCACCGGAAGAACGGCTACCGG
CACCTGAAGGACAGCGACGAGGAAGAGAACGTCTGATAATCTAGACGGCGCGCCCAC
CCAGCGGCCGCATACAGCAGCAATTGGCAAGCTGCTTACATAGAACTCGCGGCGATT
GGCATGCCGCCTTAAAATTTTTATTTTATTTTTCTTTTCTTTTCCGAATCGGATTTT
GTTTTTAATATTTCAAAAAAAAAAAAAAAAAAAAAAAAAAAAAAAAAAAGGGTCGGC
ATGGCATCTCCACCTCCTCGCGGTCCGACCTGGGCATCCGAAGGAGGACGCACGTCC
ACTCGGATGGCTAAGGGAGAGCCACGTTTAAACCAGCTCCAATTCGCCCTATAGTGA
GTCGTATTACGCGCGCTCACTGGCCGTCGTTTTACAACGTCGTGACTGGGAAAACCC
TGGCGTTACCCAACTTAATCGCCTTGCAGCACATCCCCCTTTCGCCAGCTGGCGTAA
TAGCGAAGAGGCCCGCACCGATCGCCCTTCCCA

FIG. 16F

ACAGTTGCGCAGCCTGAATGGCGAATGGGACGCGCCCTGTAGCGGCGCATTAAGCGC
GGCGGGTGTGGTGGTTACGCGCAGCGTGACCGCTACACTTGCCAGCGCCCTAGCGCC
CGCTCCTTTCGCTTTCTTCCCTTCCTTTCTCGCCACGTTCGCCGGCTTTCCCCGTCA
AGCTCTAAATCGGGGGCTCCCTTTAGGGTTCCGATTTAGTGCTTTACGGCACCTCGA
CCCCAAAAAACTTGATTAGGGTGATGGTTCACGTAGTGGGCCATCGCCCTGATAGAC
GGTTTTTCGCCCTTTGACGTTGGAGTCCACGTTCTTTAATAGTGGACTCTTGTTCCA
AACTGGAACAACACTCAACCCTATCTCGGTCTATTCTTTTGATTTATAAGGGATTTT
GCCGATTTCGGCCTATTGGTTAAAAAATGAGCTGATTTAACAAAAATTTAACGCGAA
TTTTAACAAAATATTAACGCTTACAATTTAGGTGGCACTTTTCGGGGAAATGTGCGC
GGAACCCCTATTTGTTTATTTTTCTAAATACATTCAAATATGTATCCGCTCATGAGA
CAATAACCCTGATAAATGCTTCAATAATATTGAAAAAGGAAGAGTATGAGTATTCAA
CATTTCCGTGTCGCCCTTATTCCCTTTTTTGCGGCATTTTGCCTTCCTGTTTTTGCT
CACCCAGAAACGCTGGTGAAAGTAAAAGATGCTGAAGATCAGTTGGGTGCACGAGTG
GGTTACATCGAACTGGATCTCAACAGCGGTAAGATCCTTGAGAGTTTTCGCCCCGAA
GAACGTTTTCCAATGATGAGCACTTTTAAAGTTCTGCTATGTGGCGCGGTATTATCC
CGTATTGACGCCGGGCAAGAGCAACTCGGTCGCCGCATACACTATTCTCAGAATGAC
TTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTG
ACAACGATCGGAGGACCGAAGGAGCTAACCGCTTTTTTGCACAACATGGGGGATCAT
GTAACTCGCCTTGATCGTTGGGAACCGGAGCTGAATGAAGCCATACCAAACGACGAG
CGTGACACCACGATGCCTGTAGCAATGGCAACAACGTTGCGCAAACTATTAACTGGC
GAACTACTTACTCTAGCTTCCCGGCAACAATTAATAGACTGGATGGAGGCGGATAAA
GTTGCAGGACCACTTCTGCGCTCGGCCCTTCCGGCTGGCTGGTTTATTGCTGATAAA
TCTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGAA
CGAAATAGACAGATCGCTGAGATAGGTGCCTCACTGATTAAGCATTGGTAACTGTCA
GACCAAGTTTACTCATATATACTTTAGATTGATTTAAAACTTCATTTTTAATTTAAA
AGGATCTAGGTGAAGATCCTTTTTGATAATCTCATGACCAAAATCCCTTAACGTGAG
TTTTCGTTCCACTGAGCGTCAGACCCCGTAGAAAAGATCAAAGGATCTTCTTGAGAT
CCTTTTTTTCTGCGCGTAATCTGCTGCTTGCAAACAAAAAAACCACCGCTACCAGCG
GTGGTTTGTTTGCCGGATCAAGAGCTACCAACTCTTTTTCCGAAGGTAACTGGCTTC
AGCAGAGCGCAGATACCAAATACTGTTCTTCTA

FIG. 16G

GTGTAGCCGTAGTTAGGCCACCACTTCAAGAACTCTGTAGCACCGCCTACATACCTC
GCTCTGCTAATCCTGTTACCAGTGGCTGCTGCCAGTGGCGATAAGTCGTGTCTTACC
GGGTTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATACCTA
CAGCGTGAGCTATGAGAAAGCGCCACGCTTCCCGAAGGGAGAAAGGCGGACAGGTAT
CCGGTAAGCGGCAGGGTCGGAACAGGAGAGCGCACGAGGGAGCTTCCAGGGGGAAAC
GCCTGGTATCTTTATAGTCCTGTCGGGTTTCGCCACCTCTGACTTGAGCGTCGATTT
TTGTGATGCTCGTCAGGGGGGCGGAGCCTATGGAAAAACGCCAGCAACGCGGCCTTT
TTACGGTTCCTGGCCTTTTGCTGGCCTTTTGCTCACATGTTCTTTCCTGCGTTATCC
CCTGATTCTGTGGATAACCGTATTACCGCCTTTGAGTGAGCTGATACCGCTCGCCGC
AGCCGAACGACCGAGCGCAGCGAGTCAGTGAGCGAGGAAGCGGAAGAGCGCCCAATA
CGCAAACCGCCTCTCCCCGCGCGTTGGCCGATTCATTAATGCAGCTGGCACGACAGG
TTTCCCGACTGGAAAGCGGGCAGTGAGCGCAACGCAATTAATGTGAGTTAGCTCACT
CATTAGGCACCCCAGGCTTTACACTTTATGCTCCCGGCTCGTATGTTGTGTGGAATT
GTGAGCGGATAACAATTTCACACAGGAAACAGCTATGACCATGATTACGCCAAGCGC
GCAATTAACCCTCACTAAAGGGAACAAAAGCTGGGTACCGGGCCCACGCGTAATACG
ACTCACTATAG

Plasmid encoding T7G-TC83R-merlinCMV.gB (A323)

FIG. 16H

VZV1 RNA 7 μg 3w post 3°

VZV2 RNA 1 µg 3w post 3°

ANTIGEN DELIVERY PLATFORMS

CROSS-REFERENCE TO RELATED APPLICATIONS

This is a Continuation of U.S. patent application Ser. No. 16/114,621, filed Aug. 28, 2018, which is a Continuation of U.S. patent application Ser. No. 13/878,835, filed Oct. 10, 2013 (now abandoned), which is the U.S. National Stage application submitted under 35 U.S.C. § 371 for International Application No. PCT/US2011/55834, filed Oct. 11, 2011, which claims priority to U.S. Provisional Application No. 61/391,960, filed Oct. 11, 2010, all of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: VN54076D1_US_Seq_Listing.txt; created Jun. 28, 2021, size: 614,614 bytes).

BACKGROUND

Herpes viruses are widespread and cause a wide range of diseases in humans that in the worst cases can lead to substantial morbidity and mortality, primarily in immunocompromised individuals (e.g., transplant recipients and HIV-infected individuals). Humans are susceptible to infection by at least eight herpes viruses. Herpes simplex virus-1 (HSV-1, HHV-1), Herpes simplex virus-2 (HSV-2, HHV-2) and Varicella zoster virus (VZV, HHV-3) are alpha-subfamily viruses, cytomegalovirus (CMV, HHV-5) and Roseoloviruses (HHV-6 and HHV-7) are beta-subfamily viruses, Epstein-Barr virus (EBV, HHV-4) and Kaposi's sarcoma-associated herpesvirus (KSHV, HHV-8) are gamma-subfamily viruses that infect humans.

CMV infection leads to substantial morbidity and mortality in immunocompromised individuals (e.g., transplant recipients and HIV-infected individuals) and congenital infection can result in devastating defects in neurological development in neonates. CMV envelope glycoproteins gB, gH, gL, gM and gN represent attractive vaccine candidates as they are expressed on the viral surface and can elicit protective virus-neutralizing humoral immune responses. Some CMV vaccine strategies have targeted the major surface glycoprotein B (gB), which can induce a dominant antibody response. (Go and Pollard, JID 197:1631-1633 (2008)). CMV glycoprotein gB can induce a neutralizing antibody response, and a large fraction of the antibodies that neutralize infection of fibroblasts in sera from CMV-positive patients is directed against gB (Britt 1990). Similarly, it has been reported that gH and gM/gN are targets of the immune response to natural infection (Urban et al (1996) J. Gen. Virol. 77(Pt. 7):1537-47; Mach et al (2000) J. Virol. 74(24): 11881-92).

Complexes of CMV proteins are also attractive vaccine candidates because they appear to be involved in important processes in the viral life cycle. For example, the gH/gL/gO complex seems to have important roles in both fibroblast and epithelial/endothelial cell entry. The prevailing model suggests that the gH/gL/gO complex mediates infection of fibroblasts. hCMV gO-null mutants produce small plaques on fibroblasts and very low titer virus indicating a role in entry (Dunn (2003), Proc. Natl. Acad. Sci. USA 100:14223-28; Hobom (2000) J. Virol. 74:7720-29). Recent studies suggest that gO is not incorporated into virions with gH/gL, but may act as a molecular chaperone, increasing gH/gL export from the ER to the Golgi apparatus and incorporation into virions (Ryckman (2009) J. Virol 82:60-70). Through pulse-chase experiments, it was shown that small amounts of gO remain bound to gH/gL for long periods of time but most gO dissociates and or is degraded from the gH/gL/gO complex, as it is not found in extracellular virions or secreted from cells. When gO was deleted from a clinical strain of CMV (TR) those viral particles had significantly reduced amounts of gH/gL incorporated into the virion. Additionally, gO deleted from TR virus also inhibited entry into epithelial and endothelial cells, suggesting that gH/gL is also required for epithelial/endothelial cell entry (Wille (2010) J. Virol. 84(5):2585-96).

CMV gH/gL can also associate with UL128, UL130, and UL131A (referred to here as UL131) and form a pentameric complex that is required for entry into several cell types, including epithelial cells, endothelial cells, and dendritic cells (Hahn et al (2004) J. Virol. 78(18):10023-33; Wang and Shenk (2005) Proc. Natl. Acad. Sci USA 102(50):18153-8; Gerna et al (2005). J. Gen. Virol. 84(Pt 6):1431-6; Ryckman et al (2008) J. Virol. 82:60-70). In contrast, this complex is not required for infection of fibroblasts. Laboratory hCMV isolates carry mutations in the UL128-UL131 locus, and mutations arise in clinical isolates after only a few passages in cultured fibroblasts (Akter et al (2003) J. Gen. Virol. 84(Pt 5):1117-22). During natural infection, the pentameric complex elicits antibodies that neutralize infection of epithelial cells, endothelial cells (and likely any other cell type where the pentameric complex mediates viral entry) with very high potency (Macagno et al (2010) J. Virol. 84(2):1005-13). It also appears that antibodies to this complex contribute significantly to the ability of human sera to neutralize infection of epithelial cells (Genini et al (2011) J. Clin. Virol. 52(2):113-8).

U.S. Pat. No. 5,767,250 discloses methods for making certain CMV protein complexes that contain gH and gL. The complexes are produced by introducing a DNA construct that encodes gH and a DNA construct that encodes gL into a cell so that the gH and gL are co-expressed.

WO 2004/076645 describes recombinant DNA molecules that encode CMV proteins. According to this document, combinations of distinct DNA molecules that encode different CMV proteins, can be introduced into cells to cause co-expression of the encoded CMV proteins. When gM and gN were co-expressed in this way, they formed a disulfide-linked complex. Rabbits immunized with DNA constructs that produced the gM/gN complex or with a DNA construct encoding gB produced equivalent neutralizing antibody responses.

A need exists for nucleic acids that encode two or more herpes virus proteins, for methods of expressing two or more herpes virus proteins in the same cell, and for immunization methods that produce better immune responses.

SUMMARY OF THE INVENTION

The invention relates to platforms for co-delivery of two or more herpesvirus proteins, such as cytomegalovirus (CMV) proteins, to cells, particularly proteins that form complexes in vivo. In one aspect, the invention is a recombinant polycistronic nucleic acid molecules that contain a first sequence encoding a first herpesvirus (e.g., CMV)

protein or fragment thereof, and a second sequence encoding a second herpesvirus (e.g., CMV) protein or fragment thereof.

For example, the invention provides a self-replicating RNA molecule comprising a polynucleotide which comprises a) a first nucleotide sequence encoding a first protein or fragment thereof from a herpes virus; and b) a second nucleotide sequence encoding a second protein or fragment thereof from the herpes virus. The first nucleotide sequence and second nucleotide sequence are operably linked to one or more control elements so that when the self-replicating RNA molecule is introduced into a suitable cell, the first and second herpes virus proteins or fragments thereof are produced in an amount sufficient for the formation of a complex in the cell that contains the first and second proteins or fragments. Preferably, the first protein and the second protein are not the same protein or fragments of the same protein, the first protein is not a fragment of the second protein, and the second protein is not a fragment of the first protein. The first nucleotide sequence can be operably linked to a first control element and the second nucleotide sequence can be operably linked to a second control element.

The self-replicating RNA molecule can further comprise a third nucleotide sequence encoding a third protein or fragment thereof from said herpes virus, optionally a fourth nucleotide sequence encoding a fourth protein or fragment thereof from said herpes virus; and optionally a fifth nucleotide sequence encoding a fifth protein or fragment thereof from said herpes virus. When sequences encoding additional proteins or fragments from a herpes virus are present (i.e., the third, fourth and fifth nucleotide sequences) they are operably linked to one or more control elements. In one example of a pentacistronic construct, the first nucleotide sequence is operably linked to a first control element, the second nucleotide sequence is operably linked to a second control element, the third nucleotide sequence is operably linked to a third control element, the fourth nucleotide sequence is operably linked to a fourth control element, and the fifth nucleotide sequence is operably linked to a fifth control element. The control elements present in the construct (e.g., first, second, third, fourth and fifth control elements) can be independently selected from the group consisting of a subgenomic promoter, an IRES, and a viral (e.g., FMDV) 2A site.

The herpes virus can be HSV-1, 1, HSV-2, VZV, EBV type 1, EBV type 2, CMV, HHV-6 type A, HHV-6 type B, HHV-7 and HHV-8. In some embodiments, the recombinant polycistronic nucleic acid molecule (e.g., self replicating RNA) encodes gH or a fragment thereof and gL or a fragment thereof of any one of these herpes viruses. In more particular embodiments, the herpes virus is CMV or VZV.

When the recombinant polycistronic nucleic acid molecule (e.g., self replicating RNA) encodes two or more VZV proteins, the proteins can be selected from the group consisting of gB, gE, gH, gI, gL and a fragment (e.g., of at least 10 amino acids) thereof. In some embodiments, the recombinant polycistronic nucleic acid molecule (e.g., self replicating RNA) encodes VZV gH or a fragment thereof and VZV gL or a fragment thereof.

In a particular example, the invention provides a self-replicating RNA molecule comprising a polynucleotide which comprises a) a first sequence encoding a first cytomegalovirus (CMV) protein or fragment thereof; and b) a second sequence encoding a second CMV protein or fragment thereof. The first sequence and second sequence are operably linked to one or more control elements so that when the self-replicating RNA molecule is introduced into a suitable cell, the first and second CMV proteins are produced in an amount sufficient for the formation of a complex in the cell that contains the first and second CMV proteins or fragments.

The first CMV protein and the second CMV protein are independently selected from the group consisting of gB, gH, gL; gO; gM, gN; UL128, UL130, UL131, and a fragment of any one of the foregoing. Preferably, the first CMV protein and the second CMV protein are not the same protein or fragments of the same protein, the first CMV protein is not a fragment of the second CMV protein, and the second CMV protein is not a fragment of the first CMV protein. If desired, the self-replicating RNA molecule can further comprise a third sequence encoding a third CMV protein, wherein the third sequences is operably linked to a control element. Similarly, additional sequences encoding additional CMV proteins (e.g., a fourth sequence encoding a fourth CMV protein, a fifth sequence encoding a fifth CMV protein) can be included. The control elements can be independently selected from the group consisting of a subgenomic promoter, and IRES, and a viral 2A site.

In some embodiments, the self replicating nucleic acid molecule encodes the CMV proteins gH and gL. In other embodiments, the self-replicating RNA molecule encodes the CMV proteins gH, gL, and gO. In other embodiments, the self-replicating RNA molecule encodes the CMV proteins gH, gL, UL128, UL130 and UL131.

The self replicating RNA molecules can be an alphavirus replicon. In such instances, the alphavirus replicon can be delivered in the form of an alphavirus replicon particle (VRP). The self replicating RNA molecule can also be in the form of a "naked" RNA molecule.

The invention also relates to a recombinant DNA molecule that encodes a self replicating RNA molecule as described herein. In some embodiments, the recombinant DNA molecule is a plasmid. In some embodiments, the recombinant DNA molecule includes a mammalian promoter that drive transcription of the encoded self replicating RNA molecule.

The invention also relates to compositions that comprise a self-replicating RNA molecule as described herein and a pharmaceutically acceptable vehicle. The self-replicating RNA molecule can be "naked." In some embodiments, the composition comprises a self-replicating RNA molecule that encodes the CMV proteins gH and gL. In other embodiments, the composition further comprises a self-replicating RNA molecule that encodes the CMV protein gB. The composition can also contain an RNA delivery system such as a liposome, a polymeric nanoparticle, an oil-in-water cationic nanoemulsion or combinations thereof. For example, the self-replicating RNA molecule can be encapsulated in a liposome.

In certain embodiments, the composition comprises a VRP that contains a alphavirus replicon that encodes two or more CMV proteins. In some embodiments, the VRP comprises a replicon that encodes CMV gH and gL. If desired, the composition can further comprising a second VRP containing a replicon that encodes CMV gB. The composition can also comprise an adjuvant.

The invention also relates to methods of forming a CMV protein complex. In some embodiments a self-replicating RNA encoding two or more CMV proteins is delivered to a cell, the cell is maintained under conditions suitable for expression of the CMV proteins, wherein a CMV protein complex is formed. In other embodiments, a VRP that contains a self-replicating RNA encoding two or more CMV proteins is delivered to a cell, the cell is maintained under conditions suitable for expression of the CMV proteins, wherein a CMV protein complex is formed. The method can be used to form a CMV protein complex in a cell in vivo.

The invention also relates to a method for inducing an immune response in an individual. In some embodiments, a self-replicating RNA encoding two or more CMV proteins is administered to the individual. The self-replicating RNA molecule can be administered as a composition that contains an RNA delivery system, such as a liposome. In other embodiments, a VRP that contains a self-replicating RNA encoding two or more CMV proteins is administered to the individual. In preferred embodiments, the self-replicating RNA molecule encodes CMV proteins gH and gL. Preferably, the induced immune response comprises the production of neutralizing anti-CMV antibodies. More preferably, the neutralizing antibodies are complement-independent.

The invention also relates to a method of inhibiting CMV entry into a cell comprising contacting the cell with a self-replicating RNA molecule that encodes two or more CMV proteins, such as gH and gL. The cell can be selected from the group consisting of an epithelial cell, an endothelial cell, a fibroblast and combinations thereof. In some embodiments, the cell is contacted with a VRP that contains a self-replicating RNA encoding two or more CMV proteins.

The invention also relates to the use of a self-replicating RNA molecule that encodes two or more CMV proteins (e.g., a VRP, a composition comprising the self-replicating RNA molecule and a liposome) form a CMV protein complex in a cell, to induce an immune response or to inhibit CMV entry into a cell.

BRIEF DESCRIPTION OF THE DRAWINGS

FIG. 2A, Schematic of the gB constructs ("gB FL", full-length gB; soluble gBs "gB sol 750" and "gB sol 692") described in Example 1. Two different soluble versions of gB were constructed; gB sol 750 lacks the transmembrane spanning domain and cytoplasmic domain, gB sol 692 also lacks a hydrophobic region and is similar to the gB sol described in Reap et al. (2007) Clin. Vacc. Immunol. 14:748-55. FIG. 2B, Schematic of the gB replicon vectors used to produce viral replication particles (VRPs). FIG. 2C, Schematic of the gH constructs ("gH FL", full-length gH; soluble gH "gH sol") described in Example 1. A single soluble version of gH was constructed which lacked the transmembrane spanning domain. FIG. 2D, Schematic of the gH replicon vectors used to produce VRPs. FIG. 2E, Schematic of gL construct described in Example 1. FIG. 2F, Schematic of the gL replicon vector used to produce VRPs. In FIGS. 2B, 2D and 2F, "NSP1," "NSP2," "NSP3," and "NSP4," are alphavirus nonstructural proteins 1-4, respectively, required for replication of the virus.

FIG. 3A, Serum dilution curves for all sera analyzed in ARPE-19 cells in the presence of complement. FIG. 3B, 50% neutralization titers for the sera samples. Virus incubated with pre-immune sera yielded low neutralization at low dilutions (1:40-1:80). gB (FL, sol 750, sol 692) sera had very strong neutralizing activity with 50% neutralization titers between 1:1800-1:2100. All gB immunized mice yielded a similar neutralization profile. gH (FL, sol) sera had neutralizing activity with 50% neutralization titers around 1:160. See Example 1.

Lanes 10 and 11 are from lysates infected with tricistronic gH/gL/gO-VRP. Lane 11 shows that gL was immunoprecipitated using the gH antibody. (See asterisk). Molecular Weight markers are also shown (MW). See Example 3.

Figure 6A:
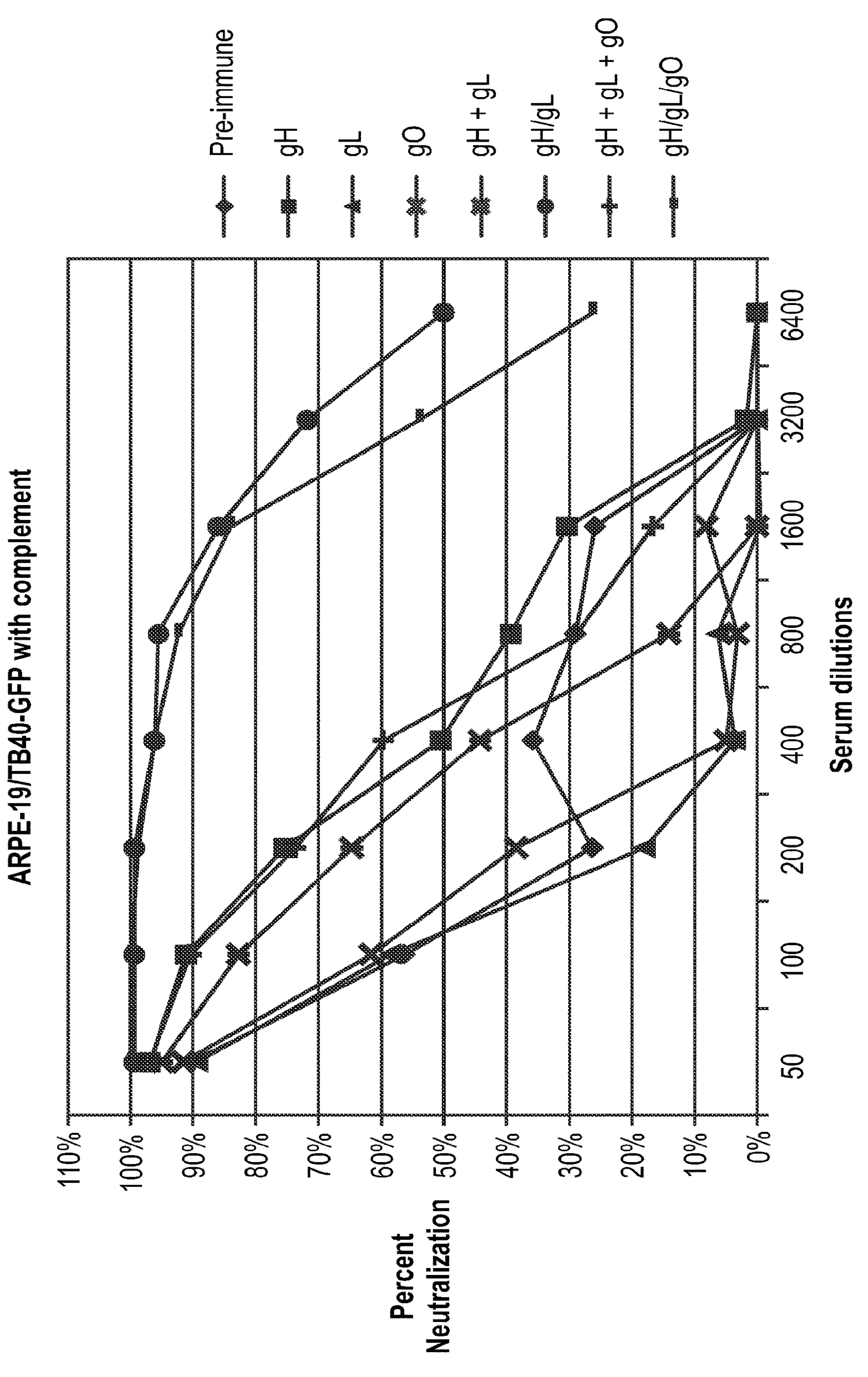
Figure 6B:
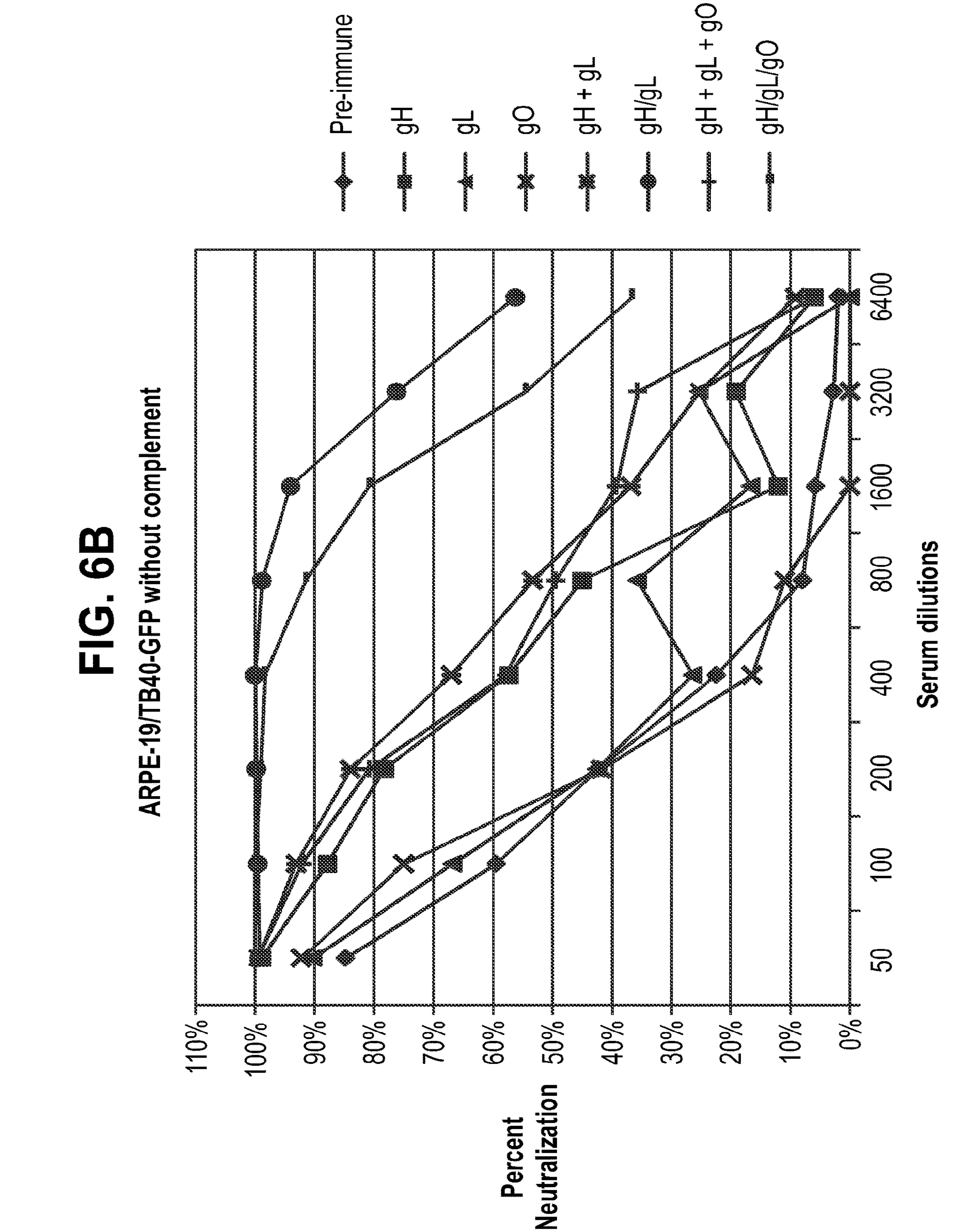
Figure 6C:
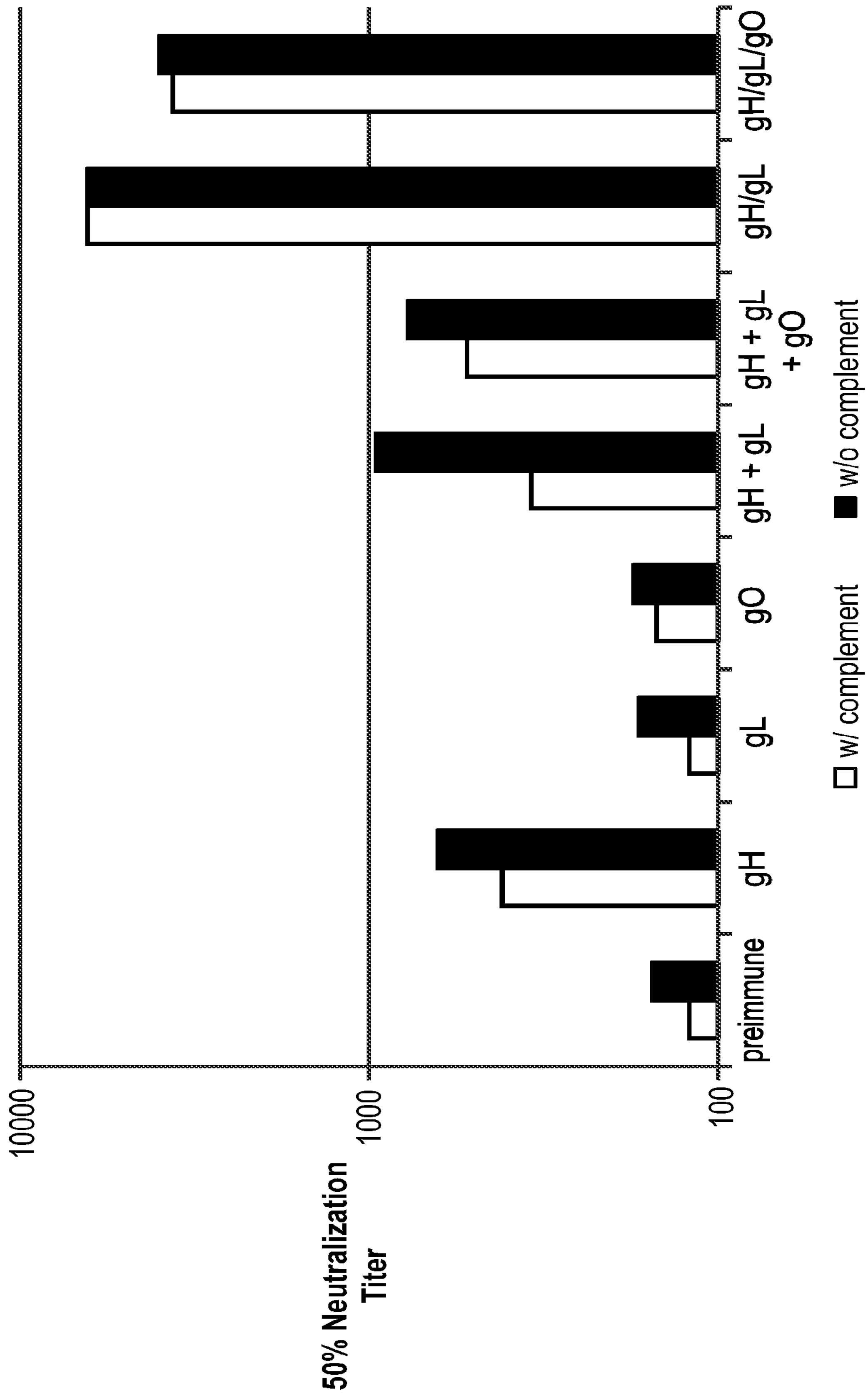

FIGS. 6A-6C shows that VRPs that affect gH/gL complex formation in vitro induce potent immune response to CMV which is qualitatively and quantitatively superior to the response to gB VRPs. FIG. 6A and FIG. 6B show serum dilution curves for gH, gL, gO, gH+gL, gH+gL+gO, gH/gL and gH/gL/gO VRP-immunized mice in neutralization of TB40-UL32-EGFP infection of ARPE-19 cells in the presence (FIG. 6A) or absence (FIG. 6B) of complement. Various dilutions of sera were pre-incubated with TB40UL32E-GFP in the presence or absence of guinea pig complement and then added to ARPE-19 epithelial cells. After 5 day infection with the virus, GFP-positive cells were counted. FIG. 6C is a graph showing 50% neutralization titers obtained in the presence and absence of complement. "3wp3," three weeks post-third immunization. VRPs expressing single CMV proteins (gH, gL, gO VRPs or co-administered gH, gL and gO VRPs) did not enhance neutralizing activity beyond that of gH alone. In contrast, sera from mice immunized with bicistronic gH/gL or tricistronic gH/gL/gO VRPs demonstrated potent neutralizing responses. Moreover, the potent neutralizing responses were similar in the presence and absence of guinea pig complement, showing that polycistronic VRPs successfully induced a complement-independent immune response. See Example 4.

Figure 7A:
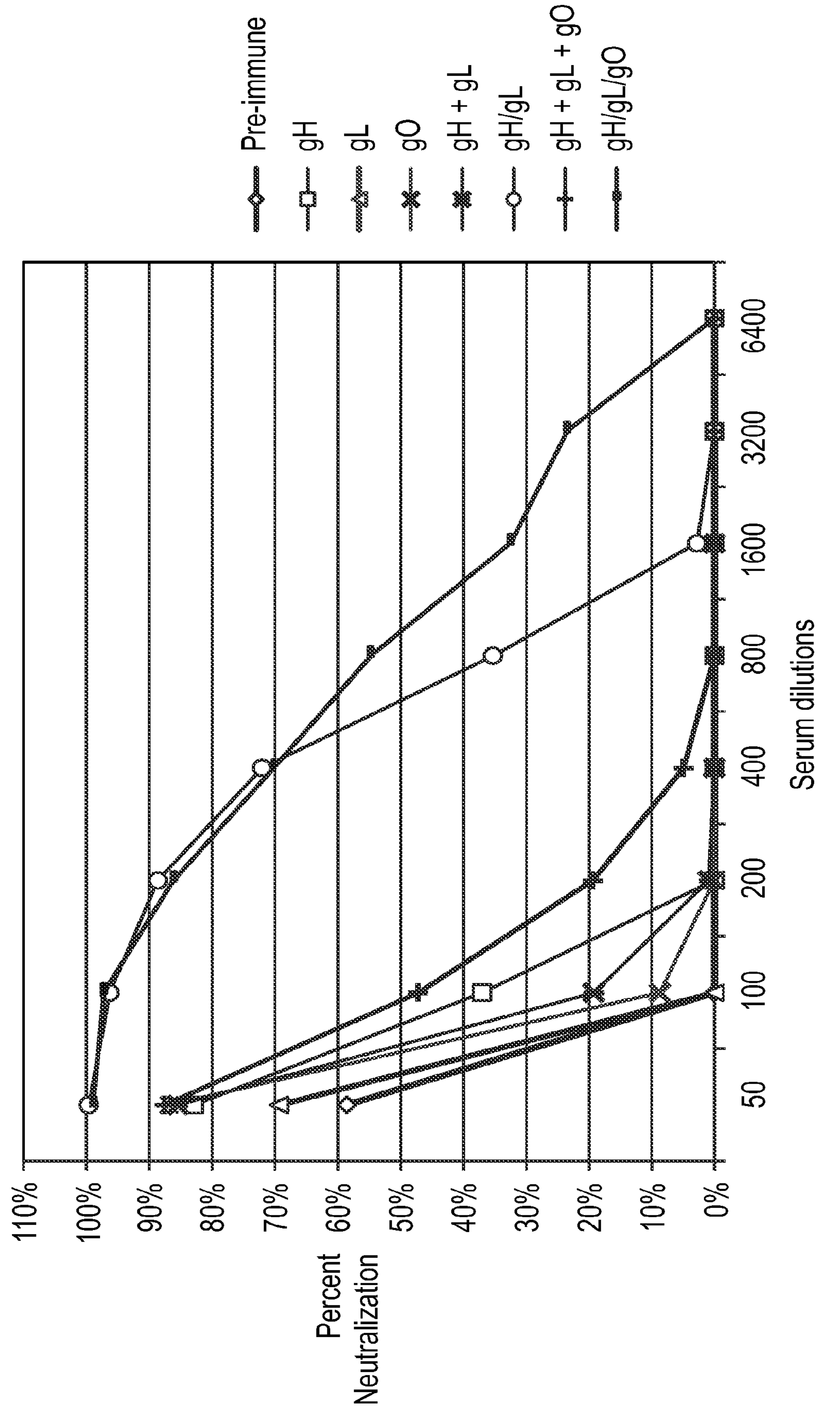
Figure 7B:
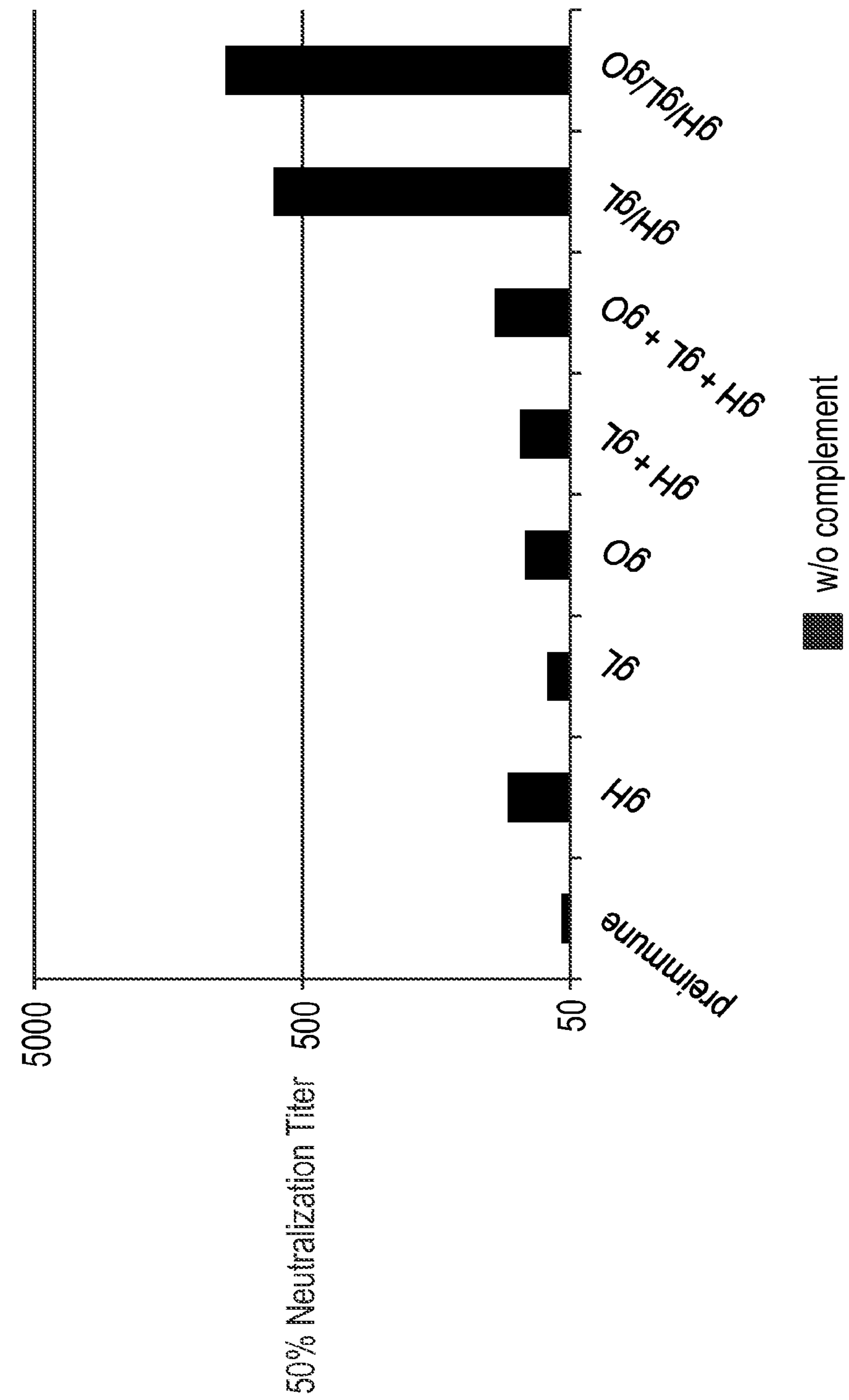

FIGS. 7A and 7B shows that VRPs that affect gH/gL complex formation in vitro induced antibodies that potently neutralized infection of MRC-5 fibroblast cells. FIG. 7A shows serum dilution curves for gH, gL, gO, gH+gL, gH+gL+gO, gH/gL and gH/gL/gO VRP-immunized mice in MRC-5 cells in the absence of complement. Various dilutions of sera were pre-incubated with TB40GFP in the presence or absence of guinea pig complement and then added to MRC-5 fibroblast cells. After 5 day infection with the virus, GFP-positive cells were counted. FIG. 7B is a graph showing 50% neutralization titers obtained in a MRC-5 fibroblast cell model in the absence of complement. "3wp3," three weeks post-third immunization. VRPs expressing single CMV proteins (gH, gL, gO VRPs or co-administered gH, gL and gO VRPs) did not enhance neutralizing activity beyond that of gH alone. In contrast, sera from mice immunized with bicistronic gH/gL or tricistronic gH/gL/gO VRPs demonstrated extremely potent neutralizing responses. See Example 4.

Figure 8A:
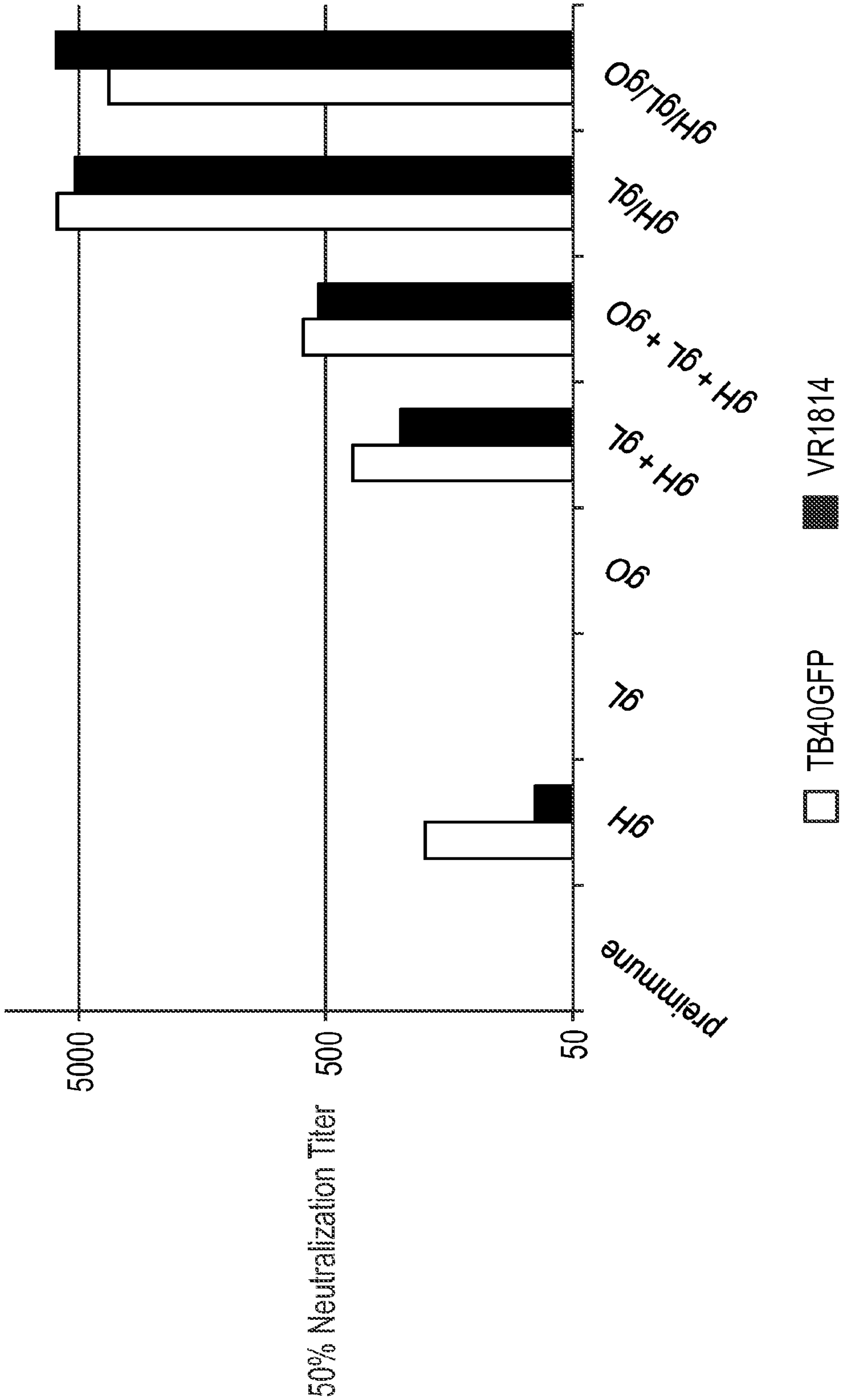
Figure 8B:
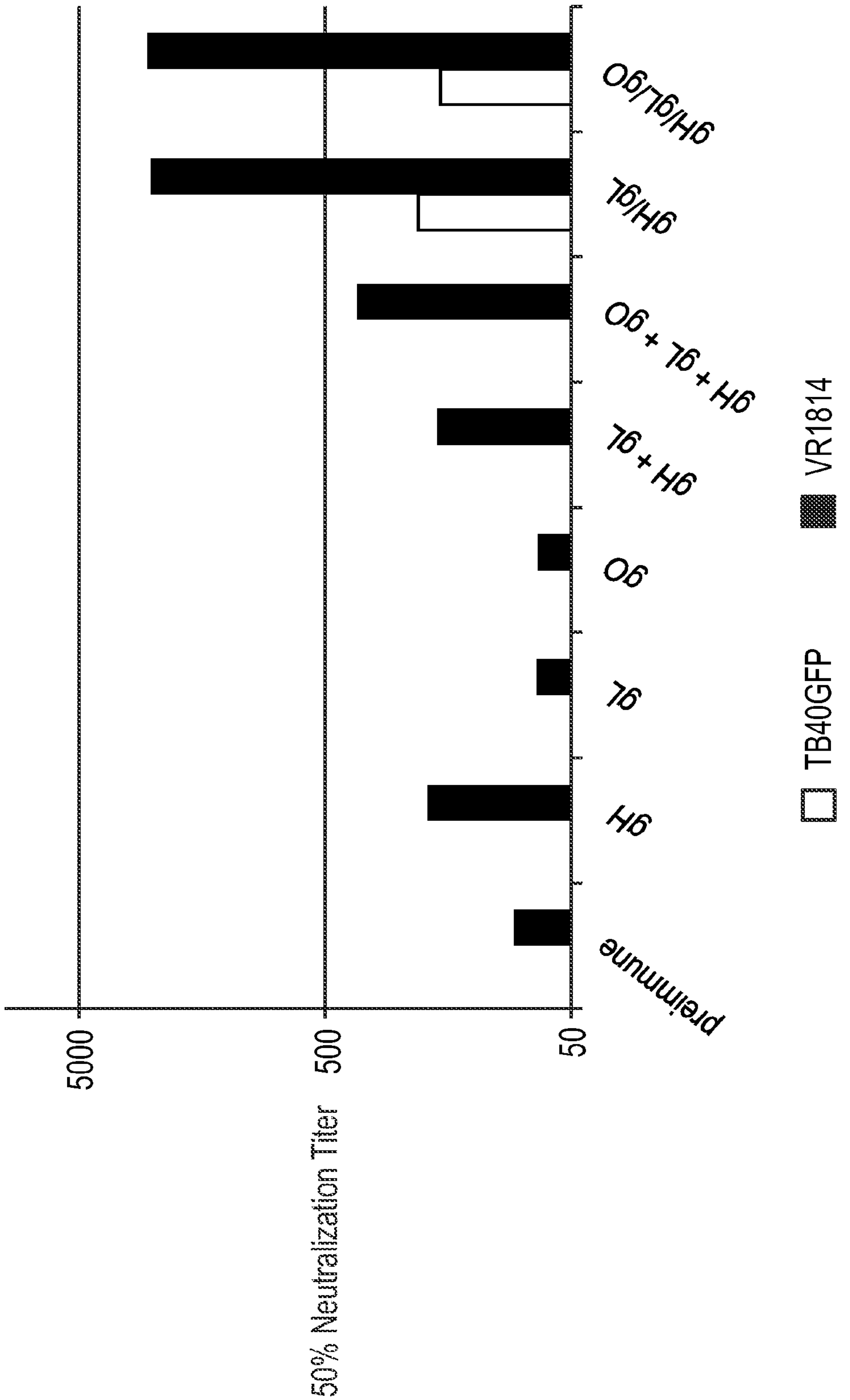

FIGS. 8A and 8B are graphs showing that the neutralizing antibodies induced by delivery of the polycistronic VRPs were cross-neutralizing antibodies. The sera from mice immunized with gH/gL and gH/gL/gO VRPs were able to neutralize TB40UL32E-GFP and VR1814 clinical strains of CMV in both ARPE-19 epithelial cells (FIG. 8A) and MRC-5 fibroblast cells (FIG. 8B) in the absence of guinea pig complement in an IE-1 neutralization assay.

Figure 9:
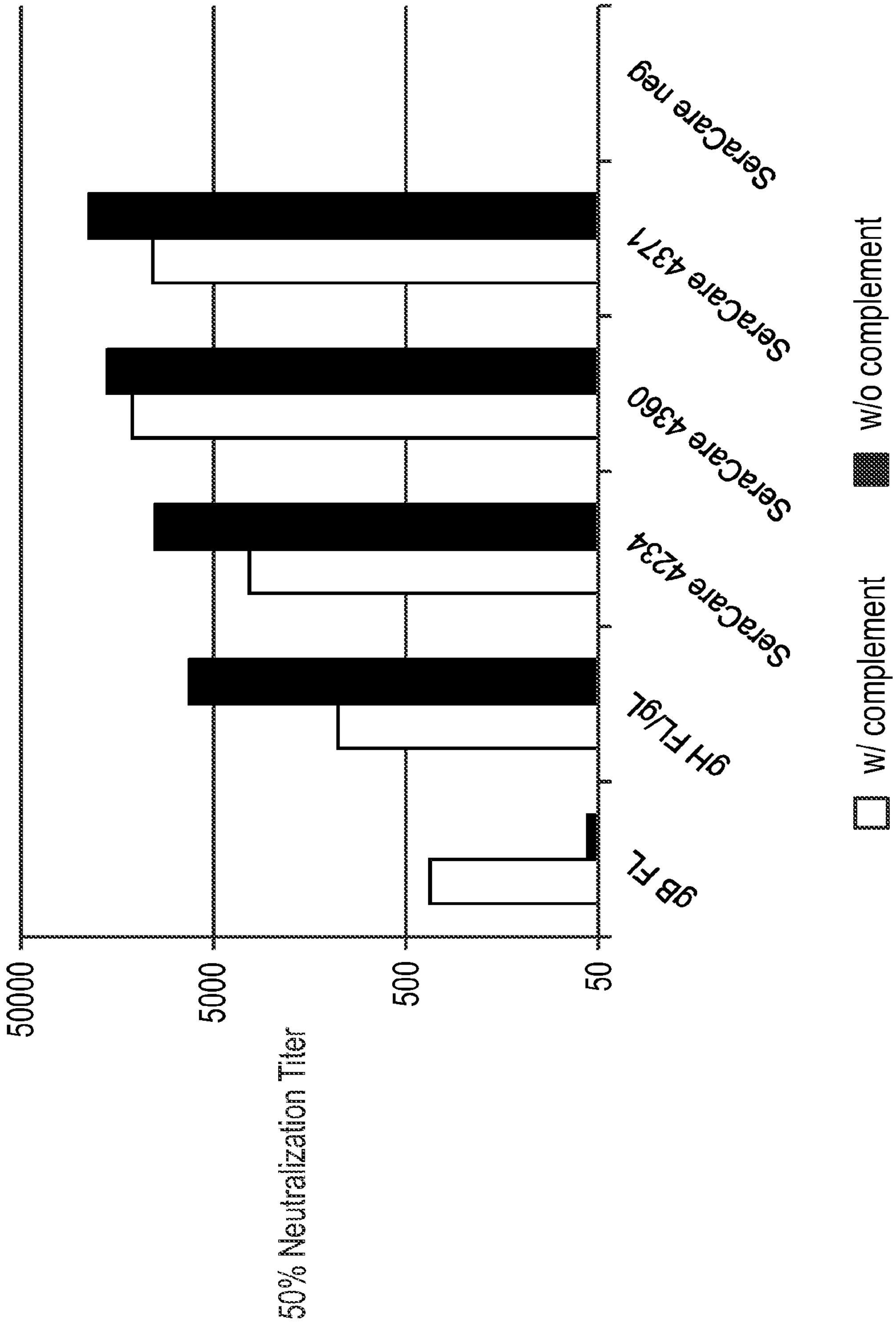

FIG. 9 is a graph showing that the neutralizing antibodies elicited against gH FL/gL are complement-independent and similar to natural immunity in titer. Mice were immunized with gB FL or gH FL/gL VRPs at $1\times10^6$ IU, 3 times, 3 weeks apart before the terminal bleed. Sera was analyzed for ability to neutralize TB40UL32E-EGFP CMV infection of ARPE-19 cells in the presence and absence of guinea pig complement in a neutralization assay. Unlike antibodies elicited by gB, antibodies elicited by gH FL/gL are complement-independent. Furthermore, gH FL/gL antibodies in these vaccinated mice were similar in titer to those found in naturally infected human subjects.

Figure 10:
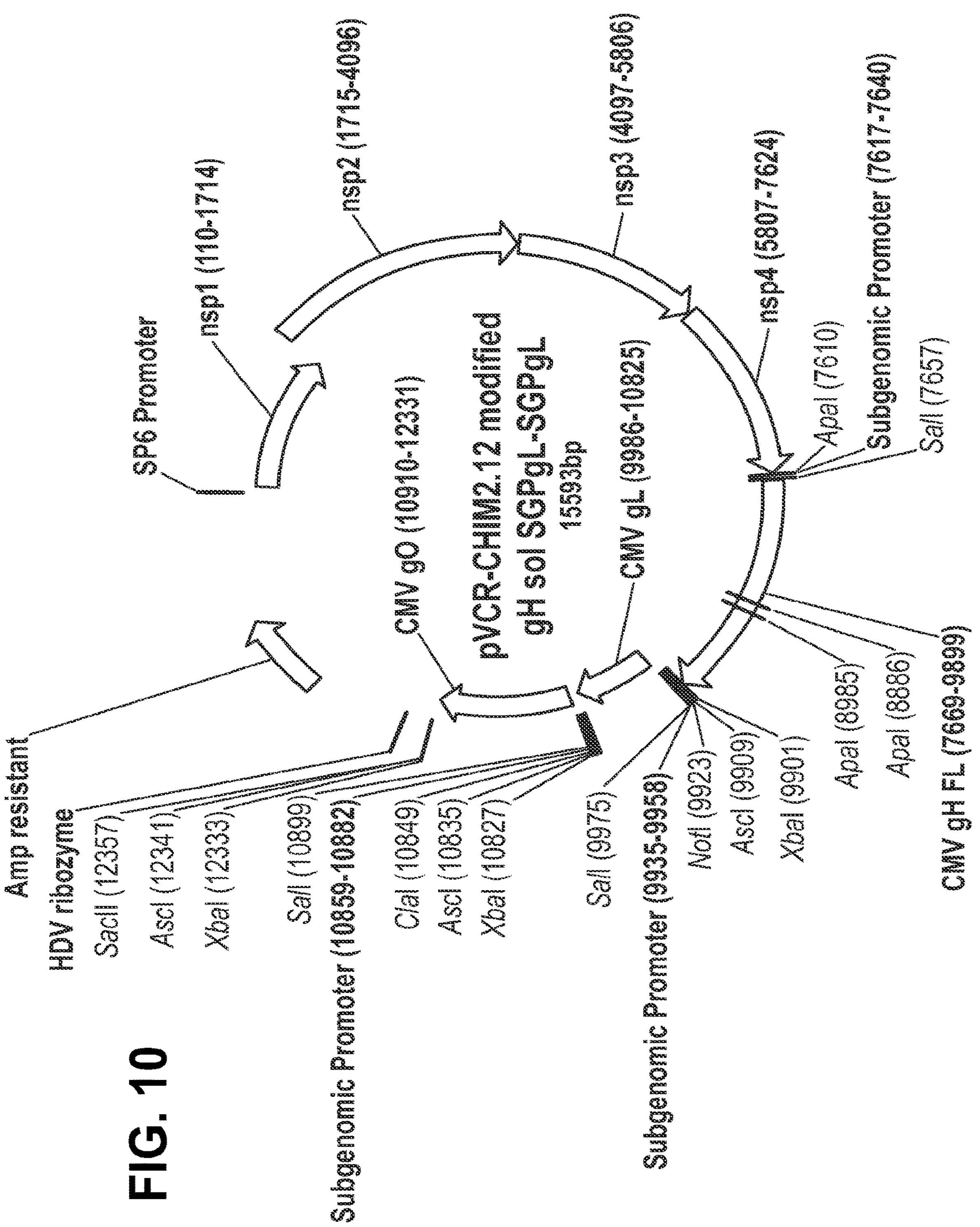

FIG. 10 shows a plasmid map for pVCR modified gH-SGPgL-SGPgO.

Figure 11:
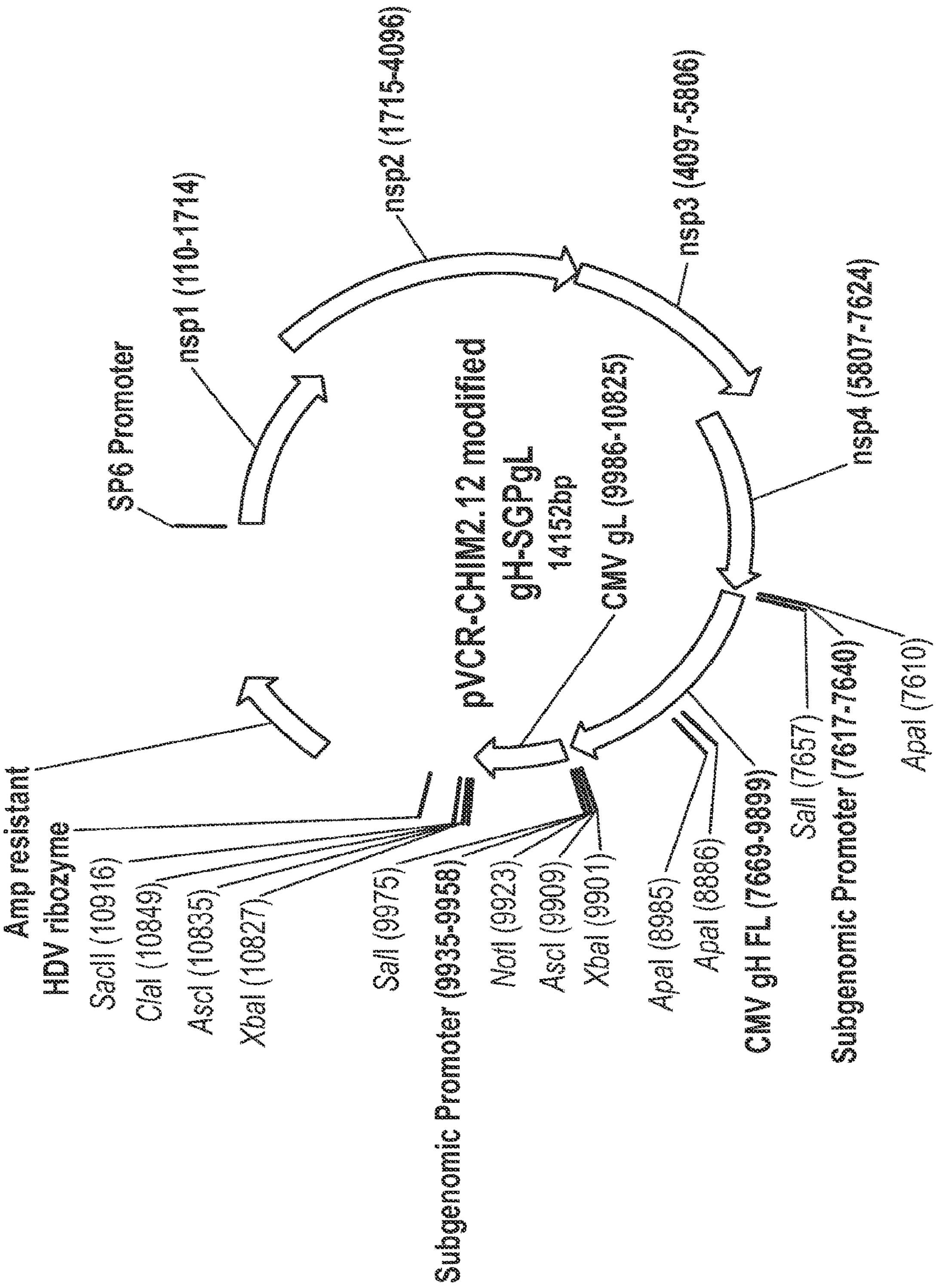

FIG. 11 show a plasmid map for pVCR modified gH-SGPgL.

Figure 12:
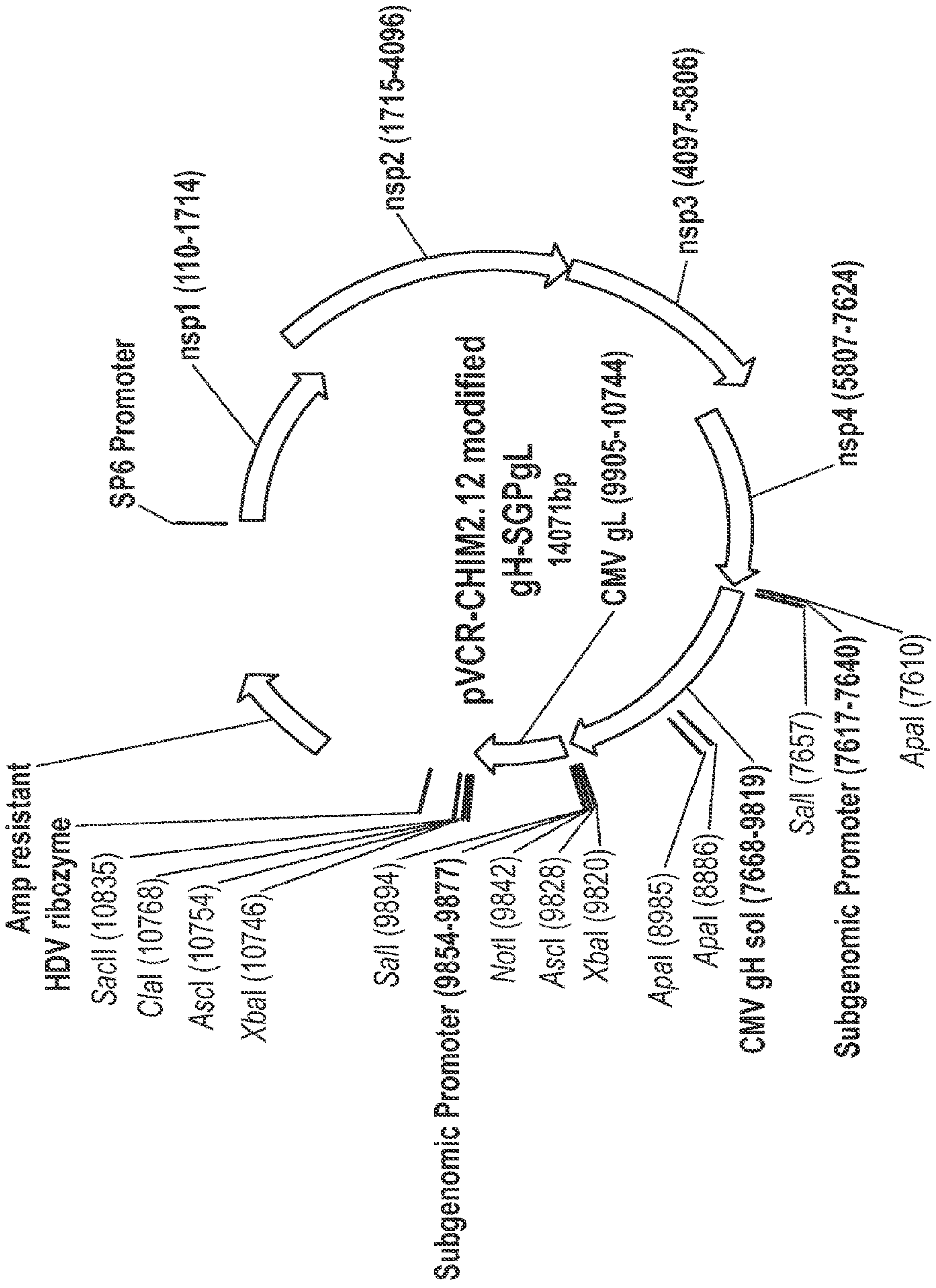

FIG. 12 show a plasmid map for pVCR modified gH sol-SGPgL.

Figure 13:
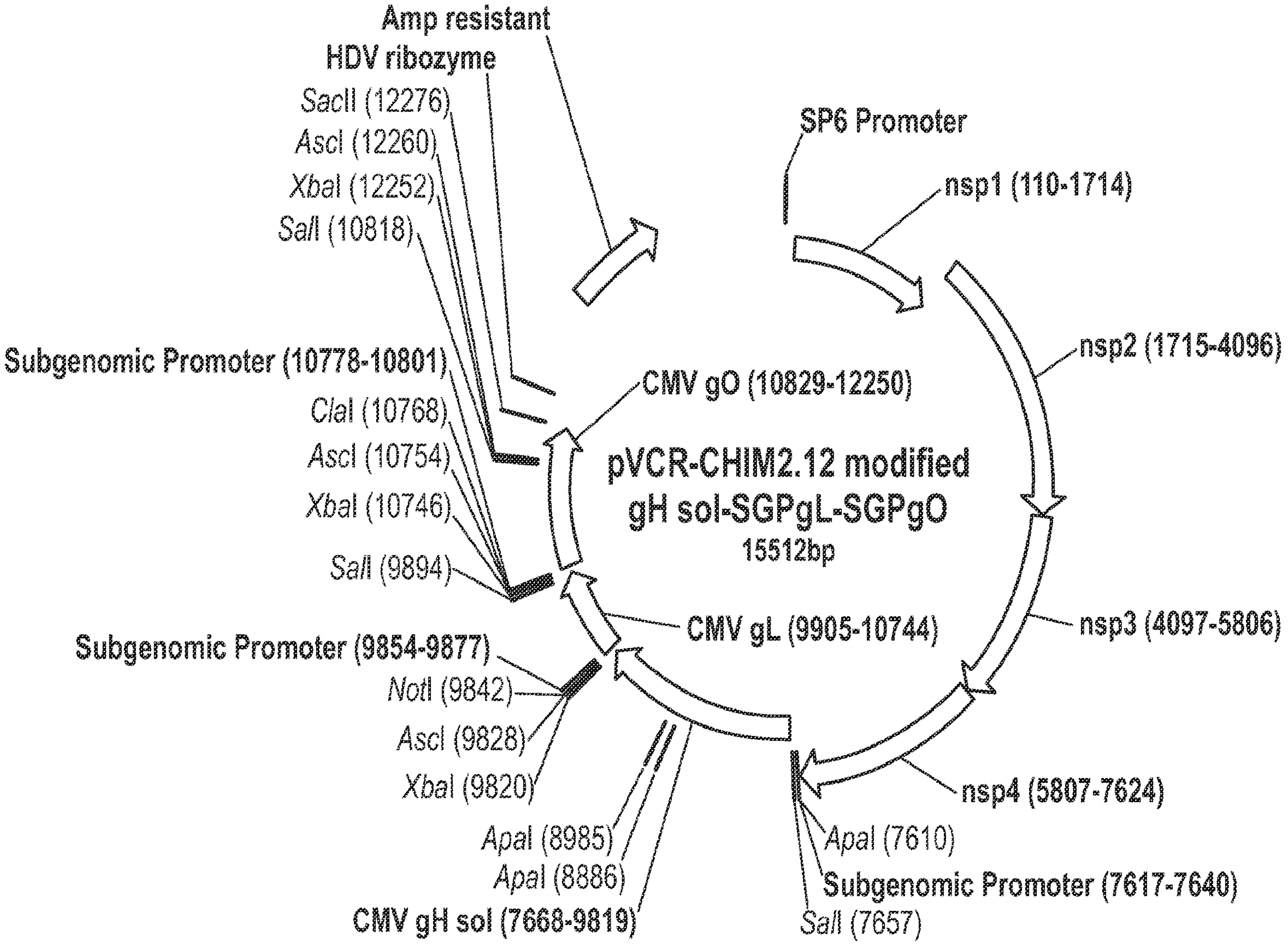

FIG. 13 show a plasmid map for pVCR modified gH sol-SGPgL-SGPgO.

FIG. 14A-14H show the nucleotide sequence (SEQ ID NO: 83) of the plasmid encoding the A160 self-replicating RNA molecule which encodes CMV surface glycoprotein H (gH) and CMV surface glycoprotein L (gL). The nucleotide sequences encoding gH and gL are underlined.

FIG. 15A-15H show the nucleotide sequence (SEQ ID NO: 84) of the plasmid encoding the A322 self-replicating RNA molecule which encodes the soluble form of CMV surface glycoprotein H (gHsol) and CMV surface glycoprotein L (gL). The nucleotide sequences encoding gHsol and gL are underlined.

FIG. 16A-16H show the nucleotide sequence (SEQ ID NO: 85) of the plasmid encoding the A323 self-replicating RNA molecule which encodes CMV surface glycoprotein B (gB). The nucleotide sequence encoding gB is underlined.

Figure 17A:
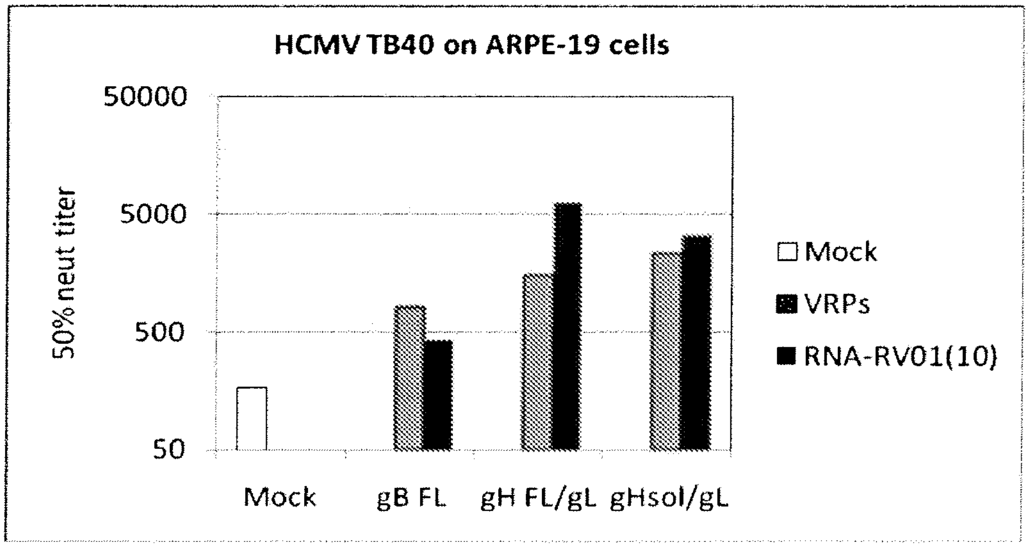
Figure 17B:
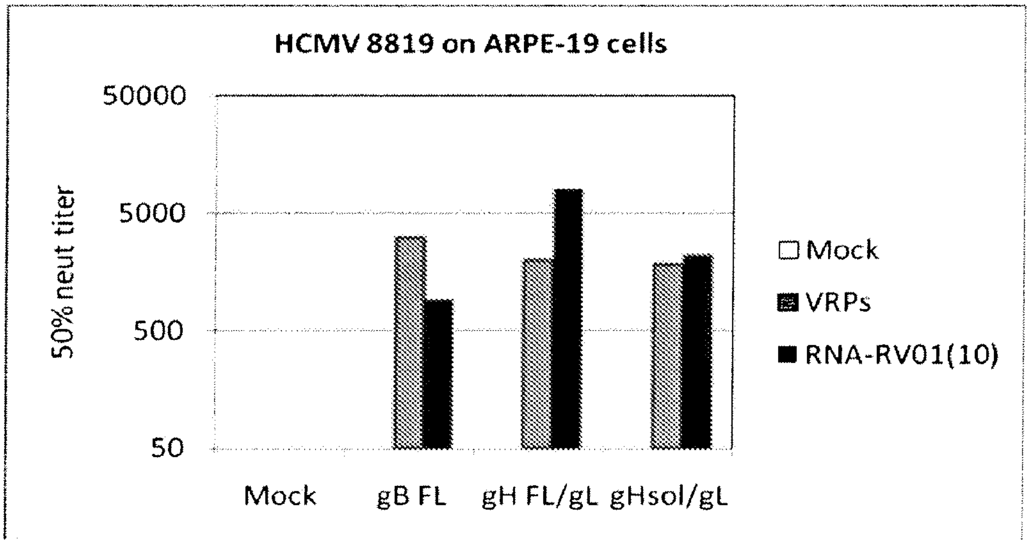
Figure 18:
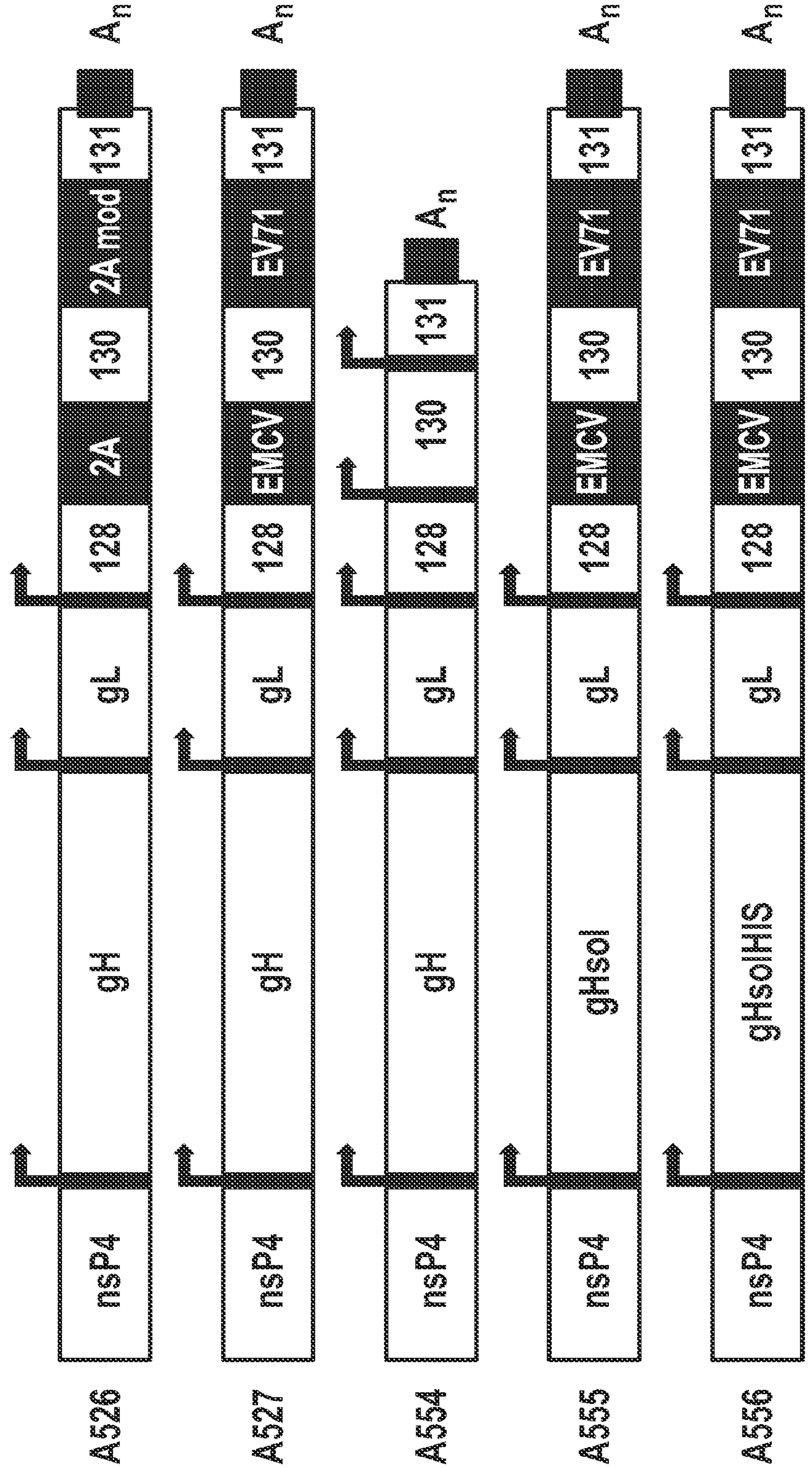

FIGS. 17A and 17B are histograms showing 50% neutralizing titers of sera from mice that were immunized with VRP or self-replicating RNA. FIG. 17A shows 50% neutralizing titers against human CMV strain TB40UL32E-EGFP ("TB40) on ARPE-19 cells, and FIG. 17B shows 50% neutralizing titers against human CMV strain 8819 on ARPE-19 cells FIG. 18 is a schematic of petacistronic RNA replicons, A526 (SEQ ID NO:56), A527 (SEQ ID NO:57), A554 (SEQ ID NO:65), A555 (SEQ ID NO:66) and A556 (SEQ ID NO:67), that encode five CMV proteins. Subgenomic promoters are shown by arrows, other control elements are labeled.

Figure 19:
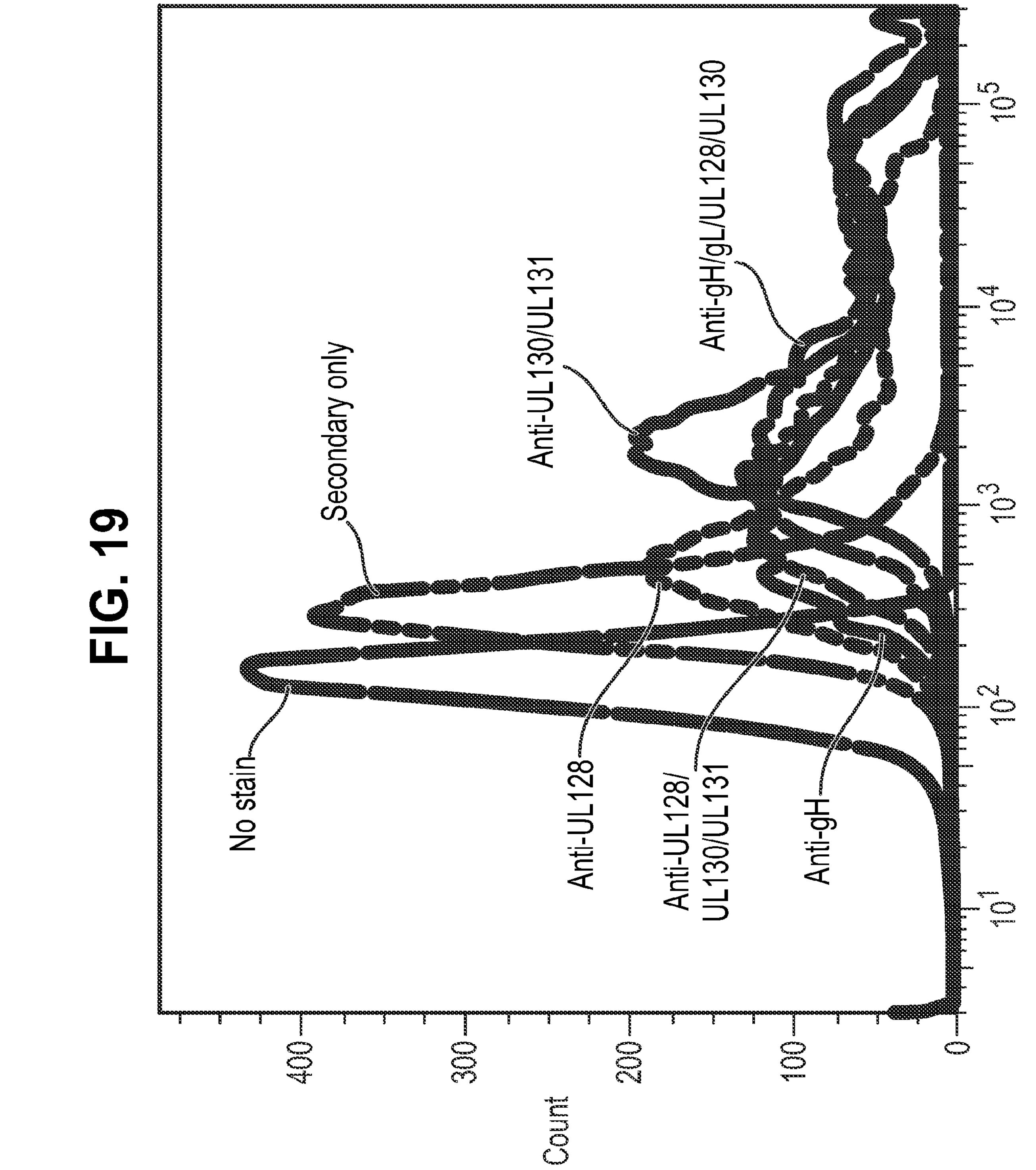

FIG. 19 is a fluorescence histogram showing that BHKV cells transfected with the A527 RNA replicon express the gH/gL/UL128/UL130/UL131 pentameric complex. Cell stain was performed using antibodies that bind a conformational epitope present on the pentameric complex (Macagno (2010) J. Virol. 84(2):1005-13).

Figure 20:
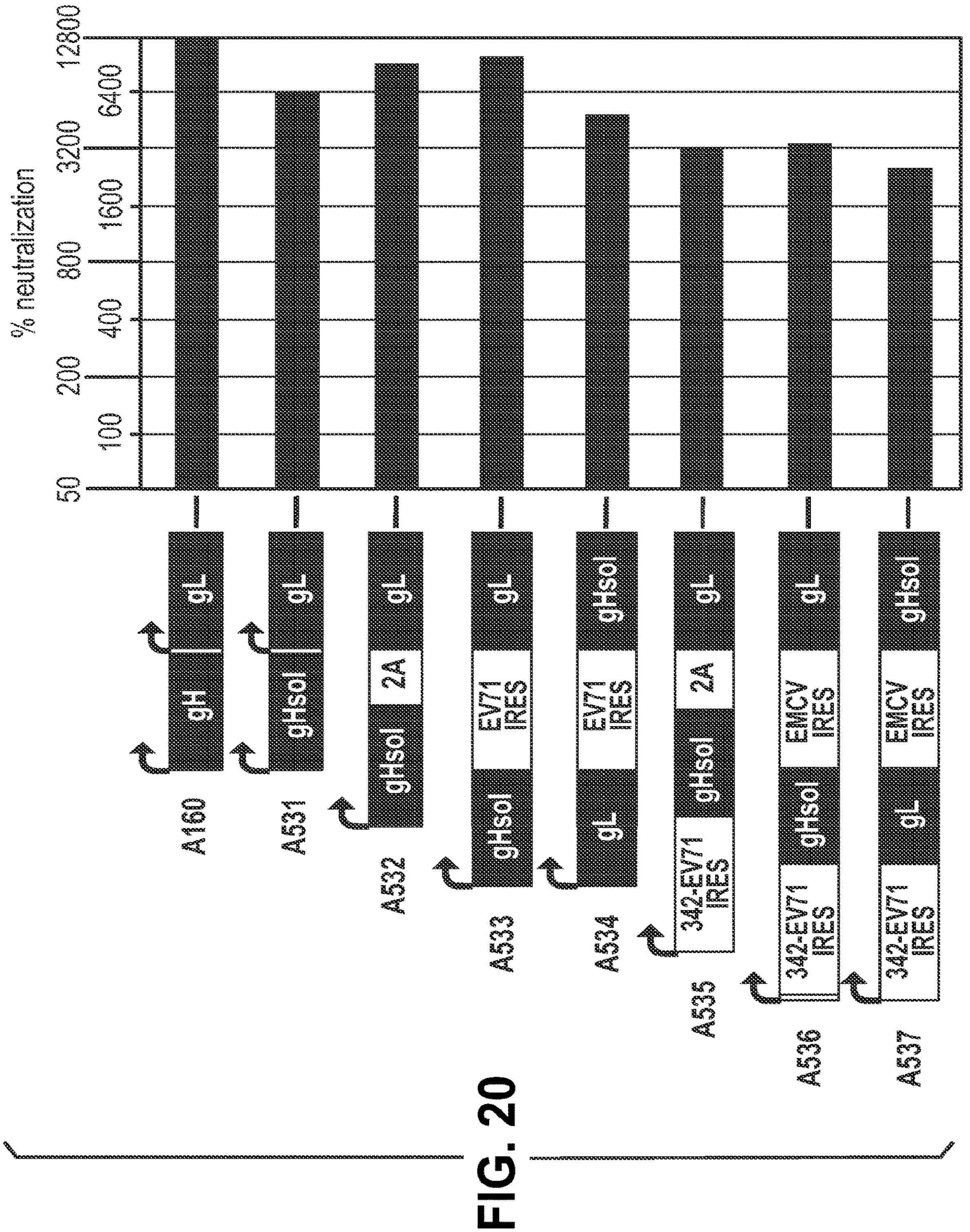

FIG. 20 is a schematic and graph. The schematic shows bicistronic RNA replicons, A160 and A531-A537, that encode CMV gH and gL. The graph shows neutralizing activity of immune sera from mice immunized with VRPs that contained the replicons.

Figure 21:
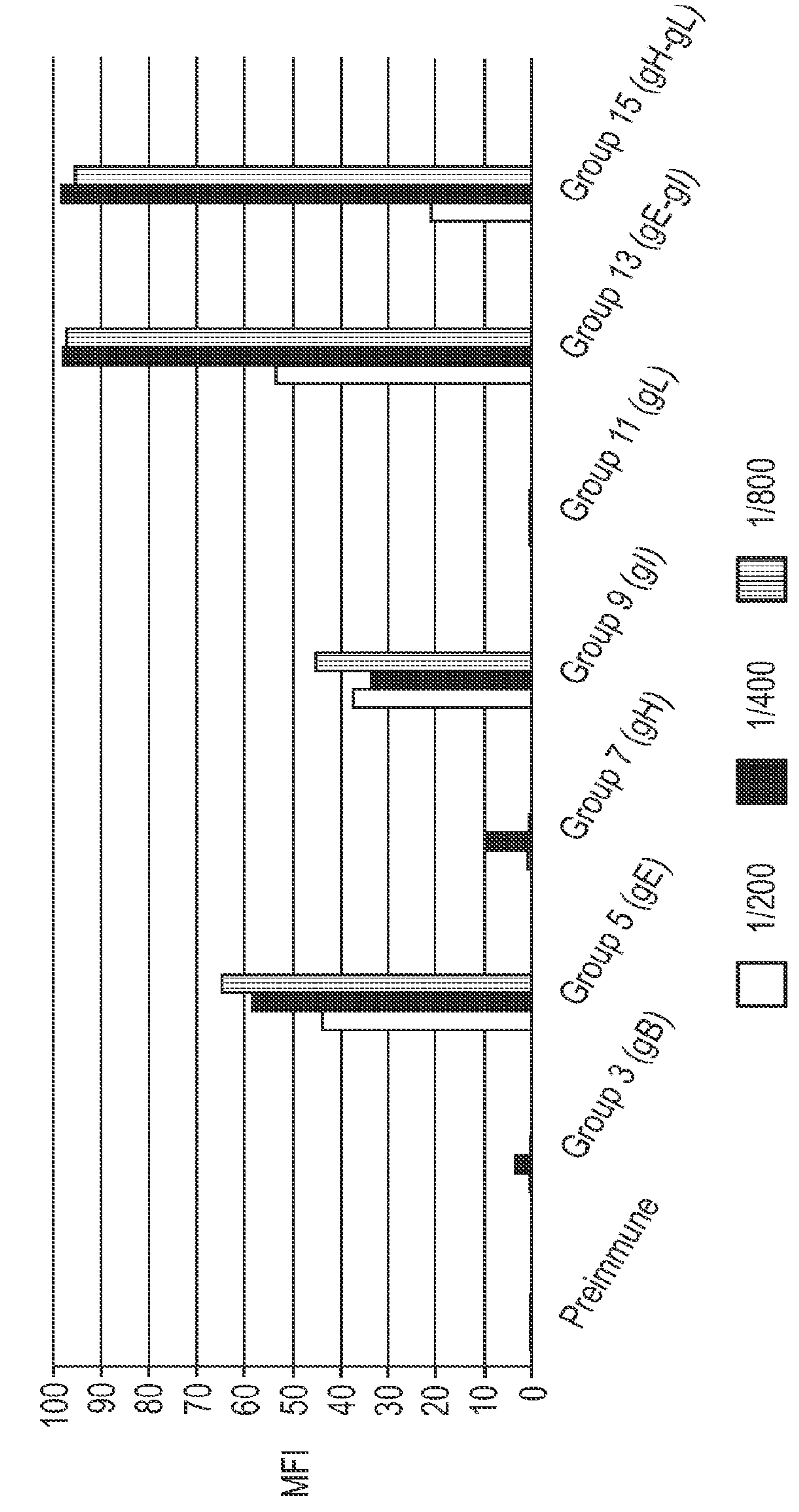

FIG. 21 is a graph showing anti-VZV protein antibody response in immune sera from mice immunized with monocistronic RNA replicons that encoded VZV proteins or bicistronic RNA replicons that encoded VZV gE and gI, or gH and gL. The mice were immunized with 7 μg RNA formulated with a CNE (see, Example 7).

Figure 22:
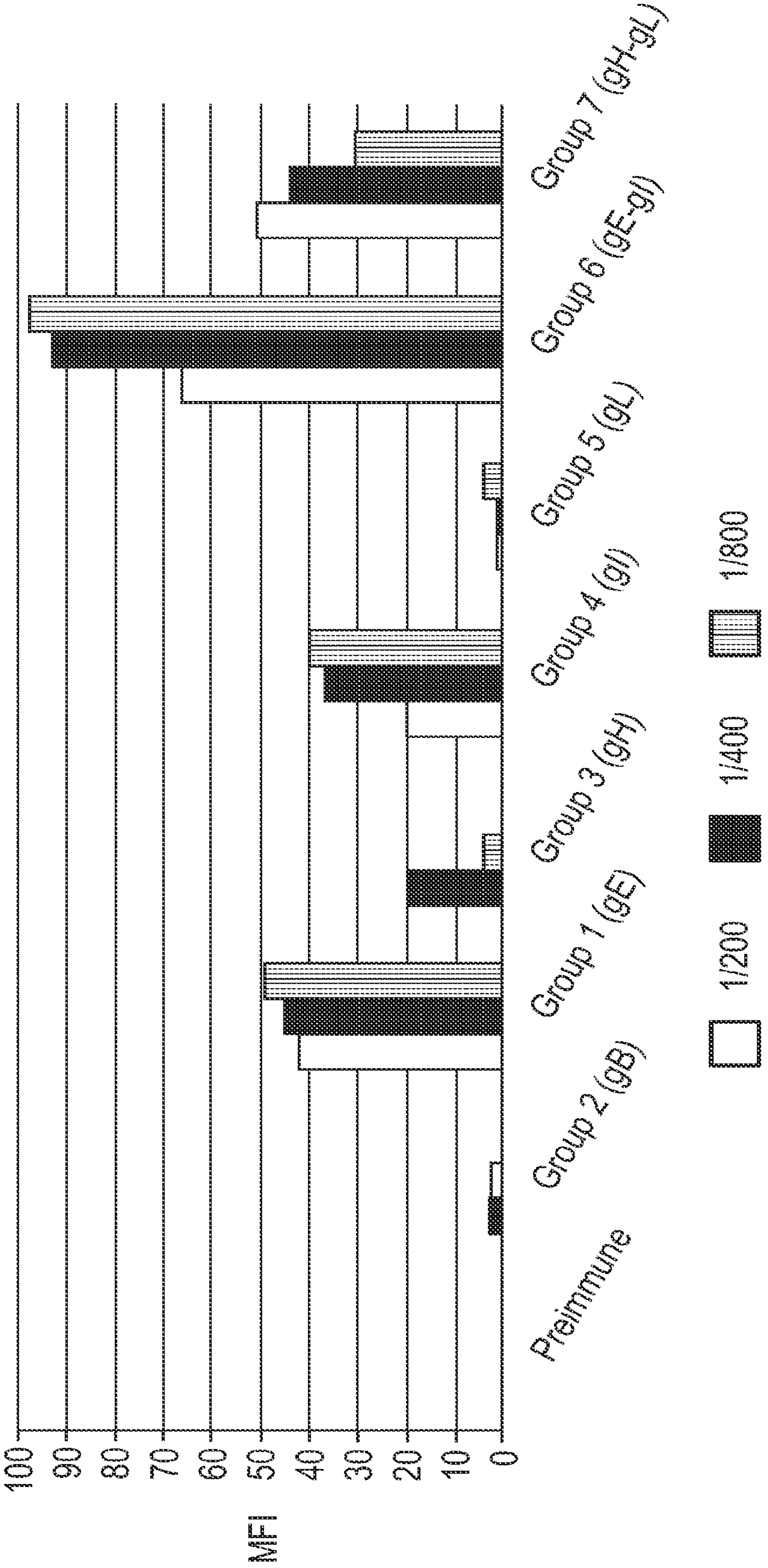

FIG. 22 is a graph showing anti-VZV protein antibody response in immune sera from mice immunized with monocistronic RNA replicons that encoded VZV proteins or bicistronic RNA replicons that encoded VZV gE and gI, or gH and gL. The mice were immunized with 1 μg RNA formulated with a CNE (see, Example 7).

DETAILED DESCRIPTION

The invention provides platforms for co-delivery of herpesvirus proteins, such as cytomegalovirus (CMV) proteins, to cells, particularly proteins that form complexes in vivo. In some embodiments, these proteins and the complexes they form elicit potent neutralizing antibodies. The immune response produced by co-delivery of herpesvirus (e.g., CMV) proteins, particularly those that form complexes in vivo (e.g., gH/gL), can be superior to the immune response produced using other approaches. For example, an RNA molecule (e.g., a replicon) that encodes both gH and gL of CMV can induce better neutralizing titers and/or protective immunity in comparison to an RNA molecule that encodes gB, an RNA molecule that encodes gH, an RNA molecule that encodes gL, or even a mixture of RNA molecules that individually encode gH or gL. Further, a replicon encoding gH/gL/UL128/UL130/UL131 can provide responses superior to those encoding only gH/gL.

In a general aspect, the invention relates to platforms for delivery of two or more herpesvirus (e.g., CMV) proteins to cells. The platforms comprise recombinant polycistronic nucleic acid molecules that contain a first sequence encoding a first herpesvirus (e.g., CMV) protein or fragment thereof, and a second sequence encoding a second herpesvirus (e.g., CMV) protein or fragment thereof. If desired, one or more additional sequences encoding additional proteins, for example, a third herpesvirus (e.g., CMV) protein or fragment thereof, a fourth herpesvirus (e.g., CMV) protein or fragment thereof, a fifth herpesvirus (e.g., CMV) protein or fragment thereof etc. can be present in the recombinant polycistronic nucleic acid molecule. The sequences encoding herpesvirus (e.g., CMV) proteins or fragments thereof are operably linked to one or more suitable control elements so that the herpesvirus (e.g., CMV) proteins or fragments are produced by a cell that contains the recombinant polycistronic nucleic acid.

In the polycistronic nucleic acids described herein, the encoded first and second herpesvirus proteins or fragments, and the encoded third, forth and fifth herpes virus proteins or fragments, if present, generally and preferably are from the same herpes virus. In certain examples, all herpes virus proteins or fragments encoded by a polycistronic vector are CMV proteins or VZV proteins.

The recombinant polycistronic nucleic acid molecules described herein provide the advantage of delivering sequences that encode two or more herpesvirus (e.g., CMV) proteins to a cell, and driving the expression of the herpesvirus (e.g., CMV) proteins at sufficient levels to result in the formation of a protein complex containing the two or more herpesvirus (e.g., CMV) proteins in vivo. Using this approach, the two or more encoded herpesvirus (e.g., CMV) proteins can be expressed at sufficient intracellular levels for the formation of herpesvirus (e.g., CMV) protein complexes (e.g., gH/gL). For example, the encoded herpesvirus (e.g., CMV) proteins or fragments thereof can be expressed at substantially the same level, or if desired, at different levels by selecting appropriate expression control sequences (e.g., promoters, IRES, 2A site etc.). This is significantly more efficient way to produce protein complexes in vivo than by co-delivering two or more individual DNA molecules that encode different herpesvirus (e.g., CMV) to the same cell, which can be inefficient and highly variable. See, e.g., WO 2004/076645.

The recombinant polycistronic nucleic acid molecule can be based on any desired nucleic acid such as DNA (e.g., plasmid or viral DNA) or RNA. Any suitable DNA or RNA can be used as the nucleic acid vector that carries the open reading frames that encode herpesvirus (e.g., CMV) proteins or fragments thereof. Suitable nucleic acid vectors have the capacity to carry and drive expression of more than one protein gene. Such nucleic acid vectors are known in the art and include, for example, plasmids, DNA obtained from DNA viruses such as vaccinia virus vectors (e.g., NYVAC, see U.S. Pat. No. 5,494,807), and poxvirus vectors (e.g., ALVAC canarypox vector, Sanofi Pasteur), and RNA obtained from suitable RNA viruses such as an alphavirus. If desired, the recombinant polycistronic nucleic acid molecule can be modified, e.g., contain modified nucleobases and or linkages as described further herein. Preferably, the polycistronic nucleic acid molecule is an RNA molecule.

In some aspects, the recombinant polycistronic nucleic acid molecule is a DNA molecule such as plasmid DNA. Such DNA molecules can, for example, encode a polycistronic replicon and contain a mammalian promoter that drives transcription of the replicon. Recombinant polycistronic nucleic acid molecules or this type can be administered to a mammal and then be transcribed in situ to produce a polycistronic replicon that expresses herpesvirus proteins.

In some aspects, the invention is a polycistronic nucleic acid molecule that contains a sequence encoding a herpesvirus gH or fragment thereof, and a herpesvirus gL or a fragment thereof. The gH and gL proteins, or fragments thereof, can be from any desired herpes virus such as HSV-1, HSV-2, VZV, EBV type 1, EBV type 2, CMV, HHV-6 type A, HHV-6 type B, HHV-7, KSHV, and the like. Preferably, the herpesvirus is VZV, HSV-2, HSV-1, EBV (type 1 or type 2) or CMV. More preferably, the herpesvirus is VZV, HSV-2 or CMV. Even more preferably, the herpesvirus is CMV. The sequences of gH and gL proteins and of nucleic acids that encode the proteins from these viruses are well known in the art. Exemplary sequences are identified in Table 1. The polycistronic nucleic acid molecule can contain a first sequence encoding a gH protein disclosed in Table 1, or a fragment thereof, or a sequence that is at least about 90%, 91%, 92%, 93%, 94%, 95%, 96%, 97%, 98%, or 99% identical thereto. The polycistronic nucleic acid molecule can also contain a second sequence encoding a gL protein disclosed in Table 1, or a fragment thereof, or a sequence that is at least about 90%, 91%, 92%, 93%, 94%, 95%, 96%, 97%, 98%, or 99% identical thereto.

TABLE 1

| Virus | gH accession number | gL accession number |
|---|---|---|
| HSV-1 (HHV-1) | NP_044623.1 | NP_044602.1 |
| HSV-2 (HHV-2) | NP_044491.1 | NP_044470.1 |
| VZV (HHV-3) | NP_040160.1 | NP_040182.1 |
| EBV type 1 (HHV-4) | YP_401700.1 | YP_401678.1 |
| EBV type 2 (HHV-4) | YP_001129496.1 | YP_001129472.1 |
| CMV (HHV-5) | YP_081523.1 | YP_081555.1 |
| HHV-6 type A | NP_042941.1 | NP_042975.1 |
| HHV-6 type B | NP_050229.1 | NP_050261.1 |
| HHV-7 | YP_073788.1 | YP_073820.1 |
| KSHV (HHV-8) | YP_001129375.1 | YP_001129399.1 |

In this description of the invention, to facilitate a clear description of the nucleic acids, particular sequence components are referred to as a "first sequence," a "second sequence," etc. It is to be understood that the first and second sequences can appear in any desired order or orientation, and that no particular order or orientation is intended by the words "first", "second" etc. Similarly, protein complexes are referred to by listing the proteins that are present in the complex, e.g., gH/gL. This is intended to describe the complex by the proteins that are present in the complex and does not indicate relative amounts of the proteins or the order or orientation of sequences that encode the proteins on a recombinant nucleic acid.

Certain preferred embodiments, such as alphavirus VRP and self-replicating RNA that contain sequences encoding CMV proteins, are further described herein. It is intended that the sequences encoding CMV proteins in such preferred embodiments, can be replaced with sequences encoding proteins, such as gH and gL from other herpesviruses.

Alphavirus VRP Platforms

In some embodiments, CMV proteins are delivered to a cell using alphavirus replicon particles (VRP) which employ polycistronic replicons (or vectors) as described below. As used herein, "polycistronic" includes bicistronic vectors as well as vectors comprising three or more cistrons. Cistrons in a polycistronic vector can encode CMV proteins from the same CMV strains or from different CMV strains. The cistrons can be oriented in any 5'-3' order. Any nucleotide sequence encoding a CMV protein can be used to produce the protein. Exemplary sequences useful for preparing the polycistronic nucleic acids that encode two or more CMV proteins or fragments thereof are described herein.

As used herein, the term "alphavirus" has its conventional meaning in the art and includes various species such as Venezuelan equine encephalitis virus (VEE; e.g., Trinidad donkey, TC83CR, etc.), Semliki Forest virus (SFV), Sindbis virus, Ross River virus, Western equine encephalitis virus, Eastern equine encephalitis virus, Chikungunya virus, S.A. AR86 virus, Everglades virus, Mucambo virus, Barmah Forest virus, Middelburg virus, Pixuna virus, O'nyong-nyong virus, Getah virus, Sagiyama virus, Bebaru virus, Mayaro virus, Una virus, Aura virus, Whataroa virus, Banbanki virus, Kyzylagach virus, Highlands J virus, Fort Morgan virus, Ndumu virus, and Buggy Creek virus. The term alphavirus may also include chimeric alphaviruses (e.g., as described by Perri et al., (2003) J. Virol. 77(19): 10394-403) that contain genome sequences from more than one alphavirus.

An "alphavirus replicon particle" (VRP) or "replicon particle" is an alphavirus replicon packaged with alphavirus structural proteins.

An "alphavirus replicon" (or "replicon") is an RNA molecule which can direct its own amplification in vivo in a target cell. The replicon encodes the polymerase(s) which catalyze RNA amplification (nsP1, nsP2, nsP3, nsP4) and contains cis RNA sequences required for replication which are recognized and utilized by the encoded polymerase(s). An alphavirus replicon typically contains the following ordered elements: 5' viral sequences required in cis for replication, sequences which encode biologically active alphavirus nonstructural proteins (nsP1, nsP2, nsP3, nsP4), 3' viral sequences required in cis for replication, and a polyadenylate tract. An alphavirus replicon also may contain one or more viral subgenomic "junction region" promoters directing the expression of heterologous nucleotide sequences, which may, in certain embodiments, be modified in order to increase or reduce viral transcription of the subgenomic fragment and heterologous sequence(s) to be expressed. Other control elements can be used, as described below.

Alphavirus replicons encoding CMV proteins are used to produce VRPs. Such alphavirus replicons comprise sequences encoding at least two CMV proteins or fragments thereof. These sequences are operably linked to one or more suitable control elements, such as a subgenomic promoter, an IRES (e.g., EMCV, EV71), and a viral 2A site, which can be the same or different. Delivery of components of these complexes using the polycistronic vectors disclosed herein is an efficient way of providing nucleic acid sequences that encode two or more CMV proteins in desired relative amounts; whereas if multiple alphavirus constructs were used to deliver individual CMV proteins for complex formation, efficient co-delivery of VRPs would be required.

Any combination of suitable control elements can be used in any order. In one example, a single subgenomic promoter is operable linked to two sequences encoding two different CMV proteins, and an IRES is positioned between the two coding sequences. In another example, two sequences that encode two different CMV proteins are operably linked to separate promoters. In still another example, the two sequences that encode two different CMV proteins are operably linked to a single promoter. The two sequences that encode two different CMV proteins are linked to each other through a nucleotide sequence encoding a viral 2A site, and thus encode a single amino acid chain that contain the amino acid sequences of both CMV proteins. The viral 2A site in this context is used to generate two CMV proteins from encoded polyprotein.

Subgenomic Promoters

Subgenomic promoters, also known as junction region promoters can be used to regulate protein expression. Alphaviral subgenomic promoters regulate expression of alphaviral structural proteins. See Strauss and Strauss, "The alphaviruses: gene expression, replication, and evolution," Microbiol Rev. 1994 September; 58(3):491-562. A polycistronic polynucleotide can comprise a subgenomic promoter from any alphavirus. When two or more subgenomic promoters are present in a polycistronic polynucleotide, the promoters can be the same or different. For example, the subgenomic promoter can have the sequence CTCTCTACGGCTAACCTGAATGGA (SEQ ID NO: 1). In certain embodiments, subgenomic promoters can be modified in order to increase or reduce viral transcription of the proteins. See U.S. Pat. No. 6,592,874.

Internal Ribosomal Entry Site (IRES)

In some embodiments, one or more control elements is an internal ribosomal entry site (IRES). An IRES allows multiple proteins to be made from a single mRNA transcript as ribosomes bind to each IRES and initiate translation in the absence of a 5'-cap, which is normally required to initiate translation of protein in eukaryotic cells. For example, the IRES can be EV71 (SEQ ID NO:50) or EMCV (SEQ ID NO:49).

Viral 2A Site

The FMDV 2A protein is a short peptide that serves to separate the structural proteins of FMDV from a nonstructural protein (FMDV 2B). Early work on this peptide suggested that it acts as an autocatalytic protease, but other work (e.g., Donnelly et al., (2001), J. Gen. Virol. 82, 1013-1025) suggest that this short sequence and the following single amino acid of FMDV 2B (Gly) acts as a translational stop-start. Regardless of the precise mode of action, the sequence can be inserted between two polypeptides, and effect the production of multiple individual polypeptides from a single open reading frame. In the context of this invention, FMDV 2A sequences can be inserted between the sequences encoding at least two CMV proteins, allowing for their synthesis as part of a single open reading frame. For example, the open reading frame may encode a gH protein and a gL protein separated by a sequence encoding a viral 2A site. A single mRNA is transcribed then, during the translation step, the gH and gL peptides are produced separately due to the activity of the viral 2A site. Any suitable viral 2A sequence may be used. Often, a viral 2A site comprises the consensus sequence Asp-Valle-Glu-X-Asn-Pro-Gly-Pro, where X is any amino acid (SEQ ID NO: 2). For example, the Foot and Mouth Disease Virus 2A peptide sequence is DVESNPGP (SEQ ID NO: 3). See Trichas et al., "Use of the viral 2A peptide for bicistronic expression in transgenic mice," BMC Biol. 2008 Sep. 15; 6:40, and Halpin et al., "Self-processing 2A-polyproteins—a system for co-ordinate expression of multiple proteins in transgenic plants," Plant J. 1999 February; 17(4):453-9.

In some embodiments an alphavirus replicon is a chimeric replicon, such as a VEE-Sindbis chimeric replicon (VCR) or a VEE strain TC83 replicon (TC83R) or a TC83-Sindbis chimeric replicon (TC83CR). In some embodiments a VCR contains the packaging signal and 3' UTR from a Sindbis replicon in place of sequences in nsP3 and at the 3' end of the VEE replicon; see Perri et al., *J. Virol.* 77, 10394-403, 2003. In some embodiments, a TC83CR contains the packaging signal and 3' UTR from a Sindbis replicon in place of sequences in nsP3 and at the 3' end of a VEE strain TC83replicon.

Producing VRPs

Methods of preparing VRPs are well known in the art. In some embodiments an alphavirus is assembled into a VRP using a packaging cell. An "alphavirus packaging cell" (or "packaging cell") is a cell that contains one or more alphavirus structural protein expression cassettes and that produces recombinant alphavirus particles after introduction of an alphavirus replicon, eukaryotic layered vector initiation system (e.g., U.S. Pat. No. 5,814,482), or recombinant alphavirus particle. The one or more different alphavirus structural protein cassettes serve as "helpers" by providing the alphavirus structural proteins. An "alphavirus structural protein cassette" is an expression cassette that encodes one or more alphavirus structural proteins and comprises at least one and up to five copies (i.e., 1, 2, 3, 4, or 5) of an alphavirus replicase recognition sequence. Structural protein expression cassettes typically comprise, from 5' to 3', a 5' sequence which initiates transcription of alphavirus RNA, an optional alphavirus subgenomic region promoter, a nucleotide sequence encoding the alphavirus structural protein, a 3' untranslated region (which also directs RNA transcription), and a polyA tract. See, e.g., WO 2010/019437.

In preferred embodiments two different alphavirus structural protein cassettes ("split" defective helpers) are used in a packaging cell to minimize recombination events which could produce a replication-competent virus. In some embodiments an alphavirus structural protein cassette encodes the capsid protein (C) but not either of the glycoproteins (E2 and E1). In some embodiments an alphavirus structural protein cassette encodes the capsid protein and either the E1 or E2 glycoproteins (but not both). In some embodiments an alphavirus structural protein cassette encodes the E2 and E1 glycoproteins but not the capsid protein. In some embodiments an alphavirus structural protein cassette encodes the E1 or E2 glycoprotein (but not both) and not the capsid protein.

In some embodiments, VRPs are produced by the simultaneous introduction of replicons and helper RNAs into cells of various sources. Under these conditions, for example, BHKV cells ($1\times10^7$) are electroporated at, for example, 220 volts, 1000 μF, 2 manually pulses with 10 μg replicon RNA: 6 μg defective helper Cap RNA: 10 μg defective helper Gly RNA, alphavirus containing supernatant is collected ~24 hours later. Replicons and/or helpers can also be introduced in DNA forms which launch suitable RNAs within the transfected cells.

A packaging cell may be a mammalian cell or a non-mammalian cell, such as an insect (e.g., SF9) or avian cell (e.g., a primary chick or duck fibroblast or fibroblast cell line). See U.S. Pat. No. 7,445,924. Avian sources of cells include, but are not limited to, avian embryonic stem cells such as EB66® (VIVALIS); chicken cells, including chicken embryonic stem cells such as EBx® cells, chicken embryonic fibroblasts, and chicken embryonic germ cells; duck cells such as the AGE1.CR and AGE1.CR.pIX cell lines (ProBioGen) which are described, for example, in Vaccine 27:4975-4982 (2009) and WO2005/042728); and geese cells. In some embodiments, a packaging cell is a primary duck fibroblast or duck retinal cell line, such as AGE.CR (PROBIOGEN).

Mammalian sources of cells for simultaneous nucleic acid introduction and/or packaging cells include, but are not limited to, human or non-human primate cells, including PerC6 (PER.C6) cells (CRUCELL N.V.), which are described, for example, in WO 01/38362 and WO 02/40665, as well as deposited under ECACC deposit number 96022940); MRC-5 (ATCC CCL-171); WI-38 (ATCC CCL-75); fetal rhesus lung cells (ATCC CL-160); human embryonic kidney cells (e.g., 293 cells, typically transformed by sheared adenovirus type 5 DNA); VERO cells from monkey kidneys); cells of horse, cow (e.g., MDBK cells), sheep, dog (e.g., MDCK cells from dog kidneys, ATCC CCL34 MDCK (NBL2) or MDCK 33016, deposit number DSM ACC 2219 as described in WO 97/37001); cat, and rodent (e.g., hamster cells such as BHK21-F, HKCC cells, or Chinese hamster ovary (CHO) cells), and may be obtained from a wide variety of developmental stages, including for example, adult, neonatal, fetal, and embryo.

In some embodiments a packaging cell is stably transformed with one or more structural protein expression cassette(s). Structural protein expression cassettes can be introduced into cells using standard recombinant DNA techniques, including transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun" methods, and DEAE- or calcium phosphate-mediated transfection. Structural protein expression cassettes typically are introduced into a host cell as DNA molecules, but can also be introduced as in vitro-transcribed RNA. Each expression cassette can be introduced separately or substantially simultaneously.

In some embodiments, stable alphavirus packaging cell lines are used to produce recombinant alphavirus particles. These are alphavirus-permissive cells comprising DNA cassettes expressing the defective helper RNA stably integrated into their genomes. See Polo et al., *Proc. Natl. Acad. Sci. USA* 96, 4598-603, 1999. The helper RNAs are constitutively expressed but the alphavirus structural proteins are not, because the genes are under the control of an alphavirus subgenomic promoter (Polo et al., 1999). Upon introduction of an alphavirus replicon into the genome of a packaging cell by transfection or VRP infection, replicase enzymes are produced and trigger expression of the capsid and glycoprotein genes on the helper RNAs, and output VRPs are produced. Introduction of the replicon can be accomplished by a variety of methods, including both transfection and infection with a seed stock of alphavirus replicon particles. The packaging cell is then incubated under conditions and for a time sufficient to produce packaged alphavirus replicon particles in the culture supernatant.

Thus, packaging cells allow VRPs to act as self-propagating viruses. This technology allows VRPs to be produced in much the same manner, and using the same equipment, as that used for live attenuated vaccines or other viral vectors that have producer cell lines available, such as replication-incompetent adenovirus vectors grown in cells expressing the adenovirus E1A and E1B genes.

In some embodiments, a two-step process is used: the first step comprises producing a seed stock of alphavirus replicon particles by transfecting a packaging cell with a replicon RNA or plasmid DNA-based replicon. A much larger stock of replicon particles is then produced in a second step, by infecting a fresh culture of packaging cells with the seed stock. This infection can be performed using various multiplicities of infection (MOI), including a MOI=0.00001, 0.00005, 0.0001, 0.0005, 0.001, 0.005, 0.01, 0.05, 0.1, 0.5, 1.0, 3, 5, 10 or 20. In some embodiments infection is performed at a low MOI (e.g., less than 1). Over time, replicon particles can be harvested from packaging cells infected with the seed stock. In some embodiments, replicon particles can then be passaged in yet larger cultures of naive packaging cells by repeated low-multiplicity infection, resulting in commercial scale preparations with the same high titer.

Self-Replicating RNA Platforms

Two or more CMV proteins can be produced by expression of recombinant nucleic acids that encode the proteins in the cells of a subject. Preferably, the recombinant nucleic acid molecules encode two or more CMV proteins, e.g., are polycistronic. As defined above, "polycistronic" includes bicistronic. Preferred nucleic acids that can be administered to a subject to cause the production of CMV proteins are self-replicating RNA molecules. The self-replicating RNA molecules of the invention are based on the genomic RNA of RNA viruses, but lack the genes encoding one or more structural proteins. The self-replicating RNA molecules are capable of being translated to produce non-structural proteins of the RNA virus and CMV proteins encoded by the self-replicating RNA.

The self-replicating RNA generally contains at least one or more genes selected from the group consisting of viral replicase, viral proteases, viral helicases and other nonstructural viral proteins, and also comprise 5'- and 3'-end cis-active replication sequences, and a heterologous sequences that encodes two or more desired CMV proteins. A subgenomic promoter that directs expression of the heterologous sequence(s) can be included in the self-replicating RNA. If desired, a heterologous sequence may be fused in frame to other coding regions in the self-replicating RNA and/or may be under the control of an internal ribosome entry site (IRES).

Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sindbis virus (SIN), Semliki forest virus and Venezuelan equine encephalitis virus (VEE), one or more genes encoding viral structural proteins, such as capsid and/or envelope glycoproteins, can be omitted. If desired, self-replicating RNA molecules of the invention can be designed to induce production of infectious viral particles that are attenuated or virulent, or to produce viral particles that are capable of a single round of subsequent infection.

A self-replicating RNA molecule can, when delivered to a vertebrate cell even without any proteins, lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus the delivered RNA leads to the production of multiple daughter RNAs. These transcripts are antisense relative to the delivered RNA and may be translated themselves to provide in situ expression of encoded CMV protein, or may be transcribed to provide further transcripts with the same sense as the delivered RNA which are translated to provide in situ expression of the encoded CMV protein(s).

One suitable system for achieving self-replication is to use an alphavirus-based RNA replicon, such as an alphavirus replicon as described herein. These + stranded replicons are translated after delivery to a cell to produce a replicase (or replicase-transcriptase). The replicase is translated as a polyprotein which auto cleaves to provide a replication complex which creates genomic − strand copies of the + strand delivered RNA. These − strand transcripts can themselves be transcribed to give further copies of the + stranded parent RNA and also to give rise to one or more subgenomic transcript which encodes two or more CMV proteins. Translation of the subgenomic transcript thus leads to in situ expression of the CMV protein(s) by the infected cell. Suitable alphavirus replicons can use a replicase from a Sindbis virus, a Semliki forest virus, an eastern equine encephalitis virus, a Venezuelan equine encephalitis virus, etc.

A preferred self-replicating RNA molecule thus encodes (i) a RNA-dependent RNA polymerase which can transcribe RNA from the self-replicating RNA molecule and (ii) two or more CMV proteins or fragments thereof. The polymerase can be an alphavirus replicase e.g. comprising alphavirus protein nsP4. Protein nsP4 is the key catalytic component of the replicase.

Whereas natural alphavirus genomes encode structural virion proteins in addition to the non-structural replicase polyprotein, it is preferred that an alphavirus based self-replicating RNA molecule of the invention does not encode all alphavirus structural proteins. Thus the self replicating RNA can lead to the production of genomic RNA copies of itself in a cell, but not to the production of RNA-containing alphavirus virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self replicating RNAs of the invention and their place is taken by gene(s) encoding the desired gene product (CMV protein or fragment thereof), such that the subgenomic transcript encodes the desired gene product rather than the structural alphavirus virion proteins.

Thus a self-replicating RNA molecule useful with the invention have two sequences that encode different CMV proteins or fragments thereof. The sequences encoding the CMV proteins or fragments can be in any desired orientation, and can be operably linked to the same or separate promoters. If desired, the sequences encoding the CMV proteins or fragments can be part of a single open reading frame. In some embodiments the RNA may have one or more additional (downstream) sequences or open reading frames e.g. that encode other additional CMV proteins or fragments thereof. A self-replicating RNA molecule can have a 5' sequence which is compatible with the encoded replicase.

In one aspect, the self-replicating RNA molecule is derived from or based on an alphavirus, such as an alphavirus replicon as defined herein. In other aspects, the self-replicating RNA molecule is derived from or based on a virus other than an alphavirus, preferably, a positive-stranded RNA viruses, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro virus (ATCC VR-66; ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

The self-replicating RNA molecules of the invention can contain one or more modified nucleotides and therefore have improved stability and be resistant to degradation and clearance in vivo, and other advantages. Without wishing to be bound by any particular theory, it is believed that self-replicating RNA molecules that contain modified nucleotides avoid or reduce stimulation of endosomal and cytoplasmic immune receptors when the self-replicating RNA is delivered into a cell. This permits self-replication, amplification and expression of protein to occur. This also reduces safety concerns relative to self-replicating RNA that does not contain modified nucleotides, because the self-replicating RNA that contains modified nucleotides reduce activation of the innate immune system and subsequent undesired consequences (e.g., inflammation at injection site, irritation at injection site, pain, and the like). It is also believed that the RNA molecules produced as a result of self-replication are recognized as foreign nucleic acids by the cytoplasmic immune receptors. Thus, self-replicating RNA molecules that contain modified nucleotides provide for efficient amplification of the RNA in a host cell and expression of CMV proteins, as well as adjuvant effects.

The RNA sequence can be modified with respect to its codon usage, for example, to increase translation efficacy and half-life of the RNA. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap 0 structure can provide stability and translational efficacy to the RNA molecule. The 5' cap of the RNA molecule may be further modified by a 2'-O-Methyltransferase which results in the generation of a cap 1 structure (m7Gppp [m2'-O] N), which may further increases translation efficacy. A cap 1 structure may also increase in vivo potency.

As used herein, "modified nucleotide" refers to a nucleotide that contains one or more chemical modifications (e.g., substitutions) in or on the nitrogenous base of the nucleoside (e.g., cytosine (C), thymine (T) or uracil (U), adenine (A) or guanine (G)). If desired, a self replicating RNA molecule can contain chemical modifications in or on the sugar moiety of the nucleoside (e.g., ribose, deoxyribose, modified ribose, modified deoxyribose, six-membered sugar analog, or open-chain sugar analog), or the phosphate.

The self-replicating RNA molecules can contain at least one modified nucleotide, that preferably is not part of the 5' cap (e.g., in addition to the modification that are part of the 5" cap). Accordingly, the self-replicating RNA molecule can contain a modified nucleotide at a single position, can contain a particular modified nucleotide (e.g., pseudouridine, N6-methyladenosine, 5-methylcytidine, 5-methyluridine) at two or more positions, or can contain two, three, four, five, six, seven, eight, nine, ten or more modified nucleotides (e.g., each at one or more positions). Preferably, the self-replicating RNA molecules comprise modified nucleotides that contain a modification on or in the nitrogenous base, but do not contain modified sugar or phosphate moieties.

In some examples, between 0.001% and 99% or 100% of the nucleotides in a self-replicating RNA molecule are modified nucleotides. For example, 0.001%-25%, 0.01%-25%, 0.1%-25%, or 1%-25% of the nucleotides in a self-replicating RNA molecule are modified nucleotides.

In other examples, between 0.001% and 99% or 100% of a particular unmodified nucleotide in a self-replicating RNA molecule is replaced with a modified nucleotide. For example, about 1% of the nucleotides in the self-replicating RNA molecule that contain uridine can be modified, such as by replacement of uridine with pseudouridine. In other examples, the desired amount (percentage) of two, three, or four particular nucleotides (nucleotides that contain uridine, cytidine, guanosine, or adenine) in a self-replicating RNA molecule are modified nucleotides. For example, 0.001%-25%, 0.01%-25%, 0.1%-25, or 1%-25% of a particular nucleotide in a self-replicating RNA molecule are modified nucleotides. In other examples, 0.001%-20%, 0.001%-15%, 0.001%-10%, 0.01%-20%, 0.01%-15%, 0.1%-25, 0.01%-10%, 1%-20%, 1%-15%, 1%-10%, or about 5%, about 10%, about 15%, about 20% of a particular nucleotide in a self-replicating RNA molecule are modified nucleotides.

It is preferred that less than 100% of the nucleotides in a self-replicating RNA molecule are modified nucleotides. It is also preferred that less than 100% of a particular nucleotide in a self-replicating RNA molecule are modified nucleotides. Thus, preferred self-replicating RNA molecules comprise at least some unmodified nucleotides.

There are more than 96 naturally occurring nucleoside modifications found on mammalian RNA. See, e.g., Limbach et al., *Nucleic Acids Research,* 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated herein by reference in their entirety, and many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxy-isopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-O-methyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Any one or any combination of these modified nucleobases may be included in the self-replicating RNA of the invention. Many of these modified nucleobases and their corresponding ribonucleosides are available from commercial suppliers.

If desired, the self-replicating RNA molecule can contain phosphoramidate, phosphorothioate, and/or methylphosphonate linkages.

Self-replicating RNA molecules that comprise at least one modified nucleotide can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

Suitable synthetic methods can be used alone, or in combination with one or more other methods (e.g., recombinant DNA or RNA technology), to produce a self-replicating RNA molecule that contain one or more modified nucleotides. Suitable methods for de novo synthesis are well-known in the art and can be adapted for particular applications. Exemplary methods include, for example, chemical synthesis using suitable protecting groups such as CEM (Masuda et al., (2007) *Nucleic Acids Symposium Series* 51:3-4), the β-cyanoethyl phosphoramidite method (Beaucage S L et al. (1981) *Tetrahedron Lett* 22:1859); nucleoside H-phosphonate method (Garegg P et al. (1986) *Tetrahedron Lett* 27:4051-4; Froehler B C et al. (1986) *Nucl Acid Res* 14:5399-407; Garegg P et al. (1986) *Tetrahedron Lett* 27:4055-8; Gaffney B L et al. (1988) *Tetrahedron Lett* 29:2619-22). These chemistries can be performed or adapted for use with automated nucleic acid synthesizers that are commercially available. Additional suitable synthetic methods are disclosed in Uhlmann et al. (1990) *Chem Rev* 90:544-84, and Goodchild J (1990) *Bioconjugate Chem* 1: 165. Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like. Suitable methods for transcription, translation and expression of nucleic acid sequences are known and conventional in the art. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast Saccharomyces, Eds. Strathern et al., Cold Spring Harbor Press, Vols. I and II, 1982; and Sambrook et al., Molecular Cloning: A Laboratory Manual, Cold Spring Harbor Press, 1989.)

The presence and/or quantity of one or more modified nucleotides in a self-replicating RNA molecule can be determined using any suitable method. For example, a self-replicating RNA can be digested to monophosphates (e.g., using nuclease P1) and dephosphorylated (e.g., using a suitable phosphatase such as CIAP), and the resulting nucleosides analyzed by reversed phase HPLC (e.g., using a YMC Pack ODS-AQ column (5 micron, 4.6×250 mm) and elute using a gradient, 30% B (0-5 min) to 100% B (5-13 min) and at 100% B (13-40) min, flow Rate (0.7 ml/min), UV detection (wavelength: 260 nm), column temperature (30° C.). Buffer A (20 mM acetic acid-ammonium acetate pH 3.5), buffer B (20 mM acetic acid-ammonium acetate pH 3.5/methanol [90/10])).

The self-replicating RNA may be associated with a delivery system. The self-replicating RNA may be administered with or without an adjuvant.

RNA Delivery Systems

The self-replicating RNA described herein are suitable for delivery in a variety of modalities, such as naked RNA delivery or in combination with lipids, polymers or other compounds that facilitate entry into the cells. Self-replicating RNA molecules can be introduced into target cells or subjects using any suitable technique, e.g., by direct injection, microinjection, electroporation, lipofection, biolystics, and the like. The self-replicating RNA molecule may also be introduced into cells by way of receptor-mediated endocytosis. See e.g., U.S. Pat. No. 6,090,619; Wu and Wu, J. Biol. Chem., 263:14621 (1988); and Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine residues (SEQ ID NO:4)), which is itself coupled to an integrin receptor-binding moiety (e.g., a cyclic peptide having the sequence Arg-Gly-Asp (SEQ ID NO:5).

The self-replicating RNA molecules can be delivered into cells via amphiphiles. See e.g., U.S. Pat. No. 6,071,890. Typically, a nucleic acid molecule may form a complex with the cationic amphiphile. Mammalian cells contacted with the complex can readily take it up.

The self-replicating RNA can be delivered as naked RNA (e.g. merely as an aqueous solution of RNA) but, to enhance entry into cells and also subsequent intercellular effects, the self-replicating RNA is preferably administered in combination with a delivery system, such as a particulate or emulsion delivery system. A large number of delivery systems are well known to those of skill in the art. Such delivery systems include, for example liposome-based delivery (Debs and Zhu (1993) WO 93/24640; Mannino and Gould-Fogerite (1988) BioTechniques 6(7): 682-691; Rose U.S. Pat. No. 5,279,833; Brigham (1991) WO 91/06309; and Felgner et al. (1987) Proc. Natl. Acad. Sci. USA 84: 7413-7414), as well as use of viral vectors (e.g., adenoviral (see, e.g., Berns et al. (1995) Ann. NY Acad. Sci. 772: 95-104; Ali et al. (1994) Gene Ther. 1: 367-384; and Haddada et al. (1995) Curr. Top. Microbiol. Immunol. 199 (Pt 3): 297-306 for review), papillomaviral, retroviral (see, e.g., Buchscher et al. (1992) J. Virol. 66(5) 2731-2739; Johann et al. (1992) J. Virol. 66 (5): 1635-1640 (1992); Sommerfelt et al., (1990) Virol. 176:58-59; Wilson et al. (1989) J. Virol. 63:2374-2378; Miller et al., J. Virol. 65:2220-2224 (1991); Wong-Staal et al., PCT/US94/05700, and Rosenburg and Fauci (1993) in Fundamental Immunology, Third Edition Paul (ed) Raven Press, Ltd., New York and the references therein, and Yu et al., Gene Therapy (1994) supra.), and adeno-associated viral vectors (see, West et al. (1987) Virology 160:38-47; Carter et al. (1989) U.S. Pat. No. 4,797,368; Carter et al. WO 93/24641 (1993); Kotin (1994) Human Gene Therapy 5:793-801; Muzyczka (1994) J. Clin. Invst. 94:1351 and Samulski (supra) for an overview of AAV vectors; see also, Lebkowski, U.S. Pat. No. 5,173,414; Tratschin et al. (1985) Mol. Cell. Biol. 5(11):3251-3260; Tratschin, et al. (1984) Mol. Cell. Biol., 4:2072-2081; Hermonat and Muzyczka (1984) Proc. Natl. Acad. Sci. USA, 81:6466-6470; McLaughlin et al. (1988) and Samulski et al. (1989) J. Virol., 63:03822-3828), and the like.

Three particularly useful delivery systems are (i) liposomes, (ii) non-toxic and biodegradable polymer microparticles, and (iii) cationic submicron oil-in-water emulsions.

Liposomes

Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic. Suitable classes of phospholipid include, but are not limited to, phosphatidylethanolamines, phosphatidylcholines, phosphatidylserines, and phosphatidylglycerols, and some useful phospholipids are listed in Table 2. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC and dodecylphosphocholine. The lipids can be saturated or unsaturated.

Liposomes can be formed from a single lipid or from a mixture of lipids. A mixture may comprise (i) a mixture of anionic lipids (ii) a mixture of cationic lipids (iii) a mixture of zwitterionic lipids (iv) a mixture of anionic lipids and cationic lipids (v) a mixture of anionic lipids and zwitterionic lipids (vi) a mixture of zwitterionic lipids and cationic lipids or (vii) a mixture of anionic lipids, cationic lipids and zwitterionic lipids. Similarly, a mixture may comprise both saturated and unsaturated lipids. For example, a mixture may comprise DSPC (zwitterionic, saturated), DlinDMA (cationic, unsaturated), and/or DMPG (anionic, saturated). Where a mixture of lipids is used, not all of the component lipids in the mixture need to be amphiphilic e.g. one or more amphiphilic lipids can be mixed with cholesterol.

The hydrophilic portion of a lipid can be PEGylated (i.e. modified by covalent attachment of a polyethylene glycol). This modification can increase stability and prevent non-specific adsorption of the liposomes. For instance, lipids can be conjugated to PEG using techniques such as those disclosed in Heyes et al. (2005) *J Controlled Release* 107:276-87.

A mixture of DSPC, DlinDMA, PEG-DMPG and cholesterol can be used to form liposomes. A separate aspect of the invention is a liposome comprising DSPC, DlinDMA, PEG-DMG and cholesterol. This liposome preferably encapsulates RNA, such as a self-replicating RNA e.g. encoding an immunogen.

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter ≤50 nm, and LUVs have a diameter >50 nm. Liposomes useful with of the invention are ideally LUVs with a diameter in the range of 50-220 nm. For a composition comprising a population of LUVs with different diameters: (i) at least 80% by number should have diameters in the range of 20-220 nm, (ii) the average diameter (Zav, by intensity) of the population is ideally in the range of 40-200 nm, and/or (iii) the diameters should have a polydispersity index <0.2.

Techniques for preparing suitable liposomes are well known in the art e.g. see Liposomes: Methods and Protocols, Volume 1: Pharmaceutical Nanocarriers: Methods and Protocols. (ed. Weissig). Humana Press, 2009. ISBN 160327359X; Liposome Technology, volumes I, II & III. (ed. Gregoriadis). Informa Healthcare, 2006; and Functional Polymer Colloids and Microparticles volume 4 (Microspheres, microcapsules & liposomes). (eds. Arshady & Guyot). Citus Books, 2002. One useful method involves mixing (i) an ethanolic solution of the lipids (ii) an aqueous solution of the nucleic acid and (iii) buffer, followed by mixing, equilibration, dilution and purification (Heyes et al. (2005) *J Controlled Release* 107:276-87.).

RNA is preferably encapsulated within the liposomes, and so the liposome forms a outer layer around an aqueous RNA-containing core. This encapsulation has been found to protect RNA from RNase digestion. The liposomes can include some external RNA (e.g. on the surface of the liposomes), but preferably, at least half of the RNA (and ideally substantially all of it) is encapsulated.

Polymeric Microparticles

Various polymers can form microparticles to encapsulate or adsorb RNA. The use of a substantially non-toxic polymer means that a recipient can safely receive the particles, and the use of a biodegradable polymer means that the particles can be metabolised after delivery to avoid long-term persistence. Useful polymers are also sterilisable, to assist in preparing pharmaceutical grade formulations.

Suitable non-toxic and biodegradable polymers include, but are not limited to, poly(α-hydroxy acids), polyhydroxy butyric acids, polylactones (including polycaprolactones), polydioxanones, polyvalerolactone, polyorthoesters, polyanhydrides, polycyanoacrylates, tyrosine-derived polycarbonates, polyvinyl-pyrrolidinones or polyester-amides, and combinations thereof.

In some embodiments, the microparticles are formed from poly(α-hydroxy acids), such as a poly(lactides) ("PLA"), copolymers of lactide and glycolide such as a poly(D,L-lactide-co-glycolide) ("PLG"), and copolymers of D,L-lactide and caprolactone. Useful PLG polymers include those having a lactide/glycolide molar ratio ranging, for example, from 20:80 to 80:20 e.g. 25:75, 40:60, 45:55, 55:45, 60:40, 75:25. Useful PLG polymers include those having a molecular weight between, for example, 5,000-200,000 Da e.g. between 10,000-100,000, 20,000-70,000, 40,000-50,000 Da.

The microparticles ideally have a diameter in the range of 0.02 μm to 8 μm. For a composition comprising a population of microparticles with different diameters at least 80% by number should have diameters in the range of 0.03-7 μm.

Techniques for preparing suitable microparticles are well known in the art e.g. see Functional Polymer Colloids and Microparticles volume 4 (Microspheres, microcapsules & liposomes). (eds. Arshady & Guyot). Citus Books, 2002; *Polymers in Drug Delivery*. (eds. Uchegbu & Schatzlein). CRC Press, 2006. (in particular chapter 7) and *Microparticulate Systems for the Delivery of Proteins and Vaccines*. (eds. Cohen & Bernstein). CRC Press, 1996. To facilitate adsorption of RNA, a microparticle may include a cationic surfactant and/or lipid e.g. as disclosed in O'Hagan et al. (2001) *J Virology* 75:9037-9043; and Singh et al. (2003) *Pharmaceutical Research* 20: 247-251. An alternative way of making polymeric microparticles is by molding and curing e.g. as disclosed in WO2009/132206.

Microparticles of the invention can have a zeta potential of between 40-100 mV. RNA can be adsorbed to the microparticles, and adsorption is facilitated by including cationic materials (e.g. cationic lipids) in the microparticle.

Oil-In-Water Cationic Emulsions

Oil-in-water emulsions are known for adjuvanting influenza vaccines e.g. the MF59™ adjuvant in the FLUAD™ product, and the AS03 adjuvant in the PREPANDRIX™ product. RNA delivery can be accomplished with the use of an oil-in-water emulsion, provided that the emulsion includes one or more cationic molecules. For instance, a cationic lipid can be included in the emulsion to provide a positively charged droplet surface to which negatively-charged RNA can attach.

The emulsion comprises one or more oils. Suitable oil(s) include those from, for example, an animal (such as fish) or a vegetable source. The oil is ideally biodegradable (metabolizable) and biocompatible. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α, β, γ, δ, ε or ξ tocopherols can be used, but α-tocopherols are preferred. D-α-tocopherol and DL-α-tocopherol can both be used. A preferred α-tocopherol is DL-α-tocopherol. An oil combination comprising squalene and a tocopherol (e.g. DL-(α-tocopherol) can be used.

Preferred emulsions comprise squalene, a shark liver oil which is a branched, unsaturated terpenoid ($C_{30}H_{50}$; $[(CH_3)_2C[{=}CHCH_2CH_2C(CH_3)]_2{=}CHCH_2\text{-}]_2$; 2,6,10,15,19,23-hexamethyl-2,6,10,14,18,22-tetracosahexaene; CAS RN 7683-64-9).

The oil in the emulsion may comprise a combination of oils e.g. squalene and at least one further oil.

The aqueous component of the emulsion can be plain water (e.g. w.f.i.) or can include further components e.g. solutes. For instance, it may include salts to form a buffer e.g. citrate or phosphate salts, such as sodium salts. Typical buffers include: a phosphate buffer, a Tris buffer; a borate buffer; a succinate buffer; a histidine buffer, or a citrate buffer. A buffered aqueous phase is preferred, and buffers will typically be included in the 5-20 mM range.

The emulsion also includes a cationic lipid. Preferably this lipid is a surfactant so that it can facilitate formation and stabilization of the emulsion. Useful cationic lipids generally contains a nitrogen atom that is positively charged under physiological conditions e.g. as a tertiary or quaternary amine. This nitrogen can be in the hydrophilic head group of an amphiphilic surfactant. Useful cationic lipids include, but are not limited to: 1,2-dioleoyloxy-3-(trimethylammonio) propane (DOTAP), 3'-[N—(N',N'-Dimethylaminoethane)-carbamoyl]Cholesterol (DC Cholesterol), dimethyldioctadecyl-ammonium (DDA e.g. the bromide), 1,2-Dimyristoyl-3-Trimethyl-AmmoniumPropane (DMTAP), dipalmitoyl (C16:0)trimethyl ammonium propane (DPTAP), distearoyltrimethylammonium propane (DSTAP). Other useful cationic lipids are: benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC), cetyl trimethylammonium chloride (CTAC), N,N',N'-polyoxyethylene (10)-N-tallow-1,3-diaminopropane, dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemetha-naminium chloride (DEBDA), dialkyldimetylammonium salts, [1-(2,3-dioleyloxy)-propyl]-N,N,N, trimethylammonium chloride, 1,2-diacyl-3-(trimethylammonio) propane (acyl group=dimyristoyl, dipalmitoyl, distearoyl, dioleoyl), 1,2-diacyl-3 (dimethylammonio)propane (acyl group=dimyristoyl, dipalmitoyl, distearoyl, dioleoyl), 1,2-dioleoyl-3-(4'-trimethyl-ammonio) butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes (C12Me6; C12BU6), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group (C^GluPhCnN), ditetradecyl glutamate ester with pendant amino group (Cl4GIuCnN+), cationic derivatives of cholesterol, including but not limited to cholesteryl-3 β-oxysuccinamidoethylenetrimethylammonium salt, cholesteryl-3 β-oxysuccinamidoethylene-dimethylamine, cholesteryl-3 β-carboxyamidoethylenetrimethylammonium salt, and cholesteryl-3 β-carboxyamidoethylenedimethylamine. Other useful cationic lipids are described in US 2008/0085870 and US 2008/0057080, which are incorporated herein by reference. The cationic lipid is preferably biodegradable (metabolizable) and biocompatible.

In addition to the oil and cationic lipid, an emulsion can include a non-ionic surfactant and/or a zwitterionic surfactant. Such surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the Spans), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin and Triton X-100.

Mixtures of these surfactants can be included in the emulsion e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxy-polyethoxyethanol (Triton X-100) is also suitable. Another useful combination comprises laureth 9 plus a polyoxyethylene sorbitan ester and/or an octoxynol. Useful mixtures can comprise a surfactant with a HLB value in the range of 10-20 (e.g. polysorbate 80, with a HLB of 15.0) and a surfactant with a HLB value in the range of 1-10 (e.g. sorbitan trioleate, with a HLB of 1.8).

Preferred amounts of oil (% by volume) in the final emulsion are between 2-20% e.g. 5-15%, 6-14%, 7-13%, 8-12%. A squalene content of about 4-6% or about 9-11% is particularly useful.

Preferred amounts of surfactants (% by weight) in the final emulsion are between 0.001% and 8%. For example: polyoxyethylene sorbitan esters (such as polysorbate 80) 0.2 to 4%, in particular between 0.4-0.6%, between 0.45-0.55%, about 0.5% or between 1.5-2%, between 1.8-2.2%, between 1.9-2.1%, about 2%, or 0.85-0.95%, or about 1%; sorbitan esters (such as sorbitan trioleate) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth 9) 0.1 to 8%, preferably 0.1 to 10% and in particular 0.1 to 1% or about 0.5%.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (excess oil).

An important parameter for ensuring immunostimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 250 nm e.g. less than 200 nm, less than 150 nm. The average droplet size is usefully in the range of 80-180 nm. Ideally, at least 80% (by number) of the emulsion's oil droplets are less than 250 nm in diameter, and preferably at least 90%. Apparatuses for determining the average droplet size in an emulsion, and the size distribution, are commercially available. These typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan).

Ideally, the distribution of droplet sizes (by number) has only one maximum i.e. there is a single population of droplets distributed around an average (mode), rather than having two maxima. Preferred emulsions have a polydispersity of <0.4 e.g. 0.3, 0.2, or less.

Suitable emulsions with submicron droplets and a narrow size distribution can be obtained by the use of microfluidization. This technique reduces average oil droplet size by propelling streams of input components through geometrically fixed channels at high pressure and high velocity. These streams contact channel walls, chamber walls and each other. The results shear, impact and cavitation forces cause a reduction in droplet size. Repeated steps of microfluidization can be performed until an emulsion with a desired droplet size average and distribution are achieved.

As an alternative to microfluidization, thermal methods can be used to cause phase inversion. These methods can also provide a submicron emulsion with a tight particle size distribution.

Preferred emulsions can be filter sterilized i.e. their droplets can pass through a 220 nm filter. As well as providing a sterilization, this procedure also removes any large droplets in the emulsion.

In certain embodiments, the cationic lipid in the emulsion is DOTAP. The cationic oil-in-water emulsion may comprise from about 0.5 mg/ml to about 25 mg/ml DOTAP. For example, the cationic oil-in-water emulsion may comprise DOTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 12 mg/ml, about 18 mg/ml, about 20 mg/ml, about 21.8 mg/ml, about 24 mg/ml, etc. In an exemplary embodiment, the cationic oil-in-water emulsion comprises from about 0.8 mg/ml to about 1.6 mg/ml DOTAP, such as 0.8 mg/ml, 1.2 mg/ml, 1.4 mg/ml or 1.6 mg/ml.

In certain embodiments, the cationic lipid is DC Cholesterol. The cationic oil-in-water emulsion may comprise DC Cholesterol at from about 0.1 mg/ml to about 5 mg/ml DC Cholesterol. For example, the cationic oil-in-water emulsion may comprise DC Cholesterol from about 0.1 mg/ml to about 5 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.62 mg/ml to about 5 mg/ml, from about 1 mg/ml to about 5 mg/ml, from about 1.5 mg/ml to about 5 mg/ml, from about 2 mg/ml to about 5 mg/ml, from about 2.46 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, from about 0.1 mg/ml to about 4.92 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.46 mg/ml, from about 0.1 mg/ml to about 2 mg/ml, from about 0.1 mg/ml to about 1.5 mg/ml, from about 0.1 mg/ml to about 1 mg/ml, from about 0.1 mg/ml to about 0.62 mg/ml, about 0.15 mg/ml, about 0.3 mg/ml, about 0.6 mg/ml, about 0.62 mg/ml, about 0.9 mg/ml, about 1.2 mg/ml, about 2.46 mg/ml, about 4.92 mg/ml, etc. In an exemplary embodiment, the cationic oil-in-water emulsion comprises from about 0.62 mg/ml to about 4.92 mg/ml DC Cholesterol, such as 2.46 mg/ml.

In certain embodiments, the cationic lipid is DDA. The cationic oil-in-water emulsion may comprise from about 0.1 mg/ml to about 5 mg/ml DDA. For example, the cationic oil-in-water emulsion may comprise DDA at from about 0.1 mg/ml to about 5 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.5 mg/ml, from about 0.1 mg/ml to about 2 mg/ml, from about 0.1 mg/ml to about 1.5 mg/ml, from about 0.1 mg/ml to about 1.45 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.6 mg/ml to about 5 mg/ml, from about 0.73 mg/ml to about 5 mg/ml, from about 0.8 mg/ml to about 5 mg/ml, from about 0.9 mg/ml to about 5 mg/ml, from about 1.0 mg/ml to about 5 mg/ml, from about 1.2 mg/ml to about 5 mg/ml, from about 1.45 mg/ml to about 5 mg/ml, from about 2 mg/ml to about 5 mg/ml, from about 2.5 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, about 1.2 mg/ml, about 1.45 mg/ml, etc. Alternatively, the cationic oil-in-water emulsion may comprise DDA at about 20 mg/ml, about 21 mg/ml, about 21.5 mg/ml, about 21.6 mg/ml, about 25 mg/ml. In an exemplary embodiment, the cationic oil-in-water emulsion comprises from about 0.73 mg/ml to about 1.45 mg/ml DDA, such as 1.45 mg/ml.

Catheters or like devices may be used to deliver the self-replicating RNA molecules of the invention, as naked RNA or in combination with a delivery system, into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

The present invention includes the use of suitable delivery systems, such as liposomes, polymer microparticles or submicron emulsion microparticles with encapsulated or adsorbed self-replicating RNA, to deliver a self-replicating RNA molecule that encodes two or more CMV proteins, for example, to elicit an immune response alone, or in combination with another macromolecule. The invention includes liposomes, microparticles and submicron emulsions with adsorbed and/or encapsulated self-replicating RNA molecules, and combinations thereof.

The self-replicating RNA molecules associated with liposomes and submicron emulsion microparticles can be effectively delivered to a host cell, and can induce an immune response to the protein encoded by the self-replicating RNA.

Polycistronic self replicating RNA molecules that encode CMV proteins, and VRPs produced using polycistronic alphavirus replicons, can be used to form CMV protein complexes in a cell. Complexes include, but are not limited to, gB/gH/gL; gH/gL; gH/gL/gO; gM/gN; gH/gL/UL128/UL130/UL131; and UL128/UL130/UL131.

In some embodiments combinations of VRPs are delivered to a cell. Combinations include, but are not limited to:

1. a gH/gL VRP and another VRP;
2. a gH/gL VRP and a gB VRP;
3. a gH/gL/gO VRP and a gB VRP;
4. a gB VRP and a gH/gL/UL128/UL130/UL131 VRP;
5. a gB VRP and UL128/UL130/UL131 VRP;
6. a gB VRP and a gM/gN VRP;
7. a gB VRP, a gH/gL VRP, and a UL128/UL130/UL131 VRP;
8. a gB VRP, a gH/gL/gO VRP, and a UL128/UL130/UL131 VRP;
9. a gB VRP, a gM/gN VRP, a gH/gL VRP, and a UL128/UL130/UL131 VRP;
10. a gB VRP, a gM/gN VRP, a gH/gL/O VRP, and a UL128/UL130/UL131 VRP;
11. a gH/gL VRP and a UL128/UL130/UL131 VRP; and In some embodiments combinations of self-replicating RNA molecules are delivered to a cell. Combinations include, but are not limited to:

1. a self-replicating RNA molecule encoding gH/gL and a self-replicating RNA molecule encoding another protein;
2. a self-replicating RNA molecule encoding gH and gL and a self-replicating RNA molecule encoding gB;
3. a self-replicating RNA molecule encoding gH, gL and gO and a self-replicating RNA molecule encoding gB;
4. a self-replicating RNA molecule encoding gB and a self-replicating RNA molecule encoding gH, gL, UL128, UL130 and UL131;
5. a self-replicating RNA molecule encoding gB and a self-replicating RNA molecule encoding UL128, UL130 and UL131;
6. a self-replicating RNA molecule encoding gB and a self-replicating RNA molecule encoding gM and gN;
7. a self-replicating RNA molecule encoding gB, a self-replicating RNA molecule encoding gH and gL, and a self-replicating RNA molecule encoding UL128, UL130 and UL131;
8. a self-replicating RNA molecule encoding gB, a self-replicating RNA molecule encoding gH, gL, and gO, and a self-replicating RNA molecule encoding UL128, UL130 and UL131;
9. a self-replicating RNA molecule encoding gB, a self-replicating RNA molecule encoding gM and gN, a self-replicating RNA molecule encoding gH and gL, and a self-replicating RNA molecule encoding UL128, UL130 and UL131;
10. a self-replicating RNA molecule encoding gB, a self-replicating RNA molecule encoding gM and gN, a self-replicating RNA molecule encoding gH, gL and gO, and a self-replicating RNA molecule encoding UL128, UL130 and UL131;
11. a self-replicating RNA molecule encoding gH and gL, and a self-replicating RNA molecule encoding UL128, UL130 and UL131; and CMV Proteins Suitable CMV proteins include gB, gH, gL, gO, and can be from any CMV strain. Other suitable CMV proteins include UL128, UL130 and UL131, and can be from any CMV strain. For example, CMV proteins can be from Merlin, AD169, VR1814, Towne, Toledo, TR, PH, TB40, or Fix strains of CMV. Exemplary CMV proteins and fragments are described herein. These proteins and fragments can be encoded by any suitable nucleotide sequence, including sequences that are codon optimized or deoptimized for expression in a desired host, such as a human cell. Exemplary sequences of CMV proteins and nucleic acids encoding the proteins are provided in Table 2

TABLE 2

| | |
|---|---|
| Full length gH polynucleotide | (CMV gH FL) SEQ ID NO: 31 |
| Full length gH polypeptide | (CMV gH FL) SEQ ID NO: 32 |
| Full length gL polynucleotide | (CMV gL FL) SEQ ID NO: 35 |
| Full length gL polypeptide | (CMV gL FL) SEQ ID NO: 36 |
| Full length gO polynucleotide | (CMV gO FL) SEQ ID NO: 41 |
| Full length gO polypeptide | (CMV gO FL) SEQ ID NO: 42 |
| gH sol polynucleotide | (CMV gH sol) SEQ ID NO: 33 |
| gH sol polypeptide | (CMV gH sol) SEQ ID NO: 34 |
| Full length UL128 polynucleotide | (CMV UL128 FL) SEQ ID NO: 43 |
| Full length UL128 polypeptide | (CMV UL128 FL) SEQ ID NO: 44 |
| Full length UL130 polynucleotide | (CMV UL130 FL) SEQ ID NO: 45 |
| Full length UL130 polypeptide | (CMV UL130 FL) SEQ ID NO: 46 |
| Full length UL131 polynucleotide | (CMV UL131 FL) SEQ ID NO: 47 |
| Full length UL131 polypeptide | (CMV UL131 FL) SEQ ID NO: 48 |
| Full length gB polynucleotide | (CMV gB FL) SEQ ID NO: 25 |
| Full length gB polypeptide | (CMV gB FL) SEQ ID NO: 26 |
| gB sol 750 polynucleotide | (CMV gB 750) SEQ ID NO: 27 |
| gB sol 750 polypeptide | (CMV gB 750) SEQ ID NO: 28 |
| gB sol 692 polynucleotide | (CMV gB 692) SEQ ID NO: 29 |
| gB sol 692 polypeptide | (CMV gB 692) SEQ ID NO: 30 |
| Full length gM polynucleotide | (CMV gM FL) SEQ ID NO: 37 |
| Full length gM polypeptide | (CMV gM FL) SEQ ID NO: 38 |
| Full length gN polynucleotide | (CMV gN FL) SEQ ID NO: 39 |
| Full length gN polypeptide | (CMV gN FL) SEQ ID NO: 40 |

CMV gB Proteins

A gB protein can be full length or can omit one or more regions of the protein. Alternatively, fragments of a gB protein can be used. gB amino acids are numbered according to the full-length gB amino acid sequence (CMV gB FL) shown in SEQ ID NO: 26, which is 907 amino acids long. Suitable regions of a gB protein, which can be excluded from the full-length protein or included as fragments include: the signal sequence (amino acids 1-24), a gB-DLD disintegrin-like domain (amino acids 57-146), a furin cleavage site (amino acids 459-460), a heptad repeat region (679-693), a membrane spanning domain (amino acids 751-771), and a cytoplasmic domain from amino acids 771-906. In some embodiments a gB protein includes amino acids 67-86 (Neutralizing Epitope AD2) and/or amino acids 532-635 (Immunodominant Epitope AD1). Specific examples of gB fragments, include "gB sol 692," which includes the first 692 amino acids of gB, and "gB sol 750," which includes the first 750 amino acids of gB. The signal sequence, amino acids 1-24, can be present or absent from gB sol 692 and gB sol 750 as desired. Optionally, the gB protein can be a gB fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, or 875 amino acids. A gB fragment can begin at any of residue number: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, or 897.

Optionally, a gB fragment can extend further into the N-terminus by 5, 10, 20, or 30 amino acids from the starting residue of the fragment. Optionally, a gB fragment can extend further into the C-terminus by 5, 10, 20, or 30 amino acids from the last residue of the fragment.

CMV gH Proteins

In some embodiments, a gH protein is a full-length gH protein (CMV gH FL, SEQ ID NO: 32, for example, which is a 742 amino acid protein). gH has a membrane spanning domain and a cytoplasmic domain starting at position 716 to position 743. Removing amino acids from 717 to 743 provides a soluble gH (e.g., CMV gH sol, SEQ ID NO: 34). In some embodiments the gH protein can be a gH fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, or 725 amino acids. Optionally, the gH protein can be a gH fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, or 725 amino acids. A gH fragment can begin at any of residue number: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, or 732.

gH residues are numbered according to the full-length gH amino acid sequence (CMV gH FL) shown in SEQ ID NO: 32. Optionally, a gH fragment can extend further into the N-terminus by 5, 10, 20, or 30 amino acids from the starting residue of the fragment. Optionally, a gH fragment can extend further into the C-terminus by 5, 10, 20, or 30 amino acids from the last residue of the fragment.

CMV gL Proteins

In some embodiments a gL protein is a full-length gL protein (CMV gL FL, SEQ ID NO: 36, for example, which is a 278 amino acid protein). In some embodiments a gL fragment can be used. For example, the number of amino acids in the fragment can comprise 10, 15, 20, 30, 40, 50, 60, 70, 80, 90, 100, 125, 150, 175, 200, 225, or 250 amino acids. A gL fragment can begin at any of residue number: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, or 268.

gL residues are numbered according to the full-length gL amino acid sequence (CMV gL FL) shown in SEQ ID NO: 36. Optionally, a gL fragment can extend further into the N-terminus by 5, 10, 20, or 30 amino acids from the starting residue of the fragment. Optionally, a gL fragment can extend further into the C-terminus by 5, 10, 20, or 30 amino acids from the last residue of the fragment.

CMV gO Proteins

In some embodiments, a gO protein is a full-length gO protein (CMV gO FL, SEQ ID NO: 42, for example, which is a 472 amino acid protein). In some embodiments the gO protein can be a gO fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, 350, 375, 400, 425, or 450 amino acids. A gO fragment can begin at any of residue number: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, or 462.

gO residues are numbered according to the full-length gO amino acid sequence (CMV gO FL) shown in SEQ ID NO: 42. Optionally, a gO fragment can extend further into the N-terminus by 5, 10, 20, or 30 amino acids from the starting residue of the fragment. Optionally, a gO fragment can extend further into the C-terminus by 5, 10, 20, or 30 amino acids from the last residue of the fragment.

CMV gM Proteins

In some embodiments, a gM protein is a full-length gM protein (CMV gM FL, SEQ ID NO: 38, for example, which is a 371 amino acid protein). In some embodiments the gM protein can be a gM fragment of 10 amino acids or longer. For example, the number of amino acids in the fragment can comprise 10, 15, 20, 30, 40, 50, 60, 70, 80, 90, 100, 125, 150, 175, 200, 225, 250, 275, 300, 325, or 350 amino acids. A gM fragment can begin at any of residue number: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, or 361.

gM residues are numbered according to the full-length gM amino acid sequence (CMV gM FL) shown in SEQ ID NO: 38. Optionally, a gM fragment can extend further into the N-terminus by 5, 10, 20, or 30 amino acids from the starting residue of the fragment. Optionally, a gM fragment can extend further into the C-terminus by 5, 10, 20, or 30 amino acids from the last residue of the fragment.

CMV gN Proteins

In some embodiments, a gN protein is a full-length gN protein (CMV gN FL, SEQ ID NO: 40, for example, which is a 135 amino acid protein). In some embodiments the gN protein can be a gN fragment of 10 amino acids or longer. For example, the number of amino acids in the fragment can comprise 10, 15, 20, 30, 40, 50, 60, 70, 80, 90, 100, or 125 amino acids. A gN fragment can begin at any of residue number: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125.

gN residues are numbered according to the full-length gN amino acid sequence (CMV gN FL) shown in SEQ ID NO: 40. Optionally, a gN fragment can extend further into the N-terminus by 5, 10, 20, or 30 amino acids from the starting residue of the fragment. Optionally, a gN fragment can extend further into the C-terminus by 5, 10, 20, or 30 amino acids from the last residue of the fragment.

CMV UL128 Proteins

In some embodiments, a UL128 protein is a full-length UL128 protein (CMV UL128 FL, SEQ ID NO: 44, for example, which is a 171 amino acid protein). In some embodiments the UL128 protein can be a UL128 fragment of 10 amino acids or longer. For example, the number of amino acids in the fragment can comprise 10, 15, 20, 30, 40, 50, 60, 70, 80, 90, 100, 125, or 150 amino acids. A UL128 fragment can begin at any of residue number: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or 161.

UL128 residues are numbered according to the full-length UL128 amino acid sequence (CMV UL128 FL) shown in SEQ ID NO: 44. Optionally, a UL128 fragment can extend further into the N-terminus by 5, 10, 20, or 30 amino acids from the starting residue of the fragment. Optionally, a UL128 fragment can extend further into the C-terminus by 5, 10, 20, or 30 amino acids from the last residue of the fragment.

CMV UL130 Proteins

In some embodiments, a UL130 protein is a full-length UL130 protein (CMV UL130 FL, SEQ ID NO: 46, for example, which is a 214 amino acid protein). In some embodiments the UL130 protein can be a UL130 fragment of 10 amino acids or longer. For example, the number of amino acids in the fragment can comprise 10, 15, 20, 30, 40, 50, 60, 70, 80, 90, 100, 125, 150, 175, or 200 amino acids. A UL130 fragment can begin at any of residue number: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, or 204.

UL130 residues are numbered according to the full-length UL130 amino acid sequence (CMV UL130 FL) shown in SEQ ID NO: 46. Optionally, a UL130 fragment can extend further into the N-terminus by 5, 10, 20, or 30 amino acids from the starting residue of the fragment. Optionally, a UL130 fragment can extend further into the C-terminus by 5, 10, 20, or 30 amino acids from the last residue of the fragment.

CMV UL131 Proteins

In some embodiments, a UL131 protein is a full-length UL131 protein (CMV UL131, SEQ ID NO: 48, for example, which is a 129 amino acid protein). In some embodiments the UL131 protein can be a UL131 fragment of 10 amino acids or longer. For example, the number of amino acids in the fragment can comprise 10, 15, 20, 30, 40, 50, 60, 70, 80, 90, 100, 125, 150, 175, or 200 amino acids. A UL131 fragment can begin at any of residue number: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119.

UL131 residues are numbered according to the full-length UL131 amino acid sequence (CMV UL131 FL) shown in SEQ ID NO: 48. Optionally, a UL131 fragment can extend further into the N-terminus by 5, 10, 20, or 30 amino acids from the starting residue of the fragment. Optionally, a UL131 fragment can extend further into the C-terminus by 5, 10, 20, or 30 amino acids from the last residue of the fragment.

As stated above, the invention relates to recombinant polycistronic nucleic acid molecules that contain a first sequence encoding a first herpesvirus protein or fragment thereof, and a second sequence encoding a second herpesvirus protein or fragment thereof. Accordingly, the foregoing description of certain preferred embodiments, such as alphavirus VRPs and self-replicating RNAs that contain sequences encoding two or more CMV proteins or fragments thereof, is illustrative of the invention but does not limit the scope of the invention. It will be appreciated that the sequences encoding CMV proteins in such preferred embodiments, can be replaced with sequences encoding proteins, such as gH and gL, or fragments thereof that are 10 amino acids long or longer, from other herpesviruses such as HHV-1, HHV-2, HHV-3, HHV-4, HHV-6, HHV-7 and HHV-8. For example, suitable VZV (HHV-3) proteins include gB, gE, gH, gI, and gL, and fragments thereof that are 10 amino acids long or longer, and can be from any VZV strain. For example, VZV proteins or fragments thereof can be from pOka, Dumas, HJO, CA123, or DR strains of VZV. These exemplary VZV proteins and fragments thereof can be encoded by any suitable nucleotide sequence, including sequences that are codon optimized or deoptimized for expression in a desired host, such as a human cell. Exemplary sequences of VZV proteins are provided herein.

For example, in one embodiment, the polycistronic nucleic acid molecule contains a first sequence encoding a VZV gH protein or fragment thereof, and a second sequence encoding a VZV gL protein or fragment thereof.

In some embodiments, each of the sequences encoding a herpes virus protein or fragment that are present in the polycistronic nucleic acid molecule is operably linked to its own control elements. For example, each sequences encoding a herpes virus protein or fragment is operably linked to its own subgenomic promoter. Thus the polycistronic nucleic acid molecule, such as an alphavirus replicon, can contain two, three, four or five subgenomic promoters, each of which controls expression of a herpes virus protein or fragment. When this type of polycistronic nucleic acid molecule is a self replicating RNA, such as an alphavirus replicon, it can be packaged as a VRP, or associate or formulated with an RNA delivery system.

Methods and Uses

In some embodiments, self-replicating RNA molecules or VRPs are administered to an individual to stimulate an immune response. In such embodiments, self-replicating RNA molecules or VRPs typically are present in a composition which may comprise a pharmaceutically acceptable carrier and, optionally, an adjuvant. See, e.g., U.S. Pat. Nos. 6,299,884; 7,641,911; 7,306,805; and US 2007/0207090.

The immune response can comprise a humoral immune response, a cell-mediated immune response, or both. In some embodiments an immune response is induced against each delivered CMV protein. A cell-mediated immune response can comprise a Helper T-cell ($T_h$) response, a CD8+ cytotoxic T-cell (CTL) response, or both. In some embodiments the immune response comprises a humoral immune response, and the antibodies are neutralizing antibodies. Neutralizing antibodies block viral infection of cells. CMV infects epithelial cells and also fibroblast cells. In some embodiments the immune response reduces or prevents infection of both cell types. Neutralizing antibody responses can be complement-dependent or complement-independent. In some embodiments the neutralizing antibody response is complement-independent. In some embodiments the neutralizing antibody response is cross-neutralizing; i.e., an antibody generated against an administered composition neutralizes a CMV virus of a strain other than the strain used in the composition.

A useful measure of antibody potency in the art is "50% neutralization titer." To determine 50% neutralizing titer, serum from immunized animals is diluted to assess how dilute serum can be yet retain the ability to block entry of 50% of viruses into cells. For example, a titer of 700 means that serum retained the ability to neutralize 50% of virus after being diluted 700-fold. Thus, higher titers indicate more potent neutralizing antibody responses. In some embodiments, this titer is in a range having a lower limit of about 200, about 400, about 600, about 800, about 1000, about 1500, about 2000, about 2500, about 3000, about 3500, about 4000, about 4500, about 5000, about 5500, about 6000, about 6500, or about 7000. The 50% neutralization titer range can have an upper limit of about 400, about 600, about 800, about 1000, about 1500, about 200, about 2500, about 3000, about 3500, about 4000, about 4500, about 5000, about 5500, about 6000, about 6500, about 7000, about 8000, about 9000, about 10000, about 11000, about 12000, about 13000, about 14000, about 15000, about 16000, about 17000, about 18000, about 19000, about 20000, about 21000, about 22000, about 23000, about 24000, about 25000, about 26000, about 27000, about 28000, about 29000, or about 30000. For example, the 50% neutralization titer can be about 3000 to about 6500. "About" means plus or minus 10% of the recited value. Neutralization titer can be measured as described in the specific examples, below.

An immune response can be stimulated by administering VRPs or self-replicating RNA to an individual, typically a mammal, including a human. In some embodiments the immune response induced is a protective immune response, i.e., the response reduces the risk or severity of CMV infection. Stimulating a protective immune response is particularly desirable in some populations particularly at risk from CMV infection and disease. For example, at-risk populations include solid organ transplant (SOT) patients, bone marrow transplant patients, and hematopoietic stem cell transplant (HSCT) patients. VRPs can be administered to a transplant donor pre-transplant, or a transplant recipient pre- and/or post-transplant. Because vertical transmission from mother to child is a common source of infecting infants, administering VRPs or self-replicating RNA to a woman who can become pregnant is particularly useful.

Any suitable route of administration can be used. For example, a composition can be administered intra-muscularly, intra-peritoneally, sub-cutaneously, or trans-dermally. Some embodiments will be administered through an intra-mucosal route such as intra-orally, intra-nasally, intra-vaginally, and intra-rectally. Compositions can be administered according to any suitable schedule.

All patents, patent applications, and references cited in this disclosure, including nucleotide and amino acid sequences referred to by accession number, are expressly incorporated herein by reference. The above disclosure is a general description. A more complete understanding can be obtained by reference to the following specific examples, which are provided for purposes of illustration only.

Example 1

Delivery of Individual CMV Antigens Using a VRP Platform

Each of CMV glycoproteins gB and gH induce neutralizing responses, and gB is the dominant antigen among antibodies in human sera that neutralize infection of fibroblasts (Britt et al. (1990) J. Virol. 64(3):1079-85). The following experiments demonstrate in mice a neutralizing response against these antigens delivered using a VRP platform.

Each CMV antigen was cloned into a pcDNA-6His vector (Invitrogen) and tested for protein expression before cloning into an alphavirus replicon vector, pVCR 2.1 SalI/XbaI derived from the plasmid described by Perri et al. (J. Virol 77(19)10394-10403 (2003)) producing the constructs shown in FIG. 2. pVCR 2.1 SalI/XbaI is a self-replicating RNA vector that, when electroporated with defective helper capsid and glycoprotein RNA, forms an infectious alphavirus particle.

pVCR vectors were used to make RNA which was electroporated into baby hamster kidney (BHKV) cells in the presence of defective helper capsid and glycoprotein RNAs derived from Venezuelan equine encephalitis virus (VEE). After electroporation, the supernatant containing secreted alphavirus vector particles (VRPs) was collected, purified, titered, and used for mouse immunization studies. Mice were immunized with $1\times10^6$ infectious units (IU)/mouse in a series of two immunizations, three weeks apart. The terminal bleed was three weeks after the second immunization.

Monocistronic gB, gH and gL VRPs

Figure 1:
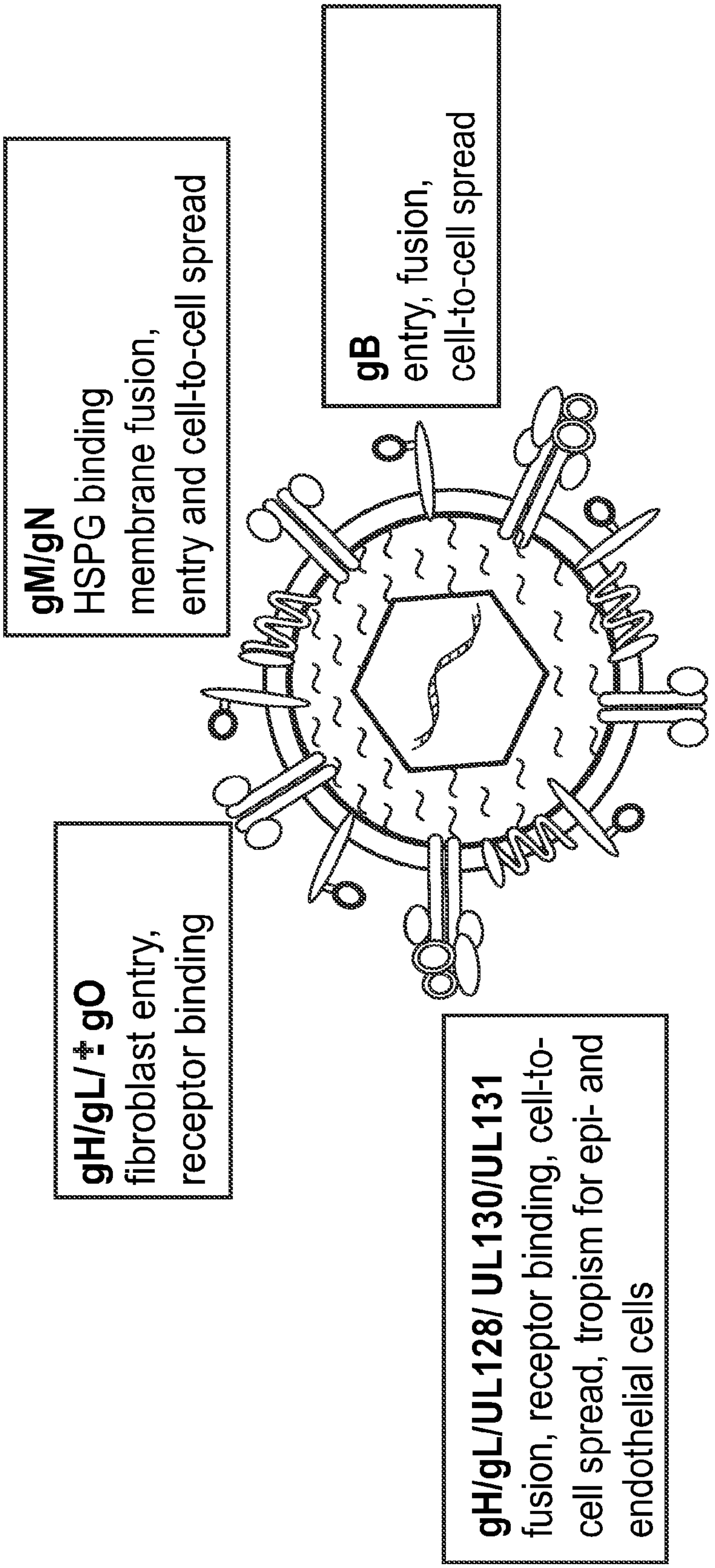
FIG. 1 is a schematic of CMV identifying known glycoprotein complexes involved in CMV entry into target cells. Envelope glycoproteins represent attractive vaccine candidates as they are expressed on the viral surface and can elicit protective and long lasting virus-neutralizing humoral immune responses. The structural glycoproteins mediating these processes can be divided into two classes; those that are conserved throughout the herpes virus family and those that are not. Among those that are conserved are gB, gH, gL, gM and gN. Many of these glycoproteins form complexes with one another (gH/gL/±gO; gH/gL/UL128/UL130/UL131; gM/gN) to facilitate localization to the viral surface and to carry out their functions in viral attachment, entry and cell fusion.
Figure 2A:
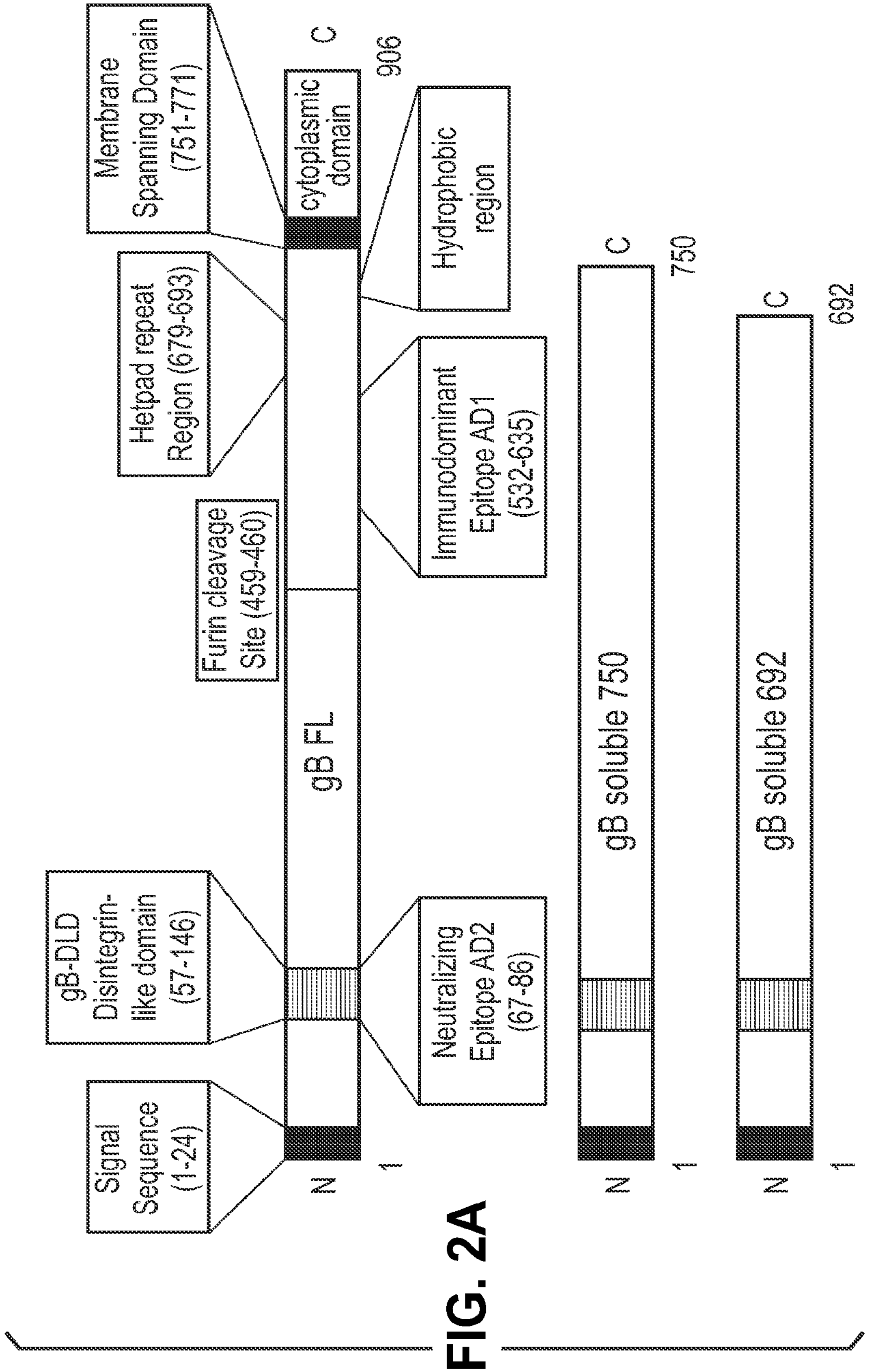
FIGS. 2A-2F are schematics of CMV constructs.
Figure 2B:
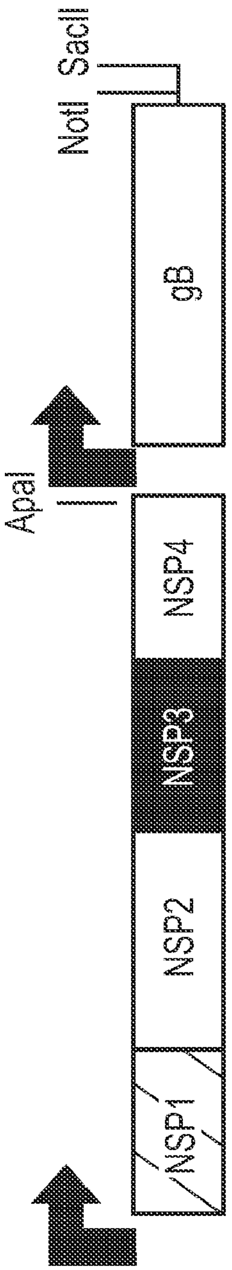
Figure 2C:
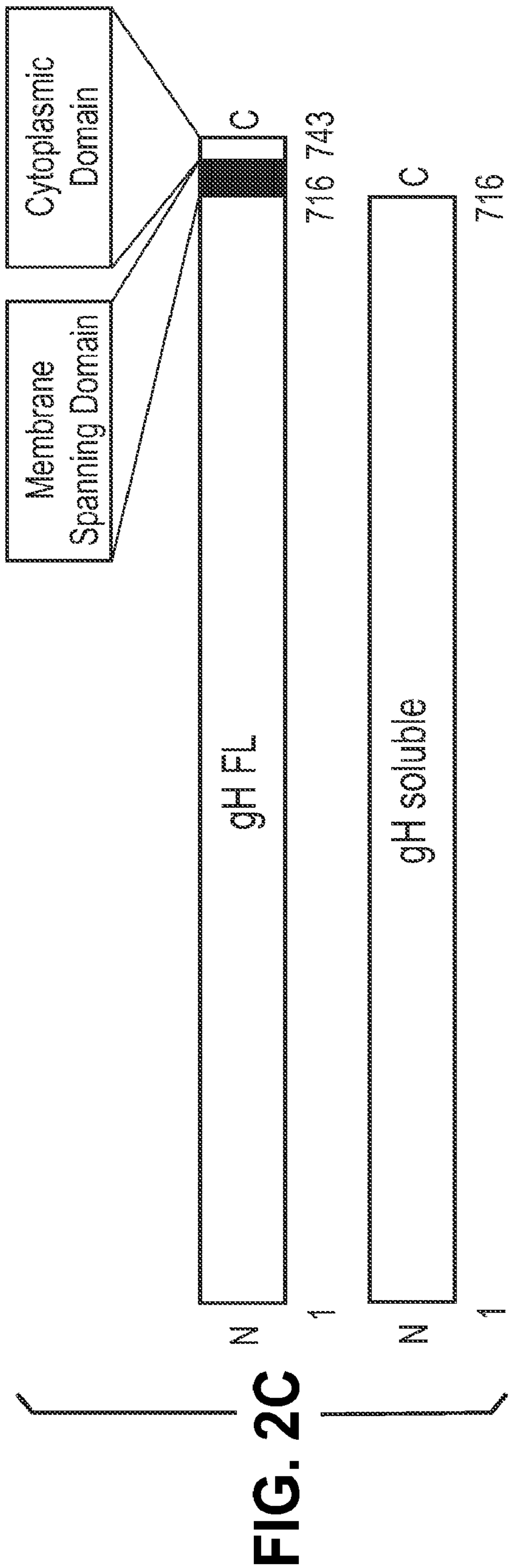
Figure 2D:
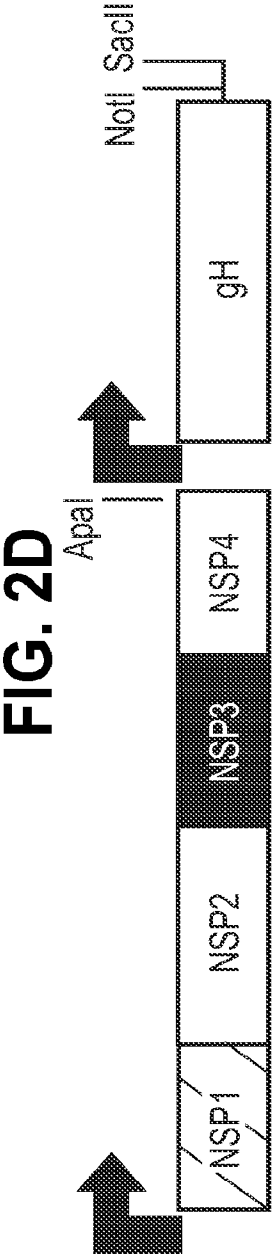
Figure 2E:
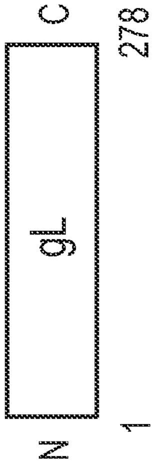
Figure 2F:
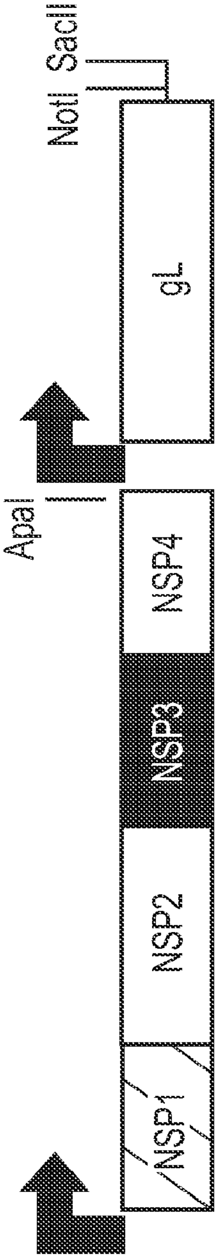

Two different versions of soluble gB were constructed: "gB sol 750" lacks the transmembrane spanning domain and cytoplasmic domain; and "gB sol 692" also lacks a hydrophobic region (FIG. 2A) and is similar to the Reap et al. construct. A soluble gH which lacks the transmembrane spanning domain and cytoplasmic domain ("gH sol 716") was also constructed (FIG. 2C). Sera from immunized mice were screened in several assays. Immunoblot (data not shown) and immunofluorescence assays were used to confirm specific antibody responses to the antigens. Neutralization assays were used to demonstrate that the elicited antibody responses were able to neutralize CMV infection.

Sera from immunized mice were examined by immunofluorescence for recognition of gB in 293T cells transfected with constructs expressing gB-6His. Cells were probed with either anti-His antibodies ("anti-6His"), a monoclonal gB antibody ("anti-gB 27-156"), or collected pooled mouse sera. Pre-immune serum was negative in all cases. In cells transfected with constructs expressing gB FL-6His, fixed, and permeabilized, anti-6His staining revealed an expression pattern of surface expression with a punctate cytoplasmic pattern most likely corresponding to the endocytic/exocytic trafficking pathway. Both anti-gB 27-156 and the pooled mouse sera showed a similar expression pattern. Sera from mice immunized with each of gB FL VRPs, gB sol 750 VRPs, and gB sol 692 VRPs showed the same expression pattern.

Mice immunized with gH FL VRPs and gH sol 716 VRPs produced antibodies specific to gH. Immunofluorescence analysis of 293T cells transfected with constructs expressing gH FL-6His detected strong recognition of gH by anti-6His, anti-gH, and pooled mouse sera. Sera collected from mice immunized with gL VRPs produced a specific antibody response as determined by immunoblot analysis and immunofluorescence. gL VRPs failed to elicit a neutralizing response.

Figure 3A:
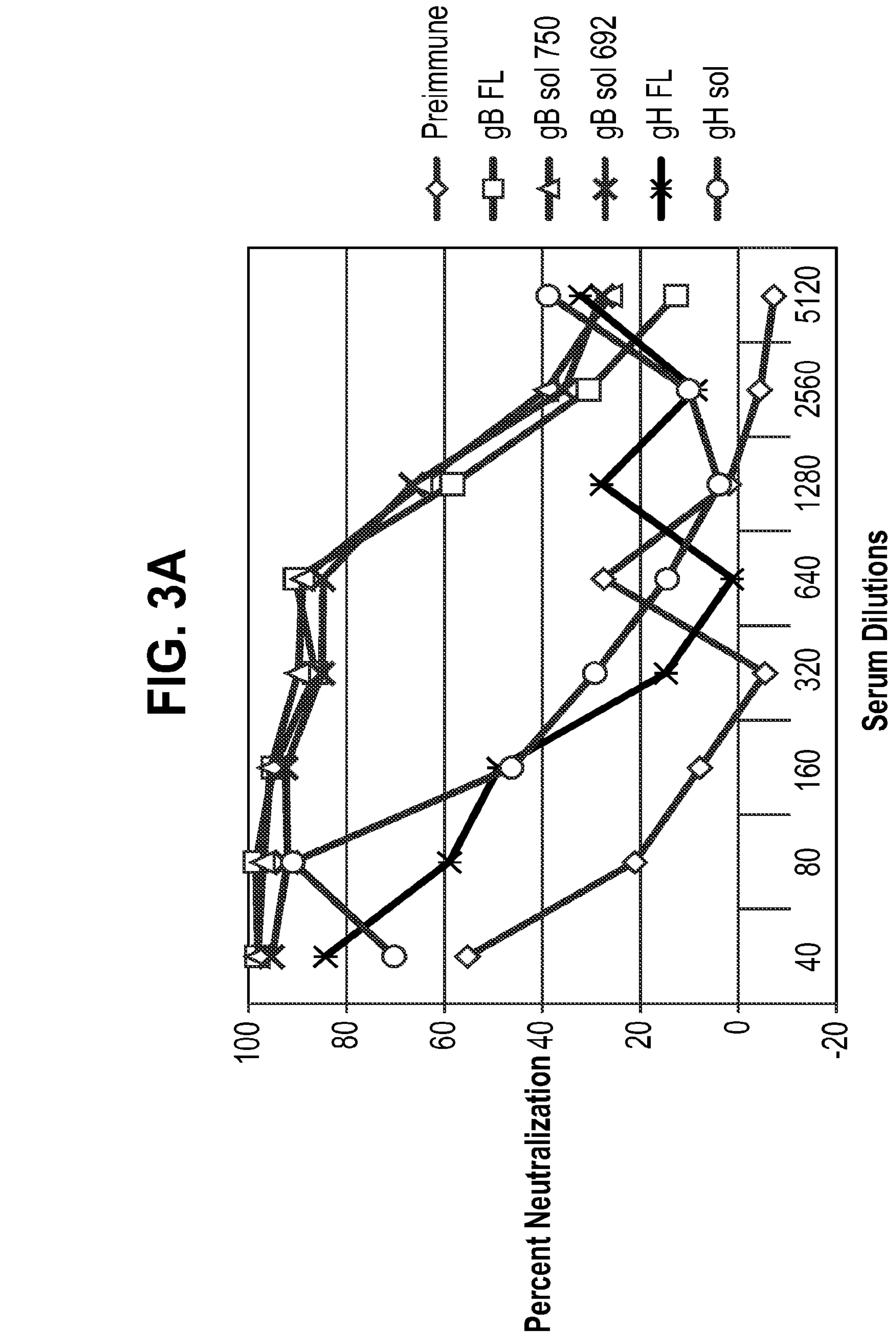
FIGS. 3A and 3B show that mice immunized with gB (FL, sol 750, sol 692) or gH (FL, sol) VRPs induced antibody responses that were neutralizing in the presence of guinea pig complement. The neutralization assay was done by pre-incubating the CMV virus strain TB40UL32E-GFP (which encodes the enhanced green fluorescent protein-GFP, Sampaio et al (2005) J. Virol. 79(5):2754-67), with mouse sera and guinea pig complement before infection of ARPE-19 epithelial cells. Five days post-infection, the number of GFP positive cells was determined.
Figure 3B:
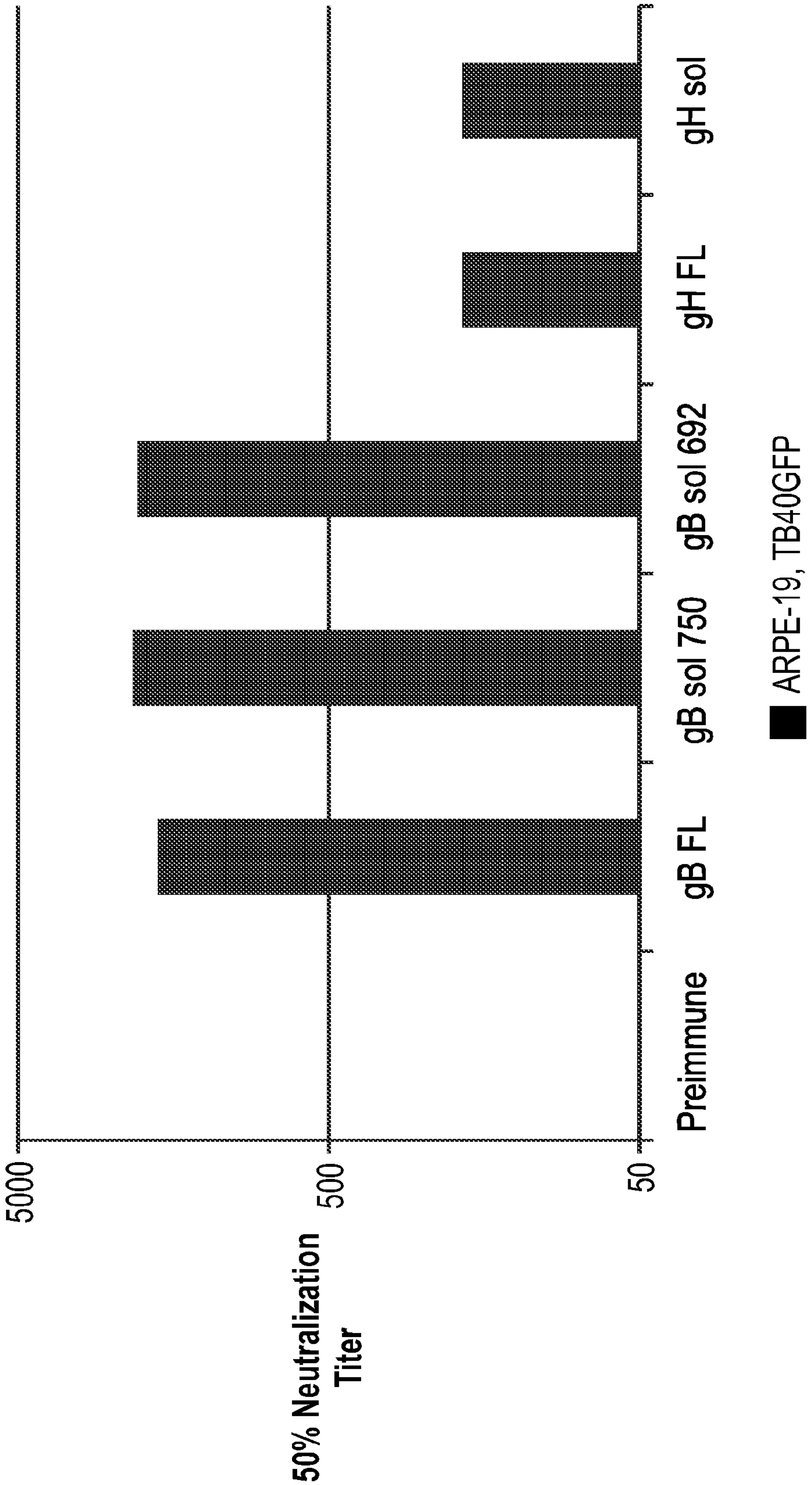

Sera from mice immunized with gB VRPs or gH VRPs were analyzed for the presence of neutralizing antibodies using a CMV neutralization assay. Sera at various dilutions were pre-incubated with CMV virus TB40UL32EGFP ("TB40-GFP," a clinical isolate engineered to express GFP and then added to ARPE-19 epithelial cells and incubated for 5 days. At 5 days post-infection, the GFP-positive cells were counted. In this assay, cells incubated with serum containing neutralizing antibodies have fewer GFP-positive cells compared to cells incubated with virus alone or with virus incubated with pre-immune sera. Sera from mice immunized with gB VRPs, gB FL VRPs, gB sol 750 VRPs, or gB sol 692 VRPs had strong neutralizing activity in the presence of guinea pig complement (50% neutralization titer at a serum dilution of 1:1280-1:2560; FIG. 3). Sera from mice immunized with gH FL VRPs or gH sol VRPs had some neutralizing activity that was independent of guinea pig complement (FIG. 3).

Example 2

Construction of Polycistronic Alphavirus Vectors

CMV produces several multi-protein complexes during infection. To determine whether a single replicon expressing all components of a desired complex can be used to produce the CMV complex in a subject, or whether components of the complex could be co-delivered from multiple replicon vectors, we designed a platform that allows controlled expression of multiple CMV proteins.

An alphavirus vector (pVCR 2.1 SalI/XbaI) was modified to allow assembly of multiple subgenomic promoters (SGP) and genes of interest (GOI). pVCR 2.1SalI/XbaI ApaI site at 11026-31 bp was changed from GGGCCC (SEQ ID NO: 7) to GGCGCC (SEQ ID NO: 8). ClaI and PmlI restriction sites added in the region immediately downstream of the first subgenomic promoter and SalI-XbaI insert sites. The sequence at 7727-7754 bp was changed from ctcgatgtacttccgaggaactgatgtg (SEQ ID NO: 9) to ATCGATGTACTTCCGAGGAACTCACGTG (SEQ ID NO: 10).

A shuttling vector system was designed to allow insertion of a GOI directly downstream of a SGP using the SalI-XbaI sites. pcDNA 3.1 (−) C was modified as follows. Three SalI sites were deleted: positions 1046-1051 bp, 3332-3337 bp and 5519-21, 1-3 bp from GTCGAC (SEQ ID NO: 11) to GTCTAC (SEQ ID NO: 12). pcDNA 3.1 (−) C was modified to mutate an XbaI site at position 916-921 bp from TCTAGA (SEQ ID NO: 13) to TCAAGA (SEQ ID NO: 14).

pcDNA 3.1 (–) C was modified to add a ClaI site and SacII site at positions 942-947 (ClaI) and 950-955 (SacII) bp from ctggatatctgcag (SEQ ID NO: 15) to ATCGATATCCGCGG (SEQ ID NO: 16).

Once the restriction sites were added and the resulting sequence was verified, the region from bp 7611-7689 (ctataactctctacggctaacctgaatggactacgacatagtctagtcgac-caagcctctagacggc gcgcccaccca) (SEQ ID NO: 17) was amplified from the modified pVCR 2.1 alphavirus vector using the following primers

```
Forward SGP S-X Not F:
                                          (SEQ ID NO: 18)
5'ATAAGAATGCGGCCGCCTATAACTCTCTACGGCTAACC 3'

Reverse SGP S-X Cla R:
                                          (SEQ ID NO: 19)
5'CCATCGATTGGGTGGGCGCGCCGTCTAG3'
or

Forward SGP S-X Cla F:
                                          (SEQ ID NO: 20)
5'CCATCGATCTATAACTCTCTACGGCTAACC3'
and

Reverse SGP S-X Sac R:
                                        (S SEQ ID NO: 21)
5'TCCCCGCGGTGGGTGGGCGCGCCGTCTAG 3'.
```

The amplified regions were added into the modified pcDNA 3.1(–)C vector to make shuttling vectors (pcDNA SV) between appropriate sites (NotI-ClaI or ClaI-SacII). Insertion of the NotI-SGP Sal-Xba-ClaI forms pcDNA SV cassette 2, insertion of the ClaI-SGP Sal-Xba-SacII forms pcDNA SV cassette 3. These SV cassettes were sequenced. The pcDNA SV cassette 2 contains an additional 12 bp between the XbaI site and the ClaI site (CCACTGTGATCG) (SEQ ID NO: 22) because the ClaI site was not cut in the pcDNA SV cassette 2 vector. A PmlI site was therefore added. For pcDNA SV cassette 2, the PmlI site was inserted at bp 1012 (CACGTG) (SEQ ID NO: 23). For cassette 3, PmlI site was added at bp 935-940 (ACTGTG (SEQ ID NO: 24) was changed to CACGTG (SEQ ID NO: 23).

For each polycistronic vector the first gene was inserted directly into the pVCR 2.1 modified vector using the SalI-XbaI sites. The second gene was ligated into pcDNA SV cassette 2 using SalI-XbaI and excised using NotI-PmlI, NotI-SacII or PCRed using primers for NotI-ClaI and digested using NotI and ClaI. The resulting insert SGP-SalI-GOI-Xba was ligated into the modified pVCR 2.1 vector using NotI-PmlI, NotI-SacII, or NotI-ClaI sites. The NotI-ClaI insert was used only when a desired gene in the construct contained a PmlI site.

In some cases a third gene was ligated into pcDNA SV cassette 3 using SalI-XbaI and excised using PmlI-SacII or PCRed using primers for ClaI-SacII and digested using ClaI and SacII. The resulting insert SGP-SalI-GOI-XbaI was ligated into the modified pVCR 2.1 using PmlI-SacII or ClaI-SacII.

SalI-XbaI digestion was used to validate construction of the polycistronic vector DNA. After digestion with SalI-XbaI, agarose gel electrophoresis was performed to confirm the presence of the GOIs. The polycistronic vector DNA was then linearized with PmeI overnight, purified using Qiagen's PCR purification kit, and used as template to make RNA using the Ambion mMessage mMachine kit. RNA quality was checked by running a sample aliquot on an RNA agarose gel.

Expression from a Polycistronic Vector

Figure 4A:
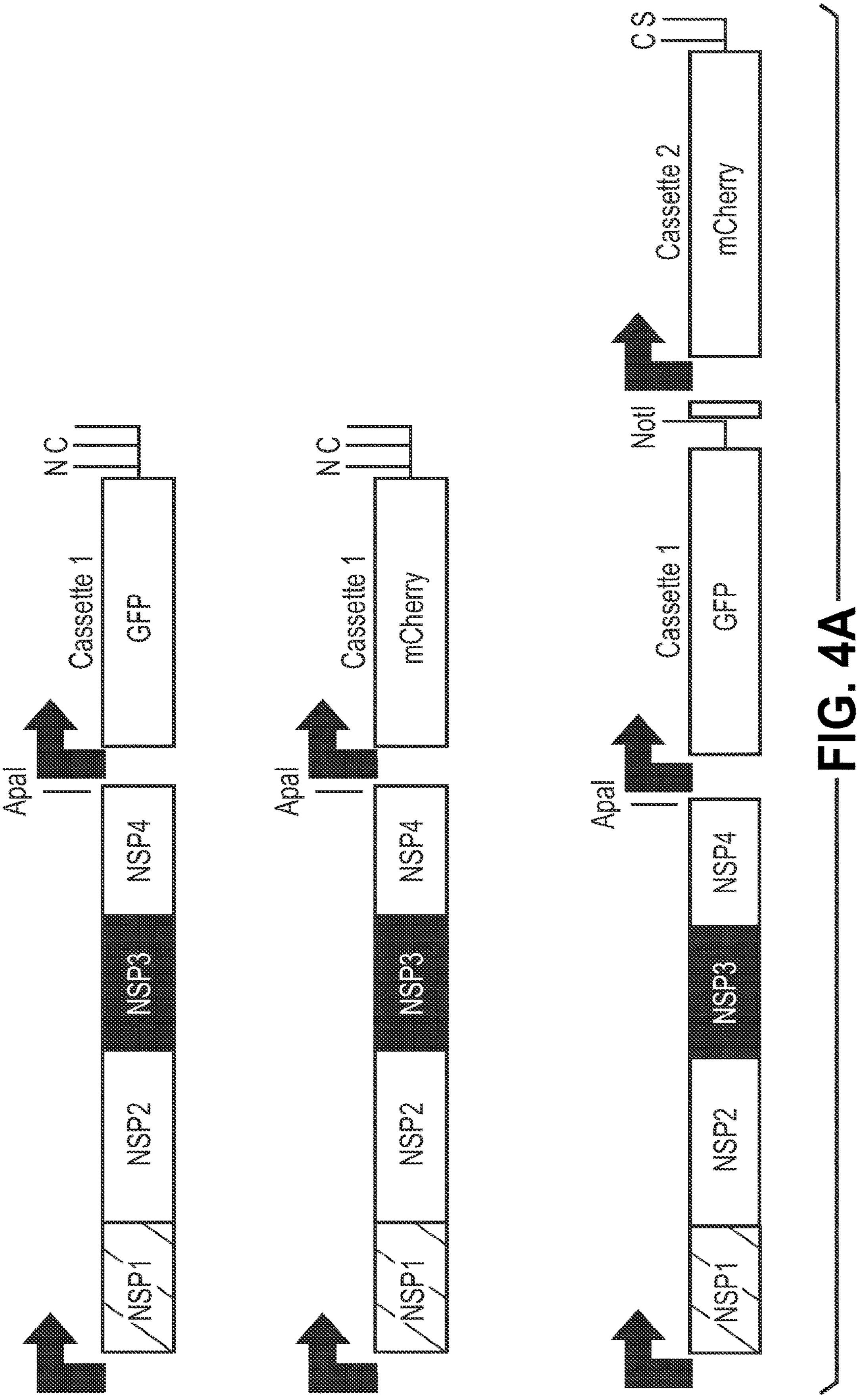
FIG. 4A is a schematic illustration of monocistronic replicons encoding green fluorescent protein (GFP) or red fluorescent protein (mCherry) and a bicistronic replicon encoding GFP and mCherry. "NSP1," "NSP2," "NSP3," and "NSP4," are alphavirus nonstructural proteins 1-4, respectively. The polycistronic alphavirus replicon system was designed by making modifications to the existing alphavirus replicon system to accommodate multiple subgenomic promoters driving genes of interest.

Fluorescent proteins GFP (green fluorescent protein) and mCherry (red fluorescent protein) were used as the GOIs to assess the ability of the polycistronic vector to express two proteins. We prepared a bicistronic vector in which GFP would be expressed using a first subgenomic promoter and mCherry would be expressed from a second subgenomic promoter (FIG. 4A). Polynucleotides containing coding sequences for these proteins were inserted using SalI-XbaI sites. The first polynucleotide (GFP) was inserted directly into the modified alphavirus replicon vector. The second polynucleotide (mCherry) was inserted first into a shuttling vector that contains a subgenomic promoter directly upstream of the coding sequence. A fragment containing both the second subgenomic promoter and the second polynucleotide was isolated and ligated into the modified alphavirus replicon vector containing the first polynucleotide, providing an alphavirus replicon with multiple subgenomic promoters.

VRPs were produced in BHKV cells by electroporating replicon RNAs with defective helper RNAs for Cap and Gly. The VRPs were harvested 24 hours after electroporation and used to infect BHKV cells at a multiplicity of infection (MOI) of 20 infectious units (IU) per cell.

Figure 4B:
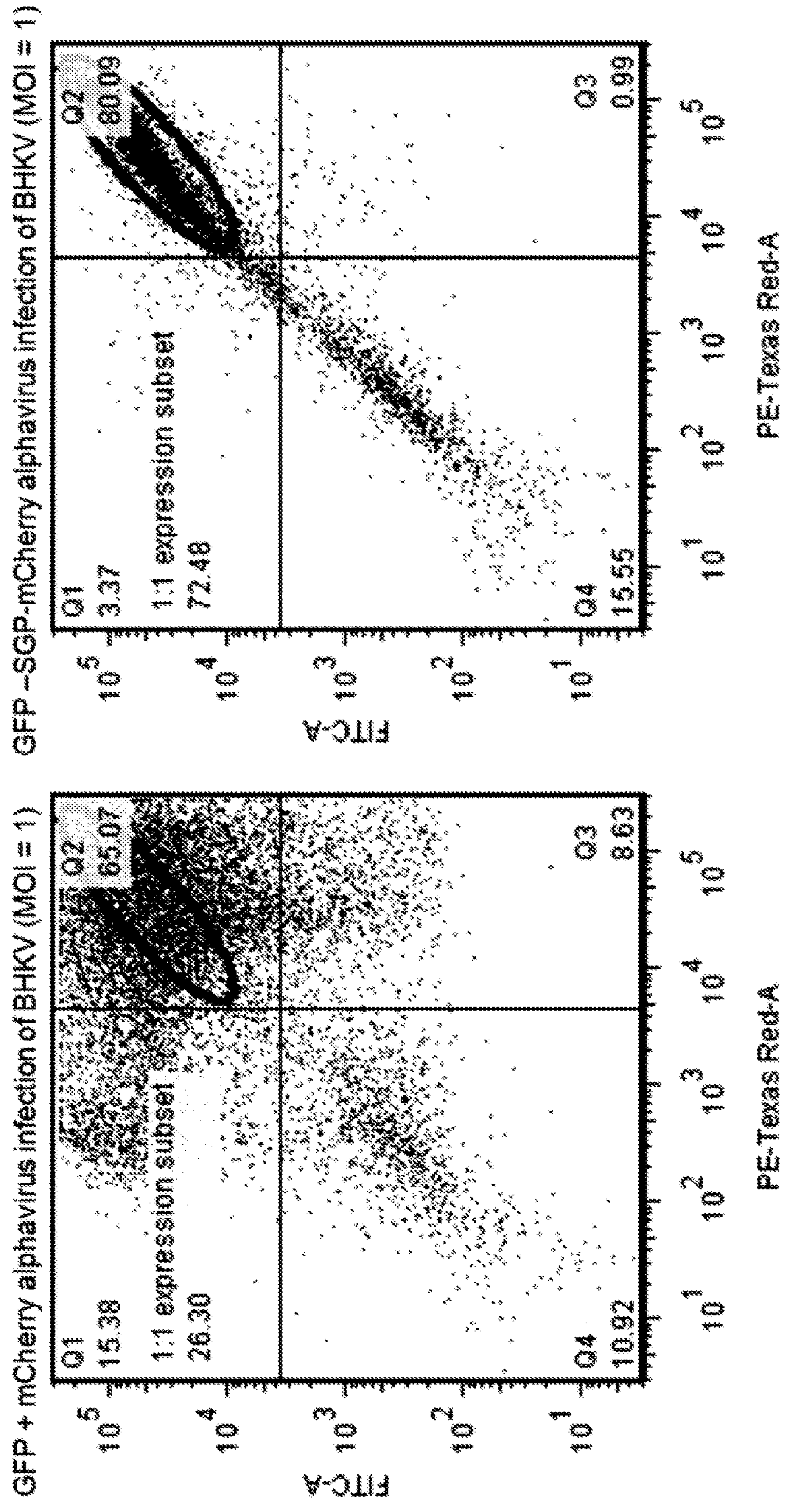
FIG. 4B are fluorescence plots showing FACS analysis of BHKV cells infected with VRPs containing mono- and bicistronic RNAs. Polycistronic alphavirus VRPs yield more cells expressing both genes of interest at approximately equal amounts (GFP and mCherry; 72.48%) than co-infection of GFP VRP+mCherry VRP (26.30%). See Example 2.

The experiment tested four sets of VRPs: one VRP expressing only GFP; one VRP expressing mCherry; one VRP expressing only GFP and one VRP expressing only mCherry, both at MOI of 20 IU/cell; and one VRP containing the bicistronic vector GFP(1)-SGPmCherry(2). VRP-infected BHKV cells were examined 24 hours post-infection to determine percent of colocalization. Nearly all the cells were positive for GFP or mCherry when singly infected. Cells infected with two separate VRPs appeared either green or red. Very few cells were yellow, indicating that few cells expressed GFP and mCherry at equal levels and that there was a low level of co-infection. These data were confirmed using FACS analysis (FIG. 4B).

In contrast, cells infected with alphavirus containing the bicistronic vector GFP(1)-SGPmCherry(2) were all yellow, which indicates approximately equal expression of GFP and mCherry. This study demonstrates that multiple proteins can be expressed successfully from a single polycistronic alphavirus replicon vector.

Example 3

Production of CMV Complexes

This example demonstrates that CMV protein complexes can be formed in a cell after delivery of the complex components from a polycistronic alphavirus replicon vector.

gH/gL and gH/gL/gO Complexes

Figure 5A:
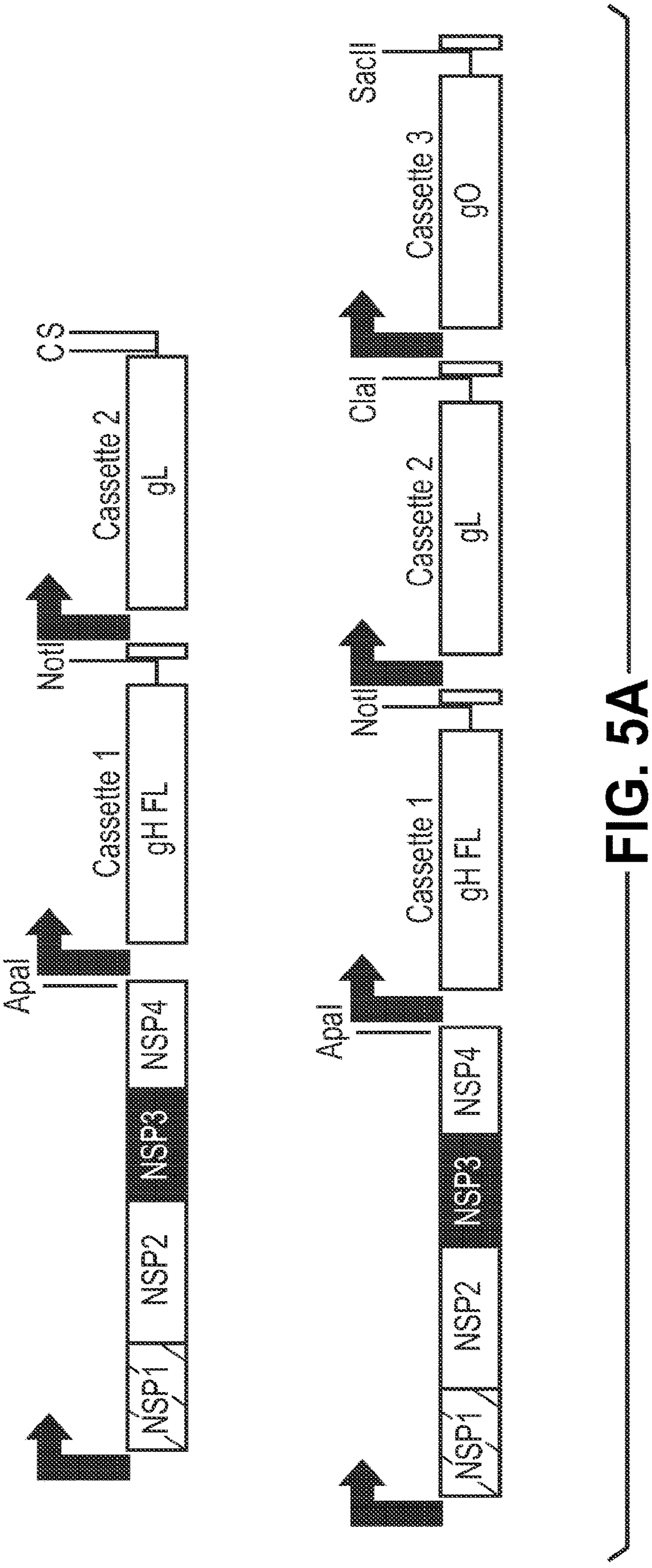
FIG. 5A is a schematic illustration of construction of polycistronic alphavirus replicon constructs encoding gH/gL and gH/gL/gO.
Figure 5B:
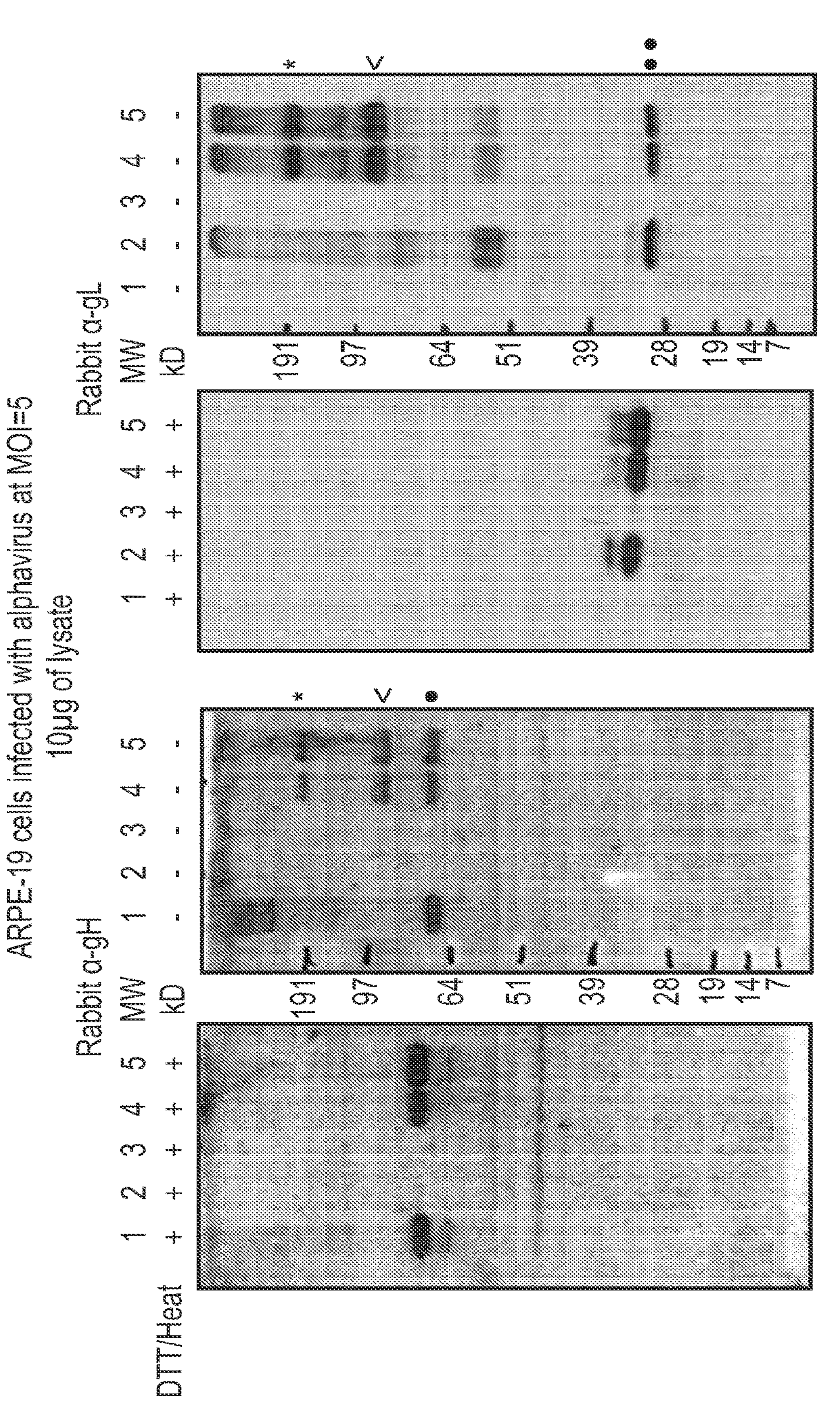
FIG. 5B show that gH/gL form a complex in vitro. VRPs containing replicons encoding gH, gL, gO, gH/gL or gH/gL/gO were produced in BHKV cells. The resulting VRPs were used to infect ARPE-19 cells to demonstrate complex formation in vitro. The alphavirus infected ARPE-19 cells were harvested and analyzed for the presence of gH and gL. ARPE-19 cells infected with VRPs encoding gH/gL produced disulfide linked complexes of gH/gL (see in the absence of DTT, heat). gO did not detectably alter the gH/gL association. The left hand blot shows expression of gH protein. The right hand blot shows expression of gL protein. Molecular weight markers are indicated between the blots. •=monomeric gH, ••=monomeric gL, <=heterodimer (gH+gL), *=dimer of heterodimers.

Polycistronic gH/gL and gH/gL/gO alphavirus replicons were constructed as described above (shown schematically in FIG. 5A). VRPs containing gH, gL, gO, gH/gL and gH/gL/gO encoding replicons were produced in BHKV cells as described above and used to infect BHKV cells to demonstrate complex formation in vitro. VRP infected ARPE-19 cells produced disulfide linked complexes of gH/gL. gO did not detectably alter gH/gL association (FIG. 5B).

Immunofluorescence studies were conducted to evaluate the localization of gH and gL delivered alone and when delivered using a polycistronic alphavirus to look at relocalization of the proteins when co-expressed. gH localization did not appear to change in the presence or absence of gL, or gL/gO. gL localization d change when in the presence of gH and gH/gO.

Figure 5C:
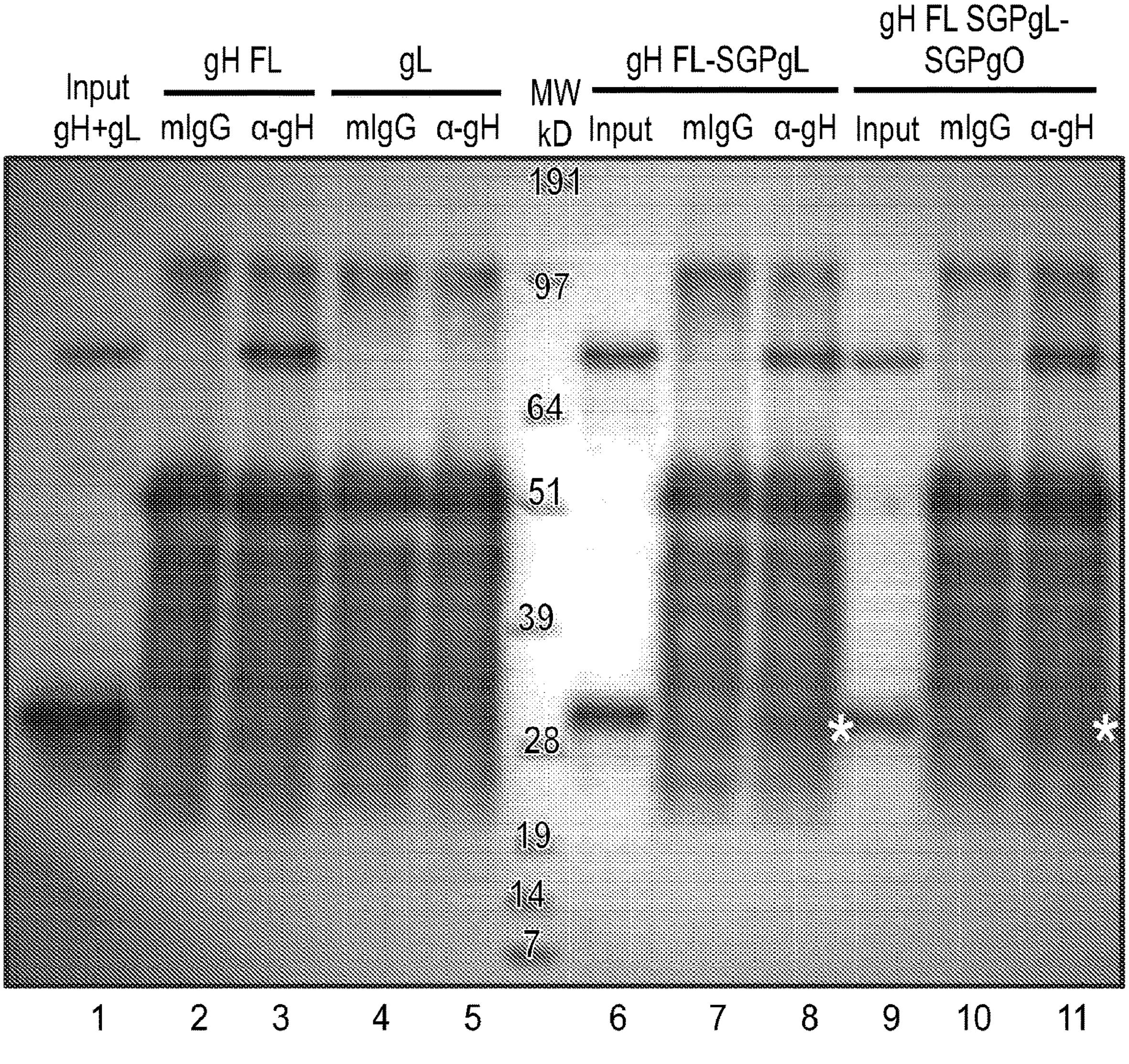
FIG. 5C shows immunoprecipitation of gH and gH/gL complexes from BHKV cells infected with VRPs. Immunoprecipitation was performed using mouse IgG antibodies as a control (Lanes 2, 4, 7, and 10) or mouse anti-gH antibodies (Genway) to immunoprecipitate gH (Lanes 3, 5, 8, and 11). Western blots were performed using pooled rabbit anti-gL antibody and rabbit anti-gH antibody. Lanes 1, 6, and 9 show gH protein (upper band ~75 kDa) and gL protein (lower band ~30 kDa) for reference. Lanes 2 and 3 are lysates infected with gH-VRP. Lane 2 shows that the control antibody did not immunoprecipitate gH. Lane 3 shows the anti-gH antibody immunoprecipitated gH. Lanes 4 and 5 are from lysates infected with gL-VRP only. No gH protein was immunoprecipitated. Lanes 7 and 8 are from lysates infected with bicistronic gH/gL-VRP. Lane 8 shows that gL was immunoprecipitated using the gH antibody. (See asterisk).

Finally, gH/gL association was examined via immunoprecipitation. A commercial gH antibody (Genway) was used to investigate the association of gH and gL. In all cases, the gH antibody efficiently immunoprecipitated gH (FIG. 5C). When no gH was present, gL was not immunoprecipitated. When gL was expressed in the presence of gH or gH/gO, there was association of gL with gH (FIG. 5C).

The relocalization of gL in the presence of gH and the association of gH/gL (with or without gO) indicates that all components of the polycistronic alphavirus replicons were expressed and associated to form a complex.

Example 4

VRPs that Effect gH/gL Complex Formation In Vitro Induce Potent Immune Response to CMV which is Qualitatively and Quantitatively Superior to the Immune Response Elicited to gB VRPs.

This example demonstrates the induction of robust immune responses to complexes formed by delivering polycistronic gH/gL VRPs or gH/gL/gO VRPs compared with immune responses obtained using VRPs delivering single components or single-component VRPs administered in combination or to responses elicited by gB VRPs.

Mice were infected three times with VRPs administered 3 weeks apart ($10^6$ IU per mouse; 5 BalbC mice/group). Sera collected from immunizations with single and polycistronic VRPs were screened for neutralizing antibodies using a CMV neutralization assay as described above. Neutralization titer was measured as follows. Various dilutions of sera were pre-incubated with TB40-UL32-EGFP in the presence or absence of guinea pig complement and then added to ARPE-19 epithelial cells or MRC-5 fibroblast cells and incubated for 5 days. After 5 days infection with the virus, GFP-positive cells were counted. Results for the ARPE-19 cells are shown in FIG. 6A, FIG. 6B, and FIG. 6C. Results for the MRC-5 cells are shown in FIG. 7A and FIG. 7B.

Sera from mice immunized with gH FL VRPs had low complement-independent neutralizing activity (FIG. 6A and FIG. 6B). No neutralizing activity was observed using sera from mice immunized with only gL or gO in the presence or absence of guinea pig complement. (FIG. 6C) Pooled sera from immunization with several CMV gB proteins (gB FL, gB sol 750, and gB sol 692) demonstrated strong neutralizing activity in the presence of guinea pig complement, with a 50% neutralization titer at 1:1280 sera dilution. However, there was no neutralizing activity in the absence of guinea pig complement in ARPE-19 cells for the pooled gB sera. VRPs expressing single CMV proteins (gH- or gL-VRPs or co-administering gH-, gL-, and gO-VRPs at $10^6$ IU/mouse/VRP) did not enhance neutralizing activity beyond that of gH alone.

In contrast, sera from mice immunized with bicistronic gH/gL or tricistronic gH/gL/gO VRPs ($1 \times 10^6$ IU/mouse) demonstrated robust neutralizing responses. Moreover, the responses were similar in the presence and absence of guinea pig complement, showing that polycistronic VRPs successfully induced a complement-independent immune response. (FIG. 6C.) The 50% neutralization titer was 1:3500-6400+ sera dilution in ARPE-19 cells with TB40-GFP CMV virus. This titer is approximately 3-4 fold higher titer than the 50% complement-dependent neutralization titer for gB pooled sera.

Results in the MRC-5 fibroblast cells were similar to those in ARPE-19 cells (FIGS. 7A and 7B). Sera from mice immunized with bicistronic gH/gL or tricistronic gH/gL/gO VRPs demonstrated strong neutralizing activity compared to sera from mice immunized with VRPs encoding gH alone, gL alone, or gO alone and to sera from mice immunized by coadministration of gH VRPs and gL VRPs, or coadministration of gH VRPs, gL VRPs, and gO VRPs. These results demonstrate that administration of the polycistronic VRPs induced an immune response that provides good complement-independent neutralization of CMV infection of fibroblast cells. To assess the breadth and potency of the gH/gL immune sera against different strains of CMV, we compared the ability of the sera to block infection of fibroblasts and epithelial cells with six different strains of CMV. FIG. 8 shows that the gH/gL sera potently neutralize infection of both cell types with a broad range of strains.

These data also demonstrate strong neutralizing activity for sera from mice immunized with the polycistronic VRPs but not with mixed pools of VRPs expressing only one protein. This shows that polycistronic replicons that encode the components of a protein complex on a single replicon result in efficient production of the complex in situ. Moreover, because Merlin strain CMV proteins were used to stimulate these responses, the in vitro data obtained using TB40 strain CMV virus demonstrates that the neutralizing antibodies induced by delivery of the polycistronic VRPs are cross-neutralizing antibodies.

Example 5

RNA Synthesis

Plasmid DNA encoding alphavirus replicons (see FIGS. 14-16) served as a template for synthesis of RNA in vitro. Alphavirus replicons contain the genetic elements required for RNA replication but lack those encoding gene products necessary for particle assembly; the structural genes of the alphavirus genome are replaced by sequences encoding a heterologous protein. Upon delivery of the replicons to eukaryotic cells, the positive-stranded RNA is translated to produce four non-structural proteins, which together replicate the genomic RNA and transcribe abundant subgenomic mRNAs encoding the heterologous gene product or gene of interest (GOI). Due to the lack of expression of the alphavirus structural proteins, replicons are incapable of inducing the generation of infectious particles. A bacteriophage (T7 or SP6) promoter upstream of the alphavirus cDNA facilitates the synthesis of the replicon RNA in vitro and the hepatitis delta virus (HDV) ribozyme immediately downstream of the poly(A)-tail generates the correct 3'-end through its self-cleaving activity.

In order to allow the formation of an antigenic protein complex, the expression of the individual components of said complex in the same cell is of paramount importance. In theory, this can be accomplished by co-transfecting cells with the genes encoding the individual components. However, in case of non-virally or VRP delivered alphavirus replicon RNAs, this strategy is hampered by inefficient co-delivery of multiple RNAs to the same cell or, alternatively, by inefficient launch of multiple self-replicating RNAs in an individual cell. A potentially more efficient way to facilitate co-expression of components of a protein complex is to deliver the respective genes as part of the same self-replicating RNA molecule. To this end, we engineered alphavirus replicon constructs encoding multiple genes of interest. Every GOI is preceded by its own subgenomic promoter which is recognized by the alphavirus transcription machinery. Thereby, multiple subgenomic messenger RNA species are synthesized in an individual cell allowing the assembly of multi-component protein complexes.

Following linearization of the plasmid DNA downstream of the HDV ribozyme with a suitable restriction endonuclease, run-off transcripts were synthesized in vitro using T7 bacteriophage derived DNA-dependent RNA polymerase. Transcriptions were performed for 2 hours at 37° C. in the presence of 7.5 mM of each of the nucleoside triphosphates (ATP, CTP, GTP and UTP) following the instructions provided by the manufacturer (Ambion, Austin, Tex.). Following transcription, the template DNA was digested with TURBO DNase (Ambion, Austin, Tex.). The replicon RNA was precipitated with LiCl and reconstituted in nuclease-free water. Uncapped RNA was capped post-transcriptionally with Vaccinia Capping Enzyme (VCE) using the ScriptCap $m^7G$ Capping System (Epicentre Biotechnologies, Madison, Wis.) as outlined in the user manual. Post-transcriptionally capped RNA was precipitated with LiCl and reconstituted in nuclease-free water. The concentration of the RNA samples was determined by measuring the optical density at 260 nm. Integrity of the in vitro transcripts was confirmed by denaturing agarose gel electrophoresis.

Lipid Nanoparticle (LNP) Formulation 1,2-dilinoleyloxy-N,N-dimethyl-3-aminopropane (DlinDMA) was synthesized using a previously published procedure [Heyes, J., Palmer, L., Bremner, K., MacLachlan, I. Cationic lipid saturation influences intracellular delivery of encapsulated nucleic acids. Journal of Controlled Release, 107: 276-287 (2005)]. 1,2-Diastearoyl-sn-glycero-3-phosphocholine (DSPC) was purchased from Genzyme. Cholesterol was obtained from Sigma-Aldrich (St. Lois, Mo.). 1,2-dimyristoyl-sn-glycero-3-phosphoethanolamine-N-[methoxy(polyethylene glycol)-2000] (ammonium salt) (PEG DMG 2000), was obtained from Avanti Polar Lipids.

LNPs (RV01(14)) were formulated using the following method. 150 μg batch, (PES hollow fibers and no mustang): Fresh lipid stock solutions in ethanol were prepared. 37 mg of DlinDMA, 11.8 mg of DSPC, 27.8 mg of Cholesterol and 8.07 mg of PEG DMG 2000 were weighed and dissolved in 7.55 mL of ethanol. The freshly prepared lipid stock solution was gently rocked at 37° C. for about 15 min to form a homogenous mixture. Then, 453 μL of the stock was added to 1.547 mL ethanol to make a working lipid stock solution of 2 mL. This amount of lipids was used to form LNPs with 150 μg RNA at a 8:1 N:P (Nitrogen to Phosphate) ratio. The protonatable nitrogen on DlinDMA (the cationic lipid) and phosphates on the RNA are used for this calculation. Each μg of self-replicating RNA molecule was assumed to contain 3 nmoles of anionic phosphate, each μg of DlinDMA was assumed to contains 1.6 nmoles of cationic nitrogen. A 2 mL working solution of RNA was also prepared from a stock solution of ~1 μg/μL in 100 mM citrate buffer (pH 6) (Teknova). Three 20 mL glass vials (with stir bars) were rinsed with RNase Away solution (Molecular BioProducts) and washed with plenty of MilliQ water before use to decontaminate the vials of RNAses. One of the vials was used for the RNA working solution and the others for collecting the lipid and RNA mixes (as described later). The working lipid and RNA solutions were heated at 37° C. for 10 min before being loaded into 3 cc luer-lok syringes (BD Medical). 2 mL of citrate buffer (pH 6) was loaded in another 3 cc syringe. Syringes containing RNA and the lipids were connected to a T mixer (PEEK™ 500 μm ID junction) using FEP tubing([fluorinated ethylene-propylene] 2 mm ID×3 mm OD, Idex Health Science, Oak Harbor, Wash.). The outlet from the T mixer was also FEP tubing (2 mm ID×3 mm). The third syringe containing the citrate buffer was connected to a separate piece of tubing (2 mm ID×3 mm OD). All syringes were then driven at a flow rate of 7 mL/min using a syringe pump (from kdScientific, model no. KDS-220). The tube outlets were positioned to collect the mixtures in a 20 mL glass vial (while stirring). The stir bar was taken out and the ethanol/aqueous solution was allowed to equilibrate to room temperature for 1 h. Then the mixture was loaded in a 5 cc syringe (BD Medical), which was fitted to a piece of FEP tubing (2 mm ID×3 mm OD) and in another 5 cc syringe with equal length of FEP tubing, an equal volume of 100 mM citrate buffer (pH 6) was loaded. The two syringes were driven at 7 mL/min flow rate using a syringe pump and the final mixture collected in a 20 mL glass vial (while stirring). Next, LNPs were concentrated to 2 mL and dialyzed against 10-15 volumes of 1×PBS (from Teknova) using the Tangential Flow Filtration (TFF) system before recovering the final product. The TFF system and hollow fiber filtration membranes were purchased from Spectrum Labs and were used according to the manufacturer's guidelines. Polyethersulfone (PES) hollow fiber filtration membranes (part number P-C1-100E-100-01N) with a 100 kD pore size cutoff and 20 $cm^2$ surface area were used. For in vitro and in vivo experiments, formulations were diluted to the required RNA concentration with 1×PBS (from Teknova).

Particle Size

Particle size was measured using a Zetasizer Nano ZS (Malvern Instruments, Worcestershire, UK) according to the manufacturer's instructions. Particle sizes are reported as the Z average with the polydispersity index (pdi). Liposomes were diluted in 1×PBS before measurement.

Encapsulation Efficiency and RNA Concentration

The percentage of encapsulated RNA and RNA concentration were determined by Quant-iT RiboGreen RNA reagent kit (Invitrogen). Manufacturer's instructions were followed in the assay. The ribosomal RNA standard provided in the kit was used to generate a standard curve. LNPs either obtained from method 1 or methods 2-5 were diluted ten fold or one hundred fold respectively in 1×TE buffer (from kit), before addition of the dye. Separately, LNPs were diluted ten or 100 fold in 1×TE buffer containing 0.5% Triton X (Sigma-Aldrich), before addition of the dye. Thereafter an equal amount of dye was added to each solution and then ~180 μL of each solution after dye addition was loaded in duplicate into a 96 well tissue culture plate (obtained from VWR, catalog #353072). The fluorescence (Ex 485 nm, Em 528 nm) was read on a microplate reader (from BioTek Instruments, Inc.).

Triton X was used to disrupt the LNPs, providing a fluorescence reading corresponding to the total RNA amount and the sample without Triton X provided fluorescence corresponding to the unencapsulated RNA. % RNA encapsulation was determined as follows: LNP RNA Encapsulation (%)=$[(F_t-F_i)/F_t]\times100$, where $F_t$ is the fluorescence intensity of LNPs with triton X addition and $F_i$ is the fluorescence intensity of the LNP solution without detergent addition. These values ($F_t$ and $F_i$) were obtained after subtraction from blank (1×TE buffer) fluorescence intensity. The concentration of encapsulated RNA was obtained by comparing $F_t-F_i$ with the standard curve generated. All LNP formulations were dosed in vivo based on the encapsulated dose.

Viral Replicon Particles (VRP)

To compare RNA vaccines to traditional RNA-vectored approaches for achieving in vivo expression of reporter genes or antigens, we utilized viral replicon particles (VRPs), produced in BHK cells by the methods described by Perri et al. (J. Virol 77(19):10394-10403 (2003)), coding for expression of the same antigens as the corresponding RNA constructs. In this system, the antigen consisted of alphavirus chimeric replicons (VCR) derived from the genome of Venezuelan equine encephalitis virus (VEEV) engineered to contain the 3' terminal sequences (3' UTR) of Sindbis virus and a Sindbis virus packaging signal (PS) (see FIG. 2 of Perri et al). The replicons were packaged into VRPs by co-electroporating them into baby hamster kidney (BHK) cells along with defective helper RNAs encoding the Sindbis virus capsid and glycoprotein genes (see FIG. 2 of Perri et al). The VRPs were then harvested and partially purified by ultracentrifugation on a sucrose cushion and concentrated on an Amicon concentrator. The resulting VRP stock was titrated by standard methods and inoculated into animals in culture fluid or other isotonic buffers. An alphavirus replicon particle chimera derived from venezuelan equine encephalitis and sindbis viruses is a potent gene-based vaccine delivery vector. J. Virol. 77, 10394-10403.

Murine Immunogenicity Studies

Groups of 10 female BALB/c mice aged 8-10 weeks and weighing about 20 g were immunized with $1\times10^6$ IU (VRP) or 1.0 μg (RNA) at day 0, 21 and 42 with bleeds taken 3 weeks after the $2^{nd}$ and 3 weeks after the $3^{rd}$ vaccinations. All animals were injected in the quadriceps in the two hind legs each getting an equivalent volume (50 μl per site).

Micro Neutralization Assay

Serum samples were tested for the presence of neutralizing antibodies by an infection reduction neutralization test. Two-fold serial dilutions of HI-serum (in DMEM with 10% HI FBS) were added to an equal volume of CMV (strain TB40 or clinical isolate 8819) previously titered to give approximately 200 IU/50 μl. The VR1814, Towne, AD169 strains and the clinical isolate 8822 were also used. Serum/virus mixtures were incubated for 2 hours at 37° C. and 5% $CO_2$, to allow virus neutralization to occur, and then 50 μl of this mixture (containing approximately 200 IU) was inoculated on duplicate wells of ARPE-19 cells in 96 half well plates. Plates were incubated for 40-44 hours. Unless otherwise noted, the number of positive infected foci was determined by immunostaining with an AlexaFluor 488 conjugated IE1 CMV monoclonal antibody followed by automated counting. The neutralization titer is defined as the reciprocal of the serum dilution producing a 50% reduction in number of positive virus foci per well, relative to controls (no serum).

Immunogenicity of gH/gL VRPs and LNP Formulated RNA

The A323 replicon that expresses the surface glycoprotein B (gB) of CMV, the A160 replicon that expresses the membrane complex of the full-length glycoprotein H and L (gH/gL) and the A322 replicon that expresses the membrane complex of the soluble form of glycoprotein H and L (gHsol/gL) were used for this experiment. BALB/c mice, 10 animals per group, were given bilateral intramuscular vaccinations (50 μL per leg) on days 0, 21 and 42 with VRPs expressing gB ($1\times10^6$ IU), VRPs expressing gH/gL ($1\times10^6$ IU), VRP's expressing gHsol/gL ($1\times10^6$ IU) and PBS as the controls. The three test groups received self-replicating RNA (A160, A322 or A323) formulated in LNP (RV01(14). Serum was collected for immunological analysis on days 39 (3wp2) and 63 (3wp3).

Results

The size and percentage of encapsulated RNA in the RV01(14) formulations made for the experiment are shown in Table 3.

TABLE 3

| RV# | Lipid Composition (% moles of total) | RNA | pKa of cationic lipid | Particle Size Zav (nm) | pdI | Percent RNA Encapsulation |
|---|---|---|---|---|---|---|
| RV01 (14) | DlinDMA 40%, DSPC-10%, Chol- 48%, PEG DMG 2k-2% | gB FL | 5.8 | 170 | 0.098 | 88.3 |
| RV01 (14) | DlinDMA 40%, DSPC-10%, Chol- 48%, PEG DMG 2k-2% | gH FL/gL | 5.8 | 168.8 | 0.144 | 87.4 |
| RV01 (14) | DlinDMA 40%, DSPC-10%, Chol- 48%, PEG DMG 2k-2% | gHsol/gL | 5.8 | 162 | 0.131 | 90 |

The 50% neutralizing titers for the terminal sera (day 63, three weeks after final vaccination) are shown in Table 4.

TABLE 4

| | | ARPE-19, HCMV TB40 | | | ARPE-19, HCMV 8819 | | |
|---|---|---|---|---|---|---|---|
| | | pool #1 | pool #2 | average | pool #1 | pool #2 | average |
| Preimmune serum | — | 126 | 212 | 169 | 50 | 50 | 50 |
| gB FL VRP | $10^6$ IU | 1332 | 295 | 814 | 5085 | 1031 | 3058 |
| gB FL RNA-RV01(14) | 1 μg | 686 | 179 | 433 | 1261 | 557 | 909 |
| gH FL/gL VRP | $10^6$ IU | 1425 | 1624 | 1525 | 2496 | 1374 | 1935 |
| gH FL/gL RNA-RV01(14) | 1 μg | 6196 | 6390 | 6293 | 5800 | 10267 | 8034 |
| gH sol/gL VRP | $10^6$ IU | 2375 | 2254 | 2315 | 1733 | 1924 | 1829 |
| gH sol/gL RNA-RV01(14) | 1 μg | 4600 | 2062 | 3331 | 2912 | 1533 | 2223 |

RNA expressing either a full-length or a presumed soluble form of the HCMV gH/gL complex elicit high titers of neutralizing antibody, as assayed on epithelial cells using two different HCMV strains. The average titers elicited by the gH/gL RNAs are at least as high as the average titer for the corresponding gH/gL VRPs (see FIG. 17).

Example 6 Bicistronic and Pentacistronic Nucleic Acids Encoding CMV Proteins

Additional bicistronic and pentacistronic alphavirus replicons that express glycoprotein complexes from human cytomegalovirus (HCMV) were prepared, and are shown schematically in FIGS. 18 and 20. The alphavirus replicons were based on venezuelan equine encephalitis virus (VEE). The replicons were packaged into viral replicon particles (VRPs), encapsulated in lipid nanoparticles (LNP), or formulated with a cationic nanoemulsion (CNE). Expression of the encoded HCMV proteins and protein complexes from each of the replicons was confirmed by immunoblot, co-immunoprecipitation, and flow cytometry. Flow cytometry was used to verify expression of the pentameric gH/gL/UL128/UL130/UL131 complex from pentameric replicons encoding the protein components of the complex, using human monoclonal antibodies specific to conformational epitopes present on the pentameric complex (Macagno et al (2010), J. Virol. 84(2):1005-13). FIG. 19 shows that these antibodies bind to BHKV cells transfected with replicon RNA expressing the HCMV gH/gL/UL128/UL130/UL131 pentameric complex (A527). Similar results were obtained when cells were infected with VRPs made from the same replicon construct. This shows that replicons designed to express the pentameric complex do indeed express the desired antigen and not the potential byproduct gH/gL.

The VRPs, RNA encapsulated in LNPs, and RNA formulated with CNE were used to immunize Balb/c mice by intramuscular injections in the rear quadriceps. The mice were immunized three times, three weeks apart, and serum samples were collected prior to each immunization as well as three weeks after the third and final immunization. The sera were evaluated in microneutralization assays to measure the potency of the neutralizing antibody response that was elicited by the vaccinations. The titers are expressed as 50% neutralizing titer.

The immunogenicity of a number of different configurations of a bicistronic expression cassette for a soluble HCMV gH/gL complex in VRPs was assessed. FIG. 20 shows that VRPs expressing the membrane-anchored, full-length gH/gL complex elicited potent neutralizing antibodies at slightly higher titers than the soluble complex (gHsol/gL) expressed from a similar bicistronic expression cassette. Changing the order of the genes encoding gHsol and gL or replacing one of the subgenomic promoters with an IRES or an FMDV 2A site did not substantially improve immunogenicity.

The breadth and potency of HCMV neutralizing activity in sera from mice immunized with VEE/SIN VRPs expressing gH/gL was assessed by using the sera to block infection of fibroblasts and epithelial cells with different strains of HCMV. Table 5 shows that gH/gL immune sera were broadly and potently neutralizing against six different strains of HCMV on both cell types in the absence of complement. Addition of complement had a slight negative effect on the neutralizing potency of the sera.

TABLE 5

Neutralizing antibody titers in sera from mice immunized with pVCR-derived VRPs expressing gH/gL.

| | | Serum from mice immunized with pVCR-derived VRPs expressing gH/gL | |
|---|---|---|---|
| HCMV Strain | Cell | Without complement | With complement |
| Towne | Fibroblasts | 5244 | 4081 |
| AD169 | (MRC-5) | 2126 | 2208 |
| TB40-UL32-EGFP | | 678 | 505 |
| VR1814 | | 4764 | 2126 |
| TB40-UL32-EGFP | Epithelial cells | 5602 | 3247 |
| VR1814 | (ARPE-19) | 6510 | 2420 |
| 8819 (clinical isolate) | | 8706 | 5242 |
| 8822 (clinical isolate) | | 3427 | 2684 |

The immunogenicity of LNP-encapsulated RNAs encoding the pentameric complex (A526 and A527) compared to LNP-encapsulated RNA (A160) and VRPs (pVCR modified gH-SGPgL) expressing gH/gL was assessed. Table 6 shows that replicons expressing the pentameric complex elicited more potently neutralizing antibodies than replicons expressing gH/gL.

TABLE 6

Neutralizing antibody titers.

| Replicon | Titer post $1^{st}$ | Titer post $2^{nd}$ | Titer post $3^{rd}$ |
|---|---|---|---|
| C313 pVCR modified gH-SGP-gL VRP $10^6$ IU | 126 | 6,296 | 26,525 |
| A160 gH FL/gL 1 μg LNP | 347 | 9,848 | 42,319 |
| A526 Pentameric 2A 1 μg LNP | 179 | 12,210 | 80,000 |
| A527 Pentameric IRES 1 μg LNP | 1,510 | 51,200 | 130,000 |

The pentacistronic VEE-based RNA replicon that elicited the highest titers of neutralizing antibodies (A527) was packaged as VRPs and the immunogenicity of the VRPs were compared to gH/gL-expressing VRPs and LNP-encapsulated replicons expressing gH/gL and pentameric complex. Table 7 shows that VRPs expressing the pentameric complex elicited higher titers of neutralizing antibodies than VRPs expressing gH/gL. Moreover, $10^6$ infectious units of VRPs are at least as potent as 1 μg of LNP-encapsulated RNA when the VRPs and the RNA encoded the same protein complexes.

TABLE 7

Neutralizing antibody titers. Sera were collected three weeks after the second immunization.

| Replicon | 50% Neutralizing Titer |
|---|---|
| A160 gH FL/gL VRP $10^6$ IU | 14,833 |
| A527 Pentameric IRES VRP $10^6$ IU | 51,200 |
| A160 gH FL/gL LNP 0.01 μg | 4,570 |
| A160 gH FL/gL LNP 0.1 μg | 9,415 |
| A160 gH FL/gL LNP 1 μg | 14,427 |
| A527 Pentameric IRES 0.01 μg LNP | 12,693 |
| A527 Pentameric IRES 0.1 μg LNP | 10,309 |
| A527 Pentameric IRES 1 μg LNP | 43,157 |

The breadth and potency of HCMV neutralizing activity in sera from mice immunized with VEE-based RNA encoding the pentameric complex (A527) was assessed by using the sera to block infection of fibroblasts and epithelial cells with different strains of HCMV. Table 8 shows that anti-gH/ gL/UL128/UL130/UL131 immune sera broadly and potently neutralized infection of epithelial cells. This effect was complement independent. In contrast, the sera had a reduced or not detectable effect on infection of fibroblasts. These results are what is expected for immune sera that contains mostly antibodies specific for the gH/gL/UL128/UL130/UL131 pentameric complex, because the pentameric complex is not required for infection of fibroblasts and, consequently, antibodies to UL128, UL130, and UL131 do not block infection of fibroblasts (Adler et al (2006), J. Gen. Virol. 87(Pt. 9):2451-60; Wang and Shenk (2005), Proc. Natl. Acad. Sci. USA 102(50):18153-8). Thus, these data demonstrate that the pentameric replicons encoding the gH/gL/UL128/UL130/UL131pentameric complex specifically elicit antibodies to the complex in vivo.

TABLE 8

Neutralizing antibody titers in sera from mice immunized with the A527 RNA replicon encapsulated in LNPs. The replicon expresses the HCMV pentameric complex using subgenomic promoters and IRESes.

| HCMV Strain | Cell | Serum from mice immunized with A527 pentameric IRES RNA in LNPs: Without complement | With complement |
|---|---|---|---|
| Towne | Fibroblasts | 3433 | 1574 |
| AD169 | (MRC-5) | 2292 | <1000 |
| TB40-UL32-EGFP | | <1000 | <1000 |
| VR1814 | | 4683 | 1324 |
| TB40-UL32-EGFP | Epithelial cells | 86991 | 59778 |
| VR1814 | (ARPE-19) | 82714 | 37293 |
| 8819 (clinical isolate) | | 94418 | 43269 |
| 8822 (clinical isolate) | | 85219 | 49742 |

To see if bicistronic and pentacistronic replicons expressing the gH/gL and pentameric complexes would elicit neutralizing antibodies in different formulations, cotton rats were immunized with bicistronic or pentacistronic replicons mixed with a cationic nanoemulsion (CNE). Table 9 shows that replicons in CNE elicited comparable neutralizing antibody titers to the same replicons encapsulated in LNPs.

TABLE 9

Neutralizing antibody titers. The sera were collected three weeks after the second immunization.

| Replicon | 50% Neutralizing Titer |
|---|---|
| A160 gH FL/gL VRP $10^6$ IU | 594 |
| A160 gH FL/gL 1 μg LNP | 141 |
| A527 Pentameric IRES 1 μg LNP | 4,416 |
| A160 gH FL/gL 1 μg CNE | 413 |
| A527 Pentameric IRES 1 μg CNE | 4,411 |

Example 7. Replicons Encoding VZV Proteins

Nucleic acids encoding VZV proteins were cloned into a VEE replicon vector to produce monocystronic replicons that encode gB, gH, gL, gE, and gI, and to produce bicistronic replicons that encode gH/gL or gE/gI. In the bicistronic replicons, expression of each VZV open reading frame was driven by a separate subgenomic promoter.

To prepare replicon RNA, plasmid encoding the replicon was linearized by digestion with PmeI, and the linearized plasmid was extracted with phenol/chloroform/isoamylalchohol, precipitated in sodium acetate/ethanol and resuspended in 20 μl of RNase-free water.

RNA was prepared by In vitro transcription of 1 μg of linearized DNA using the MEGAscript T7 kit (AMBION #AM1333). A 20 μl reaction was set up according to the manufacturer's instruction without cap analog and incubated for 2 hours at 32° C. TURBO DNase (1 μl) was added and the mixture was incubate for 30 min. at 32° C. RNase-free water (30 μl) and ammonium acetate solution (30 μl) were added. The solution was mixed and chilled for at least 30 min at −20° C. Then the solution was centrifuged at maximum speed for 25 min. at 4° C. The supernatant was discarded, and the pellet was rinsed with 70% ethanol, and again centrifuged at maximum speed for 10 min. at 4° C. The pellet was air dried and resuspended in 50 μl of RNase-free water. The concentration of RNA was measured and quality was check on a denaturing gel.

The RNA was capped using the ScriptCap m7G Capping System (Epicentre #SCCE0625). The reaction was scaled by combining the RNA and RNase-free water. The RNA was then denatured for 5-10 min. at 65° C. The denatured RNA was transferred quickly to ice and the following reagents were added in the following order: ScriptCap Capping Buffer, 10 mM GTP, 2 mM SAM fresh prepared, ScriptGuard RNase inhibitor, and ScriptCap Capping Enzyme. The mixture was incubated for 60 min. at 37° C. The reaction was stopped by adding RNase-free water and 7.5 M LiCl, mixing well and storing the mixture for at least 30 min at −20° C. Then, the mixture was centrifuged at maximum speed for 25 min. at 4° C., the pellet was rinsed with 70% ethanol, again centrifuged at maximum speed for 10 min. at 4° C. and the pellet was air dried. The pellet was resuspended in RNase-free water. The concentration of RNA was measured and quality was checked on a denaturing gel.

RNA Transfection

Cells (BHK-V cells) were seeded on 6-well plates brought to 90-95% confluence at the time of transfection. For each transfection 3 μg of RNA was diluted in 50 mL OPTIMEM media in a first tube. Lipofectamine 2000 was added to a second tube contained 50 mL OPTIMEM media. The first and second tubes were combined and kept for 20 min. at room temperature. The culture media in the 6-well plates were replaced with fresh media, and the RNA-Lipofectamine complex was placed onto the cells, and mixed by gently rocking the plate. The plates were incubated for 24 hours at 37° C. in a $CO_2$ incubator.

Expression of the VZV proteins in transfected cells was assessed by western blot and immunofluorescence. For western blots, lysates of transfected cells were separated by electrophoresis (5 μg total proteins/lane) and blotted. A cleared viral suspension (7 μg total protein/lane) derived from the OKA/Merck vaccine strain was used as a positive control. Blots were probed using commercially available antibodies (1:1000 dilution) that bind VZV proteins.

For immunofluorescence, transfected cells were harvested and seeded in 96 well plate, and intracellular staining was performed using commercially available mouse mAbs (dilution range 1:100 1:400). Cell pellets were fixed and permeabilized with Citofix-Citoperm solutions. A secondary reagent, Alexa488 labelled goat anti-mouse $F(ab')_2$ (1:400 final dilution), was used.

Expression of VZV proteins gE and gI was detected in cells transfected with monocistronic constructs (gE or gI), and expression of both gE and gI was detected in cells transfected with a bicistronic gE/gI construct in western blots using commercially available mouse antibodies, 13B1 for gE and 8C4 for gI. Expression of VZV protein gB was detected in cells transfected with a monocistronic construct encoding gB, by immunofluorescence using commercially available antibody 10G6. Expression of the VZV protein complex gH/gL, was detected by immunofluorescence in cells transfected with monocistronic gH and monocistronic gL, or with a bicistronic gH/gL construct. The gH/gL complex was detected using commercially available antibody SG3.

Murine Immunogenicity Studies

Groups of 8 female BALB/c mice aged 6-8 weeks and weighing about 20 g were immunized intramuscularly with 7.0 or 1.0 μg of replicon RNA formulated with a CNE or LNP (RV01) at day 0, 21 and 42. Blood samples were taken from the immunized animals 3 weeks after the 2nd immunization and 3 weeks after the 3rd immunization. The groups are shown in Table 10.

TABLE 10

| Group | Antigen | Dose (micrograms) | Formulation |
|---|---|---|---|
| Study 1 | | | |
| 1 | YFP | 7 | CNE |
| 2 | YFP | 1 | CNE |
| 3 | gB | 7 | CNE |
| 4 | gB | 1 | CNE |
| 5 | gE | 7 | CNE |
| 6 | gE | 1 | CNE |
| 7 | gH | 7 | CNE |
| 8 | gH | 1 | CNE |
| 9 | gI | 7 | CNE |
| 10 | gI | 1 | CNE |
| 11 | gL | 7 | CNE |
| 12 | gL | 1 | CNE |
| 13 | gE/gI | 7 | CNE |
| 14 | gE/gI | 1 | CNE |
| 15 | gH/gL | 7 | CNE |
| 16 | gH/gL | 1 | CNE |
| Study 2 | | | |
| 1 | gB | 1 | RV01 |
| 2 | gE | 1 | RV01 |
| 3 | gH | 1 | RV01 |
| 4 | gI | 1 | RV01 |
| 5 | gL | 1 | RV01 |
| 6 | gE/gI | 1 | RV01 |
| 7 | gH/gL | 1 | RV01 |

Immune Response to VZV Antigens

Serum samples were tested for the presence of antibodies to gB, by intracellular staining of VZV-replicon transfected MRC-5 cells. MRC-5 cells were maintained in Dulbecco Modified Eagle's Medium with 10% fetal bovine serum. VZV Oka strain inoculum (obtained from ATCC) was used to infect MRC-5 cell culture and infected whole cells were used for subpassage of virus. The ratio between infected and un-infected cells was 1:10. 30 hrs post infection cells were trypsin-dispersed for seeding in a 96 well plate to perform an intracellular staining with pools of mice sera (dilution range 1:200 to 1:800) obtained after immunization. Commercial mAbs were used as controls to quantify the infection level. Cell pellets ware fixed and permeabilized with Citofix-Citoperm solutions. A secondary reagent, Alexa488 labelled goat anti-mouse $F(ab')_2$ was used (1:400 final dilution).

Commercial antibodies to gB (10G6), gH (SG3), and gE (13B1 (SBA) and 8612 (Millipore)) were used as positive controls, and each intracellularly stained infected MRC-5 cells. Immune sera obtained 3 weeks after the third immunization with either 1 or 7 μg of RNA formulated with CNE or LNP were diluted 1/200, 1/400 and 1/800 and used to intracellularly stain infected MRC-5 cells. The results are shown in FIG. 21 (Study 1, groups 1, 5, 7, 9, 11, 13 and 15, CNE formulation) and FIG. 22 (Study 2, groups 1-7, LNP formulation).

Neutralizing Assay

Each immunized mouse serum was serially diluted by two fold increments starting at 1:20 in standard culture medium, and added to the equal volume of VZV suspension in the presence of guinea pig complement. After incubation for 1 hour at 37° C., the human epithelial cell line A549, was added. Infected cells can be measured after one week of culture by counting plaques formed in the culture under microscope. From the plaque number the % inhibition at each serum dilution was calculated. A chart for each serum sample was made by plotting the value of % inhibition against the logarithmic scale the dilution factor. Subsequently an approximate line of relationship between dilution factor and % inhibition was drawn. Then the 50% neutralization titer was determined as the dilution factor where the line crossed at the value of 50% inhibition.

Table 11 shows that sera obtained from mice immunized with monocistronic gE, bicistronic gE/gI, and bicistronic gH/gL contained robust neutralizing antibody titers.

TABLE 11

Neutralization titers of pooled sera from mice immunized with 7 μg RNA

| Control (YFP) | gB | gE | gI | gE/gI | gH | gL | gH/gL |
|---|---|---|---|---|---|---|---|
| <20 | <20 | 1111 | <20 | 440 | <20 | <20 | 1070 |
| <20 | <20 | 413 | 51 | >2560 | <20 | <20 | >2560 |
| <20 | <20 | >2560 | <20 | 1031 | <20 | <20 | >2560 |
| <20 | 20 | 2128 | <20 | 1538 | <20 | <20 | >2560 |
| <20 | 20 | 861 | <20 | 636 | 20 | <20 | >2560 |
| <20 | <20 | 1390 | <20 | 2339 | <20 | <20 | >2560 |
| <20 | <20 | 969 | <20 | 1903 | <20 | <20 | 900 |
| <20 | <20 | 1011 | 20 | 1969 | 20 | <20 | >2560 |
| <20* | <20* | <20* | <20* | <20* | <20* | <20* | <20* |

*pre-immune pooled sera

REFERENCES

Britt W J, Alford C A. Cytomegalovirus. In Fields B N, Knipe D M, Howley P M (ed.). Fields Virology, 3rd edition, Philadelphia, Pa.: Lippincott/Raven; 1996. p. 2493-523.

Chee M S, Bankier A T, Beck S, Bohni R, Brown C M, Cerny R, Horsnell T, Hutchinson C A, Kouzarides T, Martignetti J A, Preddie E, Satchwell S C, Tomlinson P, Weston K M and Barrell B G. 1990. Analysis of the protein-coding content of the sequence of human cytomegalovirus strain AD169. Curr. Top. Microbiol. Immunol. 154:125-70.

Davison A J, Dolan A, Akter P, Addison C, Dargan D J, Alcendor D J, McGeoch D J and Hayward G S. 2003. The human cytomegalovirus genome revisited: comparison with the chimpanzee cytomegalovirus genome. J. Gen. Virol. 84:17-28. (Erratum, 84:1053).

Crumpacker C S and Wadhwa S. 2005. Cytomegalovirus, p 1786-1800. In G. L. Mandell, J. E. Bennett, and R. Dolin (ed.), Principles and practice of infectious diseases, vol 2. Elsevier, Philadelphia, Pa.

Pomeroy C and Englund J A. 1987. Cyotmegalovirus: epidemiology and infection control. Am J Infect Control 15: 107-119.

Murphy E, Yu D, Grimwood J, Schmutz J, Dickson M, Jarvis M A, Nelson J A, Myers R M and Shenk T E. 2003. Coding potential of laboratory and clinical strains of cytomegalovirus. Proc. Natl. Acad. Sci. USA 100:14976-81.

Mocarski E S and Tan Courcelle C. 2001. Cytomegalovirus and their replication, p. 2629-73. In D M Knipe and P M Howley (ed.) Fields Virology, 4th edition, vol. 2. Lippincott Williams and Wilkins, Philadelphia, Pa.

Compton T. 2004. Receptors and immune sensors: the complex entry path of human cytomegalovirus. Trends Cell. Bio. 14(1): 5-8.

Britt W J and Alford C A. 2004. Human cytomegalovirus virion proteins. Hum. Immunol. 65:395-402.

Varnum S M, Streblow D N, Monroe M E, Smith P, Auberry K J, Pasa-Tolic L, Wang D, Camp I I D G, Rodland K, Wiley, Britt W, Shenk T, Smith R D and Nelson J A. 2004. Identification of proteins in human cytomegalovirus (HCMV) particles: the HCMV proteome. J. Virol. 78:10960-66. (Erratum, 78:13395).

Ljungman P, Griffiths P and Paya C. 2002. Definitions of cytomegalovirus infection and disease in transplant recipients. Clin. Infect. Dis. 34:1094-97.

Rubin R. 2002. Clinical approach to infection in the compromised host, p. 573-679. In R. Rubin and L S Young (ed), Infection in the organ transplant recipient. Kluwer Academic Press, New York, N.Y.

Stagno S and Britt W J. 2005. Cytomegalovirus, p. 389-424. In J S Remington and J O Klein (ed), Infectious diseases of the fetus and newborn infant, 6th edition. WB Saunders, Philadelphia, Pa.

Britt W J, Vugler L, Butfiloski E J and Stephens E B. 1990. Cell surface expression of human cytomegalovirus (HCMV) gp55-116 (gB): use of HCMV-vaccinia recombinant virus infected cells in analysis of the human neutralizing antibody response. J. Virol. 64:1079-85.

Reap E A, Dryga S A, Morris J, Rivers B, Norberg P K, Olmsted R A and Chulay J D. 2007. Cellular and Humoral Immune Responses to Alphavirus Replicon Vaccines expressing Cytomegalovirus pp 65, IL1 and gB proteins. Clin. Vacc. Immunol. 14:748-55.

Balasuriya U B R, Heidner H W, Hedges J F, Williams J C, Davis N L, Johnston R E and MacLachlan N J. 2000. Expression of the two major envelope proteins of equine arteritis virus as a heterodimer is necessary for induction of neutralizing antibodies in mice immunized with recombinant Venezuelan equine encephalitis virus replicon particles. J. Virol. 74:10623-30.

Dunn W, Chou C, Li H, Hai R, Patterson D, Stoic V, Zhu H and Liu F. 2003. Functional profiling of a human cytomegalovirus genome. Proc. Natl. Acad. Sci USA 100: 14223-28.

Hobom U, Brune W, Messerle M, Hahn G and Kosinowski U H. 2000. Fast screening procedures for random transposon libraries of cloned herpesvirus genomes: mutational analysis of human cytomegalovirus envelope glycoprotein genes. J. Virol. 74:7720-29.

Ryckman B J, Chase M C and Johnson D C. 2009. HCMV T R strain glycoprotein 0 acts as a chaperone promoting gH/gL incorporation into virions, but is not present in virions. J. Virol.

Wille P T, Knoche A J, Nelson J A, Jarvis M A and Johnson J C. 2009. An HCMV gO-null mutant fails to incorporate gH/gL into the virion envelope and is unable to enter fibroblasts, epithelial, and endothelial cells. J. Virol.

Shimamura M, Mach M and Britt W J. 2006. Human Cytomegalovirus infection elicits a glycoprotein M (gM)/gN-specific virus-neutralizing antibody response. J. Virol. 80:4591-4600.

Cha T A, Tom E, Kemble G W, Duke G M, Mocarski E S and Spaete R R. 1996. Human cytomegalovirus clinical isolates carry at least 19 genes not found in laboratory strains. J. Virol. 70:78-83.

Wang D and Shenk T. 2005. Human cytomegalovirus virion protein complex required for epithelial and endothelial cell tropism. Proc. Natl. Acad. Sci. USA 102:18153-58.

Adler B, Scrivano L, Ruzcics Z, Rupp B, Sinzger C and Kosinowski U. 2006. Role of human cytomegalovirus UL131A in cell type-specific virus entry and release. J. Gen. Virol. 87:2451-60.

Ryckman B J, Rainish B L, Chase M C, Borton J A, Nelson J A, Jarvis J A and Johnson D C. 2008. Characterization of the human cytomegalovirus gH/gL/UL128-UL131 complex that mediates entry into epithelial and endothelial cells. J. Virol. 82: 60-70.

SEQUENCES

```
CMV gB FL (SEQ ID NO: 25):
1-
atggaaagccggatctggtgcctggtcgtgtgcgtgaacctgtgcatcgtgtgcctgggagc
cgccgtgagcagcagcagcaccagaggcaccagcgccacacacagccaccacagcagccaca
ccacctctgccgcccacagcagatccggcagcgtgtcccagagagtgaccagcagccagacc
gtgtcccacggcgtgaacgagacaatctacaacaccaccctgaagtacggcgacgtcgtggg
cgtgaataccaccaagtacccctacagagtgtgcagcatggcccagggcaccgacctgatca
gattcgagcggaacatcgtgtgcaccagcatgaagcccatcaacgaggacctggacgagggc
atcatggtggtgtacaagagaaacatcgtggcccacaccttcaaagtgcgggtgtaccagaa
```

-continued

| SEQUENCES |
|---|

ggtgctgaccttccggcggagctacgcctacatccacaccacatacctgctgggcagcaaca
ccgagtacgtggcccctcccatgtgggagatccaccacatcaacagccacagccagtgctac
agcagctacagccgcgtgatcgccggcacagtgttcgtggcctaccaccgggacagctacga
gaacaagaccatgcagctgatgcccgacgactacagcaacacccacagcaccagatacgtga
ccgtgaaggaccagtggcacagcagaggcagcacctggctgtaccgggagacatgcaacctg
aactgcatggtcaccatcaccaccgccagaagcaagtacccttaccacttcttcgccacctc
caccggcgacgtggtggacatcagccccttctacaacggcaccaaccggaacgccagctact
tcggcgagaacgccgacaagttcttcatcttccccaactacaccatcgtgtccgacttcggc
agacccaacagcgctctggaaacccacagactggtggcctttctggaacgggccgacagcgt
gatcagctgggacatccaggacgagaagaacgtgacctgccagctgaccttctgggaggcct
ctgagagaaccatcagaagcgaggccgaggacagctaccacttcagcagcgccaagatgacc
gccaccttcctgagcaagaaacaggaagtgaacatgagcgactccgccctggactgcgtgag
ggacgaggccatcaacaagctgcagcagatcttcaacaccagctacaaccagacctacgaga
agtatggcaatgtgtccgtgttcgagacaacaggcggcctggtggtgttctggcagggcatc
aagcagaaaagcctggtggagctggaacggctcgccaaccggtccagcctgaacctgaccca
caaccggaccaagcggagcaccgacggcaacaacgcaacccacctgtccaacatggaaagcg
tgcacaacctggtgtacgcacagctgcagttcacctacgacaccctgcggggctacatcaac
agagccctggcccagatcgccgaggcttggtgcgtggaccagcggcggaccctggaagtgtt
caaagagctgtccaagatcaaccccagcgccatcctgagcgccatctacaacaagcctatcg
ccgccagattcatgggcgacgtgctgggcctggccagctgcgtgaccatcaaccagaccagc
gtgaaggtgctgcgggacatgaacgtgaaagagagcccaggccgctgctactccagacccgt
ggtcatcttcaacttcgccaacagctcctacgtgcagtacggccagctgggcgaggacaacg
agatcctgctggggaaccaccggaccgaggaatgccagctgcccagcctgaagatctttatc
gccggcaacagcgcctacgagtatgtggactacctgttcaagcggatgatcgacctgagcag
catctccaccgtggacagcatgatcgccctggacatcgacccccctggaaaacaccgacttcc
gggtgctggaactgtacagccagaaagagctgcggagcagcaacgtgttcgacctggaagag
atcatgcgggagttcaacagctacaagcagcgcgtgaaatacgtggaggacaaggtggtgga
ccccctgcctccttacctgaagggcctggacgacctgatgagcggactgggcgctgccggaa
aagccgtgggagtggccattggagctgtgggcggagctgtggcctctgtcgtggaaggcgtc
gccacctttctgaagaaccccttcggcgccttcaccatcatcctggtggccattgccgtcgt
gatcatcacctacctgatctacacccggcagcggagactgtgtacccagcccctgcagaacc
tgttcccctacctggtgtccgccgatggcaccacagtgaccagcggctccaccaaggatacc
agcctgcaggccccacccagctacgaagagagcgtgtacaacagcggcagaaagggccctgg
ccctcccagctctgatgccagcacagccgcccctccctacaccaacgagcaggcctaccaga
tgctgctggccctggctagactggatgccgagcagagggcccagcagaacggcaccgacagc
ctggatggcagaaccggcacccaggacaagggccagaagcccaacctgctggaccggctgcg
gcaccggaagaacggctaccggcacctgaaggacagcgacgaggaagagaacgtctgataa
-2727

CMV gB FL (SEQ ID NO: 26):
MESRIWCLVVCVNLCIVCLGAAVSSSSTRGTSATHSHHSSHTTSAAHSRSGSVSQRVTSSQT
VSHGVNETIYNTTLKYGDVVGVNTTKYPYRVCSMAQGTDLIRFERNIVCTSMKPINEDLDEG
IMVVYKRNIVAHTFKVRVYQKVLTFRRSYAYIHTTYLLGSNTEYVAPPMWEIHHINSHSQCY
SSYSRVIAGTVFVAYHRDSYENKTMQLMPDDYSNTHSTRYVTVKDQWHSRGSTWLYRETCNL
NCMVTITTARSKYPYHFFATSTGDVVDISPFYNGTNRNASYFGENADKFFIFPNYTIVSDFG
RPNSALETHRLVAFLERADSVISWDIQDEKNVTCQLTFWEASERTIRSEAEDSYHFSSAKMT
ATFLSKKQEVNMSDSALDCVRDEAINKLQQIFNTSYNQTYEKYGNVSVFETTGGLVVFWQGI
KQKSLVELERLANRSSLNLTHNRTKRSTDGNNATHLSNMESVHNLVYAQLQFTYDTLRGYIN
RALAQIAEAWCVDQRRTLEVFKELSKINPSAILSAIYNKPIAARFMGDVLGLASCVTINQTS
VKVLRDMNVKESPGRCYSRPVVIFNFANSSYVQYGQLGEDNEILLGNHRTEECQLPSLKIFI
AGNSAYEYVDYLFKRMIDLSSISTVDSMIALDIDPLENTDFRVLELYSQKELRSSNVFDLEE
IMREFNSYKQRVKYVEDKVVDPLPPYLKGLDDLMSGLGAAGKAVGVAIGAVGGAVASVVEGV
ATFLKNPFGAFTIILVAIAVVIITYLIYTRQRRLCTQPLQNLFPYLVSADGTTVTSGSTKDT
SLQAPPSYEESVYNSGRKGPGPPSSDASTAAPPYTNEQAYQMLLALARLDAEQRAQQNGTDS
LDGRTGTQDKGQKPNLLDRLRHRKNGYRHLKDSDEEENV--

CMV gB sol 750 (SEQ ID NO: 27):
1-
atggaaagccggatctggtgcctggtcgtgtgcgtgaacctgtgcatcgtgtgcctgggagc
cgccgtgagcagcagcagcaccagaggcaccagcgccacacacagccaccacagcagccaca
ccacctctgccgcccacagcagatccggcagcgtgtcccagagagtgaccagcagccagacc
gtgtcccacggcgtgaacgagacaatctacaacaccaccctgaagtacggcgacgtcgtggg
cgtgaataccaccaagtacccctacagagtgtgcagcatggcccagggcaccgacctgatca
gattcgagcggaacatcgtgtgcaccagcatgaagcccatcaacgaggacctggacgagggc
atcatggtggtgtacaagagaaacatcgtggcccacaccttcaaagtgcgggtgtaccagaa
ggtgctgaccttccggcggagctacgcctacatccacaccacatacctgctgggcagcaaca
ccgagtacgtggcccctcccatgtgggagatccaccacatcaacagccacagccagtgctac
agcagctacagccgcgtgatcgccggcacagtgttcgtggcctaccaccgggacagctacga
gaacaagaccatgcagctgatgcccgacgactacagcaacacccacagcaccagatacgtga
ccgtgaaggaccagtggcacagcagaggcagcacctggctgtaccgggagacatgcaacctg
aactgcatggtcaccatcaccaccgccagaagcaagtacccttaccacttcttcgccacctc
caccggcgacgtggtggacatcagccccttctacaacggcaccaaccggaacgccagctact
tcggcgagaacgccgacaagttcttcatcttccccaactacaccatcgtgtccgacttcggc
agacccaacagcgctctggaaacccacagactggtggcctttctggaacgggccgacagcgt
gatcagctgggacatccaggacgagaagaacgtgacctgccagctgaccttctgggaggcct
ctgagagaaccatcagaagcgaggccgaggacagctaccacttcagcagcgccaagatgacc
gccaccttcctgagcaagaaacaggaagtgaacatgagcgactccgccctggactgcgtgag -continued

| SEQUENCES |
|---|

ggacgaggccatcaacaagctgcagcagatcttcaacaccagctacaaccagacctacgaga
agtatggcaatgtgtccgtgttcgagacaacaggcggcctggtggtgttctggcagggcatc
aagcagaaaagcctggtggagctggaacggctcgccaaccggtccagcctgaacctgaccca
caaccggaccaagcggagcaccgacggcaacaacgcaacccacctgtccaacatggaaagcg
tgcacaacctggtgtacgcacagctgcagttcacctacgacaccctgcggggctacatcaac
agagccctggcccagatcgccgaggcttggtgcgtggaccagcggcggaccctggaagtgtt
caaagagctgtccaagatcaaccccagcgccatcctgagcgccatctacaacaagcctatcg
ccgccagattcatgggcgacgtgctgggcctggccagctgcgtgaccatcaaccagaccagc
gtgaaggtgctgcgggacatgaacgtgaaagagagcccaggccgctgctactccagacccgt
ggtcatcttcaacttcgccaacagctcctacgtgcagtacggccagctgggcgaggacaacg
agatcctgctggggaaccaccggaccgaggaatgccagctgcccagcctgaagatctttatc
gccggcaacagcgcctacgagtatgtggactacctgttcaagcggatgatcgacctgagcag
catctccaccgtggacagcatgatcgccctggacatcgacccccctggaaaacaccgacttcc
gggtgctggaactgtacagccagaaagagctgcggagcagcaacgtgttcgacctggaagag
atcatgcgggagttcaacagctacaagcagcgcgtgaaatacgtggaggacaaggtggtgga
ccccctgcctccttacctgaagggcctggacgacctgatgagcggactgggcgctgccggaa
aagccgtgggagtggccattggagctgtgggcggagctgtggcctctgtcgtggaaggcgtc
gccacctttctgaagaactgataa-2256

Cmv gB sol 750 (SEQ ID NO: 28):
MESRIWCLVVCVNLCIVCLGAAVSSSSTRGTSATHSHHSSHTTSAAHSRSGSVSQRVTSSQT
VSHGVNETIYNTTLKYGDVVGVNTTKYPYRVCSMAQGTDLIRFERNIVCTSMKPINEDLDEG
IMVVYKRNIVAHTFKVRVYQKVLTFRRSYAYIHTTYLLGSNTEYVAPPMWEIHHINSHSQCY
SSYSRVIAGTVFVAYHRDSYENKTMQLMPDDYSNTHSTRYVTVKDQWHSRGSTWLYRETCNL
NCMVTITTARSKYPYHFFATSTGDVVDISPFYNGTNRNASYFGENADKFFIFPNYTIVSDFG
RPNSALETHRLVAFLERADSVISWDIQDEKNVTCQLTFWEASERTIRSEAEDSYHFSSAKMT
ATFLSKKQEVNMSDSALDCVRDEAINKLQQIFNTSYNQTYEKYGNVSVFETTGGLVVFWQGI
KQKSLVELERLANRSSLNLTHNRTKRSTDGNNATHLSNMESVHNLVYAQLQFTYDTLRGYIN
RALAQIAEAWCVDQRRTLEVFKELSKINPSAILSAIYNKPIAARFMGDVLGLASCVTINQTS
VKVLRDMNVKESPGRCYSRPVVIFNFANSSYVQYGQLGEDNEILLGNHRTEECQLPSLKIFI
AGNSAYEYVDYLFKRMIDLSSISTVDSMIALDIDPLENTDFRVLELYSQKELRSSNVFDLEE
IMREFNSYKQRVKYVEDKVVDPLPPYLKGLDDLMSGLGAAGKAVGVAIGAVGGAVASVVEGV
ATFLKN--

CMV gB sol 692 (SEQ ID NO: 29):
1-
atggaaagccggatctggtgcctggtcgtgtgcgtgaacctgtgcatcgtgtgcctgggagc
cgccgtgagcagcagcagcaccagaggcaccagcgccacacacagccaccacagcagccaca
ccacctctgccgcccacagcagatccggcagcgtgtcccagagagtgaccagcagccagacc
gtgtcccacggcgtgaacgagacaatctacaacaccaccctgaagtacggcgacgtcgtggg
cgtgaataccaccaagtacccctacagagtgtgcagcatggcccagggcaccgacctgatca
gattcgagcggaacatcgtgtgcaccagcatgaagcccatcaacgaggacctggacgagggc
atcatggtggtgtacaagagaaacatcgtggcccacaccttcaaagtgcgggtgtaccagaa
ggtgctgaccttccggcggagctacgcctacatccacaccacatacctgctgggcagcaaca
ccgagtacgtggcccctcccatgtgggagatccaccacatcaacagccacagccagtgctac
agcagctacagccgcgtgatcgccggcacagtgttcgtggcctaccaccgggacagctacga
gaacaagaccatgcagctgatgcccgacgactacagcaacacccacagcaccagatacgtga
ccgtgaaggaccagtggcacagcagaggcagcacctggctgtaccgggagacatgcaacctg
aactgcatggtcaccatcaccaccgccagaagcaagtacccttaccacttcttcgccacctc
caccggcgacgtggtggacatcagccccttctacaacggcaccaaccggaacgccagctact
tcggcgagaacgccgacaagttcttcatcttccccaactacaccatcgtgtccgacttcggc
agacccaacagcgctctggaaacccacagactggtggcctttctggaacgggccgacagcgt
gatcagctgggacatccaggacgagaagaacgtgacctgccagctgaccttctgggaggcct
ctgagagaaccatcagaagcgaggccgaggacagctaccacttcagcagcgccaagatgacc
gccaccttcctgagcaagaaacaggaagtgaacatgagcgactccgccctggactgcgtgag
ggacgaggccatcaacaagctgcagcagatcttcaacaccagctacaaccagacctacgaga
agtatggcaatgtgtccgtgttcgagacaacaggcggcctggtggtgttctggcagggcatc
aagcagaaaagcctggtggagctggaacggctcgccaaccggtccagcctgaacctgaccca
caaccggaccaagcggagcaccgacggcaacaacgcaacccacctgtccaacatggaaagcg
tgcacaacctggtgtacgcacagctgcagttcacctacgacaccctgcggggctacatcaac
agagccctggcccagatcgccgaggcttggtgcgtggaccagcggcggaccctggaagtgtt
caaagagctgtccaagatcaaccccagcgccatcctgagcgccatctacaacaagcctatcg
ccgccagattcatgggcgacgtgctgggcctggccagctgcgtgaccatcaaccagaccagc
gtgaaggtgctgcgggacatgaacgtgaaagagagcccaggccgctgctactccagacccgt
ggtcatcttcaacttcgccaacagctcctacgtgcagtacggccagctgggcgaggacaacg
agatcctgctggggaaccaccggaccgaggaatgccagctgcccagcctgaagatctttatc
gccggcaacagcgcctacgagtatgtggactacctgttcaagcggatgatcgacctgagcag
catctccaccgtggacagcatgatcgccctggacatcgacccccctggaaaacaccgacttcc
gggtgctggaactgtacagccagaaagagctgcggagcagcaacgtgttcgacctggaagag
atcatgcgggagttcaacagctacaagcagtgataa-2082

Cmv gB sol 692 (SEQ ID NO: 30);
MESRIWCLVVCVNLCIVCLGAAVSSSSTRGTSATHSHHSSHTTSAAHSRSGSVSQRVT
SSQTVSHGVNETIYNTTLKYGDVVGVNTTKYPYRVCSMAQGTDLIRFERNIVCTSMK
PINEDLDEGIMVVYKRNIVAHTFKVRVYQKVLTFRRSYAYIHTTYLLGSNTEYVAPP
MWEIHHINSHSQCYSSYSRVIAGTVFVAYHRDSYENKTMQLMPDDYSNTHSTRYVT
VKDQWHSRGSTWLYRETCNLNCMVTITTARSKYPYHFFATSTGDVVDISPFYNGTN -continued

| SEQUENCES |
|---|

RNASYFGENADKFFIFPNYTIVSDFGRPNSALETHRLVAFLERADSVISWDIQDEKNV
TCQLTFWEASERTIRSEAEDSYHFSSAKMTATFLSKKQEVNMSDSALDCVRDEAINK
LQQIFNTSYNQTYEKYGNVSVFETTGGLVVFWQGIKQKSLVELERLANRSSLNLTHN
RTKRSTDGNNATHLSNMESVHNLVYAQLQFTYDTLRGYINRALAQIAEAWCVDQR
RTLEVFKELSKINPSAILSAIYNKPIAARFMGDVLGLASCVTINQTSVKVLRDMNVKE
SPGRCYSRPVVIFNFANSSYVQYGQLGEDNEILLGNHRTEECQLPSLKIFIAGNSAYEY
VDYLFKRMIDLSSISTVDSMIALDIDPLENTDFRVLELYSQKELRSSNVFDLEEIMREF
NSYKQ-

CMV gH FL (SEQ ID NO: 31):
1-
atgaggcctggcctgccctcctacctgatcatcctggccgtgtgcctgttcagccacctgctgtccagcagatac
ggcgccgaggccgtgagcgagcccctggacaaggctttccacctgctgctgaacacctacggcagacccatccgg
tttctgcgggagaacaccacccagtgcacctacaacagcagcctgcggaacagcaccgtcgtgagagagaacgcc
atcagcttcaactttttccagagctacaaccagtactacgtgttccacatgcccagatgcctgtttgccggccct
ctggccgagcagttcctgaaccaggtggacctgaccgagacactggaaagataccagcagcggctgaatacctac
gccctggtgtccaaggacctggccagctaccggtcctttagccagcagctcaaggctcaggatagcctcggcgag
cagcctaccaccgtgccccctcccatcgacctgagcatcccccacgtgtggatgcctccccagaccacccctcac
ggctggaccgagagccacaccacctccggcctgcacagaccccacttcaaccagacctgcatcctgttcgacggc
cacgacctgctgtttagcaccgtgacccccctgcctgcaccagggcttctacctgatcgacgagctgagatacgtg
aagatcaccctgaccgaggatttcttcgtggtcaccgtgtccatcgacgacgacaccccccatgctgctgatcttc
ggccacctgcccagagtgctgttcaaggccccctaccagcgggacaacttcatcctgcggcagaccgagaagcac
gagctgctggtgctggtcaagaaggaccagctgaaccggcactcctacctgaaggaccccgacttcctggacgcc
gccctggacttcaactacctggacctgagcgccctgctgagaaacagcttccacagatacgccgtggacgtgctg
aagtccggacggtgccagatgctcgatcggcggaccgtggagatggccttcgcctatgccctcgccctgttcgcc
gctgccagacaggaagaggctggcgcccaggtgtcagtgcccagagccctggatagacaggccgccctgctgcag
atccaggaattcatgatcacctgcctgagccagacccccccctagaaccaccctgctgctgtaccccacagccgtg
gatctggccaagagggccctgtggacccccaaccagatcaccgacatcacaagcctcgtgcggctcgtgtacatc
ctgagcaagcagaaccagcagcacctgatccccagtgggccctgagacagatcgccgacttcgccctgaagctg
cacaagacccatctggccagctttctgagcgccttcgccaggcaggaactgtacctgatgggcagcctggtccac
agcatgctggtgcataccaccgagcggcgggagatcttcatcgtggagacaggcctgtgtagcctggccgagctg
tcccactttacccagctgctggcccaccctcaccacgagtacctgagcgacctgtacaccccctgcagcagcagc
ggcagacgggaccacagcctggaacggctgaccagactgttccccgatgccaccgtgcctgctacagtgcctgcc
gccctgtccatcctgtccaccatgcagcccagcaccctggaaaccttccccgacctgttctgcctgcccctgggc
gagagctttagcgccctgaccgtgtccgagcacgtgtcctacatcgtgaccaatcagtacctgatcaagggcatc
agctaccccgtgtccaccacagtcgtgggccagagcctgatcatcacccagaccgacagccagaccaagtgcgag
ctgacccggaacatgcacaccacacacagcatcaccgtggccctgaacatcagcctggaaaactgcgctttctgt
cagtctgccctgctggaatacgacgatacccagggcgtgatcaacatcatgtacatgcacgacagcgacgacgtg
ctgttcgccctggaccccctacaacgaggtggtggtgtccagcccccggacccactacctgatgctgctgaagaac
ggcaccgtgctggaagtgaccgacgtggtggtggacgccaccgacagcagactgctgatgatgagcgtgtacgcc
ctgagcgccatcatcggcatctacctgctgtaccggatgctgaaaacctgctgataa-2232

Cmv gH FL (SEQ ID NO: 32);
MRPGLPSYLIILAVCLFSHLLSSRYGAEAVSEPLDKAFHLLLNTYGRPIRFLRENTTQCTYN
SSLRNSTVVRENAISFNFFQSYNQYYVFHMPRCLFAGPLAEQFLNQVDLTETLERYQQRLNT
YALVSKDLASYRSFSQQLKAQDSLGEQPTTVPPPIDLSIPHVWMPPQTTPHGWTESHTTSGL
HRPHFNQTCILFDGHDLLFSTVTPCLHQGFYLIDELRYVKITLTEDFFVVTVSIDDDTPMLL
IFGHLPRVLFKAPYQRDNFILRQTEKHELLVLVKKDQLNRHSYLKDPDFLDAALDFNYLDLS
ALLRNSFHRYAVDVLKSGRCQMLDRRTVEMAFAYALALFAAARQEEAGAQVSVPRALDRQAA
LLQIQEFMITCLSQTPPRTTLLLYPTAVDLAKRALWTPNQITDITSLVRLVYILSKQNQQHL
IPQWALRQIADFALKLHKTHLASFLSAFARQELYLMGSLVHSMLVHTTERREIFIVETGLCS
LAELSHFTQLLAHPHHEYLSDLYTPCSSSGRRDHSLERLTRLFPDATVPATVPAALSILSTM
QPSTLETFPDLFCLPLGESFSALTVSEHVSYIVTNQYLIKGISYPVSTTVVGQSLIITQTDS
QTKCELTRNMHTTHSITVALNISLENCAFCQSALLEYDDTQGVINIMYMHDSDDVLFALDPY
NEVVVSSPRTHYLMLLKNGTVLEVTDVVVDATDSRLLMMSVYALSAIIGIYLLYRMLKTC--

CMV gH sol (SEQ ID NO: 33):
1-
atgaggcctggcctgccctcctacctgatcatcctggccgtgtgcctgttcagccacctgct
gtccagcagatacggcgccgaggccgtgagcgagcccctggacaaggctttccacctgctgc
tgaacacctacggcagacccatccggtttctgcgggagaacaccacccagtgcacctacaac
agcagcctgcggaacagcaccgtcgtgagagagaacgccatcagcttcaactttttccagag
ctacaaccagtactacgtgttccacatgcccagatgcctgtttgccggccctctggccgagc
agttcctgaaccaggtggacctgaccgagacactggaaagataccagcagcggctgaatacc
tacgccctggtgtccaaggacctggccagctaccggtcctttagccagcagctcaaggctca
ggatagcctcggcgagcagcctaccaccgtgccccctcccatcgacctgagcatcccccacg
tgtggatgcctccccagaccacccctcacggctggaccgagagccacaccacctccggcctg
cacagaccccacttcaaccagacctgcatcctgttcgacggccacgacctgctgtttagcac
cgtgacccccctgcctgcaccagggcttctacctgatcgacgagctgagatacgtgaagatca
ccctgaccgaggatttcttcgtggtcaccgtgtccatcgacgacgacaccccccatgctgctg
atcttcggccacctgcccagagtgctgttcaaggccccctaccagcgggacaacttcatcct
gcggcagaccgagaagcacgagctgctggtgctggtcaagaaggaccagctgaaccggcact
cctacctgaaggaccccgacttcctggacgccgccctggacttcaactacctggacctgagc
gccctgctgagaaacagcttccacagatacgccgtggacgtgctgaagtccggacggtgcca
gatgctcgatcggcggaccgtggagatggccttcgcctatgccctcgccctgttcgccgctg
ccagacaggaagaggctggcgcccaggtgtcagtgcccagagccctggatagacaggccgcc
ctgctgcagatccaggaattcatgatcacctgcctgagccagacccccccctagaaccaccct -continued

SEQUENCES gctgctgtaccccacagccgtggatctggccaagagggccctgtggacccccaaccagatca
ccgacatcacaagcctcgtgcggctcgtgtacatcctgagcaagcagaaccagcagcacctg
atcccccagtgggccctgagacagatcgccgacttcgccctgaagctgcacaagacccatct
ggccagctttctgagcgccttcgccaggcaggaactgtacctgatgggcagcctggtccaca
gcatgctggtgcataccaccgagcggcgggagatcttcatcgtggagacaggcctgtgtagc
ctggccgagctgtcccactttacccagctgctggcccaccctcaccacgagtacctgagcga
cctgtacacccccctgcagcagcagcggcagacgggaccacagcctggaacggctgaccagac
tgttccccgatgccaccgtgcctgctacagtgcctgccgccctgtccatcctgtccaccatg
cagcccagcaccctggaaaccttccccgacctgttctgcctgcccctgggcgagagctttag
cgccctgaccgtgtccgagcacgtgtcctacatcgtgaccaatcagtacctgatcaagggca
tcagctaccccgtgtccaccacagtcgtgggccagagcctgatcatcacccagaccgacagc
cagaccaagtgcgagctgacccggaacatgcacaccacacacagcatcaccgtggccctgaa
catcagcctggaaaactgcgctttctgtcagtctgccctgctggaatacgacgatacccagg
gcgtgatcaacatcatgtacatgcacgacagcgacgacgtgctgttcgccctggacccctac
aacgaggtggtggtgtccagcccccggacccactacctgatgctgctgaagaacggcaccgt
gctggaagtgaccgacgtggtggtggacgccaccgactgataa-2151

CMV gH sol (SEQ ID NO: 34);
MRPGLPSYLIIILAVCLFSHLLSSRYGAEAVSEPLDKAFHLLLNTYGRPIRFLRENTTQCTYN
SSLRNSTVVRENAISFNFFQSYNQYYVFHMPRCLFAGPLAEQFLNQVDLTETLERYQQRLNT
YALVSKDLASYRSFSQQLKAQDSLGEQPTTVPPPIDLSIPHVWMPPQTTPHGWTESHTTSGL
HRPHFNQTCILFDGHDLLFSTVTPCLHQGFYLIDELRYVKITLTEDFFVVTVSIDDDTPMLL
IFGHLPRVLFKAPYQRDNFILRQTEKHELLVLVKKDQLNRHSYLKDPDFLDAALDFNYLDLS
ALLRNSFHRYAVDVLKSGRCQMLDRRTVEMAFAYALALFAAARQEEAGAQVSVPRALDRQAA
LLQIQEFMITCLSQTPPRTTLLLYPTAVDLAKRALWTPNQITDITSLVRLVYILSKQNQQHL
IPQWALRQIADFALKLHKTHLASFLSAFARQELYLMGSLVHSMLVHTTERREIFIVETGLCS
LAELSHFTQLLAHPHHEYLSDLYTPCSSSGRRDHSLERLTRLFPDATVPATVPAALSILSTM
QPSTLETFPDLFCLPLGESFSALTVSEHVSYIVTNQYLIKGISYPVSTTVVGQSLIITQTDS
QTKCELTRNMHTTHSITVALNISLENCAFCQSALLEYDDTQGVINIMYMHDSDDVLFALDPY
NEVVVSSPRTHYLMLLKNGTVLEVTDVVVDATD--

CMV gL fl (SEQ ID NO: 35):
1-
atgtgcagaaggcccgactgcggcttcagcttcagccctggacccgtgatcctgctgtggtg
ctgcctgctgctgcctatcgtgtcctctgccgccgtgtctgtggcccctacagccgccgaga
aggtgccagccgagtgccccgagctgaccagaagatgcctgctgggcgaggtgttcgagggc
gacaagtacgagagctggctgcggcccctggtcaacgtgaccggcagagatggcccccctgag
ccagctgatccggtacagacccgtgacccccgaggccgccaatagcgtgctgctggacgagg
ccttcctggataccctggccctgctgtacaacaaccccgaccagctgagagccctgctgacc
ctgctgtccagcgacaccgcccccagatggatgaccgtgatgcggggctacagcgagtgtgg
agatggcagccctgccgtgtacacctgcgtggacgacctgtgcagaggctacgacctgacca
gactgagctacggccggtccatcttcacagagcacgtgctgggcttcgagctggtgcccccc
agcctgttcaacgtggtggtggccatccggaacgaggccaccagaaccaacagagccgtgcg
gctgcctgtgtctacagccgctgcacctgagggcatcacactgttctacggcctgtacaacg
ccgtgaaagagttctgcctccggcaccagctggatccccccctgctgagacacctggacaag
tactacgccggcctgcccccagagctgaagcagaccagagtgaacctgcccgcccacagcag
atatggccctcaggccgtggacgccagatgataa-840

CMV gL FL (SEQ ID NO: 36);
MCRRPDCGFSFSPGPVILLWCCLLLPIVSSAAVSVAPTAAEKVPAECPELTRRCLLGEVFEG
DKYESWLRPLVNVTGRDGPLSQLIRYRPVTPEAANSVLLDEAFLDTLALLYNNPDQLRALLT
LLSSDTAPRWMTVMRGYSECGDGSPAVYTCVDDLCRGYDLTRLSYGRSIFTEHVLGFELVPP
SLFNVVVAIRNEATRTNRAVRLPVSTAAAPEGITLFYGLYNAVKEFCLRHQLDPPLLRHLDK
YYAGLPPELKQTRVNLPAHSRYGPQAVDAR--

CMV gM FL (SEQ ID NO: 37):
1-
atggcccccagccacgtggacaaagtgaacacccggacttggagcgccagcatcgtgttcat
ggtgctgaccttcgtgaacgtgtccgtgcacctggtgctgtccaacttcccccacctgggct
acccctgcgtgtactaccacgtggtggacttcgagcggctgaacatgagcgcctacaacgtg
atgcacctgcacacccccatgctgtttctggacagcgtgcagctcgtgtgctacgccgtgtt
catgcagctggtgtttctggccgtgaccatctactacctcgtgtgctggatcaagatcagca
tgcggaaggacaagggcatgagcctgaaccagagcacccgggacatcagctacatgggcgac
agcctgaccgccttcctgttcatcctgagcatggacaccttccagctgttcaccctgaccat
gagcttccggctgcccagcatgatcgccttcatggccgccgtgcactttttctgtctgacca
tcttcaacgtgtccatggtcacccagtaccggtcctacaagcggagcctgttcttcttctcc
cggctgcaccccaagctgaagggcaccgtgcagttccggaccctgatcgtgaacctggtgga
ggtggccctgggcttcaataccaccgtggtggctatggccctgtgctacggcttcggcaaca
acttcttcgtgcggaccggccatatggtgctggccgtgttcgtggtgtacgccatcatcagc
atcatctactttctgctgatcgaggccgtgttcttccagtacgtgaaggtgcagttcggcta
ccatctgggcgcctttttcggcctgtgcggcctgatctaccccatcgtgcagtacgacacct
tcctgagcaacgagtaccggaccggcatcagctggtccttcggaatgctgttcttcatctgg
gccatgttcaccacctgcagagccgtgcggtacttcagaggcagaggcagcggctccgtgaa
gtaccaggccctggccacagcctctggcgaagaggtggccgccctgagccaccacgacagcc
tggaaagcagacggctgcgggaggaagaggacgacgacgacgaggacttcgaggacgcctga
taa-1119

-continued

| SEQUENCES |
|---|

CMV gM FL (SEQ ID NO: 38);
MAPSHVDKVNTRTWSASIVFMVLTFVNVSVHLVLSNFPHLGYPCVYYHVVDFERLNMSAYNV
MHLHTPMLFLDSVQLVCYAVFMQLVFLAVTIYYLVCWIKISMRKDKGMSLNQSTRDISYMGD
SLTAFLFILSMDTFQLFTLTMSFRLPSMIAFMAAVHFFCLTIFNVSMVTQYRSYKRSLFFFS
RLHPKLKGTVQFRTLIVNLVEVALGFNTTVVAMALCYGFGNNFFVRTGHMVLAVFVVYAIIS
IIYFLLIEAVFFQYVKVQFGYHLGAFFGLCGLIYPIVQYDTFLSNEYRTGISWSFGMLFFIW
AMFTTCRAVRYFRGRGSGSVKYQALATASGEEVAALSHHDSLESRRLREEEDDDDEDFEDA-
-

CMV gN FL (SEQ ID NO: 39):
1-
atggaatggaacaccctggtcctgggcctgctggtgctgtctgtcgtggccagcagcaacaa
cacatccacagccagcacccctagacctagcagcagcacccacgccagcactaccgtgaagg
ctaccaccgtggccaccacaagcaccaccactgctaccagcaccagctccaccacctctgcc
aagcctggctctaccacacacgaccccaacgtgatgaggccccacgcccacaacgacttcta
caacgctcactgcaccagccacatgtacgagctgtccctgagcagctttgccgcctggtgga
ccatgctgaacgccctgatcctgatgggcgccttctgcatcgtgctgcggcactgctgcttc
cagaacttcaccgccaccaccaccaagggctactgataa-411

CMV gN FL (SEQ ID NO: 40);
MEWNTLVLGLLVLSVVASSNNTSTASTPRPSSSTHASTTVKATTVATTSTTATSTSSTTSA
KPGSTTHDPNVMRPHAHNDFYNAHCTSHMYELSLSSFAAWWTMLNALILMGAFCIVLRHCCF
QNFTATTTKGY--

CMV gO FL (SEQ ID NO: 41):
1-
atgggcaagaaagaaatgatcatggtcaagggcatccccaagatcatgctgctgattagcat
cacctttctgctgctgtccctgatcaactgcaacgtgctggtcaacagccggggcaccagaa
gatcctggccctacaccgtgctgtcctaccggggcaaagagatcctgaagaagcagaaagag
gacatcctgaagcggctgatgagcaccagcagcgacggctaccggttcctgatgtaccccag
ccagcagaaattccacgccatcgtgatcagcatggacaagttccccaggactacatcctgg
ccggacccatccggaacgacagcatcacccacatgtggttcgacttctacagcacccagctg
cggaagcccgccaaatacgtgtacagcgagtacaaccacaccgcccacaagatcaccctgag
gcctcccccttgtggcaccgtgcccagcatgaactgcctgagcgagatgctgaacgtgtcca
agcggaacgacaccggcgagaagggctgcggcaacttcaccaccttcaaccccatgttcttc
aacgtgccccggtggaacaccaagctgtacatcggcagcaacaaagtgaacgtggacagcca
gaccatctactttctgggcctgaccgccctgctgctgagatacgcccagcggaactgcaccc
ggtccttctacctggtcaacgccatgagccggaacctgttccgggtgcccaagtacatcaac
ggcaccaagctgaagaacaccatgcggaagctgaagcggaagcaggccctggtcaaagagca
gccccagaagaagaacaagaagtcccagagcaccaccaccccctacctgagctacaccacct
ccaccgccttcaacgtgaccaccaacgtgacctacagcgccacagccgccgtgaccagagtg
gccacaagcaccaccggctaccggcccgacagcaactttatgaagtccatcatggccaccca
gctgagagatctggccacctgggtgtacaccaccctgcggtacagaaacgagccctttctgca
agcccgaccggaacagaaccgccgtgagcgagttcatgaagaatacccacgtgctgatcaga
aacgagacaccctacaccatctacggcaccctggacatgagcagcctgtactacaacgagac
aatgagcgtggagaacgagacagccagcgacaacaacgaaaccaccccccacctcccccagca
cccggttccagcggaccttcatcgacccccctgtgggactacctggacagcctgctgttcctg
gacaagatccggaacttcagcctgcagctgcccgcctacggcaatctgacccccccctgagca
cagaagggccgccaacctgagcaccctgaacagcctgtggtggtggagccagtgataa-
1422

CMV gO FL (SEQ ID NO: 42);
MGKKEMIMVKGIPKIMLLISITFLLLSLINCNVLVNSRGTRRSWPYTVLSYRGKEILKKQKE
DILKRLMSTSSDGYRFLMYPSQQKFHAIVISMDKFPQDYILAGPIRNDSITHMWFDFYSTQL
RKPAKYVYSEYNHTAHKITLRPPPCGTVPSMNCLSEMLNVSKRNDTGEKGCGNFTTFNPMFF
NVPRWNTKLYIGSNKVNVDSQTIYFLGLTALLLRYAQRNCTRSFYLVNAMSRNLFRVPKYIN
GTKLKNTMRKLKRKQALVKEQPQKKNKKSQSTTTPYLSYTTSTAFNVTTNVTYSATAAVTRV
ATSTTGYRPDSNFMKSIMATQLRDLATWVYTTLRYRNEPFCKPDRNRTAVSEFMKNTHVLIR
NETPYTIYGTLDMSSLYYNETMSVENETASDNNETTPTSPSTRFQRTFIDPLWDYLDSLLFL
DKIRNFSLQLPAYGNLTPPEHRRAANLSTLNSLWWWSQ--

CMV UL128 FL (SEQ ID NO: 43):
1-
atgagccccaaggacctgaccccccttcctgacaaccctgtggctgctcctgggccatagcag
agtgcctagagtgcgggccgaggaatgctgcgagttcatcaacgtgaaccaccccccccgagc
ggtgctacgacttcaagatgtgcaaccggttcaccgtggccctgagatgccccgacggcgaa
gtgtgctacagccccgagaaaaccgccgagatccggggcatcgtgaccaccatgacccacag
cctgacccggcaggtggtgcacaacaagctgaccagctgcaactacaacccccctgtacctgg
aagccgacggccggatcagatgcggcaaagtgaacgacaaggcccagtacctgctgggagcc
gccggaagcgtgccctaccggtggatcaacctggaatacgacaagatcacccggatcgtggg
cctggaccagtacctggaaagcgtgaagaagcacaagcggctggacgtgtgcagagccaaga
tgggctacatgctgcagtgataa-519

CMV UL128 FL (SEQ ID NO: 44);
MSPKDLTPFLTTLWLLLGHSRVPRVRAEECCEFINVNHPPERCYDFKMCNRFTVALRCPDGE
VCYSPEKTAEIRGIVTTMTHSLTRQVVHNKLTSCNYNPLYLEADGRIRCGKVNDKAQYLLGA
AGSVPYRWINLEYDKITRIVGLDQYLESVKKHKRLDVCRAKMGYMLQ--

-continued

SEQUENCES

CMV UL130 FL (SEQ ID NO: 45):
1-
atgctgcggctgctgctgagacaccacttccactgcctgctgctgtgtgccgtgtgggccac
cccttgtctggccagcccttggagcaccctgaccgccaaccagaaccctagcccccccttggt
ccaagctgacctacagcaagccccacgacgccgccaccttctactgccccttctgtacccc
agccctcccagaagccccctgcagttcagcggcttccagagagtgtccaccggccctgagtg
ccggaacgagacactgtacctgctgtacaaccgggagggccagacactggtggagcggagca
gcacctgggtgaaaaaagtgatctggtatctgagcggccggaaccagaccatcctgcagcgg
atgcccagaaccgccagcaagcccagcgacggcaacgtgcagatcagcgtggaggacgccaa
aatcttcggcgcccacatggtgcccaagcagaccaagctgctgagattcgtggtcaacgacg
gcaccagatatcagatgtgcgtgatgaagctggaaagctgggcccacgtgttccgggactac
tccgtgagcttccaggtccggctgaccttcaccgaggccaacaaccagacctacaccttctg
cacccaccccaacctgatcgtgtgataa-648

CMV UL130 FL (SEQ ID NO: 46);
MLRLLLRHHFHCLLLCAVWATPCLASPWSTLTANQNPSPPWSKLTYSKPHDAATFYCPFLYP
SPPRSPLQFSGFQRVSTGPECRNETLYLLYNREGQTLVERSSTWVKKVIWYLSGRNQTILQR
MPRTASKPSDGNVQISVEDAKIFGAHMVPKQTKLLRFVVNDGTRYQMCVMKLESWAHVERDY
SVSFQVRLTFTEANNQTYTFCTHPNLIV--

CMV UL131 FL (SEQ ID NO: 47):
1-
atgcggctgtgcagagtgtggctgtccgtgtgcctgtgtgccgtggtgctgggccagtgcca
gagagagacagccgagaagaacgactactaccgggtgccccactactgggatgcctgcagca
gagccctgcccgaccagacccggtacaaatacgtggagcagctcgtggacctgaccctgaac
taccactacgacgccagccacggcctggacaacttcgacgtgctgaagcggatcaacgtgac
cgaggtgtccctgctgatcagcgacttccggcggcagaacagaagaggcggcaccaacaagc
ggaccaccttcaacgccgctggctctctggcccctcacgccagatccctggaattcagcgtg
cggctgttcgccaactgataa-393

CMV UL131 FL (SEQ ID NO: 48);
MRLCRVWLSVOLCAVVLGQCQRETAEKNDYYRVPHYWDACSRALPDQTRYKYVEQLVDLTLN
YHYDASHGLDNFDVLKRINVTEVSLLISDFRRQNRRGGTNKRTTFNAAGSLAPHARSLEFSV
RLFAN--

EMCV IRES nucleotide sequence (SEQ ID NO: 49);
aacgttactggccgaagccgcttggaataaggccggtgtgcgtttgtctatatgttattttc
caccatattgccgtcttttggcaatgtgagggcccggaaacctggccctgtcttcttgacga
gcattcctaggggtctttcccctctcgccaaaggaatgcaaggtctgttgaatgtcgtgaag
gaagcagttcctctggaagcttcttgaagacaaacaacgtctgtagcgaccctttgcaggca
gcggaaccccccacctggcgacaggtgcctctgcggccaaaagccacgtgtataagatacac
ctgcaaaggcggcacaaccccagtgccacgttgtgagttggatagttgtggaaagagtcaaa
tggctctcctcaagcgtattcaacaaggggctgaaggatgcccagaaggtaccccattgtat
gggatctgatctggggcctcggtgcacatgctttacatgtgtttagtcgaggttaaaaaaac
gtctaggccccccgaaccacggggacgtggttttcctttgaaaaacacgataat EV71 IRES nucleotide sequence (SEQ ID NO: 50);
gtacctttgtacgcctgttttatacccctccctgatttgcaacttagaagcaacgcaaacc
agatcaatagtaggtgtgacataccagtcgcatcttgatcaagcacttctgtatccccggac
cgagtatcaatagactgtgcacacggttgaaggagaaaacgtccgttacccggctaactact
tcgagaagcctagtaacgccattgaagttgcagagtgtttcgctcagcactccccccgtgta
gatcaggtcgatgagtcaccgcattccccacgggcgaccgtggcggtggctgcgttggcggc
ctgcctatggggtaacccataggacgctctaatacggacatggcgtgaagagtctattgagc
tagttagtagtcctccggcccctgaatgcggctaatcctaactgcggagcacataccccttaa
tccaaagggcagtgtgtcgtaacgggcaactctgcagcggaaccgactactttgggtgtccg
tgtttcctttttattcttgtattggctgcttatggtgacaattaaagaattgttaccatatag
ctattggattggccatccagtgtcaaacagagctattgtatatctctttgttggattcacac
ctctcactcttgaaacgttacacaccctcaattacattatactgctgaacacgaagcg VEE Subgenomic Promoter (SEQ ID NO: 51):
5'-CTCTCTACGGCTAACCTGAATGGA-3' pVCR modified vector gH sol-SGP gL (SEQ ID NO: 52):
cgcgtcggctacaattaatacataaccttatgtatcatacacatacgatttaggtgacacta
tagatgggcggcgcatgagagaagcccagaccaattacctacccaaaatggagaaagttcac
gttgacatcgaggaagacagcccattcctcagagctttgcagcggagcttcccgcagtttga
ggtagaagccaagcaggtcactgataatgaccatgctaatgccagagcgttttcgcatctgg
cttcaaaactgatcgaaacggaggtggacccatccgacacgatccttgacattggaagtgcg
cccgcccgcagaatgtattctaagcacaagtatcattgtatctgtccgatgagatgtgcgga
agatccggacagattgtataagtatgcaactaagctgaagaaaaactgtaaggaaataactg
ataaggaattggacaagaaaatgaaggagctcgccgccgtcatgagcgaccctgacctggaa
actgagactatgtgcctccacgacgacgagtcgtgtcgctacgaagggcaagtcgctgttta
ccaggatgtatacgcggttgacggaccgacaagtctctatcaccaagccaataagggagtta
gagtcgcctactggataggctttgacaccacccctttttatgtttaagaacttggctggagca
tatccatcatactctaccaactgggccgacgaaaccgtgttaacggctcgtaacataggcct
atgcagctctgacgttatggagcggtcacgtagagggatgtccattcttagaaagaagtatt -continued

| SEQUENCES |
| --- |
| tgaaaccatccaacaatgttctattctctgttggctcgaccatctaccacgagaagagggac<br>ttactgaggagctggcacctgccgtctgtatttcacttacgtggcaagcaaaattacacatg<br>tcggtgtgagactatagttagttgcgacgggtacgtcgttaaaagaatagctatcagtccag<br>gcctgtatgggaagccttcaggctatgctgctacgatgcaccgcgagggattcttgtgctgc<br>aaagtgacagacacattgaacggggagagggtctcttttcccgtgtgcacgtatgtgccagc<br>tacattgtgtgaccaaatgactggcatactggcaacagatgtcagtgcggacgacgcgcaaa<br>aactgctggttgggctcaaccagcgtatagtcgtcaacggtcgcacccagagaaacaccaat<br>accatgaaaaattacctttgcccgtagtggcccaggcatttgctaggtgggcaaaggaata<br>taaggaagatcaagaagatgaaaggccactaggactacgagatagacagttagtcatggggt<br>gttgttgggcttttagaaggcacaagataacatctatttataagcgcccggatacccaaacc<br>atcatcaaagtgaacagcgatttccactcattcgtgctgcccaggataggcagtaacacatt<br>ggagatcgggctgagaacaagaatcaggaaaatgttagaggagcacaaggagccgtcacctc<br>tcattaccgccgaggacgtacaagaagctaagtgcgcagccgatgaggctaaggaggtgcgt<br>gaagccgaggagttgcgcgcagctctaccacctttggcagctgatgttgaggagcccactct<br>ggaagccgatgtagacttgatgttacaagaggctggggccggctcagtggagacacctcgtg<br>gcttgataaaggttaccagctacgctggcgaggacaagatcggctcttacgctgtgctttct<br>ccgcaggctgtactcaagagtgaaaaattatcttgcatccaccctctcgctgaacaagtcat<br>agtgataacacactctggccgaaaagggcgttatgccgtggaaccataccatggtaaagtag<br>tggtgccagagggacatgcaatacccgtccaggactttcaagctctgagtgaaagtgccacc<br>attgtgtacaacgaacgtgagttcgtaaacaggtacctgcaccatattgccacacatggagg<br>agcgctgaacactgatgaagaatattacaaaactgtcaagcccagcgagcacgacggcgaat<br>acctgtacgacatcgacaggaaacagtgcgtcaagaaagaactagtcactgggctagggctc<br>acaggcgagctggtggatcctcccttccatgaattcgcctacgagagtctgagaacacgacc<br>agccgctccttaccaagtaccaaccataggggtgtatggcgtgccaggatcaggcaagtctg<br>gcatcattaaaagcgcagtcaccaaaaaagatctagtggtgagcgccaagaaagaaaactgt<br>gcagaaattataagggacgtcaagaaaatgaaagggctggacgtcaatgccagaactgtgga<br>ctcagtgctcttgaatggatgcaaacaccccgtagagaccctgtatattgacgaagcttttg<br>cttgtcatgcaggtactctcagagcgctcatagccattataagacctaaaaaggcagtgctc<br>tgcggggatcccaaacagtgcggtttttttaacatgatgtgcctgaaagtgcattttaacca<br>cgagatttgcacacaagtcttccacaaaagcatctctcgccgttgcactaaatctgtgactt<br>cggtcgtctcaaccttgttttacgacaaaaaaatgagaacgacgaatccgaaagagactaag<br>attgtgattgacactaccggcagtaccaaacctaagcaggacgatctcattctcacttgttt<br>cagagggtgggtgaagcagttgcaaatagattacaaaggcaacgaaataatgacggcagctg<br>cctctcaagggctgacccgtaaaggtgtgtatgccgttcggtacaaggtgaatgaaaatcct<br>ctgtacgcacccacctcagaacatgtgaacgtcctactgacccgcacggaggaccgcatcgt<br>gtggaaaacactagccggcgacccatggataaaaacactgactgccaagtaccctgggaatt<br>tcactgccacgatagaggagtggcaagcagagcatgatgccatcatgaggcacatcttggag<br>agaccggaccctaccgacgtcttccagaataaggcaaacgtgtgttgggccaaggctttagt<br>gccggtgctgaagaccgctggcatagacatgaccactgaacaatggaacactgtggattatt<br>ttgaaacggacaaagctcactcagcagagatagtattgaaccaactatgcgtgaggttcttt<br>ggactcgatctggactccggtctattttctgcacccactgttccgttatccattaggaataa<br>tcactgggataactccccgtcgcctaacatgtacgggctgaataaagaagtggtccgtcagc<br>tctctcgcaggtacccacaactgcctcgggcagttgccactggaagagtctatgacatgaac<br>actggtacactgcgcaattatgatccgcgcataaacctagtacctgtaaacagaagactgcc<br>tcatgctttagtcctccaccataatgaacacccacagagtgacttttcttcattcgtcagca<br>aattgaagggcagaactgtcctggtggtcggggaaaagttgtccgtcccaggcaaaatggtt<br>gactggttgtcagaccggcctgaggctaccttcagagctcggctggatttaggcatcccagg<br>tgatgtgcccaaatatgacataatatttgttaatgtgaggaccccatataaataccatcact<br>atcagcagtgtgaagaccatgccattaagcttagcatgttgaccaagaaagcttgtctgcat<br>ctgaatcccggcggaacctgtgtcagcataggttatggttacgctgacagggccagcgaaag<br>catcattggtgctatagcgcggcagttcaagttttcccgggtatgcaaaccgaaatcctcac<br>ttgaagagacggaagttctgtttgtattcattgggtacgatcgcaaggcccgtacgcacaat<br>ccttacaagctttcatcaaccttgaccaacatttatacaggttccagactccacgaagccgg<br>atgtgcaccctcatatcatgtggtgcgaggggatattgccacggccaccgaaggagtgatta<br>taaatgctgctaacagcaaaggacaacctggcggaggggtgtgcggagcgctgtataagaaa<br>ttcccggaaagcttcgatttacagccgatcgaagtaggaaaagcgcgactggtcaaaggtgc<br>agctaaacatatcattcatgccgtaggaccaaacttcaacaaagtttcggaggttgaaggtg<br>acaaacagttggcagaggcttatgagtccatcgctaagattgtcaacgataacaattacaag<br>tcagtagcgattccactgttgtccaccggcatcttttccgggaacaaagatcgactaaccca<br>atcattgaaccatttgctgacagctttagacaccactgatgcagatgtagccatatactgca<br>gggacaagaaatgggaaatgactctcaaggaagcagtggctaggagagaagcagtggaggag<br>atatgcatatccgacgactcttcagtgacagaacctgatgcagagctggtgagggtgcatcc<br>gaagagttctttggctggaaggaagggctacagcacaagcgatggcaaaactttctcatatt<br>tggaagggaccaagtttcaccaggcggccaaggatatagcagaaattaatgccatgtggccc<br>gttgcaacggaggccaatgagcaggtatgcatgtatatcctcggagaaagcatgagcagtat<br>taggtcgaaatgccccgtcgaagagtcggaagcctcctcaccacctagcacgctgccttgct<br>tgtgcatccatgccatgactccagaaagagtacagcgcctaaaagcctcacgtccagaacaa<br>attactgtgtgctcatcctttccattgccgaagtatagaatcactggtgtgcagaagatcca<br>atgctcccagcctatattgttctcaccgaaagtgcctgcgtatattcatccaaggaagtatc<br>tcgtggaaacaccaccggtagacgagactccggagccatcggcagagaaccaatccacagag<br>gggacacctgaacaaccaccacttataaccgaggatgagaccaggactagaacgcctgagcc<br>gatcatcatcgaagaggaagaagaggatagcataagtttgctgtcagatggcccgacccacc<br>aggtgctgcaagtcgaggcagacattcacgggccgccctctgtatctagctcatcctggtcc<br>attcctcatgcatccgactttgatgtggacagtttatccatacttgacaccctggagggagc<br>tagcgtgaccagcggggcaacgtcagccgagactaactcttacttcgcaaagagtatggagt<br>ttctggcgcgaccggtgcctgcgcctcgaacagtattcaggaaccctccacatcccgctccg<br>cgcacaagaacaccgtcacttgcacccagcagggcctgctcgagagggatcacgggagaaac |

-continued

| SEQUENCES |
| --- |

cgtgggatacgcggttacacacaatagcgagggcttcttgctatgcaaagttactgacacag
taaaaggagaacgggtatcgttccctgtgtgcacgtacatcccggccaccataaactcgaga
accagcctggtctccaacccgccaggcgtaaatagggtgattacaagagaggagtttgaggc
gttcgtagcacaacaacaatgacggtttgatgcgggtgcatacatcttttcctccgacaccg
gtcaagggcatttacaacaaaaatcagtaaggcaaacggtgctatccgaagtggtgttggag
aggaccgaattggagatttcgtatgccccgcgcctcgaccaagaaaaagaagaattactacg
caagaaattacagttaaatcccacacctgctaacagaagcagataccagtccaggaaggtgg
agaacatgaaagccataacagctagacgtattctgcaaggcctagggcattatttgaaggca
gaaggaaaagtggagtgctaccgaaccctgcatcctgttcctttgtattcatctagtgtgaa
ccgtgccttttcaagccccaaggtcgcagtggaagcctgtaacgccatgttgaaagagaact
ttccgactgtggcttcttactgtattattccagagtacgatgcctatttggacatggttgac
ggagcttcatgctgcttagacactgccagtttttgccctgcaaagctgcgcagctttccaaa
gaaacactcctatttggaacccacaatacgatcggcagtgccttcagcgatccagaacacgc
tccagaacgtcctggcagctgccacaaaaagaaattgcaatgtcacgcaaatgagagaattg
cccgtattggattcggcggcctttaatgtggaatgcttcaagaaatatgcgtgtaataatga
atattgggaaacgtttaaagaaaaccccatcaggcttactgaagaaaacgtggtaaattaca
ttaccaaattaaaaggaccaaaagctgctgctctttttgcgaagacacataatttgaatatg
ttgcaggacataccaatggacaggtttgtaatggacttaaagagagacgtgaaagtgactcc
aggaacaaaacatactgaagaacggcccaaggtacaggtgatccaggctgccgatccgctag
caacagcgtatctgtgcggaatccaccgagagctggttaggagattaaatgcggtcctgctt
ccgaacattcatacactgtttgatatgtcggctgaagactttgacgctattatagccgagca
cttccagcctggggattgtgttctggaaactgacatcgcgtcgtttgataaaagtgaggacg
acgccatggctctgaccgcgttaatgattctggaagacttaggtgtggacgcagagctgttg
acgctgattgaggcggctttcggcgaaatttcatcaatacatttgcccactaaaactaaatt
taaattcggagccatgatgaaatctggaatgttcctcacactgtttgtgaacacagtcatta
acattgtaatcgcaagcagagtgttgagagaacggctaaccggatcaccatgtgcagcattc
attggagatgacaatatcgtgaaaggagtcaaatcggacaaattaatggcagacaggtgcgc
cacctggttgaatatggaagtcaagattatagatgctgtggtgggcgagaaagcgccttatt
tctgtggagggtttattttgtgtgactccgtgaccggcacagcgtgccgtgtggcagacccc
ctaaaaaggctgtttaagcttggcaaacctctggcagcagacgatgaacatgatgatgacag
gagaagggcattgcatgaagagtcaacacgctggaaccgagtgggtattctttcagagctgt
gcaaggcagtagaatcaaggtatgaaaccgtaggaacttccatcatagttatggccatgact
actctagctagcagtgttaaatcattcagctacctgagaggggcccctataactctctacgg
ctaacctgaatggactacgacatagtctagtcgacgccaccatgaggcctggcctgccctcc
tacctgatcatcctggccgtgtgcctgttcagccacctgctgtccagcagatacggcgccga
ggccgtgagcgagcccctggacaaggctttccacctgctgctgaacacctacggcagaccca
tccggtttctgcgggagaacaccacccagtgcacctacaacagcagcctgcggaacagcacc
gtcgtgagagagaacgccatcagcttcaacttttttccagagctacaaccagtactacgtgtt
ccacatgcccagatgcctgtttgccggccctctggccgagcagttcctgaaccaggtggacc
tgaccgagacactggaaagataccagcagcggctgaatacctacgccctggtgtccaaggac
ctggccagctaccggtcctttagccagcagctcaaggctcaggatagcctcggcgagcagcc
taccaccgtgccccctcccatcgacctgagcatcccccacgtgtggatgcctccccagacca
cccctcacggctggaccgagagccacaccacctccggcctgcacagaccccacttcaaccag
acctgcatcctgttcgacggccacgacctgctgtttagcaccgtgacccccctgcctgcacca
gggcttctacctgatcgacgagctgagatacgtgaagatcaccctgaccgaggatttcttcg
tggtcaccgtgtccatcgacgacgacacccccatgctgctgatcttcggccacctgcccaga
gtgctgttcaaggcccccctaccagcgggacaacttcatcctgcggcagaccgagaagcacga
gctgctggtgctggtcaagaaggaccagctgaaccggcactcctacctgaaggaccccgact
tcctggacgccgccctggacttcaactacctggacctgagcgccctgctgagaaacagcttc
cacagatacgccgtggacgtgctgaagtccggacggtgccagatgctcgatcggcggaccgt
ggagatggccttcgcctatgccctcgccctgttcgccgctgccagacaggaagaggctggcg
cccaggtgtcagtgcccagagccctggatagacaggccgccctgctgcagatccaggaattc
atgatcacctgcctgagccagaccccccctagaaccaccctgctgctgtaccccacagccgt
ggatctggccaagagggccctgtggaccccccaaccagatcaccgacatcacaagcctcgtgc
ggctcgtgtacatcctgagcaagcagaaccagcagcacctgatccccccagtgggccctgaga
cagatcgccgacttcgccctgaagctgcacaagacccatctggccagctttctgagcgcctt
cgccaggcaggaactgtacctgatgggcagcctggtccacagcatgctggtgcataccaccg
agcggcgggagatcttcatcgtggagacaggcctgtgtagcctggccgagctgtcccacttt
acccagctgctggcccaccctcaccacgagtacctgagcgacctgtacacccctgcagcag
cagcggcagacgggaccacagcctggaacggctgaccagactgttccccgatgccaccgtgc
ctgctacagtgcctgccgccctgtccatcctgtccaccatgcagcccagcaccctggaaacc
ttccccgacctgttctgcctgcccctgggcgagagctttagcgccctgaccgtgtccgagca
cgtgtcctacatcgtgaccaatcagtacctgatcaagggcatcagctaccccgtgtccacca
cagtcgtgggccagagcctgatcatcacccagaccgacagccagaccaagtgcgagctgacc
cggaacatgcacaccacacacagcatcaccgtggccctgaacatcagcctggaaaactgcgc
tttctgtcagtctgccctgctggaatacgacgatacccagggcgtgatcaacatcatgtaca
tgcacgacagcgacgacgtgctgttcgccctggacccctacaacgaggtggtggtgtccagc
ccccggacccactacctgatgctgctgaagaacggcaccgtgctggaagtgaccgacgtggt
ggtggacgccaccgactgataatctagacggcgcgcccacccagcggccgcctataactctc
tacggctaacctgaatggactacgacatagtctagtcgacgccaccatgtgcagaaggcccg
actgcggcttcagcttcagccctggacccgtgatcctgctgtggtgctgcctgctgctgcct
atcgtgtcctctgccgccgtgtctgtggcccctacagccgccgagaaggtgccagccgagtg
ccccgagctgaccagaagatgcctgctgggcgaggtgttcgagggcgacaagtacgagagct
ggctgcggcccctggtcaacgtgaccggcagagatggcccccctgagccagctgatccggtac
agacccgtgacccccgaggccgccaatagcgtgctgctggacgaggccttcctggataccct
ggccctgctgtacaacaaccccgaccagctgagagccctgctgaccctgctgtccagcgaca
ccgcccccagatggatgaccgtgatgcggggctacagcgagtgtggagatggcagccctgcc -continued

SEQUENCES gtgtacacctgcgtggacgacctgtgcagaggctacgacctgaccagactgagctacggccg
gtccatcttcacagagcacgtgctgggcttcgagctggtgcccccccagcctgttcaacgtgg
tggtggccatccggaacgaggccaccagaaccaacagagccgtgcggctgcctgtgtctaca
gccgctgcacctgagggcatcacactgttctacggcctgtacaacgccgtgaaagagttctg
cctccggcaccagctggatccccccctgctgagacacctggacaagtactacgccggcctgc
cccagagctgaagcagaccagagtgaacctgcccgcccacagcagatatggccctcaggcc
gtggacgccagatgataatctagacggcgcgcccacccaatcgatgtacttccgaggaactc
acgtgcataatgcatcaggctggtacattagatccccgcttaccgcgggcaatatagcaaca
ctaaaaactcgatgtacttccgaggaagcgcagtgcataatgctgcgcagtgttgccacata
accactatattaaccatttatctagcggacgccaaaaactcaatgtatttctgaggaagcgt
ggtgcataatgccacgcagcgtctgcataacttttattatttcttttattaatcaacaaaat
tttgttttaacatttcaaaaaaaaaaaaaaaaaaaaaaaaaaaaaaaaaaaaaaaaagggtc
ggcatggcatctccacctcctcgcggtccgacctgggcatccgaaggaggacgcacgtccac
tcggatggctaagggagagccacgagctcctgtttaaaccagctccaattcgccctatagtg
agtcgtattacgcgcgctcactggccgtcgttttacaacgtcgtgactgggaaaaccctggc
gttacccaacttaatcgccttgcagcacatccccctttcgccagctggcgtaatagcgaaga
ggcccgcaccgatcgcccttcccaacagttgcgcagcctgaatggcgaatgggacgcgccct
gtagcggcgcattaagcgcggcgggtgtggtggttacgcgcagcgtgaccgctacacttgcc
agcgccctagcgcccgctcctttcgctttcttcccttcctttctcgccacgttcgccggctt
tccccgtcaagctctaaatcgggggctccctttagggttccgatttagtgctttacggcacc
tcgaccccaaaaaacttgattagggtgatggttcacgtagtgggccatcgccctgatagacg
gtttttcgccctttgacgttggagtccacgttctttaatagtggactcttgttccaaactgg
aacaacactcaaccctatctcggtctattcttttgatttataagggattttgccgatttcgg
cctattggttaaaaaatgagctgatttaacaaaaatttaacgcgaattttaacaaaatatta
acgcttacaatttaggtggcacttttcggggaaatgtgcgcggaacccctatttgtttattt
ttctaaatacattcaaatatgtatccgctcatgagacaataaccctgataaatgcttcaata
atattgaaaaaggaagagtatgagtattcaacatttccgtgtcgcccttattcccttttttg
cggcattttgccttcctgtttttgctcacccagaaacgctggtgaaagtaaaagatgctgaa
gatcagttgggtgcacgagtgggttacatcgaactggatctcaacagcggtaagatccttga
gagttttcgccccgaagaacgttttccaatgatgagcacttttaaagttctgctatgtggcg
cggtattatcccgtattgacgccgggcaagagcaactcggtcgccgcatacactattctcag
aatgacttggttgagtactcaccagtcacagaaaagcatcttacggatggcatgacagtaag
agaattatgcagtgctgccataaccatgagtgataacactgcggccaacttacttctgacaa
cgatcggaggaccgaaggagctaaccgcttttttgcacaacatgggggatcatgtaactcgc
cttgatcgttgggaaccggagctgaatgaagccataccaaacgacgagcgtgacaccacgat
gcctgtagcaatggcaacaacgttgcgcaaactattaactggcgaactacttactctagctt
cccggcaacaattaatagactggatggaggcggataaagttgcaggaccacttctgcgctcg
gcccttccggctggctggtttattgctgataaatctggagccggtgagcgtgggtctcgcgg
tatcattgcagcactggggccagatggtaagccctcccgtatcgtagttatctacacgacgg
ggagtcaggcaactatggatgaacgaaatagacagatcgctgagataggtgcctcactgatt
aagcattggtaactgtcagaccaagtttactcatatatactttagattgatttaaaacttca
tttttaatttaaaaggatctaggtgaagatcctttttgataatctcatgaccaaaatccctt
aacgtgagttttcgttccactgagcgtcagaccccgtagaaaagatcaaaggatcttcttga
gatcctttttttctgcgcgtaatctgctgcttgcaaacaaaaaaaccaccgctaccagcggt
ggtttgtttgccggatcaagagctaccaactctttttccgaaggtaactggcttcagcagag
cgcagataccaaatactgttcttctagtgtagccgtagttaggccaccacttcaagaactct
gtagcaccgcctacatacctcgctctgctaatcctgttaccagtggctgctgccagtggcga
taagtcgtgtcttaccgggttggactcaagacgatagttaccggataaggcgcagcggtcgg
gctgaacggggggttcgtgcacacagcccagcttggagcgaacgacctacaccgaactgaga
tacctacagcgtgagctatgagaaagcgccacgcttcccgaagggagaaaggcggacaggta
tccggtaagcggcagggtcggaacaggagagcgcacgagggagcttccagggggaaacgcct
ggtatctttatagtcctgtcgggtttcgccacctctgacttgagcgtcgatttttgtgatgc
tcgtcaggggggcggagcctatggaaaaacgccagcaacgcggcctttttacggttcctggc
cttttgctggccttttgctcacatgttctttcctgcgttatcccctgattctgtggataacc
gtattaccgcctttgagtgagctgataccgctcgccgcagccgaacgaccgagcgcagcgag
tcagtgagcgaggaagcggaagagcgcccaatacgcaaaccgcctctccccgcgcgttggcc
gattcattaatgcagctggcacgacaggtttcccgactggaaagcgggcagtgagcgcaacg
caattaatgtgagttagctcactcattaggcaccccaggctttacactttatgctcccggct
cgtatgttgtgtggaattgtgagcggataacaatttcacacaggaaacagctatgaccatga
ttacgccaagcgcgcaattaaccctcactaaagggaacaaaagctgggtaccggcgcca pVCR modified vector gH FL-SGP gL (SEQ ID NO: 53):
cgcgtcggctacaattaatacataaccttatgtatcatacacatacgatttaggtgacacta
tagatgggcggcgcatgagagaagcccagaccaattacctacccaaaatggagaaagttcac
gttgacatcgaggaagacagcccattcctcagagctttgcagcggagcttcccgcagtttga
ggtagaagccaagcaggtcactgataatgaccatgctaatgccagagcgttttcgcatctgg
cttcaaaactgatcgaaacggaggtggacccatccgacacgatccttgacattggaagtgcg
cccgcccgcagaatgtattctaagcacaagtatcattgtatctgtccgatgagatgtgcgga
agatccggacagattgtataagtatgcaactaagctgaagaaaaactgtaaggaaataactg
ataaggaattggacaagaaaatgaaggagctcgccgccgtcatgagcgaccctgacctggaa
actgagactatgtgcctccacgacgacgagtcgtgtcgctacgaagggcaagtcgctgttta
ccaggatgtatacgcggttgacggaccgacaagtctctatcaccaagccaataagggagtta
gagtcgcctactggataggctttgacaccacccctttatgtttaagaacttggctggagca
tatccatcatactctaccaactgggccgacgaaaccgtgttaacggctcgtaacataggcct
atgcagctctgacgttatggagcggtcacgtagagggatgtccattcttagaaagaagtatt
tgaaaccatccaacaatgttctattctctgttggctcgaccatctaccacgagaagagggac
ttactgaggagctggcacctgccgtctgtatttcacttacgtggcaagcaaaattacacatg -continued

| SEQUENCES |
|---|
| tcggtgtgagactatagttagttgcgacgggtacgtcgttaaaagaatagctatcagtccag<br>gcctgtatgggaagccttcaggctatgctgctacgatgcaccgcgagggattcttgtgctgc<br>aaagtgacagacacattgaacggggagagggtctcttttcccgtgtgcacgtatgtgccagc<br>tacattgtgtgaccaaatgactggcatactggcaacagatgtcagtgcggacgacgcgcaaa<br>aactgctggttgggctcaaccagcgtatagtcgtcaacggtcgcacccagagaaacaccaat<br>accatgaaaaattacctttgcccgtagtggcccaggcatttgctaggtgggcaaaggaata<br>taaggaagatcaagaagatgaaaggccactaggactacgagatagacagttagtcatggggt<br>gttgttgggcttttagaaggcacaagataacatctatttataagcgcccggatacccaaacc<br>atcatcaaagtgaacagcgatttccactcattcgtgctgcccaggataggcagtaacacatt<br>ggagatcgggctgagaacaagaatcaggaaaatgttagaggagcacaaggagccgtcacctc<br>tcattaccgccgaggacgtacaagaagctaagtgcgcagccgatgaggctaaggaggtgcgt<br>gaagccgaggagttgcgcgcagctctaccacctttggcagctgatgttgaggagcccactct<br>ggaagccgatgtagacttgatgttacaagaggctggggccggctcagtggagacacctcgtg<br>gcttgataaaggttaccagctacgctggcgaggacaagatcggctcttacgctgtgctttct<br>ccgcaggctgtactcaagagtgaaaaattatcttgcatccaccctctcgctgaacaagtcat<br>agtgataacacactctggccgaaaagggcgttatgccgtggaaccataccatggtaaagtag<br>tggtgccagagggacatgcaatacccgtccaggactttcaagctctgagtgaaagtgccacc<br>attgtgtacaacgaacgtgagttcgtaaacaggtacctgcaccatattgccacacatggagg<br>agcgctgaacactgatgaagaatattacaaaactgtcaagcccagcgagcacgacggcgaat<br>acctgtacgacatcgacaggaaacagtgcgtcaagaaagaactagtcactgggctagggctc<br>acaggcgagctggtggatcctcccttccatgaattcgcctacgagagtctgagaacacgacc<br>agccgctccttaccaagtaccaaccataggggtgtatggcgtgccaggatcaggcaagtctg<br>gcatcattaaaagcgcagtcaccaaaaaagatctagtggtgagcgccaagaaagaaaactgt<br>gcagaaattataagggacgtcaagaaaatgaaagggctggacgtcaatgccagaactgtgga<br>ctcagtgctcttgaatggatgcaaacaccccgtagagaccctgtatattgacgaagcttttg<br>cttgtcatgcaggtactctcagagcgctcatagccattataagacctaaaaaggcagtgctc<br>tgcggggatcccaaacagtgcggtttttttaacatgatgtgcctgaaagtgcattttaacca<br>cgagatttgcacacaagtcttccacaaaagcatctctcgccgttgcactaaatctgtgactt<br>cggtcgtctcaaccttgttttacgacaaaaaaatgagaacgacgaatccgaaagagactaag<br>attgtgattgacactaccggcagtaccaaacctaagcaggacgatctcattctcacttgttt<br>cagagggtgggtgaagcagttgcaaatagattacaaaggcaacgaaataatgacggcagctg<br>cctctcaagggctgacccgtaaaggtgtgtatgccgttcggtacaaggtgaatgaaaatcct<br>ctgtacgcacccacctcagaacatgtgaacgtcctactgacccgcacggaggaccgcatcgt<br>gtggaaaacactagccggcgacccatggataaaaacactgactgccaagtaccctgggaatt<br>tcactgccacgatagaggagtggcaagcagagcatgatgccatcatgaggcacatcttggag<br>agaccggaccctaccgacgtcttccagaataaggcaaacgtgtgttgggccaaggctttagt<br>gccggtgctgaagaccgctggcatagacatgaccactgaacaatggaacactgtggattatt<br>ttgaaacggacaaagctcactcagcagagatagtattgaaccaactatgcgtgaggttcttt<br>ggactcgatctggactccggtctattttctgcacccactgttccgttatccattaggaataa<br>tcactgggataactccccgtcgcctaacatgtacgggctgaataaagaagtggtccgtcagc<br>tctctcgcaggtacccacaactgcctcgggcagttgccactggaagagtctatgacatgaac<br>actggtacactgcgcaattatgatccgcgcataaacctagtacctgtaaacagaagactgcc<br>tcatgctttagtcctccaccataatgaacacccacagagtgacttttcttcattcgtcagca<br>aattgaagggcagaactgtcctggtggtcggggaaaagttgtccgtcccaggcaaaatggtt<br>gactggttgtcagaccggcctgaggctaccttcagagctcggctggatttaggcatcccagg<br>tgatgtgcccaaatatgacataatatttgttaatgtgaggaccccatataaataccatcact<br>atcagcagtgtgaagaccatgccattaagcttagcatgttgaccaagaaagcttgtctgcat<br>ctgaatcccggcggaacctgtgtcagcataggttatggttacgctgacagggccagcgaaag<br>catcattggtgctatagcgcggcagttcaagttttcccgggtatgcaaaccgaaatcctcac<br>ttgaagagacggaagttctgtttgtattcattgggtacgatcgcaaggcccgtacgcacaat<br>ccttacaagctttcatcaaccttgaccaacatttatacaggttccagactccacgaagccgg<br>atgtgcaccctcatatcatgtggtgcgagggatattgccacggccaccgaaggagtgatta<br>taaatgctgctaacagcaaaggacaacctggcggaggggtgtgcggagcgctgtataagaaa<br>ttcccggaaagcttcgatttacagccgatcgaagtaggaaaagcgcgactggtcaaaggtgc<br>agctaaacatatcattcatgccgtaggaccaaacttcaacaaagtttcggaggttgaaggtg<br>acaaacagttggcagaggcttatgagtccatcgctaagattgtcaacgataacaattacaag<br>tcagtagcgattccactgttgtccaccggcatcttttccgggaacaaagatcgactaaccca<br>atcattgaaccatttgctgacagctttagacaccactgatgcagatgtagccatatactgca<br>gggacaagaaatgggaaatgactctcaaggaagcagtggctaggagagaagcagtggaggag<br>atatgcatatccgacgactcttcagtgacagaacctgatgcagagctggtgagggtgcatcc<br>gaagagttctttggctggaaggaagggctacagcacaagcgatggcaaaactttctcatatt<br>tggaagggaccaagtttcaccaggcggccaaggatatagcagaaattaatgccatgtggccc<br>gttgcaacggaggccaatgagcaggtatgcatgtatatcctcggagaaagcatgagcagtat<br>taggtcgaaatgccccgtcgaagagtcggaagcctcctcaccacctagcacgctgccttgct<br>tgtgcatccatgccatgactccagaaagagtacagcgcctaaaagcctcacgtccagaacaa<br>attactgtgtgctcatcctttccattgccgaagtatagaatcactggtgtgcagaagatcca<br>atgctcccagcctatattgttctcaccgaaagtgcctgcgtatattcatccaaggaagtatc<br>tcgtggaaacaccaccggtagacgagactccggagccatcggcagagaaccaatccacagag<br>gggacacctgaacaaccaccacttataaccgaggatgagaccaggactagaacgcctgagcc<br>gatcatcatcgaagaggaagaagaggatagcataagtttgctgtcagatggcccgacccacc<br>aggtgctgcaagtcgaggcagacattcacgggccgccctctgtatctagctcatcctggtcc<br>attcctcatgcatccgactttgatgtggacagtttatccatacttgacaccctggagggagc<br>tagcgtgaccagcggggcaacgtcagccgagactaactcttacttcgcaaagagtatggagt<br>ttctggcgcgaccggtgcctgcgcctcgaacagtattcaggaaccctccacatcccgctccg<br>cgcacaagaacaccgtcacttgcacccagcagggcctgctcgagagggatcacgggagaaac<br>cgtgggatacgcggttacacacaatagcgagggcttcttgctatgcaaagttactgacacag<br>taaaaggagaacgggtatcgttccctgtgtgcacgtacatcccggccaccataaactcgaga |

-continued

| SEQUENCES |
|---|
| accagcctggtctccaacccgccaggcgtaaatagggtgattacaagagaggagtttgaggc<br>gttcgtagcacaacaacaatgacggtttgatgcgggtgcatacatcttttcctccgacaccg<br>gtcaagggcatttacaacaaaaatcagtaaggcaaacggtgctatccgaagtggtgttggag<br>aggaccgaattggagatttcgtatgccccgcgcctcgaccaagaaaaagaagaattactacg<br>caagaaattacagttaaatcccacacctgctaacagaagcagataccagtccaggaaggtgg<br>agaacatgaaagccataacagctagacgtattctgcaaggcctagggcattatttgaaggca<br>gaaggaaaagtggagtgctaccgaaccctgcatcctgttcctttgtattcatctagtgtgaa<br>ccgtgccttttcaagccccaaggtcgcagtggaagcctgtaacgccatgttgaaagagaact<br>ttccgactgtggcttcttactgtattattccagagtacgatgcctatttggacatggttgac<br>ggagcttcatgctgcttagacactgccagttttttgccctgcaaagctgcgcagctttccaaa<br>gaaacactcctatttggaacccacaatacgatcggcagtgccttcagcgatccagaacacgc<br>tccagaacgtcctggcagctgccacaaaaagaaattgcaatgtcacgcaaatgagagaattg<br>cccgtattggattcggcggcctttaatgtggaatgcttcaagaaatatgcgtgtaataatga<br>atattgggaaacgtttaaagaaaaccccatcaggcttactgaagaaaacgtggtaaattaca<br>ttaccaaattaaaaggaccaaaagctgctgctcttttttgcgaagacacataatttgaatatg<br>ttgcaggacataccaatggacaggtttgtaatggacttaaagagagacgtgaaagtgactcc<br>aggaacaaaacatactgaagaacggcccaaggtacaggtgatccaggctgccgatccgctag<br>caacagcgtatctgtgcggaatccaccgagagctggttaggagattaaatgcggtcctgctt<br>ccgaacattcatacactgtttgatatgtcggctgaagactttgacgctattatagccgagca<br>cttccagcctggggattgtgttctggaaactgacatcgcgtcgtttgataaaagtgaggacg<br>acgccatggctctgaccgcgttaatgattctggaagacttaggtgtggacgcagagctgttg<br>acgctgattgaggcggctttcggcgaaatttcatcaatacatttgcccactaaaactaaatt<br>taaattcggagccatgatgaaatctggaatgttcctcacactgtttgtgaacacagtcatta<br>acattgtaatcgcaagcagagtgttgagagaacggctaaccggatcaccatgtgcagcattc<br>attggagatgacaatatcgtgaaaggagtcaaatcggacaaattaatggcagacaggtgcgc<br>cacctggttgaatatggaagtcaagattatagatgctgtggtgggcgagaaagcgccttatt<br>tctgtggagggtttattttgtgtgactccgtgaccggcacagcgtgccgtgtggcagacccc<br>ctaaaaaggctgtttaagcttggcaaacctctggcagcagacgatgaacatgatgatgacag<br>gagaagggcattgcatgaagagtcaacacgctggaaccgagtgggtattctttcagagctgt<br>gcaaggcagtagaatcaaggtatgaaaccgtaggaacttccatcatagttatggccatgact<br>actctagctagcagtgttaaatcattcagctacctgagaggggcccctataactctctacgg<br>ctaacctgaatggactacgacatagtctagtcgacgccaccatgaggcctggcctgccctcc<br>tacctgatcatcctggccgtgtgcctgttcagccacctgctgtccagcagatacggcgccga<br>ggccgtgagcgagcccctggacaaggctttccacctgctgctgaacacctacggcagaccca<br>tccggtttctgcgggagaacaccacccagtgcacctacaacagcagcctgcggaacagcacc<br>gtcgtgagagagaacgccatcagcttcaactttttccagagctacaaccagtactacgtgtt<br>ccacatgcccagatgcctgtttgccggccctctggccgagcagttcctgaaccaggtggacc<br>tgaccgagacactggaaagataccagcagcggctgaatacctacgccctggtgtccaaggac<br>ctggccagctaccggtcctttagccagcagctcaaggctcaggatagcctcggcgagcagcc<br>taccaccgtgcccccctcccatcgacctgagcatcccccacgtgtggatgcctccccagacca<br>cccctcacggctggaccgagagccacaccacctccggcctgcacagaccccacttcaaccag<br>acctgcatcctgttcgacggccacgacctgctgtttagcaccgtgacccccctgcctgcacca<br>gggcttctacctgatcgacgagctgagatacgtgaagatcaccctgaccgaggatttcttcg<br>tggtcaccgtgtccatcgacgacgacacccccatgctgctgatcttcggccacctgcccaga<br>gtgctgttcaaggcccccctaccagcgggacaacttcatcctgcggcagaccgagaagcacga<br>gctgctggtgctggtcaagaaggaccagctgaaccggcactcctacctgaaggaccccgact<br>tcctggacgccgccctggacttcaactacctggacctgagcgccctgctgagaaacagcttc<br>cacagatacgccgtggacgtgctgaagtccggacggtgccagatgctcgatcggcggaccgt<br>ggagatggccttcgcctatgccctcgccctgttcgccgctgccagacaggaagaggctggcg<br>cccaggtgtcagtgcccagagccctggatagacaggccgccctgctgcagatccaggaattc<br>atgatcacctgcctgagccagacccccccctagaaccaccctgctgctgtaccccacagccgt<br>ggatctggccaagagggccctgtggacccccaaccagatcaccgacatcacaagcctcgtgc<br>ggctcgtgtacatcctgagcaagcagaaccagcagcacctgatcccccagtgggccctgaga<br>cagatcgccgacttcgccctgaagctgcacaagacccatctggccagctttctgagcgcctt<br>cgccaggcaggaactgtacctgatgggcagcctggtccacagcatgctggtgcataccaccg<br>agcggcgggagatcttcatcgtggagacaggcctgtgtagcctggccgagctgtcccacttt<br>acccagctgctggcccaccctcaccacgagtacctgagcgacctgtacaccccctgcagcag<br>cagcggcagacgggaccacagcctggaacggctgaccagactgttccccgatgccaccgtgc<br>ctgctacagtgcctgccgccctgtccatcctgtccaccatgcagcccagcaccctggaaacc<br>ttccccgacctgttctgcctgccccctgggcgagagctttagcgccctgaccgtgtccgagca<br>cgtgtcctacatcgtgaccaatcagtacctgatcaagggcatcagctaccccgtgtccacca<br>cagtcgtgggccagagcctgatcatcacccagaccgacagccagaccaagtgcgagctgacc<br>cggaacatgcacaccacacacagcatcaccgtggccctgaacatcagcctggaaaactgcgc<br>tttctgtcagtctgccctgctggaatacgacgatacccagggcgtgatcaacatcatgtaca<br>tgcacgacagcgacgacgtgctgttcgccctggacccctacaacgaggtggtggtgtccagc<br>ccccggacccactacctgatgctgctgaagaacggcaccgtgctggaagtgaccgacgtggt<br>ggtggacgccaccgacagcagactgctgatgatgagcgtgtacgccctgagcgccatcatcg<br>gcatctacctgctgtaccggatgctgaaaacctgctgataatctagacggcgcgcccaccca<br>gcggccgcctataactctctacggctaacctgaatggactacgacatagtctagtcgacgcc<br>accatgtgcagaaggcccgactgcggcttcagcttcagccctggacccgtgatcctgctgtg<br>gtgctgcctgctgctgcctatcgtgtcctctgccgccgtgtctgtggcccctacagccgccg<br>agaaggtgccagccgagtgccccgagctgaccagaagatgcctgctgggcgaggtgttcgag<br>ggcgacaagtacgagagctggctgcggcccctggtcaacgtgaccggcagagatggcccccct<br>gagccagctgatccggtacagacccgtgacccccgaggccgccaatagcgtgctgctggacg<br>aggccttcctggataccctggccctgctgtacaacaaccccgaccagctgagagccctgctg<br>accctgctgtccagcgacaccgcccccagatggatgaccgtgatgcggggctacagcgagtg<br>tggagatggcagccctgccgtgtacacctgcgtggacgacctgtgcagaggctacgacctga |

-continued

| SEQUENCES |
| --- |

ccagactgagctacggccggtccatcttcacagagcacgtgctgggcttcgagctggtgccc
cccagcctgttcaacgtggtggtggccatccggaacgaggccaccagaaccaacagagccgt
gcggctgcctgtgtctacagccgctgcacctgagggcatcacactgttctacggcctgtaca
acgccgtgaaagagttctgcctccggcaccagctggatcccccctgctgagacacctggac
aagtactacgccggcctgcccccagagctgaagcagaccagagtgaacctgcccgcccacag
cagatatggccctcaggccgtggacgccagatgataatctagacggcgcgcccacccaatcg
atgtacttccgaggaactcacgtgcataatgcatcaggctggtacattagatccccgcttac
cgcgggcaatatagcaacactaaaaactcgatgtacttccgaggaagcgcagtgcataatgc
tgcgcagtgttgccacataaccactatattaaccatttatctagcggacgccaaaaactcaa
tgtatttctgaggaagcgtggtgcataatgccacgcagcgtctgcataacttttattatttc
ttttattaatcaacaaaatttgtttttaacatttcaaaaaaaaaaaaaaaaaaaaaaaaaa
aaaaaaaaaaaaaagggtcggcatggcatctccacctcctcgcggtccgacctgggcatccg
aaggaggacgcacgtccactcggatggctaagggagagccacgagctcctgtttaaaccagc
tccaattcgccctatagtgagtcgtattacgcgcgctcactggccgtcgttttacaacgtcg
tgactgggaaaaccctggcgttacccaacttaatcgccttgcagcacatcccccttttcgcca
gctggcgtaatagcgaagaggcccgcaccgatcgcccttcccaacagttgcgcagcctgaat
ggcgaatgggacgcgccctgtagcggcgcattaagcgcggcgggtgtggtggttacgcgcag
cgtgaccgctacacttgccagcgccctagcgcccgctcctttcgctttcttcccttcctttc
tcgccacgttcgccggctttccccgtcaagctctaaatcgggggctccctttagggttccga
tttagtgctttacggcacctcgaccccaaaaaacttgattagggtgatggttcacgtagtgg
gccatcgccctgatagacggtttttcgccctttgacgttggagtccacgttctttaatagtg
gactcttgttccaaactggaacaacactcaaccctatctcggtctattcttttgatttataa
gggattttgccgatttcggcctattggttaaaaaatgagctgatttaacaaaaatttaacgc
gaattttaacaaaatattaacgcttacaatttaggtggcacttttcggggaaatgtgcgcgg
aacccctatttgtttatttttctaaatacattcaaatatgtatccgctcatgagacaataac
cctgataaatgcttcaataatattgaaaaaggaagagtatgagtattcaacatttccgtgtc
gcccttattcccttttttgcggcattttgccttcctgtttttgctcacccagaaacgctggt
gaaagtaaaagatgctgaagatcagttgggtgcacgagtgggttacatcgaactggatctca
acagcggtaagatccttgagagttttcgccccgaagaacgttttccaatgatgagcactttt
aaagttctgctatgtggcgcggtattatcccgtattgacgccgggcaagagcaactcggtcg
ccgcatacactattctcagaatgacttggttgagtactcaccagtcacagaaaagcatctta
cggatggcatgacagtaagagaattatgcagtgctgccataaccatgagtgataacactgcg
gccaacttacttctgacaacgatcggaggaccgaaggagctaaccgcttttttgcacaacat
gggggatcatgtaactcgccttgatcgttgggaaccggagctgaatgaagccataccaaacg
acgagcgtgacaccacgatgcctgtagcaatggcaacaacgttgcgcaaactattaactggc
gaactacttactctagcttcccggcaacaattaatagactggatggaggcggataaagttgc
aggaccacttctgcgctcggcccttccggctggctggtttattgctgataaatctggagccg
gtgagcgtgggtctcgcggtatcattgcagcactggggccagatggtaagccctcccgtatc
gtagttatctacacgacggggagtcaggcaactatggatgaacgaaatagacagatcgctga
gataggtgcctcactgattaagcattggtaactgtcagaccaagtttactcatatatacttt
agattgatttaaaacttcatttttaatttaaaaggatctaggtgaagatcctttttgataat
ctcatgaccaaaatcccttaacgtgagttttcgttccactgagcgtcagaccccgtagaaaa
gatcaaaggatcttcttgagatcctttttttctgcgcgtaatctgctgcttgcaaacaaaaa
aaccaccgctaccagcggtggtttgtttgccggatcaagagctaccaactctttttccgaag
gtaactggcttcagcagagcgcagataccaaatactgttcttctagtgtagccgtagttagg
ccaccacttcaagaactctgtagcaccgcctacatacctcgctctgctaatcctgttaccag
tggctgctgccagtggcgataagtcgtgtcttaccgggttggactcaagacgatagttaccg
gataaggcgcagcggtcgggctgaacggggggttcgtgcacacagcccagcttggagcgaac
gacctacaccgaactgagatacctacagcgtgagctatgagaaagcgccacgcttcccgaag
ggagaaaggcggacaggtatccggtaagcggcagggtcggaacaggagagcgcacgagggag
cttccagggggaaacgcctggtatctttatagtcctgtcgggtttcgccacctctgacttga
gcgtcgatttttgtgatgctcgtcaggggggcggagcctatggaaaaacgccagcaacgcgg
cctttttacggttcctggccttttgctggccttttgctcacatgttctttcctgcgttatcc
cctgattctgtggataaccgtattaccgcctttgagtgagctgataccgctcgccgcagccg
aacgaccgagcgcagcgagtcagtgagcgaggaagcggaagagcgcccaatacgcaaaccgc
ctctccccgcgcgttggccgattcattaatgcagctggcacgacaggtttcccgactggaaa
gcgggcagtgagcgcaacgcaattaatgtgagttagctcactcattaggcaccccaggcttt
acactttatgctcccggctcgtatgttgtgtggaattgtgagcggataacaatttcacacag
gaaacagctatgaccatgattacgccaagcgcgcaattaaccctcactaaagggaacaaaag
ctgggtaccggcgcca pVCR modified vector gH sol-SGP gL-SGP gO (SEQ ID NO: 54):
cgcgtcggctacaattaatacataaccttatgtatcatacacatacgatttaggtgacacta
tagatgggcggcgcatgagagaagcccagaccaattacctacccaaaatggagaaagttcac
gttgacatcgaggaagacagcccattcctcagagctttgcagcggagcttcccgcagtttga
ggtagaagccaagcaggtcactgataatgaccatgctaatgccagagcgttttcgcatctgg
cttcaaaactgatcgaaacggaggtggacccatccgacacgatccttgacattggaagtgcg
cccgcccgcagaatgtattctaagcacaagtatcattgtatctgtccgatgagatgtgcgga
agatccggacagattgtataagtatgcaactaagctgaagaaaaactgtaaggaaataactg
ataaggaattggacaagaaaatgaaggagctcgccgccgtcatgagcgaccctgacctggaa
actgagactatgtgcctccacgacgacgagtcgtgtcgctacgaagggcaagtcgctgttta
ccaggatgtatacgcggttgacggaccgacaagtctctatcaccaagccaataagggagtta
gagtcgcctactggataggctttgacaccaccccttttatgtttaagaacttggctggagca
tatccatcatactctaccaactgggccgacgaaaccgtgttaacggctcgtaacataggcct
atgcagctctgacgttatggagcggtcacgtagagggatgtccattcttagaaagaagtatt
tgaaaccatccaacaatgttctattctctgttggctcgaccatctaccacgagaagagggac
ttactgaggagctggcacctgccgtctgtatttcacttacgtggcaagcaaaattacacatg -continued

| SEQUENCES |
| --- |
| tcggtgtgagactatagttagttgcgacgggtacgtcgttaaaagaatagctatcagtccag<br>gcctgtatgggaagccttcaggctatgctgctacgatgcaccgcgagggattcttgtgctgc<br>aaagtgacagacacattgaacggggagagggtctcttttcccgtgtgcacgtatgtgccagc<br>tacattgtgtgaccaaatgactggcatactggcaacagatgtcagtgcggacgacgcgcaaa<br>aactgctggttgggctcaaccagcgtatagtcgtcaacggtcgcacccagagaaacaccaat<br>accatgaaaaattacctttttgcccgtagtggcccaggcatttgctaggtgggcaaaggaata<br>taaggaagatcaagaagatgaaaggccactaggactacgagatagacagttagtcatggggt<br>gttgttgggcttttagaaggcacaagataacatctatttataagcgcccggatacccaaacc<br>atcatcaaagtgaacagcgatttccactcattcgtgctgcccaggataggcagtaacacatt<br>ggagatcgggctgagaacaagaatcaggaaaatgttagaggagcacaaggagccgtcacctc<br>tcattaccgccgaggacgtacaagaagctaagtgcgcagccgatgaggctaaggaggtgcgt<br>gaagccgaggagttgcgcgcagctctaccacctttggcagctgatgttgaggagcccactct<br>ggaagccgatgtagacttgatgttacaagaggctggggccggctcagtggagacacctcgtg<br>gcttgataaaggttaccagctacgctggcgaggacaagatcggctcttacgctgtgctttct<br>ccgcaggctgtactcaagagtgaaaaattatcttgcatccaccctctcgctgaacaagtcat<br>agtgataacacactctggccgaaaagggcgttatgccgtggaaccataccatggtaaagtag<br>tggtgccagagggacatgcaatacccgtccaggactttcaagctctgagtgaaagtgccacc<br>attgtgtacaacgaacgtgagttcgtaaacaggtacctgcaccatattgccacacatggagg<br>agcgctgaacactgatgaagaatattacaaaactgtcaagcccagcgagcacgacggcgaat<br>acctgtacgacatcgacaggaaacagtgcgtcaagaaagaactagtcactgggctagggctc<br>acaggcgagctggtggatcctcccttccatgaattcgcctacgagagtctgagaacacgacc<br>agccgctccttaccaagtaccaaccataggggtgtatggcgtgccaggatcaggcaagtctg<br>gcatcattaaaagcgcagtcaccaaaaaagatctagtggtgagcgccaagaaagaaaactgt<br>gcagaaattataagggacgtcaagaaaatgaaagggctggacgtcaatgccagaactgtgga<br>ctcagtgctcttgaatggatgcaaacaccccgtagagaccctgtatattgacgaagcttttg<br>cttgtcatgcaggtactctcagagcgctcatagccattataagacctaaaaaggcagtgctc<br>tgcggggatcccaaacagtgcggtttttttaacatgatgtgcctgaaagtgcattttaacca<br>cgagatttgcacacaagtcttccacaaaagcatctctcgccgttgcactaaatctgtgactt<br>cggtcgtctcaaccttgttttacgacaaaaaaatgagaacgacgaatccgaaagagactaag<br>attgtgattgacactaccggcagtaccaaacctaagcaggacgatctcattctcacttgttt<br>cagagggtgggtgaagcagttgcaaatagattacaaaggcaacgaaataatgacggcagctg<br>cctctcaagggctgacccgtaaaggtgtgtatgccgttcggtacaaggtgaatgaaaatcct<br>ctgtacgcacccacctcagaacatgtgaacgtcctactgacccgcacggaggaccgcatcgt<br>gtggaaaacactagccggcgacccatggataaaaacactgactgccaagtaccctgggaatt<br>tcactgccacgatagaggagtggcaagcagagcatgatgccatcatgaggcacatcttggag<br>agaccggaccctaccgacgtcttccagaataaggcaaacgtgtgttgggccaaggctttagt<br>gccggtgctgaagaccgctggcatagacatgaccactgaacaatggaacactgtggattatt<br>ttgaaacggacaaagctcactcagcagagatagtattgaaccaactatgcgtgaggttcttt<br>ggactcgatctggactccggtctattttctgcacccactgttccgttatccattaggaataa<br>tcactgggataactccccgtcgcctaacatgtacgggctgaataaagaagtggtccgtcagc<br>tctctcgcaggtacccacaactgcctcgggcagttgccactggaagagtctatgacatgaac<br>actggtacactgcgcaattatgatccgcgcataaacctagtacctgtaaacagaagactgcc<br>tcatgctttagtcctccaccataatgaacacccacagagtgacttttcttcattcgtcagca<br>aattgaagggcagaactgtcctggtggtcggggaaaagttgtccgtcccaggcaaaatggtt<br>gactggttgtcagaccggcctgaggctaccttcagagctcggctggatttaggcatcccagg<br>tgatgtgcccaaatatgacataatatttgttaatgtgaggaccccatataaataccatcact<br>atcagcagtgtgaagaccatgccattaagcttagcatgttgaccaagaaagcttgtctgcat<br>ctgaatcccggcggaacctgtgtcagcataggttatggttacgctgacagggccagcgaaag<br>catcattggtgctatagcgcggcagttcaagttttcccgggtatgcaaaccgaaatcctcac<br>ttgaagagacggaagttctgtttgtattcattgggtacgatcgcaaggcccgtacgcacaat<br>ccttacaagctttcatcaaccttgaccaacatttatacaggttccagactccacgaagccgg<br>atgtgcaccctcatatcatgtggtgcgaggggatattgccacggccaccgaaggagtgatta<br>taaatgctgctaacagcaaaggacaacctggcggaggggtgtgcggagcgctgtataagaaa<br>ttcccggaaagcttcgatttacagccgatcgaagtaggaaaagcgcgactggtcaaaggtgc<br>agctaaacatatcattcatgccgtaggaccaaacttcaacaaagtttcggaggttgaaggtg<br>acaaacagttggcagaggcttatgagtccatcgctaagattgtcaacgataacaattacaag<br>tcagtagcgattccactgttgtccaccggcatcttttccgggaacaaagatcgactaaccca<br>atcattgaaccatttgctgacagctttagacaccactgatgcagatgtagccatatactgca<br>gggacaagaaatgggaaatgactctcaaggaagcagtggctaggagagaagcagtggaggag<br>atatgcatatccgacgactcttcagtgacagaacctgatgcagagctggtgagggtgcatcc<br>gaagagttctttggctggaaggaagggctacagcacaagcgatggcaaaactttctcatatt<br>tggaagggaccaagtttcaccaggcggccaaggatatagcagaaattaatgccatgtggccc<br>gttgcaacggaggccaatgagcaggtatgcatgtatatcctcggagaaagcatgagcagtat<br>taggtcgaaatgccccgtcgaagagtcggaagcctcctcaccacctagcacgctgccttgct<br>tgtgcatccatgccatgactccagaaagagtacagcgcctaaaagcctcacgtccagaacaa<br>attactgtgtgctcatcctttccattgccgaagtatagaatcactggtgtgcagaagatcca<br>atgctcccagcctatattgttctcaccgaaagtgcctgcgtatattcatccaaggaagtatc<br>tcgtggaaacaccaccggtagacgagactccggagccatcggcagagaaccaatccacagag<br>gggacacctgaacaaccaccacttataaccgaggatgagaccaggactagaacgcctgagcc<br>gatcatcatcgaagaggaagaagaggatagcataagtttgctgtcagatggcccgacccacc<br>aggtgctgcaagtcgaggcagacattcacgggccgccctctgtatctagctcatcctggtcc<br>attcctcatgcatccgactttgatgtggacagtttatccatacttgacaccctggagggagc<br>tagcgtgaccagcggggcaacgtcagccgagactaactcttacttcgcaaagagtatggagt<br>ttctggcgcgaccggtgcctgcgcctcgaacagtattcaggaaccctccacatcccgctccg<br>cgcacaagaacaccgtcacttgcacccagcagggcctgctcgagagggatcacgggagaaac<br>cgtgggatacgcggttacacacaatagcgagggcttcttgctatgcaaagttactgacacag<br>taaaaggagaacgggtatcgttccctgtgtgcacgtacatcccggccaccataaactcgaga |

-continued

| SEQUENCES |
| --- |
| accagcctggtctccaacccgccaggcgtaaatagggtgattacaagagaggagtttgaggc<br>gttcgtagcacaacaacaatgacggtttgatgcgggtgcatacatcttttcctccgacaccg<br>gtcaagggcatttacaacaaaaatcagtaaggcaaacggtgctatccgaagtggtgttggag<br>aggaccgaattggagatttcgtatgccccgcgcctcgaccaagaaaaagaagaattactacg<br>caagaaattacagttaaatcccacacctgctaacagaagcagataccagtccaggaaggtgg<br>agaacatgaaagccataacagctagacgtattctgcaaggcctagggcattatttgaaggca<br>gaaggaaaagtggagtgctaccgaaccctgcatcctgttcctttgtattcatctagtgtgaa<br>ccgtgccttttcaagccccaaggtcgcagtggaagcctgtaacgccatgttgaaagagaact<br>ttccgactgtggcttcttactgtattattccagagtacgatgcctatttggacatggttgac<br>ggagcttcatgctgcttagacactgccagttttgccctgcaaagctgcgcagctttccaaa<br>gaaacactcctatttggaacccacaatacgatcggcagtgccttcagcgatccagaacacgc<br>tccagaacgtcctggcagctgccacaaaaagaaattgcaatgtcacgcaaatgagagaattg<br>cccgtattggattcggcggcctttaatgtggaatgcttcaagaaatatgcgtgtaataatga<br>atattgggaaacgtttaaagaaaaccccatcaggcttactgaagaaaacgtggtaaattaca<br>ttaccaaattaaaaggaccaaaagctgctgctcttttgcgaagacacataatttgaatatg<br>ttgcaggacataccaatggacaggtttgtaatggacttaaagagagacgtgaaagtgactcc<br>aggaacaaaacatactgaagaacggcccaaggtacaggtgatccaggctgccgatccgctag<br>caacagcgtatctgtgcggaatccaccgagagctggttaggagattaaatgcggtcctgctt<br>ccgaacattcatacactgtttgatatgtcggctgaagactttgacgctattatagccgagca<br>cttccagcctggggattgtgttctggaaactgacatcgcgtcgtttgataaaagtgaggacg<br>acgccatggctctgaccgcgttaatgattctggaagacttaggtgtggacgcagagctgttg<br>acgctgattgaggcggctttcggcgaaatttcatcaatacatttgcccactaaaactaaatt<br>taaattcggagccatgatgaaatctggaatgttcctcacactgtttgtgaacacagtcatta<br>acattgtaatcgcaagcagagtgttgagagaacggctaaccggatcaccatgtgcagcattc<br>attggagatgacaatatcgtgaaaggagtcaaatcggacaaattaatggcagacaggtgcgc<br>cacctggttgaatatggaagtcaagattatagatgctgtggtgggcgagaaagcgccttatt<br>tctgtggagggtttattttgtgtgactccgtgaccggcacagcgtgccgtgtggcagacccc<br>ctaaaaaggctgtttaagcttggcaaacctctggcagcagacgatgaacatgatgatgacag<br>gagaagggcattgcatgaagagtcaacacgctggaaccgagtgggtattctttcagagctgt<br>gcaaggcagtagaatcaaggtatgaaaccgtaggaacttccatcatagttatggccatgact<br>actctagctagcagtgttaaatcattcagctacctgagaggggcccctataactctctacgg<br>ctaacctgaatggactacgacatagtctagtcgacgccaccatgaggcctggcctgccctcc<br>tacctgatcatcctggccgtgtgcctgttcagccacctgctgtccagcagatacggcgccga<br>ggccgtgagcgagcccctggacaaggctttccacctgctgctgaacacctacggcagaccca<br>tccggtttctgcgggagaacaccacccagtgcacctacaacagcagcctgcggaacagcacc<br>gtcgtgagagagaacgccatcagcttcaactttttccagagctacaaccagtactacgtgtt<br>ccacatgcccagatgcctgtttgccggccctctggccgagcagttcctgaaccaggtggacc<br>tgaccgagacactggaaagataccagcagcggctgaatacctacgccctggtgtccaaggac<br>ctggccagctaccggtcctttagccagcagctcaaggctcaggatagcctcggcgagcagcc<br>taccaccgtgcccccctcccatcgacctgagcatcccccacgtgtggatgcctccccagacca<br>cccctcacggctggaccgagagccacaccacctccggcctgcacagaccccacttcaaccag<br>acctgcatcctgttcgacggccacgacctgctgtttagcaccgtgacccccctgcctgcacca<br>gggcttctacctgatcgacgagctgagatacgtgaagatcaccctgaccgaggatttcttcg<br>tggtcaccgtgtccatcgacgacgacacccccatgctgctgatcttcggccacctgcccaga<br>gtgctgttcaaggcccccctaccagcgggacaacttcatcctgcggcagaccgagaagcacga<br>gctgctggtgctggtcaagaaggaccagctgaaccggcactcctacctgaaggaccccgact<br>tcctggacgccgccctggacttcaactacctggacctgagcgccctgctgagaaacagcttc<br>cacagatacgccgtggacgtgctgaagtccggacggtgccagatgctcgatcggcggaccgt<br>ggagatggccttcgcctatgccctcgccctgttcgccgctgccagacaggaagaggctggcg<br>cccaggtgtcagtgcccagagccctggatagacaggccgccctgctgcagatccaggaattc<br>atgatcacctgcctgagccagacccccccctagaaccaccctgctgctgtaccccacagccgt<br>ggatctggccaagagggccctgtggacccccaaccagatcaccgacatcacaagcctcgtgc<br>ggctcgtgtacatcctgagcaagcagaaccagcagcacctgatcccccagtgggccctgaga<br>cagatcgccgacttcgccctgaagctgcacaagacccatctggccagctttctgagcgcctt<br>cgccaggcaggaactgtacctgatgggcagcctggtccacagcatgctggtgcataccaccg<br>agcggcgggagatcttcatcgtggagacaggcctgtgtagcctggccgagctgtcccacttt<br>acccagctgctggcccaccctcaccacgagtacctgagcgacctgtacacccccctgcagcag<br>cagcggcagacgggaccacagcctggaacggctgaccagactgttccccgatgccaccgtgc<br>ctgctacagtgcctgccgccctgtccatcctgtccaccatgcagcccagcaccctggaaacc<br>ttccccgacctgttctgcctgcccctgggcgagagctttagcgccctgaccgtgtccgagca<br>cgtgtcctacatcgtgaccaatcagtacctgatcaagggcatcagctaccccgtgtccacca<br>cagtcgtgggccagagcctgatcatcacccagaccgacagccagaccaagtgcgagctgacc<br>cggaacatgcacaccacacacagcatcaccgtggccctgaacatcagcctggaaaactgcgc<br>tttctgtcagtctgccctgctggaatacgacgatacccagggcgtgatcaacatcatgtaca<br>tgcacgacagcgacgacgtgctgttcgccctggacccctacaacgaggtggtggtgtccagc<br>ccccggacccactacctgatgctgctgaagaacggcaccgtgctggaagtgaccgacgtggt<br>ggtggacgccaccgactgataatctagacggcgcgcccacccagcggccgcctataactctc<br>tacggctaacctgaatggactacgacatagtctagtcgacgccaccatgtgcagaaggcccg<br>actgcggcttcagcttcagccctggacccgtgatcctgctgtggtgctgcctgctgctgcct<br>atcgtgtcctctgccgccgtgtctgtggcccctacagccgccgagaaggtgccagccgagtg<br>ccccgagctgaccagaagatgcctgctgggcgaggtgttcgagggcgacaagtacgagagct<br>ggctgcggcccctggtcaacgtgaccggcagagatggcccccctgagccagctgatccggtac<br>agacccgtgacccccgaggccgccaatagcgtgctgctggacgaggccttcctggataccct<br>ggccctgctgtacaacaaccccgaccagctgagagccctgctgaccctgctgtccagcgaca<br>ccgcccccagatggatgaccgtgatgcggggctacagcgagtgtggagatggcagccctgcc<br>gtgtacacctgcgtggacgacctgtgcagaggctacgacctgaccagactgagctacggccg<br>gtccatcttcacagagcacgtgctgggcttcgagctggtgcccccagcctgttcaacgtgg |

-continued

SEQUENCES tggtggccatccggaacgaggccaccagaaccaacagagccgtgcggctgcctgtgtctaca
gccgctgcacctgagggcatcacactgttctacggcctgtacaacgccgtgaaagagttctg
cctccggcaccagctggatccccccctgctgagacacctggacaagtactacgccggcctgc
cccagagctgaagcagaccagagtgaacctgcccgcccacagcagatatggccctcaggcc
gtggacgccagatgataatctagacggcgcgcccacccaatcgatctataactctctacggc
taacctgaatggactacgacatagtctagtcgacgccaccatgggcaagaaagaaatgatca
tggtcaagggcatccccaagatcatgctgctgattagcatcacctttctgctgctgtccctg
atcaactgcaacgtgctggtcaacagccggggcaccagaagatcctggccctacaccgtgct
gtcctaccggggcaaagagatcctgaagaagcagaaagaggacatcctgaagcggctgatga
gcaccagcagcgacggctaccggttcctgatgtaccccagccagcagaaattccacgccatc
gtgatcagcatggacaagttcccccaggactacatcctggccggacccatccggaacgacag
catcacccacatgtggttcgacttctacagcacccagctgcggaagcccgccaaatacgtgt
acagcgagtacaaccacaccgcccacaagatcaccctgaggcctccccccttgtggcaccgtg
cccagcatgaactgcctgagcgagatgctgaacgtgtccaagcggaacgacaccggcgagaa
gggctgcggcaacttcaccaccttcaaccccatgttcttcaacgtgccccggtggaacacca
agctgtacatcggcagcaacaaagtgaacgtggacagccagaccatctactttctgggcctg
accgccctgctgctgagatacgcccagcggaactgcacccggtccttctacctggtcaacgc
catgagccggaacctgttccgggtgcccaagtacatcaacggcaccaagctgaagaacacca
tgcggaagctgaagcggaagcaggccctggtcaaagagcagccccagaagaagaacaagaag
tcccagagcaccaccaccccctacctgagctacaccacctccaccgccttcaacgtgaccac
caacgtgacctacagcgccacagccgccgtgaccagagtggccacaagcaccaccggctacc
ggcccgacagcaactttatgaagtccatcatggccacccagctgagagatctggccacctgg
gtgtacaccaccctgcggtacagaaacgagcccttctgcaagcccgaccggaacagaaccgc
cgtgagcgagttcatgaagaatacccacgtgctgatcagaaacgagacaccctacaccatct
acggcaccctggacatgagcagcctgtactacaacgagacaatgagcgtggagaacgagaca
gccagcgacaacaacgaaaccacccccacctcccccagcacccggttccagcggaccttcat
cgacccccctgtgggactacctggacagcctgctgttcctggacaagatccggaacttcagcc
tgcagctgcccgcctacggcaatctgacccccctgagcacagaagggccgccaacctgagc
accctgaacagcctgtggtggtggagccagtgataatctagacggcgcgcccacccaccgcg
ggcaatatagcaacactaaaaactcgatgtacttccgaggaagcgcagtgcataatgctgcg
cagtgttgccacataaccactatattaaccatttatctagcggacgccaaaaactcaatgta
tttctgaggaagcgtggtgcataatgccacgcagcgtctgcataacttttattatttctttt
attaatcaacaaaatttgtttttaacatttcaaaaaaaaaaaaaaaaaaaaaaaaaaaaaaa
aaaaaaaaaagggtcggcatggcatctccacctcctcgcggtccgacctgggcatccgaagg
aggacgcacgtccactcggatggctaagggagagccacgagctcctgtttaaaccagctcca
attcgccctatagtgagtcgtattacgcgcgctcactggccgtcgttttacaacgtcgtgac
tgggaaaaccctggcgttacccaacttaatcgccttgcagcacatccccctttcgccagctg
gcgtaatagcgaagaggcccgcaccgatcgcccttcccaacagttgcgcagcctgaatggcg
aatgggacgcgccctgtagcggcgcattaagcgcggcgggtgtggtggttacgcgcagcgtg
accgctacacttgccagcgccctagcgcccgctcctttcgctttcttcccttcctttctcgc
cacgttcgccggctttccccgtcaagctctaaatcgggggctccctttagggttccgattta
gtgctttacggcacctcgaccccaaaaaacttgattagggtgatggttcacgtagtgggcca
tcgccctgatagacggtttttcgccctttgacgttggagtccacgttctttaatagtggact
cttgttccaaactggaacaacactcaaccctatctcggtctattcttttgatttataaggga
ttttgccgatttcggcctattggttaaaaaatgagctgatttaacaaaaatttaacgcgaat
tttaacaaaatattaacgcttacaatttaggtggcacttttcggggaaatgtgcgcggaacc
cctatttgtttatttttctaaatacattcaaatatgtatccgctcatgagacaataaccctg
ataaatgcttcaataatattgaaaaaggaagagtatgagtattcaacatttccgtgtcgccc
ttattcccttttttgcggcattttgccttcctgtttttgctcacccagaaacgctggtgaaa
gtaaaagatgctgaagatcagttgggtgcacgagtgggttacatcgaactggatctcaacag
cggtaagatccttgagagttttcgccccgaagaacgttttccaatgatgagcacttttaaag
ttctgctatgtggcgcggtattatcccgtattgacgccgggcaagagcaactcggtcgccgc
atacactattctcagaatgacttggttgagtactcaccagtcacagaaaagcatcttacgga
tggcatgacagtaagagaattatgcagtgctgccataaccatgagtgataacactgcggcca
acttacttctgacaacgatcggaggaccgaaggagctaaccgcttttttgcacaacatgggg
gatcatgtaactcgccttgatcgttgggaaccggagctgaatgaagccataccaaacgacga
gcgtgacaccacgatgcctgtagcaatggcaacaacgttgcgcaaactattaactggcgaac
tacttactctagcttcccggcaacaattaatagactggatggaggcggataaagttgcagga
ccacttctgcgctcggcccttccggctggctggtttattgctgataaatctggagccggtga
gcgtgggtctcgcggtatcattgcagcactggggccagatggtaagccctcccgtatcgtag
ttatctacacgacggggagtcaggcaactatggatgaacgaaatagacagatcgctgagata
ggtgcctcactgattaagcattggtaactgtcagaccaagtttactcatatatactttagat
tgatttaaaacttcatttttaatttaaaaggatctaggtgaagatcctttttgataatctca
tgaccaaaatcccttaacgtgagttttcgttccactgagcgtcagaccccgtagaaaagatc
aaaggatcttcttgagatcctttttttctgcgcgtaatctgctgcttgcaaacaaaaaaacc
accgctaccagcggtggtttgtttgccggatcaagagctaccaactctttttccgaaggtaa
ctggcttcagcagagcgcagataccaaatactgttcttctagtgtagccgtagttaggccac
cacttcaagaactctgtagcaccgcctacatacctcgctctgctaatcctgttaccagtggc
tgctgccagtggcgataagtcgtgtcttaccgggttggactcaagacgatagttaccggata
aggcgcagcggtcgggctgaacggggggttcgtgcacacagcccagcttggagcgaacgacc
tacaccgaactgagatacctacagcgtgagctatgagaaagcgccacgcttcccgaagggag
aaaggcggacaggtatccggtaagcggcagggtcggaacaggagagcgcacgagggagcttc
cagggggaaacgcctggtatctttatagtcctgtcgggtttcgccacctctgacttgagcgt
cgatttttgtgatgctcgtcaggggggcggagcctatggaaaaacgccagcaacgcggcctt
tttacggttcctggccttttgctggccttttgctcacatgttctttcctgcgttatcccctg
attctgtggataaccgtattaccgcctttgagtgagctgataccgctcgccgcagccgaacg
accgagcgcagcgagtcagtgagcgaggaagcggaagagcgcccaatacgcaaaccgcctct -continued

SEQUENCES ccccgcgcgttggccgattcattaatgcagctggcacgacaggtttcccgactggaaagcgg
gcagtgagcgcaacgcaattaatgtgagttagctcactcattaggcaccccaggctttacac
tttatgctcccggctcgtatgttgtgtggaattgtgagcggataacaatttcacacaggaaa
cagctatgaccatgattacgccaagcgcgcaattaaccctcactaaagggaacaaaagctgg
gtaccggcgcca pVCR modified vector gH FL-SGP gL-SGP gO (SEQ ID NO: 55):
cgcgtcggctacaattaatacataaccttatgtatcatacacatacgatttaggtgacacta
tagatgggcggcgcatgagagaagcccagaccaattacctacccaaaatggagaaagttcac
gttgacatcgaggaagacagcccattcctcagagctttgcagcggagcttcccgcagtttga
ggtagaagccaagcaggtcactgataatgaccatgctaatgccagagcgttttcgcatctgg
cttcaaaactgatcgaaacggaggtggacccatccgacacgatccttgacattggaagtgcg
cccgcccgcagaatgtattctaagcacaagtatcattgtatctgtccgatgagatgtgcgga
agatccggacagattgtataagtatgcaactaagctgaagaaaaactgtaaggaaataactg
ataaggaattggacaagaaaatgaaggagctcgccgccgtcatgagcgaccctgacctggaa
actgagactatgtgcctccacgacgacgagtcgtgtcgctacgaagggcaagtcgctgttta
ccaggatgtatacgcggttgacggaccgacaagtctctatcaccaagccaataagggagtta
gagtcgcctactggataggctttgacaccaccccttttatgtttaagaacttggctggagca
tatccatcatactctaccaactgggccgacgaaaccgtgttaacggctcgtaacataggcct
atgcagctctgacgttatggagcggtcacgtagagggatgtccattcttagaaagaagtatt
tgaaaccatccaacaatgttctattctctgttggctcgaccatctaccacgagaagagggac
ttactgaggagctggcacctgccgtctgtatttcacttacgtggcaagcaaaattacacatg
tcggtgtgagactatagttagttgcgacgggtacgtcgttaaaagaatagctatcagtccag
gcctgtatgggaagccttcaggctatgctgctacgatgcaccgcgagggattcttgtgctgc
aaagtgacagacacattgaacggggagagggtctcttttcccgtgtgcacgtatgtgccagc
tacattgtgtgaccaaatgactggcatactggcaacagatgtcagtgcggacgacgcgcaaa
aactgctggttgggctcaaccagcgtatagtcgtcaacggtcgcacccagagaaacaccaat
accatgaaaaattaccttttgcccgtagtggcccaggcatttgctaggtgggcaaaggaata
taaggaagatcaagaagatgaaaggccactaggactacgagatagacagttagtcatggggt
gttgttgggcttttagaaggcacaagataacatctatttataagcgcccggatacccaaacc
atcatcaaagtgaacagcgatttccactcattcgtgctgcccaggataggcagtaacacatt
ggagatcgggctgagaacaagaatcaggaaaatgttagaggagcacaaggagccgtcacctc
tcattaccgccgaggacgtacaagaagctaagtgcgcagccgatgaggctaaggaggtgcgt
gaagccgaggagttgcgcgcagctctaccacctttggcagctgatgttgaggagcccactct
ggaagccgatgtagacttgatgttacaagaggctggggccggctcagtggagacacctcgtg
gcttgataaaggttaccagctacgctggcgaggacaagatcggctcttacgctgtgctttct
ccgcaggctgtactcaagagtgaaaaattatcttgcatccaccctctcgctgaacaagtcat
agtgataacacactctggccgaaaagggcgttatgccgtggaaccataccatggtaaagtag
tggtgccagagggacatgcaatacccgtccaggactttcaagctctgagtgaaagtgccacc
attgtgtacaacgaacgtgagttcgtaaacaggtacctgcaccatattgccacacatggagg
agcgctgaacactgatgaagaatattacaaaactgtcaagcccagcgagcacgacggcgaat
acctgtacgacatcgacaggaaacagtgcgtcaagaaagaactagtcactgggctagggctc
acaggcgagctggtggatcctcccttccatgaattcgcctacgagagtctgagaacacgacc
agccgctccttaccaagtaccaaccataggggtgtatggcgtgccaggatcaggcaagtctg
gcatcattaaaagcgcagtcaccaaaaaagatctagtggtgagcgccaagaaagaaaactgt
gcagaaattataagggacgtcaagaaaatgaaagggctggacgtcaatgccagaactgtgga
ctcagtgctcttgaatggatgcaaacaccccgtagagaccctgtatattgacgaagcttttg
cttgtcatgcaggtactctcagagcgctcatagccattataagacctaaaaaggcagtgctc
tgcggggatcccaaacagtgcggtttttttaacatgatgtgcctgaaagtgcattttaacca
cgagatttgcacacaagtcttccacaaaagcatctctcgccgttgcactaaatctgtgactt
cggtcgtctcaaccttgttttacgacaaaaaaatgagaacgacgaatccgaaagagactaag
attgtgattgacactaccggcagtaccaaacctaagcaggacgatctcattctcacttgttt
cagagggtgggtgaagcagttgcaaatagattacaaaggcaacgaaataatgacggcagctg
cctctcaagggctgacccgtaaaggtgtgtatgccgttcggtacaaggtgaatgaaaatcct
ctgtacgcacccacctcagaacatgtgaacgtcctactgacccgcacggaggaccgcatcgt
gtggaaaacactagccggcgacccatggataaaaacactgactgccaagtaccctgggaatt
tcactgccacgatagaggagtggcaagcagagcatgatgccatcatgaggcacatcttggag
agaccggaccctaccgacgtcttccagaataaggcaaacgtgtgttgggccaaggctttagt
gccggtgctgaagaccgctggcatagacatgaccactgaacaatggaacactgtggattatt
ttgaaacggacaaagctcactcagcagagatagtattgaaccaactatgcgtgaggttcttt
ggactcgatctggactccggtctattttctgcacccactgttccgttatccattaggaataa
tcactgggataactccccgtcgcctaacatgtacgggctgaataaagaagtggtccgtcagc
tctctcgcaggtacccacaactgcctcgggcagttgccactggaagagtctatgacatgaac
actggtacactgcgcaattatgatccgcgcataaacctagtacctgtaaacagaagactgcc
tcatgctttagtcctccaccataatgaacacccacagagtgacttttcttcattcgtcagca
aattgaagggcagaactgtcctggtggtcggggaaaagttgtccgtcccaggcaaaatggtt
gactggttgtcagaccggcctgaggctaccttcagagctcggctggatttaggcatcccagg
tgatgtgcccaaatatgacataatatttgttaatgtgaggaccccatataaataccatcact
atcagcagtgtgaagaccatgccattaagcttagcatgttgaccaagaaagcttgtctgcat
ctgaatcccggcggaacctgtgtcagcataggttatggttacgctgacagggccagcgaaag
catcattggtgctatagcgcggcagttcaagttttcccgggtatgcaaaccgaaatcctcac
ttgaagagacggaagttctgtttgtattcattgggtacgatcgcaaggcccgtacgcacaat
ccttacaagctttcatcaaccttgaccaacatttatacaggttccagactccacgaagccgg
atgtgcaccctcatatcatgtggtgcgaggggatattgccacggccaccgaaggagtgatta
taaatgctgctaacagcaaaggacaacctggcggaggggtgtgcggagcgctgtataagaaa
ttcccggaaagcttcgatttacagccgatcgaagtaggaaaagcgcgactggtcaaaggtgc
agctaaacatatcattcatgccgtaggaccaaacttcaacaaagtttcggaggttgaaggtg -continued

| SEQUENCES |
| --- |
| acaaacagttggcagaggcttatgagtccatcgctaagattgtcaacgataacaattacaag<br>tcagtagcgattccactgttgtccaccggcatcttttccgggaacaaagatcgactaaccca<br>atcattgaaccatttgctgacagctttagacaccactgatgcagatgtagccatatactgca<br>gggacaagaaatgggaaatgactctcaaggaagcagtggctaggagagaagcagtggaggag<br>atatgcatatccgacgactcttcagtgacagaacctgatgcagagctggtgagggtgcatcc<br>gaagagttctttggctggaaggaagggctacagcacaagcgatggcaaaactttctcatatt<br>tggaagggaccaagtttcaccaggcggccaaggatatagcagaaattaatgccatgtggccc<br>gttgcaacggaggccaatgagcaggtatgcatgtatatcctcggagaaagcatgagcagtat<br>taggtcgaaatgccccgtcgaagagtcggaagcctcctcaccacctagcacgctgccttgct<br>tgtgcatccatgccatgactccagaaagagtacagcgcctaaaagcctcacgtccagaacaa<br>attactgtgtgctcatcctttccattgccgaagtatagaatcactggtgtgcagaagatcca<br>atgctcccagcctatattgttctcaccgaaagtgcctgcgtatattcatccaaggaagtatc<br>tcgtggaaacaccaccggtagacgagactccggagccatcggcagagaaccaatccacagag<br>gggacacctgaacaaccaccacttataaccgaggatgagaccaggactagaacgcctgagcc<br>gatcatcatcgaagaggaagaagaggatagcataagtttgctgtcagatggcccgacccacc<br>aggtgctgcaagtcgaggcagacattcacgggccgccctctgtatctagctcatcctggtcc<br>attcctcatgcatccgactttgatgtggacagtttatccatacttgacaccctggagggagc<br>tagcgtgaccagcggggcaacgtcagccgagactaactcttacttcgcaaagagtatggagt<br>ttctggcgcgaccggtgcctgcgcctcgaacagtattcaggaaccctccacatcccgctccg<br>cgcacaagaacaccgtcacttgcacccagcagggcctgctcgagagggatcacgggagaaac<br>cgtgggatacgcggttacacacaatagcgagggcttcttgctatgcaaagttactgacacag<br>taaaaggagaacgggtatcgttccctgtgtgcacgtacatcccggccaccataaactcgaga<br>accagcctggtctccaacccgccaggcgtaaatagggtgattacaagagaggagtttgaggc<br>gttcgtagcacaacaacaatgacggtttgatgcgggtgcatacatcttttcctccgacaccg<br>gtcaagggcatttacaacaaaaatcagtaaggcaaacggtgctatccgaagtggtgttggag<br>aggaccgaattggagatttcgtatgccccgcgcctcgaccaagaaaaagaagaattactacg<br>caagaaattacagttaaatcccacacctgctaacagaagcagataccagtccaggaaggtgg<br>agaacatgaaagccataacagctagacgtattctgcaaggcctagggcattatttgaaggca<br>gaaggaaaagtggagtgctaccgaaccctgcatcctgttcctttgtattcatctagtgtgaa<br>ccgtgccttttcaagccccaaggtcgcagtggaagcctgtaacgccatgttgaaagagaact<br>ttccgactgtggcttcttactgtattattccagagtacgatgcctatttggacatggttgac<br>ggagcttcatgctgcttagacactgccagtttttgccctgcaaagctgcgcagctttccaaa<br>gaaacactcctatttggaacccacaatacgatcggcagtgccttcagcgatccagaacacgc<br>tccagaacgtcctggcagctgccacaaaaagaaattgcaatgtcacgcaaatgagagaattg<br>cccgtattggattcggcggcctttaatgtggaatgcttcaagaaatatgcgtgtaataatga<br>atattgggaaacgtttaaagaaaccccatcaggcttactgaagaaaacgtggtaaattaca<br>ttaccaaattaaaaggaccaaaagctgctgctctttttgcgaagacacataatttgaatatg<br>ttgcaggacataccaatggacaggtttgtaatggacttaaagagagacgtgaaagtgactcc<br>aggaacaaaacatactgaagaacggcccaaggtacaggtgatccaggctgccgatccgctag<br>caacagcgtatctgtgcggaatccaccgagagctggttaggagattaaatgcggtcctgctt<br>ccgaacattcatacactgtttgatatgtcggctgaagactttgacgctattatagccgagca<br>cttccagcctggggattgtgttctggaaactgacatcgcgtcgtttgataaaagtgaggacg<br>acgccatggctctgaccgcgttaatgattctggaagacttaggtgtggacgcagagctgttg<br>acgctgattgaggcggctttcggcgaaatttcatcaatacatttgcccactaaaactaaatt<br>taaattcggagccatgatgaaatctggaatgttcctcacactgtttgtgaacacagtcatta<br>acattgtaatcgcaagcagagtgttgagagaacggctaaccggatcaccatgtgcagcattc<br>attggagatgacaatatcgtgaaaggagtcaaatcggacaaattaatggcagacaggtgcgc<br>cacctggttgaatatggaagtcaagattatagatgctgtggtgggcgagaaagcgccttatt<br>tctgtggagggtttattttgtgtgactccgtgaccggcacagcgtgccgtgtggcagacccc<br>ctaaaaaggctgtttaagcttggcaaacctctggcagcagacgatgaacatgatgatgacag<br>gagaagggcattgcatgaagagtcaacacgctggaaccgagtgggtattctttcagagctgt<br>gcaaggcagtagaatcaaggtatgaaaccgtaggaacttccatcatagttatggccatgact<br>actctagctagcagtgttaaatcattcagctacctgagaggggcccctataactctctacgg<br>ctaacctgaatggactacgacatagtctagtcgacgccaccatgaggcctggcctgccctcc<br>tacctgatcatcctggccgtgtgcctgttcagccacctgctgtccagcagatacggcgccga<br>ggccgtgagcgagcccctggacaaggctttccacctgctgctgaacacctacggcagaccca<br>tccggtttctgcgggagaacaccacccagtgcacctacaacagcagcctgcggaacagcacc<br>gtcgtgagagagaacgccatcagcttcaactttttccagagctacaaccagtactacgtgtt<br>ccacatgcccagatgcctgtttgccggccctctggccgagcagttcctgaaccaggtggacc<br>tgaccgagacactggaaagataccagcagcggctgaatacctacgccctggtgtccaaggac<br>ctggccagctaccggtcctttagccagcagctcaaggctcaggatagcctcggcgagcagcc<br>taccaccgtgccccctcccatcgacctgagcatcccccacgtgtggatgcctccccagacca<br>cccctcacggctggaccgagagccacaccacctccggcctgcacagaccccacttcaaccag<br>acctgcatcctgttcgacggccacgacctgctgtttagcaccgtgacccctgcctgcacca<br>gggcttctacctgatcgacgagctgagatacgtgaagatcaccctgaccgaggatttcttcg<br>tggtcaccgtgtccatcgacgacgacacccccatgctgctgatcttcggccacctgcccaga<br>gtgctgttcaaggcccctaccagcgggacaacttcatcctgcggcagaccgagaagcacga<br>gctgctggtgctggtcaagaaggaccagctgaaccggcactcctacctgaaggaccccgact<br>tcctggacgccgccctggacttcaactacctggacctgagcgccctgctgagaaacagcttc<br>cacagatacgccgtggacgtgctgaagtccggacggtgccagatgctcgatcggcggaccgt<br>ggagatggccttcgcctatgccctcgccctgttcgccgctgccagacaggaagaggctggcg<br>cccaggtgtcagtgcccagagccctggatagacaggccgccctgctgcagatccaggaattc<br>atgatcacctgcctgagccagacccccctagaaccaccctgctgctgtaccccacagccgt<br>ggatctggccaagagggccctgtggacccccaaccagatcaccgacatcacaagcctcgtgc<br>ggctcgtgtacatcctgagcaagcagaaccagcagcacctgatcccccagtgggccctgaga<br>cagatcgccgacttcgccctgaagctgcacaagacccatctggccagctttctgagcgcctt<br>cgccaggcaggaactgtacctgatgggcagcctggtccacagcatgctggtgcataccaccg |

-continued

| SEQUENCES |
| --- |
| agcggcgggagatcttcatcgtggagacaggcctgtgtagcctggccgagctgtcccacttt<br>acccagctgctggcccaccctcaccacgagtacctgagcgacctgtacacccccctgcagcag<br>cagcggcagacgggaccacagcctggaacggctgaccagactgttccccgatgccaccgtgc<br>ctgctacagtgcctgccgccctgtccatcctgtccaccatgcagcccagcaccctggaaacc<br>ttccccgacctgttctgcctgcccctgggcgagagctttagcgccctgaccgtgtccgagca<br>cgtgtcctacatcgtgaccaatcagtacctgatcaagggcatcagctaccccgtgtccacca<br>cagtcgtgggccagagcctgatcatcacccagaccgacagccagaccaagtgcgagctgacc<br>cggaacatgcacaccacacacagcatcaccgtggccctgaacatcagcctggaaaactgcgc<br>tttctgtcagtctgccctgctggaatacgacgatacccagggcgtgatcaacatcatgtaca<br>tgcacgacagcgacgacgtgctgttcgccctggacccctacaacgaggtggtggtgtccagc<br>ccccggacccactacctgatgctgctgaagaacggcaccgtgctggaagtgaccgacgtggt<br>ggtggacgccaccgacagcagactgctgatgatgagcgtgtacgccctgagcgccatcatcg<br>gcatctacctgctgtaccggatgctgaaaacctgctgataatctagacggcgcgcccaccca<br>gcggccgcctataactctctacggctaacctgaatggactacgacatagtctagtcgacgcc<br>accatgtgcagaaggcccgactgcggcttcagcttcagccctggacccgtgatcctgctgtg<br>gtgctgcctgctgctgcctatcgtgtcctctgccgccgtgtctgtggcccctacagccgccg<br>agaaggtgccagccgagtgccccgagctgaccagaagatgcctgctgggcgaggtgttcgag<br>ggcgacaagtacgagagctggctgcggcccctggtcaacgtgaccggcagagatggcccccct<br>gagccagctgatccggtacagacccgtgacccccgaggccgccaatagcgtgctgctggacg<br>aggccttcctggataccctggccctgctgtacaacaaccccgaccagctgagagccctgctg<br>accctgctgtccagcgacaccgcccccagatggatgaccgtgatgcggggctacagcgagtg<br>tggagatggcagccctgccgtgtacacctgcgtggacgacctgtgcagaggctacgacctga<br>ccagactgagctacggccggtccatcttcacagagcacgtgctgggcttcgagctggtgccc<br>cccagcctgttcaacgtggtggtggccatccggaacgaggccaccagaaccaacagagccgt<br>gcggctgcctgtgtctacagccgctgcacctgagggcatcacactgttctacggcctgtaca<br>acgccgtgaaagagttctgcctccggcaccagctggatcccccccctgctgagacacctggac<br>aagtactacgccggcctgcccccagagctgaagcagaccagagtgaacctgcccgcccacag<br>cagatatggccctcaggccgtggacgccagatgataatctagacggcgcgcccacccaatcg<br>atctataactctctacggctaacctgaatggactacgacatagtctagtcgacgccaccatg<br>ggcaagaaagaaatgatcatggtcaagggcatccccaagatcatgctgctgattagcatcac<br>ctttctgctgctgtccctgatcaactgcaacgtgctggtcaacagccggggcaccagaagat<br>cctggccctacaccgtgctgtcctaccggggcaaagagatcctgaagaagcagaaagaggac<br>atcctgaagcggctgatgagcaccagcagcgacggctaccggttcctgatgtaccccagcca<br>gcagaaattccacgccatcgtgatcagcatggacaagttcccccaggactacatcctggccg<br>gacccatccggaacgacagcatcacccacatgtggttcgacttctacagcacccagctgcgg<br>aagcccgccaaatacgtgtacagcgagtacaaccacaccgcccacaagatcaccctgaggcc<br>tccccccttgtggcaccgtgcccagcatgaactgcctgagcgagatgctgaacgtgtccaagc<br>ggaacgacaccggcgagaagggctgcggcaacttcaccaccttcaaccccatgttcttcaac<br>gtgccccggtggaacaccaagctgtacatcggcagcaacaaagtgaacgtggacagccagac<br>catctactttctgggcctgaccgccctgctgctgagatacgcccagcggaactgcacccggt<br>ccttctacctggtcaacgccatgagccggaacctgttccgggtgcccaagtacatcaacggc<br>accaagctgaagaacaccatgcggaagctgaagcggaagcaggccctggtcaaagagcagcc<br>ccagaagaagaacaagaagtcccagagcaccaccacccccctacctgagctacaccacctcca<br>ccgccttcaacgtgaccaccaacgtgacctacagcgccacagccgccgtgaccagagtggcc<br>acaagcaccaccggctaccggcccgacagcaactttatgaagtccatcatggccacccagct<br>gagagatctggccacctgggtgtacaccaccctgcggtacagaaacgagcccttctgcaagc<br>ccgaccggaacagaaccgccgtgagcgagttcatgaagaatacccacgtgctgatcagaaac<br>gagacaccctacaccatctacggcaccctggacatgagcagcctgtactacaacgagacaat<br>gagcgtggagaacgagacagccagcgacaacaacgaaaccacccccacctcccccagcaccc<br>ggttccagcggaccttcatcgacccccctgtgggactacctggacagcctgctgttcctggac<br>aagatccggaacttcagcctgcagctgcccgcctacggcaatctgaccccccctgagcacag<br>aagggccgccaacctgagcaccctgaacagcctgtggtggtggagccagtgataatctagac<br>ggcgcgcccacccaccgcgggcaatatagcaacactaaaaactcgatgtacttccgaggaag<br>cgcagtgcataatgctgcgcagtgttgccacataaccactatattaaccatttatctagcgg<br>acgccaaaaactcaatgtatttctgaggaagcgtggtgcataatgccacgcagcgtctgcat<br>aacttttattatttcttttattaatcaacaaaatttgtttttaacatttcaaaaaaaaaaa<br>aaaaaaaaaaaaaaaaaaaaaaaaaaaagggtcggcatggcatctccacctcctcgcggtc<br>cgacctgggcatccgaaggaggacgcacgtccactcggatggctaagggagagccacgagct<br>cctgtttaaaccagctccaattcgccctatagtgagtcgtattacgcgcgctcactggccgt<br>cgttttacaacgtcgtgactgggaaaaccctggcgttacccaacttaatcgccttgcagcac<br>atccccctttcgccagctggcgtaatagcgaagaggcccgcaccgatcgcccttcccaacag<br>ttgcgcagcctgaatggcgaatgggacgcgccctgtagcggcgcattaagcgcggcgggtgt<br>ggtggttacgcgcagcgtgaccgctacacttgccagcgccctagcgcccgctcctttcgctt<br>tcttcccttcctttctcgccacgttcgccggctttccccgtcaagctctaaatcgggggctc<br>cctttagggttccgatttagtgctttacggcacctcgaccccaaaaaacttgattagggtga<br>tggttcacgtagtgggccatcgccctgatagacggtttttcgccctttgacgttggagtcca<br>cgttctttaatagtggactcttgttccaaactggaacaacactcaaccctatctcggtctat<br>tcttttgatttataagggattttgccgatttcggcctattggttaaaaaatgagctgattta<br>acaaaaatttaacgcgaattttaacaaaatattaacgcttacaatttaggtggcacttttcg<br>gggaaatgtgcgcggaacccctatttgtttatttttctaaatacattcaaatatgtatccgc<br>tcatgagacaataaccctgataaatgcttcaataatattgaaaaaggaagagtatgagtatt<br>caacatttccgtgtcgcccttattcccttttttgcggcattttgccttcctgtttttgctca<br>cccagaaacgctggtgaaagtaaaagatgctgaagatcagttgggtgcacgagtgggttaca<br>tcgaactggatctcaacagcggtaagatccttgagagttttcgccccgaagaacgttttcca<br>atgatgagcacttttaaagttctgctatgtggcgcggtattatcccgtattgacgccgggca<br>agagcaactcggtcgccgcatacactattctcagaatgacttggttgagtactcaccagtca<br>cagaaaagcatcttacggatggcatgacagtaagagaattatgcagtgctgccataaccatg |

-continued

SEQUENCES agtgataacactgcggccaacttacttctgacaacgatcggaggaccgaaggagctaaccgc
tttttgcacaacatgggggatcatgtaactcgccttgatcgttgggaaccggagctgaatg
aagccataccaaacgacgagcgtgacaccacgatgcctgtagcaatggcaacaacgttgcgc
aaactattaactggcgaactacttactctagcttcccggcaacaattaatagactggatgga
ggcggataaagttgcaggaccacttctgcgctcggcccttccggctggctggtttattgctg
ataaatctggagccggtgagcgtgggtctcgcggtatcattgcagcactggggccagatggt
aagccctcccgtatcgtagttatctacacgacggggagtcaggcaactatggatgaacgaaa
tagacagatcgctgagataggtgcctcactgattaagcattggtaactgtcagaccaagttt
actcatatatactttagattgatttaaaacttcatttttaatttaaaaggatctaggtgaag
atcctttttgataatctcatgaccaaaatcccttaacgtgagttttcgttccactgagcgtc
agaccccgtagaaaagatcaaaggatcttcttgagatcctttttttctgcgcgtaatctgct
gcttgcaaacaaaaaaaccaccgctaccagcggtggtttgtttgccggatcaagagctacca
actctttttccgaaggtaactggcttcagcagagcgcagataccaaatactgttcttctagt
gtagccgtagttaggccaccacttcaagaactctgtagcaccgcctacatacctcgctctgc
taatcctgttaccagtggctgctgccagtggcgataagtcgtgtcttaccgggttggactca
agacgatagttaccggataaggcgcagcggtcgggctgaacggggggttcgtgcacacagcc
cagcttggagcgaacgacctacaccgaactgagatacctacagcgtgagctatgagaaagcg
ccacgcttcccgaagggagaaaggcggacaggtatccggtaagcggcagggtcggaacagga
gagcgcacgagggagcttccagggggaaacgcctggtatctttatagtcctgtcgggtttcg
ccacctctgacttgagcgtcgatttttgtgatgctcgtcaggggggcggagcctatggaaaa
acgccagcaacgcggcctttttacggttcctggccttttgctggccttttgctcacatgttc
tttcctgcgttatcccctgattctgtggataaccgtattaccgcctttgagtgagctgatac
cgctcgccgcagccgaacgaccgagcgcagcgagtcagtgagcgaggaagcggaagagcgcc
caatacgcaaaccgcctctccccgcgcgttggccgattcattaatgcagctggcacgacagg
tttcccgactggaaagcgggcagtgagcgcaacgcaattaatgtgagttagctcactcatta
ggcaccccaggctttacactttatgctcccggctcgtatgttgtgtggaattgtgagcggat
aacaatttcacacaggaaacagctatgaccatgattacgccaagcgcgcaattaaccctcac
taaagggaacaaaagctgggtaccggcgcca A526 Vector: SGP-gH-SGP-gL-SGP-UL128-2A-UL130-2Amod-UL131 (SEQ ID NO: 56):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT
GTGCGGAAGATCCGGACAGATTGTATAAGTATGCAACTAAGCTGAAGAAAAACTGTAAGGAAATAACTGATAAGG
AATTGGACAAGAAAATGAAGGAGCTCGCCGCCGTCATGAGCGACCCTGACCTGGAAACTGAGACTATGTGCCTCC
ACGACGACGAGTCGTGTCGCTACGAAGGGCAAGTCGCTGTTTACCAGGATGTATACGCGGTTGACGGACCGACAA
GTCTCTATCACCAAGCCAATAAGGGAGTTAGAGTCGCCTACTGGATAGGCTTTGACACCACCCCTTTTATGTTTA
AGAACTTGGCTGGAGCATATCCATCATACTCTACCAACTGGGCCGACGAAACCGTGTTAACGGCTCGTAACATAG
GCCTATGCAGCTCTGACGTTATGGAGCGGTCACGTAGAGGGATGTCCATTCTTAGAAAGAAGTATTTGAAACCAT
CCAACAATGTTCTATTCTCTGTTGGCTCGACCATCTACCACGAGAAGAGGGACTTACTGAGGAGCTGGCACCTGC
CGTCTGTATTTCACTTACGTGGCAAGCAAAATTACACATGTCGGTGTGAGACTATAGTTAGTTGCGACGGGTACG
TCGTTAAAAGAATAGCTATCAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCGTGTGCACGTATGTGCCAG
CTACATTGTGTGACCAAATGACTGGCATACTGGCAACAGATGTCAGTGCGGACGACGCGCAAAAACTGCTGGTTG
GGCTCAACCAGCGTATAGTCGTCAACGGTCGCACCCAGAGAAACACCAATACCATGAAAAATTACCTTTTGCCCG
TAGTGGCCCAGGCATTTGCTAGGTGGGCAAAGGAATATAAGGAAGATCAAGAAGATGAAAGGCCACTAGGACTAC
GAGATAGACAGTTAGTCATGGGGTGTTGTTGGGCTTTTAGAAGGCACAAGATAACATCTATTTATAAGCGCCCGG
ATACCCAAACCATCATCAAAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCACCTCTCATTACCGCCGAGG
ACGTACAAGAAGCTAAGTGCGCAGCCGATGAGGCTAAGGAGGTGCGTGAAGCCGAGGAGTTGCGCGCAGCTCTAC
CACCTTTGGCAGCTGATGTTGAGGAGCCCACTCTGGAAGCCGATGTAGACTTGATGTTACAAGAGGCTGGGGCCG
GCTCAGTGGAGACACCTCGTGGCTTGATAAAGGTTACCAGCTACGATGGCGAGGACAAGATCGGCTCTTACGCTG
TGCTTTCTCCGCAGGCTGTACTCAAGAGTGAAAAATTATCTTGCATCCACCCTCTCGCTGAACAAGTCATAGTGA
TAACACACTCTGGCCGAAAAGGGCGTTATGCCGTGGAACCATACCATGGTAAAGTAGTGGTGCCAGAGGGACATG
CAATACCCGTCCAGGACTTTCAAGCTCTGAGTGAAAGTGCCACCATTGTGTACAACGAACGTGAGTTCGTAAACA
GGTACCTGCACCATATTGCCACACATGGAGGAGCGCTGAACACTGATGAAGAATATTACAAAACTGTCAAGCCCA
GCGAGCACGACGGCGAATACCTGTACGACATCGACAGGAAACAGTGCGTCAAGAAAGAACTAGTCACTGGGCTAG
GGCTCACAGGCGAGCTGGTGGATCCTCCCTTCCATGAATTCGCCTACGAGAGTCTGAGAACACGACCAGCCGCTC
CTTACCAAGTACCAACCATAGGGGTGTATGGCGTGCCAGGATCAGGCAAGTCTGGCATCATTAAAAGCGCAGTCA
CCAAAAAAGATCTAGTGGTGAGCGCCAAGAAAGAAAACTGTGCAGAAATTATAAGGGACGTCAAGAAAATGAAAG
GGCTGGACGTCAATGCCAGAACTGTGGACTCAGTGCTCTTGAATGGATGCAAACACCCCGTAGAGACCCTGTATA
TTGACGAAGCTTTTGCTTGTCATGCAGGTACTCTCAGAGCGCTCATAGCCATTATAAGACCTAAAAAGGCAGTGC
TCTGCGGGGATCCCAAACAGTGCGGTTTTTTTAACATGATGTGCCTGAAAGTGCATTTTAACCACGAGATTTGCA
CACAAGTCTTCCACAAAAGCATCTCTCGCCGTTGCACTAAATCTGTGACTTCGGTCGTCTCAACCTTGTTTTACG
ACAAAAAAATGAGAACGACGAATCCGAAAGAGACTAAGATTGTGATTGACACTACCGGCAGTACCAAACCTAAGC
AGGACGATCTCATTCTCACTTGTTTCAGAGGGTGGGTGAAGCAGTTGCAAATAGATTACAAAGGCAACGAAATAA
TGACGGCAGCTGCCTCTCAAGGGCTGACCCGTAAAGGTGTGTATGCCGTTCGGTACAAGGTGAATGAAAATCCTC
TGTACGCACCCACCTCAGAACATGTGAACGTCCTACTGACCCGCACGGAGGACCGCATCGTGTGGAAAACACTAG
CCGGCGACCCATGGATAAAAACACTGACTGCCAAGTACCCTGGGAATTTCACTGCCACGATAGAGGAGTGGCAAG
CAGAGCATGATGCCATCATGAGGCACATCTTGGAGAGACCGGACCCTACCGACGTCTTCCAGAATAAGGCAAACG
TGTGTTGGGCCAAGGCTTTAGTGCCGGTGCTGAAGACCGCTGGCATAGACATGACCACTGAACAATGGAACACTG
TGGATTATTTTGAAACGGACAAAGCTCACTCAGCAGAGATAGTATTGAACCAACTATGCGTGAGGTTCTTTGGAC
TCGATCTGGACTCCGGTCTATTTTCTGCACCCACTGTTCCGTTATCCATTAGGAATAATCACTGGGATAACTCCC
CGTCGCCTAACATGTACGGGCTGAATAAAGAAGTGGTCCGTCAGCTCTCTCGCAGGTACCCACAACTGCCTCGGG
CAGTTGCCACTGGAAGAGTCTATGACATGAACACTGGTACACTGCGCAATTATGATCCGCGCATAAACCTAGTAC
CTGTAAACAGAAGACTGCCTCATGCTTTAGTCCTCCACCATAATGAACACCCACAGAGTGACTTTTCTTCATTCG -continued

SEQUENCES

TCAGCAAATTGAAGGGCAGAACTGTCCTGGTGGTCGGGGAAAAGTTGTCCGTCCCAGGCAAAATGGTTGACTGGT
TGTCAGACCGGCCTGAGGCTACCTTCAGAGCTCGGCTGGATTTAGGCATCCCAGGTGATGTGCCCAAATATGACA
TAATATTTGTTAATGTGAGGACCCCATATAAATACCATCACTATCAGCAGTGTGAAGACCATGCCATTAAGCTTA
GCATGTTGACCAAGAAAGCTTGTCTGCATCTGAATCCCGGCGGAACCTGTGTCAGCATAGGTTATGGTTACGCTG
ACAGGGCCAGCGAAAGCATCATTGGTGCTATAGCGCGGCAGTTCAAGTTTTCCCGGGTATGCAAACCGAAATCCT
CACTTGAAGAGACGGAAGTTCTGTTTGTATTCATTGGGTACGATCGCAAGGCCCGTACGCACAATCCTTACAAGC
TTTCATCAACCTTGACCAACATTTATACAGGTTCCAGACTCCACGAAGCCGGATGTGCACCCTCATATCATGTGG
TGCGAGGGGATATTGCCACGGCCACCGAAGGAGTGATTATAAATGCTGCTAACAGCAAAGGACAACCTGGCGGAG
GGGTGTGCGGAGCGCTGTATAAGAAATTCCCGGAAAGCTTCGATTTACAGCCGATCGAAGTAGGAAAAGCGCGAC
TGGTCAAAGGTGCAGCTAAACATATCATTCATGCCGTAGGACCAAACTTCAACAAAGTTTCGGAGGTTGAAGGTG
ACAAACAGTTGGCAGAGGCTTATGAGTCCATCGCTAAGATTGTCAACGATAACAATTACAAGTCAGTAGCGATTC
CACTGTTGTCCACCGGCATCTTTTCCGGGAACAAAGATCGACTAACCCAATCATTGAACCATTTGCTGACAGCTT
TAGACACCACTGATGCAGATGTAGCCATATACTGCAGGGACAAGAAATGGGAAATGACTCTCAAGGAAGCAGTGG
CTAGGAGAGAAGCAGTGGAGGAGATATGCATATCCGACGACTCTTCAGTGACAGAACCTGATGCAGAGCTGGTGA
GGGTGCATCCGAAGAGTTCTTTGGCTGGAAGGAAGGGCTACAGCACAAGCGATGGCAAAACTTTCTCATATTTGG
AAGGGACCAAGTTTCACCAGGCGGCCAAGGATATAGCAGAAATTAATGCCATGTGGCCCGTTGCAACGGAGGCCA
ATGAGCAGGTATGCATGTATATCCTCGGAGAAAGCATGAGCAGTATTAGGTCGAAATGCCCCGTCGAAGAGTCGG
AAGCCTCCACACCACCTAGCACGCTGCCTTGCTTGTGCATCCATGCCATGACTCCAGAAAGAGTACAGCGCCTAA
AAGCCTCACGTCCAGAACAAATTACTGTGTGCTCATCCTTTCCATTGCCGAAGTATAGAATCACTGGTGTGCAGA
AGATCCAATGCTCCCAGCCTATATTGTTCTCACCGAAAGTGCCTGCGTATATTCATCCAAGGAAGTATCTCGTGG
AAACACCACCGGTAGACGAGACTCCGGAGCCATCGGCAGAGAACCAATCCACAGAGGGGACACCTGAACAACCAC
CACTTATAACCGAGGATGAGACCAGGACTAGAACGCCTGAGCCGATCATCATCGAAGAGGAAGAAGAGGATAGCA
TAAGTTTGCTGTCAGATGGCCCGACCCACCAGGTGCTGCAAGTCGAGGCAGACATTCACGGGCCGCCCTCTGTAT
CTAGCTCATCCTGGTCCATTCCTCATGCATCCGACTTTGATGTGGACAGTTTATCCATACTTGACACCCTGGAGG
GAGCTAGCGTGACCAGCGGGGCAACGTCAGCCGAGACTAACTCTTACTTCGCAAAGAGTATGGAGTTTCTGGCGC
GACCGGTGCCTGCGCCTCGAACAGTATTCAGGAACCCTCCACATCCCGCTCCGCGCACAAGAACACCGTCACTTG
CACCCAGCAGGGCCTGCTCGAGAACCAGCCTAGTTTCCACCCCGCCAGGCGTGAATAGGGTGATCACTAGAGAGG
AGCTCGAGGCGCTTACCCCGTCACGCACTCCTAGCAGGTCGGTCTCGAGAACCAGCCTGGTCTCCAACCCGCCAG
GCGTAAATAGGGTGATTACAAGAGAGGAGTTTGAGGCGTTCGTAGCACAACAACAATGACGGTTTGATGCGGGTG
CATACATCTTTTCCTCCGACACCGGTCAAGGGCATTTACAACAAAAATCAGTAAGGCAAACGGTGCTATCCGAAG
TGGTGTTGGAGAGGACCGAATTGGAGATTTCGTATGCCCCGCGCCTCGACCAAGAAAAAGAAGAATTACTACGCA
AGAAATTACAGTTAAATCCCACACCTGCTAACAGAAGCAGATACCAGTCCAGGAAGGTGGAGAACATGAAAGCCA
TAACAGCTAGACGTATTCTGCAAGGCCTAGGGCATTATTTGAAGGCAGAAGGAAAAGTGGAGTGCTACCGAACCC
TGCATCCTGTTCCTTTGTATTCATCTAGTGTGAACCGTGCCTTTTCAAGCCCCAAGGTCGCAGTGGAAGCCTGTA
ACGCCATGTTGAAAGAGAACTTTCCGACTGTGGCTTCTTACTGTATTATTCCAGAGTACGATGCCTATTTGGACA
TGGTTGACGGAGCTTCATGCTGCTTAGACACTGCCAGTTTTTGCCCTGCAAAGCTGCGCAGCTTTCCAAAGAAAC
ACTCCTATTTGGAACCCACAATACGATCGGCAGTGCCTTCAGCGATCCAGAACACGCTCCAGAACGTCCTGGCAG
CTGCCACAAAAAGAAATTGCAATGTCACGCAAATGAGAGAATTGCCCGTATTGGATTCGGCGGCCTTTAATGTGG
AATGCTTCAAGAAATATGCGTGTAATAATGAATATTGGGAAACGTTTAAAGAAAACCCCATCAGGCTTACTGAAG
AAAACGTGGTAAATTACATTACCAAATTAAAAGGACCAAAAGCTGCTGCTCTTTTTGCGAAGACACATAATTTGA
ATATGTTGCAGGACATACCAATGGACAGGTTTGTAATGGACTTAAAGAGAGACGTGAAAGTGACTCCAGGAACAA
AACATACTGAAGAACGGCCCAAGGTACAGGTGATCCAGGCTGCCGATCCGCTAGCAACAGCGTATCTGTGCGGAA
TCCACCGAGAGCTGGTTAGGAGATTAAATGCGGTCCTGCTTCCGAACATTCATACACTGTTTGATATGTCGGCTG
AAGACTTTGACGCTATTATAGCCGAGCACTTCCAGCCTGGGGATTGTGTTCTGGAAACTGACATCGCGTCGTTTG
ATAAAAGTGAGGACGACGCCATGGCTCTGACCGCGTTAATGATTCTGGAAGACTTAGGTGTGGACGCAGAGCTGT
TGACGCTGATTGAGGCGGCTTTCGGCGAAATTTCATCAATACATTTGCCCACTAAAACTAAATTTAAATTCGGAG
CCATGATGAAATCTGGAATGTTCCTCACACTGTTTGTGAACACAGTCATTAACATTGTAATCGCAAGCAGAGTGT
TGAGAGAACGGCTAACCGGATCACCATGTGCAGCATTCATTGGAGATGACAATATCGTGAAAGGAGTCAAATCGG
ACAAATTAATGGCAGACAGGTGCGCCACCTGGTTGAATATGGAAGTCAAGATTATAGATGCTGTGGTGGGCGAGA
AAGCGCCTTATTTCTGTGGAGGGTTTATTTTGTGTGACTCCGTGACCGGCACAGCGTGCCGTGTGGCAGACCCCC
TAAAAAGGCTGTTTAAGCTTGGCAAACCTCTGGCAGCAGACGATGAACATGATGATGACAGGAGAAGGGCATTGC
ATGAAGAGTCAACACGCTGGAACCGAGTGGGTATTCTTTCAGAGCTGTGCAAGGCAGTAGAATCAAGGTATGAAA
CCGTAGGAACTTCCATCATAGTTATGGCCATGACTACTCTAGCTAGCAGTGTTAAATCATTCAGCTACCTGAGAG
GGGCCCCTATAACTCTCTACGGCTAACCTGAATGGACTACGACATAGTCTAGTCCGCCAAGATGAGGCCTGGCCT
GCCCTCCTACCTGATCATCCTGGCCGTGTGCCTGTTCAGCCACCTGCTGTCCAGCAGATACGGCGCCGAGGCCGT
GAGCGAGCCCCTGGACAAGGCTTTCCACCTGCTGCTGAACACCTACGGCAGACCCATCCGGTTTCTGCGGGAGAA
CACCACCCAGTGCACCTACAACAGCAGCCTGCGGAACAGCACCGTCGTGAGAGAGAACGCCATCAGCTTCAACTT
TTTCCAGAGCTACAACCAGTACTACGTGTTCCACATGCCCAGATGCCTGTTTGCCGGCCCTCTGGCCGAGCAGTT
CCTGAACCAGGTGGACCTGACCGAGACACTGGAAAGATACCAGCAGCGGCTGAATACCTACGCCCTGGTGTCCAA
GGACCTGGCCAGCTACCGGTCCTTTAGCCAGCAGCTCAAGGCTCAGGATAGCCTCGGCGAGCAGCCTACCACCGT
GCCCCCTCCCATCGACCTGAGCATCCCCCACGTGTGGATGCCTCCCCAGACCACCCCTCACGGCTGGACCGAGAG
CCACACCACCTCCGGCCTGCACAGACCCCACTTCAACCAGACCTGCATCCTGTTCGACGGCCACGACCTGCTGTT
TAGCACCGTGACCCCCTGCCTGCACCAGGGCTTCTACCTGATCGACGAGCTGAGATACGTGAAGATCACCCTGAC
CGAGGATTTCTTCGTGGTCACCGTGTCCATCGACGACGACACCCCCATGCTGCTGATCTTCGGCCACCTGCCCAG
AGTGCTGTTCAAGGCCCCCTACCAGCGGGACAACTTCATCCTGCGGCAGACCGAGAAGCACGAGCTGCTGGTGCT
GGTCAAGAAGGACCAGCTGAACCGGCACTCCTACCTGAAGGACCCCGACTTCCTGGACGCCGCCCTGGACTTCAA
CTACCTGGACCTGAGCGCCCTGCTGAGAAACAGCTTCCACAGATACGCCGTGGACGTGCTGAAGTCCGGACGGTG
CCAGATGCTCGATCGGCGGACCGTGGAGATGGCCTTCGCCTATGCCCTCGCCCTGTTCGCCGCTGCCAGACAGGA
AGAGGCTGGCGCCCAGGTGTCAGTGCCCAGAGCCCTGGATAGACAGGCCGCCCTGCTGCAGATCCAGGAATTCAT
GATCACCTGCCTGAGCCAGACCCCCCCTAGAACCACCCTGCTGCTGTACCCCACAGCCGTGGATCTGGCCAAGAG
GGCCCTGTGGACCCCCAACCAGATCACCGACATCACAAGCCTCGTGCGGCTCGTGTACATCCTGAGCAAGCAGAA
CCAGCAGCACCTGATCCCCCAGTGGGCCCTGAGACAGATCGCCGACTTCGCCCTGAAGCTGCACAAGACCCATCT
GGCCAGCTTTCTGAGCGCCTTCGCCAGGCAGGAACTGTACCTGATGGGCAGCCTGGTCCACAGCATGCTGGTGCA
TACCACCGAGCGGCGGGAGATCTTCATCGTGGAGACAGGCCTGTGTAGCCTGGCCGAGCTGTCCCACTTTACCCA
GCTGCTGGCCCACCCTCACCACGAGTACCTGAGCGACCTGTACACCCCCTGCAGCAGCAGCGGCAGACGGGACCA
CAGCCTGGAACGGCTGACCAGACTGTTCCCCGATGCCACCGTGCCTGCTACAGTGCCTGCCGCCCTGTCCATCCT
GTCCACCATGCAGCCCAGCACCCTGGAAACCTTCCCCGACCTGTTCTGCCTGCCCCTGGGCGAGAGCTTTAGCGC

-continued

SEQUENCES

CCTGACCGTGTCCGAGCACGTGTCCTACATCGTGACCAATCAGTACCTGATCAAGGGCATCAGCTACCCCGTGTC
CACCACAGTCGTGGGCCAGAGCCTGATCATCACCCAGACCGACAGCCAGACCAAGTGCGAGCTGACCCGGAACAT
GCACACCACACACAGCATCACCGTGGCCCTGAACATCAGCCTGGAAAACTGCGCTTTCTGTCAGTCTGCCCTGCT
GGAATACGACGATACCCAGGGCGTGATCAACATCATGTACATGCACGACAGCGACGACGTGCTGTTCGCCCTGGA
CCCCTACAACGAGGTGGTGGTGTCCAGCCCCCGGACCCACTACCTGATGCTGCTGAAGAACGGCACCGTGCTGGA
AGTGACCGACGTGGTGGTGGACGCCACCGACAGCAGACTGCTGATGATGAGCGTGTACGCCCTGAGCGCCATCAT
CGGCATCTACCTGCTGTACCGGATGCTGAAAACCTGCTGATAATCTAGAGGCCCCTATAACTCTCTACGGCTAAC
CTGAATGGACTACGACATAGTCTAGTCCGCCAAGATGTGCAGAAGGCCCGACTGCGGCTTCAGCTTCAGCCCTGG
ACCCGTGATCCTGCTGTGGTGCTGCCTGCTGCTGCCTATCGTGTCCTCTGCCGCCGTGTCTGTGGCCCCTACAGC
CGCCGAGAAGGTGCCAGCCGAGTGCCCCGAGCTGACCAGAAGATGCCTGCTGGGCGAGGTGTTCGAGGGCGACAA
GTACGAGAGCTGGCTGCGGCCCCTGGTCAACGTGACCGGCAGAGATGGCCCCCTGAGCCAGCTGATCCGGTACAG
ACCCGTGACCCCCGAGGCCGCCAATAGCGTGCTGCTGGACGAGGCCTTCCTGGATACCCTGGCCCTGCTGTACAA
CAACCCCGACCAGCTGAGAGCCCTGCTGACCCTGCTGTCCAGCGACACCGCCCCCAGATGGATGACCGTGATGCG
GGGCTACAGCGAGTGTGGAGATGGCAGCCCTGCCGTGTACACCTGCGTGGACGACCTGTGCAGAGGCTACGACCT
GACCAGACTGAGCTACGGCCGGTCCATCTTCACAGAGCACGTGCTGGGCTTCGAGCTGGTGCCCCCCAGCCTGTT
CAACGTGGTGGTGGCCATCCGGAACGAGGCCACCAGAACCAACAGAGCCGTGCGGCTGCCTGTGTCTACAGCCGC
TGCACCTGAGGGCATCACACTGTTCTACGGCCTGTACAACGCCGTGAAAGAGTTCTGCCTCCGGCACCAGCTGGA
TCCCCCCCTGCTGAGACACCTGGACAAGTACTACGCCGGCCTGCCCCCAGAGCTGAAGCAGACCAGAGTGAACCT
GCCCGCCCACAGCAGATATGGCCCTCAGGCCGTGGACGCCAGATGATAACGCCGGCGGCCCCTATAACTCTCTAC
GGCTAACCTGAATGGACTACGACATAGTCTAGTCCGCCAAGATGAGCCCCAAGGACCTGACCCCCTTCCTGACAA
CCCTGTGGCTGCTCCTGGGCCATAGCAGAGTGCCTAGAGTGCGGGCCGAGGAATGCTGCGAGTTCATCAACGTGA
ACCACCCCCCCGAGCGGTGCTACGACTTCAAGATGTGCAACCGGTTCACCGTGGCCCTGAGATGCCCCGACGGCG
AAGTGTGCTACAGCCCCGAGAAAACCGCCGAGATCCGGGGCATCGTGACCACCATGACCCACAGCCTGACCCGGC
AGGTGGTGCACAACAAGCTGACCAGCTGCAACTACAACCCCCTGTACCTGGAAGCCGACGGCCGGATCAGATGCG
GCAAAGTGAACGACAAGGCCCAGTACCTGCTGGGAGCCGCCGGAAGCGTGCCCTACCGGTGGATCAACCTGGAAT
ACGACAAGATCACCCGGATCGTGGGCCTGGACCAGTACCTGGAAAGCGTGAAGAAGCACAAGCGGCTGGACGTGT
GCAGAGCCAAGATGGGCTACATGCTGCAGCTGTTGAATTTTGACCTTCTTAAGCTTGCGGGAGACGTCGAGTCCA
ACCCCGGGCCCATGCTGCGGCTGCTGCTGAGACACCACTTCCACTGCCTGCTGCTGTGTGCCGTGTGGGCCACCC
CTTGTCTGGCCAGCCCTTGGAGCACCCTGACCGCCAACCAGAACCCTAGCCCCCCTTGGTCCAAGCTGACCTACA
GCAAGCCCCACGACGCCGCCACCTTCTACTGCCCCTTTCTGTACCCCAGCCCTCCCAGAAGCCCCCTGCAGTTCA
GCGGCTTCCAGAGAGTGTCCACCGGCCCTGAGTGCCGGAACGAGACACTGTACCTGCTGTACAACCGGGAGGGCC
AGACACTGGTGGAGCGGAGCAGCACCTGGGTGAAAAAAGTGATCTGGTATCTGAGCGGCCGGAACCAGACCATCC
TGCAGCGGATGCCCAGAACCGCCAGCAAGCCCAGCGACGGCAACGTGCAGATCAGCGTGGAGGACGCCAAAATCT
TCGGCGCCCACATGGTGCCCAAGCAGACCAAGCTGCTGAGATTCGTGGTCAACGACGGCACCAGATATCAGATGT
GCGTGATGAAGCTGGAAAGCTGGGCCCACGTGTTCCGGGACTACTCCGTGAGCTTCCAGGTCCGGCTGACCTTCA
CCGAGGCCAACAACCAGACCTACACCTTCTGCACCCACCCCAACCTGATCGTGCTGCTGAACTTCGACCTGCTGA
AGCTGGCCGGCGACGTGGAGAGCAACCCCGGCCCCCATATGCGGCTGTGCAGAGTGTGGCTGTCCGTGTGCCTGT
GTGCCGTGGTGCTGGGCCAGTGCCAGAGAGAGACAGCCGAGAAGAACGACTACTACCGGGTGCCCCACTACTGGG
ATGCCTGCAGCAGAGCCCTGCCCGACCAGACCCGGTACAAATACGTGGAGCAGCTCGTGGACCTGACCCTGAACT
ACCACTACGACGCCAGCCACGGCCTGGACAACTTCGACGTGCTGAAGCGGATCAACGTGACCGAGGTGTCCCTGC
TGATCAGCGACTTCCGGCGGCAGAACAGAAGAGGCGGCACCAACAAGCGGACCACCTTCAACGCCGCTGGCTCTC
TGGCCCCTCACGCCAGATCCCTGGAATTCAGCGTGCGGCTGTTCGCCAACTGATAACGTTGCATCCTGCAGGATA
CAGCAGCAATTGGCAAGCTGCTTACATAGAACTCGCGGCGATTGGCATGCCGCCTTAAAATTTTTATTTTATTTT
TCTTTTCTTTTCCGAATCGGATTTTGTTTTTAATATTTCAAAAAAAAAAAAAAAAAAAAAAAAAAAAAAAAAAAAG
GGTCGGCATGGCATCTCCACCTCCTCGCGGTCCGACCTGGGCATCCGAAGGAGGACGCACGTCCACTCGGATGGC
TAAGGGAGAGCCACGTTTAAACGCTAGAGCAAGACGTTTCCCGTTGAATATGGCTCATAACACCCCTTGTATTAC
TGTTTATGTAAGCAGACAGTTTTATTGTTCATGATGATATATTTTTATCTTGTGCAATGTAACATCAGAGATTTT
GAGACACAACGTGGCTTTGTTGAATAAATCGAACTTTTGCTGAGTTGAAGGATCAGATCACGCATCTTCCCGACA
ACGCAGACCGTTCCGTGGCAAAGCAAAAGTTCAAAATCACCAACTGGTCCACCTACAACAAAGCTCTCATCAACC
GTGGCTCCCTCACTTTCTGGCTGGATGATGGGGCGATTCAGGCCTGGTATGAGTCAGCAACACCTTCTTCACGAG
GCAGACCTCAGCGCTAGCGGAGTGTATACTGGCTTACTATGTTGGCACTGATGAGGGTGTCAGTGAAGTGCTTCA
TGTGGCAGGAGAAAAAAGGCTGCACCGGTGCGTCAGCAGAATATGTGATACAGGATATATTCCGCTTCCTCGCTC
ACTGACTCGCTACGCTCGGTCGTTCGACTGCGGCGAGCGGAAATGGCTTACGAACGGGGCGGAGATTTCCTGGAA
GATGCCAGGAAGATACTTAACAGGGAAGTGAGAGGGCCGCGGCAAAGCCGTTTTTCCATAGGCTCCGCCCCCCTG
ACAAGCATCACGAAATCTGACGCTCAAATCAGTGGTGGCGAAACCCGACAGGACTATAAAGATACCAGGCGTTTC
CCCTGGCGGCTCCCTCGTGCGCTCTCCTGTTCCTGCCTTTCGGTTTACCGGTGTCATTCCGCTGTTATGGCCGCG
TTTGTCTCATTCCACGCCTGACACTCAGTTCCGGGTAGGCAGTTCGCTCCAAGCTGGACTGTATGCACGAACCCC
CCGTTCAGTCCGACCGCTGCGCCTTATCCGGTAACTATCGTCTTGAGTCCAACCCGGAAAGACATGCAAAAGCAC
CACTGGCAGCAGCCACTGGTAATTGATTTAGAGGAGTTAGTCTTGAAGTCATGCGCCGGTTAAGGCTAAACTGAA
AGGACAAGTTTTGGTGACTGCGCTCCTCCAAGCCAGTTACCTCGGTTCAAAGAGTTGGTAGCTCAGAGAACCTTC
GAAAAACCGCCCTGCAAGGCGGTTTTTTCGTTTTCAGAGCAAGAGATTACGCGCAGACCAAAACGATCTCAAGAA
GATCATCTTATTAAGGGGTCTGACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCTAAAGTATATATGAGTAAACT
TGGTCTGACAGTTATTAGAAAAATTCATCCAGCAGACGATAAAACGCAATACGCTGGCTATCCGGTGCCGCAATG
CCATACAGCACCAGAAAACGATCCGCCCATTCGCCGCCCAGTTCTTCCGCAATATCACGGGTGGCCAGCGCAATA
TCCTGATAACGATCCGCCACGCCCAGACGGCCGCAATCAATAAAGCCGCTAAAACGGCCATTTTCCACCATAATG
TTCGGCAGGCACGCATCACCATGGGTCACCACCAGATCTTCGCCATCCGGCATGCTCGCTTTCAGACGCGCAAAC
AGCTCTGCCGGTGCCAGGCCCTGATGTTCTTCATCCAGATCATCCTGATCCACCAGGCCCGCTTCCATACGGGTA
CGCGCACGTTCAATACGATGTTTCGCCTGATGATCAAACGGACAGGTCGCCGGGTCCAGGGTATGCAGACGACGC
ATGGCATCCGCCATAATGCTCACTTTTTCTGCCGGCGCCAGATGGCTAGACAGCAGATCCTGACCCGGCACTTCG
CCCAGCAGCAGCCAATCACGGCCCGCTTCGGTCACCACATCCAGCACCGCCGCACACGGAACACCGGTGGTGGCC
AGCCAGCTCAGACGCGCCGCTTCATCCTGCAGCTCGTTCAGCGCACCGCTCAGATCGGTTTTCACAAACAGCACC
GGACGACCCTGCGCGCTCAGACGAAACACCGCCGCATCAGAGCAGCCAATGGTCTGCTGCGCCCAATCATAGCCA
AACAGACGTTCCACCCACGCTGCCGGGCTACCCGCATGCAGGCCATCCTGTTCAATCATACTCTTCCTTTTTCAA
TATTATTGAAGCATTTATCAGGGTTATTGTCTCATGAGCGGATACATATTTGAATGTATTTAGAAAAATAAACAA
ATAGGGGTTCCGCGCACATTTCCCCGAAAAGTGCCACCTAAATTGTAAGCGTTAATATTTTGTTAAAATTCGCGT
TAAATTTTTGTTAAATCAGCTCATTTTTTAACCAATAGGCCGAAATCGGCAAAATCCCTTATAAATCAAAAGAAT

-continued

SEQUENCES

AGACCGAGATAGGGTTGAGTGGCCGCTACAGGGCGCTCCCATTCGCCATTCAGGCTGCGCAACTGTTGGGAAGGG
CGTTTCGGTGCGGGCCTCTTCGCTATTACGCCAGCTGGCGAAAGGGGGATGTGCTGCAAGGCGATTAAGTTGGGT
AACGCCAGGGTTTTCCCAGTCACACGCGTAATACGACTCACTATAG

A527 Vector: SGP-gH-SGP-gL-SGP-UL128-EMCV-UL130-EV71-UL131 (SEQ ID NO: 57):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT
GTGCGGAAGATCCGGACAGATTGTATAAGTATGCAACTAAGCTGAAGAAAAACTGTAAGGAAATAACTGATAAGG
AATTGGACAAGAAAATGAAGGAGCTCGCCGCCGTCATGAGCGACCCTGACCTGGAAACTGAGACTATGTGCCTCC
ACGACGACGAGTCGTGTCGCTACGAAGGGCAAGTCGCTGTTTACCAGGATGTATACGCGGTTGACGGACCGACAA
GTCTCTATCACCAAGCCAATAAGGGAGTTAGAGTCGCCTACTGGATAGGCTTTGACACCACCCCTTTTATGTTTA
AGAACTTGGCTGGAGCATATCCATCATACTCTACCAACTGGGCCGACGAAACCGTGTTAACGGCTCGTAACATAG
GCCTATGCAGCTCTGACGTTATGGAGCGGTCACGTAGAGGGATGTCCATTCTTAGAAAGAAGTATTTGAAACCAT
CCAACAATGTTCTATTCTCTGTTGGCTCGACCATCTACCACGAGAAGAGGGACTTACTGAGGAGCTGGCACCTGC
CGTCTGTATTTCACTTACGTGGCAAGCAAAATTACACATGTCGGTGTGAGACTATAGTTAGTTGCGACGGGTACG
TCGTTAAAAGAATAGCTATCAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCGTGTGCACGTATGTGCCAG
CTACATTGTGTGACCAAATGACTGGCATACTGGCAACAGATGTCAGTGCGGACGACGCGCAAAAACTGCTGGTTG
GGCTCAACCAGCGTATAGTCGTCAACGGTCGCACCCAGAGAAACACCAATACCATGAAAAATTACCTTTTGCCCG
TAGTGGCCCAGGCATTTGCTAGGTGGGCAAAGGAATATAAGGAAGATCAAGAAGATGAAAGGCCACTAGGACTAC
GAGATAGACAGTTAGTCATGGGGTGTTGTTGGGCTTTTAGAAGGCACAAGATAACATCTATTTATAAGCGCCCGG
ATACCCAAACCATCATCAAAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCACCTCTCATTACCGCCGAGG
ACGTACAAGAAGCTAAGTGCGCAGCCGATGAGGCTAAGGAGGTGCGTGAAGCCGAGGAGTTGCGCGCAGCTCTAC
CACCTTTGGCAGCTGATGTTGAGGAGCCCACTCTGGAAGCCGATGTAGACTTGATGTTACAAGAGGCTGGGGCCG
GCTCAGTGGAGACACCTCGTGGCTTGATAAAGGTTACCAGCTACGATGGCGAGGACAAGATCGGCTCTTACGCTG
TGCTTTCTCCGCAGGCTGTACTCAAGAGTGAAAAATTATCTTGCATCCACCCTCTCGCTGAACAAGTCATAGTGA
TAACACACTCTGGCCGAAAAGGGCGTTATGCCGTGGAACCATACCATGGTAAAGTAGTGGTGCCAGAGGGACATG
CAATACCCGTCCAGGACTTTCAAGCTCTGAGTGAAAGTGCCACCATTGTGTACAACGAACGTGAGTTCGTAAACA
GGTACCTGCACCATATTGCCACACATGGAGGAGCGCTGAACACTGATGAAGAATATTACAAAACTGTCAAGCCCA
GCGAGCACGACGGCGAATACCTGTACGACATCGACAGGAAACAGTGCGTCAAGAAAGAACTAGTCACTGGGCTAG
GGCTCACAGGCGAGCTGGTGGATCCTCCCTTCCATGAATTCGCCTACGAGAGTCTGAGAACACGACCAGCCGCTC
CTTACCAAGTACCAACCATAGGGGTGTATGGCGTGCCAGGATCAGGCAAGTCTGGCATCATTAAAAGCGCAGTCA
CCAAAAAAGATCTAGTGGTGAGCGCCAAGAAAGAAAACTGTGCAGAAATTATAAGGGACGTCAAGAAAATGAAAG
GGCTGGACGTCAATGCCAGAACTGTGGACTCAGTGCTCTTGAATGGATGCAAACACCCCGTAGAGACCCTGTATA
TTGACGAAGCTTTTGCTTGTCATGCAGGTACTCTCAGAGCGCTCATAGCCATTATAAGACCTAAAAAGGCAGTGC
TCTGCGGGGATCCCAAACAGTGCGGTTTTTTTAACATGATGTGCCTGAAAGTGCATTTTAACCACGAGATTTGCA
CACAAGTCTTCCACAAAAGCATCTCTCGCCGTTGCACTAAATCTGTGACTTCGGTCGTCTCAACCTTGTTTTACG
ACAAAAAAATGAGAACGACGAATCCGAAAGAGACTAAGATTGTGATTGACACTACCGGCAGTACCAAACCTAAGC
AGGACGATCTCATTCTCACTTGTTTCAGAGGGTGGGTGAAGCAGTTGCAAATAGATTACAAAGGCAACGAAATAA
TGACGGCAGCTGCCTCTCAAGGGCTGACCCGTAAAGGTGTGTATGCCGTTCGGTACAAGGTGAATGAAAATCCTC
TGTACGCACCCACCTCAGAACATGTGAACGTCCTACTGACCCGCACGGAGGACCGCATCGTGTGGAAAACACTAG
CCGGCGACCCATGGATAAAAACACTGACTGCCAAGTACCCTGGGAATTTCACTGCCACGATAGAGGAGTGGCAAG
CAGAGCATGATGCCATCATGAGGCACATCTTGGAGAGACCGGACCCTACCGACGTCTTCCAGAATAAGGCAAACG
TGTGTTGGGCCAAGGCTTTAGTGCCGGTGCTGAAGACCGCTGGCATAGACATGACCACTGAACAATGGAACACTG
TGGATTATTTTGAAACGGACAAAGCTCACTCAGCAGAGATAGTATTGAACCAACTATGCGTGAGGTTCTTTGGAC
TCGATCTGGACTCCGGTCTATTTTCTGCACCCACTGTTCCGTTATCCATTAGGAATAATCACTGGGATAACTCCC
CGTCGCCTAACATGTACGGGCTGAATAAAGAAGTGGTCCGTCAGCTCTCTCGCAGGTACCCACAACTGCCTCGGG
CAGTTGCCACTGGAAGAGTCTATGACATGAACACTGGTACACTGCGCAATTATGATCCGCGCATAAACCTAGTAC
CTGTAAACAGAAGACTGCCTCATGCTTTAGTCCTCCACCATAATGAACACCCACAGAGTGACTTTTCTTCATTCG
TCAGCAAATTGAAGGGCAGAACTGTCCTGGTGGTCGGGGAAAAGTTGTCCGTCCCAGGCAAAATGGTTGACTGGT
TGTCAGACCGGCCTGAGGCTACCTTCAGAGCTCGGCTGGATTTAGGCATCCCAGGTGATGTGCCCAAATATGACA
TAATATTTGTTAATGTGAGGACCCCATATAAATACCATCACTATCAGCAGTGTGAAGACCATGCCATTAAGCTTA
GCATGTTGACCAAGAAAGCTTGTCTGCATCTGAATCCCGGCGGAACCTGTGTCAGCATAGGTTATGGTTACGCTG
ACAGGGCCAGCGAAAGCATCATTGGTGCTATAGCGCGGCAGTTCAAGTTTTCCCGGGTATGCAAACCGAAATCCT
CACTTGAAGAGACGGAAGTTCTGTTTGTATTCATTGGGTACGATCGCAAGGCCCGTACGCACAATCCTTACAAGC
TTTCATCAACCTTGACCAACATTTATACAGGTTCCAGACTCCACGAAGCCGGATGTGCACCCTCATATCATGTGG
TGCGAGGGGATATTGCCACGGCCACCGAAGGAGTGATTATAAATGCTGCTAACAGCAAAGGACAACCTGGCGGAG
GGGTGTGCGGAGCGCTGTATAAGAAATTCCCGGAAAGCTTCGATTTACAGCCGATCGAAGTAGGAAAAGCGCGAC
TGGTCAAAGGTGCAGCTAAACATATCATTCATGCCGTAGGACCAAACTTCAACAAAGTTTCGGAGGTTGAAGGTG
ACAAACAGTTGGCAGAGGCTTATGAGTCCATCGCTAAGATTGTCAACGATAACAATTACAAGTCAGTAGCGATTC
CACTGTTGTCCACCGGCATCTTTTCCGGGAACAAAGATCGACTAACCCAATCATTGAACCATTTGCTGACAGCTT
TAGACACCACTGATGCAGATGTAGCCATATACTGCAGGGACAAGAAATGGGAAATGACTCTCAAGGAAGCAGTGG
CTAGGAGAGAAGCAGTGGAGGAGATATGCATATCCGACGACTCTTCAGTGACAGAACCTGATGCAGAGCTGGTGA
GGGTGCATCCGAAGAGTTCTTTGGCTGGAAGGAAGGGCTACAGCACAAGCGATGGCAAAACTTTCTCATATTTGG
AAGGGACCAAGTTTCACCAGGCGGCCAAGGATATAGCAGAAATTAATGCCATGTGGCCCGTTGCAACGGAGGCCA
ATGAGCAGGTATGCATGTATATCCTCGGAGAAAGCATGAGCAGTATTAGGTCGAAATGCCCCGTCGAAGAGTCGG
AAGCCTCCACACCACCTAGCACGCTGCCTTGCTTGTGCATCCATGCCATGACTCCAGAAAGAGTACAGCGCCTAA
AAGCCTCACGTCCAGAACAAATTACTGTGTGCTCATCCTTTCCATTGCCGAAGTATAGAATCACTGGTGTGCAGA
AGATCCAATGCTCCCAGCCTATATTGTTCTCACCGAAAGTGCCTGCGTATATTCATCCAAGGAAGTATCTCGTGG
AAACACCACCGGTAGACGAGACTCCGGAGCCATCGGCAGAGAACCAATCCACAGAGGGGACACCTGAACAACCAC
CACTTATAACCGAGGATGAGACCAGGACTAGAACGCCTGAGCCGATCATCATCGAAGAGGAAGAAGAGGATAGCA
TAAGTTTGCTGTCAGATGGCCCGACCCACCAGGTGCTGCAAGTCGAGGCAGACATTCACGGGCCGCCCTCTGTAT
CTAGCTCATCCTGGTCCATTCCTCATGCATCCGACTTTGATGTGGACAGTTTATCCATACTTGACACCCTGGAGG -continued

SEQUENCES

GAGCTAGCGTGACCAGCGGGGCAACGTCAGCCGAGACTAACTCTTACTTCGCAAAGAGTATGGAGTTTCTGGCGC
GACCGGTGCCTGCGCCTCGAACAGTATTCAGGAACCCTCCACATCCCGCTCCGCGCACAAGAACACCGTCACTTG
CACCCAGCAGGGCCTGCTCGAGAACCAGCCTAGTTTCCACCCCGCCAGGCGTGAATAGGGTGATCACTAGAGAGG
AGCTCGAGGCGCTTACCCCGTCACGCACTCCTAGCAGGTCGGTCTCGAGAACCAGCCTGGTCTCCAACCCGCCAG
GCGTAAATAGGGTGATTACAAGAGAGGAGTTTGAGGCGTTCGTAGCACAACAACAATGACGGTTTGATGCGGGTG
CATACATCTTTTCCTCCGACACCGGTCAAGGGCATTTACAACAAAAATCAGTAAGGCAAACGGTGCTATCCGAAG
TGGTGTTGGAGAGGACCGAATTGGAGATTTCGTATGCCCCGCGCCTCGACCAAGAAAAAGAAGAATTACTACGCA
AGAAATTACAGTTAAATCCCACACCTGCTAACAGAAGCAGATACCAGTCCAGGAAGGTGGAGAACATGAAAGCCA
TAACAGCTAGACGTATTCTGCAAGGCCTAGGGCATTATTTGAAGGCAGAAGGAAAAGTGGAGTGCTACCGAACCC
TGCATCCTGTTCCTTTGTATTCATCTAGTGTGAACCGTGCCTTTTCAAGCCCCAAGGTCGCAGTGGAAGCCTGTA
ACGCCATGTTGAAAGAGAACTTTCCGACTGTGGCTTCTTACTGTATTATTCCAGAGTACGATGCCTATTTGGACA
TGGTTGACGGAGCTTCATGCTGCTTAGACACTGCCAGTTTTTGCCCTGCAAAGCTGCGCAGCTTTCCAAAGAAAC
ACTCCTATTTGGAACCCACAATACGATCGGCAGTGCCTTCAGCGATCCAGAACACGCTCCAGAACGTCCTGGCAG
CTGCCACAAAAAGAAATTGCAATGTCACGCAAATGAGAGAATTGCCCGTATTGGATTCGGCGGCCTTTAATGTGG
AATGCTTCAAGAAATATGCGTGTAATAATGAATATTGGGAAACGTTTAAAGAAAACCCCATCAGGCTTACTGAAG
AAAACGTGGTAAATTACATTACCAAATTAAAAGGACCAAAAGCTGCTGCTCTTTTTGCGAAGACACATAATTTGA
ATATGTTGCAGGACATACCAATGGACAGGTTTGTAATGGACTTAAAGAGAGACGTGAAAGTGACTCCAGGAACAA
AACATACTGAAGAACGGCCCAAGGTACAGGTGATCCAGGCTGCCGATCCGCTAGCAACAGCGTATCTGTGCGGAA
TCCACCGAGAGCTGGTTAGGAGATTAAATGCGGTCCTGCTTCCGAACATTCATACACTGTTTGATATGTCGGCTG
AAGACTTTGACGCTATTATAGCCGAGCACTTCCAGCCTGGGGATTGTGTTCTGGAAACTGACATCGCGTCGTTTG
ATAAAAGTGAGGACGACGCCATGGCTCTGACCGCGTTAATGATTCTGGAAGACTTAGGTGTGGACGCAGAGCTGT
TGACGCTGATTGAGGCGGCTTTCGGCGAAATTTCATCAATACATTTGCCCACTAAAACTAAATTTAAATTCGGAG
CCATGATGAAATCTGGAATGTTCCTCACACTGTTTGTGAACACAGTCATTAACATTGTAATCGCAAGCAGAGTGT
TGAGAGAACGGCTAACCGGATCACCATGTGCAGCATTCATTGGAGATGACAATATCGTGAAAGGAGTCAAATCGG
ACAAATTAATGGCAGACAGGTGCGCCACCTGGTTGAATATGGAAGTCAAGATTATAGATGCTGTGGTGGGCGAGA
AAGCGCCTTATTTCTGTGGAGGGTTTATTTTGTGTGACTCCGTGACCGGCACAGCGTGCCGTGTGGCAGACCCCC
TAAAAAGGCTGTTTAAGCTTGGCAAACCTCTGGCAGCAGACGATGAACATGATGATGACAGGAGAAGGGCATTGC
ATGAAGAGTCAACACGCTGGAACCGAGTGGGTATTCTTTCAGAGCTGTGCAAGGCAGTAGAATCAAGGTATGAAA
CCGTAGGAACTTCCATCATAGTTATGGCCATGACTACTCTAGCTAGCAGTGTTAAATCATTCAGCTACCTGAGAG
GGGCCCCTATAACTCTCTACGGCTAACCTGAATGGACTACGACATAGTCTAGTCCGCCAAGATGAGGCCTGGCCT
GCCCTCCTACCTGATCATCCTGGCCGTGTGCCTGTTCAGCCACCTGCTGTCCAGCAGATACGGCGCCGAGGCCGT
GAGCGAGCCCCTGGACAAGGCTTTCCACCTGCTGCTGAACACCTACGGCAGACCCATCCGGTTTCTGCGGGAGAA
CACCACCCAGTGCACCTACAACAGCAGCCTGCGGAACAGCACCGTCGTGAGAGAGAACGCCATCAGCTTCAACTT
TTTCCAGAGCTACAACCAGTACTACGTGTTCCACATGCCCAGATGCCTGTTTGCCGGCCCTCTGGCCGAGCAGTT
CCTGAACCAGGTGGACCTGACCGAGACACTGGAAAGATACCAGCAGCGGCTGAATACCTACGCCCTGGTGTCCAA
GGACCTGGCCAGCTACCGGTCCTTTAGCCAGCAGCTCAAGGCTCAGGATAGCCTCGGCGAGCAGCCTACCACCGT
GCCCCCTCCCATCGACCTGAGCATCCCCCACGTGTGGATGCCTCCCCAGACCACCCCTCACGGCTGGACCGAGAG
CCACACCACCTCCGGCCTGCACAGACCCCACTTCAACCAGACCTGCATCCTGTTCGACGGCCACGACCTGCTGTT
TAGCACCGTGACCCCCTGCCTGCACCAGGGCTTCTACCTGATCGACGAGCTGAGATACGTGAAGATCACCCTGAC
CGAGGATTTCTTCGTGGTCACCGTGTCCATCGACGACGACACCCCCATGCTGCTGATCTTCGGCCACCTGCCCAG
AGTGCTGTTCAAGGCCCCCTACCAGCGGGACAACTTCATCCTGCGGCAGACCGAGAAGCACGAGCTGCTGGTGCT
GGTCAAGAAGGACCAGCTGAACCGGCACTCCTACCTGAAGGACCCCGACTTCCTGGACGCCGCCCTGGACTTCAA
CTACCTGGACCTGAGCGCCCTGCTGAGAAACAGCTTCCACAGATACGCCGTGGACGTGCTGAAGTCCGGACGGTG
CCAGATGCTCGATCGGCGGACCGTGGAGATGGCCTTCGCCTATGCCCTCGCCCTGTTCGCCGCTGCCAGACAGGA
AGAGGCTGGCGCCCAGGTGTCAGTGCCCAGAGCCCTGGATAGACAGGCCGCCCTGCTGCAGATCCAGGAATTCAT
GATCACCTGCCTGAGCCAGACCCCCCCTAGAACCACCCTGCTGCTGTACCCCACAGCCGTGGATCTGGCCAAGAG
GGCCCTGTGGACCCCCAACCAGATCACCGACATCACAAGCCTCGTGCGGCTCGTGTACATCCTGAGCAAGCAGAA
CCAGCAGCACCTGATCCCCCAGTGGGCCCTGAGACAGATCGCCGACTTCGCCCTGAAGCTGCACAAGACCCATCT
GGCCAGCTTTCTGAGCGCCTTCGCCAGGCAGGAACTGTACCTGATGGGCAGCCTGGTCCACAGCATGCTGGTGCA
TACCACCGAGCGGCGGGAGATCTTCATCGTGGAGACAGGCCTGTGTAGCCTGGCCGAGCTGTCCCACTTTACCCA
GCTGCTGGCCCACCCTCACCACGAGTACCTGAGCGACCTGTACACCCCCTGCAGCAGCAGCGGCAGACGGGACCA
CAGCCTGGAACGGCTGACCAGACTGTTCCCCGATGCCACCGTGCCTGCTACAGTGCCTGCCGCCCTGTCCATCCT
GTCCACCATGCAGCCCAGCACCCTGGAAACCTTCCCCGACCTGTTCTGCCTGCCCCTGGGCGAGAGCTTTAGCGC
CCTGACCGTGTCCGAGCACGTGTCCTACATCGTGACCAATCAGTACCTGATCAAGGGCATCAGCTACCCCGTGTC
CACCACAGTCGTGGGCCAGAGCCTGATCATCACCCAGACCGACAGCCAGACCAAGTGCGAGCTGACCCGGAACAT
GCACACCACACACAGCATCACCGTGGCCCTGAACATCAGCCTGGAAAACTGCGCTTTCTGTCAGTCTGCCCTGCT
GGAATACGACGATACCCAGGGCGTGATCAACATCATGTACATGCACGACAGCGACGACGTGCTGTTCGCCCTGGA
CCCCTACAACGAGGTGGTGGTGTCCAGCCCCCGGACCCACTACCTGATGCTGCTGAAGAACGGCACCGTGCTGGA
AGTGACCGACGTGGTGGTGGACGCCACCGACAGCAGACTGCTGATGATGAGCGTGTACGCCCTGAGCGCCATCAT
CGGCATCTACCTGCTGTACCGGATGCTGAAAACCTGCTGATAATCTAGAGGCCCCTATAACTCTCTACGGCTAAC
CTGAATGGACTACGACATAGTCTAGTCCGCCAAGATGTGCAGAAGGCCCGACTGCGGCTTCAGCTTCAGCCCTGG
ACCCGTGATCCTGCTGTGGTGCTGCCTGCTGCTGCCTATCGTGTCCTCTGCCGCCGTGTCTGTGGCCCCTACAGC
CGCCGAGAAGGTGCCAGCCGAGTGCCCCGAGCTGACCAGAAGATGCCTGCTGGGCGAGGTGTTCGAGGGCGACAA
GTACGAGAGCTGGCTGCGGCCCCTGGTCAACGTGACCGGCAGAGATGGCCCCCTGAGCCAGCTGATCCGGTACAG
ACCCGTGACCCCCGAGGCCGCCAATAGCGTGCTGCTGGACGAGGCCTTCCTGGATACCCTGGCCCTGCTGTACAA
CAACCCCGACCAGCTGAGAGCCCTGCTGACCCTGCTGTCCAGCGACACCGCCCCCAGATGGATGACCGTGATGCG
GGGCTACAGCGAGTGTGGAGATGGCAGCCCTGCCGTGTACACCTGCGTGGACGACCTGTGCAGAGGCTACGACCT
GACCAGACTGAGCTACGGCCGGTCCATCTTCACAGAGCACGTGCTGGGCTTCGAGCTGGTGCCCCCCAGCCTGTT
CAACGTGGTGGTGGCCATCCGGAACGAGGCCACCAGAACCAACAGAGCCGTGCGGCTGCCTGTGTCTACAGCCGC
TGCACCTGAGGGCATCACACTGTTCTACGGCCTGTACAACGCCGTGAAAGAGTTCTGCCTCCGGCACCAGCTGGA
TCCCCCCCTGCTGAGACACCTGGACAAGTACTACGCCGGCCTGCCCCCAGAGCTGAAGCAGACCAGAGTGAACCT
GCCCGCCCACAGCAGATATGGCCCTCAGGCCGTGGACGCCAGATGATAACGCCGGCGGCCCCTATAACTCTCTAC
GGCTAACCTGAATGGACTACGACATAGTCTAGTCCGCCAAGATGAGCCCCAAGGACCTGACCCCCTTCCTGACAA
CCCTGTGGCTGCTCCTGGGCCATAGCAGAGTGCCTAGAGTGCGGGCCGAGGAATGCTGCGAGTTCATCAACGTGA
ACCACCCCCCCGAGCGGTGCTACGACTTCAAGATGTGCAACCGGTTCACCGTGGCCCTGAGATGCCCCGACGGCG
AAGTGTGCTACAGCCCCGAGAAAACCGCCGAGATCCGGGGCATCGTGACCACCATGACCCACAGCCTGACCCGGC
AGGTGGTGCACAACAAGCTGACCAGCTGCAACTACAACCCCCTGTACCTGGAAGCCGACGGCCGGATCAGATGCG

-continued

SEQUENCES

GCAAAGTGAACGACAAGGCCCAGTACCTGCTGGGAGCCGCCGGAAGCGTGCCCTACCGGTGGATCAACCTGGAAT
ACGACAAGATCACCCGGATCGTGGGCCTGGACCAGTACCTGGAAAGCGTGAAGAAGCACAAGCGGCTGGACGTGT
GCAGAGCCAAGATGGGCTACATGCTGCAGTGATAAGGCGCGCCAACGTTACTGGCCGAAGCCGCTTGGAATAAGG
CCGGTGTGCGTTTGTCTATATGTTATTTTCCACCATATTGCCGTCTTTTGGCAATGTGAGGGCCCGGAAACCTGG
CCCTGTCTTCTTGACGAGCATTCCTAGGGGTCTTTCCCCTCTCGCCAAAGGAATGCAAGGTCTGTTGAATGTCGT
GAAGGAAGCAGTTCCTCTGGAAGCTTCTTGAAGACAAACAACGTCTGTAGCGACCCTTTGCAGGCAGCGGAACCC
CCCACCTGGCGACAGGTGCCTCTGCGGCCAAAAGCCACGTGTATAAGATACACCTGCAAAGGCGGCACAACCCCA
GTGCCACGTTGTGAGTTGGATAGTTGTGGAAAGAGTCAAATGGCTCTCCTCAAGCGTATTCAACAAGGGGCTGAA
GGATGCCCAGAAGGTACCCCATTGTATGGGATCTGATCTGGGGCCTCGGTGCACATGCTTTACATGTGTTTAGTC
GAGGTTAAAAAAACGTCTAGGCCCCCCGAACCACGGGGACGTGGTTTTCCTTTGAAAAACACGATAATATGCTGC
GGCTGCTGCTGAGACACCACTTCCACTGCCTGCTGCTGTGTGCCGTGTGGGCCACCCCTTGTCTGGCCAGCCCTT
GGAGCACCCTGACCGCCAACCAGAACCCTAGCCCCCCTTGGTCCAAGCTGACCTACAGCAAGCCCCACGACGCCG
CCACCTTCTACTGCCCCTTTCTGTACCCCAGCCCTCCCAGAAGCCCCCTGCAGTTCAGCGGCTTCCAGAGAGTGT
CCACCGGCCCTGAGTGCCGGAACGAGACACTGTACCTGCTGTACAACCGGGAGGGCCAGACACTGGTGGAGCGGA
GCAGCACCTGGGTGAAAAAAGTGATCTGGTATCTGAGCGGCCGGAACCAGACCATCCTGCAGCGGATGCCCAGAA
CCGCCAGCAAGCCCAGCGACGGCAACGTGCAGATCAGCGTGGAGGACGCCAAAATCTTCGGAGCCCACATGGTGC
CCAAGCAGACCAAGCTGCTGAGATTCGTGGTCAACGACGGCACCAGATATCAGATGTGCGTGATGAAGCTGGAAA
GCTGGGCCCACGTGTTCCGGGACTACTCCGTGAGCTTCCAGGTCCGGCTGACCTTCACCGAGGCCAACAACCAGA
CCTACACCTTCTGCACCCACCCCAACCTGATCGTGTGATAAGTACCTTTGTACGCCTGTTTTATACCCCCTCCCT
GATTTGCAACTTAGAAGCAACGCAAACCAGATCAATAGTAGGTGTGACATACCAGTCGCATCTTGATCAAGCACT
TCTGTATCCCCGGACCGAGTATCAATAGACTGTGCACACGGTTGAAGGAGAAAACGTCCGTTACCCGGCTAACTA
CTTCGAGAAGCCTAGTAACGCCATTGAAGTTGCAGAGTGTTTCGCTCAGCACTCCCCCCGTGTAGATCAGGTCGA
TGAGTCACCGCATTCCCCACGGGCGACCGTGGCGGTGGCTGCGTTGGCGGCCTGCCTATGGGGTAACCCATAGGA
CGCTCTAATACGGACATGGCGTGAAGAGTCTATTGAGCTAGTTAGTAGTCCTCCGGCCCCTGAATGCGGCTAATC
CTAACTGCGGAGCACATACCCTTAATCCAAAGGGCAGTGTGTCGTAACGGGCAACTCTGCAGCGGAACCGACTAC
TTTGGGTGTCCGTGTTTCTTTTTATTCTTGTATTGGCTGCTTATGGTGACAATTAAAGAATTGTTACCATATAGC
TATTGGATTGGCCATCCAGTGTCAAACAGAGCTATTGTATATCTCTTTGTTGGATTCACACCTCTCACTCTTGAA
ACGTTACACACCCTCAATTACATTATACTGCTGAACACGAAGCGCATATGCGGCTGTGCAGAGTGTGGCTGTCCG
TGTGCCTGTGTGCCGTGGTGCTGGGCCAGTGCCAGAGAGAGACAGCCGAGAAGAACGACTACTACCGGGTGCCCC
ACTACTGGGATGCCTGCAGCAGAGCCCTGCCCGACCAGACCCGGTACAAATACGTGGAGCAGCTCGTGGACCTGA
CCCTGAACTACCACTACGACGCCAGCCACGGCCTGGACAACTTCGACGTGCTGAAGCGGATCAACGTGACCGAGG
TGTCCCTGCTGATCAGCGACTTCCGGCGGCAGAACAGAAGAGGCGGCACCAACAAGCGGACCACCTTCAACGCCG
CTGGCTCTCTGGCCCCTCACGCCAGATCCTGGAATTCAGCGTGCGGCTGTTCGCCAACTGATAACGTTGCATCC
TGCAGGATACAGCAGCAATTGGCAAGCTGCTTACATAGAACTCGCGGCGATTGGCATGCCGCCTTAAAATTTTTA
TTTTATTTTCTTTTCTTTTCCGAATCGGATTTTGTTTTTAATATTTCAAAAAAAAAAAAAAAAAAAAAAAAAAAA
AAAAAAAAGGGTCGGCATGGCATCTCCACCTCCTCGCGGTCCGACCTGGGCATCCGAAGGAGGACGCACGTCCAC
TCGGATGGCTAAGGGAGAGCCACGTTTAAACGCTAGAGCAAGACGTTTCCCGTTGAATATGGCTCATAACACCCC
TTGTATTACTGTTTATGTAAGCAGACAGTTTTATTGTTCATGATGATATATTTTTATCTTGTGCAATGTAACATC
AGAGATTTTGAGACACAACGTGGCTTTGTTGAATAAATCGAACTTTTGCTGAGTTGAAGGATCAGATCACGCATC
TTCCCGACAACGCAGACCGTTCCGTGGCAAAGCAAAAGTTCAAAATCACCAACTGGTCCACCTACAACAAAGCTC
TCATCAACCGTGGCTCCCTCACTTTCTGGCTGGATGATGGGGCGATTCAGGCCTGGTATGAGTCAGCAACACCTT
CTTCACGAGGCAGACCTCAGCGCTAGCGGAGTGTATACTGGCTTACTATGTTGGCACTGATGAGGGTGTCAGTGA
AGTGCTTCATGTGGCAGGAGAAAAAAGGCTGCACCGGTGCGTCAGCAGAATATGTGATACAGGATATATTCCGCT
TCCTCGCTCACTGACTCGCTACGCTCGGTCGTTCGACTGCGGCGAGCGGAAATGGCTTACGAACGGGGCGGAGAT
TTCCTGGAAGATGCCAGGAAGATACTTAACAGGGAAGTGAGAGGGCCGCGGCAAAGCCGTTTTTCCATAGGCTCC
GCCCCCCTGACAAGCATCACGAAATCTGACGCTCAAATCAGTGGTGGCGAAACCCGACAGGACTATAAAGATACC
AGGCGTTTCCCCCTGGCGGCTCCCTCGTGCGCTCTCCTGTTCCTGCCTTTCGGTTTACCGGTGTCATTCCGCTGTT
ATGGCCGCGTTTGTCTCATTCCACGCCTGACACTCAGTTCCGGGTAGGCAGTTCGCTCCAAGCTGGACTGTATGC
ACGAACCCCCCGTTCAGTCCGACCGCTGCGCCTTATCCGGTAACTATCGTCTTGAGTCCAACCCGGAAAGACATG
CAAAAGCACCACTGGCAGCAGCCACTGGTAATTGATTTAGAGGAGTTAGTCTTGAAGTCATGCGCCGGTTAAGGC
TAAACTGAAAGGACAAGTTTTGGTGACTGCGCTCCTCCAAGCCAGTTACCTCGGTTCAAAGAGTTGGTAGCTCAG
AGAACCTTCGAAAAACCGCCCTGCAAGGCGGTTTTTTCGTTTTCAGAGCAAGAGATTACGCGCAGACCAAAACGA
TCTCAAGAAGATCATCTTATTAAGGGGTCTGACGCTCAGTGGAACGAAAACTCACGTTAAGGGATTTTGGTCATG
AGATTATCAAAAAGGATCTTCACCTAGATCCTTTTAAATTAAAAATGAAGTTTTAAATCAATCTAAAGTATATAT
GAGTAAACTTGGTCTGACAGTTATTAGAAAAATTCATCCAGCAGACGATAAAACGCAATACGCTGGCTATCCGGT
GCCGCAATGCCATACAGCACCAGAAAACGATCCGCCCATTCGCCGCCCAGTTCTTCCGCAATATCACGGGTGGCC
AGCGCAATATCCTGATAACGATCCGCCACGCCCAGACGGCCGCAATCAATAAAGCCGCTAAAACGGCCATTTTCC
ACCATAATGTTCGGCAGGCACGCATCACCATGGGTCACCACCAGATCTTCGCCATCCGGCATGCTCGCTTTCAGA
CGCGCAAACAGCTCTGCCGGTGCCAGGCCCTGATGTTCTTCATCCAGATCATCCTGATCCACCAGGCCCGCTTCC
ATACGGGTACGCGCACGTTCAATACGATGTTTCGCCTGATGATCAAACGGACAGGTCGCCGGGTCCAGGGTATGC
AGACGACGCATGGCATCCGCCATAATGCTCACTTTTTCTGCCGGCGCCAGATGGCTAGACAGCAGATCCTGACCC
GGCACTTCGCCCAGCAGCAGCCAATCACGGCCCGCTTCGGTCACCACATCCAGCACCGCCGCACACGGAACACCG
GTGGTGGCCAGCCAGCTCAGACGCGCCGCTTCATCCTGCAGCTCGTTCAGCGCACCGCTCAGATCGGTTTTCACA
AACAGCACCGGACGACCCTGCGCGCTCAGACGAAACACCGCCGCATCAGAGCAGCCAATGGTCTGCTGCGCCCAA
TCATAGCCAAACAGACGTTCCACCCACGCTGCCGGGCTACCCGCATGCAGGCCATCCTGTTCAATCATACTCTTC
CTTTTTCAATATTATTGAAGCATTTATCAGGGTTATTGTCTCATGAGCGGATACATATTTGAATGTATTTAGAAA
AATAAACAAATAGGGGTTCCGCGCACATTTCCCCGAAAAGTGCCACCTAAATTGTAAGCGTTAATATTTTGTTAA
AATTCGCGTTAAATTTTTGTTAAATCAGCTCATTTTTTAACCAATAGGCCGAAATCGGCAAAATCCCTTATAAAT
CAAAAGAATAGACCGAGATAGGGTTGAGTGGCCGCTACAGGGCGCTCCCATTCGCCATTCAGGCTGCGCAACTGT
TGGGAAGGGCGTTTCGGTGCGGGCCTCTTCGCTATTACGCCAGCTGGCGAAAGGGGGATGTGCTGCAAGGCGATT
AAGTTGGGTAACGCCAGGGTTTTCCCAGTCACACGCGTAATACGACTCACTATAG

A531 Vector: SGP-gHsol-SGP-gL (SEQ ID NO: 58):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT -continued

| SEQUENCES |
| --- |
| GTGCGGAAGATCCGGACAGATTGTATAAGTATGCAACTAAGCTGAAGAAAAACTGTAAGGAAATAACTGATAAGG |
| AATTGGACAAGAAAATGAAGGAGCTCGCCGCCGTCATGAGCGACCCTGACCTGGAAACTGAGACTATGTGCCTCC |
| ACGACGACGAGTCGTGTCGCTACGAAGGGCAAGTCGCTGTTTACCAGGATGTATACGCGGTTGACGGACCGACAA |
| GTCTCTATCACCAAGCCAATAAGGGAGTTAGAGTCGCCTACTGGATAGGCTTTGACACCACCCCTTTTATGTTTA |
| AGAACTTGGCTGGAGCATATCCATCATACTCTACCAACTGGGCCGACGAAACCGTGTTAACGGCTCGTAACATAG |
| GCCTATGCAGCTCTGACGTTATGGAGCGGTCACGTAGAGGGATGTCCATTCTTAGAAAGAAGTATTTGAAACCAT |
| CCAACAATGTTCTATTCTCTGTTGGCTCGACCATCTACCACGAGAAGAGGGACTTACTGAGGAGCTGGCACCTGC |
| CGTCTGTATTTCACTTACGTGGCAAGCAAAATTACACATGTCGGTGTGAGACTATAGTTAGTTGCGACGGGTACG |
| TCGTTAAAAGAATAGCTATCAGTCCAGGCCTGTATGGGAAGCCTTCAGGCTATGCTGCTACGATGCACCGCGAGG |
| GATTCTTGTGCTGCAAAGTGACAGACACATTGAACGGGGAGAGGGTCTCTTTTCCCGTGTGCACGTATGTGCCAG |
| CTACATTGTGTGACCAAATGACTGGCATACTGGCAACAGATGTCAGTGCGGACGACGCGCAAAAACTGCTGGTTG |
| GGCTCAACCAGCGTATAGTCGTCAACGGTCGCACCCAGAGAAACACCAATACCATGAAAAATTACCTTTTGCCCG |
| TAGTGGCCCAGGCATTTGCTAGGTGGGCAAAGGAATATAAGGAAGATCAAGAAGATGAAAGGCCACTAGGACTAC |
| GAGATAGACAGTTAGTCATGGGGTGTTGTTGGGCTTTTAGAAGGCACAAGATAACATCTATTTATAAGCGCCCGG |
| ATACCCAAACCATCATCAAAGTGAACAGCGATTTCCACTCATTCGTGCTGCCCAGGATAGGCAGTAACACATTGG |
| AGATCGGGCTGAGAACAAGAATCAGGAAAATGTTAGAGGAGCACAAGGAGCCGTCACCTCTCATTACCGCCGAGG |
| ACGTACAAGAAGCTAAGTGCGCAGCCGATGAGGCTAAGGAGGTGCGTGAAGCCGAGGAGTTGCGCGCAGCTCTAC |
| CACCTTTGGCAGCTGATGTTGAGGAGCCCACTCTGGAAGCCGATGTCGACTTGATGTTACAAGAGGCTGGGGCCG |
| GCTCAGTGGAGACACCTCGTGGCTTGATAAAGGTTACCAGCTACGATGGCGAGGACAAGATCGGCTCTTACGCTG |
| TGCTTTCTCCGCAGGCTGTACTCAAGAGTGAAAAATTATCTTGCATCCACCCTCTCGCTGAACAAGTCATAGTGA |
| TAACACACTCTGGCCGAAAAGGGCGTTATGCCGTGGAACCATACCATGGTAAAGTAGTGGTGCCAGAGGGACATG |
| CAATACCCGTCCAGGACTTTCAAGCTCTGAGTGAAAGTGCCACCATTGTGTACAACGAACGTGAGTTCGTAAACA |
| GGTACCTGCACCATATTGCCACACATGGAGGAGCGCTGAACACTGATGAAGAATATTACAAAACTGTCAAGCCCA |
| GCGAGCACGACGGCGAATACCTGTACGACATCGACAGGAAACAGTGCGTCAAGAAAGAACTAGTCACTGGGCTAG |
| GGCTCACAGGCGAGCTGGTGGATCCTCCCTTCCATGAATTCGCCTACGAGAGTCTGAGAACACGACCAGCCGCTC |
| CTTACCAAGTACCAACCATAGGGGTGTATGGCGTGCCAGGATCAGGCAAGTCTGGCATCATTAAAAGCGCAGTCA |
| CCAAAAAAGATCTAGTGGTGAGCGCCAAGAAAGAAAACTGTGCAGAAATTATAAGGGACGTCAAGAAAATGAAAG |
| GGCTGGACGTCAATGCCAGAACTGTGGACTCAGTGCTCTTGAATGGATGCAAACACCCCGTAGAGACCCTGTATA |
| TTGACGAAGCTTTTGCTTGTCATGCAGGTACTCTCAGAGCGCTCATAGCCATTATAAGACCTAAAAAGGCAGTGC |
| TCTGCGGGGATCCCAAACAGTGCGGTTTTTTAACATGATGTGCCTGAAAGTGCATTTTAACCACGAGATTTGCA |
| CACAAGTCTTCCACAAAAGCATCTCTCGCCGTTGCACTAAATCTGTGACTTCGGTCGTCTCAACCTTGTTTTACG |
| ACAAAAAAATGAGAACGACGAATCCGAAAGAGACTAAGATTGTGATTGACACTACCGGCAGTACCAAACCTAAGC |
| AGGACGATCTCATTCTCACTTGTTTCAGAGGGTGGGTGAAGCAGTTGCAAATAGATTACAAAGGCAACGAAATAA |
| TGACGGCAGCTGCCTCTCAAGGGCTGACCCGTAAAGGTGTGTATGCCGTTCGGTACAAGGTGAATGAAAATCCTC |
| TGTACGCACCCACCTCAGAACATGTGAACGTCCTACTGACCCGCACGGAGGACCGCATCGTGTGGAAAACACTAG |
| CCGGCGACCCATGGATAAAAACACTGACTGCCAAGTACCCTGGGAATTTCACTGCCACGATAGAGGAGTGGCAAG |
| CAGAGCATGATGCCATCATGAGGCACATCTTGGAGAGACCGGACCCTACCGACGTCTTCCAGAATAAGGCAAACG |
| TGTGTTGGGCCAAGGCTTTAGTGCCGGTGCTGAAGACCGCTGGCATAGACATGACCACTGAACAATGGAACACTG |
| TGGATTATTTTGAAACGGACAAAGCTCACTCAGCAGAGATAGTATTGAACCAACTATGCGTGAGGTTCTTTGGAC |
| TCGATCTGGACTCCGGTCTATTTTCTGCACCCACTGTTCCGTTATCCATTAGGAATAATCACTGGGATAACTCCC |
| CGTCGCCTAACATGTACGGGCTGAATAAAGAAGTGGTCCGTCAGCTCTCTCGCAGGTACCCACAACTGCCTCGGG |
| CAGTTGCCACTGGAAGAGTCTATGACATGAACACTGGTACACTGCGCAATTATGATCCGCGCATAAACCTAGTAC |
| CTGTAAACAGAAGACTGCCTCATGCTTTAGTCCTCCACCATAATGAACACCCACAGAGTGACTTTTCTTCATTCG |
| TCAGCAAATTGAAGGGCAGAACTGTCCTGGTGGTCGGGGAAAAGTTGTCCGTCCCAGGCAAAATGGTTGACTGGT |
| TGTCAGACCGGCCTGAGGCTACCTTCAGAGCTCGGCTGGATTTAGGCATCCCAGGTGATGTGCCCAAATATGACA |
| TAATATTTGTTAATGTGAGGACCCCATATAAATACCATCACTATCAGCAGTGTGAAGACCATGCCATTAAGCTTA |
| GCATGTTGACCAAGAAAGCTTGTCTGCATCTGAATCCCGGCGGAACCTGTGTCAGCATAGGTTATGGTTACGCTG |
| ACAGGGCCAGCGAAAGCATCATTGGTGCTATAGCGCGGCAGTTCAAGTTTTCCCGGGTATGCAAACCGAAATCCT |
| CACTTGAAGAGACGGAAGTTCTGTTTGTATTCATTGGGTACGATCGCAAGGCCCGTACGCACAATCCTTACAAGC |
| TTTCATCAACCTTGACCAACATTTATACAGGTTCCAGACTCCACGAAGCCGGATGTGCACCCTCATATCATGTGG |
| TGCGAGGGGATATTGCCACGGCCACCGAAGGAGTGATTATAAATGCTGCTAACAGCAAAGGACAACCTGGCGGAG |
| GGGTGTGCGGAGCGCTGTATAAGAAATTCCCGGAAAGCTTCGATTTACAGCCGATCGAAGTAGGAAAAGCGCGAC |
| TGGTCAAAGGTGCAGCTAAACATATCATTCATGCCGTAGGACCAAACTTCAACAAAGTTTCGGAGGTTGAAGGTG |
| ACAAACAGTTGGCAGAGGCTTATGAGTCCATCGCTAAGATTGTCAACGATAACAATTACAAGTCAGTAGCGATTC |
| CACTGTTGTCCACCGGCATCTTTTCCGGGAACAAAGATCGACTAACCCAATCATTGAACCATTTGCTGACAGCTT |
| TAGACACCACTGATGCAGATGTAGCCATATACTGCAGGGACAAGAAATGGGAAATGACTCTCAAGGAAGCAGTGG |
| CTAGGAGAGAAGCAGTGGAGGAGATATGCATATCCGACGACTCTTCAGTGACAGAACCTGATGCAGAGCTGGTGA |
| GGGTGCATCCGAAGAGTTCTTTGGCTGGAAGGAAGGGCTACAGCACAAGCGATGGCAAAACTTTCTCATATTTGG |
| AAGGGACCAAGTTTCACCAGGCGGCCAAGGATATAGCAGAAATTAATGCCATGTGGCCCGTTGCAACGGAGGCCA |
| ATGAGCAGGTATGCATGTATATCCTCGGAGAAAGCATGAGCAGTATTAGGTCGAAATGCCCCGTCGAAGAGTCGG |
| AAGCCTCCACACCACCTAGCACGCTGCCTTGCTTGTGCATCCATGCCATGACTCCAGAAAGAGTACAGCGCCTAA |
| AAGCCTCACGTCCAGAACAAATTACTGTGTGCTCATCCTTTCCATTGCCGAAGTATAGAATCACTGGTGTGCAGA |
| AGATCCAATGCTCCCAGCCTATATTGTTCTCACCGAAAGTGCCTGCGTATATTCATCCAAGGAAGTATCTCGTGG |
| AAACACCACCGGTAGACGAGACTCCGGAGCCATCGGCAGAGAACCAATCCACAGAGGGGACACCTGAACAACCAC |
| CACTTATAACCGAGGATGAGACCAGGACTAGAACGCCTGAGCCGATCATCATCGAAGAGGAAGAAGAGGATAGCA |
| TAAGTTTGCTGTCAGATGGCCCGACCCACCAGGTGCTGCAAGTCGAGGCAGACATTCACGGGCCGCCCTCTGTAT |
| CTAGCTCATCCTGGTCCATTCCTCATGCATCCGACTTTGATGTGGACAGTTTATCCATACTTGACACCCTGGAGG |
| GAGCTAGCGTGACCAGCGGGGCAACGTCAGCCGAGACTAACTCTTACTTCGCAAAGAGTATGGAGTTTCTGGCGC |
| GACCGGTGCCTGCGCCTCGAACAGTATTCAGGAACCCTCCACATCCCGCTCCGCGCACAAGAACACCGTCACTTG |
| CACCCAGCAGGGCCTGCTCGAGAACCAGCCTAGTTTCCACCCCGCCAGGCGTGAATAGGGTGATCACTAGAGAGG |
| AGCTCGAGGCGCTTACCCCGTCACGCACTCCTAGCAGGTCGGTCTCGAGAACCAGCCTGGTCTCCAACCCGCCAG |
| GCGTAAATAGGGTGATTACAAGAGAGGAGTTTGAGGCGTTCGTAGCACAACAACAATGACGGTTTGATGCGGGTG |
| CATACATCTTTTCCTCCGACACCGGTCAAGGGCATTTACAACAAAAATCAGTAAGGCAAACGGTGCTATCCGAAG |
| TGGTGTTGGAGAGGACCGAATTGGAGATTTCGTATGCCCCGCGCCTCGACCAAGAAAAAGAAGAATTACTACGCA |
| AGAAATTACAGTTAAATCCCACACCTGCTAACAGAAGCAGATACCAGTCCAGGAAGGTGGAGAACATGAAAGCCA |
| TAACAGCTAGACGTATTCTGCAAGGCCTAGGGCATTATTTGAAGGCAGAAGGAAAAGTGGAGTGCTACCGAACCC |
| TGCATCCTGTTCCTTTGTATTCATCTAGTGTGAACCGTGCCTTTTCAAGCCCCAAGGTCGCAGTGGAAGCCTGTA |

-continued

| SEQUENCES |
|---|

ACGCCATGTTGAAAGAGAACTTTCCGACTGTGGCTTCTTACTGTATTATTCCAGAGTACGATGCCTATTTGGACA
TGGTTGACGGAGCTTCATGCTGCTTAGACACTGCCAGTTTTTGCCCTGCAAAGCTGCGCAGCTTTCCAAAGAAAC
ACTCCTATTTGGAACCCACAATACGATCGGCAGTGCCTTCAGCGATCCAGAACACGCTCCAGAACGTCCTGGCAG
CTGCCACAAAAAGAAATTGCAATGTCACGCAAATGAGAGAATTGCCCGTATTGGATTCGGCGGCCTTTAATGTGG
AATGCTTCAAGAAATATGCGTGTAATAATGAATATTGGGAAACGTTTAAAGAAAACCCCATCAGGCTTACTGAAG
AAAACGTGGTAAATTACATTACCAAATTAAAAGGACCAAAAGCTGCTGCTCTTTTTGCGAAGACACATAATTTGA
ATATGTTGCAGGACATACCAATGGACAGGTTTGTAATGGACTTAAAGAGAGACGTGAAAGTGACTCCAGGAACAA
AACATACTGAAGAACGGCCCAAGGTACAGGTGATCCAGGCTGCCGATCCGCTAGCAACAGCGTATCTGTGCGGAA
TCCACCGAGAGCTGGTTAGGAGATTAAATGCGGTCCTGCTTCCGAACATTCATACACTGTTTGATATGTCGGCTG
AAGACTTTGACGCTATTATAGCCGAGCACTTCCAGCCTGGGGATTGTGTTCTGGAAACTGACATCGCGTCGTTTG
ATAAAAGTGAGGACGACGCCATGGCTCTGACCGCGTTAATGATTCTGGAAGACTTAGGTGTGGACGCAGAGCTGT
TGACGCTGATTGAGGCGGCTTTCGGCGAAATTTCATCAATACATTTGCCCACTAAAACTAAATTTAAATTCGGAG
CCATGATGAAATCTGGAATGTTCCTCACACTGTTTGTGAACACAGTCATTAACATTGTAATCGCAAGCAGAGTGT
TGAGAGAACGGCTAACCGGATCACCATGTGCAGCATTCATTGGAGATGACAATATCGTGAAAGGAGTCAAATCGG
ACAAATTAATGGCAGACAGGTGCGCCACCTGGTTGAATATGGAAGTCAAGATTATAGATGCTGTGGTGGGCGAGA
AAGCGCCTTATTTCTGTGGAGGGTTTATTTTGTGTGACTCCGTGACCGGCACAGCGTGCCGTGTGGCAGACCCCC
TAAAAAGGCTGTTTAAGCTTGGCAAACCTCTGGCAGCAGACGATGAACATGATGATGACAGGAGAAGGGCATTGC
ATGAAGAGTCAACACGCTGGAACCGAGTGGGTATTCTTTCAGAGCTGTGCAAGGCAGTAGAATCAAGGTATGAAA
CCGTAGGAACTTCCATCATAGTTATGGCCATGACTACTCTAGCTAGCAGTGTTAAATCATTCAGCTACCTGAGAG
GGGCCCCTATAACTCTCTACGGCTAACCTGAATGGACTACGACATAGTCTAGTCCGCCAAGATGAGGCCTGGCCT
GCCCTCCTACCTGATCATCCTGGCCGTGTGCCTGTTCAGCCACCTGCTGTCCAGCAGATACGGCGCCGAGGCCGT
GAGCGAGCCCCTGGACAAGGCTTTCCACCTGCTGCTGAACACCTACGGCAGACCCATCCGGTTTCTGCGGGAGAA
CACCACCCAGTGCACCTACAACAGCAGCCTGCGGAACAGCACCGTCGTGAGAGAGAACGCCATCAGCTTCAACTT
TTTCCAGAGCTACAACCAGTACTACGTGTTCCACATGCCCAGATGCCTGTTTGCCGGCCCTCTGGCCGAGCAGTT
CCTGAACCAGGTGGACCTGACCGAGACACTGGAAAGATACCAGCAGCGGCTGAATACCTACGCCCTGGTGTCCAA
GGACCTGGCCAGCTACCGGTCCTTTAGCCAGCAGCTCAAGGCTCAGGATAGCCTCGGCGAGCAGCCTACCACCGT
GCCCCCTCCCATCGACCTGAGCATCCCCCACGTGTGGATGCCTCCCCAGACCACCCCTCACGGCTGGACCGAGAG
CCACACCACCTCCGGCCTGCACAGACCCCACTTCAACCAGACCTGCATCCTGTTCGACGGCCACGACCTGCTGTT
TAGCACCGTGACCCCCTGCCTGCACCAGGGCTTCTACCTGATCGACGAGCTGAGATACGTGAAGATCACCCTGAC
CGAGGATTTCTTCGTGGTCACCGTGTCCATCGACGACGACACCCCCATGCTGCTGATCTTCGGCCACCTGCCCAG
AGTGCTGTTCAAGGCCCCCTACCAGCGGGACAACTTCATCCTGCGGCAGACCGAGAAGCACGAGCTGCTGGTGCT
GGTCAAGAAGGACCAGCTGAACCGGCACTCCTACCTGAAGGACCCCGACTTCCTGGACGCCGCCCTGGACTTCAA
CTACCTGGACCTGAGCGCCCTGCTGAGAAACAGCTTCCACAGATACGCCGTGGACGTGCTGAAGTCCGGACGGTG
CCAGATGCTCGATCGGCGGACCGTGGAGATGGCCTTCGCCTATGCCCTCGCCCTGTTCGCCGCTGCCAGACAGGA
AGAGGCTGGCGCCCAGGTGTCAGTGCCCAGAGCCCTGGATAGACAGGCCGCCCTGCTGCAGATCCAGGAATTCAT
GATCACCTGCCTGAGCCAGACCCCCCCTAGAACCACCCTGCTGCTGTACCCCACAGCCGTGGATCTGGCCAAGAG
GGCCCTGTGGACCCCCAACCAGATCACCGACATCACAAGCCTCGTGCGGCTCGTGTACATCCTGAGCAAGCAGAA
CCAGCAGCACCTGATCCCCCAGTGGGCCCTGAGACAGATCGCCGACTTCGCCCTGAAGCTGCACAAGACCCATCT
GGCCAGCTTTCTGAGCGCCTTCGCCAGGCAGGAACTGTACCTGATGGGCAGCCTGGTCCACAGCATGCTGGTGCA
TACCACCGAGCGGCGGGAGATCTTCATCGTGGAGACAGGCCTGTGTAGCCTGGCCGAGCTGTCCCACTTTACCCA
GCTGCTGGCCCACCCTCACCACGAGTACCTGAGCGACCTGTACACCCCCTGCAGCAGCAGCGGCAGACGGGACCA
CAGCCTGGAACGGCTGACCAGACTGTTCCCCGATGCCACCGTGCCTGCTACAGTGCCTGCCGCCCTGTCCATCCT
GTCCACCATGCAGCCCAGCACCCTGGAAACCTTCCCCGACCTGTTCTGCCTGCCCCTGGGCGAGAGCTTTAGCGC
CCTGACCGTGTCCGAGCACGTGTCCTACATCGTGACCAATCAGTACCTGATCAAGGGCATCAGCTACCCCGTGTC
CACCACAGTCGTGGGCCAGAGCCTGATCATCACCCAGACCGACAGCCAGACCAAGTGCGAGCTGACCCGGAACAT
GCACACCACACACAGCATCACCGTGGCCCTGAACATCAGCCTGGAAAACTGCGCTTTCTGTCAGTCTGCCCTGCT
GGAATACGACGATACCCAGGGCGTGATCAACATCATGTACATGCACGACAGCGACGACGTGCTGTTCGCCCTGGA
CCCCTACAACGAGGTGGTGGTGTCCAGCCCCCGGACCCACTACCTGATGCTGCTGAAGAACGGCACCGTGCTGGA
AGTGACCGACGTGGTGGTGGACGCCACCGACGATAATCTAGAGGCCCCTATAACTCTCTACGGCTAACCTGAAT
GGACTACGACATAGTCTAGTCCGCCAAGATGTGCAGAAGGCCCGACTGCGGCTTCAGCTTCAGCCCTGGACCCGT
GATCCTGCTGTGGTGCTGCCTGCTGCTGCCTATCGTGTCCTCTGCCGCCGTGTCTGTGGCCCCTACAGCCGCCGA
GAAGGTGCCAGCCGAGTGCCCCGAGCTGACCAGAAGATGCCTGCTGGGCGAGGTGTTCGAGGGCGACAAGTACGA
GAGCTGGCTGCGGCCCCTGGTCAACGTGACCGGCAGAGATGGCCCCCTGAGCCAGCTGATCCGGTACAGACCCGT
GACCCCCGAGGCCGCCAATAGCGTGCTGCTGGACGAGGCCTTCCTGGATACCCTGGCCCTGCTGTACAACAACCC
CGACCAGCTGAGAGCCCTGCTGACCCTGCTGTCCAGCGACACCGCCCCCAGATGGATGACCGTGATGCGGGGCTA
CAGCGAGTGTGGAGATGGCAGCCCTGCCGTGTACACCTGCGTGGACGACCTGTGCAGAGGCTACGACCTGACCAG
ACTGAGCTACGGCCGGTCCATCTTCACAGAGCACGTGCTGGGCTTCGAGCTGGTGCCCCCCAGCCTGTTCAACGT
GGTGGTGGCCATCCGGAACGAGGCCACCAGAACCAACAGAGCCGTGCGGCTGCCTGTGTCTACAGCCGCTGCACC
TGAGGGCATCACACTGTTCTACGGCCTGTACAACGCCGTGAAAGAGTTCTGCCTCCGGCACCAGCTGGATCCCCC
CCTGCTGAGACACCTGGACAAGTACTACGCCGGCCTGCCCCCAGAGCTGAAGCAGACCAGAGTGAACCTGCCCGC
CCACAGCAGATATGGCCCTCAGGCCGTGGACGCCAGATGATAAGCGGCCGCATACAGCAGCAATTGGCAAGCTGC
TTACATAGAACTCGCGGCGATTGGCATGCCGCCTTAAAATTTTTATTTTATTTTTCTTTTCTTTTCCGAATCGGA
TTTTGTTTTTAATATTTCAAAAAAAAAAAAAAAAAAAAAAAAAAAAAAAAAAAAAAAGGGTCGGCATGGCATCTCCACC
TCCTCGCGGTCCGACCTGGGCATCCGAAGGAGGACGCACGTCCACTCGGATGGCTAAGGGAGAGCCACGTTTAAA
CACGTGATATCTGGCCTCATGGGCCTTCCTTTCACTGCCCGCTTTCCAGTCGGGAAACCTGTCGTGCCAGCTGCA
TTAACATGGTCATAGCTGTTTCCTTGCGTATTGGGCGCTCTCCGCTTCCTCGCTCACTGACTCGCTGCGCTCGGT
CGTTCGGGTAAAGCCTGGGGTGCCTAATGAGCAAAAGGCCAGCAAAAGGCCAGGAACCGTAAAAAGGCCGCGTTG
CTGGCGTTTTTCCATAGGCTCCGCCCCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTTTCTCATAGCTCACGCTGTAGGTATCTC
AGTTCGGTGTAGGTCGTTCGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCTAACTACGGCTACACTAGAAGA
ACAGTATTTGGTATCTGCGCTCTGCTGAAGCCAGTTACCTTCGGAAAAAGAGTTGGTAGCTCTTGATCCGGCAAA
CAAACCACCGCTGGTAGCGGTGGTTTTTTTGTTTGCAAGCAGCAGATTACGCGCAGAAAAAAAGGATCTCAAGAA
GATCCTTTGATCTTTTCTACGGGGTCTGACGCTCAGTGGAACGAAAACTCACGTTAAGGGATTTGGTCATGAGA
TTATCAAAAAGGATCTTCACCTAGATCCTTTTAAATTAAAAATGAAGTTTTAAATCAATCTAAAGTATATATGAG

-continued

| SEQUENCES |
|---|

TAAACTTGGTCTGACAGTTATTAGAAAAATTCATCCAGCAGACGATAAAACGCAATACGCTGGCTATCCGGTGCC
GCAATGCCATACAGCACCAGAAAACGATCCGCCCATTCGCCGCCCAGTTCTTCCGCAATATCACGGGTGGCCAGC
GCAATATCCTGATAACGATCCGCCACGCCCAGACGGCCGCAATCAATAAAGCCGCTAAAACGGCCATTTTCCACC
ATAATGTTCGGCAGGCACGCATCACCATGGGTCACCACCAGATCTTCGCCATCCGGCATGCTCGCTTTCAGACGC
GCAAACAGCTCTGCCGGTGCCAGGCCCTGATGTTCTTCATCCAGATCATCCTGATCCACCAGGCCCGCTTCCATA
CGGGTACGCGCACGTTCAATACGATGTTTCGCCTGATGATCAAACGGACAGGTCGCCGGGTCCAGGGTATGCAGA
CGACGCATGGCATCCGCCATAATGCTCACTTTTTCTGCCGGCGCCAGATGGCTAGACAGCAGATCCTGACCCGGC
ACTTCGCCCAGCAGCAGCCAATCACGGCCCGCTTCGGTCACCACATCCAGCACCGCCGCACACGGAACACCGGTG
GTGGCCAGCCAGCTCAGACGCGCCGCTTCATCCTGCAGCTCGTTCAGCGCACCGCTCAGATCGGTTTTCACAAAC
AGCACCGGACGACCCTGCGCGCTCAGACGAAACACCGCCGCATCAGAGCAGCCAATGGTCTGCTGCGCCCAATCA
TAGCCAAACAGACGTTCCACCCACGCTGCCGGGCTACCCGCATGCAGGCCATCCTGTTCAATCATACTCTTCCTT
TTTCAATATTATTGAAGCATTTATCAGGGTTATTGTCTCATGAGCGGATACATATTTGAATGTATTTAGAAAAAT
AAACAAATAGGGGTTCCGCGCACATTTCCCCGAAAAGTGCCACCTAAATTGTAAGCGTTAATATTTTGTTAAAAT
TCGCGTTAAATTTTTGTTAAATCAGCTCATTTTTTAACCAATAGGCCGAAATCGGCAAAATCCCTTATAAATCAA
AAGAATAGACCGAGATAGGGTTGAGTGGCCGCTACAGGGCGCTCCCATTCGCCATTCAGGCTGCGCAACTGTTGG
GAAGGGCGTTTCGGTGCGGGCCTCTTCGCTATTACGCCAGCTGGCGAAAGGGGGATGTGCTGCAAGGCGATTAAG
TTGGGTAACGCCAGGGTTTTCCCAGTCACACGCGTAATACGACTCACTATAG

A532 Vector: SGP-gHsol-2A-gL (SEQ ID NO: 59):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT
GTGCGGAAGATCCGGACAGATTGTATAAGTATGCAACTAAGCTGAAGAAAAACTGTAAGGAAATAACTGATAAGG
AATTGGACAAGAAAATGAAGGAGCTCGCCGCCGTCATGAGCGACCCTGACCTGGAAACTGAGACTATGTGCCTCC
ACGACGACGAGTCGTGTCGCTACGAAGGGCAAGTCGCTGTTTACCAGGATGTATACGCGGTTGACGGACCGACAA
GTCTCTATCACCAAGCCAATAAGGGAGTTAGAGTCGCCTACTGGATAGGCTTTGACACCACCCCTTTTATGTTTA
AGAACTTGGCTGGAGCATATCCATCATACTCTACCAACTGGGCCGACGAAACCGTGTTAACGGCTCGTAACATAG
GCCTATGCAGCTCTGACGTTATGGAGCGGTCACGTAGAGGGATGTCCATTCTTAGAAAGAAGTATTTGAAACCAT
CCAACAATGTTCTATTCTCTGTTGGCTCGACCATCTACCACGAGAAGAGGGACTTACTGAGGAGCTGGCACCTGC
CGTCTGTATTTCACTTACGTGGCAAGCAAAATTACACATGTCGGTGTGAGACTATAGTTAGTTGCGACGGGTACG
TCGTTAAAAGAATAGCTATCAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCGTGTGCACGTATGTGCCAG
CTACATTGTGTGACCAAATGACTGGCATACTGGCAACAGATGTCAGTGCGGACGACGCGCAAAAACTGCTGGTTG
GGCTCAACCAGCGTATAGTCGTCAACGGTCGCACCCAGAGAAACACCAATACCATGAAAAATTACCTTTTGCCCG
TAGTGGCCCAGGCATTTGCTAGGTGGGCAAAGGAATATAAGGAAGATCAAGAAGATGAAAGGCCACTAGGACTAC
GAGATAGACAGTTAGTCATGGGGTGTTGTTGGGCTTTTAGAAGGCACAAGATAACATCTATTTATAAGCGCCCGG
ATACCCAAACCATCATCAAAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCACCTCTCATTACCGCCGAGG
ACGTACAAGAAGCTAAGTGCGCAGCCGATGAGGCTAAGGAGGTGCGTGAAGCCGAGGAGTTGCGCGCAGCTCTAC
CACCTTTGGCAGCTGATGTTGAGGAGCCCACTCTGGAAGCCGATGTCGACTTGATGTTACAAGAGGCTGGGGCCG
GCTCAGTGGAGACACCTCGTGGCTTGATAAAGGTTACCAGCTACGATGGCGAGGACAAGATCGGCTCTTACGCTG
TGCTTTCTCCGCAGGCTGTACTCAAGAGTGAAAAATTATCTTGCATCCACCCTCTCGCTGAACAAGTCATAGTGA
TAACACACTCTGGCCGAAAAGGGCGTTATGCCGTGGAACCATACCATGGTAAAGTAGTGGTGCCAGAGGGACATG
CAATACCCGTCCAGGACTTTCAAGCTCTGAGTGAAAGTGCCACCATTGTGTACAACGAACGTGAGTTCGTAAACA
GGTACCTGCACCATATTGCCACACATGGAGGAGCGCTGAACACTGATGAAGAATATTACAAAACTGTCAAGCCCA
GCGAGCACGACGGCGAATACCTGTACGACATCGACAGGAAACAGTGCGTCAAGAAAGAACTAGTCACTGGGCTAG
GGCTCACAGGCGAGCTGGTGGATCCTCCCTTCCATGAATTCGCCTACGAGAGTCTGAGAACACGACCAGCCGCTC
CTTACCAAGTACCAACCATAGGGGTGTATGGCGTGCCAGGATCAGGCAAGTCTGGCATCATTAAAAGCGCAGTCA
CCAAAAAAGATCTAGTGGTGAGCGCCAAGAAAGAAAACTGTGCAGAAATTATAAGGGACGTCAAGAAAATGAAAG
GGCTGGACGTCAATGCCAGAACTGTGGACTCAGTGCTCTTGAATGGATGCAAACACCCCGTAGAGACCCTGTATA
TTGACGAAGCTTTTGCTTGTCATGCAGGTACTCTCAGAGCGCTCATAGCCATTATAAGACCTAAAAAGGCAGTGC
TCTGCGGGGATCCCAAACAGTGCGGTTTTTTTAACATGATGTGCCTGAAAGTGCATTTTAACCACGAGATTTGCA
CACAAGTCTTCCACAAAAGCATCTCTCGCCGTTGCACTAAATCTGTGACTTCGGTCGTCTCAACCTTGTTTTACG
ACAAAAAAATGAGAACGACGAATCCGAAAGAGACTAAGATTGTGATTGACACTACCGGCAGTACCAAACCTAAGC
AGGACGATCTCATTCTCACTTGTTTCAGAGGGTGGGTGAAGCAGTTGCAAATAGATTACAAAGGCAACGAAATAA
TGACGGCAGCTGCCTCTCAAGGGCTGACCCGTAAAGGTGTGTATGCCGTTCGGTACAAGGTGAATGAAAATCCTC
TGTACGCACCCACCTCAGAACATGTGAACGTCCTACTGACCCGCACGGAGGACCGCATCGTGTGGAAAACACTAG
CCGGCGACCCATGGATAAAAACACTGACTGCCAAGTACCCTGGGAATTTCACTGCCACGATAGAGGAGTGGCAAG
CAGAGCATGATGCCATCATGAGGCACATCTTGGAGAGACCGGACCCTACCGACGTCTTCCAGAATAAGGCAAACG
TGTGTTGGGCCAAGGCTTTAGTGCCGGTGCTGAAGACCGCTGGCATAGACATGACCACTGAACAATGGAACACTG
TGGATTATTTTGAAACGGACAAAGCTCACTCAGCAGAGATAGTATTGAACCAACTATGCGTGAGGTTCTTTGGAC
TCGATCTGGACTCCGGTCTATTTTCTGCACCCACTGTTCCGTTATCCATTAGGAATAATCACTGGGATAACTCCC
CGTCGCCTAACATGTACGGGCTGAATAAAGAAGTGGTCCGTCAGCTCTCTCGCAGGTACCCACAACTGCCTCGGG
CAGTTGCCACTGGAAGAGTCTATGACATGAACACTGGTACACTGCGCAATTATGATCCGCGCATAAACCTAGTAC
CTGTAAACAGAAGACTGCCTCATGCTTTAGTCCTCCACCATAATGAACACCCACAGAGTGACTTTTCTTCATTCG
TCAGCAAATTGAAGGGCAGAACTGTCCTGGTGGTCGGGGAAAAGTTGTCCGTCCCAGGCAAAATGGTTGACTGGT
TGTCAGACCGGCCTGAGGCTACCTTCAGAGCTCGGCTGGATTTAGGCATCCCAGGTGATGTGCCCAAATATGACA
TAATATTTGTTAATGTGAGGACCCCATATAAATACCATCACTATCAGCAGTGTGAAGACCATGCCATTAAGCTTA
GCATGTTGACCAAGAAAGCTTGTCTGCATCTGAATCCCGGCGGAACCTGTGTCAGCATAGGTTATGGTTACGCTG
ACAGGGCCAGCGAAAGCATCATTGGTGCTATAGCGCGGCAGTTCAAGTTTTCCCGGGTATGCAAACCGAAATCCT
CACTTGAAGAGACGGAAGTTCTGTTTGTATTCATTGGGTACGATCGCAAGGCCCGTACGCACAATCCTTACAAGC
TTTCATCAACCTTGACCAACATTTATACAGGTTCCAGACTCCACGAAGCCGGATGTGCACCCTCATATCATGTGG
TGCGAGGGGATATTGCCACGGCCACCGAAGGAGTGATTATAAATGCTGCTAACAGCAAAGGACAACCTGGCGGAG
GGGTGTGCGGAGCGCTGTATAAGAAATTCCCGGAAAGCTTCGATTTACAGCCGATCGAAGTAGGAAAAGCGCGAC
TGGTCAAAGGTGCAGCTAAACATATCATTCATGCCGTAGGACCAAACTTCAACAAAGTTTCGGAGGTTGAAGGTG
ACAAACAGTTGGCAGAGGCTTATGAGTCCATCGCTAAGATTGTCAACGATAACAATTACAAGTCAGTAGCGATTC -continued

SEQUENCES

CACTGTTGTCCACCGGCATCTTTTCCGGGAACAAAGATCGACTAACCCAATCATTGAACCATTTGCTGACAGCTT
TAGACACCACTGATGCAGATGTAGCCATATACTGCAGGGACAAGAAATGGGAAATGACTCTCAAGGAAGCAGTGG
CTAGGAGAGAAGCAGTGGAGGAGATATGCATATCCGACGACTCTTCAGTGACAGAACCTGATGCAGAGCTGGTGA
GGGTGCATCCGAAGAGTTCTTTGGCTGGAAGGAAGGGCTACAGCACAAGCGATGGCAAAACTTTCTCATATTTGG
AAGGGACCAAGTTTCACCAGGCGGCCAAGGATATAGCAGAAATTAATGCCATGTGGCCCGTTGCAACGGAGGCCA
ATGAGCAGGTATGCATGTATATCCTCGGAGAAAGCATGAGCAGTATTAGGTCGAAATGCCCCGTCGAAGAGTCGG
AAGCCTCCACACCACCTAGCACGCTGCCTTGCTTGTGCATCCATGCCATGACTCCAGAAAGAGTACAGCGCCTAA
AAGCCTCACGTCCAGAACAAATTACTGTGTGCTCATCCTTTCCATTGCCGAAGTATAGAATCACTGGTGTGCAGA
AGATCCAATGCTCCCAGCCTATATTGTTCTCACCGAAAGTGCCTGCGTATATTCATCCAAGGAAGTATCTCGTGG
AAACACCACCGGTAGACGAGACTCCGGAGCCATCGGCAGAGAACCAATCCACAGAGGGGACACCTGAACAACCAC
CACTTATAACCGAGGATGAGACCAGGACTAGAACGCCTGAGCCGATCATCATCGAAGAGGAAGAAGAGGATAGCA
TAAGTTTGCTGTCAGATGGCCCGACCCACCAGGTGCTGCAAGTCGAGGCAGACATTCACGGGCCGCCCTCTGTAT
CTAGCTCATCCTGGTCCATTCCTCATGCATCCGACTTTGATGTGGACAGTTTATCCATACTTGACACCCTGGAGG
GAGCTAGCGTGACCAGCGGGGCAACGTCAGCCGAGACTAACTCTTACTTCGCAAAGAGTATGGAGTTTCTGGCGC
GACCGGTGCCTGCGCCTCGAACAGTATTCAGGAACCCTCCACATCCCGCTCCGCGCACAAGAACACCGTCACTTG
CACCCAGCAGGGCCTGCTCGAGAACCAGCCTAGTTTCCACCCCGCCAGGCGTGAATAGGGTGATCACTAGAGAGG
AGCTCGAGGCGCTTACCCCGTCACGCACTCCTAGCAGGTCGGTCTCGAGAACCAGCCTGGTCTCCAACCCGCCAG
GCGTAAATAGGGTGATTACAAGAGAGGAGTTTGAGGCGTTCGTAGCACAACAACAATGACGGTTTGATGCGGGTG
CATACATCTTTTCCTCCGACACCGGTCAAGGGCATTTACAACAAAAATCAGTAAGGCAAACGGTGCTATCCGAAG
TGGTGTTGGAGAGGACCGAATTGGAGATTTCGTATGCCCCGCGCCTCGACCAAGAAAAAGAAGAATTACTACGCA
AGAAATTACAGTTAAATCCCACACCTGCTAACAGAAGCAGATACCAGTCCAGGAAGGTGGAGAACATGAAAGCCA
TAACAGCTAGACGTATTCTGCAAGGCCTAGGGCATTATTTGAAGGCAGAAGGAAAAGTGGAGTGCTACCGAACCC
TGCATCCTGTTCCTTTGTATTCATCTAGTGTGAACCGTGCCTTTTCAAGCCCCAAGGTCGCAGTGGAAGCCTGTA
ACGCCATGTTGAAAGAGAACTTTCCGACTGTGGCTTCTTACTGTATTATTCCAGAGTACGATGCCTATTTGGACA
TGGTTGACGGAGCTTCATGCTGCTTAGACACTGCCAGTTTTTGCCCTGCAAAGCTGCGCAGCTTTCCAAAGAAAC
ACTCCTATTTGGAACCCACAATACGATCGGCAGTGCCTTCAGCGATCCAGAACACGCTCCAGAACGTCCTGGCAG
CTGCCACAAAAAGAAATTGCAATGTCACGCAAATGAGAGAATTGCCCGTATTGGATTCGGCGGCCTTTAATGTGG
AATGCTTCAAGAAATATGCGTGTAATAATGAATATTGGGAAACGTTTAAAGAAAACCCCATCAGGCTTACTGAAG
AAAACGTGGTAAATTACATTACCAAATTAAAAGGACCAAAAGCTGCTGCTCTTTTTGCGAAGACACATAATTTGA
ATATGTTGCAGGACATACCAATGGACAGGTTTGTAATGGACTTAAAGAGAGACGTGAAAGTGACTCCAGGAACAA
AACATACTGAAGAACGGCCCAAGGTACAGGTGATCCAGGCTGCCGATCCGCTAGCAACAGCGTATCTGTGCGGAA
TCCACCGAGAGCTGGTTAGGAGATTAAATGCGGTCCTGCTTCCGAACATTCATACACTGTTTGATATGTCGGCTG
AAGACTTTGACGCTATTATAGCCGAGCACTTCCAGCCTGGGGATTGTGTTCTGGAAACTGACATCGCGTCGTTTG
ATAAAAGTGAGGACGACGCCATGGCTCTGACCGCGTTAATGATTCTGGAAGACTTAGGTGTGGACGCAGAGCTGT
TGACGCTGATTGAGGCGGCTTTCGGCGAAATTTCATCAATACATTTGCCCACTAAAACTAAATTTAAATTCGGAG
CCATGATGAAATCTGGAATGTTCCTCACACTGTTTGTGAACACAGTCATTAACATTGTAATCGCAAGCAGAGTGT
TGAGAGAACGGCTAACCGGATCACCATGTGCAGCATTCATTGGAGATGACAATATCGTGAAAGGAGTCAAATCGG
ACAAATTAATGGCAGACAGGTGCGCCACCTGGTTGAATATGGAAGTCAAGATTATAGATGCTGTGGTGGGCGAGA
AAGCGCCTTATTTCTGTGGAGGGTTTATTTTGTGTGACTCCGTGACCGGCACAGCGTGCCGTGTGGCAGACCCCC
TAAAAAGGCTGTTTAAGCTTGGCAAACCTCTGGCAGCAGACGATGAACATGATGATGACAGGAGAAGGGCATTGC
ATGAAGAGTCAACACGCTGGAACCGAGTGGGTATTCTTTCAGAGCTGTGCAAGGCAGTAGAATCAAGGTATGAAA
CCGTAGGAACTTCCATCATAGTTATGGCCATGACTACTCTAGCTAGCAGTGTTAAATCATTCAGCTACCTGAGAG
GGGCCCCTATAACTCTCTACGGCTAACCTGAATGGACTACGACATAGTCTAGTCCGCCAAGATGAGGCCTGGCCT
GCCCTCCTACCTGATCATCCTGGCCGTGTGCCTGTTCAGCCACCTGCTGTCCAGCAGATACGGCGCCGAGGCCGT
GAGCGAGCCCCTGGACAAGGCTTTCCACCTGCTGCTGAACACCTACGGCAGACCCATCCGGTTTCTGCGGGAGAA
CACCACCCAGTGCACCTACAACAGCAGCCTGCGGAACAGCACCGTCGTGAGAGAGAACGCCATCAGCTTCAACTT
TTTCCAGAGCTACAACCAGTACTACGTGTTCCACATGCCCAGATGCCTGTTTGCCGGCCCTCTGGCCGAGCAGTT
CCTGAACCAGGTGGACCTGACCGAGACACTGGAAAGATACCAGCAGCGGCTGAATACCTACGCCCTGGTGTCCAA
GGACCTGGCCAGCTACCGGTCCTTTAGCCAGCAGCTCAAGGCTCAGGATAGCCTCGGCGAGCAGCCTACCACCGT
GCCCCCTCCCATCGACCTGAGCATCCCCCACGTGTGGATGCCTCCCCAGACCACCCCTCACGGCTGGACCGAGAG
CCACACCACCTCCGGCCTGCACAGACCCCACTTCAACCAGACCTGCATCCTGTTCGACGGCCACGACCTGCTGTT
TAGCACCGTGACCCCCTGCCTGCACCAGGGCTTCTACCTGATCGACGAGCTGAGATACGTGAAGATCACCCTGAC
CGAGGATTTCTTCGTGGTCACCGTGTCCATCGACGACGACACCCCCATGCTGCTGATCTTCGGCCACCTGCCCAG
AGTGCTGTTCAAGGCCCCCTACCAGCGGGACAACTTCATCCTGCGGCAGACCGAGAAGCACGAGCTGCTGGTGCT
GGTCAAGAAGGACCAGCTGAACCGGCACTCCTACCTGAAGGACCCCGACTTCCTGGACGCCGCCCTGGACTTCAA
CTACCTGGACCTGAGCGCCCTGCTGAGAAACAGCTTCCACAGATACGCCGTGGACGTGCTGAAGTCCGGACGGTG
CCAGATGCTCGATCGGCGGACCGTGGAGATGGCCTTCGCCTATGCCCTCGCCCTGTTCGCCGCTGCCAGACAGGA
AGAGGCTGGCGCCCAGGTGTCAGTGCCCAGAGCCCTGGATAGACAGGCCGCCCTGCTGCAGATCCAGGAATTCAT
GATCACCTGCCTGAGCCAGACCCCCCCTAGAACCACCCTGCTGCTGTACCCCACAGCCGTGGATCTGGCCAAGAG
GGCCCTGTGGACCCCCAACCAGATCACCGACATCACAAGCCTCGTGCGGCTCGTGTACATCCTGAGCAAGCAGAA
CCAGCAGCACCTGATCCCCCAGTGGGCCCTGAGACAGATCGCCGACTTCGCCCTGAAGCTGCACAAGACCCATCT
GGCCAGCTTTCTGAGCGCCTTCGCCAGGCAGGAACTGTACCTGATGGGCAGCCTGGTCCACAGCATGCTGGTGCA
TACCACCGAGCGGCGGGAGATCTTCATCGTGGAGACAGGCCTGTGTAGCCTGGCCGAGCTGTCCCACTTTACCCA
GCTGCTGGCCCACCCTCACCACGAGTACCTGAGCGACCTGTACACCCCCTGCAGCAGCAGCGGCAGACGGGACCA
CAGCCTGGAACGGCTGACCAGACTGTTCCCCGATGCCACCGTGCCTGCTACAGTGCCTGCCGCCCTGTCCATCCT
GTCCACCATGCAGCCCAGCACCCTGGAAACCTTCCCCGACCTGTTCTGCCTGCCCCTGGGCGAGAGCTTTAGCGC
CCTGACCGTGTCCGAGCACGTGTCCTACATCGTGACCAATCAGTACCTGATCAAGGGCATCAGCTACCCCGTGTC
CACCACAGTCGTGGGCCAGAGCCTGATCATCACCCAGACCGACAGCCAGACCAAGTGCGAGCTGACCCGGAACAT
GCACACCACACACAGCATCACCGTGGCCCTGAACATCAGCCTGGAAAACTGCGCTTTCTGTCAGTCTGCCCTGCT
GGAATACGACGATACCCAGGGCGTGATCAACATCATGTACATGCACGACAGCGACGACGTGCTGTTCGCCCTGGA
CCCCTACAACGAGGTGGTGGTGTCCAGCCCCCGGACCCACTACCTGATGCTGCTGAAGAACGGCACCGTGCTGGA
AGTGACCGACGTGGTGGTGGACGCCACCGACCTGTTGAATTTTGACCTTCTTAAGCTTGCGGGAGACGTCGAGTC
CAACCCCGGGCCCATGTGCAGAAGGCCCGACTGCGGCTTCAGCTTCAGCCCTGGACCCGTGATCCTGCTGTGGTG
CTGCCTGCTGCTGCCTATCGTGTCCTCTGCCGCCGTGTCTGTGGCCCCTACAGCCGCCGAGAAGGTGCCAGCCGA
GTGCCCCGAGCTGACCAGAAGATGCCTGCTGGGCGAGGTGTTCGAGGGCGACAAGTACGAGAGCTGGCTGCGGCC
CCTGGTCAACGTGACCGGCAGAGATGGCCCCCTGAGCCAGCTGATCCGGTACAGACCCGTGACCCCCGAGGCCGC
CAATAGCGTGCTGCTGGACGAGGCCTTCCTGGATACCCTGGCCCTGCTGTACAACAACCCCGACCAGCTGAGAGC

-continued

SEQUENCES

CCTGCTGACCCTGCTGTCCAGCGACACCGCCCCCAGATGGATGACCGTGATGCGGGGCTACAGCGAGTGTGGAGA
TGGCAGCCCTGCCGTGTACACCTGCGTGGACGACCTGTGCAGAGGCTACGACCTGACCAGACTGAGCTACGGCCG
GTCCATCTTCACAGAGCACGTGCTGGGCTTCGAGCTGGTGCCCCCCAGCCTGTTCAACGTGGTGGTGGCCATCCG
GAACGAGGCCACCAGAACCAACAGAGCCGTGCGGCTGCCTGTGTCTACAGCCGCTGCACCTGAGGGCATCACACT
GTTCTACGGCCTGTACAACGCCGTGAAAGAGTTCTGCCTCCGGCACCAGCTGGATCCCCCCCTGCTGAGACACCT
GGACAAGTACTACGCCGGCCTGCCCCCAGAGCTGAAGCAGACCAGAGTGAACCTGCCCGCCCACAGCAGATATGG
CCCTCAGGCCGTGGACGCCAGATGATAAGCGGCCGCATACAGCAGCAATTGGCAAGCTGCTTACATAGAACTCGC
GGCGATTGGCATGCCGCCTTAAAATTTTTATTTTATTTTTCTTTTCTTTTCCGAATCGGATTTTGTTTTTAATAT
TTCAAAAAAAAAAAAAAAAAAAAAAAAAAAAAAAAAAAAAAGGGTCGGCATGGCATCTCCACCTCCTCGCGGTCCGAC
CTGGGCATCCGAAGGAGGACGCACGTCCACTCGGATGGCTAAGGGAGAGCCACGTTTAAACACGTGATATCTGGC
CTCATGGGCCTTCCTTTCACTGCCCGCTTTCCAGTCGGGAAACCTGTCGTGCCAGCTGCATTAACATGGTCATAG
CTGTTTCCTTGCGTATTGGGCGCTCTCCGCTTCCTCGCTCACTGACTCGCTGCGCTCGGTCGTTCGGGTAAAGCC
TGGGGTGCCTAATGAGCAAAAGGCCAGCAAAAGGCCAGGAACCGTAAAAAGGCCGCGTTGCTGGCGTTTTTCCAT
AGGCTCCGCCCCCCTGACGAGCATCACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCTGTAGGTATCTCAGTTCGGTGTAGGTC
GTTCGCTCCAAGCTGGGCTGTGTGCACGAACCCCCCGTTCAGCCCGACCGCTGCGCCTTATCCGGTAACTATCGT
CTTGAGTCCAACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAACAGTATTTGGTATC
TGCGCTCTGCTGAAGCCAGTTACCTTCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATGAGATTATCAAAAAGGATC
TTCACCTAGATCCTTTTAAATTAAAAATGAAGTTTTAAATCAATCTAAAGTATATATGAGTAAACTTGGTCTGAC
AGTTATTAGAAAAATTCATCCAGCAGACGATAAAACGCAATACGCTGGCTATCCGGTGCCGCAATGCCATACAGC
ACCAGAAAACGATCCGCCCATTCGCCGCCCAGTTCTTCCGCAATATCACGGGTGGCCAGCGCAATATCCTGATAA
CGATCCGCCACGCCCAGACGGCCGCAATCAATAAAGCCGCTAAAACGGCCATTTTCCACCATAATGTTCGGCAGG
CACGCATCACCATGGGTCACCACCAGATCTTCGCCATCCGGCATGCTCGCTTTCAGACGCGCAAACAGCTCTGCC
GGTGCCAGGCCCTGATGTTCTTCATCCAGATCATCCTGATCCACCAGGCCCGCTTCCATACGGGTACGCGCACGT
TCAATACGATGTTTCGCCTGATGATCAAACGGACAGGTCGCCGGGTCCAGGGTATGCAGACGACGCATGGCATCC
GCCATAATGCTCACTTTTTCTGCCGGCGCCAGATGGCTAGACAGCAGATCCTGACCCGGCACTTCGCCCAGCAGC
AGCCAATCACGGCCCGCTTCGGTCACCACATCCAGCACCGCCGCACACGGAACACCGGTGGTGGCCAGCCAGCTC
AGACGCGCCGCTTCATCCTGCAGCTCGTTCAGCGCACCGCTCAGATCGGTTTTCACAAACAGCACCGGACGACCC
TGCGCGCTCAGACGAAACACCGCCGCATCAGAGCAGCCAATGGTCTGCTGCGCCCAATCATAGCCAAACAGACGT
TCCACCCACGCTGCCGGGCTACCCGCATGCAGGCCATCCTGTTCAATCATACTCTTCCTTTTTCAATATTATTGA
AGCATTTATCAGGGTTATTGTCTCATGAGCGGATACATATTTGAATGTATTTAGAAAAATAAACAAATAGGGGTT
CCGCGCACATTTCCCCGAAAAGTGCCACCTAAATTGTAAGCGTTAATATTTTGTTAAAATTCGCGTTAAATTTTT
GTTAAATCAGCTCATTTTTTAACCAATAGGCCGAAATCGGCAAAATCCCTTATAAATCAAAAGAATAGACCGAGA
TAGGGTTGAGTGGCCGCTACAGGGCGCTCCCATTCGCCATTCAGGCTGCGCAACTGTTGGGAAGGGCGTTTCGGT
GCGGGCCTCTTCGCTATTACGCCAGCTGGCGAAAGGGGGATGTGCTGCAAGGCGATTAAGTTGGGTAACGCCAGG
GTTTTCCCAGTCACACGCGTAATACGACTCACTATAG

A533 Vector: SGP-gHsol-EV71-gL (SEQ ID NO: 60):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT
GTGCGGAAGATCCGGACAGATTGTATAAGTATGCAACTAAGCTGAAGAAAAACTGTAAGGAAATAACTGATAAGG
AATTGGACAAGAAAATGAAGGAGCTCGCCGCCGTCATGAGCGACCCTGACCTGGAAACTGAGACTATGTGCCTCC
ACGACGACGAGTCGTGTCGCTACGAAGGGCAAGTCGCTGTTTACCAGGATGTATACGCGGTTGACGGACCGACAA
GTCTCTATCACCAAGCCAATAAGGGAGTTAGAGTCGCCTACTGGATAGGCTTTGACACCACCCCTTTTATGTTTA
AGAACTTGGCTGGAGCATATCCATCATACTCTACCAACTGGGCCGACGAAACCGTGTTAACGGCTCGTAACATAG
GCCTATGCAGCTCTGACGTTATGGAGCGGTCACGTAGAGGGATGTCCATTCTTAGAAAGAAGTATTTGAAACCAT
CCAACAATGTTCTATTCTCTGTTGGCTCGACCATCTACCACGAGAAGAGGGACTTACTGAGGAGCTGGCACCTGC
CGTCTGTATTTCACTTACGTGGCAAGCAAAATTACACATGTCGGTGTGAGACTATAGTTAGTTGCGACGGGTACG
TCGTTAAAAGAATAGCTATCAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCGTGTGCACGTATGTGCCAG
CTACATTGTGTGACCAAATGACTGGCATACTGGCAACAGATGTCAGTGCGGACGACGCGCAAAAACTGCTGGTTG
GGCTCAACCAGCGTATAGTCGTCAACGGTCGCACCCAGAGAAACACCAATACCATGAAAAATTACCTTTTGCCCG
TAGTGGCCCAGGCATTTGCTAGGTGGGCAAAGGAATATAAGGAAGATCAAGAAGATGAAAGGCCACTAGGACTAC
GAGATAGACAGTTAGTCATGGGGTGTTGTTGGGCTTTTAGAAGGCACAAGATAACATCTATTTATAAGCGCCCGG
ATACCCAAACCATCATCAAAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCACCTCTCATTACCGCCGAGG
ACGTACAAGAAGCTAAGTGCGCAGCCGATGAGGCTAAGGAGGTGCGTGAAGCCGAGGAGTTGCGCGCAGCTCTAC
CACCTTTGGCAGCTGATGTTGAGGAGCCCACTCTGGAAGCCGATGTCGACTTGATGTTACAAGAGGCTGGGGCCG
GCTCAGTGGAGACACCTCGTGGCTTGATAAAGGTTACCAGCTACGATGGCGAGGACAAGATCGGCTCTTACGCTG
TGCTTTCTCCGCAGGCTGTACTCAAGAGTGAAAAATTATCTTGCATCCACCCTCTCGCTGAACAAGTCATAGTGA
TAACACACTCTGGCCGAAAAGGGCGTTATGCCGTGGAACCATACCATGGTAAAGTAGTGGTGCCAGAGGGACATG
CAATACCCGTCCAGGACTTTCAAGCTCTGAGTGAAAGTGCCACCATTGTGTACAACGAACGTGAGTTCGTAAACA
GGTACCTGCACCATATTGCCACACATGGAGGAGCGCTGAACACTGATGAAGAATATTACAAAACTGTCAAGCCCA
GCGAGCACGACGGCGAATACCTGTACGACATCGACAGGAAACAGTGCGTCAAGAAAGAACTAGTCACTGGGCTAG
GGCTCACAGGCGAGCTGGTGGATCCTCCCTTCCATGAATTCGCCTACGAGAGTCTGAGAACACGACCAGCCGCTC
CTTACCAAGTACCAACCATAGGGGTGTATGGCGTGCCAGGATCAGGCAAGTCTGGCATCATTAAAAGCGCAGTCA
CCAAAAAAGATCTAGTGGTGAGCGCCAAGAAAGAAAACTGTGCAGAAATTATAAGGGACGTCAAGAAAATGAAAG
GGCTGGACGTCAATGCCAGAACTGTGGACTCAGTGCTCTTGAATGGATGCAAACACCCCGTAGAGACCCTGTATA
TTGACGAAGCTTTTGCTTGTCATGCAGGTACTCTCAGAGCGCTCATAGCCATTATAAGACCTAAAAAGGCAGTGC
TCTGCGGGGATCCCAAACAGTGCGGTTTTTTTAACATGATGTGCCTGAAAGTGCATTTTAACCACGAGATTTGCA
CACAAGTCTTCCACAAAAGCATCTCTCGCCGTTGCACTAAATCTGTGACTTCGGTCGTCTCAACCTTGTTTTACG -continued

| SEQUENCES |
|---|
| ACAAAAAAATGAGAACGACGAATCCGAAAGAGACTAAGATTGTGATTGACACTACCGGCAGTACCAAACCTAAGC<br>AGGACGATCTCATTCTCACTTGTTTCAGAGGGTGGGTGAAGCAGTTGCAAATAGATTACAAAGGCAACGAAATAA<br>TGACGGCAGCTGCCTCTCAAGGGCTGACCCGTAAAGGTGTGTATGCCGTTCGGTACAAGGTGAATGAAAATCCTC<br>TGTACGCACCCACCTCAGAACATGTGAACGTCCTACTGACCCGCACGGAGGACCGCATCGTGTGGAAAACACTAG<br>CCGGCGACCCATGGATAAAAACACTGACTGCCAAGTACCCTGGGAATTTCACTGCCACGATAGAGGAGTGGCAAG<br>CAGAGCATGATGCCATCATGAGGCACATCTTGGAGAGACCGGACCCTACCGACGTCTTCCAGAATAAGGCAAACG<br>TGTGTTGGGCCAAGGCTTTAGTGCCGGTGCTGAAGACCGCTGGCATAGACATGACCACTGAACAATGGAACACTG<br>TGGATTATTTTGAAACGGACAAAGCTCACTCAGCAGAGATAGTATTGAACCAACTATGCGTGAGGTTCTTTGGAC<br>TCGATCTGGACTCCGGTCTATTTTCTGCACCCACTGTTCCGTTATCCATTAGGAATAATCACTGGGATAACTCCC<br>CGTCGCCTAACATGTACGGGCTGAATAAAGAAGTGGTCCGTCAGCTCTCTCGCAGGTACCCACAACTGCCTCGGG<br>CAGTTGCCACTGGAAGAGTCTATGACATGAACACTGGTACACTGCGCAATTATGATCCGCGCATAAACCTAGTAC<br>CTGTAAACAGAAGACTGCCTCATGCTTTAGTCCTCCACCATAATGAACACCCACAGAGTGACTTTTCTTCATTCG<br>TCAGCAAATTGAAGGGCAGAACTGTCCTGGTGGTCGGGGAAAAGTTGTCCGTCCCAGGCAAAATGGTTGACTGGT<br>TGTCAGACCGGCCTGAGGCTACCTTCAGAGCTCGGCTGGATTTAGGCATCCCAGGTGATGTGCCCAAATATGACA<br>TAATATTTGTTAATGTGAGGACCCCATATAAATACCATCACTATCAGCAGTGTGAAGACCATGCCATTAAGCTTA<br>GCATGTTGACCAAGAAAGCTTGTCTGCATCTGAATCCCGGCGGAACCTGTGTCAGCATAGGTTATGGTTACGCTG<br>ACAGGGCCAGCGAAAGCATCATTGGTGCTATAGCGCGGCAGTTCAAGTTTTCCCGGGTATGCAAACCGAAATCCT<br>CACTTGAAGAGACGGAAGTTCTGTTTGTATTCATTGGGTACGATCGCAAGGCCCGTACGCACAATCCTTACAAGC<br>TTTCATCAACCTTGACCAACATTTATACAGGTTCCAGACTCCACGAAGCCGGATGTGCACCCTCATATCATGTGG<br>TGCGAGGGGATATTGCCACGGCCACCGAAGGAGTGATTATAAATGCTGCTAACAGCAAAGGACAACCTGGCGGAG<br>GGGTGTGCGGAGCGCTGTATAAGAAATTCCCGGAAAGCTTCGATTTACAGCCGATCGAAGTAGGAAAAGCGCGAC<br>TGGTCAAAGGTGCAGCTAAACATATCATTCATGCCGTAGGACCAAACTTCAACAAAGTTTCGGAGGTTGAAGGTG<br>ACAAACAGTTGGCAGAGGCTTATGAGTCCATCGCTAAGATTGTCAACGATAACAATTACAAGTCAGTAGCGATTC<br>CACTGTTGTCCACCGGCATCTTTTCCGGGAACAAAGATCGACTAACCCAATCATTGAACCATTTGCTGACAGCTT<br>TAGACACCACTGATGCAGATGTAGCCATATACTGCAGGGACAAGAAATGGGAAATGACTCTCAAGGAAGCAGTGG<br>CTAGGAGAGAAGCAGTGGAGGAGATATGCATATCCGACGACTCTTCAGTGACAGAACCTGATGCAGAGCTGGTGA<br>GGGTGCATCCGAAGAGTTCTTTGGCTGGAAGGAAGGGCTACAGCACAAGCGATGGCAAAACTTTCTCATATTTGG<br>AAGGGACCAAGTTTCACCAGGCGGCCAAGGATATAGCAGAAATTAATGCCATGTGGCCCGTTGCAACGGAGGCCA<br>ATGAGCAGGTATGCATGTATATCCTCGGAGAAAGCATGAGCAGTATTAGGTCGAAATGCCCCGTCGAAGAGTCGG<br>AAGCCTCCACACCACCTAGCACGCTGCCTTGCTTGTGCATCCATGCCATGACTCCAGAAAGAGTACAGCGCCTAA<br>AAGCCTCACGTCCAGAACAAATTACTGTGTGCTCATCCTTTCCATTGCCGAAGTATAGAATCACTGGTGTGCAGA<br>AGATCCAATGCTCCCAGCCTATATTGTTCTCACCGAAAGTGCCTGCGTATATTCATCCAAGGAAGTATCTCGTGG<br>AAACACCACCGGTAGACGAGACTCCGGAGCCATCGGCAGAGAACCAATCCACAGAGGGGACACCTGAACAACCAC<br>CACTTATAACCGAGGATGAGACCAGGACTAGAACGCCTGAGCCGATCATCATCGAAGAGGAAGAAGAGGATAGCA<br>TAAGTTTGCTGTCAGATGGCCCGACCCACCAGGTGCTGCAAGTCGAGGCAGACATTCACGGGCCGCCCTCTGTAT<br>CTAGCTCATCCTGGTCCATTCCTCATGCATCCGACTTTGATGTGGACAGTTTATCCATACTTGACACCCTGGAGG<br>GAGCTAGCGTGACCAGCGGGGCAACGTCAGCCGAGACTAACTCTTACTTCGCAAAGAGTATGGAGTTTCTGGCGC<br>GACCGGTGCCTGCGCCTCGAACAGTATTCAGGAACCCTCCACATCCCGCTCCGCGCACAAGAACACCGTCACTTG<br>CACCCAGCAGGGCCTGCTCGAGAACCAGCCTAGTTTCCACCCCGCCAGGCGTGAATAGGGTGATCACTAGAGAGG<br>AGCTCGAGGCGCTTACCCCGTCACGCACTCCTAGCAGGTCGGTCTCGAGAACCAGCCTGGTCTCCAACCCGCCAG<br>GCGTAAATAGGGTGATTACAAGAGAGGAGTTTGAGGCGTTCGTAGCACAACAACAATGACGGTTTGATGCGGGTG<br>CATACATCTTTTCCTCCGACACCGGTCAAGGGCATTTACAACAAAAATCAGTAAGGCAAACGGTGCTATCCGAAG<br>TGGTGTTGGAGAGGACCGAATTGGAGATTTCGTATGCCCCGCGCCTCGACCAAGAAAAAGAAGAATTACTACGCA<br>AGAAATTACAGTTAAATCCCACACCTGCTAACAGAAGCAGATACCAGTCCAGGAAGGTGGAGAACATGAAAGCCA<br>TAACAGCTAGACGTATTCTGCAAGGCCTAGGGCATTATTTGAAGGCAGAAGGAAAAGTGGAGTGCTACCGAACCC<br>TGCATCCTGTTCCTTTGTATTCATCTAGTGTGAACCGTGCCTTTTCAAGCCCCAAGGTCGCAGTGGAAGCCTGTA<br>ACGCCATGTTGAAAGAGAACTTTCCGACTGTGGCTTCTTACTGTATTATTCCAGAGTACGATGCCTATTTGGACA<br>TGGTTGACGGAGCTTCATGCTGCTTAGACACTGCCAGTTTTTGCCCTGCAAAGCTGCGCAGCTTTCCAAAGAAAC<br>ACTCCTATTTGGAACCCACAATACGATCGGCAGTGCCTTCAGCGATCCAGAACACGCTCCAGAACGTCCTGGCAG<br>CTGCCACAAAAAGAAATTGCAATGTCACGCAAATGAGAGAATTGCCCGTATTGGATTCGGCGGCCTTTAATGTGG<br>AATGCTTCAAGAAATATGCGTGTAATAATGAATATTGGGAAACGTTTAAAGAAAACCCCATCAGGCTTACTGAAG<br>AAAACGTGGTAAATTACATTACCAAATTAAAAGGACCAAAAGCTGCTGCTCTTTTTGCGAAGACACATAATTTGA<br>ATATGTTGCAGGACATACCAATGGACAGGTTTGTAATGGACTTAAAGAGAGACGTGAAAGTGACTCCAGGAACAA<br>AACATACTGAAGAACGGCCCAAGGTACAGGTGATCCAGGCTGCCGATCCGCTAGCAACAGCGTATCTGTGCGGAA<br>TCCACCGAGAGCTGGTTAGGAGATTAAATGCGGTCCTGCTTCCGAACATTCATACACTGTTTGATATGTCGGCTG<br>AAGACTTTGACGCTATTATAGCCGAGCACTTCCAGCCTGGGGATTGTGTTCTGGAAACTGACATCGCGTCGTTTG<br>ATAAAAGTGAGGACGACGCCATGGCTCTGACCGCGTTAATGATTCTGGAAGACTTAGGTGTGGACGCAGAGCTGT<br>TGACGCTGATTGAGGCGGCTTTCGGCGAAATTTCATCAATACATTTGCCCACTAAAACTAAATTTAAATTCGGAG<br>CCATGATGAAATCTGGAATGTTCCTCACACTGTTTGTGAACACAGTCATTAACATTGTAATCGCAAGCAGAGTGT<br>TGAGAGAACGGCTAACCGGATCACCATGTGCAGCATTCATTGGAGATGACAATATCGTGAAAGGAGTCAAATCGG<br>ACAAATTAATGGCAGACAGGTGCGCCACCTGGTTGAATATGGAAGTCAAGATTATAGATGCTGTGGTGGGCGAGA<br>AAGCGCCTTATTTCTGTGGAGGGTTTATTTTGTGTGACTCCGTGACCGGCACAGCGTGCCGTGTGGCAGACCCCC<br>TAAAAAGGCTGTTTAAGCTTGGCAAACCTCTGGCAGCAGACGATGAACATGATGATGACAGGAGAAGGGCATTGC<br>ATGAAGAGTCAACACGCTGGAACCGAGTGGGTATTCTTTCAGAGCTGTGCAAGGCAGTAGAATCAAGGTATGAAA<br>CCGTAGGAACTTCCATCATAGTTATGGCCATGACTACTCTAGCTAGCAGTGTTAAATCATTCAGCTACCTGAGAG<br>GGGCCCCTATAACTCTCTACGGCTAACCTGAATGGACTACGACATAGTCTAGTCCGCCAAG**ATGAGGCCTGGCCT**<br>**GCCCTCCTACCTGATCATCCTGGCCGTGTGCCTGTTCAGCCACCTGCTGTCCAGCAGATACGGCGCCGAGGCCGT**<br>**GAGCGAGCCCCTGGACAAGGCTTTCCACCTGCTGCTGAACACCTACGGCAGACCCATCCGGTTTCTGCGGGAGAA**<br>**CACCACCCAGTGCACCTACAACAGCAGCCTGCGGAACAGCACCGTCGTGAGAGAGAACGCCATCAGCTTCAACTT**<br>**TTTCCAGAGCTACAACCAGTACTACGTGTTCCACATGCCCAGATGCCTGTTTGCCGGCCCTCTGGCCGAGCAGTT**<br>CCTGAACCAGGTGGACCTGACCGAGACACTGGAAAGATACCAGCAGCGGCTGAATACCTACGCCCTGGTGTCCAA<br>**GGACCTGGCCAGCTACCGGTCCTTTAGCCAGCAGCTCAAGGCTCAGGATAGCCTCGGCGAGCAGCCTACCACCGT**<br>**GCCCCCTCCCATCGACCTGAGCATCCCCCACGTGTGGATGCCTCCCCAGACCACCCCTCACGGCTGGACCGAGAG**<br>**CCACACCACCTCCGGCCTGCACAGACCCCACTTCAACCAGACCTGCATCCTGTTCGACGGCCACGACCTGCTGTT**<br>**TAGCACCGTGACCCCCTGCCTGCACCAGGGCTTCTACCTGATCGACGAGCTGAGATACGTGAAGATCACCCTGAC**<br>**CGAGGATTTCTTCGTGGTCACCGTGTCCATCGACGACGACACCCCCATGCTGCTGATCTTCGGCCACCTGCCCAG**<br>**AGTGCTGTTCAAGGCCCCCTACCAGCGGGACAACTTCATCCTGCGGCAGACCGAGAAGCACGAGCTGCTGGTGCT** |

-continued

SEQUENCES

GGTCAAGAAGGACCAGCTGAACCGGCACTCCTACCTGAAGGACCCCGACTTCCTGGACGCCGCCCTGGACTTCAA
CTACCTGGACCTGAGCGCCCTGCTGAGAAACAGCTTCCACAGATACGCCGTGGACGTGCTGAAGTCCGGACGGTG
CCAGATGCTCGATCGGCGGACCGTGGAGATGGCCTTCGCCTATGCCCTCGCCCTGTTCGCCGCTGCCAGACAGGA
AGAGGCTGGCGCCCAGGTGTCAGTGCCCAGAGCCCTGGATAGACAGGCCGCCCTGCTGCAGATCCAGGAATTCAT
GATCACCTGCCTGAGCCAGACCCCCCCTAGAACCACCCTGCTGCTGTACCCCACAGCCGTGGATCTGGCCAAGAG
GGCCCTGTGGACCCCCAACCAGATCACCGACATCACAAGCCTCGTGCGGCTCGTGTACATCCTGAGCAAGCAGAA
CCAGCAGCACCTGATCCCCCAGTGGGCCCTGAGACAGATCGCCGACTTCGCCCTGAAGCTGCACAAGACCCATCT
GGCCAGCTTTCTGAGCGCCTTCGCCAGGCAGGAACTGTACCTGATGGGCAGCCTGGTCCACAGCATGCTGGTGCA
TACCACCGAGCGGCGGGAGATCTTCATCGTGGAGACAGGCCTGTGTAGCCTGGCCGAGCTGTCCCACTTTACCCA
GCTGCTGGCCCACCCTCACCACGAGTACCTGAGCGACCTGTACACCCCCTGCAGCAGCAGCGGCAGACGGGACCA
CAGCCTGGAACGGCTGACCAGACTGTTCCCCGATGCCACCGTGCCTGCTACAGTGCCTGCCGCCCTGTCCATCCT
GTCCACCATGCAGCCCAGCACCCTGGAAACCTTCCCCGACCTGTTCTGCCTGCCCCTGGGCGAGAGCTTTAGCGC
CCTGACCGTGTCCGAGCACGTGTCCTACATCGTGACCAATCAGTACCTGATCAAGGGCATCAGCTACCCCGTGTC
CACCACAGTCGTGGGCCAGAGCCTGATCATCACCCAGACCGACAGCCAGACCAAGTGCGAGCTGACCCGGAACAT
GCACACCACACACAGCATCACCGTGGCCCTGAACATCAGCCTGGAAAACTGCGCTTTCTGTCAGTCTGCCCTGCT
GGAATACGACGATACCCAGGGCGTGATCAACATCATGTACATGCACGACAGCGACGACGTGCTGTTCGCCCTGGA
CCCCTACAACGAGGTGGTGGTGTCCAGCCCCCGGACCCACTACCTGATGCTGCTGAAGAACGGCACCGTGCTGGA
AGTGACCGACGTGGTGGTGGACGCCACCGACTGATAATCTAGATTAAAACAGCTGTGGGTTGTTCCCACCCACAG
GGCCCACTGGGCGCTAGCACTCTGATTTTACGAAATCCTTGTGCGCCTGTTTTATATCCCTTCCCTAATTCGAAA
CGTAGAAGCAATGCGCACCACTGATCAATAGTAGGCGTAACGCGCCAGTTACGTCATGATCAAGCATATCTGTTC
CCCCGGACTGAGTATCAATAGACTGCTTACGCGGTTGAAGGAGAAAACGTTCGTTATCCGGCTAACTACTTCGAG
AAGCCCAGTAACACCATGGAAGCTGCAGGGTGTTTCGCTCAGCACTTCCCCCGTGTAGATCAGGTCGATGAGCCA
CTGCAATCCCCACAGGTGACTGTGGCAGTGGCTGCGTTGGCGGCCTGCCTATGGGGAGACCCATAGGACGCTCTA
ATGTGGACATGGTGCGAAGAGCCTATTGAGCTAGTTAGTAGTCCTCCGGCCCCTGAATGCGGCTAATCCTAACTG
CGGAGCACATGCCTTCAACCCAGAGGGTAGTGTGTCGTAATGGGCAACTCTGCAGCGGAACCGACTACTTTGGGT
GTCCGTGTTTCTTTTTATTCTTATATTGGCTGCTTATGGTGACAATTACAGAATTGTTACCATATAGCTATTGGA
TTGGCCATCCGGTGTGTAATAGAGCTGTTATATACCTATTTGTTGGCTTTGTACCACTAACTTTAAAATCTATAA
CTACCCTCAACTTTATATTAACCCTCAATACAGTTGAACATGTGCAGAAGGCCCGACTGCGGCTTCAGCTTCAGC
CCTGGACCCGTGATCCTGCTGTGGTGCTGCCTGCTGCTGCCTATCGTGTCCTCTGCCGCCGTGTCTGTGGCCCCT
ACAGCCGCCGAGAAGGTGCCAGCCGAGTGCCCCGAGCTGACCAGAAGATGCCTGCTGGGCGAGGTGTTCGAGGGC
GACAAGTACGAGAGCTGGCTGCGGCCCCTGGTCAACGTGACCGGCAGAGATGGCCCCCTGAGCCAGCTGATCCGG
TACAGACCCGTGACCCCCGAGGCCGCCAATAGCGTGCTGCTGGACGAGGCCTTCCTGGATACCCTGGCCCTGCTG
TACAACAACCCCGACCAGCTGAGAGCCCTGCTGACCCTGCTGTCCAGCGACACCGCCCCCAGATGGATGACCGTG
ATGCGGGGCTACAGCGAGTGTGGAGATGGCAGCCCTGCCGTGTACACCTGCGTGGACGACCTGTGCAGAGGCTAC
GACCTGACCAGACTGAGCTACGGCCGGTCCATCTTCACAGAGCACGTGCTGGGCTTCGAGCTGGTGCCCCCCAGC
CTGTTCAACGTGGTGGTGGCCATCCGGAACGAGGCCACCAGAACCAACAGAGCCGTGCGGCTGCCTGTGTCTACA
GCCGCTGCACCTGAGGGCATCACACTGTTCTACGGCCTGTACAACGCCGTGAAAGAGTTCTGCCTCCGGCACCAG
CTGGATCCCCCCCTGCTGAGACACCTGGACAAGTACTACGCCGGCCTGCCCCCAGAGCTGAAGCAGACCAGAGTG
AACCTGCCCGCCCACAGCAGATATGGCCCTCAGGCCGTGGACGCCAGATGATAAGCGGCCGCATACAGCAGCAAT
TGGCAAGCTGCTTACATAGAACTCGCGGCGATTGGCATGCCGCCTTAAAATTTTTATTTTATTTTTCTTTTCTTT
TCCGAATCGGATTTTGTTTTTAATATTTCAAAAAAAAAAAAAAAAAAAAAAAAAAAAAAAAAAAGGGTCGGCATG
GCATCTCCACCTCCTCGCGGTCCGACCTGGGCATCCGAAGGAGGACGCACGTCCACTCGGATGGCTAAGGGAGAG
CCACGTTTAAACACGTGATATCTGGCCTCATGGGCCTTCCTTTCACTGCCCGCTTTCCAGTCGGGAAACCTGTCG
TGCCAGCTGCATTAACATGGTCATAGCTGTTTCCTTGCGTATTGGGCGCTCTCCGCTTCCTCGCTCACTGACTCG
CTGCGCTCGGTCGTTCGGGTAAAGCCTGGGGTGCCTAATGAGCAAAAGGCCAGCAAAAGGCCAGGAACCGTAAAA
AGGCCGCGTTGCTGGCGTTTTTCCATAGGCTCCGCCCCCCTGACGAGCATCACAAAAATCGACGCTCAAGTCAGA
GGTGGCGAAACCCGACAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCACTGGCAGCAGCCA
CTGGTAACAGGATTAGCAGAGCGAGGTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAATGAAGTTTTAAATCAATCTAAA
GTATATATGAGTAAACTTGGTCTGACAGTTATTAGAAAAATTCATCCAGCAGACGATAAAACGCAATACGCTGGC
TATCCGGTGCCGCAATGCCATACAGCACCAGAAAACGATCCGCCCATTCGCCGCCCAGTTCTTCCGCAATATCAC
GGGTGGCCAGCGCAATATCCTGATAACGATCCGCCACGCCCAGACGGCCGCAATCAATAAAGCCGCTAAAACGGC
CATTTTCCACCATAATGTTCGGCAGGCACGCATCACCATGGGTCACCACCAGATCTTCGCCATCCGGCATGCTCG
CTTTCAGACGCGCAAACAGCTCTGCCGGTGCCAGGCCCTGATGTTCTTCATCCAGATCATCCTGATCCACCAGGC
CCGCTTCCATACGGGTACGCGCACGTTCAATACGATGTTTCGCCTGATGATCAAACGGACAGGTCGCCGGGTCCA
GGGTATGCAGACGACGCATGGCATCCGCCATAATGCTCACTTTTTCTGCCGGCGCCAGATGGCTAGACAGCAGAT
CCTGACCCGGCACTTCGCCCAGCAGCAGCCAATCACGGCCCGCTTCGGTCACCACATCCAGCACCGCCGCACACG
GAACACCGGTGGTGGCCAGCCAGCTCAGACGCGCCGCTTCATCCTGCAGCTCGTTCAGCGCACCGCTCAGATCGG
TTTTCACAAACAGCACCGGACGACCCTGCGCGCTCAGACGAAACACCGCCGCATCAGAGCAGCCAATGGTCTGCT
GCGCCCAATCATAGCCAAACAGACGTTCCACCCACGCTGCCGGGCTACCCGCATGCAGGCCATCCTGTTCAATCA
TACTCTTCCTTTTTCAATATTATTGAAGCATTTATCAGGGTTATTGTCTCATGAGCGGATACATATTTGAATGTA
TTTAGAAAAATAAACAAATAGGGGTTCCGCGCACATTTCCCCGAAAAGTGCCACCTAAATTGTAAGCGTTAATAT
TTTGTTAAAATTCGCGTTAAATTTTTGTTAAATCAGCTCATTTTTTAACCAATAGGCCGAAATCGGCAAAATCCC
TTATAAATCAAAAGAATAGACCGAGATAGGGTTGAGTGGCCGCTACAGGGCGCTCCCATTCGCCATTCAGGCTGC
GCAACTGTTGGGAAGGGCGTTTCGGTGCGGGCCTCTTCGCTATTACGCCAGCTGGCGAAAGGGGGATGTGCTGCA
AGGCGATTAAGTTGGGTAACGCCAGGGTTTTCCCAGTCACACGCGTAATACGACTCACTATAG

A534 Vector: SGP-gL-EV71-gH (SEQ ID NO: 61):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA -continued

| SEQUENCES |
| --- |
| TCCTTGACATTGGAAGTGCGCCCGCCCGCAGAATGTATTCTAAGCACAAGTATCATTGTATCTGTCCGATGAGAT<br>GTGCGGAAGATCCGGACAGATTGTATAAGTATGCAACTAAGCTGAAGAAAAACTGTAAGGAAATAACTGATAAGG<br>AATTGGACAAGAAAATGAAGGAGCTCGCCGCCGTCATGAGCGACCCTGACCTGGAAACTGAGACTATGTGCCTCC<br>ACGACGACGAGTCGTGTCGCTACGAAGGGCAAGTCGCTGTTTACCAGGATGTATACGCGGTTGACGGACCGACAA<br>GTCTCTATCACCAAGCCAATAAGGGAGTTAGAGTCGCCTACTGGATAGGCTTTGACACCACCCCTTTTATGTTTA<br>AGAACTTGGCTGGAGCATATCCATCATACTCTACCAACTGGGCCGACGAAACCGTGTTAACGGCTCGTAACATAG<br>GCCTATGCAGCTCTGACGTTATGGAGCGGTCACGTAGAGGGATGTCCATTCTTAGAAAGAAGTATTTGAAACCAT<br>CCAACAATGTTCTATTCTCTGTTGGCTCGACCATCTACCACGAGAAGAGGGACTTACTGAGGAGCTGGCACCTGC<br>CGTCTGTATTTCACTTACGTGGCAAGCAAAATTACACATGTCGGTGTGAGACTATAGTTAGTTGCGACGGGTACG<br>TCGTTAAAAGAATAGCTATCAGTCCAGGCCTGTATGGGAAGCCTTCAGGCTATGCTGCTACGATGCACCGCGAGG<br>GATTCTTGTGCTGCAAAGTGACAGACACATTGAACGGGGAGAGGGTCTCTTTTCCCGTGTGCACGTATGTGCCAG<br>CTACATTGTGTGACCAAATGACTGGCATACTGGCAACAGATGTCAGTGCGGACGACGCGCAAAAACTGCTGGTTG<br>GGCTCAACCAGCGTATAGTCGTCAACGGTCGCACCCAGAGAAACACCAATACCATGAAAAATTACCTTTTGCCCG<br>TAGTGGCCCAGGCATTTGCTAGGTGGGCAAAGGAATATAAGGAAGATCAAGAAGATGAAAGGCCACTAGGACTAC<br>GAGATAGACAGTTAGTCATGGGGTGTTGTTGGGCTTTTAGAAGGCACAAGATAACATCTATTTATAAGCGCCCGG<br>ATACCCAAACCATCATCAAAGTGAACAGCGATTTCCACTCATTCGTGCTGCCCAGGATAGGCAGTAACACATTGG<br>AGATCGGGCTGAGAACAAGAATCAGGAAAATGTTAGAGGAGCACAAGGAGCCGTCACCTCTCATTACCGCCGAGG<br>ACGTACAAGAAGCTAAGTGCGCAGCCGATGAGGCTAAGGAGGTGCGTGAAGCCGAGGAGTTGCGCGCAGCTCTAC<br>CACCTTTGGCAGCTGATGTTGAGGAGCCCACTCTGGAAGCCGATGTCGACTTGATGTTACAAGAGGCTGGGGCCG<br>GCTCAGTGGAGACACCTCGTGGCTTGATAAAGGTTACCAGCTACGATGGCGAGGACAAGATCGGCTCTTACGCTG<br>TGCTTTCTCCGCAGGCTGTACTCAAGAGTGAAAAATTATCTTGCATCCACCCTCTCGCTGAACAAGTCATAGTGA<br>TAACACACTCTGGCCGAAAAGGGCGTTATGCCGTGGAACCATACCATGGTAAAGTAGTGGTGCCAGAGGGACATG<br>CAATACCCGTCCAGGACTTTCAAGCTCTGAGTGAAAGTGCCACCATTGTGTACAACGAACGTGAGTTCGTAAACA<br>GGTACCTGCACCATATTGCCACACATGGAGGAGCGCTGAACACTGATGAAGAATATTACAAAACTGTCAAGCCCA<br>GCGAGCACGACGGCGAATACCTGTACGACATCGACAGGAAACAGTGCGTCAAGAAAGAACTAGTCACTGGGCTAG<br>GGCTCACAGGCGAGCTGGTGGATCCTCCCTTCCATGAATTCGCCTACGAGAGTCTGAGAACACGACCAGCCGCTC<br>CTTACCAAGTACCAACCATAGGGGTGTATGGCGTGCCAGGATCAGGCAAGTCTGGCATCATTAAAAGCGCAGTCA<br>CCAAAAAAGATCTAGTGGTGAGCGCCAAGAAAGAAAACTGTGCAGAAATTATAAGGGACGTCAAGAAAATGAAAG<br>GGCTGGACGTCAATGCCAGAACTGTGGACTCAGTGCTCTTGAATGGATGCAAACACCCCGTAGAGACCCTGTATA<br>TTGACGAAGCTTTTGCTTGTCATGCAGGTACTCTCAGAGCGCTCATAGCCATTATAAGACCTAAAAAGGCAGTGC<br>TCTGCGGGGATCCCAAACAGTGCGGTTTTTTAACATGATGTGCCTGAAAGTGCATTTTAACCACGAGATTTGCA<br>CACAAGTCTTCCACAAAAGCATCTCTCGCCGTTGCACTAAATCTGTGACTTCGGTCGTCTCAACCTTGTTTTACG<br>ACAAAAAAATGAGAACGACGAATCCGAAAGAGACTAAGATTGTGATTGACACTACCGGCAGTACCAAACCTAAGC<br>AGGACGATCTCATTCTCACTTGTTTCAGAGGGTGGGTGAAGCAGTTGCAAATAGATTACAAAGGCAACGAAATAA<br>TGACGGCAGCTGCCTCTCAAGGGCTGACCCGTAAAGGTGTGTATGCCGTTCGGTACAAGGTGAATGAAAATCCTC<br>TGTACGCACCCACCTCAGAACATGTGAACGTCCTACTGACCCGCACGGAGGACCGCATCGTGTGGAAAACACTAG<br>CCGGCGACCCATGGATAAAAACACTGACTGCCAAGTACCCTGGGAATTTCACTGCCACGATAGAGGAGTGGCAAG<br>CAGAGCATGATGCCATCATGAGGCACATCTTGGAGAGACCGGACCCTACCGACGTCTTCCAGAATAAGGCAAACG<br>TGTGTTGGGCCAAGGCTTTAGTGCCGGTGCTGAAGACCGCTGGCATAGACATGACCACTGAACAATGGAACACTG<br>TGGATTATTTTGAAACGGACAAAGCTCACTCAGCAGAGATAGTATTGAACCAACTATGCGTGAGGTTCTTTGGAC<br>TCGATCTGGACTCCGGTCTATTTTCTGCACCCACTGTTCCGTTATCCATTAGGAATAATCACTGGGATAACTCCC<br>CGTCGCCTAACATGTACGGGCTGAATAAAGAAGTGGTCCGTCAGCTCTCTCGCAGGTACCCACAACTGCCTCGGG<br>CAGTTGCCACTGGAAGAGTCTATGACATGAACACTGGTACACTGCGCAATTATGATCCGCGCATAAACCTAGTAC<br>CTGTAAACAGAAGACTGCCTCATGCTTTAGTCCTCCACCATAATGAACACCCACAGAGTGACTTTTCTTCATTCG<br>TCAGCAAATTGAAGGGCAGAACTGTCCTGGTGGTCGGGGAAAAGTTGTCCGTCCCAGGCAAAATGGTTGACTGGT<br>TGTCAGACCGGCCTGAGGCTACCTTCAGAGCTCGGCTGGATTTAGGCATCCCAGGTGATGTGCCCAAATATGACA<br>TAATATTTGTTAATGTGAGGACCCCATATAAATACCATCACTATCAGCAGTGTGAAGACCATGCCATTAAGCTTA<br>GCATGTTGACCAAGAAAGCTTGTCTGCATCTGAATCCCGGCGGAACCTGTGTCAGCATAGGTTATGGTTACGCTG<br>ACAGGGCCAGCGAAAGCATCATTGGTGCTATAGCGCGGCAGTTCAAGTTTTCCCGGGTATGCAAACCGAAATCCT<br>CACTTGAAGAGACGGAAGTTCTGTTTGTATTCATTGGGTACGATCGCAAGGCCCGTACGCACAATCCTTACAAGC<br>TTTCATCAACCTTGACCAACATTTATACAGGTTCCAGACTCCACGAAGCCGGATGTGCACCCTCATATCATGTGG<br>TGCGAGGGGATATTGCCACGGCCACCGAAGGAGTGATTATAAATGCTGCTAACAGCAAAGGACAACCTGGCGGAG<br>GGGTGTGCGGAGCGCTGTATAAGAAATTCCCGGAAAGCTTCGATTTACAGCCGATCGAAGTAGGAAAAGCGCGAC<br>TGGTCAAAGGTGCAGCTAAACATATCATTCATGCCGTAGGACCAAACTTCAACAAAGTTTCGGAGGTTGAAGGTG<br>ACAAACAGTTGGCAGAGGCTTATGAGTCCATCGCTAAGATTGTCAACGATAACAATTACAAGTCAGTAGCGATTC<br>CACTGTTGTCCACCGGCATCTTTTCCGGGAACAAAGATCGACTAACCCAATCATTGAACCATTTGCTGACAGCTT<br>TAGACACCACTGATGCAGATGTAGCCATATACTGCAGGGACAAGAAATGGGAAATGACTCTCAAGGAAGCAGTGG<br>CTAGGAGAGAAGCAGTGGAGGAGATATGCATATCCGACGACTCTTCAGTGACAGAACCTGATGCAGAGCTGGTGA<br>GGGTGCATCCGAAGAGTTCTTTGGCTGGAAGGAAGGGCTACAGCACAAGCGATGGCAAAACTTTCTCATATTTGG<br>AAGGGACCAAGTTTCACCAGGCGGCCAAGGATATAGCAGAAATTAATGCCATGTGGCCCGTTGCAACGGAGGCCA<br>ATGAGCAGGTATGCATGTATATCCTCGGAGAAAGCATGAGCAGTATTAGGTCGAAATGCCCCGTCGAAGAGTCGG<br>AAGCCTCCACACCACCTAGCACGCTGCCTTGCTTGTGCATCCATGCCATGACTCCAGAAAGAGTACAGCGCCTAA<br>AAGCCTCACGTCCAGAACAAATTACTGTGTGCTCATCCTTTCCATTGCCGAAGTATAGAATCACTGGTGTGCAGA<br>AGATCCAATGCTCCCAGCCTATATTGTTCTCACCGAAAGTGCCTGCGTATATTCATCCAAGGAAGTATCTCGTGG<br>AAACACCACCGGTAGACGAGACTCCGGAGCCATCGGCAGAGAACCAATCCACAGAGGGGACACCTGAACAACCAC<br>CACTTATAACCGAGGATGAGACCAGGACTAGAACGCCTGAGCCGATCATCATCGAAGAGGAAGAAGAGGATAGCA<br>TAAGTTTGCTGTCAGATGGCCCGACCCACCAGGTGCTGCAAGTCGAGGCAGACATTCACGGGCCGCCCTCTGTAT<br>CTAGCTCATCCTGGTCCATTCCTCATGCATCCGACTTTGATGTGGACAGTTTATCCATACTTGACACCCTGGAGG<br>GAGCTAGCGTGACCAGCGGGGCAACGTCAGCCGAGACTAACTCTTACTTCGCAAAGAGTATGGAGTTTCTGGCGC<br>GACCGGTGCCTGCGCCTCGAACAGTATTCAGGAACCCTCCACATCCCGCTCCGCGCACAAGAACACCGTCACTTG<br>CACCCAGCAGGGCCTGCTCGAGAACCAGCCTAGTTTCCACCCCGCCAGGCGTGAATAGGGTGATCACTAGAGAGG<br>AGCTCGAGGCGCTTACCCCGTCACGCACTCCTAGCAGGTCGGTCTCGAGAACCAGCCTGGTCTCCAACCCGCCAG<br>GCGTAAATAGGGTGATTACAAGAGAGGAGTTTGAGGCGTTCGTAGCACAACAACAATGACGGTTTGATGCGGGTG<br>CATACATCTTTTCCTCCGACACCGGTCAAGGGCATTTACAACAAAAATCAGTAAGGCAAACGGTGCTATCCGAAG<br>TGGTGTTGGAGAGGACCGAATTGGAGATTTCGTATGCCCCGCGCCTCGACCAAGAAAAAGAAGAATTACTACGCA<br>AGAAATTACAGTTAAATCCCACACCTGCTAACAGAAGCAGATACCAGTCCAGGAAGGTGGAGAACATGAAAGCCA<br>TAACAGCTAGACGTATTCTGCAAGGCCTAGGGCATTATTTGAAGGCAGAAGGAAAAGTGGAGTGCTACCGAACCC |

-continued

SEQUENCES

TGCATCCTGTTCCTTTGTATTCATCTAGTGTGAACCGTGCCTTTTCAAGCCCCAAGGTCGCAGTGGAAGCCTGTA
ACGCCATGTTGAAAGAGAACTTTCCGACTGTGGCTTCTTACTGTATTATTCCAGAGTACGATGCCTATTTGGACA
TGGTTGACGGAGCTTCATGCTGCTTAGACACTGCCAGTTTTTGCCCTGCAAAGCTGCGCAGCTTTCCAAAGAAAC
ACTCCTATTTGGAACCCACAATACGATCGGCAGTGCCTTCAGCGATCCAGAACACGCTCCAGAACGTCCTGGCAG
CTGCCACAAAAAGAAATTGCAATGTCACGCAAATGAGAGAATTGCCCGTATTGGATTCGGCGGCCTTTAATGTGG
AATGCTTCAAGAAATATGCGTGTAATAATGAATATTGGGAAACGTTTAAAGAAAACCCCATCAGGCTTACTGAAG
AAAACGTGGTAAATTACATTACCAAATTAAAAGGACCAAAAGCTGCTGCTCTTTTTGCGAAGACACATAATTTGA
ATATGTTGCAGGACATACCAATGGACAGGTTTGTAATGGACTTAAAGAGAGACGTGAAAGTGACTCCAGGAACAA
AACATACTGAAGAACGGCCCAAGGTACAGGTGATCCAGGCTGCCGATCCGCTAGCAACAGCGTATCTGTGCGGAA
TCCACCGAGAGCTGGTTAGGAGATTAAATGCGGTCCTGCTTCCGAACATTCATACACTGTTTGATATGTCGGCTG
AAGACTTTGACGCTATTATAGCCGAGCACTTCCAGCCTGGGGATTGTGTTCTGGAAACTGACATCGCGTCGTTTG
ATAAAAGTGAGGACGACGCCATGGCTCTGACCGCGTTAATGATTCTGGAAGACTTAGGTGTGGACGCAGAGCTGT
TGACGCTGATTGAGGCGGCTTTCGGCGAAATTTCATCAATACATTTGCCCACTAAAACTAAATTTAAATTCGGAG
CCATGATGAAATCTGGAATGTTCCTCACACTGTTTGTGAACACAGTCATTAACATTGTAATCGCAAGCAGAGTGT
TGAGAGAACGGCTAACCGGATCACCATGTGCAGCATTCATTGGAGATGACAATATCGTGAAAGGAGTCAAATCGG
ACAAATTAATGGCAGACAGGTGCGCCACCTGGTTGAATATGGAAGTCAAGATTATAGATGCTGTGGTGGGCGAGA
AAGCGCCTTATTTCTGTGGAGGGTTTATTTTGTGTGACTCCGTGACCGGCACAGCGTGCCGTGTGGCAGACCCCC
TAAAAAGGCTGTTTAAGCTTGGCAAACCTCTGGCAGCAGACGATGAACATGATGATGACAGGAGAAGGGCATTGC
ATGAAGAGTCAACACGCTGGAACCGAGTGGGTATTCTTTCAGAGCTGTGCAAGGCAGTAGAATCAAGGTATGAAA
CCGTAGGAACTTCCATCATAGTTATGGCCATGACTACTCTAGCTAGCAGTGTTAAATCATTCAGCTACCTGAGAG
GGGCCCCTATAACTCTCTACGGCTAACCTGAATGGACTACGACATAGTCTAGTCCGCCAAGATGTGCAGAAGGCC
CGACTGCGGCTTCAGCTTCAGCCCTGGACCCGTGATCCTGCTGTGGTGCTGCCTGCTGCTGCCTATCGTGTCCTC
TGCCGCCGTGTCTGTGGCCCCTACAGCCGCCGAGAAGGTGCCAGCCGAGTGCCCCGAGCTGACCAGAAGATGCCT
GCTGGGCGAGGTGTTCGAGGGCGACAAGTACGAGAGCTGGCTGCGGCCCCTGGTCAACGTGACCGGCAGAGATGG
CCCCCTGAGCCAGCTGATCCGGTACAGACCCGTGACCCCCGAGGCCGCCAATAGCGTGCTGCTGGACGAGGCCTT
CCTGGATACCCTGGCCCTGCTGTACAACAACCCCGACCAGCTGAGAGCCCTGCTGACCCTGCTGTCCAGCGACAC
CGCCCCCAGATGGATGACCGTGATGCGGGGCTACAGCGAGTGTGGAGATGGCAGCCCTGCCGTGTACACCTGCGT
GGACGACCTGTGCAGAGGCTACGACCTGACCAGACTGAGCTACGGCCGGTCCATCTTCACAGAGCACGTGCTGGG
CTTCGAGCTGGTGCCCCCCAGCCTGTTCAACGTGGTGGTGGCCATCCGGAACGAGGCCACCAGAACCAACAGAGC
CGTGCGGCTGCCTGTGTCTACAGCCGCTGCACCTGAGGGCATCACACTGTTCTACGGCCTGTACAACGCCGTGAA
AGAGTTCTGCCTCCGGCACCAGCTGGATCCCCCCCTGCTGAGACACCTGGACAAGTACTACGCCGGCCTGCCCCC
AGAGCTGAAGCAGACCAGAGTGAACCTGCCCGCCCACAGCAGATATGGCCCTCAGGCCGTGGACGCCAGATGATA
ATCTAGATTAAAACAGCTGTGGGTTGTTCCCACCCACAGGGCCCACTGGGCGCTAGCACTCTGATTTTACGAAAT
CCTTGTGCGCCTGTTTTATATCCCTTCCCTAATTCGAAACGTAGAAGCAATGCGCACCACTGATCAATAGTAGGC
GTAACGCGCCAGTTACGTCATGATCAAGCATATCTGTTCCCCCGGACTGAGTATCAATAGACTGCTTACGCGGTT
GAAGGAGAAAACGTTCGTTATCCGGCTAACTACTTCGAGAAGCCCAGTAACACCATGGAAGCTGCAGGGTGTTTC
GCTCAGCACTTCCCCCGTGTAGATCAGGTCGATGAGCCACTGCAATCCCCACAGGTGACTGTGGCAGTGGCTGCG
TTGGCGGCCTGCCTATGGGGAGACCCATAGGACGCTCTAATGTGGACATGGTGCGAAGAGCCTATTGAGCTAGTT
AGTAGTCCTCCGGCCCCTGAATGCGGCTAATCCTAACTGCGGAGCACATGCCTTCAACCCAGAGGGTAGTGTGTC
GTAATGGGCAACTCTGCAGCGGAACCGACTACTTTGGGTGTCCGTGTTTCTTTTTATTCTTATATTGGCTGCTTA
TGGTGACAATTACAGAATTGTTACCATATAGCTATTGGATTGGCCATCCGGTGTGTAATAGAGCTGTTATATACC
TATTTGTTGGCTTTGTACCACTAACTTTAAAATCTATAACTACCCTCAACTTTATATTAACCCTCAATACAGTTG
AACATGAGGCCTGGCCTGCCCTCCTACCTGATCATCCTGGCCGTGTGCCTGTTCAGCCACCTGCTGTCCAGCAGA
TACGGCGCCGAGGCCGTGAGCGAGCCCCTGGACAAGGCTTTCCACCTGCTGCTGAACACCTACGGCAGACCCATC
CGGTTTCTGCGGGAGAACACCACCCAGTGCACCTACAACAGCAGCCTGCGGAACAGCACCGTCGTGAGAGAGAAC
GCCATCAGCTTCAACTTTTTCCAGAGCTACAACCAGTACTACGTGTTCCACATGCCCAGATGCCTGTTTGCCGGC
CCTCTGGCCGAGCAGTTCCTGAACCAGGTGGACCTGACCGAGACACTGGAAAGATACCAGCAGCGGCTGAATACC
TACGCCCTGGTGTCCAAGGACCTGGCCAGCTACCGGTCCTTTAGCCAGCAGCTCAAGGCTCAGGATAGCCTCGGC
GAGCAGCCTACCACCGTGCCCCCTCCCATCGACCTGAGCATCCCCCACGTGTGGATGCCTCCCCAGACCACCCCT
CACGGCTGGACCGAGAGCCACACCACCTCCGGCCTGCACAGACCCCACTTCAACCAGACCTGCATCCTGTTCGAC
GGCCACGACCTGCTGTTTAGCACCGTGACCCCCTGCCTGCACCAGGGCTTCTACCTGATCGACGAGCTGAGATAC
GTGAAGATCACCCTGACCGAGGATTTCTTCGTGGTCACCGTGTCCATCGACGACGACACCCCCATGCTGCTGATC
TTCGGCCACCTGCCCAGAGTGCTGTTCAAGGCCCCCTACCAGCGGGACAACTTCATCCTGCGGCAGACCGAGAAG
CACGAGCTGCTGGTGCTGGTCAAGAAGGACCAGCTGAACCGGCACTCCTACCTGAAGGACCCCGACTTCCTGGAC
GCCGCCCTGGACTTCAACTACCTGGACCTGAGCGCCCTGCTGAGAAACAGCTTCCACAGATACGCCGTGGACGTG
CTGAAGTCCGGACGGTGCCAGATGCTCGATCGGCGGACCGTGGAGATGGCCTTCGCCTATGCCCTCGCCCTGTTC
GCCGCTGCCAGACAGGAAGAGGCTGGCGCCCAGGTGTCAGTGCCCAGAGCCCTGGATAGACAGGCCGCCCTGCTG
CAGATCCAGGAATTCATGATCACCTGCCTGAGCCAGACCCCCCCTAGAACCACCCTGCTGCTGTACCCCACAGCC
GTGGATCTGGCCAAGAGGGCCCTGTGGACCCCCAACCAGATCACCGACATCACAAGCCTCGTGCGGCTCGTGTAC
ATCCTGAGCAAGCAGAACCAGCAGCACCTGATCCCCCAGTGGGCCCTGAGACAGATCGCCGACTTCGCCCTGAAG
CTGCACAAGACCCATCTGGCCAGCTTTCTGAGCGCCTTCGCCAGGCAGGAACTGTACCTGATGGGCAGCCTGGTC
CACAGCATGCTGGTGCATACCACCGAGCGGCGGGAGATCTTCATCGTGGAGACAGGCCTGTGTAGCCTGGCCGAG
CTGTCCCACTTTACCCAGCTGCTGGCCCACCCTCACCACGAGTACCTGAGCGACCTGTACACCCCCTGCAGCAGC
AGCGGCAGACGGGACCACAGCCTGGAACGGCTGACCAGACTGTTCCCCGATGCCACCGTGCCTGCTACAGTGCCT
GCCGCCCTGTCCATCCTGTCCACCATGCAGCCCAGCACCCTGGAAACCTTCCCCGACCTGTTCTGCCTGCCCCTG
GGCGAGAGCTTTAGCGCCCTGACCGTGTCCGAGCACGTGTCCTACATCGTGACCAATCAGTACCTGATCAAGGGC
ATCAGCTACCCCGTGTCCACCACAGTCGTGGGCCAGAGCCTGATCATCACCCAGACCGACAGCCAGACCAAGTGC
GAGCTGACCCGGAACATGCACACCACACACAGCATCACCGTGGCCCTGAACATCAGCCTGGAAAACTGCGCTTTC
TGTCAGTCTGCCCTGCTGGAATACGACGATACCCAGGGCGTGATCAACATCATGTACATGCACGACAGCGACGAC
GTGCTGTTCGCCCTGGACCCCTACAACGAGGTGGTGGTGTCCAGCCCCCGGACCCACTACCTGATGCTGCTGAAG
AACGGCACCGTGCTGGAAGTGACCGACGTGGTGGTGGACGCCACCGACTGATAAGCGGCCGCATACAGCAGCAAT
TGGCAAGCTGCTTACATAGAACTCGCGGCGATTGGCATGCCGCCTTAAAATTTTTATTTTATTTTTCTTTTCTTT
TCCGAATCGGATTTTGTTTTTAATATTTCAAAAAAAAAAAAAAAAAAAAAAAAAAAAAAAAAAAAAGGGTCGGCATG
GCATCTCCACCTCCTCGCGGTCCGACCTGGGCATCCGAAGGAGGACGCACGTCCACTCGGATGGCTAAGGGAGAG
CCACGTTTAAACACGTGATATCTGGCCTCATGGGCCTTCCTTTCACTGCCCGCTTTCCAGTCGGGAAACCTGTCG
TGCCAGCTGCATTAACATGGTCATAGCTGTTTCCTTGCGTATTGGGCGCTCTCCGCTTCCTCGCTCACTGACTCG
CTGCGCTCGGTCGTTCGGGTAAAGCCTGGGGTGCCTAATGAGCAAAAGGCCAGCAAAAGGCCAGGAACCGTAAAA

-continued

| SEQUENCES |
| --- |

AGGCCGCGTTGCTGGCGTTTTTCCATAGGCTCCGCCCCCCTGACGAGCATCACAAAAATCGACGCTCAAGTCAGA
GGTGGCGAAACCCGACAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCACTGGCAGCAGCCA
CTGGTAACAGGATTAGCAGAGCGAGGTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAATGAAGTTTTAAATCAATCTAAA
GTATATATGAGTAAACTTGGTCTGACAGTTATTAGAAAAATTCATCCAGCAGACGATAAAACGCAATACGCTGGC
TATCCGGTGCCGCAATGCCATACAGCACCAGAAAACGATCCGCCCATTCGCCGCCCAGTTCTTCCGCAATATCAC
GGGTGGCCAGCGCAATATCCTGATAACGATCCGCCACGCCCAGACGGCCGCAATCAATAAAGCCGCTAAAACGGC
CATTTTCCACCATAATGTTCGGCAGGCACGCATCACCATGGGTCACCACCAGATCTTCGCCATCCGGCATGCTCG
CTTTCAGACGCGCAAACAGCTCTGCCGGTGCCAGGCCCTGATGTTCTTCATCCAGATCATCCTGATCCACCAGGC
CCGCTTCCATACGGGTACGCGCACGTTCAATACGATGTTTCGCCTGATGATCAAACGGACAGGTCGCCGGGTCCA
GGGTATGCAGACGACGCATGGCATCCGCCATAATGCTCACTTTTTCTGCCGGCGCCAGATGGCTAGACAGCAGAT
CCTGACCCGGCACTTCGCCCAGCAGCAGCCAATCACGGCCCGCTTCGGTCACCACATCCAGCACCGCCGCACACG
GAACACCGGTGGTGGCCAGCCAGCTCAGACGCGCCGCTTCATCCTGCAGCTCGTTCAGCGCACCGCTCAGATCGG
TTTTCACAAACAGCACCGGACGACCCTGCGCGCTCAGACGAAACACCGCCGCATCAGAGCAGCCAATGGTCTGCT
GCGCCCAATCATAGCCAAACAGACGTTCCACCCACGCTGCCGGGCTACCCGCATGCAGGCCATCCTGTTCAATCA
TACTCTTCCTTTTTCAATATTATTGAAGCATTTATCAGGGTTATTGTCTCATGAGCGGATACATATTTGAATGTA
TTTAGAAAAATAAACAAATAGGGGTTCCGCGCACATTTCCCCGAAAAGTGCCACCTAAATTGTAAGCGTTAATAT
TTTGTTAAAATTCGCGTTAAATTTTTGTTAAATCAGCTCATTTTTTAACCAATAGGCCGAAATCGGCAAAATCCC
TTATAAATCAAAAGAATAGACCGAGATAGGGTTGAGTGGCCGCTACAGGGCGCTCCCATTCGCCATTCAGGCTGC
GCAACTGTTGGGAAGGGCGTTTCGGTGCGGGCCTCTTCGCTATTACGCCAGCTGGCGAAAGGGGGATGTGCTGCA
AGGCGATTAAGTTGGGTAACGCCAGGGTTTTCCCAGTCACACGCGTAATACGACTCACTATAG

A535 Vector: SGP-342-EV71-gHsol-2A-gL (SEQ ID NO: 62):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT
GTGCGGAAGATCCGGACAGATTGTATAAGTATGCAACTAAGCTGAAGAAAAACTGTAAGGAAATAACTGATAAGG
AATTGGACAAGAAAATGAAGGAGCTCGCCGCCGTCATGAGCGACCCTGACCTGGAAACTGAGACTATGTGCCTCC
ACGACGACGAGTCGTGTCGCTACGAAGGGCAAGTCGCTGTTTACCAGGATGTATACGCGGTTGACGGACCGACAA
GTCTCTATCACCAAGCCAATAAGGGAGTTAGAGTCGCCTACTGGATAGGCTTTGACACCACCCCTTTTATGTTTA
AGAACTTGGCTGGAGCATATCCATCATACTCTACCAACTGGGCCGACGAAACCGTGTTAACGGCTCGTAACATAG
GCCTATGCAGCTCTGACGTTATGGAGCGGTCACGTAGAGGGATGTCCATTCTTAGAAAGAAGTATTTGAAACCAT
CCAACAATGTTCTATTCTCTGTTGGCTCGACCATCTACCACGAGAAGAGGGACTTACTGAGGAGCTGGCACCTGC
CGTCTGTATTTCACTTACGTGGCAAGCAAAATTACACATGTCGGTGTGAGACTATAGTTAGTTGCGACGGGTACG
TCGTTAAAAGAATAGCTATCAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCGTGTGCACGTATGTGCCAG
CTACATTGTGTGACCAAATGACTGGCATACTGGCAACAGATGTCAGTGCGGACGACGCGCAAAAACTGCTGGTTG
GGCTCAACCAGCGTATAGTCGTCAACGGTCGCACCCAGAGAAACACCAATACCATGAAAAATTACCTTTTGCCCG
TAGTGGCCCAGGCATTTGCTAGGTGGGCAAAGGAATATAAGGAAGATCAAGAAGATGAAAGGCCACTAGGACTAC
GAGATAGACAGTTAGTCATGGGGTGTTGTTGGGCTTTTAGAAGGCACAAGATAACATCTATTTATAAGCGCCCGG
ATACCCAAACCATCATCAAAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCACCTCTCATTACCGCCGAGG
ACGTACAAGAAGCTAAGTGCGCAGCCGATGAGGCTAAGGAGGTGCGTGAAGCCGAGGAGTTGCGCGCAGCTCTAC
CACCTTTGGCAGCTGATGTTGAGGAGCCCACTCTGGAAGCCGATGTCGACTTGATGTTACAAGAGGCTGGGGCCG
GCTCAGTGGAGACACCTCGTGGCTTGATAAAGGTTACCAGCTACGATGGCGAGGACAAGATCGGCTCTTACGCTG
TGCTTTCTCCGCAGGCTGTACTCAAGAGTGAAAAATTATCTTGCATCCACCCTCTCGCTGAACAAGTCATAGTGA
TAACACACTCTGGCCGAAAAGGGCGTTATGCCGTGGAACCATACCATGGTAAAGTAGTGGTGCCAGAGGGACATG
CAATACCCGTCCAGGACTTTCAAGCTCTGAGTGAAAGTGCCACCATTGTGTACAACGAACGTGAGTTCGTAAACA
GGTACCTGCACCATATTGCCACACATGGAGGAGCGCTGAACACTGATGAAGAATATTACAAAACTGTCAAGCCCA
GCGAGCACGACGGCGAATACCTGTACGACATCGACAGGAAACAGTGCGTCAAGAAAGAACTAGTCACTGGGCTAG
GGCTCACAGGCGAGCTGGTGGATCCTCCCTTCCATGAATTCGCCTACGAGAGTCTGAGAACACGACCAGCCGCTC
CTTACCAAGTACCAACCATAGGGGTGTATGGCGTGCCAGGATCAGGCAAGTCTGGCATCATTAAAAGCGCAGTCA
CCAAAAAAGATCTAGTGGTGAGCGCCAAGAAAGAAAACTGTGCAGAAATTATAAGGGACGTCAAGAAAATGAAAG
GGCTGGACGTCAATGCCAGAACTGTGGACTCAGTGCTCTTGAATGGATGCAAACACCCCGTAGAGACCCTGTATA
TTGACGAAGCTTTTGCTTGTCATGCAGGTACTCTCAGAGCGCTCATAGCCATTATAAGACCTAAAAAGGCAGTGC
TCTGCGGGGATCCCAAACAGTGCGGTTTTTTTAACATGATGTGCCTGAAAGTGCATTTTAACCACGAGATTTGCA
CACAAGTCTTCCACAAAAGCATCTCTCGCCGTTGCACTAAATCTGTGACTTCGGTCGTCTCAACCTTGTTTTACG
ACAAAAAAATGAGAACGACGAATCCGAAAGAGACTAAGATTGTGATTGACACTACCGGCAGTACCAAACCTAAGC
AGGACGATCTCATTCTCACTTGTTTCAGAGGGTGGGTGAAGCAGTTGCAAATAGATTACAAAGGCAACGAAATAA
TGACGGCAGCTGCCTCTCAAGGGCTGACCCGTAAAGGTGTGTATGCCGTTCGGTACAAGGTGAATGAAAATCCTC
TGTACGCACCCACCTCAGAACATGTGAACGTCCTACTGACCCGCACGGAGGACCGCATCGTGTGGAAAACACTAG
CCGGCGACCCATGGATAAAAACACTGACTGCCAAGTACCCTGGGAATTTCACTGCCACGATAGAGGAGTGGCAAG
CAGAGCATGATGCCATCATGAGGCACATCTTGGAGAGACCGGACCCTACCGACGTCTTCCAGAATAAGGCAAACG
TGTGTTGGGCCAAGGCTTTAGTGCCGGTGCTGAAGACCGCTGGCATAGACATGACCACTGAACAATGGAACACTG
TGGATTATTTTGAAACGGACAAAGCTCACTCAGCAGAGATAGTATTGAACCAACTATGCGTGAGGTTCTTTGGAC
TCGATCTGGACTCCGGTCTATTTTCTGCACCCACTGTTCCGTTATCCATTAGGAATAATCACTGGGATAACTCCC
CGTCGCCTAACATGTACGGGCTGAATAAAGAAGTGGTCCGTCAGCTCTCTCGCAGGTACCCACAACTGCCTCGGG
CAGTTGCCACTGGAAGAGTCTATGACATGAACACTGGTACACTGCGCAATTATGATCCGCGCATAAACCTAGTAC
CTGTAAACAGAAGACTGCCTCATGCTTTAGTCCTCCACCATAATGAACACCCACAGAGTGACTTTTCTTCATTCG
TCAGCAAATTGAAGGGCAGAACTGTCCTGGTGGTCGGGGAAAAGTTGTCCGTCCCAGGCAAAATGGTTGACTGGT -continued

| SEQUENCES |
|---|
| TGTCAGACCGGCCTGAGGCTACCTTCAGAGCTCGGCTGGATTTAGGCATCCCAGGTGATGTGCCCAAATATGACA<br>TAATATTTGTTAATGTGAGGACCCCATATAAATACCATCACTATCAGCAGTGTGAAGACCATGCCATTAAGCTTA<br>GCATGTTGACCAAGAAAGCTTGTCTGCATCTGAATCCCGGCGGAACCTGTGTCAGCATAGGTTATGGTTACGCTG<br>ACAGGGCCAGCGAAAGCATCATTGGTGCTATAGCGCGGCAGTTCAAGTTTTCCCGGGTATGCAAACCGAAATCCT<br>CACTTGAAGAGACGGAAGTTCTGTTTGTATTCATTGGGTACGATCGCAAGGCCCGTACGCACAATCCTTACAAGC<br>TTTCATCAACCTTGACCAACATTTATACAGGTTCCAGACTCCACGAAGCCGGATGTGCACCCTCATATCATGTGG<br>TGCGAGGGGATATTGCCACGGCCACCGAAGGAGTGATTATAAATGCTGCTAACAGCAAAGGACAACCTGGCGGAG<br>GGGTGTGCGGAGCGCTGTATAAGAAATTCCCGGAAAGCTTCGATTTACAGCCGATCGAAGTAGGAAAAGCGCGAC<br>TGGTCAAAGGTGCAGCTAAACATATCATTCATGCCGTAGGACCAAACTTCAACAAAGTTTCGGAGGTTGAAGGTG<br>ACAAACAGTTGGCAGAGGCTTATGAGTCCATCGCTAAGATTGTCAACGATAACAATTACAAGTCAGTAGCGATTC<br>CACTGTTGTCCACCGGCATCTTTTCCGGGAACAAAGATCGACTAACCCAATCATTGAACCATTTGCTGACAGCTT<br>TAGACACCACTGATGCAGATGTAGCCATATACTGCAGGGACAAGAAATGGGAAATGACTCTCAAGGAAGCAGTGG<br>CTAGGAGAGAAGCAGTGGAGGAGATATGCATATCCGACGACTCTTCAGTGACAGAACCTGATGCAGAGCTGGTGA<br>GGGTGCATCCGAAGAGTTCTTTGGCTGGAAGGAAGGGCTACAGCACAAGCGATGGCAAAACTTTCTCATATTTGG<br>AAGGGACCAAGTTTCACCAGGCGGCCAAGGATATAGCAGAAATTAATGCCATGTGGCCCGTTGCAACGGAGGCCA<br>ATGAGCAGGTATGCATGTATATCCTCGGAGAAAGCATGAGCAGTATTAGGTCGAAATGCCCCGTCGAAGAGTCGG<br>AAGCCTCCACACCACCTAGCACGCTGCCTTGCTTGTGCATCCATGCCATGACTCCAGAAAGAGTACAGCGCCTAA<br>AAGCCTCACGTCCAGAACAAATTACTGTGTGCTCATCCTTTCCATTGCCGAAGTATAGAATCACTGGTGTGCAGA<br>AGATCCAATGCTCCCAGCCTATATTGTTCTCACCGAAAGTGCCTGCGTATATTCATCCAAGGAAGTATCTCGTGG<br>AAACACCACCGGTAGACGAGACTCCGGAGCCATCGGCAGAGAACCAATCCACAGAGGGGACACCTGAACAACCAC<br>CACTTATAACCGAGGATGAGACCAGGACTAGAACGCCTGAGCCGATCATCATCGAAGAGGAAGAAGAGGATAGCA<br>TAAGTTTGCTGTCAGATGGCCCGACCCACCAGGTGCTGCAAGTCGAGGCAGACATTCACGGGCCGCCCTCTGTAT<br>CTAGCTCATCCTGGTCCATTCCTCATGCATCCGACTTTGATGTGGACAGTTTATCCATACTTGACACCCTGGAGG<br>GAGCTAGCGTGACCAGCGGGGCAACGTCAGCCGAGACTAACTCTTACTTCGCAAAGAGTATGGAGTTTCTGGCGC<br>GACCGGTGCCTGCGCCTCGAACAGTATTCAGGAACCCTCCACATCCCGCTCCGCGCACAAGAACACCGTCACTTG<br>CACCCAGCAGGGCCTGCTCGAGAACCAGCCTAGTTTCCACCCCGCCAGGCGTGAATAGGGTGATCACTAGAGAGG<br>AGCTCGAGGCGCTTACCCCGTCACGCACTCCTAGCAGGTCGGTCTCGAGAACCAGCCTGGTCTCCAACCCGCCAG<br>GCGTAAATAGGGTGATTACAAGAGAGGAGTTTGAGGCGTTCGTAGCACAACAACAATGACGGTTTGATGCGGGTG<br>CATACATCTTTTCCTCCGACACCGGTCAAGGGCATTTACAACAAAAATCAGTAAGGCAAACGGTGCTATCCGAAG<br>TGGTGTTGGAGAGGACCGAATTGGAGATTTCGTATGCCCCGCGCCTCGACCAAGAAAAAGAAGAATTACTACGCA<br>AGAAATTACAGTTAAATCCCACACCTGCTAACAGAAGCAGATACCAGTCCAGGAAGGTGGAGAACATGAAAGCCA<br>TAACAGCTAGACGTATTCTGCAAGGCCTAGGGCATTATTTGAAGGCAGAAGGAAAAGTGGAGTGCTACCGAACCC<br>TGCATCCTGTTCCTTTGTATTCATCTAGTGTGAACCGTGCCTTTTCAAGCCCCAAGGTCGCAGTGGAAGCCTGTA<br>ACGCCATGTTGAAAGAGAACTTTCCGACTGTGGCTTCTTACTGTATTATTCCAGAGTACGATGCCTATTTGGACA<br>TGGTTGACGGAGCTTCATGCTGCTTAGACACTGCCAGTTTTTGCCCTGCAAAGCTGCGCAGCTTTCCAAAGAAAC<br>ACTCCTATTTGGAACCCACAATACGATCGGCAGTGCCTTCAGCGATCCAGAACACGCTCCAGAACGTCCTGGCAG<br>CTGCCACAAAAAGAAATTGCAATGTCACGCAAATGAGAGAATTGCCCGTATTGGATTCGGCGGCCTTTAATGTGG<br>AATGCTTCAAGAAATATGCGTGTAATAATGAATATTGGGAAACGTTTAAAGAAAACCCCATCAGGCTTACTGAAG<br>AAAACGTGGTAAATTACATTACCAAATTAAAAGGACCAAAAGCTGCTGCTCTTTTTGCGAAGACACATAATTTGA<br>ATATGTTGCAGGACATACCAATGGACAGGTTTGTAATGGACTTAAAGAGAGACGTGAAAGTGACTCCAGGAACAA<br>AACATACTGAAGAACGGCCCAAGGTACAGGTGATCCAGGCTGCCGATCCGCTAGCAACAGCGTATCTGTGCGGAA<br>TCCACCGAGAGCTGGTTAGGAGATTAAATGCGGTCCTGCTTCCGAACATTCATACACTGTTTGATATGTCGGCTG<br>AAGACTTTGACGCTATTATAGCCGAGCACTTCCAGCCTGGGGATTGTGTTCTGGAAACTGACATCGCGTCGTTTG<br>ATAAAAGTGAGGACGACGCCATGGCTCTGACCGCGTTAATGATTCTGGAAGACTTAGGTGTGGACGCAGAGCTGT<br>TGACGCTGATTGAGGCGGCTTTCGGCGAAATTTCATCAATACATTTGCCCACTAAAACTAAATTTAAATTCGGAG<br>CCATGATGAAATCTGGAATGTTCCTCACACTGTTTGTGAACACAGTCATTAACATTGTAATCGCAAGCAGAGTGT<br>TGAGAGAACGGCTAACCGGATCACCATGTGCAGCATTCATTGGAGATGACAATATCGTGAAAGGAGTCAAATCGG<br>ACAAATTAATGGCAGACAGGTGCGCCACCTGGTTGAATATGGAAGTCAAGATTATAGATGCTGTGGTGGGCGAGA<br>AAGCGCCTTATTTCTGTGGAGGGTTTATTTTGTGTGACTCCGTGACCGGCACAGCGTGCCGTGTGGCAGACCCCC<br>TAAAAAGGCTGTTTAAGCTTGGCAAACCTCTGGCAGCAGACGATGAACATGATGATGACAGGAGAAGGGCATTGC<br>ATGAAGAGTCAACACGCTGGAACCGAGTGGGTATTCTTTCAGAGCTGTGCAAGGCAGTAGAATCAAGGTATGAAA<br>CCGTAGGAACTTCCATCATAGTTATGGCCATGACTACTCTAGCTAGCAGTGTTAAATCATTCAGCTACCTGAGAG<br>GGGCCCCTATAACTCTCTACGGCTAACCTGAATGGACTACGACATAGTCTAGTCCGCCAAGCTATTCCAGAAGTA<br>GTGAGGAGGCTTTTTTGGAGGCCTAGGCTTTTGCAAAAAGCTTGTATATCCATTTTCGGATCTGATCAAGAGACA<br>GGATGAGGATCGTTTCGCATGATTGAATAAGATGGATTGCACGTAGGTTCTCCGGCCGCTTGGGTGGAGAGGCTA<br>TTCGGCTATGACTGGGCACAACTGACAATCGGCTGCTCTGATGCCGCCGTGATCCGGTTGTCAGCGCAGGGGCGC<br>CCGGTTCTTTTTGTCAAGACCGACCTGTCCGGTGCCCTGAATGAACTGAAGGACGAGGCAGCGCGGCTATCGTGG<br>CTGGCCACGACGGGCGTTCCTTGCGCAGTCTAGACTGGCGCGCCAAACCTGCAGGTTAAAACAGCTGTGGGTTGT<br>TCCCACCCACAGGGCCCACTGGGCGCTAGCACTCTGATTTTACGAAATCCTTGTGCGCCTGTTTTATATCCCTTC<br>CCTAATTCGAAACGTAGAAGCAATGCGCACCACTGATCAATAGTAGGCGTAACGCGCCAGTTACGTCATGATCAA<br>GCATATCTGTTCCCCCGGACTGAGTATCAATAGACTGCTTACGCGGTTGAAGGAGAAAACGTTCGTTATCCGGCT<br>AACTACTTCGAGAAGCCCAGTAACACCATGGAAGCTGCAGGGTGTTTCGCTCAGCACTTCCCCCGTGTAGATCAG<br>GTCGATGAGCCACTGCAATCCCCACAGGTGACTGTGGCAGTGGCTGCGTTGGCGGCCTGCCTATGGGGAGACCCA<br>TAGGACGCTCTAATGTGGACATGGTGCGAAGAGCCTATTGAGCTAGTTAGTAGTCCTCCGGCCCCTGAATGCGGC<br>TAATCCTAACTGCGGAGCACATGCCTTCAACCCAGAGGGTAGTGTGTCGTAATGGGCAACTCTGCAGCGGAACCG<br>ACTACTTTGGGTGTCCGTGTTTCTTTTTATTCTTATATTGGCTGCTTATGGTGACAATTACAGAATTGTTACCAT<br>ATAGCTATTGGATTGGCCATCCGGTGTGTAATAGAGCTGTTATATACCTATTTGTTGGCTTTGTACCACTAACTT<br>TAAAATCTATAACTACCCTCAACTTTATATTAACCCTCAATACAGTTGAAC**ATGAGGCCTGGCCTGCCCTCCTAC**<br>**CTGATCATCCTGGCCGTGTGCCTGTTCAGCCACCTGCTGTCCAGCAGATACGGCGCCGAGGCCGTGAGCGAGCCC**<br>**CTGGACAAGGCTTTCCACCTGCTGCTGAACACCTACGGCAGACCCATCCGGTTTCTGCGGGAGAACACCACCCAG**<br>**TGCACCTACAACAGCAGCCTGCGGAACAGCACCGTCGTGAGAGAGAACGCCATCAGCTTCAACTTTTTCCAGAGC**<br>**TACAACCAGTACTACGTGTTCCACATGCCCAGATGCCTGTTTGCCGGCCCTCTGGCCGAGCAGTTCCTGAACCAG**<br>**GTGGACCTGACCGAGACACTGGAAAGATACCAGCAGCGGCTGAATACCTACGCCCTGGTGTCCAAGGACCTGGCC**<br>**AGCTACCGGTCCTTTAGCCAGCAGCTCAAGGCTCAGGATAGCCTCGGCGAGCAGCCTACCACCGTGCCCCCTCCC**<br>**ATCGACCTGAGCATCCCCCACGTGTGGATGCCTCCCCAGACCACCCCTCACGGCTGGACCGAGAGCCACACCACC**<br>**TCCGGCCTGCACAGACCCCACTTCAACCAGACCTGCATCCTGTTCGACGGCCACGACCTGCTGTTTAGCACCGTG**<br>**ACCCCCTGCCTGCACCAGGGCTTCTACCTGATCGACGAGCTGAGATACGTGAAGATCACCCTGACCGAGGATTTC** |

-continued

| SEQUENCES |
| --- |

TTCGTGGTCACCGTGTCCATCGACGACGACACCCCCATGCTGCTGATCTTCGGCCACCTGCCCAGAGTGCTGTTC
AAGGCCCCCTACCAGCGGGACAACTTCATCCTGCGGCAGACCGAGAAGCACGAGCTGCTGGTGCTGGTCAAGAAG
GACCAGCTGAACCGGCACTCCTACCTGAAGGACCCCGACTTCCTGGACGCCGCCCTGGACTTCAACTACCTGGAC
CTGAGCGCCCTGCTGAGAAACAGCTTCCACAGATACGCCGTGGACGTGCTGAAGTCCGGACGGTGCCAGATGCTC
GATCGGCGGACCGTGGAGATGGCCTTCGCCTATGCCCTCGCCCTGTTCGCCGCTGCCAGACAGGAAGAGGCTGGC
GCCCAGGTGTCAGTGCCCAGAGCCCTGGATAGACAGGCCGCCCTGCTGCAGATCCAGGAATTCATGATCACCTGC
CTGAGCCAGACCCCCCCTAGAACCACCCTGCTGCTGTACCCCACAGCCGTGGATCTGGCCAAGAGGGCCCTGTGG
ACCCCCAACCAGATCACCGACATCACAAGCCTCGTGCGGCTCGTGTACATCCTGAGCAAGCAGAACCAGCAGCAC
CTGATCCCCCAGTGGGCCCTGAGACAGATCGCCGACTTCGCCCTGAAGCTGCACAAGACCCATCTGGCCAGCTTT
CTGAGCGCCTTCGCCAGGCAGGAACTGTACCTGATGGGCAGCCTGGTCCACAGCATGCTGGTGCATACCACCGAG
CGGCGGGAGATCTTCATCGTGGAGACAGGCCTGTGTAGCCTGGCCGAGCTGTCCCACTTTACCCAGCTGCTGGCC
CACCCTCACCACGAGTACCTGAGCGACCTGTACACCCCCTGCAGCAGCAGCGGCAGACGGGACCACAGCCTGGAA
CGGCTGACCAGACTGTTCCCCGATGCCACCGTGCCTGCTACAGTGCCTGCCGCCCTGTCCATCCTGTCCACCATG
CAGCCCAGCACCCTGGAAACCTTCCCCGACCTGTTCTGCCTGCCCCTGGGCGAGAGCTTTAGCGCCCTGACCGTG
TCCGAGCACGTGTCCTACATCGTGACCAATCAGTACCTGATCAAGGGCATCAGCTACCCCGTGTCCACCACAGTC
GTGGGCCAGAGCCTGATCATCACCCAGACCGACAGCCAGACCAAGTGCGAGCTGACCCGGAACATGCACACCACA
CACAGCATCACCGTGGCCCTGAACATCAGCCTGGAAAACTGCGCTTTCTGTCAGTCTGCCCTGCTGGAATACGAC
GATACCCAGGGCGTGATCAACATCATGTACATGCACGACAGCGACGACGTGCTGTTCGCCCTGGACCCCTACAAC
GAGGTGGTGGTGTCCAGCCCCCGGACCCACTACCTGATGCTGCTGAAGAACGGCACCGTGCTGGAAGTGACCGAC
GTGGTGGTGGACGCCACCGACCTGTTGAATTTTGACCTTCTTAAGCTTGCGGGAGACGTCGAGTCCAACCCCGGG
CCCATGTGCAGAAGGCCCGACTGCGGCTTCAGCTTCAGCCCTGGACCCGTGATCCTGCTGTGGTGCTGCCTGCTG
CTGCCTATCGTGTCCTCTGCCGCCGTGTCTGTGGCCCCTACAGCCGCCGAGAAGGTGCCAGCCGAGTGCCCCGAG
CTGACCAGAAGATGCCTGCTGGGCGAGGTGTTCGAGGGCGACAAGTACGAGAGCTGGCTGCGGCCCCTGGTCAAC
GTGACCGGCAGAGATGGCCCCCTGAGCCAGCTGATCCGGTACAGACCCGTGACCCCCGAGGCCGCCAATAGCGTG
CTGCTGGACGAGGCCTTCCTGGATACCCTGGCCCTGCTGTACAACAACCCCGACCAGCTGAGAGCCCTGCTGACC
CTGCTGTCCAGCGACACCGCCCCCAGATGGATGACCGTGATGCGGGGCTACAGCGAGTGTGGAGATGGCAGCCCT
GCCGTGTACACCTGCGTGGACGACCTGTGCAGAGGCTACGACCTGACCAGACTGAGCTACGGCCGGTCCATCTTC
ACAGAGCACGTGCTGGGCTTCGAGCTGGTGCCCCCCAGCCTGTTCAACGTGGTGGTGGCCATCCGGAACGAGGCC
ACCAGAACCAACAGAGCCGTGCGGCTGCCTGTGTCTACAGCCGCTGCACCTGAGGGCATCACACTGTTCTACGGC
CTGTACAACGCCGTGAAAGAGTTCTGCCTCCGGCACCAGCTGGATCCCCCCCTGCTGAGACACCTGGACAAGTAC
TACGCCGGCCTGCCCCCAGAGCTGAAGCAGACCAGAGTGAACCTGCCCGCCCACAGCAGATATGGCCCTCAGGCC
GTGGACGCCAGATGATAAGCGGCCGCATACAGCAGCAATTGGCAAGCTGCTTACATAGAACTCGCGGCGATTGGC
ATGCCGCCTTAAAATTTTTATTTTATTTTTTCTTTTCTTTTCCGAATCGGATTTTGTTTTTAATATTTCAAAAAAA
AAAAAAAAAAAAAAAAAAAAAAAAAAAAAAAGGGTCGGCATGGCATCTCCACCTCCTCGCGGTCCGACCTGGGCATCC
GAAGGAGGACGCACGTCCACTCGGATGGCTAAGGGAGAGCCACGTTTAAACACGTGATATCTGGCCTCATGGGCC
TTCCTTTCACTGCCCGCTTTCCAGTCGGGAAACCTGTCGTGCCAGCTGCATTAACATGGTCATAGCTGTTTCCTT
GCGTATTGGGCGCTCTCCGCTTCCTCGCTCACTGACTCGCTGCGCTCGGTCGTTCGGGTAAAGCCTGGGGTGCCT
AATGAGCAAAAGGCCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTCAGTTCGGTGTAGGTCGTTCGCTCCA
AGCTGGGCTGTGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGGTATGTAGGCG
GTGCTACAGAGTTCTTGAAGTGGTGGCCTAACTACGGCTACACTAGAAGAACAGTATTTGGTATCTGCGCTCTGC
TGAAGCCAGTTACCTTCGGAAAAAGAGTTGGTAGCTCTTGATCCGGCAAACAAACCACCGCTGGTAGCGGTGGTT
TTTTTGTTTGCAAGCAGCAGATTACGCGCAGAAAAAAAGGATCTCAAGAAGATCCTTTGATCTTTTCTACGGGGT
CTGACGCTCAGTGGAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCTGACAGTTATTAGA
AAAATTCATCCAGCAGACGATAAAACGCAATACGCTGGCTATCCGGTGCCGCAATGCCATACAGCACCAGAAAAC
GATCCGCCCATTCGCCGCCCAGTTCTTCCGCAATATCACGGGTGGCCAGCGCAATATCCTGATAACGATCCGCCA
CGCCCAGACGGCCGCAATCAATAAAGCCGCTAAAACGGCCATTTTCCACCATAATGTTCGGCAGGCACGCATCAC
CATGGGTCACCACCAGATCTTCGCCATCCGGCATGCTCGCTTTCAGACGCGCAAACAGCTCTGCCGGTGCCAGGC
CCTGATGTTCTTCATCCAGATCATCCTGATCCACCAGGCCCGCTTCCATACGGGTACGCGCACGTTCAATACGAT
GTTTCGCCTGATGATCAAACGGACAGGTCGCCGGGTCCAGGGTATGCAGACGACGCATGGCATCCGCCATAATGC
TCACTTTTTCTGCCGGCGCCAGATGGCTAGACAGCAGATCCTGACCCGGCACTTCGCCCAGCAGCAGCCAATCAC
GGCCCGCTTCGGTCACCACATCCAGCACCGCCGCACACGGAACACCGGTGGTGGCCAGCCAGCTCAGACGCGCCG
CTTCATCCTGCAGCTCGTTCAGCGCACCGCTCAGATCGGTTTTCACAAACAGCACCGGACGACCCTGCGCGCTCA
GACGAAACACCGCCGCATCAGAGCAGCCAATGGTCTGCTGCGCCCAATCATAGCCAAACAGACGTTCCACCCACG
CTGCCGGGCTACCCGCATGCAGGCCATCCTGTTCAATCATACTCTTCCTTTTTCAATATTATTGAAGCATTTATC
AGGGTTATTGTCTCATGAGCGGATACATATTTGAATGTATTTAGAAAAATAAACAAATAGGGGTTCCGCGCACAT
TTCCCCGAAAAGTGCCACCTAAATTGTAAGCGTTAATATTTTGTTAAAATTCGCGTTAAATTTTTGTTAAATCAG
CTCATTTTTTAACCAATAGGCCGAAATCGGCAAAATCCCTTATAAATCAAAAGAATAGACCGAGATAGGGTTGAG
TGGCCGCTACAGGGCGCTCCCATTCGCCATTCAGGCTGCGCAACTGTTGGGAAGGGCGTTTCGGTGCGGGCCTCT
TCGCTATTACGCCAGCTGGCGAAAGGGGGATGTGCTGCAAGGCGATTAAGTTGGGTAACGCCAGGGTTTTCCCAG
TCACACGCGTAATACGACTCACTATAG

A536 Vector: S GP-342-EV71-gHsol-EMCV-gL (SEQ ID NO :63):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT
GTGCGGAAGATCCGGACAGATTGTATAAGTATGCAACTAAGCTGAAGAAAAACTGTAAGGAAATAACTGATAAGG
AATTGGACAAGAAAATGAAGGAGCTCGCCGCCGTCATGAGCGACCCTGACCTGGAAACTGAGACTATGTGCCTCC
ACGACGACGAGTCGTGTCGCTACGAAGGGCAAGTCGCTGTTTACCAGGATGTATACGCGGTTGACGGACCGACAA
GTCTCTATCACCAAGCCAATAAGGGAGTTAGAGTCGCCTACTGGATAGGCTTTGACACCACCCCTTTTATGTTTA
AGAACTTGGCTGGAGCATATCCATCATACTCTACCAACTGGGCCGACGAAACCGTGTTAACGGCTCGTAACATAG
GCCTATGCAGCTCTGACGTTATGGAGCGGTCACGTAGAGGGATGTCCATTCTTAGAAAGAAGTATTTGAAACCAT -continued

| SEQUENCES |
|---|
| CCAACAATGTTCTATTCTCTGTTGGCTCGACCATCTACCACGAGAAGAGGGACTTACTGAGGAGCTGGCACCTGC |
| CGTCTGTATTTCACTTACGTGGCAAGCAAAATTACACATGTCGGTGTGAGACTATAGTTAGTTGCGACGGGTACG |
| TCGTTAAAAGAATAGCTATCAGTCCAGGCCTGTATGGGAAGCCTTCAGGCTATGCTGCTACGATGCACCGCGAGG |
| GATTCTTGTGCTGCAAAGTGACAGACACATTGAACGGGGAGAGGGTCTCTTTTCCCGTGTGCACGTATGTGCCAG |
| CTACATTGTGTGACCAAATGACTGGCATACTGGCAACAGATGTCAGTGCGGACGACGCGCAAAAACTGCTGGTTG |
| GGCTCAACCAGCGTATAGTCGTCAACGGTCGCACCCAGAGAAACACCAATACCATGAAAAATTACCTTTTGCCCG |
| TAGTGGCCCAGGCATTTGCTAGGTGGGCAAAGGAATATAAGGAAGATCAAGAAGATGAAAGGCCACTAGGACTAC |
| GAGATAGACAGTTAGTCATGGGGTGTTGTTGGGCTTTTAGAAGGCACAAGATAACATCTATTTATAAGCGCCCGG |
| ATACCCAAACCATCATCAAAGTGAACAGCGATTTCCACTCATTCGTGCTGCCCAGGATAGGCAGTAACACATTGG |
| AGATCGGGCTGAGAACAAGAATCAGGAAAATGTTAGAGGAGCACAAGGAGCCGTCACCTCTCATTACCGCCGAGG |
| ACGTACAAGAAGCTAAGTGCGCAGCCGATGAGGCTAAGGAGGTGCGTGAAGCCGAGGAGTTGCGCGCAGCTCTAC |
| CACCTTTGGCAGCTGATGTTGAGGAGCCCACTCTGGAAGCCGATGTCGACTTGATGTTACAAGAGGCTGGGGCCG |
| GCTCAGTGGAGACACCTCGTGGCTTGATAAAGGTTACCAGCTACGATGGCGAGGACAAGATCGGCTCTTACGCTG |
| TGCTTTCTCCGCAGGCTGTACTCAAGAGTGAAAAATTATCTTGCATCCACCCTCTCGCTGAACAAGTCATAGTGA |
| TAACACACTCTGGCCGAAAAGGGCGTTATGCCGTGGAACCATACCATGGTAAAGTAGTGGTGCCAGAGGGACATG |
| CAATACCCGTCCAGGACTTTCAAGCTCTGAGTGAAAGTGCCACCATTGTGTACAACGAACGTGAGTTCGTAAACA |
| GGTACCTGCACCATATTGCCACACATGGAGGAGCGCTGAACACTGATGAAGAATATTACAAAACTGTCAAGCCCA |
| GCGAGCACGACGGCGAATACCTGTACGACATCGACAGGAAACAGTGCGTCAAGAAAGAACTAGTCACTGGGCTAG |
| GGCTCACAGGCGAGCTGGTGGATCCTCCCTTCCATGAATTCGCCTACGAGAGTCTGAGAACACGACCAGCCGCTC |
| CTTACCAAGTACCAACCATAGGGGTGTATGGCGTGCCAGGATCAGGCAAGTCTGGCATCATTAAAAGCGCAGTCA |
| CCAAAAAAGATCTAGTGGTGAGCGCCAAGAAAGAAAACTGTGCAGAAATTATAAGGGACGTCAAGAAAATGAAAG |
| GGCTGGACGTCAATGCCAGAACTGTGGACTCAGTGCTCTTGAATGGATGCAAACACCCCGTAGAGACCCTGTATA |
| TTGACGAAGCTTTTGCTTGTCATGCAGGTACTCTCAGAGCGCTCATAGCCATTATAAGACCTAAAAAGGCAGTGC |
| TCTGCGGGGATCCCAAACAGTGCGGTTTTTTAACATGATGTGCCTGAAAGTGCATTTTAACCACGAGATTTGCA |
| CACAAGTCTTCCACAAAAGCATCTCTCGCCGTTGCACTAAATCTGTGACTTCGGTCGTCTCAACCTTGTTTTACG |
| ACAAAAAAATGAGAACGACGAATCCGAAAGAGACTAAGATTGTGATTGACACTACCGGCAGTACCAAACCTAAGC |
| AGGACGATCTCATTCTCACTTGTTTCAGAGGGTGGGTGAAGCAGTTGCAAATAGATTACAAAGGCAACGAAATAA |
| TGACGGCAGCTGCCTCTCAAGGGCTGACCCGTAAAGGTGTGTATGCCGTTCGGTACAAGGTGAATGAAAATCCTC |
| TGTACGCACCCACCTCAGAACATGTGAACGTCCTACTGACCCGCACGGAGGACCGCATCGTGTGGAAAACACTAG |
| CCGGCGACCCATGGATAAAAACACTGACTGCCAAGTACCCTGGGAATTTCACTGCCACGATAGAGGAGTGGCAAG |
| CAGAGCATGATGCCATCATGAGGCACATCTTGGAGAGACCGGACCCTACCGACGTCTTCCAGAATAAGGCAAACG |
| TGTGTTGGGCCAAGGCTTTAGTGCCGGTGCTGAAGACCGCTGGCATAGACATGACCACTGAACAATGGAACACTG |
| TGGATTATTTTGAAACGGACAAAGCTCACTCAGCAGAGATAGTATTGAACCAACTATGCGTGAGGTTCTTTGGAC |
| TCGATCTGGACTCCGGTCTATTTTCTGCACCCACTGTTCCGTTATCCATTAGGAATAATCACTGGGATAACTCCC |
| CGTCGCCTAACATGTACGGGCTGAATAAAGAAGTGGTCCGTCAGCTCTCTCGCAGGTACCCACAACTGCCTCGGG |
| CAGTTGCCACTGGAAGAGTCTATGACATGAACACTGGTACACTGCGCAATTATGATCCGCGCATAAACCTAGTAC |
| CTGTAAACAGAAGACTGCCTCATGCTTTAGTCCTCCACCATAATGAACACCCACAGAGTGACTTTTCTTCATTCG |
| TCAGCAAATTGAAGGGCAGAACTGTCCTGGTGGTCGGGGAAAAGTTGTCCGTCCCAGGCAAAATGGTTGACTGGT |
| TGTCAGACCGGCCTGAGGCTACCTTCAGAGCTCGGCTGGATTTAGGCATCCCAGGTGATGTGCCCAAATATGACA |
| TAATATTTGTTAATGTGAGGACCCCATATAAATACCATCACTATCAGCAGTGTGAAGACCATGCCATTAAGCTTA |
| GCATGTTGACCAAGAAAGCTTGTCTGCATCTGAATCCCGGCGGAACCTGTGTCAGCATAGGTTATGGTTACGCTG |
| ACAGGGCCAGCGAAAGCATCATTGGTGCTATAGCGCGGCAGTTCAAGTTTTCCCGGGTATGCAAACCGAAATCCT |
| CACTTGAAGAGACGGAAGTTCTGTTTGTATTCATTGGGTACGATCGCAAGGCCCGTACGCACAATCCTTACAAGC |
| TTTCATCAACCTTGACCAACATTTATACAGGTTCCAGACTCCACGAAGCCGGATGTGCACCCTCATATCATGTGG |
| TGCGAGGGGATATTGCCACGGCCACCGAAGGAGTGATTATAAATGCTGCTAACAGCAAAGGACAACCTGGCGGAG |
| GGGTGTGCGGAGCGCTGTATAAGAAATTCCCGGAAAGCTTCGATTTACAGCCGATCGAAGTAGGAAAAGCGCGAC |
| TGGTCAAAGGTGCAGCTAAACATATCATTCATGCCGTAGGACCAAACTTCAACAAAGTTTCGGAGGTTGAAGGTG |
| ACAAACAGTTGGCAGAGGCTTATGAGTCCATCGCTAAGATTGTCAACGATAACAATTACAAGTCAGTAGCGATTC |
| CACTGTTGTCCACCGGCATCTTTTCCGGGAACAAAGATCGACTAACCCAATCATTGAACCATTTGCTGACAGCTT |
| TAGACACCACTGATGCAGATGTAGCCATATACTGCAGGGACAAGAAATGGGAAATGACTCTCAAGGAAGCAGTGG |
| CTAGGAGAGAAGCAGTGGAGGAGATATGCATATCCGACGACTCTTCAGTGACAGAACCTGATGCAGAGCTGGTGA |
| GGGTGCATCCGAAGAGTTCTTTGGCTGGAAGGAAGGGCTACAGCACAAGCGATGGCAAAACTTTCTCATATTTGG |
| AAGGGACCAAGTTTCACCAGGCGGCCAAGGATATAGCAGAAATTAATGCCATGTGGCCCGTTGCAACGGAGGCCA |
| ATGAGCAGGTATGCATGTATATCCTCGGAGAAAGCATGAGCAGTATTAGGTCGAAATGCCCCGTCGAAGAGTCGG |
| AAGCCTCCACACCACCTAGCACGCTGCCTTGCTTGTGCATCCATGCCATGACTCCAGAAAGAGTACAGCGCCTAA |
| AAGCCTCACGTCCAGAACAAATTACTGTGTGCTCATCCTTTCCATTGCCGAAGTATAGAATCACTGGTGTGCAGA |
| AGATCCAATGCTCCCAGCCTATATTGTTCTCACCGAAAGTGCCTGCGTATATTCATCCAAGGAAGTATCTCGTGG |
| AAACACCACCGGTAGACGAGACTCCGGAGCCATCGGCAGAGAACCAATCCACAGAGGGGACACCTGAACAACCAC |
| CACTTATAACCGAGGATGAGACCAGGACTAGAACGCCTGAGCCGATCATCATCGAAGAGGAAGAAGAGGATAGCA |
| TAAGTTTGCTGTCAGATGGCCCGACCCACCAGGTGCTGCAAGTCGAGGCAGACATTCACGGGCCGCCCTCTGTAT |
| CTAGCTCATCCTGGTCCATTCCTCATGCATCCGACTTTGATGTGGACAGTTTATCCATACTTGACACCCTGGAGG |
| GAGCTAGCGTGACCAGCGGGGCAACGTCAGCCGAGACTAACTCTTACTTCGCAAAGAGTATGGAGTTTCTGGCGC |
| GACCGGTGCCTGCGCCTCGAACAGTATTCAGGAACCCTCCACATCCCGCTCCGCGCACAAGAACACCGTCACTTG |
| CACCCAGCAGGGCCTGCTCGAGAACCAGCCTAGTTTCCACCCCGCCAGGCGTGAATAGGGTGATCACTAGAGAGG |
| AGCTCGAGGCGCTTACCCCGTCACGCACTCCTAGCAGGTCGGTCTCGAGAACCAGCCTGGTCTCCAACCCGCCAG |
| GCGTAAATAGGGTGATTACAAGAGAGGAGTTTGAGGCGTTCGTAGCACAACAACAATGACGGTTTGATGCGGGTG |
| CATACATCTTTTCCTCCGACACCGGTCAAGGGCATTTACAACAAAAATCAGTAAGGCAAACGGTGCTATCCGAAG |
| TGGTGTTGGAGAGGACCGAATTGGAGATTTCGTATGCCCCGCGCCTCGACCAAGAAAAAGAAGAATTACTACGCA |
| AGAAATTACAGTTAAATCCCACACCTGCTAACAGAAGCAGATACCAGTCCAGGAAGGTGGAGAACATGAAAGCCA |
| TAACAGCTAGACGTATTCTGCAAGGCCTAGGGCATTATTTGAAGGCAGAAGGAAAAGTGGAGTGCTACCGAACCC |
| TGCATCCTGTTCCTTTGTATTCATCTAGTGTGAACCGTGCCTTTTCAAGCCCCAAGGTCGCAGTGGAAGCCTGTA |
| ACGCCATGTTGAAAGAGAACTTTCCGACTGTGGCTTCTTACTGTATTATTCCAGAGTACGATGCCTATTTGGACA |
| TGGTTGACGGAGCTTCATGCTGCTTAGACACTGCCAGTTTTTGCCCTGCAAAGCTGCGCAGCTTTCCAAAGAAAC |
| ACTCCTATTTGGAACCCACAATACGATCGGCAGTGCCTTCAGCGATCCAGAACACGCTCCAGAACGTCCTGGCAG |
| CTGCCACAAAAAGAAATTGCAATGTCACGCAAATGAGAGAATTGCCCGTATTGGATTCGGCGGCCTTTAATGTGG |
| AATGCTTCAAGAAATATGCGTGTAATAATGAATATTGGGAAACGTTTAAAGAAAACCCCATCAGGCTTACTGAAG |
| AAAACGTGGTAAATTACATTACCAAATTAAAAGGACCAAAAGCTGCTGCTCTTTTTGCGAAGACACATAATTTGA |

-continued

SEQUENCES

ATATGTTGCAGGACATACCAATGGACAGGTTTGTAATGGACTTAAAGAGAGACGTGAAAGTGACTCCAGGAACAA
AACATACTGAAGAACGGCCCAAGGTACAGGTGATCCAGGCTGCCGATCCGCTAGCAACAGCGTATCTGTGCGGAA
TCCACCGAGAGCTGGTTAGGAGATTAAATGCGGTCCTGCTTCCGAACATTCATACACTGTTTGATATGTCGGCTG
AAGACTTTGACGCTATTATAGCCGAGCACTTCCAGCCTGGGGATTGTGTTCTGGAAACTGACATCGCGTCGTTTG
ATAAAAGTGAGGACGACGCCATGGCTCTGACCGCGTTAATGATTCTGGAAGACTTAGGTGTGGACGCAGAGCTGT
TGACGCTGATTGAGGCGGCTTTCGGCGAAATTTCATCAATACATTTGCCCACTAAAACTAAATTTAAATTCGGAG
CCATGATGAAATCTGGAATGTTCCTCACACTGTTTGTGAACACAGTCATTAACATTGTAATCGCAAGCAGAGTGT
TGAGAGAACGGCTAACCGGATCACCATGTGCAGCATTCATTGGAGATGACAATATCGTGAAAGGAGTCAAATCGG
ACAAATTAATGGCAGACAGGTGCGCCACCTGGTTGAATATGGAAGTCAAGATTATAGATGCTGTGGTGGGCGAGA
AAGCGCCTTATTTCTGTGGAGGGTTTATTTTGTGTGACTCCGTGACCGGCACAGCGTGCCGTGTGGCAGACCCCC
TAAAAAGGCTGTTTAAGCTTGGCAAACCTCTGGCAGCAGACGATGAACATGATGATGACAGGAGAAGGGCATTGC
ATGAAGAGTCAACACGCTGGAACCGAGTGGGTATTCTTTCAGAGCTGTGCAAGGCAGTAGAATCAAGGTATGAAA
CCGTAGGAACTTCCATCATAGTTATGGCCATGACTACTCTAGCTAGCAGTGTTAAATCATTCAGCTACCTGAGAG
GGGCCCCTATAACTCTCTACGGCTAACCTGAATGGACTACGACATAGTCTAGTCCGCCAAGCTATTCCAGAAGTA
GTGAGGAGGCTTTTTGGAGGCCTAGGCTTTTGCAAAAAGCTTGTATATCCATTTTCGGATCTGATCAAGAGACA
GGATGAGGATCGTTTCGCATGATTGAATAAGATGGATTGCACGTAGGTTCTCCGGCCGCTTGGGTGGAGAGGCTA
TTCGGCTATGACTGGGCACAACTGACAATCGGCTGCTCTGATGCCGCCGTGATCCGGTTGTCAGCGCAGGGGCGC
CCGGTTCTTTTTGTCAAGACCGACCTGTCCGGTGCCCTGAATGAACTGAAGGACGAGGCAGCGCGGCTATCGTGG
CTGGCCACGACGGGCGTTCCTTGCGCAGTCTAGACTGGCGCGCCAAACCTGCAGGTTAAAACAGCTGTGGGTTGT
TCCCACCCACAGGGCCCACTGGGCGCTAGCACTCTGATTTTACGAAATCCTTGTGCGCCTGTTTTATATCCCTTC
CCTAATTCGAAACGTAGAAGCAATGCGCACCACTGATCAATAGTAGGCGTAACGCGCCAGTTACGTCATGATCAA
GCATATCTGTTCCCCCGGACTGAGTATCAATAGACTGCTTACGCGGTTGAAGGAGAAAACGTTCGTTATCCGGCT
AACTACTTCGAGAAGCCCAGTAACACCATGGAAGCTGCAGGGTGTTTCGCTCAGCACTTCCCCCGTGTAGATCAG
GTCGATGAGCCACTGCAATCCCCACAGGTGACTGTGGCAGTGGCTGCGTTGGCGGCCTGCCTATGGGGAGACCCA
TAGGACGCTCTAATGTGGACATGGTGCGAAGAGCCTATTGAGCTAGTTAGTAGTCCTCCGGCCCCTGAATGCGGC
TAATCCTAACTGCGGAGCACATGCCTTCAACCCAGAGGGTAGTGTGTCGTAATGGGCAACTCTGCAGCGGAACCG
ACTACTTTGGGTGTCCGTGTTTCTTTTTATTCTTATATTGGCTGCTTATGGTGACAATTACAGAATTGTTACCAT
ATAGCTATTGGATTGGCCATCCGGTGTGTAATAGAGCTGTTATATACCTATTTGTTGGCTTTGTACCACTAACTT
TAAAATCTATAACTACCCTCAACTTTATATTAACCCTCAATACAGTTGAACATGAGGCCTGGCCTGCCCTCCTAC
CTGATCATCCTGGCCGTGTGCCTGTTCAGCCACCTGCTGTCCAGCAGATACGGCGCCGAGGCCGTGAGCGAGCCC
CTGGACAAGGCTTTCCACCTGCTGCTGAACACCTACGGCAGACCCATCCGGTTTCTGCGGGAGAACACCACCCAG
TGCACCTACAACAGCAGCCTGCGGAACAGCACCGTCGTGAGAGAGAACGCCATCAGCTTCAACTTTTTCCAGAGC
TACAACCAGTACTACGTGTTCCACATGCCCAGATGCCTGTTTGCCGGCCCTCTGGCCGAGCAGTTCCTGAACCAG
GTGGACCTGACCGAGACACTGGAAAGATACCAGCAGCGGCTGAATACCTACGCCCTGGTGTCCAAGGACCTGGCC
AGCTACCGGTCCTTTAGCCAGCAGCTCAAGGCTCAGGATAGCCTCGGCGAGCAGCCTACCACCGTGCCCCCTCCC
ATCGACCTGAGCATCCCCCACGTGTGGATGCCTCCCCAGACCACCCCTCACGGCTGGACCGAGAGCCACACCACC
TCCGGCCTGCACAGACCCCACTTCAACCAGACCTGCATCCTGTTCGACGGCCACGACCTGCTGTTTAGCACCGTG
ACCCCCTGCCTGCACCAGGGCTTCTACCTGATCGACGAGCTGAGATACGTGAAGATCACCCTGACCGAGGATTTC
TTCGTGGTCACCGTGTCCATCGACGACGACACCCCCATGCTGCTGATCTTCGGCCACCTGCCCAGAGTGCTGTTC
AAGGCCCCCTACCAGCGGGACAACTTCATCCTGCGGCAGACCGAGAAGCACGAGCTGCTGGTGCTGGTCAAGAAG
GACCAGCTGAACCGGCACTCCTACCTGAAGGACCCCGACTTCCTGGACGCCGCCCTGGACTTCAACTACCTGGAC
CTGAGCGCCCTGCTGAGAAACAGCTTCCACAGATACGCCGTGGACGTGCTGAAGTCCGGACGGTGCCAGATGCTC
GATCGGCGGACCGTGGAGATGGCCTTCGCCTATGCCCTCGCCCTGTTCGCCGCTGCCAGACAGGAAGAGGCTGGC
GCCCAGGTGTCAGTGCCCAGAGCCCTGGATAGACAGGCCGCCCTGCTGCAGATCCAGGAATTCATGATCACCTGC
CTGAGCCAGACCCCCCCTAGAACCACCCTGCTGCTGTACCCCACAGCCGTGGATCTGGCCAAGAGGGCCCTGTGG
ACCCCCAACCAGATCACCGACATCACAAGCCTCGTGCGGCTCGTGTACATCCTGAGCAAGCAGAACCAGCAGCAC
CTGATCCCCCAGTGGGCCCTGAGACAGATCGCCGACTTCGCCCTGAAGCTGCACAAGACCCATCTGGCCAGCTTT
CTGAGCGCCTTCGCCAGGCAGGAACTGTACCTGATGGGCAGCCTGGTCCACAGCATGCTGGTGCATACCACCGAG
CGGCGGGAGATCTTCATCGTGGAGACAGGCCTGTGTAGCCTGGCCGAGCTGTCCCACTTTACCCAGCTGCTGGCC
CACCCTCACCACGAGTACCTGAGCGACCTGTACACCCCCTGCAGCAGCAGCGGCAGACGGGACCACAGCCTGGAA
CGGCTGACCAGACTGTTCCCCGATGCCACCGTGCCTGCTACAGTGCCTGCCGCCCTGTCCATCCTGTCCACCATG
CAGCCCAGCACCCTGGAAACCTTCCCCGACCTGTTCTGCCTGCCCCTGGGCGAGAGCTTTAGCGCCCTGACCGTG
TCCGAGCACGTGTCCTACATCGTGACCAATCAGTACCTGATCAAGGGCATCAGCTACCCCGTGTCCACCACAGTC
GTGGGCCAGAGCCTGATCATCACCCAGACCGACAGCCAGACCAAGTGCGAGCTGACCCGGAACATGCACACCACA
CACAGCATCACCGTGGCCCTGAACATCAGCCTGGAAAACTGCGCTTTCTGTCAGTCTGCCCTGCTGGAATACGAC
GATACCCAGGGCGTGATCAACATCATGTACATGCACGACAGCGACGACGTGCTGTTCGCCCTGGACCCCTACAAC
GAGGTGGTGGTGTCCAGCCCCCGGACCCACTACCTGATGCTGCTGAAGAACGGCACCGTGCTGGAAGTGACCGAC
GTGGTGGTGGACGCCACCGACTGATAACGCCGGCGCCCCCCCCTAACGTTACTGGCCGAAGCCGCTTGGAATAAG
GCCGGTGTGCGTTTGTCTATATGTTATTTTCCACCATATTGCCGTCTTTTGGCAATGTGAGGGCCCGGAAACCTG
GCCCTGTCTTCTTGACGAGCATTCCTAGGGGTCTTTCCCCTCTCGCCAAAGGAATGCAAGGTCTGTTGAATGTCG
TGAAGGAAGCAGTTCCTCTGGAAGCTTCTTGAAGACAAACAACGTCTGTAGCGACCCTTTGCAGGCAGCGGAACC
CCCCACCTGGCGACAGGTGCCTCTGCGGCCAAAAGCCACGTGTATAAGATACACCTGCAAAGGCGGCACAACCCC
AGTGCCACGTTGTGAGTTGGATAGTTGTGGAAAGAGTCAAATGGCTCTCCTCAAGCGTATTCAACAAGGGGCTGA
AGGATGCCCAGAAGGTACCCCATTGTATGGGATCTGATCTGGGGCCTCGGTGCACATGCTTTACATGTGTTTAGT
CGAGGTTAAAAAAACGTCTAGGCCCCCCGAACCACGGGGACGTGGTTTTCCTTTGAAAAACACGATAATAATATG
TGCAGAAGGCCCGACTGCGGCTTCAGCTTCAGCCCTGGACCCGTGATCCTGCTGTGGTGCTGCCTGCTGCTGCCT
ATCGTGTCCTCTGCCGCCGTGTCTGTGGCCCCTACAGCCGCCGAGAAGGTGCCAGCCGAGTGCCCCGAGCTGACC
AGAAGATGCCTGCTGGGCGAGGTGTTCGAGGGCGACAAGTACGAGAGCTGGCTGCGGCCCCTGGTCAACGTGACC
GGCAGAGATGGCCCCCTGAGCCAGCTGATCCGGTACAGACCCGTGACCCCCGAGGCCGCCAATAGCGTGCTGCTG
GACGAGGCCTTCCTGGATACCCTGGCCCTGCTGTACAACAACCCCGACCAGCTGAGAGCCCTGCTGACCCTGCTG
TCCAGCGACACCGCCCCCAGATGGATGACCGTGATGCGGGGCTACAGCGAGTGTGGAGATGGCAGCCCTGCCGTG
TACACCTGCGTGGACGACCTGTGCAGAGGCTACGACCTGACCAGACTGAGCTACGGCCGGTCCATCTTCACAGAG
CACGTGCTGGGCTTCGAGCTGGTGCCCCCCAGCCTGTTCAACGTGGTGGTGGCCATCCGGAACGAGGCCACCAGA
ACCAACAGAGCCGTGCGGCTGCCTGTGTCTACAGCCGCTGCACCTGAGGGCATCACACTGTTCTACGGCCTGTAC
AACGCCGTGAAAGAGTTCTGCCTCCGGCACCAGCTGGATCCCCCCCTGCTGAGACACCTGGACAAGTACTACGCC
GGCCTGCCCCCAGAGCTGAAGCAGACCAGAGTGAACCTGCCCGCCCACAGCAGATATGGCCCTCAGGCCGTGGAC
GCCAGATGATAAGCGGCCGCATACAGCAGCAATTGGCAAGCTGCTTACATAGAACTCGCGGCGATTGGCATGCCG

-continued

SEQUENCES

CCTTAAAATTTTTATTTTATTTTTCTTTTCTTTTCCGAATCGGATTTTGTTTTTAATATTTCAAAAAAAAAAAA
AAAAAAAAAAAAAAAAAAAAAAAGGGTCGGCATGGCATCTCCACCTCCTCGCGGTCCGACCTGGGCATCCGAAGGA
GGACGCACGTCCACTCGGATGGCTAAGGGAGAGCCACGTTTAAACACGTGATATCTGGCCTCATGGGCCTTCCTT
TCACTGCCCGCTTTCCAGTCGGGAAACCTGTCGTGCCAGCTGCATTAACATGGTCATAGCTGTTTCCTTGCGTAT
TGGGCGCTCTCCGCTTCCTCGCTCACTGACTCGCTGCGCTCGGTCGTTCGGGTAAAGCCTGGGGTGCCTAATGAG
CAAAAGGCCAGCAAAAGGCCAGGAACCGTAAAAAGGCCGCGTTGCTGGCGTTTTTCCATAGGCTCCGCCCCCCTG
ACGAGCATCACAAAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTTGAGTCCAACCCGG
TAAGACACGACTTATCGCCACTGGCAGCAGCCACTGGTAACAGGATTAGCAGAGCGAGGTATGTAGGCGGTGCTA
CAGAGTTCTTGAAGTGGTGGCCTAACTACGGCTACACTAGAAGAACAGTATTTGGTATCTGCGCTCTGCTGAAGC
CAGTTACCTTCGGAAAAAGAGTTGGTAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCTTTGATCTTTTCTACGGGGTCTGACG
CTCAGTGGAACGAAAACTCACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTGACAGTTATTAGAAAAATT
CATCCAGCAGACGATAAAACGCAATACGCTGGCTATCCGGTGCCGCAATGCCATACAGCACCAGAAAACGATCCG
CCCATTCGCCGCCCAGTTCTTCCGCAATATCACGGGTGGCCAGCGCAATATCCTGATAACGATCCGCCACGCCCA
GACGGCCGCAATCAATAAAGCCGCTAAAACGGCCATTTTCCACCATAATGTTCGGCAGGCACGCATCACCATGGG
TCACCACCAGATCTTCGCCATCCGGCATGCTCGCTTTCAGACGCGCAAACAGCTCTGCCGGTGCCAGGCCCTGAT
GTTCTTCATCCAGATCATCCTGATCCACCAGGCCCGCTTCCATACGGGTACGCGCACGTTCAATACGATGTTTCG
CCTGATGATCAAACGGACAGGTCGCCGGGTCCAGGGTATGCAGACGACGCATGGCATCCGCCATAATGCTCACTT
TTTCTGCCGGCGCCAGATGGCTAGACAGCAGATCCTGACCCGGCACTTCGCCCAGCAGCAGCCAATCACGGCCCG
CTTCGGTCACCACATCCAGCACCGCCGCACACGGAACACCGGTGGTGGCCAGCCAGCTCAGACGCGCCGCTTCAT
CCTGCAGCTCGTTCAGCGCACCGCTCAGATCGGTTTTCACAAACAGCACCGGACGACCCTGCGCGCTCAGACGAA
ACACCGCCGCATCAGAGCAGCCAATGGTCTGCTGCGCCCAATCATAGCCAAACAGACGTTCCACCCACGCTGCCG
GGCTACCCGCATGCAGGCCATCCTGTTCAATCATACTCTTCCTTTTTCAATATTATTGAAGCATTTATCAGGGTT
ATTGTCTCATGAGCGGATACATATTTGAATGTATTTAGAAAAATAAACAAATAGGGGTTCCGCGCACATTTCCCC
GAAAAGTGCCACCTAAATTGTAAGCGTTAATATTTTGTTAAAATTCGCGTTAAATTTTTGTTAAATCAGCTCATT
TTTTAACCAATAGGCCGAAATCGGCAAAATCCCTTATAAATCAAAAGAATAGACCGAGATAGGGTTGAGTGGCCG
CTACAGGGCGCTCCCATTCGCCATTCAGGCTGCGCAACTGTTGGGAAGGGCGTTTCGGTGCGGGCCTCTTCGCTA
TTACGCCAGCTGGCGAAAGGGGGATGTGCTGCAAGGCGATTAAGTTGGGTAACGCCAGGGTTTTCCCAGTCACAC
GCGTAATACGACTCACTATAG

A537 Vector: SGP-342-EV71-gL-EMCV-gHsol (SEQ ID NO :64):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT
GTGCGGAAGATCCGGACAGATTGTATAAGTATGCAACTAAGCTGAAGAAAAACTGTAAGGAAATAACTGATAAGG
AATTGGACAAGAAAATGAAGGAGCTCGCCGCCGTCATGAGCGACCCTGACCTGGAAACTGAGACTATGTGCCTCC
ACGACGACGAGTCGTGTCGCTACGAAGGGCAAGTCGCTGTTTACCAGGATGTATACGCGGTTGACGGACCGACAA
GTCTCTATCACCAAGCCAATAAGGGAGTTAGAGTCGCCTACTGGATAGGCTTTGACACCACCCCTTTTATGTTTA
AGAACTTGGCTGGAGCATATCCATCATACTCTACCAACTGGGCCGACGAAACCGTGTTAACGGCTCGTAACATAG
GCCTATGCAGCTCTGACGTTATGGAGCGGTCACGTAGAGGGATGTCCATTCTTAGAAAGAAGTATTTGAAACCAT
CCAACAATGTTCTATTCTCTGTTGGCTCGACCATCTACCACGAGAAGAGGGACTTACTGAGGAGCTGGCACCTGC
CGTCTGTATTTCACTTACGTGGCAAGCAAAATTACACATGTCGGTGTGAGACTATAGTTAGTTGCGACGGGTACG
TCGTTAAAAGAATAGCTATCAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCGTGTGCACGTATGTGCCAG
CTACATTGTGTGACCAAATGACTGGCATACTGGCAACAGATGTCAGTGCGGACGACGCGCAAAAACTGCTGGTTG
GGCTCAACCAGCGTATAGTCGTCAACGGTCGCACCCAGAGAAACACCAATACCATGAAAAATTACCTTTTGCCCG
TAGTGGCCCAGGCATTTGCTAGGTGGGCAAAGGAATATAAGGAAGATCAAGAAGATGAAAGGCCACTAGGACTAC
GAGATAGACAGTTAGTCATGGGGTGTTGTTGGGCTTTTAGAAGGCACAAGATAACATCTATTTATAAGCGCCCGG
ATACCCAAACCATCATCAAAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCACCTCTCATTACCGCCGAGG
ACGTACAAGAAGCTAAGTGCGCAGCCGATGAGGCTAAGGAGGTGCGTGAAGCCGAGGAGTTGCGCGCAGCTCTAC
CACCTTTGGCAGCTGATGTTGAGGAGCCCACTCTGGAAGCCGATGTCGACTTGATGTTACAAGAGGCTGGGGCCG
GCTCAGTGGAGACACCTCGTGGCTTGATAAAGGTTACCAGCTACGATGGCGAGGACAAGATCGGCTCTTACGCTG
TGCTTTCTCCGCAGGCTGTACTCAAGAGTGAAAAATTATCTTGCATCCACCCTCTCGCTGAACAAGTCATAGTGA
TAACACACTCTGGCCGAAAAGGGCGTTATGCCGTGGAACCATACCATGGTAAAGTAGTGGTGCCAGAGGGACATG
CAATACCCGTCCAGGACTTTCAAGCTCTGAGTGAAAGTGCCACCATTGTGTACAACGAACGTGAGTTCGTAAACA
GGTACCTGCACCATATTGCCACACATGGAGGAGCGCTGAACACTGATGAAGAATATTACAAAACTGTCAAGCCCA
GCGAGCACGACGGCGAATACCTGTACGACATCGACAGGAAACAGTGCGTCAAGAAAGAACTAGTCACTGGGCTAG
GGCTCACAGGCGAGCTGGTGGATCCTCCCTTCCATGAATTCGCCTACGAGAGTCTGAGAACACGACCAGCCGCTC
CTTACCAAGTACCAACCATAGGGGTGTATGGCGTGCCAGGATCAGGCAAGTCTGGCATCATTAAAAGCGCAGTCA
CCAAAAAAGATCTAGTGGTGAGCGCCAAGAAAGAAAACTGTGCAGAAATTATAAGGGACGTCAAGAAAATGAAAG
GGCTGGACGTCAATGCCAGAACTGTGGACTCAGTGCTCTTGAATGGATGCAAACACCCCGTAGAGACCCTGTATA
TTGACGAAGCTTTTGCTTGTCATGCAGGTACTCTCAGAGCGCTCATAGCCATTATAAGACCTAAAAAGGCAGTGC
TCTGCGGGGATCCCAAACAGTGCGGTTTTTTTAACATGATGTGCCTGAAAGTGCATTTTAACCACGAGATTTGCA
CACAAGTCTTCCACAAAAGCATCTCTCGCCGTTGCACTAAATCTGTGACTTCGGTCGTCTCAACCTTGTTTTACG
ACAAAAAAATGAGAACGACGAATCCGAAAGAGACTAAGATTGTGATTGACACTACCGGCAGTACCAAACCTAAGC
AGGACGATCTCATTCTCACTTGTTTCAGAGGGTGGGTGAAGCAGTTGCAAATAGATTACAAAGGCAACGAAATAA
TGACGGCAGCTGCCTCTCAAGGGCTGACCCGTAAAGGTGTGTATGCCGTTCGGTACAAGGTGAATGAAAATCCTC
TGTACGCACCCACCTCAGAACATGTGAACGTCCTACTGACCCGCACGGAGGACCGCATCGTGTGGAAAACACTAG
CCGGCGACCCATGGATAAAAACACTGACTGCCAAGTACCCTGGGAATTTCACTGCCACGATAGAGGAGTGGCAAG
CAGAGCATGATGCCATCATGAGGCACATCTTGGAGAGACCGGACCCTACCGACGTCTTCCAGAATAAGGCAAACG
TGTGTTGGGCCAAGGCTTTAGTGCCGGTGCTGAAGACCGCTGGCATAGACATGACCACTGAACAATGGAACACTG -continued

| SEQUENCES |
| --- |
| TGGATTATTTTGAAACGGACAAAGCTCACTCAGCAGAGATAGTATTGAACCAACTATGCGTGAGGTTCTTTGGAC<br>TCGATCTGGACTCCGGTCTATTTTCTGCACCCACTGTTCCGTTATCCATTAGGAATAATCACTGGGATAACTCCC<br>CGTCGCCTAACATGTACGGGCTGAATAAAGAAGTGGTCCGTCAGCTCTCTCGCAGGTACCCACAACTGCCTCGGG<br>CAGTTGCCACTGGAAGAGTCTATGACATGAACACTGGTACACTGCGCAATTATGATCCGCGCATAAACCTAGTAC<br>CTGTAAACAGAAGACTGCCTCATGCTTTAGTCCTCCACCATAATGAACACCCACAGAGTGACTTTTCTTCATTCG<br>TCAGCAAATTGAAGGGCAGAACTGTCCTGGTGGTCGGGGAAAAGTTGTCCGTCCCAGGCAAAATGGTTGACTGGT<br>TGTCAGACCGGCCTGAGGCTACCTTCAGAGCTCGGCTGGATTTAGGCATCCCAGGTGATGTGCCCAAATATGACA<br>TAATATTTGTTAATGTGAGGACCCCATATAAATACCATCACTATCAGCAGTGTGAAGACCATGCCATTAAGCTTA<br>GCATGTTGACCAAGAAAGCTTGTCTGCATCTGAATCCCGGCGGAACCTGTGTCAGCATAGGTTATGGTTACGCTG<br>ACAGGGCCAGCGAAAGCATCATTGGTGCTATAGCGCGGCAGTTCAAGTTTTCCCGGGTATGCAAACCGAAATCCT<br>CACTTGAAGAGACGGAAGTTCTGTTTGTATTCATTGGGTACGATCGCAAGGCCCGTACGCACAATCCTTACAAGC<br>TTTCATCAACCTTGACCAACATTTATACAGGTTCCAGACTCCACGAAGCCGGATGTGCACCCTCATATCATGTGG<br>TGCGAGGGGATATTGCCACGGCCACCGAAGGAGTGATTATAAATGCTGCTAACAGCAAAGGACAACCTGGCGGAG<br>GGGTGTGCGGAGCGCTGTATAAGAAATTCCCGGAAAGCTTCGATTTACAGCCGATCGAAGTAGGAAAAGCGCGAC<br>TGGTCAAAGGTGCAGCTAAACATATCATTCATGCCGTAGGACCAAACTTCAACAAAGTTTCGGAGGTTGAAGGTG<br>ACAAACAGTTGGCAGAGGCTTATGAGTCCATCGCTAAGATTGTCAACGATAACAATTACAAGTCAGTAGCGATTC<br>CACTGTTGTCCACCGGCATCTTTTCCGGGAACAAAGATCGACTAACCCAATCATTGAACCATTTGCTGACAGCTT<br>TAGACACCACTGATGCAGATGTAGCCATATACTGCAGGGACAAGAAATGGGAAATGACTCTCAAGGAAGCAGTGG<br>CTAGGAGAGAAGCAGTGGAGGAGATATGCATATCCGACGACTCTTCAGTGACAGAACCTGATGCAGAGCTGGTGA<br>GGGTGCATCCGAAGAGTTCTTTGGCTGGAAGGAAGGGCTACAGCACAAGCGATGGCAAAACTTTCTCATATTTGG<br>AAGGGACCAAGTTTCACCAGGCGGCCAAGGATATAGCAGAAATTAATGCCATGTGGCCCGTTGCAACGGAGGCCA<br>ATGAGCAGGTATGCATGTATATCCTCGGAGAAAGCATGAGCAGTATTAGGTCGAAATGCCCCGTCGAAGAGTCGG<br>AAGCCTCCACACCACCTAGCACGCTGCCTTGCTTGTGCATCCATGCCATGACTCCAGAAAGAGTACAGCGCCTAA<br>AAGCCTCACGTCCAGAACAAATTACTGTGTGCTCATCCTTTCCATTGCCGAAGTATAGAATCACTGGTGTGCAGA<br>AGATCCAATGCTCCCAGCCTATATTGTTCTCACCGAAAGTGCCTGCGTATATTCATCCAAGGAAGTATCTCGTGG<br>AAACACCACCGGTAGACGAGACTCCGGAGCCATCGGCAGAGAACCAATCCACAGAGGGGACACCTGAACAACCAC<br>CACTTATAACCGAGGATGAGACCAGGACTAGAACGCCTGAGCCGATCATCATCGAAGAGGAAGAAGAGGATAGCA<br>TAAGTTTGCTGTCAGATGGCCCGACCCACCAGGTGCTGCAAGTCGAGGCAGACATTCACGGGCCGCCCTCTGTAT<br>CTAGCTCATCCTGGTCCATTCCTCATGCATCCGACTTTGATGTGGACAGTTTATCCATACTTGACACCCTGGAGG<br>GAGCTAGCGTGACCAGCGGGGCAACGTCAGCCGAGACTAACTCTTACTTCGCAAAGAGTATGGAGTTTCTGGCGC<br>GACCGGTGCCTGCGCCTCGAACAGTATTCAGGAACCCTCCACATCCCGCTCCGCGCACAAGAACACCGTCACTTG<br>CACCCAGCAGGGCCTGCTCGAGAACCAGCCTAGTTTCCACCCCGCCAGGCGTGAATAGGGTGATCACTAGAGAGG<br>AGCTCGAGGCGCTTACCCCGTCACGCACTCCTAGCAGGTCGGTCTCGAGAACCAGCCTGGTCTCCAACCCGCCAG<br>GCGTAAATAGGGTGATTACAAGAGAGGAGTTTGAGGCGTTCGTAGCACAACAACAATGACGGTTTGATGCGGGTG<br>CATACATCTTTTCCTCCGACACCGGTCAAGGGCATTTACAACAAAAATCAGTAAGGCAAACGGTGCTATCCGAAG<br>TGGTGTTGGAGAGGACCGAATTGGAGATTTCGTATGCCCCGCGCCTCGACCAAGAAAAAGAAGAATTACTACGCA<br>AGAAATTACAGTTAAATCCCACACCTGCTAACAGAAGCAGATACCAGTCCAGGAAGGTGGAGAACATGAAAGCCA<br>TAACAGCTAGACGTATTCTGCAAGGCCTAGGGCATTATTTGAAGGCAGAAGGAAAAGTGGAGTGCTACCGAACCC<br>TGCATCCTGTTCCTTTGTATTCATCTAGTGTGAACCGTGCCTTTTCAAGCCCCAAGGTCGCAGTGGAAGCCTGTA<br>ACGCCATGTTGAAAGAGAACTTTCCGACTGTGGCTTCTTACTGTATTATTCCAGAGTACGATGCCTATTTGGACA<br>TGGTTGACGGAGCTTCATGCTGCTTAGACACTGCCAGTTTTTGCCCTGCAAAGCTGCGCAGCTTTCCAAAGAAAC<br>ACTCCTATTTGGAACCCACAATACGATCGGCAGTGCCTTCAGCGATCCAGAACACGCTCCAGAACGTCCTGGCAG<br>CTGCCACAAAAAGAAATTGCAATGTCACGCAAATGAGAGAATTGCCCGTATTGGATTCGGCGGCCTTTAATGTGG<br>AATGCTTCAAGAAATATGCGTGTAATAATGAATATTGGGAAACGTTTAAAGAAAACCCCATCAGGCTTACTGAAG<br>AAAACGTGGTAAATTACATTACCAAATTAAAAGGACCAAAAGCTGCTGCTCTTTTTGCGAAGACACATAATTTGA<br>ATATGTTGCAGGACATACCAATGGACAGGTTTGTAATGGACTTAAAGAGAGACGTGAAAGTGACTCCAGGAACAA<br>AACATACTGAAGAACGGCCCAAGGTACAGGTGATCCAGGCTGCCGATCCGCTAGCAACAGCGTATCTGTGCGGAA<br>TCCACCGAGAGCTGGTTAGGAGATTAAATGCGGTCCTGCTTCCGAACATTCATACACTGTTTGATATGTCGGCTG<br>AAGACTTTGACGCTATTATAGCCGAGCACTTCCAGCCTGGGGATTGTGTTCTGGAAACTGACATCGCGTCGTTTG<br>ATAAAAGTGAGGACGACGCCATGGCTCTGACCGCGTTAATGATTCTGGAAGACTTAGGTGTGGACGCAGAGCTGT<br>TGACGCTGATTGAGGCGGCTTTCGGCGAAATTTCATCAATACATTTGCCCACTAAAACTAAATTTAAATTCGGAG<br>CCATGATGAAATCTGGAATGTTCCTCACACTGTTTGTGAACACAGTCATTAACATTGTAATCGCAAGCAGAGTGT<br>TGAGAGAACGGCTAACCGGATCACCATGTGCAGCATTCATTGGAGATGACAATATCGTGAAAGGAGTCAAATCGG<br>ACAAATTAATGGCAGACAGGTGCGCCACCTGGTTGAATATGGAAGTCAAGATTATAGATGCTGTGGTGGGCGAGA<br>AAGCGCCTTATTTCTGTGGAGGGTTTATTTTGTGTGACTCCGTGACCGGCACAGCGTGCCGTGTGGCAGACCCCC<br>TAAAAAGGCTGTTTAAGCTTGGCAAACCTCTGGCAGCAGACGATGAACATGATGATGACAGGAGAAGGGCATTGC<br>ATGAAGAGTCAACACGCTGGAACCGAGTGGGTATTCTTTCAGAGCTGTGCAAGGCAGTAGAATCAAGGTATGAAA<br>CCGTAGGAACTTCCATCATAGTTATGGCCATGACTACTCTAGCTAGCAGTGTTAAATCATTCAGCTACCTGAGAG<br>GGGCCCCTATAACTCTCTACGGCTAACCTGAATGGACTACGACATAGTCTAGTCCGCCAAGCTATTCCAGAAGTA<br>GTGAGGAGGCTTTTTTGGAGGCCTAGGCTTTTGCAAAAAGCTTGTATATCCATTTTCGGATCTGATCAAGAGACA<br>GGATGAGGATCGTTTCGCATGATTGAATAAGATGGATTGCACGTAGGTTCTCCGGCCGCTTGGGTGGAGAGGCTA<br>TTCGGCTATGACTGGGCACAACTGACAATCGGCTGCTCTGATGCCGCCGTGATCCGGTTGTCAGCGCAGGGGCGC<br>CCGGTTCTTTTTGTCAAGACCGACCTGTCCGGTGCCCTGAATGAACTGAAGGACGAGGCAGCGCGGCTATCGTGG<br>CTGGCCACGACGGGCGTTCCTTGCGCAGTCTAGACTGGCGCGCCAAACCTGCAGGTTAAAACAGCTGTGGGTTGT<br>TCCCACCCACAGGGCCCACTGGGCGCTAGCACTCTGATTTTACGAAATCCTTGTGCGCCTGTTTTATATCCCTTC<br>CCTAATTCGAAACGTAGAAGCAATGCGCACCACTGATCAATAGTAGGCGTAACGCGCCAGTTACGTCATGATCAA<br>GCATATCTGTTCCCCCGGACTGAGTATCAATAGACTGCTTACGCGGTTGAAGGAGAAAACGTTCGTTATCCGGCT<br>AACTACTTCGAGAAGCCCAGTAACACCATGGAAGCTGCAGGGTGTTTCGCTCAGCACTTCCCCCGTGTAGATCAG<br>GTCGATGAGCCACTGCAATCCCCACAGGTGACTGTGGCAGTGGCTGCGTTGGCGGCCTGCCTATGGGGAGACCCA<br>TAGGACGCTCTAATGTGGACATGGTGCGAAGAGCCTATTGAGCTAGTTAGTAGTCCTCCGGCCCCTGAATGCGGC<br>TAATCCTAACTGCGGAGCACATGCCTTCAACCCAGAGGGTAGTGTGTCGTAATGGGCAACTCTGCAGCGGAACCG<br>ACTACTTTGGGTGTCCGTGTTTCTTTTTATTCTTATATTGGCTGCTTATGGTGACAATTACAGAATTGTTACCAT<br>ATAGCTATTGGATTGGCCATCCGGTGTGTAATAGAGCTGTTATATACCTATTTGTTGGCTTTGTACCACTAACTT<br>**TAAAATCTATAACTACCCTCAACTTTATATTAACCCTCAATACAGTTGAACATGTGCAGAAGGCCCGACTGCGGC**<br>**TTCAGCTTCAGCCCTGGACCCGTGATCCTGCTGTGGTGCTGCCTGCTGCTGCCTATCGTGTCCTCTGCCGCCGTG**<br>**TCTGTGGCCCCTACAGCCGCCGAGAAGGTGCCAGCCGAGTGCCCCGAGCTGACCAGAAGATGCCTGCTGGGCGAG**<br>**GTGTTCGAGGGCGACAAGTACGAGAGCTGGCTGCGGCCCCTGGTCAACGTGACCGGCAGAGATGGCCCCCTGAGC** |

-continued

SEQUENCES

CAGCTGATCCGGTACAGACCCGTGACCCCCGAGGCCGCCAATAGCGTGCTGCTGGACGAGGCCTTCCTGGATACC
CTGGCCCTGCTGTACAACAACCCCGACCAGCTGAGAGCCCTGCTGACCCTGCTGTCCAGCGACACCGCCCCCAGA
TGGATGACCGTGATGCGGGGCTACAGCGAGTGTGGAGATGGCAGCCCTGCCGTGTACACCTGCGTGGACGACCTG
TGCAGAGGCTACGACCTGACCAGACTGAGCTACGGCCGGTCCATCTTCACAGAGCACGTGCTGGGCTTCGAGCTG
GTGCCCCCCAGCCTGTTCAACGTGGTGGTGGCCATCCGGAACGAGGCCACCAGAACCAACAGAGCCGTGCGGCTG
CCTGTGTCTACAGCCGCTGCACCTGAGGGCATCACACTGTTCTACGGCCTGTACAACGCCGTGAAAGAGTTCTGC
CTCCGGCACCAGCTGGATCCCCCCCTGCTGAGACACCTGGACAAGTACTACGCCGGCCTGCCCCCAGAGCTGAAG
CAGACCAGAGTGAACCTGCCCGCCCACAGCAGATATGGCCCTCAGGCCGTGGACGCCAGATGATAACGCCGGCGC
CCCCCCCTAACGTTACTGGCCGAAGCCGCTTGGAATAAGGCCGGTGTGCGTTTGTCTATATGTTATTTTCCACCA
TATTGCCGTCTTTTGGCAATGTGAGGGCCCGGAAACCTGGCCCTGTCTTCTTGACGAGCATTCCTAGGGGTCTTT
CCCCTCTCGCCAAAGGAATGCAAGGTCTGTTGAATGTCGTGAAGGAAGCAGTTCCTCTGGAAGCTTCTTGAAGAC
AAACAACGTCTGTAGCGACCCTTTGCAGGCAGCGGAACCCCCCACCTGGCGACAGGTGCCTCTGCGGCCAAAAGC
CACGTGTATAAGATACACCTGCAAAGGCGGCACAACCCCAGTGCCACGTTGTGAGTTGGATAGTTGTGGAAAGAG
TCAAATGGCTCTCCTCAAGCGTATTCAACAAGGGGCTGAAGGATGCCCAGAAGGTACCCCATTGTATGGGATCTG
ATCTGGGGCCTCGGTGCACATGCTTTACATGTGTTTAGTCGAGGTTAAAAAAACGTCTAGGCCCCCCGAACCACG
GGGACGTGGTTTTCCTTTGAAAAACACGATAATAATATGAGGCCTGGCCTGCCCTCCTACCTGATCATCCTGGCC
GTGTGCCTGTTCAGCCACCTGCTGTCCAGCAGATACGGCGCCGAGGCCGTGAGCGAGCCCCTGGACAAGGCTTTC
CACCTGCTGCTGAACACCTACGGCAGACCCATCCGGTTTCTGCGGGAGAACACCACCCAGTGCACCTACAACAGC
AGCCTGCGGAACAGCACCGTCGTGAGAGAGAACGCCATCAGCTTCAACTTTTTCCAGAGCTACAACCAGTACTAC
GTGTTCCACATGCCCAGATGCCTGTTTGCCGGCCCTCTGGCCGAGCAGTTCCTGAACCAGGTGGACCTGACCGAG
ACACTGGAAAGATACCAGCAGCGGCTGAATACCTACGCCCTGGTGTCCAAGGACCTGGCCAGCTACCGGTCCTTT
AGCCAGCAGCTCAAGGCTCAGGATAGCCTCGGCGAGCAGCCTACCACCGTGCCCCCTCCCATCGACCTGAGCATC
CCCCACGTGTGGATGCCTCCCCAGACCACCCCTCACGGCTGGACCGAGAGCCACACCACCTCCGGCCTGCACAGA
CCCCACTTCAACCAGACCTGCATCCTGTTCGACGGCCACGACCTGCTGTTTAGCACCGTGACCCCCTGCCTGCAC
CAGGGCTTCTACCTGATCGACGAGCTGAGATACGTGAAGATCACCCTGACCGAGGATTTCTTCGTGGTCACCGTG
TCCATCGACGACGACACCCCCATGCTGCTGATCTTCGGCCACCTGCCCAGAGTGCTGTTCAAGGCCCCCTACCAG
CGGGACAACTTCATCCTGCGGCAGACCGAGAAGCACGAGCTGCTGGTGCTGGTCAAGAAGGACCAGCTGAACCGG
CACTCCTACCTGAAGGACCCCGACTTCCTGGACGCCGCCCTGGACTTCAACTACCTGGACCTGAGCGCCCTGCTG
AGAAACAGCTTCCACAGATACGCCGTGGACGTGCTGAAGTCCGGACGGTGCCAGATGCTCGATCGGCGGACCGTG
GAGATGGCCTTCGCCTATGCCCTCGCCCTGTTCGCCGCTGCCAGACAGGAAGAGGCTGGCGCCCAGGTGTCAGTG
CCCAGAGCCCTGGATAGACAGGCCGCCCTGCTGCAGATCCAGGAATTCATGATCACCTGCCTGAGCCAGACCCCC
CCTAGAACCACCCTGCTGCTGTACCCCACAGCCGTGGATCTGGCCAAGAGGGCCCTGTGGACCCCCAACCAGATC
ACCGACATCACAAGCCTCGTGCGGCTCGTGTACATCCTGAGCAAGCAGAACCAGCAGCACCTGATCCCCCAGTGG
GCCCTGAGACAGATCGCCGACTTCGCCCTGAAGCTGCACAAGACCCATCTGGCCAGCTTTCTGAGCGCCTTCGCC
AGGCAGGAACTGTACCTGATGGGCAGCCTGGTCCACAGCATGCTGGTGCATACCACCGAGCGGCGGGAGATCTTC
ATCGTGGAGACAGGCCTGTGTAGCCTGGCCGAGCTGTCCCACTTTACCCAGCTGCTGGCCCACCCTCACCACGAG
TACCTGAGCGACCTGTACACCCCCTGCAGCAGCAGCGGCAGACGGGACCACAGCCTGGAACGGCTGACCAGACTG
TTCCCCGATGCCACCGTGCCTGCTACAGTGCCTGCCGCCCTGTCCATCCTGTCCACCATGCAGCCCAGCACCCTG
GAAACCTTCCCCGACCTGTTCTGCCTGCCCCTGGGCGAGAGCTTTAGCGCCCTGACCGTGTCCGAGCACGTGTCC
TACATCGTGACCAATCAGTACCTGATCAAGGGCATCAGCTACCCCGTGTCCACCACAGTCGTGGGCCAGAGCCTG
ATCATCACCCAGACCGACAGCCAGACCAAGTGCGAGCTGACCCGGAACATGCACACCACACACAGCATCACCGTG
GCCCTGAACATCAGCCTGGAAAACTGCGCTTTCTGTCAGTCTGCCCTGCTGGAATACGACGATACCCAGGGCGTG
ATCAACATCATGTACATGCACGACAGCGACGACGTGCTGTTCGCCCTGGACCCCTACAACGAGGTGGTGGTGTCC
AGCCCCCGGACCCACTACCTGATGCTGCTGAAGAACGGCACCGTGCTGGAAGTGACCGACGTGGTGGTGGACGCC
ACCGACTGATAAGCGGCCGCATACAGCAGCAATTGGCAAGCTGCTTACATAGAACTCGCGGCGATTGGCATGCCG
CCTTAAAATTTTTATTTTATTTTTCTTTTCTTTTCCGAATCGGATTTTGTTTTTAATATTTCAAAAAAAAAAAAA
AAAAAAAAAAAAAAAAAAAAAAAGGGTCGGCATGGCATCTCCACCTCCTCGCGGTCCGACCTGGGCATCCGAAGGA
GGACGCACGTCCACTCGGATGGCTAAGGGAGAGCCACGTTTAAACACGTGATATCTGGCCTCATGGGCCTTCCTT
TCACTGCCCGCTTTCCAGTCGGGAAACCTGTCGTGCCAGCTGCATTAACATGGTCATAGCTGTTTCCTTGCGTAT
TGGGCGCTCTCCGCTTCCTCGCTCACTGACTCGCTGCGCTCGGTCGTTCGGGTAAAGCCTGGGGTGCCTAATGAG
CAAAAGGCCAGCAAAAGGCCAGGAACCGTAAAAAGGCCGCGTTGCTGGCGTTTTTCCATAGGCTCCGCCCCCCTG
ACGAGCATCACAAAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTTGAGTCCAACCCGG
TAAGACACGACTTATCGCCACTGGCAGCAGCCACTGGTAACAGGATTAGCAGAGCGAGGTATGTAGGCGGTGCTA
CAGAGTTCTTGAAGTGGTGGCCTAACTACGGCTACACTAGAAGAACAGTATTTGGTATCTGCGCTCTGCTGAAGC
CAGTTACCTTCGGAAAAAGAGTTGGTAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCTTTGATCTTTTCTACGGGGTCTGACG
CTCAGTGGAACGAAAACTCACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTGACAGTTATTAGAAAAATT
CATCCAGCAGACGATAAAACGCAATACGCTGGCTATCCGGTGCCGCAATGCCATACAGCACCAGAAAACGATCCG
CCCATTCGCCGCCCAGTTCTTCCGCAATATCACGGGTGGCCAGCGCAATATCCTGATAACGATCCGCCACGCCCA
GACGGCCGCAATCAATAAAGCCGCTAAAACGGCCATTTTCCACCATAATGTTCGGCAGGCACGCATCACCATGGG
TCACCACCAGATCTTCGCCATCCGGCATGCTCGCTTTCAGACGCGCAAACAGCTCTGCCGGTGCCAGGCCCTGAT
GTTCTTCATCCAGATCATCCTGATCCACCAGGCCCGCTTCCATACGGGTACGCGCACGTTCAATACGATGTTTCG
CCTGATGATCAAACGGACAGGTCGCCGGGTCCAGGGTATGCAGACGACGCATGGCATCCGCCATAATGCTCACTT
TTTCTGCCGGCGCCAGATGGCTAGACAGCAGATCCTGACCCGGCACTTCGCCCAGCAGCAGCCAATCACGGCCCG
CTTCGGTCACCACATCCAGCACCGCCGCACACGGAACACCGGTGGTGGCCAGCCAGCTCAGACGCGCCGCTTCAT
CCTGCAGCTCGTTCAGCGCACCGCTCAGATCGGTTTTCACAAACAGCACCGGACGACCCTGCGCGCTCAGACGAA
ACACCGCCGCATCAGAGCAGCCAATGGTCTGCTGCGCCCAATCATAGCCAAACAGACGTTCCACCCACGCTGCCG
GGCTACCCGCATGCAGGCCATCCTGTTCAATCATACTCTTCCTTTTTCAATATTATTGAAGCATTTATCAGGGTT
ATTGTCTCATGAGCGGATACATATTTGAATGTATTTAGAAAAATAAACAAATAGGGGTTCCGCGCACATTTCCCC
GAAAAGTGCCACCTAAATTGTAAGCGTTAATATTTTGTTAAAATTCGCGTTAAATTTTTGTTAAATCAGCTCATT
TTTTAACCAATAGGCCGAAATCGGCAAAATCCCTTATAAATCAAAAGAATAGACCGAGATAGGGTTGAGTGGCCG
CTACAGGGCGCTCCCATTCGCCATTCAGGCTGCGCAACTGTTGGGAAGGGCGTTTCGGTGCGGGCCTCTTCGCTA

-continued

| SEQUENCES |
| --- |

TTACGCCAGCTGGCGAAAGGGGGATGTGCTGCAAGGCGATTAAGTTGGGTAACGCCAGGGTTTTCCCAGTCACAC
GCGTAATACGACTCACTATAG

A554 Vector: SGP-gH-SGP-gL-SGP-UL128-SGP-UL130-SGP-UL131 (SEQ ID NO: 65)
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT
GTGCGGAAGATCCGGACAGATTGTATAAGTATGCAACTAAGCTGAAGAAAAACTGTAAGGAAATAACTGATAAGG
AATTGGACAAGAAAATGAAGGAGCTCGCCGCCGTCATGAGCGACCCTGACCTGGAAACTGAGACTATGTGCCTCC
ACGACGACGAGTCGTGTCGCTACGAAGGGCAAGTCGCTGTTTACCAGGATGTATACGCGGTTGACGGACCGACAA
GTCTCTATCACCAAGCCAATAAGGGAGTTAGAGTCGCCTACTGGATAGGCTTTGACACCACCCCTTTTATGTTTA
AGAACTTGGCTGGAGCATATCCATCATACTCTACCAACTGGGCCGACGAAACCGTGTTAACGGCTCGTAACATAG
GCCTATGCAGCTCTGACGTTATGGAGCGGTCACGTAGAGGGATGTCCATTCTTAGAAAGAAGTATTTGAAACCAT
CCAACAATGTTCTATTCTCTGTTGGCTCGACCATCTACCACGAGAAGAGGGACTTACTGAGGAGCTGGCACCTGC
CGTCTGTATTTCACTTACGTGGCAAGCAAAATTACACATGTCGGTGTGAGACTATAGTTAGTTGCGACGGGTACG
TCGTTAAAAGAATAGCTATCAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCGTGTGCACGTATGTGCCAG
CTACATTGTGTGACCAAATGACTGGCATACTGGCAACAGATGTCAGTGCGGACGACGCGCAAAAACTGCTGGTTG
GGCTCAACCAGCGTATAGTCGTCAACGGTCGCACCCAGAGAAACACCAATACCATGAAAAATTACCTTTTGCCCG
TAGTGGCCCAGGCATTTGCTAGGTGGGCAAAGGAATATAAGGAAGATCAAGAAGATGAAAGGCCACTAGGACTAC
GAGATAGACAGTTAGTCATGGGGTGTTGTTGGGCTTTTAGAAGGCACAAGATAACATCTATTTATAAGCGCCCGG
ATACCCAAACCATCATCAAAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCACCTCTCATTACCGCCGAGG
ACGTACAAGAAGCTAAGTGCGCAGCCGATGAGGCTAAGGAGGTGCGTGAAGCCGAGGAGTTGCGCGCAGCTCTAC
CACCTTTGGCAGCTGATGTTGAGGAGCCCACTCTGGAAGCCGATGTAGACTTGATGTTACAAGAGGCTGGGGCCG
GCTCAGTGGAGACACCTCGTGGCTTGATAAAGGTTACCAGCTACGATGGCGAGGACAAGATCGGCTCTTACGCTG
TGCTTTCTCCGCAGGCTGTACTCAAGAGTGAAAAATTATCTTGCATCCACCCTCTCGCTGAACAAGTCATAGTGA
TAACACACTCTGGCCGAAAAGGGCGTTATGCCGTGGAACCATACCATGGTAAAGTAGTGGTGCCAGAGGGACATG
CAATACCCGTCCAGGACTTTCAAGCTCTGAGTGAAAGTGCCACCATTGTGTACAACGAACGTGAGTTCGTAAACA
GGTACCTGCACCATATTGCCACACATGGAGGAGCGCTGAACACTGATGAAGAATATTACAAAACTGTCAAGCCCA
GCGAGCACGACGGCGAATACCTGTACGACATCGACAGGAAACAGTGCGTCAAGAAAGAACTAGTCACTGGGCTAG
GGCTCACAGGCGAGCTGGTGGATCCTCCCTTCCATGAATTCGCCTACGAGAGTCTGAGAACACGACCAGCCGCTC
CTTACCAAGTACCAACCATAGGGGTGTATGGCGTGCCAGGATCAGGCAAGTCTGGCATCATTAAAAGCGCAGTCA
CCAAAAAAGATCTAGTGGTGAGCGCCAAGAAAGAAAACTGTGCAGAAATTATAAGGGACGTCAAGAAAATGAAAG
GGCTGGACGTCAATGCCAGAACTGTGGACTCAGTGCTCTTGAATGGATGCAAACACCCCGTAGAGACCCTGTATA
TTGACGAAGCTTTTGCTTGTCATGCAGGTACTCTCAGAGCGCTCATAGCCATTATAAGACCTAAAAAGGCAGTGC
TCTGCGGGGATCCCAAACAGTGCGGTTTTTTAACATGATGTGCCTGAAAGTGCATTTTAACCACGAGATTTGCA
CACAAGTCTTCCACAAAAGCATCTCTCGCCGTTGCACTAAATCTGTGACTTCGGTCGTCTCAACCTTGTTTTACG
ACAAAAAAATGAGAACGACGAATCCGAAAGAGACTAAGATTGTGATTGACACTACCGGCAGTACCAAACCTAAGC
AGGACGATCTCATTCTCACTTGTTTCAGAGGGTGGGTGAAGCAGTTGCAAATAGATTACAAAGGCAACGAAATAA
TGACGGCAGCTGCCTCTCAAGGGCTGACCCGTAAAGGTGTGTATGCCGTTCGGTACAAGGTGAATGAAAATCCTC
TGTACGCACCCACCTCAGAACATGTGAACGTCCTACTGACCCGCACGGAGGACCGCATCGTGTGGAAAACACTAG
CCGGCGACCCATGGATAAAAACACTGACTGCCAAGTACCCTGGGAATTTCACTGCCACGATAGAGGAGTGGCAAG
CAGAGCATGATGCCATCATGAGGCACATCTTGGAGAGACCGGACCCTACCGACGTCTTCCAGAATAAGGCAAACG
TGTGTTGGGCCAAGGCTTTAGTGCCGGTGCTGAAGACCGCTGGCATAGACATGACCACTGAACAATGGAACACTG
TGGATTATTTTGAAACGGACAAAGCTCACTCAGCAGAGATAGTATTGAACCAACTATGCGTGAGGTTCTTTGGAC
TCGATCTGGACTCCGGTCTATTTTCTGCACCCACTGTTCCGTTATCCATTAGGAATAATCACTGGGATAACTCCC
CGTCGCCTAACATGTACGGGCTGAATAAAGAAGTGGTCCGTCAGCTCTCTCGCAGGTACCCACAACTGCCTCGGG
CAGTTGCCACTGGAAGAGTCTATGACATGAACACTGGTACACTGCGCAATTATGATCCGCGCATAAACCTAGTAC
CTGTAAACAGAAGACTGCCTCATGCTTTAGTCCTCCACCATAATGAACACCCACAGAGTGACTTTTCTTCATTCG
TCAGCAAATTGAAGGGCAGAACTGTCCTGGTGGTCGGGGAAAAGTTGTCCGTCCCAGGCAAAATGGTTGACTGGT
TGTCAGACCGGCCTGAGGCTACCTTCAGAGCTCGGCTGGATTTAGGCATCCCAGGTGATGTGCCCAAATATGACA
TAATATTTGTTAATGTGAGGACCCCATATAAATACCATCACTATCAGCAGTGTGAAGACCATGCCATTAAGCTTA
GCATGTTGACCAAGAAAGCTTGTCTGCATCTGAATCCCGGCGGAACCTGTGTCAGCATAGGTTATGGTTACGCTG
ACAGGGCCAGCGAAAGCATCATTGGTGCTATAGCGCGGCAGTTCAAGTTTTCCCGGGTATGCAAACCGAAATCCT
CACTTGAAGAGACGGAAGTTCTGTTTGTATTCATTGGGTACGATCGCAAGGCCCGTACGCACAATCCTTACAAGC
TTTCATCAACCTTGACCAACATTTATACAGGTTCCAGACTCCACGAAGCCGGATGTGCACCCTCATATCATGTGG
TGCGAGGGGATATTGCCACGGCCACCGAAGGAGTGATTATAAATGCTGCTAACAGCAAAGGACAACCTGGCGGAG
GGGTGTGCGGAGCGCTGTATAAGAAATTCCCGGAAAGCTTCGATTTACAGCCGATCGAAGTAGGAAAAGCGCGAC
TGGTCAAAGGTGCAGCTAAACATATCATTCATGCCGTAGGACCAAACTTCAACAAAGTTTCGGAGGTTGAAGGTG
ACAAACAGTTGGCAGAGGCTTATGAGTCCATCGCTAAGATTGTCAACGATAACAATTACAAGTCAGTAGCGATTC
CACTGTTGTCCACCGGCATCTTTTCCGGGAACAAAGATCGACTAACCCAATCATTGAACCATTTGCTGACAGCTT
TAGACACCACTGATGCAGATGTAGCCATATACTGCAGGGACAAGAAATGGGAAATGACTCTCAAGGAAGCAGTGG
CTAGGAGAGAAGCAGTGGAGGAGATATGCATATCCGACGACTCTTCAGTGACAGAACCTGATGCAGAGCTGGTGA
GGGTGCATCCGAAGAGTTCTTTGGCTGGAAGGAAGGGCTACAGCACAAGCGATGGCAAAACTTTCTCATATTTGG
AAGGGACCAAGTTTCACCAGGCGGCCAAGGATATAGCAGAAATTAATGCCATGTGGCCCGTTGCAACGGAGGCCA
ATGAGCAGGTATGCATGTATATCCTCGGAGAAAGCATGAGCAGTATTAGGTCGAAATGCCCCGTCGAAGAGTCGG
AAGCCTCCACACCACCTAGCACGCTGCCTTGCTTGTGCATCCATGCCATGACTCCAGAAAGAGTACAGCGCCTAA
AAGCCTCACGTCCAGAACAAATTACTGTGTGCTCATCCTTTCCATTGCCGAAGTATAGAATCACTGGTGTGCAGA
AGATCCAATGCTCCCAGCCTATATTGTTCTCACCGAAAGTGCCTGCGTATATTCATCCAAGGAAGTATCTCGTGG
AAACACCACCGGTAGACGAGACTCCGGAGCCATCGGCAGAGAACCAATCCACAGAGGGGACACCTGAACAACCAC
CACTTATAACCGAGGATGAGACCAGGACTAGAACGCCTGAGCCGATCATCATCGAAGAGGAAGAAGAGGATAGCA
TAAGTTTGCTGTCAGATGGCCCGACCCACCAGGTGCTGCAAGTCGAGGCAGACATTCACGGGCCGCCCTCTGTAT
CTAGCTCATCCTGGTCCATTCCTCATGCATCCGACTTTGATGTGGACAGTTTATCCATACTTGACACCCTGGAGG
GAGCTAGCGTGACCAGCGGGGCAACGTCAGCCGAGACTAACTCTTACTTCGCAAAGAGTATGGAGTTTCTGGCGC
GACCGGTGCCTGCGCCTCGAACAGTATTCAGGAACCCTCCACATCCCGCTCCGCGCACAAGAACACCGTCACTTG -continued

SEQUENCES

CACCCAGCAGGGCCTGCTCGAGAACCAGCCTAGTTTCCACCCCGCCAGGCGTGAATAGGGTGATCACTAGAGAGG
AGCTCGAGGCGCTTACCCCGTCACGCACTCCTAGCAGGTCGGTCTCGAGAACCAGCCTGGTCTCCAACCCGCCAG
GCGTAAATAGGGTGATTACAAGAGAGGAGTTTGAGGCGTTCGTAGCACAACAACAATGACGGTTTGATGCGGGTG
CATACATCTTTTCCTCCGACACCGGTCAAGGGCATTTACAACAAAAATCAGTAAGGCAAACGGTGCTATCCGAAG
TGGTGTTGGAGAGGACCGAATTGGAGATTTCGTATGCCCCGCGCCTCGACCAAGAAAAAGAAGAATTACTACGCA
AGAAATTACAGTTAAATCCCACACCTGCTAACAGAAGCAGATACCAGTCCAGGAAGGTGGAGAACATGAAAGCCA
TAACAGCTAGACGTATTCTGCAAGGCCTAGGGCATTATTTGAAGGCAGAAGGAAAAGTGGAGTGCTACCGAACCC
TGCATCCTGTTCCTTTGTATTCATCTAGTGTGAACCGTGCCTTTTCAAGCCCCAAGGTCGCAGTGGAAGCCTGTA
ACGCCATGTTGAAAGAGAACTTTCCGACTGTGGCTTCTTACTGTATTATTCCAGAGTACGATGCCTATTTGGACA
TGGTTGACGGAGCTTCATGCTGCTTAGACACTGCCAGTTTTTGCCCTGCAAAGCTGCGCAGCTTTCCAAAGAAAC
ACTCCTATTTGGAACCCACAATACGATCGGCAGTGCCTTCAGCGATCCAGAACACGCTCCAGAACGTCCTGGCAG
CTGCCACAAAAAGAAATTGCAATGTCACGCAAATGAGAGAATTGCCCGTATTGGATTCGGCGGCCTTTAATGTGG
AATGCTTCAAGAAATATGCGTGTAATAATGAATATTGGGAAACGTTTAAAGAAAACCCCATCAGGCTTACTGAAG
AAAACGTGGTAAATTACATTACCAAATTAAAAGGACCAAAAGCTGCTGCTCTTTTTGCGAAGACACATAATTTGA
ATATGTTGCAGGACATACCAATGGACAGGTTTGTAATGGACTTAAAGAGAGACGTGAAAGTGACTCCAGGAACAA
AACATACTGAAGAACGGCCCAAGGTACAGGTGATCCAGGCTGCCGATCCGCTAGCAACAGCGTATCTGTGCGGAA
TCCACCGAGAGCTGGTTAGGAGATTAAATGCGGTCCTGCTTCCGAACATTCATACACTGTTTGATATGTCGGCTG
AAGACTTTGACGCTATTATAGCCGAGCACTTCCAGCCTGGGGATTGTGTTCTGGAAACTGACATCGCGTCGTTTG
ATAAAAGTGAGGACGACGCCATGGCTCTGACCGCGTTAATGATTCTGGAAGACTTAGGTGTGGACGCAGAGCTGT
TGACGCTGATTGAGGCGGCTTTCGGCGAAATTTCATCAATACATTTGCCCACTAAAACTAAATTTAAATTCGGAG
CCATGATGAAATCTGGAATGTTCCTCACACTGTTTGTGAACACAGTCATTAACATTGTAATCGCAAGCAGAGTGT
TGAGAGAACGGCTAACCGGATCACCATGTGCAGCATTCATTGGAGATGACAATATCGTGAAAGGAGTCAAATCGG
ACAAATTAATGGCAGACAGGTGCGCCACCTGGTTGAATATGGAAGTCAAGATTATAGATGCTGTGGTGGGCGAGA
AAGCGCCTTATTTCTGTGGAGGGTTTATTTTGTGTGACTCCGTGACCGGCACAGCGTGCCGTGTGGCAGACCCCC
TAAAAAGGCTGTTTAAGCTTGGCAAACCTCTGGCAGCAGACGATGAACATGATGATGACAGGAGAAGGGCATTGC
ATGAAGAGTCAACACGCTGGAACCGAGTGGGTATTCTTTCAGAGCTGTGCAAGGCAGTAGAATCAAGGTATGAAA
CCGTAGGAACTTCCATCATAGTTATGGCCATGACTACTCTAGCTAGCAGTGTTAAATCATTCAGCTACCTGAGAG
GGGCCCCTATAACTCTCTACGGCTAACCTGAATGGACTACGACATAGTCTAGTCCGCCAAGATGAGGCCTGGCCT
GCCCTCCTACCTGATCATCCTGGCCGTGTGCCTGTTCAGCCACCTGCTGTCCAGCAGATACGGCGCCGAGGCCGT
GAGCGAGCCCCTGGACAAGGCTTTCCACCTGCTGCTGAACACCTACGGCAGACCCATCCGGTTTCTGCGGGAGAA
CACCACCCAGTGCACCTACAACAGCAGCCTGCGGAACAGCACCGTCGTGAGAGAGAACGCCATCAGCTTCAACTT
TTTCCAGAGCTACAACCAGTACTACGTGTTCCACATGCCCAGATGCCTGTTTGCCGGCCCTCTGGCCGAGCAGTT
CCTGAACCAGGTGGACCTGACCGAGACACTGGAAAGATACCAGCAGCGGCTGAATACCTACGCCCTGGTGTCCAA
GGACCTGGCCAGCTACCGGTCCTTTAGCCAGCAGCTCAAGGCTCAGGATAGCCTCGGCGAGCAGCCTACCACCGT
GCCCCCTCCCATCGACCTGAGCATCCCCCACGTGTGGATGCCTCCCCAGACCACCCCTCACGGCTGGACCGAGAG
CCACACCACCTCCGGCCTGCACAGACCCCACTTCAACCAGACCTGCATCCTGTTCGACGGCCACGACCTGCTGTT
TAGCACCGTGACCCCCTGCCTGCACCAGGGCTTCTACCTGATCGACGAGCTGAGATACGTGAAGATCACCCTGAC
CGAGGATTTCTTCGTGGTCACCGTGTCCATCGACGACGACACCCCCATGCTGCTGATCTTCGGCCACCTGCCCAG
AGTGCTGTTCAAGGCCCCCTACCAGCGGGACAACTTCATCCTGCGGCAGACCGAGAAGCACGAGCTGCTGGTGCT
GGTCAAGAAGGACCAGCTGAACCGGCACTCCTACCTGAAGGACCCCGACTTCCTGGACGCCGCCCTGGACTTCAA
CTACCTGGACCTGAGCGCCCTGCTGAGAAACAGCTTCCACAGATACGCCGTGGACGTGCTGAAGTCCGGACGGTG
CCAGATGCTCGATCGGCGGACCGTGGAGATGGCCTTCGCCTATGCCCTCGCCCTGTTCGCCGCTGCCAGACAGGA
AGAGGCTGGCGCCCAGGTGTCAGTGCCCAGAGCCCTGGATAGACAGGCCGCCCTGCTGCAGATCCAGGAATTCAT
GATCACCTGCCTGAGCCAGACCCCCCCTAGAACCACCCTGCTGCTGTACCCCACAGCCGTGGATCTGGCCAAGAG
GGCCCTGTGGACCCCCAACCAGATCACCGACATCACAAGCCTCGTGCGGCTCGTGTACATCCTGAGCAAGCAGAA
CCAGCAGCACCTGATCCCCCAGTGGGCCCTGAGACAGATCGCCGACTTCGCCCTGAAGCTGCACAAGACCCATCT
GGCCAGCTTTCTGAGCGCCTTCGCCAGGCAGGAACTGTACCTGATGGGCAGCCTGGTCCACAGCATGCTGGTGCA
TACCACCGAGCGGCGGGAGATCTTCATCGTGGAGACAGGCCTGTGTAGCCTGGCCGAGCTGTCCCACTTTACCCA
GCTGCTGGCCCACCCTCACCACGAGTACCTGAGCGACCTGTACACCCCCTGCAGCAGCAGCGGCAGACGGGACCA
CAGCCTGGAACGGCTGACCAGACTGTTCCCCGATGCCACCGTGCCTGCTACAGTGCCTGCCGCCCTGTCCATCCT
GTCCACCATGCAGCCCAGCACCCTGGAAACCTTCCCCGACCTGTTCTGCCTGCCCCTGGGCGAGAGCTTTAGCGC
CCTGACCGTGTCCGAGCACGTGTCCTACATCGTGACCAATCAGTACCTGATCAAGGGCATCAGCTACCCCGTGTC
CACCACAGTCGTGGGCCAGAGCCTGATCATCACCCAGACCGACAGCCAGACCAAGTGCGAGCTGACCCGGAACAT
GCACACCACACACAGCATCACCGTGGCCCTGAACATCAGCCTGGAAAACTGCGCTTTCTGTCAGTCTGCCCTGCT
GGAATACGACGATACCCAGGGCGTGATCAACATCATGTACATGCACGACAGCGACGACGTGCTGTTCGCCCTGGA
CCCCTACAACGAGGTGGTGGTGTCCAGCCCCCGGACCCACTACCTGATGCTGCTGAAGAACGGCACCGTGCTGGA
AGTGACCGACGTGGTGGTGGACGCCACCGACAGCAGACTGCTGATGATGAGCGTGTACGCCCTGAGCGCCATCAT
CGGCATCTACCTGCTGTACCGGATGCTGAAAACCTGCTGATAATCTAGAGGCCCCTATAACTCTCTACGGCTAAC
CTGAATGGACTACGACATAGTCTAGTCCGCCAAGATGTGCAGAAGGCCCGACTGCGGCTTCAGCTTCAGCCCTGG
ACCCGTGATCCTGCTGTGGTGCTGCCTGCTGCTGCCTATCGTGTCCTCTGCCGCCGTGTCTGTGGCCCCTACAGC
CGCCGAGAAGGTGCCAGCCGAGTGCCCCGAGCTGACCAGAAGATGCCTGCTGGGCGAGGTGTTCGAGGGCGACAA
GTACGAGAGCTGGCTGCGGCCCCTGGTCAACGTGACCGGCAGAGATGGCCCCCTGAGCCAGCTGATCCGGTACAG
ACCCGTGACCCCCGAGGCCGCCAATAGCGTGCTGCTGGACGAGGCCTTCCTGGATACCCTGGCCCTGCTGTACAA
CAACCCCGACCAGCTGAGAGCCCTGCTGACCCTGCTGTCCAGCGACACCGCCCCCAGATGGATGACCGTGATGCG
GGGCTACAGCGAGTGTGGAGATGGCAGCCCTGCCGTGTACACCTGCGTGGACGACCTGTGCAGAGGCTACGACCT
GACCAGACTGAGCTACGGCCGGTCCATCTTCACAGAGCACGTGCTGGGCTTCGAGCTGGTGCCCCCCAGCCTGTT
CAACGTGGTGGTGGCCATCCGGAACGAGGCCACCAGAACCAACAGAGCCGTGCGGCTGCCTGTGTCTACAGCCGC
TGCACCTGAGGGCATCACACTGTTCTACGGCCTGTACAACGCCGTGAAAGAGTTCTGCCTCCGGCACCAGCTGGA
TCCCCCCCTGCTGAGACACCTGGACAAGTACTACGCCGGCCTGCCCCCAGAGCTGAAGCAGACCAGAGTGAACCT
GCCCGCCCACAGCAGATATGGCCCTCAGGCCGTGGACGCCAGATGATAACGCCGGCGGCCCCTATAACTCTCTAC
GGCTAACCTGAATGGACTACGACATAGTCTAGTCCGCCAAGATGAGCCCCAAGGACCTGACCCCCTTCCTGACAA
CCCTGTGGCTGCTCCTGGGCCATAGCAGAGTGCCTAGAGTGCGGGCCGAGGAATGCTGCGAGTTCATCAACGTGA
ACCACCCCCCCGAGCGGTGCTACGACTTCAAGATGTGCAACCGGTTCACCGTGGCCCTGAGATGCCCCGACGGCG
AAGTGTGCTACAGCCCCGAGAAAACCGCCGAGATCCGGGGCATCGTGACCACCATGACCCACAGCCTGACCCGGC
AGGTGGTGCACAACAAGCTGACCAGCTGCAACTACAACCCCCTGTACCTGGAAGCCGACGGCCGGATCAGATGCG
GCAAAGTGAACGACAAGGCCCAGTACCTGCTGGGAGCCGCCGGAAGCGTGCCCTACCGGTGGATCAACCTGGAAT
ACGACAAGATCACCCGGATCGTGGGCCTGGACCAGTACCTGGAAAGCGTGAAGAAGCACAAGCGGCTGGACGTGT

-continued

SEQUENCES

GCAGAGCCAAGATGGGCTACATGCTGCAGTGATAAGGCGCGCCGCCCCTATAACTCTCTACGGCTAACCTGAATG
GACTACGACATAGTCTAGTCCGCCAAGATGCTGCGGCTGCTGCTGAGACACCACTTCCACTGCCTGCTGCTGTGT
GCCGTGTGGGCCACCCCTTGTCTGGCCAGCCCTTGGAGCACCCTGACCGCCAACCAGAACCCTAGCCCCCCTTGG
TCCAAGCTGACCTACAGCAAGCCCCACGACGCCGCCACCTTCTACTGCCCCTTTCTGTACCCCAGCCCTCCCAGA
AGCCCCCTGCAGTTCAGCGGCTTCCAGAGAGTGTCCACCGGCCCTGAGTGCCGGAACGAGACACTGTACCTGCTG
TACAACCGGGAGGGCCAGACACTGGTGGAGCGGAGCAGCACCTGGGTGAAAAAAGTGATCTGGTATCTGAGCGGC
CGGAACCAGACCATCCTGCAGCGGATGCCCAGAACCGCCAGCAAGCCCAGCGACGGCAACGTGCAGATCAGCGTG
GAGGACGCCAAAATCTTCGGAGCCCACATGGTGCCCAAGCAGACCAAGCTGCTGAGATTCGTGGTCAACGACGGC
ACCAGATATCAGATGTGCGTGATGAAGCTGGAAAGCTGGGCCCACGTGTTCCGGGACTACTCCGTGAGCTTCCAG
GTCCGGCTGACCTTCACCGAGGCCAACAACCAGACCTACACCTTCTGCACCCACCCCAACCTGATCGTGTGATAA
GCGGCCGCGCCCCTATAACTCTCTACGGCTAACCTGAATGGACTACGACATAGTCTAGTCCGCCAAGATGCGGCT
GTGCAGAGTGTGGCTGTCCGTGTGCCTGTGTGCCGTGGTGCTGGGCCAGTGCCAGAGAGAGACAGCCGAGAAGAA
CGACTACTACCGGGTGCCCCACTACTGGGATGCCTGCAGCAGAGCCCTGCCCGACCAGACCCGGTACAAATACGT
GGAGCAGCTCGTGGACCTGACCCTGAACTACCACTACGACGCCAGCCACGGCCTGGACAACTTCGACGTGCTGAA
GCGGATCAACGTGACCGAGGTGTCCCTGCTGATCAGCGACTTCCGGCGGCAGAACAGAAGAGGCGGCACCAACAA
GCGGACCACCTTCAACGCCGCTGGCTCTCTGGCCCCTCACGCCAGATCCCTGGAATTCAGCGTGCGGCTGTTCGC
CAACTGATAACGTTGCATCCTGCAGGATACAGCAGCAATTGGCAAGCTGCTTACATAGAACTCGCGGCGATTGGC
ATGCCGCCTTAAAATTTTTATTTTATTTTTCTTTTCTTTTCCGAATCGGATTTTGTTTTTAATATTTCAAAAAAA
AAAAAAAAAAAAAAAAAAAAAAAAAAAAAAGGGTCGGCATGGCATCTCCACCTCCTCGCGGTCCGACCTGGGCATCC
GAAGGAGGACGCACGTCCACTCGGATGGCTAAGGGAGAGCCACGTTTAAACGCTAGAGCAAGACGTTTCCCGTTG
AATATGGCTCATAACACCCCTTGTATTACTGTTTATGTAAGCAGACAGTTTTATTGTTCATGATGATATATTTTT
ATCTTGTGCAATGTAACATCAGAGATTTTGAGACACAACGTGGCTTTGTTGAATAAATCGAACTTTTGCTGAGTT
GAAGGATCAGATCACGCATCTTCCCGACAACGCAGACCGTTCCGTGGCAAAGCAAAAGTTCAAAATCACCAACTG
GTCCACCTACAACAAAGCTCTCATCAACCGTGGCTCCCTCACTTTCTGGCTGGATGATGGGGCGATTCAGGCCTG
GTATGAGTCAGCAACACCTTCTTCACGAGGCAGACCTCAGCGCTAGCGGAGTGTATACTGGCTTACTATGTTGGC
ACTGATGAGGGTGTCAGTGAAGTGCTTCATGTGGCAGGAGAAAAAAGGCTGCACCGGTGCGTCAGCAGAATATGT
GATACAGGATATATTCCGCTTCCTCGCTCACTGACTCGCTACGCTCGGTCGTTCGACTGCGGCGAGCGGAAATGG
CTTACGAACGGGGCGGAGATTTCCTGGAAGATGCCAGGAAGATACTTAACAGGGAAGTGAGAGGGCCGCGGCAAA
GCCGTTTTTCCATAGGCTCCGCCCCCCTGACAAGCATCACGAAATCTGACGCTCAAATCAGTGGTGGCGAAACCC
GACAGGACTATAAAGATACCAGGCGTTTCCCCCTGGCGGCTCCCTCGTGCGCTCTCCTGTTCCTGCCTTTCGGTTT
ACCGGTGTCATTCCGCTGTTATGGCCGCGTTTGTCTCATTCCACGCCTGACACTCAGTTCCGGGTAGGCAGTTCG
CTCCAAGCTGGACTGTATGCACGAACCCCCCGTTCAGTCCGACCGCTGCGCCTTATCCGGTAACTATCGTCTTGA
GTCCAACCCGGAAAGACATGCAAAAGCACCACTGGCAGCAGCCACTGGTAATTGATTTAGAGGAGTTAGTCTTGA
AGTCATGCGCCGGTTAAGGCTAAACTGAAAGGACAAGTTTTGGTGACTGCGCTCCTCCAAGCCAGTTACCTCGGT
TCAAAGAGTTGGTAGCTCAGAGAACCTTCGAAAAACCGCCCTGCAAGGCGGTTTTTTCGTTTTCAGAGCAAGAGA
TTACGCGCAGACCAAAACGATCTCAAGAAGATCATCTTATTAAGGGGTCTGACGCTCAGTGGAACGAAAACTCAC
GTTAAGGGATTTTGGTCATGAGATTATCAAAAAGGATCTTCACCTAGATCCTTTTAAATTAAAAATGAAGTTTTA
AATCAATCTAAAGTATATATGAGTAAACTTGGTCTGACAGTTATTAGAAAAATTCATCCAGCAGACGATAAAACG
CAATACGCTGGCTATCCGGTGCCGCAATGCCATACAGCACCAGAAAACGATCCGCCCATTCGCCGCCCAGTTCTT
CCGCAATATCACGGGTGGCCAGCGCAATATCCTGATAACGATCCGCCACGCCCAGACGGCCGCAATCAATAAAGC
CGCTAAAACGGCCATTTTCCACCATAATGTTCGGCAGGCACGCATCACCATGGGTCACCACCAGATCTTCGCCAT
CCGGCATGCTCGCTTTCAGACGCGCAAACAGCTCTGCCGGTGCCAGGCCCTGATGTTCTTCATCCAGATCATCCT
GATCCACCAGGCCCGCTTCCATACGGGTACGCGCACGTTCAATACGATGTTTCGCCTGATGATCAAACGGACAGG
TCGCCGGGTCCAGGGTATGCAGACGACGCATGGCATCCGCCATAATGCTCACTTTTTCTGCCGGCGCCAGATGGC
TAGACAGCAGATCCTGACCCGGCACTTCGCCCAGCAGCAGCCAATCACGGCCCGCTTCGGTCACCACATCCAGCA
CCGCCGCACACGGAACACCGGTGGTGGCCAGCCAGCTCAGACGCGCCGCTTCATCCTGCAGCTCGTTCAGCGCAC
CGCTCAGATCGGTTTTCACAAACAGCACCGGACGACCCTGCGCGCTCAGACGAAACACCGCCGCATCAGAGCAGC
CAATGGTCTGCTGCGCCCAATCATAGCCAAACAGACGTTCCACCCACGCTGCCGGGCTACCCGCATGCAGGCCAT
CCTGTTCAATCATACTCTTCCTTTTTCAATATTATTGAAGCATTTATCAGGGTTATTGTCTCATGAGCGGATACA
TATTTGAATGTATTTAGAAAAATAAACAAATAGGGGTTCCGCGCACATTTCCCCGAAAAGTGCCACCTAAATTGT
AAGCGTTAATATTTTGTTAAAATTCGCGTTAAATTTTTGTTAAATCAGCTCATTTTTTAACCAATAGGCCGAAAT
CGGCAAAATCCCTTATAAATCAAAAGAATAGACCGAGATAGGGTTGAGTGGCCGCTACAGGGCGCTCCCATTCGC
CATTCAGGCTGCGCAACTGTTGGGAAGGGCGTTTCGGTGCGGGCCTCTTCGCTATTACGCCAGCTGGCGAAAGGG
GGATGTGCTGCAAGGCGATTAAGTTGGGTAACGCCAGGGTTTTCCCAGTCACACGCGTAATACGACTCACTATAG

A555 Vector: SGP-gHsol-SGP-gL-SGP-UL128-SGP-UL130-SGP-UL131 (SEQ ID NO: 66):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT
GTGCGGAAGATCCGGACAGATTGTATAAGTATGCAACTAAGCTGAAGAAAAACTGTAAGGAAATAACTGATAAGG
AATTGGACAAGAAAATGAAGGAGCTCGCCGCCGTCATGAGCGACCCTGACCTGGAAACTGAGACTATGTGCCTCC
ACGACGACGAGTCGTGTCGCTACGAAGGGCAAGTCGCTGTTTACCAGGATGTATACGCGGTTGACGGACCGACAA
GTCTCTATCACCAAGCCAATAAGGGAGTTAGAGTCGCCTACTGGATAGGCTTTGACACCACCCCTTTTATGTTTA
AGAACTTGGCTGGAGCATATCCATCATACTCTACCAACTGGGCCGACGAAACCGTGTTAACGGCTCGTAACATAG
GCCTATGCAGCTCTGACGTTATGGAGCGGTCACGTAGAGGGATGTCCATTCTTAGAAAGAAGTATTTGAAACCAT
CCAACAATGTTCTATTCTCTGTTGGCTCGACCATCTACCACGAGAAGAGGGACTTACTGAGGAGCTGGCACCTGC
CGTCTGTATTTCACTTACGTGGCAAGCAAAATTACACATGTCGGTGTGAGACTATAGTTAGTTGCGACGGGTACG
TCGTTAAAAGAATAGCTATCAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCGTGTGCACGTATGTGCCAG
CTACATTGTGTGACCAAATGACTGGCATACTGGCAACAGATGTCAGTGCGGACGACGCGCAAAAACTGCTGGTTG
GGCTCAACCAGCGTATAGTCGTCAACGGTCGCACCCAGAGAAACACCAATACCATGAAAAATTACCTTTTGCCCG
TAGTGGCCCAGGCATTTGCTAGGTGGGCAAAGGAATATAAGGAAGATCAAGAAGATGAAAGGCCACTAGGACTAC
GAGATAGACAGTTAGTCATGGGGTGTTGTTGGGCTTTTAGAAGGCACAAGATAACATCTATTTATAAGCGCCCGG
ATACCCAAACCATCATCAAAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCACCTCTCATTACCGCCGAGG
ACGTACAAGAAGCTAAGTGCGCAGCCGATGAGGCTAAGGAGGTGCGTGAAGCCGAGGAGTTGCGCGCAGCTCTAC -continued

| SEQUENCES |
|---|
| CACCTTTGGCAGCTGATGTTGAGGAGCCCACTCTGGAAGCCGATGTAGACTTGATGTTACAAGAGGCTGGGGCCG<br>GCTCAGTGGAGACACCTCGTGGCTTGATAAAGGTTACCAGCTACGATGGCGAGGACAAGATCGGCTCTTACGCTG<br>TGCTTTCTCCGCAGGCTGTACTCAAGAGTGAAAAATTATCTTGCATCCACCCTCTCGCTGAACAAGTCATAGTGA<br>TAACACACTCTGGCCGAAAAGGGCGTTATGCCGTGGAACCATACCATGGTAAAGTAGTGGTGCCAGAGGGACATG<br>CAATACCCGTCCAGGACTTTCAAGCTCTGAGTGAAAGTGCCACCATTGTGTACAACGAACGTGAGTTCGTAAACA<br>GGTACCTGCACCATATTGCCACACATGGAGGAGCGCTGAACACTGATGAAGAATATTACAAAACTGTCAAGCCCA<br>GCGAGCACGACGGCGAATACCTGTACGACATCGACAGGAAACAGTGCGTCAAGAAAGAACTAGTCACTGGGCTAG<br>GGCTCACAGGCGAGCTGGTGGATCCTCCCTTCCATGAATTCGCCTACGAGAGTCTGAGAACACGACCAGCCGCTC<br>CTTACCAAGTACCAACCATAGGGGTGTATGGCGTGCCAGGATCAGGCAAGTCTGGCATCATTAAAAGCGCAGTCA<br>CCAAAAAAGATCTAGTGGTGAGCGCCAAGAAAGAAAACTGTGCAGAAATTATAAGGGACGTCAAGAAAATGAAAG<br>GGCTGGACGTCAATGCCAGAACTGTGGACTCAGTGCTCTTGAATGGATGCAAACACCCCGTAGAGACCCTGTATA<br>TTGACGAAGCTTTTGCTTGTCATGCAGGTACTCTCAGAGCGCTCATAGCCATTATAAGACCTAAAAAGGCAGTGC<br>TCTGCGGGGATCCCAAACAGTGCGGTTTTTTTAACATGATGTGCCTGAAAGTGCATTTTAACCACGAGATTTGCA<br>CACAAGTCTTCCACAAAAGCATCTCTCGCCGTTGCACTAAATCTGTGACTTCGGTCGTCTCAACCTTGTTTTACG<br>ACAAAAAAATGAGAACGACGAATCCGAAAGAGACTAAGATTGTGATTGACACTACCGGCAGTACCAAACCTAAGC<br>AGGACGATCTCATTCTCACTTGTTTCAGAGGGTGGGTGAAGCAGTTGCAAATAGATTACAAAGGCAACGAAATAA<br>TGACGGCAGCTGCCTCTCAAGGGCTGACCCGTAAAGGTGTGTATGCCGTTCGGTACAAGGTGAATGAAAATCCTC<br>TGTACGCACCCACCTCAGAACATGTGAACGTCCTACTGACCCGCACGGAGGACCGCATCGTGTGGAAAACACTAG<br>CCGGCGACCCATGGATAAAAACACTGACTGCCAAGTACCCTGGGAATTTCACTGCCACGATAGAGGAGTGGCAAG<br>CAGAGCATGATGCCATCATGAGGCACATCTTGGAGAGACCGGACCCTACCGACGTCTTCCAGAATAAGGCAAACG<br>TGTGTTGGGCCAAGGCTTTAGTGCCGGTGCTGAAGACCGCTGGCATAGACATGACCACTGAACAATGGAACACTG<br>TGGATTATTTTGAAACGGACAAAGCTCACTCAGCAGAGATAGTATTGAACCAACTATGCGTGAGGTTCTTTGGAC<br>TCGATCTGGACTCCGGTCTATTTTCTGCACCCACTGTTCCGTTATCCATTAGGAATAATCACTGGGATAACTCCC<br>CGTCGCCTAACATGTACGGGCTGAATAAAGAAGTGGTCCGTCAGCTCTCTCGCAGGTACCCACAACTGCCTCGGG<br>CAGTTGCCACTGGAAGAGTCTATGACATGAACACTGGTACACTGCGCAATTATGATCCGCGCATAAACCTAGTAC<br>CTGTAAACAGAAGACTGCCTCATGCTTTAGTCCTCCACCATAATGAACACCCACAGAGTGACTTTTCTTCATTCG<br>TCAGCAAATTGAAGGGCAGAACTGTCCTGGTGGTCGGGGAAAAGTTGTCCGTCCCAGGCAAAATGGTTGACTGGT<br>TGTCAGACCGGCCTGAGGCTACCTTCAGAGCTCGGCTGGATTTAGGCATCCCAGGTGATGTGCCCAAATATGACA<br>TAATATTTGTTAATGTGAGGACCCCATATAAATACCATCACTATCAGCAGTGTGAAGACCATGCCATTAAGCTTA<br>GCATGTTGACCAAGAAAGCTTGTCTGCATCTGAATCCCGGCGGAACCTGTGTCAGCATAGGTTATGGTTACGCTG<br>ACAGGGCCAGCGAAAGCATCATTGGTGCTATAGCGCGGCAGTTCAAGTTTTCCCGGGTATGCAAACCGAAATCCT<br>CACTTGAAGAGACGGAAGTTCTGTTTGTATTCATTGGGTACGATCGCAAGGCCCGTACGCACAATCCTTACAAGC<br>TTTCATCAACCTTGACCAACATTTATACAGGTTCCAGACTCCACGAAGCCGGATGTGCACCCTCATATCATGTGG<br>TGCGAGGGGATATTGCCACGGCCACCGAAGGAGTGATTATAAATGCTGCTAACAGCAAAGGACAACCTGGCGGAG<br>GGGTGTGCGGAGCGCTGTATAAGAAATTCCCGGAAAGCTTCGATTTACAGCCGATCGAAGTAGGAAAAGCGCGAC<br>TGGTCAAAGGTGCAGCTAAACATATCATTCATGCCGTAGGACCAAACTTCAACAAAGTTTCGGAGGTTGAAGGTG<br>ACAAACAGTTGGCAGAGGCTTATGAGTCCATCGCTAAGATTGTCAACGATAACAATTACAAGTCAGTAGCGATTC<br>CACTGTTGTCCACCGGCATCTTTTCCGGGAACAAAGATCGACTAACCCAATCATTGAACCATTTGCTGACAGCTT<br>TAGACACCACTGATGCAGATGTAGCCATATACTGCAGGGACAAGAAATGGGAAATGACTCTCAAGGAAGCAGTGG<br>CTAGGAGAGAAGCAGTGGAGGAGATATGCATATCCGACGACTCTTCAGTGACAGAACCTGATGCAGAGCTGGTGA<br>GGGTGCATCCGAAGAGTTCTTTGGCTGGAAGGAAGGGCTACAGCACAAGCGATGGCAAAACTTTCTCATATTTGG<br>AAGGGACCAAGTTTCACCAGGCGGCCAAGGATATAGCAGAAATTAATGCCATGTGGCCCGTTGCAACGGAGGCCA<br>ATGAGCAGGTATGCATGTATATCCTCGGAGAAAGCATGAGCAGTATTAGGTCGAAATGCCCCGTCGAAGAGTCGG<br>AAGCCTCCACACCACCTAGCACGCTGCCTTGCTTGTGCATCCATGCCATGACTCCAGAAAGAGTACAGCGCCTAA<br>AAGCCTCACGTCCAGAACAAATTACTGTGTGCTCATCCTTTCCATTGCCGAAGTATAGAATCACTGGTGTGCAGA<br>AGATCCAATGCTCCCAGCCTATATTGTTCTCACCGAAAGTGCCTGCGTATATTCATCCAAGGAAGTATCTCGTGG<br>AAACACCACCGGTAGACGAGACTCCGGAGCCATCGGCAGAGAACCAATCCACAGAGGGGACACCTGAACAACCAC<br>CACTTATAACCGAGGATGAGACCAGGACTAGAACGCCTGAGCCGATCATCATCGAAGAGGAAGAAGAGGATAGCA<br>TAAGTTTGCTGTCAGATGGCCCGACCCACCAGGTGCTGCAAGTCGAGGCAGACATTCACGGGCCGCCCTCTGTAT<br>CTAGCTCATCCTGGTCCATTCCTCATGCATCCGACTTTGATGTGGACAGTTTATCCATACTTGACACCCTGGAGG<br>GAGCTAGCGTGACCAGCGGGGCAACGTCAGCCGAGACTAACTCTTACTTCGCAAAGAGTATGGAGTTTCTGGCGC<br>GACCGGTGCCTGCGCCTCGAACAGTATTCAGGAACCCTCCACATCCCGCTCCGCGCACAAGAACACCGTCACTTG<br>CACCCAGCAGGGCCTGCTCGAGAACCAGCCTAGTTTCCACCCCGCCAGGCGTGAATAGGGTGATCACTAGAGAGG<br>AGCTCGAGGCGCTTACCCCGTCACGCACTCCTAGCAGGTCGGTCTCGAGAACCAGCCTGGTCTCCAACCCGCCAG<br>GCGTAAATAGGGTGATTACAAGAGAGGAGTTTGAGGCGTTCGTAGCACAACAACAATGACGGTTTGATGCGGGTG<br>CATACATCTTTTCCTCCGACACCGGTCAAGGGCATTTACAACAAAAATCAGTAAGGCAAACGGTGCTATCCGAAG<br>TGGTGTTGGAGAGGACCGAATTGGAGATTTCGTATGCCCCGCGCCTCGACCAAGAAAAAGAAGAATTACTACGCA<br>AGAAATTACAGTTAAATCCCACACCTGCTAACAGAAGCAGATACCAGTCCAGGAAGGTGGAGAACATGAAAGCCA<br>TAACAGCTAGACGTATTCTGCAAGGCCTAGGGCATTATTTGAAGGCAGAAGGAAAAGTGGAGTGCTACCGAACCC<br>TGCATCCTGTTCCTTTGTATTCATCTAGTGTGAACCGTGCCTTTTCAAGCCCCAAGGTCGCAGTGGAAGCCTGTA<br>ACGCCATGTTGAAAGAGAACTTTCCGACTGTGGCTTCTTACTGTATTATTCCAGAGTACGATGCCTATTTGGACA<br>TGGTTGACGGAGCTTCATGCTGCTTAGACACTGCCAGTTTTTGCCCTGCAAAGCTGCGCAGCTTTCCAAAGAAAC<br>ACTCCTATTTGGAACCCACAATACGATCGGCAGTGCCTTCAGCGATCCAGAACACGCTCCAGAACGTCCTGGCAG<br>CTGCCACAAAAAGAAATTGCAATGTCACGCAAATGAGAGAATTGCCCGTATTGGATTCGGCGGCCTTTAATGTGG<br>AATGCTTCAAGAAATATGCGTGTAATAATGAATATTGGGAAACGTTTAAAGAAAACCCCATCAGGCTTACTGAAG<br>AAAACGTGGTAAATTACATTACCAAATTAAAAGGACCAAAAGCTGCTGCTCTTTTTGCGAAGACACATAATTTGA<br>ATATGTTGCAGGACATACCAATGGACAGGTTTGTAATGGACTTAAAGAGAGACGTGAAAGTGACTCCAGGAACAA<br>AACATACTGAAGAACGGCCCAAGGTACAGGTGATCCAGGCTGCCGATCCGCTAGCAACAGCGTATCTGTGCGGAA<br>TCCACCGAGAGCTGGTTAGGAGATTAAATGCGGTCCTGCTTCCGAACATTCATACACTGTTTGATATGTCGGCTG<br>AAGACTTTGACGCTATTATAGCCGAGCACTTCCAGCCTGGGGATTGTGTTCTGGAAACTGACATCGCGTCGTTTG<br>ATAAAAGTGAGGACGACGCCATGGCTCTGACCGCGTTAATGATTCTGGAAGACTTAGGTGTGGACGCAGAGCTGT<br>TGACGCTGATTGAGGCGGCTTTCGGCGAAATTTCATCAATACATTTGCCCACTAAAACTAAATTTAAATTCGGAG<br>CCATGATGAAATCTGGAATGTTCCTCACACTGTTTGTGAACACAGTCATTAACATTGTAATCGCAAGCAGAGTGT<br>TGAGAGAACGGCTAACCGGATCACCATGTGCAGCATTCATTGGAGATGACAATATCGTGAAAGGAGTCAAATCGG<br>ACAAATTAATGGCAGACAGGTGCGCCACCTGGTTGAATATGGAAGTCAAGATTATAGATGCTGTGGTGGGCGAGA<br>AAGCGCCTTATTTCTGTGGAGGGTTTATTTTGTGTGACTCCGTGACCGGCACAGCGTGCCGTGTGGCAGACCCCC<br>TAAAAAGGCTGTTTAAGCTTGGCAAACCTCTGGCAGCAGACGATGAACATGATGATGACAGGAGAAGGGCATTGC |

-continued

| SEQUENCES |
| --- |
| ATGAAGAGTCAACACGCTGGAACCGAGTGGGTATTCTTTCAGAGCTGTGCAAGGCAGTAGAATCAAGGTATGAAA<br>CCGTAGGAACTTCCATCATAGTTATGGCCATGACTACTCTAGCTAGCAGTGTTAAATCATTCAGCTACCTGAGAG<br>GGGCCCCTATAACTCTCTACGGCTAACCTGAATGGACTACGACATAGTCTAGTCCGCCAAG**ATGAGGCCTGGCCT**<br>**GCCCTCCTACCTGATCATCCTGGCCGTGTGCCTGTTCAGCCACCTGCTGTCCAGCAGATACGGCGCCGAGGCCGT**<br>**GAGCGAGCCCCTGGACAAGGCTTTCCACCTGCTGCTGAACACCTACGGCAGACCCATCCGGTTTCTGCGGGAGAA**<br>**CACCACCCAGTGCACCTACAACAGCAGCCTGCGGAACAGCACCGTCGTGAGAGAGAACGCCATCAGCTTCAACTT**<br>**TTTCCAGAGCTACAACCAGTACTACGTGTTCCACATGCCCAGATGCCTGTTTGCCGGCCCTCTGGCCGAGCAGTT**<br>**CCTGAACCAGGTGGACCTGACCGAGACACTGGAAAGATACCAGCAGCGGCTGAATACCTACGCCCTGGTGTCCAA**<br>**GGACCTGGCCAGCTACCGGTCCTTTAGCCAGCAGCTCAAGGCTCAGGATAGCCTCGGCGAGCAGCCTACCACCGT**<br>**GCCCCCTCCCATCGACCTGAGCATCCCCCACGTGTGGATGCCTCCCCAGACCACCCCTCACGGCTGGACCGAGAG**<br>**CCACACCACCTCCGGCCTGCACAGACCCCACTTCAACCAGACCTGCATCCTGTTCGACGGCCACGACCTGCTGTT**<br>**TAGCACCGTGACCCCCTGCCTGCACCAGGGCTTCTACCTGATCGACGAGCTGAGATACGTGAAGATCACCCTGAC**<br>**CGAGGATTTCTTCGTGGTCACCGTGTCCATCGACGACGACACCCCCATGCTGCTGATCTTCGGCCACCTGCCCAG**<br>**AGTGCTGTTCAAGGCCCCCTACCAGCGGGACAACTTCATCCTGCGGCAGACCGAGAAGCACGAGCTGCTGGTGCT**<br>**GGTCAAGAAGGACCAGCTGAACCGGCACTCCTACCTGAAGGACCCCGACTTCCTGGACGCCGCCCTGGACTTCAA**<br>**CTACCTGGACCTGAGCGCCCTGCTGAGAAACAGCTTCCACAGATACGCCGTGGACGTGCTGAAGTCCGGACGGTG**<br>**CCAGATGCTCGATCGGCGGACCGTGGAGATGGCCTTCGCCTATGCCCTCGCCCTGTTCGCCGCTGCCAGACAGGA**<br>**AGAGGCTGGCGCCCAGGTGTCAGTGCCCAGAGCCCTGGATAGACAGGCCGCCCTGCTGCAGATCCAGGAATTCAT**<br>GATCACCTGCCTGAGCCAGACCCCCCCTAGAACCACCCTGCTGCTGTACCCCACAGCCGTGGATCTGGCCAAGAG<br>**GGCCCTGTGGACCCCCAACCAGATCACCGACATCACAAGCCTCGTGCGGCTCGTGTACATCCTGAGCAAGCAGAA**<br>**CCAGCAGCACCTGATCCCCCAGTGGGCCCTGAGACAGATCGCCGACTTCGCCCTGAAGCTGCACAAGACCCATCT**<br>**GGCCAGCTTTCTGAGCGCCTTCGCCAGGCAGGAACTGTACCTGATGGGCAGCCTGGTCCACAGCATGCTGGTGCA**<br>**TACCACCGAGCGGCGGGAGATCTTCATCGTGGAGACAGGCCTGTGTAGCCTGGCCGAGCTGTCCCACTTTACCCA**<br>**GCTGCTGGCCCACCCTCACCACGAGTACCTGAGCGACCTGTACACCCCCTGCAGCAGCAGCGGCAGACGGGACCA**<br>**CAGCCTGGAACGGCTGACCAGACTGTTCCCCGATGCCACCGTGCCTGCTACAGTGCCTGCCGCCCTGTCCATCCT**<br>**GTCCACCATGCAGCCCAGCACCCTGGAAACCTTCCCCGACCTGTTCTGCCTGCCCCTGGGCGAGAGCTTTAGCGC**<br>**CCTGACCGTGTCCGAGCACGTGTCCTACATCGTGACCAATCAGTACCTGATCAAGGGCATCAGCTACCCCGTGTC**<br>**CACCACAGTCGTGGGCCAGAGCCTGATCATCACCCAGACCGACAGCCAGACCAAGTGCGAGCTGACCCGGAACAT**<br>**GCACACCACACACAGCATCACCGTGGCCCTGAACATCAGCCTGGAAAACTGCGCTTTCTGTCAGTCTGCCCTGCT**<br>**GGAATACGACGATACCCAGGGCGTGATCAACATCATGTACATGCACGACAGCGACGACGTGCTGTTCGCCCTGGA**<br>**CCCCTACAACGAGGTGGTGGTGTCCAGCCCCCGGACCCACTACCTGATGCTGCTGAAGAACGGCACCGTGCTGGA**<br>**AGTGACCGACGTGGTGGTGGACGCCACCGAC**TGATAATCTAGAGGCCCCTATAACTCTCTACGGCTAACCTGAAT<br>GGACTACGACATAGTCTAGTCCGCCAAG**ATGTGCAGAAGGCCCGACTGCGGCTTCAGCTTCAGCCCTGGACCCGT**<br>**GATCCTGCTGTGGTGCTGCCTGCTGCTGCCTATCGTGTCCTCTGCCGCCGTGTCTGTGGCCCCTACAGCCGCCGA**<br>**GAAGGTGCCAGCCGAGTGCCCCGAGCTGACCAGAAGATGCCTGCTGGGCGAGGTGTTCGAGGGCGACAAGTACGA**<br>**GAGCTGGCTGCGGCCCCTGGTCAACGTGACCGGCAGAGATGGCCCCCTGAGCCAGCTGATCCGGTACAGACCCGT**<br>**GACCCCCGAGGCCGCCAATAGCGTGCTGCTGGACGAGGCCTTCCTGGATACCCTGGCCCTGCTGTACAACAACCC**<br>**CGACCAGCTGAGAGCCCTGCTGACCCTGCTGTCCAGCGACACCGCCCCCAGATGGATGACCGTGATGCGGGGCTA**<br>**CAGCGAGTGTGGAGATGGCAGCCCTGCCGTGTACACCTGCGTGGACGACCTGTGCAGAGGCTACGACCTGACCAG**<br>**ACTGAGCTACGGCCGGTCCATCTTCACAGAGCACGTGCTGGGCTTCGAGCTGGTGCCCCCCAGCCTGTTCAACGT**<br>**GGTGGTGGCCATCCGGAACGAGGCCACCAGAACCAACAGAGCCGTGCGGCTGCCTGTGTCTACAGCCGCTGCACC**<br>**TGAGGGCATCACACTGTTCTACGGCCTGTACAACGCCGTGAAAGAGTTCTGCCTCCGGCACCAGCTGGATCCCCC**<br>**CCTGCTGAGACACCTGGACAAGTACTACGCCGGCCTGCCCCCAGAGCTGAAGCAGACCAGAGTGAACCTGCCCGC**<br>**CCACAGCAGATATGGCCCTCAGGCCGTGGACGCCAGATG**ATAACGCCGGCGGCCCCTATAACTCTCTACGGCTAA<br>CCTGAATGGACTACGACATAGTCTAGTCCGCCAAG**ATGAGCCCCAAGGACCTGACCCCCTTCCTGACAACCCTGT**<br>**GGCTGCTCCTGGGCCATAGCAGAGTGCCTAGAGTGCGGGCCGAGGAATGCTGCGAGTTCATCAACGTGAACCACC**<br>**CCCCCGAGCGGTGCTACGACTTCAAGATGTGCAACCGGTTCACCGTGGCCCTGAGATGCCCCGACGGCGAAGTGT**<br>**GCTACAGCCCCGAGAAAACCGCCGAGATCCGGGGCATCGTGACCACCATGACCCACAGCCTGACCCGGCAGGTGG**<br>**TGCACAACAAGCTGACCAGCTGCAACTACAACCCCCTGTACCTGGAAGCCGACGGCCGGATCAGATGCGGCAAAG**<br>**TGAACGACAAGGCCCAGTACCTGCTGGGAGCCGCCGGAAGCGTGCCCTACCGGTGGATCAACCTGGAATACGACA**<br>**AGATCACCCGGATCGTGGGCCTGGACCAGTACCTGGAAAGCGTGAAGAAGCACAAGCGGCTGGACGTGTGCAGAG**<br>**CCAAGATGGGCTACATGCTGCAG**TGATAAGGCGCGCCAACGTTACTGGCCGAAGCCGCTTGGAATAAGGCCGGTG<br>TGCGTTTGTCTATATGTTATTTTCCACCATATTGCCGTCTTTTGGCAATGTGAGGGCCCGGAAACCTGGCCCTGT<br>CTTCTTGACGAGCATTCCTAGGGGTCTTTCCCCTCTCGCCAAAGGAATGCAAGGTCTGTTGAATGTCGTGAAGGA<br>AGCAGTTCCTCTGGAAGCTTCTTGAAGACAAACAACGTCTGTAGCGACCCTTTGCAGGCAGCGGAACCCCCCACC<br>TGGCGACAGGTGCCTCTGCGGCCAAAAGCCACGTGTATAAGATACACCTGCAAAGGCGGCACAACCCCAGTGCCA<br>CGTTGTGAGTTGGATAGTTGTGGAAAGAGTCAAATGGCTCTCCTCAAGCGTATTCAACAAGGGGCTGAAGGATGC<br>CCAGAAGGTACCCCATTGTATGGGATCTGATCTGGGGCCTCGGTGCACATGCTTTACATGTGTTTAGTCGAGGTT<br>AAAAAAACGTCTAGGCCCCCCGAACCACGGGGACGTGGTTTTCCTTTGAAAAACACGATAAT**ATGCTGCGGCTGC**<br>**TGCTGAGACACCACTTCCACTGCCTGCTGCTGTGTGCCGTGTGGGCCACCCCTTGTCTGGCCAGCCCTTGGAGCA**<br>**CCCTGACCGCCAACCAGAACCCTAGCCCCCCTTGGTCCAAGCTGACCTACAGCAAGCCCCACGACGCCGCCACCT**<br>**TCTACTGCCCCTTTCTGTACCCCAGCCCTCCCAGAAGCCCCCTGCAGTTCAGCGGCTTCCAGAGAGTGTCCACCG**<br>**GCCCTGAGTGCCGGAACGAGACACTGTACCTGCTGTACAACCGGGAGGGCCAGACACTGGTGGAGCGGAGCAGCA**<br>**CCTGGGTGAAAAAAGTGATCTGGTATCTGAGCGGCCGGAACCAGACCATCCTGCAGCGGATGCCCAGAACCGCCA**<br>**GCAAGCCCAGCGACGGCAACGTGCAGATCAGCGTGGAGGACGCCAAAATCTTCGGAGCCCACATGGTGCCCAAGC**<br>**AGACCAAGCTGCTGAGATTCGTGGTCAACGACGGCACCAGATATCAGATGTGCGTGATGAAGCTGGAAAGCTGGG**<br>**CCCACGTGTTCCGGGACTACTCCGTGAGCTTCCAGGTCCGGCTGACCTTCACCGAGGCCAACAACCAGACCTACA**<br>**CCTTCTGCACCCACCCCAACCTGATCGTG**TGATAAGTACCTTTGTACGCCTGTTTTATACCCCCTCCCTGATTTG<br>CAACTTAGAAGCAACGCAAACCAGATCAATAGTAGGTGTGACATACCAGTCGCATCTTGATCAAGCACTTCTGTA<br>TCCCCGGACCGAGTATCAATAGACTGTGCACACGGTTGAAGGAGAAAACGTCCGTTACCCGGCTAACTACTTCGA<br>GAAGCCTAGTAACGCCATTGAAGTTGCAGAGTGTTTCGCTCAGCACTCCCCCCGTGTAGATCAGGTCGATGAGTC<br>ACCGCATTCCCCACGGGCGACCGTGGCGGTGGCTGCGTTGGCGGCCTGCCTATGGGGTAACCCATAGGACGCTCT<br>AATACGGACATGGCGTGAAGAGTCTATTGAGCTAGTTAGTAGTCCTCCGGCCCCTGAATGCGGCTAATCCTAACT<br>GCGGAGCACATACCCTTAATCCAAAGGGCAGTGTGTCGTAACGGGCAACTCTGCAGCGGAACCGACTACTTTGGG<br>TGTCCGTGTTTCTTTTTATTCTTGTATTGGCTGCTTATGGTGACAATTAAAGAATTGTTACCATATAGCTATTGG<br>ATTGGCCATCCAGTGTCAAACAGAGCTATTGTATATCTCTTTGTTGGATTCACACCTCTCACTCTTGAAACGTTA<br>CACACCCTCAATTACATTATACTGCTGAACACGAAGCGCAT**ATGCGGCTGTGCAGAGTGTGGCTGTCCGTGTGCC** |

-continued

SEQUENCES

TGTGTGCCGTGGTGCTGGGCCAGTGCCAGAGAGAGACAGCCGAGAAGAACGACTACTACCGGGTGCCCCACTACT
GGGATGCCTGCAGCAGAGCCCTGCCCGACCAGACCCGGTACAAATACGTGGAGCAGCTCGTGGACCTGACCCTGA
ACTACCACTACGACGCCAGCCACGGCCTGGACAACTTCGACGTGCTGAAGCGGATCAACGTGACCGAGGTGTCCC
TGCTGATCAGCGACTTCCGGCGGCAGAACAGAAGAGGCGGCACCAACAAGCGGACCACCTTCAACGCCGCTGGCT
CTCTGGCCCCTCACGCCAGATCCCTGGAATTCAGCGTGCGGCTGTTCGCCAACTGATAACGTTGCATCCTGCAGG
ATACAGCAGCAATTGGCAAGCTGCTTACATAGAACTCGCGGCGATTGGCATGCCGCCTTAAAATTTTTATTTTAT
TTTTCTTTTCTTTTCCGAATCGGATTTTGTTTTTAATATTTCAAAAAAAAAAAAAAAAAAAAAAAAAAAAAAAAA
AAGGGTCGGCATGGCATCTCCACCTCCTCGCGGTCCGACCTGGGCATCCGAAGGAGGACGCACGTCCACTCGGAT
GGCTAAGGGAGAGCCACGTTTAAACGCTAGAGCAAGACGTTTCCCGTTGAATATGGCTCATAACACCCCTTGTAT
TACTGTTTATGTAAGCAGACAGTTTTATTGTTCATGATGATATATTTTTATCTTGTGCAATGTAACATCAGAGAT
TTTGAGACACAACGTGGCTTTGTTGAATAAATCGAACTTTTGCTGAGTTGAAGGATCAGATCACGCATCTTCCCG
ACAACGCAGACCGTTCCGTGGCAAAGCAAAAGTTCAAAATCACCAACTGGTCCACCTACAACAAAGCTCTCATCA
ACCGTGGCTCCCTCACTTTCTGGCTGGATGATGGGGCGATTCAGGCCTGGTATGAGTCAGCAACACCTTCTTCAC
GAGGCAGACCTCAGCGCTAGCGGAGTGTATACTGGCTTACTATGTTGGCACTGATGAGGGTGTCAGTGAAGTGCT
TCATGTGGCAGGAGAAAAAAGGCTGCACCGGTGCGTCAGCAGAATATGTGATACAGGATATATTCCGCTTCCTCG
CTCACTGACTCGCTACGCTCGGTCGTTCGACTGCGGCGAGCGGAAATGGCTTACGAACGGGGCGGAGATTTCCTG
GAAGATGCCAGGAAGATACTTAACAGGGAAGTGAGAGGGCCGCGGCAAAGCCGTTTTTCCATAGGCTCCGCCCCC
CTGACAAGCATCACGAAATCTGACGCTCAAATCAGTGGTGGCGAAACCCGACAGGACTATAAAGATACCAGGCGT
TTCCCCTGGCGGCTCCCTCGTGCGCTCTCCTGTTCCTGCCTTTCGGTTTACCGGTGTCATTCCGCTGTTATGGCC
GCGTTTGTCTCATTCCACGCCTGACACTCAGTTCCGGGTAGGCAGTTCGCTCCAAGCTGGACTGTATGCACGAAC
CCCCCGTTCAGTCCGACCGCTGCGCCTTATCCGGTAACTATCGTCTTGAGTCCAACCCGGAAAGACATGCAAAAG
CACCACTGGCAGCAGCCACTGGTAATTGATTTAGAGGAGTTAGTCTTGAAGTCATGCGCCGGTTAAGGCTAAACT
GAAAGGACAAGTTTTGGTGACTGCGCTCCTCCAAGCCAGTTACCTCGGTTCAAAGAGTTGGTAGCTCAGAGAACC
TTCGAAAAACCGCCCTGCAAGGCGGTTTTTTCGTTTTCAGAGCAAGAGATTACGCGCAGACCAAAACGATCTCAA
GAAGATCATCTTATTAAGGGGTCTGACGCTCAGTGGAACGAAAACTCACGTTAAGGGATTTTGGTCATGAGATTA
TCAAAAAGGATCTTCACCTAGATCCTTTTAAATTAAAAATGAAGTTTTAAATCAATCTAAAGTATATATGAGTAA
ACTTGGTCTGACAGTTATTAGAAAAATTCATCCAGCAGACGATAAAACGCAATACGCTGGCTATCCGGTGCCGCA
ATGCCATACAGCACCAGAAAACGATCCGCCCATTCGCCGCCCAGTTCTTCCGCAATATCACGGGTGGCCAGCGCA
ATATCCTGATAACGATCCGCCACGCCCAGACGGCCGCAATCAATAAAGCCGCTAAAACGGCCATTTTCCACCATA
ATGTTCGGCAGGCACGCATCACCATGGGTCACCACCAGATCTTCGCCATCCGGCATGCTCGCTTTCAGACGCGCA
AACAGCTCTGCCGGTGCCAGGCCCTGATGTTCTTCATCCAGATCATCCTGATCCACCAGGCCCGCTTCCATACGG
GTACGCGCACGTTCAATACGATGTTTCGCCTGATGATCAAACGGACAGGTCGCCGGGTCCAGGGTATGCAGACGA
CGCATGGCATCCGCCATAATGCTCACTTTTTCTGCCGGCGCCAGATGGCTAGACAGCAGATCCTGACCCGGCACT
TCGCCCAGCAGCAGCCAATCACGGCCCGCTTCGGTCACCACATCCAGCACCGCCGCACACGGAACACCGGTGGTG
GCCAGCCAGCTCAGACGCGCCGCTTCATCCTGCAGCTCGTTCAGCGCACCGCTCAGATCGGTTTTCACAAACAGC
ACCGGACGACCCTGCGCGCTCAGACGAAACACCGCCGCATCAGAGCAGCCAATGGTCTGCTGCGCCCAATCATAG
CCAAACAGACGTTCCACCCACGCTGCCGGGCTACCCGCATGCAGGCCATCCTGTTCAATCATACTCTTCCTTTTT
CAATATTATTGAAGCATTTATCAGGGTTATTGTCTCATGAGCGGATACATATTTGAATGTATTTAGAAAAATAAA
CAAATAGGGGTTCCGCGCACATTTCCCCGAAAAGTGCCACCTAAATTGTAAGCGTTAATATTTTGTTAAAATTCG
CGTTAAATTTTTGTTAAATCAGCTCATTTTTTAACCAATAGGCCGAAATCGGCAAAATCCCTTATAAATCAAAAG
AATAGACCGAGATAGGGTTGAGTGGCCGCTACAGGGCGCTCCCATTCGCCATTCAGGCTGCGCAACTGTTGGGAA
GGGCGTTTCGGTGCGGGCCTCTTCGCTATTACGCCAGCTGGCGAAAGGGGGATGTGCTGCAAGGCGATTAAGTTG
GGTAACGCCAGGGTTTTCCCAGTCACACGCGTAATACGACTCACTATAG

A556 Vector: SGP-gHso16His-SGP-gL-SGP-UL128-SGP-UL130-SGP-UL131 (SEQ ID NO: 67):
ATAGGCGGCGCATGAGAGAAGCCCAGACCAATTACCTACCCAAAATGGAGAAAGTTCACGTTGACATCGAGGAAG
ACAGCCCATTCCTCAGAGCTTTGCAGCGGAGCTTCCCGCAGTTTGAGGTAGAAGCCAAGCAGGTCACTGATAATG
ACCATGCTAATGCCAGAGCGTTTTCGCATCTGGCTTCAAAACTGATCGAAACGGAGGTGGACCCATCCGACACGA
TCCTTGACATTGGAAGTGCGCCCGCCCGCAGAATGTATTCTAAGCACAAGTATCATTGTATCTGTCCGATGAGAT
GTGCGGAAGATCCGGACAGATTGTATAAGTATGCAACTAAGCTGAAGAAAAACTGTAAGGAAATAACTGATAAGG
AATTGGACAAGAAAATGAAGGAGCTCGCCGCCGTCATGAGCGACCCTGACCTGGAAACTGAGACTATGTGCCTCC
ACGACGACGAGTCGTGTCGCTACGAAGGGCAAGTCGCTGTTTACCAGGATGTATACGCGGTTGACGGACCGACAA
GTCTCTATCACCAAGCCAATAAGGGAGTTAGAGTCGCCTACTGGATAGGCTTTGACACCACCCCTTTTATGTTTA
AGAACTTGGCTGGAGCATATCCATCATACTCTACCAACTGGGCCGACGAAACCGTGTTAACGGCTCGTAACATAG
GCCTATGCAGCTCTGACGTTATGGAGCGGTCACGTAGAGGGATGTCCATTCTTAGAAAGAAGTATTTGAAACCAT
CCAACAATGTTCTATTCTCTGTTGGCTCGACCATCTACCACGAGAAGAGGGACTTACTGAGGAGCTGGCACCTGC
CGTCTGTATTTCACTTACGTGGCAAGCAAAATTACACATGTCGGTGTGAGACTATAGTTAGTTGCGACGGGTACG
TCGTTAAAAGAATAGCTATCAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCGTGTGCACGTATGTGCCAG
CTACATTGTGTGACCAAATGACTGGCATACTGGCAACAGATGTCAGTGCGGACGACGCGCAAAAACTGCTGGTTG
GGCTCAACCAGCGTATAGTCGTCAACGGTCGCACCCAGAGAAACACCAATACCATGAAAAATTACCTTTTGCCCG
TAGTGGCCCAGGCATTTGCTAGGTGGGCAAAGGAATATAAGGAAGATCAAGAAGATGAAAGGCCACTAGGACTAC
GAGATAGACAGTTAGTCATGGGGTGTTGTTGGGCTTTTAGAAGGCACAAGATAACATCTATTTATAAGCGCCCGG
ATACCCAAACCATCATCAAAGTGAACAGCGATTTCCACTCATTCGTGCTGCCCAGGATAGGCAGTAACACATTGG
AGATCGGGCTGAGAACAAGAATCAGGAAAATGTTAGAGGAGCACAAGGAGCCGTCACCTCTCATTACCGCCGAGG
ACGTACAAGAAGCTAAGTGCGCAGCCGATGAGGCTAAGGAGGTGCGTGAAGCCGAGGAGTTGCGCGCAGCTCTAC
CACCTTTGGCAGCTGATGTTGAGGAGCCCACTCTGGAAGCCGATGTAGACTTGATGTTACAAGAGGCTGGGGCCG
GCTCAGTGGAGACACCTCGTGGCTTGATAAAGGTTACCAGCTACGATGGCGAGGACAAGATCGGCTCTTACGCTG
TGCTTTCTCCGCAGGCTGTACTCAAGAGTGAAAAATTATCTTGCATCCACCCTCTCGCTGAACAAGTCATAGTGA
TAACACACTCTGGCCGAAAAGGGCGTTATGCCGTGGAACCATACCATGGTAAAGTAGTGGTGCCAGAGGGACATG
CAATACCCGTCCAGGACTTTCAAGCTCTGAGTGAAAGTGCCACCATTGTGTACAACGAACGTGAGTTCGTAAACA
GGTACCTGCACCATATTGCCACACATGGAGGAGCGCTGAACACTGATGAAGAATATTACAAAACTGTCAAGCCCA
GCGAGCACGACGGCGAATACCTGTACGACATCGACAGGAAACAGTGCGTCAAGAAAGAACTAGTCACTGGGCTAG
GGCTCACAGGCGAGCTGGTGGATCCTCCCTTCCATGAATTCGCCTACGAGAGTCTGAGAACACGACCAGCCGCTC
CTTACCAAGTACCAACCATAGGGGTGTATGGCGTGCCAGGATCAGGCAAGTCTGGCATCATTAAAAGCGCAGTCA
CCAAAAAAGATCTAGTGGTGAGCGCCAAGAAAGAAAACTGTGCAGAAATTATAAGGGACGTCAAGAAAATGAAAG -continued

| SEQUENCES |
|---|
| GGCTGGACGTCAATGCCAGAACTGTGGACTCAGTGCTCTTGAATGGATGCAAACACCCCGTAGAGACCCTGTATA<br>TTGACGAAGCTTTTGCTTGTCATGCAGGTACTCTCAGAGCGCTCATAGCCATTATAAGACCTAAAAAGGCAGTGC<br>TCTGCGGGGATCCCAAACAGTGCGGTTTTTTAACATGATGTGCCTGAAAGTGCATTTTAACCACGAGATTTGCA<br>CACAAGTCTTCCACAAAAGCATCTCTCGCCGTTGCACTAAATCTGTGACTTCGGTCGTCTCAACCTTGTTTTACG<br>ACAAAAAAATGAGAACGACGAATCCGAAAGAGACTAAGATTGTGATTGACACTACCGGCAGTACCAAACCTAAGC<br>AGGACGATCTCATTCTCACTTGTTTCAGAGGGTGGGTGAAGCAGTTGCAAATAGATTACAAAGGCAACGAAATAA<br>TGACGGCAGCTGCCTCTCAAGGGCTGACCCGTAAAGGTGTGTATGCCGTTCGGTACAAGGTGAATGAAAATCCTC<br>TGTACGCACCCACCTCAGAACATGTGAACGTCCTACTGACCCGCACGGAGGACCGCATCGTGTGGAAAACACTAG<br>CCGGCGACCCATGGATAAAAACACTGACTGCCAAGTACCCTGGGAATTTCACTGCCACGATAGAGGAGTGGCAAG<br>CAGAGCATGATGCCATCATGAGGCACATCTTGGAGAGACCGGACCCTACCGACGTCTTCCAGAATAAGGCAAACG<br>TGTGTTGGGCCAAGGCTTTAGTGCCGGTGCTGAAGACCGCTGGCATAGACATGACCACTGAACAATGGAACACTG<br>TGGATTATTTTGAAACGGACAAAGCTCACTCAGCAGAGATAGTATTGAACCAACTATGCGTGAGGTTCTTTGGAC<br>TCGATCTGGACTCCGGTCTATTTTCTGCACCCACTGTTCCGTTATCCATTAGGAATAATCACTGGGATAACTCCC<br>CGTCGCCTAACATGTACGGGCTGAATAAAGAAGTGGTCCGTCAGCTCTCTCGCAGGTACCCACAACTGCCTCGGG<br>CAGTTGCCACTGGAAGAGTCTATGACATGAACACTGGTACACTGCGCAATTATGATCCGCGCATAAACCTAGTAC<br>CTGTAAACAGAAGACTGCCTCATGCTTTAGTCCTCCACCATAATGAACACCCACAGAGTGACTTTTCTTCATTCG<br>TCAGCAAATTGAAGGGCAGAACTGTCCTGGTGGTCGGGGAAAAGTTGTCCGTCCCAGGCAAAATGGTTGACTGGT<br>TGTCAGACCGGCCTGAGGCTACCTTCAGAGCTCGGCTGGATTTAGGCATCCCAGGTGATGTGCCCAAATATGACA<br>TAATATTTGTTAATGTGAGGACCCCATATAAATACCATCACTATCAGCAGTGTGAAGACCATGCCATTAAGCTTA<br>GCATGTTGACCAAGAAAGCTTGTCTGCATCTGAATCCCGGCGGAACCTGTGTCAGCATAGGTTATGGTTACGCTG<br>ACAGGGCCAGCGAAAGCATCATTGGTGCTATAGCGCGGCAGTTCAAGTTTTCCCGGGTATGCAAACCGAAATCCT<br>CACTTGAAGAGACGGAAGTTCTGTTTGTATTCATTGGGTACGATCGCAAGGCCCGTACGCACAATCCTTACAAGC<br>TTTCATCAACCTTGACCAACATTTATACAGGTTCCAGACTCCACGAAGCCGGATGTGCACCCTCATATCATGTGG<br>TGCGAGGGGATATTGCCACGGCCACCGAAGGAGTGATTATAAATGCTGCTAACAGCAAAGGACAACCTGGCGGAG<br>GGGTGTGCGGAGCGCTGTATAAGAAATTCCCGGAAAGCTTCGATTTACAGCCGATCGAAGTAGGAAAAGCGCGAC<br>TGGTCAAAGGTGCAGCTAAACATATCATTCATGCCGTAGGACCAAACTTCAACAAAGTTTCGGAGGTTGAAGGTG<br>ACAAACAGTTGGCAGAGGCTTATGAGTCCATCGCTAAGATTGTCAACGATAACAATTACAAGTCAGTAGCGATTC<br>CACTGTTGTCCACCGGCATCTTTTCCGGGAACAAAGATCGACTAACCCAATCATTGAACCATTTGCTGACAGCTT<br>TAGACACCACTGATGCAGATGTAGCCATATACTGCAGGGACAAGAAATGGGAAATGACTCTCAAGGAAGCAGTGG<br>CTAGGAGAGAAGCAGTGGAGGAGATATGCATATCCGACGACTCTTCAGTGACAGAACCTGATGCAGAGCTGGTGA<br>GGGTGCATCCGAAGAGTTCTTTGGCTGGAAGGAAGGGCTACAGCACAAGCGATGGCAAAACTTTCTCATATTTGG<br>AAGGGACCAAGTTTCACCAGGCGGCCAAGGATATAGCAGAAATTAATGCCATGTGGCCCGTTGCAACGGAGGCCA<br>ATGAGCAGGTATGCATGTATATCCTCGGAGAAAGCATGAGCAGTATTAGGTCGAAATGCCCCGTCGAAGAGTCGG<br>AAGCCTCCACACCACCTAGCACGCTGCCTTGCTTGTGCATCCATGCCATGACTCCAGAAAGAGTACAGCGCCTAA<br>AAGCCTCACGTCCAGAACAAATTACTGTGTGCTCATCCTTTCCATTGCCGAAGTATAGAATCACTGGTGTGCAGA<br>AGATCCAATGCTCCCAGCCTATATTGTTCTCACCGAAAGTGCCTGCGTATATTCATCCAAGGAAGTATCTCGTGG<br>AAACACCACCGGTAGACGAGACTCCGGAGCCATCGGCAGAGAACCAATCCACAGAGGGGACACCTGAACAACCAC<br>CACTTATAACCGAGGATGAGACCAGGACTAGAACGCCTGAGCCGATCATCATCGAAGAGGAAGAAGAGGATAGCA<br>TAAGTTTGCTGTCAGATGGCCCGACCCACCAGGTGCTGCAAGTCGAGGCAGACATTCACGGGCCGCCCTCTGTAT<br>CTAGCTCATCCTGGTCCATTCCTCATGCATCCGACTTTGATGTGGACAGTTTATCCATACTTGACACCCTGGAGG<br>GAGCTAGCGTGACCAGCGGGGCAACGTCAGCCGAGACTAACTCTTACTTCGCAAAGAGTATGGAGTTTCTGGCGC<br>GACCGGTGCCTGCGCCTCGAACAGTATTCAGGAACCCTCCACATCCCGCTCCGCGCACAAGAACACCGTCACTTG<br>CACCCAGCAGGGCCTGCTCGAGAACCAGCCTAGTTTCCACCCCGCCAGGCGTGAATAGGGTGATCACTAGAGAGG<br>AGCTCGAGGCGCTTACCCCGTCACGCACTCCTAGCAGGTCGGTCTCGAGAACCAGCCTGGTCTCCAACCCGCCAG<br>GCGTAAATAGGGTGATTACAAGAGAGGAGTTTGAGGCGTTCGTAGCACAACAACAATGACGGTTTGATGCGGGTG<br>CATACATCTTTTCCTCCGACACCGGTCAAGGGCATTTACAACAAAAATCAGTAAGGCAAACGGTGCTATCCGAAG<br>TGGTGTTGGAGAGGACCGAATTGGAGATTTCGTATGCCCCGCGCCTCGACCAAGAAAAAGAAGAATTACTACGCA<br>AGAAATTACAGTTAAATCCCACACCTGCTAACAGAAGCAGATACCAGTCCAGGAAGGTGGAGAACATGAAAGCCA<br>TAACAGCTAGACGTATTCTGCAAGGCCTAGGGCATTATTTGAAGGCAGAAGGAAAAGTGGAGTGCTACCGAACCC<br>TGCATCCTGTTCCTTTGTATTCATCTAGTGTGAACCGTGCCTTTTCAAGCCCCAAGGTCGCAGTGGAAGCCTGTA<br>ACGCCATGTTGAAAGAGAACTTTCCGACTGTGGCTTCTTACTGTATTATTCCAGAGTACGATGCCTATTTGGACA<br>TGGTTGACGGAGCTTCATGCTGCTTAGACACTGCCAGTTTTTGCCCTGCAAAGCTGCGCAGCTTTCCAAAGAAAC<br>ACTCCTATTTGGAACCCACAATACGATCGGCAGTGCCTTCAGCGATCCAGAACACGCTCCAGAACGTCCTGGCAG<br>CTGCCACAAAAAGAAATTGCAATGTCACGCAAATGAGAGAATTGCCCGTATTGGATTCGGCGGCCTTTAATGTGG<br>AATGCTTCAAGAAATATGCGTGTAATAATGAATATTGGGAAACGTTTAAAGAAAACCCCATCAGGCTTACTGAAG<br>AAAACGTGGTAAATTACATTACCAAATTAAAAGGACCAAAAGCTGCTGCTCTTTTTGCGAAGACACATAATTTGA<br>ATATGTTGCAGGACATACCAATGGACAGGTTTGTAATGGACTTAAAGAGAGACGTGAAAGTGACTCCAGGAACAA<br>AACATACTGAAGAACGGCCCAAGGTACAGGTGATCCAGGCTGCCGATCCGCTAGCAACAGCGTATCTGTGCGGAA<br>TCCACCGAGAGCTGGTTAGGAGATTAAATGCGGTCCTGCTTCCGAACATTCATACACTGTTTGATATGTCGGCTG<br>AAGACTTTGACGCTATTATAGCCGAGCACTTCCAGCCTGGGGATTGTGTTCTGGAAACTGACATCGCGTCGTTTG<br>ATAAAAGTGAGGACGACGCCATGGCTCTGACCGCGTTAATGATTCTGGAAGACTTAGGTGTGGACGCAGAGCTGT<br>TGACGCTGATTGAGGCGGCTTTCGGCGAAATTTCATCAATACATTTGCCCACTAAAACTAAATTTAAATTCGGAG<br>CCATGATGAAATCTGGAATGTTCCTCACACTGTTTGTGAACACAGTCATTAACATTGTAATCGCAAGCAGAGTGT<br>TGAGAGAACGGCTAACCGGATCACCATGTGCAGCATTCATTGGAGATGACAATATCGTGAAAGGAGTCAAATCGG<br>ACAAATTAATGGCAGACAGGTGCGCCACCTGGTTGAATATGGAAGTCAAGATTATAGATGCTGTGGTGGGCGAGA<br>AAGCGCCTTATTTCTGTGGAGGGTTTATTTTGTGTGACTCCGTGACCGGCACAGCGTGCCGTGTGGCAGACCCCC<br>TAAAAAGGCTGTTTAAGCTTGGCAAACCTCTGGCAGCAGACGATGAACATGATGATGACAGGAGAAGGGCATTGC<br>ATGAAGAGTCAACACGCTGGAACCGAGTGGGTATTCTTTCAGAGCTGTGCAAGGCAGTAGAATCAAGGTATGAAA<br>CCGTAGGAACTTCCATCATAGTTATGGCCATGACTACTCTAGCTAGCAGTGTTAAATCATTCAGCTACCTGAGAG<br>GGGCCCCTATAACTCTCTACGGCTAACCTGAATGGACTACGACATAGTCTAGTCCGCCAAG**ATGAGGCCTGGCCT**<br>**GCCCTCCTACCTGATCATCCTGGCCGTGTGCCTGTTCAGCCACCTGCTGTCCAGCAGATACGGCGCCGAGGCCGT**<br>**GAGCGAGCCCCTGGACAAGGCTTTCCACCTGCTGCTGAACACCTACGGCAGACCCATCCGGTTTCTGCGGGAGAA**<br>**CACCACCCAGTGCACCTACAACAGCAGCCTGCGGAACAGCACCGTCGTGAGAGAGAACGCCATCAGCTTCAACTT**<br>**TTTCCAGAGCTACAACCAGTACTACGTGTTCCACATGCCCAGATGCCTGTTTGCCGGCCCTCTGGCCGAGCAGTT**<br>**CCTGAACCAGGTGGACCTGACCGAGACACTGGAAAGATACCAGCAGCGGCTGAATACCTACGCCCTGGTGTCCAA**<br>**GGACCTGGCCAGCTACCGGTCCTTTAGCCAGCAGCTCAAGGCTCAGGATAGCCTCGGCGAGCAGCCTACCACCGT**<br>**GCCCCCTCCCATCGACCTGAGCATCCCCCACGTGTGGATGCCTCCCCAGACCACCCCTCACGGCTGGACCGAGAG** |

-continued

SEQUENCES

CCACACCACCTCCGGCCTGCACAGACCCCACTTCAACCAGACCTGCATCCTGTTCGACGGCCACGACCTGCTGTT
TAGCACCGTGACCCCCTGCCTGCACCAGGGCTTCTACCTGATCGACGAGCTGAGATACGTGAAGATCACCCTGAC
CGAGGATTTCTTCGTGGTCACCGTGTCCATCGACGACGACACCCCCATGCTGCTGATCTTCGGCCACCTGCCCAG
AGTGCTGTTCAAGGCCCCCTACCAGCGGGACAACTTCATCCTGCGGCAGACCGAGAAGCACGAGCTGCTGGTGCT
GGTCAAGAAGGACCAGCTGAACCGGCACTCCTACCTGAAGGACCCCGACTTCCTGGACGCCGCCCTGGACTTCAA
CTACCTGGACCTGAGCGCCCTGCTGAGAAACAGCTTCCACAGATACGCCGTGGACGTGCTGAAGTCCGGACGGTG
CCAGATGCTCGATCGGCGGACCGTGGAGATGGCCTTCGCCTATGCCCTCGCCCTGTTCGCCGCTGCCAGACAGGA
AGAGGCTGGCGCCCAGGTGTCAGTGCCCAGAGCCCTGGATAGACAGGCCGCCCTGCTGCAGATCCAGGAATTCAT
GATCACCTGCCTGAGCCAGACCCCCCCTAGAACCACCCTGCTGCTGTACCCCACAGCCGTGGATCTGGCCAAGAG
GGCCCTGTGGACCCCCAACCAGATCACCGACATCACAAGCCTCGTGCGGCTCGTGTACATCCTGAGCAAGCAGAA
CCAGCAGCACCTGATCCCCCAGTGGGCCCTGAGACAGATCGCCGACTTCGCCCTGAAGCTGCACAAGACCCATCT
GGCCAGCTTTCTGAGCGCCTTCGCCAGGCAGGAACTGTACCTGATGGGCAGCCTGGTCCACAGCATGCTGGTGCA
TACCACCGAGCGGCGGGAGATCTTCATCGTGGAGACAGGCCTGTGTAGCCTGGCCGAGCTGTCCCACTTTACCCA
GCTGCTGGCCCACCCTCACCACGAGTACCTGAGCGACCTGTACACCCCCTGCAGCAGCAGCGGCAGACGGGACCA
CAGCCTGGAACGGCTGACCAGACTGTTCCCCGATGCCACCGTGCCTGCTACAGTGCCTGCCGCCCTGTCCATCCT
GTCCACCATGCAGCCCAGCACCCTGGAAACCTTCCCCGACCTGTTCTGCCTGCCCCTGGGCGAGAGCTTTAGCGC
CCTGACCGTGTCCGAGCACGTGTCCTACATCGTGACCAATCAGTACCTGATCAAGGGCATCAGCTACCCCGTGTC
CACCACAGTCGTGGGCCAGAGCCTGATCATCACCCAGACCGACAGCCAGACCAAGTGCGAGCTGACCCGGAACAT
GCACACCACACACAGCATCACCGTGGCCCTGAACATCAGCCTGGAAAACTGCGCTTTCTGTCAGTCTGCCCTGCT
GGAATACGACGATACCCAGGGCGTGATCAACATCATGTACATGCACGACAGCGACGACGTGCTGTTCGCCCTGGA
CCCCTACAACGAGGTGGTGGTGTCCAGCCCCCGGACCCACTACCTGATGCTGCTGAAGAACGGCACCGTGCTGGA
AGTGACCGACGTGGTGGTGGACGCCACCGACGGCAGCGGATCTGGGTCCCACCATCACCATCACCATTGATAATC
TAGAGGCCCCTATAACTCTCTACGGCTAACCTGAATGGACTACGACATAGTCTAGTCCGCCAAGATGTGCAGAAG
GCCCGACTGCGGCTTCAGCTTCAGCCCTGGACCCGTGATCCTGCTGTGGTGCTGCCTGCTGCTGCCTATCGTGTC
CTCTGCCGCCGTGTCTGTGGCCCCTACAGCCGCCGAGAAGGTGCCAGCCGAGTGCCCCGAGCTGACCAGAAGATG
CCTGCTGGGCGAGGTGTTCGAGGGCGACAAGTACGAGAGCTGGCTGCGGCCCCTGGTCAACGTGACCGGCAGAGA
TGGCCCCCTGAGCCAGCTGATCCGGTACAGACCCGTGACCCCCGAGGCCGCCAATAGCGTGCTGCTGGACGAGGC
CTTCCTGGATACCCTGGCCCTGCTGTACAACAACCCCGACCAGCTGAGAGCCCTGCTGACCCTGCTGTCCAGCGA
CACCGCCCCCAGATGGATGACCGTGATGCGGGGCTACAGCGAGTGTGGAGATGGCAGCCCTGCCGTGTACACCTG
CGTGGACGACCTGTGCAGAGGCTACGACCTGACCAGACTGAGCTACGGCCGGTCCATCTTCACAGAGCACGTGCT
GGGCTTCGAGCTGGTGCCCCCCAGCCTGTTCAACGTGGTGGTGGCCATCCGGAACGAGGCCACCAGAACCAACAG
AGCCGTGCGGCTGCCTGTGTCTACAGCCGCTGCACCTGAGGGCATCACACTGTTCTACGGCCTGTACAACGCCGT
GAAAGAGTTCTGCCTCCGGCACCAGCTGGATCCCCCCCTGCTGAGACACCTGGACAAGTACTACGCCGGCCTGCC
CCCAGAGCTGAAGCAGACCAGAGTGAACCTGCCCGCCCACAGCAGATATGGCCCTCAGGCCGTGGACGCCAGATG
ATAACGCCGGCGGCCCCTATAACTCTCTACGGCTAACCTGAATGGACTACGACATAGTCTAGTCCGCCAAGATGA
GCCCCAAGGACCTGACCCCCTTCCTGACAACCCTGTGGCTGCTCCTGGGCCATAGCAGAGTGCCTAGAGTGCGGG
CCGAGGAATGCTGCGAGTTCATCAACGTGAACCACCCCCCCGAGCGGTGCTACGACTTCAAGATGTGCAACCGGT
TCACCGTGGCCCTGAGATGCCCCGACGGCGAAGTGTGCTACAGCCCCGAGAAAACCGCCGAGATCCGGGGCATCG
TGACCACCATGACCCACAGCCTGACCCGGCAGGTGGTGCACAACAAGCTGACCAGCTGCAACTACAACCCCCTGT
ACCTGGAAGCCGACGGCCGGATCAGATGCGGCAAAGTGAACGACAAGGCCCAGTACCTGCTGGGAGCCGCCGGAA
GCGTGCCCTACCGGTGGATCAACCTGGAATACGACAAGATCACCCGGATCGTGGGCCTGGACCAGTACCTGGAAA
GCGTGAAGAAGCACAAGCGGCTGGACGTGTGCAGAGCCAAGATGGGCTACATGCTGCAGTGATAAGGCGCGCCAA
CGTTACTGGCCGAAGCCGCTTGGAATAAGGCCGGTGTGCGTTTGTCTATATGTTATTTTCCACCATATTGCCGTC
TTTTGGCAATGTGAGGGCCCGGAAACCTGGCCCTGTCTTCTTGACGAGCATTCCTAGGGGTCTTTCCCCTCTCGC
CAAAGGAATGCAAGGTCTGTTGAATGTCGTGAAGGAAGCAGTTCCTCTGGAAGCTTCTTGAAGACAAACAACGTC
TGTAGCGACCCTTTGCAGGCAGCGGAACCCCCCACCTGGCGACAGGTGCCTCTGCGGCCAAAAGCCACGTGTATA
AGATACACCTGCAAAGGCGGCACAACCCCAGTGCCACGTTGTGAGTTGGATAGTTGTGGAAAGAGTCAAATGGCT
CTCCTCAAGCGTATTCAACAAGGGGCTGAAGGATGCCCAGAAGGTACCCCATTGTATGGGATCTGATCTGGGGCC
TCGGTGCACATGCTTTACATGTGTTTAGTCGAGGTTAAAAAAACGTCTAGGCCCCCCGAACCACGGGGACGTGGT
TTTCCTTTGAAAAACACGATAATATGCTGCGGCTGCTGCTGAGACACCACTTCCACTGCCTGCTGCTGTGTGCCG
TGTGGGCCACCCCTTGTCTGGCCAGCCCTTGGAGCACCCTGACCGCCAACCAGAACCCTAGCCCCCCTTGGTCCA
AGCTGACCTACAGCAAGCCCCACGACGCCGCCACCTTCTACTGCCCCTTTCTGTACCCCAGCCCTCCCAGAAGCC
CCCTGCAGTTCAGCGGCTTCCAGAGAGTGTCCACCGGCCCTGAGTGCCGGAACGAGACACTGTACCTGCTGTACA
ACCGGGAGGGCCAGACACTGGTGGAGCGGAGCAGCACCTGGGTGAAAAAAGTGATCTGGTATCTGAGCGGCCGGA
ACCAGACCATCCTGCAGCGGATGCCCAGAACCGCCAGCAAGCCCAGCGACGGCAACGTGCAGATCAGCGTGGAGG
ACGCCAAAATCTTCGGAGCCCACATGGTGCCCAAGCAGACCAAGCTGCTGAGATTCGTGGTCAACGACGGCACCA
GATATCAGATGTGCGTGATGAAGCTGGAAAGCTGGGCCCACGTGTTCCGGGACTACTCCGTGAGCTTCCAGGTCC
GGCTGACCTTCACCGAGGCCAACAACCAGACCTACACCTTCTGCACCCACCCCAACCTGATCGTGTGATAAGTAC
CTTTGTACGCCTGTTTTATACCCCCTCCCTGATTTGCAACTTAGAAGCAACGCAAACCAGATCAATAGTAGGTGT
GACATACCAGTCGCATCTTGATCAAGCACTTCTGTATCCCCGGACCGAGTATCAATAGACTGTGCACACGGTTGA
AGGAGAAAACGTCCGTTACCCGGCTAACTACTTCGAGAAGCCTAGTAACGCCATTGAAGTTGCAGAGTGTTTCGC
TCAGCACTCCCCCCGTGTAGATCAGGTCGATGAGTCACCGCATTCCCCACGGGCGACCGTGGCGGTGGCTGCGTT
GGCGGCCTGCCTATGGGGTAACCCATAGGACGCTCTAATACGGACATGGCGTGAAGAGTCTATTGAGCTAGTTAG
TAGTCCTCCGGCCCCTGAATGCGGCTAATCCTAACTGCGGAGCACATACCCTTAATCCAAAGGGCAGTGTGTCGT
AACGGGCAACTCTGCAGCGGAACCGACTACTTTGGGTGTCCGTGTTTCTTTTTATTCTTGTATTGGCTGCTTATG
GTGACAATTAAAGAATTGTTACCATATAGCTATTGGATTGGCCATCCAGTGTCAAACAGAGCTATTGTATATCTC
TTTGTTGGATTCACACCTCTCACTCTTGAAACGTTACACACCCTCAATTACATTATACTGCTGAACACGAAGCGC
ATATGCGGCTGTGCAGAGTGTGGCTGTCCGTGTGCCTGTGTGCCGTGGTGCTGGGCCAGTGCCAGAGAGAGACAG
CCGAGAAGAACGACTACTACCGGGTGCCCCACTACTGGGATGCCTGCAGCAGAGCCCTGCCCGACCAGACCCGGT
ACAAATACGTGGAGCAGCTCGTGGACCTGACCCTGAACTACCACTACGACGCCAGCCACGGCCTGGACAACTTCG
ACGTGCTGAAGCGGATCAACGTGACCGAGGTGTCCCTGCTGATCAGCGACTTCCGGCGGCAGAACAGAAGAGGCG
GCACCAACAAGCGGACCACCTTCAACGCCGCTGGCTCTCTGGCCCCTCACGCCAGATCCCTGGAATTCAGCGTGC
GGCTGTTCGCCAACTGATAACGTTGCATCCTGCAGGATACAGCAGCAATTGGCAAGCTGCTTACATAGAACTCGC
GGCGATTGGCATGCCGCCTTAAAATTTTTATTTTATTTTTCTTTTCTTTTCCGAATCGGATTTTGTTTTTAATAT
TTCAAAAAAAAAAAAAAAAAAAAAAAAAAAAAAAAAAAAAGGGTCGGCATGGCATCTCCACCTCCTCGCGGTCCGAC
CTGGGCATCCGAAGGAGGACGCACGTCCACTCGGATGGCTAAGGGAGAGCCACGTTTAAACGCTAGAGCAAGACG
TTTCCCGTTGAATATGGCTCATAACACCCCTTGTATTACTGTTTATGTAAGCAGACAGTTTTATTGTTCATGATG

-continued

SEQUENCES

ATATATTTTTATCTTGTGCAATGTAACATCAGAGATTTTGAGACACAACGTGGCTTTGTTGAATAAATCGAACTT
TTGCTGAGTTGAAGGATCAGATCACGCATCTTCCCGACAACGCAGACCGTTCCGTGGCAAAGCAAAAGTTCAAAA
TCACCAACTGGTCCACCTACAACAAAGCTCTCATCAACCGTGGCTCCCTCACTTTCTGGCTGGATGATGGGGCGA
TTCAGGCCTGGTATGAGTCAGCAACACCTTCTTCACGAGGCAGACCTCAGCGCTAGCGGAGTGTATACTGGCTTA
CTATGTTGGCACTGATGAGGGTGTCAGTGAAGTGCTTCATGTGGCAGGAGAAAAAAGGCTGCACCGGTGCGTCAG
CAGAATATGTGATACAGGATATATTCCGCTTCCTCGCTCACTGACTCGCTACGCTCGGTCGTTCGACTGCGGCGA
GCGGAAATGGCTTACGAACGGGGCGGAGATTTCCTGGAAGATGCCAGGAAGATACTTAACAGGGAAGTGAGAGGG
CCGCGGCAAAGCCGTTTTTCCATAGGCTCCGCCCCCCTGACAAGCATCACGAAATCTGACGCTCAAATCAGTGGT
GGCGAAACCCGACAGGACTATAAAGATACCAGGCGTTTCCCCTGGCGGCTCCCTCGTGCGCTCTCCTGTTCCTGC
CTTTCGGTTTACCGGTGTCATTCCGCTGTTATGGCCGCGTTTGTCTCATTCCACGCCTGACACTCAGTTCCGGGT
AGGCAGTTCGCTCCAAGCTGGACTGTATGCACGAACCCCCCGTTCAGTCCGACCGCTGCGCCTTATCCGGTAACT
ATCGTCTTGAGTCCAACCCGGAAAGACATGCAAAAGCACCACTGGCAGCAGCCACTGGTAATTGATTTAGAGGAG
TTAGTCTTGAAGTCATGCGCCGGTTAAGGCTAAACTGAAAGGACAAGTTTTGGTGACTGCGCTCCTCCAAGCCAG
TTACCTCGGTTCAAAGAGTTGGTAGCTCAGAGAACCTTCGAAAAACCGCCCTGCAAGGCGGTTTTTTCGTTTTCA
GAGCAAGAGATTACGCGCAGACCAAAACGATCTCAAGAAGATCATCTTATTAAGGGGTCTGACGCTCAGTGGAAC
GAAAACTCACGTTAAGGGATTTTGGTCATGAGATTATCAAAAAGGATCTTCACCTAGATCCTTTTAAATTAAAAA
TGAAGTTTTAAATCAATCTAAAGTATATATGAGTAAACTTGGTCTGACAGTTATTAGAAAAATTCATCCAGCAGA
CGATAAAACGCAATACGCTGGCTATCCGGTGCCGCAATGCCATACAGCACCAGAAAACGATCCGCCCATTCGCCG
CCCAGTTCTTCCGCAATATCACGGGTGGCCAGCGCAATATCCTGATAACGATCCGCCACGCCCAGACGGCCGCAA
TCAATAAAGCCGCTAAAACGGCCATTTTCCACCATAATGTTCGGCAGGCACGCATCACCATGGGTCACCACCAGA
TCTTCGCCATCCGGCATGCTCGCTTTCAGACGCGCAAACAGCTCTGCCGGTGCCAGGCCCTGATGTTCTTCATCC
AGATCATCCTGATCCACCAGGCCCGCTTCCATACGGGTACGCGCACGTTCAATACGATGTTTCGCCTGATGATCA
AACGGACAGGTCGCCGGGTCCAGGGTATGCAGACGACGCATGGCATCCGCCATAATGCTCACTTTTTCTGCCGGC
GCCAGATGGCTAGACAGCAGATCCTGACCCGGCACTTCGCCCAGCAGCAGCCAATCACGGCCCGCTTCGGTCACC
ACATCCAGCACCGCCGCACACGGAACACCGGTGGTGGCCAGCCAGCTCAGACGCGCCGCTTCATCCTGCAGCTCG
TTCAGCGCACCGCTCAGATCGGTTTTCACAAACAGCACCGGACGACCCTGCGCGCTCAGACGAAACACCGCCGCA
TCAGAGCAGCCAATGGTCTGCTGCGCCCAATCATAGCCAAACAGACGTTCCACCCACGCTGCCGGGCTACCCGCA
TGCAGGCCATCCTGTTCAATCATACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCACATTTCCCCGAAAAGTGCCA
CCTAAATTGTAAGCGTTAATATTTTGTTAAAATTCGCGTTAAATTTTTGTTAAATCAGCTCATTTTTTAACCAAT
AGGCCGAAATCGGCAAAATCCCTTATAAATCAAAAGAATAGACCGAGATAGGGTTGAGTGGCCGCTACAGGGCGC
TCCCATTCGCCATTCAGGCTGCGCAACTGTTGGGAAGGGCGTTTCGGTGCGGGCCTCTTCGCTATTACGCCAGCT
GGCGAAAGGGGGATGTGCTGCAAGGCGATTAAGTTGGGTAACGCCAGGGTTTTCCCAGTCACACGCGTAATACGA
CTCACTATAG

VZV gB (SEQ ID NO: 68):
MFVTAVVSVSPSSFYESLQVEPTQSEDITRSAHLGDGDEIREAIHKSQDAETKPTFYVCPPP
TGSTIVRLEPPRTCPDYHLGKNFTEGIAVVYKENIAAYKFKATVYYKDVIVSTAWAGSSYTQ
ITNRYADRVPIPVSEITDTIDKFGKCSSKATYVRNNHKVEAFNEDKNPQDMPLIASKYNSVG
SKAWHTTNDTYMVAGTPGTYRTGTSVNCIIEEVEARSIFPYDSFGLSTGDIIYMSPFFGLRD
GAYREHSNYAMDRFHQFEGYRQRDLDTRALLEPAARNFLVTPHLTVGWNWKPKRTEVCSLVK
WREVEDVVRDEYAHNFRFTMKTLSTTFISETNEFNLNQIHLSQCVKEEARAIINRIYTTRYN
SSHVRTGDIQTYLARGGFVVVFQPLLSNSLARLYLQELVRENTNHSPQKHPTRNTRSRRSVP
VELRANRTITTTSSVEFAMLQFTYDHIQEHVNEMLARISSSWCQLQNRERALWSGLFPINPS
ALASTILDQRVKARILGDVISVSNCPELGSDTRIILQNSMRVSGSTTRCYSRPLISIVSLNG
SGTVEGQLGTDNELIMSRDLLEPCVANHKRYFLFGHHYVYYEDYRYVREIAVHDVGMISTYV
DLNLTLLKDREFMPLQVYTRDELRDTGLLDYSEIQRRNQMHSLRFYDIDKVVQYDSGTAIMQ
GMAQFFQGLGTAGQAVGHVVLGATGALLSTVHGFTTFLSNPFGALAVGLLVLAGLVAAFFAY
RYVLKLKTSPMKALYPLTTKGLKQLPEGMDPFAEKPNATDTPIEEIGDSQNTEPSVNSGFDP
DKFREAQEMIKYMTLVSAAERQESKARKKNKTSALLTSRLTGLALRNRRGYSRVRTENVTGV

VZV gH (SEQ ID NO: 69):
MFALVLAVVILPLWTTANKSYVTPTPATRSIGHMSALLREYSDRNMSLKLEAFYPTGFDEEL
IKSLHWGNDRKHVFLVIVKVNPTTHEGDVGLVIFPKYLLSPYHFKAEHRAPFPAGRFGFLSH
PVTPDVSFFDSSFAPYLTTQHLVAFTTFPPNPLVWHLERAETAATAERPFGVSLLPARPTVP
KNTILEHKAHFATWDALARHTFFSAEAIITNSTLRIHVPLFGSVWPIRYWATGSVLLTSDSG
RVEVNIGVGFMSSLISLSSGLPIELIVVPHTVKLNAVTSDTTWFQLNPPGPDPGPSYRVYLL
GRGLDMNFSKHATVDICAYPEESLDYRYHLSMAHTEALRMTTKADQHDINEESYYHIAARIA
TSIFALSEMGRTTEYFLLDEIVDVQYQLKFLNYILMRIGAGAHPNTISGTSDLIFADPSQLH
DELSLLFGQVKPANVDYFISYDEARDQLKTAYALSRGQDHVNALSLARRVIMSIYKGLLVKQ
NLNATERQALFFASMILLNFREGLENSSRVLDGRTTLLLMTSMCTAAHATQAALNIQEGLAY
LNPSKHMFTIPNVYSPCMGSLRTDLTEEIHVMNLLSAIPTRPGLNEVLHTQLDESEIFDAAF
KTMMIFTTWTAKDLHILHTHVPEVFTCQDAAARNGEYVLILPAVQGHSYVITRNKPQRGLVY
SLADVDVYNPISVVYLSKDTCVSEHGVIETVALPHPDNLKECLYCGSVFLRYLTTGAIMDII
IIDSKDTERQLAAMGNSTIPPFNPDMHGDDSKAVLLFPNGTVVTLLGFERRQAIRMSGQYLG
ASLGGAFLAVVGFGIIGWMLCGNSRLREYNKIPLT

VZV gL (SEQ ID NO: 70):
MASHKWLLQMIVFLKTITIAYCLHLQDDTPLFFGAKPLSDVSLIITEPCVSSVYEAWDYAAP
PVSNLSEALSGIVVKTKCPVPEVILWFKDKQMAYWTNPYVTLKGLTQSVGEEHKSGDIRDAL
LDALSGVWVDSTPSSTNIPENGCVWGADRLFQRVCQ

VZV gI (SEQ ID NO: 71):
MFLIQCLISAVIFYIQVTNALIFKGDHVSLQVNSSLTSILIPMQNDNYTEIKGQLVFIGEQL
PTGTNYSGTLELLYADTVAFCFRSVQVIRYDGCPRIRTSAFISCRYKHSWHYGNSTDRISTE
PDAGVMLKITKPGINDAGVYVLLVRLDHSRSTDGFILGVNVYTAGSHHNIHGVIYTSPSLQN
GYSTRALFQQARLCDLPATPKGSGTSLFQHMLDLRAGKSLEDNPWLHEDVVTTETKSVVKEG

-continued

| SEQUENCES |
| --- |

IENHVYPTDMSTLPEKSLNDPPENLLIIIPIVASVMILTAMVIVIVISVKRRRIKKHPIYRP
NTKTRRGIQNATPESDVMLEAAIAQLATIREESPPHSVVNPFVK

VZV gE (SEQ ID NO: 72):
MGTVNKPVVGVLMGFGIITGTLRITNPVRASVLRYDDFHIDEDKLDTNSVYEPYYHSDHAES
SWVNRGESSRKAYDHNSPYIWPRNDYDGFLENAHEHHGVYNQGRGIDSGERLMQPTQMSAQE
DLGDDTGIHVIPTLNGDDRHKIVNVDQRQYGDVFKGDLNPKPQGQRLIEVSVEENHPFTLRA
PIQRIYGVRYTETWSFLPSLTCTGDAAPAIQHICLKHTTCFQDVVVDVDCAENTKEDQLAEI
SYRFQGKKEADQPWIVVNTSTLFDELELDPPEIEPGVLKVLRTEKQYLGVYIWNMRGSDGTS
TYATFLVTWKGDEKTRNPTPAVTPQPRGAEFHMWNYHSHVFSVGDTFSLAMHLQYKIHEAPF
DLLLEWLYVPIDPTCQPMRLYSTCLYHPNAPQCLSHMNSGCTFTSPHLAQRVASTVYQNCEH
ADNYTAYCLGISHMEPSFGLILHDGGTTLKFVDTPESLSGLYVFVVYFNGHVEAVAYTVVST
VDHFVNAIEERGFPPTAGQPPATTKPKEITPVNPGTSPLLRYAAWTGGLAAVVLLCLVIFLI
CTAKRMRVKAYRVDKSPYNQSMYYAGLPVDDFEDSESTDTEEEFGNAIGGSHGGSSYTVYID
KTR

VZV VEERep.SGPgB (SEQ ID NO: 73):
1_
ataggcggcgcatgagagaagcccagaccaattacctacccaaaatggagaaagttcacgttgacatc
gaggaagacagcccattcctcagagctttgcagcggagcttcccgcagtttgaggtagaagccaagca
ggtcactgataatgaccatgctaatgccagagcgttttcgcatctggcttcaaaactgatcgaaacgg
aggtggacccatccgacacgatccttgacattggaagtgcgcccgcccgcagaatgtattctaagcac
aagtatcattgtatctgtccgatgagatgtgcggaagatccggacagattgtataagtatgcaactaa
gctgaagaaaaactgtaaggaaataactgataaggaattggacaagaaaatgaaggagctcgccgccg
tcatgagcgaccctgacctggaaactgagactatgtgcctccacgacgacgagtcgtgtcgctacgaa
gggcaagtcgctgtttaccaggatgtatacgcggttgacggaccgacaagtctctatcaccaagccaa
taagggagttagagtcgcctactggataggctttgacaccaccccttttatgtttaagaacttggctg
gagcatatccatcatactctaccaactgggccgacgaaaccgtgttaacggctcgtaacataggccta
tgcagctctgacgttatggagcggtcacgtagagggatgtccattcttagaaagaagtatttgaaacc
atccaacaatgttctattctctgttggctcgaccatctaccacgagaagagggacttactgaggagct
ggcacctgccgtctgtatttcacttacgtggcaagcaaaattacacatgtcggtgtgagactatagtt
agttgcgacgggtacgtcgttaaaagaatagctatcagtccaggcctgtatgggaagccttcaggcta
tgctgctacgatgcaccgcgagggattcttgtgctgcaaagtgacagacacattgaacggggagaggg
tctcttttcccgtgtgcacgtatgtgccagctacattgtgtgaccaaatgactggcatactggcaaca
gatgtcagtgcggacgacgcgcaaaaactgctggttgggctcaaccagcgtatagtcgtcaacggtcg
cacccagagaaacaccaataccatgaaaaattacctttttgcccgtagtggcccaggcatttgctaggt
gggcaaaggaatataaggaagatcaagaagatgaaaggccactaggactacgagatagacagttagtc
atggggtgttgttgggcttttagaaggcacaagataacatctatttataagcgcccggatacccaaac
catcatcaaagtgaacagcgatttccactcattcgtgctgcccaggataggcagtaacacattggaga
tcgggctgagaacaagaatcaggaaaatgttagaggagcacaaggagccgtcacctctcattaccgcc
gaggacgtacaagaagctaagtgcgcagccgatgaggctaaggaggtgcgtgaagccgaggagttgcg
cgcagctctaccacctttggcagctgatgttgaggagcccactctggaagccgatgtagacttgatgt
tacaagaggctggggccggctcagtggagacacctcgtggcttgataaaggttaccagctacgatggc
gaggacaagatcggctcttacgctgtgctttctccgcaggctgtactcaagagtgaaaaattatcttg
catccaccctctcgctgaacaagtcatagtgataacacactctggccgaaaagggcgttatgccgtgg
aaccataccatggtaaagtagtggtgccagagggacatgcaatacccgtccaggactttcaagctctg
agtgaaagtgccaccattgtgtacaacgaacgtgagttcgtaaacaggtacctgcaccatattgccac
acatggaggagcgctgaacactgatgaagaatattacaaaactgtcaagcccagcgagcacgacggcg
aatacctgtacgacatcgacaggaaacagtgcgtcaagaaagaactagtcactgggctagggctcaca
ggcgagctggtggatcctcccttccatgaattcgcctacgagagtctgagaacacgaccagccgctcc
ttaccaagtaccaaccatagggggtgtatggcgtgccaggatcaggcaagtctggcatcattaaaagcg
cagtcaccaaaaaagatctagtggtgagcgccaagaaagaaaactgtgcagaaattataagggacgtc
aagaaaatgaaagggctggacgtcaatgccagaactgtggactcagtgctcttgaatggatgcaaaca
ccccgtagagaccctgtatattgacgaagcttttgcttgtcatgcaggtactctcagagcgctcatag
ccattataagacctaaaaaggcagtgctctgcggggatcccaaacagtgcggtttttttaacatgatg
tgcctgaaagtgcattttaaccacgagatttgcacacaagtcttccacaaaagcatctctcgccgttg
cactaaatctgtgacttcggtcgtctcaaccttgttttacgacaaaaaaatgagaacgacgaatccga
aagagactaagattgtgattgacactaccggcagtaccaaacctaagcaggacgatctcattctcact
tgtttcagagggtgggtgaagcagttgcaaatagattacaaaggcaacgaaataatgacggcagctgc
ctctcaagggctgacccgtaaaggtgtgtatgccgttcggtacaaggtgaatgaaaatcctctgtacg
cacccacctcagaacatgtgaacgtcctactgacccgcacggaggaccgcatcgtgtggaaaacacta
gccggcgacccatggataaaaacactgactgccaagtaccctgggaatttcactgccacgatagagga
gtggcaagcagagcatgatgccatcatgaggcacatcttggagagaccggaccctaccgacgtcttcc
agaataaggcaaacgtgtgttgggccaaggctttagtgccggtgctgaagaccgctggcatagacatg
accactgaacaatggaacactgtggattattttgaaacggacaaagctcactcagcagagatagtatt
gaaccaactatgcgtgaggttctttggactcgatctggactccggtctattttctgcacccactgttc
cgttatccattaggaataatcactgggataactccccgtcgcctaacatgtacgggctgaataaagaa
gtggtccgtcagctctctcgcaggtacccacaactgcctcgggcagttgccactggaagagtctatga
catgaacactggtacactgcgcaattatgatccgcgcataaacctagtacctgtaaacagaagactgc
ctcatgctttagtcctccaccataatgaacacccacagagtgacttttcttcattcgtcagcaaattg
aagggcagaactgtcctggtggtcggggaaaagttgtccgtcccaggcaaaatggttgactggttgtc
agaccggcctgaggctaccttcagagctcggctggatttaggcatcccaggtgatgtgcccaaatatg
acataatatttgttaatgtgaggaccccatataaataccatcactatcagcagtgtgaagaccatgcc
attaagcttagcatgttgaccaagaaagcttgtctgcatctgaatcccggcggaacctgtgtcagcat
aggttatggttacgctgacagggccagcgaaagcatcattggtgctatagcgcggcagttcaagtttt
cccgggtatgcaaaccgaaatcctcacttgaagagacggaagttctgtttgtattcattgggtacgat
cgcaaggcccgtacgcacaatccttacaagctttcatcaaccttgaccaacatttatacaggttccag -continued

| SEQUENCES |
| --- |
| actccacgaagccggatgtgcaccctcatatcatgtggtgcgaggggatattgccacggccaccgaag<br>gagtgattataaatgctgctaacagcaaaggacaacctggcggaggggtgtgcggagcgctgtataag<br>aaattcccggaaagcttcgatttacagccgatcgaagtaggaaaagcgcgactggtcaaaggtgcagc<br>taaacatatcattcatgccgtaggaccaaacttcaacaaagtttcggaggttgaaggtgacaaacagt<br>tggcagaggcttatgagtccatcgctaagattgtcaacgataacaattacaagtcagtagcgattcca<br>ctgttgtccaccggcatcttttccgggaacaaagatcgactaacccaatcattgaaccatttgctgac<br>agctttagacaccactgatgcagatgtagccatatactgcagggacaagaaatgggaaatgactctca<br>aggaagcagtggctaggagagaagcagtggaggagatatgcatatccgacgactcttcagtgacagaa<br>cctgatgcagagctggtgagggtgcatccgaagagttctttggctggaaggaagggctacagcacaag<br>cgatggcaaaactttctcatatttggaagggaccaagtttcaccaggcggccaaggatatagcagaaa<br>ttaatgccatgtggcccgttgcaacggaggccaatgagcaggtatgcatgtatatcctcggagaaagc<br>atgagcagtattaggtcgaaatgccccgtcgaagagtcggaagcctccacaccacctagcacgctgcc<br>ttgcttgtgcatccatgccatgactccagaaagagtacagcgcctaaaagcctcacgtccagaacaaa<br>ttactgtgtgctcatcctttccattgccgaagtatagaatcactggtgtgcagaagatccaatgctcc<br>cagcctatattgttctcaccgaaagtgcctgcgtatattcatccaaggaagtatctcgtggaaacacc<br>accggtagacgagactccggagccatcggcagagaaccaatccacagaggggacacctgaacaaccac<br>cacttataaccgaggatgagaccaggactagaacgcctgagccgatcatcatcgaagaggaagaagag<br>gatagcataagtttgctgtcagatggcccgacccaccaggtgctgcaagtcgaggcagacattcacgg<br>gccgccctctgtatctagctcatcctggtccattcctcatgcatccgactttgatgtggacagtttat<br>ccatacttgacaccctggagggagctagcgtgaccagcggggcaacgtcagccgagactaactcttac<br>ttcgcaaagagtatggagtttctggcgcgaccggtgcctgcgcctcgaacagtattcaggaaccctcc<br>acatcccgctccgcgcacaagaacaccgtcacttgcacccagcagggcctgctcgagaaccagcctag<br>tttccaccccgccaggcgtgaatagggtgatcactagagaggagctcgaggcgcttaccccgtcacgc<br>actcctagcaggtcggtctcgagaaccagcctggtctccaacccgccaggcgtaaatagggtgattac<br>aagagaggagtttgaggcgttcgtagcacaacaacaatgacggtttgatgcgggtgcatacatctttt<br>cctccgacaccggtcaagggcatttacaacaaaaatcagtaaggcaaacggtgctatccgaagtggtg<br>ttggagaggaccgaattggagatttcgtatgccccgcgcctcgaccaagaaaaagaagaattactacg<br>caagaaattacagttaaatcccacacctgctaacagaagcagataccagtccaggaaggtggagaaca<br>tgaaagccataacagctagacgtattctgcaaggcctagggcattatttgaaggcagaaggaaaagtg<br>gagtgctaccgaaccctgcatcctgttcctttgtattcatctagtgtgaaccgtgccttttcaagccc<br>caaggtcgcagtggaagcctgtaacgccatgttgaaagagaactttccgactgtggcttcttactgta<br>ttattccagagtacgatgcctatttggacatggttgacggagcttcatgctgcttagacactgccagt<br>ttttgccctgcaaagctgcgcagctttccaaagaaacactcctatttggaacccacaatacgatcggc<br>agtgccttcagcgatccagaacacgctccagaacgtcctggcagctgccacaaaaagaaattgcaatg<br>tcacgcaaatgagagaattgcccgtattggattcggcggcctttaatgtggaatgcttcaagaaatat<br>gcgtgtaataatgaatattgggaaacgtttaaagaaaaccccatcaggcttactgaagaaaacgtggt<br>aaattacattaccaaattaaaaggaccaaaagctgctgctctttttgcgaagacacataatttgaata<br>tgttgcaggacataccaatggacaggtttgtaatggacttaaagagagacgtgaaagtgactccagga<br>acaaaacatactgaagaacggcccaaggtacaggtgatccaggctgccgatccgctagcaacagcgta<br>tctgtgcggaatccaccgagagctggttaggagattaaatgcggtcctgcttccgaacattcatacac<br>tgtttgatatgtcggctgaagactttgacgctattatagccgagcacttccagcctggggattgtgtt<br>ctggaaactgacatcgcgtcgtttgataaaagtgaggacgacgccatggctctgaccgcgttaatgat<br>tctggaagacttaggtgtggacgcagagctgttgacgctgattgaggcggctttcggcgaaatttcat<br>caatacatttgcccactaaaactaaatttaaattcggagccatgatgaaatctggaatgttcctcaca<br>ctgtttgtgaacacagtcattaacattgtaatcgcaagcagagtgttgagagaacggctaaccggatc<br>accatgtgcagcattcattggagatgacaatatcgtgaaaggagtcaaatcggacaaattaatggcag<br>acaggtgcgccacctggttgaatatggaagtcaagattatagatgctgtggtgggcgagaaagcgcct<br>tatttctgtggagggtttattttgtgactccgtgaccggcacagcgtgccgtgtggcagacccccct<br>aaaaaggctgtttaagcttggcaaacctctggcagcagacgatgaacatgatgatgacaggagaaggg<br>cattgcatgaagagtcaacacgctggaaccgagtgggtattctttcagagctgtgcaaggcagtagaa<br>tcaaggtatgaaaccgtaggaacttccatcatagttatggccatgactactctagctagcagtgttaa<br>atcattcagctacctgagaggggcccctataactctctacggctaacctgaatggactacgacatagt<br>ctagtcgagtctagtcgacgccaccatgttcgtgaccgccgtggtgtccgtgtcccccagcagctttt<br>acgagagcctgcaggtcgagcccacccagagcgaggacatcacaagatctgcccacctgggcgacggc<br>gacgagatcagagaggccatccacaagagccaggacgccgagacaaagcccaccttctacgtgtgccc<br>cccacctaccggctctacaattgtgcggctggaacccccagaacctgccctgattaccacctgggca<br>agaacttcaccgagggaattgccgtggtgtacaaagagaatatcgccgcctacaagttcaaggccacc<br>gtgtactacaaggacgtgatcgtgtccaccgcctgggccggcagcagctacacccagatcaccaacag<br>atacgccgaccgggtgcccatccccgtgtctgagatcaccgacaccatcgacaagttcggcaagtgca<br>gcagcaaggccacctacgtgcggaacaaccacaaggtggaagccttcaacgaggacaagaaccccag<br>gacatgcccctgatcgccagcaagtacaacagcgtgggctccaaggcctggcacaccaccaacgacac<br>ctacatggtggccggcacccccggcacatacagaacaggcaccagcgtgaactgcatcatcgaggaag<br>tggaagcccggtccatcttcccatacgacagcttcggcctgagcaccggcgacattatctacatgagc<br>cctttcttcggcctgcgggacggcgcctacagagagcacagcaactacgccatggaccggttccacca<br>gttcgagggctacagacagcgggacctggacacaagagccctgctggaacctgccgccagaaacttcc<br>tggtcacccctcacctgaccgtgggctggaactggaagcccaagcggaccgaagtgtgcagcctggtc<br>aagtggcgcgaggtggaagatgtcgtgcgggatgagtacgcccacaacttccggttcaccatgaagac<br>cctgagcaccaccttcatcagcgagacaaacgagttcaacctgaaccagatccacctgagccagtgcg<br>tgaaagaggaagccagagccatcatcaaccggatctacaccacccggtacaacagcagccacgtgcgg<br>accggcgatatccagacctatctggctagaggcggcttcgtggtggtgtttcagcccctgctgagcaa<br>cagcctggctagactgtacctgcaggaactcgtcagagagaacaccaaccacagcccccagaagcacc<br>ccacccggaataccagatccagacgcagcgtgcccgtggaactgagagccaaccggaccatcaccacc<br>accagcagcgtggaattcgccatgctgcagttcacctacgaccacatccaggaacacgtgaacgagat<br>gctggcccggatcagcagcagttggtgccagctgcagaatcgggaaagggccctgtggtccggcctgt<br>tccccatcaatccaagcgccctggccagcaccatcctggaccagagagtgaaggccagaatcctgggg<br>gacgtgatcagcgtgtccaactgtcctgagctgggcagcgacacccggatcatcctgcagaacagcat<br>gcgggtgtccggcagcaccaccagatgctacagcagacccctgatcagcatcgtgtccctgaacggca |

SEQUENCES gcggcacagtggaaggccagctgggcaccgataacgagctgatcatgagccgggacctgctcgaaccc
tgcgtggccaatcacaagcggtactttctgttcggccaccactacgtgtactatgaggactacagata
cgtgcgcgagatcgccgtgcacgacgtgggcatgatcagcacctacgtggacctgaacctgaccctgc
tgaaggaccgcgagttcatgccactgcaggtctacacccgggacgagctgagagataccggcctgctg
gactacagcgagatccagcggcggaaccagatgcactccctgcggttctacgacatcgacaaggtggt
gcagtacgacagcggcaccgccatcatgcagggcatggcccagttctttcagggcctgggaacagccg
gacaggccgtgggacatgtggtgctgggagctacaggcgccctgctgtctaccgtgcacggcttcacc
acctttctgagcaaccccttcggagccctggctgtgggactgctggtcctggctggactggtggccgc
cttctttgcctaccgctacgtgctgaagctgaaaaccagccccatgaaggccctgtacccccctgacca
ccaagggcctgaagcagctgctgagggcatggacccccttcgccgagaagcccaatgccaccgacacc
cccatcgaggaaatcggcgacagccagaacaccgagccctccgtgaacagcggcttcgaccccgacaa
gtttcgcgaggcccaggaaatgatcaagtacatgaccctggtgtctgctgccgagcggcaggaaagca
aggcccggaagaagaacaagacctccgccctgctgaccagcagactgacaggactggccctgcggaac
agacggggctatagcagagtgcggaccgagaatgtgaccggcgtgtaatctagacgcggccgcataca
gcagcaattggcaagctgcttacatagaactcgcggcgattggcatgccgccttaaaatttttatttt
atttttcttttcttttccgaatcggattttgtttttaatatttcaaaaaaaaaaaaaaaaaaaaaaaa
aaaaaaaaaaaagggtcggcatggcatctccacctcctcgcggtccgacctgggcatccgaaggaggac
gcacgtccactcggatggctaagggagagccacgtttaaaccagctccaattcgccctatagtgagtc
gtattacgcgcgctcactggccgtcgttttacaacgtcgtgactgggaaaaccctggcgttacccaac
ttaatcgccttgcagcacatccccctttcgccagctggcgtaatagcgaagaggcccgcaccgatcgc
ccttcccaacagttgcgcagcctgaatggcgaatgggacgcgccctgtagcggcgcattaagcgcggc
gggtgtggtggttacgcgcagcgtgaccgctacacttgccagcgccctagcgcccgctcctttcgctt
tcttcccttcctttctcgccacgttcgccggctttccccgtcaagctctaaatcgggggctccctttta
gggttccgatttagtgctttacggcacctcgaccccaaaaaacttgattagggtgatggttcacgtag
tgggccatcgccctgatagacggtttttcgccctttgacgttggagtccacgttctttaatagtggac
tcttgttccaaactggaacaacactcaaccctatctcggtctattcttttgatttataagggattttg
ccgatttcggcctattggttaaaaaatgagctgatttaacaaaaatttaacgcgaattttaacaaaat
attaacgcttacaatttaggtggcacttttcggggaaatgtgcgcggaacccctatttgtttattttt
ctaaatacattcaaatatgtatccgctcatgagacaataaccctgataaatgcttcaataatattgaa
aaaggaagagtatgagtattcaacatttccgtgtcgcccttattcccttttttgcggcattttgcctt
cctgtttttgctcacccagaaacgctggtgaaagtaaaagatgctgaagatcagttgggtgcacgagt
gggttacatcgaactggatctcaacagcggtaagatccttgagagttttcgccccgaagaacgttttc
caatgatgagcacttttaaagttctgctatgtggcgcggtattatcccgtattgacgccgggcaagag
caactcggtcgccgcatacactattctcagaatgacttggttgagtactcaccagtcacagaaaagca
tcttacggatggcatgacagtaagagaattatgcagtgctgccataaccatgagtgataacactgcgg
ccaacttacttctgacaacgatcggaggaccgaaggagctaaccgcttttttgcacaacatgggggat
catgtaactcgccttgatcgttgggaaccggagctgaatgaagccataccaaacgacgagcgtgacac
cacgatgcctgtagcaatggcaacaacgttgcgcaaactattaactggcgaactacttactctagctt
cccggcaacaattaatagactggatggaggcggataaagttgcaggaccacttctgcgctcggccctt
ccggctggctggtttattgctgataaatctggagccggtgagcgtgggtctcgcggtatcattgcagc
actggggccagatggtaagccctcccgtatcgtagttatctacacgacggggagtcaggcaactatgg
atgaacgaaatagacagatcgctgagataggtgcctcactgattaagcattggtaactgtcagaccaa
gtttactcatatatactttagattgatttaaaacttcatttttaatttaaaaggatctaggtgaagat
cctttttgataatctcatgaccaaaatcccttaacgtgagttttcgttccactgagcgtcagaccccg
tagaaaagatcaaaggatcttcttgagatcctttttttctgcgcgtaatctgctgcttgcaaacaaaa
aaaccaccgctaccagcggtggtttgtttgccggatcaagagctaccaactctttttccgaaggtaac
tggcttcagcagagcgcagataccaaatactgttcttctagtgtagccgtagttaggccaccacttca
agaactctgtagcaccgcctacatacctcgctctgctaatcctgttaccagtggctgctgccagtggc
gataagtcgtgtcttaccgggttggactcaagacgatagttaccggataaggcgcagcggtcgggctg
aacggggggttcgtgcacacagcccagcttggagcgaacgacctacaccgaactgagatacctacagc
gtgagctatgagaaagcgccacgcttcccgaagggagaaaggcggacaggtatccggtaagcggcagg
gtcggaacaggagagcgcacgagggagcttccagggggaaacgcctggtatctttatagtcctgtcgg
gtttcgccacctctgacttgagcgtcgatttttgtgatgctcgtcaggggggcggagcctatggaaaa
acgccagcaacgcggcctttttacggttcctggccttttgctggccttttgctcacatgttctttcct
gcgttatcccctgattctgtggataaccgtattaccgcctttgagtgagctgataccgctcgccgcag
ccgaacgaccgagcgcagcgagtcagtgagcgaggaagcggaagagcgcccaatacgcaaaccgcctc
tccccgcgcgttggccgattcattaatgcagctggcacgacaggtttcccgactggaaagcgggcagt
gagcgcaacgcaattaatgtgagttagctcactcattaggcaccccaggctttacactttatgctccc
ggctcgtatgttgtgtggaattgtgagcggataacaatttcacacaggaaacagctatgaccatgatt
acgccaagcgcgcaattaaccctcactaaagggaacaaaagctgggtaccgggcccacgcgtaatacg
actcactatag_13339

VZV VEERep.SGPgH (SEQ ID NO: 74):
1_
ataggcggcgcatgagagaagcccagaccaattacctacccaaaatggagaaagttcacgttgacatc
gaggaagacagcccattcctcagagctttgcagcggagcttcccgcagtttgaggtagaagccaagca
ggtcactgataatgaccatgctaatgccagagcgttttcgcatctggcttcaaaactgatcgaaacgg
aggtggacccatccgacacgatccttgacattggaagtgcgcccgcccgcagaatgtattctaagcac
aagtatcattgtatctgtccgatgagatgtgcggaagatccggacagattgtataagtatgcaactaa
gctgaagaaaaactgtaaggaaataactgataaggaattggacaagaaaatgaaggagctcgccgccg
tcatgagcgaccctgacctggaaactgagactatgtgcctccacgacgacgagtcgtgtcgctacgaa
gggcaagtcgctgtttaccaggatgtatacgcggttgacggaccgacaagtctctatcaccaagccaa
taagggagttagagtcgcctactggataggctttgacaccaccccttttatgtttaagaacttggctg
gagcatatccatcatactctaccaactgggccgacgaaaccgtgttaacggctcgtaacataggccta
tgcagctctgacgttatggagcggtcacgtagagggatgtccattcttagaaagaagtatttgaaacc
atccaacaatgttctattctctgttggctcgaccatctaccacgagaagagggacttactgaggagct
ggcacctgccgtctgtatttcacttacgtggcaagcaaaattacacatgtcggtgtgagactatagtt -continued

| SEQUENCES |
| --- |
| agttgcgacgggtacgtcgttaaaagaatagctatcagtccaggcctgtatgggaagccttcaggcta<br>tgctgctacgatgcaccgcgagggattcttgtgctgcaaagtgacagacacattgaacggggagaggg<br>tctcttttcccgtgtgcacgtatgtgccagctacattgtgtgaccaaatgactggcatactggcaaca<br>gatgtcagtgcggacgacgcgcaaaaactgctggttgggctcaaccagcgtatagtcgtcaacggtcg<br>cacccagagaaacaccaataccatgaaaaattaccttttgcccgtagtggcccaggcatttgctaggt<br>gggcaaaggaatataaggaagatcaagaagatgaaaggccactaggactacgagatagacagttagtc<br>atggggtgttgttgggcttttagaaggcacaagataacatctatttataagcgcccggatacccaaac<br>catcatcaaagtgaacagcgatttccactcattcgtgctgcccaggataggcagtaacacattggaga<br>tcgggctgagaacaagaatcaggaaaatgttagaggagcacaaggagccgtcacctctcattaccgcc<br>gaggacgtacaagaagctaagtgcgcagccgatgaggctaaggaggtgcgtgaagccgaggagttgcg<br>cgcagctctaccacctttggcagctgatgttgaggagcccactctggaagccgatgtagacttgatgt<br>tacaagaggctggggccggctcagtggagacacctcgtggcttgataaaggttaccagctacgatggc<br>gaggacaagatcggctcttacgctgtgctttctccgcaggctgtactcaagagtgaaaaattatcttg<br>catccaccctctcgctgaacaagtcatagtgataacacactctggccgaaaagggcgttatgccgtgg<br>aaccataccatggtaaagtagtggtgccagagggacatgcaatacccgtccaggactttcaagctctg<br>agtgaaagtgccaccattgtgtacaacgaacgtgagttcgtaaacaggtacctgcaccatattgccac<br>acatggaggagcgctgaacactgatgaagaatattacaaaactgtcaagcccagcgagcacgacggcg<br>aatacctgtacgacatcgacaggaaacagtgcgtcaagaaagaactagtcactgggctagggctcaca<br>ggcgagctggtggatcctcccttccatgaattcgcctacgagagtctgagaacacgaccagccgctcc<br>ttaccaagtaccaaccataggggtgtatggcgtgccaggatcaggcaagtctggcatcattaaaagcg<br>cagtcaccaaaaaagatctagtggtgagcgccaagaaagaaaactgtgcagaaattataagggacgtc<br>aagaaaatgaaagggctggacgtcaatgccagaactgtggactcagtgctcttgaatggatgcaaaca<br>ccccgtagagaccctgtatattgacgaagcttttgcttgtcatgcaggtactctcagagcgctcatag<br>ccattataagacctaaaaaggcagtgctctgcggggatcccaaacagtgcggtttttttaacatgatg<br>tgcctgaaagtgcattttaaccacgagatttgcacacaagtcttccacaaaagcatctctcgccgttg<br>cactaaatctgtgacttcggtcgtctcaaccttgttttacgacaaaaaaatgagaacgacgaatccga<br>aagagactaagattgtgattgacactaccggcagtaccaaacctaagcaggacgatctcattctcact<br>tgtttcagagggtgggtgaagcagttgcaaatagattacaaaggcaacgaaataatgacggcagctgc<br>ctctcaagggctgacccgtaaaggtgtgtatgccgttcggtacaaggtgaatgaaaatcctctgtacg<br>cacccacctcagaacatgtgaacgtcctactgacccgcacggaggaccgcatcgtgtggaaaacacta<br>gccggcgacccatggataaaaacactgactgccaagtaccctgggaatttcactgccacgatagagga<br>gtggcaagcagagcatgatgccatcatgaggcacatcttggagagaccggaccctaccgacgtcttcc<br>agaataaggcaaacgtgtgttgggccaaggctttagtgccggtgctgaagaccgctggcatagacatg<br>accactgaacaatggaacactgtggattatttgaaacggacaaagctcactcagcagagatagtatt<br>gaaccaactatgcgtgaggttctttggactcgatctggactccggtctattttctgcacccactgttc<br>cgttatccattaggaataatcactgggataactccccgtcgcctaacatgtacgggctgaataaagaa<br>gtggtccgtcagctctctcgcaggtacccacaactgcctcgggcagttgccactggaagagtctatga<br>catgaacactggtacactgcgcaattatgatccgcgcataaacctagtacctgtaaacagaagactgc<br>ctcatgctttagtcctccaccataatgaacacccacagagtgacttttcttcattcgtcagcaaattg<br>aagggcagaactgtcctggtggtcggggaaaagttgtccgtcccaggcaaaatggttgactggttgtc<br>agaccggcctgaggctaccttcagagctcggctggatttaggcatcccaggtgatgtgcccaaatatg<br>acataatatttgttaatgtgaggaccccatataaataccatcactatcagcagtgtgaagaccatgcc<br>attaagcttagcatgttgaccaagaaagcttgtctgcatctgaatcccggcggaacctgtgtcagcat<br>aggttatggttacgctgacagggccagcgaaagcatcattggtgctatagcgcggcagttcaagtttt<br>cccgggtatgcaaaccgaaatcctcacttgaagagacggaagttctgtttgtattcattgggtacgat<br>cgcaaggcccgtacgcacaatccttacaagctttcatcaaccttgaccaacatttatacaggttccag<br>actccacgaagccggatgtgcaccctcatatcatgtggtgcgaggggatattgccacggccaccgaag<br>gagtgattataaatgctgctaacagcaaaggacaacctggcggaggggtgtgcggagcgctgtataag<br>aaattcccggaaagcttcgatttacagccgatcgaagtaggaaaagcgcgactggtcaaaggtgcagc<br>taaacatatcattcatgccgtaggaccaaacttcaacaaagtttcggaggttgaaggtgacaaacagt<br>tggcagaggcttatgagtccatcgctaagattgtcaacgataacaattacaagtcagtagcgattcca<br>ctgttgtccaccggcatcttttccgggaacaaagatcgactaacccaatcattgaaccatttgctgac<br>agctttagacaccactgatgcagatgtagccatatactgcagggacaagaaatgggaaatgactctca<br>aggaagcagtggctaggagagaagcagtggaggagatatgcatatccgacgactcttcagtgacagaa<br>cctgatgcagagctggtgagggtgcatccgaagagttctttggctggaaggaagggctacagcacaag<br>cgatggcaaaactttctcatatttggaagggaccaagtttcaccaggcggccaaggatatagcagaaa<br>ttaatgccatgtggcccgttgcaacggaggccaatgagcaggtatgcatgtatatcctcggagaaagc<br>atgagcagtattaggtcgaaatgccccgtcgaagagtcggaagcctccacaccacctagcacgctgcc<br>ttgcttgtgcatccatgccatgactccagaaagagtacagcgcctaaaagcctcacgtccagaacaaa<br>ttactgtgtgctcatcctttccattgccgaagtatagaatcactggtgtgcagaagatccaatgctcc<br>cagcctatattgttctcaccgaaagtgcctgcgtatattcatccaaggaagtatctcgtggaaacacc<br>accggtagacgagactccggagccatcggcagagaaccaatccacagaggggacacctgaacaaccac<br>cacttataaccgaggatgagaccaggactagaacgcctgagccgatcatcatcgaagaggaagaagag<br>gatagcataagtttgctgtcagatggcccgacccaccaggtgctgcaagtcgaggcagacattcacgg<br>gccgccctctgtatctagctcatcctggtccattcctcatgcatccgactttgatgtggacagtttat<br>ccatacttgacaccctggagggagctagcgtgaccagcggggcaacgtcagccgagactaactcttac<br>ttcgcaaagagtatggagtttctggcgcgaccggtgcctgcgcctcgaacagtattcaggaaccctcc<br>acatcccgctccgcgcacaagaacaccgtcacttgcacccagcagggcctgctcgagaaccagcctag<br>tttccaccccgccaggcgtgaatagggtgatcactagagaggagctcgaggcgcttaccccgtcacgc<br>actcctagcaggtcggtctcgagaaccagcctggtctccaacccgccaggcgtaaatagggtgattac<br>aagagaggagtttgaggcgttcgtagcacaacaacaatgacggtttgatgcgggtgcatacatctttt<br>cctccgacaccggtcaagggcatttacaacaaaaatcagtaaggcaaacggtgctatccgaagtggtg<br>ttggagaggaccgaattggagatttcgtatgccccgcgcctcgaccaagaaaaagaagaattactacg<br>caagaaattacagttaaatcccacacctgctaacagaagcagataccagtccaggaaggtggagaaca<br>tgaaagccataacagctagacgtattctgcaaggcctagggcattatttgaaggcagaaggaaaagtg<br>gagtgctaccgaaccctgcatcctgttcctttgtattcatctagtgtgaaccgtgccttttcaagccc<br>caaggtcgcagtggaagcctgtaacgccatgttgaaagagaactttccgactgtggcttcttactgta |

-continued

| SEQUENCES |
| --- |
| ttattccagagtacgatgcctatttggacatggttgacggagcttcatgctgcttagacactgccagt<br>ttttgccctgcaaagctgcgcagctttccaaagaaacactcctatttggaacccacaatacgatcggc<br>agtgccttcagcgatccagaacacgctccagaacgtcctggcagctgccacaaaaagaaattgcaatg<br>tcacgcaaatgagagaattgcccgtattggattcggcggcctttaatgtggaatgcttcaagaaatat<br>gcgtgtaataatgaatattgggaaacgtttaaagaaaaccccatcaggcttactgaagaaaacgtggt<br>aaattacattaccaaattaaaaggaccaaaagctgctgctcttttttgcgaagacacataatttgaata<br>tgttgcaggacataccaatggacaggtttgtaatggacttaaagagagacgtgaaagtgactccagga<br>acaaaacatactgaagaacggcccaaggtacaggtgatccaggctgccgatccgctagcaacagcgta<br>tctgtgcggaatccaccgagagctggttaggagattaaatgcggtcctgcttccgaacattcatacac<br>tgtttgatatgtcggctgaagactttgacgctattatagccgagcacttccagcctggggattgtgtt<br>ctggaaactgacatcgcgtcgtttgataaaagtgaggacgacgccatggctctgaccgcgttaatgat<br>tctggaagacttaggtgtggacgcagagctgttgacgctgattgaggcggctttcggcgaaatttcat<br>caatacatttgcccactaaaactaaatttaaattcggagccatgatgaaatctggaatgttcctcaca<br>ctgtttgtgaacacagtcattaacattgtaatcgcaagcagagtgttgagagaacggctaaccggatc<br>accatgtgcagcattcattggagatgacaatatcgtgaaaggagtcaaatcggacaaattaatggcag<br>acaggtgcgccacctggttgaatatggaagtcaagattatagatgctgtggtgggcgagaaagcgcct<br>tatttctgtggagggtttattttgtgtgactccgtgaccggcacagcgtgccgtgtggcagacccccct<br>aaaaaggctgtttaagcttggcaaacctctggcagcagacgatgaacatgatgatgacaggagaaggg<br>cattgcatgaagagtcaacacgctggaaccgagtgggtattctttcagagctgtgcaaggcagtagaa<br>tcaaggtatgaaaccgtaggaacttccatcatagttatggccatgactactctagctagcagtgttaa<br>atcattcagctacctgagaggggcccctataactctctacggctaacctgaatggactacgacatagt<br>ctagtcgagtctagtcgacgccaccatgttcgccctggtgctggccgtggtcatcctgcctctgtgga<br>ccaccgccaacaagagctacgtgacccccacacccgccaccagatccatcggacacatgagcgccctg<br>ctgagagagtacagcgaccggaacatgagcctgaagctggaagccttctaccccaccggcttcgacga<br>ggaactgatcaagagcctgcactggggcaacgaccggaagcacgtgttcctcgtgatcgtgaaagtga<br>accccaccacccacgagggcgacgtcggcctggtcatcttccccaagtacctgctgagcccctaccac<br>ttcaaggccgagcacagagccccttccctgctggccgctttggctttctgagccaccctgtgacccc<br>cgacgtgtcattcttcgacagcagcttcgcccccctacctgaccacacagcacctggtggccttcacca<br>ccttccccccccaatcctctcgtgtggcacctggaaagagccgagacagccgccaccgccgaaagacct<br>tttggcgtgtccctgctgcccgccagacctaccgtgcccaagaacaccatcctggaacacaaggccca<br>cttcgccacctgggatgccctggccagacacaccttctttagcgccgaggccatcatcaccaacagca<br>ccctgagaatccacgtgcccctgttcggcagcgtgtggcccatcagatactgggccacaggcagcgtg<br>ctgctgaccagcgatagcggcagagtggaagtgaacatcggcgtgggcttcatgagcagcctgatcag<br>cctgagcagcggcctgcccatcgagctgattgtggtgccccacaccgtgaagctgaacgccgtgacca<br>gcgacaccacctggttccagctgaacccccctggccctgatcctggccctagttacagagtgtacctg<br>ctgggcagaggcctggacatgaacttcagcaagcacgccaccgtggacatctgcgcctaccctgagga<br>aagcctggactacagataccacctgagcatggcccacaccgaggccctgagaatgaccaccaaggccg<br>accagcacgacatcaacgaggaaagctactaccacattgccgccagaatcgccaccagcatcttcgcc<br>ctgagcgagatgggccggaccaccgagtactttctgctggacgagatcgtggacgtgcagtaccagct<br>gaagttcctgaactacatcctgatgcggatcggcgctggcgcccaccctaataccatcagcggcacca<br>gcgacctgatcttcgccgatcctagccagctgcacgacgagctgagcctgctgttcggccaggtcaaa<br>cccgccaacgtggactacttcatcagctacgacgaggcccgggaccagctgaaaacagcctacgccct<br>gtccagaggccaggatcatgtgaacgccctgtccctggccaggcgcgtgatcatgagcatctacaagg<br>gcctgctggtcaagcagaacctgaacgccaccgagcggcaggccctgttcttcgccagcatgatcctg<br>ctgaacttcagagagggcctggaaaacagcagccgggtgctggatggcagaaccaccctgctgctgat<br>gaccagcatgtgcacagccgcccatgccacacaggccgccctgaatatccaggaaggcctggcttacc<br>tgaaccccagcaagcacatgttcaccatccccaacgtgtacagcccctgcatgggcagcctgagaacc<br>gacctgaccgaagagatccacgtgatgaacctgctgtccgccatccccaccagacccggactgaatga<br>ggtgctgcacacccagctggacgagtccgagatcttcgacgccgccttcaagaccatgatgatcttta<br>ccacctggaccgccaaggacctgcacatcctgcacacacacgtgcccgaggtgttcacatgccaagat<br>gccgccgctcggaacggcgagtatgtgctgattctgcctgccgtgcagggccacagctacgtgatcac<br>ccggaacaagccccagcggggcctggtgtatagcctggctgacgtggacgtgtacaaccccatcagcg<br>tggtgtacctgagcaaggatacctgcgtgtccgagcacggcgtgatcgaaacagtggccctgccccac<br>cccgacaacctgaaagagtgcctgtactgcggctccgtgttcctgcggtatctgaccaccggcgccat<br>catggacatcatcatcatcgacagcaaggacaccgagagacagctggccgccatgggcaacagcacca<br>tccccccccttcaaccccgacatgcacggcgacgatagcaaggccgtgctgctgttccccaacggcacc<br>gtggtcacactgctgggcttcgagcggagacaggccatcagaatgagcggccagtacctgggcgcctc<br>tctgggtggtgcctttctggccgtcgtgggctttggcatcatcggctggatgctgtgcggcaacagca<br>gactgcgcgagtacaacaagatcccccctgacctaatctagacgcggccgcatacagcagcaattggca<br>agctgcttacatagaactcgcggcgattggcatgccgccttaaaatttttatttttattttttcttttct<br>tttccgaatcggattttgtttttaatatttcaaaaaaaaaaaaaaaaaaaaaaaaaaaaaaaaaaaaagg<br>gtcggcatggcatctccacctcctcgcggtccgacctgggcatccgaaggaggacgcacgtccactcg<br>gatggctaagggagagccacgtttaaaccagctccaattcgccctatagtgagtcgtattacgcgcgc<br>tcactggccgtcgttttacaacgtcgtgactgggaaaaccctggcgttacccaacttaatcgccttgc<br>agcacatccccctttcgccagctggcgtaatagcgaagaggcccgcaccgatcgcccttcccaacagt<br>tgcgcagcctgaatggcgaatgggacgcgccctgtagcggcgcattaagcgcggcgggtgtggtggtt<br>acgcgcagcgtgaccgctacacttgccagcgccctagcgcccgctcctttcgctttcttcccttcctt<br>tctcgccacgttcgccggctttccccgtcaagctctaaatcgggggctccctttagggttccgattta<br>gtgctttacggcacctcgaccccaaaaaacttgattagggtgatggttcacgtagtgggccatcgccc<br>tgatagacggtttttcgccctttgacgttggagtccacgttctttaatagtggactcttgttccaaac<br>tggaacaacactcaaccctatctcggtctattcttttgatttataagggattttgccgatttcggcct<br>attggttaaaaaatgagctgatttaacaaaaatttaacgcgaattttaacaaaatattaacgcttaca<br>atttaggtggcacttttcggggaaatgtgcgcggaacccctatttgtttatttttctaaatacattca<br>aatatgtatccgctcatgagacaataaccctgataaatgcttcaataatattgaaaaaggaagagtat<br>gagtattcaacatttccgtgtcgcccttattcccttttttgcggcattttgccttcctgtttttgctc<br>acccagaaacgctggtgaaagtaaaagatgctgaagatcagttgggtgcacgagtgggttacatcgaa<br>ctggatctcaacagcggtaagatccttgagagttttcgccccgaagaacgttttccaatgatgagcac |

-continued

SEQUENCES ttttaaagttctgctatgtggcgcggtattatcccgtattgacgccgggcaagagcaactcggtcgcc
gcatacactattctcagaatgacttggttgagtactcaccagtcacagaaaagcatcttacggatggc
atgacagtaagagaattatgcagtgctgccataaccatgagtgataacactgcggccaacttacttct
gacaacgatcggaggaccgaaggagctaaccgcttttttgcacaacatgggggatcatgtaactcgcc
ttgatcgttgggaaccggagctgaatgaagccataccaaacgacgagcgtgacaccacgatgcctgta
gcaatggcaacaacgttgcgcaaactattaactggcgaactacttactctagcttcccggcaacaatt
aatagactggatggaggcggataaagttgcaggaccacttctgcgctcggcccttccggctggctggt
ttattgctgataaatctggagccggtgagcgtgggtctcgcggtatcattgcagcactggggccagat
ggtaagccctcccgtatcgtagttatctacacgacggggagtcaggcaactatggatgaacgaaatag
acagatcgctgagataggtgcctcactgattaagcattggtaactgtcagaccaagtttactcatata
tactttagattgatttaaaacttcatttttaatttaaaaggatctaggtgaagatcctttttgataat
ctcatgaccaaaatcccttaacgtgagttttcgttccactgagcgtcagaccccgtagaaaagatcaa
aggatcttcttgagatcctttttttctgcgcgtaatctgctgcttgcaaacaaaaaaaccaccgctac
cagcggtggtttgtttgccggatcaagagctaccaactctttttccgaaggtaactggcttcagcaga
gcgcagataccaaatactgttcttctagtgtagccgtagttaggccaccacttcaagaactctgtagc
accgcctacatacctcgctctgctaatcctgttaccagtggctgctgccagtggcgataagtcgtgtc
ttaccgggttggactcaagacgatagttaccggataaggcgcagcggtcgggctgaacggggggttcg
tgcacacagcccagcttggagcgaacgacctacaccgaactgagatacctacagcgtgagctatgaga
aagcgccacgcttcccgaagggagaaaggcggacaggtatccggtaagcggcagggtcggaacaggag
agcgcacgagggagcttccagggggaaacgcctggtatctttatagtcctgtcgggtttcgccacctc
tgacttgagcgtcgatttttgtgatgctcgtcaggggggcggagcctatggaaaaacgccagcaacgc
ggcctttttacggttcctggccttttgctggccttttgctcacatgttctttcctgcgttatcccctg
attctgtggataaccgtattaccgcctttgagtgagctgataccgctcgccgcagccgaacgaccgag
cgcagcgagtcagtgagcgaggaagcggaagagcgcccaatacgcaaaccgcctctccccgcgcgttg
gccgattcattaatgcagctggcacgacaggtttcccgactggaaagcgggcagtgagcgcaacgcaa
ttaatgtgagttagctcactcattaggcaccccaggctttacactttatgctcccggctcgtatgttg
tgtggaattgtgagcggataacaatttcacacaggaaacagctatgaccatgattacgccaagcgcgc
aattaaccctcactaaagggaacaaaagctgggtaccgggcccacgcgtaatacgactcactatag_1
3258

VZV VEERep.SGPgL (SEQ ID NO: 75):
1_
ataggcggcgcatgagagaagcccagaccaattacctacccaaaatggagaaagttcacgttgacatc
gaggaagacagcccattcctcagagctttgcagcggagcttcccgcagtttgaggtagaagccaagca
ggtcactgataatgaccatgctaatgccagagcgttttcgcatctggcttcaaaactgatcgaaacgg
aggtggacccatccgacacgatccttgacattggaagtgcgcccgcccgcagaatgtattctaagcac
aagtatcattgtatctgtccgatgagatgtgcggaagatccggacagattgtataagtatgcaactaa
gctgaagaaaaactgtaaggaaataactgataaggaattggacaagaaaatgaaggagctcgccgccg
tcatgagcgaccctgacctggaaactgagactatgtgcctccacgacgacgagtcgtgtcgctacgaa
gggcaagtcgctgtttaccaggatgtatacgcggttgacggaccgacaagtctctatcaccaagccaa
taagggagttagagtcgcctactggataggctttgacaccaccccttttatgtttaagaacttggctg
gagcatatccatcatactctaccaactgggccgacgaaaccgtgttaacggctcgtaacataggccta
tgcagctctgacgttatggagcggtcacgtagagggatgtccattcttagaaagaagtatttgaaacc
atccaacaatgttctattctctgttggctcgaccatctaccacgagaagagggacttactgaggagct
ggcacctgccgtctgtatttcacttacgtggcaagcaaaattacacatgtcggtgtgagactatagtt
agttgcgacgggtacgtcgttaaaagaatagctatcagtccaggcctgtatgggaagccttcaggcta
tgctgctacgatgcaccgcgagggattcttgtgctgcaaagtgacagacacattgaacggggagaggg
tctcttttcccgtgtgcacgtatgtgccagctacattgtgtgaccaaatgactggcatactggcaaca
gatgtcagtgcggacgacgcgcaaaaactgctggttgggctcaaccagcgtatagtcgtcaacggtcg
cacccagagaaacaccaataccatgaaaaattaccttttgcccgtagtggcccaggcatttgctaggt
gggcaaaggaatataaggaagatcaagaagatgaaaggccactaggactacgagatagacagttagtc
atggggtgttgttgggcttttagaaggcacaagataacatctatttataagcgcccggatacccaaac
catcatcaaagtgaacagcgatttccactcattcgtgctgcccaggataggcagtaacacattggaga
tcgggctgagaacaagaatcaggaaaatgttagaggagcacaaggagccgtcacctctcattaccgcc
gaggacgtacaagaagctaagtgcgcagccgatgaggctaaggaggtgcgtgaagccgaggagttgcg
cgcagctctaccacctttggcagctgatgttgaggagcccactctggaagccgatgtagacttgatgt
tacaagaggctggggccggctcagtggagacacctcgtggcttgataaaggttaccagctacgatggc
gaggacaagatcggctcttacgctgtgctttctccgcaggctgtactcaagagtgaaaaattatcttg
catccaccctctcgctgaacaagtcatagtgataacacactctggccgaaaagggcgttatgccgtgg
aaccataccatggtaaagtagtggtgccagagggacatgcaatacccgtccaggactttcaagctctg
agtgaaagtgccaccattgtgtacaacgaacgtgagttcgtaaacaggtacctgcaccatattgccac
acatggaggagcgctgaacactgatgaagaatattacaaaactgtcaagcccagcgagcacgacggcg
aatacctgtacgacatcgacaggaaacagtgcgtcaagaaagaactagtcactgggctagggctcaca
ggcgagctggtggatcctcccttccatgaattcgcctacgagagtctgagaacacgaccagccgctcc
ttaccaagtaccaaccataggggtgtatggcgtgccaggatcaggcaagtctggcatcattaaaagcg
cagtcaccaaaaaagatctagtggtgagcgccaagaaagaaaactgtgcagaaattataaggacgtc
aagaaaatgaaagggctggacgtcaatgccagaactgtggactcagtgctcttgaatggatgcaaaca
ccccgtagagaccctgtatattgacgaagcttttgcttgtcatgcaggtactctcagagcgctcatag
ccattataagacctaaaaaggcagtgctctgcggggatcccaaacagtgcggtttttttaacatgatg
tgcctgaaagtgcattttaaccacgagatttgcacacaagtcttccacaaaagcatctctcgccgttg
cactaaatctgtgacttcggtcgtctcaaccttgttttacgacaaaaaaatgagaacgacgaatccga
aagagactaagattgtgattgacactaccggcagtaccaaacctaagcaggacgatctcattctcact
tgtttcagagggtgggtgaagcagttgcaaatagattacaaaggcaacgaaataatgacggcagctgc
ctctcaagggctgacccgtaaaggtgtgtatgccgttcggtacaaggtgaatgaaaatcctctgtacg
cacccacctcagaacatgtgaacgtcctactgacccgcacggaggaccgcatcgtgtggaaaacacta
gccggcgacccatggataaaaacactgactgccaagtaccctgggaatttcactgccacgatagagga
gtggcaagcagagcatgatgccatcatgaggcacatcttggagagaccggaccctaccgacgtcttcc -continued

| SEQUENCES |
| --- |
| agaataaggcaaacgtgtgttgggccaaggctttagtgccggtgctgaagaccgctggcatagacatg<br>accactgaacaatggaacactgtggattattttgaaacggacaaagctcactcagcagagatagtatt<br>gaaccaactatgcgtgaggttctttggactcgatctggactccggtctattttctgcacccactgttc<br>cgttatccattaggaataatcactgggataactccccgtcgcctaacatgtacgggctgaataaagaa<br>gtggtccgtcagctctctcgcaggtacccacaactgcctcgggcagttgccactggaagagtctatga<br>catgaacactggtacactgcgcaattatgatccgcgcataaacctagtacctgtaaacagaagactgc<br>ctcatgctttagtcctccaccataatgaacacccacagagtgacttttcttcattcgtcagcaaattg<br>aagggcagaactgtcctggtggtcggggaaaagttgtccgtcccaggcaaaatggttgactggttgtc<br>agaccggcctgaggctaccttcagagctcggctggatttaggcatcccaggtgatgtgcccaaatatg<br>acataatatttgttaatgtgaggaccccatataaataccatcactatcagcagtgtgaagaccatgcc<br>attaagcttagcatgttgaccaagaaagcttgtctgcatctgaatcccggcggaacctgtgtcagcat<br>aggttatggttacgctgacagggccagcgaaagcatcattggtgctatagcgcggcagttcaagtttt<br>cccgggtatgcaaaccgaaatcctcacttgaagagacggaagttctgtttgtattcattgggtacgat<br>cgcaaggcccgtacgcacaatccttacaagctttcatcaaccttgaccaacatttatacaggttccag<br>actccacgaagccggatgtgcaccctcatatcatgtggtgcgaggggatattgccacggccaccgaag<br>gagtgattataaatgctgctaacagcaaaggacaacctggcggaggggtgtgcggagcgctgtataag<br>aaattcccggaaagcttcgatttacagccgatcgaagtaggaaaagcgcgactggtcaaaggtgcagc<br>taaacatatcattcatgccgtaggaccaaacttcaacaaagtttcggaggttgaaggtgacaaacagt<br>tggcagaggcttatgagtccatcgctaagattgtcaacgataacaattacaagtcagtagcgattcca<br>ctgttgtccaccggcatcttttccgggaacaaagatcgactaacccaatcattgaaccatttgctgac<br>agctttagacaccactgatgcagatgtagccatatactgcagggacaagaaatgggaaatgactctca<br>aggaagcagtggctaggagagaagcagtggaggagatatgcatatccgacgactcttcagtgacagaa<br>cctgatgcagagctggtgagggtgcatccgaagagttctttggctggaaggaagggctacagcacaag<br>cgatggcaaaactttctcatatttggaagggaccaagtttcaccaggcggccaaggatatagcagaaa<br>ttaatgccatgtggcccgttgcaacggaggccaatgagcaggtatgcatgtatatcctcggagaaagc<br>atgagcagtattaggtcgaaatgccccgtcgaagagtcggaagcctccacaccacctagcacgctgcc<br>ttgcttgtgcatccatgccatgactccagaaagagtacagcgcctaaaagcctcacgtccagaacaaa<br>ttactgtgtgctcatcctttccattgccgaagtatagaatcactggtgtgcagaagatccaatgctcc<br>cagcctatattgttctcaccgaaagtgcctgcgtatattcatccaaggaagtatctcgtggaaacacc<br>accggtagacgagactccggagccatcggcagagaaccaatccacagaggggacacctgaacaaccac<br>cacttataaccgaggatgagaccaggactagaacgcctgagccgatcatcatcgaagaggaagaagag<br>gatagcataagtttgctgtcagatggcccgacccaccaggtgctgcaagtcgaggcagacattcacgg<br>gccgccctctgtatctagctcatcctggtccattcctcatgcatccgactttgatgtggacagtttat<br>ccatacttgacaccctggagggagctagcgtgaccagcggggcaacgtcagccgagactaactcttac<br>ttcgcaaagagtatggagtttctggcgcgaccggtgcctgcgcctcgaacagtattcaggaaccctcc<br>acatcccgctccgcgcacaagaacaccgtcacttgcacccagcagggcctgctcgagaaccagcctag<br>tttccaccccgccaggcgtgaatagggtgatcactagagaggagctcgaggcgcttaccccgtcacgc<br>actcctagcaggtcggtctcgagaaccagcctggtctccaacccgccaggcgtaaatagggtgattac<br>aagagaggagtttgaggcgttcgtagcacaacaacaatgacggtttgatgcgggtgcatacatctttt<br>cctccgacaccggtcaagggcatttacaacaaaaatcagtaaggcaaacggtgctatccgaagtggtg<br>ttggagaggaccgaattggagatttcgtatgccccgcgcctcgaccaagaaaaagaagaattactacg<br>caagaaattacagttaaatcccacacctgctaacagaagcagataccagtccaggaaggtggagaaca<br>tgaaagccataacagctagacgtattctgcaaggcctagggcattatttgaaggcagaaggaaaagtg<br>gagtgctaccgaaccctgcatcctgttcctttgtattcatctagtgtgaaccgtgccttttcaagccc<br>caaggtcgcagtggaagcctgtaacgccatgttgaaagagaactttccgactgtggcttcttactgta<br>ttattccagagtacgatgcctatttggacatggttgacggagcttcatgctgcttagacactgccagt<br>ttttgccctgcaaagctgcgcagctttccaaagaaacactcctatttggaacccacaatacgatcggc<br>agtgccttcagcgatccagaacacgctccagaacgtcctggcagctgccacaaaaagaaattgcaatg<br>tcacgcaaatgagagaattgcccgtattggattcggcggcctttaatgtggaatgcttcaagaaatat<br>gcgtgtaataatgaatattgggaaacgtttaaagaaaaccccatcaggcttactgaagaaaacgtggt<br>aaattacattaccaaattaaaaggaccaaaagctgctgctctttttgcgaagacacataatttgaata<br>tgttgcaggacataccaatggacaggtttgtaatggacttaaagagagacgtgaaagtgactccagga<br>acaaaacatactgaagaacggcccaaggtacaggtgatccaggctgccgatccgctagcaacagcgta<br>tctgtgcggaatccaccgagagctggttaggagattaaatgcggtcctgcttccgaacattcatacac<br>tgtttgatatgtcggctgaagactttgacgctattatagccgagcacttccagcctggggattgtgtt<br>ctggaaactgacatcgcgtcgtttgataaaagtgaggacgacgccatggctctgaccgcgttaatgat<br>tctggaagacttaggtgtggacgcagagctgttgacgctgattgaggcggctttcggcgaaatttcat<br>caatacatttgcccactaaaactaaatttaaattcggagccatgatgaaatctggaatgttcctcaca<br>ctgtttgtgaacacagtcattaacattgtaatcgcaagcagagtgttgagagaacggctaaccggatc<br>accatgtgcagcattcattggagatgacaatatcgtgaaaggagtcaaatcggacaaattaatggcag<br>acaggtgcgccacctggttgaatatggaagtcaagattatagatgctgtggtgggcgagaaagcgcct<br>tatttctgtggagggtttattttgtgtgactccgtgaccggcacagcgtgccgtgtggcagacccccct<br>aaaaaggctgtttaagcttggcaaacctctggcagcagacgatgaacatgatgatgacaggagaaggg<br>cattgcatgaagagtcaacacgctggaaccgagtgggtattctttcagagctgtgcaaggcagtagaa<br>tcaaggtatgaaaccgtaggaacttccatcatagttatggccatgactactctagctagcagtgttaa<br>atcattcagctacctgagaggggcccctataactctctacggctaacctgaatggactacgacatagt<br>ctagtcgagtctagtcgacgccaccatggccagccacaagtggctgctgcagatgatcgtgttcctga<br>aaaccatcacaatcgcctactgcctgcatctgcaggacgacacccctctgttcttcggcgccaagcct<br>ctgagcgacgtgtccctgatcatcaccgagccttgcgtgtccagcgtgtacgaggcctgggattatgc<br>cgcccctcccgtgtccaatctgagcgaagccctgagcggcatcgtggtcaagaccaagtgccccgtgc<br>ccgaagtgatcctgtggttcaaggacaagcagatggcctactggaccaacccttacgtgaccctgaag<br>ggcctgacccagagcgtgggcgaggaacacaagagcggcgacatcagagatgccctgctggatgccct<br>gtccggtgtctgggtggacagcacaccctccagcaccaacatccccgagaacggctgtgtgtggggag<br>ccgaccggctgttccagagagtgtgtcagtaatctagacgcggccgcatacagcagcaattggcaagc<br>tgcttacatagaactcgcggcgattggcatgccgccttaaaatttttattttattttttcttttctttt<br>ccgaatcggattttgtttttaatatttcaaaaaaaaaaaaaaaaaaaaaaaaaaaaaaaaaaagggtc<br>ggcatggcatctccacctcctcgcggtccgacctgggcatccgaaggaggacgcacgtccactcggat |

-continued

| SEQUENCES |
| --- |

ggctaagggagagccacgtttaaaccagctccaattcgccctatagtgagtcgtattacgcgcgctca
ctggccgtcgttttacaacgtcgtgactgggaaaaccctggcgttacccaacttaatcgccttgcagc
acatccccctttcgccagctggcgtaatagcgaagaggcccgcaccgatcgcccttcccaacagttgc
gcagcctgaatggcgaatgggacgcgccctgtagcggcgcattaagcgcggcgggtgtggtggttacg
cgcagcgtgaccgctacacttgccagcgccctagcgcccgctcctttcgctttcttcccttcctttct
cgccacgttcgccggctttccccgtcaagctctaaatcgggggctccctttagggttccgatttagtg
ctttacggcacctcgaccccaaaaaacttgattagggtgatggttcacgtagtgggccatcgccctga
tagacggtttttcgccctttgacgttggagtccacgttctttaatagtggactcttgttccaaactgg
aacaacactcaaccctatctcggtctattcttttgatttataagggattttgccgatttcggcctatt
ggttaaaaaatgagctgatttaacaaaaatttaacgcgaattttaacaaaatattaacgcttacaatt
taggtggcacttttcggggaaatgtgcgcggaacccctatttgtttatttttctaaatacattcaaat
atgtatccgctcatgagacaataaccctgataaatgcttcaataatattgaaaaaggaagagtatgag
tattcaacatttccgtgtcgcccttattcccttttttgcggcattttgccttcctgtttttgctcacc
cagaaacgctggtgaaagtaaaagatgctgaagatcagttgggtgcacgagtgggttacatcgaactg
gatctcaacagcggtaagatccttgagagttttcgccccgaagaacgttttccaatgatgagcacttt
taaagttctgctatgtggcgcggtattatcccgtattgacgccgggcaagagcaactcggtcgccgca
tacactattctcagaatgacttggttgagtactcaccagtcacagaaaagcatcttacggatggcatg
acagtaagagaattatgcagtgctgccataaccatgagtgataacactgcggccaacttacttctgac
aacgatcggaggaccgaaggagctaaccgcttttttgcacaacatgggggatcatgtaactcgccttg
atcgttgggaaccggagctgaatgaagccataccaaacgacgagcgtgacaccacgatgcctgtagca
atggcaacaacgttgcgcaaactattaactggcgaactacttactctagcttcccggcaacaattaat
agactggatggaggcggataaagttgcaggaccacttctgcgctcggcccttccggctggctggttta
ttgctgataaatctggagccggtgagcgtgggtctcgcggtatcattgcagcactggggccagatggt
aagccctcccgtatcgtagttatctacacgacggggagtcaggcaactatggatgaacgaaatagaca
gatcgctgagataggtgcctcactgattaagcattggtaactgtcagaccaagtttactcatatatac
tttagattgatttaaaacttcatttttaatttaaaaggatctaggtgaagatcctttttgataatctc
atgaccaaaatcccttaacgtgagttttcgttccactgagcgtcagaccccgtagaaaagatcaaagg
atcttcttgagatcctttttttctgcgcgtaatctgctgcttgcaaacaaaaaaaccaccgctaccag
cggtggtttgtttgccggatcaagagctaccaactctttttccgaaggtaactggcttcagcagagcg
cagataccaaatactgttcttctagtgtagccgtagttaggccaccacttcaagaactctgtagcacc
gcctacatacctcgctctgctaatcctgttaccagtggctgctgccagtggcgataagtcgtgtctta
ccgggttggactcaagacgatagttaccggataaggcgcagcggtcgggctgaacggggggttcgtgc
acacagcccagcttggagcgaacgacctacaccgaactgagatacctacagcgtgagctatgagaaag
cgccacgcttcccgaagggagaaaggcggacaggtatccggtaagcggcagggtcggaacaggagagc
gcacgagggagcttccagggggaaacgcctggtatctttatagtcctgtcgggtttcgccacctctga
cttgagcgtcgatttttgtgatgctcgtcaggggggcggagcctatggaaaaacgccagcaacgcggc
ctttttacggttcctggccttttgctggccttttgctcacatgttctttcctgcgttatcccctgatt
ctgtggataaccgtattaccgcctttgagtgagctgataccgctcgccgcagccgaacgaccgagcgc
agcgagtcagtgagcgaggaagcggaagagcgcccaatacgcaaaccgcctctccccgcgcgttggcc
gattcattaatgcagctggcacgacaggtttcccgactggaaagcgggcagtgagcgcaacgcaatta
atgtgagttagctcactcattaggcaccccaggctttacactttatgctcccggctcgtatgttgtgt
ggaattgtgagcggataacaatttcacacaggaaacagctatgaccatgattacgccaagcgcgcaat
taaccctcactaaagggaacaaaagctgggtaccgggcccacgcgtaatacgactcactatag_1121
5

VZV VEERep.SGPgH-SGPgL (SEQ ID NO: 76)
1_
ataggcggcgcatgagagaagcccagaccaattacctacccaaaatggagaaagttcacgttgacatc
gaggaagacagcccattcctcagagctttgcagcggagcttcccgcagtttgaggtagaagccaagca
ggtcactgataatgaccatgctaatgccagagcgttttcgcatctggcttcaaaactgatcgaaacgg
aggtggacccatccgacacgatccttgacattggaagtgcgcccgcccgcagaatgtattctaagcac
aagtatcattgtatctgtccgatgagatgtgcggaagatccggacagattgtataagtatgcaactaa
gctgaagaaaaactgtaaggaaataactgataaggaattggacaagaaaatgaaggagctcgccgccg
tcatgagcgaccctgacctggaaactgagactatgtgcctccacgacgacgagtcgtgtcgctacgaa
gggcaagtcgctgtttaccaggatgtatacgcggttgacggaccgacaagtctctatcaccaagccaa
taagggagttagagtcgcctactggataggctttgacaccaccccttttatgtttaagaacttggctg
gagcatatccatcatactctaccaactgggccgacgaaaccgtgttaacggctcgtaacataggccta
tgcagctctgacgttatggagcggtcacgtagagggatgtccattcttagaaagaagtatttgaaacc
atccaacaatgttctattctctgttggctcgaccatctaccacgagaagagggacttactgaggagct
ggcacctgccgtctgtatttcacttacgtggcaagcaaaattacacatgtcggtgtgagactatagtt
agttgcgacgggtacgtcgttaaaagaatagctatcagtccaggcctgtatgggaagccttcaggcta
tgctgctacgatgcaccgcgagggattcttgtgctgcaaagtgacagacacattgaacggggagaggg
tctcttttcccgtgtgcacgtatgtgccagctacattgtgtgaccaaatgactggcatactggcaaca
gatgtcagtgcggacgacgcgcaaaaactgctggttgggctcaaccagcgtatagtcgtcaacggtcg
cacccagagaaacaccaataccatgaaaaattacctttgcccgtagtggcccaggcatttgctaggt
gggcaaaggaatataaggaagatcaagaagatgaaaggccactaggactacgagatagacagttagtc
atggggtgttgttgggcttttagaaggcacaagataacatctatttataagcgcccggatacccaaac
catcatcaaagtgaacagcgatttccactcattcgtgctgcccaggataggcagtaacacattggaga
tcgggctgagaacaagaatcaggaaaatgttagaggagcacaaggagccgtcacctctcattaccgcc
gaggacgtacaagaagctaagtgcgcagccgatgaggctaaggaggtgcgtgaagccgaggagttgcg
cgcagctctaccacctttggcagctgatgttgaggagcccactctggaagccgatgtagacttgatgt
tacaagaggctggggccggctcagtggagacacctcgtggcttgataaaggttaccagctacgatggc
gaggacaagatcggctcttacgctgtgctttctccgcaggctgtactcaagagtgaaaaattatcttg
catccaccctctcgctgaacaagtcatagtgataacacactctggccgaaaagggcgttatgccgtgg
aaccataccatggtaaagtagtggtgccagagggacatgcaatacccgtccaggactttcaagctctg
agtgaaagtgccaccattgtgtacaacgaacgtgagttcgtaaacaggtacctgcaccatattgccac
acatggaggagcgctgaacactgatgaagaatattacaaaactgtcaagcccagcgagcacgacggcg -continued

SEQUENCES aatacctgtacgacatcgacaggaaacagtgcgtcaagaaagaactagtcactgggctagggctcaca
ggcgagctggtggatcctcccttccatgaattcgcctacgagagtctgagaacacgaccagccgctcc
ttaccaagtaccaaccatagggtgtatggcgtgccaggatcaggcaagtctggcatcattaaaagcg
cagtcaccaaaaaagatctagtggtgagcgccaagaaagaaaactgtgcagaaattataagggacgtc
aagaaaatgaaagggctggacgtcaatgccagaactgtggactcagtgctcttgaatggatgcaaaca
ccccgtagagaccctgtatattgacgaagcttttgcttgtcatgcaggtactctcagagcgctcatag
ccattataagacctaaaaaggcagtgctctgcggggatcccaaacagtgcggtttttttaacatgatg
tgcctgaaagtgcattttaaccacgagatttgcacacaagtcttccacaaaagcatctctcgccgttg
cactaaatctgtgacttcggtcgtctcaaccttgttttacgacaaaaaaatgagaacgacgaatccga
aagagactaagattgtgattgacactaccggcagtaccaaacctaagcaggacgatctcattctcact
tgtttcagagggtgggtgaagcagttgcaaatagattacaaaggcaacgaaataatgacggcagctgc
ctctcaagggctgacccgtaaaggtgtgtatgccgttcggtacaaggtgaatgaaaatcctctgtacg
cacccacctcagaacatgtgaacgtcctactgacccgcacggaggaccgcatcgtgtggaaaacacta
gccggcgacccatggataaaaacactgactgccaagtaccctgggaatttcactgccacgatagagga
gtggcaagcagagcatgatgccatcatgaggcacatcttggagagaccggaccctaccgacgtcttcc
agaataaggcaaacgtgtgttgggccaaggctttagtgccggtgctgaagaccgctggcatagacatg
accactgaacaatggaacactgtggattattttgaaacggacaaagctcactcagcagagatagtatt
gaaccaactatgcgtgaggttctttggactcgatctggactccggtctattttctgcacccactgttc
cgttatccattaggaataatcactgggataactccccgtcgcctaacatgtacgggctgaataaagaa
gtggtccgtcagctctctcgcaggtacccacaactgcctcgggcagttgccactggaagagtctatga
catgaacactggtacactgcgcaattatgatccgcgcataaacctagtacctgtaaacagaagactgc
ctcatgctttagtcctccaccataatgaacacccacagagtgacttttcttcattcgtcagcaaattg
aagggcagaactgtcctggtggtcggggaaaagttgtccgtcccaggcaaaatggttgactggttgtc
agaccggcctgaggctaccttcagagctcggctggatttaggcatcccaggtgatgtgcccaaatatg
acataatatttgttaatgtgaggaccccatataaataccatcactatcagcagtgtgaagaccatgcc
attaagcttagcatgttgaccaagaaagcttgtctgcatctgaatcccggcggaacctgtgtcagcat
aggttatggttacgctgacagggccagcgaaagcatcattggtgctatagcgcggcagttcaagtttt
cccgggtatgcaaaccgaaatcctcacttgaagagacggaagttctgtttgtattcattgggtacgat
cgcaaggcccgtacgcacaatccttacaagctttcatcaaccttgaccaacatttatacaggttccag
actccacgaagccggatgtgcaccctcatatcatgtggtgcgaggggatattgccacggccaccgaag
gagtgattataaatgctgctaacagcaaaggacaacctggcggagggggtgtgcggagcgctgtataag
aaattcccggaaagcttcgatttacagccgatcgaagtaggaaaagcgcgactggtcaaaggtgcagc
taaacatatcattcatgccgtaggaccaaacttcaacaaagtttcggaggttgaaggtgacaaacagt
tggcagaggcttatgagtccatcgctaagattgtcaacgataacaattacaagtcagtagcgattcca
ctgttgtccaccggcatcttttccgggaacaaagatcgactaacccaatcattgaaccatttgctgac
agctttagacaccactgatgcagatgtagccatatactgcagggacaagaaatgggaaatgactctca
aggaagcagtggctaggagagaagcagtggaggagatatgcatatccgacgactcttcagtgacagaa
cctgatgcagagctggtgagggtgcatccgaagagttctttggctggaaggaagggctacagcacaag
cgatggcaaaactttctcatatttggaagggaccaagtttcaccaggcggccaaggatatagcagaaa
ttaatgccatgtggcccgttgcaacggaggccaatgagcaggtatgcatgtatatcctcggagaaagc
atgagcagtattaggtcgaaatgccccgtcgaagagtcggaagcctccacaccacctagcacgctgcc
ttgcttgtgcatccatgccatgactccagaaagagtacagcgcctaaaagcctcacgtccagaacaaa
ttactgtgtgctcatcctttccattgccgaagtatagaatcactggtgtgcagaagatccaatgctcc
cagcctatattgttctcaccgaaagtgcctgcgtatattcatccaaggaagtatctcgtggaaacacc
accggtagacgagactccggagccatcggcagagaaccaatccacagaggggacacctgaacaaccac
cacttataaccgaggatgagaccaggactagaacgcctgagccgatcatcatcgaagaggaagaagag
gatagcataagtttgctgtcagatggcccgacccaccaggtgctgcaagtcgaggcagacattcacgg
gccgccctctgtatctagctcatcctggtccattcctcatgcatccgactttgatgtggacagtttat
ccatacttgacaccctggagggagctagcgtgaccagcggggcaacgtcagccgagactaactcttac
ttcgcaaagagtatggagtttctggcgcgaccggtgcctgcgcctcgaacagtattcaggaaccctcc
acatcccgctccgcgcacaagaacaccgtcacttgcacccagcagggcctgctcgagaaccagcctag
tttccaccccgccaggcgtgaatagggtgatcactagagaggagctcgaggcgcttaccccgtcacgc
actcctagcaggtcggtctcgagaaccagcctggtctccaacccgccaggcgtaaatagggtgattac
aagagaggagtttgaggcgttcgtagcacaacaacaatgacggtttgatgcgggtgcatacatctttt
cctccgacaccggtcaagggcatttacaacaaaaatcagtaaggcaaacggtgctatccgaagtggtg
ttggagaggaccgaattggagatttcgtatgccccgcgcctcgaccaagaaaaagaagaattactacg
caagaaattacagttaaatcccacacctgctaacagaagcagataccagtccaggaaggtggagaaca
tgaaagccataacagctagacgtattctgcaaggcctagggcattatttgaaggcagaaggaaaagtg
gagtgctaccgaaccctgcatcctgttcctttgtattcatctagtgtgaaccgtgccttttcaagccc
caaggtcgcagtggaagcctgtaacgccatgttgaaagagaactttccgactgtggcttcttactgta
ttattccagagtacgatgcctatttggacatggttgacggagcttcatgctgcttagacactgccagt
tttgccctgcaaagctgcgcagctttccaaagaaacactcctatttggaacccacaatacgatcggc
agtgccttcagcgatccagaacacgctccagaacgtcctggcagctgccacaaaaagaaattgcaatg
tcacgcaaatgagagaattgcccgtattggattcggcggcctttaatgtggaatgcttcaagaaatat
gcgtgtaataatgaatattgggaaacgtttaaagaaaaccccatcaggcttactgaagaaaacgtggt
aaattacattaccaaattaaaaggaccaaaagctgctgctctttttgcgaagacacataatttgaata
tgttgcaggacataccaatggacaggtttgtaatggacttaaagagagacgtgaaagtgactccagga
acaaaacatactgaagaacggcccaaggtacaggtgatccaggctgccgatccgctagcaacagcgta
tctgtgcggaatccaccgagagctggttaggagattaaatgcggtcctgcttccgaacattcatacac
tgtttgatatgtcggctgaagactttgacgctattatagccgagcacttccagcctggggattgtgtt
ctggaaactgacatcgcgtcgtttgataaaagtgaggacgacgccatggctctgaccgcgttaatgat
tctggaagacttaggtgtggacgcagagctgttgacgctgattgaggcggctttcggcgaaatttcat
caatacatttgcccactaaaactaaatttaaattcggagccatgatgaaatctggaatgttcctcaca
ctgtttgtgaacacagtcattaacattgtaatcgcaagcagagtgttgagagaacggctaaccggatc
accatgtgcagcattcattggagatgacaatatcgtgaaaggagtcaaatcggacaaattaatggcag
acaggtgcgccacctggttgaatatggaagtcaagattatagatgctgtggtgggcgagaaagcgcct
tatttctgtggagggtttattttgtgtgactccgtgaccggcacagcgtgccgtgtggcagacccccct -continued

| SEQUENCES |
|---|
| aaaaaggctgtttaagcttggcaaacctctggcagcagacgatgaacatgatgatgacaggagaaggg<br>cattgcatgaagagtcaacacgctggaaccgagtgggtattctttcagagctgtgcaaggcagtagaa<br>tcaaggtatgaaaccgtaggaacttccatcatagttatggccatgactactctagctagcagtgttaa<br>atcattcagctacctgagaggggcccctataactctctacggctaacctgaatggactacgacatagt<br>ctagtcgagtctagtcgacgccaccatgttcgccctggtgctggccgtggtcatcctgcctctgtgga<br>ccaccgccaacaagagctacgtgacccccacacccgccaccagatccatcggacacatgagcgccctg<br>ctgagagagtacagcgaccggaacatgagcctgaagctggaagccttctaccccaccggcttcgacga<br>ggaactgatcaagagcctgcactggggcaacgaccggaagcacgtgttcctcgtgatcgtgaaagtga<br>accccaccacccacgagggcgacgtcggcctggtcatcttccccaagtacctgctgagcccctaccac<br>ttcaaggccgagcacagagccccttccctgctggccgctttggctttctgagccaccctgtgacccc<br>cgacgtgtcattcttcgacagcagcttcgcccccctacctgaccacacagcacctggtggccttcacca<br>ccttccccccccaatcctctcgtgtggcacctggaaagagccgagacagccgccaccgccgaaagacct<br>tttggcgtgtccctgctgcccgccagacctaccgtgcccaagaacaccatcctggaacacaaggccca<br>cttcgccacctgggatgccctggccagacacaccttctttagcgccgaggccatcatcaccaacagca<br>ccctgagaatccacgtgcccctgttcggcagcgtgtggcccatcagatactgggccacaggcagcgtg<br>ctgctgaccagcgatagcggcagagtggaagtgaacatcggcgtgggcttcatgagcagcctgatcag<br>cctgagcagcggcctgcccatcgagctgattgtggtgccccacaccgtgaagctgaacgccgtgacca<br>gcgacaccacctggttccagctgaaccccctggccctgatcctggccctagttacagagtgtacctg<br>ctgggcagaggcctggacatgaacttcagcaagcacgccaccgtggacatctgcgcctaccctgagga<br>aagcctggactacagataccacctgagcatggcccacaccgaggccctgagaatgaccaccaaggccg<br>accagcacgacatcaacgaggaaagctactaccacattgccgccagaatcgccaccagcatcttcgcc<br>ctgagcgagatgggccggaccaccgagtactttctgctggacgagatcgtggacgtgcagtaccagct<br>gaagttcctgaactacatcctgatgcggatcggcgctggcgcccaccctaataccatcagcggcacca<br>gcgacctgatcttcgccgatcctagccagctgcacgacgagctgagcctgctgttcggccaggtcaaa<br>cccgccaacgtggactacttcatcagctacgacgaggcccgggaccagctgaaaacagcctacgccct<br>gtccagaggccaggatcatgtgaacgccctgtccctggccaggcgcgtgatcatgagcatctacaagg<br>gcctgctggtcaagcagaacctgaacgccaccgagcggcaggccctgttcttcgccagcatgatcctg<br>ctgaacttcagagagggcctggaaaacagcagccgggtgctggatggcagaaccaccctgctgctgat<br>gaccagcatgtgcacagccgcccatgccacacaggccgccctgaatatccaggaaggcctggcttacc<br>tgaaccccagcaagcacatgttcaccatccccaacgtgtacagcccctgcatgggcagcctgagaacc<br>gacctgaccgaagagatccacgtgatgaacctgctgtccgccatccccaccagacccggactgaatga<br>ggtgctgcacacccagctggacgagtccgagatcttcgacgccgccttcaagaccatgatgatcttta<br>ccacctggaccgccaaggacctgcacatcctgcacacacacgtgcccgaggtgttcacatgccaagat<br>gccgccgctcggaacggcgagtatgtgctgattctgcctgccgtgcagggccacagctacgtgatcac<br>ccggaacaagccccagcggggcctggtgtatagcctggctgacgtggacgtgtacaaccccatcagcg<br>tggtgtacctgagcaaggatacctgcgtgtccgagcacggcgtgatcgaaacagtggccctgccccac<br>cccgacaacctgaaagagtgcctgtactgcggctccgtgttcctgcggtatctgaccaccggcgccat<br>catggacatcatcatcatcgacagcaaggacaccgagagacagctggccgccatgggcaacagcacca<br>tcccccccttcaaccccgacatgcacggcgacgatagcaaggccgtgctgctgttccccaacggcacc<br>gtggtcacactgctgggcttcgagcggagacaggccatcagaatgagcggccagtacctgggcgcctc<br>tctgggtggtgcctttctggccgtcgtgggctttggcatcatcggctggatgctgtgcggcaacagca<br>gactgcgcgagtacaacaagatcccccctgacctaatctagacgtcgcgaccacccaggatccgcctat<br>aactctctacggctaacctgaatggactacgacatagtctagtcgacgccaccatggccagccacaag<br>tggctgctgcagatgatcgtgttcctgaaaaccatcacaatcgcctactgcctgcatctgcaggacga<br>cacccctctgttcttcggcgccaagcctctgagcgacgtgtccctgatcatcaccgagccttgcgtgt<br>ccagcgtgtacgaggcctgggattatgccgcccctcccgtgtccaatctgagcgaagccctgagcggc<br>atcgtggtcaagaccaagtgccccgtgcccgaagtgatcctgtggttcaaggacaagcagatggccta<br>ctggaccaacccttacgtgaccctgaagggcctgacccagagcgtgggcgaggaacacaagagcggcg<br>acatcagagatgccctgctggatgccctgtccggtgtctgggtggacagcacaccctccagcaccaac<br>atccccgagaacggctgtgtgtggggagccgaccggctgttccagagagtgtgtcagtaatctagacg<br>cggccgcatacagcagcaattggcaagctgcttacatagaactcgcggcgattggcatgccgccttaa<br>aatttttattttattttcttttcttttccgaatcggattttgtttttaatatttcaaaaaaaaaaaaa<br>aaaaaaaaaaaaaaaaaaaaaaagggtcggcatggcatctccacctcctcgcggtccgacctgggcat<br>ccgaaggaggacgcacgtccactcggatggctaagggagagccacgtttaaaccagctccaattcgcc<br>ctatagtgagtcgtattacgcgcgctcactggccgtcgttttacaacgtcgtgactgggaaaaccctg<br>gcgttacccaacttaatcgccttgcagcacatccccctttcgccagctggcgtaatagcgaagaggcc<br>cgcaccgatcgcccttcccaacagttgcgcagcctgaatggcgaatggacgcgccctgtagcggcgc<br>attaagcgcggcgggtgtggtggttacgcgcagcgtgaccgctacacttgccagcgccctagcgcccg<br>ctcctttcgctttcttcccttcctttctcgccacgttcgccggctttccccgtcaagctctaaatcgg<br>gggctccctttagggttccgatttagtgctttacggcacctcgaccccaaaaaacttgattagggtga<br>tggttcacgtagtgggccatcgccctgatagacggtttttcgccctttgacgttggagtccacgttct<br>ttaatagtggactcttgttccaaactggaacaacactcaaccctatctcggtctattcttttgattta<br>taagggattttgccgatttcggcctattggttaaaaaatgagctgatttaacaaaaatttaacgcgaa<br>ttttaacaaaatattaacgcttacaatttaggtggcacttttcggggaaatgtgcgcggaacccctat<br>ttgtttatttttctaaatacattcaaatatgtatccgctcatgagacaataaccctgataaatgcttc<br>aataatattgaaaaaggaagagtatgagtattcaacatttccgtgtcgcccttattcccttttttgcg<br>gcattttgccttcctgtttttgctcacccagaaacgctggtgaaagtaaaagatgctgaagatcagtt<br>gggtgcacgagtgggttacatcgaactggatctcaacagcggtaagatccttgagagttttcgccccg<br>aagaacgttttccaatgatgagcacttttaaagttctgctatgtggcgcggtattatcccgtattgac<br>gccgggcaagagcaactcggtcgccgcatacactattctcagaatgacttggttgagtactcaccagt<br>cacagaaaagcatcttacggatggcatgacagtaagagaattatgcagtgctgccataaccatgagtg<br>ataacactgcggccaacttacttctgacaacgatcggaggaccgaaggagctaaccgcttttttgcac<br>aacatgggggatcatgtaactcgccttgatcgttgggaaccggagctgaatgaagccataccaaacga<br>cgagcgtgacaccacgatgcctgtagcaatggcaacaacgttgcgcaaactattaactggcgaactac<br>ttactctagcttcccggcaacaattaatagactggatggaggcggataaagttgcaggaccacttctg<br>cgctcggcccttccggctggctggtttattgctgataaatctggagccggtgagcgtgggtctcgcgg<br>tatcattgcagcactggggccagatggtaagccctcccgtatcgtagttatctacacgacggggagtc |

-continued

SEQUENCES aggcaactatggatgaacgaaatagacagatcgctgagataggtgcctcactgattaagcattggtaa
ctgtcagaccaagtttactcatatatactttagattgatttaaaacttcatttttaatttaaaaggat
ctaggtgaagatcctttttgataatctcatgaccaaaatcccttaacgtgagttttcgttccactgag
cgtcagaccccgtagaaaagatcaaaggatcttcttgagatcctttttttctgcgcgtaatctgctgc
ttgcaaacaaaaaaaccaccgctaccagcggtggtttgtttgccggatcaagagctaccaactctttt
tccgaaggtaactggcttcagcagagcgcagataccaaatactgttcttctagtgtagccgtagttag
gccaccacttcaagaactctgtagcaccgcctacatacctcgctctgctaatcctgttaccagtggct
gctgccagtggcgataagtcgtgtcttaccgggttggactcaagacgatagttaccggataaggcgca
gcggtcgggctgaacggggggttcgtgcacacagcccagcttggagcgaacgacctacaccgaactga
gatacctacagcgtgagctatgagaaagcgccacgcttcccgaagggagaaaggcggacaggtatccg
gtaagcggcagggtcggaacaggagagcgcacgagggagcttccagggggaaacgcctggtatcttta
tagtcctgtcgggtttcgccacctctgacttgagcgtcgatttttgtgatgctcgtcaggggggcgga
gcctatggaaaaacgccagcaacgcggcctttttacggttcctggccttttgctggccttttgctcac
atgttctttcctgcgttatcccctgattctgtggataaccgtattaccgcctttgagtgagctgatac
cgctcgccgcagccgaacgaccgagcgcagcgagtcagtgagcgaggaagcggaagagcgcccaatac
gcaaaccgcctctccccgcgcgttggccgattcattaatgcagctggcacgacaggtttcccgactgg
aaagcgggcagtgagcgcaacgcaattaatgtgagttagctcactcattaggcaccccaggctttaca
ctttatgctcccggctcgtatgttgtgtggaattgtgagcggataacaatttcacacaggaaacagct
atgaccatgattacgccaagcgcgcaattaaccctcactaaagggaacaaaagctgggtaccgggccc
acgcgtaatacgactcactatag_13827

VZV VEERep.SGPgE (SEQ ID NO: 77):
1_
ataggcggcgcatgagagaagcccagaccaattacctacccaaaatggagaaagttcacgttgacatc
gaggaagacagcccattcctcagagctttgcagcggagcttcccgcagtttgaggtagaagccaagca
ggtcactgataatgaccatgctaatgccagagcgttttcgcatctggcttcaaaactgatcgaaacgg
aggtggacccatccgacacgatccttgacattggaagtgcgcccgcccgcagaatgtattctaagcac
aagtatcattgtatctgtccgatgagatgtgcggaagatccggacagattgtataagtatgcaactaa
gctgaagaaaaactgtaaggaaataactgataaggaattggacaagaaaatgaaggagctcgccgccg
tcatgagcgaccctgacctggaaactgagactatgtgcctccacgacgacgagtcgtgtcgctacgaa
gggcaagtcgctgtttaccaggatgtatacgcggttgacggaccgacaagtctctatcaccaagccaa
taagggagttagagtcgcctactggataggctttgacaccaccccttttatgtttaagaacttggctg
gagcatatccatcatactctaccaactgggccgacgaaaccgtgttaacggctcgtaacataggccta
tgcagctctgacgttatggagcggtcacgtagagggatgtccattcttagaaagaagtatttgaaacc
atccaacaatgttctattctctgttggctcgaccatctaccacgagaagagggacttactgaggagct
ggcacctgccgtctgtatttcacttacgtggcaagcaaaattacacatgtcggtgtgagactatagtt
agttgcgacgggtacgtcgttaaaagaatagctatcagtccaggcctgtatgggaagccttcaggcta
tgctgctacgatgcaccgcgagggattcttgtgctgcaaagtgacagacacattgaacggggagaggg
tctcttttcccgtgtgcacgtatgtgccagctacattgtgtgaccaaatgactggcatactggcaaca
gatgtcagtgcggacgacgcgcaaaaactgctggttgggctcaaccagcgtatagtcgtcaacggtcg
cacccagagaaacaccaataccatgaaaaattacctttgcccgtagtggcccaggcatttgctaggt
gggcaaaggaatataaggaagatcaagaagatgaaaggccactaggactacgagatagacagttagtc
atggggtgttgttgggcttttagaaggcacaagataacatctatttataagcgcccggatacccaaac
catcatcaaagtgaacagcgatttccactcattcgtgctgcccaggataggcagtaacacattggaga
tcgggctgagaacaagaatcaggaaaatgttagaggagcacaaggagccgtcacctctcattaccgcc
gaggacgtacaagaagctaagtgcgcagccgatgaggctaaggaggtgcgtgaagccgaggagttgcg
cgcagctctaccacctttggcagctgatgttgaggagcccactctggaagccgatgtagacttgatgt
tacaagaggctggggccggctcagtggagacacctcgtggcttgataaaggttaccagctacgatggc
gaggacaagatcggctcttacgctgtgctttctccgcaggctgtactcaagagtgaaaaattatcttg
catccaccctctcgctgaacaagtcatagtgataacacactctggccgaaaagggcgttatgccgtgg
aaccataccatggtaaagtagtggtgccagagggacatgcaatacccgtccaggactttcaagctctg
agtgaaagtgccaccattgtgtacaacgaacgtgagttcgtaaacaggtacctgcaccatattgccac
acatggaggagcgctgaacactgatgaagaatattacaaaactgtcaagcccagcgagcacgacggcg
aatacctgtacgacatcgacaggaaacagtgcgtcaagaaagaactagtcactgggctagggctcaca
ggcgagctggtggatcctcccttccatgaattcgcctacgagagtctgagaacacgaccagccgctcc
ttaccaagtaccaaccataggggtgtatggcgtgccaggatcaggcaagtctggcatcattaaaagcg
cagtcaccaaaaaagatctagtggtgagcgccaagaaagaaaactgtgcagaaattataagggacgtc
aagaaaatgaaagggctggacgtcaatgccagaactgtggactcagtgctcttgaatggatgcaaaca
ccccgtagagaccctgtatattgacgaagcttttgcttgtcatgcaggtactctcagagcgctcatag
ccattataagacctaaaaaggcagtgctctgcggggatcccaaacagtgcggtttttttaacatgatg
tgcctgaaagtgcattttaaccacgagatttgcacacaagtcttccacaaaagcatctctcgccgttg
cactaaatctgtgacttcggtcgtctcaaccttgttttacgacaaaaaaatgagaacgacgaatccga
aagagactaagattgtgattgacactaccggcagtaccaaacctaagcaggacgatctcattctcact
tgtttcagagggtgggtgaagcagttgcaaatagattacaaaggcaacgaaataatgacggcagctgc
ctctcaagggctgacccgtaaaggtgtgtatgccgttcggtacaaggtgaatgaaaatcctctgtacg
cacccacctcagaacatgtgaacgtcctactgacccgcacggaggaccgcatcgtgtggaaaacacta
gccggcgacccatggataaaaacactgactgccaagtaccctgggaatttcactgccacgatagagga
gtggcaagcagagcatgatgccatcatgaggcacatcttggagagaccggaccctaccgacgtcttcc
agaataaggcaaacgtgtgttgggccaaggctttagtgccggtgctgaagaccgctggcatagacatg
accactgaacaatggaacactgtggattattttgaaacggacaaagctcactcagcagagatagtatt
gaaccaactatgcgtgaggttctttggactcgatctggactccggtctattttctgcacccactgttc
cgttatccattaggaataatcactgggataactccccgtcgcctaacatgtacgggctgaataaagaa
gtggtccgtcagctctctcgcaggtacccacaactgcctcgggcagttgccactggaagagtctatga
catgaacactggtacactgcgcaattatgatccgcgcataaacctagtacctgtaaacagaagactgc
ctcatgctttagtcctccaccataatgaacacccacagagtgacttttcttcattcgtcagcaaattg
aagggcagaactgtcctggtggtcggggaaaagttgtccgtcccaggcaaaatggttgactggttgtc
agaccggcctgaggctaccttcagagctcggctggatttaggcatcccaggtgatgtgcccaaatatg -continued

SEQUENCES acataatatttgttaatgtgaggaccccatataaataccatcactatcagcagtgtgaagaccatgcc
attaagcttagcatgttgaccaagaaagcttgtctgcatctgaatcccggcggaacctgtgtcagcat
aggttatggttacgctgacagggccagcgaaagcatcattggtgctatagcgcggcagttcaagtttt
cccgggtatgcaaaccgaaatcctcacttgaagagacggaagttctgtttgtattcattgggtacgat
cgcaaggcccgtacgcacaatccttacaagctttcatcaaccttgaccaacatttatacaggttccag
actccacgaagccggatgtgcaccctcatatcatgtggtgcgaggggatattgccacggccaccgaag
gagtgattataaatgctgctaacagcaaaggacaacctggcggaggggtgtgcggagcgctgtataag
aaattcccggaaagcttcgatttacagccgatcgaagtaggaaaagcgcgactggtcaaaggtgcagc
taaacatatcattcatgccgtaggaccaaacttcaacaaagtttcggaggttgaaggtgacaaacagt
tggcagaggcttatgagtccatcgctaagattgtcaacgataacaattacaagtcagtagcgattcca
ctgttgtccaccggcatcttttccgggaacaaagatcgactaacccaatcattgaaccatttgctgac
agctttagacaccactgatgcagatgtagccatatactgcagggacaagaaatgggaaatgactctca
aggaagcagtggctaggagagaagcagtggaggagatatgcatatccgacgactcttcagtgacagaa
cctgatgcagagctggtgagggtgcatccgaagagttctttggctggaaggaagggctacagcacaag
cgatggcaaaactttctcatatttggaagggaccaagtttcaccaggcggccaaggatatagcagaaa
ttaatgccatgtggcccgttgcaacggaggccaatgagcaggtatgcatgtatatcctcggagaaagc
atgagcagtattaggtcgaaatgccccgtcgaagagtcggaagcctccacaccacctagcacgctgcc
ttgcttgtgcatccatgccatgactccagaaagagtacagcgcctaaaagcctcacgtccagaacaaa
ttactgtgtgctcatcctttccattgccgaagtatagaatcactggtgtgcagaagatccaatgctcc
cagcctatattgttctcaccgaaagtgcctgcgtatattcatccaaggaagtatctcgtggaaacacc
accggtagacgagactccggagccatcggcagagaaccaatccacagaggggacacctgaacaaccac
cacttataaccgaggatgagaccaggactagaacgcctgagccgatcatcatcgaagaggaagaagag
gatagcataagtttgctgtcagatggcccgacccaccaggtgctgcaagtcgaggcagacattcacgg
gccgccctctgtatctagctcatcctggtccattcctcatgcatccgactttgatgtggacagtttat
ccatacttgacaccctggagggagctagcgtgaccagcggggcaacgtcagccgagactaactcttac
ttcgcaaagagtatggagtttctggcgcgaccggtgcctgcgcctcgaacagtattcaggaaccctcc
acatcccgctccgcgcacaagaacaccgtcacttgcacccagcagggcctgctcgagaaccagcctag
tttccaccccgccaggcgtgaatagggtgatcactagagaggagctcgaggcgcttaccccgtcacgc
actcctagcaggtcggtctcgagaaccagcctggtctccaacccgccaggcgtaaatagggtgattac
aagagaggagtttgaggcgttcgtagcacaacaacaatgacggtttgatgcgggtgcatacatctttt
cctccgacaccggtcaagggcatttacaacaaaaatcagtaaggcaaacggtgctatccgaagtggtg
ttggagaggaccgaattggagatttcgtatgccccgcgcctcgaccaagaaaaagaagaattactacg
caagaaattacagttaaatcccacacctgctaacagaagcagataccagtccaggaaggtggagaaca
tgaaagccataacagctagacgtattctgcaaggcctagggcattatttgaaggcagaaggaaaagtg
gagtgctaccgaaccctgcatcctgttcctttgtattcatctagtgtgaaccgtgccttttcaagccc
caaggtcgcagtggaagcctgtaacgccatgttgaaagagaactttccgactgtggcttcttactgta
ttattccagagtacgatgcctatttggacatggttgacggagcttcatgctgcttagacactgccagt
tttgccctgcaaagctgcgcagctttccaaagaaacactcctatttggaacccacaatacgatcggc
agtgccttcagcgatccagaacacgctccagaacgtcctggcagctgccacaaaaagaaattgcaatg
tcacgcaaatgagagaattgcccgtattggattcggcggcctttaatgtggaatgcttcaagaaatat
gcgtgtaataatgaatattgggaaacgtttaaagaaaaccccatcaggcttactgaagaaaacgtggt
aaattacattaccaaattaaaaggaccaaaagctgctgctctttttgcgaagacacataatttgaata
tgttgcaggacataccaatggacaggtttgtaatggacttaaagagagacgtgaaagtgactccagga
acaaaacatactgaagaacggcccaaggtacaggtgatccaggctgccgatccgctagcaacagcgta
tctgtgcggaatccaccgagagctggttaggagattaaatgcggtcctgcttccgaacattcatacac
tgtttgatatgtcggctgaagactttgacgctattatagccgagcacttccagcctggggattgtgtt
ctggaaactgacatcgcgtcgtttgataaaagtgaggacgacgccatggctctgaccgcgttaatgat
tctggaagacttaggtgtggacgcagagctgttgacgctgattgaggcggctttcggcgaaatttcat
caatacatttgcccactaaaactaaatttaaattcggagccatgatgaaatctggaatgttcctcaca
ctgtttgtgaacacagtcattaacattgtaatcgcaagcagagtgttgagagaacggctaaccggatc
accatgtgcagcattcattggagatgacaatatcgtgaaaggagtcaaatcggacaaattaatggcag
acaggtgcgccacctggttgaatatggaagtcaagattatagatgctgtggtgggcgagaaagcgcct
tatttctgtggagggtttattttgtgtgactccgtgaccggcacagcgtgccgtgtggcagacccccct
aaaaaggctgtttaagcttggcaaacctctggcagcagacgatgaacatgatgatgacaggagaaggg
cattgcatgaagagtcaacacgctggaaccgagtgggtattctttcagagctgtgcaaggcagtagaa
tcaaggtatgaaaccgtaggaacttccatcatagttatggccatgactactctagctagcagtgttaa
atcattcagctacctgagaggggcccctataactctctacggctaacctgaatggactacgacatagt
ctagtcgagtctagtcgacgccaccatgggcaccgtgaacaagcctgtcgtgggcgtgctgatgggct
tcggcatcatcaccggcaccctgagaatcaccaaccctgtgcgggccagcgtgctgagatacgacgac
ttccacatcgacgaggacaagctggacaccaacagcgtgtacgagccctactaccacagcgaccacgc
cgagagcagctgggtcaacagaggcgagagcagccggaaggcctacgaccacaacagcccctacatct
ggccccggaacgactacgacggcttcctggaaaacgcccacgagcaccacggcgtgtacaatcagggc
agaggcatcgacagcggcgagagactgatgcagcccacacagatgagcgcccaggaagatctgggcga
cgacacaggcatccacgtgatccccaccctgaacggcgacgaccggcacaagatcgtgaacgtggacc
agcggcagtacggcgacgtgttcaagggcgacctgaaccctaagccccagggccagagactgatcgag
gtgtccgtggaagagaaccaccccttcaccctgagagcccccatccagagaatctacggcgtgcggta
taccgagacttggagcttcctgcccagcctgacctgtacaggcgacgccgctcctgccatccagcaca
tctgcctgaagcacaccacctgtttccaggacgtggtggtggacgtggactgcgccgagaacaccaaa
gaggaccagctggccgagatcagctaccggttccagggcaagaaagaggccgaccagccctggatcgt
ggtcaataccagcaccctgttcgacgagctggaactggacccccccgagattgaacccggcgtgctga
aggtgctgcggaccgagaagcagtacctgggcgtgtacatctggaacatgcggggctccgacggcacc
tctacctacgccaccttcctggtcacatggaagggcgacgagaaaacccggaaccctacccctgccgt
gacccctcagcctagaggcgccgagttccatatgtggaattaccactcccacgtgttcagcgtgggcg
acaccttcagcctggccatgcatctgcagtacaagatccacgaggccccctt cgacctgctgctggaa
tggctgtacgtgcccatcgaccctacctgccagcccatgcggctgtacagcacctgtctgtaccaccc
caacgcccctcagtgcctgagccacatgaacagcggctgcaccttcaccagccctcacctggctcaga
gggtggccagcaccgtgtaccagaattgcgagcacgccgacaactacaccgcctactgcctgggcatc -continued

SEQUENCES agccacatggaacccagcttcggcctgatcctgcacgatggcggcaccaccctgaagttcgtggacac
acccgagagcctgagcggcctgtacgtgttcgtggtgtacttcaacggccacgtggaagccgtggcct
acaccgtggtgtccaccgtggaccacttcgtgaacgccatcgaggaaagaggcttcccacccacagcc
ggacagcctccagccaccaccaagcccaaagaaatcacccccgtgaaccccggcaccagcccccctgct
gagatatgctgcttggacaggcggactggccgctgtggtgctgctgtgcctggtcatcttcctgatct
gcaccgccaagcggatgagagtgaaggcctaccgggtggacaagtcccccctacaaccagagcatgtac
tacgccggcctgcccgtggacgatttcgaggatagcgagagcaccgacaccgaggaagagttcggcaa
cgccatcggcggatctcacggcggcagcagctacaccgtgtacatcgacaagaccagataatctagac
gcggccgcatacagcagcaattggcaagctgcttacatagaactcgcggcgattggcatgccgcctta
aaatttttattttattttttcttttcttttccgaatcggattttgtttttaatatttcaaaaaaaaaa
aaaaaaaaaaaaaaaaaaaaaaaaagggtcggcatggcatctccacctcctcgcggtccgacctgggca
tccgaaggaggacgcacgtccactcggatggctaagggagagccacgtttaaaccagctccaattcgc
cctatagtgagtcgtattacgcgcgctcactggccgtcgttttacaacgtcgtgactgggaaaaccct
ggcgttacccaacttaatcgccttgcagcacatccccctttcgccagctggcgtaatagcgaagaggc
ccgcaccgatcgcccttcccaacagttgcgcagcctgaatggcgaatgggacgcgccctgtagcggcg
cattaagcgcggcgggtgtggtggttacgcgcagcgtgaccgctacacttgccagcgccctagcgccc
gctcctttcgctttcttcccttcctttctcgccacgttcgccggctttccccgtcaagctctaaatcg
ggggctccctttagggttccgatttagtgctttacggcacctcgaccccaaaaaacttgattagggtg
atggttcacgtagtgggccatcgccctgatagacggtttttcgccctttgacgttggagtccacgttc
tttaatagtggactcttgttccaaactggaacaacactcaaccctatctcggtctattcttttgattt
ataagggattttgccgatttcggcctattggttaaaaaatgagctgatttaacaaaaatttaacgcga
attttaacaaaatattaacgcttacaatttaggtggcacttttcggggaaatgtgcgcggaacccta
tttgtttatttttctaaatacattcaaatatgtatccgctcatgagacaataaccctgataaatgctt
caataatattgaaaaaggaagagtatgagtattcaacatttccgtgtcgcccttattcccttttttgc
ggcattttgccttcctgtttttgctcacccagaaacgctggtgaaagtaaaagatgctgaagatcagt
tgggtgcacgagtgggttacatcgaactggatctcaacagcggtaagatccttgagagttttcgcccc
gaagaacgttttccaatgatgagcacttttaaagttctgctatgtggcgcggtattatcccgtattga
cgccgggcaagagcaactcggtcgccgcatacactattctcagaatgacttggttgagtactcaccag
tcacagaaaagcatcttacggatggcatgacagtaagagaattatgcagtgctgccataaccatgagt
gataacactgcggccaacttacttctgacaacgatcggaggaccgaaggagctaaccgcttttttgca
caacatgggggatcatgtaactcgccttgatcgttgggaaccggagctgaatgaagccataccaaacg
acgagcgtgacaccacgatgcctgtagcaatggcaacaacgttgcgcaaactattaactggcgaacta
cttactctagcttcccggcaacaattaatagactggatggaggcggataaagttgcaggaccacttct
gcgctcggcccttccggctggctggtttattgctgataaatctggagccggtgagcgtgggtctcgcg
gtatcattgcagcactggggccagatggtaagccctcccgtatcgtagttatctacacgacggggagt
caggcaactatggatgaacgaaatagacagatcgctgagataggtgcctcactgattaagcattggta
actgtcagaccaagtttactcatatatactttagattgatttaaaacttcatttttaatttaaaagga
tctaggtgaagatcctttttgataatctcatgaccaaaatcccttaacgtgagttttcgttccactga
gcgtcagaccccgtagaaaagatcaaaggatcttcttgagatcctttttttctgcgcgtaatctgctg
cttgcaaacaaaaaaaccaccgctaccagcggtggtttgtttgccggatcaagagctaccaactcttt
ttccgaaggtaactggcttcagcagagcgcagataccaaatactgttcttctagtgtagccgtagtta
ggccaccacttcaagaactctgtagcaccgcctacatacctcgctctgctaatcctgttaccagtggc
tgctgccagtggcgataagtcgtgtcttaccgggttggactcaagacgatagttaccggataaggcgc
agcggtcgggctgaacggggggttcgtgcacacagcccagcttggagcgaacgacctacaccgaactg
agatacctacagcgtgagctatgagaaagcgccacgcttcccgaagggagaaaggcggacaggtatcc
ggtaagcggcagggtcggaacaggagagcgcacgagggagcttccagggggaaacgcctggtatcttt
atagtcctgtcgggtttcgccacctctgacttgagcgtcgatttttgtgatgctcgtcaggggggcgg
agcctatggaaaaacgccagcaacgcggcctttttacggttcctggccttttgctggccttttgctca
catgttctttcctgcgttatcccctgattctgtggataaccgtattaccgcctttgagtgagctgata
ccgctcgccgcagccgaacgaccgagcgcagcgagtcagtgagcgaggaagcggaagagcgcccaata
cgcaaaccgcctctccccgcgcgttggccgattcattaatgcagctggcacgacaggtttcccgactg
gaaagcgggcagtgagcgcaacgcaattaatgtgagttagctcactcattaggcaccccaggctttac
actttatgctcccggctcgtatgttgtgtggaattgtgagcggataacaatttcacacaggaaacagc
tatgaccatgattacgccaagcgcgcaattaaccctcactaaagggaacaaaagctgggtaccgggcc
cacgcgtaatacgactcactatag_12604

VZV VEERep.SGPgI (SEQ ID NO: 78)
1_
ataggcggcgcatgagagaagcccagaccaattacctacccaaaatggagaaagttcacgttgacatc
gaggaagacagcccattcctcagagctttgcagcggagcttcccgcagtttgaggtagaagccaagca
ggtcactgataatgaccatgctaatgccagagcgttttcgcatctggcttcaaaactgatcgaaacgg
aggtggacccatccgacacgatccttgacattggaagtgcgcccgcccgcagaatgtattctaagcac
aagtatcattgtatctgtccgatgagatgtgcggaagatccggacagattgtataagtatgcaactaa
gctgaagaaaaactgtaaggaaataactgataaggaattggacaagaaaatgaaggagctcgccgccg
tcatgagcgaccctgacctggaaactgagactatgtgcctccacgacgacgagtcgtgtcgctacgaa
gggcaagtcgctgtttaccaggatgtatacgcggttgacggaccgacaagtctctatcaccaagccaa
taagggagttagagtcgcctactggataggctttgacaccacccctttatgtttaagaacttggctg
gagcatatccatcatactctaccaactgggccgacgaaaccgtgttaacggctcgtaacataggccta
tgcagctctgacgttatggagcggtcacgtagagggatgtccattcttagaaagaagtatttgaaacc
atccaacaatgttctattctctgttggctcgaccatctaccacgagaagagggacttactgaggagct
ggcacctgccgtctctgtatttcacttacgtggcaagcaaaattacacatgtcggtgtgagactatagtt
agttgcgacgggtacgtcgttaaaagaatagctatcagtccaggcctgtatgggaagccttcaggcta
tgctgctacgatgcaccgcgagggattcttgtgctgcaaagtgacagacacattgaacggggagaggg
tctcttttcccgtgtgcacgtatgtgccagctacattgtgtgaccaaatgactggcatactggcaaca
gatgtcagtgcggacgacgcgcaaaaactgctggttgggctcaaccagcgtatagtcgtcaacggtcg
cacccagagaaacaccaataccatgaaaaattacctttgcccgtagtggcccaggcatttgctaggt
gggcaaaggaatataaggaagatcaagaagatgaaaggccactaggactacgagatagacagttagtc -continued

| SEQUENCES |
| --- |
| atggggtgttgttgggcttttagaaggcacaagataacatctatttataagcgcccggatacccaaac<br>catcatcaaagtgaacagcgatttccactcattcgtgctgcccaggataggcagtaacacattggaga<br>tcgggctgagaacaagaatcaggaaaatgttagaggagcacaaggagccgtcacctctcattaccgcc<br>gaggacgtacaagaagctaagtgcgcagccgatgaggctaaggaggtgcgtgaagccgaggagttgcg<br>cgcagctctaccacctttggcagctgatgttgaggagcccactctggaagccgatgtagacttgatgt<br>tacaagaggctggggccggctcagtggagacacctcgtggcttgataaaggttaccagctacgatggc<br>gaggacaagatcggctcttacgctgtgctttctccgcaggctgtactcaagagtgaaaaattatcttg<br>catccaccctctcgctgaacaagtcatagtgataacacactctggccgaaaagggcgttatgccgtgg<br>aaccataccatggtaaagtagtggtgccagagggacatgcaatacccgtccaggactttcaagctctg<br>agtgaaagtgccaccattgtgtacaacgaacgtgagttcgtaaacaggtacctgcaccatattgccac<br>acatggaggagcgctgaacactgatgaagaatattacaaaactgtcaagcccagcgagcacgacggcg<br>aatacctgtacgacatcgacaggaaacagtgcgtcaagaaagaactagtcactgggctagggctcaca<br>ggcgagctggtggatcctcccttccatgaattcgcctacgagagtctgagaacacgaccagccgctcc<br>ttaccaagtaccaaccataggggtgtatggcgtgccaggatcaggcaagtctggcatcattaaaagcg<br>cagtcaccaaaaaagatctagtggtgagcgccaagaaagaaaactgtgcagaaattataagggacgtc<br>aagaaaatgaaagggctggacgtcaatgccagaactgtggactcagtgctcttgaatggatgcaaaca<br>ccccgtagagaccctgtatattgacgaagcttttgcttgtcatgcaggtactctcagagcgctcatag<br>ccattataagacctaaaaaggcagtgctctgcggggatcccaaacagtgcggtttttttaacatgatg<br>tgcctgaaagtgcattttaaccacgagatttgcacacaagtcttccacaaaagcatctctcgccgttg<br>cactaaatctgtgacttcggtcgtctcaaccttgttttacgacaaaaaaatgagaacgacgaatccga<br>aagagactaagattgtgattgacactaccggcagtaccaaacctaagcaggacgatctcattctcact<br>tgtttcagagggtgggtgaagcagttgcaaatagattacaaaggcaacgaaataatgacggcagctgc<br>ctctcaagggctgacccgtaaaggtgtgtatgccgttcggtacaaggtgaatgaaaatcctctgtacg<br>cacccacctcagaacatgtgaacgtcctactgacccgcacggaggaccgcatcgtgtggaaaacacta<br>gccggcgacccatggataaaaacactgactgccaagtaccctgggaatttcactgccacgatagagga<br>gtggcaagcagagcatgatgccatcatgaggcacatcttggagagaccggaccctaccgacgtcttcc<br>agaataaggcaaacgtgtgttgggccaaggctttagtgccggtgctgaagaccgctggcatagacatg<br>accactgaacaatggaacactgtggattattttgaaacggacaaagctcactcagcagagatagtatt<br>gaaccaactatgcgtgaggttctttggactcgatctggactccggtctattttctgcacccactgttc<br>cgttatccattaggaataatcactgggataactccccgtcgcctaacatgtacgggctgaataaagaa<br>gtggtccgtcagctctctcgcaggtacccacaactgcctcgggcagttgccactggaagagtctatga<br>catgaacactggtacactgcgcaattatgatccgcgcataaacctagtacctgtaaacagaagactgc<br>ctcatgctttagtcctccaccataatgaacacccacagagtgactttttcttcattcgtcagcaaattg<br>aagggcagaactgtcctggtggtcggggaaaagttgtccgtcccaggcaaaatggttgactggttgtc<br>agaccggcctgaggctaccttcagagctcggctggatttaggcatcccaggtgatgtgcccaaatatg<br>acataatatttgttaatgtgaggaccccatataaataccatcactatcagcagtgtgaagaccatgcc<br>attaagcttagcatgttgaccaagaaagcttgtctgcatctgaatcccggcggaacctgtgtcagcat<br>aggttatggttacgctgacagggccagcgaaagcatcattggtgctatagcgcggcagttcaagtttt<br>cccgggtatgcaaaccgaaatcctcacttgaagagacggaagttctgtttgtattcattgggtacgat<br>cgcaaggcccgtacgcacaatccttacaagctttcatcaaccttgaccaacatttatacaggttccag<br>actccacgaagccggatgtgcaccctcatatcatgtggtgcgaggggatattgccacggccaccgaag<br>gagtgattataaatgctgctaacagcaaaggacaacctggcggagggggtgtgcggagcgctgtataag<br>aaattcccggaaagcttcgatttacagccgatcgaagtaggaaaagcgcgactggtcaaaggtgcagc<br>taaacatatcattcatgccgtaggaccaaacttcaacaaagtttcggaggttgaaggtgacaaacagt<br>tggcagaggcttatgagtccatcgctaagattgtcaacgataacaattacaagtcagtagcgattcca<br>ctgttgtccaccggcatcttttccgggaacaaagatcgactaacccaatcattgaaccatttgctgac<br>agctttagacaccactgatgcagatgtagccatatactgcagggacaagaaatgggaaatgactctca<br>aggaagcagtggctaggagagaagcagtggaggagatatgcatatccgacgactcttcagtgacagaa<br>cctgatgcagagctggtgagggtgcatccgaagagttctttggctggaaggaagggctacagcacaag<br>cgatggcaaaactttctcatatttggaagggaccaagtttcaccaggcggccaaggatatagcagaaa<br>ttaatgccatgtggcccgttgcaacggaggccaatgagcaggtatgcatgtatatcctcggagaaagc<br>atgagcagtattaggtcgaaatgccccgtcgaagagtcggaagcctccacaccacctagcacgctgcc<br>ttgcttgtgcatccatgccatgactccagaaagagtacagcgcctaaaagcctcacgtccagaacaaa<br>ttactgtgtgctcatcctttccattgccgaagtatagaatcactggtgtgcagaagatccaatgctcc<br>cagcctatattgttctcaccgaaagtgcctgcgtatattcatccaaggaagtatctcgtggaaacacc<br>accggtagacgagactccggagccatcggcagagaaccaatccacagaggggacacctgaacaaccac<br>cacttataaccgaggatgagaccaggactagaacgcctgagccgatcatcatcgaagaggaagaagag<br>gatagcataagtttgctgtcagatggcccgacccaccaggtgctgcaagtcgaggcagacattcacgg<br>gccgccctctgtatctagctcatcctggtccattcctcatgcatccgactttgatgtggacagtttat<br>ccatacttgacaccctggagggagctagcgtgaccagcggggcaacgtcagccgagactaactcttac<br>ttcgcaaagagtatggagtttctggcgcgaccggtgcctgcgcctcgaacagtattcaggaaccctcc<br>acatcccgctccgcgcacaagaacaccgtcacttgcacccagcagggcctgctcgagaaccagcctag<br>tttccaccccgccaggcgtgaatagggtgatcactagagaggagctcgaggcgcttaccccgtcacgc<br>actcctagcaggtcggtctcgagaaccagcctggtctccaacccgccaggcgtaaatagggtgattac<br>aagagaggagtttgaggcgttcgtagcacaacaacaatgacggtttgatgcgggtgcatacatctttt<br>cctccgacaccggtcaagggcatttacaacaaaaatcagtaaggcaaacggtgctatccgaagtggtg<br>ttggagaggaccgaattggagatttcgtatgccccgcgcctcgaccaagaaaaagaagaattactacg<br>caagaaattacagttaaatcccacacctgctaacagaagcagataccagtccaggaaggtggagaaca<br>tgaaagccataacagctagacgtattctgcaaggcctagggcattatttgaaggcagaaggaaaagtg<br>gagtgctaccgaaccctgcatcctgttcctttgtattcatctagtgtgaaccgtgccttttcaagccc<br>caaggtcgcagtggaagcctgtaacgccatgttgaaagagaactttccgactgtggcttcttactgta<br>ttattccagagtacgatgcctatttggacatggttgacggagcttcatgctgcttagacactgccagt<br>ttttgccctgcaaagctgcgcagctttccaaagaaacactcctatttggaacccacaatacgatcggc<br>agtgccttcagcgatccagaacacgctccagaacgtcctggcagctgccacaaaaagaaattgcaatg<br>tcacgcaaatgagagaattgcccgtattggattcggcggcctttaatgtggaatgcttcaagaaatat<br>gcgtgtaataatgaatattgggaaacgtttaaagaaaaccccatcaggcttactgaagaaaacgtggt<br>aaattacattaccaaattaaaaggaccaaaagctgctgctctttttgcgaagacacataatttgaata |

-continued

| SEQUENCES |
|---|
| tgttgcaggacataccaatggacaggtttgtaatggacttaaagagagacgtgaaagtgactccagga<br>acaaaacatactgaagaacggcccaaggtacaggtgatccaggctgccgatccgctagcaacagcgta<br>tctgtgcggaatccaccgagagctggttaggagattaaatgcggtcctgcttccgaacattcatacac<br>tgtttgatatgtcggctgaagactttgacgctattatagccgagcacttccagcctggggattgtgtt<br>ctggaaactgacatcgcgtcgtttgataaaagtgaggacgacgccatggctctgaccgcgttaatgat<br>tctggaagacttaggtgtggacgcagagctgttgacgctgattgaggcggctttcggcgaaatttcat<br>caatacatttgcccactaaaactaaatttaaattcggagccatgatgaaatctggaatgttcctcaca<br>ctgtttgtgaacacagtcattaacattgtaatcgcaagcagagtgttgagagaacggctaaccggatc<br>accatgtgcagcattcattggagatgacaatatcgtgaaaggagtcaaatcggacaaattaatggcag<br>acaggtgcgccacctggttgaatatggaagtcaagattatagatgctgtggtgggcgagaaagcgcct<br>tatttctgtggagggtttattttgtgtgactccgtgaccggcacagcgtgccgtgtggcagacccccct<br>aaaaaggctgtttaagcttggcaaacctctggcagcagacgatgaacatgatgatgacaggagaaggg<br>cattgcatgaagagtcaacacgctggaaccgagtgggtattctttcagagctgtgcaaggcagtagaa<br>tcaaggtatgaaaccgtaggaacttccatcatagttatggccatgactactctagctagcagtgttaa<br>atcattcagctacctgagaggggcccctataactctctacggctaacctgaatggactacgacatagt<br>ctagtcgagtctagtcgacgccaccatgtttctgatccagtgcctgatcagcgccgtgatcttctata<br>ttcaagtcacaaacgccctgatctttaagggcgaccacgtgtcactgcaggtcaacagcagcctgacc<br>agcatcctgatccccatgcagaacgacaattacaccgagatcaagggccagctggtgttcatcggcga<br>gcagctgcccaccggcaccaattacagcggcaccctggaactgctgtacgccgataccgtggccttct<br>gcttcagaagcgtgcaggtcatcagatacgacggctgcccccggatcagaaccagcgccttcatcagc<br>tgccggtacaagcacagctggcactacggcaacagcaccgaccggatcagcaccgaacctgatgccgg<br>cgtgatgctgaagatcaccaagcccggcatcaacgacgccggcgtgtacgtgctgctcgtgcggctgg<br>atcacagcagaagcaccgacggcttcatcctgggcgtgaacgtgtacaccgccggcagccaccacaac<br>atccacggcgtgatctacaccagccccagcctgcagaacggctacagcaccagagccctgttccagca<br>ggccagactgtgcgatctgcccgccacacctaagggcagcggcacaagcctgtttcagcacatgctgg<br>acctgagagccggcaagagcctggaagataacccctggctgcacgaggacgtggtcaccaccgagaca<br>aagagcgtggtcaaagagggcatcgagaaccacgtgtaccccaccgacatgagcaccctgcccgagaa<br>gtccctgaacgacccccctgagaacctgctgatcatcatccccatcgtggccagcgtgatgatcctga<br>ccgccatggtcatcgtgatcgtgatcagcgtgaagcggcggagaatcaagaagcaccccatctaccgg<br>cccaacaccaagaccagacggggcatccagaacgccacccctgagtccgacgtgatgctggaagccgc<br>cattgcccagctggccaccatcagagaggaaagccccccctcacagcgtcgtgaaccccttcgtgaagt<br>aatctagacgcggccgcatacagcagcaattggcaagctgcttacatagaactcgcggcgattggcat<br>gccgccttaaaatttttattttattttttcttttcttttccgaatcggattttgtttttaatatttcaa<br>aaaaaaaaaaaaaaaaaaaaaaaaaaaaaaaagggtcggcatggcatctccacctcctcgcggtccg<br>acctgggcatccgaaggaggacgcacgtccactcggatggctaagggagagccacgtttaaaccagct<br>ccaattcgccctatagtgagtcgtattacgcgcgctcactggccgtcgttttacaacgtcgtgactgg<br>gaaaaccctggcgttacccaacttaatcgccttgcagcacatccccctttcgccagctggcgtaatag<br>cgaagaggcccgcaccgatcgcccttcccaacagttgcgcagcctgaatggcgaatgggacgcgccct<br>gtagcggcgcattaagcgcggcgggtgtggtggttacgcgcagcgtgaccgctacacttgccagcgcc<br>ctagcgcccgctcctttcgctttcttcccttcctttctcgccacgttcgccggctttccccgtcaagc<br>tctaaatcgggggctccctttagggttccgatttagtgctttacggcacctcgaccccaaaaaacttg<br>attagggtgatggttcacgtagtgggccatcgccctgatagacggtttttcgccctttgacgttggag<br>tccacgttctttaatagtggactcttgttccaaactggaacaacactcaaccctatctcggtctattc<br>ttttgatttataagggattttgccgatttcggcctattggttaaaaaatgagctgatttaacaaaaat<br>ttaacgcgaattttaacaaaatattaacgcttacaatttaggtggcacttttcggggaaatgtgcgcg<br>gaacccctatttgtttatttttctaaatacattcaaatatgtatccgctcatgagacaataaccctga<br>taaatgcttcaataatattgaaaaaggaagagtatgagtattcaacatttccgtgtcgcccttattcc<br>cttttttgcggcattttgccttcctgtttttgctcacccagaaacgctggtgaaagtaaaagatgctg<br>aagatcagttgggtgcacgagtgggttacatcgaactggatctcaacagcggtaagatccttgagagt<br>tttcgccccgaagaacgttttccaatgatgagcacttttaaagttctgctatgtggcgcggtattatc<br>ccgtattgacgccgggcaagagcaactcggtcgccgcatacactattctcagaatgacttggttgagt<br>actcaccagtcacagaaaagcatcttacggatggcatgacagtaagagaattatgcagtgctgccata<br>accatgagtgataacactgcggccaacttacttctgacaacgatcggaggaccgaaggagctaaccgc<br>ttttttgcacaacatgggggatcatgtaactcgccttgatcgttgggaaccggagctgaatgaagcca<br>taccaaacgacgagcgtgacaccacgatgcctgtagcaatggcaacaacgttgcgcaaactattaact<br>ggcgaactacttactctagcttcccggcaacaattaatagactggatggaggcggataaagttgcagg<br>accacttctgcgctcggcccttccggctggctggtttattgctgataaatctggagccggtgagcgtg<br>ggtctcgcggtatcattgcagcactggggccagatggtaagccctcccgtatcgtagttatctacacg<br>acggggagtcaggcaactatggatgaacgaaatagacagatcgctgagataggtgcctcactgattaa<br>gcattggtaactgtcagaccaagtttactcatatatactttagattgatttaaaacttcatttttaat<br>ttaaaaggatctaggtgaagatcctttttgataatctcatgaccaaaatcccttaacgtgagttttcg<br>ttccactgagcgtcagaccccgtagaaaagatcaaaggatcttcttgagatcctttttttctgcgcgt<br>aatctgctgcttgcaaacaaaaaaaccaccgctaccagcggtggtttgtttgccggatcaagagctac<br>caactctttttccgaaggtaactggcttcagcagagcgcagataccaaatactgttcttctagtgtag<br>ccgtagttaggccaccacttcaagaactctgtagcaccgcctacatacctcgctctgctaatcctgtt<br>accagtggctgctgccagtggcgataagtcgtgtcttaccgggttggactcaagacgatagttaccgg<br>ataaggcgcagcggtcgggctgaacggggggttcgtgcacacagcccagcttggagcgaacgacctac<br>accgaactgagatacctacagcgtgagctatgagaaagcgccacgcttcccgaagggagaaaggcgga<br>caggtatccggtaagcggcagggtcggaacaggagagcgcacgagggagcttccagggggaaacgcct<br>ggtatctttatagtcctgtcgggtttcgccacctctgacttgagcgtcgatttttgtgatgctcgtca<br>ggggggcggagcctatggaaaaacgccagcaacgcggcctttttacggttcctggccttttgctggcc<br>ttttgctcacatgttctttcctgcgttatcccctgattctgtggataaccgtattaccgcctttgagt<br>gagctgataccgctcgccgcagccgaacgaccgagcgcagcgagtcagtgagcgaggaagcggaagag<br>cgcccaatacgcaaaccgcctctccccgcgcgttggccgattcattaatgcagctggcacgacaggtt<br>tcccgactggaaagcgggcagtgagcgcaacgcaattaatgtgagttagctcactcattaggcacccc<br>aggctttacactttatgctcccggctcgtatgttgtgtggaattgtgagcggataacaatttcacaca |

-continued

SEQUENCES ggaaacagctatgaccatgattacgccaagcgcgcaattaaccctcactaaagggaacaaaagctggg
taccgggccccacgcgtaatacgactcactatag_11797

VZV VEErep.SGPgE-SGPgI (SEQ ID NO: 79):
1_
ataggcggcgcatgagagaagcccagaccaattacctacccaaaatggagaaagttcacgttgacatc
gaggaagacagcccattcctcagagctttgcagcggagcttcccgcagtttgaggtagaagccaagca
ggtcactgataatgaccatgctaatgccagagcgttttcgcatctggcttcaaaactgatcgaaacgg
aggtggacccatccgacacgatccttgacattggaagtgcgcccgcccgcagaatgtattctaagcac
aagtatcattgtatctgtccgatgagatgtgcggaagatccggacagattgtataagtatgcaactaa
gctgaagaaaaactgtaaggaaataactgataaggaattggacaagaaaatgaaggagctcgccgccg
tcatgagcgaccctgacctggaaactgagactatgtgcctccacgacgacgagtcgtgtcgctacgaa
gggcaagtcgctgtttaccaggatgtatacgcggttgacggaccgacaagtctctatcaccaagccaa
taagggagttagagtcgcctactggataggctttgacaccaccccttttatgtttaagaacttggctg
gagcatatccatcatactctaccaactgggccgacgaaaccgtgttaacggctcgtaacataggccta
tgcagctctgacgttatggagcggtcacgtagagggatgtccattcttagaaagaagtatttgaaacc
atccaacaatgttctattctctgttggctcgaccatctaccacgagaagagggacttactgaggagct
ggcacctgccgtctgtatttcacttacgtggcaagcaaaattacacatgtcggtgtgagactatagtt
agttgcgacgggtacgtcgttaaaagaatagctatcagtccaggcctgtatgggaagccttcaggcta
tgctgctacgatgcaccgcgagggattcttgtgctgcaaagtgacagacacattgaacggggagaggg
tctcttttcccgtgtgcacgtatgtgccagctacattgtgtgaccaaatgactggcatactggcaaca
gatgtcagtgcggacgacgcgcaaaaactgctggttgggctcaaccagcgtatagtcgtcaacggtcg
cacccagagaaacaccaataccatgaaaaattaccttttgcccgtagtggcccaggcatttgctaggt
gggcaaaggaatataaggaagatcaagaagatgaaaggccactaggactacgagatagacagttagtc
atggggtgttgttgggcttttagaaggcacaagataacatctatttataagcgcccggatacccaaac
catcatcaaagtgaacagcgatttccactcattcgtgctgcccaggataggcagtaacacattggaga
tcgggctgagaacaagaatcaggaaaatgttagaggagcacaaggagccgtcacctctcattaccgcc
gaggacgtacaagaagctaagtgcgcagccgatgaggctaaggaggtgcgtgaagccgaggagttgcg
cgcagctctaccacctttggcagctgatgttgaggagcccactctggaagccgatgtagacttgatgt
tacaagaggctggggccggctcagtggagacacctcgtggcttgataaaggttaccagctacgatggc
gaggacaagatcggctcttacgctgtgctttctccgcaggctgtactcaagagtgaaaaattatcttg
catccaccctctcgctgaacaagtcatagtgataacacactctggccgaaaagggcgttatgccgtgg
aaccataccatggtaaagtagtggtgccagagggacatgcaatacccgtccaggactttcaagctctg
agtgaaagtgccaccattgtgtacaacgaacgtgagttcgtaaacaggtacctgcaccatattgccac
acatggaggagcgctgaacactgatgaagaatattacaaaactgtcaagcccagcgagcacgacggcg
aatacctgtacgacatcgacaggaaacagtgcgtcaagaaagaactagtcactgggctagggctcaca
ggcgagctggtggatcctcccttccatgaattcgcctacgagagtctgagaacacgaccagccgctcc
ttaccaagtaccaaccataggggtgtatggcgtgccaggatcaggcaagtctggcatcattaaaagcg
cagtcaccaaaaaagatctagtggtgagcgccaagaaagaaaactgtgcagaaattataagggacgtc
aagaaaatgaaagggctggacgtcaatgccagaactgtggactcagtgctcttgaatggatgcaaaca
ccccgtagagaccctgtatattgacgaagcttttgcttgtcatgcaggtactctcagagcgctcatag
ccattataagacctaaaaaggcagtgctctgcggggatcccaaacagtgcggtttttttaacatgatg
tgcctgaaagtgcattttaaccacgagatttgcacacaagtcttccacaaaagcatctctcgccgttg
cactaaatctgtgacttcggtcgtctcaaccttgttttacgacaaaaaaatgagaacgacgaatccga
aagagactaagattgtgattgacactaccggcagtaccaaacctaagcaggacgatctcattctcact
tgtttcagagggtgggtgaagcagttgcaaatagattacaaaggcaacgaaataatgacggcagctgc
ctctcaagggctgacccgtaaaggtgtgtatgccgttcggtacaaggtgaatgaaaatcctctgtacg
cacccacctcagaacatgtgaacgtcctactgacccgcacggaggaccgcatcgtgtggaaaacacta
gccggcgacccatggataaaaacactgactgccaagtaccctgggaatttcactgccacgatagagga
gtggcaagcagagcatgatgccatcatgaggcacatcttggagagaccggaccctaccgacgtcttcc
agaataaggcaaacgtgtgttgggccaaggctttagtgccggtgctgaagaccgctggcatagacatg
accactgaacaatggaacactgtggattattttgaaacggacaaagctcactcagcagagatagtatt
gaaccaactatgcgtgaggttctttggactcgatctggactccggtctattttctgcacccactgttc
cgttatccattaggaataatcactgggataactccccgtcgcctaacatgtacgggctgaataaagaa
gtggtccgtcagctctctcgcaggtacccacaactgcctcgggcagttgccactggaagagtctatga
catgaacactggtacactgcgcaattatgatccgcgcataaacctagtacctgtaaacagaagactgc
ctcatgctttagtcctccaccataatgaacacccacagagtgacttttcttcattcgtcagcaaattg
aagggcagaactgtcctggtggtcggggaaaagttgtccgtcccaggcaaaatggttgactggttgtc
agaccggcctgaggctaccttcagagctcggctggatttaggcatcccaggtgatgtgcccaaatatg
acataatatttgttaatgtgaggaccccatataaataccatcactatcagcagtgtgaagaccatgcc
attaagcttagcatgttgaccaagaaagcttgtctgcatctgaatcccggcggaacctgtgtcagcat
aggttatggttacgctgacagggccagcgaaagcatcattggtgctatagcgcggcagttcaagtttt
cccgggtatgcaaaccgaaatcctcacttgaagagacggaagttctgtttgtattcattgggtacgat
cgcaaggcccgtacgcacaatccttacaagctttcatcaaccttgaccaacatttatacaggttccag
actccacgaagccggatgtgcaccctcatatcatgtggtgcgaggggatattgccacggccaccgaag
gagtgattataaatgctgctaacagcaaaggacaacctggcggaggggtgtgcggagcgctgtataag
aaattcccggaaagcttcgatttacagccgatcgaagtaggaaaagcgcgactggtcaaaggtgcagc
taaacatatcattcatgccgtaggaccaaacttcaacaaagtttcggaggttgaaggtgacaaacagt
tggcagaggcttatgagtccatcgctaagattgtcaacgataacaattacaagtcagtagcgattcca
ctgttgtccaccggcatcttttccgggaacaaagatcgactaacccaatcattgaaccatttgctgac
agctttagacaccactgatgcagatgtagccatatactgcagggacaagaaatgggaaatgactctca
aggaagcagtggctaggagagaagcagtggaggagatatgcatatccgacgactcttcagtgacagaa
cctgatgcagagctggtgagggtgcatccgaagagttctttggctggaaggaagggctacagcacaag
cgatggcaaaactttctcatatttggaagggaccaagtttcaccaggcggccaaggatatagcagaaa
ttaatgccatgtggcccgttgcaacggaggccaatgagcaggtatgcatgtatatcctcggagaaagc
atgagcagtattaggtcgaaatgccccgtcgaagagtcggaagcctccacaccacctagcacgctgcc
ttgcttgtgcatccatgccatgactccagaaagagtacagcgcctaaaagcctcacgtccagaacaaa -continued

| SEQUENCES |
| --- |
| ttactgtgtgctcatcctttccattgccgaagtatagaatcactggtgtgcagaagatccaatgctcc<br>cagcctatattgttctcaccgaaagtgcctgcgtatattcatccaaggaagtatctcgtggaaacacc<br>accggtagacgagactccggagccatcggcagagaaccaatccacagaggggacacctgaacaaccac<br>cacttataaccgaggatgagaccaggactagaacgcctgagccgatcatcatcgaagaggaagaagag<br>gatagcataagtttgctgtcagatggcccgacccaccaggtgctgcaagtcgaggcagacattcacgg<br>gccgccctctgtatctagctcatcctggtccattcctcatgcatccgactttgatgtggacagtttat<br>ccatacttgacaccctggagggagctagcgtgaccagcggggcaacgtcagccgagactaactcttac<br>ttcgcaaagagtatggagtttctggcgcgaccggtgcctgcgcctcgaacagtattcaggaaccctcc<br>acatcccgctccgcgcacaagaacaccgtcacttgcacccagcagggcctgctcgagaaccagcctag<br>tttccaccccgccaggcgtgaatagggtgatcactagagaggagctcgaggcgcttaccccgtcacgc<br>actcctagcaggtcggtctcgagaaccagcctggtctccaacccgccaggcgtaaatagggtgattac<br>aagagaggagtttgaggcgttcgtagcacaacaacaatgacggtttgatgcgggtgcatacatctttt<br>cctccgacaccggtcaagggcatttacaacaaaaatcagtaaggcaaacggtgctatccgaagtggtg<br>ttggagaggaccgaattggagatttcgtatgccccgcgcctcgaccaagaaaaagaagaattactacg<br>caagaaattacagttaaatcccacacctgctaacagaagcagataccagtccaggaaggtggagaaca<br>tgaaagccataacagctagacgtattctgcaaggcctagggcattatttgaaggcagaaggaaaagtg<br>gagtgctaccgaaccctgcatcctgttcctttgtattcatctagtgtgaaccgtgccttttcaagccc<br>caaggtcgcagtggaagcctgtaacgccatgttgaaagagaactttccgactgtggcttcttactgta<br>ttattccagagtacgatgcctatttggacatggttgacggagcttcatgctgcttagacactgccagt<br>ttttgccctgcaaagctgcgcagctttccaaagaaacactcctatttggaacccacaatacgatcggc<br>agtgccttcagcgatccagaacacgctccagaacgtcctggcagctgccacaaaaagaaattgcaatg<br>tcacgcaaatgagagaattgcccgtattggattcggcggcctttaatgtggaatgcttcaagaaatat<br>gcgtgtaataatgaatattgggaaacgtttaaagaaaaccccatcaggcttactgaagaaaacgtggt<br>aaattacattaccaaattaaaaggaccaaaagctgctgctctttttgcgaagacacataatttgaata<br>tgttgcaggacataccaatggacaggtttgtaatggacttaaagagagacgtgaaagtgactccagga<br>acaaaacatactgaagaacggcccaaggtacaggtgatccaggctgccgatccgctagcaacagcgta<br>tctgtgcggaatccaccgagagctggttaggagattaaatgcggtcctgcttccgaacattcatacac<br>tgtttgatatgtcggctgaagactttgacgctattatagccgagcacttccagcctggggattgtgtt<br>ctggaaactgacatcgcgtcgtttgataaaagtgaggacgacgccatggctctgaccgcgttaatgat<br>tctggaagacttaggtgtggacgcagagctgttgacgctgattgaggcggctttcggcgaaatttcat<br>caatacatttgcccactaaaactaaatttaaattcggagccatgatgaaatctggaatgttcctcaca<br>ctgtttgtgaacacagtcattaacattgtaatcgcaagcagagtgttgagagaacggctaaccggatc<br>accatgtgcagcattcattggagatgacaatatcgtgaaaggagtcaaatcggacaaattaatggcag<br>acaggtgcgccacctggttgaatatggaagtcaagattatagatgctgtggtgggcgagaaagcgcct<br>tatttctgtggagggtttattttgtgtgactccgtgaccggcacagcgtgccgtgtggcagacccccct<br>aaaaaggctgtttaagcttggcaaacctctggcagcagacgatgaacatgatgatgacaggagaaggg<br>cattgcatgaagagtcaacacgctggaaccgagtgggtattctttcagagctgtgcaaggcagtagaa<br>tcaaggtatgaaaccgtaggaacttccatcatagttatggccatgactactctagctagcagtgttaa<br>atcattcagctacctgagaggggcccctataactctctacggctaacctgaatggactacgacatagt<br>ctagtcgagtctagtcgacgccaccatgggcaccgtgaacaagcctgtcgtgggcgtgctgatgggct<br>tcggcatcatcaccggcaccctgagaatcaccaaccctgtgcgggccagcgtgctgagatacgacgac<br>ttccacatcgacgaggacaagctggacaccaacagcgtgtacgagccctactaccacagcgaccacgc<br>cgagagcagctgggtcaacagaggcgagagcagccggaaggcctacgaccacaacagcccctacatct<br>ggccccggaacgactacgacggcttcctggaaaacgcccacgagcaccacggcgtgtacaatcagggc<br>agaggcatcgacagcggcgagagactgatgcagcccacacagatgagcgcccaggaagatctgggcga<br>cgacacaggcatccacgtgatccccaccctgaacggcgacgaccggcacaagatcgtgaacgtggacc<br>agcggcagtacggcgacgtgttcaagggcgacctgaaccctaagccccagggccagagactgatcgag<br>gtgtccgtggaagagaaccaccccttcaccctgagagcccccatccagagaatctacggcgtgcggta<br>taccgagacttggagcttcctgcccagcctgacctgtacaggcgacgccgctcctgccatccagcaca<br>tctgcctgaagcacaccacctgtttccaggacgtggtggtggacgtggactgcgccgagaacaccaaa<br>gaggaccagctggccgagatcagctaccggttccagggcaagaaagaggccgaccagccctggatcgt<br>ggtcaataccagcaccctgttcgacgagctggaactggacccccccgagattgaacccggcgtgctga<br>aggtgctgcggaccgagaagcagtacctgggcgtgtacatctggaacatgcggggctccgacggcacc<br>tctacctacgccaccttcctggtcacatggaagggcgacgagaaaacccggaaccctaccccctgccgt<br>gacccctcagcctagaggcgccgagttccatatgtggaattaccactcccacgtgttcagcgtgggcg<br>acaccttcagcctggccatgcatctgcagtacaagatccacgaggccccccttcgacctgctgctggaa<br>tggctgtacgtgcccatcgaccctacctgccagcccatgcggctgtacagcacctgtctgtaccaccc<br>caacgcccctcagtgcctgagccacatgaacagcggctgcaccttcaccagccctcacctggctcaga<br>gggtggccagcaccgtgtaccagaattgcgagcacgccgacaactacaccgcctactgcctgggcatc<br>agccacatggaacccagcttcggcctgatcctgcacgatggcggcaccaccctgaagttcgtggacac<br>acccgagagcctgagcggcctgtacgtgttcgtggtgtacttcaacggccacgtggaagccgtggcct<br>acaccgtggtgtccaccgtggaccacttcgtgaacgccatcgaggaaagaggcttcccacccacagcc<br>ggacagcctccagccaccaccaagcccaaagaaatcaccccccgtgaaccccggcaccagccccctgct<br>gagatatgctgcttggacaggcggactggccgctgtggtgctgctgtgcctggtcatcttcctgatct<br>gcaccgccaagcggatgagagtgaaggcctaccgggtggacaagtcccccctacaaccagagcatgtac<br>tacgccggcctgcccgtggacgatttcgaggatagcgagagcaccgacaccgaggaagagttcggcaa<br>cgccatcggcggatctcacggcggcagcagctacaccgtgtacatcgacaagaccagataatctagac<br>gtcgcgaccacccaggatccgcctataactctctacggctaacctgaatggactacgacatagtctag<br>tcgacgccaccatgtttctgatccagtgcctgatcagcgccgtgatcttctatattcaagtcacaaac<br>gccctgatctttaagggcgaccacgtgtcactgcaggtcaacagcagcctgaccagcatcctgatccc<br>catgcagaacgacaattacaccgagatcaagggccagctggtgttcatcggcgagcagctgcccaccg<br>gcaccaattacagcggcaccctggaactgctgtacgccgataccgtggccttctgcttcagaagcgtg<br>caggtcatcagatacgacggctgcccccggatcagaaccagcgccttcatcagctgccggtacaagca<br>cagctggcactacggcaacagcaccgaccggatcagcaccgaacctgatgccggcgtgatgctgaaga<br>tcaccaagcccggcatcaacgacgccggcgtgtacgtgctgctcgtgcggctggatcacagcagaagc<br>accgacggcttcatcctgggcgtgaacgtgtacaccgccggcagccaccacaacatccacggcgtgat<br>ctacaccagccccagcctgcagaacggctacagcaccagagccctgttccagcaggccagactgtgcg |

-continued

| SEQUENCES |
|---|

atctgcccgccacacctaagggcagcggcacaagcctgtttcagcacatgctggacctgagagccggc
aagagcctggaagataacccctggctgcacgaggacgtggtcaccaccgagacaaagagcgtggtcaa
agagggcatcgagaaccacgtgtaccccaccgacatgagcaccctgcccgagaagtccctgaacgacc
cccctgagaacctgctgatcatcatccccatcgtggccagcgtgatgatcctgaccgccatggtcatc
gtgatcgtgatcagcgtgaagcggcggagaatcaagaagcaccccatctaccggcccaacaccaagac
cagacggggcatccagaacgccacccctgagtccgacgtgatgctggaagccgccattgcccagctgg
ccaccatcagagaggaaagcccccctcacagcgtcgtgaaccccttcgtgaagtaatctagacgcggc
cgcatacagcagcaattggcaagctgcttacatagaactcgcggcgattggcatgccgccttaaaatt
tttattttattttcttttcttttccgaatcggattttgtttttaatatttcaaaaaaaaaaaaaaaaa
aaaaaaaaaaaaaaaaaaagggtcggcatggcatctccacctcctcgcggtccgacctgggcatccga
aggaggacgcacgtccactcggatggctaagggagagccacgtttaaaccagctccaattcgccctat
agtgagtcgtattacgcgcgctcactggccgtcgttttacaacgtcgtgactgggaaaaccctggcgt
tacccaacttaatcgccttgcagcacatccccctttcgccagctggcgtaatagcgaagaggcccgca
ccgatcgcccttcccaacagttgcgcagcctgaatggcgaatgggacgcgccctgtagcggcgcatta
agcgcggcgggtgtggtggttacgcgcagcgtgaccgctacacttgccagcgccctagcgcccgctcc
tttcgctttcttcccttcctttctcgccacgttcgccggctttccccgtcaagctctaaatcgggggc
tccctttagggttccgatttagtgctttacggcacctcgaccccaaaaaacttgattagggtgatggt
tcacgtagtgggccatcgccctgatagacggtttttcgccctttgacgttggagtccacgttctttaa
tagtggactcttgttccaaactggaacaacactcaaccctatctcggtctattcttttgatttataag
ggattttgccgatttcggcctattggttaaaaaatgagctgatttaacaaaaatttaacgcgaatttt
aacaaaatattaacgcttacaatttaggtggcacttttcggggaaatgtgcgcggaacccctatttgt
ttatttttctaaatacattcaaatatgtatccgctcatgagacaataaccctgataaatgcttcaata
atattgaaaaaggaagagtatgagtattcaacatttccgtgtcgcccttattcccttttttgcggcat
tttgccttcctgtttttgctcacccagaaacgctggtgaaagtaaaagatgctgaagatcagttgggt
gcacgagtgggttacatcgaactggatctcaacagcggtaagatccttgagagttttcgccccgaaga
acgttttccaatgatgagcacttttaaagttctgctatgtggcgcggtattatcccgtattgacgccg
ggcaagagcaactcggtcgccgcatacactattctcagaatgacttggttgagtactcaccagtcaca
gaaaagcatcttacggatggcatgacagtaagagaattatgcagtgctgccataaccatgagtgataa
cactgcggccaacttacttctgacaacgatcggaggaccgaaggagctaaccgcttttttgcacaaca
tgggggatcatgtaactcgccttgatcgttgggaaccggagctgaatgaagccataccaaacgacgag
cgtgacaccacgatgcctgtagcaatggcaacaacgttgcgcaaactattaactggcgaactacttac
tctagcttcccggcaacaattaatagactggatggaggcggataaagttgcaggaccacttctgcgct
cggcccttccggctggctggtttattgctgataaatctggagccggtgagcgtgggtctcgcggtatc
attgcagcactggggccagatggtaagccctcccgtatcgtagttatctacacgacggggagtcaggc
aactatggatgaacgaaatagacagatcgctgagataggtgcctcactgattaagcattggtaactgt
cagaccaagtttactcatatatactttagattgatttaaaacttcatttttaatttaaaaggatctag
gtgaagatcctttttgataatctcatgaccaaaatcccttaacgtgagttttcgttccactgagcgtc
agaccccgtagaaaagatcaaaggatcttcttgagatcctttttttctgcgcgtaatctgctgcttgc
aaacaaaaaaaccaccgctaccagcggtggtttgtttgccggatcaagagctaccaactctttttccg
aaggtaactggcttcagcagagcgcagataccaaatactgttcttctagtgtagccgtagttaggcca
ccacttcaagaactctgtagcaccgcctacatacctcgctctgctaatcctgttaccagtggctgctg
ccagtggcgataagtcgtgtcttaccgggttggactcaagacgatagttaccggataaggcgcagcgg
tcgggctgaacggggggttcgtgcacacagcccagcttggagcgaacgacctacaccgaactgagata
cctacagcgtgagctatgagaaagcgccacgcttcccgaagggagaaaggcggacaggtatccggtaa
gcggcagggtcggaacaggagagcgcacgagggagcttccagggggaaacgcctggtatctttatagt
cctgtcgggtttcgccacctctgacttgagcgtcgatttttgtgatgctcgtcaggggggcggagcct
atggaaaaacgccagcaacgcggcctttttacggttcctggccttttgctggccttttgctcacatgt
tctttcctgcgttatcccctgattctgtggataaccgtattaccgcctttgagtgagctgataccgct
cgccgcagccgaacgaccgagcgcagcgagtcagtgagcgaggaagcggaagagcgcccaatacgcaa
accgcctctccccgcgcgttggccgattcattaatgcagctggcacgacaggtttcccgactggaaag
cgggcagtgagcgcaacgcaattaatgtgagttagctcactcattaggcaccccaggctttacacttt
atgctcccggctcgtatgttgtgtggaattgtgagcggataacaatttcacacaggaaacagctatga
ccatgattacgccaagcgcgcaattaaccctcactaaagggaacaaaagctgggtaccgggcccacgc
gtaatacgactcactatag_13775

VEE-based replicon encoding eGFP (SEQ ID NO: 80)

```
                                                    nsP1
                                             ~~~~~~~~~~~~~~~~~~
  1    ATAGGCGGCG CATGAGAGAA GCCCAGACCA ATTACCTACC CAAAATGGAG AAAGTTCACG
                             nsP1
       ~~~~~~~~~~~~~~~~~~~~~~~~~~~~~~~~~~~~~~~~~~~~~~~~~~~~~~~~~~~~~~~~~~
 61    TTGACATCGA GGAAGACAGC CCATTCCTCA GAGCTTTGCA GCGGAGCTTC CCGCAGTTTG
                             nsP1
       ~~~~~~~~~~~~~~~~~~~~~~~~~~~~~~~~~~~~~~~~~~~~~~~~~~~~~~~~~~~~~~~~~~
121    AGGTAGAAGC CAAGCAGGTC ACTGATAATG ACCATGCTAA TGCCAGAGCG TTTTCGCATC
                             nsP1
       ~~~~~~~~~~~~~~~~~~~~~~~~~~~~~~~~~~~~~~~~~~~~~~~~~~~~~~~~~~~~~~~~~~
181    TGGCTTCAAA ACTGATCGAA ACGGAGGTGG ACCCATCCGA CACGATCCTT GACATTGGAA
                             nsP1
       ~~~~~~~~~~~~~~~~~~~~~~~~~~~~~~~~~~~~~~~~~~~~~~~~~~~~~~~~~~~~~~~~~~
241    GTGCGCCCGC CCGCAGAATG TATTCTAAGC ACAAGTATCA TTGTATCTGT CCGATGAGAT
                             nsP1
       ~~~~~~~~~~~~~~~~~~~~~~~~~~~~~~~~~~~~~~~~~~~~~~~~~~~~~~~~~~~~~~~~~~
301    GTGCGGAAGA TCCGGACAGA TTGTATAAGT ATGCAACTAA GCTGAAGAAA AACTGTAAGG
                             nsP1
       ~~~~~~~~~~~~~~~~~~~~~~~~~~~~~~~~~~~~~~~~~~~~~~~~~~~~~~~~~~~~~~~~~~
361    AAATAACTGA TAAGGAATTG GACAAGAAAA TGAAGGAGCT CGCCGCCGTC ATGAGCGACC
```

-continued

SEQUENCES

```
                             nsP1
        ~~~~~~~~~~~~~~~~~~~~~~~~~~~~~~~~~~~~~~~~~~~~~~~~~~~~~~~~~~~~~~~~~
   421  CTGACCTGGA AACTGAGACT ATGTGCCTCC ACGACGACGA GTCGTGTCGC TACGAAGGGC
                             nsP1
        ~~~~~~~~~~~~~~~~~~~~~~~~~~~~~~~~~~~~~~~~~~~~~~~~~~~~~~~~~~~~~~~~~
   481  AAGTCGCTGT TTACCAGGAT GTATACGCGG TTGACGGACC GACAAGTCTC TATCACCAAG
                             nsP1
        ~~~~~~~~~~~~~~~~~~~~~~~~~~~~~~~~~~~~~~~~~~~~~~~~~~~~~~~~~~~~~~~~~
   541  CCAATAAGGG AGTTAGAGTC GCCTACTGGA TAGGCTTTGA CACCACCCCT TTTATGTTTA
                             nsP1
        ~~~~~~~~~~~~~~~~~~~~~~~~~~~~~~~~~~~~~~~~~~~~~~~~~~~~~~~~~~~~~~~~~
   601  AGAACTTGGC TGGAGCATAT CCATCATACT CTACCAACTG GGCCGACGAA ACCGTGTTAA
                             nsP1
        ~~~~~~~~~~~~~~~~~~~~~~~~~~~~~~~~~~~~~~~~~~~~~~~~~~~~~~~~~~~~~~~~~
   661  CGGCTCGTAA CATAGGCCTA TGCAGCTCTG ACGTTATGGA GCGGTCACGT AGAGGGATGT
                             nsP1
        ~~~~~~~~~~~~~~~~~~~~~~~~~~~~~~~~~~~~~~~~~~~~~~~~~~~~~~~~~~~~~~~~~
   721  CCATTCTTAG AAAGAAGTAT TTGAAACCAT CCAACAATGT TCTATTCTCT GTTGGCTCGA
                             nsP1
        ~~~~~~~~~~~~~~~~~~~~~~~~~~~~~~~~~~~~~~~~~~~~~~~~~~~~~~~~~~~~~~~~~
   781  CCATCTACCA CGAGAAGAGG GACTTACTGA GGAGCTGGCA CCTGCCGTCT GTATTTCACT
                             nsP1
        ~~~~~~~~~~~~~~~~~~~~~~~~~~~~~~~~~~~~~~~~~~~~~~~~~~~~~~~~~~~~~~~~~
   841  TACGTGGCAA GCAAAATTAC ACATGTCGGT GTGAGACTAT AGTTAGTTGC GACGGGTACG
                             nsP1
        ~~~~~~~~~~~~~~~~~~~~~~~~~~~~~~~~~~~~~~~~~~~~~~~~~~~~~~~~~~~~~~~~~
   901  TCGTTAAAAG AATAGCTATC AGTCCAGGCC TGTATGGGAA GCCTTCAGGC TATGCTGCTA
                             nsP1
        ~~~~~~~~~~~~~~~~~~~~~~~~~~~~~~~~~~~~~~~~~~~~~~~~~~~~~~~~~~~~~~~~~
   961  CGATGCACCG CGAGGGATTC TTGTGCTGCA AAGTGACAGA CACATTGAAC GGGGAGAGGG
                             nsP1
        ~~~~~~~~~~~~~~~~~~~~~~~~~~~~~~~~~~~~~~~~~~~~~~~~~~~~~~~~~~~~~~~~~
  1021  TCTCTTTTCC CGTGTGCACG TATGTGCCAG CTACATTGTG TGACCAAATG ACTGGCATAC
                             nsP1
        ~~~~~~~~~~~~~~~~~~~~~~~~~~~~~~~~~~~~~~~~~~~~~~~~~~~~~~~~~~~~~~~~~
  1081  TGGCAACAGA TGTCAGTGCG GACGACGCGC AAAAACTGCT GGTTGGGCTC AACCAGCGTA
                             nsP1
        ~~~~~~~~~~~~~~~~~~~~~~~~~~~~~~~~~~~~~~~~~~~~~~~~~~~~~~~~~~~~~~~~~
  1141  TAGTCGTCAA CGGTCGCACC CAGAGAAACA CCAATACCAT GAAAAATTAC CTTTTGCCCG
                             nsP1
        ~~~~~~~~~~~~~~~~~~~~~~~~~~~~~~~~~~~~~~~~~~~~~~~~~~~~~~~~~~~~~~~~~
  1201  TAGTGGCCCA GGCATTTGCT AGGTGGGCAA AGGAATATAA GGAAGATCAA GAAGATGAAA
                             nsP1
        ~~~~~~~~~~~~~~~~~~~~~~~~~~~~~~~~~~~~~~~~~~~~~~~~~~~~~~~~~~~~~~~~~
  1261  GGCCACTAGG ACTACGAGAT AGACAGTTAG TCATGGGGTG TTGTTGGGCT TTTAGAAGGC
                             nsP1
        ~~~~~~~~~~~~~~~~~~~~~~~~~~~~~~~~~~~~~~~~~~~~~~~~~~~~~~~~~~~~~~~~~
  1321  ACAAGATAAC ATCTATTTAT AAGCGCCCGG ATACCCAAAC CATCATCAAA GTGAACAGCG
                             nsP1
        ~~~~~~~~~~~~~~~~~~~~~~~~~~~~~~~~~~~~~~~~~~~~~~~~~~~~~~~~~~~~~~~~~
  1381  ATTTCCACTC ATTCGTGCTG CCCAGGATAG GCAGTAACAC ATTGGAGATC GGGCTGAGAA
                             nsP1
        ~~~~~~~~~~~~~~~~~~~~~~~~~~~~~~~~~~~~~~~~~~~~~~~~~~~~~~~~~~~~~~~~~
  1441  CAAGAATCAG GAAAATGTTA GAGGAGCACA AGGAGCCGTC ACCTCTCATT ACCGCCGAGG
                             nsP1
        ~~~~~~~~~~~~~~~~~~~~~~~~~~~~~~~~~~~~~~~~~~~~~~~~~~~~~~~~~~~~~~~~~
  1501  ACGTACAAGA AGCTAAGTGC GCAGCCGATG AGGCTAAGGA GGTGCGTGAA GCCGAGGAGT
                             nsP1
        ~~~~~~~~~~~~~~~~~~~~~~~~~~~~~~~~~~~~~~~~~~~~~~~~~~~~~~~~~~~~~~~~~
  1561  TGCGCGCAGC TCTACCACCT TTGGCAGCTG ATGTTGAGGA GCCCACTCTG GAAGCCGATG
                                                     nsP2
                                ~~~~~~~~~~~~~~~~~~~~~~~~~~~~~~~~~~
             nsP1
        ~~~~~~~~~~~~~~~~~~~~~~~~~~~~~~~
  1621  TAGACTTGAT GTTACAAGAG GCTGGGGCCG GCTCAGTGGA GACACCTCGT GGCTTGATAA
                             nsP2
        ~~~~~~~~~~~~~~~~~~~~~~~~~~~~~~~~~~~~~~~~~~~~~~~~~~~~~~~~~~~~~~~~~
  1681  AGGTTACCAG CTACGATGGC GAGGACAAGA TCGGCTCTTA CGCTGTGCTT TCTCCGCAGG
                             nsP2
        ~~~~~~~~~~~~~~~~~~~~~~~~~~~~~~~~~~~~~~~~~~~~~~~~~~~~~~~~~~~~~~~~~
  1741  CTGTACTCAA GAGTGAAAAA TTATCTTGCA TCCACCCTCT CGCTGAACAA GTCATAGTGA
                             nsP2
        ~~~~~~~~~~~~~~~~~~~~~~~~~~~~~~~~~~~~~~~~~~~~~~~~~~~~~~~~~~~~~~~~~
  1801  TAACACACTC TGGCCGAAAA GGGCGTTATG CCGTGGAACC ATACCATGGT AAAGTAGTGG
                             nsP2
        ~~~~~~~~~~~~~~~~~~~~~~~~~~~~~~~~~~~~~~~~~~~~~~~~~~~~~~~~~~~~~~~~~
  1861  TGCCAGAGGG ACATGCAATA CCCGTCCAGG ACTTTCAAGC TCTGAGTGAA AGTGCCACCA
```

-continued

| SEQUENCES |
|---|

```
                              nsP2
           ~~~~~~~~~~~~~~~~~~~~~~~~~~~~~~~~~~~~~~~~~~~~~~~~~~~~~~~~~~~~~~~~~~~~~~
1921       TTGTGTACAA CGAACGTGAG TTCGTAAACA GGTACCTGCA CCATATTGCC ACACATGGAG
                              nsP2
           ~~~~~~~~~~~~~~~~~~~~~~~~~~~~~~~~~~~~~~~~~~~~~~~~~~~~~~~~~~~~~~~~~~~~~~
1981       GAGCGCTGAA CACTGATGAA GAATATTACA AAACTGTCAA GCCCAGCGAG CACGACGGCG
                              nsP2
           ~~~~~~~~~~~~~~~~~~~~~~~~~~~~~~~~~~~~~~~~~~~~~~~~~~~~~~~~~~~~~~~~~~~~~~
2041       AATACCTGTA CGACATCGAC AGGAAACAGT GCGTCAAGAA AGAACTAGTC ACTGGGCTAG
                              nsP2
           ~~~~~~~~~~~~~~~~~~~~~~~~~~~~~~~~~~~~~~~~~~~~~~~~~~~~~~~~~~~~~~~~~~~~~~
2101       GGCTCACAGG CGAGCTGGTG GATCCTCCCT TCCATGAATT CGCCTACGAG AGTCTGAGAA
                              nsP2
           ~~~~~~~~~~~~~~~~~~~~~~~~~~~~~~~~~~~~~~~~~~~~~~~~~~~~~~~~~~~~~~~~~~~~~~
2161       CACGACCAGC CGCTCCTTAC CAAGTACCAA CCATAGGGGT GTATGGCGTG CCAGGATCAG
                              nsP2
           ~~~~~~~~~~~~~~~~~~~~~~~~~~~~~~~~~~~~~~~~~~~~~~~~~~~~~~~~~~~~~~~~~~~~~~
2221       GCAAGTCTGG CATCATTAAA AGCGCAGTCA CCAAAAAAGA TCTAGTGGTG AGCGCCAAGA
                              nsP2
           ~~~~~~~~~~~~~~~~~~~~~~~~~~~~~~~~~~~~~~~~~~~~~~~~~~~~~~~~~~~~~~~~~~~~~~
2281       AAGAAAACTG TGCAGAAATT ATAAGGGACG TCAAGAAAAT GAAAGGGCTG GACGTCAATG
                              nsP2
           ~~~~~~~~~~~~~~~~~~~~~~~~~~~~~~~~~~~~~~~~~~~~~~~~~~~~~~~~~~~~~~~~~~~~~~
2341       CCAGAACTGT GGACTCAGTG CTCTTGAATG GATGCAAACA CCCCGTAGAG ACCCTGTATA
                              nsP2
           ~~~~~~~~~~~~~~~~~~~~~~~~~~~~~~~~~~~~~~~~~~~~~~~~~~~~~~~~~~~~~~~~~~~~~~
2401       TTGACGAAGC TTTTGCTTGT CATGCAGGTA CTCTCAGAGC GCTCATAGCC ATTATAAGAC
                              nsP2
           ~~~~~~~~~~~~~~~~~~~~~~~~~~~~~~~~~~~~~~~~~~~~~~~~~~~~~~~~~~~~~~~~~~~~~~
2461       CTAAAAAGGC AGTGCTCTGC GGGGATCCCA AACAGTGCGG TTTTTTTAAC ATGATGTGCC
                              nsP2
           ~~~~~~~~~~~~~~~~~~~~~~~~~~~~~~~~~~~~~~~~~~~~~~~~~~~~~~~~~~~~~~~~~~~~~~
2521       TGAAAGTGCA TTTTAACCAC GAGATTTGCA CACAAGTCTT CCACAAAAGC ATCTCTCGCC
                              nsP2
           ~~~~~~~~~~~~~~~~~~~~~~~~~~~~~~~~~~~~~~~~~~~~~~~~~~~~~~~~~~~~~~~~~~~~~~
2581       GTTGCACTAA ATCTGTGACT TCGGTCGTCT CAACCTTGTT TTACGACAAA AAAATGAGAA
                              nsP2
           ~~~~~~~~~~~~~~~~~~~~~~~~~~~~~~~~~~~~~~~~~~~~~~~~~~~~~~~~~~~~~~~~~~~~~~
2641       CGACGAATCC GAAAGAGACT AAGATTGTGA TTGACACTAC CGGCAGTACC AAACCTAAGC
                              nsP2
           ~~~~~~~~~~~~~~~~~~~~~~~~~~~~~~~~~~~~~~~~~~~~~~~~~~~~~~~~~~~~~~~~~~~~~~
2701       AGGACGATCT CATTCTCACT TGTTTCAGAG GGTGGGTGAA GCAGTTGCAA ATAGATTACA
                              nsP2
           ~~~~~~~~~~~~~~~~~~~~~~~~~~~~~~~~~~~~~~~~~~~~~~~~~~~~~~~~~~~~~~~~~~~~~~
2761       AAGGCAACGA AATAATGACG GCAGCTGCCT CTCAAGGGCT GACCCGTAAA GGTGTGTATG
                              nsP2
           ~~~~~~~~~~~~~~~~~~~~~~~~~~~~~~~~~~~~~~~~~~~~~~~~~~~~~~~~~~~~~~~~~~~~~~
2821       CCGTTCGGTA CAAGGTGAAT GAAAATCCTC TGTACGCACC CACCTCAGAA CATGTGAACG
                              nsP2
           ~~~~~~~~~~~~~~~~~~~~~~~~~~~~~~~~~~~~~~~~~~~~~~~~~~~~~~~~~~~~~~~~~~~~~~
2881       TCCTACTGAC CCGCACGGAG GACCGCATCG TGTGGAAAAC ACTAGCCGGC GACCCATGGA
                              nsP2
           ~~~~~~~~~~~~~~~~~~~~~~~~~~~~~~~~~~~~~~~~~~~~~~~~~~~~~~~~~~~~~~~~~~~~~~
2941       TAAAAACACT GACTGCCAAG TACCCTGGGA ATTTCACTGC CACGATAGAG GAGTGGCAAG
                              nsP2
           ~~~~~~~~~~~~~~~~~~~~~~~~~~~~~~~~~~~~~~~~~~~~~~~~~~~~~~~~~~~~~~~~~~~~~~
3001       CAGAGCATGA TGCCATCATG AGGCACATCT TGGAGAGACC GGACCCTACC GACGTCTTCC
                              nsP2
           ~~~~~~~~~~~~~~~~~~~~~~~~~~~~~~~~~~~~~~~~~~~~~~~~~~~~~~~~~~~~~~~~~~~~~~
3061       AGAATAAGGC AAACGTGTGT TGGGCCAAGG CTTTAGTGCC GGTGCTGAAG ACCGCTGGCA
                              nsP2
           ~~~~~~~~~~~~~~~~~~~~~~~~~~~~~~~~~~~~~~~~~~~~~~~~~~~~~~~~~~~~~~~~~~~~~~
3121       TAGACATGAC CACTGAACAA TGGAACACTG TGGATTATTT TGAAACGGAC AAAGCTCACT
                              nsP2
           ~~~~~~~~~~~~~~~~~~~~~~~~~~~~~~~~~~~~~~~~~~~~~~~~~~~~~~~~~~~~~~~~~~~~~~
3181       CAGCAGAGAT AGTATTGAAC CAACTATGCG TGAGGTTCTT TGGACTCGAT CTGGACTCCG
                              nsP2
           ~~~~~~~~~~~~~~~~~~~~~~~~~~~~~~~~~~~~~~~~~~~~~~~~~~~~~~~~~~~~~~~~~~~~~~
3241       GTCTATTTTC TGCACCCACT GTTCCGTTAT CCATTAGGAA TAATCACTGG GATAACTCCC
                              nsP2
           ~~~~~~~~~~~~~~~~~~~~~~~~~~~~~~~~~~~~~~~~~~~~~~~~~~~~~~~~~~~~~~~~~~~~~~
3301       CGTCGCCTAA CATGTACGGG CTGAATAAAG AAGTGGTCCG TCAGCTCTCT CGCAGGTACC
                              nsP2
           ~~~~~~~~~~~~~~~~~~~~~~~~~~~~~~~~~~~~~~~~~~~~~~~~~~~~~~~~~~~~~~~~~~~~~~
3361       CACAACTGCC TCGGGCAGTT GCCACTGGAA GAGTCTATGA CATGAACACT GGTACACTGC
                              nsP2
           ~~~~~~~~~~~~~~~~~~~~~~~~~~~~~~~~~~~~~~~~~~~~~~~~~~~~~~~~~~~~~~~~~~~~~~
```

-continued

SEQUENCES

```
3421   GCAATTATGA TCCGCGCATA AACCTAGTAC CTGTAAACAG AAGACTGCCT CATGCTTTAG
                                nsP2
       ~~~~~~~~~~~~~~~~~~~~~~~~~~~~~~~~~~~~~~~~~~~~~~~~~~~~~~~~~~~~~~~~~
3481   TCCTCCACCA TAATGAACAC CCACAGAGTG ACTTTTCTTC ATTCGTCAGC AAATTGAAGG
                                nsP2
       ~~~~~~~~~~~~~~~~~~~~~~~~~~~~~~~~~~~~~~~~~~~~~~~~~~~~~~~~~~~~~~~~~
3541   GCAGAACTGT CCTGGTGGTC GGGGAAAAGT TGTCCGTCCC AGGCAAAATG GTTGACTGGT
                                nsP2
       ~~~~~~~~~~~~~~~~~~~~~~~~~~~~~~~~~~~~~~~~~~~~~~~~~~~~~~~~~~~~~~~~~
3601   TGTCAGACCG GCCTGAGGCT ACCTTCAGAG CTCGGCTGGA TTTAGGCATC CCAGGTGATG
                                nsP2
       ~~~~~~~~~~~~~~~~~~~~~~~~~~~~~~~~~~~~~~~~~~~~~~~~~~~~~~~~~~~~~~~~~
3661   TGCCCAAATA TGACATAATA TTTGTTAATG TGAGGACCCC ATATAAATAC CATCACTATC
                                nsP2
       ~~~~~~~~~~~~~~~~~~~~~~~~~~~~~~~~~~~~~~~~~~~~~~~~~~~~~~~~~~~~~~~~~
3721   AGCAGTGTGA AGACCATGCC ATTAAGCTTA GCATGTTGAC CAAGAAAGCT TGTCTGCATC
                                nsP2
       ~~~~~~~~~~~~~~~~~~~~~~~~~~~~~~~~~~~~~~~~~~~~~~~~~~~~~~~~~~~~~~~~~
3781   TGAATCCCGG CGGAACCTGT GTCAGCATAG GTTATGGTTA CGCTGACAGG GCCAGCGAAA
                                nsP2
       ~~~~~~~~~~~~~~~~~~~~~~~~~~~~~~~~~~~~~~~~~~~~~~~~~~~~~~~~~~~~~~~~~
3841   GCATCATTGG TGCTATAGCG CGGCAGTTCA AGTTTTCCCG GGTATGCAAA CCGAAATCCT
                                nsP2
       ~~~~~~~~~~~~~~~~~~~~~~~~~~~~~~~~~~~~~~~~~~~~~~~~~~~~~~~~~~~~~~~~~
3901   CACTTGAAGA GACGGAAGTT CTGTTTGTAT TCATTGGGTA CGATCGCAAG GCCCGTACGC
                                nsP2
       ~~~~~~~~~~~~~~~~~~~~~~~~~~~~~~~~~~~~~~~~~~~~~~~~~~~~~~~~~~~~~~~~~
3961   ACAATCCTTA CAAGCTTTCA TCAACCTTGA CCAACATTTA TACAGGTTCC AGACTCCACG
                                      nsP3
             ~~~~~~~~~~~~~~~~~~~~~~~~~~~~~~~~~~~~~~~~~~~~~~~~~~~~~
          nsP2
       ~~~~~~~~~~~~
4021   AAGCCGGATG TGCACCCTCA TATCATGTGG TGCGAGGGGA TATTGCCACG GCCACCGAAG
                                nsP3
       ~~~~~~~~~~~~~~~~~~~~~~~~~~~~~~~~~~~~~~~~~~~~~~~~~~~~~~~~~~~~~~~~~
4081   GAGTGATTAT AAATGCTGCT AACAGCAAAG GACAACCTGG CGGAGGGGTG TGCGGAGCGC
                                nsP3
       ~~~~~~~~~~~~~~~~~~~~~~~~~~~~~~~~~~~~~~~~~~~~~~~~~~~~~~~~~~~~~~~~~
4141   TGTATAAGAA ATTCCCGGAA AGCTTCGATT TACAGCCGAT CGAAGTAGGA AAAGCGCGAC
                                nsP3
       ~~~~~~~~~~~~~~~~~~~~~~~~~~~~~~~~~~~~~~~~~~~~~~~~~~~~~~~~~~~~~~~~~
4201   TGGTCAAAGG TGCAGCTAAA CATATCATTC ATGCCGTAGG ACCAAACTTC AACAAAGTTT
                                nsP3
       ~~~~~~~~~~~~~~~~~~~~~~~~~~~~~~~~~~~~~~~~~~~~~~~~~~~~~~~~~~~~~~~~~
4261   CGGAGGTTGA AGGTGACAAA CAGTTGGCAG AGGCTTATGA GTCCATCGCT AAGATTGTCA
                                nsP3
       ~~~~~~~~~~~~~~~~~~~~~~~~~~~~~~~~~~~~~~~~~~~~~~~~~~~~~~~~~~~~~~~~~
4321   ACGATAACAA TTACAAGTCA GTAGCGATTC CACTGTTGTC CACCGGCATC TTTTCCGGGA
                                nsP3
       ~~~~~~~~~~~~~~~~~~~~~~~~~~~~~~~~~~~~~~~~~~~~~~~~~~~~~~~~~~~~~~~~~
4381   ACAAAGATCG ACTAACCCAA TCATTGAACC ATTTGCTGAC AGCTTTAGAC ACCACTGATG
                                nsP3
       ~~~~~~~~~~~~~~~~~~~~~~~~~~~~~~~~~~~~~~~~~~~~~~~~~~~~~~~~~~~~~~~~~
4441   CAGATGTAGC CATATACTGC AGGGACAAGA AATGGGAAAT GACTCTCAAG GAAGCAGTGG
                                nsP3
       ~~~~~~~~~~~~~~~~~~~~~~~~~~~~~~~~~~~~~~~~~~~~~~~~~~~~~~~~~~~~~~~~~
4501   CTAGGAGAGA AGCAGTGGAG GAGATATGCA TATCCGACGA CTCTTCAGTG ACAGAACCTG
                                nsP3
       ~~~~~~~~~~~~~~~~~~~~~~~~~~~~~~~~~~~~~~~~~~~~~~~~~~~~~~~~~~~~~~~~~
4561   ATGCAGAGCT GGTGAGGGTG CATCCGAAGA GTTCTTTGGC TGGAAGGAAG GGCTACAGCA
                                nsP3
       ~~~~~~~~~~~~~~~~~~~~~~~~~~~~~~~~~~~~~~~~~~~~~~~~~~~~~~~~~~~~~~~~~
4621   CAAGCGATGG CAAAACTTTC TCATATTTGG AAGGGACCAA GTTTCACCAG GCGGCCAAGG
                                nsP3
       ~~~~~~~~~~~~~~~~~~~~~~~~~~~~~~~~~~~~~~~~~~~~~~~~~~~~~~~~~~~~~~~~~
4681   ATATAGCAGA AATTAATGCC ATGTGGCCCG TTGCAACGGA GGCCAATGAG CAGGTATGCA
                                nsP3
       ~~~~~~~~~~~~~~~~~~~~~~~~~~~~~~~~~~~~~~~~~~~~~~~~~~~~~~~~~~~~~~~~~
4741   TGTATATCCT CGGAGAAAGC ATGAGCAGTA TTAGGTCGAA ATGCCCCGTC GAAGAGTCGG
                                nsP3
       ~~~~~~~~~~~~~~~~~~~~~~~~~~~~~~~~~~~~~~~~~~~~~~~~~~~~~~~~~~~~~~~~~
4801   AAGCCTCCAC ACCACCTAGC ACGCTGCCTT GCTTGTGCAT CCATGCCATG ACTCCAGAAA
                                nsP3
       ~~~~~~~~~~~~~~~~~~~~~~~~~~~~~~~~~~~~~~~~~~~~~~~~~~~~~~~~~~~~~~~~~
4861   GAGTACAGCG CCTAAAAGCC TCACGTCCAG AACAAATTAC TGTGTGCTCA TCCTTTCCAT
                                nsP3
       ~~~~~~~~~~~~~~~~~~~~~~~~~~~~~~~~~~~~~~~~~~~~~~~~~~~~~~~~~~~~~~~~~
```

-continued

SEQUENCES

```
4921  TGCCGAAGTA TAGAATCACT GGTGTGCAGA AGATCCAATG CTCCCAGCCT ATATTGTTCT
                          nsP3
      ~~~~~~~~~~~~~~~~~~~~~~~~~~~~~~~~~~~~~~~~~~~~~~~~~~~~~~~~~~~~~~~~~~
4981  CACCGAAAGT GCCTGCGTAT ATTCATCCAA GGAAGTATCT CGTGGAAACA CCACCGGTAG
                          nsP3
      ~~~~~~~~~~~~~~~~~~~~~~~~~~~~~~~~~~~~~~~~~~~~~~~~~~~~~~~~~~~~~~~~~~
5041  ACGAGACTCC GGAGCCATCG GCAGAGAACC AATCCACAGA GGGGACACCT GAACAACCAC
                          nsP3
      ~~~~~~~~~~~~~~~~~~~~~~~~~~~~~~~~~~~~~~~~~~~~~~~~~~~~~~~~~~~~~~~~~~
5101  CACTTATAAC CGAGGATGAG ACCAGGACTA GAACGCCTGA GCCGATCATC ATCGAAGAGG
                          nsP3
      ~~~~~~~~~~~~~~~~~~~~~~~~~~~~~~~~~~~~~~~~~~~~~~~~~~~~~~~~~~~~~~~~~~
5161  AAGAAGAGGA TAGCATAAGT TTGCTGTCAG ATGGCCCGAC CCACCAGGTG CTGCAAGTCG
                          nsP3
      ~~~~~~~~~~~~~~~~~~~~~~~~~~~~~~~~~~~~~~~~~~~~~~~~~~~~~~~~~~~~~~~~~~
5221  AGGCAGACAT TCACGGGCCG CCCTCTGTAT CTAGCTCATC CTGGTCCATT CCTCATGCAT
                          nsP3
      ~~~~~~~~~~~~~~~~~~~~~~~~~~~~~~~~~~~~~~~~~~~~~~~~~~~~~~~~~~~~~~~~~~
5281  CCGACTTTGA TGTGGACAGT TTATCCATAC TTGACACCCT GGAGGGAGCT AGCGTGACCA
                          nsP3
      ~~~~~~~~~~~~~~~~~~~~~~~~~~~~~~~~~~~~~~~~~~~~~~~~~~~~~~~~~~~~~~~~~~
5341  GCGGGGCAAC GTCAGCCGAG ACTAACTCTT ACTTCGCAAA GAGTATGGAG TTTCTGGCGC
                          nsP3
      ~~~~~~~~~~~~~~~~~~~~~~~~~~~~~~~~~~~~~~~~~~~~~~~~~~~~~~~~~~~~~~~~~~
5401  GACCGGTGCC TGCGCCTCGA ACAGTATTCA GGAACCCTCC ACATCCCGCT CCGCGCACAA
                          nsP3
      ~~~~~~~~~~~~~~~~~~~~~~~~~~~~~~~~~~~~~~~~~~~~~~~~~~~~~~~~~~~~~~~~~~
5461  GAACACCGTC ACTTGCACCC AGCAGGGCCT GCTCGAGAAC CAGCCTAGTT TCCACCCCGC
                          nsP3
      ~~~~~~~~~~~~~~~~~~~~~~~~~~~~~~~~~~~~~~~~~~~~~~~~~~~~~~~~~~~~~~~~~~
5521  CAGGCGTGAA TAGGGTGATC ACTAGAGAGG AGCTCGAGGC GCTTACCCCG TCACGCACTC
                          nsP3
      ~~~~~~~~~~~~~~~~~~~~~~~~~~~~~~~~~~~~~~~~~~~~~~~~~~~~~~~~~~~~~~~~~~
5581  CTAGCAGGTC GGTCTCGAGA ACCAGCCTGG TCTCCAACCC GCCAGGCGTA AATAGGGTGA
                                                    nsP4
                                            ~~~~~~~~~~~~~~~~~~~~

                nsP3
      ~~~~~~~~~~~~~~~~~~~~~~~~~~~~~~~~~~~~~~~~~~~~~~
5641  TTACAAGAGA GGAGTTTGAG GCGTTCGTAG CACAACAACA ATGACGGTTT GATGCGGGTG
                          nsP4
      ~~~~~~~~~~~~~~~~~~~~~~~~~~~~~~~~~~~~~~~~~~~~~~~~~~~~~~~~~~~~~~~~~~
5701  CATACATCTT TTCCTCCGAC ACCGGTCAAG GGCATTTACA ACAAAAATCA GTAAGGCAAA
                          nsP4
      ~~~~~~~~~~~~~~~~~~~~~~~~~~~~~~~~~~~~~~~~~~~~~~~~~~~~~~~~~~~~~~~~~~
5761  CGGTGCTATC CGAAGTGGTG TTGGAGAGGA CCGAATTGGA GATTTCGTAT GCCCCGCGCC
                          nsP4
      ~~~~~~~~~~~~~~~~~~~~~~~~~~~~~~~~~~~~~~~~~~~~~~~~~~~~~~~~~~~~~~~~~~
5821  TCGACCAAGA AAAAGAAGAA TTACTACGCA AGAAATTACA GTTAAATCCC ACACCTGCTA
                          nsP4
      ~~~~~~~~~~~~~~~~~~~~~~~~~~~~~~~~~~~~~~~~~~~~~~~~~~~~~~~~~~~~~~~~~~
5881  ACAGAAGCAG ATACCAGTCC AGGAAGGTGG AGAACATGAA AGCCATAACA GCTAGACGTA
                          nsP4
      ~~~~~~~~~~~~~~~~~~~~~~~~~~~~~~~~~~~~~~~~~~~~~~~~~~~~~~~~~~~~~~~~~~
5941  TTCTGCAAGG CCTAGGGCAT TATTTGAAGG CAGAAGGAAA AGTGGAGTGC TACCGAACCC
                          nsP4
      ~~~~~~~~~~~~~~~~~~~~~~~~~~~~~~~~~~~~~~~~~~~~~~~~~~~~~~~~~~~~~~~~~~
6001  TGCATCCTGT TCCTTTGTAT TCATCTAGTG TGAACCGTGC CTTTTCAAGC CCCAAGGTCG
                          nsP4
      ~~~~~~~~~~~~~~~~~~~~~~~~~~~~~~~~~~~~~~~~~~~~~~~~~~~~~~~~~~~~~~~~~~
6061  CAGTGGAAGC CTGTAACGCC ATGTTGAAAG AGAACTTTCC GACTGTGGCT TCTTACTGTA
                          nsP4
      ~~~~~~~~~~~~~~~~~~~~~~~~~~~~~~~~~~~~~~~~~~~~~~~~~~~~~~~~~~~~~~~~~~
6121  TTATTCCAGA GTACGATGCC TATTTGGACA TGGTTGACGG AGCTTCATGC TGCTTAGACA
                          nsP4
      ~~~~~~~~~~~~~~~~~~~~~~~~~~~~~~~~~~~~~~~~~~~~~~~~~~~~~~~~~~~~~~~~~~
6181  CTGCCAGTTT TTGCCCTGCA AAGCTGCGCA GCTTTCCAAA GAAACACTCC TATTTGGAAC
                          nsP4
      ~~~~~~~~~~~~~~~~~~~~~~~~~~~~~~~~~~~~~~~~~~~~~~~~~~~~~~~~~~~~~~~~~~
6241  CCACAATACG ATCGGCAGTG CCTTCAGCGA TCCAGAACAC GCTCCAGAAC GTCCTGGCAG
                          nsP4
      ~~~~~~~~~~~~~~~~~~~~~~~~~~~~~~~~~~~~~~~~~~~~~~~~~~~~~~~~~~~~~~~~~~
6301  CTGCCACAAA AAGAAATTGC AATGTCACGC AAATGAGAGA ATTGCCCGTA TTGGATTCGG
                          nsP4
      ~~~~~~~~~~~~~~~~~~~~~~~~~~~~~~~~~~~~~~~~~~~~~~~~~~~~~~~~~~~~~~~~~~
6361  CGGCCTTTAA TGTGGAATGC TTCAAGAAAT ATGCGTGTAA TAATGAATAT TGGGAAACGT
                          nsP4
      ~~~~~~~~~~~~~~~~~~~~~~~~~~~~~~~~~~~~~~~~~~~~~~~~~~~~~~~~~~~~~~~~~~
```

-continued

| SEQUENCES |
| --- |

```
6421   TTAAAGAAAA CCCCATCAGG CTTACTGAAG AAAACGTGGT AAATTACATT ACCAAATTAA
                             nsP4
       ~~~~~~~~~~~~~~~~~~~~~~~~~~~~~~~~~~~~~~~~~~~~~~~~~~~~~~~~~~~~~~~~
6481   AAGGACCAAA AGCTGCTGCT CTTTTTGCGA AGACACATAA TTTGAATATG TTGCAGGACA
                             nsP4
       ~~~~~~~~~~~~~~~~~~~~~~~~~~~~~~~~~~~~~~~~~~~~~~~~~~~~~~~~~~~~~~~~
6541   TACCAATGGA CAGGTTTGTA ATGGACTTAA AGAGAGACGT GAAAGTGACT CCAGGAACAA
                             nsP4
       ~~~~~~~~~~~~~~~~~~~~~~~~~~~~~~~~~~~~~~~~~~~~~~~~~~~~~~~~~~~~~~~~
6601                         nsP4
                             nsP4
       ~~~~~~~~~~~~~~~~~~~~~~~~~~~~~~~~~~~~~~~~~~~~~~~~~~~~~~~~~~~~~~~~
6661   CGTATCTGTG CGGAATCCAC CGAGAGCTGG TTAGGAGATT AAATGCGGTC CTGCTTCCGA
                             nsP4
       ~~~~~~~~~~~~~~~~~~~~~~~~~~~~~~~~~~~~~~~~~~~~~~~~~~~~~~~~~~~~~~~~
6721   ACATTCATAC ACTGTTTGAT ATGTCGGCTG AAGACTTTGA CGCTATTATA GCCGAGCACT
                             nsP4
       ~~~~~~~~~~~~~~~~~~~~~~~~~~~~~~~~~~~~~~~~~~~~~~~~~~~~~~~~~~~~~~~~
6781   TCCAGCCTGG GGATTGTGTT CTGGAAACTG ACATCGCGTC GTTTGATAAA AGTGAGGACG
                             nsP4
       ~~~~~~~~~~~~~~~~~~~~~~~~~~~~~~~~~~~~~~~~~~~~~~~~~~~~~~~~~~~~~~~~
6841   ACGCCATGGC TCTGACCGCG TTAATGATTC TGGAAGACTT AGGTGTGGAC GCAGAGCTGT
                             nsP4
       ~~~~~~~~~~~~~~~~~~~~~~~~~~~~~~~~~~~~~~~~~~~~~~~~~~~~~~~~~~~~~~~~
6901   TGACGCTGAT TGAGGCGGCT TTCGGCGAAA TTTCATCAAT ACATTTGCCC ACTAAAACTA
                             nsP4
       ~~~~~~~~~~~~~~~~~~~~~~~~~~~~~~~~~~~~~~~~~~~~~~~~~~~~~~~~~~~~~~~~
6961   AATTTAAATT CGGAGCCATG ATGAAATCTG GAATGTTCCT CACACTGTTT GTGAACACAG
                             nsP4
       ~~~~~~~~~~~~~~~~~~~~~~~~~~~~~~~~~~~~~~~~~~~~~~~~~~~~~~~~~~~~~~~~
7021   TCATTAACAT TGTAATCGCA AGCAGAGTGT TGAGAGAACG GCTAACCGGA TCACCATGTG
                             nsP4
       ~~~~~~~~~~~~~~~~~~~~~~~~~~~~~~~~~~~~~~~~~~~~~~~~~~~~~~~~~~~~~~~~
7081   CAGCATTCAT TGGAGATGAC AATATCGTGA AAGGAGTCAA ATCGGACAAA TTAATGGCAG
                             nsP4
       ~~~~~~~~~~~~~~~~~~~~~~~~~~~~~~~~~~~~~~~~~~~~~~~~~~~~~~~~~~~~~~~~
7141   ACAGGTGCGC CACCTGGTTG AATATGGAAG TCAAGATTAT AGATGCTGTG GTGGGCGAGA
                             nsP4
       ~~~~~~~~~~~~~~~~~~~~~~~~~~~~~~~~~~~~~~~~~~~~~~~~~~~~~~~~~~~~~~~~
7201   AAGCGCCTTA TTTCTGTGGA GGGTTTATTT TGTGTGACTC CGTGACCGGC ACAGCGTGCC
                             nsP4
       ~~~~~~~~~~~~~~~~~~~~~~~~~~~~~~~~~~~~~~~~~~~~~~~~~~~~~~~~~~~~~~~~
7261   GTGTGGCAGA CCCCCTAAAA AGGCTGTTTA AGCTTGGCAA ACCTCTGGCA GCAGACGATG
                             nsP4
       ~~~~~~~~~~~~~~~~~~~~~~~~~~~~~~~~~~~~~~~~~~~~~~~~~~~~~~~~~~~~~~~~
7321   AACATGATGA TGACAGGAGA AGGGCATTGC ATGAAGAGTC AACACGCTGG AACCGAGTGG
                             nsP4
       ~~~~~~~~~~~~~~~~~~~~~~~~~~~~~~~~~~~~~~~~~~~~~~~~~~~~~~~~~~~~~~~~
7381   GTATTCTTTC AGAGCTGTGC AAGGCAGTAG AATCAAGGTA TGAAACCGTA GGAACTTCCA
                             nsP4
       ~~~~~~~~~~~~~~~~~~~~~~~~~~~~~~~~~~~~~~~~~~~~~~~~~~~~~~~~~~~~~~~~
7441   TCATAGTTAT GGCCATGACT ACTCTAGCTA GCAGTGTTAA ATCATTCAGC TACCTGAGAG
               subgenomic promoter
             ~~~~~~~~~~~~~~~~~~~~~~~~~
            nsP4
       ~~~~~~~~~~~~~~~~~~~~~~~~~~~~
7501   GGGCCCCTAT AACTCTCTAC GGCTAACCTG AATGGACTAC GACATAGTCT AGTCGACGCC
                              eGFP
       ~~~~~~~~~~~~~~~~~~~~~~~~~~~~~~~~~~~~~~~~~~~~~~~~~~~~~~~~~~~~~
7561   ACCATGGTGA GCAAGGGCGA GGAGCTGTTC ACCGGGGTGG TGCCCATCCT GGTCGAGCTG
                              eGFP
       ~~~~~~~~~~~~~~~~~~~~~~~~~~~~~~~~~~~~~~~~~~~~~~~~~~~~~~~~~~~~~~~~
7621   GACGGCGACG TAAACGGCCA CAAGTTCAGC GTGTCCGGCG AGGGCGAGGG CGATGCCACC
                              eGFP
       ~~~~~~~~~~~~~~~~~~~~~~~~~~~~~~~~~~~~~~~~~~~~~~~~~~~~~~~~~~~~~~~~
7681   TACGGCAAGC TGACCCTGAA GTTCATCTGC ACCACCGGCA AGCTGCCCGT GCCCTGGCCC
                              eGFP
       ~~~~~~~~~~~~~~~~~~~~~~~~~~~~~~~~~~~~~~~~~~~~~~~~~~~~~~~~~~~~~~~~
7741   ACCCTCGTGA CCACCCTGAC CTACGGCGTG CAGTGCTTCA GCCGCTACCC CGACCACATG
                              eGFP
       ~~~~~~~~~~~~~~~~~~~~~~~~~~~~~~~~~~~~~~~~~~~~~~~~~~~~~~~~~~~~~~~~
7801   AAGCAGCACG ACTTCTTCAA GTCCGCCATG CCCGAAGGCT ACGTCCAGGA GCGCACCATC
                              eGFP
       ~~~~~~~~~~~~~~~~~~~~~~~~~~~~~~~~~~~~~~~~~~~~~~~~~~~~~~~~~~~~~~~~
7861   TTCTTCAAGG ACGACGGCAA CTACAAGACC CGCGCCGAGG TGAAGTTCGA GGGCGACACC
                              eGFP
       ~~~~~~~~~~~~~~~~~~~~~~~~~~~~~~~~~~~~~~~~~~~~~~~~~~~~~~~~~~~~~~~~
```

-continued

SEQUENCES

```
7921   CTGGTGAACC GCATCGAGCT GAAGGGCATC GACTTCAAGG AGGACGGCAA CATCCTGGGG
                                eGFP
       ~~~~~~~~~~~~~~~~~~~~~~~~~~~~~~~~~~~~~~~~~~~~~~~~~~~~~~~~~~~~~~~~~~
7981   CACAAGCTGG AGTACAACTA CAACAGCCAC AACGTCTATA TCATGGCCGA CAAGCAGAAG
                                eGFP
       ~~~~~~~~~~~~~~~~~~~~~~~~~~~~~~~~~~~~~~~~~~~~~~~~~~~~~~~~~~~~~~~~~~
8041   AACGGCATCA AGGTGAACTT CAAGATCCGC CACAACATCG AGGACGGCAG CGTGCAGCTC
                                eGFP
       ~~~~~~~~~~~~~~~~~~~~~~~~~~~~~~~~~~~~~~~~~~~~~~~~~~~~~~~~~~~~~~~~~~
8101   GCCGACCACT ACCAGCAGAA CACCCCCATC GGCGACGGCC CCGTGCTGCT GCCCGACAAC
                                eGFP
       ~~~~~~~~~~~~~~~~~~~~~~~~~~~~~~~~~~~~~~~~~~~~~~~~~~~~~~~~~~~~~~~~~~
8161   CACTACCTGA GCACCCAGTC CGCCCTGAGC AAAGACCCCA ACGAGAAGCG CGATCACATG
                                eGFP
       ~~~~~~~~~~~~~~~~~~~~~~~~~~~~~~~~~~~~~~~~~~~~~~~~~~~~~~~~~~~~~~~~~~
8221   GTCCTGCTGG AGTTCGTGAC CGCCGCCGGG ATCACTCTCG GCATGGACGA GCTGTACAAG
       eGFP                                        3'UTR
       ~~~~~~                         ~~~~~~~~~~~~~~~~~~~~~~~~~~~
8281   TGATAATCTA GACGGCGCGC CCACCCAGCG GCCGCATACA GCAGCAATTG GCAAGCTGCT
                              3'UTR
       ~~~~~~~~~~~~~~~~~~~~~~~~~~~~~~~~~~~~~~~~~~~~~~~~~~~~~~~~~~~~~~~~~~
8341   TACATAGAAC TCGCGGCGAT TGGCATGCCG CCTTAAAATT TTTATTTTAT TTTTCTTTTC
             3'UTR
       ~~~~~~~~~~~~~~~~~~~~~~~~~~~~~~~~~~~
8401   TTTTCCGAAT CGGATTTTGT TTTTAATATT TCAAAAAAAA AAAAAAAAAA AAAAAAAAAA
                              HDV ribozyme
       ~~~~~~~~~~~~~~~~~~~~~~~~~~~~~~~~~~~~~~~~~~~~~~~~~~~~~~~~~~
8461   AAAAAAAGGG TCGGCATGGC ATCTCCACCT CCTCGCGGTC CGACCTGGGC ATCCGAAGGA
            HDV ribozyme
       ~~~~~~~~~~~~~~~~~~~~~~~~~~~~~~~~~~~~~~~~
8521   GGACGCACGT CCACTCGGAT GGCTAAGGGA GAGCCACGTT TAAACCAGCT CCAATTCGCC
8581   CTATAGTGAG TCGTATTACG CGCGCTCACT GGCCGTCGTT TTACAACGTC GTGACTGGGA
8641   AAACCCTGGC GTTACCCAAC TTAATCGCCT TGCAGCACAT CCCCCTTTCG CCAGCTGGCG
8701   TAATAGCGAA GAGGCCCGCA CCGATCGCCC TTCCCAACAG TTGCGCAGCC TGAATGGCGA
8761   ATGGGACGCG CCCTGTAGCG GCGCATTAAG CGCGGCGGGT GTGGTGGTTA CGCGCAGCGT
8821   GACCGCTACA CTTGCCAGCG CCCTAGCGCC CGCTCCTTTC GCTTTCTTCC CTTCCTTTCT
8881   CGCCACGTTC GCCGGCTTTC CCCGTCAAGC TCTAAATCGG GGGCTCCCTT TAGGGTTCCG
8941   ATTTAGTGCT TTACGGCACC TCGACCCCAA AAAACTTGAT TAGGGTGATG GTTCACGTAG
9001   TGGGCCATCG CCCTGATAGA CGGTTTTTCG CCCTTTGACG TTGGAGTCCA CGTTCTTTAA
9061   TAGTGGACTC TTGTTCCAAA CTGGAACAAC ACTCAACCCT ATCTCGGTCT ATTCTTTTGA
9121   TTTATAAGGG ATTTTGCCGA TTTCGGCCTA TTGGTTAAAA AATGAGCTGA TTTAACAAAA
9181   ATTTAACGCG AATTTTAACA AAATATTAAC GCTTACAATT TAGGTGGCAC TTTTCGGGGA
9241   AATGTGCGCG GAACCCCTAT TTGTTTATTT TTCTAAATAC ATTCAAATAT GTATCCGCTC
                                                                 bla
                                                             ~~~~~~~~~
9301   ATGAGACAAT AACCCTGATA AATGCTTCAA TAATATTGAA AAAGGAAGAG TATGAGTATT
                               bla
       ~~~~~~~~~~~~~~~~~~~~~~~~~~~~~~~~~~~~~~~~~~~~~~~~~~~~~~~~~~~~~~~~~~
9361   CAACATTTCC GTGTCGCCCT TATTCCCTTT TTTGCGGCAT TTTGCCTTCC TGTTTTTGCT
                               bla
       ~~~~~~~~~~~~~~~~~~~~~~~~~~~~~~~~~~~~~~~~~~~~~~~~~~~~~~~~~~~~~~~~~~
9421   CACCCAGAAA CGCTGGTGAA AGTAAAAGAT GCTGAAGATC AGTTGGGTGC ACGAGTGGGT
                               bla
       ~~~~~~~~~~~~~~~~~~~~~~~~~~~~~~~~~~~~~~~~~~~~~~~~~~~~~~~~~~~~~~~~~~
9481   TACATCGAAC TGGATCTCAA CAGCGGTAAG ATCCTTGAGA GTTTTCGCCC CGAAGAACGT
                               bla
       ~~~~~~~~~~~~~~~~~~~~~~~~~~~~~~~~~~~~~~~~~~~~~~~~~~~~~~~~~~~~~~~~~~
9541   TTTCCAATGA TGAGCACTTT TAAAGTTCTG CTATGTGGCG CGGTATTATC CCGTATTGAC
                               bla
       ~~~~~~~~~~~~~~~~~~~~~~~~~~~~~~~~~~~~~~~~~~~~~~~~~~~~~~~~~~~~~~~~~~
9601   GCCGGGCAAG AGCAACTCGG TCGCCGCATA CACTATTCTC AGAATGACTT GGTTGAGTAC
                               bla
       ~~~~~~~~~~~~~~~~~~~~~~~~~~~~~~~~~~~~~~~~~~~~~~~~~~~~~~~~~~~~~~~~~~
9661   TCACCAGTCA CAGAAAAGCA TCTTACGGAT GGCATGACAG TAAGAGAATT ATGCAGTGCT
                               bla
       ~~~~~~~~~~~~~~~~~~~~~~~~~~~~~~~~~~~~~~~~~~~~~~~~~~~~~~~~~~~~~~~~~~
9721   GCCATAACCA TGAGTGATAA CACTGCGGCC AACTTACTTC TGACAACGAT CGGAGGACCG
                               bla
       ~~~~~~~~~~~~~~~~~~~~~~~~~~~~~~~~~~~~~~~~~~~~~~~~~~~~~~~~~~~~~~~~~~
9781   AAGGAGCTAA CCGCTTTTTT GCACAACATG GGGGATCATG TAACTCGCCT TGATCGTTGG
                               bla
       ~~~~~~~~~~~~~~~~~~~~~~~~~~~~~~~~~~~~~~~~~~~~~~~~~~~~~~~~~~~~~~~~~~
9841   GAACCGGAGC TGAATGAAGC CATACCAAAC GACGAGCGTG ACACCACGAT GCCTGTAGCA
                               bla
       ~~~~~~~~~~~~~~~~~~~~~~~~~~~~~~~~~~~~~~~~~~~~~~~~~~~~~~~~~~~~~~~~~~
9901   ATGGCAACAA CGTTGCGCAA ACTATTAACT GGCGAACTAC TTACTCTAGC TTCCCGGCAA
                               bla
```

-continued

SEQUENCES

```
        ~~~~~~~~~~~~~~~~~~~~~~~~~~~~~~~~~~~~~~~~~~~~~~~~~~~~~~~~~~~~~~~~~
   9961 CAATTAATAG ACTGGATGGA GGCGGATAAA GTTGCAGGAC CACTTCTGCG CTCGGCCCTT
                             bla
        ~~~~~~~~~~~~~~~~~~~~~~~~~~~~~~~~~~~~~~~~~~~~~~~~~~~~~~~~~~~~~~~~~
  10021 CCGGCTGGCT GGTTTATTGC TGATAAATCT GGAGCCGGTG AGCGTGGGTC TCGCGGTATC
                             bla
        ~~~~~~~~~~~~~~~~~~~~~~~~~~~~~~~~~~~~~~~~~~~~~~~~~~~~~~~~~~~~~~~~~
  10081 ATTGCAGCAC TGGGGCCAGA TGGTAAGCCC TCCCGTATCG TAGTTATCTA CACGACGGGG
                             bla
        ~~~~~~~~~~~~~~~~~~~~~~~~~~~~~~~~~~~~~~~~~~~~~~~~~~~~~~~~~~~~~~~~~
  10141 AGTCAGGCAA CTATGGATGA ACGAAATAGA CAGATCGCTG AGATAGGTGC CTCACTGATT
           bla
        ~~~~~~~~~
  10201 AAGCATTGGT AACTGTCAGA CCAAGTTTAC TCATATATAC TTTAGATTGA TTTAAAACTT
  10261 CATTTTTAAT TTAAAAGGAT CTAGGTGAAG ATCCTTTTTG ATAATCTCAT GACCAAAATC
  10321 CCTTAACGTG AGTTTTCGTT CCACTGAGCG TCAGACCCCG TAGAAAAGAT CAAAGGATCT
  10381 TCTTGAGATC CTTTTTTTCT GCGCGTAATC TGCTGCTTGC AAACAAAAAA ACCACCGCTA
  10441 CCAGCGGTGG TTTGTTTGCC GGATCAAGAG CTACCAACTC TTTTTCCGAA GGTAACTGGC
  10501 TTCAGCAGAG CGCAGATACC AAATACTGTT CTTCTAGTGT AGCCGTAGTT AGGCCACCAC
  10561 TTCAAGAACT CTGTAGCACC GCCTACATAC CTCGCTCTGC TAATCCTGTT ACCAGTGGCT
  10621 GCTGCCAGTG GCGATAAGTC GTGTCTTACC GGGTTGGACT CAAGACGATA GTTACCGGAT
  10681 AAGGCGCAGC GGTCGGGCTG AACGGGGGGT TCGTGCACAC AGCCCAGCTT GGAGCGAACG
  10741 ACCTACACCG AACTGAGATA CCTACAGCGT GAGCTATGAG AAAGCGCCAC GCTTCCCGAA
  10801 GGGAGAAAGG CGGACAGGTA TCCGGTAAGC GGCAGGGTCG GAACAGGAGA GCGCACGAGG
  10861 GAGCTTCCAG GGGGAAACGC CTGGTATCTT TATAGTCCTG TCGGGTTTCG CCACCTCTGA
  10921 CTTGAGCGTC GATTTTTGTG ATGCTCGTCA GGGGGGCGGA GCCTATGGAA AAACGCCAGC
  10981 AACGCGGCCT TTTTACGGTT CCTGGCCTTT TGCTGGCCTT TTGCTCACAT GTTCTTTCCT
  11041 GCGTTATCCC CTGATTCTGT GGATAACCGT ATTACCGCCT TTGAGTGAGC TGATACCGCT
  11101 CGCCGCAGCC GAACGACCGA GCGCAGCGAG TCAGTGAGCG AGGAAGCGGA AGAGCGCCCA
  11161 ATACGCAAAC CGCCTCTCCC CGCGCGTTGG CCGATTCATT AATGCAGCTG GCACGACAGG
  11221 TTTCCCGACT GGAAAGCGGG CAGTGAGCGC AACGCAATTA ATGTGAGTTA GCTCACTCAT
  11281 TAGGCACCCC AGGCTTTACA CTTTATGCTC CCGGCTCGTA TGTTGTGTGG AATTGTGAGC
  11341 GGATAACAAT TTCACACAGG AAACAGCTAT GACCATGATT ACGCCAAGCG CGCAATTAAC
  11401 CCTCACTAAA GGGAACAAAA GCTGGGTACC GGGCCCACGC GTAATACGAC TCACTATAG

VEE cap helper
                             5'UTR
        ~~~~~~~~~~~~~~~~~~~~~~~~~~~~~~~~~~~~~~~~~~~~~~~~
                                                     nsP1
                                              ~~~~~~~~~~~~~~~~~
      1 ATAGGCGGCG CATGAGAGAA GCCCAGACCA ATTACCTACC CAAATAGGAG AAAGTTCACG
                             nsP1
        ~~~~~~~~~~~~~~~~~~~~~~~~~~~~~~~~~~~~~~~~~~~~~~~~~~~~~~~~~~~~~~~~~
     61 TTGACATCGA GGAAGACAGC CCATTCCTCA GAGCTTTGCA GCGGAGCTTC CCGCAGTTTG
                             nsP1
        ~~~~~~~~~~~~~~~~~~~~~~~~~~~~~~~~~~~~~~~~~~~~~~~~~~~~~~~~~~~~~~~~~
    121 AGGTAGAAGC CAAGCAGGTC ACTGATAATG ACCATGCTAA TGCCAGAGCG TTTTCGCATC
                             nsP1
        ~~~~~~~~~~~~~~~~~~~~~~~~~~~~~~~~~~~~~~~~~~~~~~~~~~~~~~~~~~~~~~~~~
    181 TGGCTTCAAA ACTGATCGAA ACGGAGGTGG ACCCATCCGA CACGATCCTT GACATTGGAC
                             nsP1
        ~~~~~~~~~~~~~~~~~~~~~~~~~~~~~~~~~~~~~~~~~~~~~~~~~~~~~~~~~~~~~~~~~
    241 GGACCGACCA TGTTCCCGTT CCAGCCAATG TATCCGATGC AGCCAATGCC CTATCGCAAC
                            VEECAP
        ~~~~~~~~~~~~~~~~~~~~~~~~~~~~~~~~~~~~~~~~~~~~~~~~~~~~~~~~~~~~~~~~~
    301 CCGTTCGCGG CCCCGCGCAG GCCCTGGTTC CCCAGAACCG ACCCTTTTCT GGCGATGCAG
                            VEECAP
        ~~~~~~~~~~~~~~~~~~~~~~~~~~~~~~~~~~~~~~~~~~~~~~~~~~~~~~~~~~~~~~~~~
    361 GTGCAGGAAT TAACCCGCTC GATGGCTAAC CTGACGTTCA AGCAACGCCG GGACGCGCCA
                            VEECAP
        ~~~~~~~~~~~~~~~~~~~~~~~~~~~~~~~~~~~~~~~~~~~~~~~~~~~~~~~~~~~~~~~~~
    421 CCTGAGGGGC CATCCGCTAA GAAACCGAAG AAGGAGGCCT CGCAAAAACA GAAAGGGGGA
                            VEECAP
        ~~~~~~~~~~~~~~~~~~~~~~~~~~~~~~~~~~~~~~~~~~~~~~~~~~~~~~~~~~~~~~~~~
    481 GGCCAAGGGA AGAAGAAGAA GAACCAAGGG AAGAAGAAGG CTAAGACAGG GCCGCCTAAT
                            VEECAP
        ~~~~~~~~~~~~~~~~~~~~~~~~~~~~~~~~~~~~~~~~~~~~~~~~~~~~~~~~~~~~~~~~~
    541 CCGAAGGCAC AGAATGGAAA CAAGAAGAAG ACCAACAAGA AACCAGGCAA GAGACAGCGC
                            VEECAP
        ~~~~~~~~~~~~~~~~~~~~~~~~~~~~~~~~~~~~~~~~~~~~~~~~~~~~~~~~~~~~~~~~~
    601 ATGGTCATGA AATTGGAATC TGACAAGACG TTCCCAATCA TGTTGGAAGG GAAGATAAAC
                            VEECAP
        ~~~~~~~~~~~~~~~~~~~~~~~~~~~~~~~~~~~~~~~~~~~~~~~~~~~~~~~~~~~~~~~~~
                                                H152G
                                                 ~~~
    661 GGCTACGCTT GTGTGGTCGG AGGGAAGTTA TTCAGGCCGA TGGGTGTGGA AGGCAAGATC
                            VEECAP
```

-continued

| SEQUENCES |
|---|

```
     ~~~~~~~~~~~~~~~~~~~~~~~~~~~~~~~~~~~~~~~~~~~~~~~~~~~~~~~~~~~~~~~~~
 721 GACAACGACG TTCTGGCCGC GCTTAAGACG AAGAAAGCAT CCAAATACGA TCTTGAGTAT
                         VEECAP
     ~~~~~~~~~~~~~~~~~~~~~~~~~~~~~~~~~~~~~~~~~~~~~~~~~~~~~~~~~~~~~~~~~
 781 GCAGATGTGC CACAGAACAT GCGGGCCGAT ACATTCAAAT ACACCCATGA GAAACCCCAA
                         VEECAP
     ~~~~~~~~~~~~~~~~~~~~~~~~~~~~~~~~~~~~~~~~~~~~~~~~~~~~~~~~~~~~~~~~~
 841 GGCTATTACA GCTGGCATCA TGGAGCAGTC CAATATGAAA ATGGGCGTTT CACGGTGCCG
                         VEECAP
     ~~~~~~~~~~~~~~~~~~~~~~~~~~~~~~~~~~~~~~~~~~~~~~~~~~~~~~~~~~~~~~~~~
 901 AAAGGAGTTG GGGCCAAGGG AGACAGCGGA CGACCCATTC TGGATAACCA GGGACGGGTG
                         VEECAP
     ~~~~~~~~~~~~~~~~~~~~~~~~~~~~~~~~~~~~~~~~~~~~~~~~~~~~~~~~~~~~~~~~~
 961 GTCGCTATTG TGCTGGGAGG TGTGAATGAA GGATCTAGGA CAGCCCTTTC AGTCGTCATG
                         VEECAP
     ~~~~~~~~~~~~~~~~~~~~~~~~~~~~~~~~~~~~~~~~~~~~~~~~~~~~~~~~~~~~~~~~~
1021 TGGAACGAGA AGGGAGTTAC CGTGAAGTAT ACTCCGGAGA ACTGCGAGCA ATGGTAATAG
     VEECAP                          3'UTR
     ~~~          ~~~~~~~~~~~~~~~~~~~~~~~~~~~~~~~~~~~~~~~~~~~~~~~~~~~~
1081 TAAGCGGCCG CATACAGCAG CAATTGGCAA GCTGCTTACA TAGAACTCGC GGCGATTGGC
                         3'UTR
     ~~~~~~~~~~~~~~~~~~~~~~~~~~~~~~~~~~~~~~~~~~~~~~~~~~~~~~~~~~~~~~~~~
1141 ATGCCGCCTT AAAATTTTTA TTTTATTTTT CTTTTCTTTT CCGAATCGGA TTTTGTTTTT
     3'UTR                                        HDV ribozyme
     ~~~~~~~~                                    ~~~~~~~~~~~~~~~~~~~~
1201 AATATTTCAA AAAAAAAAAA AAAAAAAAAA AAAAAAAAAA AAAGGGTCGG CATGGCATCT
                      HDV ribozyme
     ~~~~~~~~~~~~~~~~~~~~~~~~~~~~~~~~~~~~~~~~~~~~~~~~~~~~~~~~~~~~~~~~~
1261 CCACCTCCTC GCGGTCCGAC CTGGGCATCC GAAGGAGGAC GCACGTCCAC TCGGATGGCT
     HDV ribozyme
     ~~~~~~~~~~~~~~
1321 AAGGGAGAGC CACGTTTAAA CACGTGATAT CTGGCCTCAT GGGCCTTCCT TTCACTGCCC
1381 GCTTTCCAGT CGGGAAACCT GTCGTGCCAG CTGCATTAAC ATGGTCATAG CTGTTTCCTT
1441 GCGTATTGGG CGCTCTCCGC TTCCTCGCTC ACTGACTCGC TGCGCTCGGT CGTTCGGGTA
                                    colE1
                ~~~~~~~~~~~~~~~~~~~~~~~~~~~~~~~~~~~~~~~~~~~~~~
1501 AAGCCTGGGG TGCCTAATGA GCAAAAGGCC AGCAAAAGGC CAGGAACCGT AAAAAGGCCG
                                    colE1
     ~~~~~~~~~~~~~~~~~~~~~~~~~~~~~~~~~~~~~~~~~~~~~~~~~~~~~~~~~~~~~~~~~
1561 CGTTGCTGGC GTTTTTCCAT AGGCTCCGCC CCCCTGACGA GCATCACAAA AATCGACGCT
                                    colE1
     ~~~~~~~~~~~~~~~~~~~~~~~~~~~~~~~~~~~~~~~~~~~~~~~~~~~~~~~~~~~~~~~~~
1621 CAAGTCAGAG GTGGCGAAAC CCGACAGGAC TATAAAGATA CCAGGCGTTT CCCCCTGGAA
                                    colE1
     ~~~~~~~~~~~~~~~~~~~~~~~~~~~~~~~~~~~~~~~~~~~~~~~~~~~~~~~~~~~~~~~~~
1681 GCTCCCTCGT GCGCTCTCCT GTTCCGACCC TGCCGCTTAC CGGATACCTG TCCGCCTTTC
                                    colE1
     ~~~~~~~~~~~~~~~~~~~~~~~~~~~~~~~~~~~~~~~~~~~~~~~~~~~~~~~~~~~~~~~~~
1741 TCCCTTCGGG AAGCGTGGCG CTTTCTCATA GCTCACGCTG TAGGTATCTC AGTTCGGTGT
                                    colE1
     ~~~~~~~~~~~~~~~~~~~~~~~~~~~~~~~~~~~~~~~~~~~~~~~~~~~~~~~~~~~~~~~~~
1801 AGGTCGTTCG CTCCAAGCTG GGCTGTGTGC ACGAACCCCC CGTTCAGCCC GACCGCTGCG
                                    colE1
     ~~~~~~~~~~~~~~~~~~~~~~~~~~~~~~~~~~~~~~~~~~~~~~~~~~~~~~~~~~~~~~~~~
1861 CCTTATCCGG TAACTATCGT CTTGAGTCCA ACCCGGTAAG ACACGACTTA TCGCCACTGG
                                    colE1
     ~~~~~~~~~~~~~~~~~~~~~~~~~~~~~~~~~~~~~~~~~~~~~~~~~~~~~~~~~~~~~~~~~
1921 CAGCAGCCAC TGGTAACAGG ATTAGCAGAG CGAGGTATGT AGGCGGTGCT ACAGAGTTCT
                                    colE1
     ~~~~~~~~~~~~~~~~~~~~~~~~~~~~~~~~~~~~~~~~~~~~~~~~~~~~~~~~~~~~~~~~~
1981 TGAAGTGGTG GCCTAACTAC GGCTACACTA GAAGAACAGT ATTTGGTATC TGCGCTCTGC
                                    colE1
     ~~~~~~~~~~~~~~~~~~~~~~~~~~~~~~~~~~~~~~~~~~~~~~~~~~~~~~~~~~~~~~~~~
2041 TGAAGCCAGT TACCTTCGGA AAAAGAGTTG GTAGCTCTTG ATCCGGCAAA CAAACCACCG
                                    colE1
     ~~~~~~~~~~~~~~~~~~~~~~~~~~~~~~~~~~~~~~~~~~~~~~~~~~~~~~~~~~~~~~~~~
2101 CTGGTAGCGG TGGTTTTTTT GTTTGCAAGC AGCAGATTAC GCGCAGAAAA AAAGGATCTC
        colE1
     ~~~~~~~~~~~~~~~~~~~~~~~~~~~
2161 AAGAAGATCC TTTGATCTTT TCTACGGGGT CTGACGCTCA GTGGAACGAA AACTCACGTT
2221 AAGGGATTTT GGTCATGAGA TTATCAAAAA GGATCTTCAC CTAGATCCTT TTAAATTAAA
2281 AATGAAGTTT TAAATCAATC TAAAGTATAT ATGAGTAAAC TTGGTCTGAC AGTTATTAGA
                                                          ~~~
                          KanR
2341 AAAATTCATC CAGCAGACGA TAAAACGCAA TACGCTGGCT ATCCGGTGCC GCAATGCCAT
     ~~~~~~~~~~~~~~~~~~~~~~~~~~~~~~~~~~~~~~~~~~~~~~~~~~~~~~~~~~~~~~~~~
                          KanR
```

-continued

SEQUENCES

```
2401   ACAGCACCAG AAAACGATCC GCCCATTCGC CGCCCAGTTC TTCCGCAATA TCACGGGTGG
       ~~~~~~~~~~~~~~~~~~~~~~~~~~~~~~~~~~~~~~~~~~~~~~~~~~~~~~~~~~~~~~~~~
                                 KanR
2461   CCAGCGCAAT ATCCTGATAA CGATCCGCCA CGCCCAGACG GCCGCAATCA ATAAAGCCGC
       ~~~~~~~~~~~~~~~~~~~~~~~~~~~~~~~~~~~~~~~~~~~~~~~~~~~~~~~~~~~~~~~~~
                                 KanR
2521   TAAAACGGCC ATTTTCCACC ATAATGTTCG GCAGGCACGC ATCACCATGG GTCACCACCA
       ~~~~~~~~~~~~~~~~~~~~~~~~~~~~~~~~~~~~~~~~~~~~~~~~~~~~~~~~~~~~~~~~~
                                 KanR
2581   GATCTTCGCC ATCCGGCATG CTCGCTTTCA GACGCGCAAA CAGCTCTGCC GGTGCCAGGC
       ~~~~~~~~~~~~~~~~~~~~~~~~~~~~~~~~~~~~~~~~~~~~~~~~~~~~~~~~~~~~~~~~~
                                 KanR
2641   CCTGATGTTC TTCATCCAGA TCATCCTGAT CCACCAGGCC CGCTTCCATA CGGGTACGCG
       ~~~~~~~~~~~~~~~~~~~~~~~~~~~~~~~~~~~~~~~~~~~~~~~~~~~~~~~~~~~~~~~~~
                                 KanR
2701   CACGTTCAAT ACGATGTTTC GCCTGATGAT CAAACGGACA GGTCGCCGGG TCCAGGGTAT
       ~~~~~~~~~~~~~~~~~~~~~~~~~~~~~~~~~~~~~~~~~~~~~~~~~~~~~~~~~~~~~~~~~
                                 KanR
2761   GCAGACGACG CATGGCATCC GCCATAATGC TCACTTTTTC TGCCGGCGCC AGATGGCTAG
       ~~~~~~~~~~~~~~~~~~~~~~~~~~~~~~~~~~~~~~~~~~~~~~~~~~~~~~~~~~~~~~~~~
                                 KanR
2821   ACAGCAGATC CTGACCCGGC ACTTCGCCCA GCAGCAGCCA ATCACGGCCC GCTTCGGTCA
       ~~~~~~~~~~~~~~~~~~~~~~~~~~~~~~~~~~~~~~~~~~~~~~~~~~~~~~~~~~~~~~~~~
                                 KanR
2881   CCACATCCAG CACCGCCGCA CACGGAACAC CGGTGGTGGC CAGCCAGCTC AGACGCGCCG
       ~~~~~~~~~~~~~~~~~~~~~~~~~~~~~~~~~~~~~~~~~~~~~~~~~~~~~~~~~~~~~~~~~
                                 KanR
2941   CTTCATCCTG CAGCTCGTTC AGCGCACCGC TCAGATCGGT TTTCACAAAC AGCACCGGAC
       ~~~~~~~~~~~~~~~~~~~~~~~~~~~~~~~~~~~~~~~~~~~~~~~~~~~~~~~~~~~~~~~~~
                                 KanR
3001   GACCCTGCGC GCTCAGACGA AACACCGCCG CATCAGAGCA GCCAATGGTC TGCTGCGCCC
       ~~~~~~~~~~~~~~~~~~~~~~~~~~~~~~~~~~~~~~~~~~~~~~~~~~~~~~~~~~~~~~~~~
                                 KanR
3061   AATCATAGCC AAACAGACGT TCCACCCACG CTGCCGGGCT ACCCGCATGC AGGCCATCCT
       ~~~~~~~~~~~~~~~~~~~~~~~~~~~~~~~~~~~~~~~~~~~~~~~~~~~~~~~~~~~~~~~~~
                                 KanR
3121   GTTCAATCAT ACTCTTCCTT TTTCAATATT ATTGAAGCAT TTATCAGGGT TATTGTCTCA
       ~~~~~~~~~~~
       KanR
3181   TGAGCGGATA CATATTTGAA TGTATTTAGA AAAATAAACA AATAGGGGTT CCGCGCACAT
3241   TTCCCCGAAA AGTGCCACCT AAATTGTAAG CGTTAATATT TTGTTAAAAT TCGCGTTAAA
3301   TTTTTGTTAA ATCAGCTCAT TTTTTAACCA ATAGGCCGAA ATCGGCAAAA TCCCTTATAA
3361   ATCAAAAGAA TAGACCGAGA TAGGGTTGAG TGGCCGCTAC AGGGCGCTCC CATTCGCCAT
3421   TCAGGCTGCG CAACTGTTGG GAAGGGCGTT TCGGTGCGGG CCTCTTCGCT ATTACGCCAG
3481   CTGGCGAAAG GGGGATGTGC TGCAAGGCGA TTAAGTTGGG TAACGCCAGG GTTTTCCCAG
            T7 promoter
         ~~~~~~~~~~~~~~~~~~~~
3541   TCACACGCGT AATACGACTC ACTATAG
```

VEE gly helper

```
                  5'UTR
       ~~~~~~~~~~~~~~~~~~~~~~~~~~~~~~~~~~~~~~~~~~~~~~~~
                                                     nsP1
                                                 ~~~~~~~~~~~~~~~~~
   1   ATAGGCGGCG CATGAGAGAA GCCCAGACCA ATTACCTACC CAAATAGGAG AAAGTTCACG
                                 nsP1
       ~~~~~~~~~~~~~~~~~~~~~~~~~~~~~~~~~~~~~~~~~~~~~~~~~~~~~~~~~~~~~~~~~
  61   TTGACATCGA GGAAGACAGC CCATTCCTCA GAGCTTTGCA GCGGAGCTTC CCGCAGTTTG
                                 nsP1
       ~~~~~~~~~~~~~~~~~~~~~~~~~~~~~~~~~~~~~~~~~~~~~~~~~~~~~~~~~~~~~~~~~
 121   AGGTAGAAGC CAAGCAGGTC ACTGATAATG ACCATGCTAA TGCCAGAGCG TTTTCGCATC
                                 nsP1
       ~~~~~~~~~~~~~~~~~~~~~~~~~~~~~~~~~~~~~~~~~~~~~~~~~~~~~~~~~~~~~~~~
 181   TGGCTTCAAA ACTGATCGAA ACGGAGGTGG ACCCATCCGA CACGATCCTT GACATTGGAC
                                    VEE GLY
       ~~~~~~~~~~~~~~~~~~~~~~~~~~~~~~~~~~~~~~~~~~~~~~~~~~~~~~~
 241   GGACCGACCA TGTCACTAGT GACCACCATG TGTCTGCTCG CCAATGTGAC GTTCCCATGT
                            VEE GLY
       ~~~~~~~~~~~~~~~~~~~~~~~~~~~~~~~~~~~~~~~~~~~~~~~~~~~~~~~~~~~~~~~~~
 301   GCTCAACCAC CAATTTGCTA CGACAGAAAA CCAGCAGAGA CTTTGGCCAT GCTCAGCGTT
                            VEE GLY
       ~~~~~~~~~~~~~~~~~~~~~~~~~~~~~~~~~~~~~~~~~~~~~~~~~~~~~~~~~~~~~~~~~
 361   AACGTTGACA ACCCGGGCTA CGATGAGCTG CTGGAAGCAG CTGTTAAGTG CCCCGGAAGG
                            VEE GLY
       ~~~~~~~~~~~~~~~~~~~~~~~~~~~~~~~~~~~~~~~~~~~~~~~~~~~~~~~~~~~~~~~~~
 421   AAAAGGAGAT CCACCGAGGA GCTGTTTAAT GAGTATAAGC TAACGCGCCC TTACATGGCC
                            VEE GLY
```

-continued

| SEQUENCES |
|---|

```
      ~~~~~~~~~~~~~~~~~~~~~~~~~~~~~~~~~~~~~~~~~~~~~~~~~~~~~~~~~~~~~~~~~~
 481  AGATGCATCA GATGTGCAGT TGGGAGCTGC CATAGTCCAA TAGCAATCGA GGCAGTAAAG
                     VEE GLY
      ~~~~~~~~~~~~~~~~~~~~~~~~~~~~~~~~~~~~~~~~~~~~~~~~~~~~~~~~~~~~~~~~~~
 541  AGCGACGGGC ACGACGGTTA TGTTAGACTT CAGACTTCCT CGCAGTATGG CCTGGATTCC
                     VEE GLY
      ~~~~~~~~~~~~~~~~~~~~~~~~~~~~~~~~~~~~~~~~~~~~~~~~~~~~~~~~~~~~~~~~~~
 601  TCCGGCAACT TAAAGGGCAG GACCATGCGG TATGACATGC ACGGGACCAT TAAAGAGATA
                     VEE GLY
      ~~~~~~~~~~~~~~~~~~~~~~~~~~~~~~~~~~~~~~~~~~~~~~~~~~~~~~~~~~~~~~~~~~
 661  CCACTACATC AAGTGTCACT CTATACATCT CGCCCGTGTC ACATTGTGGA TGGGCACGGT
                     VEE GLY
      ~~~~~~~~~~~~~~~~~~~~~~~~~~~~~~~~~~~~~~~~~~~~~~~~~~~~~~~~~~~~~~~~~~
 721  TATTTCCTGC TTGCCAGGTG CCCGGCAGGG GACTCCATCA CCATGGAATT TAAGAAAGAT
                     VEE GLY
      ~~~~~~~~~~~~~~~~~~~~~~~~~~~~~~~~~~~~~~~~~~~~~~~~~~~~~~~~~~~~~~~~~~
 781  TCCGTCAGAC ACTCCTGCTC GGTGCCGTAT GAAGTGAAAT TTAATCCTGT AGGCAGAGAA
                     VEE GLY
      ~~~~~~~~~~~~~~~~~~~~~~~~~~~~~~~~~~~~~~~~~~~~~~~~~~~~~~~~~~~~~~~~~~
 841  CTCTATACTC ATCCCCCAGA ACACGGAGTA GAGCAAGCGT GCCAAGTCTA CGCACATGAT
                     VEE GLY
      ~~~~~~~~~~~~~~~~~~~~~~~~~~~~~~~~~~~~~~~~~~~~~~~~~~~~~~~~~~~~~~~~~~
 901  GCACAGAACA GAGGAGCTTA TGTCGAGATG CACCTCCCGG GCTCAGAAGT GGACAGCAGT
                     VEE GLY
      ~~~~~~~~~~~~~~~~~~~~~~~~~~~~~~~~~~~~~~~~~~~~~~~~~~~~~~~~~~~~~~~~~~
 961  TTGGTTTCCT TGAGCGGCAG TTCAGTCACC GTGACACCTC CTGATGGGAC TAGCGCCCTG
                     VEE GLY
      ~~~~~~~~~~~~~~~~~~~~~~~~~~~~~~~~~~~~~~~~~~~~~~~~~~~~~~~~~~~~~~~~~~
1021  GTGGAATGCG AGTGTGGCGG CACAAAGATC TCCGAGACCA TCAACAAGAC AAAACAGTTC
                     VEE GLY
      ~~~~~~~~~~~~~~~~~~~~~~~~~~~~~~~~~~~~~~~~~~~~~~~~~~~~~~~~~~~~~~~~~~
1081  AGCCAGTGCA CAAAGAAGGA GCAGTGCAGA GCATATCGGC TGCAGAACGA TAAGTGGGTG
                     VEE GLY
      ~~~~~~~~~~~~~~~~~~~~~~~~~~~~~~~~~~~~~~~~~~~~~~~~~~~~~~~~~~~~~~~~~~
1141  TATAATTCTG ACAAACTGCC CAAAGCAGCG GGAGCCACCT TAAAAGGAAA ACTGCATGTC
                     VEE GLY
      ~~~~~~~~~~~~~~~~~~~~~~~~~~~~~~~~~~~~~~~~~~~~~~~~~~~~~~~~~~~~~~~~~~
1201  CCATTCTTGC TGGCAGACGG CAAATGCACC GTGCCTCTAG CACCAGAACC TATGATAACC
                     VEE GLY
      ~~~~~~~~~~~~~~~~~~~~~~~~~~~~~~~~~~~~~~~~~~~~~~~~~~~~~~~~~~~~~~~~~~
1261  TTCGGTTTCA GATCAGTGTC ACTGAAACTG CACCCTAAGA ATCCCACATA TCTAATCACC
                     VEE GLY
      ~~~~~~~~~~~~~~~~~~~~~~~~~~~~~~~~~~~~~~~~~~~~~~~~~~~~~~~~~~~~~~~~~~
1321  CGCCAACTTG CTGATGAGCC TCACTACACG CACGAGCTCA TATCTGAACC AGCTGTTAGG
                     VEE GLY
      ~~~~~~~~~~~~~~~~~~~~~~~~~~~~~~~~~~~~~~~~~~~~~~~~~~~~~~~~~~~~~~~~~~
1381  AATTTTACCG TCACCGAAAA AGGGTGGGAG TTTGTATGGG GAAACCACCC GCCGAAAAGG
                     VEE GLY
      ~~~~~~~~~~~~~~~~~~~~~~~~~~~~~~~~~~~~~~~~~~~~~~~~~~~~~~~~~~~~~~~~~~
1441  TTTTGGGCAC AGGAAACAGC ACCCGGAAAT CCACATGGGC TACCGCACGA GGTGATAACT
                     VEE GLY
      ~~~~~~~~~~~~~~~~~~~~~~~~~~~~~~~~~~~~~~~~~~~~~~~~~~~~~~~~~~~~~~~~~~
1501  CATTATTACC ACAGATACCC TATGTCCACC ATCCTGGGTT TGTCAATTTG TGCCGCCATT
                     VEE GLY
      ~~~~~~~~~~~~~~~~~~~~~~~~~~~~~~~~~~~~~~~~~~~~~~~~~~~~~~~~~~~~~~~~~~
1561  GCAACCGTTT CCGTTGCAGC GTCTACCTGG CTGTTTTGCA GATCTAGAGT TGCGTGCCTA
                     VEE GLY
      ~~~~~~~~~~~~~~~~~~~~~~~~~~~~~~~~~~~~~~~~~~~~~~~~~~~~~~~~~~~~~~~~~~
1621  ACTCCTTACC GGCTAACACC TAACGCTAGG ATACCATTTT GTCTGGCTGT GCTTTGCTGC
                     VEE GLY
      ~~~~~~~~~~~~~~~~~~~~~~~~~~~~~~~~~~~~~~~~~~~~~~~~~~~~~~~~~~~~~~~~~~
1681  GCCCGCACTG CCCGGGCCGA GACCACCTGG GAGTCCTTGG ATCACCTATG GAACAATAAC
                     VEE GLY
      ~~~~~~~~~~~~~~~~~~~~~~~~~~~~~~~~~~~~~~~~~~~~~~~~~~~~~~~~~~~~~~~~~~
1741  CAACAGATGT TCTGGATTCA ATTGCTGATC CCTCTGGCCG CCTTGATCGT AGTGACTCGC
                     VEE GLY
      ~~~~~~~~~~~~~~~~~~~~~~~~~~~~~~~~~~~~~~~~~~~~~~~~~~~~~~~~~~~~~~~~~~
1801  CTGCTCAGGT GCGTGTGCTG TGTCGTGCCT TTTTTAGTCA TGGCCGGCGC CGCAGGCGCC
                     VEE GLY
      ~~~~~~~~~~~~~~~~~~~~~~~~~~~~~~~~~~~~~~~~~~~~~~~~~~~~~~~~~~~~~~~~~~
1861  GGCGCCTACG AGCACGCGAC CACGATGCCG AGCCAAGCGG GAATCTCGTA TAACACTATA
                     VEE GLY
      ~~~~~~~~~~~~~~~~~~~~~~~~~~~~~~~~~~~~~~~~~~~~~~~~~~~~~~~~~~~~~~~~~~
1921  GTCAACAGAG CAGGCTACGC ACCACTCCCT ATCAGCATAA CACCAACAAA GATCAAGCTG
                     VEE GLY
      ~~~~~~~~~~~~~~~~~~~~~~~~~~~~~~~~~~~~~~~~~~~~~~~~~~~~~~~~~~~~~~~~~~
1981  ATACCTACAG TGAACTTGGA GTACGTCACC TGCCACTACA AAACAGGAAT GGATTCACCA
```

-continued

SEQUENCES

```
                   VEE GLY
       ~~~~~~~~~~~~~~~~~~~~~~~~~~~~~~~~~~~~~~~~~~~~~~~~~~~~~~~~~~~~~~~~~
2041   GCCATCAAAT GCTGCGGATC TCAGGAATGC ACTCCAACTT ACAGGCCTGA TGAACAGTGC
                   VEE GLY
       ~~~~~~~~~~~~~~~~~~~~~~~~~~~~~~~~~~~~~~~~~~~~~~~~~~~~~~~~~~~~~~~~~
2101   AAAGTCTTCA CAGGGGTTTA CCCGTTCATG TGGGGTGGTG CATATTGCTT TTGCGACACT
                   VEE GLY
       ~~~~~~~~~~~~~~~~~~~~~~~~~~~~~~~~~~~~~~~~~~~~~~~~~~~~~~~~~~~~~~~~~
2161   GAGAACACCC AAGTCAGCAA GGCCTACGTA ATGAAATCTG ACGACTGCCT TGCGGATCAT
                   VEE GLY
       ~~~~~~~~~~~~~~~~~~~~~~~~~~~~~~~~~~~~~~~~~~~~~~~~~~~~~~~~~~~~~~~~~
2221   GCTGAAGCAT ATAAAGCGCA CACAGCCTCA GTGCAGGCGT TCCTCAACAT CACAGTGGGA
                   VEE GLY
       ~~~~~~~~~~~~~~~~~~~~~~~~~~~~~~~~~~~~~~~~~~~~~~~~~~~~~~~~~~~~~~~~~
2281   GAACACTCTA TTGTGACTAC CGTGTATGTG AATGGAGAAA CTCCTGTGAA TTTCAATGGG
                   VEE GLY
       ~~~~~~~~~~~~~~~~~~~~~~~~~~~~~~~~~~~~~~~~~~~~~~~~~~~~~~~~~~~~~~~~~
2341   GTCAAAATAA CTGCAGGTCC GCTTTCCACA GCTTGGACAC CCTTTGATCG CAAAATCGTG
                   VEE GLY
       ~~~~~~~~~~~~~~~~~~~~~~~~~~~~~~~~~~~~~~~~~~~~~~~~~~~~~~~~~~~~~~~~~
2401   CAGTATGCCG GGAGATCTA TAATTATGAT TTTCCTGAGT ATGGGGCAGG ACAACCAGGA
                   VEE GLY
       ~~~~~~~~~~~~~~~~~~~~~~~~~~~~~~~~~~~~~~~~~~~~~~~~~~~~~~~~~~~~~~~~~
2461   GCATTTGGAG ATATACAATC CAGAACAGTC TCAAGCTCTG ATCTGTATGC CAATACCAAC
                   VEE GLY
       ~~~~~~~~~~~~~~~~~~~~~~~~~~~~~~~~~~~~~~~~~~~~~~~~~~~~~~~~~~~~~~~~~
2521   CTAGTGCTGC AGAGACCCAA AGCAGGAGCG ATCCACGTGC CATACACTCA GGCACCTTCG
                   VEE GLY
       ~~~~~~~~~~~~~~~~~~~~~~~~~~~~~~~~~~~~~~~~~~~~~~~~~~~~~~~~~~~~~~~~~
2581   GGTTTTGAGC AATGGAAGAA AGATAAAGCT CCATCATTGA AATTTACCGC CCCTTTCGGA
                   VEE GLY
       ~~~~~~~~~~~~~~~~~~~~~~~~~~~~~~~~~~~~~~~~~~~~~~~~~~~~~~~~~~~~~~~~~
2641   TGCGAAATAT ATACAAACCC CATTCGCGCC GAAAACTGTG CTGTAGGGTC AATTCCATTA
                   VEE GLY
       ~~~~~~~~~~~~~~~~~~~~~~~~~~~~~~~~~~~~~~~~~~~~~~~~~~~~~~~~~~~~~~~~~
2701   GCCTTTGACA TTCCCGACGC CTTGTTCACC AGGGTGTCAG AAACACCGAC ACTTTCAGCG
                   VEE GLY
       ~~~~~~~~~~~~~~~~~~~~~~~~~~~~~~~~~~~~~~~~~~~~~~~~~~~~~~~~~~~~~~~~~
2761   GCCGAATGCA CTCTTAACGA GTGCGTGTAT TCTTCCGACT TTGGTGGGAT CGCCACGGTC
                   VEE GLY
       ~~~~~~~~~~~~~~~~~~~~~~~~~~~~~~~~~~~~~~~~~~~~~~~~~~~~~~~~~~~~~~~~~
2821   AAGTACTCGG CCAGCAAGTC AGGCAAGTGC GCAGTCCATG TGCCATCAGG GACTGCTACC
                   VEE GLY
       ~~~~~~~~~~~~~~~~~~~~~~~~~~~~~~~~~~~~~~~~~~~~~~~~~~~~~~~~~~~~~~~~~
2881   CTAAAAGAAG CAGCAGTCGA GCTAACCGAG CAAGGGTCGG CGACTATCCA TTTCTCGACC
                   VEE GLY
       ~~~~~~~~~~~~~~~~~~~~~~~~~~~~~~~~~~~~~~~~~~~~~~~~~~~~~~~~~~~~~~~~~
2941   GCAAATATCC ACCCGGAGTT CAGGCTCCAA ATATGCACAT CATATGTTAC GTGCAAAGGT
                   VEE GLY
       ~~~~~~~~~~~~~~~~~~~~~~~~~~~~~~~~~~~~~~~~~~~~~~~~~~~~~~~~~~~~~~~~~
3001   GATTGTCACC CCCCGAAAGA CCATATTGTG ACACACCCTC AGTATCACGC CCAAACATTT
                   VEE GLY
       ~~~~~~~~~~~~~~~~~~~~~~~~~~~~~~~~~~~~~~~~~~~~~~~~~~~~~~~~~~~~~~~~~
3061   ACAGCCGCGG TGTCAAAAAC CGCGTGGACG TGGTTAACAT CCCTGCTGGG AGGATCAGCC
                   VEE GLY
       ~~~~~~~~~~~~~~~~~~~~~~~~~~~~~~~~~~~~~~~~~~~~~~~~~~~~~~~~~~~~~~~~~
3121   GTAATTATTA TAATTGGCTT GGTGCTGGCT ACTATTGTGG CCATGTACGT GCTGACCAAC
       VEE GLY                        3'UTR
       ~~~~~~~~~~~~~~~~~~~~~~~ ~~~~~~~~~~~~~~~~~~~~~~~~~~~~~~~~~~
3181   CAGAAACATA ATTAATAGTA AGCGGCCGCA TACAGCAGCA ATTGGCAAGC TGCTTACATA
                    3'UTR
       ~~~~~~~~~~~~~~~~~~~~~~~~~~~~~~~~~~~~~~~~~~~~~~~~~~~~~~~~~~~~~~~~~
3241   GAACTCGCGG CGATTGGCAT GCCGCCTTAA AATTTTTATT TTATTTTTCT TTTCTTTTCC
       3'UTR
       ~~~~~~~~~~~~~~~~~~~~~~~~~~~~
3301   GAATCGGATT TTGTTTTTAA TATTTCAAAA AAAAAAAAAA AAAA AAAAAAAAAA
                  HDV ribozyme
       ~~~~~~~~~~~~~~~~~~~~~~~~~~~~~~~~~~~~~~~~~~~~~~~~~~~~~~~~~~~~~~~~
3361   AGGGTCGGCA TGGCATCTCC ACCTCCTCGC GGTCCGACCT GGGCATCCGA AGGAGGACGC
          HDV ribozyme
       ~~~~~~~~~~~~~~~~~~~~~~~~~~~~~~~~~~
3421   ACGTCCACTC GGATGGCTAA GGGAGAGCCA CGTTTAAACA CGTGATATCT GGCCTCATGG
3481   GCCTTCCTTT CACTGCCCGC TTTCCAGTCG GGAAACCTGT CGTGCCAGCT GCATTAACAT
3541   GGTCATAGCT GTTTCCTTGC GTATTGGGCG CTCTCCGCTT CCTCGCTCAC TGACTCGCTG
                                          colE1
                                ~~~~~~~~~~~~~~~~~~~~~~~~~~~
3601   CGCTCGGTCG TTCGGGTAAA GCCTGGGGTG CCTAATGAGC AAAAGGCCAG CAAAAGGCCA
```

-continued

SEQUENCES

```
                            colE1
         ~~~~~~~~~~~~~~~~~~~~~~~~~~~~~~~~~~~~~~~~~~~~~~~~~~~~~~~~~~~~
3661     GGAACCGTAA AAAGGCCGCG TTGCTGGCGT TTTTCCATAG GCTCCGCCCC CCTGACGAGC
                            colE1
         ~~~~~~~~~~~~~~~~~~~~~~~~~~~~~~~~~~~~~~~~~~~~~~~~~~~~~~~~~~~~
3721     ATCACAAAAA TCGACGCTCA AGTCAGAGGT GGCGAAACCC GACAGGACTA TAAAGATACC
                            colE1
         ~~~~~~~~~~~~~~~~~~~~~~~~~~~~~~~~~~~~~~~~~~~~~~~~~~~~~~~~~~~~
3781     AGGCGTTTCC CCCTGGAAGC TCCCTCGTGC GCTCTCCTGT TCCGACCCTG CCGCTTACCG
                            colE1
         ~~~~~~~~~~~~~~~~~~~~~~~~~~~~~~~~~~~~~~~~~~~~~~~~~~~~~~~~~~~~
3841     GATACCTGTC CGCCTTTCTC CCTTCGGGAA GCGTGGCGCT TTCTCATAGC TCACGCTGTA
                            colE1
         ~~~~~~~~~~~~~~~~~~~~~~~~~~~~~~~~~~~~~~~~~~~~~~~~~~~~~~~~~~~~
3901     GGTATCTCAG TTCGGTGTAG GTCGTTCGCT CCAAGCTGGG CTGTGTGCAC GAACCCCCCG
                            colE1
         ~~~~~~~~~~~~~~~~~~~~~~~~~~~~~~~~~~~~~~~~~~~~~~~~~~~~~~~~~~~~
3961     TTCAGCCCGA CCGCTGCGCC TTATCCGGTA ACTATCGTCT TGAGTCCAAC CCGGTAAGAC
                            colE1
         ~~~~~~~~~~~~~~~~~~~~~~~~~~~~~~~~~~~~~~~~~~~~~~~~~~~~~~~~~~~~
4021     ACGACTTATC GCCACTGGCA GCAGCCACTG GTAACAGGAT TAGCAGAGCG AGGTATGTAG
                            colE1
         ~~~~~~~~~~~~~~~~~~~~~~~~~~~~~~~~~~~~~~~~~~~~~~~~~~~~~~~~~~~~
4081     GCGGTGCTAC AGAGTTCTTG AAGTGGTGGC CTAACTACGG CTACACTAGA AGAACAGTAT
                            colE1
         ~~~~~~~~~~~~~~~~~~~~~~~~~~~~~~~~~~~~~~~~~~~~~~~~~~~~~~~~~~~~
4141     TTGGTATCTG CGCTCTGCTG AAGCCAGTTA CCTTCGGAAA AAGAGTTGGT AGCTCTTGAT
                            colE1
         ~~~~~~~~~~~~~~~~~~~~~~~~~~~~~~~~~~~~~~~~~~~~~~~~~~~~~~~~~~~~
4201     CCGGCAAACA AACCACCGCT GGTAGCGGTG GTTTTTTTGT TTGCAAGCAG CAGATTACGC
                     colE1
         ~~~~~~~~~~~~~~~~~~~~~~~~~~~~~~~~~~~~~~~~~~~
4261     GCAGAAAAAA AGGATCTCAA GAAGATCCTT TGATCTTTTC TACGGGGTCT GACGCTCAGT
4321     GGAACGAAAA CTCACGTTAA GGGATTTTGG TCATGAGATT ATCAAAAAGG ATCTTCACCT
4381     AGATCCTTTT AAATTAAAAA TGAAGTTTTA AATCAATCTA AAGTATATAT GAGTAAACTT
4441     GGTCTGACAG TTATTAGAAA AATTCATCCA GCAGACGATA AAACGCAATA CGCTGGCTAT
                    ~~~~~~~~~~~~~~~~~~~~~~~~~~~~~~~~~~~~~~~~~~~~~~~~
                                   KanR
4501     CCGGTGCCGC AATGCCATAC AGCACCAGAA AACGATCCGC CCATTCGCCG CCCAGTTCTT
         ~~~~~~~~~~~~~~~~~~~~~~~~~~~~~~~~~~~~~~~~~~~~~~~~~~~~~~~~~~~~
                             KanR
4561     CCGCAATATC ACGGGTGGCC AGCGCAATAT CCTGATAACG ATCCGCCACG CCCAGACGGC
         ~~~~~~~~~~~~~~~~~~~~~~~~~~~~~~~~~~~~~~~~~~~~~~~~~~~~~~~~~~~~
                             KanR
4621     CGCAATCAAT AAAGCCGCTA AAACGGCCAT TTTCCACCAT AATGTTCGGC AGGCACGCAT
         ~~~~~~~~~~~~~~~~~~~~~~~~~~~~~~~~~~~~~~~~~~~~~~~~~~~~~~~~~~~~
                             KanR
4681     CACCATGGGT CACCACCAGA TCTTCGCCAT CCGGCATGCT CGCTTTCAGA CGCGCAAACA
         ~~~~~~~~~~~~~~~~~~~~~~~~~~~~~~~~~~~~~~~~~~~~~~~~~~~~~~~~~~~~
                             KanR
4741     GCTCTGCCGG TGCCAGGCCC TGATGTTCTT CATCCAGATC ATCCTGATCC ACCAGGCCCG
         ~~~~~~~~~~~~~~~~~~~~~~~~~~~~~~~~~~~~~~~~~~~~~~~~~~~~~~~~~~~~
                             KanR
4801     CTTCCATACG GGTACGCGCA CGTTCAATAC GATGTTTCGC CTGATGATCA AACGGACAGG
         ~~~~~~~~~~~~~~~~~~~~~~~~~~~~~~~~~~~~~~~~~~~~~~~~~~~~~~~~~~~~
                             KanR
4861     TCGCCGGGTC CAGGGTATGC AGACGACGCA TGGCATCCGC CATAATGCTC ACTTTTTCTG
         ~~~~~~~~~~~~~~~~~~~~~~~~~~~~~~~~~~~~~~~~~~~~~~~~~~~~~~~~~~~~
                             KanR
4921     CCGGCGCCAG ATGGCTAGAC AGCAGATCCT GACCCGGCAC TTCGCCCAGC AGCAGCCAAT
         ~~~~~~~~~~~~~~~~~~~~~~~~~~~~~~~~~~~~~~~~~~~~~~~~~~~~~~~~~~~~
                             KanR
4981     CACGGCCCGC TTCGGTCACC ACATCCAGCA CCGCCGCACA CGGAACACCG GTGGTGGCCA
         ~~~~~~~~~~~~~~~~~~~~~~~~~~~~~~~~~~~~~~~~~~~~~~~~~~~~~~~~~~~~
                             KanR
5041     GCCAGCTCAG ACGCGCCGCT TCATCCTGCA GCTCGTTCAG CGCACCGCTC AGATCGGTTT
         ~~~~~~~~~~~~~~~~~~~~~~~~~~~~~~~~~~~~~~~~~~~~~~~~~~~~~~~~~~~~
                             KanR
5101     TCACAAACAG CACCGGACGA CCCTGCGCGC TCAGACGAAA CACCGCCGCA TCAGAGCAGC
         ~~~~~~~~~~~~~~~~~~~~~~~~~~~~~~~~~~~~~~~~~~~~~~~~~~~~~~~~~~~~
                             KanR
5161     CAATGGTCTG CTGCGCCCAA TCATAGCCAA ACAGACGTTC CACCCACGCT GCCGGGCTAC
         ~~~~~~~~~~~~~~~~~~~~~~~~~~~~~~~~~~~~~~~~~~~~~~~~~~~~~~~~~~~~
                             KanR
5221     CCGCATGCAG GCCATCCTGT TCAATCATAC TCTTCCTTTT TCAATATTAT TGAAGCATTT
         ~~~~~~~~~~~~~~~~~~~~~~~~~~~
              KanR
```

-continued

| SEQUENCES | |
|---|---|
| 5281 | ATCAGGGTTA TTGTCTCATG AGCGGATACA TATTTGAATG TATTTAGAAA AATAAACAAA |
| 5341 | TAGGGGTTCC GCGCACATTT CCCCGAAAAG TGCCACCTAA ATTGTAAGCG TTAATATTTT |
| 5401 | GTTAAAATTC GCGTTAAATT TTTGTTAAAT CAGCTCATTT TTTAACCAAT AGGCCGAAAT |
| 5461 | CGGCAAAATC CCTTATAAAT CAAAAGAATA GACCGAGATA GGGTTGAGTG GCCGCTACAG |
| 5521 | GGCGCTCCCA TTCGCCATTC AGGCTGCGCA ACTGTTGGGA AGGGCGTTTC GGTGCGGGCC |
| 5581 | TCTTCGCTAT TACGCCAGCT GGCGAAAGGG GGATGTGCTG CAAGGCGATT AAGTTGGGTA |
| | T7 promoter<br>~~~~~~~~~~~~~~~~~~~~ |
| 5641 | ACGCCAGGGT TTTCCCAGTC ACACGCGTAA TACGACTCAC TATAG |

The invention claimed is:

1. A method of forming a protein complex comprising:

delivering to a cell, a self-replicating RNA molecule comprising a polynucleotide that comprises:

a) a first nucleotide sequence encoding a first protein or fragment thereof from cytomegalovirus (CMV), wherein the first nucleotide sequence is operably linked to a first subgenomic promoter and followed by b);

b) a second nucleotide sequence encoding a second protein or fragment thereof from said CMV, wherein the second nucleotide sequence is operably linked to a second subgenomic promoter and followed by c);

c) a third nucleotide sequence encoding a third protein or fragment thereof from said CMV, wherein the third nucleotide sequence is operably linked to a third subgenomic promoter and followed by d);

d) a fourth nucleotide sequence encoding a fourth protein or fragment thereof from said CMV, wherein the fourth nucleotide sequence is operably linked to an IRES or a viral 2A site and followed by e); and e) a fifth nucleotide sequence encoding a fifth protein or fragment thereof from said CMV, wherein the fifth nucleotide sequence is operably linked to an IRES or a viral 2A site, wherein the first protein is gH, the second protein is gL, the third protein is UL128, the fourth protein is UL130, and the fifth protein is UL131; and maintaining the cell under conditions suitable for expression of the self-replicating RNA molecule, wherein the first, second, third, fourth and fifth CMV proteins or fragments thereof are expressed in an amount sufficient for the formation of a gH/gL/UL128/UL130/UL131 pentameric complex.

2. The method of claim 1, wherein the first protein consists of SEQ ID NO: 32 or a fragment thereof.

3. The method of claim 1, wherein the second protein consists of SEQ ID NO: 36 or a fragment thereof.

4. The method of claim 1, wherein the third protein consists of SEQ ID NO: 44 or a fragment thereof.

5. The method of claim 1, wherein the fourth protein consists of SEQ ID NO: 46 or a fragment thereof.

6. The method of claim 1, wherein the fifth protein consists of SEQ ID NO: 48 or a fragment thereof.

7. The method of claim 1, wherein the first protein consists of SEQ ID NO: 32 or a fragment thereof; the second protein consists of SEQ ID NO: 36 or a fragment thereof; the third protein consists of SEQ ID NO: 44 or a fragment thereof; the fourth protein consists of SEQ ID NO: 46 or a fragment thereof; and the fifth protein consists of SEQ ID NO: 48 or a fragment thereof.

8. The method of claim 7, wherein the self-replicating RNA molecule is encoded by a DNA sequence selected from the group consisting of SEQ ID NO: 56 (vector A526) and SEQ ID NO: 57 (vector A527).

9. The method of claim 1, wherein the self-replicating RNA molecule is an alphavirus replicon.

10. The method of claim 1, wherein the first, second and/or third subgenomic promoter comprises SEQ ID NO:51.

11. The method of claim 1, wherein the IRES, when present, comprises SEQ ID NO:49 or SEQ ID NO:50.

12. The method of claim 1, wherein the viral 2A site, when present, comprises SEQ ID NO:2.

13. The method of claim 12, wherein the viral 2A site, when present, comprises SEQ ID NO:3.

14. The method of claim 1, comprising delivering the self-replicating RNA molecule and an RNA delivery system to the cell.

15. The method of claim 14, wherein the RNA delivery system is a liposome, a polymeric nanoparticle, a lipid nanoparticle (LNP), an oil-in-water cationic nanoemulsion or combinations thereof.

16. The method of claim 1, wherein a recombinant DNA molecule encodes the self-replicating RNA molecule.

17. The method of claim 16, wherein the recombinant DNA molecule is a plasmid.

18. The method of claim 17, wherein the recombinant DNA molecule comprises a DNA sequence selected from the group consisting of SEQ ID NO: 56 (vector A526) and SEQ ID NO: 57 (vector A527).

19. The method of claim 1, wherein the cell is in vivo.

* * * * *

SEQUENCE LISTING

<160> NUMBER OF SEQ ID NOS: 85

<210> SEQ ID NO 1
<211> LENGTH: 24
<212> TYPE: DNA
<213> ORGANISM: Venezuelan equine encephalitis virus

<400> SEQUENCE: 1
ctctctacgg ctaacctgaa tgga 24

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic consensus sequence"
<220> FEATURE:
<221> NAME/KEY: VARIANT
<222> LOCATION: (2)..(2)
<223> OTHER INFORMATION: /replace="Ile"
<220> FEATURE:
<221> NAME/KEY: MOD_RES
<222> LOCATION: (4)..(4)
<223> OTHER INFORMATION: Any amino acid

<400> SEQUENCE: 2

Asp Val Glu Xaa Asn Pro Gly Pro
1 5

<210> SEQ ID NO 3
<211> LENGTH: 8
<212> TYPE: PRT
<213> ORGANISM: Foot and mouth disease virus

<400> SEQUENCE: 3

Asp Val Glu Ser Asn Pro Gly Pro
1 5

<210> SEQ ID NO 4
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"
<220> FEATURE:
<221> NAME/KEY: misc_feature
<222> LOCATION: (1)..(100)
<223> OTHER INFORMATION: /note="This sequence may encompass 3 to 100
'Lys' residues"

<400> SEQUENCE: 4

```
Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys Lys
                85                  90                  95

Lys Lys Lys Lys
            100


<210> SEQ ID NO 5
<211> LENGTH: 3
<212> TYPE: PRT
<213> ORGANISM: Unknown
<220> FEATURE:
<221> NAME/KEY: source
<223> OTHER INFORMATION: /note="Description of Unknown: integrin
      receptor-binding moiety peptide"

<400> SEQUENCE: 5

Arg Gly Asp
1


<210> SEQ ID NO 6
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 6

His His His His His His
1               5


<210> SEQ ID NO 7
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7

gggccc                                                                  6


<210> SEQ ID NO 8
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8

ggcgcc                                                                  6
```

<210> SEQ ID NO 9
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 9
ctcgatgtac ttccgaggaa ctgatgtg 28

<210> SEQ ID NO 10
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 10
atcgatgtac ttccgaggaa ctcacgtg 28

<210> SEQ ID NO 11
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 11 gtcgac 6

<210> SEQ ID NO 12
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 12 gtctac 6

<210> SEQ ID NO 13
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 13 tctaga 6

<210> SEQ ID NO 14
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 14 tcaaga 6

<210> SEQ ID NO 15
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 15
ctggatatct gcag 14

<210> SEQ ID NO 16
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
atcgatatcc gcgg 14

<210> SEQ ID NO 17
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 17
ctataactct ctacggctaa cctgaatgga ctacgacata gtctagtcga ccaagcctct 60
agacggcgcg cccaccca 78

<210> SEQ ID NO 18
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 18
ataagaatgc ggccgcctat aactctctac ggctaacc 38

<210> SEQ ID NO 19
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 19
ccatcgattg ggtgggcgcg ccgtctag 28

<210> SEQ ID NO 20
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 20
ccatcgatct ataactctct acggctaacc 30

<210> SEQ ID NO 21
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 21
tccccgcggt gggtgggcgc gccgtctag 29

<210> SEQ ID NO 22
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 22
ccactgtgat cg 12

<210> SEQ ID NO 23
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 23 cacgtg 6

<210> SEQ ID NO 24
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24 actgtg 6

<210> SEQ ID NO 25
<211> LENGTH: 2727
<212> TYPE: DNA
<213> ORGANISM: Human herpesvirus 5

<400> SEQUENCE: 25
atggaaagcc ggatctggtg cctggtcgtg tgcgtgaacc tgtgcatcgt gtgcctggga 60

-continued

```
gccgccgtga gcagcagcag caccagaggc accagcgcca cacacagcca ccacagcagc    120
cacaccacct ctgccgccca cagcagatcc ggcagcgtgt cccagagagt gaccagcagc    180
cagaccgtgt cccacggcgt gaacgagaca atctacaaca ccaccctgaa gtacggcgac    240
gtcgtgggcg tgaataccac caagtacccc tacagagtgt gcagcatggc ccagggcacc    300
gacctgatca gattcgagcg gaacatcgtg tgcaccagca tgaagcccat caacgaggac    360
ctggacgagg gcatcatggt ggtgtacaag agaaacatcg tggcccacac cttcaaagtg    420
cgggtgtacc agaaggtgct gaccttccgg cggagctacg cctacatcca caccacatac    480
ctgctgggca gcaacaccga gtacgtggcc cctcccatgt gggagatcca ccacatcaac    540
agccacagcc agtgctacag cagctacagc cgcgtgatcg ccggcacagt gttcgtggcc    600
taccaccggg acagctacga gaacaagacc atgcagctga tgcccgacga ctacagcaac    660
acccacagca ccagatacgt gaccgtgaag gaccagtggc acagcagagg cagcacctgg    720
ctgtaccggg agacatgcaa cctgaactgc atggtcacca tcaccaccgc cagaagcaag    780
taccccttacc acttcttcgc cacctccacc ggcgacgtgg tggacatcag cccctttctac    840
aacggcacca accggaacgc cagctacttc ggcgagaacg ccgacaagtt cttcatcttc    900
cccaactaca ccatcgtgtc cgacttcggc agacccaaca gcgctctgga aacccacaga    960
ctggtggcct ttctggaacg ggccgacagc gtgatcagct gggacatcca ggacgagaag   1020
aacgtgacct gccagctgac cttctgggag gcctctgaga gaaccatcag aagcgaggcc   1080
gaggacagct accacttcag cagcgccaag atgaccgcca ccttcctgag caagaaacag   1140
gaagtgaaca tgagcgactc cgccctggac tgcgtgaggg acgaggccat caacaagctg   1200
cagcagatct tcaacaccag ctacaaccag acctacgaga agtatggcaa tgtgtccgtg   1260
ttcgagacaa caggcggcct ggtggtgttc tggcagggca tcaagcagaa aagcctggtg   1320
gagctggaac ggctcgccaa ccggtccagc ctgaacctga cccacaaccg gaccaagcgg   1380
agcaccgacg gcaacaacgc aacccacctg tccaacatgg aaagcgtgca caacctggtg   1440
tacgcacagc tgcagttcac ctacgacacc ctgcggggct acatcaacag agccctggcc   1500
cagatcgccg aggcttggtg cgtggaccag cggcggaccc tggaagtgtt caaagagctg   1560
tccaagatca accccagcgc catcctgagc gccatctaca acaagcctat cgccgccaga   1620
ttcatgggcg acgtgctggg cctggccagc tgcgtgacca tcaaccagac cagcgtgaag   1680
gtgctgcggg acatgaacgt gaaagagagc ccaggccgct gctactccag acccgtggtc   1740
atcttcaact tcgccaacag ctcctacgtg cagtacggcc agctgggcga ggacaacgag   1800
atcctgctgg ggaaccaccg gaccgaggaa tgccagctgc ccagcctgaa gatctttatc   1860
gccggcaaca gcgcctacga gtatgtggac tacctgttca agcggatgat cgacctgagc   1920
agcatctcca ccgtggacag catgatcgcc ctggacatcg accccctgga aaacaccgac   1980
ttccgggtgc tggaactgta cagccagaaa gagctgcgga gcagcaacgt gttcgacctg   2040
gaagagatca tgcgggagtt caacagctac aagcagcgcg tgaaatacgt ggaggacaag   2100
gtggtggacc ccctgcctcc ttacctgaag ggcctggacg acctgatgag cggactgggc   2160
gctgccggaa aagccgtggg agtggccatt ggagctgtgg gcggagctgt ggcctctgtc   2220
gtggaaggcg tcgccacctt tctgaagaac cccttcggcg ccttcaccat catcctggtg   2280
gccattgccg tcgtgatcat cacctacctg atctacaccc ggcagcggag actgtgtacc   2340
cagcccctgc agaacctgtt cccctacctg gtgtccgccg atggcaccac agtgaccagc   2400
ggctccacca aggataccag cctgcaggcc ccacccagct acgaagagag cgtgtacaac   2460
```

agcggcagaa agggccctgg ccctcccagc tctgatgcca gcacagccgc ccctccctac 2520
accaacgagc aggcctacca gatgctgctg gccctggcta gactggatgc cgagcagagg 2580
gcccagcaga acggcaccga cagcctggat ggcagaaccg gcacccagga caagggccag 2640
aagcccaacc tgctggaccg gctgcggcac cggaagaacg gctaccggca cctgaaggac 2700
agcgacgagg aagagaacgt ctgataa 2727

<210> SEQ ID NO 26
<211> LENGTH: 907
<212> TYPE: PRT
<213> ORGANISM: Human herpesvirus 5

<400> SEQUENCE: 26

Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

-continued

```
Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
```

```
            740                 745                 750

Gly Ala Phe Thr Ile Ile Leu Val Ala Ile Ala Val Val Ile Ile Thr
        755                 760                 765

Tyr Leu Ile Tyr Thr Arg Gln Arg Arg Leu Cys Thr Gln Pro Leu Gln
    770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Ala Arg Leu Asp Ala Glu Gln Arg Ala Gln Gln Asn
    850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Glu Asn Val
            900                 905
```

<210> SEQ ID NO 27
<211> LENGTH: 2256
<212> TYPE: DNA
<213> ORGANISM: Human herpesvirus 5

<400> SEQUENCE: 27

```
atggaaagcc ggatctggtg cctggtcgtg tgcgtgaacc tgtgcatcgt gtgcctggga     60

gccgccgtga gcagcagcag caccagaggc accagcgcca cacacagcca ccacagcagc    120

cacaccacct ctgccgccca cagcagatcc ggcagcgtgt cccagagagt gaccagcagc    180

cagaccgtgt cccacggcgt gaacgagaca atctacaaca ccaccctgaa gtacggcgac    240

gtcgtgggcg tgaataccac caagtacccc tacagagtgt gcagcatggc ccagggcacc    300

gacctgatca gattcgagcg gaacatcgtg tgcaccagca tgaagcccat caacgaggac    360

ctggacgagg gcatcatggt ggtgtacaag agaaacatcg tggcccacac cttcaaagtg    420

cgggtgtacc agaaggtgct gaccttccgg cggagctacg cctacatcca caccacatac    480

ctgctgggca gcaacaccga gtacgtggcc cctcccatgt gggagatcca ccacatcaac    540

agccacagcc agtgctacag cagctacagc cgcgtgatcg ccggcacagt gttcgtggcc    600

taccaccggg acagctacga gaacaagacc atgcagctga tgcccgacga ctacagcaac    660

acccacagca ccagatacgt gaccgtgaag gaccagtggc acagcagagg cagcacctgg    720

ctgtaccggg agacatgcaa cctgaactgc atggtcacca tcaccaccgc cagaagcaag    780

taccccttacc acttcttcgc cacctccacc ggcgacgtgg tggacatcag ccccttctac    840

aacggcacca accggaacgc cagctacttc ggcgagaacg ccgacaagtt cttcatcttc    900

cccaactaca ccatcgtgtc cgacttcggc agacccaaca gcgctctgga aacccacaga    960

ctggtggcct ttctggaacg ggccgacagc gtgatcagct gggacatcca ggacgagaag   1020

aacgtgacct gccagctgac cttctgggag gcctctgaga gaaccatcag aagcgaggcc   1080

gaggacagct accacttcag cagcgccaag atgaccgcca ccttcctgag caagaaacag   1140

gaagtgaaca tgagcgactc cgccctggac tgcgtgaggg acgaggccat caacaagctg   1200
```

```
cagcagatct tcaacaccag ctacaaccag acctacgaga agtatggcaa tgtgtccgtg   1260

ttcgagacaa caggcggcct ggtggtgttc tggcagggca tcaagcagaa aagcctggtg   1320

gagctggaac ggctcgccaa ccggtccagc ctgaacctga cccacaaccg gaccaagcgg   1380

agcaccgacg gcaacaacgc aacccacctg tccaacatgg aaagcgtgca caacctggtg   1440

tacgcacagc tgcagttcac ctacgacacc ctgcggggct acatcaacag agccctggcc   1500

cagatcgccg aggcttggtg cgtggaccag cggcggaccc tggaagtgtt caaagagctg   1560

tccaagatca accccagcgc catcctgagc gccatctaca acaagcctat cgccgccaga   1620

ttcatgggcg acgtgctggg cctggccagc tgcgtgacca tcaaccagac cagcgtgaag   1680

gtgctgcggg acatgaacgt gaaagagagc ccaggccgct gctactccag acccgtggtc   1740

atcttcaact tcgccaacag ctcctacgtg cagtacggcc agctgggcga ggacaacgag   1800

atcctgctgg ggaaccaccg gaccgaggaa tgccagctgc ccagcctgaa gatctttatc   1860

gccggcaaca gcgcctacga gtatgtggac tacctgttca agcggatgat cgacctgagc   1920

agcatctcca ccgtggacag catgatcgcc ctggacatcg acccccctgga aaacaccgac   1980

ttccgggtgc tggaactgta cagccagaaa gagctgcgga gcagcaacgt gttcgacctg   2040

gaagagatca tgcgggagtt caacagctac aagcagcgcg tgaaatacgt ggaggacaag   2100

gtggtggacc ccctgcctcc ttacctgaag ggcctggacg acctgatgag cggactgggc   2160

gctgccggaa aagccgtggg agtggccatt ggagctgtgg gcggagctgt ggcctctgtc   2220

gtggaaggcg tcgccacctt tctgaagaac tgataa                             2256
```

<210> SEQ ID NO 28
<211> LENGTH: 750
<212> TYPE: PRT
<213> ORGANISM: Human herpesvirus 5

<400> SEQUENCE: 28

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
```

-continued

```
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605
```

```
Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn
            740                 745                 750
```

<210> SEQ ID NO 29
<211> LENGTH: 2082
<212> TYPE: DNA
<213> ORGANISM: Human herpesvirus 5

<400> SEQUENCE: 29

```
atggaaagcc ggatctggtg cctggtcgtg tgcgtgaacc tgtgcatcgt gtgcctggga      60

gccgccgtga gcagcagcag caccagaggc accagcgcca cacacagcca ccacagcagc     120

cacaccacct ctgccgccca cagcagatcc ggcagcgtgt cccagagagt gaccagcagc     180

cagaccgtgt cccacggcgt gaacgagaca atctacaaca ccaccctgaa gtacggcgac     240

gtcgtgggcg tgaataccac caagtacccc tacagagtgt gcagcatggc ccagggcacc     300

gacctgatca gattcgagcg gaacatcgtg tgcaccagca tgaagcccat caacgaggac     360

ctggacgagg gcatcatggt ggtgtacaag agaaacatcg tggcccacac cttcaaagtg     420

cgggtgtacc agaaggtgct gaccttccgg cggagctacg cctacatcca caccacatac     480

ctgctgggca gcaacaccga gtacgtggcc cctcccatgt gggagatcca ccacatcaac     540

agccacagcc agtgctacag cagctacagc cgcgtgatcg ccggcacagt gttcgtggcc     600

taccaccggg acagctacga gaacaagacc atgcagctga tgcccgacga ctacagcaac     660

acccacagca ccagatacgt gaccgtgaag gaccagtggc acagcagagg cagcacctgg     720

ctgtaccggg agacatgcaa cctgaactgc atggtcacca tcaccaccgc cagaagcaag     780

taccccttacc acttcttcgc cacctccacc ggcgacgtgg tggacatcag cccccttctac     840

aacggcacca accggaacgc cagctacttc ggcgagaacg ccgacaagtt cttcatcttc     900

cccaactaca ccatcgtgtc cgacttcggc agacccaaca gcgctctgga aacccacaga     960

ctggtggcct ttctggaacg ggccgacagc gtgatcagct gggacatcca ggacgagaag    1020

aacgtgacct gccagctgac cttctgggag gcctctgaga gaaccatcag aagcgaggcc    1080

gaggacagct accacttcag cagcgccaag atgaccgcca ccttcctgag caagaaacag    1140

gaagtgaaca tgagcgactc cgccctggac tgcgtgaggg acgaggccat caacaagctg    1200

cagcagatct tcaacaccag ctacaaccag acctacgaga agtatggcaa tgtgtccgtg    1260

ttcgagacaa caggcggcct ggtggtgttc tggcagggca tcaagcagaa aagcctggtg    1320
```

```
gagctggaac ggctcgccaa ccggtccagc ctgaacctga cccacaaccg gaccaagcgg   1380

agcaccgacg gcaacaacgc aacccacctg tccaacatgg aaagcgtgca caacctggtg   1440

tacgcacagc tgcagttcac ctacgacacc ctgcggggct acatcaacag agccctggcc   1500

cagatcgccg aggcttggtg cgtggaccag cggcggaccc tggaagtgtt caaagagctg   1560

tccaagatca accccagcgc catcctgagc gccatctaca acaagcctat cgccgccaga   1620

ttcatgggcg acgtgctggg cctggccagc tgcgtgacca tcaaccagac cagcgtgaag   1680

gtgctgcggg acatgaacgt gaaagagagc ccaggccgct gctactccag acccgtggtc   1740

atcttcaact tcgccaacag ctcctacgtg cagtacggcc agctgggcga ggacaacgag   1800

atcctgctgg ggaaccaccg gaccgaggaa tgccagctgc ccagcctgaa gatctttatc   1860

gccggcaaca gcgcctacga gtatgtggac tacctgttca agcggatgat cgacctgagc   1920

agcatctcca ccgtggacag catgatcgcc ctggacatcg accccctgga aaacaccgac   1980

ttccgggtgc tggaactgta cagccagaaa gagctgcgga gcagcaacgt gttcgacctg   2040

gaagagatca tgcgggagtt caacagctac aagcagtgat aa                      2082
```

```
<210> SEQ ID NO 30
<211> LENGTH: 692
<212> TYPE: PRT
<213> ORGANISM: Human herpesvirus 5

<400> SEQUENCE: 30

Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240
```

-continued

Leu Tyr Arg Glu Thr Cys Asn Leu Asn Cys Met Val Thr Ile Thr Thr
245 250 255

Ala Arg Ser Lys Tyr Pro Tyr His Phe Phe Ala Thr Ser Thr Gly Asp
260 265 270

Val Val Asp Ile Ser Pro Phe Tyr Asn Gly Thr Asn Arg Asn Ala Ser
275 280 285

Tyr Phe Gly Glu Asn Ala Asp Lys Phe Phe Ile Phe Pro Asn Tyr Thr
290 295 300

Ile Val Ser Asp Phe Gly Arg Pro Asn Ser Ala Leu Glu Thr His Arg
305 310 315 320

Leu Val Ala Phe Leu Glu Arg Ala Asp Ser Val Ile Ser Trp Asp Ile
325 330 335

Gln Asp Glu Lys Asn Val Thr Cys Gln Leu Thr Phe Trp Glu Ala Ser
340 345 350

Glu Arg Thr Ile Arg Ser Glu Ala Glu Asp Ser Tyr His Phe Ser Ser
355 360 365

Ala Lys Met Thr Ala Thr Phe Leu Ser Lys Lys Gln Glu Val Asn Met
370 375 380

Ser Asp Ser Ala Leu Asp Cys Val Arg Asp Glu Ala Ile Asn Lys Leu
385 390 395 400

Gln Gln Ile Phe Asn Thr Ser Tyr Asn Gln Thr Tyr Glu Lys Tyr Gly
405 410 415

Asn Val Ser Val Phe Glu Thr Thr Gly Gly Leu Val Val Phe Trp Gln
420 425 430

Gly Ile Lys Gln Lys Ser Leu Val Glu Leu Glu Arg Leu Ala Asn Arg
435 440 445

Ser Ser Leu Asn Leu Thr His Asn Arg Thr Lys Arg Ser Thr Asp Gly
450 455 460

Asn Asn Ala Thr His Leu Ser Asn Met Glu Ser Val His Asn Leu Val
465 470 475 480

Tyr Ala Gln Leu Gln Phe Thr Tyr Asp Thr Leu Arg Gly Tyr Ile Asn
485 490 495

Arg Ala Leu Ala Gln Ile Ala Glu Ala Trp Cys Val Asp Gln Arg Arg
500 505 510

Thr Leu Glu Val Phe Lys Glu Leu Ser Lys Ile Asn Pro Ser Ala Ile
515 520 525

Leu Ser Ala Ile Tyr Asn Lys Pro Ile Ala Ala Arg Phe Met Gly Asp
530 535 540

Val Leu Gly Leu Ala Ser Cys Val Thr Ile Asn Gln Thr Ser Val Lys
545 550 555 560

Val Leu Arg Asp Met Asn Val Lys Glu Ser Pro Gly Arg Cys Tyr Ser
565 570 575

Arg Pro Val Val Ile Phe Asn Phe Ala Asn Ser Ser Tyr Val Gln Tyr
580 585 590

Gly Gln Leu Gly Glu Asp Asn Glu Ile Leu Leu Gly Asn His Arg Thr
595 600 605

Glu Glu Cys Gln Leu Pro Ser Leu Lys Ile Phe Ile Ala Gly Asn Ser
610 615 620

Ala Tyr Glu Tyr Val Asp Tyr Leu Phe Lys Arg Met Ile Asp Leu Ser
625 630 635 640

Ser Ile Ser Thr Val Asp Ser Met Ile Ala Leu Asp Ile Asp Pro Leu
645 650 655

-continued

```
Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln
    690


<210> SEQ ID NO 31
<211> LENGTH: 2232
<212> TYPE: DNA
<213> ORGANISM: Human herpesvirus 5

<400> SEQUENCE: 31

atgaggcctg gcctgccctc ctacctgatc atcctggccg tgtgcctgtt cagccacctg     60

ctgtccagca gatacggcgc cgaggccgtg agcgagcccc tggacaaggc tttccacctg    120

ctgctgaaca cctacggcag acccatccgg tttctgcggg agaacaccac ccagtgcacc    180

tacaacagca gcctgcggaa cagcaccgtc gtgagagaga acgccatcag cttcaacttt    240

ttccagagct acaaccagta ctacgtgttc cacatgccca gatgcctgtt tgccggccct    300

ctggccgagc agttcctgaa ccaggtggac ctgaccgaga cactggaaag ataccagcag    360

cggctgaata cctacgccct ggtgtccaag gacctggcca gctaccggtc ctttagccag    420

cagctcaagg ctcaggatag cctcggcgag cagcctacca ccgtgccccc tcccatcgac    480

ctgagcatcc cccacgtgtg gatgcctccc cagaccaccc ctcacggctg gaccgagagc    540

cacaccacct ccggcctgca cagaccccac ttcaaccaga cctgcatcct gttcgacggc    600

cacgacctgc tgtttagcac cgtgaccccc tgcctgcacc agggcttcta cctgatcgac    660

gagctgagat acgtgaagat caccctgacc gaggatttct tcgtggtcac cgtgtccatc    720

gacgacgaca cccccatgct gctgatcttc ggccacctgc ccagagtgct gttcaaggcc    780

ccctaccagc gggacaactt catcctgcgg cagaccgaga agcacgagct gctggtgctg    840

gtcaagaagg accagctgaa ccggcactcc tacctgaagg accccgactt cctggacgcc    900

gccctggact tcaactacct ggacctgagc gccctgctga gaaacagctt ccacagatac    960

gccgtggacg tgctgaagtc cggacggtgc cagatgctcg atcggcggac cgtggagatg   1020

gccttcgcct atgccctcgc cctgttcgcc gctgccagac aggaagaggc tggcgcccag   1080

gtgtcagtgc ccagagccct ggatagacag gccgccctgc tgcagatcca ggaattcatg   1140

atcacctgcc tgagccagac cccccctaga accaccctgc tgctgtaccc cacagccgtg   1200

gatctggcca agagggccct gtggaccccc aaccagatca ccgacatcac aagcctcgtg   1260

cggctcgtgt acatcctgag caagcagaac cagcagcacc tgatccccca gtgggccctg   1320

agacagatcg ccgacttcgc cctgaagctg cacaagaccc atctggccag ctttctgagc   1380

gccttcgcca ggcaggaact gtacctgatg ggcagcctgg tccacagcat gctggtgcat   1440

accaccgagc ggcgggagat cttcatcgtg gagacaggcc tgtgtagcct ggccgagctg   1500

tcccacttta cccagctgct ggcccaccct caccacgagt acctgagcga cctgtacacc   1560

ccctgcagca gcagcggcag acgggaccac agcctggaac ggctgaccag actgttcccc   1620

gatgccaccg tgcctgctac agtgcctgcc gccctgtcca tcctgtccac catgcagccc   1680

agcaccctgg aaaccttccc cgacctgttc tgcctgcccc tgggcgagag ctttagcgcc   1740

ctgaccgtgt ccgagcacgt gtcctacatc gtgaccaatc agtacctgat caagggcatc   1800

agctaccccg tgtccaccac agtcgtgggc cagagcctga tcatcaccca gaccgacagc   1860
```

-continued cagaccaagt gcgagctgac ccggaacatg cacaccacac acagcatcac cgtggccctg 1920
aacatcagcc tggaaaactg cgctttctgt cagtctgccc tgctggaata cgacgatacc 1980
cagggcgtga tcaacatcat gtacatgcac gacagcgacg acgtgctgtt cgccctggac 2040
ccctacaacg aggtggtggt gtccagcccc cggacccact acctgatgct gctgaagaac 2100
ggcaccgtgc tggaagtgac cgacgtggtg gtggacgcca ccgacagcag actgctgatg 2160
atgagcgtgt acgccctgag cgccatcatc ggcatctacc tgctgtaccg gatgctgaaa 2220
acctgctgat aa 2232

<210> SEQ ID NO 32
<211> LENGTH: 742
<212> TYPE: PRT
<213> ORGANISM: Human herpesvirus 5

<400> SEQUENCE: 32

Met Arg Pro Gly Leu Pro Ser Tyr Leu Ile Ile Leu Ala Val Cys Leu
1 5 10 15

Phe Ser His Leu Leu Ser Ser Arg Tyr Gly Ala Glu Ala Val Ser Glu
20 25 30

Pro Leu Asp Lys Ala Phe His Leu Leu Leu Asn Thr Tyr Gly Arg Pro
35 40 45

Ile Arg Phe Leu Arg Glu Asn Thr Thr Gln Cys Thr Tyr Asn Ser Ser
50 55 60

Leu Arg Asn Ser Thr Val Val Arg Glu Asn Ala Ile Ser Phe Asn Phe
65 70 75 80

Phe Gln Ser Tyr Asn Gln Tyr Tyr Val Phe His Met Pro Arg Cys Leu
85 90 95

Phe Ala Gly Pro Leu Ala Glu Gln Phe Leu Asn Gln Val Asp Leu Thr
100 105 110

Glu Thr Leu Glu Arg Tyr Gln Gln Arg Leu Asn Thr Tyr Ala Leu Val
115 120 125

Ser Lys Asp Leu Ala Ser Tyr Arg Ser Phe Ser Gln Gln Leu Lys Ala
130 135 140

Gln Asp Ser Leu Gly Glu Gln Pro Thr Thr Val Pro Pro Pro Ile Asp
145 150 155 160

Leu Ser Ile Pro His Val Trp Met Pro Pro Gln Thr Thr Pro His Gly
165 170 175

Trp Thr Glu Ser His Thr Thr Ser Gly Leu His Arg Pro His Phe Asn
180 185 190

Gln Thr Cys Ile Leu Phe Asp Gly His Asp Leu Leu Phe Ser Thr Val
195 200 205

Thr Pro Cys Leu His Gln Gly Phe Tyr Leu Ile Asp Glu Leu Arg Tyr
210 215 220

Val Lys Ile Thr Leu Thr Glu Asp Phe Phe Val Val Thr Val Ser Ile
225 230 235 240

Asp Asp Asp Thr Pro Met Leu Leu Ile Phe Gly His Leu Pro Arg Val
245 250 255

Leu Phe Lys Ala Pro Tyr Gln Arg Asp Asn Phe Ile Leu Arg Gln Thr
260 265 270

Glu Lys His Glu Leu Leu Val Leu Val Lys Lys Asp Gln Leu Asn Arg
275 280 285

His Ser Tyr Leu Lys Asp Pro Asp Phe Leu Asp Ala Ala Leu Asp Phe
290 295 300

-continued

Asn Tyr Leu Asp Leu Ser Ala Leu Leu Arg Asn Ser Phe His Arg Tyr
305 310 315 320

Ala Val Asp Val Leu Lys Ser Gly Arg Cys Gln Met Leu Asp Arg Arg
325 330 335

Thr Val Glu Met Ala Phe Ala Tyr Ala Leu Ala Leu Phe Ala Ala Ala
340 345 350

Arg Gln Glu Glu Ala Gly Ala Gln Val Ser Val Pro Arg Ala Leu Asp
355 360 365

Arg Gln Ala Ala Leu Leu Gln Ile Gln Glu Phe Met Ile Thr Cys Leu
370 375 380

Ser Gln Thr Pro Pro Arg Thr Thr Leu Leu Leu Tyr Pro Thr Ala Val
385 390 395 400

Asp Leu Ala Lys Arg Ala Leu Trp Thr Pro Asn Gln Ile Thr Asp Ile
405 410 415

Thr Ser Leu Val Arg Leu Val Tyr Ile Leu Ser Lys Gln Asn Gln Gln
420 425 430

His Leu Ile Pro Gln Trp Ala Leu Arg Gln Ile Ala Asp Phe Ala Leu
435 440 445

Lys Leu His Lys Thr His Leu Ala Ser Phe Leu Ser Ala Phe Ala Arg
450 455 460

Gln Glu Leu Tyr Leu Met Gly Ser Leu Val His Ser Met Leu Val His
465 470 475 480

Thr Thr Glu Arg Arg Glu Ile Phe Ile Val Glu Thr Gly Leu Cys Ser
485 490 495

Leu Ala Glu Leu Ser His Phe Thr Gln Leu Leu Ala His Pro His His
500 505 510

Glu Tyr Leu Ser Asp Leu Tyr Thr Pro Cys Ser Ser Ser Gly Arg Arg
515 520 525

Asp His Ser Leu Glu Arg Leu Thr Arg Leu Phe Pro Asp Ala Thr Val
530 535 540

Pro Ala Thr Val Pro Ala Ala Leu Ser Ile Leu Ser Thr Met Gln Pro
545 550 555 560

Ser Thr Leu Glu Thr Phe Pro Asp Leu Phe Cys Leu Pro Leu Gly Glu
565 570 575

Ser Phe Ser Ala Leu Thr Val Ser Glu His Val Ser Tyr Ile Val Thr
580 585 590

Asn Gln Tyr Leu Ile Lys Gly Ile Ser Tyr Pro Val Ser Thr Thr Val
595 600 605

Val Gly Gln Ser Leu Ile Ile Thr Gln Thr Asp Ser Gln Thr Lys Cys
610 615 620

Glu Leu Thr Arg Asn Met His Thr Thr His Ser Ile Thr Val Ala Leu
625 630 635 640

Asn Ile Ser Leu Glu Asn Cys Ala Phe Cys Gln Ser Ala Leu Leu Glu
645 650 655

Tyr Asp Asp Thr Gln Gly Val Ile Asn Ile Met Tyr Met His Asp Ser
660 665 670

Asp Asp Val Leu Phe Ala Leu Asp Pro Tyr Asn Glu Val Val Val Ser
675 680 685

Ser Pro Arg Thr His Tyr Leu Met Leu Leu Lys Asn Gly Thr Val Leu
690 695 700

Glu Val Thr Asp Val Val Val Asp Ala Thr Asp Ser Arg Leu Leu Met
705 710 715 720

Met Ser Val Tyr Ala Leu Ser Ala Ile Ile Gly Ile Tyr Leu Leu Tyr

```
                725                 730                 735

Arg Met Leu Lys Thr Cys
            740


<210> SEQ ID NO 33
<211> LENGTH: 2151
<212> TYPE: DNA
<213> ORGANISM: Human herpesvirus 5

<400> SEQUENCE: 33

atgaggcctg gcctgccctc ctacctgatc atcctggccg tgtgcctgtt cagccacctg      60

ctgtccagca gatacggcgc cgaggccgtg agcgagcccc tggacaaggc tttccacctg     120

ctgctgaaca cctacggcag acccatccgg tttctgcggg agaacaccac ccagtgcacc     180

tacaacagca gcctgcggaa cagcaccgtc gtgagagaga acgccatcag cttcaacttt     240

ttccagagct acaaccagta ctacgtgttc cacatgccca gatgcctgtt tgccggccct     300

ctggccgagc agttcctgaa ccaggtggac ctgaccgaga cactggaaag ataccagcag     360

cggctgaata cctacgccct ggtgtccaag gacctggcca gctaccggtc ctttagccag     420

cagctcaagg ctcaggatag cctcggcgag cagcctacca ccgtgccccc tcccatcgac     480

ctgagcatcc cccacgtgtg gatgcctccc cagaccaccc ctcacggctg gaccgagagc     540

cacaccacct ccggcctgca cagaccccac ttcaaccaga cctgcatcct gttcgacggc     600

cacgacctgc tgtttagcac cgtgaccccc tgcctgcacc agggcttcta cctgatcgac     660

gagctgagat acgtgaagat caccctgacc gaggatttct tcgtggtcac cgtgtccatc     720

gacgacgaca cccccatgct gctgatcttc ggccacctgc ccagagtgct gttcaaggcc     780

ccctaccagc gggacaactt catcctgcgg cagaccgaga agcacgagct gctggtgctg     840

gtcaagaagg accagctgaa ccggcactcc tacctgaagg accccgactt cctggacgcc     900

gccctggact tcaactacct ggacctgagc gccctgctga gaaacagctt ccacagatac     960

gccgtggacg tgctgaagtc cggacggtgc cagatgctcg atcggcggac cgtggagatg    1020

gccttcgcct atgccctcgc cctgttcgcc gctgccagac aggaagaggc tggcgcccag    1080

gtgtcagtgc ccagagccct ggatagacag gccgccctgc tgcagatcca ggaattcatg    1140

atcacctgcc tgagccagac ccccccctaga accaccctgc tgctgtaccc cacagccgtg    1200

gatctggcca agagggccct gtggaccccc aaccagatca ccgacatcac aagcctcgtg    1260

cggctcgtgt acatcctgag caagcagaac cagcagcacc tgatccccca gtgggccctg    1320

agacagatcg ccgacttcgc cctgaagctg cacaagaccc atctggccag ctttctgagc    1380

gccttcgcca ggcaggaact gtacctgatg ggcagcctgg tccacagcat gctggtgcat    1440

accaccgagc ggcgggagat cttcatcgtg gagacaggcc tgtgtagcct ggccgagctg    1500

tcccacttta cccagctgct ggcccaccct caccacgagt acctgagcga cctgtacacc    1560

ccctgcagca gcagcggcag acgggaccac agcctggaac ggctgaccag actgttcccc    1620

gatgccaccg tgcctgctac agtgcctgcc gccctgtcca tcctgtccac catgcagccc    1680

agcaccctgg aaaccttccc cgacctgttc tgcctgcccc tgggcgagag ctttagcgcc    1740

ctgaccgtgt ccgagcacgt gtcctacatc gtgaccaatc agtacctgat caagggcatc    1800

agctaccccg tgtccaccac agtcgtgggc cagagcctga tcatcaccca gaccgacagc    1860

cagaccaagt gcgagctgac ccggaacatg cacaccacac acagcatcac cgtggccctg    1920

aacatcagcc tggaaaactg cgctttctgt cagtctgccc tgctggaata cgacgatacc    1980
```

```
cagggcgtga tcaacatcat gtacatgcac gacagcgacg acgtgctgtt cgccctggac   2040

ccctacaacg aggtggtggt gtccagcccc cggacccact acctgatgct gctgaagaac   2100

ggcaccgtgc tggaagtgac cgacgtggtg gtggacgcca ccgactgata a            2151


<210> SEQ ID NO 34
<211> LENGTH: 715
<212> TYPE: PRT
<213> ORGANISM: Human herpesvirus 5

<400> SEQUENCE: 34

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350
```

```
Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685

Ser Pro Arg Thr His Tyr Leu Met Leu Leu Lys Asn Gly Thr Val Leu
    690                 695                 700

Glu Val Thr Asp Val Val Val Asp Ala Thr Asp
705                 710                 715
```

<210> SEQ ID NO 35
<211> LENGTH: 840
<212> TYPE: DNA
<213> ORGANISM: Human herpesvirus 5

<400> SEQUENCE: 35

```
atgtgcagaa ggcccgactg cggcttcagc ttcagccctg gacccgtgat cctgctgtgg      60
```

```
tgctgcctgc tgctgcctat cgtgtcctct gccgccgtgt ctgtggcccc tacagccgcc    120

gagaaggtgc cagccgagtg ccccgagctg accagaagat gcctgctggg cgaggtgttc    180

gagggcgaca agtacgagag ctggctgcgg cccctggtca acgtgaccgg cagagatggc    240

cccctgagcc agctgatccg gtacagaccc gtgacccccg aggccgccaa tagcgtgctg    300

ctggacgagg ccttcctgga taccctggcc ctgctgtaca acaaccccga ccagctgaga    360

gccctgctga ccctgctgtc cagcgacacc gcccccagat ggatgaccgt gatgcggggc    420

tacagcgagt gtggagatgg cagccctgcc gtgtacacct gcgtggacga cctgtgcaga    480

ggctacgacc tgaccagact gagctacggc cggtccatct tcacagagca cgtgctgggc    540

ttcgagctgg tgcccccccag cctgttcaac gtggtggtgg ccatccggaa cgaggccacc    600

agaaccaaca gagccgtgcg gctgcctgtg tctacagccg ctgcacctga gggcatcaca    660

ctgttctacg gcctgtacaa cgccgtgaaa gagttctgcc tccggcacca gctggatccc    720

cccctgctga gacacctgga caagtactac gccggcctgc ccccagagct gaagcagacc    780

agagtgaacc tgcccgccca cagcagatat ggccctcagg ccgtggacgc cagatgataa    840
```

```
<210> SEQ ID NO 36
<211> LENGTH: 278
<212> TYPE: PRT
<213> ORGANISM: Human herpesvirus 5

<400> SEQUENCE: 36

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys
    50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240
```

```
Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275


<210> SEQ ID NO 37
<211> LENGTH: 1119
<212> TYPE: DNA
<213> ORGANISM: Human herpesvirus 5

<400> SEQUENCE: 37

atggccccca gccacgtgga caaagtgaac acccggactt ggagcgccag catcgtgttc      60

atggtgctga ccttcgtgaa cgtgtccgtg cacctggtgc tgtccaactt cccccacctg     120

ggctacccct gcgtgtacta ccacgtggtg gacttcgagc ggctgaacat gagcgcctac     180

aacgtgatgc acctgcacac ccccatgctg tttctggaca gcgtgcagct cgtgtgctac     240

gccgtgttca tgcagctggt gtttctggcc gtgaccatct actacctcgt gtgctggatc     300

aagatcagca tgcggaagga caagggcatg agcctgaacc agagcacccg ggacatcagc     360

tacatgggcg acagcctgac cgccttcctg ttcatcctga gcatggacac cttccagctg     420

ttcaccctga ccatgagctt ccggctgccc agcatgatcg ccttcatggc cgccgtgcac     480

tttttctgtc tgaccatctt caacgtgtcc atggtcaccc agtaccggtc ctacaagcgg     540

agcctgttct tcttctcccg gctgcacccc aagctgaagg gcaccgtgca gttccggacc     600

ctgatcgtga acctggtgga ggtggccctg ggcttcaata ccaccgtggt ggctatggcc     660

ctgtgctacg gcttcggcaa caacttcttc gtgcggaccg gccatatggt gctggccgtg     720

ttcgtggtgt acgccatcat cagcatcatc tactttctgc tgatcgaggc cgtgttcttc     780

cagtacgtga aggtgcagtt cggctaccat ctgggcgcct tttcggcct gtgcggcctg      840

atctacccca tcgtgcagta cgacaccttc ctgagcaacg agtaccggac cggcatcagc     900

tggtccttcg gaatgctgtt cttcatctgg gccatgttca ccacctgcag agccgtgcgg     960

tacttcagag gcagaggcag cggctccgtg aagtaccagg ccctggccac agcctctggc    1020

gaagaggtgg ccgccctgag ccaccacgac agcctggaaa gcagacggct gcgggaggaa    1080

gaggacgacg acgacgagga cttcgaggac gcctgataa                          1119


<210> SEQ ID NO 38
<211> LENGTH: 371
<212> TYPE: PRT
<213> ORGANISM: Human herpesvirus 5

<400> SEQUENCE: 38

Met Ala Pro Ser His Val Asp Lys Val Asn Thr Arg Thr Trp Ser Ala
1               5                   10                  15

Ser Ile Val Phe Met Val Leu Thr Phe Val Asn Val Ser Val His Leu
            20                  25                  30

Val Leu Ser Asn Phe Pro His Leu Gly Tyr Pro Cys Val Tyr Tyr His
        35                  40                  45

Val Val Asp Phe Glu Arg Leu Asn Met Ser Ala Tyr Asn Val Met His
    50                  55                  60

Leu His Thr Pro Met Leu Phe Leu Asp Ser Val Gln Leu Val Cys Tyr
65                  70                  75                  80
```

-continued

```
Ala Val Phe Met Gln Leu Val Phe Leu Ala Val Thr Ile Tyr Tyr Leu
                85                  90                  95

Val Cys Trp Ile Lys Ile Ser Met Arg Lys Asp Lys Gly Met Ser Leu
            100                 105                 110

Asn Gln Ser Thr Arg Asp Ile Ser Tyr Met Gly Asp Ser Leu Thr Ala
        115                 120                 125

Phe Leu Phe Ile Leu Ser Met Asp Thr Phe Gln Leu Phe Thr Leu Thr
    130                 135                 140

Met Ser Phe Arg Leu Pro Ser Met Ile Ala Phe Met Ala Ala Val His
145                 150                 155                 160

Phe Phe Cys Leu Thr Ile Phe Asn Val Ser Met Val Thr Gln Tyr Arg
                165                 170                 175

Ser Tyr Lys Arg Ser Leu Phe Phe Phe Ser Arg Leu His Pro Lys Leu
            180                 185                 190

Lys Gly Thr Val Gln Phe Arg Thr Leu Ile Val Asn Leu Val Glu Val
        195                 200                 205

Ala Leu Gly Phe Asn Thr Thr Val Val Ala Met Ala Leu Cys Tyr Gly
    210                 215                 220

Phe Gly Asn Asn Phe Phe Val Arg Thr Gly His Met Val Leu Ala Val
225                 230                 235                 240

Phe Val Val Tyr Ala Ile Ile Ser Ile Ile Tyr Phe Leu Leu Ile Glu
                245                 250                 255

Ala Val Phe Phe Gln Tyr Val Lys Val Gln Phe Gly Tyr His Leu Gly
            260                 265                 270

Ala Phe Phe Gly Leu Cys Gly Leu Ile Tyr Pro Ile Val Gln Tyr Asp
        275                 280                 285

Thr Phe Leu Ser Asn Glu Tyr Arg Thr Gly Ile Ser Trp Ser Phe Gly
    290                 295                 300

Met Leu Phe Phe Ile Trp Ala Met Phe Thr Thr Cys Arg Ala Val Arg
305                 310                 315                 320

Tyr Phe Arg Gly Arg Gly Ser Gly Ser Val Lys Tyr Gln Ala Leu Ala
                325                 330                 335

Thr Ala Ser Gly Glu Glu Val Ala Ala Leu Ser His His Asp Ser Leu
            340                 345                 350

Glu Ser Arg Arg Leu Arg Glu Glu Glu Asp Asp Asp Asp Glu Asp Phe
        355                 360                 365

Glu Asp Ala
    370
```

<210> SEQ ID NO 39
<211> LENGTH: 411
<212> TYPE: DNA
<213> ORGANISM: Human herpesvirus 5

<400> SEQUENCE: 39

```
atggaatgga acaccctggt cctgggcctg ctggtgctgt ctgtcgtggc cagcagcaac      60

aacacatcca cagccagcac ccctagacct agcagcagca cccacgccag cactaccgtg     120

aaggctacca ccgtggccac cacaagcacc accactgcta ccagcaccag ctccaccacc     180

tctgccaagc ctggctctac cacacacgac cccaacgtga tgaggcccca cgcccacaac     240

gacttctaca acgctcactg caccagccac atgtacgagc tgtccctgag cagctttgcc     300

gcctggtgga ccatgctgaa cgccctgatc ctgatgggcg ccttctgcat cgtgctgcgg     360

cactgctgct tccagaactt caccgccacc accaccaagg gctactgata a              411
```

<210> SEQ ID NO 40
<211> LENGTH: 135
<212> TYPE: PRT
<213> ORGANISM: Human herpesvirus 5

<400> SEQUENCE: 40

```
Met Glu Trp Asn Thr Leu Val Leu Gly Leu Leu Val Leu Ser Val Val
1               5                   10                  15

Ala Ser Ser Asn Asn Thr Ser Thr Ala Ser Thr Pro Arg Pro Ser Ser
            20                  25                  30

Ser Thr His Ala Ser Thr Thr Val Lys Ala Thr Thr Val Ala Thr Thr
        35                  40                  45

Ser Thr Thr Thr Ala Thr Ser Thr Ser Ser Thr Thr Ser Ala Lys Pro
    50                  55                  60

Gly Ser Thr Thr His Asp Pro Asn Val Met Arg Pro His Ala His Asn
65                  70                  75                  80

Asp Phe Tyr Asn Ala His Cys Thr Ser His Met Tyr Glu Leu Ser Leu
                85                  90                  95

Ser Ser Phe Ala Ala Trp Trp Thr Met Leu Asn Ala Leu Ile Leu Met
            100                 105                 110

Gly Ala Phe Cys Ile Val Leu Arg His Cys Cys Phe Gln Asn Phe Thr
        115                 120                 125

Ala Thr Thr Thr Lys Gly Tyr
    130                 135
```

<210> SEQ ID NO 41
<211> LENGTH: 1422
<212> TYPE: DNA
<213> ORGANISM: Human herpesvirus 5

<400> SEQUENCE: 41

```
atgggcaaga aagaaatgat catggtcaag ggcatcccca agatcatgct gctgattagc     60

atcacctttc tgctgctgtc cctgatcaac tgcaacgtgc tggtcaacag ccggggcacc    120

agaagatcct ggccctacac cgtgctgtcc taccggggca aagagatcct gaagaagcag    180

aaagaggaca tcctgaagcg gctgatgagc accagcagcg acggctaccg gttcctgatg    240

taccccagcc agcagaaatt ccacgccatc gtgatcagca tggacaagtt cccccaggac    300

tacatcctgg ccggacccat ccggaacgac agcatcaccc acatgtggtt cgacttctac    360

agcacccagc tgcggaagcc cgccaaatac gtgtacagcg agtacaacca caccgcccac    420

aagatcaccc tgaggcctcc cccttgtggc accgtgccca gcatgaactg cctgagcgag    480

atgctgaacg tgtccaagcg gaacgacacc ggcgagaagg gctgcggcaa cttcaccacc    540

ttcaacccca tgttcttcaa cgtgccccgg tggaacacca agctgtacat cggcagcaac    600

aaagtgaacg tggacagcca gaccatctac tttctgggcc tgaccgccct gctgctgaga    660

tacgcccagc ggaactgcac ccggtccttc tacctggtca acgccatgag ccggaacctg    720

ttccgggtgc ccaagtacat caacggcacc aagctgaaga acaccatgcg gaagctgaag    780

cggaagcagg ccctggtcaa agagcagccc cagaagaaga acaagaagtc ccagagcacc    840

accacccccct acctgagcta caccacctcc accgccttca acgtgaccac caacgtgacc    900

tacagcgcca cagccgccgt gaccagagtg gccacaagca ccaccggcta ccggcccgac    960

agcaacttta tgaagtccat catggccacc cagctgagag atctggccac ctgggtgtac   1020

accaccctgc ggtacagaaa cgagcccttc tgcaagcccg accggaacag aaccgccgtg   1080
```

```
agcgagttca tgaagaatac ccacgtgctg atcagaaacg agacacccta caccatctac   1140

ggcaccctgg acatgagcag cctgtactac aacgagacaa tgagcgtgga gaacgagaca   1200

gccagcgaca acaacgaaac cacccccacc tcccccagca cccggttcca gcggaccttc   1260

atcgaccccc tgtgggacta cctggacagc ctgctgttcc tggacaagat ccggaacttc   1320

agcctgcagc tgcccgccta cggcaatctg acccccccctg agcacagaag ggccgccaac   1380

ctgagcaccc tgaacagcct gtggtggtgg agccagtgat aa                      1422


<210> SEQ ID NO 42
<211> LENGTH: 472
<212> TYPE: PRT
<213> ORGANISM: Human herpesvirus 5

<400> SEQUENCE: 42

Met Gly Lys Lys Glu Met Ile Met Val Lys Gly Ile Pro Lys Ile Met
1               5                   10                  15

Leu Leu Ile Ser Ile Thr Phe Leu Leu Leu Ser Leu Ile Asn Cys Asn
            20                  25                  30

Val Leu Val Asn Ser Arg Gly Thr Arg Arg Ser Trp Pro Tyr Thr Val
        35                  40                  45

Leu Ser Tyr Arg Gly Lys Glu Ile Leu Lys Lys Gln Lys Glu Asp Ile
    50                  55                  60

Leu Lys Arg Leu Met Ser Thr Ser Ser Asp Gly Tyr Arg Phe Leu Met
65                  70                  75                  80

Tyr Pro Ser Gln Gln Lys Phe His Ala Ile Val Ile Ser Met Asp Lys
                85                  90                  95

Phe Pro Gln Asp Tyr Ile Leu Ala Gly Pro Ile Arg Asn Asp Ser Ile
            100                 105                 110

Thr His Met Trp Phe Asp Phe Tyr Ser Thr Gln Leu Arg Lys Pro Ala
        115                 120                 125

Lys Tyr Val Tyr Ser Glu Tyr Asn His Thr Ala His Lys Ile Thr Leu
    130                 135                 140

Arg Pro Pro Pro Cys Gly Thr Val Pro Ser Met Asn Cys Leu Ser Glu
145                 150                 155                 160

Met Leu Asn Val Ser Lys Arg Asn Asp Thr Gly Glu Lys Gly Cys Gly
                165                 170                 175

Asn Phe Thr Thr Phe Asn Pro Met Phe Phe Asn Val Pro Arg Trp Asn
            180                 185                 190

Thr Lys Leu Tyr Ile Gly Ser Asn Lys Val Asn Val Asp Ser Gln Thr
        195                 200                 205

Ile Tyr Phe Leu Gly Leu Thr Ala Leu Leu Leu Arg Tyr Ala Gln Arg
    210                 215                 220

Asn Cys Thr Arg Ser Phe Tyr Leu Val Asn Ala Met Ser Arg Asn Leu
225                 230                 235                 240

Phe Arg Val Pro Lys Tyr Ile Asn Gly Thr Lys Leu Lys Asn Thr Met
                245                 250                 255

Arg Lys Leu Lys Arg Lys Gln Ala Leu Val Lys Glu Gln Pro Gln Lys
            260                 265                 270

Lys Asn Lys Lys Ser Gln Ser Thr Thr Thr Pro Tyr Leu Ser Tyr Thr
        275                 280                 285

Thr Ser Thr Ala Phe Asn Val Thr Thr Asn Val Thr Tyr Ser Ala Thr
    290                 295                 300

Ala Ala Val Thr Arg Val Ala Thr Ser Thr Thr Gly Tyr Arg Pro Asp
305                 310                 315                 320
```

Ser Asn Phe Met Lys Ser Ile Met Ala Thr Gln Leu Arg Asp Leu Ala
325 330 335

Thr Trp Val Tyr Thr Thr Leu Arg Tyr Arg Asn Glu Pro Phe Cys Lys
340 345 350

Pro Asp Arg Asn Arg Thr Ala Val Ser Glu Phe Met Lys Asn Thr His
355 360 365

Val Leu Ile Arg Asn Glu Thr Pro Tyr Thr Ile Tyr Gly Thr Leu Asp
370 375 380

Met Ser Ser Leu Tyr Tyr Asn Glu Thr Met Ser Val Glu Asn Glu Thr
385 390 395 400

Ala Ser Asp Asn Asn Glu Thr Thr Pro Thr Ser Pro Ser Thr Arg Phe
405 410 415

Gln Arg Thr Phe Ile Asp Pro Leu Trp Asp Tyr Leu Asp Ser Leu Leu
420 425 430

Phe Leu Asp Lys Ile Arg Asn Phe Ser Leu Gln Leu Pro Ala Tyr Gly
435 440 445

Asn Leu Thr Pro Pro Glu His Arg Arg Ala Ala Asn Leu Ser Thr Leu
450 455 460

Asn Ser Leu Trp Trp Trp Ser Gln
465 470

<210> SEQ ID NO 43
<211> LENGTH: 519
<212> TYPE: DNA
<213> ORGANISM: Human herpesvirus 5

<400> SEQUENCE: 43
atgagcccca aggacctgac cccttcctg acaaccctgt ggctgctcct gggccatagc 60
agagtgccta gagtgcgggc cgaggaatgc tgcgagttca tcaacgtgaa ccaccccccc 120
gagcggtgct acgacttcaa gatgtgcaac cggttcaccg tggccctgag atgccccgac 180
ggcgaagtgt gctacagccc cgagaaaacc gccgagatcc ggggcatcgt gaccaccatg 240
acccacagcc tgacccggca ggtggtgcac aacaagctga ccagctgcaa ctacaacccc 300
ctgtacctgg aagccgacgg ccggatcaga tgcggcaaag tgaacgacaa ggcccagtac 360
ctgctgggag ccgccggaag cgtgccctac cggtggatca acctggaata cgacaagatc 420
acccggatcg tgggcctgga ccagtacctg gaaagcgtga agaagcacaa gcggctggac 480
gtgtgcagag ccaagatggg ctacatgctg cagtgataa 519

<210> SEQ ID NO 44
<211> LENGTH: 171
<212> TYPE: PRT
<213> ORGANISM: Human herpesvirus 5

<400> SEQUENCE: 44

Met Ser Pro Lys Asp Leu Thr Pro Phe Leu Thr Thr Leu Trp Leu Leu
1 5 10 15

Leu Gly His Ser Arg Val Pro Arg Val Arg Ala Glu Glu Cys Cys Glu
20 25 30

Phe Ile Asn Val Asn His Pro Pro Glu Arg Cys Tyr Asp Phe Lys Met
35 40 45

Cys Asn Arg Phe Thr Val Ala Leu Arg Cys Pro Asp Gly Glu Val Cys
50 55 60

Tyr Ser Pro Glu Lys Thr Ala Glu Ile Arg Gly Ile Val Thr Thr Met
65 70 75 80

Thr His Ser Leu Thr Arg Gln Val Val His Asn Lys Leu Thr Ser Cys
85 90 95

Asn Tyr Asn Pro Leu Tyr Leu Glu Ala Asp Gly Arg Ile Arg Cys Gly
100 105 110

Lys Val Asn Asp Lys Ala Gln Tyr Leu Leu Gly Ala Ala Gly Ser Val
115 120 125

Pro Tyr Arg Trp Ile Asn Leu Glu Tyr Asp Lys Ile Thr Arg Ile Val
130 135 140

Gly Leu Asp Gln Tyr Leu Glu Ser Val Lys Lys His Lys Arg Leu Asp
145 150 155 160

Val Cys Arg Ala Lys Met Gly Tyr Met Leu Gln
165 170

<210> SEQ ID NO 45
<211> LENGTH: 648
<212> TYPE: DNA
<213> ORGANISM: Human herpesvirus 5

<400> SEQUENCE: 45
atgctgcggc tgctgctgag acaccacttc cactgcctgc tgctgtgtgc cgtgtgggcc 60
accccttgtc tggccagccc ttggagcacc ctgaccgcca accagaaccc tagccccccct 120 tggtccaagc tgacctacag caagccccac gacgccgcca ccttctactg cccctttctg 180
taccccagcc ctcccagaag ccccctgcag ttcagcggct tccagagagt gtccaccggc 240
cctgagtgcc ggaacgagac actgtacctg ctgtacaacc gggagggcca gacactggtg 300
gagcggagca gcacctgggt gaaaaaagtg atctggtatc tgagcggccg gaaccagacc 360
atcctgcagc ggatgcccag aaccgccagc aagcccagcg acggcaacgt gcagatcagc 420
gtggaggacg ccaaaatctt cggcgcccac atggtgccca agcagaccaa gctgctgaga 480
ttcgtggtca acgacggcac cagatatcag atgtgcgtga tgaagctgga aagctgggcc 540
cacgtgttcc gggactactc cgtgagcttc caggtccggc tgaccttcac cgaggccaac 600
aaccagacct acaccttctg cacccacccc aacctgatcg tgtgataa 648

<210> SEQ ID NO 46
<211> LENGTH: 214
<212> TYPE: PRT
<213> ORGANISM: Human herpesvirus 5

<400> SEQUENCE: 46

Met Leu Arg Leu Leu Leu Arg His His Phe His Cys Leu Leu Leu Cys
1 5 10 15

Ala Val Trp Ala Thr Pro Cys Leu Ala Ser Pro Trp Ser Thr Leu Thr
20 25 30

Ala Asn Gln Asn Pro Ser Pro Pro Trp Ser Lys Leu Thr Tyr Ser Lys
35 40 45

Pro His Asp Ala Ala Thr Phe Tyr Cys Pro Phe Leu Tyr Pro Ser Pro
50 55 60

Pro Arg Ser Pro Leu Gln Phe Ser Gly Phe Gln Arg Val Ser Thr Gly
65 70 75 80

Pro Glu Cys Arg Asn Glu Thr Leu Tyr Leu Leu Tyr Asn Arg Glu Gly
85 90 95

Gln Thr Leu Val Glu Arg Ser Ser Thr Trp Val Lys Lys Val Ile Trp
100 105 110

Tyr Leu Ser Gly Arg Asn Gln Thr Ile Leu Gln Arg Met Pro Arg Thr

```
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
    210


<210> SEQ ID NO 47
<211> LENGTH: 393
<212> TYPE: DNA
<213> ORGANISM: Human herpesvirus 5

<400> SEQUENCE: 47

atgcggctgt gcagagtgtg gctgtccgtg tgcctgtgtg ccgtggtgct gggccagtgc      60

cagagagaga cagccgagaa gaacgactac taccgggtgc cccactactg ggatgcctgc     120

agcagagccc tgcccgacca gacccggtac aaatacgtgg agcagctcgt ggacctgacc     180

ctgaactacc actacgacgc cagccacggc ctggacaact tcgacgtgct gaagcggatc     240

aacgtgaccg aggtgtccct gctgatcagc gacttccggc ggcagaacag aagaggcggc     300

accaacaagc ggaccacctt caacgccgct ggctctctgg cccctcacgc cagatccctg     360

gaattcagcg tgcggctgtt cgccaactga taa                                  393


<210> SEQ ID NO 48
<211> LENGTH: 129
<212> TYPE: PRT
<213> ORGANISM: Human herpesvirus 5

<400> SEQUENCE: 48

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn


<210> SEQ ID NO 49
<211> LENGTH: 550
```

<212> TYPE: DNA
<213> ORGANISM: Encephalomyocarditis virus

<400> SEQUENCE: 49
aacgttactg gccgaagccg cttggaataa ggccggtgtg cgtttgtcta tatgttattt 60
tccaccatat tgccgtcttt tggcaatgtg agggcccgga aacctggccc tgtcttcttg 120
acgagcattc ctaggggtct ttcccctctc gccaaaggaa tgcaaggtct gttgaatgtc 180
gtgaaggaag cagttcctct ggaagcttct tgaagacaaa caacgtctgt agcgaccctt 240
tgcaggcagc ggaacccccc acctggcgac aggtgcctct gcggccaaaa gccacgtgta 300
taagatacac ctgcaaaggc ggcacaaccc cagtgccacg ttgtgagttg gatagttgtg 360
gaaagagtca aatggctctc ctcaagcgta ttcaacaagg ggctgaagga tgcccagaag 420
gtaccccatt gtatgggatc tgatctgggg cctcggtgca catgctttac atgtgtttag 480
tcgaggttaa aaaaacgtct aggccccccg aaccacgggg acgtggtttt cctttgaaaa 540
acacgataat 550

<210> SEQ ID NO 50
<211> LENGTH: 678
<212> TYPE: DNA
<213> ORGANISM: Human enterovirus 71

<400> SEQUENCE: 50
gtacctttgt acgcctgttt tatacccccct ccctgatttg caacttagaa gcaacgcaaa 60
ccagatcaat agtaggtgtg acataccagt cgcatcttga tcaagcactt ctgtatcccc 120
ggaccgagta tcaatagact gtgcacacgg ttgaaggaga aaacgtccgt tacccggcta 180
actacttcga gaagcctagt aacgccattg aagttgcaga gtgtttcgct cagcactccc 240
cccgtgtaga tcaggtcgat gagtcaccgc attccccacg ggcgaccgtg gcggtggctg 300
cgttggcggc ctgcctatgg ggtaacccat aggacgctct aatacggaca tggcgtgaag 360
agtctattga gctagttagt agtcctccgg cccctgaatg cggctaatcc taactgcgga 420
gcacataccc ttaatccaaa gggcagtgtg tcgtaacggg caactctgca gcggaaccga 480
ctactttggg tgtccgtgtt tcttttttatt cttgtattgg ctgcttatgg tgacaattaa 540
agaattgtta ccatatagct attggattgg ccatccagtg tcaaacagag ctattgtata 600
tctctttgtt ggattcacac ctctcactct tgaaacgtta cacaccctca attacattat 660
actgctgaac acgaagcg 678

<210> SEQ ID NO 51
<211> LENGTH: 24
<212> TYPE: DNA
<213> ORGANISM: Venezuelan equine encephalitis virus

<400> SEQUENCE: 51
ctctctacgg ctaacctgaa tgga 24

<210> SEQ ID NO 52
<211> LENGTH: 14071
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 52

-continued

```
cgcgtcggct acaattaata cataacctta tgtatcatac acatacgatt taggtgacac     60
tatagatggg cggcgcatga gagaagccca gaccaattac ctacccaaaa tggagaaagt    120
tcacgttgac atcgaggaag acagcccatt cctcagagct ttgcagcgga gcttcccgca    180
gtttgaggta gaagccaagc aggtcactga taatgaccat gctaatgcca gagcgttttc    240
gcatctggct tcaaaactga tcgaaacgga ggtggaccca tccgacacga tccttgacat    300
tggaagtgcg cccgcccgca gaatgtattc taagcacaag tatcattgta tctgtccgat    360
gagatgtgcg gaagatccgg acagattgta taagtatgca actaagctga agaaaaactg    420
taaggaaata actgataagg aattggacaa gaaaatgaag gagctcgccg ccgtcatgag    480
cgaccctgac ctggaaactg agactatgtg cctccacgac gacgagtcgt gtcgctacga    540
agggcaagtc gctgtttacc aggatgtata cgcggttgac ggaccgacaa gtctctatca    600
ccaagccaat aagggagtta gagtcgccta ctggataggc tttgacacca ccccttttat    660
gtttaagaac ttggctggag catatccatc atactctacc aactgggccg acgaaaccgt    720
gttaacggct cgtaacatag gcctatgcag ctctgacgtt atggagcggt cacgtagagg    780
gatgtccatt cttagaaaga agtatttgaa accatccaac aatgttctat tctctgttgg    840
ctcgaccatc taccacgaga agagggactt actgaggagc tggcacctgc cgtctgtatt    900
tcacttacgt ggcaagcaaa attacacatg tcggtgtgag actatagtta gttgcgacgg    960
gtacgtcgtt aaaagaatag ctatcagtcc aggcctgtat gggaagcctt caggctatgc   1020
tgctacgatg caccgcgagg gattcttgtg ctgcaaagtg acagacacat tgaacgggga   1080
gagggtctct tttcccgtgt gcacgtatgt gccagctaca ttgtgtgacc aaatgactgg   1140
catactggca acagatgtca gtgcggacga cgcgcaaaaa ctgctggttg ggctcaacca   1200
gcgtatagtc gtcaacggtc gcacccagag aaacaccaat accatgaaaa attacctttt   1260
gcccgtagtg gcccaggcat ttgctaggtg ggcaaaggaa tataaggaag atcaagaaga   1320
tgaaaggcca ctaggactac gagatagaca gttagtcatg gggtgttgtt gggcttttag   1380
aaggcacaag ataacatcta tttataagcg cccggatacc caaaccatca tcaaagtgaa   1440
cagcgatttc cactcattcg tgctgcccag gataggcagt aacacattgg agatcgggct   1500
gagaacaaga atcaggaaaa tgttagagga gcacaaggag ccgtcacctc tcattaccgc   1560
cgaggacgta caagaagcta agtgcgcagc cgatgaggct aaggaggtgc gtgaagccga   1620
ggagttgcgc gcagctctac cacctttggc agctgatgtt gaggagccca ctctggaagc   1680
cgatgtagac ttgatgttac aagaggctgg ggccggctca gtggagacac ctcgtggctt   1740
gataaaggtt accagctacg ctggcgagga caagatcggc tcttacgctg tgctttctcc   1800
gcaggctgta ctcaagagtg aaaaattatc ttgcatccac cctctcgctg aacaagtcat   1860
agtgataaca cactctggcc gaaaagggcg ttatgccgtg gaaccatacc atggtaaagt   1920
agtggtgcca gagggacatg caatacccgt ccaggacttt caagctctga gtgaaagtgc   1980
caccattgtg tacaacgaac gtgagttcgt aaacaggtac ctgcaccata ttgccacaca   2040
tggaggagcg ctgaacactg atgaagaata ttacaaaact gtcaagccca gcgagcacga   2100
cggcgaatac ctgtacgaca tcgacaggaa acagtgcgtc aagaaagaac tagtcactgg   2160
gctagggctc acaggcgagc tggtggatcc tcccttccat gaattcgcct acgagagtct   2220
gagaacacga ccagccgctc cttaccaagt accaaccata ggggtgtatg gcgtgccagg   2280
atcaggcaag tctggcatca ttaaaagcgc agtcaccaaa aaagatctag tggtgagcgc   2340
caagaaagaa aactgtgcag aaattataag ggacgtcaag aaaatgaaag ggctggacgt   2400
```

caatgccaga actgtggact cagtgctctt gaatggatgc aaacaccccg tagagaccct 2460
gtatattgac gaagcttttg cttgtcatgc aggtactctc agagcgctca tagccattat 2520
aagacctaaa aaggcagtgc tctgcgggga tcccaaacag tgcggttttt ttaacatgat 2580
gtgcctgaaa gtgcatttta accacgagat ttgcacacaa gtcttccaca aaagcatctc 2640
tcgccgttgc actaaatctg tgacttcggt cgtctcaacc ttgttttacg acaaaaaaat 2700
gagaacgacg aatccgaaag agactaagat tgtgattgac actaccggca gtaccaaacc 2760
taagcaggac gatctcattc tcacttgttt cagagggtgg gtgaagcagt tgcaaataga 2820
ttacaaaggc aacgaaataa tgacggcagc tgcctctcaa gggctgaccc gtaaaggtgt 2880
gtatgccgtt cggtacaagg tgaatgaaaa tcctctgtac gcacccacct cagaacatgt 2940
gaacgtccta ctgacccgca cggaggaccg catcgtgtgg aaaacactag ccggcgaccc 3000
atggataaaa acactgactg ccaagtaccc tgggaatttc actgccacga tagaggagtg 3060
gcaagcagag catgatgcca tcatgaggca catcttggag agaccggacc ctaccgacgt 3120
cttccagaat aaggcaaacg tgtgttgggc caaggcttta gtgccggtgc tgaagaccgc 3180
tggcatagac atgaccactg aacaatggaa cactgtggat tattttgaaa cggacaaagc 3240
tcactcagca gagatagtat tgaaccaact atgcgtgagg ttctttggac tcgatctgga 3300
ctccggtcta ttttctgcac ccactgttcc gttatccatt aggaataatc actgggataa 3360
ctccccgtcg cctaacatgt acgggctgaa taaagaagtg gtccgtcagc tctctcgcag 3420
gtacccacaa ctgcctcggg cagttgccac tggaagagtc tatgacatga acactggtac 3480
actgcgcaat tatgatccgc gcataaacct agtacctgta aacagaagac tgcctcatgc 3540
tttagtcctc caccataatg aacacccaca gagtgacttt tcttcattcg tcagcaaatt 3600
gaagggcaga actgtcctgg tggtcgggga aaagttgtcc gtcccaggca aaatggttga 3660
ctggttgtca gaccggcctg aggctacctt cagagctcgg ctggatttag gcatcccagg 3720
tgatgtgccc aaatatgaca taatatttgt taatgtgagg accccatata aataccatca 3780
ctatcagcag tgtgaagacc atgccattaa gcttagcatg ttgaccaaga aagcttgtct 3840
gcatctgaat cccggcggaa cctgtgtcag cataggttat ggttacgctg acagggccag 3900
cgaaagcatc attggtgcta tagcgcggca gttcaagttt tcccgggtat gcaaaccgaa 3960
atcctcactt gaagagacgg aagttctgtt tgtattcatt gggtacgatc gcaaggcccg 4020
tacgcacaat ccttacaagc tttcatcaac cttgaccaac atttatacag gttccagact 4080
ccacgaagcc ggatgtgcac cctcatatca tgtggtgcga ggggatattg ccacggccac 4140
cgaaggagtg attataaatg ctgctaacag caaaggacaa cctggcggag ggtgtgcgg 4200
agcgctgtat aagaaattcc cggaaagctt cgatttacag ccgatcgaag taggaaaagc 4260
gcgactggtc aaaggtgcag ctaaacatat cattcatgcc gtaggaccaa acttcaacaa 4320
agtttcggag gttgaaggtg acaaacagtt ggcagaggct tatgagtcca tcgctaagat 4380
tgtcaacgat aacaattaca agtcagtagc gattccactg ttgtccaccg gcatcttttc 4440
cgggaacaaa gatcgactaa cccaatcatt gaaccatttg ctgacagctt tagacaccac 4500
tgatgcagat gtagccatat actgcaggga caagaaatgg gaaatgactc tcaaggaagc 4560
agtggctagg agagaagcag tggaggagat atgcatatcc gacgactctt cagtgacaga 4620
acctgatgca gagctggtga gggtgcatcc gaagagttct ttggctggaa ggaagggcta 4680
cagcacaagc gatggcaaaa ctttctcata tttggaaggg accaagtttc accaggcggc 4740

-continued

```
caaggatata gcagaaatta atgccatgtg gcccgttgca acggaggcca atgagcaggt   4800
atgcatgtat atcctcggag aaagcatgag cagtattagg tcgaaatgcc ccgtcgaaga   4860
gtcggaagcc tcctcaccac ctagcacgct gccttgcttg tgcatccatg ccatgactcc   4920
agaaagagta cagcgcctaa aagcctcacg tccagaacaa attactgtgt gctcatcctt   4980
tccattgccg aagtatagaa tcactggtgt gcagaagatc caatgctccc agcctatatt   5040
gttctcaccg aaagtgcctg cgtatattca tccaaggaag tatctcgtgg aaacaccacc   5100
ggtagacgag actccggagc catcggcaga gaaccaatcc acagagggga cacctgaaca   5160
accaccactt ataaccgagg atgagaccag gactagaacg cctgagccga tcatcatcga   5220
agaggaagaa gaggatagca taagtttgct gtcagatggc ccgacccacc aggtgctgca   5280
agtcgaggca gacattcacg ggccgccctc tgtatctagc tcatcctggt ccattcctca   5340
tgcatccgac tttgatgtgg acagtttatc catacttgac accctggagg gagctagcgt   5400
gaccagcggg gcaacgtcag ccgagactaa ctcttacttc gcaaagagta tggagtttct   5460
ggcgcgaccg gtgcctgcgc ctcgaacagt attcaggaac cctccacatc ccgctccgcg   5520
cacaagaaca ccgtcacttg cacccagcag ggcctgctcg agagggatca cgggagaaac   5580
cgtgggatac gcggttacac acaatagcga gggcttcttg ctatgcaaag ttactgacac   5640
agtaaaagga gaacgggtat cgttccctgt gtgcacgtac atcccggcca ccataaactc   5700
gagaaccagc ctggtctcca acccgccagg cgtaaatagg gtgattacaa gagaggagtt   5760
tgaggcgttc gtagcacaac aacaatgacg gtttgatgcg ggtgcataca tcttttcctc   5820
cgacaccggt caagggcatt tacaacaaaa atcagtaagg caaacggtgc tatccgaagt   5880
ggtgttggag aggaccgaat tggagatttc gtatgccccg cgcctcgacc aagaaaaaga   5940
agaattacta cgcaagaaat tacagttaaa tcccacacct gctaacagaa gcagatacca   6000
gtccaggaag gtggagaaca tgaaagccat aacagctaga cgtattctgc aaggcctagg   6060
gcattatttg aaggcagaag gaaaagtgga gtgctaccga accctgcatc ctgttccttt   6120
gtattcatct agtgtgaacc gtgccttttc aagccccaag gtcgcagtgg aagcctgtaa   6180
cgccatgttg aaagagaact ttccgactgt ggcttcttac tgtattattc cagagtacga   6240
tgcctatttg gacatggttg acggagcttc atgctgctta gacactgcca gtttttgccc   6300
tgcaaagctg cgcagctttc caaagaaaca ctcctatttg gaacccacaa tacgatcggc   6360
agtgccttca gcgatccaga acacgctcca gaacgtcctg gcagctgcca caaaaagaaa   6420
ttgcaatgtc acgcaaatga gagaattgcc cgtattggat tcggcggcct ttaatgtgga   6480
atgcttcaag aaatatgcgt gtaataatga atattgggaa acgtttaaag aaaaccccat   6540
caggcttact gaagaaaacg tggtaaatta cattaccaaa ttaaaaggac caaaagctgc   6600
tgctcttttt gcgaagacac ataatttgaa tatgttgcag gacataccaa tggacaggtt   6660
tgtaatggac ttaaagagag acgtgaaagt gactccagga acaaaacata ctgaagaacg   6720
gcccaaggta caggtgatcc aggctgccga tccgctagca acagcgtatc tgtgcggaat   6780
ccaccgagag ctggttagga gattaaatgc ggtcctgctt ccgaacattc atacactgtt   6840
tgatatgtcg gctgaagact ttgacgctat tatagccgag cacttccagc ctggggattg   6900
tgttctggaa actgacatcg cgtcgtttga taaaagtgag gacgacgcca tggctctgac   6960
cgcgttaatg attctggaag acttaggtgt ggacgcagag ctgttgacgc tgattgaggc   7020
ggctttcggc gaaatttcat caatacattt gcccactaaa actaaattta aattcggagc   7080
catgatgaaa tctggaatgt tcctcacact gtttgtgaac acagtcatta acattgtaat   7140
```

cgcaagcaga gtgttgagag aacggctaac cggatcacca tgtgcagcat tcattggaga 7200
tgacaatatc gtgaaaggag tcaaatcgga caaattaatg gcagacaggt gcgccacctg 7260
gttgaatatg gaagtcaaga ttatagatgc tgtggtgggc gagaaagcgc cttatttctg 7320
tggagggttt attttgtgtg actccgtgac cggcacagcg tgccgtgtgg cagaccccct 7380
aaaaaggctg tttaagcttg gcaaacctct ggcagcagac gatgaacatg atgatgacag 7440
gagaagggca ttgcatgaag agtcaacacg ctggaaccga gtgggtattc tttcagagct 7500
gtgcaaggca gtagaatcaa ggtatgaaac cgtaggaact tccatcatag ttatggccat 7560
gactactcta gctagcagtg ttaaatcatt cagctacctg agaggggccc ctataactct 7620
ctacggctaa cctgaatgga ctacgacata gtctagtcga cgccaccatg aggcctggcc 7680
tgccctccta cctgatcatc ctggccgtgt gcctgttcag ccacctgctg tccagcagat 7740
acggcgccga ggccgtgagc gagcccctgg acaaggcttt ccacctgctg ctgaacacct 7800
acggcagacc catccggttt ctgcgggaga acaccaccca gtgcacctac aacagcagcc 7860
tgcggaacag caccgtcgtg agagagaacg ccatcagctt caactttttc cagagctaca 7920
accagtacta cgtgttccac atgcccagat gcctgtttgc cggccctctg gccgagcagt 7980
tcctgaacca ggtggacctg accgagacac tggaaagata ccagcagcgg ctgaatacct 8040
acgccctggt gtccaaggac ctggccagct accggtcctt tagccagcag ctcaaggctc 8100
aggatagcct cggcgagcag cctaccaccg tgccccctcc catcgacctg agcatccccc 8160
acgtgtggat gcctccccag accacccctc acggctggac cgagagccac accacctccg 8220
gcctgcacag accccacttc aaccagacct gcatcctgtt cgacggccac gacctgctgt 8280
ttagcaccgt gacccccctgc ctgcaccagg gcttctacct gatcgacgag ctgagatacg 8340
tgaagatcac cctgaccgag gatttcttcg tggtcaccgt gtccatcgac gacgacaccc 8400
ccatgctgct gatcttcggc cacctgccca gagtgctgtt caaggccccc taccagcggg 8460
acaacttcat cctgcggcag accgagaagc acgagctgct ggtgctggtc aagaaggacc 8520
agctgaaccg gcactcctac ctgaaggacc ccgacttcct ggacgccgcc ctggacttca 8580
actacctgga cctgagcgcc ctgctgagaa acagcttcca cagatacgcc gtggacgtgc 8640
tgaagtccgg acggtgccag atgctcgatc ggcggaccgt ggagatggcc ttcgcctatg 8700
ccctcgccct gttcgccgct gccagacagg aagaggctgg cgcccaggtg tcagtgccca 8760
gagccctgga tagacaggcc gccctgctgc agatccagga attcatgatc acctgcctga 8820
gccagacccc ccctagaacc accctgctgc tgtaccccac agccgtggat ctggccaaga 8880
gggccctgtg gacccccaac cagatcaccg acatcacaag cctcgtgcgg ctcgtgtaca 8940
tcctgagcaa gcagaaccag cagcacctga tcccccagtg ggccctgaga cagatcgccg 9000
acttcgccct gaagctgcac aagacccatc tggccagctt tctgagcgcc ttcgccaggc 9060
aggaactgta cctgatgggc agcctggtcc acagcatgct ggtgcatacc accgagcggc 9120
gggagatctt catcgtggag acaggcctgt gtagcctggc cgagctgtcc cactttaccc 9180
agctgctggc ccaccctcac cacgagtacc tgagcgacct gtacaccccc tgcagcagca 9240
gcggcagacg ggaccacagc ctggaacggc tgaccagact gttccccgat gccaccgtgc 9300
ctgctacagt gcctgccgcc ctgtccatcc tgtccaccat gcagcccagc accctggaaa 9360
ccttccccga cctgttctgc ctgcccctgg gcgagagctt tagcgccctg accgtgtccg 9420
agcacgtgtc ctacatcgtg accaatcagt acctgatcaa gggcatcagc taccccgtgt 9480

-continued ccaccacagt cgtgggccag agcctgatca tcacccagac cgacagccag accaagtgcg 9540
agctgacccg gaacatgcac accacacaca gcatcaccgt ggccctgaac atcagcctgg 9600
aaaactgcgc tttctgtcag tctgccctgc tggaatacga cgatacccag ggcgtgatca 9660
acatcatgta catgcacgac agcgacgacg tgctgttcgc cctggacccc tacaacgagg 9720
tggtggtgtc cagcccccgg acccactacc tgatgctgct gaagaacggc accgtgctgg 9780
aagtgaccga cgtggtggtg gacgccaccg actgataatc tagacggcgc gcccacccag 9840
cggccgccta taactctcta cggctaacct gaatggacta cgacatagtc tagtcgacgc 9900
caccatgtgc agaaggcccg actgcggctt cagcttcagc cctggacccg tgatcctgct 9960
gtggtgctgc ctgctgctgc ctatcgtgtc ctctgccgcc gtgtctgtgg cccctacagc 10020
cgccgagaag gtgccagccg agtgccccga gctgaccaga agatgcctgc tgggcgaggt 10080
gttcgagggc gacaagtacg agagctggct gcggcccctg gtcaacgtga ccggcagaga 10140
tggccccctg agccagctga tccggtacag acccgtgacc cccgaggccg ccaatagcgt 10200
gctgctggac gaggccttcc tggataccct ggccctgctg tacaacaacc ccgaccagct 10260
gagagccctg ctgaccctgc tgtccagcga caccgccccc agatggatga ccgtgatgcg 10320
gggctacagc gagtgtggag atggcagccc tgccgtgtac acctgcgtgg acgacctgtg 10380
cagaggctac gacctgacca gactgagcta cggccggtcc atcttcacag agcacgtgct 10440
gggcttcgag ctggtgcccc ccagcctgtt caacgtggtg gtggccatcc ggaacgaggc 10500
caccagaacc aacagagccg tgcggctgcc tgtgtctaca gccgctgcac ctgagggcat 10560
cacactgttc tacggcctgt acaacgccgt gaaagagttc tgcctccggc accagctgga 10620
tccccccctg ctgagacacc tggacaagta ctacgccggc ctgcccccag agctgaagca 10680
gaccagagtg aacctgcccg cccacagcag atatggccct caggccgtgg acgccagatg 10740
ataatctaga cggcgcgccc acccaatcga tgtacttccg aggaactcac gtgcataatg 10800
catcaggctg gtacattaga tccccgctta ccgcgggcaa tatagcaaca ctaaaaactc 10860
gatgtacttc cgaggaagcg cagtgcataa tgctgcgcag tgttgccaca taaccactat 10920
attaaccatt tatctagcgg acgccaaaaa ctcaatgtat ttctgaggaa gcgtggtgca 10980
taatgccacg cagcgtctgc ataactttta ttatttcttt tattaatcaa caaaattttg 11040
tttttaacat ttcaaaaaaa aaaaaaaaaa aaaaaaaaaa aaaaaaaaaa aaagggtcgg 11100
catggcatct ccacctcctc gcggtccgac ctgggcatcc gaaggaggac gcacgtccac 11160
tcggatggct aagggagagc cacgagctcc tgtttaaacc agctccaatt cgccctatag 11220
tgagtcgtat tacgcgcgct cactggccgt cgttttacaa cgtcgtgact gggaaaaccc 11280
tggcgttacc caacttaatc gccttgcagc acatccccct ttcgccagct ggcgtaatag 11340
cgaagaggcc cgcaccgatc gcccttccca acagttgcgc agcctgaatg gcgaatggga 11400
cgcgccctgt agcggcgcat taagcgcggc gggtgtggtg gttacgcgca gcgtgaccgc 11460
tacacttgcc agcgccctag cgcccgctcc tttcgctttc ttcccttcct ttctcgccac 11520
gttcgccggc tttccccgtc aagctctaaa tcgggggctc cctttagggt tccgatttag 11580
tgctttacgg cacctcgacc ccaaaaaact tgattagggt gatggttcac gtagtgggcc 11640
atcgccctga tagacggttt ttcgcccttt gacgttggag tccacgttct ttaatagtgg 11700
actcttgttc caaactggaa caacactcaa ccctatctcg gtctattctt ttgatttata 11760
agggattttg ccgatttcgg cctattggtt aaaaaatgag ctgatttaac aaaaatttaa 11820
cgcgaatttt aacaaaatat taacgcttac aatttaggtg gcactttctg gggaaatgtg 11880

-continued

```
cgcggaaccc ctatttgttt atttttctaa atacattcaa atatgtatcc gctcatgaga  11940
caataaccct gataaatgct tcaataatat tgaaaaagga agagtatgag tattcaacat  12000
ttccgtgtcg cccttattcc cttttttgcg gcattttgcc ttcctgtttt tgctcaccca  12060
gaaacgctgg tgaaagtaaa agatgctgaa gatcagttgg gtgcacgagt gggttacatc  12120
gaactggatc tcaacagcgg taagatcctt gagagttttc gccccgaaga acgttttcca  12180
atgatgagca cttttaaagt tctgctatgt ggcgcggtat tatcccgtat tgacgccggg  12240
caagagcaac tcggtcgccg catacactat tctcagaatg acttggttga gtactcacca  12300
gtcacagaaa agcatcttac ggatggcatg acagtaagag aattatgcag tgctgccata  12360
accatgagtg ataacactgc ggccaactta cttctgacaa cgatcggagg accgaaggag  12420
ctaaccgctt ttttgcacaa catgggggat catgtaactc gccttgatcg ttgggaaccg  12480
gagctgaatg aagccatacc aaacgacgag cgtgacacca cgatgcctgt agcaatggca  12540
acaacgttgc gcaaactatt aactggcgaa ctacttactc tagcttcccg gcaacaatta  12600
atagactgga tggaggcgga taaagttgca ggaccacttc tgcgctcggc ccttccggct  12660
ggctggttta ttgctgataa atctggagcc ggtgagcgtg ggtctcgcgg tatcattgca  12720
gcactggggc cagatggtaa gccctcccgt atcgtagtta tctacacgac ggggagtcag  12780
gcaactatgg atgaacgaaa tagacagatc gctgagatag gtgcctcact gattaagcat  12840
tggtaactgt cagaccaagt ttactcatat atactttaga ttgatttaaa acttcatttt  12900
taatttaaaa ggatctaggt gaagatcctt tttgataatc tcatgaccaa aatcccttaa  12960
cgtgagtttt cgttccactg agcgtcagac cccgtagaaa agatcaaagg atcttcttga  13020
gatccttttt ttctgcgcgt aatctgctgc ttgcaaacaa aaaaaccacc gctaccagcg  13080
gtggtttgtt tgccggatca agagctacca actctttttc cgaaggtaac tggcttcagc  13140
agagcgcaga taccaaatac tgttcttcta gtgtagccgt agttaggcca ccacttcaag  13200
aactctgtag caccgcctac atacctcgct ctgctaatcc tgttaccagt ggctgctgcc  13260
agtggcgata agtcgtgtct taccgggttg gactcaagac gatagttacc ggataaggcg  13320
cagcggtcgg gctgaacggg gggttcgtgc acacagccca gcttggagcg aacgacctac  13380
accgaactga gatacctaca gcgtgagcta tgagaaagcg ccacgcttcc cgaagggaga  13440
aaggcggaca ggtatccggt aagcggcagg gtcggaacag gagagcgcac gagggagctt  13500
ccagggggaa acgcctggta tctttatagt cctgtcgggt ttcgccacct ctgacttgag  13560
cgtcgatttt tgtgatgctc gtcagggggg cggagcctat ggaaaaacgc cagcaacgcg  13620
gcctttttac ggttcctggc cttttgctgg ccttttgctc acatgttctt tcctgcgtta  13680
tcccctgatt ctgtggataa ccgtattacc gcctttgagt gagctgatac cgctcgccgc  13740
agccgaacga ccgagcgcag cgagtcagtg agcgaggaag cggaagagcg cccaatacgc  13800
aaaccgcctc tccccgcgcg ttggccgatt cattaatgca gctggcacga caggtttccc  13860
gactggaaag cgggcagtga gcgcaacgca attaatgtga gttagctcac tcattaggca  13920
ccccaggctt tacactttat gctcccggct cgtatgttgt gtggaattgt gagcggataa  13980
caatttcaca caggaaacag ctatgaccat gattacgcca agcgcgcaat taaccctcac  14040
taaagggaac aaaagctggg taccggcgcc a                                 14071
```

<210> SEQ ID NO 53
<211> LENGTH: 14152
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53

```
cgcgtcggct acaattaata cataacctta tgtatcatac acatacgatt taggtgacac     60
tatagatggg cggcgcatga gagaagccca gaccaattac ctacccaaaa tggagaaagt    120
tcacgttgac atcgaggaag acagcccatt cctcagagct ttgcagcgga gcttcccgca    180
gtttgaggta gaagccaagc aggtcactga taatgaccat gctaatgcca gagcgttttc    240
gcatctggct tcaaaactga tcgaaacgga ggtggaccca tccgacacga tccttgacat    300
tggaagtgcg cccgcccgca gaatgtattc taagcacaag tatcattgta tctgtccgat    360
gagatgtgcg gaagatccgg acagattgta taagtatgca actaagctga agaaaaactg    420
taaggaaata actgataagg aattggacaa gaaaatgaag gagctcgccg ccgtcatgag    480
cgaccctgac ctggaaactg agactatgtg cctccacgac gacgagtcgt gtcgctacga    540
agggcaagtc gctgtttacc aggatgtata cgcggttgac ggaccgacaa gtctctatca    600
ccaagccaat aagggagtta gagtcgccta ctggataggc tttgacacca ccccttttat    660
gtttaagaac ttggctggag catatccatc atactctacc aactgggccg acgaaaccgt    720
gttaacggct cgtaacatag gcctatgcag ctctgacgtt atggagcggt cacgtagagg    780
gatgtccatt cttagaaaga agtatttgaa accatccaac aatgttctat tctctgttgg    840
ctcgaccatc taccacgaga agagggactt actgaggagc tggcacctgc cgtctgtatt    900
tcacttacgt ggcaagcaaa attacacatg tcggtgtgag actatagtta gttgcgacgg    960
gtacgtcgtt aaaagaatag ctatcagtcc aggcctgtat gggaagcctt caggctatgc   1020
tgctacgatg caccgcgagg gattcttgtg ctgcaaagtg acagacacat tgaacgggga   1080
gagggtctct ttcccgtgt gcacgtatgt gccagctaca ttgtgtgacc aaatgactgg   1140
catactggca acagatgtca gtgcggacga cgcgcaaaaa ctgctggttg ggctcaacca   1200
gcgtatagtc gtcaacggtc gcacccagag aaacaccaat accatgaaaa attacctttt   1260
gcccgtagtg gcccaggcat ttgctaggtg ggcaaaggaa tataaggaag atcaagaaga   1320
tgaaaggcca ctaggactac gagatagaca gttagtcatg gggtgttgtt gggcttttag   1380
aaggcacaag ataacatcta tttataagcg cccggatacc caaaccatca tcaaagtgaa   1440
cagcgatttc cactcattcg tgctgcccag gataggcagt aacacattgg agatcgggct   1500
gagaacaaga atcaggaaaa tgttagagga gcacaaggag ccgtcacctc tcattaccgc   1560
cgaggacgta caagaagcta agtgcgcagc cgatgaggct aaggaggtgc gtgaagccga   1620
ggagttgcgc gcagctctac cacctttggc agctgatgtt gaggagccca ctctggaagc   1680
cgatgtagac ttgatgttac aagaggctgg ggccggctca gtggagacac ctcgtggctt   1740
gataaaggtt accagctacg ctggcgagga caagatcggc tcttacgctg tgctttctcc   1800
gcaggctgta ctcaagagtg aaaaattatc ttgcatccac cctctcgctg aacaagtcat   1860
agtgataaca cactctggcc gaaaagggcg ttatgccgtg gaaccatacc atggtaaagt   1920
agtggtgcca gagggacatg caatacccgt ccaggacttt caagctctga gtgaaagtgc   1980
caccattgtg tacaacgaac gtgagttcgt aaacaggtac ctgcaccata ttgccacaca   2040
tggaggagcg ctgaacactg atgaagaata ttacaaaact gtcaagccca gcgagcacga   2100
cggcgaatac ctgtacgaca tcgacaggaa acagtgcgtc aagaaagaac tagtcactgg   2160
```

gctagggctc acaggcgagc tggtggatcc tcccttccat gaattcgcct acgagagtct 2220
gagaacacga ccagccgctc cttaccaagt accaaccata ggggtgtatg gcgtgccagg 2280
atcaggcaag tctggcatca ttaaaagcgc agtcaccaaa aaagatctag tggtgagcgc 2340
caagaaagaa aactgtgcag aaattataag ggacgtcaag aaaatgaaag ggctggacgt 2400
caatgccaga actgtggact cagtgctctt gaatggatgc aaacaccccg tagagaccct 2460
gtatattgac gaagcttttg cttgtcatgc aggtactctc agagcgctca tagccattat 2520
aagacctaaa aaggcagtgc tctgcgggga tcccaaacag tgcggttttt ttaacatgat 2580
gtgcctgaaa gtgcatttta accacgagat ttgcacacaa gtcttccaca aaagcatctc 2640
tcgccgttgc actaaatctg tgacttcggt cgtctcaacc ttgttttacg acaaaaaaat 2700
gagaacgacg aatccgaaag agactaagat tgtgattgac actaccggca gtaccaaacc 2760
taagcaggac gatctcattc tcacttgttt cagagggtgg gtgaagcagt tgcaaataga 2820
ttacaaaggc aacgaaataa tgacggcagc tgcctctcaa gggctgaccc gtaaaggtgt 2880
gtatgccgtt cggtacaagg tgaatgaaaa tcctctgtac gcacccacct cagaacatgt 2940
gaacgtccta ctgacccgca cggaggaccg catcgtgtgg aaaacactag ccggcgaccc 3000
atggataaaa acactgactg ccaagtaccc tgggaatttc actgccacga tagaggagtg 3060
gcaagcagag catgatgcca tcatgaggca catcttggag agaccggacc ctaccgacgt 3120
cttccagaat aaggcaaacg tgtgttgggc caaggcttta gtgccggtgc tgaagaccgc 3180
tggcatagac atgaccactg aacaatggaa cactgtggat tattttgaaa cggacaaagc 3240
tcactcagca gagatagtat tgaaccaact atgcgtgagg ttctttggac tcgatctgga 3300
ctccggtcta ttttctgcac ccactgttcc gttatccatt aggaataatc actgggataa 3360
ctccccgtcg cctaacatgt acgggctgaa taaagaagtg gtccgtcagc tctctcgcag 3420
gtacccacaa ctgcctcggg cagttgccac tggaagagtc tatgacatga acactggtac 3480
actgcgcaat tatgatccgc gcataaacct agtacctgta aacagaagac tgcctcatgc 3540
tttagtcctc caccataatg aacacccaca gagtgacttt tcttcattcg tcagcaaatt 3600
gaagggcaga actgtcctgg tggtcgggga aaagttgtcc gtcccaggca aaatggttga 3660
ctggttgtca gaccggcctg aggctacctt cagagctcgg ctggatttag gcatcccagg 3720
tgatgtgccc aaatatgaca taatatttgt taatgtgagg accccatata aataccatca 3780
ctatcagcag tgtgaagacc atgccattaa gcttagcatg ttgaccaaga aagcttgtct 3840
gcatctgaat cccggcggaa cctgtgtcag cataggttat ggttacgctg acagggccag 3900
cgaaagcatc attggtgcta tagcgcggca gttcaagttt tcccgggtat gcaaaccgaa 3960
atcctcactt gaagagacgg aagttctgtt tgtattcatt gggtacgatc gcaaggcccg 4020
tacgcacaat ccttacaagc tttcatcaac cttgaccaac atttatacag gttccagact 4080
ccacgaagcc ggatgtgcac cctcatatca tgtggtgcga ggggatattg ccacggccac 4140
cgaaggagtg attataaatg ctgctaacag caaaggacaa cctggcggag ggggtgtgcgg 4200 agcgctgtat aagaaattcc cggaaagctt cgatttacag ccgatcgaag taggaaaagc 4260
gcgactggtc aaaggtgcag ctaaacatat cattcatgcc gtaggaccaa acttcaacaa 4320
agtttcggag gttgaaggtg acaaacagtt ggcagaggct tatgagtcca tcgctaagat 4380
tgtcaacgat aacaattaca agtcagtagc gattccactg ttgtccaccg gcatcttttc 4440
cgggaacaaa gatcgactaa cccaatcatt gaaccatttg ctgacagctt tagacaccac 4500

-continued

```
tgatgcagat gtagccatat actgcaggga caagaaatgg gaaatgactc tcaaggaagc   4560
agtggctagg agagaagcag tggaggagat atgcatatcc gacgactctt cagtgacaga   4620
acctgatgca gagctggtga gggtgcatcc gaagagttct ttggctggaa ggaagggcta   4680
cagcacaagc gatggcaaaa ctttctcata tttggaaggg accaagtttc accaggcggc   4740
caaggatata gcagaaatta atgccatgtg gcccgttgca acggaggcca atgagcaggt   4800
atgcatgtat atcctcggag aaagcatgag cagtattagg tcgaaatgcc ccgtcgaaga   4860
gtcggaagcc tcctcaccac ctagcacgct gccttgcttg tgcatccatg ccatgactcc   4920
agaaagagta cagcgcctaa aagcctcacg tccagaacaa attactgtgt gctcatcctt   4980
tccattgccg aagtatagaa tcactggtgt gcagaagatc caatgctccc agcctatatt   5040
gttctcaccg aaagtgcctg cgtatattca tccaaggaag tatctcgtgg aaacaccacc   5100
ggtagacgag actccggagc catcggcaga gaaccaatcc acagagggga cacctgaaca   5160
accaccactt ataaccgagg atgagaccag gactagaacg cctgagccga tcatcatcga   5220
agaggaagaa gaggatagca taagtttgct gtcagatggc ccgacccacc aggtgctgca   5280
agtcgaggca gacattcacg ggccgccctc tgtatctagc tcatcctggt ccattcctca   5340
tgcatccgac tttgatgtgg acagtttatc catacttgac accctggagg gagctagcgt   5400
gaccagcggg gcaacgtcag ccgagactaa ctcttacttc gcaaagagta tggagtttct   5460
ggcgcgaccg gtgcctgcgc ctcgaacagt attcaggaac cctccacatc ccgctccgcg   5520
cacaagaaca ccgtcacttg cacccagcag ggcctgctcg agagggatca cgggagaaac   5580
cgtgggatac gcggttacac acaatagcga gggcttcttg ctatgcaaag ttactgacac   5640
agtaaaagga gaacgggtat cgttccctgt gtgcacgtac atcccggcca ccataaactc   5700
gagaaccagc ctggtctcca acccgccagg cgtaaatagg gtgattacaa gagaggagtt   5760
tgaggcgttc gtagcacaac aacaatgacg gtttgatgcg ggtgcataca tcttttcctc   5820
cgacaccggt caagggcatt tacaacaaaa atcagtaagg caaacggtgc tatccgaagt   5880
ggtgttggag aggaccgaat tggagatttc gtatgccccg cgcctcgacc aagaaaaaga   5940
agaattacta cgcaagaaat tacagttaaa tcccacacct gctaacagaa gcagatacca   6000
gtccaggaag gtggagaaca tgaaagccat aacagctaga cgtattctgc aaggcctagg   6060
gcattatttg aaggcagaag gaaaagtgga gtgctaccga accctgcatc ctgttccttt   6120
gtattcatct agtgtgaacc gtgccttttc aagccccaag gtcgcagtgg aagcctgtaa   6180
cgccatgttg aaagagaact ttccgactgt ggcttcttac tgtattattc cagagtacga   6240
tgcctatttg gacatggttg acggagcttc atgctgctta gacactgcca gtttttgccc   6300
tgcaaagctg cgcagctttc caaagaaaca ctcctatttg gaacccacaa tacgatcggc   6360
agtgccttca gcgatccaga acacgctcca gaacgtcctg gcagctgcca caaaaagaaa   6420
ttgcaatgtc acgcaaatga gagaattgcc cgtattggat tcggcggcct ttaatgtgga   6480
atgcttcaag aaatatgcgt gtaataatga atattgggaa acgtttaaag aaaacccat    6540
caggcttact gaagaaaacg tggtaaatta cattaccaaa ttaaaaggac caaaagctgc   6600
tgctcttttt gcgaagacac ataatttgaa tatgttgcag gacataccaa tggacaggtt   6660
tgtaatggac ttaaagagag acgtgaaagt gactccagga acaaaacata ctgaagaacg   6720
gcccaaggta caggtgatcc aggctgccga tccgctagca acagcgtatc tgtgcggaat   6780
ccaccgagag ctggttagga gattaaatgc ggtcctgctt ccgaacattc atacactgtt   6840
tgatatgtcg gctgaagact ttgacgctat tatagccgag cacttccagc ctggggattg   6900
```

-continued tgttctggaa actgacatcg cgtcgtttga taaaagtgag gacgacgcca tggctctgac 6960
cgcgttaatg attctggaag acttaggtgt ggacgcagag ctgttgacgc tgattgaggc 7020
ggctttcggc gaaatttcat caatacattt gcccactaaa actaaattta aattcggagc 7080
catgatgaaa tctggaatgt tcctcacact gtttgtgaac acagtcatta acattgtaat 7140
cgcaagcaga gtgttgagag aacggctaac cggatcacca tgtgcagcat tcattggaga 7200
tgacaatatc gtgaaaggag tcaaatcgga caaattaatg gcagacaggt gcgccacctg 7260
gttgaatatg gaagtcaaga ttatagatgc tgtggtgggc gagaaagcgc cttatttctg 7320
tggagggttt attttgtgtg actccgtgac cggcacagcg tgccgtgtgg cagacccccct 7380
aaaaaggctg tttaagcttg gcaaacctct ggcagcagac gatgaacatg atgatgacag 7440
gagaagggca ttgcatgaag agtcaacacg ctggaaccga gtgggtattc tttcagagct 7500
gtgcaaggca gtagaatcaa ggtatgaaac cgtaggaact tccatcatag ttatggccat 7560
gactactcta gctagcagtg ttaaatcatt cagctacctg agaggggccc ctataactct 7620
ctacggctaa cctgaatgga ctacgacata gtctagtcga cgccaccatg aggcctggcc 7680
tgccctccta cctgatcatc ctggccgtgt gcctgttcag ccacctgctg tccagcagat 7740
acggcgccga ggccgtgagc gagcccctgg acaaggcttt ccacctgctg ctgaacacct 7800
acggcagacc catccggttt ctgcgggaga acaccaccca gtgcacctac aacagcagcc 7860
tgcggaacag caccgtcgtg agagagaacg ccatcagctt caactttttc cagagctaca 7920
accagtacta cgtgttccac atgcccagat gcctgtttgc cggccctctg gccgagcagt 7980
tcctgaacca ggtggacctg accgagacac tggaaagata ccagcagcgg ctgaatacct 8040
acgccctggt gtccaaggac ctggccagct accggtcctt tagccagcag ctcaaggctc 8100
aggatagcct cggcgagcag cctaccaccg tgccccctcc catcgacctg agcatccccc 8160
acgtgtggat gcctccccag accacccctc acggctggac cgagagccac accacctccg 8220
gcctgcacag accccacttc aaccagacct gcatcctgtt cgacggccac gacctgctgt 8280
ttagcaccgt gacccccctgc ctgcaccagg gcttctacct gatcgacgag ctgagatacg 8340
tgaagatcac cctgaccgag gatttcttcg tggtcaccgt gtccatcgac gacgacaccc 8400
ccatgctgct gatcttcggc cacctgccca gagtgctgtt caaggccccc taccagcggg 8460
acaacttcat cctgcggcag accgagaagc acgagctgct ggtgctggtc aagaaggacc 8520
agctgaaccg gcactcctac ctgaaggacc ccgacttcct ggacgccgcc ctggacttca 8580
actacctgga cctgagcgcc ctgctgagaa acagcttcca cagatacgcc gtggacgtgc 8640
tgaagtccgg acggtgccag atgctcgatc ggcggaccgt ggagatggcc ttcgcctatg 8700
ccctcgccct gttcgccgct gccagacagg aagaggctgg cgcccaggtg tcagtgccca 8760
gagccctgga tagacaggcc gccctgctgc agatccagga attcatgatc acctgcctga 8820
gccagacccc ccctagaacc accctgctgc tgtaccccac agccgtggat ctggccaaga 8880
gggccctgtg gacccccaac cagatcaccg acatcacaag cctcgtgcgg ctcgtgtaca 8940
tcctgagcaa gcagaaccag cagcacctga tcccccagtg ggccctgaga cagatcgccg 9000
acttcgccct gaagctgcac aagacccatc tggccagctt tctgagcgcc ttcgccaggc 9060
aggaactgta cctgatgggc agcctggtcc acagcatgct ggtgcatacc accgagcggc 9120
gggagatctt catcgtggag acaggcctgt gtagcctggc cgagctgtcc cactttaccc 9180
agctgctggc ccaccctcac cacgagtacc tgagcgacct gtacaccccc tgcagcagca 9240
gcggcagacg ggaccacagc ctggaacggc tgaccagact gttccccgat gccaccgtgc 9300
ctgctacagt gcctgccgcc ctgtccatcc tgtccaccat gcagcccagc accctggaaa 9360
ccttccccga cctgttctgc ctgcccctgg gcgagagctt tagcgccctg accgtgtccg 9420
agcacgtgtc ctacatcgtg accaatcagt acctgatcaa gggcatcagc taccccgtgt 9480
ccaccacagt cgtgggccag agcctgatca tcacccagac cgacagccag accaagtgcg 9540
agctgacccg gaacatgcac accacacaca gcatcaccgt ggccctgaac atcagcctgg 9600
aaaactgcgc tttctgtcag tctgccctgc tggaatacga cgatacccag ggcgtgatca 9660
acatcatgta catgcacgac agcgacgacg tgctgttcgc cctggacccc tacaacgagg 9720
tggtggtgtc cagcccccgg acccactacc tgatgctgct gaagaacggc accgtgctgg 9780
aagtgaccga cgtggtggtg gacgccaccg acagcagact gctgatgatg agcgtgtacg 9840
ccctgagcgc catcatcggc atctacctgc tgtaccggat gctgaaaacc tgctgataat 9900
ctagacggcg cgcccaccca gcggccgcct ataactctct acggctaacc tgaatggact 9960
acgacatagt ctagtcgacg ccaccatgtg cagaaggccc gactgcggct tcagcttcag 10020
ccctggaccc gtgatcctgc tgtggtgctg cctgctgctg cctatcgtgt cctctgccgc 10080
cgtgtctgtg gcccctacag ccgccgagaa ggtgccagcc gagtgccccg agctgaccag 10140
aagatgcctg ctgggcgagg tgttcgaggg cgacaagtac gagagctggc tgcggcccct 10200
ggtcaacgtg accggcagag atggccccct gagccagctg atccggtaca gacccgtgac 10260
ccccgaggcc gccaatagcg tgctgctgga cgaggccttc ctggataccc tggccctgct 10320
gtacaacaac cccgaccagc tgagagccct gctgaccctg ctgtccagcg acaccgcccc 10380
cagatggatg accgtgatgc ggggctacag cgagtgtgga gatggcagcc ctgccgtgta 10440
cacctgcgtg gacgacctgt gcagaggcta cgacctgacc agactgagct acggccggtc 10500
catcttcaca gagcacgtgc tgggcttcga gctggtgccc cccagcctgt tcaacgtggt 10560
ggtggccatc cggaacgagg ccaccagaac caacagagcc gtgcggctgc ctgtgtctac 10620
agccgctgca cctgagggca tcacactgtt ctacggcctg tacaacgccg tgaaagagtt 10680
ctgcctccgg caccagctgg atcccccccct gctgagacac ctggacaagt actacgccgg 10740
cctgccccca gagctgaagc agaccagagt gaacctgccc gcccacagca gatatggccc 10800
tcaggccgtg gacgccagat gataatctag acggcgcgcc cacccaatcg atgtacttcc 10860
gaggaactca cgtgcataat gcatcaggct ggtacattag atccccgctt accgcgggca 10920
atatagcaac actaaaaact cgatgtactt ccgaggaagc gcagtgcata atgctgcgca 10980
gtgttgccac ataaccacta tattaaccat ttatctagcg gacgccaaaa actcaatgta 11040
tttctgagga agcgtggtgc ataatgccac gcagcgtctg cataactttt attatttctt 11100
ttattaatca acaaaatttt gtttttaaca tttcaaaaaa aaaaaaaaaa aaaaaaaaaa 11160
aaaaaaaaaa aaaagggtcg gcatggcatc tccacctcct cgcggtccga cctgggcatc 11220
cgaaggagga cgcacgtcca ctcggatggc taagggagag ccacgagctc ctgtttaaac 11280
cagctccaat tcgccctata gtgagtcgta ttacgcgcgc tcactggccg tcgttttaca 11340
acgtcgtgac tgggaaaacc ctggcgttac ccaacttaat cgccttgcag cacatccccc 11400
tttcgccagc tggcgtaata gcgaagaggc ccgcaccgat cgcccttccc aacagttgcg 11460
cagcctgaat ggcgaatggg acgcgccctg tagcggcgca ttaagcgcgg cgggtgtggt 11520
ggttacgcgc agcgtgaccg ctacacttgc cagcgcccta gcgcccgctc ctttcgcttt 11580
cttcccttcc tttctcgcca cgttcgccgg ctttccccgt caagctctaa atcgggggct 11640

-continued

```
ccctttaggg ttccgattta gtgctttacg gcacctcgac cccaaaaaac ttgattaggg  11700
tgatggttca cgtagtgggc catcgccctg atagacggtt tttcgccctt tgacgttgga  11760
gtccacgttc tttaatagtg gactcttgtt ccaaactgga acaacactca accctatctc  11820
ggtctattct tttgatttat aagggatttt gccgatttcg gcctattggt taaaaaatga  11880
gctgatttaa caaaaattta acgcgaattt taacaaaata ttaacgctta caatttaggt  11940
ggcacttttc ggggaaatgt gcgcggaacc cctatttgtt tatttttcta aatacattca  12000
aatatgtatc cgctcatgag acaataaccc tgataaatgc ttcaataata ttgaaaaagg  12060
aagagtatga gtattcaaca tttccgtgtc gcccttattc ccttttttgc ggcattttgc  12120
cttcctgttt ttgctcaccc agaaacgctg gtgaaagtaa aagatgctga agatcagttg  12180
ggtgcacgag tgggttacat cgaactggat ctcaacagcg gtaagatcct tgagagtttt  12240
cgccccgaag aacgttttcc aatgatgagc acttttaaag ttctgctatg tggcgcggta  12300
ttatcccgta ttgacgccgg gcaagagcaa ctcggtcgcc gcatacacta ttctcagaat  12360
gacttggttg agtactcacc agtcacagaa aagcatctta cggatggcat gacagtaaga  12420
gaattatgca gtgctgccat aaccatgagt gataacactg cggccaactt acttctgaca  12480
acgatcggag gaccgaagga gctaaccgct tttttgcaca acatggggga tcatgtaact  12540
cgccttgatc gttgggaacc ggagctgaat gaagccatac caaacgacga gcgtgacacc  12600
acgatgcctg tagcaatggc aacaacgttg cgcaaactat taactggcga actacttact  12660
ctagcttccc ggcaacaatt aatagactgg atggaggcgg ataaagttgc aggaccactt  12720
ctgcgctcgg cccttccggc tggctggttt attgctgata aatctggagc cggtgagcgt  12780
gggtctcgcg gtatcattgc agcactgggg ccagatggta agccctcccg tatcgtagtt  12840
atctacacga cggggagtca ggcaactatg gatgaacgaa atagacagat cgctgagata  12900
ggtgcctcac tgattaagca ttggtaactg tcagaccaag tttactcata tatactttag  12960
attgatttaa aacttcattt ttaatttaaa aggatctagg tgaagatcct ttttgataat  13020
ctcatgacca aaatccctta acgtgagttt tcgttccact gagcgtcaga ccccgtagaa  13080
aagatcaaag gatcttcttg agatcctttt tttctgcgcg taatctgctg cttgcaaaca  13140
aaaaaaccac cgctaccagc ggtggtttgt ttgccggatc aagagctacc aactcttttt  13200
ccgaaggtaa ctggcttcag cagagcgcag ataccaaata ctgttcttct agtgtagccg  13260
tagttaggcc accacttcaa gaactctgta gcaccgccta catacctcgc tctgctaatc  13320
ctgttaccag tggctgctgc cagtggcgat aagtcgtgtc ttaccgggtt ggactcaaga  13380
cgatagttac cggataaggc gcagcggtcg ggctgaacgg ggggttcgtg cacacagccc  13440
agcttggagc gaacgaccta caccgaactg agatacctac agcgtgagct atgagaaagc  13500
gccacgcttc ccgaagggag aaaggcggac aggtatccgg taagcggcag ggtcggaaca  13560
ggagagcgca cgagggagct tccaggggga aacgcctggt atctttatag tcctgtcggg  13620
tttcgccacc tctgacttga gcgtcgattt ttgtgatgct cgtcaggggg gcggagccta  13680
tggaaaaacg ccagcaacgc ggccttttta cggttcctgg ccttttgctg gccttttgct  13740
cacatgttct ttcctgcgtt atcccctgat tctgtggata accgtattac cgcctttgag  13800
tgagctgata ccgctcgccg cagccgaacg accgagcgca gcgagtcagt gagcgaggaa  13860
gcggaagagc gcccaatacg caaaccgcct ctccccgcgc gttggccgat tcattaatgc  13920
agctggcacg acaggtttcc cgactggaaa gcgggcagtg agcgcaacgc aattaatgtg  13980
```

agttagctca ctcattaggc accccaggct ttacacttta tgctcccggc tcgtatgttg 14040
tgtggaattg tgagcggata acaatttcac acaggaaaca gctatgacca tgattacgcc 14100
aagcgcgcaa ttaaccctca ctaaagggaa caaaagctgg gtaccggcgc ca 14152

<210> SEQ ID NO 54
<211> LENGTH: 15512
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54
cgcgtcggct acaattaata cataacctta tgtatcatac acatacgatt taggtgacac 60
tatagatggg cggcgcatga gagaagccca gaccaattac ctacccaaaa tggagaaagt 120
tcacgttgac atcgaggaag acagcccatt cctcagagct ttgcagcgga gcttcccgca 180
gtttgaggta gaagccaagc aggtcactga taatgaccat gctaatgcca gagcgttttc 240
gcatctggct tcaaaactga tcgaaacgga ggtggaccca tccgacacga tccttgacat 300
tggaagtgcg cccgcccgca gaatgtattc taagcacaag tatcattgta tctgtccgat 360
gagatgtgcg gaagatccgg acagattgta taagtatgca actaagctga agaaaaactg 420
taaggaaata actgataagg aattggacaa gaaaatgaag gagctcgccg ccgtcatgag 480
cgaccctgac ctggaaactg agactatgtg cctccacgac gacgagtcgt gtcgctacga 540
agggcaagtc gctgtttacc aggatgtata cgcggttgac ggaccgacaa gtctctatca 600
ccaagccaat aagggagtta gagtcgccta ctggataggc tttgacacca ccccttttat 660
gtttaagaac ttggctggag catatccatc atactctacc aactgggccg acgaaaccgt 720
gttaacggct cgtaacatag gcctatgcag ctctgacgtt atggagcggt cacgtagagg 780
gatgtccatt cttagaaaga agtatttgaa accatccaac aatgttctat tctctgttgg 840
ctcgaccatc taccacgaga agagggactt actgaggagc tggcacctgc cgtctgtatt 900
tcacttacgt ggcaagcaaa attacacatg tcggtgtgag actatagtta gttgcgacgg 960
gtacgtcgtt aaaagaatag ctatcagtcc aggcctgtat gggaagcctt caggctatgc 1020
tgctacgatg caccgcgagg gattcttgtg ctgcaaagtg acagacacat tgaacgggga 1080
gagggtctct ttcccgtgt gcacgtatgt gccagctaca ttgtgtgacc aaatgactgg 1140
catactggca acagatgtca gtgcggacga cgcgcaaaaa ctgctggttg ggctcaacca 1200
gcgtatagtc gtcaacggtc gcacccagag aaacaccaat accatgaaaa attacctttt 1260
gcccgtagtg gcccaggcat ttgctaggtg ggcaaaggaa tataaggaag atcaagaaga 1320
tgaaaggcca ctaggactac gagatagaca gttagtcatg gggtgttgtt gggcttttag 1380
aaggcacaag ataacatcta tttataagcg cccggatacc caaaccatca tcaaagtgaa 1440
cagcgatttc cactcattcg tgctgcccag gataggcagt aacacattgg agatcgggct 1500
gagaacaaga atcaggaaaa tgttagagga gcacaaggag ccgtcacctc tcattaccgc 1560
cgaggacgta caagaagcta agtgcgcagc cgatgaggct aaggaggtgc gtgaagccga 1620
ggagttgcgc gcagctctac cacctttggc agctgatgtt gaggagccca ctctggaagc 1680
cgatgtagac ttgatgttac aagaggctgg ggccggctca gtggagacac ctcgtggctt 1740
gataaaggtt accagctacg ctggcgagga caagatcggc tcttacgctg tgctttctcc 1800
gcaggctgta ctcaagagtg aaaaattatc ttgcatccac cctctcgctg aacaagtcat 1860
agtgataaca cactctggcc gaaaagggcg ttatgccgtg gaaccatacc atggtaaagt 1920
agtggtgcca gagggacatg caatacccgt ccaggacttt caagctctga gtgaaagtgc 1980
caccattgtg tacaacgaac gtgagttcgt aaacaggtac ctgcaccata ttgccacaca 2040
tggaggagcg ctgaacactg atgaagaata ttacaaaact gtcaagccca gcgagcacga 2100
cggcgaatac ctgtacgaca tcgacaggaa acagtgcgtc aagaaagaac tagtcactgg 2160
gctagggctc acaggcgagc tggtggatcc tcccttccat gaattcgcct acgagagtct 2220
gagaacacga ccagccgctc cttaccaagt accaaccata ggggtgtatg gcgtgccagg 2280
atcaggcaag tctggcatca ttaaaagcgc agtcaccaaa aaagatctag tggtgagcgc 2340
caagaaagaa aactgtgcag aaattataag ggacgtcaag aaaatgaaag ggctggacgt 2400
caatgccaga actgtggact cagtgctctt gaatggatgc aaacaccccg tagagaccct 2460
gtatattgac gaagcttttg cttgtcatgc aggtactctc agagcgctca tagccattat 2520
aagacctaaa aaggcagtgc tctgcgggga tcccaaacag tgcggttttt ttaacatgat 2580
gtgcctgaaa gtgcatttta accacgagat ttgcacacaa gtcttccaca aaagcatctc 2640
tcgccgttgc actaaatctg tgacttcggt cgtctcaacc ttgttttacg acaaaaaaat 2700
gagaacgacg aatccgaaag agactaagat tgtgattgac actaccggca gtaccaaacc 2760
taagcaggac gatctcattc tcacttgttt cagagggtgg gtgaagcagt tgcaaataga 2820
ttacaaaggc aacgaaataa tgacggcagc tgcctctcaa gggctgaccc gtaaaggtgt 2880
gtatgccgtt cggtacaagg tgaatgaaaa tcctctgtac gcacccacct cagaacatgt 2940
gaacgtccta ctgacccgca cggaggaccg catcgtgtgg aaaacactag ccggcgaccc 3000
atggataaaa acactgactg ccaagtaccc tgggaatttc actgccacga tagaggagtg 3060
gcaagcagag catgatgcca tcatgaggca catcttggag agaccggacc ctaccgacgt 3120
cttccagaat aaggcaaacg tgtgttgggc caaggcttta gtgccggtgc tgaagaccgc 3180
tggcatagac atgaccactg aacaatggaa cactgtggat tattttgaaa cggacaaagc 3240
tcactcagca gagatagtat tgaaccaact atgcgtgagg ttctttggac tcgatctgga 3300
ctccggtcta ttttctgcac ccactgttcc gttatccatt aggaataatc actgggataa 3360
ctccccgtcg cctaacatgt acgggctgaa taaagaagtg gtccgtcagc tctctcgcag 3420
gtacccacaa ctgcctcggg cagttgccac tggaagagtc tatgacatga acactggtac 3480
actgcgcaat tatgatccgc gcataaacct agtacctgta aacagaagac tgcctcatgc 3540
tttagtcctc caccataatg aacacccaca gagtgacttt tcttcattcg tcagcaaatt 3600
gaagggcaga actgtcctgg tggtcgggga aaagttgtcc gtcccaggca aaatggttga 3660
ctggttgtca gaccggcctg aggctacctt cagagctcgg ctggatttag gcatcccagg 3720
tgatgtgccc aaatatgaca taatatttgt taatgtgagg accccatata aataccatca 3780
ctatcagcag tgtgaagacc atgccattaa gcttagcatg ttgaccaaga aagcttgtct 3840
gcatctgaat cccggcggaa cctgtgtcag cataggttat ggttacgctg acagggccag 3900
cgaaagcatc attggtgcta tagcgcggca gttcaagttt tcccgggtat gcaaaccgaa 3960
atcctcactt gaagagacgg aagttctgtt tgtattcatt gggtacgatc gcaaggcccg 4020
tacgcacaat ccttacaagc tttcatcaac cttgaccaac atttatacag gttccagact 4080
ccacgaagcc ggatgtgcac cctcatatca tgtggtgcga ggggatattg ccacggccac 4140
cgaaggagtg attataaatg ctgctaacag caaaggacaa cctggcggag ggtgtgcgg 4200

-continued agcgctgtat aagaaattcc cggaaagctt cgatttacag ccgatcgaag taggaaaagc 4260
gcgactggtc aaaggtgcag ctaaacatat cattcatgcc gtaggaccaa acttcaacaa 4320
agtttcggag gttgaaggtg acaaacagtt ggcagaggct tatgagtcca tcgctaagat 4380
tgtcaacgat aacaattaca agtcagtagc gattccactg ttgtccaccg gcatcttttc 4440
cgggaacaaa gatcgactaa cccaatcatt gaaccatttg ctgacagctt tagacaccac 4500
tgatgcagat gtagccatat actgcaggga caagaaatgg gaaatgactc tcaaggaagc 4560
agtggctagg agagaagcag tggaggagat atgcatatcc gacgactctt cagtgacaga 4620
acctgatgca gagctggtga gggtgcatcc gaagagttct ttggctggaa ggaagggcta 4680
cagcacaagc gatggcaaaa ctttctcata tttggaaggg accaagtttc accaggcggc 4740
caaggatata gcagaaatta atgccatgtg gcccgttgca acggaggcca atgagcaggt 4800
atgcatgtat atcctcggag aaagcatgag cagtattagg tcgaaatgcc ccgtcgaaga 4860
gtcggaagcc tcctcaccac ctagcacgct gccttgcttg tgcatccatg ccatgactcc 4920
agaaagagta cagcgcctaa aagcctcacg tccagaacaa attactgtgt gctcatcctt 4980
tccattgccg aagtatagaa tcactggtgt gcagaagatc caatgctccc agcctatatt 5040
gttctcaccg aaagtgcctg cgtatattca tccaaggaag tatctcgtgg aaacaccacc 5100
ggtagacgag actccggagc catcggcaga gaaccaatcc acagagggga cacctgaaca 5160
accaccactt ataaccgagg atgagaccag gactagaacg cctgagccga tcatcatcga 5220
agaggaagaa gaggatagca taagtttgct gtcagatggc ccgacccacc aggtgctgca 5280
agtcgaggca gacattcacg ggccgccctc tgtatctagc tcatcctggt ccattcctca 5340
tgcatccgac tttgatgtgg acagtttatc catacttgac accctggagg gagctagcgt 5400
gaccagcggg gcaacgtcag ccgagactaa ctcttacttc gcaaagagta tggagtttct 5460
ggcgcgaccg gtgcctgcgc ctcgaacagt attcaggaac cctccacatc ccgctccgcg 5520
cacaagaaca ccgtcacttg cacccagcag ggcctgctcg agagggatca cgggagaaac 5580
cgtgggatac gcggttacac acaatagcga gggcttcttg ctatgcaaag ttactgacac 5640
agtaaaagga gaacgggtat cgttccctgt gtgcacgtac atcccggcca ccataaactc 5700
gagaaccagc ctggtctcca acccgccagg cgtaaatagg gtgattacaa gagaggagtt 5760
tgaggcgttc gtagcacaac aacaatgacg gtttgatgcg ggtgcataca tcttttcctc 5820
cgacaccggt caagggcatt tacaacaaaa atcagtaagg caaacggtgc tatccgaagt 5880
ggtgttggag aggaccgaat tggagatttc gtatgccccg cgcctcgacc aagaaaaaga 5940
agaattacta cgcaagaaat tacagttaaa tcccacacct gctaacagaa gcagatacca 6000
gtccaggaag gtggagaaca tgaaagccat aacagctaga cgtattctgc aaggcctagg 6060
gcattatttg aaggcagaag gaaaagtgga gtgctaccga accctgcatc ctgttccttt 6120
gtattcatct agtgtgaacc gtgccttttc aagccccaag gtcgcagtgg aagcctgtaa 6180
cgccatgttg aaagagaact ttccgactgt ggcttcttac tgtattattc cagagtacga 6240
tgcctatttg gacatggttg acggagcttc atgctgctta gacactgcca gtttttgccc 6300
tgcaaagctg cgcagctttc caaagaaaca ctcctatttg gaacccacaa tacgatcggc 6360
agtgccttca gcgatccaga acacgctcca gaacgtcctg gcagctgcca caaaaagaaa 6420
ttgcaatgtc acgcaaatga gagaattgcc cgtattggat tcggcggcct ttaatgtgga 6480
atgcttcaag aaatatgcgt gtaataatga atattgggaa acgtttaaag aaaaccccat 6540
caggcttact gaagaaaacg tggtaaatta cattaccaaa ttaaaaggac caaaagctgc 6600

-continued

```
tgctcttttt gcgaagacac ataatttgaa tatgttgcag gacataccaa tggacaggtt   6660
tgtaatggac ttaaagagag acgtgaaagt gactccagga acaaaacata ctgaagaacg   6720
gcccaaggta caggtgatcc aggctgccga tccgctagca acagcgtatc tgtgcggaat   6780
ccaccgagag ctggttagga gattaaatgc ggtcctgctt ccgaacattc atacactgtt   6840
tgatatgtcg gctgaagact ttgacgctat tatagccgag cacttccagc ctggggattg   6900
tgttctggaa actgacatcg cgtcgtttga taaaagtgag gacgacgcca tggctctgac   6960
cgcgttaatg attctggaag acttaggtgt ggacgcagag ctgttgacgc tgattgaggc   7020
ggctttcggc gaaatttcat caatacattt gcccactaaa actaaattta aattcggagc   7080
catgatgaaa tctggaatgt tcctcacact gtttgtgaac acagtcatta acattgtaat   7140
cgcaagcaga gtgttgagag aacggctaac cggatcacca tgtgcagcat tcattggaga   7200
tgacaatatc gtgaaaggag tcaaatcgga caaattaatg gcagacaggt gcgccacctg   7260
gttgaatatg gaagtcaaga ttatagatgc tgtggtgggc gagaaagcgc cttatttctg   7320
tggagggttt attttgtgtg actccgtgac cggcacagcg tgccgtgtgg cagaccccct   7380
aaaaaggctg tttaagcttg gcaaacctct ggcagcagac gatgaacatg atgatgacag   7440
gagaagggca ttgcatgaag agtcaacacg ctggaaccga gtgggtattc tttcagagct   7500
gtgcaaggca gtagaatcaa ggtatgaaac cgtaggaact tccatcatag ttatggccat   7560
gactactcta gctagcagtg ttaaatcatt cagctacctg agaggggccc ctataactct   7620
ctacggctaa cctgaatgga ctacgacata gtctagtcga cgccaccatg aggcctggcc   7680
tgccctccta cctgatcatc ctggccgtgt gcctgttcag ccacctgctg tccagcagat   7740
acggcgccga ggccgtgagc gagcccctgg acaaggcttt ccacctgctg ctgaacacct   7800
acggcagacc catccggttt ctgcgggaga acaccaccca gtgcacctac aacagcagcc   7860
tgcggaacag caccgtcgtg agagagaacg ccatcagctt caactttttc cagagctaca   7920
accagtacta cgtgttccac atgcccagat gcctgtttgc cggccctctg gccgagcagt   7980
tcctgaacca ggtggacctg accgagacac tggaaagata ccagcagcgg ctgaatacct   8040
acgccctggt gtccaaggac ctggccagct accggtcctt tagccagcag ctcaaggctc   8100
aggatagcct cggcgagcag cctaccaccg tgccccctcc catcgacctg agcatccccc   8160
acgtgtggat gcctccccag accacccctc acggctggac cgagagccac accacctccg   8220
gcctgcacag accccacttc aaccagacct gcatcctgtt cgacggccac gacctgctgt   8280
ttagcaccgt gacccctgc ctgcaccagg gcttctacct gatcgacgag ctgagatacg   8340
tgaagatcac cctgaccgag gatttcttcg tggtcaccgt gtccatcgac gacgacaccc   8400
ccatgctgct gatcttcggc cacctgccca gagtgctgtt caaggccccc taccagcggg   8460
acaacttcat cctgcggcag accgagaagc acgagctgct ggtgctggtc aagaaggacc   8520
agctgaaccg gcactcctac ctgaaggacc ccgacttcct ggacgccgcc ctggacttca   8580
actacctgga cctgagcgcc ctgctgagaa acagcttcca cagatacgcc gtggacgtgc   8640
tgaagtccgg acggtgccag atgctcgatc ggcggaccgt ggagatggcc ttcgcctatg   8700
ccctcgccct gttcgccgct gccagacagg aagaggctgg cgcccaggtg tcagtgccca   8760
gagccctgga tagacaggcc gccctgctgc agatccagga attcatgatc acctgcctga   8820
gccagacccc ccctagaacc accctgctgc tgtaccccac agccgtggat ctggccaaga   8880
gggccctgtg gacccccaac cagatcaccg acatcacaag cctcgtgcgg ctcgtgtaca   8940
```

-continued

```
tcctgagcaa gcagaaccag cagcacctga tcccccagtg ggccctgaga cagatcgccg   9000
acttcgccct gaagctgcac aagacccatc tggccagctt tctgagcgcc ttcgccaggc   9060
aggaactgta cctgatgggc agcctggtcc acagcatgct ggtgcatacc accgagcggc   9120
gggagatctt catcgtggag acaggcctgt gtagcctggc cgagctgtcc cactttaccc   9180
agctgctggc ccaccctcac cacgagtacc tgagcgacct gtacaccccc tgcagcagca   9240
gcggcagacg ggaccacagc ctggaacggc tgaccagact gttccccgat gccaccgtgc   9300
ctgctacagt gcctgccgcc ctgtccatcc tgtccaccat gcagcccagc accctggaaa   9360
ccttccccga cctgttctgc ctgcccctgg gcgagagctt tagcgccctg accgtgtccg   9420
agcacgtgtc ctacatcgtg accaatcagt acctgatcaa gggcatcagc taccccgtgt   9480
ccaccacagt cgtgggccag agcctgatca tcacccagac cgacagccag accaagtgcg   9540
agctgacccg gaacatgcac accacacaca gcatcaccgt ggccctgaac atcagcctgg   9600
aaaactgcgc tttctgtcag tctgccctgc tggaatacga cgatacccag ggcgtgatca   9660
acatcatgta catgcacgac agcgacgacg tgctgttcgc cctggacccc tacaacgagg   9720
tggtggtgtc cagcccccgg acccactacc tgatgctgct gaagaacggc accgtgctgg   9780
aagtgaccga cgtggtggtg gacgccaccg actgataatc tagacggcgc gcccacccag   9840
cggccgccta taactctcta cggctaacct gaatggacta cgacatagtc tagtcgacgc   9900
caccatgtgc agaaggcccg actgcggctt cagcttcagc cctggacccg tgatcctgct   9960
gtggtgctgc ctgctgctgc ctatcgtgtc ctctgccgcc gtgtctgtgg cccctacagc  10020
cgccgagaag gtgccagccg agtgccccga gctgaccaga agatgcctgc tgggcgaggt  10080
gttcgagggc gacaagtacg agagctggct gcggcccctg gtcaacgtga ccggcagaga  10140
tggcccccctg agccagctga tccggtacag acccgtgacc cccgaggccg ccaatagcgt  10200
gctgctggac gaggccttcc tggataccct ggccctgctg tacaacaacc ccgaccagct  10260
gagagccctg ctgaccctgc tgtccagcga caccgccccc agatggatga ccgtgatgcg  10320
gggctacagc gagtgtggag atggcagccc tgccgtgtac acctgcgtgg acgacctgtg  10380
cagaggctac gacctgacca gactgagcta cggccggtcc atcttcacag agcacgtgct  10440
gggcttcgag ctggtgcccc ccagcctgtt caacgtggtg gtggccatcc ggaacgaggc  10500
caccagaacc aacagagccg tgcggctgcc tgtgtctaca gccgctgcac ctgagggcat  10560
cacactgttc tacggcctgt acaacgccgt gaaagagttc tgcctccggc accagctgga  10620
tcccccccctg ctgagacacc tggacaagta ctacgccggc ctgccccccag agctgaagca  10680
gaccagagtg aacctgcccg cccacagcag atatggccct caggccgtgg acgccagatg  10740
ataatctaga cggcgcgccc acccaatcga tctataactc tctacggcta acctgaatgg  10800
actacgacat agtctagtcg acgccaccat gggcaagaaa gaaatgatca tggtcaaggg  10860
catccccaag atcatgctgc tgattagcat cacctttctg ctgctgtccc tgatcaactg  10920
caacgtgctg gtcaacagcc ggggcaccag aagatcctgg ccctacaccg tgctgtccta  10980
ccggggcaaa gagatcctga agaagcagaa agaggacatc ctgaagcggc tgatgagcac  11040
cagcagcgac ggctaccggt tcctgatgta ccccagccag cagaaattcc acgccatcgt  11100
gatcagcatg gacaagttcc cccaggacta catcctggcc ggacccatcc ggaacgacag  11160
catcacccac atgtggttcg acttctacag cacccagctg cggaagcccg ccaaatacgt  11220
gtacagcgag tacaaccaca ccgcccacaa gatcaccctg aggcctcccc cttgtggcac  11280
cgtgcccagc atgaactgcc tgagcgagat gctgaacgtg tccaagcgga acgacaccgg  11340
```

cgagaagggc tgcggcaact tcaccacctt caaccccatg ttcttcaacg tgccccggtg 11400
gaacaccaag ctgtacatcg gcagcaacaa agtgaacgtg gacagccaga ccatctactt 11460
tctgggcctg accgccctgc tgctgagata cgcccagcgg aactgcaccc ggtccttcta 11520
cctggtcaac gccatgagcc ggaacctgtt ccgggtgccc aagtacatca acggcaccaa 11580
gctgaagaac accatgcgga agctgaagcg gaagcaggcc ctggtcaaag agcagcccca 11640
gaagaagaac aagaagtccc agagcaccac cacccccctac ctgagctaca ccacctccac 11700
cgccttcaac gtgaccacca acgtgaccta cagcgccaca gccgccgtga ccagagtggc 11760
cacaagcacc accggctacc ggcccgacag caactttatg aagtccatca tggccaccca 11820
gctgagagat ctggccacct gggtgtacac caccctgcgg tacagaaacg agcccttctg 11880
caagcccgac cggaacagaa ccgccgtgag cgagttcatg aagaataccc acgtgctgat 11940
cagaaacgag acaccctaca ccatctacgg caccctggac atgagcagcc tgtactacaa 12000
cgagacaatg agcgtggaga acgagacagc cagcgacaac aacgaaacca cccccacctc 12060
ccccagcacc cggttccagc ggaccttcat cgacccccctg tgggactacc tggacagcct 12120
gctgttcctg gacaagatcc ggaacttcag cctgcagctg cccgcctacg gcaatctgac 12180 ccccccctgag cacagaaggg ccgccaacct gagcaccctg aacagcctgt ggtggtggag 12240
ccagtgataa tctagacggc gcgcccaccc accgcgggca atatagcaac actaaaaact 12300
cgatgtactt ccgaggaagc gcagtgcata atgctgcgca gtgttgccac ataaccacta 12360
tattaaccat ttatctagcg gacgccaaaa actcaatgta tttctgagga agcgtggtgc 12420
ataatgccac gcagcgtctg cataactttt attatttctt ttattaatca acaaaatttt 12480
gtttttaaca tttcaaaaaa aaaaaaaaaa aaaaaaaaaa aaaaaaaaaa aaaagggtcg 12540
gcatggcatc tccacctcct cgcggtccga cctgggcatc cgaaggagga cgcacgtcca 12600
ctcggatggc taagggagag ccacgagctc ctgtttaaac cagctccaat tcgccctata 12660
gtgagtcgta ttacgcgcgc tcactggccg tcgttttaca acgtcgtgac tgggaaaacc 12720
ctggcgttac ccaacttaat cgccttgcag cacatccccc tttcgccagc tggcgtaata 12780
gcgaagaggc ccgcaccgat cgcccttccc aacagttgcg cagcctgaat ggcgaatggg 12840
acgcgccctg tagcggcgca ttaagcgcgg cgggtgtggt ggttacgcgc agcgtgaccg 12900
ctacacttgc cagcgcccta gcgcccgctc ctttcgcttt cttcccttcc tttctcgcca 12960
cgttcgccgg ctttccccgt caagctctaa atcgggggct ccctttaggg ttccgattta 13020
gtgctttacg gcacctcgac cccaaaaaac ttgattaggg tgatggttca cgtagtgggc 13080
catcgccctg atagacggtt tttcgccctt tgacgttgga gtccacgttc tttaatagtg 13140
gactcttgtt ccaaactgga acaacactca accctatctc ggtctattct tttgatttat 13200
aagggatttt gccgatttcg gcctattggt taaaaaatga gctgatttaa caaaaattta 13260
acgcgaattt taacaaaata ttaacgctta caatttaggt ggcacttttc ggggaaatgt 13320
gcgcggaacc cctatttgtt tatttttcta aatacattca aatatgtatc cgctcatgag 13380
acaataaccc tgataaatgc ttcaataata ttgaaaaagg aagagtatga gtattcaaca 13440
tttccgtgtc gcccttattc ccttttttgc ggcattttgc cttcctgttt ttgctcaccc 13500
agaaacgctg gtgaaagtaa aagatgctga agatcagttg ggtgcacgag tgggttacat 13560
cgaactggat ctcaacagcg gtaagatcct tgagagtttt cgccccgaag aacgttttcc 13620
aatgatgagc acttttaaag ttctgctatg tggcgcggta ttatcccgta ttgacgccgg 13680
gcaagagcaa ctcggtcgcc gcatacacta ttctcagaat gacttggttg agtactcacc 13740
agtcacagaa aagcatctta cggatggcat gacagtaaga gaattatgca gtgctgccat 13800
aaccatgagt gataacactg cggccaactt acttctgaca acgatcggag gaccgaagga 13860
gctaaccgct tttttgcaca acatggggga tcatgtaact cgccttgatc gttgggaacc 13920
ggagctgaat gaagccatac caaacgacga gcgtgacacc acgatgcctg tagcaatggc 13980
aacaacgttg cgcaaactat taactggcga actacttact ctagcttccc ggcaacaatt 14040
aatagactgg atggaggcgg ataaagttgc aggaccactt ctgcgctcgg cccttccggc 14100
tggctggttt attgctgata aatctggagc cggtgagcgt gggtctcgcg gtatcattgc 14160
agcactgggg ccagatggta agccctcccg tatcgtagtt atctacacga cggggagtca 14220
ggcaactatg gatgaacgaa atagacagat cgctgagata ggtgcctcac tgattaagca 14280
ttggtaactg tcagaccaag tttactcata tatactttag attgatttaa aacttcattt 14340
ttaatttaaa aggatctagg tgaagatcct ttttgataat ctcatgacca aaatccctta 14400
acgtgagttt tcgttccact gagcgtcaga ccccgtagaa aagatcaaag gatcttcttg 14460
agatcctttt tttctgcgcg taatctgctg cttgcaaaca aaaaaaccac cgctaccagc 14520
ggtggtttgt ttgccggatc aagagctacc aactcttttt ccgaaggtaa ctggcttcag 14580
cagagcgcag ataccaaata ctgttcttct agtgtagccg tagttaggcc accacttcaa 14640
gaactctgta gcaccgccta catacctcgc tctgctaatc ctgttaccag tggctgctgc 14700
cagtggcgat aagtcgtgtc ttaccgggtt ggactcaaga cgatagttac cggataaggc 14760
gcagcggtcg ggctgaacgg ggggttcgtg cacacagccc agcttggagc gaacgaccta 14820
caccgaactg agatacctac agcgtgagct atgagaaagc gccacgcttc ccgaagggag 14880
aaaggcggac aggtatccgg taagcggcag ggtcggaaca ggagagcgca cgagggagct 14940
tccaggggga aacgcctggt atctttatag tcctgtcggg tttcgccacc tctgacttga 15000
gcgtcgattt ttgtgatgct cgtcaggggg gcggagccta tggaaaaacg ccagcaacgc 15060
ggccttttta cggttcctgg ccttttgctg gccttttgct cacatgttct ttcctgcgtt 15120
atcccctgat tctgtggata accgtattac cgcctttgag tgagctgata ccgctcgccg 15180
cagccgaacg accgagcgca gcgagtcagt gagcgaggaa gcggaagagc gcccaatacg 15240
caaaccgcct ctccccgcgc gttggccgat tcattaatgc agctggcacg acaggtttcc 15300
cgactggaaa gcgggcagtg agcgcaacgc aattaatgtg agttagctca ctcattaggc 15360
accccaggct ttacacttta tgctcccggc tcgtatgttg tgtggaattg tgagcggata 15420
acaatttcac acaggaaaca gctatgacca tgattacgcc aagcgcgcaa ttaaccctca 15480
ctaaagggaa caaaagctgg gtaccggcgc ca 15512

<210> SEQ ID NO 55
<211> LENGTH: 15593
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55
cgcgtcggct acaattaata cataacctta tgtatcatac acatacgatt taggtgacac 60
tatagatggg cggcgcatga gagaagccca gaccaattac ctacccaaaa tggagaaagt 120
tcacgttgac atcgaggaag acagcccatt cctcagagct ttgcagcgga gcttcccgca 180

```
gtttgaggta gaagccaagc aggtcactga taatgaccat gctaatgcca gagcgttttc    240
gcatctggct tcaaaactga tcgaaacgga ggtggaccca tccgacacga tccttgacat    300
tggaagtgcg cccgcccgca gaatgtattc taagcacaag tatcattgta tctgtccgat    360
gagatgtgcg gaagatccgg acagattgta taagtatgca actaagctga agaaaaactg    420
taaggaaata actgataagg aattggacaa gaaaatgaag gagctcgccg ccgtcatgag    480
cgaccctgac ctggaaactg agactatgtg cctccacgac gacgagtcgt gtcgctacga    540
agggcaagtc gctgtttacc aggatgtata cgcggttgac ggaccgacaa gtctctatca    600
ccaagccaat aagggagtta gagtcgccta ctggataggc tttgacacca ccccttttat    660
gtttaagaac ttggctggag catatccatc atactctacc aactgggccg acgaaaccgt    720
gttaacggct cgtaacatag gcctatgcag ctctgacgtt atggagcggt cacgtagagg    780
gatgtccatt cttagaaaga agtatttgaa accatccaac aatgttctat tctctgttgg    840
ctcgaccatc taccacgaga agagggactt actgaggagc tggcacctgc cgtctgtatt    900
tcacttacgt ggcaagcaaa attacacatg tcggtgtgag actatagtta gttgcgacgg    960
gtacgtcgtt aaaagaatag ctatcagtcc aggcctgtat gggaagcctt caggctatgc   1020
tgctacgatg caccgcgagg gattcttgtg ctgcaaagtg acagacacat tgaacgggga   1080
gagggtctct ttcccgtgt gcacgtatgt gccagctaca ttgtgtgacc aaatgactgg   1140
catactggca acagatgtca gtgcggacga cgcgcaaaaa ctgctggttg ggctcaacca   1200
gcgtatagtc gtcaacggtc gcacccagag aaacaccaat accatgaaaa attacctttt   1260
gcccgtagtg gcccaggcat ttgctaggtg ggcaaaggaa tataaggaag atcaagaaga   1320
tgaaaggcca ctaggactac gagatagaca gttagtcatg gggtgttgtt gggcttttag   1380
aaggcacaag ataacatcta tttataagcg cccggatacc caaaccatca tcaaagtgaa   1440
cagcgatttc cactcattcg tgctgcccag gataggcagt aacacattgg agatcgggct   1500
gagaacaaga atcaggaaaa tgttagagga gcacaaggag ccgtcacctc tcattaccgc   1560
cgaggacgta caagaagcta agtgcgcagc cgatgaggct aaggaggtgc gtgaagccga   1620
ggagttgcgc gcagctctac cacctttggc agctgatgtt gaggagccca ctctggaagc   1680
cgatgtagac ttgatgttac aagaggctgg ggccggctca gtggagacac ctcgtggctt   1740
gataaaggtt accagctacg ctggcgagga caagatcggc tcttacgctg tgctttctcc   1800
gcaggctgta ctcaagagtg aaaaattatc ttgcatccac cctctcgctg aacaagtcat   1860
agtgataaca cactctggcc gaaaagggcg ttatgccgtg gaaccatacc atggtaaagt   1920
agtggtgcca gagggacatg caatacccgt ccaggacttt caagctctga gtgaaagtgc   1980
caccattgtg tacaacgaac gtgagttcgt aaacaggtac ctgcaccata ttgccacaca   2040
tggaggagcg ctgaacactg atgaagaata ttacaaaact gtcaagccca gcgagcacga   2100
cggcgaatac ctgtacgaca tcgacaggaa acagtgcgtc aagaaagaac tagtcactgg   2160
gctagggctc acaggcgagc tggtggatcc tcccttccat gaattcgcct acgagagtct   2220
gagaacacga ccagccgctc cttaccaagt accaaccata ggggtgtatg gcgtgccagg   2280
atcaggcaag tctggcatca ttaaaagcgc agtcaccaaa aaagatctag tggtgagcgc   2340
caagaaagaa aactgtgcag aaattataag ggacgtcaag aaaatgaaag ggctggacgt   2400
caatgccaga actgtggact cagtgctctt gaatggatgc aaacaccccg tagagaccct   2460
gtatattgac gaagcttttg cttgtcatgc aggtactctc agagcgctca tagccattat   2520
```

-continued

```
aagacctaaa aaggcagtgc tctgcgggga tcccaaacag tgcggttttt ttaacatgat   2580
gtgcctgaaa gtgcatttta accacgagat ttgcacacaa gtcttccaca aaagcatctc   2640
tcgccgttgc actaaatctg tgacttcggt cgtctcaacc ttgttttacg acaaaaaaat   2700
gagaacgacg aatccgaaag agactaagat tgtgattgac actaccggca gtaccaaacc   2760
taagcaggac gatctcattc tcacttgttt cagagggtgg gtgaagcagt tgcaaataga   2820
ttacaaaggc aacgaaataa tgacggcagc tgcctctcaa gggctgaccc gtaaaggtgt   2880
gtatgccgtt cggtacaagg tgaatgaaaa tcctctgtac gcacccacct cagaacatgt   2940
gaacgtccta ctgacccgca cggaggaccg catcgtgtgg aaaacactag ccggcgaccc   3000
atggataaaa acactgactg ccaagtaccc tgggaatttc actgccacga tagaggagtg   3060
gcaagcagag catgatgcca tcatgaggca catcttggag agaccggacc ctaccgacgt   3120
cttccagaat aaggcaaacg tgtgttgggc caaggcttta gtgccggtgc tgaagaccgc   3180
tggcatagac atgaccactg aacaatggaa cactgtggat tattttgaaa cggacaaagc   3240
tcactcagca gagatagtat tgaaccaact atgcgtgagg ttctttggac tcgatctgga   3300
ctccggtcta ttttctgcac ccactgttcc gttatccatt aggaataatc actgggataa   3360
ctccccgtcg cctaacatgt acgggctgaa taaagaagtg gtccgtcagc tctctcgcag   3420
gtacccacaa ctgcctcggg cagttgccac tggaagagtc tatgacatga acactggtac   3480
actgcgcaat tatgatccgc gcataaacct agtacctgta aacagaagac tgcctcatgc   3540
tttagtcctc caccataatg aacacccaca gagtgacttt tcttcattcg tcagcaaatt   3600
gaagggcaga actgtcctgg tggtcgggga aaagttgtcc gtcccaggca aaatggttga   3660
ctggttgtca gaccggcctg aggctacctt cagagctcgg ctggatttag gcatcccagg   3720
tgatgtgccc aaatatgaca taatatttgt taatgtgagg accccatata aataccatca   3780
ctatcagcag tgtgaagacc atgccattaa gcttagcatg ttgaccaaga aagcttgtct   3840
gcatctgaat cccggcggaa cctgtgtcag cataggttat ggttacgctg acagggccag   3900
cgaaagcatc attggtgcta tagcgcggca gttcaagttt tcccgggtat gcaaaccgaa   3960
atcctcactt gaagagacgg aagttctgtt tgtattcatt gggtacgatc gcaaggcccg   4020
tacgcacaat ccttacaagc tttcatcaac cttgaccaac atttatacag gttccagact   4080
ccacgaagcc ggatgtgcac cctcatatca tgtggtgcga ggggatattg ccacggccac   4140
cgaaggagtg attataaatg ctgctaacag caaaggacaa cctggcggag ggggtgtgcgg   4200
agcgctgtat aagaaattcc cggaaagctt cgatttacag ccgatcgaag taggaaaagc   4260
gcgactggtc aaaggtgcag ctaaacatat cattcatgcc gtaggaccaa acttcaacaa   4320
agtttcggag gttgaaggtg acaaacagtt ggcagaggct tatgagtcca tcgctaagat   4380
tgtcaacgat aacaattaca agtcagtagc gattccactg ttgtccaccg gcatcttttc   4440
cgggaacaaa gatcgactaa cccaatcatt gaaccatttg ctgacagctt tagacaccac   4500
tgatgcagat gtagccatat actgcaggga caagaaatgg gaaatgactc tcaaggaagc   4560
agtggctagg agagaagcag tggaggagat atgcatatcc gacgactctt cagtgacaga   4620
acctgatgca gagctggtga gggtgcatcc gaagagttct ttggctggaa ggaagggcta   4680
cagcacaagc gatggcaaaa ctttctcata tttggaaggg accaagtttc accaggcggc   4740
caaggatata gcagaaatta atgccatgtg gcccgttgca acggaggcca atgagcaggt   4800
atgcatgtat atcctcggag aaagcatgag cagtattagg tcgaaatgcc ccgtcgaaga   4860
gtcggaagcc tcctcaccac ctagcacgct gccttgcttg tgcatccatg ccatgactcc   4920
```

-continued agaaagagta cagcgcctaa aagcctcacg tccagaacaa attactgtgt gctcatcctt 4980
tccattgccg aagtatagaa tcactggtgt gcagaagatc caatgctccc agcctatatt 5040
gttctcaccg aaagtgcctg cgtatattca tccaaggaag tatctcgtgg aaacaccacc 5100
ggtagacgag actccggagc catcggcaga gaaccaatcc acagagggga cacctgaaca 5160
accaccactt ataaccgagg atgagaccag gactagaacg cctgagccga tcatcatcga 5220
agaggaagaa gaggatagca taagtttgct gtcagatggc ccgacccacc aggtgctgca 5280
agtcgaggca gacattcacg ggccgccctc tgtatctagc tcatcctggt ccattcctca 5340
tgcatccgac tttgatgtgg acagtttatc catacttgac accctggagg gagctagcgt 5400
gaccagcggg gcaacgtcag ccgagactaa ctcttacttc gcaaagagta tggagtttct 5460
ggcgcgaccg gtgcctgcgc ctcgaacagt attcaggaac cctccacatc ccgctccgcg 5520
cacaagaaca ccgtcacttg cacccagcag ggcctgctcg agagggatca cgggagaaac 5580
cgtgggatac gcggttacac acaatagcga gggcttcttg ctatgcaaag ttactgacac 5640
agtaaaagga gaacgggtat cgttccctgt gtgcacgtac atcccggcca ccataaactc 5700
gagaaccagc ctggtctcca acccgccagg cgtaaatagg gtgattacaa gagaggagtt 5760
tgaggcgttc gtagcacaac aacaatgacg gtttgatgcg ggtgcataca tcttttcctc 5820
cgacaccggt caagggcatt tacaacaaaa atcagtaagg caaacggtgc tatccgaagt 5880
ggtgttggag aggaccgaat tggagatttc gtatgccccg cgcctcgacc aagaaaaaga 5940
agaattacta cgcaagaaat tacagttaaa tcccacacct gctaacagaa gcagatacca 6000
gtccaggaag gtggagaaca tgaaagccat aacagctaga cgtattctgc aaggcctagg 6060
gcattatttg aaggcagaag gaaaagtgga gtgctaccga accctgcatc ctgttccttt 6120
gtattcatct agtgtgaacc gtgccttttc aagccccaag gtcgcagtgg aagcctgtaa 6180
cgccatgttg aaagagaact ttccgactgt ggcttcttac tgtattattc cagagtacga 6240
tgcctatttg gacatggttg acggagcttc atgctgctta gacactgcca gtttttgccc 6300
tgcaaagctg cgcagctttc caaagaaaca ctcctatttg gaacccacaa tacgatcggc 6360
agtgccttca gcgatccaga acacgctcca gaacgtcctg gcagctgcca caaaaagaaa 6420
ttgcaatgtc acgcaaatga gagaattgcc cgtattggat tcggcggcct ttaatgtgga 6480
atgcttcaag aaatatgcgt gtaataatga atattgggaa acgtttaaag aaaaccccat 6540
caggcttact gaagaaaacg tggtaaatta cattaccaaa ttaaaaggac caaaagctgc 6600
tgctcttttt gcgaagacac ataatttgaa tatgttgcag gacataccaa tggacaggtt 6660
tgtaatggac ttaaagagag acgtgaaagt gactccagga acaaaacata ctgaagaacg 6720
gcccaaggta caggtgatcc aggctgccga tccgctagca acagcgtatc tgtgcggaat 6780
ccaccgagag ctggttagga gattaaatgc ggtcctgctt ccgaacattc atacactgtt 6840
tgatatgtcg gctgaagact ttgacgctat tatagccgag cacttccagc ctggggattg 6900
tgttctggaa actgacatcg cgtcgtttga taaaagtgag gacgacgcca tggctctgac 6960
cgcgttaatg attctggaag acttaggtgt ggacgcagag ctgttgacgc tgattgaggc 7020
ggctttcggc gaaatttcat caatacattt gcccactaaa actaaattta aattcggagc 7080
catgatgaaa tctggaatgt tcctcacact gtttgtgaac acagtcatta acattgtaat 7140
cgcaagcaga gtgttgagag aacggctaac cggatcacca tgtgcagcat tcattggaga 7200
tgacaatatc gtgaaaggag tcaaatcgga caaattaatg gcagacaggt gcgccacctg 7260

-continued gttgaatatg gaagtcaaga ttatagatgc tgtggtgggc gagaaagcgc cttatttctg 7320
tggagggttt attttgtgtg actccgtgac cggcacagcg tgccgtgtgg cagacccccct 7380 aaaaaggctg tttaagcttg gcaaacctct ggcagcagac gatgaacatg atgatgacag 7440
gagaagggca ttgcatgaag agtcaacacg ctggaaccga gtgggtattc tttcagagct 7500
gtgcaaggca gtagaatcaa ggtatgaaac cgtaggaact tccatcatag ttatggccat 7560
gactactcta gctagcagtg ttaaatcatt cagctacctg agaggggccc ctataactct 7620
ctacggctaa cctgaatgga ctacgacata gtctagtcga cgccaccatg aggcctggcc 7680
tgccctccta cctgatcatc ctggccgtgt gcctgttcag ccacctgctg tccagcagat 7740
acggcgccga ggccgtgagc gagcccctgg acaaggcttt ccacctgctg ctgaacacct 7800
acggcagacc catccggttt ctgcgggaga acaccaccca gtgcacctac aacagcagcc 7860
tgcggaacag caccgtcgtg agagagaacg ccatcagctt caactttttc cagagctaca 7920
accagtacta cgtgttccac atgcccagat gcctgtttgc cggccctctg gccgagcagt 7980
tcctgaacca ggtggacctg accgagacac tggaaagata ccagcagcgg ctgaatacct 8040
acgccctggt gtccaaggac ctggccagct accggtcctt tagccagcag ctcaaggctc 8100
aggatagcct cggcgagcag cctaccaccg tgccccctcc catcgacctg agcatccccc 8160
acgtgtggat gcctccccag accacccctc acggctggac cgagagccac accacctccg 8220
gcctgcacag accccacttc aaccagacct gcatcctgtt cgacggccac gacctgctgt 8280
ttagcaccgt gaccccctgc ctgcaccagg gcttctacct gatcgacgag ctgagatacg 8340
tgaagatcac cctgaccgag gatttcttcg tggtcaccgt gtccatcgac gacgacaccc 8400
ccatgctgct gatcttcggc cacctgccca gagtgctgtt caaggccccc taccagcggg 8460
acaacttcat cctgcggcag accgagaagc acgagctgct ggtgctggtc aagaaggacc 8520
agctgaaccg gcactcctac ctgaaggacc ccgacttcct ggacgccgcc ctggacttca 8580
actacctgga cctgagcgcc ctgctgagaa acagcttcca cagatacgcc gtggacgtgc 8640
tgaagtccgg acggtgccag atgctcgatc ggcggaccgt ggagatggcc ttcgcctatg 8700
ccctcgccct gttcgccgct gccagacagg aagaggctgg cgcccaggtg tcagtgccca 8760
gagccctgga tagacaggcc gccctgctgc agatccagga attcatgatc acctgcctga 8820
gccagacccc ccctagaacc accctgctgc tgtaccccac agccgtggat ctggccaaga 8880
gggccctgtg gacccccaac cagatcaccg acatcacaag cctcgtgcgg ctcgtgtaca 8940
tcctgagcaa gcagaaccag cagcacctga tcccccagtg ggccctgaga cagatcgccg 9000
acttcgccct gaagctgcac aagacccatc tggccagctt tctgagcgcc ttcgccaggc 9060
aggaactgta cctgatgggc agcctggtcc acagcatgct ggtgcatacc accgagcggc 9120
gggagatctt catcgtggag acaggcctgt gtagcctggc cgagctgtcc cactttaccc 9180
agctgctggc ccaccctcac cacgagtacc tgagcgacct gtacaccccc tgcagcagca 9240
gcggcagacg ggaccacagc ctggaacggc tgaccagact gttccccgat gccaccgtgc 9300
ctgctacagt gcctgccgcc ctgtccatcc tgtccaccat gcagcccagc accctggaaa 9360
ccttccccga cctgttctgc ctgcccctgg gcgagagctt tagcgccctg accgtgtccg 9420
agcacgtgtc ctacatcgtg accaatcagt acctgatcaa gggcatcagc taccccgtgt 9480
ccaccacagt cgtgggccag agcctgatca tcacccagac cgacagccag accaagtgcg 9540
agctgacccg gaacatgcac accacacaca gcatcaccgt ggccctgaac atcagcctgg 9600
aaaactgcgc tttctgtcag tctgccctgc tggaatacga cgatacccag ggcgtgatca 9660

```
acatcatgta catgcacgac agcgacgacg tgctgttcgc cctggacccc tacaacgagg   9720
tggtggtgtc cagccccccgg acccactacc tgatgctgct gaagaacggc accgtgctgg   9780
aagtgaccga cgtggtggtg gacgccaccg acagcagact gctgatgatg agcgtgtacg   9840
ccctgagcgc catcatcggc atctacctgc tgtaccggat gctgaaaacc tgctgataat   9900
ctagacggcg cgcccaccca gcggccgcct ataactctct acggctaacc tgaatggact   9960
acgacatagt ctagtcgacg ccaccatgtg cagaaggccc gactgcggct tcagcttcag  10020
ccctggaccc gtgatcctgc tgtggtgctg cctgctgctg cctatcgtgt cctctgccgc  10080
cgtgtctgtg gcccctacag ccgccgagaa ggtgccagcc gagtgccccg agctgaccag  10140
aagatgcctg ctgggcgagg tgttcgaggg cgacaagtac gagagctggc tgcggcccct  10200
ggtcaacgtg accggcagag atggccccct gagccagctg atccggtaca gacccgtgac  10260
ccccgaggcc gccaatagcg tgctgctgga cgaggccttc ctggataccc tggccctgct  10320
gtacaacaac cccgaccagc tgagagccct gctgaccctg ctgtccagcg acaccgcccc  10380
cagatggatg accgtgatgc ggggctacag cgagtgtgga gatggcagcc ctgccgtgta  10440
cacctgcgtg gacgacctgt gcagaggcta cgacctgacc agactgagct acggccggtc  10500
catcttcaca gagcacgtgc tgggcttcga gctggtgccc cccagcctgt tcaacgtggt  10560
ggtggccatc cggaacgagg ccaccagaac caacagagcc gtgcggctgc ctgtgtctac  10620
agccgctgca cctgagggca tcacactgtt ctacggcctg tacaacgccg tgaaagagtt  10680
ctgcctccgg caccagctgg atcccccccct gctgagacac ctggacaagt actacgccgg  10740
cctgccccca gagctgaagc agaccagagt gaacctgccc gcccacagca gatatggccc  10800
tcaggccgtg gacgccagat gataatctag acggcgcgcc cacccaatcg atctataact  10860
ctctacggct aacctgaatg gactacgaca tagtctagtc gacgccacca tgggcaagaa  10920
agaaatgatc atggtcaagg gcatccccaa gatcatgctg ctgattagca tcacctttct  10980
gctgctgtcc ctgatcaact gcaacgtgct ggtcaacagc cggggcacca gaagatcctg  11040
gccctacacc gtgctgtcct accggggcaa agagatcctg aagaagcaga aagaggacat  11100
cctgaagcgg ctgatgagca ccagcagcga cggctaccgg ttcctgatgt accccagcca  11160
gcagaaattc cacgccatcg tgatcagcat ggacaagttc ccccaggact acatcctggc  11220
cggacccatc cggaacgaca gcatcaccca catgtggttc gacttctaca gcacccagct  11280
gcggaagccc gccaaatacg tgtacagcga gtacaaccac accgcccaca agatcaccct  11340
gaggcctccc ccttgtggca ccgtgcccag catgaactgc ctgagcgaga tgctgaacgt  11400
gtccaagcgg aacgacaccg gcgagaaggg ctgcggcaac ttcaccacct tcaaccccat  11460
gttcttcaac gtgccccggt ggaacaccaa gctgtacatc ggcagcaaca aagtgaacgt  11520
ggacagccag accatctact ttctgggcct gaccgccctg ctgctgagat acgcccagcg  11580
gaactgcacc cggtccttct acctggtcaa cgccatgagc cggaacctgt tccgggtgcc  11640
caagtacatc aacggcacca agctgaagaa caccatgcgg aagctgaagc ggaagcaggc  11700
cctggtcaaa gagcagcccc agaagaagaa caagaagtcc cagagcacca ccaccccccta  11760
cctgagctac accacctcca ccgccttcaa cgtgaccacc aacgtgacct acagcgccac  11820
agccgccgtg accagagtgg ccacaagcac caccggctac cggcccgaca gcaactttat  11880
gaagtccatc atggccaccc agctgagaga tctggccacc tgggtgtaca ccaccctgcg  11940
gtacagaaac gagcccttct gcaagcccga ccggaacaga accgccgtga gcgagttcat  12000
```

-continued

```
gaagaatacc cacgtgctga tcagaaacga gacaccctac accatctacg gcaccctgga  12060
catgagcagc ctgtactaca acgagacaat gagcgtggag aacgagacag ccagcgacaa  12120
caacgaaacc acccccacct cccccagcac ccggttccag cggaccttca tcgacccccct  12180
gtgggactac ctggacagcc tgctgttcct ggacaagatc cggaacttca gcctgcagct  12240
gcccgcctac ggcaatctga cccccctga gcacagaagg gccgccaacc tgagcaccct  12300
gaacagcctg tggtggtgga gccagtgata atctagacgg cgcgcccacc caccgcgggc  12360
aatatagcaa cactaaaaac tcgatgtact tccgaggaag cgcagtgcat aatgctgcgc  12420
agtgttgcca cataaccact atattaacca tttatctagc ggacgccaaa aactcaatgt  12480
atttctgagg aagcgtggtg cataatgcca cgcagcgtct gcataacttt tattatttct  12540
tttattaatc aacaaaattt tgtttttaac atttcaaaaa aaaaaaaaaa aaaaaaaaaa  12600
aaaaaaaaaa aaaaagggtc ggcatggcat ctccacctcc tcgcggtccg acctgggcat  12660
ccgaaggagg acgcacgtcc actcggatgg ctaagggaga gccacgagct cctgtttaaa  12720
ccagctccaa ttcgccctat agtgagtcgt attacgcgcg ctcactggcc gtcgttttac  12780
aacgtcgtga ctgggaaaac cctggcgtta cccaacttaa tcgccttgca gcacatcccc  12840
ctttcgccag ctggcgtaat agcgaagagg cccgcaccga tcgcccttcc caacagttgc  12900
gcagcctgaa tggcgaatgg gacgcgccct gtagcggcgc attaagcgcg gcgggtgtgg  12960
tggttacgcg cagcgtgacc gctacacttg ccagcgccct agcgcccgct cctttcgctt  13020
tcttcccttc ctttctcgcc acgttcgccg gctttccccg tcaagctcta aatcgggggc  13080
tccctttagg gttccgattt agtgctttac ggcacctcga ccccaaaaaa cttgattagg  13140
gtgatggttc acgtagtggg ccatcgccct gatagacggt ttttcgccct ttgacgttgg  13200
agtccacgtt ctttaatagt ggactcttgt tccaaactgg aacaacactc aaccctatct  13260
cggtctattc ttttgattta taagggattt tgccgatttc ggcctattgg ttaaaaaatg  13320
agctgattta acaaaaattt aacgcgaatt ttaacaaaat attaacgctt acaatttagg  13380
tggcactttt cggggaaatg tgcgcggaac ccctatttgt ttatttttct aaatacattc  13440
aaatatgtat ccgctcatga gacaataacc ctgataaatg cttcaataat attgaaaaag  13500
gaagagtatg agtattcaac atttccgtgt cgcccttatt cccttttttg cggcattttg  13560
ccttcctgtt tttgctcacc cagaaacgct ggtgaaagta aaagatgctg aagatcagtt  13620
gggtgcacga gtgggttaca tcgaactgga tctcaacagc ggtaagatcc ttgagagttt  13680
tcgccccgaa gaacgttttc caatgatgag cacttttaaa gttctgctat gtggcgcggt  13740
attatcccgt attgacgccg ggcaagagca actcggtcgc cgcatacact attctcagaa  13800
tgacttggtt gagtactcac cagtcacaga aaagcatctt acggatggca tgacagtaag  13860
agaattatgc agtgctgcca taaccatgag tgataacact gcggccaact tacttctgac  13920
aacgatcgga ggaccgaagg agctaaccgc ttttttgcac aacatggggg atcatgtaac  13980
tcgccttgat cgttgggaac cggagctgaa tgaagccata ccaaacgacg agcgtgacac  14040
cacgatgcct gtagcaatgg caacaacgtt gcgcaaacta ttaactggcg aactacttac  14100
tctagcttcc cggcaacaat taatagactg gatggaggcg gataaagttg caggaccact  14160
tctgcgctcg gcccttccgg ctggctggtt tattgctgat aaatctggag ccggtgagcg  14220
tgggtctcgc ggtatcattg cagcactggg gccagatggt aagccctccc gtatcgtagt  14280
tatctacacg acggggagtc aggcaactat ggatgaacga aatagacaga tcgctgagat  14340
aggtgcctca ctgattaagc attggtaact gtcagaccaa gtttactcat atatacttta  14400
```

gattgattta aaacttcatt tttaatttaa aaggatctag gtgaagatcc tttttgataa 14460
tctcatgacc aaaatccctt aacgtgagtt ttcgttccac tgagcgtcag accccgtaga 14520
aaagatcaaa ggatcttctt gagatccttt ttttctgcgc gtaatctgct gcttgcaaac 14580
aaaaaaacca ccgctaccag cggtggtttg tttgccggat caagagctac caactctttt 14640
tccgaaggta actggcttca gcagagcgca gataccaaat actgttcttc tagtgtagcc 14700
gtagttaggc caccacttca agaactctgt agcaccgcct acatacctcg ctctgctaat 14760
cctgttacca gtggctgctg ccagtggcga taagtcgtgt cttaccgggt tggactcaag 14820
acgatagtta ccggataagg cgcagcggtc gggctgaacg gggggttcgt gcacacagcc 14880
cagcttggag cgaacgacct acaccgaact gagataccta cagcgtgagc tatgagaaag 14940
cgccacgctt cccgaaggga gaaaggcgga caggtatccg gtaagcggca gggtcggaac 15000
aggagagcgc acgagggagc ttccaggggg aaacgcctgg tatctttata gtcctgtcgg 15060
gtttcgccac ctctgacttg agcgtcgatt tttgtgatgc tcgtcagggg ggcggagcct 15120
atggaaaaac gccagcaacg cggccttttt acggttcctg gccttttgct ggccttttgc 15180
tcacatgttc tttcctgcgt tatcccctga ttctgtggat aaccgtatta ccgcctttga 15240
gtgagctgat accgctcgcc gcagccgaac gaccgagcgc agcgagtcag tgagcgagga 15300
agcggaagag cgcccaatac gcaaaccgcc tctccccgcg cgttggccga ttcattaatg 15360
cagctggcac gacaggtttc ccgactggaa agcgggcagt gagcgcaacg caattaatgt 15420
gagttagctc actcattagg caccccaggc tttacacttt atgctcccgg ctcgtatgtt 15480
gtgtggaatt gtgagcggat aacaatttca cacaggaaac agctatgacc atgattacgc 15540
caagcgcgca attaaccctc actaaaggga acaaaagctg ggtaccggcg cca 15593

<210> SEQ ID NO 56
<211> LENGTH: 15271
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 56
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780

-continued

```
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
```

```
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
```

caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga cccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gatgaggcct ggcctgccct cctacctgat catcctggcc gtgtgcctgt tcagccacct 7620
gctgtccagc agatacggcg ccgaggccgt gagcgagccc ctggacaagg ctttccacct 7680
gctgctgaac acctacggca gacccatccg gtttctgcgg gagaacacca cccagtgcac 7740
ctacaacagc agcctgcgga acagcaccgt cgtgagagag aacgccatca gcttcaactt 7800
tttccagagc tacaaccagt actacgtgtt ccacatgccc agatgcctgt ttgccggccc 7860
tctggccgag cagttcctga accaggtgga cctgaccgag acactggaaa gataccagca 7920

-continued

```
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga cccccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgacagca gactgctgat   9720
gatgagcgtg tacgccctga gcgccatcat cggcatctac ctgctgtacc ggatgctgaa   9780
aacctgctga taatctagag gcccctataa ctctctacgg ctaacctgaa tggactacga   9840
catagtctag tccgccaaga tgtgcagaag gcccgactgc ggcttcagct tcagccctgg   9900
acccgtgatc ctgctgtggt gctgcctgct gctgcctatc gtgtcctctg ccgccgtgtc   9960
tgtggcccct acagccgccg agaaggtgcc agccgagtgc cccgagctga ccagaagatg  10020
cctgctgggc gaggtgttcg agggcgacaa gtacgagagc tggctgcggc ccctggtcaa  10080
cgtgaccggc agagatggcc ccctgagcca gctgatccgg tacagacccg tgacccccga  10140
ggccgccaat agcgtgctgc tggacgaggc cttcctggat accctggccc tgctgtacaa  10200
caaccccgac cagctgagag ccctgctgac cctgctgtcc agcgacaccg cccccagatg  10260
```

-continued

```
gatgaccgtg atgcggggct acagcgagtg tggagatggc agccctgccg tgtacacctg  10320
cgtggacgac ctgtgcagag gctacgacct gaccagactg agctacggcc ggtccatctt  10380
cacagagcac gtgctgggct tcgagctggt gccccccagc ctgttcaacg tggtggtggc  10440
catccggaac gaggccacca gaaccaacag agccgtgcgg ctgcctgtgt ctacagccgc  10500
tgcacctgag ggcatcacac tgttctacgg cctgtacaac gccgtgaaag agttctgcct  10560
ccggcaccag ctggatcccc ccctgctgag acacctggac aagtactacg ccggcctgcc  10620
cccagagctg aagcagacca gagtgaacct gcccgcccac agcagatatg gccctcaggc  10680
cgtggacgcc agatgataac gccggcggcc cctataactc tctacggcta acctgaatgg  10740
actacgacat agtctagtcc gccaagatga gccccaagga cctgaccccc ttcctgacaa  10800
ccctgtggct gctcctgggc catagcagag tgcctagagt gcgggccgag gaatgctgcg  10860
agttcatcaa cgtgaaccac ccccccgagc ggtgctacga cttcaagatg tgcaaccggt  10920
tcaccgtggc cctgagatgc cccgacggcg aagtgtgcta cagccccgag aaaaccgccg  10980
agatccgggg catcgtgacc accatgaccc acagcctgac ccggcaggtg gtgcacaaca  11040
agctgaccag ctgcaactac aaccccctgt acctggaagc cgacggccgg atcagatgcg  11100
gcaaagtgaa cgacaaggcc cagtacctgc tgggagccgc cggaagcgtg ccctaccggt  11160
ggatcaacct ggaatacgac aagatcaccc ggatcgtggg cctggaccag tacctggaaa  11220
gcgtgaagaa gcacaagcgg ctggacgtgt gcagagccaa gatgggctac atgctgcagc  11280
tgttgaattt tgaccttctt aagcttgcgg gagacgtcga gtccaacccc gggcccatgc  11340
tgcggctgct gctgagacac cacttccact gcctgctgct gtgtgccgtg tgggccaccc  11400
cttgtctggc cagcccttgg agcaccctga ccgccaacca gaaccctagc ccccccttggt  11460
ccaagctgac ctacagcaag ccccacgacg ccgccacctt ctactgcccc tttctgtacc  11520
ccagccctcc cagaagcccc ctgcagttca gcggcttcca gagagtgtcc accggccctg  11580
agtgccggaa cgagacactg tacctgctgt acaaccggga gggccagaca ctggtggagc  11640
ggagcagcac ctgggtgaaa aaagtgatct ggtatctgag cggccggaac cagaccatcc  11700
tgcagcggat gcccagaacc gccagcaagc ccagcgacgg caacgtgcag atcagcgtgg  11760
aggacgccaa aatcttcggc gcccacatgg tgcccaagca gaccaagctg ctgagattcg  11820
tggtcaacga cggcaccaga tatcagatgt gcgtgatgaa gctggaaagc tgggcccacg  11880
tgttccggga ctactccgtg agcttccagg tccggctgac cttcaccgag gccaacaacc  11940
agacctacac cttctgcacc caccccaacc tgatcgtgct gctgaacttc gacctgctga  12000
agctggccgg cgacgtggag agcaaccccg gcccccatat gcggctgtgc agagtgtggc  12060
tgtccgtgtg cctgtgtgcc gtggtgctgg gccagtgcca gagagagaca gccgagaaga  12120
acgactacta ccgggtgccc cactactggg atgcctgcag cagagccctg cccgaccaga  12180
cccggtacaa atacgtggag cagctcgtgg acctgaccct gaactaccac tacgacgcca  12240
gccacggcct ggacaacttc gacgtgctga agcggatcaa cgtgaccgag gtgtccctgc  12300
tgatcagcga cttccggcgg cagaacagaa gaggcggcac caacaagcgg accaccttca  12360
acgccgctgg ctctctggcc cctcacgcca gatccctgga attcagcgtg cggctgttcg  12420
ccaactgata acgttgcatc ctgcaggata cagcagcaat tggcaagctg cttacataga  12480
actcgcggcg attggcatgc cgccttaaaa tttttatttt atttttcttt tcttttccga  12540
atcggatttt gtttttaata tttcaaaaaa aaaaaaaaaa aaaaaaaaaa aaaaaaaaag  12600
ggtcggcatg gcatctccac ctcctcgcgg tccgacctgg gcatccgaag gaggacgcac  12660
```

gtccactcgg atggctaagg gagagccacg tttaaacgct agagcaagac gtttcccgtt 12720
gaatatggct cataacaccc cttgtattac tgtttatgta agcagacagt tttattgttc 12780
atgatgatat atttttatct tgtgcaatgt aacatcagag attttgagac acaacgtggc 12840
tttgttgaat aaatcgaact tttgctgagt tgaaggatca gatcacgcat cttcccgaca 12900
acgcagaccg ttccgtggca aagcaaaagt tcaaaatcac caactggtcc acctacaaca 12960
aagctctcat caaccgtggc tccctcactt tctggctgga tgatggggcg attcaggcct 13020
ggtatgagtc agcaacacct tcttcacgag gcagacctca gcgctagcgg agtgtatact 13080
ggcttactat gttggcactg atgagggtgt cagtgaagtg cttcatgtgg caggagaaaa 13140
aaggctgcac cggtgcgtca gcagaatatg tgatacagga tatattccgc ttcctcgctc 13200
actgactcgc tacgctcggt cgttcgactg cggcgagcgg aaatggctta cgaacggggc 13260
ggagatttcc tggaagatgc caggaagata cttaacaggg aagtgagagg gccgcggcaa 13320
agccgttttt ccataggctc cgcccccctg acaagcatca cgaaatctga cgctcaaatc 13380
agtggtggcg aaacccgaca ggactataaa gataccaggc gtttcccctg gcggctccct 13440
cgtgcgctct cctgttcctg cctttcggtt taccggtgtc attccgctgt tatggccgcg 13500
tttgtctcat tccacgcctg acactcagtt ccgggtaggc agttcgctcc aagctggact 13560
gtatgcacga acccccgtt cagtccgacc gctgcgcctt atccggtaac tatcgtcttg 13620
agtccaaccc ggaaagacat gcaaaagcac cactggcagc agccactggt aattgattta 13680
gaggagttag tcttgaagtc atgcgccggt taaggctaaa ctgaaaggac aagttttggt 13740
gactgcgctc ctccaagcca gttacctcgg ttcaaagagt tggtagctca gagaaccttc 13800
gaaaaaccgc cctgcaaggc ggtttttcg ttttcagagc aagagattac gcgcagacca 13860
aaacgatctc aagaagatca tcttattaag ggtctgacg ctcagtggaa cgaaaactca 13920
cgttaaggga ttttggtcat gagattatca aaaaggatct tcacctagat ccttttaaat 13980
taaaaatgaa gttttaaatc aatctaaagt atatatgagt aaacttggtc tgacagttat 14040
tagaaaaatt catccagcag acgataaaac gcaatacgct ggctatccgg tgccgcaatg 14100
ccatacagca ccagaaaacg atccgcccat tcgccgccca gttcttccgc aatatcacgg 14160
gtggccagcg caatatcctg ataacgatcc gccacgccca gacggccgca atcaataaag 14220
ccgctaaaac ggccattttc caccataatg ttcggcaggc acgcatcacc atgggtcacc 14280
accagatctt cgccatccgg catgctcgct ttcagacgcg caaacagctc tgccggtgcc 14340
aggccctgat gttcttcatc cagatcatcc tgatccacca ggcccgcttc catacgggta 14400
cgcgcacgtt caatacgatg tttcgcctga tgatcaaacg gacaggtcgc cgggtccagg 14460
gtatgcagac gacgcatggc atccgccata atgctcactt tttctgccgg cgccagatgg 14520
ctagacagca gatcctgacc cggcacttcg cccagcagca gccaatcacg gcccgcttcg 14580
gtcaccacat ccagcaccgc cgcacacgga acaccggtgg tggccagcca gctcagacgc 14640
gccgcttcat cctgcagctc gttcagcgca ccgctcagat cggttttcac aaacagcacc 14700
ggacgaccct gcgcgctcag acgaaacacc gccgcatcag agcagccaat ggtctgctgc 14760
gcccaatcat agccaaacag acgttccacc cacgctgccg ggctacccgc atgcaggcca 14820
tcctgttcaa tcatactctt cctttttcaa tattattgaa gcatttatca gggttattgt 14880
ctcatgagcg gatacatatt tgaatgtatt tagaaaaata aacaaatagg ggttccgcgc 14940
acatttcccc gaaaagtgcc acctaaattg taagcgttaa tattttgtta aaattcgcgt 15000
taaatttttg ttaaatcagc tcatttttta accaataggc cgaaatcggc aaaatccctt 15060
ataaatcaaa agaatagacc gagatagggt tgagtggccg ctacagggcg ctcccattcg 15120
ccattcaggc tgcgcaactg ttgggaaggg cgtttcggtg cgggcctctt cgctattacg 15180
ccagctggcg aaagggggat gtgctgcaag gcgattaagt tgggtaacgc cagggttttc 15240
ccagtcacac gcgtaatacg actcactata g 15271

<210> SEQ ID NO 57
<211> LENGTH: 16405
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tagacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgaggggga tattgccacg gccaccgaag 4080

-continued gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gatgaggcct ggcctgccct cctacctgat catcctggcc gtgtgcctgt tcagccacct 7620
gctgtccagc agatacggcg ccgaggccgt gagcgagccc ctggacaagg ctttccacct 7680
gctgctgaac acctacggca gacccatccg gtttctgcgg gagaacacca cccagtgcac 7740
ctacaacagc agcctgcgga acagcaccgt cgtgagagag aacgccatca gcttcaactt 7800
tttccagagc tacaaccagt actacgtgtt ccacatgccc agatgcctgt ttgccggccc 7860
tctggccgag cagttcctga accaggtgga cctgaccgag acactggaaa gataccagca 7920
gcggctgaat acctacgccc tggtgtccaa ggacctggcc agctaccggt cctttagcca 7980
gcagctcaag gctcaggata gcctcggcga gcagcctacc accgtgcccc ctcccatcga 8040
cctgagcatc ccccacgtgt ggatgcctcc ccagaccacc cctcacggct ggaccgagag 8100
ccacaccacc tccggcctgc acagacccca cttcaaccag acctgcatcc tgttcgacgg 8160
ccacgacctg ctgtttagca ccgtgacccc ctgcctgcac cagggcttct acctgatcga 8220
cgagctgaga tacgtgaaga tcaccctgac cgaggatttc ttcgtggtca ccgtgtccat 8280
cgacgacgac acccccatgc tgctgatctt cggccacctg cccagagtgc tgttcaaggc 8340
cccctaccag cgggacaact tcatcctgcg gcagaccgag aagcacgagc tgctggtgct 8400
ggtcaagaag gaccagctga accggcactc ctacctgaag gaccccgact tcctggacgc 8460
cgccctggac ttcaactacc tggacctgag cgccctgctg agaaacagct tccacagata 8520
cgccgtggac gtgctgaagt ccggacggtg ccagatgctc gatcggcgga ccgtggagat 8580
ggccttcgcc tatgccctcg ccctgttcgc cgctgccaga caggaagagg ctggcgccca 8640
ggtgtcagtg cccagagccc tggatagaca ggccgccctg ctgcagatcc aggaattcat 8700
gatcacctgc ctgagccaga cccccccctag aaccaccctg ctgctgtacc ccacagccgt 8760
ggatctggcc aagagggccc tgtggacccc caaccagatc accgacatca caagcctcgt 8820

-continued

```
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgacagca gactgctgat   9720
gatgagcgtg tacgccctga gcgccatcat cggcatctac ctgctgtacc ggatgctgaa   9780
aacctgctga taatctagag gcccctataa ctctctacgg ctaacctgaa tggactacga   9840
catagtctag tccgccaaga tgtgcagaag gcccgactgc ggcttcagct tcagccctgg   9900
acccgtgatc ctgctgtggt gctgcctgct gctgcctatc gtgtcctctg ccgccgtgtc   9960
tgtggcccct acagccgccg agaaggtgcc agccgagtgc cccgagctga ccagaagatg  10020
cctgctgggc gaggtgttcg agggcgacaa gtacgagagc tggctgcggc ccctggtcaa  10080
cgtgaccggc agagatggcc ccctgagcca gctgatccgg tacagacccg tgacccccga  10140
ggccgccaat agcgtgctgc tggacgaggc cttcctggat accctggccc tgctgtacaa  10200
caaccccgac cagctgagag ccctgctgac cctgctgtcc agcgacaccg cccccagatg  10260
gatgaccgtg atgcggggct acagcgagtg tggagatggc agccctgccg tgtacacctg  10320
cgtggacgac ctgtgcagag gctacgacct gaccagactg agctacggcc ggtccatctt  10380
cacagagcac gtgctgggct tcgagctggt gccccccagc ctgttcaacg tggtggtggc  10440
catccggaac gaggccacca gaaccaacag agccgtgcgg ctgcctgtgt ctacagccgc  10500
tgcacctgag ggcatcacac tgttctacgg cctgtacaac gccgtgaaag agttctgcct  10560
ccggcaccag ctggatcccc ccctgctgag acacctggac aagtactacg ccggcctgcc  10620
cccagagctg aagcagacca gagtgaacct gcccgcccac agcagatatg gccctcaggc  10680
cgtggacgcc agatgataac gccggcggcc cctataactc tctacggcta acctgaatgg  10740
actacgacat agtctagtcc gccaagatga gccccaagga cctgaccccc ttcctgacaa  10800
ccctgtggct gctcctgggc catagcagag tgcctagagt gcgggccgag gaatgctgcg  10860
agttcatcaa cgtgaaccac ccccccgagc ggtgctacga cttcaagatg tgcaaccggt  10920
tcaccgtggc cctgagatgc cccgacggcg aagtgtgcta cagccccgag aaaaccgccg  10980
agatccgggg catcgtgacc accatgaccc acagcctgac ccggcaggtg gtgcacaaca  11040
agctgaccag ctgcaactac aaccccctgt acctggaagc cgacggccgg atcagatgcg  11100
gcaaagtgaa cgacaaggcc cagtacctgc tgggagccgc cggaagcgtg ccctaccggt  11160
ggatcaacct ggaatacgac aagatcaccc ggatcgtggg cctggaccag tacctggaaa  11220
```

gcgtgaagaa gcacaagcgg ctggacgtgt gcagagccaa gatgggctac atgctgcagt 11280
gataaggcgc gccaacgtta ctggccgaag ccgcttggaa taaggccggt gtgcgtttgt 11340
ctatatgtta ttttccacca tattgccgtc ttttggcaat gtgagggccc ggaaacctgg 11400
ccctgtcttc ttgacgagca ttcctagggg tctttcccct ctcgccaaag gaatgcaagg 11460
tctgttgaat gtcgtgaagg aagcagttcc tctggaagct tcttgaagac aaacaacgtc 11520
tgtagcgacc ctttgcaggc agcggaaccc cccacctggc gacaggtgcc tctgcggcca 11580
aaagccacgt gtataagata cacctgcaaa ggcggcacaa ccccagtgcc acgttgtgag 11640
ttggatagtt gtggaaagag tcaaatggct ctcctcaagc gtattcaaca aggggctgaa 11700
ggatgcccag aaggtacccc attgtatggg atctgatctg gggcctcggt gcacatgctt 11760
tacatgtgtt tagtcgaggt taaaaaaacg tctaggcccc ccgaaccacg gggacgtggt 11820
tttcctttga aaaacacgat aatatgctgc ggctgctgct gagacaccac ttccactgcc 11880
tgctgctgtg tgccgtgtgg gccacccctt gtctggccag cccttggagc accctgaccg 11940
ccaaccagaa ccctagcccc ccttggtcca agctgaccta cagcaagccc cacgacgccg 12000
ccaccttcta ctgccccttt ctgtacccca gccctcccag aagccccctg cagttcagcg 12060
gcttccagag agtgtccacc ggccctgagt gccggaacga gacactgtac ctgctgtaca 12120
accgggaggg ccagacactg gtggagcgga gcagcacctg ggtgaaaaaa gtgatctggt 12180
atctgagcgg ccggaaccag accatcctgc agcggatgcc cagaaccgcc agcaagccca 12240
gcgacggcaa cgtgcagatc agcgtggagg acgccaaaat cttcggagcc cacatggtgc 12300
ccaagcagac caagctgctg agattcgtgg tcaacgacgg caccagatat cagatgtgcg 12360
tgatgaagct ggaaagctgg gcccacgtgt tccgggacta ctccgtgagc ttccaggtcc 12420
ggctgacctt caccgaggcc aacaaccaga cctacacctt ctgcacccac cccaacctga 12480
tcgtgtgata agtacctttg tacgcctgtt ttatacccc tccctgattt gcaacttaga 12540
agcaacgcaa accagatcaa tagtaggtgt gacataccag tcgcatcttg atcaagcact 12600
tctgtatccc cggaccgagt atcaatagac tgtgcacacg gttgaaggag aaaacgtccg 12660
ttacccggct aactacttcg agaagcctag taacgccatt gaagttgcag agtgtttcgc 12720
tcagcactcc ccccgtgtag atcaggtcga tgagtcaccg cattccccac gggcgaccgt 12780
ggcggtggct gcgttggcgg cctgcctatg gggtaaccca taggacgctc taatacggac 12840
atggcgtgaa gagtctattg agctagttag tagtcctccg gcccctgaat gcggctaatc 12900
ctaactgcgg agcacatacc cttaatccaa agggcagtgt gtcgtaacgg gcaactctgc 12960
agcggaaccg actactttgg gtgtccgtgt ttcttttat tcttgtattg gctgcttatg 13020
gtgacaatta aagaattgtt accatatagc tattggattg gccatccagt gtcaaacaga 13080
gctattgtat atctctttgt tggattcaca cctctcactc ttgaaacgtt acacaccctc 13140
aattacatta tactgctgaa cacgaagcgc atatgcggct gtgcagagtg tggctgtccg 13200
tgtgcctgtg tgccgtggtg ctgggccagt gccagagaga gacagccgag aagaacgact 13260
actaccgggt gccccactac tgggatgcct gcagcagagc cctgcccgac cagacccggt 13320
acaaatacgt ggagcagctc gtggacctga ccctgaacta ccactacgac gccagccacg 13380
gcctggacaa cttcgacgtg ctgaagcgga tcaacgtgac cgaggtgtcc ctgctgatca 13440
gcgacttccg gcggcagaac agaagaggcg gcaccaacaa gcggaccacc ttcaacgccg 13500
ctggctctct ggcccctcac gccagatccc tggaattcag cgtgcggctg ttcgccaact 13560
gataacgttg catcctgcag gatacagcag caattggcaa gctgcttaca tagaactcgc 13620
ggcgattggc atgccgcctt aaaattttta ttttattttt cttttctttt ccgaatcgga 13680
ttttgttttt aatatttcaa aaaaaaaaaa aaaaaaaaaa aaaaaaaaaa aaagggtcgg 13740
catggcatct ccacctcctc gcggtccgac ctgggcatcc gaaggaggac gcacgtccac 13800
tcggatggct aagggagagc cacgtttaaa cgctagagca agacgtttcc cgttgaatat 13860
ggctcataac accccttgta ttactgttta tgtaagcaga cagttttatt gttcatgatg 13920
atatattttt atcttgtgca atgtaacatc agagattttg agacacaacg tggctttgtt 13980
gaataaatcg aacttttgct gagttgaagg atcagatcac gcatcttccc gacaacgcag 14040
accgttccgt ggcaaagcaa aagttcaaaa tcaccaactg gtccacctac aacaaagctc 14100
tcatcaaccg tggctccctc actttctggc tggatgatgg ggcgattcag gcctggtatg 14160
agtcagcaac accttcttca cgaggcagac ctcagcgcta gcggagtgta tactggctta 14220
ctatgttggc actgatgagg gtgtcagtga agtgcttcat gtggcaggag aaaaaaggct 14280
gcaccggtgc gtcagcagaa tatgtgatac aggatatatt ccgcttcctc gctcactgac 14340
tcgctacgct cggtcgttcg actgcggcga gcggaaatgg cttacgaacg gggcggagat 14400
ttcctggaag atgccaggaa gatacttaac agggaagtga gagggccgcg gcaaagccgt 14460
ttttccatag gctccgcccc cctgacaagc atcacgaaat ctgacgctca aatcagtggt 14520
ggcgaaaccc gacaggacta taaagatacc aggcgtttcc cctggcggct ccctcgtgcg 14580
ctctcctgtt cctgcctttc ggtttaccgg tgtcattccg ctgttatggc cgcgtttgtc 14640
tcattccacg cctgacactc agttccgggt aggcagttcg ctccaagctg gactgtatgc 14700
acgaaccccc cgttcagtcc gaccgctgcg ccttatccgg taactatcgt cttgagtcca 14760
acccggaaag acatgcaaaa gcaccactgg cagcagccac tggtaattga tttagaggag 14820
ttagtcttga agtcatgcgc cggttaaggc taaactgaaa ggacaagttt tggtgactgc 14880
gctcctccaa gccagttacc tcggttcaaa gagttggtag ctcagagaac cttcgaaaaa 14940
ccgccctgca aggcggtttt ttcgttttca gagcaagaga ttacgcgcag accaaaacga 15000
tctcaagaag atcatcttat taaggggtct gacgctcagt ggaacgaaaa ctcacgttaa 15060
gggattttgg tcatgagatt atcaaaaagg atcttcacct agatcctttt aaattaaaaa 15120
tgaagtttta aatcaatcta aagtatatat gagtaaactt ggtctgacag ttattagaaa 15180
aattcatcca gcagacgata aaacgcaata cgctggctat ccggtgccgc aatgccatac 15240
agcaccagaa aacgatccgc ccattcgccg cccagttctt ccgcaatatc acgggtggcc 15300
agcgcaatat cctgataacg atccgccacg cccagacggc cgcaatcaat aaagccgcta 15360
aaacggccat tttccaccat aatgttcggc aggcacgcat caccatgggt caccaccaga 15420
tcttcgccat ccggcatgct cgctttcaga cgcgcaaaca gctctgccgg tgccaggccc 15480
tgatgttctt catccagatc atcctgatcc accaggcccg cttccatacg ggtacgcgca 15540
cgttcaatac gatgtttcgc ctgatgatca aacggacagg tcgccgggtc cagggtatgc 15600
agacgacgca tggcatccgc cataatgctc actttttctg ccggcgccag atggctagac 15660
agcagatcct gacccggcac ttcgcccagc agcagccaat cacggcccgc ttcggtcacc 15720
acatccagca ccgccgcaca cggaacaccg gtggtggcca gccagctcag acgcgccgct 15780
tcatcctgca gctcgttcag cgcaccgctc agatcggttt tcacaaacag caccggacga 15840
ccctgcgcgc tcagacgaaa caccgccgca tcagagcagc caatggtctg ctgcgcccaa 15900
tcatagccaa acagacgttc cacccacgct gccgggctac ccgcatgcag gccatcctgt 15960

```
tcaatcatac tcttcctttt tcaatattat tgaagcattt atcagggtta ttgtctcatg  16020

agcggataca tatttgaatg tatttagaaa aataaacaaa taggggttcc gcgcacattt  16080

ccccgaaaag tgccacctaa attgtaagcg ttaatatttt gttaaaattc gcgttaaatt  16140

tttgttaaat cagctcattt tttaaccaat aggccgaaat cggcaaaatc ccttataaat  16200

caaaagaata gaccgagata gggttgagtg gccgctacag ggcgctccca ttcgccattc  16260

aggctgcgca actgttggga agggcgtttc ggtgcgggcc tcttcgctat tacgccagct  16320

ggcgaaaggg ggatgtgctg caaggcgatt aagttgggta acgccagggt tttcccagtc  16380

acacgcgtaa tacgactcac tatag                                        16405


<210> SEQ ID NO 58
<211> LENGTH: 13102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58

ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440

caagaatcag gaaaatgtta gaggagcaca aggagccgtc acctctcatt accgccgagg   1500
```

-continued

```
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg actttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
```

cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga cccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gatgaggcct ggcctgccct cctacctgat catcctggcc gtgtgcctgt tcagccacct 7620
gctgtccagc agatacggcg ccgaggccgt gagcgagccc ctggacaagg ctttccacct 7680
gctgctgaac acctacggca gacccatccg gtttctgcgg gagaacacca cccagtgcac 7740
ctacaacagc agcctgcgga acagcaccgt cgtgagagag aacgccatca gcttcaactt 7800
tttccagagc tacaaccagt actacgtgtt cccacatgccc agatgcctgt ttgccggccc 7860
tctggccgag cagttcctga accaggtgga cctgaccgag acactggaaa gataccagca 7920
gcggctgaat acctacgccc tggtgtccaa ggacctggcc agctaccggt cctttagcca 7980
gcagctcaag gctcaggata gcctcggcga gcagcctacc accgtgcccc ctcccatcga 8040
cctgagcatc ccccacgtgt ggatgcctcc ccagaccacc cctcacggct ggaccgagag 8100
ccacaccacc tccggcctgc acagacccca cttcaaccag acctgcatcc tgttcgacgg 8160
ccacgacctg ctgtttagca ccgtgacccc ctgcctgcac cagggcttct acctgatcga 8220
cgagctgaga tacgtgaaga tcaccctgac cgaggatttc ttcgtggtca ccgtgtccat 8280
cgacgacgac acccccatgc tgctgatctt cggccacctg cccagagtgc tgttcaaggc 8340
cccctaccag cgggacaact tcatcctgcg gcagaccgag aagcacgagc tgctggtgct 8400
ggtcaagaag gaccagctga accggcactc ctacctgaag gaccccgact tcctggacgc 8460
cgccctggac ttcaactacc tggacctgag cgccctgctg agaaacagct tccacagata 8520
cgccgtggac gtgctgaagt ccggacggtg ccagatgctc gatcggcgga ccgtggagat 8580
ggccttcgcc tatgccctcg ccctgttcgc cgctgccaga caggaagagg ctggcgccca 8640

```
ggtgtcagtg cccagagccc tggatagaca ggccgccctg ctgcagatcc aggaattcat   8700
gatcacctgc ctgagccaga cccccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgactgat aatctagagg   9720
cccctataac tctctacggc taacctgaat ggactacgac atagtctagt ccgccaagat   9780
gtgcagaagg cccgactgcg gcttcagctt cagccctgga cccgtgatcc tgctgtggtg   9840
ctgcctgctg ctgcctatcg tgtcctctgc cgccgtgtct gtggccccta cagccgccga   9900
gaaggtgcca gccgagtgcc ccgagctgac cagaagatgc ctgctgggcg aggtgttcga   9960
gggcgacaag tacgagagct ggctgcggcc cctggtcaac gtgaccggca gagatggccc  10020
cctgagccag ctgatccggt acagacccgt gacccccgag gccgccaata gcgtgctgct  10080
ggacgaggcc ttcctggata ccctggccct gctgtacaac aaccccgacc agctgagagc  10140
cctgctgacc ctgctgtcca gcgacaccgc ccccagatgg atgaccgtga tgcggggcta  10200
cagcgagtgt ggagatggca gccctgccgt gtacacctgc gtggacgacc tgtgcagagg  10260
ctacgacctg accagactga gctacggccg gtccatcttc acagagcacg tgctgggctt  10320
cgagctggtg ccccccagcc tgttcaacgt ggtggtggcc atccggaacg aggccaccag  10380
aaccaacaga gccgtgcggc tgcctgtgtc tacagccgct gcacctgagg gcatcacact  10440
gttctacggc ctgtacaacg ccgtgaaaga gttctgcctc cggcaccagc tggatccccc  10500
cctgctgaga cacctggaca agtactacgc cggcctgccc ccagagctga agcagaccag  10560
agtgaacctg cccgcccaca gcagatatgg ccctcaggcc gtggacgcca gatgataagc  10620
ggccgcatac agcagcaatt ggcaagctgc ttacatagaa ctcgcggcga ttggcatgcc  10680
gccttaaaat ttttatttta tttttctttt cttttccgaa tcggattttg tttttaatat  10740
ttcaaaaaaa aaaaaaaaaa aaaaaaaaaa aaaaaaaagg gtcggcatgg catctccacc  10800
tcctcgcggt ccgacctggg catccgaagg aggacgcacg tccactcgga tggctaaggg  10860
agagccacgt ttaaacacgt gatatctggc ctcatgggcc ttcctttcac tgcccgcttt  10920
ccagtcggga aacctgtcgt gccagctgca ttaacatggt catagctgtt tccttgcgta  10980
```

ttgggcgctc tccgcttcct cgctcactga ctcgctgcgc tcggtcgttc gggtaaagcc 11040
tggggtgcct aatgagcaaa aggccagcaa aaggccagga accgtaaaaa ggccgcgttg 11100
ctggcgtttt tccataggct ccgcccccct gacgagcatc acaaaaatcg acgctcaagt 11160
cagaggtggc gaaacccgac aggactataa agataccagg cgtttccccc tggaagctcc 11220
ctcgtgcgct ctcctgttcc gaccctgccg cttaccggat acctgtccgc ctttctccct 11280
tcgggaagcg tggcgctttc tcatagctca cgctgtaggt atctcagttc ggtgtaggtc 11340
gttcgctcca agctgggctg tgtgcacgaa ccccccgttc agcccgaccg ctgcgcctta 11400
tccggtaact atcgtcttga gtccaacccg gtaagacacg acttatcgcc actggcagca 11460
gccactggta acaggattag cagagcgagg tatgtaggcg gtgctacaga gttcttgaag 11520
tggtggccta actacggcta cactagaaga acagtatttg gtatctgcgc tctgctgaag 11580
ccagttacct tcggaaaaag agttggtagc tcttgatccg gcaaacaaac caccgctggt 11640
agcggtggtt tttttgtttg caagcagcag attacgcgca gaaaaaaagg atctcaagaa 11700
gatcctttga tcttttctac ggggtctgac gctcagtgga acgaaaactc acgttaaggg 11760
attttggtca tgagattatc aaaaaggatc ttcacctaga tccttttaaa ttaaaaatga 11820
agttttaaat caatctaaag tatatatgag taaacttggt ctgacagtta ttagaaaaat 11880
tcatccagca gacgataaaa cgcaatacgc tggctatccg gtgccgcaat gccatacagc 11940
accagaaaac gatccgccca ttcgccgccc agttcttccg caatatcacg ggtggccagc 12000
gcaatatcct gataacgatc cgccacgccc agacggccgc aatcaataaa gccgctaaaa 12060
cggccatttt ccaccataat gttcggcagg cacgcatcac catgggtcac caccagatct 12120
tcgccatccg gcatgctcgc tttcagacgc gcaaacagct ctgccggtgc caggccctga 12180
tgttcttcat ccagatcatc ctgatccacc aggcccgctt ccatacgggt acgcgcacgt 12240
tcaatacgat gtttcgcctg atgatcaaac ggacaggtcg ccgggtccag ggtatgcaga 12300
cgacgcatgg catccgccat aatgctcact ttttctgccg gcgccagatg gctagacagc 12360
agatcctgac ccggcacttc gcccagcagc agccaatcac ggcccgcttc ggtcaccaca 12420
tccagcaccg ccgcacacgg aacaccggtg gtggccagcc agctcagacg cgccgcttca 12480
tcctgcagct cgttcagcgc accgctcaga tcggttttca caaacagcac cggacgaccc 12540
tgcgcgctca gacgaaacac cgccgcatca gagcagccaa tggtctgctg cgcccaatca 12600
tagccaaaca gacgttccac ccacgctgcc gggctacccg catgcaggcc atcctgttca 12660
atcatactct tcctttttca atattattga agcatttatc agggttattg tctcatgagc 12720
ggatacatat ttgaatgtat ttagaaaaat aaacaaatag gggttccgcg cacatttccc 12780
cgaaaagtgc cacctaaatt gtaagcgtta atattttgtt aaaattcgcg ttaaattttt 12840
gttaaatcag ctcatttttt aaccaatagg ccgaaatcgg caaaatccct tataaatcaa 12900
aagaatagac cgagataggg ttgagtggcc gctacagggc gctcccattc gccattcagg 12960
ctgcgcaact gttgggaagg gcgtttcggt gcgggcctct tcgctattac gccagctggc 13020
gaaaggggga tgtgctgcaa ggcgattaag ttgggtaacg ccagggtttt cccagtcaca 13080
cgcgtaatac gactcactat ag 13102

<210> SEQ ID NO 59
<211> LENGTH: 13087
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220

-continued

```
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg actttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
```

caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccacccccgc 5520 caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960

-continued

```
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgaggcct ggcctgccct cctacctgat catcctggcc gtgtgcctgt tcagccacct   7620
gctgtccagc agatacggcg ccgaggccgt gagcgagccc ctggacaagg ctttccacct   7680
gctgctgaac acctacggca gacccatccg gtttctgcgg gagaacacca cccagtgcac   7740
ctacaacagc agcctgcgga acagcaccgt cgtgagagag aacgccatca gcttcaactt   7800
tttccagagc tacaaccagt actacgtgtt ccacatgccc agatgcctgt ttgccggccc   7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga cccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
```

cagctacccc gtgtccacca cagtcgtggg ccagagcctg atcatcaccc agaccgacag 9420
ccagaccaag tgcgagctga cccggaacat gcacaccaca cacagcatca ccgtggccct 9480
gaacatcagc ctggaaaact gcgctttctg tcagtctgcc ctgctggaat acgacgatac 9540
ccagggcgtg atcaacatca tgtacatgca cgacagcgac gacgtgctgt tcgccctgga 9600
cccctacaac gaggtggtgg tgtccagccc ccggacccac tacctgatgc tgctgaagaa 9660
cggcaccgtg ctggaagtga ccgacgtggt ggtggacgcc accgacctgt tgaattttga 9720
ccttcttaag cttgcgggag acgtcgagtc caaccccggg cccatgtgca gaaggcccga 9780
ctgcggcttc agcttcagcc ctggacccgt gatcctgctg tggtgctgcc tgctgctgcc 9840
tatcgtgtcc tctgccgccg tgtctgtggc ccctacagcc gccgagaagg tgccagccga 9900
gtgccccgag ctgaccagaa gatgcctgct gggcgaggtg ttcgagggcg acaagtacga 9960
gagctggctg cggcccctgg tcaacgtgac cggcagagat ggcccccctga gccagctgat 10020 ccggtacaga cccgtgaccc ccgaggccgc caatagcgtg ctgctggacg aggccttcct 10080
ggataccctg gccctgctgt acaacaaccc cgaccagctg agagccctgc tgaccctgct 10140
gtccagcgac accgccccca gatggatgac cgtgatgcgg ggctacagcg agtgtggaga 10200
tggcagccct gccgtgtaca cctgcgtgga cgacctgtgc agaggctacg acctgaccag 10260
actgagctac ggccggtcca tcttcacaga gcacgtgctg ggcttcgagc tggtgccccc 10320
cagcctgttc aacgtggtgg tggccatccg gaacgaggcc accagaacca acagagccgt 10380
gcggctgcct gtgtctacag ccgctgcacc tgagggcatc acactgttct acggcctgta 10440
caacgccgtg aaagagttct gcctccggca ccagctggat cccccccctgc tgagacacct 10500 ggacaagtac tacgccggcc tgcccccaga gctgaagcag accagagtga acctgcccgc 10560
ccacagcaga tatggccctc aggccgtgga cgccagatga taagcggccg catacagcag 10620
caattggcaa gctgcttaca tagaactcgc ggcgattggc atgccgcctt aaaattttta 10680
ttttattttt cttttctttt ccgaatcgga ttttgttttt aatatttcaa aaaaaaaaaa 10740
aaaaaaaaaa aaaaaaaaaa aaagggtcgg catggcatct ccacctcctc gcggtccgac 10800
ctgggcatcc gaaggaggac gcacgtccac tcggatggct aagggagagc cacgtttaaa 10860
cacgtgatat ctggcctcat gggccttcct ttcactgccc gctttccagt cgggaaacct 10920
gtcgtgccag ctgcattaac atggtcatag ctgtttcctt gcgtattggg cgctctccgc 10980
ttcctcgctc actgactcgc tgcgctcggt cgttcgggta aagcctgggg tgcctaatga 11040
gcaaaaggcc agcaaaaggc caggaaccgt aaaaaggccg cgttgctggc gtttttccat 11100
aggctccgcc cccctgacga gcatcacaaa aatcgacgct caagtcagag gtggcgaaac 11160
ccgacaggac tataaagata ccaggcgttt ccccctggaa gctccctcgt gcgctctcct 11220
gttccgaccc tgccgcttac cggatacctg tccgcctttc tcccttcggg aagcgtggcg 11280
ctttctcata gctcacgctg taggtatctc agttcggtgt aggtcgttcg ctccaagctg 11340
ggctgtgtgc acgaaccccc cgttcagccc gaccgctgcg ccttatccgg taactatcgt 11400
cttgagtcca acccggtaag acacgactta tcgccactgg cagcagccac tggtaacagg 11460
attagcagag cgaggtatgt aggcggtgct acagagttct tgaagtggtg gcctaactac 11520
ggctacacta gaagaacagt atttggtatc tgcgctctgc tgaagccagt taccttcgga 11580
aaaagagttg gtagctcttg atccggcaaa caaaccaccg ctggtagcgg tggttttttt 11640
gtttgcaagc agcagattac gcgcagaaaa aaaggatctc aagaagatcc tttgatcttt 11700
tctacggggt ctgacgctca gtggaacgaa aactcacgtt aagggatttt ggtcatgaga 11760
ttatcaaaaa ggatcttcac ctagatcctt ttaaattaaa aatgaagttt taaatcaatc 11820
taaagtatat atgagtaaac ttggtctgac agttattaga aaaattcatc cagcagacga 11880
taaaacgcaa tacgctggct atccggtgcc gcaatgccat acagcaccag aaaacgatcc 11940
gcccattcgc cgcccagttc ttccgcaata tcacgggtgg ccagcgcaat atcctgataa 12000
cgatccgcca cgcccagacg gccgcaatca ataaagccgc taaaacggcc attttccacc 12060
ataatgttcg gcaggcacgc atcaccatgg gtcaccacca gatcttcgcc atccggcatg 12120
ctcgctttca gacgcgcaaa cagctctgcc ggtgccaggc cctgatgttc ttcatccaga 12180
tcatcctgat ccaccaggcc cgcttccata cgggtacgcg cacgttcaat acgatgtttc 12240
gcctgatgat caaacggaca ggtcgccggg tccagggtat gcagacgacg catggcatcc 12300
gccataatgc tcactttttc tgccggcgcc agatggctag acagcagatc ctgacccggc 12360
acttcgccca gcagcagcca atcacggccc gcttcggtca ccacatccag caccgccgca 12420
cacggaacac cggtggtggc cagccagctc agacgcgccg cttcatcctg cagctcgttc 12480
agcgcaccgc tcagatcggt tttcacaaac agcaccggac gaccctgcgc gctcagacga 12540
aacaccgccg catcagagca gccaatggtc tgctgcgccc aatcatagcc aaacagacgt 12600
tccacccacg ctgccgggct acccgcatgc aggccatcct gttcaatcat actcttcctt 12660
tttcaatatt attgaagcat ttatcagggt tattgtctca tgagcggata catatttgaa 12720
tgtatttaga aaaataaaca aataggggtt ccgcgcacat ttccccgaaa agtgccacct 12780
aaattgtaag cgttaatatt ttgttaaaat tcgcgttaaa tttttgttaa atcagctcat 12840
tttttaacca ataggccgaa atcggcaaaa tcccttataa atcaaaagaa tagaccgaga 12900
tagggttgag tggccgctac agggcgctcc cattcgccat tcaggctgcg caactgttgg 12960
gaagggcgtt tcggtgcggg cctcttcgct attacgccag ctggcgaaag ggggatgtgc 13020
tgcaaggcga ttaagttggg taacgccagg gttttcccag tcacacgcgt aatacgactc 13080
actatag 13087

<210> SEQ ID NO 60
<211> LENGTH: 13788
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 60
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600

```
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
```

taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggagggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga cccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gatgaggcct ggcctgccct cctacctgat catcctggcc gtgtgcctgt tcagccacct 7620
gctgtccagc agatacggcg ccgaggccgt gagcgagccc ctggacaagg ctttccacct 7680

-continued

```
gctgctgaac acctacggca gacccatccg gtttctgcgg gagaacacca cccagtgcac   7740
ctacaacagc agcctgcgga acagcaccgt cgtgagagag aacgccatca gcttcaactt   7800
tttccagagc tacaaccagt actacgtgtt ccacatgccc agatgcctgt ttgccggccc   7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga cccccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgactgat aatctagatt   9720
aaaacagctg tgggttgttc ccacccacag ggcccactgg gcgctagcac tctgatttta   9780
cgaaatcctt gtgcgcctgt tttatatccc ttccctaatt cgaaacgtag aagcaatgcg   9840
caccactgat caatagtagg cgtaacgcgc cagttacgtc atgatcaagc atatctgttc   9900
ccccggactg agtatcaata gactgcttac gcggttgaag gagaaaacgt tcgttatccg   9960
gctaactact tcgagaagcc cagtaacacc atggaagctg cagggtgttt cgctcagcac  10020
ttcccccgtg tagatcaggt cgatgagcca ctgcaatccc cacaggtgac tgtggcagtg  10080
```

-continued gctgcgttgg cggcctgcct atggggagac ccataggacg ctctaatgtg gacatggtgc 10140
gaagagccta ttgagctagt tagtagtcct ccggcccctg aatgcggcta atcctaactg 10200
cggagcacat gccttcaacc cagagggtag tgtgtcgtaa tgggcaactc tgcagcggaa 10260
ccgactactt tgggtgtccg tgtttctttt tattcttata ttggctgctt atggtgacaa 10320
ttacagaatt gttaccatat agctattgga ttggccatcc ggtgtgtaat agagctgtta 10380
tatacctatt tgttggcttt gtaccactaa ctttaaaatc tataactacc ctcaacttta 10440
tattaaccct caatacagtt gaacatgtgc agaaggcccg actgcggctt cagcttcagc 10500
cctggacccg tgatcctgct gtggtgctgc ctgctgctgc ctatcgtgtc ctctgccgcc 10560
gtgtctgtgg cccctacagc cgccgagaag gtgccagccg agtgccccga gctgaccaga 10620
agatgcctgc tgggcgaggt gttcgagggc gacaagtacg agagctggct gcggcccctg 10680
gtcaacgtga ccggcagaga tggcccccctg agccagctga tccggtacag acccgtgacc 10740
cccgaggccg ccaatagcgt gctgctggac gaggccttcc tggataccct ggccctgctg 10800
tacaacaacc ccgaccagct gagagccctg ctgaccctgc tgtccagcga caccgccccc 10860
agatggatga ccgtgatgcg gggctacagc gagtgtggag atggcagccc tgccgtgtac 10920
acctgcgtgg acgacctgtg cagaggctac gacctgacca gactgagcta cggccggtcc 10980
atcttcacag agcacgtgct gggcttcgag ctggtgcccc ccagcctgtt caacgtggtg 11040
gtggccatcc ggaacgaggc caccagaacc aacagagccg tgcggctgcc tgtgtctaca 11100
gccgctgcac ctgagggcat cacactgttc tacggcctgt acaacgccgt gaaagagttc 11160
tgcctccggc accagctgga tccccccctg ctgagacacc tggacaagta ctacgccggc 11220
ctgcccccag agctgaagca gaccagagtg aacctgcccg cccacagcag atatggccct 11280
caggccgtgg acgccagatg ataagcggcc gcatacagca gcaattggca agctgcttac 11340
atagaactcg cggcgattgg catgccgcct taaaattttt attttatttt tcttttcttt 11400
tccgaatcgg attttgtttt taatatttca aaaaaaaaaa aaaaaaaaaa aaaaaaaaaa 11460
aaaagggtcg gcatggcatc tccacctcct cgcggtccga cctgggcatc cgaaggagga 11520
cgcacgtcca ctcggatggc taagggagag ccacgtttaa acacgtgata tctggcctca 11580
tgggccttcc tttcactgcc cgctttccag tcgggaaacc tgtcgtgcca gctgcattaa 11640
catggtcata gctgtttcct tgcgtattgg gcgctctccg cttcctcgct cactgactcg 11700
ctgcgctcgg tcgttcgggt aaagcctggg gtgcctaatg agcaaaaggc cagcaaaagg 11760
ccaggaaccg taaaaaggcc gcgttgctgg cgtttttcca taggctccgc ccccctgacg 11820
agcatcacaa aaatcgacgc tcaagtcaga ggtggcgaaa cccgacagga ctataaagat 11880
accaggcgtt tccccctgga agctccctcg tgcgctctcc tgttccgacc ctgccgctta 11940
ccggatacct gtccgccttt ctcccttcgg gaagcgtggc gctttctcat agctcacgct 12000
gtaggtatct cagttcggtg taggtcgttc gctccaagct gggctgtgtg cacgaacccc 12060
ccgttcagcc cgaccgctgc gccttatccg gtaactatcg tcttgagtcc aacccggtaa 12120
gacacgactt atcgccactg gcagcagcca ctggtaacag gattagcaga gcgaggtatg 12180
taggcggtgc tacagagttc ttgaagtggt ggcctaacta cggctacact agaagaacag 12240
tatttggtat ctgcgctctg ctgaagccag ttaccttcgg aaaaagagtt ggtagctctt 12300
gatccggcaa acaaaccacc gctggtagcg gtggtttttt tgtttgcaag cagcagatta 12360
cgcgcagaaa aaaaggatct caagaagatc ctttgatctt ttctacgggg tctgacgctc 12420
agtggaacga aaactcacgt taagggattt tggtcatgag attatcaaaa aggatcttca 12480
cctagatcct tttaaattaa aaatgaagtt ttaaatcaat ctaaagtata tatgagtaaa 12540
cttggtctga cagttattag aaaaattcat ccagcagacg ataaaacgca atacgctggc 12600
tatccggtgc cgcaatgcca tacagcacca gaaaacgatc cgcccattcg ccgcccagtt 12660
cttccgcaat atcacgggtg gccagcgcaa tatcctgata acgatccgcc acgcccagac 12720
ggccgcaatc aataaagccg ctaaaacggc catttttccac cataatgttc ggcaggcacg 12780
catcaccatg ggtcaccacc agatcttcgc catccggcat gctcgctttc agacgcgcaa 12840
acagctctgc cggtgccagg ccctgatgtt cttcatccag atcatcctga tccaccaggc 12900
ccgcttccat acgggtacgc gcacgttcaa tacgatgttt cgcctgatga tcaaacggac 12960
aggtcgccgg gtccagggta tgcagacgac gcatggcatc cgccataatg ctcacttttt 13020
ctgccggcgc cagatggcta gacagcagat cctgacccgg cacttcgccc agcagcagcc 13080
aatcacggcc cgcttcggtc accacatcca gcaccgccgc acacggaaca ccggtggtgg 13140
ccagccagct cagacgcgcc gcttcatcct gcagctcgtt cagcgcaccg ctcagatcgg 13200
ttttcacaaa cagcaccgga cgaccctgcg cgctcagacg aaacaccgcc gcatcagagc 13260
agccaatggt ctgctgcgcc caatcatagc caaacagacg ttccacccac gctgccgggc 13320
tacccgcatg caggccatcc tgttcaatca tactcttcct ttttcaatat tattgaagca 13380
tttatcaggg ttattgtctc atgagcggat acatatttga atgtatttag aaaaataaac 13440
aaataggggt tccgcgcaca tttccccgaa aagtgccacc taaattgtaa gcgttaatat 13500
tttgttaaaa ttcgcgttaa atttttgtta aatcagctca ttttttaacc aataggccga 13560
aatcggcaaa atcccttata aatcaaaaga atagaccgag atagggttga gtggccgcta 13620
cagggcgctc ccattcgcca ttcaggctgc gcaactgttg ggaagggcgt ttcggtgcgg 13680
gcctcttcgc tattacgcca gctggcgaaa gggggatgtg ctgcaaggcg attaagttgg 13740
gtaacgccag ggttttccca gtcacacgcg taatacgact cactatag 13788

<210> SEQ ID NO 61
<211> LENGTH: 13788
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 61
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660

```
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
```

-continued cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400

```
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgtgcaga aggcccgact gcggcttcag cttcagccct ggacccgtga tcctgctgtg   7620
gtgctgcctg ctgctgccta tcgtgtcctc tgccgccgtg tctgtggccc ctacagccgc   7680
cgagaaggtg ccagccgagt gccccgagct gaccagaaga tgcctgctgg gcgaggtgtt   7740
```

-continued

```
cgagggcgac aagtacgaga gctggctgcg gcccctggtc aacgtgaccg gcagagatgg   7800
ccccctgagc cagctgatcc ggtacagacc cgtgaccccc gaggccgcca atagcgtgct   7860
gctggacgag gccttcctgg ataccctggc cctgctgtac aacaaccccg accagctgag   7920
agccctgctg accctgctgt ccagcgacac cgcccccaga tggatgaccg tgatgcgggg   7980
ctacagcgag tgtggagatg gcagccctgc cgtgtacacc tgcgtggacg acctgtgcag   8040
aggctacgac ctgaccagac tgagctacgg ccggtccatc ttcacagagc acgtgctggg   8100
cttcgagctg gtgcccccca gcctgttcaa cgtggtggtg gccatccgga acgaggccac   8160
cagaaccaac agagccgtgc ggctgcctgt gtctacagcc gctgcacctg agggcatcac   8220
actgttctac ggcctgtaca acgccgtgaa agagttctgc ctccggcacc agctggatcc   8280
ccccctgctg agacacctgg acaagtacta cgccggcctg cccccagagc tgaagcagac   8340
cagagtgaac ctgcccgccc acagcagata tggccctcag gccgtggacg ccagatgata   8400
atctagatta aaacagctgt gggttgttcc cacccacagg gcccactggg cgctagcact   8460
ctgattttac gaaatccttg tgcgcctgtt ttatatccct tccctaattc gaaacgtaga   8520
agcaatgcgc accactgatc aatagtaggc gtaacgcgcc agttacgtca tgatcaagca   8580
tatctgttcc cccggactga gtatcaatag actgcttacg cggttgaagg agaaaacgtt   8640
cgttatccgg ctaactactt cgagaagccc agtaacacca tggaagctgc agggtgtttc   8700
gctcagcact tcccccgtgt agatcaggtc gatgagccac tgcaatcccc acaggtgact   8760
gtggcagtgg ctgcgttggc ggcctgccta tggggagacc cataggacgc tctaatgtgg   8820
acatggtgcg aagagcctat tgagctagtt agtagtcctc cggcccctga atgcggctaa   8880
tcctaactgc ggagcacatg ccttcaaccc agagggtagt gtgtcgtaat gggcaactct   8940
gcagcggaac cgactacttt gggtgtccgt gtttcttttt attcttatat tggctgctta   9000
tggtgacaat tacagaattg ttaccatata gctattggat tggccatccg gtgtgtaata   9060
gagctgttat atacctattt gttggctttg taccactaac tttaaaatct ataactaccc   9120
tcaactttat attaaccctc aatacagttg aacatgaggc ctggcctgcc ctcctacctg   9180
atcatcctgg ccgtgtgcct gttcagccac ctgctgtcca gcagatacgg cgccgaggcc   9240
gtgagcgagc ccctggacaa ggctttccac ctgctgctga acacctacgg cagacccatc   9300
cggtttctgc gggagaacac cacccagtgc acctacaaca gcagcctgcg gaacagcacc   9360
gtcgtgagag agaacgccat cagcttcaac tttttccaga gctacaacca gtactacgtg   9420
ttccacatgc ccagatgcct gtttgccggc cctctggccg agcagttcct gaaccaggtg   9480
gacctgaccg agacactgga aagataccag cagcggctga atacctacgc cctggtgtcc   9540
aaggacctgg ccagctaccg gtcctttagc cagcagctca aggctcagga tagcctcggc   9600
gagcagccta ccaccgtgcc ccctcccatc gacctgagca tcccccacgt gtggatgcct   9660
ccccagacca cccctcacgg ctggaccgag agccacacca cctccggcct gcacagaccc   9720
cacttcaacc agacctgcat cctgttcgac ggccacgacc tgctgtttag caccgtgacc   9780
ccctgcctgc accagggctt ctacctgatc gacgagctga gatacgtgaa gatcaccctg   9840
accgaggatt tcttcgtggt caccgtgtcc atcgacgacg acacccccat gctgctgatc   9900
ttcggccacc tgcccagagt gctgttcaag gccccctacc agcgggacaa cttcatcctg   9960
cggcagaccg agaagcacga gctgctggtg ctggtcaaga aggaccagct gaaccggcac  10020
tcctacctga aggaccccga cttcctggac gccgccctgg acttcaacta cctggacctg  10080
agcgccctgc tgagaaacag cttccacaga tacgccgtgg acgtgctgaa gtccggacgg  10140
```

```
tgccagatgc tcgatcggcg gaccgtggag atggccttcg cctatgccct cgccctgttc  10200
gccgctgcca gacaggaaga ggctggcgcc caggtgtcag tgcccagagc cctggataga  10260
caggccgccc tgctgcagat ccaggaattc atgatcacct gcctgagcca gacccccccct  10320
agaaccaccc tgctgctgta ccccacagcc gtggatctgg ccaagagggc cctgtggacc  10380
cccaaccaga tcaccgacat cacaagcctc gtgcggctcg tgtacatcct gagcaagcag  10440
aaccagcagc acctgatccc ccagtgggcc ctgagacaga tcgccgactt cgccctgaag  10500
ctgcacaaga cccatctggc cagctttctg agcgccttcg ccaggcagga actgtacctg  10560
atgggcagcc tggtccacag catgctggtg cataccaccg agcggcggga gatcttcatc  10620
gtggagacag gcctgtgtag cctggccgag ctgtcccact ttacccagct gctggcccac  10680
cctcaccacg agtacctgag cgacctgtac accccctgca gcagcagcgg cagacgggac  10740
cacagcctgg aacggctgac cagactgttc cccgatgcca ccgtgcctgc tacagtgcct  10800
gccgccctgt ccatcctgtc caccatgcag cccagcaccc tggaaacctt ccccgacctg  10860
ttctgcctgc ccctgggcga gagctttagc gccctgaccg tgtccgagca cgtgtcctac  10920
atcgtgacca atcagtacct gatcaagggc atcagctacc ccgtgtccac cacagtcgtg  10980
ggccagagcc tgatcatcac ccagaccgac agccagacca agtgcgagct gacccggaac  11040
atgcacacca cacacagcat caccgtggcc ctgaacatca gcctggaaaa ctgcgctttc  11100
tgtcagtctg ccctgctgga atacgacgat acccagggcg tgatcaacat catgtacatg  11160
cacgacagcg acgacgtgct gttcgccctg gacccctaca acgaggtggt ggtgtccagc  11220
ccccggaccc actacctgat gctgctgaag aacggcaccg tgctggaagt gaccgacgtg  11280
gtggtggacg ccaccgactg ataagcggcc gcatacagca gcaattggca agctgcttac  11340
atagaactcg cggcgattgg catgccgcct taaaattttt attttatttt tcttttcttt  11400
tccgaatcgg attttgtttt taatatttca aaaaaaaaaa aaaaaaaaaa aaaaaaaaaa  11460
aaaagggtcg gcatggcatc tccacctcct cgcggtccga cctgggcatc cgaaggagga  11520
cgcacgtcca ctcggatggc taagggagag ccacgtttaa acacgtgata tctggcctca  11580
tgggccttcc tttcactgcc cgctttccag tcgggaaacc tgtcgtgcca gctgcattaa  11640
catggtcata gctgtttcct tgcgtattgg gcgctctccg cttcctcgct cactgactcg  11700
ctgcgctcgg tcgttcgggt aaagcctggg gtgcctaatg agcaaaaggc cagcaaaagg  11760
ccaggaaccg taaaaaggcc gcgttgctgg cgtttttcca taggctccgc ccccctgacg  11820
agcatcacaa aaatcgacgc tcaagtcaga ggtggcgaaa cccgacagga ctataaagat  11880
accaggcgtt tccccctgga agctccctcg tgcgctctcc tgttccgacc ctgccgctta  11940
ccggatacct gtccgccttt ctcccttcgg gaagcgtggc gctttctcat agctcacgct  12000
gtaggtatct cagttcggtg taggtcgttc gctccaagct gggctgtgtg cacgaacccc  12060
ccgttcagcc cgaccgctgc gccttatccg gtaactatcg tcttgagtcc aacccggtaa  12120
gacacgactt atcgccactg gcagcagcca ctggtaacag gattagcaga gcgaggtatg  12180
taggcggtgc tacagagttc ttgaagtggt ggcctaacta cggctacact agaagaacag  12240
tatttggtat ctgcgctctg ctgaagccag ttaccttcgg aaaaagagtt ggtagctctt  12300
gatccggcaa acaaaccacc gctggtagcg gtggtttttt tgtttgcaag cagcagatta  12360
cgcgcagaaa aaaaggatct caagaagatc ctttgatctt ttctacgggg tctgacgctc  12420
agtggaacga aaactcacgt taagggattt tggtcatgag attatcaaaa aggatcttca  12480
```

cctagatcct tttaaattaa aaatgaagtt ttaaatcaat ctaaagtata tatgagtaaa 12540
cttggtctga cagttattag aaaaattcat ccagcagacg ataaaacgca atacgctggc 12600
tatccggtgc cgcaatgcca tacagcacca gaaaacgatc cgcccattcg ccgcccagtt 12660
cttccgcaat atcacgggtg gccagcgcaa tatcctgata acgatccgcc acgcccagac 12720
ggccgcaatc aataaagccg ctaaaacggc cattttccac cataatgttc ggcaggcacg 12780
catcaccatg ggtcaccacc agatcttcgc catccggcat gctcgctttc agacgcgcaa 12840
acagctctgc cggtgccagg ccctgatgtt cttcatccag atcatcctga tccaccaggc 12900
ccgcttccat acgggtacgc gcacgttcaa tacgatgttt cgcctgatga tcaaacggac 12960
aggtcgccgg gtccagggta tgcagacgac gcatggcatc cgccataatg ctcacttttt 13020
ctgccggcgc cagatggcta gacagcagat cctgacccgg cacttcgccc agcagcagcc 13080
aatcacggcc cgcttcggtc accacatcca gcaccgccgc acacggaaca ccggtggtgg 13140
ccagccagct cagacgcgcc gcttcatcct gcagctcgtt cagcgcaccg ctcagatcgg 13200
ttttcacaaa cagcaccgga cgaccctgcg cgctcagacg aaacaccgcc gcatcagagc 13260
agccaatggt ctgctgcgcc caatcatagc caaacagacg ttccacccac gctgccgggc 13320
tacccgcatg caggccatcc tgttcaatca tactcttcct tttcaatat tattgaagca 13380 tttatcaggg ttattgtctc atgagcggat acatatttga atgtatttag aaaaataaac 13440
aaataggggt tccgcgcaca tttccccgaa aagtgccacc taaattgtaa gcgttaatat 13500
tttgttaaaa ttcgcgttaa atttttgtta aatcagctca ttttttaacc aataggccga 13560
aatcggcaaa atcccttata aatcaaaaga atagaccgag atagggttga gtggccgcta 13620
cagggcgctc ccattcgcca ttcaggctgc gcaactgttg ggaagggcgt ttcggtgcgg 13680
gcctcttcgc tattacgcca gctggcgaaa gggggatgtg ctgcaaggcg attaagttgg 13740
gtaacgccag ggttttccca gtcacacgcg taatacgact cactatag 13788

<210> SEQ ID NO 62
<211> LENGTH: 14202
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720

```
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
```

-continued

```
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
```

-continued

```
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gctattccag aagtagtgag gaggcttttt tggaggccta ggcttttgca aaaagcttgt   7620
atatccattt tcggatctga tcaagagaca ggatgaggat cgtttcgcat gattgaataa   7680
gatggattgc acgtaggttc tccggccgct tgggtggaga ggctattcgg ctatgactgg   7740
gcacaactga caatcggctg ctctgatgcc gccgtgatcc ggttgtcagc gcaggggcgc   7800
```

-continued ccggttcttt ttgtcaagac cgacctgtcc ggtgccctga atgaactgaa ggacgaggca 7860
gcgcggctat cgtggctggc cacgacgggc gttccttgcg cagtctagac tggcgcgcca 7920
aacctgcagg ttaaaacagc tgtgggttgt tcccacccac agggcccact gggcgctagc 7980
actctgattt tacgaaatcc ttgtgcgcct gttttatatc ccttccctaa ttcgaaacgt 8040
agaagcaatg cgcaccactg atcaatagta ggcgtaacgc gccagttacg tcatgatcaa 8100
gcatatctgt tcccccggac tgagtatcaa tagactgctt acgcggttga aggagaaaac 8160
gttcgttatc cggctaacta cttcgagaag cccagtaaca ccatggaagc tgcagggtgt 8220
ttcgctcagc acttcccccg tgtagatcag gtcgatgagc cactgcaatc cccacaggtg 8280
actgtggcag tggctgcgtt ggcggcctgc ctatggggag acccatagga cgctctaatg 8340
tggacatggt gcgaagagcc tattgagcta gttagtagtc ctccggcccc tgaatgcggc 8400
taatcctaac tgcggagcac atgccttcaa cccagagggt agtgtgtcgt aatgggcaac 8460
tctgcagcgg aaccgactac tttgggtgtc cgtgtttctt tttattctta tattggctgc 8520
ttatggtgac aattacagaa ttgttaccat atagctattg gattggccat ccggtgtgta 8580
atagagctgt tatataccta tttgttggct ttgtaccact aactttaaaa tctataacta 8640
ccctcaactt tatattaacc ctcaatacag ttgaacatga ggcctggcct gccctcctac 8700
ctgatcatcc tggccgtgtg cctgttcagc cacctgctgt ccagcagata cggcgccgag 8760
gccgtgagcg agcccctgga caaggctttc cacctgctgc tgaacaccta cggcagaccc 8820
atccggtttc tgcgggagaa caccacccag tgcacctaca acagcagcct gcggaacagc 8880
accgtcgtga gagagaacgc catcagcttc aactttttcc agagctacaa ccagtactac 8940
gtgttccaca tgcccagatg cctgtttgcc ggccctctgg ccgagcagtt cctgaaccag 9000
gtggacctga ccgagacact ggaaagatac cagcagcggc tgaataccta cgccctggtg 9060
tccaaggacc tggccagcta ccggtccttt agccagcagc tcaaggctca ggatagcctc 9120
ggcgagcagc ctaccaccgt gcccccctccc atcgacctga gcatccccca cgtgtggatg 9180
cctccccaga ccacccctca cggctggacc gagagccaca ccacctccgg cctgcacaga 9240
ccccacttca accagacctg catcctgttc gacggccacg acctgctgtt tagcaccgtg 9300 acccccctgcc tgcaccaggg cttctacctg atcgacgagc tgagatacgt gaagatcacc 9360
ctgaccgagg atttcttcgt ggtcaccgtg tccatcgacg acgacacccc catgctgctg 9420
atcttcggcc acctgcccag agtgctgttc aaggccccct accagcggga caacttcatc 9480
ctgcggcaga ccgagaagca cgagctgctg gtgctggtca agaaggacca gctgaaccgg 9540
cactcctacc tgaaggaccc cgacttcctg gacgccgccc tggacttcaa ctacctggac 9600
ctgagcgccc tgctgagaaa cagcttccac agatacgccg tggacgtgct gaagtccgga 9660
cggtgccaga tgctcgatcg gcggaccgtg gagatggcct tcgcctatgc cctcgccctg 9720
ttcgccgctg ccagacagga agaggctggc gcccaggtgt cagtgcccag agccctggat 9780
agacaggccg ccctgctgca gatccaggaa ttcatgatca cctgcctgag ccagaccccc 9840
cctagaacca ccctgctgct gtaccccaca gccgtggatc tggccaagag ggccctgtgg 9900
acccccaacc agatcaccga catcacaagc ctcgtgcggc tcgtgtacat cctgagcaag 9960
cagaaccagc agcacctgat cccccagtgg gccctgagac agatcgccga cttcgccctg 10020
aagctgcaca agacccatct ggccagcttt ctgagcgcct tcgccaggca ggaactgtac 10080
ctgatgggca gcctggtcca cagcatgctg gtgcatacca ccgagcggcg ggagatcttc 10140
atcgtggaga caggcctgtg tagcctggcc gagctgtccc actttaccca gctgctggcc 10200

-continued

```
caccctcacc acgagtacct gagcgacctg tacacccccct gcagcagcag cggcagacgg  10260
gaccacagcc tggaacggct gaccagactg ttccccgatg ccaccgtgcc tgctacagtg  10320
cctgccgccc tgtccatcct gtccaccatg cagcccagca ccctggaaac cttccccgac  10380
ctgttctgcc tgcccctggg cgagagcttt agcgccctga ccgtgtccga gcacgtgtcc  10440
tacatcgtga ccaatcagta cctgatcaag ggcatcagct accccgtgtc caccacagtc  10500
gtgggccaga gcctgatcat cacccagacc gacagccaga ccaagtgcga gctgacccgg  10560
aacatgcaca ccacacacag catcaccgtg gccctgaaca tcagcctgga aaactgcgct  10620
ttctgtcagt ctgccctgct ggaatacgac gatacccagg gcgtgatcaa catcatgtac  10680
atgcacgaca gcgacgacgt gctgttcgcc ctggacccct acaacgaggt ggtggtgtcc  10740
agcccccgga cccactacct gatgctgctg aagaacggca ccgtgctgga agtgaccgac  10800
gtggtggtgg acgccaccga cctgttgaat tttgaccttc ttaagcttgc gggagacgtc  10860
gagtccaacc ccgggcccat gtgcagaagg cccgactgcg gcttcagctt cagccctgga  10920
cccgtgatcc tgctgtggtg ctgcctgctg ctgcctatcg tgtcctctgc cgccgtgtct  10980
gtggccccta cagccgccga gaaggtgcca gccgagtgcc ccgagctgac cagaagatgc  11040
ctgctgggcg aggtgttcga gggcgacaag tacgagagct ggctgcggcc cctggtcaac  11100
gtgaccggca gagatggccc cctgagccag ctgatccggt acagacccgt gacccccgag  11160
gccgccaata gcgtgctgct ggacgaggcc ttcctggata ccctggccct gctgtacaac  11220
aaccccgacc agctgagagc cctgctgacc ctgctgtcca gcgacaccgc ccccagatgg  11280
atgaccgtga tgcggggcta cagcgagtgt ggagatggca gccctgccgt gtacacctgc  11340
gtggacgacc tgtgcagagg ctacgacctg accagactga gctacggccg gtccatcttc  11400
acagagcacg tgctgggctt cgagctggtg ccccccagcc tgttcaacgt ggtggtggcc  11460
atccggaacg aggccaccag aaccaacaga gccgtgcggc tgcctgtgtc tacagccgct  11520
gcacctgagg gcatcacact gttctacggc ctgtacaacg ccgtgaaaga gttctgcctc  11580
cggcaccagc tggatccccc cctgctgaga cacctggaca agtactacgc cggcctgccc  11640
ccagagctga agcagaccag agtgaacctg cccgcccaca gcagatatgg ccctcaggcc  11700
gtggacgcca gatgataagc ggccgcatac agcagcaatt ggcaagctgc ttacatagaa  11760
ctcgcggcga ttggcatgcc gccttaaaat ttttatttta tttttctttt cttttccgaa  11820
tcggattttg tttttaatat ttcaaaaaaa aaaaaaaaaa aaaaaaaaaa aaaaaaaagg  11880
gtcggcatgg catctccacc tcctcgcggt ccgacctggg catccgaagg aggacgcacg  11940
tccactcgga tggctaaggg agagccacgt ttaaacacgt gatatctggc ctcatgggcc  12000
ttcctttcac tgcccgcttt ccagtcggga aacctgtcgt gccagctgca ttaacatggt  12060
catagctgtt tccttgcgta ttgggcgctc tccgcttcct cgctcactga ctcgctgcgc  12120
tcggtcgttc gggtaaagcc tggggtgcct aatgagcaaa aggccagcaa aaggccagga  12180
accgtaaaaa ggccgcgttg ctggcgtttt tccataggct ccgcccccct gacgagcatc  12240
acaaaaatcg acgctcaagt cagaggtggc gaaacccgac aggactataa agataccagg  12300
cgtttccccc tggaagctcc ctcgtgcgct ctcctgttcc gaccctgccg cttaccggat  12360
acctgtccgc ctttctccct tcgggaagcg tggcgctttc tcatagctca cgctgtaggt  12420
atctcagttc ggtgtaggtc gttcgctcca agctgggctg tgtgcacgaa ccccccgttc  12480
agcccgaccg ctgcgcctta tccggtaact atcgtcttga gtccaacccg gtaagacacg  12540
```

acttatcgcc actggcagca gccactggta acaggattag cagagcgagg tatgtaggcg 12600
gtgctacaga gttcttgaag tggtggccta actacggcta cactagaaga acagtatttg 12660
gtatctgcgc tctgctgaag ccagttacct tcggaaaaag agttggtagc tcttgatccg 12720
gcaaacaaac caccgctggt agcggtggtt tttttgtttg caagcagcag attacgcgca 12780
gaaaaaaagg atctcaagaa gatcctttga tcttttctac ggggtctgac gctcagtgga 12840
acgaaaactc acgttaaggg attttggtca tgagattatc aaaaaggatc ttcacctaga 12900
tccttttaaa ttaaaaatga agttttaaat caatctaaag tatatatgag taaacttggt 12960
ctgacagtta ttagaaaaat tcatccagca gacgataaaa cgcaatacgc tggctatccg 13020
gtgccgcaat gccatacagc accagaaaac gatccgccca ttcgccgccc agttcttccg 13080
caatatcacg ggtggccagc gcaatatcct gataacgatc cgccacgccc agacggccgc 13140
aatcaataaa gccgctaaaa cggccatttt ccaccataat gttcggcagg cacgcatcac 13200
catgggtcac caccagatct tcgccatccg gcatgctcgc tttcagacgc gcaaacagct 13260
ctgccggtgc caggccctga tgttcttcat ccagatcatc ctgatccacc aggcccgctt 13320
ccatacgggt acgcgcacgt tcaatacgat gtttcgcctg atgatcaaac ggacaggtcg 13380
ccgggtccag ggtatgcaga cgacgcatgg catccgccat aatgctcact ttttctgccg 13440
gcgccagatg gctagacagc agatcctgac ccggcacttc gcccagcagc agccaatcac 13500
ggcccgcttc ggtcaccaca tccagcaccg ccgcacacgg aacaccggtg gtggccagcc 13560
agctcagacg cgccgcttca tcctgcagct cgttcagcgc accgctcaga tcggttttca 13620
caaacagcac cggacgaccc tgcgcgctca gacgaaacac cgccgcatca gagcagccaa 13680
tggtctgctg cgcccaatca tagccaaaca gacgttccac ccacgctgcc gggctacccg 13740
catgcaggcc atcctgttca atcatactct tcctttttca atattattga agcatttatc 13800
agggttattg tctcatgagc ggatacatat ttgaatgtat ttagaaaaat aaacaaatag 13860
gggttccgcg cacatttccc cgaaaagtgc cacctaaatt gtaagcgtta atattttgtt 13920
aaaattcgcg ttaaattttt gttaaatcag ctcatttttt aaccaatagg ccgaaatcgg 13980
caaaatccct tataaatcaa aagaatagac cgagataggg ttgagtggcc gctacagggc 14040
gctcccattc gccattcagg ctgcgcaact gttgggaagg gcgtttcggt gcgggcctct 14100
tcgctattac gccagctggc gaaaggggga tgtgctgcaa ggcgattaag ttgggtaacg 14160
ccagggtttt cccagtcaca cgcgtaatac gactcactat ag 14202

<210> SEQ ID NO 63
<211> LENGTH: 14721
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360

-continued

```
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
```

-continued

```
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
```

```
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
```

-continued

```
tcatagttat ggccatgact actctagcta gcagtgttaa atcattcagc tacctgagag   7500
gggcccctat aactctctac ggctaacctg aatggactac gacatagtct agtccgccaa   7560
gctattccag aagtagtgag gaggcttttt tggaggccta ggcttttgca aaaagcttgt   7620
atatccattt tcggatctga tcaagagaca ggatgaggat cgtttcgcat gattgaataa   7680
gatggattgc acgtaggttc tccggccgct tgggtggaga ggctattcgg ctatgactgg   7740
gcacaactga caatcggctg ctctgatgcc gccgtgatcc ggttgtcagc gcaggggcgc   7800
ccggttcttt ttgtcaagac cgacctgtcc ggtgccctga atgaactgaa ggacgaggca   7860
gcgcggctat cgtggctggc cacgacgggc gttccttgcg cagtctagac tggcgcgcca   7920
aacctgcagg ttaaaacagc tgtgggttgt tcccacccac agggcccact gggcgctagc   7980
actctgattt tacgaaatcc ttgtgcgcct gttttatatc ccttccctaa ttcgaaacgt   8040
agaagcaatg cgcaccactg atcaatagta ggcgtaacgc gccagttacg tcatgatcaa   8100
gcatatctgt tcccccggac tgagtatcaa tagactgctt acgcggttga aggagaaaac   8160
gttcgttatc cggctaacta cttcgagaag cccagtaaca ccatggaagc tgcagggtgt   8220
ttcgctcagc acttcccccg tgtagatcag gtcgatgagc cactgcaatc cccacaggtg   8280
actgtggcag tggctgcgtt ggcggcctgc ctatggggag acccatagga cgctctaatg   8340
tggacatggt gcgaagagcc tattgagcta gttagtagtc ctccggcccc tgaatgcggc   8400
taatcctaac tgcggagcac atgccttcaa cccagagggt agtgtgtcgt aatgggcaac   8460
tctgcagcgg aaccgactac tttgggtgtc cgtgtttctt tttattctta tattggctgc   8520
ttatggtgac aattacagaa ttgttaccat atagctattg gattggccat ccggtgtgta   8580
atagagctgt tatataccta tttgttggct ttgtaccact aactttaaaa tctataacta   8640
ccctcaactt tatattaacc ctcaatacag ttgaacatga ggcctggcct gccctcctac   8700
ctgatcatcc tggccgtgtg cctgttcagc cacctgctgt ccagcagata cggcgccgag   8760
gccgtgagcg agcccctgga caaggctttc cacctgctgc tgaacaccta cggcagaccc   8820
atccggtttc tgcgggagaa caccacccag tgcacctaca acagcagcct gcggaacagc   8880
accgtcgtga gagagaacgc catcagcttc aactttttcc agagctacaa ccagtactac   8940
gtgttccaca tgcccagatg cctgtttgcc ggccctctgg ccgagcagtt cctgaaccag   9000
gtggacctga ccgagacact ggaaagatac cagcagcggc tgaataccta cgccctggtg   9060
tccaaggacc tggccagcta ccggtccttt agccagcagc tcaaggctca ggatagcctc   9120
ggcgagcagc ctaccaccgt gccccctccc atcgacctga gcatccccca cgtgtggatg   9180
cctccccaga ccacccctca cggctggacc gagagccaca ccacctccgg cctgcacaga   9240
ccccacttca accagacctg catcctgttc gacggccacg acctgctgtt tagcaccgtg   9300
acccccctgcc tgcaccaggg cttctacctg atcgacgagc tgagatacgt gaagatcacc   9360
ctgaccgagg atttcttcgt ggtcaccgtg tccatcgacg acgacacccc catgctgctg   9420
atcttcggcc acctgcccag agtgctgttc aaggccccct accagcggga caacttcatc   9480
ctgcggcaga ccgagaagca cgagctgctg gtgctggtca agaaggacca gctgaaccgg   9540
cactcctacc tgaaggaccc cgacttcctg gacgccgccc tggacttcaa ctacctggac   9600
ctgagcgccc tgctgagaaa cagcttccac agatacgccg tggacgtgct gaagtccgga   9660
cggtgccaga tgctcgatcg gcggaccgtg gagatggcct tcgcctatgc cctcgccctg   9720
ttcgccgctg ccagacagga agaggctggc gcccaggtgt cagtgcccag agccctggat   9780
agacaggccg ccctgctgca gatccaggaa ttcatgatca cctgcctgag ccagaccccc   9840
```

-continued

```
cctagaacca ccctgctgct gtaccccaca gccgtggatc tggccaagag ggccctgtgg   9900
acccccaacc agatcaccga catcacaagc ctcgtgcggc tcgtgtacat cctgagcaag   9960
cagaaccagc agcacctgat cccccagtgg gccctgagac agatcgccga cttcgccctg  10020
aagctgcaca agacccatct ggccagcttt ctgagcgcct tcgccaggca ggaactgtac  10080
ctgatgggca gcctggtcca cagcatgctg gtgcatacca ccgagcggcg ggagatcttc  10140
atcgtggaga caggcctgtg tagcctggcc gagctgtccc actttaccca gctgctggcc  10200
caccctcacc acgagtacct gagcgacctg tacaccccct gcagcagcag cggcagacgg  10260
gaccacagcc tggaacggct gaccagactg ttccccgatg ccaccgtgcc tgctacagtg  10320
cctgccgccc tgtccatcct gtccaccatg cagcccagca ccctggaaac cttccccgac  10380
ctgttctgcc tgcccctggg cgagagcttt agcgccctga ccgtgtccga gcacgtgtcc  10440
tacatcgtga ccaatcagta cctgatcaag ggcatcagct accccgtgtc caccacagtc  10500
gtgggccaga gcctgatcat cacccagacc gacagccaga ccaagtgcga gctgacccgg  10560
aacatgcaca ccacacacag catcaccgtg gccctgaaca tcagcctgga aaactgcgct  10620
ttctgtcagt ctgccctgct ggaatacgac gatacccagg gcgtgatcaa catcatgtac  10680
atgcacgaca gcgacgacgt gctgttcgcc ctggacccct acaacgaggt ggtggtgtcc  10740
agcccccgga cccactacct gatgctgctg aagaacggca ccgtgctgga agtgaccgac  10800
gtggtggtgg acgccaccga ctgataacgc cggcgccccc ccctaacgtt actggccgaa  10860
gccgcttgga ataaggccgg tgtgcgtttg tctatatgtt attttccacc atattgccgt  10920
cttttggcaa tgtgagggcc cggaaacctg gccctgtctt cttgacgagc attcctaggg  10980
gtctttcccc tctcgccaaa ggaatgcaag gtctgttgaa tgtcgtgaag gaagcagttc  11040
ctctggaagc ttcttgaaga caaacaacgt ctgtagcgac cctttgcagg cagcggaacc  11100
ccccacctgg cgacaggtgc ctctgcggcc aaaagccacg tgtataagat acacctgcaa  11160
aggcggcaca accccagtgc cacgttgtga gttggatagt tgtggaaaga gtcaaatggc  11220
tctcctcaag cgtattcaac aaggggctga aggatgccca gaaggtaccc cattgtatgg  11280
gatctgatct ggggcctcgg tgcacatgct ttacatgtgt ttagtcgagg ttaaaaaaac  11340
gtctaggccc cccgaaccac ggggacgtgg ttttcctttg aaaaacacga taataatatg  11400
tgcagaaggc ccgactgcgg cttcagcttc agccctggac ccgtgatcct gctgtggtgc  11460
tgcctgctgc tgcctatcgt gtcctctgcc gccgtgtctg tggcccctac agccgccgag  11520
aaggtgccag ccgagtgccc cgagctgacc agaagatgcc tgctgggcga ggtgttcgag  11580
ggcgacaagt acgagagctg gctgcggccc ctggtcaacg tgaccggcag agatggcccc  11640
ctgagccagc tgatccggta cagacccgtg acccccgagg ccgccaatag cgtgctgctg  11700
gacgaggcct tcctggatac cctggccctg ctgtacaaca accccgacca gctgagagcc  11760
ctgctgaccc tgctgtccag cgacaccgcc cccagatgga tgaccgtgat gcggggctac  11820
agcgagtgtg gagatggcag ccctgccgtg tacacctgcg tggacgacct gtgcagaggc  11880
tacgacctga ccagactgag ctacggccgg tccatcttca cagagcacgt gctgggcttc  11940
gagctggtgc cccccagcct gttcaacgtg gtggtggcca tccggaacga ggccaccaga  12000
accaacagag ccgtgcggct gcctgtgtct acagccgctg cacctgaggg catcacactg  12060
ttctacggcc tgtacaacgc cgtgaaagag ttctgcctcc ggcaccagct ggatcccccc  12120
ctgctgagac acctggacaa gtactacgcc ggcctgcccc cagagctgaa gcagaccaga  12180
```

gtgaacctgc ccgcccacag cagatatggc cctcaggccg tggacgccag atgataagcg 12240
gccgcataca gcagcaattg gcaagctgct tacatagaac tcgcggcgat tggcatgccg 12300
ccttaaaatt tttattttat ttttctttc ttttccgaat cggattttgt ttttaatatt 12360
tcaaaaaaaa aaaaaaaaaa aaaaaaaaaa aaaaaaaggg tcggcatggc atctccacct 12420
cctcgcggtc cgacctgggc atccgaagga ggacgcacgt ccactcggat ggctaaggga 12480
gagccacgtt taaacacgtg atatctggcc tcatgggcct tcctttcact gcccgctttc 12540
cagtcgggaa acctgtcgtg ccagctgcat taacatggtc atagctgttt ccttgcgtat 12600
tgggcgctct ccgcttcctc gctcactgac tcgctgcgct cggtcgttcg ggtaaagcct 12660
ggggtgccta atgagcaaaa ggccagcaaa aggccaggaa ccgtaaaaag gccgcgttgc 12720
tggcgttttt ccataggctc cgcccccctg acgagcatca caaaaatcga cgctcaagtc 12780
agaggtggcg aaacccgaca ggactataaa gataccaggc gtttccccct ggaagctccc 12840
tcgtgcgctc tcctgttccg accctgccgc ttaccggata cctgtccgcc tttctccctt 12900
cgggaagcgt ggcgctttct catagctcac gctgtaggta tctcagttcg gtgtaggtcg 12960
ttcgctccaa gctgggctgt gtgcacgaac cccccgttca gcccgaccgc tgcgccttat 13020
ccggtaacta tcgtcttgag tccaacccgg taagacacga cttatcgcca ctggcagcag 13080
ccactggtaa caggattagc agagcgaggt atgtaggcgg tgctacagag ttcttgaagt 13140
ggtggcctaa ctacggctac actagaagaa cagtatttgg tatctgcgct ctgctgaagc 13200
cagttacctt cggaaaaaga gttggtagct cttgatccgg caaacaaacc accgctggta 13260
gcggtggttt ttttgtttgc aagcagcaga ttacgcgcag aaaaaaagga tctcaagaag 13320
atcctttgat cttttctacg gggtctgacg ctcagtggaa cgaaaactca cgttaaggga 13380
ttttggtcat gagattatca aaaaggatct tcacctagat ccttttaaat taaaaatgaa 13440
gttttaaatc aatctaaagt atatatgagt aaacttggtc tgacagttat tagaaaaatt 13500
catccagcag acgataaaac gcaatacgct ggctatccgg tgccgcaatg ccatacagca 13560
ccagaaaacg atccgcccat tcgccgccca gttcttccgc aatatcacgg gtggccagcg 13620
caatatcctg ataacgatcc gccacgccca gacggccgca atcaataaag ccgctaaaac 13680
ggccattttc caccataatg ttcggcaggc acgcatcacc atgggtcacc accagatctt 13740
cgccatccgg catgctcgct ttcagacgcg caaacagctc tgccggtgcc aggccctgat 13800
gttcttcatc cagatcatcc tgatccacca ggcccgcttc catacgggta cgcgcacgtt 13860
caatacgatg tttcgcctga tgatcaaacg gacaggtcgc cgggtccagg gtatgcagac 13920
gacgcatggc atccgccata atgctcactt tttctgccgg cgccagatgg ctagacagca 13980
gatcctgacc cggcacttcg cccagcagca gccaatcacg gcccgcttcg gtcaccacat 14040
ccagcaccgc cgcacacgga acaccggtgg tggccagcca gctcagacgc gccgcttcat 14100
cctgcagctc gttcagcgca ccgctcagat cggttttcac aaacagcacc ggacgaccct 14160
gcgcgctcag acgaaacacc gccgcatcag agcagccaat ggtctgctgc gcccaatcat 14220
agccaaacag acgttccacc cacgctgccg ggctacccgc atgcaggcca tcctgttcaa 14280
tcatactctt cctttttcaa tattattgaa gcatttatca gggttattgt ctcatgagcg 14340
gatacatatt tgaatgtatt tagaaaaata aacaaatagg ggttccgcgc acatttcccc 14400
gaaaagtgcc acctaaattg taagcgttaa tattttgtta aaattcgcgt taaatttttg 14460
ttaaatcagc tcatttttta accaataggc cgaaatcggc aaaatccctt ataaatcaaa 14520
agaatagacc gagatagggt tgagtggccg ctacagggcg ctcccattcg ccattcaggc 14580
tgcgcaactg ttgggaaggg cgtttcggtg cgggcctctt cgctattacg ccagctggcg 14640
aaagggggat gtgctgcaag gcgattaagt tgggtaacgc cagggttttc ccagtcacac 14700
gcgtaatacg actcactata g 14721

<210> SEQ ID NO 64
<211> LENGTH: 14721
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800

-continued

```
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
```

-continued

```
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
```

-continued

```
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gctattccag aagtagtgag gaggcttttt tggaggccta ggcttttgca aaaagcttgt   7620
atatccattt tcggatctga tcaagagaca ggatgaggat cgtttcgcat gattgaataa   7680
gatggattgc acgtaggttc tccggccgct tgggtggaga ggctattcgg ctatgactgg   7740
gcacaactga caatcggctg ctctgatgcc gccgtgatcc ggttgtcagc gcaggggcgc   7800
ccggttcttt ttgtcaagac cgacctgtcc ggtgccctga atgaactgaa ggacgaggca   7860
gcgcggctat cgtggctggc cacgacgggc gttccttgcg cagtctagac tggcgcgcca   7920
aacctgcagg ttaaaacagc tgtgggttgt tcccacccac agggcccact gggcgctagc   7980
actctgattt tacgaaatcc ttgtgcgcct gttttatatc ccttccctaa ttcgaaacgt   8040
agaagcaatg cgcaccactg atcaatagta ggcgtaacgc gccagttacg tcatgatcaa   8100
gcatatctgt tcccccggac tgagtatcaa tagactgctt acgcggttga aggagaaaac   8160
gttcgttatc cggctaacta cttcgagaag cccagtaaca ccatggaagc tgcagggtgt   8220
ttcgctcagc acttcccccg tgtagatcag gtcgatgagc cactgcaatc cccacaggtg   8280
actgtggcag tggctgcgtt ggcggcctgc ctatggggag acccatagga cgctctaatg   8340
tggacatggt gcgaagagcc tattgagcta gttagtagtc ctccggcccc tgaatgcggc   8400
taatcctaac tgcggagcac atgccttcaa cccagagggt agtgtgtcgt aatgggcaac   8460
tctgcagcgg aaccgactac tttgggtgtc cgtgtttctt tttattctta tattggctgc   8520
ttatggtgac aattacagaa ttgttaccat atagctattg gattggccat ccggtgtgta   8580
atagagctgt tatataccta tttgttggct ttgtaccact aactttaaaa tctataacta   8640
ccctcaactt tatattaacc ctcaatacag ttgaacatgt gcagaaggcc cgactgcggc   8700
ttcagcttca gccctggacc cgtgatcctg ctgtggtgct gcctgctgct gcctatcgtg   8760
tcctctgccg ccgtgtctgt ggcccctaca gccgccgaga aggtgccagc cgagtgcccc   8820
gagctgacca gaagatgcct gctgggcgag gtgttcgagg gcgacaagta cgagagctgg   8880
ctgcggcccc tggtcaacgt gaccggcaga gatggccccc tgagccagct gatccggtac   8940
```

```
agacccgtga cccccgaggc cgccaatagc gtgctgctgg acgaggcctt cctggatacc   9000
ctggccctgc tgtacaacaa ccccgaccag ctgagagccc tgctgaccct gctgtccagc   9060
gacaccgccc ccagatggat gaccgtgatg cggggctaca gcgagtgtgg agatggcagc   9120
cctgccgtgt acacctgcgt ggacgacctg tgcagaggct acgacctgac cagactgagc   9180
tacggccggt ccatcttcac agagcacgtg ctgggcttcg agctggtgcc ccccagcctg   9240
ttcaacgtgg tggtggccat ccggaacgag gccaccagaa ccaacagagc cgtgcggctg   9300
cctgtgtcta cagccgctgc acctgagggc atcacactgt tctacggcct gtacaacgcc   9360
gtgaaagagt tctgcctccg gcaccagctg gatccccccc tgctgagaca cctggacaag   9420
tactacgccg gcctgccccc agagctgaag cagaccagag tgaacctgcc cgcccacagc   9480
agatatggcc ctcaggccgt ggacgccaga tgataacgcc ggcgccccccc cctaacgtta   9540
ctggccgaag ccgcttggaa taaggccggt gtgcgtttgt ctatatgtta ttttccacca   9600
tattgccgtc ttttggcaat gtgagggccc ggaaacctgg ccctgtcttc ttgacgagca   9660
ttcctagggg tctttcccct ctcgccaaag gaatgcaagg tctgttgaat gtcgtgaagg   9720
aagcagttcc tctggaagct tcttgaagac aaacaacgtc tgtagcgacc ctttgcaggc   9780
agcggaaccc cccacctggc gacaggtgcc tctgcggcca aaagccacgt gtataagata   9840
cacctgcaaa ggcggcacaa ccccagtgcc acgttgtgag ttggatagtt gtggaaagag   9900
tcaaatggct ctcctcaagc gtattcaaca aggggctgaa ggatgcccag aaggtacccc   9960
attgtatggg atctgatctg gggcctcggt gcacatgctt tacatgtgtt tagtcgaggt  10020
taaaaaaacg tctaggcccc ccgaaccacg gggacgtggt tttcctttga aaaacacgat  10080
aataatatga ggcctggcct gccctcctac ctgatcatcc tggccgtgtg cctgttcagc  10140
cacctgctgt ccagcagata cggcgccgag gccgtgagcg agcccctgga caaggctttc  10200
cacctgctgc tgaacaccta cggcagaccc atccggtttc tgcgggagaa caccacccag  10260
tgcacctaca acagcagcct gcggaacagc accgtcgtga gagagaacgc catcagcttc  10320
aactttttcc agagctacaa ccagtactac gtgttccaca tgcccagatg cctgtttgcc  10380
ggccctctgg ccgagcagtt cctgaaccag gtggacctga ccgagacact ggaaagatac  10440
cagcagcggc tgaataccta cgccctggtg tccaaggacc tggccagcta ccggtccttt  10500
agccagcagc tcaaggctca ggatagcctc ggcgagcagc ctaccaccgt gccccctccc  10560
atcgacctga gcatccccca cgtgtggatg cctccccaga ccacccctca cggctggacc  10620
gagagccaca ccacctccgg cctgcacaga ccccacttca accagacctg catcctgttc  10680
gacggccacg acctgctgtt tagcaccgtg acccccctgcc tgcaccaggg cttctacctg  10740
atcgacgagc tgagatacgt gaagatcacc ctgaccgagg atttcttcgt ggtcaccgtg  10800
tccatcgacg acgacacccc catgctgctg atcttcggcc acctgcccag agtgctgttc  10860
aaggccccct accagcggga caacttcatc ctgcggcaga ccgagaagca cgagctgctg  10920
gtgctggtca agaaggacca gctgaaccgg cactcctacc tgaaggaccc cgacttcctg  10980
gacgccgccc tggacttcaa ctacctggac ctgagcgccc tgctgagaaa cagcttccac  11040
agatacgccg tggacgtgct gaagtccgga cggtgccaga tgctcgatcg gcggaccgtg  11100
gagatggcct tcgcctatgc cctcgccctg ttcgccgctg ccagacagga agaggctggc  11160
gcccaggtgt cagtgcccag agccctggat agacaggccg ccctgctgca gatccaggaa  11220
ttcatgatca cctgcctgag ccagaccccc cctagaacca ccctgctgct gtaccccaca  11280
```

-continued gccgtggatc tggccaagag ggccctgtgg acccccaacc agatcaccga catcacaagc 11340
ctcgtgcggc tcgtgtacat cctgagcaag cagaaccagc agcacctgat cccccagtgg 11400
gccctgagac agatcgccga cttcgccctg aagctgcaca agacccatct ggccagcttt 11460
ctgagcgcct tcgccaggca ggaactgtac ctgatgggca gcctggtcca cagcatgctg 11520
gtgcatacca ccgagcggcg ggagatcttc atcgtggaga caggcctgtg tagcctggcc 11580
gagctgtccc actttaccca gctgctggcc caccctcacc acgagtacct gagcgacctg 11640
tacacccccct gcagcagcag cggcagacgg gaccacagcc tggaacggct gaccagactg 11700
ttccccgatg ccaccgtgcc tgctacagtg cctgccgccc tgtccatcct gtccaccatg 11760
cagcccagca ccctggaaac cttccccgac ctgttctgcc tgcccctggg cgagagcttt 11820
agcgccctga ccgtgtccga gcacgtgtcc tacatcgtga ccaatcagta cctgatcaag 11880
ggcatcagct accccgtgtc caccacagtc gtgggccaga gcctgatcat cacccagacc 11940
gacagccaga ccaagtgcga gctgacccgg aacatgcaca ccacacacag catcaccgtg 12000
gccctgaaca tcagcctgga aaactgcgct ttctgtcagt ctgccctgct ggaatacgac 12060
gatacccagg gcgtgatcaa catcatgtac atgcacgaca gcgacgacgt gctgttcgcc 12120
ctggacccct acaacgaggt ggtggtgtcc agcccccgga cccactacct gatgctgctg 12180
aagaacggca ccgtgctgga agtgaccgac gtggtggtgg acgccaccga ctgataagcg 12240
gccgcataca gcagcaattg gcaagctgct tacatagaac tcgcggcgat tggcatgccg 12300
ccttaaaatt tttattttat ttttcttttc ttttccgaat cggattttgt ttttaatatt 12360
tcaaaaaaaa aaaaaaaaaa aaaaaaaaaa aaaaaaaggg tcggcatggc atctccacct 12420
cctcgcggtc cgacctgggc atccgaagga ggacgcacgt ccactcggat ggctaaggga 12480
gagccacgtt taaacacgtg atatctggcc tcatgggcct tcctttcact gcccgctttc 12540
cagtcgggaa acctgtcgtg ccagctgcat taacatggtc atagctgttt ccttgcgtat 12600
tgggcgctct ccgcttcctc gctcactgac tcgctgcgct cggtcgttcg ggtaaagcct 12660
ggggtgccta atgagcaaaa ggccagcaaa aggccaggaa ccgtaaaaag gccgcgttgc 12720
tggcgttttt ccataggctc cgcccccctg acgagcatca caaaaatcga cgctcaagtc 12780
agaggtggcg aaacccgaca ggactataaa gataccaggc gtttccccct ggaagctccc 12840
tcgtgcgctc tcctgttccg accctgccgc ttaccggata cctgtccgcc tttctccctt 12900
cgggaagcgt ggcgctttct catagctcac gctgtaggta tctcagttcg gtgtaggtcg 12960
ttcgctccaa gctgggctgt gtgcacgaac cccccgttca gcccgaccgc tgcgccttat 13020
ccggtaacta tcgtcttgag tccaacccgg taagacacga cttatcgcca ctggcagcag 13080
ccactggtaa caggattagc agagcgaggt atgtaggcgg tgctacagag ttcttgaagt 13140
ggtggcctaa ctacggctac actagaagaa cagtatttgg tatctgcgct ctgctgaagc 13200
cagttacctt cggaaaaaga gttggtagct cttgatccgg caaacaaacc accgctggta 13260
gcggtggttt ttttgtttgc aagcagcaga ttacgcgcag aaaaaaagga tctcaagaag 13320
atcctttgat cttttctacg gggtctgacg ctcagtggaa cgaaaactca cgttaaggga 13380
ttttggtcat gagattatca aaaaggatct tcacctagat ccttttaaat taaaaatgaa 13440
gttttaaatc aatctaaagt atatatgagt aaacttggtc tgacagttat tagaaaaatt 13500
catccagcag acgataaaac gcaatacgct ggctatccgg tgccgcaatg ccatacagca 13560
ccagaaaacg atccgcccat tcgccgccca gttcttccgc aatatcacgg gtggccagcg 13620
caatatcctg ataacgatcc gccacgccca gacggccgca atcaataaag ccgctaaaac 13680

-continued

```
ggccattttc caccataatg ttcggcaggc acgcatcacc atgggtcacc accagatctt  13740
cgccatccgg catgctcgct ttcagacgcg caaacagctc tgccggtgcc aggccctgat  13800
gttcttcatc cagatcatcc tgatccacca ggcccgcttc catacgggta cgcgcacgtt  13860
caatacgatg tttcgcctga tgatcaaacg gacaggtcgc cgggtccagg gtatgcagac  13920
gacgcatggc atccgccata atgctcactt tttctgccgg cgccagatgg ctagacagca  13980
gatcctgacc cggcacttcg cccagcagca gccaatcacg gcccgcttcg gtcaccacat  14040
ccagcaccgc cgcacacgga acaccggtgg tggccagcca gctcagacgc gccgcttcat  14100
cctgcagctc gttcagcgca ccgctcagat cggttttcac aaacagcacc ggacgaccct  14160
gcgcgctcag acgaaacacc gccgcatcag agcagccaat ggtctgctgc gcccaatcat  14220
agccaaacag acgttccacc cacgctgccg ggctacccgc atgcaggcca tcctgttcaa  14280
tcatactctt cctttttcaa tattattgaa gcatttatca gggttattgt ctcatgagcg  14340
gatacatatt tgaatgtatt tagaaaaata aacaaatagg ggttccgcgc acatttcccc  14400
gaaaagtgcc acctaaattg taagcgttaa tattttgtta aaattcgcgt taaatttttg  14460
ttaaatcagc tcatttttta accaataggc cgaaatcggc aaaatccctt ataaatcaaa  14520
agaatagacc gagatagggt tgagtggccg ctacagggcg ctcccattcg ccattcaggc  14580
tgcgcaactg ttgggaaggg cgtttcggtg cgggcctctt cgctattacg ccagctggcg  14640
aaagggggat gtgctgcaag gcgattaagt tgggtaacgc cagggttttc ccagtcacac  14700
gcgtaatacg actcactata g                                            14721
```

```
<210> SEQ ID NO 65
<211> LENGTH: 15300
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
```

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
```

-continued

```
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
```

-continued cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgaggggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640

-continued

```
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgaggcct ggcctgccct cctacctgat catcctggcc gtgtgcctgt tcagccacct   7620
gctgtccagc agatacggcg ccgaggccgt gagcgagccc ctggacaagg ctttccacct   7680
gctgctgaac acctacggca gacccatccg gtttctgcgg gagaacacca cccagtgcac   7740
ctacaacagc agcctgcgga acagcaccgt cgtgagagag aacgccatca gcttcaactt   7800
tttccagagc tacaaccagt actacgtgtt ccacatgccc agatgcctgt ttgccggccc   7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
```

-continued

```
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga cccccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgacagca gactgctgat   9720
gatgagcgtg tacgccctga gcgccatcat cggcatctac ctgctgtacc ggatgctgaa   9780
aacctgctga taatctagag gcccctataa ctctctacgg ctaacctgaa tggactacga   9840
catagtctag tccgccaaga tgtgcagaag gcccgactgc ggcttcagct tcagccctgg   9900
acccgtgatc ctgctgtggt gctgcctgct gctgcctatc gtgtcctctg ccgccgtgtc   9960
tgtggcccct acagccgccg agaaggtgcc agccgagtgc cccgagctga ccagaagatg  10020
cctgctgggc gaggtgttcg agggcgacaa gtacgagagc tggctgcggc ccctggtcaa  10080
cgtgaccggc agagatggcc ccctgagcca gctgatccgg tacagacccg tgacccccga  10140
ggccgccaat agcgtgctgc tggacgaggc cttcctggat accctggccc tgctgtacaa  10200
caaccccgac cagctgagag ccctgctgac cctgctgtcc agcgacaccg cccccagatg  10260
gatgaccgtg atgcggggct acagcgagtg tggagatggc agccctgccg tgtacacctg  10320
cgtggacgac ctgtgcagag gctacgacct gaccagactg agctacggcc ggtccatctt  10380
```

-continued

```
cacagagcac gtgctgggct tcgagctggt gccccccagc ctgttcaacg tggtggtggc  10440
catccggaac gaggccacca gaaccaacag agccgtgcgg ctgcctgtgt ctacagccgc  10500
tgcacctgag ggcatcacac tgttctacgg cctgtacaac gccgtgaaag agttctgcct  10560
ccggcaccag ctggatcccc ccctgctgag acacctggac aagtactacg ccggcctgcc  10620
cccagagctg aagcagacca gagtgaacct gcccgcccac agcagatatg gccctcaggc  10680
cgtggacgcc agatgataac gccggcggcc cctataactc tctacggcta acctgaatgg  10740
actacgacat agtctagtcc gccaagatga gccccaagga cctgaccccc ttcctgacaa  10800
ccctgtggct gctcctgggc catagcagag tgcctagagt gcgggccgag gaatgctgcg  10860
agttcatcaa cgtgaaccac ccccccgagc ggtgctacga cttcaagatg tgcaaccggt  10920
tcaccgtggc cctgagatgc cccgacggcg aagtgtgcta cagccccgag aaaaccgccg  10980
agatccgggg catcgtgacc accatgaccc acagcctgac ccggcaggtg gtgcacaaca  11040
agctgaccag ctgcaactac aaccccctgt acctggaagc cgacggccgg atcagatgcg  11100
gcaaagtgaa cgacaaggcc cagtacctgc tgggagccgc cggaagcgtg ccctaccggt  11160
ggatcaacct ggaatacgac aagatcaccc ggatcgtggg cctggaccag tacctggaaa  11220
gcgtgaagaa gcacaagcgg ctggacgtgt gcagagccaa gatgggctac atgctgcagt  11280
gataaggcgc gccgccccta taactctcta cggctaacct gaatggacta cgacatagtc  11340
tagtccgcca agatgctgcg gctgctgctg agacaccact tccactgcct gctgctgtgt  11400
gccgtgtggg ccaccccttg tctggccagc ccttggagca ccctgaccgc caaccagaac  11460
cctagccccc cttggtccaa gctgacctac agcaagcccc acgacgccgc caccttctac  11520
tgcccctttc tgtaccccag ccctcccaga agccccctgc agttcagcgg cttccagaga  11580
gtgtccaccg gccctgagtg ccggaacgag acactgtacc tgctgtacaa ccgggagggc  11640
cagacactgg tggagcggag cagcacctgg gtgaaaaaag tgatctggta tctgagcggc  11700
cggaaccaga ccatcctgca gcggatgccc agaaccgcca gcaagcccag cgacggcaac  11760
gtgcagatca gcgtggagga cgccaaaatc ttcggagccc acatggtgcc caagcagacc  11820
aagctgctga gattcgtggt caacgacggc accagatatc agatgtgcgt gatgaagctg  11880
gaaagctggg cccacgtgtt ccgggactac tccgtgagct tccaggtccg gctgaccttc  11940
accgaggcca acaaccagac ctacaccttc tgcacccacc ccaacctgat cgtgtgataa  12000
gcggccgcgc ccctataact ctctacggct aacctgaatg gactacgaca tagtctagtc  12060
cgccaagatg cggctgtgca gagtgtggct gtccgtgtgc ctgtgtgccg tggtgctggg  12120
ccagtgccag agagagacag ccgagaagaa cgactactac cgggtgcccc actactggga  12180
tgcctgcagc agagccctgc ccgaccagac ccggtacaaa tacgtggagc agctcgtgga  12240
cctgaccctg aactaccact acgacgccag ccacggcctg gacaacttcg acgtgctgaa  12300
gcggatcaac gtgaccgagg tgtccctgct gatcagcgac ttccggcggc agaacagaag  12360
aggcggcacc aacaagcgga ccaccttcaa cgccgctggc tctctggccc ctcacgccag  12420
atccctggaa ttcagcgtgc ggctgttcgc caactgataa cgttgcatcc tgcaggatac  12480
agcagcaatt ggcaagctgc ttacatagaa ctcgcggcga ttggcatgcc gccttaaaat  12540
ttttatttta tttttctttt cttttccgaa tcggattttg tttttaatat ttcaaaaaaa  12600
aaaaaaaaaa aaaaaaaaaa aaaaaaaagg gtcggcatgg catctccacc tcctcgcggt  12660
ccgacctggg catccgaagg aggacgcacg tccactcgga tggctaaggg agagccacgt  12720
ttaaacgcta gagcaagacg tttcccgttg aatatggctc ataacacccc ttgtattact  12780
```

gtttatgtaa gcagacagtt ttattgttca tgatgatata tttttatctt gtgcaatgta 12840
acatcagaga ttttgagaca caacgtggct ttgttgaata aatcgaactt ttgctgagtt 12900
gaaggatcag atcacgcatc ttcccgacaa cgcagaccgt tccgtggcaa agcaaaagtt 12960
caaaatcacc aactggtcca cctacaacaa agctctcatc aaccgtggct ccctcacttt 13020
ctggctggat gatggggcga ttcaggcctg gtatgagtca gcaacacctt cttcacgagg 13080
cagacctcag cgctagcgga gtgtatactg gcttactatg ttggcactga tgagggtgtc 13140
agtgaagtgc ttcatgtggc aggagaaaaa aggctgcacc ggtgcgtcag cagaatatgt 13200
gatacaggat atattccgct tcctcgctca ctgactcgct acgctcggtc gttcgactgc 13260
ggcgagcgga aatggcttac gaacggggcg gagatttcct ggaagatgcc aggaagatac 13320
ttaacaggga agtgagaggg ccgcggcaaa gccgtttttc cataggctcc gcccccctga 13380
caagcatcac gaaatctgac gctcaaatca gtggtggcga aacccgacag gactataaag 13440
ataccaggcg tttccccctgg cggctccctc gtgcgctctc ctgttcctgc ctttcggttt 13500
accggtgtca ttccgctgtt atggccgcgt ttgtctcatt ccacgcctga cactcagttc 13560
cgggtaggca gttcgctcca agctggactg tatgcacgaa ccccccgttc agtccgaccg 13620
ctgcgcctta tccggtaact atcgtcttga gtccaacccg gaaagacatg caaaagcacc 13680
actggcagca gccactggta attgatttag aggagttagt cttgaagtca tgcgccggtt 13740
aaggctaaac tgaaaggaca agttttggtg actgcgctcc tccaagccag ttacctcggt 13800
tcaaagagtt ggtagctcag agaaccttcg aaaaaccgcc ctgcaaggcg gttttttcgt 13860
tttcagagca agagattacg cgcagaccaa aacgatctca agaagatcat cttattaagg 13920
ggtctgacgc tcagtggaac gaaaactcac gttaagggat tttggtcatg agattatcaa 13980
aaaggatctt cacctagatc cttttaaatt aaaaatgaag ttttaaatca atctaaagta 14040
tatatgagta aacttggtct gacagttatt agaaaaattc atccagcaga cgataaaacg 14100
caatacgctg gctatccggt gccgcaatgc catacagcac cagaaaacga tccgcccatt 14160
cgccgcccag ttcttccgca atatcacggg tggccagcgc aatatcctga taacgatccg 14220
ccacgcccag acggccgcaa tcaataaagc cgctaaaacg gccattttcc accataatgt 14280
tcggcaggca cgcatcacca tgggtcacca ccagatcttc gccatccggc atgctcgctt 14340
tcagacgcgc aaacagctct gccggtgcca ggccctgatg ttcttcatcc agatcatcct 14400
gatccaccag gcccgcttcc atacgggtac gcgcacgttc aatacgatgt ttcgcctgat 14460
gatcaaacgg acaggtcgcc gggtccaggg tatgcagacg acgcatggca tccgccataa 14520
tgctcacttt ttctgccggc gccagatggc tagacagcag atcctgaccc ggcacttcgc 14580
ccagcagcag ccaatcacgg cccgcttcgg tcaccacatc cagcaccgcc gcacacggaa 14640
caccggtggt ggccagccag ctcagacgcg ccgcttcatc ctgcagctcg ttcagcgcac 14700
cgctcagatc ggttttcaca aacagcaccg gacgaccctg cgcgctcaga cgaaacaccg 14760
ccgcatcaga gcagccaatg gtctgctgcg cccaatcata gccaaacaga cgttccaccc 14820
acgctgccgg gctacccgca tgcaggccat cctgttcaat catactcttc ctttttcaat 14880
attattgaag catttatcag ggttattgtc tcatgagcgg atacatattt gaatgtattt 14940
agaaaaataa acaaataggg gttccgcgca catttccccg aaaagtgcca cctaaattgt 15000
aagcgttaat attttgttaa aattcgcgtt aaatttttgt taaatcagct cattttttaa 15060
ccaataggcc gaaatcggca aaatccctta taaatcaaaa gaatagaccg agatagggtt 15120
gagtggccgc tacagggcgc tcccattcgc cattcaggct gcgcaactgt tgggaagggc 15180
gtttcggtgc gggcctcttc gctattacgc cagctggcga aagggggatg tgctgcaagg 15240
cgattaagtt gggtaacgcc agggttttcc cagtcacacg cgtaatacga ctcactatag 15300

<210> SEQ ID NO 66
<211> LENGTH: 16324
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 66
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tagacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttaac atgatgtgcc 2520 tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200

-continued

```
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
```

aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gatgaggcct ggcctgccct cctacctgat catcctggcc gtgtgcctgt tcagccacct 7620
gctgtccagc agatacggcg ccgaggccgt gagcgagccc ctggacaagg ctttccacct 7680
gctgctgaac acctacggca gacccatccg gtttctgcgg gagaacacca cccagtgcac 7740
ctacaacagc agcctgcgga acagcaccgt cgtgagagag aacgccatca gcttcaactt 7800
tttccagagc tacaaccagt actacgtgtt ccacatgccc agatgcctgt ttgccggccc 7860
tctggccgag cagttcctga accaggtgga cctgaccgag acactggaaa gataccagca 7920
gcggctgaat acctacgccc tggtgtccaa ggacctggcc agctaccggt cctttagcca 7980
gcagctcaag gctcaggata gcctcggcga gcagcctacc accgtgcccc ctcccatcga 8040
cctgagcatc ccccacgtgt ggatgcctcc ccagaccacc cctcacggct ggaccgagag 8100
ccacaccacc tccggcctgc acagacccca cttcaaccag acctgcatcc tgttcgacgg 8160
ccacgacctg ctgtttagca ccgtgacccc ctgcctgcac cagggcttct acctgatcga 8220
cgagctgaga tacgtgaaga tcaccctgac cgaggatttc ttcgtggtca ccgtgtccat 8280
cgacgacgac acccccatgc tgctgatctt cggccacctg cccagagtgc tgttcaaggc 8340
cccctaccag cgggacaact tcatcctgcg gcagaccgag aagcacgagc tgctggtgct 8400
ggtcaagaag gaccagctga accggcactc ctacctgaag gaccccgact tcctggacgc 8460
cgccctggac ttcaactacc tggacctgag cgccctgctg agaaacagct tccacagata 8520
cgccgtggac gtgctgaagt ccggacggtg ccagatgctc gatcggcgga ccgtggagat 8580
ggccttcgcc tatgccctcg ccctgttcgc cgctgccaga caggaagagg ctggcgccca 8640
ggtgtcagtg cccagagccc tggatagaca ggccgccctg ctgcagatcc aggaattcat 8700
gatcacctgc ctgagccaga cccccccctag aaccaccctg ctgctgtacc ccacagccgt 8760
ggatctggcc aagagggccc tgtggacccc caaccagatc accgacatca caagcctcgt 8820
gcggctcgtg tacatcctga gcaagcagaa ccagcagcac ctgatccccc agtgggccct 8880
gagacagatc gccgacttcg ccctgaagct gcacaagacc catctggcca gctttctgag 8940

-continued

```
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaact gcgctttctg tcagtctgcc ctgctggaat acgacgatac   9540
ccagggcgtg atcaacatca tgtacatgca cgacagcgac gacgtgctgt tcgccctgga   9600
cccctacaac gaggtggtgg tgtccagccc ccggacccac tacctgatgc tgctgaagaa   9660
cggcaccgtg ctggaagtga ccgacgtggt ggtggacgcc accgactgat aatctagagg   9720
cccctataac tctctacggc taacctgaat ggactacgac atagtctagt ccgccaagat   9780
gtgcagaagg cccgactgcg gcttcagctt cagccctgga cccgtgatcc tgctgtggtg   9840
ctgcctgctg ctgcctatcg tgtcctctgc cgccgtgtct gtggccccta cagccgccga   9900
gaaggtgcca gccgagtgcc ccgagctgac cagaagatgc ctgctgggcg aggtgttcga   9960
gggcgacaag tacgagagct ggctgcggcc cctggtcaac gtgaccggca gagatggccc  10020
cctgagccag ctgatccggt acagacccgt gacccccgag gccgccaata gcgtgctgct  10080
ggacgaggcc ttcctggata ccctggccct gctgtacaac aaccccgacc agctgagagc  10140
cctgctgacc ctgctgtcca gcgacaccgc ccccagatgg atgaccgtga tgcggggcta  10200
cagcgagtgt ggagatggca gccctgccgt gtacacctgc gtggacgacc tgtgcagagg  10260
ctacgacctg accagactga gctacggccg gtccatcttc acagagcacg tgctgggctt  10320
cgagctggtg ccccccagcc tgttcaacgt ggtggtggcc atccggaacg aggccaccag  10380
aaccaacaga gccgtgcggc tgcctgtgtc tacagccgct gcacctgagg gcatcacact  10440
gttctacggc ctgtacaacg ccgtgaaaga gttctgcctc cggcaccagc tggatccccc  10500
cctgctgaga cacctggaca agtactacgc cggcctgccc ccagagctga agcagaccag  10560
agtgaacctg cccgcccaca gcagatatgg ccctcaggcc gtggacgcca gatgataacg  10620
ccggcggccc ctataactct ctacggctaa cctgaatgga ctacgacata gtctagtccg  10680
ccaagatgag ccccaaggac ctgacccccct tcctgacaac cctgtggctg ctcctgggcc  10740
atagcagagt gcctagagtg cgggccgagg aatgctgcga gttcatcaac gtgaaccacc  10800
cccccgagcg gtgctacgac ttcaagatgt gcaaccggtt caccgtggcc ctgagatgcc  10860
ccgacggcga agtgtgctac agccccgaga aaaccgccga gatccggggc atcgtgacca  10920
ccatgaccca cagcctgacc cggcaggtgg tgcacaacaa gctgaccagc tgcaactaca  10980
accccctgta cctggaagcc gacggccgga tcagatgcgg caaagtgaac gacaaggccc  11040
agtacctgct gggagccgcc ggaagcgtgc cctaccggtg gatcaacctg gaatacgaca  11100
agatcacccg gatcgtgggc ctggaccagt acctggaaag cgtgaagaag cacaagcggc  11160
tggacgtgtg cagagccaag atgggctaca tgctgcagtg ataaggcgcg ccaacgttac  11220
tggccgaagc cgcttggaat aaggccggtg tgcgtttgtc tatatgttat tttccaccat  11280
attgccgtct tttggcaatg tgagggcccg gaaacctggc cctgtcttct tgacgagcat  11340
```

```
tcctaggggt ctttcccctc tcgccaaagg aatgcaaggt ctgttgaatg tcgtgaagga  11400
agcagttcct ctggaagctt cttgaagaca aacaacgtct gtagcgaccc tttgcaggca  11460
gcggaacccc ccacctggcg acaggtgcct ctgcggccaa aagccacgtg tataagatac  11520
acctgcaaag gcggcacaac cccagtgcca cgttgtgagt tggatagttg tggaaagagt  11580
caaatggctc tcctcaagcg tattcaacaa ggggctgaag gatgcccaga aggtacccca  11640
ttgtatggga tctgatctgg ggcctcggtg cacatgcttt acatgtgttt agtcgaggtt  11700
aaaaaaacgt ctaggccccc cgaaccacgg ggacgtggtt ttcctttgaa aaacacgata  11760
atatgctgcg gctgctgctg agacaccact tccactgcct gctgctgtgt gccgtgtggg  11820
ccaccccttg tctggccagc ccttggagca ccctgaccgc caaccagaac cctagccccc  11880
cttggtccaa gctgacctac agcaagcccc acgacgccgc caccttctac tgcccctttc  11940
tgtaccccag ccctcccaga agccccctgc agttcagcgg cttccagaga gtgtccaccg  12000
gccctgagtg ccggaacgag acactgtacc tgctgtacaa ccgggagggc cagacactgg  12060
tggagcggag cagcacctgg gtgaaaaaag tgatctggta tctgagcggc cggaaccaga  12120
ccatcctgca gcggatgccc agaaccgcca gcaagcccag cgacggcaac gtgcagatca  12180
gcgtggagga cgccaaaatc ttcggagccc acatggtgcc caagcagacc aagctgctga  12240
gattcgtggt caacgacggc accagatatc agatgtgcgt gatgaagctg gaaagctggg  12300
cccacgtgtt ccgggactac tccgtgagct tccaggtccg gctgaccttc accgaggcca  12360
acaaccagac ctacaccttc tgcacccacc ccaacctgat cgtgtgataa gtacctttgt  12420
acgcctgttt tataccccct ccctgatttg caacttagaa gcaacgcaaa ccagatcaat  12480
agtaggtgtg acataccagt cgcatcttga tcaagcactt ctgtatcccc ggaccgagta  12540
tcaatagact gtgcacacgg ttgaaggaga aaacgtccgt tacccggcta actacttcga  12600
gaagcctagt aacgccattg aagttgcaga gtgtttcgct cagcactccc cccgtgtaga  12660
tcaggtcgat gagtcaccgc attccccacg ggcgaccgtg gcggtggctg cgttggcggc  12720
ctgcctatgg ggtaacccat aggacgctct aatacggaca tggcgtgaag agtctattga  12780
gctagttagt agtcctccgg cccctgaatg cggctaatcc taactgcgga gcacataccc  12840
ttaatccaaa gggcagtgtg tcgtaacggg caactctgca gcggaaccga ctactttggg  12900
tgtccgtgtt tctttttatt cttgtattgg ctgcttatgg tgacaattaa agaattgtta  12960
ccatatagct attggattgg ccatccagtg tcaaacagag ctattgtata tctctttgtt  13020
ggattcacac ctctcactct tgaaacgtta cacaccctca attacattat actgctgaac  13080
acgaagcgca tatgcggctg tgcagagtgt ggctgtccgt gtgcctgtgt gccgtggtgc  13140
tgggccagtg ccagagagag acagccgaga agaacgacta ctaccgggtg ccccactact  13200
gggatgcctg cagcagagcc ctgcccgacc agacccggta caaatacgtg gagcagctcg  13260
tggacctgac cctgaactac cactacgacg ccagccacgg cctggacaac ttcgacgtgc  13320
tgaagcggat caacgtgacc gaggtgtccc tgctgatcag cgacttccgg cggcagaaca  13380
gaagaggcgg caccaacaag cggaccacct tcaacgccgc tggctctctg gcccctcacg  13440
ccagatccct ggaattcagc gtgcggctgt tcgccaactg ataacgttgc atcctgcagg  13500
atacagcagc aattggcaag ctgcttacat agaactcgcg gcgattggca tgccgcctta  13560
aaatttttat tttattttc ttttcttttc cgaatcggat tttgttttta atatttcaaa  13620
aaaaaaaaaa aaaaaaaaaa aaaaaaaaaa aagggtcggc atggcatctc cacctcctcg  13680
```

-continued

```
cggtccgacc tgggcatccg aaggaggacg cacgtccact cggatggcta agggagagcc  13740
acgtttaaac gctagagcaa gacgtttccc gttgaatatg gctcataaca ccccttgtat  13800
tactgtttat gtaagcagac agttttattg ttcatgatga tatattttta tcttgtgcaa  13860
tgtaacatca gagattttga gacacaacgt ggctttgttg aataaatcga acttttgctg  13920
agttgaagga tcagatcacg catcttcccg acaacgcaga ccgttccgtg gcaaagcaaa  13980
agttcaaaat caccaactgg tccacctaca acaaagctct catcaaccgt ggctccctca  14040
ctttctggct ggatgatggg gcgattcagg cctggtatga gtcagcaaca ccttcttcac  14100
gaggcagacc tcagcgctag cggagtgtat actggcttac tatgttggca ctgatgaggg  14160
tgtcagtgaa gtgcttcatg tggcaggaga aaaaaggctg caccggtgcg tcagcagaat  14220
atgtgataca ggatatattc cgcttcctcg ctcactgact cgctacgctc ggtcgttcga  14280
ctgcggcgag cggaaatggc ttacgaacgg ggcggagatt tcctggaaga tgccaggaag  14340
atacttaaca gggaagtgag agggccgcgg caaagccgtt tttccatagg ctccgccccc  14400
ctgacaagca tcacgaaatc tgacgctcaa atcagtggtg gcgaaacccg acaggactat  14460
aaagatacca ggcgtttccc ctggcggctc cctcgtgcgc tctcctgttc ctgcctttcg  14520
gtttaccggt gtcattccgc tgttatggcc gcgtttgtct cattccacgc ctgacactca  14580
gttccgggta ggcagttcgc tccaagctgg actgtatgca cgaacccccc gttcagtccg  14640
accgctgcgc cttatccggt aactatcgtc ttgagtccaa cccggaaaga catgcaaaag  14700
caccactggc agcagccact ggtaattgat ttagaggagt tagtcttgaa gtcatgcgcc  14760
ggttaaggct aaactgaaag gacaagtttt ggtgactgcg ctcctccaag ccagttacct  14820
cggttcaaag agttggtagc tcagagaacc ttcgaaaaac cgccctgcaa ggcggttttt  14880
tcgttttcag agcaagagat tacgcgcaga ccaaaacgat ctcaagaaga tcatcttatt  14940
aaggggtctg acgctcagtg gaacgaaaac tcacgttaag ggattttggt catgagatta  15000
tcaaaaagga tcttcaccta gatcctttta aattaaaaat gaagttttaa atcaatctaa  15060
agtatatatg agtaaacttg gtctgacagt tattagaaaa attcatccag cagacgataa  15120
aacgcaatac gctggctatc cggtgccgca atgccataca gcaccagaaa acgatccgcc  15180
cattcgccgc ccagttcttc cgcaatatca cgggtggcca gcgcaatatc ctgataacga  15240
tccgccacgc ccagacggcc gcaatcaata aagccgctaa aacggccatt ttccaccata  15300
atgttcggca ggcacgcatc accatgggtc accaccagat cttcgccatc cggcatgctc  15360
gctttcagac gcgcaaacag ctctgccggt gccaggccct gatgttcttc atccagatca  15420
tcctgatcca ccaggcccgc ttccatacgg gtacgcgcac gttcaatacg atgtttcgcc  15480
tgatgatcaa acggacaggt cgccgggtcc agggtatgca gacgacgcat ggcatccgcc  15540
ataatgctca ctttttctgc cggcgccaga tggctagaca gcagatcctg acccggcact  15600
tcgcccagca gcagccaatc acggcccgct tcggtcacca catccagcac cgccgcacac  15660
ggaacaccgg tggtggccag ccagctcaga cgcgccgctt catcctgcag ctcgttcagc  15720
gcaccgctca gatcggtttt cacaaacagc accggacgac cctgcgcgct cagacgaaac  15780
accgccgcat cagagcagcc aatggtctgc tgcgcccaat catagccaaa cagacgttcc  15840
acccacgctg ccgggctacc cgcatgcagg ccatcctgtt caatcatact cttccttttt  15900
caatattatt gaagcattta tcagggttat tgtctcatga gcggatacat atttgaatgt  15960
atttagaaaa ataaacaaat aggggttccg cgcacatttc cccgaaaagt gccacctaaa  16020
ttgtaagcgt taatattttg ttaaaattcg cgttaaattt ttgttaaatc agctcatttt  16080
```

ttaaccaata ggccgaaatc ggcaaaatcc cttataaatc aaaagaatag accgagatag 16140
ggttgagtgg ccgctacagg gcgctcccat tcgccattca ggctgcgcaa ctgttgggaa 16200
gggcgtttcg gtgcgggcct cttcgctatt acgccagctg gcgaaagggg gatgtgctgc 16260
aaggcgatta agttgggtaa cgccagggtt ttcccagtca cacgcgtaat acgactcact 16320
atag 16324

<210> SEQ ID NO 67
<211> LENGTH: 16360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tagacttgat gttacaagag gctggggccg gctcagtgga gacacctcgt ggcttgataa 1680

-continued

```
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
```

-continued gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420

-continued

```
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgaggcct ggcctgccct cctacctgat catcctggcc gtgtgcctgt tcagccacct   7620
gctgtccagc agatacggcg ccgaggccgt gagcgagccc ctggacaagg ctttccacct   7680
gctgctgaac acctacggca gacccatccg gtttctgcgg gagaacacca cccagtgcac   7740
ctacaacagc agcctgcgga acagcaccgt cgtgagagag aacgccatca gcttcaactt   7800
tttccagagc tacaaccagt actacgtgtt ccacatgccc agatgcctgt ttgccggccc   7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac acccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga cccccccctag aaccaccctg ctgctgtacc ccacagccgt   8760
ggatctggcc aagagggccc tgtggacccc caaccagatc accgacatca caagcctcgt   8820
```

gcggctcgtg tacatcctga gcaagcagaa ccagcagcac ctgatccccc agtgggccct 8880
gagacagatc gccgacttcg ccctgaagct gcacaagacc catctggcca gctttctgag 8940
cgccttcgcc aggcaggaac tgtacctgat gggcagcctg gtccacagca tgctggtgca 9000
taccaccgag cggcgggaga tcttcatcgt ggagacaggc ctgtgtagcc tggccgagct 9060
gtcccacttt acccagctgc tggcccaccc tcaccacgag tacctgagcg acctgtacac 9120
cccctgcagc agcagcggca gacgggacca cagcctggaa cggctgacca gactgttccc 9180
cgatgccacc gtgcctgcta cagtgcctgc cgccctgtcc atcctgtcca ccatgcagcc 9240
cagcaccctg gaaaccttcc ccgacctgtt ctgcctgccc ctgggcgaga gctttagcgc 9300
cctgaccgtg tccgagcacg tgtcctacat cgtgaccaat cagtacctga tcaagggcat 9360
cagctacccc gtgtccacca cagtcgtggg ccagagcctg atcatcaccc agaccgacag 9420
ccagaccaag tgcgagctga cccggaacat gcacaccaca cacagcatca ccgtggccct 9480
gaacatcagc ctggaaaact gcgctttctg tcagtctgcc ctgctggaat acgacgatac 9540
ccagggcgtg atcaacatca tgtacatgca cgacagcgac gacgtgctgt tcgccctgga 9600
cccctacaac gaggtggtgg tgtccagccc ccggacccac tacctgatgc tgctgaagaa 9660
cggcaccgtg ctggaagtga ccgacgtggt ggtggacgcc accgacggca gcggatctgg 9720
gtcccaccat caccatcacc attgataatc tagaggcccc tataactctc tacggctaac 9780
ctgaatggac tacgacatag tctagtccgc caagatgtgc agaaggcccg actgcggctt 9840
cagcttcagc cctggacccg tgatcctgct gtggtgctgc ctgctgctgc ctatcgtgtc 9900
ctctgccgcc gtgtctgtgg cccctacagc cgccgagaag gtgccagccg agtgccccga 9960
gctgaccaga agatgcctgc tgggcgaggt gttcgagggc gacaagtacg agagctggct 10020
gcggcccctg gtcaacgtga ccggcagaga tggccccctg agccagctga tccggtacag 10080
acccgtgacc cccgaggccg ccaatagcgt gctgctggac gaggccttcc tggataccct 10140
ggccctgctg tacaacaacc ccgaccagct gagagccctg ctgaccctgc tgtccagcga 10200
caccgccccc agatggatga ccgtgatgcg gggctacagc gagtgtggag atggcagccc 10260
tgccgtgtac acctgcgtgg acgacctgtg cagaggctac gacctgacca gactgagcta 10320
cggccggtcc atcttcacag agcacgtgct gggcttcgag ctggtgcccc ccagcctgtt 10380
caacgtggtg gtggccatcc ggaacgaggc caccagaacc aacagagccg tgcggctgcc 10440
tgtgtctaca gccgctgcac ctgagggcat cacactgttc tacggcctgt acaacgccgt 10500
gaaagagttc tgcctccggc accagctgga tcccccccctg ctgagacacc tggacaagta 10560
ctacgccggc ctgcccccag agctgaagca gaccagagtg aacctgcccg cccacagcag 10620
atatggccct caggccgtgg acgccagatg ataacgccgg cggcccctat aactctctac 10680
ggctaacctg aatggactac gacatagtct agtccgccaa gatgagcccc aaggacctga 10740
cccccttcct gacaaccctg tggctgctcc tgggccatag cagagtgcct agagtgcggg 10800
ccgaggaatg ctgcgagttc atcaacgtga accacccccc cgagcggtgc tacgacttca 10860
agatgtgcaa ccggttcacc gtggccctga gatgccccga cggcgaagtg tgctacagcc 10920
ccgagaaaac cgccgagatc cggggcatcg tgaccaccat gacccacagc ctgacccggc 10980
aggtggtgca caacaagctg accagctgca actacaaccc cctgtacctg gaagccgacg 11040
gccggatcag atgcggcaaa gtgaacgaca aggcccagta cctgctggga gccgccggaa 11100
gcgtgcccta ccggtggatc aacctggaat acgacaagat cacccggatc gtgggcctgg 11160
accagtacct ggaaagcgtg aagaagcaca agcggctgga cgtgtgcaga gccaagatgg 11220
gctacatgct gcagtgataa ggcgcgccaa cgttactggc cgaagccgct tggaataagg 11280
ccggtgtgcg tttgtctata tgttattttc caccatattg ccgtcttttg gcaatgtgag 11340
ggcccggaaa cctggccctg tcttcttgac gagcattcct aggggtcttt cccctctcgc 11400
caaaggaatg caaggtctgt tgaatgtcgt gaaggaagca gttcctctgg aagcttcttg 11460
aagacaaaca acgtctgtag cgaccctttg caggcagcgg aaccccccac ctggcgacag 11520
gtgcctctgc ggccaaaagc cacgtgtata agatacacct gcaaaggcgg cacaacccca 11580
gtgccacgtt gtgagttgga tagttgtgga aagagtcaaa tggctctcct caagcgtatt 11640
caacaagggg ctgaaggatg cccagaaggt accccattgt atgggatctg atctggggcc 11700
tcggtgcaca tgctttacat gtgtttagtc gaggttaaaa aaacgtctag gccccccgaa 11760
ccacggggac gtggttttcc tttgaaaaac acgataatat gctgcggctg ctgctgagac 11820
accacttcca ctgcctgctg ctgtgtgccg tgtgggccac cccttgtctg gccagccctt 11880
ggagcaccct gaccgccaac cagaacccta gcccccccttg gtccaagctg acctacagca 11940
agccccacga cgccgccacc ttctactgcc cctttctgta ccccagccct cccagaagcc 12000
ccctgcagtt cagcggcttc cagagagtgt ccaccggccc tgagtgccgg aacgagacac 12060
tgtacctgct gtacaaccgg gagggccaga cactggtgga gcggagcagc acctgggtga 12120
aaaaagtgat ctggtatctg agcggccgga accagaccat cctgcagcgg atgcccagaa 12180
ccgccagcaa gcccagcgac ggcaacgtgc agatcagcgt ggaggacgcc aaaatcttcg 12240
gagcccacat ggtgcccaag cagaccaagc tgctgagatt cgtggtcaac gacggcacca 12300
gatatcagat gtgcgtgatg aagctggaaa gctgggccca cgtgttccgg gactactccg 12360
tgagcttcca ggtccggctg accttcaccg aggccaacaa ccagacctac accttctgca 12420
cccaccccaa cctgatcgtg tgataagtac ctttgtacgc ctgttttata ccccctccct 12480
gatttgcaac ttagaagcaa cgcaaaccag atcaatagta ggtgtgacat accagtcgca 12540
tcttgatcaa gcacttctgt atccccggac cgagtatcaa tagactgtgc acacggttga 12600
aggagaaaac gtccgttacc cggctaacta cttcgagaag cctagtaacg ccattgaagt 12660
tgcagagtgt ttcgctcagc actcccccccg tgtagatcag gtcgatgagt caccgcattc 12720
cccacgggcg accgtggcgg tggctgcgtt ggcggcctgc ctatggggta acccatagga 12780
cgctctaata cggacatggc gtgaagagtc tattgagcta gttagtagtc ctccggcccc 12840
tgaatgcggc taatcctaac tgcggagcac ataccottaa tccaaagggc agtgtgtcgt 12900
aacgggcaac tctgcagcgg aaccgactac tttgggtgtc cgtgtttctt tttattcttg 12960
tattggctgc ttatggtgac aattaaagaa ttgttaccat atagctattg gattggccat 13020
ccagtgtcaa acagagctat tgtatatctc tttgttggat tcacacctct cactcttgaa 13080
acgttacaca ccctcaatta cattatactg ctgaacacga agcgcatatg cggctgtgca 13140
gagtgtggct gtccgtgtgc ctgtgtgccg tggtgctggg ccagtgccag agagagacag 13200
ccgagaagaa cgactactac cgggtgcccc actactggga tgcctgcagc agagccctgc 13260
ccgaccagac ccggtacaaa tacgtggagc agctcgtgga cctgaccctg aactaccact 13320
acgacgccag ccacggcctg gacaacttcg acgtgctgaa gcggatcaac gtgaccgagg 13380
tgtccctgct gatcagcgac ttccggcggc agaacagaag aggcggcacc aacaagcgga 13440
ccaccttcaa cgccgctggc tctctggccc ctcacgccag atccctggaa ttcagcgtgc 13500
ggctgttcgc caactgataa cgttgcatcc tgcaggatac agcagcaatt ggcaagctgc 13560
ttacatagaa ctcgcggcga ttggcatgcc gccttaaaat ttttatttta tttttctttt 13620
cttttccgaa tcggattttg tttttaatat ttcaaaaaaa aaaaaaaaaa aaaaaaaaaa 13680
aaaaaaaagg gtcggcatgg catctccacc tcctcgcggt ccgacctggg catccgaagg 13740
aggacgcacg tccactcgga tggctaaggg agagccacgt ttaaacgcta gagcaagacg 13800
tttcccgttg aatatggctc ataacacccc ttgtattact gtttatgtaa gcagacagtt 13860
ttattgttca tgatgatata tttttatctt gtgcaatgta acatcagaga ttttgagaca 13920
caacgtggct ttgttgaata aatcgaactt ttgctgagtt gaaggatcag atcacgcatc 13980
ttcccgacaa cgcagaccgt tccgtggcaa agcaaaagtt caaaatcacc aactggtcca 14040
cctacaacaa agctctcatc aaccgtggct ccctcacttt ctggctggat gatggggcga 14100
ttcaggcctg gtatgagtca gcaacacctt cttcacgagg cagacctcag cgctagcgga 14160
gtgtatactg gcttactatg ttggcactga tgagggtgtc agtgaagtgc ttcatgtggc 14220
aggagaaaaa aggctgcacc ggtgcgtcag cagaatatgt gatacaggat atattccgct 14280
tcctcgctca ctgactcgct acgctcggtc gttcgactgc ggcgagcgga aatggcttac 14340
gaacggggcg gagatttcct ggaagatgcc aggaagatac ttaacaggga agtgagaggg 14400
ccgcggcaaa gccgtttttc cataggctcc gcccccctga caagcatcac gaaatctgac 14460
gctcaaatca gtggtggcga aacccgacag gactataaag ataccaggcg tttcccctgg 14520
cggctccctc gtgcgctctc ctgttcctgc ctttcggttt accggtgtca ttccgctgtt 14580
atggccgcgt ttgtctcatt ccacgcctga cactcagttc cgggtaggca gttcgctcca 14640
agctggactg tatgcacgaa ccccccgttc agtccgaccg ctgcgcctta tccggtaact 14700
atcgtcttga gtccaacccg gaaagacatg caaaagcacc actggcagca gccactggta 14760
attgatttag aggagttagt cttgaagtca tgcgccggtt aaggctaaac tgaaaggaca 14820
agttttggtg actgcgctcc tccaagccag ttacctcggt tcaaagagtt ggtagctcag 14880
agaaccttcg aaaaaccgcc ctgcaaggcg gttttttcgt tttcagagca agagattacg 14940
cgcagaccaa aacgatctca agaagatcat cttattaagg ggtctgacgc tcagtggaac 15000
gaaaactcac gttaagggat tttggtcatg agattatcaa aaaggatctt cacctagatc 15060
cttttaaatt aaaaatgaag ttttaaatca atctaaagta tatatgagta aacttggtct 15120
gacagttatt agaaaaattc atccagcaga cgataaaacg caatacgctg gctatccggt 15180
gccgcaatgc catacagcac cagaaaacga tccgcccatt cgccgcccag ttcttccgca 15240
atatcacggg tggccagcgc aatatcctga taacgatccg ccacgcccag acggccgcaa 15300
tcaataaagc cgctaaaacg gccattttcc accataatgt tcggcaggca cgcatcacca 15360
tgggtcacca ccagatcttc gccatccggc atgctcgctt tcagacgcgc aaacagctct 15420
gccggtgcca ggccctgatg ttcttcatcc agatcatcct gatccaccag gcccgcttcc 15480
atacgggtac gcgcacgttc aatacgatgt ttcgcctgat gatcaaacgg acaggtcgcc 15540
gggtccaggg tatgcagacg acgcatggca tccgccataa tgctcacttt ttctgccggc 15600
gccagatggc tagacagcag atcctgaccc ggcacttcgc ccagcagcag ccaatcacgg 15660
cccgcttcgg tcaccacatc cagcaccgcc gcacacggaa caccggtggt ggccagccag 15720
ctcagacgcg ccgcttcatc ctgcagctcg ttcagcgcac cgctcagatc ggttttcaca 15780
aacagcaccg gacgaccctg cgcgctcaga cgaaacaccg ccgcatcaga gcagccaatg 15840
gtctgctgcg cccaatcata gccaaacaga cgttccaccc acgctgccgg gctacccgca 15900

```
tgcaggccat cctgttcaat catactcttc ctttttcaat attattgaag catttatcag  15960

ggttattgtc tcatgagcgg atacatattt gaatgtattt agaaaaataa acaaataggg  16020

gttccgcgca catttccccg aaaagtgcca cctaaattgt aagcgttaat attttgttaa  16080

aattcgcgtt aaatttttgt taaatcagct cattttttaa ccaataggcc gaaatcggca  16140

aaatccctta taaatcaaaa gaatagaccg agatagggtt gagtggccgc tacagggcgc  16200

tcccattcgc cattcaggct gcgcaactgt tgggaagggc gtttcggtgc gggcctcttc  16260

gctattacgc cagctggcga aagggggatg tgctgcaagg cgattaagtt gggtaacgcc  16320

agggttttcc cagtcacacg cgtaatacga ctcactatag                        16360
```

<210> SEQ ID NO 68
<211> LENGTH: 868
<212> TYPE: PRT
<213> ORGANISM: Varicella zoster virus

<400> SEQUENCE: 68

```
Met Phe Val Thr Ala Val Val Ser Val Ser Pro Ser Ser Phe Tyr Glu
1               5                   10                  15

Ser Leu Gln Val Glu Pro Thr Gln Ser Glu Asp Ile Thr Arg Ser Ala
            20                  25                  30

His Leu Gly Asp Gly Asp Glu Ile Arg Glu Ala Ile His Lys Ser Gln
        35                  40                  45

Asp Ala Glu Thr Lys Pro Thr Phe Tyr Val Cys Pro Pro Pro Thr Gly
    50                  55                  60

Ser Thr Ile Val Arg Leu Glu Pro Pro Arg Thr Cys Pro Asp Tyr His
65                  70                  75                  80

Leu Gly Lys Asn Phe Thr Glu Gly Ile Ala Val Val Tyr Lys Glu Asn
                85                  90                  95

Ile Ala Ala Tyr Lys Phe Lys Ala Thr Val Tyr Tyr Lys Asp Val Ile
            100                 105                 110

Val Ser Thr Ala Trp Ala Gly Ser Ser Tyr Thr Gln Ile Thr Asn Arg
        115                 120                 125

Tyr Ala Asp Arg Val Pro Ile Pro Val Ser Glu Ile Thr Asp Thr Ile
    130                 135                 140

Asp Lys Phe Gly Lys Cys Ser Ser Lys Ala Thr Tyr Val Arg Asn Asn
145                 150                 155                 160

His Lys Val Glu Ala Phe Asn Glu Asp Lys Asn Pro Gln Asp Met Pro
                165                 170                 175

Leu Ile Ala Ser Lys Tyr Asn Ser Val Gly Ser Lys Ala Trp His Thr
            180                 185                 190

Thr Asn Asp Thr Tyr Met Val Ala Gly Thr Pro Gly Thr Tyr Arg Thr
        195                 200                 205

Gly Thr Ser Val Asn Cys Ile Ile Glu Glu Val Glu Ala Arg Ser Ile
    210                 215                 220

Phe Pro Tyr Asp Ser Phe Gly Leu Ser Thr Gly Asp Ile Ile Tyr Met
225                 230                 235                 240

Ser Pro Phe Phe Gly Leu Arg Asp Gly Ala Tyr Arg Glu His Ser Asn
                245                 250                 255

Tyr Ala Met Asp Arg Phe His Gln Phe Glu Gly Tyr Arg Gln Arg Asp
            260                 265                 270

Leu Asp Thr Arg Ala Leu Leu Glu Pro Ala Ala Arg Asn Phe Leu Val
        275                 280                 285

Thr Pro His Leu Thr Val Gly Trp Asn Trp Lys Pro Lys Arg Thr Glu
```

```
    290                 295                 300

Val Cys Ser Leu Val Lys Trp Arg Glu Val Glu Asp Val Val Arg Asp
305                 310                 315                 320

Glu Tyr Ala His Asn Phe Arg Phe Thr Met Lys Thr Leu Ser Thr Thr
                325                 330                 335

Phe Ile Ser Glu Thr Asn Glu Phe Asn Leu Asn Gln Ile His Leu Ser
            340                 345                 350

Gln Cys Val Lys Glu Glu Ala Arg Ala Ile Ile Asn Arg Ile Tyr Thr
        355                 360                 365

Thr Arg Tyr Asn Ser Ser His Val Arg Thr Gly Asp Ile Gln Thr Tyr
    370                 375                 380

Leu Ala Arg Gly Gly Phe Val Val Val Phe Gln Pro Leu Leu Ser Asn
385                 390                 395                 400

Ser Leu Ala Arg Leu Tyr Leu Gln Glu Leu Val Arg Glu Asn Thr Asn
                405                 410                 415

His Ser Pro Gln Lys His Pro Thr Arg Asn Thr Arg Ser Arg Arg Ser
            420                 425                 430

Val Pro Val Glu Leu Arg Ala Asn Arg Thr Ile Thr Thr Thr Ser Ser
        435                 440                 445

Val Glu Phe Ala Met Leu Gln Phe Thr Tyr Asp His Ile Gln Glu His
    450                 455                 460

Val Asn Glu Met Leu Ala Arg Ile Ser Ser Ser Trp Cys Gln Leu Gln
465                 470                 475                 480

Asn Arg Glu Arg Ala Leu Trp Ser Gly Leu Phe Pro Ile Asn Pro Ser
                485                 490                 495

Ala Leu Ala Ser Thr Ile Leu Asp Gln Arg Val Lys Ala Arg Ile Leu
            500                 505                 510

Gly Asp Val Ile Ser Val Ser Asn Cys Pro Glu Leu Gly Ser Asp Thr
        515                 520                 525

Arg Ile Ile Leu Gln Asn Ser Met Arg Val Ser Gly Ser Thr Thr Arg
    530                 535                 540

Cys Tyr Ser Arg Pro Leu Ile Ser Ile Val Ser Leu Asn Gly Ser Gly
545                 550                 555                 560

Thr Val Glu Gly Gln Leu Gly Thr Asp Asn Glu Leu Ile Met Ser Arg
                565                 570                 575

Asp Leu Leu Glu Pro Cys Val Ala Asn His Lys Arg Tyr Phe Leu Phe
            580                 585                 590

Gly His His Tyr Val Tyr Tyr Glu Asp Tyr Arg Tyr Val Arg Glu Ile
        595                 600                 605

Ala Val His Asp Val Gly Met Ile Ser Thr Tyr Val Asp Leu Asn Leu
    610                 615                 620

Thr Leu Leu Lys Asp Arg Glu Phe Met Pro Leu Gln Val Tyr Thr Arg
625                 630                 635                 640

Asp Glu Leu Arg Asp Thr Gly Leu Leu Asp Tyr Ser Glu Ile Gln Arg
                645                 650                 655

Arg Asn Gln Met His Ser Leu Arg Phe Tyr Asp Ile Asp Lys Val Val
            660                 665                 670

Gln Tyr Asp Ser Gly Thr Ala Ile Met Gln Gly Met Ala Gln Phe Phe
        675                 680                 685

Gln Gly Leu Gly Thr Ala Gly Gln Ala Val Gly His Val Val Leu Gly
    690                 695                 700

Ala Thr Gly Ala Leu Leu Ser Thr Val His Gly Phe Thr Thr Phe Leu
705                 710                 715                 720
```

```
Ser Asn Pro Phe Gly Ala Leu Ala Val Gly Leu Leu Val Leu Ala Gly
                725                 730                 735

Leu Val Ala Ala Phe Phe Ala Tyr Arg Tyr Val Leu Lys Leu Lys Thr
            740                 745                 750

Ser Pro Met Lys Ala Leu Tyr Pro Leu Thr Thr Lys Gly Leu Lys Gln
        755                 760                 765

Leu Pro Glu Gly Met Asp Pro Phe Ala Glu Lys Pro Asn Ala Thr Asp
    770                 775                 780

Thr Pro Ile Glu Glu Ile Gly Asp Ser Gln Asn Thr Glu Pro Ser Val
785                 790                 795                 800

Asn Ser Gly Phe Asp Pro Asp Lys Phe Arg Glu Ala Gln Glu Met Ile
                805                 810                 815

Lys Tyr Met Thr Leu Val Ser Ala Ala Glu Arg Gln Glu Ser Lys Ala
            820                 825                 830

Arg Lys Lys Asn Lys Thr Ser Ala Leu Leu Thr Ser Arg Leu Thr Gly
        835                 840                 845

Leu Ala Leu Arg Asn Arg Arg Gly Tyr Ser Arg Val Arg Thr Glu Asn
    850                 855                 860

Val Thr Gly Val
865


<210> SEQ ID NO 69
<211> LENGTH: 841
<212> TYPE: PRT
<213> ORGANISM: Varicella zoster virus

<400> SEQUENCE: 69

Met Phe Ala Leu Val Leu Ala Val Val Ile Leu Pro Leu Trp Thr Thr
1               5                   10                  15

Ala Asn Lys Ser Tyr Val Thr Pro Thr Pro Ala Thr Arg Ser Ile Gly
            20                  25                  30

His Met Ser Ala Leu Leu Arg Glu Tyr Ser Asp Arg Asn Met Ser Leu
        35                  40                  45

Lys Leu Glu Ala Phe Tyr Pro Thr Gly Phe Asp Glu Glu Leu Ile Lys
    50                  55                  60

Ser Leu His Trp Gly Asn Asp Arg Lys His Val Phe Leu Val Ile Val
65                  70                  75                  80

Lys Val Asn Pro Thr Thr His Glu Gly Asp Val Gly Leu Val Ile Phe
                85                  90                  95

Pro Lys Tyr Leu Leu Ser Pro Tyr His Phe Lys Ala Glu His Arg Ala
            100                 105                 110

Pro Phe Pro Ala Gly Arg Phe Gly Phe Leu Ser His Pro Val Thr Pro
        115                 120                 125

Asp Val Ser Phe Phe Asp Ser Ser Phe Ala Pro Tyr Leu Thr Thr Gln
    130                 135                 140

His Leu Val Ala Phe Thr Thr Phe Pro Pro Asn Pro Leu Val Trp His
145                 150                 155                 160

Leu Glu Arg Ala Glu Thr Ala Ala Thr Ala Glu Arg Pro Phe Gly Val
                165                 170                 175

Ser Leu Leu Pro Ala Arg Pro Thr Val Pro Lys Asn Thr Ile Leu Glu
            180                 185                 190

His Lys Ala His Phe Ala Thr Trp Asp Ala Leu Ala Arg His Thr Phe
        195                 200                 205

Phe Ser Ala Glu Ala Ile Ile Thr Asn Ser Thr Leu Arg Ile His Val
```

-continued

```
    210                 215                 220

Pro Leu Phe Gly Ser Val Trp Pro Ile Arg Tyr Trp Ala Thr Gly Ser
225                 230                 235                 240

Val Leu Leu Thr Ser Asp Ser Gly Arg Val Glu Val Asn Ile Gly Val
                245                 250                 255

Gly Phe Met Ser Ser Leu Ile Ser Leu Ser Ser Gly Leu Pro Ile Glu
            260                 265                 270

Leu Ile Val Val Pro His Thr Val Lys Leu Asn Ala Val Thr Ser Asp
        275                 280                 285

Thr Thr Trp Phe Gln Leu Asn Pro Pro Gly Pro Asp Pro Gly Pro Ser
    290                 295                 300

Tyr Arg Val Tyr Leu Leu Gly Arg Gly Leu Asp Met Asn Phe Ser Lys
305                 310                 315                 320

His Ala Thr Val Asp Ile Cys Ala Tyr Pro Glu Glu Ser Leu Asp Tyr
                325                 330                 335

Arg Tyr His Leu Ser Met Ala His Thr Glu Ala Leu Arg Met Thr Thr
            340                 345                 350

Lys Ala Asp Gln His Asp Ile Asn Glu Glu Ser Tyr Tyr His Ile Ala
        355                 360                 365

Ala Arg Ile Ala Thr Ser Ile Phe Ala Leu Ser Glu Met Gly Arg Thr
    370                 375                 380

Thr Glu Tyr Phe Leu Leu Asp Glu Ile Val Asp Val Gln Tyr Gln Leu
385                 390                 395                 400

Lys Phe Leu Asn Tyr Ile Leu Met Arg Ile Gly Ala Gly Ala His Pro
                405                 410                 415

Asn Thr Ile Ser Gly Thr Ser Asp Leu Ile Phe Ala Asp Pro Ser Gln
            420                 425                 430

Leu His Asp Glu Leu Ser Leu Leu Phe Gly Gln Val Lys Pro Ala Asn
        435                 440                 445

Val Asp Tyr Phe Ile Ser Tyr Asp Glu Ala Arg Asp Gln Leu Lys Thr
    450                 455                 460

Ala Tyr Ala Leu Ser Arg Gly Gln Asp His Val Asn Ala Leu Ser Leu
465                 470                 475                 480

Ala Arg Arg Val Ile Met Ser Ile Tyr Lys Gly Leu Leu Val Lys Gln
                485                 490                 495

Asn Leu Asn Ala Thr Glu Arg Gln Ala Leu Phe Phe Ala Ser Met Ile
            500                 505                 510

Leu Leu Asn Phe Arg Glu Gly Leu Glu Asn Ser Ser Arg Val Leu Asp
        515                 520                 525

Gly Arg Thr Thr Leu Leu Leu Met Thr Ser Met Cys Thr Ala Ala His
    530                 535                 540

Ala Thr Gln Ala Ala Leu Asn Ile Gln Glu Gly Leu Ala Tyr Leu Asn
545                 550                 555                 560

Pro Ser Lys His Met Phe Thr Ile Pro Asn Val Tyr Ser Pro Cys Met
                565                 570                 575

Gly Ser Leu Arg Thr Asp Leu Thr Glu Glu Ile His Val Met Asn Leu
            580                 585                 590

Leu Ser Ala Ile Pro Thr Arg Pro Gly Leu Asn Glu Val Leu His Thr
        595                 600                 605

Gln Leu Asp Glu Ser Glu Ile Phe Asp Ala Ala Phe Lys Thr Met Met
    610                 615                 620

Ile Phe Thr Thr Trp Thr Ala Lys Asp Leu His Ile Leu His Thr His
625                 630                 635                 640
```

Val Pro Glu Val Phe Thr Cys Gln Asp Ala Ala Ala Arg Asn Gly Glu
645 650 655

Tyr Val Leu Ile Leu Pro Ala Val Gln Gly His Ser Tyr Val Ile Thr
660 665 670

Arg Asn Lys Pro Gln Arg Gly Leu Val Tyr Ser Leu Ala Asp Val Asp
675 680 685

Val Tyr Asn Pro Ile Ser Val Val Tyr Leu Ser Lys Asp Thr Cys Val
690 695 700

Ser Glu His Gly Val Ile Glu Thr Val Ala Leu Pro His Pro Asp Asn
705 710 715 720

Leu Lys Glu Cys Leu Tyr Cys Gly Ser Val Phe Leu Arg Tyr Leu Thr
725 730 735

Thr Gly Ala Ile Met Asp Ile Ile Ile Ile Asp Ser Lys Asp Thr Glu
740 745 750

Arg Gln Leu Ala Ala Met Gly Asn Ser Thr Ile Pro Pro Phe Asn Pro
755 760 765

Asp Met His Gly Asp Asp Ser Lys Ala Val Leu Leu Phe Pro Asn Gly
770 775 780

Thr Val Val Thr Leu Leu Gly Phe Glu Arg Arg Gln Ala Ile Arg Met
785 790 795 800

Ser Gly Gln Tyr Leu Gly Ala Ser Leu Gly Gly Ala Phe Leu Ala Val
805 810 815

Val Gly Phe Gly Ile Ile Gly Trp Met Leu Cys Gly Asn Ser Arg Leu
820 825 830

Arg Glu Tyr Asn Lys Ile Pro Leu Thr
835 840

<210> SEQ ID NO 70
<211> LENGTH: 160
<212> TYPE: PRT
<213> ORGANISM: Varicella zoster virus

<400> SEQUENCE: 70

Met Ala Ser His Lys Trp Leu Leu Gln Met Ile Val Phe Leu Lys Thr
1 5 10 15

Ile Thr Ile Ala Tyr Cys Leu His Leu Gln Asp Asp Thr Pro Leu Phe
20 25 30

Phe Gly Ala Lys Pro Leu Ser Asp Val Ser Leu Ile Ile Thr Glu Pro
35 40 45

Cys Val Ser Ser Val Tyr Glu Ala Trp Asp Tyr Ala Ala Pro Pro Val
50 55 60

Ser Asn Leu Ser Glu Ala Leu Ser Gly Ile Val Val Lys Thr Lys Cys
65 70 75 80

Pro Val Pro Glu Val Ile Leu Trp Phe Lys Asp Lys Gln Met Ala Tyr
85 90 95

Trp Thr Asn Pro Tyr Val Thr Leu Lys Gly Leu Thr Gln Ser Val Gly
100 105 110

Glu Glu His Lys Ser Gly Asp Ile Arg Asp Ala Leu Leu Asp Ala Leu
115 120 125

Ser Gly Val Trp Val Asp Ser Thr Pro Ser Ser Thr Asn Ile Pro Glu
130 135 140

Asn Gly Cys Val Trp Gly Ala Asp Arg Leu Phe Gln Arg Val Cys Gln
145 150 155 160

```
<210> SEQ ID NO 71
<211> LENGTH: 354
<212> TYPE: PRT
<213> ORGANISM: Varicella zoster virus

<400> SEQUENCE: 71

Met Phe Leu Ile Gln Cys Leu Ile Ser Ala Val Ile Phe Tyr Ile Gln
1               5                   10                  15

Val Thr Asn Ala Leu Ile Phe Lys Gly Asp His Val Ser Leu Gln Val
            20                  25                  30

Asn Ser Ser Leu Thr Ser Ile Leu Ile Pro Met Gln Asn Asp Asn Tyr
        35                  40                  45

Thr Glu Ile Lys Gly Gln Leu Val Phe Ile Gly Glu Gln Leu Pro Thr
    50                  55                  60

Gly Thr Asn Tyr Ser Gly Thr Leu Glu Leu Leu Tyr Ala Asp Thr Val
65                  70                  75                  80

Ala Phe Cys Phe Arg Ser Val Gln Val Ile Arg Tyr Asp Gly Cys Pro
                85                  90                  95

Arg Ile Arg Thr Ser Ala Phe Ile Ser Cys Arg Tyr Lys His Ser Trp
            100                 105                 110

His Tyr Gly Asn Ser Thr Asp Arg Ile Ser Thr Glu Pro Asp Ala Gly
        115                 120                 125

Val Met Leu Lys Ile Thr Lys Pro Gly Ile Asn Asp Ala Gly Val Tyr
    130                 135                 140

Val Leu Leu Val Arg Leu Asp His Ser Arg Ser Thr Asp Gly Phe Ile
145                 150                 155                 160

Leu Gly Val Asn Val Tyr Thr Ala Gly Ser His His Asn Ile His Gly
                165                 170                 175

Val Ile Tyr Thr Ser Pro Ser Leu Gln Asn Gly Tyr Ser Thr Arg Ala
            180                 185                 190

Leu Phe Gln Gln Ala Arg Leu Cys Asp Leu Pro Ala Thr Pro Lys Gly
        195                 200                 205

Ser Gly Thr Ser Leu Phe Gln His Met Leu Asp Leu Arg Ala Gly Lys
    210                 215                 220

Ser Leu Glu Asp Asn Pro Trp Leu His Glu Asp Val Val Thr Thr Glu
225                 230                 235                 240

Thr Lys Ser Val Val Lys Glu Gly Ile Glu Asn His Val Tyr Pro Thr
                245                 250                 255

Asp Met Ser Thr Leu Pro Glu Lys Ser Leu Asn Asp Pro Pro Glu Asn
            260                 265                 270

Leu Leu Ile Ile Ile Pro Ile Val Ala Ser Val Met Ile Leu Thr Ala
        275                 280                 285

Met Val Ile Val Ile Val Ile Ser Val Lys Arg Arg Arg Ile Lys Lys
    290                 295                 300

His Pro Ile Tyr Arg Pro Asn Thr Lys Thr Arg Arg Gly Ile Gln Asn
305                 310                 315                 320

Ala Thr Pro Glu Ser Asp Val Met Leu Glu Ala Ala Ile Ala Gln Leu
                325                 330                 335

Ala Thr Ile Arg Glu Glu Ser Pro Pro His Ser Val Val Asn Pro Phe
            340                 345                 350

Val Lys


<210> SEQ ID NO 72
<211> LENGTH: 623
<212> TYPE: PRT
```

<213> ORGANISM: Varicella zoster virus

<400> SEQUENCE: 72

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400
```

```
Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Glu Phe Gly Asn Ala Ile Gly Gly
        595                 600                 605

Ser His Gly Gly Ser Ser Tyr Thr Val Tyr Ile Asp Lys Thr Arg
    610                 615                 620
```

<210> SEQ ID NO 73
<211> LENGTH: 13339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 73

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780
```

-continued

```
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
```

tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtcgagtct 7560
agtcgacgcc accatgttcg tgaccgccgt ggtgtccgtg tcccccagca gcttttacga 7620
gagcctgcag gtcgagccca cccagagcga ggacatcaca agatctgccc acctgggcga 7680
cggcgacgag atcagagagg ccatccacaa gagccaggac gccgagacaa agcccacctt 7740
ctacgtgtgc cccccaccta ccggctctac aattgtgcgg ctggaacccc ccagaacctg 7800
ccctgattac cacctgggca agaacttcac cgagggaatt gccgtggtgt acaaagagaa 7860

-continued

```
tatcgccgcc tacaagttca aggccaccgt gtactacaag gacgtgatcg tgtccaccgc   7920
ctgggccggc agcagctaca cccagatcac caacagatac gccgaccggg tgcccatccc   7980
cgtgtctgag atcaccgaca ccatcgacaa gttcggcaag tgcagcagca aggccaccta   8040
cgtgcggaac aaccacaagg tggaagcctt caacgaggac aagaaccccc aggacatgcc   8100
cctgatcgcc agcaagtaca acagcgtggg ctccaaggcc tggcacacca ccaacgacac   8160
ctacatggtg gccggcaccc ccggcacata cagaacaggc accagcgtga actgcatcat   8220
cgaggaagtg gaagcccggt ccatcttccc atacgacagc ttcggcctga gcaccggcga   8280
cattatctac atgagccctt tcttcggcct gcgggacggc gcctacagag agcacagcaa   8340
ctacgccatg gaccggttcc accagttcga gggctacaga cagcgggacc tggacacaag   8400
agccctgctg gaacctgccg ccagaaactt cctggtcacc cctcacctga ccgtgggctg   8460
gaactggaag cccaagcgga ccgaagtgtg cagcctggtc aagtggcgcg aggtggaaga   8520
tgtcgtgcgg gatgagtacg cccacaactt ccggttcacc atgaagaccc tgagcaccac   8580
cttcatcagc gagacaaacg agttcaacct gaaccagatc cacctgagcc agtgcgtgaa   8640
agaggaagcc agagccatca tcaaccggat ctacaccacc cggtacaaca gcagccacgt   8700
gcggaccggc gatatccaga cctatctggc tagaggcggc ttcgtggtgg tgtttcagcc   8760
cctgctgagc aacagcctgg ctagactgta cctgcaggaa ctcgtcagag agaacaccaa   8820
ccacagcccc cagaagcacc ccacccggaa taccagatcc agacgcagcg tgcccgtgga   8880
actgagagcc aaccggacca tcaccaccac cagcagcgtg gaattcgcca tgctgcagtt   8940
cacctacgac cacatccagg aacacgtgaa cgagatgctg gcccggatca gcagcagttg   9000
gtgccagctg cagaatcggg aaagggccct gtggtccggc ctgttcccca tcaatccaag   9060
cgccctggcc agcaccatcc tggaccagag agtgaaggcc agaatcctgg gggacgtgat   9120
cagcgtgtcc aactgtcctg agctgggcag cgacacccgg atcatcctgc agaacagcat   9180
gcgggtgtcc ggcagcacca ccagatgcta cagcagaccc ctgatcagca tcgtgtccct   9240
gaacggcagc ggcacagtgg aaggccagct gggcaccgat aacgagctga tcatgagccg   9300
ggacctgctc gaaccctgcg tggccaatca caagcggtac tttctgttcg gccaccacta   9360
cgtgtactat gaggactaca gatacgtgcg cgagatcgcc gtgcacgacg tgggcatgat   9420
cagcacctac gtggacctga acctgaccct gctgaaggac cgcgagttca tgccactgca   9480
ggtctacacc cgggacgagc tgagagatac cggcctgctg gactacagcg agatccagcg   9540
gcggaaccag atgcactccc tgcggttcta cgacatcgac aaggtggtgc agtacgacag   9600
cggcaccgcc atcatgcagg gcatggccca gttctttcag ggcctgggaa cagccggaca   9660
ggccgtggga catgtggtgc tgggagctac aggcgccctg ctgtctaccg tgcacggctt   9720
caccaccttt ctgagcaacc ccttcggagc cctggctgtg ggactgctgg tcctggctgg   9780
actggtggcc gccttctttg cctaccgcta cgtgctgaag ctgaaaacca gccccatgaa   9840
ggccctgtac cccctgacca ccaagggcct gaagcagctg cctgagggca tggacccctt   9900
cgccgagaag cccaatgcca ccgacacccc catcgaggaa atcggcgaca gccagaacac   9960
cgagccctcc gtgaacagcg gcttcgaccc cgacaagttt cgcgaggccc aggaaatgat  10020
caagtacatg accctggtgt ctgctgccga gcggcaggaa agcaaggccc ggaagaagaa  10080
caagacctcc gccctgctga ccagcagact gacaggactg gccctgcgga acagacgggg  10140
ctatagcaga gtgcggaccg agaatgtgac cggcgtgtaa tctagacgcg gccgcataca  10200
gcagcaattg gcaagctgct tacatagaac tcgcggcgat tggcatgccg ccttaaaatt  10260
```

```
tttattttat ttttcttttc ttttccgaat cggattttgt ttttaatatt tcaaaaaaaa  10320
aaaaaaaaaa aaaaaaaaaa aaaaaaaggg tcggcatggc atctccacct cctcgcggtc  10380
cgacctgggc atccgaagga ggacgcacgt ccactcggat ggctaaggga gagccacgtt  10440
taaaccagct ccaattcgcc ctatagtgag tcgtattacg cgcgctcact ggccgtcgtt  10500
ttacaacgtc gtgactggga aaaccctggc gttacccaac ttaatcgcct tgcagcacat  10560
ccccctttcg ccagctggcg taatagcgaa gaggcccgca ccgatcgccc ttcccaacag  10620
ttgcgcagcc tgaatggcga atgggacgcg ccctgtagcg gcgcattaag cgcggcgggt  10680
gtggtggtta cgcgcagcgt gaccgctaca cttgccagcg ccctagcgcc cgctcctttc  10740
gctttcttcc cttcctttct cgccacgttc gccggctttc cccgtcaagc tctaaatcgg  10800
gggctccctt tagggttccg atttagtgct ttacggcacc tcgaccccaa aaaacttgat  10860
tagggtgatg gttcacgtag tgggccatcg ccctgataga cggtttttcg ccctttgacg  10920
ttggagtcca cgttctttaa tagtggactc ttgttccaaa ctggaacaac actcaaccct  10980
atctcggtct attcttttga tttataaggg attttgccga tttcggccta ttggttaaaa  11040
aatgagctga tttaacaaaa atttaacgcg aattttaaca aaatattaac gcttacaatt  11100
taggtggcac ttttcgggga aatgtgcgcg gaacccctat ttgtttattt ttctaaatac  11160
attcaaatat gtatccgctc atgagacaat aaccctgata aatgcttcaa taatattgaa  11220
aaaggaagag tatgagtatt caacatttcc gtgtcgccct tattcccttt tttgcggcat  11280
tttgccttcc tgtttttgct cacccagaaa cgctggtgaa agtaaaagat gctgaagatc  11340
agttgggtgc acgagtgggt tacatcgaac tggatctcaa cagcggtaag atccttgaga  11400
gttttcgccc cgaagaacgt tttccaatga tgagcacttt taaagttctg ctatgtggcg  11460
cggtattatc ccgtattgac gccgggcaag agcaactcgg tcgccgcata cactattctc  11520
agaatgactt ggttgagtac tcaccagtca cagaaaagca tcttacggat ggcatgacag  11580
taagagaatt atgcagtgct gccataacca tgagtgataa cactgcggcc aacttacttc  11640
tgacaacgat cggaggaccg aaggagctaa ccgctttttt gcacaacatg ggggatcatg  11700
taactcgcct tgatcgttgg gaaccggagc tgaatgaagc cataccaaac gacgagcgtg  11760
acaccacgat gcctgtagca atggcaacaa cgttgcgcaa actattaact ggcgaactac  11820
ttactctagc ttcccggcaa caattaatag actggatgga ggcggataaa gttgcaggac  11880
cacttctgcg ctcggccctt ccggctggct ggtttattgc tgataaatct ggagccggtg  11940
agcgtgggtc tcgcggtatc attgcagcac tggggccaga tggtaagccc tcccgtatcg  12000
tagttatcta cacgacgggg agtcaggcaa ctatggatga acgaaataga cagatcgctg  12060
agataggtgc ctcactgatt aagcattggt aactgtcaga ccaagtttac tcatatatac  12120
tttagattga tttaaaactt catttttaat ttaaaaggat ctaggtgaag atcctttttg  12180
ataatctcat gaccaaaatc ccttaacgtg agttttcgtt ccactgagcg tcagaccccg  12240
tagaaaagat caaaggatct tcttgagatc cttttttttct gcgcgtaatc tgctgcttgc  12300
aaacaaaaaa accaccgcta ccagcggtgg tttgtttgcc ggatcaagag ctaccaactc  12360
tttttccgaa ggtaactggc ttcagcagag cgcagatacc aaatactgtt cttctagtgt  12420
agccgtagtt aggccaccac ttcaagaact ctgtagcacc gcctacatac ctcgctctgc  12480
taatcctgtt accagtggct gctgccagtg gcgataagtc gtgtcttacc gggttggact  12540
caagacgata gttaccggat aaggcgcagc ggtcgggctg aacggggggt tcgtgcacac  12600
```

-continued

```
agcccagctt ggagcgaacg acctacaccg aactgagata cctacagcgt gagctatgag  12660

aaagcgccac gcttcccgaa gggagaaagg cggacaggta tccggtaagc ggcagggtcg  12720

gaacaggaga gcgcacgagg gagcttccag ggggaaacgc ctggtatctt tatagtcctg  12780

tcgggtttcg ccacctctga cttgagcgtc gatttttgtg atgctcgtca ggggggcgga  12840

gcctatggaa aaacgccagc aacgcggcct ttttacggtt cctggccttt tgctggcctt  12900

ttgctcacat gttctttcct gcgttatccc ctgattctgt ggataaccgt attaccgcct  12960

ttgagtgagc tgataccgct cgccgcagcc gaacgaccga gcgcagcgag tcagtgagcg  13020

aggaagcgga agagcgccca atacgcaaac cgcctctccc cgcgcgttgg ccgattcatt  13080

aatgcagctg gcacgacagg tttcccgact ggaaagcggg cagtgagcgc aacgcaatta  13140

atgtgagtta gctcactcat taggcacccc aggctttaca ctttatgctc ccggctcgta  13200

tgttgtgtgg aattgtgagc ggataacaat ttcacacagg aaacagctat gaccatgatt  13260

acgccaagcg cgcaattaac cctcactaaa gggaacaaaa gctgggtacc gggcccacgc  13320

gtaatacgac tcactatag                                               13339
```

<210> SEQ ID NO 74
<211> LENGTH: 13258
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 74

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260
```

-continued

```
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
```

-continued

```
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agtttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
```

-continued

```
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgagtct   7560
agtcgacgcc accatgttcg ccctggtgct ggccgtggtc atcctgcctc tgtggaccac   7620
cgccaacaag agctacgtga cccccacacc cgccaccaga tccatcggac acatgagcgc   7680
cctgctgaga gagtacagcg accggaacat gagcctgaag ctggaagcct tctaccccac   7740
cggcttcgac gaggaactga tcaagagcct gcactggggc aacgaccgga agcacgtgtt   7800
cctcgtgatc gtgaaagtga accccaccac ccacgagggc gacgtcggcc tggtcatctt   7860
ccccaagtac ctgctgagcc cctaccactt caaggccgag cacagagccc ccttccctgc   7920
tggccgcttt ggctttctga gccaccctgt gacccccgac gtgtcattct tcgacagcag   7980
cttcgccccc tacctgacca cacagcacct ggtggccttc accaccttcc cccccaatcc   8040
tctcgtgtgg cacctggaaa gagccgagac agccgccacc gccgaaagac cttttggcgt   8100
gtccctgctg cccgccagac ctaccgtgcc caagaacacc atcctggaac acaaggccca   8160
cttcgccacc tgggatgccc tggccagaca caccttcttt agcgccgagg ccatcatcac   8220
caacagcacc ctgagaatcc acgtgcccct gttcggcagc gtgtggccca tcagatactg   8280
ggccacaggc agcgtgctgc tgaccagcga tagcggcaga gtggaagtga acatcggcgt   8340
```

-continued gggcttcatg agcagcctga tcagcctgag cagcggcctg cccatcgagc tgattgtggt 8400
gccccacacc gtgaagctga acgccgtgac cagcgacacc acctggttcc agctgaaccc 8460
ccctggccct gatcctggcc ctagttacag agtgtacctg ctgggcagag gcctggacat 8520
gaacttcagc aagcacgcca ccgtggacat ctgcgcctac cctgaggaaa gcctggacta 8580
cagataccac ctgagcatgg cccacaccga ggccctgaga atgaccacca aggccgacca 8640
gcacgacatc aacgaggaaa gctactacca cattgccgcc agaatcgcca ccagcatctt 8700
cgccctgagc gagatgggcc ggaccaccga gtactttctg ctggacgaga tcgtggacgt 8760
gcagtaccag ctgaagttcc tgaactacat cctgatgcgg atcggcgctg gcgcccaccc 8820
taataccatc agcggcacca gcgacctgat cttcgccgat cctagccagc tgcacgacga 8880
gctgagcctg ctgttcggcc aggtcaaacc cgccaacgtg gactacttca tcagctacga 8940
cgaggcccgg gaccagctga aaacagccta cgccctgtcc agaggccagg atcatgtgaa 9000
cgccctgtcc ctggccaggc gcgtgatcat gagcatctac aagggcctgc tggtcaagca 9060
gaacctgaac gccaccgagc ggcaggccct gttcttcgcc agcatgatcc tgctgaactt 9120
cagagagggc ctggaaaaca gcagccgggt gctggatggc agaaccaccc tgctgctgat 9180
gaccagcatg tgcacagccg cccatgccac acaggccgcc ctgaatatcc aggaaggcct 9240
ggcttacctg aaccccagca agcacatgtt caccatcccc aacgtgtaca gcccctgcat 9300
gggcagcctg agaaccgacc tgaccgaaga gatccacgtg atgaacctgc tgtccgccat 9360
ccccaccaga cccggactga atgaggtgct gcacacccag ctggacgagt ccgagatctt 9420
cgacgccgcc ttcaagacca tgatgatctt taccacctgg accgccaagg acctgcacat 9480
cctgcacaca cacgtgcccg aggtgttcac atgccaagat gccgccgctc ggaacggcga 9540
gtatgtgctg attctgcctg ccgtgcaggg ccacagctac gtgatcaccc ggaacaagcc 9600
ccagcggggc ctggtgtata gcctggctga cgtggacgtg tacaacccca tcagcgtggt 9660
gtacctgagc aaggatacct gcgtgtccga gcacggcgtg atcgaaacag tggccctgcc 9720
ccaccccgac aacctgaaag agtgcctgta ctgcggctcc gtgttcctgc ggtatctgac 9780
caccggcgcc atcatggaca tcatcatcat cgacagcaag gacaccgaga gacagctggc 9840
cgccatgggc aacagcacca tcccccccct caaccccgac atgcacggcg acgatagcaa 9900
ggccgtgctg ctgttcccca acggcaccgt ggtcacactg ctgggcttcg agcggagaca 9960
ggccatcaga atgagcggcc agtacctggg cgcctctctg ggtggtgcct ttctggccgt 10020
cgtgggcttt ggcatcatcg gctggatgct gtgcggcaac agcagactgc gcgagtacaa 10080
caagatcccc ctgacctaat ctagacgcgg ccgcatacag cagcaattgg caagctgctt 10140
acatagaact cgcggcgatt ggcatgccgc cttaaaattt ttattttatt tttctttttct 10200
tttccgaatc ggattttgtt tttaatattt caaaaaaaaa aaaaaaaaaa aaaaaaaaaa 10260
aaaaaagggt cggcatggca tctccacctc ctcgcggtcc gacctgggca tccgaaggag 10320
gacgcacgtc cactcggatg gctaagggag agccacgttt aaaccagctc caattcgccc 10380
tatagtgagt cgtattacgc gcgctcactg gccgtcgttt tacaacgtcg tgactgggaa 10440
aaccctggcg ttacccaact taatcgcctt gcagcacatc cccctttcgc cagctggcgt 10500
aatagcgaag aggcccgcac cgatcgccct tcccaacagt tgcgcagcct gaatggcgaa 10560
tgggacgcgc cctgtagcgg cgcattaagc gcggcgggtg tggtggttac gcgcagcgtg 10620
accgctacac ttgccagcgc cctagcgccc gctcctttcg ctttcttccc ttcctttctc 10680
gccacgttcg ccggctttcc ccgtcaagct ctaaatcggg ggctcccttt agggttccga 10740

-continued

```
tttagtgctt tacggcacct cgaccccaaa aaacttgatt agggtgatgg ttcacgtagt  10800
gggccatcgc cctgatagac ggtttttcgc cctttgacgt tggagtccac gttctttaat  10860
agtggactct tgttccaaac tggaacaaca ctcaacccta tctcggtcta ttcttttgat  10920
ttataaggga ttttgccgat ttcggcctat tggttaaaaa atgagctgat ttaacaaaaa  10980
tttaacgcga attttaacaa aatattaacg cttacaattt aggtggcact tttcggggaa  11040
atgtgcgcgg aacccctatt tgtttatttt tctaaataca ttcaaatatg tatccgctca  11100
tgagacaata accctgataa atgcttcaat aatattgaaa aaggaagagt atgagtattc  11160
aacatttccg tgtcgccctt attccctttt ttgcggcatt ttgccttcct gtttttgctc  11220
acccagaaac gctggtgaaa gtaaaagatg ctgaagatca gttgggtgca cgagtgggtt  11280
acatcgaact ggatctcaac agcggtaaga tccttgagag ttttcgcccc gaagaacgtt  11340
ttccaatgat gagcactttt aaagttctgc tatgtggcgc ggtattatcc cgtattgacg  11400
ccgggcaaga gcaactcggt cgccgcatac actattctca gaatgacttg gttgagtact  11460
caccagtcac agaaaagcat cttacggatg gcatgacagt aagagaatta tgcagtgctg  11520
ccataaccat gagtgataac actgcggcca acttacttct gacaacgatc ggaggaccga  11580
aggagctaac cgcttttttg cacaacatgg gggatcatgt aactcgcctt gatcgttggg  11640
aaccggagct gaatgaagcc ataccaaacg acgagcgtga caccacgatg cctgtagcaa  11700
tggcaacaac gttgcgcaaa ctattaactg gcgaactact tactctagct tcccggcaac  11760
aattaataga ctggatggag gcggataaag ttgcaggacc acttctgcgc tcggcccttc  11820
cggctggctg gtttattgct gataaatctg gagccggtga gcgtgggtct cgcggtatca  11880
ttgcagcact ggggccagat ggtaagccct cccgtatcgt agttatctac acgacgggga  11940
gtcaggcaac tatggatgaa cgaaatagac agatcgctga gataggtgcc tcactgatta  12000
agcattggta actgtcagac caagtttact catatatact ttagattgat ttaaaacttc  12060
atttttaatt taaaaggatc taggtgaaga tcctttttga taatctcatg accaaaatcc  12120
cttaacgtga gttttcgttc cactgagcgt cagaccccgt agaaaagatc aaaggatctt  12180
cttgagatcc tttttttctg cgcgtaatct gctgcttgca aacaaaaaaa ccaccgctac  12240
cagcggtggt ttgtttgccg gatcaagagc taccaactct ttttccgaag gtaactggct  12300
tcagcagagc gcagatacca aatactgttc ttctagtgta gccgtagtta ggccaccact  12360
tcaagaactc tgtagcaccg cctacatacc tcgctctgct aatcctgtta ccagtggctg  12420
ctgccagtgg cgataagtcg tgtcttaccg ggttggactc aagacgatag ttaccggata  12480
aggcgcagcg gtcgggctga acggggggtt cgtgcacaca gcccagcttg gagcgaacga  12540
cctacaccga actgagatac ctacagcgtg agctatgaga aagcgccacg cttcccgaag  12600
ggagaaaggc ggacaggtat ccggtaagcg gcagggtcgg aacaggagag cgcacgaggg  12660
agcttccagg gggaaacgcc tggtatcttt atagtcctgt cgggtttcgc cacctctgac  12720
ttgagcgtcg atttttgtga tgctcgtcag gggggcggag cctatggaaa aacgccagca  12780
acgcggcctt tttacggttc ctggcctttt gctggccttt tgctcacatg ttctttcctg  12840
cgttatcccc tgattctgtg gataaccgta ttaccgcctt tgagtgagct gataccgctc  12900
gccgcagccg aacgaccgag cgcagcgagt cagtgagcga ggaagcggaa gagcgcccaa  12960
tacgcaaacc gcctctcccc gcgcgttggc cgattcatta atgcagctgg cacgacaggt  13020
ttcccgactg gaaagcgggc agtgagcgca acgcaattaa tgtgagttag ctcactcatt  13080
```

aggcacccca ggctttacac tttatgctcc cggctcgtat gttgtgtgga attgtgagcg 13140
gataacaatt tcacacagga aacagctatg accatgatta cgccaagcgc gcaattaacc 13200
ctcactaaag ggaacaaaag ctgggtaccg ggcccacgcg taatacgact cactatag 13258

<210> SEQ ID NO 75
<211> LENGTH: 11215
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tagacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg tttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg actttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgaggggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200

-continued

```
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
```

aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga cccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtcgagtct 7560
agtcgacgcc accatggcca gccacaagtg gctgctgcag atgatcgtgt tcctgaaaac 7620
catcacaatc gcctactgcc tgcatctgca ggacgacacc cctctgttct tcggcgccaa 7680
gcctctgagc gacgtgtccc tgatcatcac cgagccttgc gtgtccagcg tgtacgaggc 7740
ctgggattat gccgcccctc ccgtgtccaa tctgagcgaa gccctgagcg gcatcgtggt 7800
caagaccaag tgccccgtgc ccgaagtgat cctgtggttc aaggacaagc agatggccta 7860
ctggaccaac ccttacgtga ccctgaaggg cctgacccag agcgtgggcg aggaacacaa 7920
gagcggcgac atcagagatg ccctgctgga tgccctgtcc ggtgtctggg tggacagcac 7980
accctccagc accaacatcc ccgagaacgg ctgtgtgtgg ggagccgacc ggctgttcca 8040
gagagtgtgt cagtaatcta gacgcggccg catacagcag caattggcaa gctgcttaca 8100
tagaactcgc ggcgattggc atgccgcctt aaaattttta ttttattttt cttttctttt 8160
ccgaatcgga ttttgttttt aatatttcaa aaaaaaaaaa aaaaaaaaaa aaaaaaaaaa 8220
aaagggtcgg catggcatct ccacctcctc gcggtccgac ctgggcatcc gaaggaggac 8280
gcacgtccac tcggatggct aagggagagc cacgtttaaa ccagctccaa ttcgccctat 8340
agtgagtcgt attacgcgcg ctcactggcc gtcgttttac aacgtcgtga ctgggaaaac 8400
cctggcgtta cccaacttaa tcgccttgca gcacatcccc ctttcgccag ctggcgtaat 8460
agcgaagagg cccgcaccga tcgcccttcc caacagttgc gcagcctgaa tggcgaatgg 8520
gacgcgccct gtagcggcgc attaagcgcg gcgggtgtgg tggttacgcg cagcgtgacc 8580
gctacacttg ccagcgccct agcgcccgct cctttcgctt tcttcccttc ctttctcgcc 8640
acgttcgccg gctttccccg tcaagctcta aatcgggggc tccctttagg gttccgattt 8700
agtgctttac ggcacctcga ccccaaaaaa cttgattagg gtgatggttc acgtagtggg 8760
ccatcgccct gatagacggt ttttcgccct ttgacgttgg agtccacgtt ctttaatagt 8820
ggactcttgt tccaaactgg aacaacactc aaccctatct cggtctattc ttttgattta 8880
taagggattt tgccgatttc ggcctattgg ttaaaaaatg agctgattta acaaaaattt 8940

-continued

```
aacgcgaatt ttaacaaaat attaacgctt acaatttagg tggcactttt cggggaaatg   9000
tgcgcggaac ccctatttgt ttatttttct aaatacattc aaatatgtat ccgctcatga   9060
gacaataacc ctgataaatg cttcaataat attgaaaaag gaagagtatg agtattcaac   9120
atttccgtgt cgcccttatt cccttttttg cggcattttg ccttcctgtt tttgctcacc   9180
cagaaacgct ggtgaaagta aaagatgctg aagatcagtt gggtgcacga gtgggttaca   9240
tcgaactgga tctcaacagc ggtaagatcc ttgagagttt tcgccccgaa gaacgttttc   9300
caatgatgag cacttttaaa gttctgctat gtggcgcggt attatcccgt attgacgccg   9360
ggcaagagca actcggtcgc cgcatacact attctcagaa tgacttggtt gagtactcac   9420
cagtcacaga aaagcatctt acggatggca tgacagtaag agaattatgc agtgctgcca   9480
taaccatgag tgataacact gcggccaact tacttctgac aacgatcgga ggaccgaagg   9540
agctaaccgc ttttttgcac aacatggggg atcatgtaac tcgccttgat cgttgggaac   9600
cggagctgaa tgaagccata ccaaacgacg agcgtgacac cacgatgcct gtagcaatgg   9660
caacaacgtt gcgcaaacta ttaactggcg aactacttac tctagcttcc cggcaacaat   9720
taatagactg gatggaggcg gataaagttg caggaccact tctgcgctcg gcccttccgg   9780
ctggctggtt tattgctgat aaatctggag ccggtgagcg tgggtctcgc ggtatcattg   9840
cagcactggg gccagatggt aagccctccc gtatcgtagt tatctacacg acggggagtc   9900
aggcaactat ggatgaacga aatagacaga tcgctgagat aggtgcctca ctgattaagc   9960
attggtaact gtcagaccaa gtttactcat atatacttta gattgattta aaacttcatt  10020
tttaatttaa aaggatctag gtgaagatcc tttttgataa tctcatgacc aaaatccctt  10080
aacgtgagtt ttcgttccac tgagcgtcag accccgtaga aaagatcaaa ggatcttctt  10140
gagatccttt ttttctgcgc gtaatctgct gcttgcaaac aaaaaaacca ccgctaccag  10200
cggtggtttg tttgccggat caagagctac caactctttt tccgaaggta actggcttca  10260
gcagagcgca gataccaaat actgttcttc tagtgtagcc gtagttaggc caccacttca  10320
agaactctgt agcaccgcct acatacctcg ctctgctaat cctgttacca gtggctgctg  10380
ccagtggcga taagtcgtgt cttaccgggt tggactcaag acgatagtta ccggataagg  10440
cgcagcggtc gggctgaacg gggggttcgt gcacacagcc cagcttggag cgaacgacct  10500
acaccgaact gagataccta cagcgtgagc tatgagaaag cgccacgctt cccgaaggga  10560
gaaaggcgga caggtatccg gtaagcggca gggtcggaac aggagagcgc acgagggagc  10620
ttccaggggg aaacgcctgg tatctttata gtcctgtcgg gtttcgccac ctctgacttg  10680
agcgtcgatt tttgtgatgc tcgtcagggg ggcggagcct atggaaaaac gccagcaacg  10740
cggccttttt acggttcctg gccttttgct ggccttttgc tcacatgttc tttcctgcgt  10800
tatcccctga ttctgtggat aaccgtatta ccgcctttga gtgagctgat accgctcgcc  10860
gcagccgaac gaccgagcgc agcgagtcag tgagcgagga agcggaagag cgcccaatac  10920
gcaaaccgcc tctccccgcg cgttggccga ttcattaatg cagctggcac gacaggtttc  10980
ccgactggaa agcgggcagt gagcgcaacg caattaatgt gagttagctc actcattagg  11040
caccccaggc tttacacttt atgctcccgg ctcgtatgtt gtgtggaatt gtgagcggat  11100
aacaatttca cacaggaaac agctatgacc atgattacgc caagcgcgca attaaccctc  11160
actaaaggga acaaaagctg ggtaccgggc ccacgcgtaa tacgactcac tatag        11215
```

<210> SEQ ID NO 76
<211> LENGTH: 13827

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 76
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tagacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100

-continued

```
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
```

-continued

```
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
```

-continued acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtcgagtct 7560
agtcgacgcc accatgttcg ccctggtgct ggccgtggtc atcctgcctc tgtggaccac 7620
cgccaacaag agctacgtga cccccacacc cgccaccaga tccatcggac acatgagcgc 7680
cctgctgaga gagtacagcg accggaacat gagcctgaag ctggaagcct tctaccccac 7740
cggcttcgac gaggaactga tcaagagcct gcactggggc aacgaccgga agcacgtgtt 7800
cctcgtgatc gtgaaagtga accccaccac ccacgagggc gacgtcggcc tggtcatctt 7860
ccccaagtac ctgctgagcc cctaccactt caaggccgag cacagagccc ccttccctgc 7920
tggccgcttt ggctttctga gccaccctgt gacccccgac gtgtcattct tcgacagcag 7980
cttcgccccc tacctgacca cacagcacct ggtggccttc accaccttcc cccccaatcc 8040
tctcgtgtgg cacctggaaa gagccgagac agccgccacc gccgaaagac cttttggcgt 8100
gtccctgctg cccgccagac ctaccgtgcc caagaacacc atcctggaac acaaggccca 8160
cttcgccacc tgggatgccc tggccagaca caccttcttt agcgccgagg ccatcatcac 8220
caacagcacc ctgagaatcc acgtgcccct gttcggcagc gtgtggccca tcagatactg 8280
ggccacaggc agcgtgctgc tgaccagcga tagcggcaga gtggaagtga acatcggcgt 8340
gggcttcatg agcagcctga tcagcctgag cagcggcctg cccatcgagc tgattgtggt 8400
gccccacacc gtgaagctga acgccgtgac cagcgacacc acctggttcc agctgaaccc 8460
ccctggccct gatcctggcc ctagttacag agtgtacctg ctgggcagag gcctggacat 8520
gaacttcagc aagcacgcca ccgtggacat ctgcgcctac cctgaggaaa gcctggacta 8580
cagataccac ctgagcatgg cccacaccga ggccctgaga atgaccacca aggccgacca 8640
gcacgacatc aacgaggaaa gctactacca cattgccgcc agaatcgcca ccagcatctt 8700
cgccctgagc gagatgggcc ggaccaccga gtactttctg ctggacgaga tcgtggacgt 8760
gcagtaccag ctgaagttcc tgaactacat cctgatgcgg atcggcgctg gcgcccaccc 8820
taataccatc agcggcacca gcgacctgat cttcgccgat cctagccagc tgcacgacga 8880
gctgagcctg ctgttcggcc aggtcaaacc cgccaacgtg gactacttca tcagctacga 8940
cgaggcccgg gaccagctga aaacagccta cgccctgtcc agaggccagg atcatgtgaa 9000
cgccctgtcc ctggccaggc gcgtgatcat gagcatctac aagggcctgc tggtcaagca 9060
gaacctgaac gccaccgagc ggcaggccct gttcttcgcc agcatgatcc tgctgaactt 9120
cagagagggc ctggaaaaca gcagccgggt gctggatggc agaaccaccc tgctgctgat 9180
gaccagcatg tgcacagccg cccatgccac acaggccgcc ctgaatatcc aggaaggcct 9240

-continued

```
ggcttacctg aaccccagca agcacatgtt caccatcccc aacgtgtaca gcccctgcat   9300
gggcagcctg agaaccgacc tgaccgaaga gatccacgtg atgaacctgc tgtccgccat   9360
ccccaccaga cccggactga atgaggtgct gcacacccag ctggacgagt ccgagatctt   9420
cgacgccgcc ttcaagacca tgatgatctt taccacctgg accgccaagg acctgcacat   9480
cctgcacaca cacgtgcccg aggtgttcac atgccaagat gccgccgctc ggaacggcga   9540
gtatgtgctg attctgcctg ccgtgcaggg ccacagctac gtgatcaccc ggaacaagcc   9600
ccagcggggc ctggtgtata gcctggctga cgtggacgtg tacaacccca tcagcgtggt   9660
gtacctgagc aaggatacct gcgtgtccga gcacggcgtg atcgaaacag tggccctgcc   9720
ccaccccgac aacctgaaag agtgcctgta ctgcggctcc gtgttcctgc ggtatctgac   9780
caccggcgcc atcatggaca tcatcatcat cgacagcaag gacaccgaga gacagctggc   9840
cgccatgggc aacagcacca tcccccccttc caaccccgac atgcacggcg acgatagcaa   9900
ggccgtgctg ctgttcccca acggcaccgt ggtcacactg ctgggcttcg agcggagaca   9960
ggccatcaga atgagcggcc agtacctggg cgcctctctg ggtggtgcct ttctggccgt  10020
cgtgggcttt ggcatcatcg gctggatgct gtgcggcaac agcagactgc gcgagtacaa  10080
caagatcccc ctgacctaat ctagacgtcg cgaccaccca ggatccgcct ataactctct  10140
acggctaacc tgaatggact acgacatagt ctagtcgacg ccaccatggc cagccacaag  10200
tggctgctgc agatgatcgt gttcctgaaa accatcacaa tcgcctactg cctgcatctg  10260
caggacgaca cccctctgtt cttcggcgcc aagcctctga gcgacgtgtc cctgatcatc  10320
accgagcctt gcgtgtccag cgtgtacgag gcctgggatt atgccgcccc tcccgtgtcc  10380
aatctgagcg aagccctgag cggcatcgtg gtcaagacca agtgccccgt gcccgaagtg  10440
atcctgtggt tcaaggacaa gcagatggcc tactggacca acccttacgt gaccctgaag  10500
ggcctgaccc agagcgtggg cgaggaacac aagagcggcg acatcagaga tgccctgctg  10560
gatgccctgt ccggtgtctg ggtggacagc acaccctcca gcaccaacat ccccgagaac  10620
ggctgtgtgt ggggagccga ccggctgttc cagagagtgt gtcagtaatc tagacgcggc  10680
cgcatacagc agcaattggc aagctgctta catagaactc gcggcgattg gcatgccgcc  10740
ttaaaatttt tattttattt ttcttttctt ttccgaatcg gattttgttt ttaatatttc  10800
aaaaaaaaaa aaaaaaaaaa aaaaaaaaaa aaaaagggtc ggcatggcat ctccacctcc  10860
tcgcggtccg acctgggcat ccgaaggagg acgcacgtcc actcggatgg ctaagggaga  10920
gccacgttta aaccagctcc aattcgccct atagtgagtc gtattacgcg cgctcactgg  10980
ccgtcgtttt acaacgtcgt gactgggaaa accctggcgt tacccaactt aatcgccttg  11040
cagcacatcc ccctttcgcc agctggcgta atagcgaaga ggcccgcacc gatcgccctt  11100
cccaacagtt gcgcagcctg aatggcgaat gggacgcgcc ctgtagcggc gcattaagcg  11160
cggcgggtgt ggtggttacg cgcagcgtga ccgctacact tgccagcgcc ctagcgcccg  11220
ctcctttcgc tttcttccct tcctttctcg ccacgttcgc cggctttccc cgtcaagctc  11280
taaatcgggg gctcccttta gggttccgat ttagtgcttt acggcacctc gaccccaaaa  11340
aacttgatta gggtgatggt tcacgtagtg ggccatcgcc ctgatagacg gtttttcgcc  11400
ctttgacgtt ggagtccacg ttctttaata gtggactctt gttccaaact ggaacaacac  11460
tcaaccctat ctcggtctat tcttttgatt tataagggat tttgccgatt tcggcctatt  11520
ggttaaaaaa tgagctgatt taacaaaaat ttaacgcgaa ttttaacaaa atattaacgc  11580
```

ttacaattta ggtggcactt ttcggggaaa tgtgcgcgga acccctattt gtttattttt 11640
ctaaatacat tcaaatatgt atccgctcat gagacaataa ccctgataaa tgcttcaata 11700
atattgaaaa aggaagagta tgagtattca acatttccgt gtcgccctta ttcccttttt 11760
tgcggcattt tgccttcctg tttttgctca cccagaaacg ctggtgaaag taaaagatgc 11820
tgaagatcag ttgggtgcac gagtgggtta catcgaactg gatctcaaca gcggtaagat 11880
ccttgagagt tttcgccccg aagaacgttt tccaatgatg agcactttta aagttctgct 11940
atgtggcgcg gtattatccc gtattgacgc cgggcaagag caactcggtc gccgcataca 12000
ctattctcag aatgacttgg ttgagtactc accagtcaca gaaaagcatc ttacggatgg 12060
catgacagta agagaattat gcagtgctgc cataaccatg agtgataaca ctgcggccaa 12120
cttacttctg acaacgatcg gaggaccgaa ggagctaacc gcttttttgc acaacatggg 12180
ggatcatgta actcgccttg atcgttggga accggagctg aatgaagcca taccaaacga 12240
cgagcgtgac accacgatgc ctgtagcaat ggcaacaacg ttgcgcaaac tattaactgg 12300
cgaactactt actctagctt cccggcaaca attaatagac tggatggagg cggataaagt 12360
tgcaggacca cttctgcgct cggcccttcc ggctggctgg tttattgctg ataaatctgg 12420
agccggtgag cgtgggtctc gcggtatcat tgcagcactg gggccagatg gtaagccctc 12480
ccgtatcgta gttatctaca cgacggggag tcaggcaact atggatgaac gaaatagaca 12540
gatcgctgag ataggtgcct cactgattaa gcattggtaa ctgtcagacc aagtttactc 12600
atatatactt tagattgatt taaaacttca tttttaattt aaaaggatct aggtgaagat 12660
cctttttgat aatctcatga ccaaaatccc ttaacgtgag ttttcgttcc actgagcgtc 12720
agaccccgta gaaaagatca aaggatcttc ttgagatcct ttttttctgc gcgtaatctg 12780
ctgcttgcaa acaaaaaaac caccgctacc agcggtggtt tgtttgccgg atcaagagct 12840
accaactctt tttccgaagg taactggctt cagcagagcg cagataccaa atactgttct 12900
tctagtgtag ccgtagttag gccaccactt caagaactct gtagcaccgc ctacatacct 12960
cgctctgcta atcctgttac cagtggctgc tgccagtggc gataagtcgt gtcttaccgg 13020
gttggactca agacgatagt taccggataa ggcgcagcgg tcgggctgaa cggggggttc 13080
gtgcacacag cccagcttgg agcgaacgac ctacaccgaa ctgagatacc tacagcgtga 13140
gctatgagaa agcgccacgc ttcccgaagg gagaaaggcg gacaggtatc cggtaagcgg 13200
cagggtcgga acaggagagc gcacgaggga gcttccaggg ggaaacgcct ggtatcttta 13260
tagtcctgtc gggtttcgcc acctctgact tgagcgtcga tttttgtgat gctcgtcagg 13320
ggggcggagc ctatggaaaa acgccagcaa cgcggccttt ttacggttcc tggccttttg 13380
ctggcctttt gctcacatgt tctttcctgc gttatcccct gattctgtgg ataaccgtat 13440
taccgccttt gagtgagctg ataccgctcg ccgcagccga acgaccgagc gcagcgagtc 13500
agtgagcgag gaagcggaag agcgcccaat acgcaaaccg cctctccccg cgcgttggcc 13560
gattcattaa tgcagctggc acgacaggtt tcccgactgg aaagcgggca gtgagcgcaa 13620
cgcaattaat gtgagttagc tcactcatta ggcaccccag gctttacact ttatgctccc 13680
ggctcgtatg ttgtgtggaa ttgtgagcgg ataacaattt cacacaggaa acagctatga 13740
ccatgattac gccaagcgcg caattaaccc tcactaaagg gaacaaaagc tgggtaccgg 13800
gcccacgcgt aatacgactc actatag 13827

<210> SEQ ID NO 77
<211> LENGTH: 12604

-continued

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 77
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tagacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca cccatattgcc acacatggag 1980 gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100

-continued ggctcacagg cgagctggtg gatcctccct tccatgaatt cgcctacgag agtctgagaa 2160
cacgaccagc cgctccttac caagtaccaa ccatagggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgaggggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500

```
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
```

-continued

```
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgagtct   7560
agtcgacgcc accatgggca ccgtgaacaa gcctgtcgtg ggcgtgctga tgggcttcgg   7620
catcatcacc ggcaccctga gaatcaccaa ccctgtgcgg gccagcgtgc tgagatacga   7680
cgacttccac atcgacgagg acaagctgga caccaacagc gtgtacgagc cctactacca   7740
cagcgaccac gccgagagca gctgggtcaa cagaggcgag agcagccgga aggcctacga   7800
ccacaacagc ccctacatct ggccccggaa cgactacgac ggcttcctgg aaaacgccca   7860
cgagcaccac ggcgtgtaca atcagggcag aggcatcgac agcggcgaga gactgatgca   7920
gcccacacag atgagcgccc aggaagatct gggcgacgac acaggcatcc acgtgatccc   7980
caccctgaac ggcgacgacc ggcacaagat cgtgaacgtg gaccagcggc agtacggcga   8040
cgtgttcaag ggcgacctga accctaagcc ccagggccag agactgatcg aggtgtccgt   8100
ggaagagaac cacccccttca ccctgagagc cccatccag agaatctacg gcgtgcggta   8160
taccgagact tggagcttcc tgcccagcct gacctgtaca ggcgacgccg ctcctgccat   8220
ccagcacatc tgcctgaagc acaccacctg tttccaggac gtggtggtgg acgtggactg   8280
cgccgagaac accaaagagg accagctggc cgagatcagc taccggttcc agggcaagaa   8340
agaggccgac cagccctgga tcgtggtcaa taccagcacc ctgttcgacg agctggaact   8400
ggaccccccc gagattgaac ccggcgtgct gaaggtgctg cggaccgaga agcagtacct   8460
gggcgtgtac atctggaaca tgcggggctc cgacggcacc tctacctacg ccaccttcct   8520
ggtcacatgg aagggcgacg agaaaacccg gaaccctacc cctgccgtga cccctcagcc   8580
tagaggcgcc gagttccata tgtggaatta ccactcccac gtgttcagcg tgggcgacac   8640
cttcagcctg gccatgcatc tgcagtacaa gatccacgag gccccccttcg acctgctgct   8700
ggaatggctg tacgtgccca tcgaccctac ctgccagccc atgcggctgt acagcacctg   8760
tctgtaccac cccaacgccc ctcagtgcct gagccacatg aacagcggct gcaccttcac   8820
cagccctcac ctggctcaga gggtggccag caccgtgtac cagaattgcg agcacgccga   8880
caactacacc gcctactgcc tgggcatcag ccacatggaa cccagcttcg gcctgatcct   8940
gcacgatggc ggcaccaccc tgaagttcgt ggacacaccc gagagcctga gcggcctgta   9000
cgtgttcgtg gtgtacttca acggccacgt ggaagccgtg gcctacaccg tggtgtccac   9060
cgtggaccac ttcgtgaacg ccatcgagga aagaggcttc ccacccacag ccggacagcc   9120
tccagccacc accaagccca aagaaatcac ccccgtgaac cccggcacca gcccccctgct   9180
gagatatgct gcttggacag gcggactggc cgctgtggtg ctgctgtgcc tggtcatctt   9240
```

```
cctgatctgc accgccaagc ggatgagagt gaaggcctac cgggtggaca agtcccccta   9300

caaccagagc atgtactacg ccggcctgcc cgtggacgat ttcgaggata gcgagagcac   9360

cgacaccgag gaagagttcg gcaacgccat cggcggatct cacggcggca gcagctacac   9420

cgtgtacatc gacaagacca gataatctag acgcggccgc atacagcagc aattggcaag   9480

ctgcttacat agaactcgcg gcgattggca tgccgcctta aaatttttat tttatttttc   9540

ttttcttttc cgaatcggat tttgttttta atatttcaaa aaaaaaaaaa aaaaaaaaaa   9600

aaaaaaaaaa aagggtcggc atggcatctc cacctcctcg cggtccgacc tgggcatccg   9660

aaggaggacg cacgtccact cggatggcta agggagagcc acgtttaaac cagctccaat   9720

tcgccctata gtgagtcgta ttacgcgcgc tcactggccg tcgttttaca acgtcgtgac   9780

tgggaaaacc ctggcgttac ccaacttaat cgccttgcag cacatccccc tttcgccagc   9840

tggcgtaata gcgaagaggc ccgcaccgat cgcccttccc aacagttgcg cagcctgaat   9900

ggcgaatggg acgcgccctg tagcggcgca ttaagcgcgg cgggtgtggt ggttacgcgc   9960

agcgtgaccg ctacacttgc cagcgcccta gcgcccgctc ctttcgcttt cttcccttcc  10020

tttctcgcca cgttcgccgg ctttccccgt caagctctaa atcgggggct ccctttaggg  10080

ttccgattta gtgctttacg gcacctcgac cccaaaaaac ttgattaggg tgatggttca  10140

cgtagtgggc catcgccctg atagacggtt tttcgccctt tgacgttgga gtccacgttc  10200

tttaatagtg gactcttgtt ccaaactgga acaacactca accctatctc ggtctattct  10260

tttgatttat aagggatttt gccgatttcg gcctattggt taaaaaatga gctgatttaa  10320

caaaaattta acgcgaattt taacaaaata ttaacgctta caatttaggt ggcacttttc  10380

ggggaaatgt gcgcggaacc cctatttgtt tatttttcta aatacattca aatatgtatc  10440

cgctcatgag acaataaccc tgataaatgc ttcaataata ttgaaaaagg aagagtatga  10500

gtattcaaca tttccgtgtc gcccttattc ccttttttgc ggcattttgc cttcctgttt  10560

ttgctcaccc agaaacgctg gtgaaagtaa aagatgctga agatcagttg ggtgcacgag  10620

tgggttacat cgaactggat ctcaacagcg gtaagatcct tgagagtttt cgccccgaag  10680

aacgttttcc aatgatgagc acttttaaag ttctgctatg tggcgcggta ttatcccgta  10740

ttgacgccgg gcaagagcaa ctcggtcgcc gcatacacta ttctcagaat gacttggttg  10800

agtactcacc agtcacagaa aagcatctta cggatggcat gacagtaaga gaattatgca  10860

gtgctgccat aaccatgagt gataacactg cggccaactt acttctgaca acgatcggag  10920

gaccgaagga gctaaccgct tttttgcaca acatggggga tcatgtaact cgccttgatc  10980

gttgggaacc ggagctgaat gaagccatac caaacgacga gcgtgacacc acgatgcctg  11040

tagcaatggc aacaacgttg cgcaaactat taactggcga actacttact ctagcttccc  11100

ggcaacaatt aatagactgg atggaggcgg ataaagttgc aggaccactt ctgcgctcgg  11160

cccttccggc tggctggttt attgctgata aatctggagc cggtgagcgt gggtctcgcg  11220

gtatcattgc agcactgggg ccagatggta agccctcccg tatcgtagtt atctacacga  11280

cggggagtca ggcaactatg gatgaacgaa atagacagat cgctgagata ggtgcctcac  11340

tgattaagca ttggtaactg tcagaccaag tttactcata tatactttag attgatttaa  11400

aacttcattt ttaatttaaa aggatctagg tgaagatcct ttttgataat ctcatgacca  11460

aaatccctta acgtgagttt tcgttccact gagcgtcaga ccccgtagaa aagatcaaag  11520

gatcttcttg agatcctttt tttctgcgcg taatctgctg cttgcaaaca aaaaaaccac  11580
```

cgctaccagc ggtggtttgt ttgccggatc aagagctacc aactcttttt ccgaaggtaa 11640
ctggcttcag cagagcgcag ataccaaata ctgttcttct agtgtagccg tagttaggcc 11700
accacttcaa gaactctgta gcaccgccta catacctcgc tctgctaatc ctgttaccag 11760
tggctgctgc cagtggcgat aagtcgtgtc ttaccgggtt ggactcaaga cgatagttac 11820
cggataaggc gcagcggtcg ggctgaacgg ggggttcgtg cacacagccc agcttggagc 11880
gaacgaccta caccgaactg agatacctac agcgtgagct atgagaaagc gccacgcttc 11940
ccgaagggag aaaggcggac aggtatccgg taagcggcag ggtcggaaca ggagagcgca 12000
cgagggagct tccaggggga aacgcctggt atctttatag tcctgtcggg tttcgccacc 12060
tctgacttga gcgtcgattt ttgtgatgct cgtcaggggg gcggagccta tggaaaaacg 12120
ccagcaacgc ggccttttta cggttcctgg ccttttgctg gccttttgct cacatgttct 12180
ttcctgcgtt atcccctgat tctgtggata accgtattac cgcctttgag tgagctgata 12240
ccgctcgccg cagccgaacg accgagcgca gcgagtcagt gagcgaggaa gcggaagagc 12300
gcccaatacg caaaccgcct ctccccgcgc gttggccgat tcattaatgc agctggcacg 12360
acaggtttcc cgactggaaa gcgggcagtg agcgcaacgc aattaatgtg agttagctca 12420
ctcattaggc accccaggct ttacacttta tgctcccggc tcgtatgttg tgtggaattg 12480
tgagcggata acaatttcac acaggaaaca gctatgacca tgattacgcc aagcgcgcaa 12540
ttaaccctca ctaaagggaa caaaagctgg gtaccgggcc cacgcgtaat acgactcact 12600
atag 12604

<210> SEQ ID NO 78
<211> LENGTH: 11797
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 78
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960

-continued cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tagacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttttaac atgatgtgcc 2520 tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300

-continued

```
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
```

-continued

```
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgagtct   7560
agtcgacgcc accatgtttc tgatccagtg cctgatcagc gccgtgatct tctatattca   7620
agtcacaaac gccctgatct ttaagggcga ccacgtgtca ctgcaggtca acagcagcct   7680
gaccagcatc ctgatcccca tgcagaacga caattacacc gagatcaagg gccagctggt   7740
gttcatcggc gagcagctgc ccaccggcac caattacagc ggcaccctgg aactgctgta   7800
cgccgatacc gtggccttct gcttcagaag cgtgcaggtc atcagatacg acggctgccc   7860
ccggatcaga accagcgcct tcatcagctg ccggtacaag cacagctggc actacggcaa   7920
cagcaccgac cggatcagca ccgaacctga tgccggcgtg atgctgaaga tcaccaagcc   7980
cggcatcaac gacgccggcg tgtacgtgct gctcgtgcgg ctggatcaca gcagaagcac   8040
```

-continued

```
cgacggcttc atcctgggcg tgaacgtgta caccgccggc agccaccaca acatccacgg   8100
cgtgatctac accagcccca gcctgcagaa cggctacagc accagagccc tgttccagca   8160
ggccagactg tgcgatctgc ccgccacacc taagggcagc ggcacaagcc tgtttcagca   8220
catgctggac ctgagagccg gcaagagcct ggaagataac ccctggctgc acgaggacgt   8280
ggtcaccacc gagacaaaga gcgtggtcaa agagggcatc gagaaccacg tgtaccccac   8340
cgacatgagc accctgcccg agaagtccct gaacgacccc cctgagaacc tgctgatcat   8400
catccccatc gtggccagcg tgatgatcct gaccgccatg gtcatcgtga tcgtgatcag   8460
cgtgaagcgg cggagaatca agaagcaccc catctaccgg cccaacacca agaccagacg   8520
gggcatccag aacgccaccc ctgagtccga cgtgatgctg gaagccgcca ttgcccagct   8580
ggccaccatc agagaggaaa gccccccctca cagcgtcgtg aacccccttcg tgaagtaatc   8640
tagacgcggc cgcatacagc agcaattggc aagctgctta catagaactc gcggcgattg   8700
gcatgccgcc ttaaaatttt tattttattt ttcttttctt ttccgaatcg gattttgttt   8760
ttaatatttc aaaaaaaaaa aaaaaaaaaa aaaaaaaaaa aaaaagggtc ggcatggcat   8820
ctccacctcc tcgcggtccg acctgggcat ccgaaggagg acgcacgtcc actcggatgg   8880
ctaagggaga gccacgttta aaccagctcc aattcgccct atagtgagtc gtattacgcg   8940
cgctcactgg ccgtcgtttt acaacgtcgt gactgggaaa accctggcgt tacccaactt   9000
aatcgccttg cagcacatcc ccctttcgcc agctggcgta atagcgaaga ggcccgcacc   9060
gatcgccctt cccaacagtt gcgcagcctg aatggcgaat gggacgcgcc ctgtagcggc   9120
gcattaagcg cggcgggtgt ggtggttacg cgcagcgtga ccgctacact tgccagcgcc   9180
ctagcgcccg ctcctttcgc tttcttccct tcctttctcg ccacgttcgc cggctttccc   9240
cgtcaagctc taaatcgggg gctcccttta gggttccgat ttagtgcttt acggcacctc   9300
gaccccaaaa aacttgatta gggtgatggt tcacgtagtg ggccatcgcc ctgatagacg   9360
gtttttcgcc ctttgacgtt ggagtccacg ttctttaata gtggactctt gttccaaact   9420
ggaacaacac tcaaccctat ctcggtctat tcttttgatt tataagggat tttgccgatt   9480
tcggcctatt ggttaaaaaa tgagctgatt taacaaaaat ttaacgcgaa ttttaacaaa   9540
atattaacgc ttacaattta ggtggcactt ttcggggaaa tgtgcgcgga acccctattt   9600
gtttattttt ctaaatacat tcaaatatgt atccgctcat gagacaataa ccctgataaa   9660
tgcttcaata atattgaaaa aggaagagta tgagtattca acatttccgt gtcgccctta   9720
ttcccttttt tgcggcattt tgccttcctg tttttgctca cccagaaacg ctggtgaaag   9780
taaaagatgc tgaagatcag ttgggtgcac gagtgggtta catcgaactg gatctcaaca   9840
gcggtaagat ccttgagagt tttcgccccg aagaacgttt tccaatgatg agcactttta   9900
aagttctgct atgtggcgcg gtattatccc gtattgacgc cgggcaagag caactcggtc   9960
gccgcataca ctattctcag aatgacttgg ttgagtactc accagtcaca gaaaagcatc  10020
ttacggatgg catgacagta agagaattat gcagtgctgc cataaccatg agtgataaca  10080
ctgcggccaa cttacttctg acaacgatcg gaggaccgaa ggagctaacc gcttttttgc  10140
acaacatggg ggatcatgta actcgccttg atcgttggga accggagctg aatgaagcca  10200
taccaaacga cgagcgtgac accacgatgc ctgtagcaat ggcaacaacg ttgcgcaaac  10260
tattaactgg cgaactactt actctagctt cccggcaaca attaatagac tggatggagg  10320
cggataaagt tgcaggacca cttctgcgct cggcccttcc ggctggctgg tttattgctg  10380
ataaatctgg agccggtgag cgtgggtctc gcggtatcat tgcagcactg gggccagatg  10440
```

```
gtaagccctc ccgtatcgta gttatctaca cgacggggag tcaggcaact atggatgaac  10500

gaaatagaca gatcgctgag ataggtgcct cactgattaa gcattggtaa ctgtcagacc  10560

aagtttactc atatatactt tagattgatt taaaacttca tttttaattt aaaaggatct  10620

aggtgaagat cctttttgat aatctcatga ccaaaatccc ttaacgtgag ttttcgttcc  10680

actgagcgtc agaccccgta gaaaagatca aaggatcttc ttgagatcct ttttttctgc  10740

gcgtaatctg ctgcttgcaa acaaaaaaac caccgctacc agcggtggtt tgtttgccgg  10800

atcaagagct accaactctt tttccgaagg taactggctt cagcagagcg cagataccaa  10860

atactgttct tctagtgtag ccgtagttag gccaccactt caagaactct gtagcaccgc  10920

ctacatacct cgctctgcta atcctgttac cagtggctgc tgccagtggc gataagtcgt  10980

gtcttaccgg gttggactca agacgatagt taccggataa ggcgcagcgg tcgggctgaa  11040

cggggggttc gtgcacacag cccagcttgg agcgaacgac ctacaccgaa ctgagatacc  11100

tacagcgtga gctatgagaa agcgccacgc ttcccgaagg gagaaaggcg gacaggtatc  11160

cggtaagcgg cagggtcgga acaggagagc gcacgaggga gcttccaggg ggaaacgcct  11220

ggtatcttta tagtcctgtc gggtttcgcc acctctgact tgagcgtcga tttttgtgat  11280

gctcgtcagg ggggcggagc ctatggaaaa acgccagcaa cgcggccttt ttacggttcc  11340

tggccttttg ctggcctttt gctcacatgt tctttcctgc gttatcccct gattctgtgg  11400

ataaccgtat taccgccttt gagtgagctg ataccgctcg ccgcagccga acgaccgagc  11460

gcagcgagtc agtgagcgag gaagcggaag agcgcccaat acgcaaaccg cctctccccg  11520

cgcgttggcc gattcattaa tgcagctggc acgacaggtt tcccgactgg aaagcgggca  11580

gtgagcgcaa cgcaattaat gtgagttagc tcactcatta ggcaccccag gctttacact  11640

ttatgctccc ggctcgtatg ttgtgtggaa ttgtgagcgg ataacaattt cacacaggaa  11700

acagctatga ccatgattac gccaagcgcg caattaaccc tcactaaagg gaacaaaagc  11760

tgggtaccgg gcccacgcgt aatacgactc actatag                           11797
```

```
<210> SEQ ID NO 79
<211> LENGTH: 13755
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79

ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600
```

-continued

```
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
```

cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340

-continued gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga cccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtcgagtct 7560
agtcgacgcc accatgggca ccgtgaacaa gcctgtcgtg ggcgtgctga tgggcttcgg 7620
catcatcacc ggcaccctga gaatcaccaa ccctgtgcgg gccagcgtgc tgagatacga 7680
cgacttccac atcgacgagg acaagctgga caccaacagc gtgtacgagc cctactacca 7740
cagcgaccac gccgagagca gctgggtcaa cagaggcgag agcagccgga aggcctacga 7800
ccacaacagc ccctacatct ggccccggaa cgactacgac ggcttcctgg aaaacgccca 7860
cgagcaccac ggcgtgtaca atcagggcag aggcatcgac agcggcgaga gactgatgca 7920
gcccacacag atgagcgccc aggaagatct gggcgacgac acaggcatcc acgtgatccc 7980
caccctgaac ggcgacgacc ggcacaagat cgtgaacgtg gaccagcggc agtacggcga 8040
cgtgttcaag ggcgacctga accctaagcc ccagggccag agactgatcg aggtgtccgt 8100
ggaagagaac caccccttca ccctgagagc ccccatccag agaatctacg gcgtgcggta 8160
taccgagact tggagcttcc tgcccagcct gacctgtaca ggcgacgccg ctcctgccat 8220
ccagcacatc tgcctgaagc acaccacctg tttccaggac gtggtggtgg acgtggactg 8280
cgccgagaac accaaagagg accagctggc cgagatcagc taccggttcc agggcaagaa 8340
agaggccgac cagccctgga tcgtggtcaa taccagcacc ctgttcgacg agctggaact 8400
ggaccccccc gagattgaac ccggcgtgct gaaggtgctg cggaccgaga agcagtacct 8460
gggcgtgtac atctggaaca tgcggggctc cgacggcacc tctacctacg ccaccttcct 8520
ggtcacatgg aagggcgacg agaaaacccg gaaccctacc cctgccgtga cccctcagcc 8580
tagaggcgcc gagttccata tgtggaatta ccactcccac gtgttcagcg tgggcgacac 8640
cttcagcctg gccatgcatc tgcagtacaa gatccacgag gccccccttcg acctgctgct 8700 ggaatggctg tacgtgccca tcgaccctac ctgccagccc atgcggctgt acagcacctg 8760
tctgtaccac cccaacgccc ctcagtgcct gagccacatg aacagcggct gcaccttcac 8820
cagccctcac ctggctcaga gggtggccag caccgtgtac cagaattgcg agcacgccga 8880
caactacacc gcctactgcc tgggcatcag ccacatggaa cccagcttcg gcctgatcct 8940
gcacgatggc ggcaccaccc tgaagttcgt ggacacaccc gagagcctga gcggcctgta 9000
cgtgttcgtg gtgtacttca acggccacgt ggaagccgtg gcctacaccg tggtgtccac 9060
cgtggaccac ttcgtgaacg ccatcgagga aagaggcttc ccacccacag ccggacagcc 9120
tccagccacc accaagccca aagaaatcac ccccgtgaac cccggcacca gcccccctgct 9180 gagatatgct gcttggacag gcggactggc cgctgtggtg ctgctgtgcc tggtcatctt 9240
cctgatctgc accgccaagc ggatgagagt gaaggcctac cgggtggaca agtcccccta 9300
caaccagagc atgtactacg ccggcctgcc cgtggacgat ttcgaggata gcgagagcac 9360
cgacaccgag gaagagttcg gcaacgccat cggcggatct cacggcggca gcagctacac 9420
cgtgtacatc gacaagacca gataatctag acgtcgcgac cacccaggat ccgcctataa 9480
ctctctacgg ctaacctgaa tggactacga catagtctag tcgacgccac catgtttctg 9540
atccagtgcc tgatcagcgc cgtgatcttc tatattcaag tcacaaacgc cctgatcttt 9600
aagggcgacc acgtgtcact gcaggtcaac agcagcctga ccagcatcct gatccccatg 9660
cagaacgaca attacaccga gatcaagggc cagctggtgt tcatcggcga gcagctgccc 9720
accggcacca attacagcgg caccctggaa ctgctgtacg ccgataccgt ggccttctgc 9780
ttcagaagcg tgcaggtcat cagatacgac ggctgccccc ggatcagaac cagcgccttc 9840
atcagctgcc ggtacaagca cagctggcac tacggcaaca gcaccgaccg gatcagcacc 9900
gaacctgatg ccggcgtgat gctgaagatc accaagcccg gcatcaacga cgccggcgtg 9960
tacgtgctgc tcgtgcggct ggatcacagc agaagcaccg acggcttcat cctgggcgtg 10020
aacgtgtaca ccgccggcag ccaccacaac atccacggcg tgatctacac cagccccagc 10080

-continued ctgcagaacg gctacagcac cagagccctg ttccagcagg ccagactgtg cgatctgccc 10140
gccacaccta agggcagcgg cacaagcctg tttcagcaca tgctggacct gagagccggc 10200
aagagcctgg aagataaccc ctggctgcac gaggacgtgg tcaccaccga gacaaagagc 10260
gtggtcaaag agggcatcga gaaccacgtg taccccaccg acatgagcac cctgcccgag 10320
aagtccctga acgacccccc tgagaacctg ctgatcatca tccccatcgt ggccagcgtg 10380
atgatcctga ccgccatggt catcgtgatc gtgatcagcg tgaagcggcg gagaatcaag 10440
aagcacccca tctaccggcc caacaccaag accagacggg gcatccagaa cgccacccct 10500
gagtccgacg tgatgctgga agccgccatt gcccagctgg ccaccatcag agaggaaagc 10560
ccccctcaca gcgtcgtgaa ccccttcgtg aagtaatcta gacgcggccg catacagcag 10620
caattggcaa gctgcttaca tagaactcgc ggcgattggc atgccgcctt aaaattttta 10680
ttttattttt cttttctttt ccgaatcgga ttttgttttt aatatttcaa aaaaaaaaaa 10740
aaaaaaaaaa aaaaaaaaaa aaagggtcgg catggcatct ccacctcctc gcggtccgac 10800
ctgggcatcc gaaggaggac gcacgtccac tcggatggct aagggagagc cacgtttaaa 10860
ccagctccaa ttcgccctat agtgagtcgt attacgcgcg ctcactggcc gtcgttttac 10920
aacgtcgtga ctgggaaaac cctggcgtta cccaacttaa tcgccttgca gcacatcccc 10980
ctttcgccag ctggcgtaat agcgaagagg cccgcaccga tcgcccttcc caacagttgc 11040
gcagcctgaa tggcgaatgg gacgcgccct gtagcggcgc attaagcgcg gcgggtgtgg 11100
tggttacgcg cagcgtgacc gctacacttg ccagcgccct agcgcccgct cctttcgctt 11160
tcttcccttc ctttctcgcc acgttcgccg gctttccccg tcaagctcta aatcgggggc 11220
tccctttagg gttccgattt agtgctttac ggcacctcga ccccaaaaaa cttgattagg 11280
gtgatggttc acgtagtggg ccatcgccct gatagacggt ttttcgccct ttgacgttgg 11340
agtccacgtt ctttaatagt ggactcttgt tccaaactgg aacaacactc aaccctatct 11400
cggtctattc ttttgattta taagggattt tgccgatttc ggcctattgg ttaaaaaatg 11460
agctgattta acaaaaattt aacgcgaatt ttaacaaaat attaacgctt acaatttagg 11520
tggcactttt cggggaaatg tgcgcggaac ccctatttgt ttatttttct aaatacattc 11580
aaatatgtat ccgctcatga gacaataacc ctgataaatg cttcaataat attgaaaaag 11640
gaagagtatg agtattcaac atttccgtgt cgcccttatt cccttttttg cggcattttg 11700
ccttcctgtt tttgctcacc cagaaacgct ggtgaaagta aaagatgctg aagatcagtt 11760
gggtgcacga gtgggttaca tcgaactgga tctcaacagc ggtaagatcc ttgagagttt 11820
tcgccccgaa gaacgttttc caatgatgag cacttttaaa gttctgctat gtggcgcggt 11880
attatcccgt attgacgccg ggcaagagca actcggtcgc cgcatacact attctcagaa 11940
tgacttggtt gagtactcac cagtcacaga aaagcatctt acggatggca tgacagtaag 12000
agaattatgc agtgctgcca taaccatgag tgataacact gcggccaact tacttctgac 12060
aacgatcgga ggaccgaagg agctaaccgc ttttttgcac aacatggggg atcatgtaac 12120
tcgccttgat cgttgggaac cggagctgaa tgaagccata ccaaacgacg agcgtgacac 12180
cacgatgcct gtagcaatgg caacaacgtt gcgcaaacta ttaactggcg aactacttac 12240
tctagcttcc cggcaacaat taatagactg gatggaggcg gataaagttg caggaccact 12300
tctgcgctcg gcccttccgg ctggctggtt tattgctgat aaatctggag ccggtgagcg 12360
tgggtctcgc ggtatcattg cagcactggg gccagatggt aagccctccc gtatcgtagt 12420
tatctacacg acggggagtc aggcaactat ggatgaacga aatagacaga tcgctgagat 12480

```
aggtgcctca ctgattaagc attggtaact gtcagaccaa gtttactcat atatacttta  12540

gattgattta aaacttcatt tttaatttaa aaggatctag gtgaagatcc tttttgataa  12600

tctcatgacc aaaatccctt aacgtgagtt ttcgttccac tgagcgtcag accccgtaga  12660

aaagatcaaa ggatcttctt gagatccttt ttttctgcgc gtaatctgct gcttgcaaac  12720

aaaaaaacca ccgctaccag cggtggtttg tttgccggat caagagctac caactctttt  12780

tccgaaggta actggcttca gcagagcgca gataccaaat actgttcttc tagtgtagcc  12840

gtagttaggc caccacttca agaactctgt agcaccgcct acatacctcg ctctgctaat  12900

cctgttacca gtggctgctg ccagtggcga taagtcgtgt cttaccgggt tggactcaag  12960

acgatagtta ccggataagg cgcagcggtc gggctgaacg gggggttcgt gcacacagcc  13020

cagcttggag cgaacgacct acaccgaact gagataccta cagcgtgagc tatgagaaag  13080

cgccacgctt cccgaaggga gaaaggcgga caggtatccg gtaagcggca gggtcggaac  13140

aggagagcgc acgagggagc ttccaggggg aaacgcctgg tatctttata gtcctgtcgg  13200

gtttcgccac ctctgacttg agcgtcgatt tttgtgatgc tcgtcagggg ggcggagcct  13260

atggaaaaac gccagcaacg cggccttttt acggttcctg gccttttgct ggccttttgc  13320

tcacatgttc tttcctgcgt tatcccctga ttctgtggat aaccgtatta ccgcctttga  13380

gtgagctgat accgctcgcc gcagccgaac gaccgagcgc agcgagtcag tgagcgagga  13440

agcggaagag cgcccaatac gcaaaccgcc tctccccgcg cgttggccga ttcattaatg  13500

cagctggcac gacaggtttc ccgactggaa agcgggcagt gagcgcaacg caattaatgt  13560

gagttagctc actcattagg caccccaggc tttacacttt atgctcccgg ctcgtatgtt  13620

gtgtggaatt gtgagcggat aacaatttca cacaggaaac agctatgacc atgattacgc  13680

caagcgcgca attaaccctc actaaaggga acaaaagctg ggtaccgggc ccacgcgtaa  13740

tacgactcac tatag                                                   13755
```

```
<210> SEQ ID NO 80
<211> LENGTH: 11459
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80
```

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660
```

-continued

```
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
```

-continued

```
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
```

-continued

```
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgacgcc   7560
accatggtga gcaagggcga ggagctgttc accggggtgg tgcccatcct ggtcgagctg   7620
gacggcgacg taaacggcca caagttcagc gtgtccggcg agggcgaggg cgatgccacc   7680
tacggcaagc tgaccctgaa gttcatctgc accaccggca agctgcccgt gccctggccc   7740
accctcgtga ccaccctgac ctacggcgtg cagtgcttca gccgctaccc cgaccacatg   7800
```

aagcagcacg acttcttcaa gtccgccatg cccgaaggct acgtccagga gcgcaccatc 7860
ttcttcaagg acgacggcaa ctacaagacc cgcgccgagg tgaagttcga gggcgacacc 7920
ctggtgaacc gcatcgagct gaagggcatc gacttcaagg aggacggcaa catcctgggg 7980
cacaagctgg agtacaacta caacagccac aacgtctata tcatggccga caagcagaag 8040
aacggcatca aggtgaactt caagatccgc cacaacatcg aggacggcag cgtgcagctc 8100
gccgaccact accagcagaa cacccccatc ggcgacggcc ccgtgctgct gcccgacaac 8160
cactacctga gcacccagtc cgccctgagc aaagacccca acgagaagcg cgatcacatg 8220
gtcctgctgg agttcgtgac cgccgccggg atcactctcg gcatggacga gctgtacaag 8280
tgataatcta gacggcgcgc ccacccagcg gccgcataca gcagcaattg gcaagctgct 8340
tacatagaac tcgcggcgat tggcatgccg ccttaaaatt tttattttat tttcttttc 8400
ttttccgaat cggattttgt ttttaatatt tcaaaaaaaa aaaaaaaaaa aaaaaaaaaa 8460
aaaaaaaggg tcggcatggc atctccacct cctcgcggtc cgacctgggc atccgaagga 8520
ggacgcacgt ccactcggat ggctaaggga gagccacgtt taaaccagct ccaattcgcc 8580
ctatagtgag tcgtattacg cgcgctcact ggccgtcgtt ttacaacgtc gtgactggga 8640
aaaccctggc gttacccaac ttaatcgcct tgcagcacat ccccctttcg ccagctggcg 8700
taatagcgaa gaggcccgca ccgatcgccc ttcccaacag ttgcgcagcc tgaatggcga 8760
atgggacgcg ccctgtagcg gcgcattaag cgcggcgggt gtggtggtta cgcgcagcgt 8820
gaccgctaca cttgccagcg ccctagcgcc cgctcctttc gctttcttcc cttcctttct 8880
cgccacgttc gccggctttc cccgtcaagc tctaaatcgg gggctccctt tagggttccg 8940
atttagtgct ttacggcacc tcgaccccaa aaaacttgat tagggtgatg gttcacgtag 9000
tgggccatcg ccctgataga cggtttttcg ccctttgacg ttggagtcca cgttctttaa 9060
tagtggactc ttgttccaaa ctggaacaac actcaaccct atctcggtct attcttttga 9120
tttataaggg attttgccga tttcggccta ttggttaaaa aatgagctga tttaacaaaa 9180
atttaacgcg aattttaaca aaatattaac gcttacaatt taggtggcac ttttcgggga 9240
aatgtgcgcg gaacccctat ttgtttattt ttctaaatac attcaaatat gtatccgctc 9300
atgagacaat aaccctgata aatgcttcaa taatattgaa aaaggaagag tatgagtatt 9360
caacatttcc gtgtcgccct tattcccttt tttgcggcat tttgccttcc tgtttttgct 9420
cacccagaaa cgctggtgaa agtaaaagat gctgaagatc agttgggtgc acgagtgggt 9480
tacatcgaac tggatctcaa cagcggtaag atccttgaga gttttcgccc cgaagaacgt 9540
tttccaatga tgagcacttt taaagttctg ctatgtggcg cggtattatc ccgtattgac 9600
gccgggcaag agcaactcgg tcgccgcata cactattctc agaatgactt ggttgagtac 9660
tcaccagtca cagaaaagca tcttacggat ggcatgacag taagagaatt atgcagtgct 9720
gccataacca tgagtgataa cactgcggcc aacttacttc tgacaacgat cggaggaccg 9780
aaggagctaa ccgctttttt gcacaacatg ggggatcatg taactcgcct tgatcgttgg 9840
gaaccggagc tgaatgaagc cataccaaac gacgagcgtg acaccacgat gcctgtagca 9900
atggcaacaa cgttgcgcaa actattaact ggcgaactac ttactctagc ttcccggcaa 9960
caattaatag actggatgga ggcggataaa gttgcaggac cacttctgcg ctcggccctt 10020
ccggctggct ggtttattgc tgataaatct ggagccggtg agcgtgggtc tcgcggtatc 10080
attgcagcac tggggccaga tggtaagccc tcccgtatcg tagttatcta cacgacgggg 10140

-continued agtcaggcaa ctatggatga acgaaataga cagatcgctg agataggtgc ctcactgatt 10200
aagcattggt aactgtcaga ccaagtttac tcatatatac tttagattga tttaaaactt 10260
catttttaat ttaaaaggat ctaggtgaag atcctttttg ataatctcat gaccaaaatc 10320
ccttaacgtg agttttcgtt ccactgagcg tcagaccccg tagaaaagat caaaggatct 10380
tcttgagatc ctttttttct gcgcgtaatc tgctgcttgc aaacaaaaaa accaccgcta 10440
ccagcggtgg tttgtttgcc ggatcaagag ctaccaactc tttttccgaa ggtaactggc 10500
ttcagcagag cgcagatacc aaatactgtt cttctagtgt agccgtagtt aggccaccac 10560
ttcaagaact ctgtagcacc gcctacatac ctcgctctgc taatcctgtt accagtggct 10620
gctgccagtg gcgataagtc gtgtcttacc gggttggact caagacgata gttaccggat 10680
aaggcgcagc ggtcgggctg aacggggggt tcgtgcacac agcccagctt ggagcgaacg 10740
acctacaccg aactgagata cctacagcgt gagctatgag aaagcgccac gcttcccgaa 10800
gggagaaagg cggacaggta tccggtaagc ggcagggtcg gaacaggaga gcgcacgagg 10860
gagcttccag ggggaaacgc ctggtatctt tatagtcctg tcgggtttcg ccacctctga 10920
cttgagcgtc gatttttgtg atgctcgtca ggggggcgga gcctatggaa aaacgccagc 10980
aacgcggcct ttttacggtt cctggccttt tgctggcctt ttgctcacat gttctttcct 11040
gcgttatccc ctgattctgt ggataaccgt attaccgcct ttgagtgagc tgataccgct 11100
cgccgcagcc gaacgaccga gcgcagcgag tcagtgagcg aggaagcgga agagcgccca 11160
atacgcaaac cgcctctccc cgcgcgttgg ccgattcatt aatgcagctg gcacgacagg 11220
tttcccgact ggaaagcggg cagtgagcgc aacgcaatta atgtgagtta gctcactcat 11280
taggcacccc aggctttaca ctttatgctc ccggctcgta tgttgtgtgg aattgtgagc 11340
ggataacaat ttcacacagg aaacagctat gaccatgatt acgccaagcg cgcaattaac 11400
cctcactaaa gggaacaaaa gctgggtacc gggcccacgc gtaatacgac tcactatag 11459

<210> SEQ ID NO 81
<211> LENGTH: 3567
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81
ataggcggcg catgagagaa gcccagacca attacctacc caaataggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggac 240
ggaccgacca tgttcccgtt ccagccaatg tatccgatgc agccaatgcc ctatcgcaac 300
ccgttcgcgg ccccgcgcag gccctggttc cccagaaccg accctttttct ggcgatgcag 360 gtgcaggaat taacccgctc gatggctaac ctgacgttca agcaacgccg ggacgcgcca 420
cctgaggggc catccgctaa gaaaccgaag aaggaggcct cgcaaaaaca gaaaggggga 480
ggccaaggga agaagaagaa gaaccaaggg aagaagaagg ctaagacagg gccgcctaat 540
ccgaaggcac agaatggaaa caagaagaag accaacaaga aaccaggcaa gagacagcgc 600
atggtcatga aattggaatc tgacaagacg ttcccaatca tgttggaagg gaagataaac 660
ggctacgctt gtgtggtcgg agggaagtta ttcaggccga tgggtgtgga aggcaagatc 720

-continued

```
gacaacgacg ttctggccgc gcttaagacg aagaaagcat ccaaatacga tcttgagtat    780
gcagatgtgc cacagaacat gcgggccgat acattcaaat acacccatga gaaaccccaa    840
ggctattaca gctggcatca tggagcagtc caatatgaaa atgggcgttt cacggtgccg    900
aaaggagttg gggccaaggg agacagcgga cgacccattc tggataacca gggacgggtg    960
gtcgctattg tgctgggagg tgtgaatgaa ggatctagga cagccctttc agtcgtcatg   1020
tggaacgaga agggagttac cgtgaagtat actccggaga actgcgagca atggtaatag   1080
taagcggccg catacagcag caattggcaa gctgcttaca tagaactcgc ggcgattggc   1140
atgccgcctt aaaattttta ttttattttt cttttctttt ccgaatcgga ttttgttttt   1200
aatatttcaa aaaaaaaaaa aaaaaaaaaa aaaaaaaaaa aaagggtcgg catggcatct   1260
ccacctcctc gcggtccgac ctgggcatcc gaaggaggac gcacgtccac tcggatggct   1320
aagggagagc cacgtttaaa cacgtgatat ctggcctcat gggccttcct ttcactgccc   1380
gctttccagt cgggaaacct gtcgtgccag ctgcattaac atggtcatag ctgtttcctt   1440
gcgtattggg cgctctccgc ttcctcgctc actgactcgc tgcgctcggt cgttcgggta   1500
aagcctgggg tgcctaatga gcaaaaggcc agcaaaaggc caggaaccgt aaaaaggccg   1560
cgttgctggc gtttttccat aggctccgcc cccctgacga gcatcacaaa aatcgacgct   1620
caagtcagag gtggcgaaac ccgacaggac tataaagata ccaggcgttt ccccctggaa   1680
gctccctcgt gcgctctcct gttccgaccc tgccgcttac cggatacctg tccgcctttc   1740
tcccttcggg aagcgtggcg ctttctcata gctcacgctg taggtatctc agttcggtgt   1800
aggtcgttcg ctccaagctg ggctgtgtgc acgaaccccc cgttcagccc gaccgctgcg   1860
ccttatccgg taactatcgt cttgagtcca acccggtaag acacgactta tcgccactgg   1920
cagcagccac tggtaacagg attagcagag cgaggtatgt aggcggtgct acagagttct   1980
tgaagtggtg gcctaactac ggctacacta gaagaacagt atttggtatc tgcgctctgc   2040
tgaagccagt taccttcgga aaaagagttg gtagctcttg atccggcaaa caaaccaccg   2100
ctggtagcgg tggttttttt gtttgcaagc agcagattac gcgcagaaaa aaaggatctc   2160
aagaagatcc tttgatcttt tctacggggt ctgacgctca gtggaacgaa aactcacgtt   2220
aagggatttt ggtcatgaga ttatcaaaaa ggatcttcac ctagatcctt ttaaattaaa   2280
aatgaagttt taaatcaatc taaagtatat atgagtaaac ttggtctgac agttattaga   2340
aaaattcatc cagcagacga taaaacgcaa tacgctggct atccggtgcc gcaatgccat   2400
acagcaccag aaaacgatcc gcccattcgc cgcccagttc ttccgcaata tcacgggtgg   2460
ccagcgcaat atcctgataa cgatccgcca cgcccagacg gccgcaatca ataaagccgc   2520
taaaacggcc attttccacc ataatgttcg gcaggcacgc atcaccatgg gtcaccacca   2580
gatcttcgcc atccggcatg ctcgctttca gacgcgcaaa cagctctgcc ggtgccaggc   2640
cctgatgttc ttcatccaga tcatcctgat ccaccaggcc cgcttccata cgggtacgcg   2700
cacgttcaat acgatgtttc gcctgatgat caaacggaca ggtcgccggg tccagggtat   2760
gcagacgacg catggcatcc gccataatgc tcactttttc tgccggcgcc agatggctag   2820
acagcagatc ctgacccggc acttcgccca gcagcagcca atcacggccc gcttcggtca   2880
ccacatccag caccgccgca cacggaacac cggtggtggc cagccagctc agacgcgccg   2940
cttcatcctg cagctcgttc agcgcaccgc tcagatcggt tttcacaaac agcaccggac   3000
gaccctgcgc gctcagacga aacaccgccg catcagagca gccaatggtc tgctgcgccc   3060
```

```
aatcatagcc aaacagacgt tccacccacg ctgccgggct acccgcatgc aggccatcct   3120

gttcaatcat actcttcctt tttcaatatt attgaagcat ttatcagggt tattgtctca   3180

tgagcggata catatttgaa tgtatttaga aaaataaaca aataggggtt ccgcgcacat   3240

ttccccgaaa agtgccacct aaattgtaag cgttaatatt ttgttaaaat tcgcgttaaa   3300

tttttgttaa atcagctcat tttttaacca ataggccgaa atcggcaaaa tcccttataa   3360

atcaaaagaa tagaccgaga tagggttgag tggccgctac agggcgctcc cattcgccat   3420

tcaggctgcg caactgttgg gaagggcgtt tcggtgcggg cctcttcgct attacgccag   3480

ctggcgaaag ggggatgtgc tgcaaggcga ttaagttggg taacgccagg gttttcccag   3540

tcacacgcgt aatacgactc actatag                                        3567


<210> SEQ ID NO 82
<211> LENGTH: 5685
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82

ataggcggcg catgagagaa gcccagacca attacctacc caaataggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggac    240

ggaccgacca tgtcactagt gaccaccatg tgtctgctcg ccaatgtgac gttcccatgt    300

gctcaaccac caatttgcta cgacagaaaa ccagcagaga ctttggccat gctcagcgtt    360

aacgttgaca acccgggcta cgatgagctg ctggaagcag ctgttaagtg ccccggaagg    420

aaaaggagat ccaccgagga gctgtttaat gagtataagc taacgcgccc ttacatggcc    480

agatgcatca gatgtgcagt tgggagctgc catagtccaa tagcaatcga ggcagtaaag    540

agcgacgggc acgacggtta tgttagactt cagacttcct cgcagtatgg cctggattcc    600

tccggcaact taaagggcag gaccatgcgg tatgacatgc acgggaccat taaagagata    660

ccactacatc aagtgtcact ctatacatct cgcccgtgtc acattgtgga tgggcacggt    720

tatttcctgc ttgccaggtg cccggcaggg gactccatca ccatggaatt taagaaagat    780

tccgtcagac actcctgctc ggtgccgtat gaagtgaaat ttaatcctgt aggcagagaa    840

ctctatactc atcccccaga acacggagta gagcaagcgt gccaagtcta cgcacatgat    900

gcacagaaca gaggagctta tgtcgagatg cacctcccgg gctcagaagt ggacagcagt    960

ttggtttcct tgagcggcag ttcagtcacc gtgacacctc ctgatgggac tagcgccctg   1020

gtggaatgcg agtgtggcgg cacaaagatc tccgagacca tcaacaagac aaaacagttc   1080

agccagtgca caaagaagga gcagtgcaga gcatatcggc tgcagaacga taagtgggtg   1140

tataattctg acaaactgcc caaagcagcg ggagccacct taaaaggaaa actgcatgtc   1200

ccattcttgc tggcagacgg caaatgcacc gtgcctctag caccagaacc tatgataacc   1260

ttcggtttca gatcagtgtc actgaaactg caccctaaga atcccacata tctaatcacc   1320

cgccaacttg ctgatgagcc tcactacacg cacgagctca tatctgaacc agctgttagg   1380

aattttaccg tcaccgaaaa agggtgggag tttgtatggg gaaaccaccc gccgaaaagg   1440

ttttgggcac aggaaacagc acccggaaat ccacatgggc taccgcacga ggtgataact   1500
```

-continued

```
cattattacc acagataccc tatgtccacc atcctgggtt tgtcaatttg tgccgccatt   1560
gcaaccgttt ccgttgcagc gtctacctgg ctgttttgca gatctagagt tgcgtgccta   1620
actccttacc ggctaacacc taacgctagg ataccatttt gtctggctgt gctttgctgc   1680
gcccgcactg cccgggccga gaccacctgg gagtccttgg atcacctatg gaacaataac   1740
caacagatgt tctggattca attgctgatc cctctggccg ccttgatcgt agtgactcgc   1800
ctgctcaggt gcgtgtgctg tgtcgtgcct tttttagtca tggccggcgc cgcaggcgcc   1860
ggcgcctacg agcacgcgac cacgatgccg agccaagcgg gaatctcgta taacactata   1920
gtcaacagag caggctacgc accactccct atcagcataa caccaacaaa gatcaagctg   1980
atacctacag tgaacttgga gtacgtcacc tgccactaca aaacaggaat ggattcacca   2040
gccatcaaat gctgcggatc tcaggaatgc actccaactt acaggcctga tgaacagtgc   2100
aaagtcttca caggggttta cccgttcatg tggggtggtg catattgctt ttgcgacact   2160
gagaacaccc aagtcagcaa ggcctacgta atgaaatctg acgactgcct tgcggatcat   2220
gctgaagcat ataaagcgca cacagcctca gtgcaggcgt tcctcaacat cacagtggga   2280
gaacactcta ttgtgactac cgtgtatgtg aatggagaaa ctcctgtgaa tttcaatggg   2340
gtcaaaataa ctgcaggtcc gctttccaca gcttggacac cctttgatcg caaaatcgtg   2400
cagtatgccg gggagatcta taattatgat tttcctgagt atggggcagg acaaccagga   2460
gcatttggag atatacaatc cagaacagtc tcaagctctg atctgtatgc caataccaac   2520
ctagtgctgc agagacccaa agcaggagcg atccacgtgc catacactca ggcaccttcg   2580
ggttttgagc aatggaagaa agataaagct ccatcattga aatttaccgc ccctttcgga   2640
tgcgaaatat atacaaaccc cattcgcgcc gaaaactgtg ctgtagggtc aattccatta   2700
gcctttgaca ttcccgacgc cttgttcacc agggtgtcag aaacaccgac actttcagcg   2760
gccgaatgca ctcttaacga gtgcgtgtat tcttccgact ttggtgggat cgccacggtc   2820
aagtactcgg ccagcaagtc aggcaagtgc gcagtccatg tgccatcagg gactgctacc   2880
ctaaaagaag cagcagtcga gctaaccgag caagggtcgg cgactatcca tttctcgacc   2940
gcaaatatcc acccggagtt caggctccaa atatgcacat catatgttac gtgcaaaggt   3000
gattgtcacc ccccgaaaga ccatattgtg acacaccctc agtatcacgc ccaaacattt   3060
acagccgcgg tgtcaaaaac cgcgtggacg tggttaacat ccctgctggg aggatcagcc   3120
gtaattatta taattggctt ggtgctggct actattgtgg ccatgtacgt gctgaccaac   3180
cagaaacata attaatagta agcggccgca tacagcagca attggcaagc tgcttacata   3240
gaactcgcgg cgattggcat gccgccttaa aatttttatt ttatttttct tttcttttcc   3300
gaatcggatt ttgtttttaa tatttcaaaa aaaaaaaaaa aaaaaaaaaa aaaaaaaaaa   3360
agggtcggca tggcatctcc acctcctcgc ggtccgacct gggcatccga aggaggacgc   3420
acgtccactc ggatggctaa gggagagcca cgtttaaaca cgtgatatct ggcctcatgg   3480
gccttccttt cactgcccgc tttccagtcg ggaaacctgt cgtgccagct gcattaacat   3540
ggtcatagct gtttccttgc gtattgggcg ctctccgctt cctcgctcac tgactcgctg   3600
cgctcggtcg ttcgggtaaa gcctggggtg cctaatgagc aaaaggccag caaaaggcca   3660
ggaaccgtaa aaaggccgcg ttgctggcgt ttttccatag gctccgcccc cctgacgagc   3720
atcacaaaaa tcgacgctca agtcagaggt ggcgaaaccc gacaggacta taaagatacc   3780
aggcgtttcc ccctggaagc tccctcgtgc gctctcctgt tccgaccctg ccgcttaccg   3840
```

```
gatacctgtc cgcctttctc ccttcgggaa gcgtggcgct ttctcatagc tcacgctgta   3900

ggtatctcag ttcggtgtag gtcgttcgct ccaagctggg ctgtgtgcac gaaccccccg   3960

ttcagcccga ccgctgcgcc ttatccggta actatcgtct tgagtccaac ccggtaagac   4020

acgacttatc gccactggca gcagccactg gtaacaggat tagcagagcg aggtatgtag   4080

gcggtgctac agagttcttg aagtggtggc ctaactacgg ctacactaga agaacagtat   4140

ttggtatctg cgctctgctg aagccagtta ccttcggaaa aagagttggt agctcttgat   4200

ccggcaaaca aaccaccgct ggtagcggtg gtttttttgt ttgcaagcag cagattacgc   4260

gcagaaaaaa aggatctcaa gaagatcctt tgatcttttc tacggggtct gacgctcagt   4320

ggaacgaaaa ctcacgttaa gggattttgg tcatgagatt atcaaaaagg atcttcacct   4380

agatcctttt aaattaaaaa tgaagtttta aatcaatcta aagtatatat gagtaaactt   4440

ggtctgacag ttattagaaa aattcatcca gcagacgata aaacgcaata cgctggctat   4500

ccggtgccgc aatgccatac agcaccagaa aacgatccgc ccattcgccg cccagttctt   4560

ccgcaatatc acgggtggcc agcgcaatat cctgataacg atccgccacg cccagacggc   4620

cgcaatcaat aaagccgcta aaacggccat tttccaccat aatgttcggc aggcacgcat   4680

caccatgggt caccaccaga tcttcgccat ccggcatgct cgctttcaga cgcgcaaaca   4740

gctctgccgg tgccaggccc tgatgttctt catccagatc atcctgatcc accaggcccg   4800

cttccatacg ggtacgcgca cgttcaatac gatgtttcgc ctgatgatca aacggacagg   4860

tcgccgggtc cagggtatgc agacgacgca tggcatccgc cataatgctc actttttctg   4920

ccggcgccag atggctagac agcagatcct gacccggcac ttcgcccagc agcagccaat   4980

cacggcccgc ttcggtcacc acatccagca ccgccgcaca cggaacaccg gtggtggcca   5040

gccagctcag acgcgccgct tcatcctgca gctcgttcag cgcaccgctc agatcggttt   5100

tcacaaacag caccggacga ccctgcgcgc tcagacgaaa caccgccgca tcagagcagc   5160

caatggtctg ctgcgcccaa tcatagccaa acagacgttc cacccacgct gccgggctac   5220

ccgcatgcag gccatcctgt tcaatcatac tcttcctttt tcaatattat tgaagcattt   5280

atcagggtta ttgtctcatg agcggataca tatttgaatg tatttagaaa aataaacaaa   5340

taggggttcc gcgcacattt ccccgaaaag tgccacctaa attgtaagcg ttaatatttt   5400

gttaaaattc gcgttaaatt tttgttaaat cagctcattt tttaaccaat aggccgaaat   5460

cggcaaaatc ccttataaat caaaagaata gaccgagata gggttgagtg gccgctacag   5520

ggcgctccca ttcgccattc aggctgcgca actgttggga agggcgtttc ggtgcgggcc   5580

tcttcgctat tacgccagct ggcgaaaggg ggatgtgctg caaggcgatt aagttgggta   5640

acgccagggt tttcccagtc acacgcgtaa tacgactcac tatag                    5685
```

<210> SEQ ID NO 83
<211> LENGTH: 13364
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 83

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180
```

```
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
```

```
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
```

-continued

```
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
```

-continued

```
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgacgcc   7560
accatgaggc ctggcctgcc ctcctacctg atcatcctgg ccgtgtgcct gttcagccac   7620
ctgctgtcca gcagatacgg cgccgaggcc gtgagcgagc ccctggacaa ggctttccac   7680
ctgctgctga acacctacgg cagacccatc cggtttctgc gggagaacac cacccagtgc   7740
acctacaaca gcagcctgcg gaacagcacc gtcgtgagag agaacgccat cagcttcaac   7800
tttttccaga gctacaacca gtactacgtg ttccacatgc ccagatgcct gtttgccggc   7860
cctctggccg agcagttcct gaaccaggtg gacctgaccg agacactgga aagataccag   7920
cagcggctga atacctacgc cctggtgtcc aaggacctgg ccagctaccg gtcctttagc   7980
cagcagctca aggctcagga tagcctcggc gagcagccta ccaccgtgcc ccctcccatc   8040
gacctgagca tcccccacgt gtggatgcct ccccagacca cccctcacgg ctggaccgag   8100
agccacacca cctccggcct gcacagaccc cacttcaacc agacctgcat cctgttcgac   8160
ggccacgacc tgctgtttag caccgtgacc ccctgcctgc accagggctt ctacctgatc   8220
gacgagctga gatacgtgaa gatcaccctg accgaggatt tcttcgtggt caccgtgtcc   8280
atcgacgacg acaccccccat gctgctgatc ttcggccacc tgcccagagt gctgttcaag   8340
gccccctacc agcgggacaa cttcatcctg cggcagaccg agaagcacga gctgctggtg   8400
ctggtcaaga aggaccagct gaaccggcac tcctacctga aggaccccga cttcctggac   8460
gccgccctgg acttcaacta cctggacctg agcgccctgc tgagaaacag cttccacaga   8520
tacgccgtgg acgtgctgaa gtccggacgg tgccagatgc tcgatcggcg gaccgtggag   8580
atggccttcg cctatgccct cgccctgttc gccgctgcca gacaggaaga ggctggcgcc   8640
caggtgtcag tgcccagagc cctggataga caggccgccc tgctgcagat ccaggaattc   8700
atgatcacct gcctgagcca gacccccccct agaaccaccc tgctgctgta ccccacagcc   8760
gtggatctgg ccaagagggc cctgtggacc cccaaccaga tcaccgacat cacaagcctc   8820
gtgcggctcg tgtacatcct gagcaagcag aaccagcagc acctgatccc ccagtgggcc   8880
ctgagacaga tcgccgactt cgccctgaag ctgcacaaga cccatctggc cagctttctg   8940
agcgccttcg ccaggcagga actgtacctg atgggcagcc tggtccacag catgctggtg   9000
cataccaccg agcggcggga gatcttcatc gtggagacag gcctgtgtag cctggccgag   9060
ctgtcccact ttacccagct gctggcccac cctcaccacg agtacctgag cgacctgtac   9120
accccctgca gcagcagcgg cagacgggac cacagcctgg aacggctgac cagactgttc   9180
cccgatgcca ccgtgcctgc tacagtgcct gccgccctgt ccatcctgtc caccatgcag   9240
cccagcaccc tggaaacctt ccccgacctg ttctgcctgc ccctgggcga gagctttagc   9300
gccctgaccg tgtccgagca cgtgtcctac atcgtgacca atcagtacct gatcaagggc   9360
atcagctacc ccgtgtccac cacagtcgtg ggccagagcc tgatcatcac ccagaccgac   9420
agccagacca agtgcgagct gacccggaac atgcacacca cacacagcat caccgtggcc   9480
ctgaacatca gcctggaaaa ctgcgctttc tgtcagtctg ccctgctgga atacgacgat   9540
acccagggcg tgatcaacat catgtacatg cacgacagcg acgacgtgct gttcgccctg   9600
gacccctaca acgaggtggt ggtgtccagc cccccggaccc actacctgat gctgctgaag   9660
```

-continued aacggcaccg tgctggaagt gaccgacgtg gtggtggacg ccaccgacag cagactgctg 9720
atgatgagcg tgtacgccct gagcgccatc atcggcatct acctgctgta ccggatgctg 9780
aaaacctgct gataatctag acggcgcgcc cacccagcgg ccgcctataa ctctctacgg 9840
ctaacctgaa tggactacga catagtctag tcgacgccac catgtgcaga aggcccgact 9900
gcggcttcag cttcagccct ggacccgtga tcctgctgtg gtgctgcctg ctgctgccta 9960
tcgtgtcctc tgccgccgtg tctgtggccc ctacagccgc cgagaaggtg ccagccgagt 10020
gccccgagct gaccagaaga tgcctgctgg gcgaggtgtt cgagggcgac aagtacgaga 10080
gctggctgcg gcccctggtc aacgtgaccg gcagagatgg cccccctgagc cagctgatcc 10140 ggtacagacc cgtgaccccc gaggccgcca atagcgtgct gctggacgag gccttcctgg 10200
ataccctggc cctgctgtac aacaaccccg accagctgag agccctgctg accctgctgt 10260
ccagcgacac cgcccccaga tggatgaccg tgatgcgggg ctacagcgag tgtggagatg 10320
gcagccctgc cgtgtacacc tgcgtggacg acctgtgcag aggctacgac ctgaccagac 10380
tgagctacgg ccggtccatc ttcacagagc acgtgctggg cttcgagctg gtgcccccca 10440
gcctgttcaa cgtggtggtg gccatccgga acgaggccac cagaaccaac agagccgtgc 10500
ggctgcctgt gtctacagcc gctgcacctg agggcatcac actgttctac ggcctgtaca 10560
acgccgtgaa agagttctgc ctccggcacc agctggatcc cccctgctg agacacctgg 10620 acaagtacta cgccggcctg cccccagagc tgaagcagac cagagtgaac ctgcccgccc 10680
acagcagata tggccctcag gccgtggacg ccagatgata atctagacgg cgcgcccacc 10740
cacctgcagg atacagcagc aattggcaag ctgcttacat agaactcgcg gcgattggca 10800
tgccgcctta aaatttttat tttatttttc ttttcttttc cgaatcggat tttgttttta 10860
atatttcaaa aaaaaaaaaa aaaaaaaaaa aaaaaaaaaa aagggtcggc atggcatctc 10920
cacctcctcg cggtccgacc tgggcatccg aaggaggacg cacgtccact cggatggcta 10980
agggagagcc acgtttaaac gctagagcaa gacgtttccc gttgaatatg gctcataaca 11040
ccccttgtat tactgtttat gtaagcagac agttttattg ttcatgatga tatattttta 11100
tcttgtgcaa tgtaacatca gagattttga gacacaacgt ggctttgttg aataaatcga 11160
acttttgctg agttgaagga tcagatcacg catcttcccg acaacgcaga ccgttccgtg 11220
gcaaagcaaa agttcaaaat caccaactgg tccacctaca acaaagctct catcaaccgt 11280
ggctccctca ctttctggct ggatgatggg gcgattcagg cctggtatga gtcagcaaca 11340
ccttcttcac gaggcagacc tcagcgctag cggagtgtat actggcttac tatgttggca 11400
ctgatgaggg tgtcagtgaa gtgcttcatg tggcaggaga aaaaaggctg caccggtgcg 11460
tcagcagaat atgtgataca ggatatattc cgcttcctcg ctcactgact cgctacgctc 11520
ggtcgttcga ctgcggcgag cggaaatggc ttacgaacgg ggcggagatt tcctggaaga 11580
tgccaggaag atacttaaca gggaagtgag agggccgcgg caaagccgtt tttccatagg 11640
ctccgccccc ctgacaagca tcacgaaatc tgacgctcaa atcagtggtg gcgaaacccg 11700
acaggactat aaagatacca ggcgtttccc ctggcggctc cctcgtgcgc tctcctgttc 11760
ctgcctttcg gtttaccggt gtcattccgc tgttatggcc gcgtttgtct cattccacgc 11820
ctgacactca gttccgggta ggcagttcgc tccaagctgg actgtatgca cgaacccccc 11880
gttcagtccg accgctgcgc cttatccggt aactatcgtc ttgagtccaa cccggaaaga 11940
catgcaaaag caccactggc agcagccact ggtaattgat ttagaggagt tagtcttgaa 12000

-continued

```
gtcatgcgcc ggttaaggct aaactgaaag gacaagtttt ggtgactgcg ctcctccaag  12060

ccagttacct cggttcaaag agttggtagc tcagagaacc ttcgaaaaac cgccctgcaa  12120

ggcggttttt tcgttttcag agcaagagat tacgcgcaga ccaaaacgat ctcaagaaga  12180

tcatcttatt aaggggtctg acgctcagtg gaacgaaaac tcacgttaag ggattttggt  12240

catgagatta tcaaaaagga tcttcaccta gatcctttta aattaaaaat gaagttttaa  12300

atcaatctaa agtatatatg agtaaacttg gtctgacagt taccaatgct taatcagtga  12360

ggcacctatc tcagcgatct gtctatttcg ttcatccata gttgcctgac tccccgtcgt  12420

gtagataact acgatacggg agggcttacc atctggcccc agtgctgcaa tgataccgcg  12480

agacccacgc tcaccggctc cagatttatc agcaataaac cagccagccg gaagggccga  12540

gcgcagaagt ggtcctgcaa ctttatccgc ctccatccag tctattaatt gttgccggga  12600

agctagagta agtagttcgc cagttaatag tttgcgcaac gttgttgcca ttgctgcagg  12660

catcgtggtg tcacgctcgt cgtttggtat ggcttcattc agctccggtt cccaacgatc  12720

aaggcgagtt acatgatccc ccatgttgtg caaaaaagcg gttagctcct tcggtcctcc  12780

gatcgttgtc agaagtaagt tggccgcagt gttatcactc atggttatgg cagcactgca  12840

taattctctt actgtcatgc catccgtaag atgcttttct gtgactggtg agtactcaac  12900

caagtcattc tgagaatagt gtatgcggcg accgagttgc tcttgcccgg cgtcaacacg  12960

ggataatacc gcgccacata gcagaacttt aaaagtgctc atcattggaa aacgttcttc  13020

ggggcgaaaa ctctcaagga tcttaccgct gttgagatcc agttcgatgt aacccactcg  13080

tgcacccaac tgatcttcag catcttttac tttcaccagc gtttctgggt gagcaaaaac  13140

aggaaggcaa aatgccgcaa aaaagggaat aagggcgaca cggaaatgtt gaatactcat  13200

actcttcctt tttcaatatt attgaagcat ttatcagggt tattgtctca tgagcggata  13260

catatttgaa tgtatttaga aaaataaaca aataggggtt ccgcgcacat ttccccgaaa  13320

agtgccacct gacgtgtcga gacgcgtaat acgactcact atag                  13364
```

```
<210> SEQ ID NO 84
<211> LENGTH: 13283
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
```

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660
```

cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tagacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000

-continued

```
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
```

gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtcgacgcc 7560
accatgaggc ctggcctgcc ctcctacctg atcatcctgg ccgtgtgcct gttcagccac 7620
ctgctgtcca gcagatacgg cgccgaggcc gtgagcgagc ccctggacaa ggctttccac 7680
ctgctgctga acacctacgg cagacccatc cggtttctgc gggagaacac cacccagtgc 7740
acctacaaca gcagcctgcg gaacagcacc gtcgtgagag agaacgccat cagcttcaac 7800
tttttccaga gctacaacca gtactacgtg ttccacatgc ccagatgcct gtttgccggc 7860
cctctggccg agcagttcct gaaccaggtg gacctgaccg agacactgga aagataccag 7920
cagcggctga atacctacgc cctggtgtcc aaggacctgg ccagctaccg gtcctttagc 7980
cagcagctca aggctcagga tagcctcggc gagcagccta ccaccgtgcc ccctcccatc 8040
gacctgagca tcccccacgt gtggatgcct ccccagacca cccctcacgg ctggaccgag 8100
agccacacca cctccggcct gcacagaccc cacttcaacc agacctgcat cctgttcgac 8160
ggccacgacc tgctgtttag caccgtgacc ccctgcctgc accagggctt ctacctgatc 8220
gacgagctga gatacgtgaa gatcaccctg accgaggatt tcttcgtggt caccgtgtcc 8280
atcgacgacg acaccccat gctgctgatc ttcggccacc tgcccagagt gctgttcaag 8340
gccccctacc agcgggacaa cttcatcctg cggcagaccg agaagcacga gctgctggtg 8400
ctggtcaaga aggaccagct gaaccggcac tcctacctga aggaccccga cttcctggac 8460
gccgccctgg acttcaacta cctggacctg agcgccctgc tgagaaacag cttccacaga 8520
tacgccgtgg acgtgctgaa gtccggacgg tgccagatgc tcgatcggcg gaccgtggag 8580
atggccttcg cctatgccct cgccctgttc gccgctgcca gacaggaaga ggctggcgcc 8640
caggtgtcag tgcccagagc cctggataga caggccgccc tgctgcagat ccaggaattc 8700
atgatcacct gcctgagcca gacccccct agaaccaccc tgctgctgta ccccacagcc 8760
gtggatctgg ccaagagggc cctgtggacc cccaaccaga tcaccgacat cacaagcctc 8820
gtgcggctcg tgtacatcct gagcaagcag aaccagcagc acctgatccc ccagtgggcc 8880
ctgagacaga tcgccgactt cgccctgaag ctgcacaaga cccatctggc cagctttctg 8940
agcgccttcg ccaggcagga actgtacctg atgggcagcc tggtccacag catgctggtg 9000
cataccaccg agcggcggga gatcttcatc gtggagacag gcctgtgtag cctggccgag 9060
ctgtcccact ttacccagct gctggcccac cctcaccacg agtacctgag cgacctgtac 9120
accccctgca gcagcagcgg cagacgggac cacagcctgg aacggctgac cagactgttc 9180
cccgatgcca ccgtgcctgc tacagtgcct gccgccctgt ccatcctgtc caccatgcag 9240
cccagcaccc tggaaacctt ccccgacctg ttctgcctgc ccctgggcga gagctttagc 9300
gccctgaccg tgtccgagca cgtgtcctac atcgtgacca atcagtacct gatcaagggc 9360
atcagctacc ccgtgtccac cacagtcgtg ggccagagcc tgatcatcac ccagaccgac 9420
agccagacca agtgcgagct gacccggaac atgcacacca cacacagcat caccgtggcc 9480
ctgaacatca gcctggaaaa ctgcgctttc tgtcagtctg ccctgctgga atacgacgat 9540
acccagggcg tgatcaacat catgtacatg cacgacagcg acgacgtgct gttcgccctg 9600
gacccctaca acgaggtggt ggtgtccagc cccccggaccc actacctgat gctgctgaag 9660
aacggcaccg tgctggaagt gaccgacgtg gtggtggacg ccaccgactg ataatctaga 9720
cggcgcgccc acccagcggc cgcctataac tctctacggc taacctgaat ggactacgac 9780
atagtctagt cgacgccacc atgtgcagaa ggcccgactg cggcttcagc ttcagccctg 9840
gacccgtgat cctgctgtgg tgctgcctgc tgctgcctat cgtgtcctct gccgccgtgt 9900
ctgtggcccc tacagccgcc gagaaggtgc cagccgagtg ccccgagctg accagaagat 9960
gcctgctggg cgaggtgttc gagggcgaca agtacgagag ctggctgcgg cccctggtca 10020
acgtgaccgg cagagatggc cccctgagcc agctgatccg gtacagaccc gtgacccccg 10080
aggccgccaa tagcgtgctg ctggacgagg ccttcctgga taccctggcc ctgctgtaca 10140

-continued

```
acaaccccga ccagctgaga gccctgctga ccctgctgtc cagcgacacc gcccccagat  10200
ggatgaccgt gatgcggggc tacagcgagt gtggagatgg cagccctgcc gtgtacacct  10260
gcgtggacga cctgtgcaga ggctacgacc tgaccagact gagctacggc cggtccatct  10320
tcacagagca cgtgctgggc ttcgagctgg tgccccccag cctgttcaac gtggtggtgg  10380
ccatccggaa cgaggccacc agaaccaaca gagccgtgcg gctgcctgtg tctacagccg  10440
ctgcacctga gggcatcaca ctgttctacg gcctgtacaa cgccgtgaaa gagttctgcc  10500
tccggcacca gctggatccc cccctgctga gacacctgga caagtactac gccggcctgc  10560
ccccagagct gaagcagacc agagtgaacc tgcccgccca cagcagatat ggccctcagg  10620
ccgtggacgc cagatgataa tctagacggc gcgcccaccc acctgcagga tacagcagca  10680
attggcaagc tgcttacata gaactcgcgg cgattggcat gccgccttaa aatttttatt  10740
ttattttttct tttcttttcc gaatcggatt ttgtttttaa tatttcaaaa aaaaaaaaaa  10800
aaaaaaaaaa aaaaaaaaaa agggtcggca tggcatctcc acctcctcgc ggtccgacct  10860
gggcatccga aggaggacgc acgtccactc ggatggctaa gggagagcca cgtttaaacg  10920
ctagagcaag acgtttcccg ttgaatatgg ctcataacac cccttgtatt actgtttatg  10980
taagcagaca gttttattgt tcatgatgat atatttttat cttgtgcaat gtaacatcag  11040
agattttgag acacaacgtg gctttgttga ataaatcgaa cttttgctga gttgaaggat  11100
cagatcacgc atcttcccga caacgcagac cgttccgtgg caaagcaaaa gttcaaaatc  11160
accaactggt ccacctacaa caaagctctc atcaaccgtg gctccctcac tttctggctg  11220
gatgatgggg cgattcaggc ctggtatgag tcagcaacac cttcttcacg aggcagacct  11280
cagcgctagc ggagtgtata ctggcttact atgttggcac tgatgagggt gtcagtgaag  11340
tgcttcatgt ggcaggagaa aaaaggctgc accggtgcgt cagcagaata tgtgatacag  11400
gatatattcc gcttcctcgc tcactgactc gctacgctcg gtcgttcgac tgcggcgagc  11460
ggaaatggct tacgaacggg gcggagattt cctggaagat gccaggaaga tacttaacag  11520
ggaagtgaga gggccgcggc aaagccgttt ttccataggc tccgcccccc tgacaagcat  11580
cacgaaatct gacgctcaaa tcagtggtgg cgaaacccga caggactata aagataccag  11640
gcgtttcccc tggcggctcc ctcgtgcgct ctcctgttcc tgcctttcgg tttaccggtg  11700
tcattccgct gttatggccg cgtttgtctc attccacgcc tgacactcag ttccgggtag  11760
gcagttcgct ccaagctgga ctgtatgcac gaaccccccg ttcagtccga ccgctgcgcc  11820
ttatccggta actatcgtct tgagtccaac ccggaaagac atgcaaaagc accactggca  11880
gcagccactg gtaattgatt tagaggagtt agtcttgaag tcatgcgccg gttaaggcta  11940
aactgaaagg acaagttttg gtgactgcgc tcctccaagc cagttacctc ggttcaaaga  12000
gttggtagct cagagaacct tcgaaaaacc gccctgcaag gcggtttttt cgttttcaga  12060
gcaagagatt acgcgcagac caaaacgatc tcaagaagat catcttatta aggggtctga  12120
cgctcagtgg aacgaaaact cacgttaagg gattttggtc atgagattat caaaaaggat  12180
cttcacctag atccttttaa attaaaaatg aagttttaaa tcaatctaaa gtatatatga  12240
gtaaacttgg tctgacagtt accaatgctt aatcagtgag gcacctatct cagcgatctg  12300
tctatttcgt tcatccatag ttgcctgact ccccgtcgtg tagataacta cgatacggga  12360
gggcttacca tctggcccca gtgctgcaat gataccgcga gacccacgct caccggctcc  12420
agatttatca gcaataaacc agccagccgg aagggccgag cgcagaagtg gtcctgcaac  12480
```

```
tttatccgcc tccatccagt ctattaattg ttgccgggaa gctagagtaa gtagttcgcc  12540

agttaatagt ttgcgcaacg ttgttgccat tgctgcaggc atcgtggtgt cacgctcgtc  12600

gtttggtatg gcttcattca gctccggttc ccaacgatca aggcgagtta catgatcccc  12660

catgttgtgc aaaaaagcgg ttagctcctt cggtcctccg atcgttgtca gaagtaagtt  12720

ggccgcagtg ttatcactca tggttatggc agcactgcat aattctctta ctgtcatgcc  12780

atccgtaaga tgcttttctg tgactggtga gtactcaacc aagtcattct gagaatagtg  12840

tatgcggcga ccgagttgct cttgcccggc gtcaacacgg gataataccg cgccacatag  12900

cagaacttta aaagtgctca tcattggaaa acgttcttcg gggcgaaaac tctcaaggat  12960

cttaccgctg ttgagatcca gttcgatgta acccactcgt gcacccaact gatcttcagc  13020

atcttttact ttcaccagcg tttctgggtg agcaaaaaca ggaaggcaaa atgccgcaaa  13080

aaagggaata agggcgacac ggaaatgttg aatactcata ctcttccttt ttcaatatta  13140

ttgaagcatt tatcagggtt attgtctcat gagcggatac atatttgaat gtatttagaa  13200

aaataaacaa ataggggttc cgcgcacatt tccccgaaaa gtgccacctg acgtgtcgag  13260

acgcgtaata cgactcacta tag                                          13283
```

```
<210> SEQ ID NO 85
<211> LENGTH: 13463
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
```

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200
```

-continued

```
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
```

-continued

```
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
```

ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtcgacgcc 7560
accatggaaa gccggatctg gtgcctggtc gtgtgcgtga acctgtgcat cgtgtgcctg 7620
ggagccgccg tgagcagcag cagcaccaga ggcaccagcg ccacacacag ccaccacagc 7680
agccacacca cctctgccgc ccacagcaga tccggcagcg tgtcccagag agtgaccagc 7740
agccagaccg tgtcccacgg cgtgaacgag acaatctaca acaccaccct gaagtacggc 7800
gacgtcgtgg gcgtgaatac caccaagtac ccctacagag tgtgcagcat ggcccagggc 7860
accgacctga tcagattcga gcggaacatc gtgtgcacca gcatgaagcc catcaacgag 7920
gacctggacg agggcatcat ggtggtgtac aagagaaaca tcgtggccca caccttcaaa 7980
gtgcgggtgt accagaaggt gctgaccttc cggcggagct acgcctacat ccacaccaca 8040
tacctgctgg gcagcaacac cgagtacgtg gcccctccca tgtgggagat ccaccacatc 8100
aacagccaca gccagtgcta cagcagctac agccgcgtga tcgccggcac agtgttcgtg 8160
gcctaccacc gggacagcta cgagaacaag accatgcagc tgatgcccga cgactacagc 8220
aacacccaca gcaccagata cgtgaccgtg aaggaccagt ggcacagcag aggcagcacc 8280

-continued

```
tggctgtacc gggagacatg caacctgaac tgcatggtca ccatcaccac cgccagaagc   8340
aagtaccctt accacttctt cgccacctcc accggcgacg tggtggacat cagccccttc   8400
tacaacggca ccaaccggaa cgccagctac ttcggcgaga acgccgacaa gttcttcatc   8460
ttccccaact acaccatcgt gtccgacttc ggcagaccca acagcgctct ggaaacccac   8520
agactggtgg cctttctgga acgggccgac agcgtgatca gctgggacat ccaggacgag   8580
aagaacgtga cctgccagct gaccttctgg gaggcctctg agagaaccat cagaagcgag   8640
gccgaggaca gctaccactt cagcagcgcc aagatgaccg ccaccttcct gagcaagaaa   8700
caggaagtga acatgagcga ctccgccctg gactgcgtga gggacgaggc catcaacaag   8760
ctgcagcaga tcttcaacac cagctacaac cagacctacg agaagtatgg caatgtgtcc   8820
gtgttcgaga caacaggcgg cctggtggtg ttctggcagg gcatcaagca gaaaagcctg   8880
gtggagctgg aacggctcgc caaccggtcc agcctgaacc tgacccacaa ccggaccaag   8940
cggagcaccg acggcaacaa cgcaacccac ctgtccaaca tggaaagcgt gcacaacctg   9000
gtgtacgcac agctgcagtt cacctacgac accctgcggg gctacatcaa cagagccctg   9060
gcccagatcg ccgaggcttg gtgcgtggac cagcggcgga ccctggaagt gttcaaagag   9120
ctgtccaaga tcaaccccag cgccatcctg agcgccatct acaacaagcc tatcgccgcc   9180
agattcatgg gcgacgtgct gggcctggcc agctgcgtga ccatcaacca gaccagcgtg   9240
aaggtgctgc gggacatgaa cgtgaaagag agcccaggcc gctgctactc cagacccgtg   9300
gtcatcttca acttcgccaa cagctcctac gtgcagtacg gccagctggg cgaggacaac   9360
gagatcctgc tggggaacca ccggaccgag gaatgccagc tgcccagcct gaagatcttt   9420
atcgccggca acagcgccta cgagtatgtg gactacctgt tcaagcggat gatcgacctg   9480
agcagcatct ccaccgtgga cagcatgatc gccctggaca tcgacccccct ggaaaacacc   9540
gacttccggg tgctggaact gtacagccag aaagagctgc ggagcagcaa cgtgttcgac   9600
ctggaagaga tcatgcggga gttcaacagc tacaagcagc gcgtgaaata cgtggaggac   9660
aaggtggtgg accccctgcc tccttacctg aagggcctgg acgacctgat gagcggactg   9720
ggcgctgccg gaaaagccgt gggagtggcc attggagctg tgggcggagc tgtggcctct   9780
gtcgtggaag gcgtcgccac ctttctgaag aacccttcg gcgccttcac catcatcctg   9840
gtggccattg ccgtcgtgat catcacctac ctgatctaca cccggcagcg gagactgtgt   9900
acccagcccc tgcagaacct gttcccctac ctggtgtccg ccgatggcac cacagtgacc   9960
agcggctcca ccaaggatac cagcctgcag gccccaccca gctacgaaga gagcgtgtac  10020
aacagcggca gaaagggccc tggccctccc agctctgatg ccagcacagc cgcccctccc  10080
tacaccaacg agcaggccta ccagatgctg ctggccctgg ctagactgga tgccgagcag  10140
agggcccagc agaacggcac cgacagcctg gatggcagaa ccggcaccca ggacaagggc  10200
cagaagccca acctgctgga ccggctgcgg caccggaaga acggctaccg gcacctgaag  10260
gacagcgacg aggaagagaa cgtctgataa tctagacggc gcgcccaccc agcggccgca  10320
tacagcagca attggcaagc tgcttacata gaactcgcgg cgattggcat gccgccttaa  10380
aatttttatt ttattttttct tttcttttcc gaatcggatt ttgtttttaa tatttcaaaa  10440
aaaaaaaaaa aaaaaaaaaa aaaaaaaaaa agggtcggca tggcatctcc acctcctcgc  10500
ggtccgacct gggcatccga aggaggacgc acgtccactc ggatggctaa gggagagcca  10560
cgtttaaacc agctccaatt cgccctatag tgagtcgtat tacgcgcgct cactggccgt  10620
cgttttacaa cgtcgtgact gggaaaaccc tggcgttacc caacttaatc gccttgcagc  10680
```

acatccccct ttcgccagct ggcgtaatag cgaagaggcc cgcaccgatc gcccttccca 10740
acagttgcgc agcctgaatg gcgaatggga cgcgccctgt agcggcgcat taagcgcggc 10800
gggtgtggtg gttacgcgca gcgtgaccgc tacacttgcc agcgccctag cgcccgctcc 10860
tttcgctttc ttcccttcct ttctcgccac gttcgccggc tttccccgtc aagctctaaa 10920
tcgggggctc cctttagggt tccgatttag tgctttacgg cacctcgacc ccaaaaaact 10980
tgattagggt gatggttcac gtagtgggcc atcgccctga tagacggttt ttcgcccttt 11040
gacgttggag tccacgttct ttaatagtgg actcttgttc caaactggaa caacactcaa 11100
ccctatctcg gtctattctt ttgatttata agggattttg ccgatttcgg cctattggtt 11160
aaaaaatgag ctgatttaac aaaaatttaa cgcgaatttt aacaaaatat taacgcttac 11220
aatttaggtg gcacttttcg gggaaatgtg cgcggaaccc ctatttgttt atttttctaa 11280
atacattcaa atatgtatcc gctcatgaga caataaccct gataaatgct tcaataatat 11340
tgaaaaagga agagtatgag tattcaacat ttccgtgtcg cccttattcc cttttttgcg 11400
gcattttgcc ttcctgtttt tgctcaccca gaaacgctgg tgaaagtaaa agatgctgaa 11460
gatcagttgg gtgcacgagt gggttacatc gaactggatc tcaacagcgg taagatcctt 11520
gagagttttc gccccgaaga acgttttcca atgatgagca cttttaaagt tctgctatgt 11580
ggcgcggtat tatcccgtat tgacgccggg caagagcaac tcggtcgccg catacactat 11640
tctcagaatg acttggttga gtactcacca gtcacagaaa agcatcttac ggatggcatg 11700
acagtaagag aattatgcag tgctgccata accatgagtg ataacactgc ggccaactta 11760
cttctgacaa cgatcggagg accgaaggag ctaaccgctt ttttgcacaa catgggggat 11820
catgtaactc gccttgatcg ttgggaaccg gagctgaatg aagccatacc aaacgacgag 11880
cgtgacacca cgatgcctgt agcaatggca acaacgttgc gcaaactatt aactggcgaa 11940
ctacttactc tagcttcccg gcaacaatta atagactgga tggaggcgga taaagttgca 12000
ggaccacttc tgcgctcggc ccttccggct ggctggttta ttgctgataa atctggagcc 12060
ggtgagcgtg ggtctcgcgg tatcattgca gcactggggc cagatggtaa gccctcccgt 12120
atcgtagtta tctacacgac ggggagtcag gcaactatgg atgaacgaaa tagacagatc 12180
gctgagatag gtgcctcact gattaagcat tggtaactgt cagaccaagt ttactcatat 12240
atactttaga ttgatttaaa acttcatttt taatttaaaa ggatctaggt gaagatcctt 12300
tttgataatc tcatgaccaa aatcccttaa cgtgagtttt cgttccactg agcgtcagac 12360
cccgtagaaa agatcaaagg atcttcttga gatccttttt ttctgcgcgt aatctgctgc 12420
ttgcaaacaa aaaaaccacc gctaccagcg gtggtttgtt tgccggatca agagctacca 12480
actctttttc cgaaggtaac tggcttcagc agagcgcaga taccaaatac tgttcttcta 12540
gtgtagccgt agttaggcca ccacttcaag aactctgtag caccgcctac atacctcgct 12600
ctgctaatcc tgttaccagt ggctgctgcc agtggcgata agtcgtgtct taccgggttg 12660
gactcaagac gatagttacc ggataaggcg cagcggtcgg gctgaacggg gggttcgtgc 12720
acacagccca gcttggagcg aacgacctac accgaactga gatacctaca gcgtgagcta 12780
tgagaaagcg ccacgcttcc cgaagggaga aaggcggaca ggtatccggt aagcggcagg 12840
gtcggaacag gagagcgcac gagggagctt ccagggggaa acgcctggta tctttatagt 12900
cctgtcgggt ttcgccacct ctgacttgag cgtcgatttt tgtgatgctc gtcagggggg 12960
cggagcctat ggaaaaacgc cagcaacgcg gcctttttac ggttcctggc cttttgctgg 13020

-continued

| | |
|---|---|
| ccttttgctc acatgttctt tcctgcgtta tcccctgatt ctgtggataa ccgtattacc | 13080 |
| gcctttgagt gagctgatac cgctcgccgc agccgaacga ccgagcgcag cgagtcagtg | 13140 |
| agcgaggaag cggaagagcg cccaatacgc aaaccgcctc tccccgcgcg ttggccgatt | 13200 |
| cattaatgca gctggcacga caggtttccc gactggaaag cgggcagtga gcgcaacgca | 13260 |
| attaatgtga gttagctcac tcattaggca ccccaggctt tacactttat gctcccggct | 13320 |
| cgtatgttgt gtggaattgt gagcggataa caatttcaca caggaaacag ctatgaccat | 13380 |
| gattacgcca agcgcgcaat taaccctcac taaagggaac aaaagctggg taccgggccc | 13440 |
| acgcgtaata cgactcacta tag | 13463 |